US012577222B2

(12) United States Patent
Clark

(10) Patent No.: US 12,577,222 B2
(45) Date of Patent: Mar. 17, 2026

(54) PHENETHYLAMINE COMPOUNDS SALTS, POLYMORPHIC FORMS AND METHODS OF USE THEREOF

(71) Applicant: Terran Biosciences Inc., New York, NY (US)

(72) Inventor: Samuel Clark, New York, NY (US)

(73) Assignee: Terran Biosciences Inc., Miami Beach, FL (US)

(*) Notice: Subject to any disclaimer, the term of this patent is extended or adjusted under 35 U.S.C. 154(b) by 0 days.

(21) Appl. No.: 18/418,122

(22) Filed: Jan. 19, 2024

(65) Prior Publication Data

US 2024/0327371 A1 Oct. 3, 2024

Related U.S. Application Data

(63) Continuation of application No. 18/176,441, filed on Feb. 28, 2023, now Pat. No. 11,958,821, which is a
(Continued)

(51) Int. Cl.
*C07D 317/58* (2006.01)
*A61K 45/06* (2006.01)
(Continued)

(52) U.S. Cl.
CPC ............ *C07D 317/58* (2013.01); *A61K 45/06* (2013.01); *A61P 25/22* (2018.01); *C07C 217/74* (2013.01);
(Continued)

(58) Field of Classification Search
CPC ... C07C 217/74; C07C 2602/08; C07C 57/15; C07D 317/58; C07D 317/70; A61K 45/06; A61P 25/22; C07B 2200/13
See application file for complete search history.

(56) References Cited

U.S. PATENT DOCUMENTS

| | | | |
|---|---|---|---|
| 4,058,607 | A | 11/1977 | Hennart et al. |
| 6,221,335 | B1 | 4/2001 | Foster |

(Continued)

FOREIGN PATENT DOCUMENTS

| | | | |
|---|---|---|---|
| AU | 2021106190 | A4 | 10/2021 |
| WO | WO-9639133 | A1 | 12/1996 |

(Continued)

OTHER PUBLICATIONS

Braun et al., Unraveling Complexity in the Solid Form Screening of a Pharmaceutical Salt: Why so Many Forms? Why so Few?, Crystal Growth & Design, 2017, 17, pp. 5349, 5365 (Year: 2017).*

(Continued)

*Primary Examiner* — Renee Claytor
*Assistant Examiner* — Andrew P Lee
(74) *Attorney, Agent, or Firm* — Fenwick & West LLP; Eric A. Owens; Daniel E. Manson

(57) ABSTRACT

Disclosed herein are salts and solid forms of MDMA, (R)-MDMA, (S)-MDMA, MDE, S-MDE, R-MDE, MDAI, MBDB, S-MBDB, R-MBDB, MEAI, and 5,6-Dimethoxy-2-aminoindane, including salts, solid forms of the compound and salts thereof, as well as polymorphs of solid forms. The solid forms disclosed herein may have improved properties, such as improved physical, chemical, and/or pharmacokinetic properties. Also disclosed are methods for making the salts and solid forms and methods for administering the same. The disclosed salt and solid forms of MDMA, (R)-MDMA, (S)-MDMA, MDE, S-MDE, R-MDE, MDAI, MBDB, S-MBDB, R-MBDB, MEAI, and 5,6-Dimethoxy-2-aminoindane may be useful for treating neurological disease and/or a psychiatric disorder in a subject.

38 Claims, 98 Drawing Sheets

Related U.S. Application Data continuation of application No. 17/989,673, filed on Nov. 17, 2022, which is a continuation of application No. PCT/US2022/079411, filed on Nov. 7, 2022, and a continuation of application No. PCT/US2022/079413, filed on Nov. 7, 2022, and a continuation of application No. PCT/US2022/079415, filed on Nov. 7, 2022.

(60) Provisional application No. 63/357,611, filed on Jun. 30, 2022, provisional application No. 63/326,721, filed on Apr. 1, 2022, provisional application No. 63/326,797, filed on Apr. 1, 2022, provisional application No. 63/326,802, filed on Apr. 1, 2022, provisional application No. 63/326,743, filed on Apr. 1, 2022, provisional application No. 63/326,735, filed on Apr. 1, 2022, provisional application No. 63/304,176, filed on Jan. 28, 2022, provisional application No. 63/303,588, filed on Jan. 27, 2022, provisional application No. 63/284,923, filed on Dec. 1, 2021, provisional application No. 63/284,927, filed on Dec. 1, 2021, provisional application No. 63/283,024, filed on Nov. 24, 2021, provisional application No. 63/283,017, filed on Nov. 24, 2021, provisional application No. 63/282,591, filed on Nov. 23, 2021, provisional application No. 63/280,854, filed on Nov. 18, 2021, provisional application No. 63/280,964, filed on Nov. 18, 2021, provisional application No. 63/280,960, filed on Nov. 18, 2021, provisional application No. 63/280,550, filed on Nov. 17, 2021, provisional application No. 63/280,552, filed on Nov. 17, 2021.

(51) Int. Cl.
*A61P 25/22* (2006.01)
*C07C 217/74* (2006.01)
*C07D 317/70* (2006.01)

(52) U.S. Cl.
CPC ........ *C07D 317/70* (2013.01); *C07B 2200/13* (2013.01)

(56) References Cited

U.S. PATENT DOCUMENTS

| | | | |
|---|---|---|---|
| 6,316,613 | B1 | 11/2001 | Chen et al. |
| 6,603,008 | B1 | 8/2003 | Ando et al. |
| 7,060,847 | B2 | 6/2006 | Ghoshal et al. |
| 7,517,990 | B2 | 4/2009 | Ito et al. |
| 8,877,802 | B2 | 11/2014 | Caron et al. |
| 10,406,123 | B2 | 9/2019 | Golan |
| 11,958,821 | B2 | 4/2024 | Clark |
| 2005/0130225 | A1 | 6/2005 | Zheng et al. |
| 2007/0082929 | A1 | 4/2007 | Gant et al. |
| 2007/0197695 | A1 | 8/2007 | Potyen et al. |
| 2018/0243241 | A1 | 8/2018 | Popp et al. |
| 2023/0096116 | A1 | 3/2023 | Fawaz et al. |
| 2023/0150965 | A1 | 5/2023 | Duncton et al. |
| 2023/0150966 | A1 | 5/2023 | Duncton et al. |
| 2023/0181521 | A1 | 6/2023 | Duncton et al. |
| 2023/0202998 | A1 | 6/2023 | Duncton et al. |
| 2023/0227420 | A1 | 7/2023 | Rao et al. |
| 2023/0227422 | A1 | 7/2023 | Duncton et al. |
| 2023/0278977 | A1 | 9/2023 | Fawaz et al. |
| 2024/0317724 | A1 | 9/2024 | Clark |

FOREIGN PATENT DOCUMENTS

| | | | |
|---|---|---|---|
| WO | WO2005058864 | A1 | 6/2005 |
| WO | WO2007069925 | A2 | 6/2007 |
| WO | WO2008098151 | A2 | 8/2008 |
| WO | WO2009095479 | A2 | 8/2009 |
| WO | WO2010015029 | A1 | 2/2010 |
| WO | WO-2016092547 | A1 | 6/2016 |
| WO | WO2019081764 | A1 | 5/2019 |
| WO | WO2022053696 | A1 | 3/2022 |
| WO | WO-2022232949 | A1 | 11/2022 |
| WO | WO2022256720 | A2 | 12/2022 |
| WO | WO2023283373 | A1 | 1/2023 |
| WO | WO-2023283386 | A2 | 1/2023 |
| WO | WO2023028022 | A1 | 3/2023 |
| WO | WO-2023028091 | A1 | 3/2023 |
| WO | WO2023056102 | A1 | 4/2023 |
| WO | WO-2023081895 | A1 | 5/2023 |
| WO | WO-2023081897 | A1 | 5/2023 |
| WO | WO-2023081899 | A1 | 5/2023 |
| WO | WO-2023092044 | A2 | 5/2023 |
| WO | WO2023137446 | A1 | 7/2023 |

OTHER PUBLICATIONS

Graf et al., Synchrotron far-infrared spectra for the characterisation of molecular crystals of forensic interest: Amphetamine, methamphetamine, MDA, MDMA and substituted methcathinones, Vibrational Spectroscopy, 2020, 110, pp. 1-10 (Year: 2020).*

Bijlsma et al., "Fragmentation pathways of drugs of abuse and their metabolites based on QTOF MS/MS and MS(E) accurate-mass spectra," J Mass Spectrom (Sep. 2011); 46(9):865-875.

Corkery et al., "MDAI (5,6-methylenedioxy-2-aminoindane; 6,7-dihydro-5H-cyclopenta[f][I,3]benzodioxol-6-amine; 'sparkle;' 'mindy') toxicity: a brief overview and update," Human Psychopharmacology: Clinical and Experimental, vol. 28(4):345-355, Published Jul. 2013, 11 pages.

Database STN, CAS Registry No. 284474-81-3 "Ethan-d5-amine, hydrochloride (9CI) (CA Index Name)", Chemical Abstracts Service, American Chemical Society entered Aug. 9, 2000; retrieved Mar. 24, 2023; 1 page.

Database STN, CAS Registry No. 5581-55-5 "Methan-d3-amine (9CI) (CA Index Name)", Chemical Abstracts Service, American Chemical Society entered Nov. 16, 1984; retrieved Mar. 24, 2023; 1 page.

El-Habashy et al., "Novel treatment strategies for brain tumors and metastases," Pharm Pat Anal., (May 2014); 3(3):279-296.

Erowid, Ecstasy Tablet Gallery, Retrieved from Dec. 25, 2020, URL: https://web.archive.org/web/20201225063007/https://erowid.org/chemicals/mdma/mdma_images_galleryl.shtml, 2 pages.

Erowid, MDE Images, Retrieved from Jun. 6, 2007, URL: https://web.archive.org/web/20070606024111/https://erowid.org/chemicals/mde/mde_images.shtm, 1 page.

Erowid, MDMA Dosage, Retrieved from Apr. 9, 2007, URL: https://web.archive.org/web/20070409141435/https://erowid.org/chemicals/mdma/mdma_dose.shtml, 1 page.

Foster AB "Deuterium isotope effects in the metabolism of drugs and xenobiotics: implications for drug design", Advances in drug Research. (Jan. 1, 1985); 14:1-40.

Freudenmann, R.W, et al., "The neuropsychopharmacology and toxicology of 3,4-methylenedioxy-N-ethyl-amphetamine (MDEA)", CNS Drug Reviews. (Jul. 1, 2004); 10(2):89-116.

Graf et al. "Synchrotron far-infrared spectra for the characterisation of molecular crystals of forensic interest: Amphetamine, methamphetamine, MDA, MDMA and substituted methcathinones" Vibrational Spectroscopy, (2020); 110:103115, 10 pages.

International Search Report and Written Opinion for International Application No. PCT/US2022/079411, mailed on Mar. 9, 2023, 16 pages.

International Search Report and Written Opinion for International Application No. PCT/US2022/079413, mailed on Mar. 9, 2023, 16 pages.

International Search Report and Written Opinion for International Application No. PCT/US2022/079415, dated on Mar. 3, 2023, 17 pages.

(56) References Cited

OTHER PUBLICATIONS

International Search Report and Written Opinion for International Application No. PCT/US2022/080090 dated May 15, 2023, 23 Pages.
Johnson, M.P, et al., "Neurotoxic effects of the alpha-ethyl homologue of MDMA following subacute administration", Pharmacology, biochemistry, and behavior, (May 1, 1989); 33(1): 105-108.
Liabres et al., "Molecular basis of the selective binding of MDMA enantiomers to the alpha4beta2 nicotinic receptor subtype: synthesis, pharmacological evaluation and mechanistic studies", European Journal of Medicinal Chemistry, Jun. 2014, pp. 35-46.
Matsushima K, et al., "Optical isomer analysis of 3,4-methylenedioxyamphetamine analogues and their stereoselective disposition in rats", Journal of Analytical toxicology. (Jan. 1, 1998); 22(1):33-39.
"MDE Dosage", Erowid [Online], Jan. 1, 2000—Modified Feb. 21, 2015, [retrieved on Apr. 14, 2023] 1 page, Retrieved from the Internet: https://erowid.org/chemicals/mde/mde_dose.shtml.
"MDEA", Wikipedia [Online], Last Modified Aug. 2, 2022, [retrieved on Apr. 14, 2023] 12 pages, Retrieved from the Internet: https://psychonautwiki.org/wiki/MDEA.
Morrison et al.: Isotope Effects. Organic Chemistry, 3rd Edition (1973), pp. 353-534.
Murple, First Encounter with MBI DIBI, Retrieved from Oct. 17, 2017, URL: https://web.archive.org/web/20121017041940/https://erowid.org/experiences/exp.php?ID=I 0514, 2 pages.
Nichols, D.E. et al., "Differences between the mechanism of action of MDMA, MBDB, and the classic hallucinogens. Identification of a new therapeutic class: entactogens", Journal of Psychoactive Drugs. (Oct. 1, 1986); 18(4):305-313.
Nichols, D.E. et al., "Structure-activity relationships of MDMA and related compounds: A new class of psychoactive drugs?" Annals of the New York Academy of Sciences. (Oct. 1, 1990); 600(1):613-625.
Pinterova et al. "Synthetic Aminoindanes: A Summary of Existing Knowledge," Frontiers in Psychiatry, (2017); 8:(236):1-7.
Pubchem, 5,6-dimethoxy-2,3-dihydro-1H-inden-2-amine, PubChem CID: 11041623, Date generated: Oct. 26, 2006, URL: https://pubchem.ncbi.nlm.nih.gov/compound/11041623, 8 pages.
Pubchem, 5-Methoxy-2,3-dihydro-1H-inden-2-amine, PubChem CID: 12147687, Date generated: Feb. 7, 2007, URL: https://pubchem.ncbi.nlm.nih.gov/compound/5-Methoxy-2_3-dihydro-1H-inden-2-amine, 11 pages.
Rendle et al., "Powder diffraction data for methylenedioxymethylamphetamine hydrochloride monohydrate (MDMA.HCI.H2O, Ecstasy hydrate)," Powder Diffraction, vol. 27(4):263-265, Published Dec. 2012, 3 pages.
Researchgate, How can I convert the XRD pattern taken using Cobalt-K alpha to Copper-K alpha?, published Apr. 8, 2014, Retrieved online at URL: https://www.researchgate.net/post/How-can-I-convert-the-XRD-pattern-taken-using-Cobalt-K-alpha-to-Copper-K-alpha, 8 pages.
Shulgin: #106 MDE, Retrieved from Mar. 13, 2007, URL: https://web.archive.org/web/20070313060343/https://erowid.org/library/books_online/pihkal/pihkal106.shtml, 2 pages.
Shulgin, #109 MDMA, Retrieved from Mar. 13, 2007, URL: https://web.archive.org/web/20070313060354/https://erowid.org/library/books_online/pihkal/pihkal109.shtml, 3 pages.
Shulgin, #128 METHYL-J, Retrieved Mar. 13, 2007, URL: https://web.archive.org/web/20070313060406/https://erowid.org/library/books_online/pihkal/pihkal128.shtml, 2 pages.
Shulgin et al. "PIHKAL", Transform Press. Berkeley, CA. 1991:453-923.
Spitzer M. et al., "Enantio-selective cognitive and brain activation effects of N-ethyl-3,4-methylenedioxyamphetamine in humans", Neuropharmacology. (Aug. 1, 2001); 41(2):263-271.
Steele, T.D. et al., "Stereochemical effects of 3,4-methylenedioxymethamphetamine (MDMA) and related amphetamine derivatives on inhibition of uptake of [3H]monoamines into synaptosomes from different regions of rat brain", Biochemical pharmacology. (Jul. 15, 1987); 36(14):2297-2303.
Timmins GS "Deuterated drugs: where are we now?", Expert opinion on therapeutic patents. (Jul. 29, 2014); 24(10):1067-1075.
Tonn et al.: Simultaneous analysis of diphenhydramine and a stable isotope analog (2H10)diphenhydramine using capillary gas chromatography with mass selective detection in biological fluids from chronically instrumented pregnant ewes. Biol Mass Spectrom., Nov. 1993, 22(11):633-642.
U.S. Appl. No. 17/989,673 Third Party Submission Under 37 CFR 1.290 dated Sep. 14, 2023, 31 pages.
U.S. Appl. No. 63/137,615, filed Jan. 14, 2021. Associated PCT application publication date Jul. 14, 2022, 111 pages.
U.S. Appl. No. 63/184,703, filed May 5, 2021. Associated PCT application publication date Nov. 10, 2022, 26 pages.
U.S. Appl. No. 63/236,498, filed Aug. 24, 2021. Associated PCT application publication date Mar. 2, 2023, 57 pages.
U.S. Appl. No. 63/250,978, filed Sep. 30, 2021. Associated PCT application publication date Apr. 6, 2023, 38 pages.
Whalen, RW. "Deuterium Isotope Studies on Selected Pesticides and Synergists" (1966). ETD Collection for Fordham University. AAI6613533. 24 pages. https://research.library.fordham.edu/dissertations/AAI6613533.
Wolfson et al., "MDMA-assisted psychotherapy for treatment of anxiety and other psychological distress related to life-threatening illnesses: a randomized pilot study," Scientific Reports, vol. 10:20442, Published Nov. 24, 2020, 15 pages.
Zidková et al. "Study on the metabolism of 5,6-methylenedioxy-2-aminoindane (MDAI) in rats: identification of urinary metabolites", Xenobiotica. (Jun. 3, 2017); 47(6):505-514.
Zoomgroove, Cuddle Puddle, Retrieved from Aug. 11, 2016, URL:https://web.archive.org/web/20160811183800/https://erowid.org/experiences/exp.php?ID=91055, 2 pages.
Skelton, B.W. et al., "CCDC 1825511: Experimental Crystal Structure Determination," Cambridge Crystallographic Data Centre, Feb. 23, 2018, one page, DOI: 10.5517/ccdc.csd.cc1z8lg9, [Retrieved on May 1, 2025] <URL: https://www.ccdc.cam.ac.uk/structures/search?id=doi:10.5517/ccdc.csd.cc1z8lg9&SID=DataCite>.
Van Aerts et al., "N-methyl-1-(1,3-benzodioxol-5-yl)-2-butanamine (MBDB): its properties and possible risks," Addiction Biology, Jul. 2000, 5(3):269-282.
Shimshoni et al., "Pharmacokinetic and pharmacodynamic evaluation of 5-methoxy-2-aminoindane (MEAI): A new binge-mitigating agent," Toxicology and Applied Pharmacology, Mar. 15, 2018, 343:29-39.
Awad, T., et al.; "GC-MS studies on side chain regioisomers related to substituted methylenedioxyphenethylamines: MDEA, MDMMA, and MBDB," Journal of Chromatographic Science; 48(9):726-732 (2010).
Belal, T., et al.; "GC-MS evaluation of a series of acylated derivatives of 3,4-methylenedioxymethamphetamine," J Chromatogr Sci.; 47(5):359-364 (May-Jun. 2009); doi: 10.1093/chromsci/47.5.359.
CAS Registration No. 133217-74-0, "Propanoic acid, 2,2-dimethyl-, [(chlorocarbonyl)oxy]methyl ester," Date Entered STN: Apr. 12, 1991; retrieved Aug. 26, 2024; 1 page.
CAS Registration No. 134098-68-3, "Benzenepropanoic acid, 2-(acetyloxy)-α,β,4,6-tetramethyl-," Date Entered STN: Jun. 7, 1991; retrieved Aug. 26, 2024; 1 page.
CAS Registration No. 52221-07-5, "Hexanedioic acid, 1-(1,1-dimethylethyl) ester," Date Entered STN: Nov. 16, 1984; retrieved Aug. 26, 2024; 1 page.
CAS Registration No. 628-12-6, "Carbonochloridic acid, 2-methoxyethyl ester," Date Entered STN: Nov. 16, 1984; retrieved Aug. 26, 2024; 1 page.
CAS Registration No. 63128-51-8, "Pentanedioic acid, 1-(1,1-dimethylethyl) ester," Date Entered STN: Nov. 16, 1984; retrieved Aug. 26, 2024; 1 page.
CAS Registration No. 959243-61-9, "Benzamide, N-[2-(1,3-benzodioxol-5-yl)-1-methylethyl]-N-ethyl-," Date Entered STN: Dec. 21, 2007; retrieved Aug. 26, 2024; 1 page.
Collins, M., et al.; "Identification and characterization of N-tert-butoxycarbonyl-MDMA: a new MDMA precursor," Drug Test Anal.; 9(3):399-404 (Mar. 2017); doi: 10.1002/dta.2059.

(56) References Cited

OTHER PUBLICATIONS

Dasgupta, A., et al.; "Distinguishing amphetamine and methamphetamine from other interfering sympathomimetic amines after various fluoro derivatization and analysis by gas chromatography-chemical ionization mass spectrometry," Journal of Forensic Sciences; 40(6):1077-1081 (Nov. 1995); doi: 10.1520/JFS13880J.

DATABASE Accession No. 1212453-39-8, Chemical Abstracts Service entered Mar. 21, 2010; 1 page.

DATABASE Accession No. 1212490-89-5, Chemical Abstracts Service entered Mar. 21, 2010; 1 page.

DATABASE Accession No. 1219408-40-8, Chemical Abstracts Service entered Apr. 16, 2010; 1 page.

DATABASE Accession No. 309295-75-8, Chemical Abstracts Service entered Dec. 18, 2000; 1 page.

DATABASE Accession No. 312320-67-5, Chemical Abstracts Service entered Dec. 29, 2000; 1 page.

DATABASE Accession No. 312496-54-1, Chemical Abstracts Service entered Jan. 2, 2001; 1 page.

DATABASE Accession No. 312963-09-0, Chemical Abstracts Service entered Jan. 5, 2001; 1 page.

DATABASE Accession No. 314727-02-1, Chemical Abstracts Service entered Jan. 18, 2001; 1 page.

GC-MS Spectra for MDAI HCl—Cayman Chemical Website, Item No. 9001102, 1 page (Mar. 14, 2012).

Gunnar, T., et al.; "Validated toxicological determination of 30 drugs of abuse as optimized derivatives in oral fluid by long column fast gas chromatography/electron impact mass spectrometry," Journal of Mass Spectrometry; 40(6):739-753 (2005).

Huang, Y-S., et al.; "Chiral separation of 3,4-methylenedioxymethamphetamine and related compounds in clandestine tablets and urine samples by capillary electrophoresis/fluorescence spectroscopy," Electrophoresis; 24(6):1097-1104 (Mar. 2003); doi: 10.1002/elps.200390128.

Huot et al., "Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time," The Journal of Neuroscience, May 11, 2011, 31(19):7190-7198.

International Preliminary Report on Patentability for International Application No. PCT/US2022/036410, dated Dec. 14, 2023, 7 pages.

International Preliminary Report on Patentability for International Application No. PCT/US2022/080090 dated May 30, 2024, 14 Pages.

International Search Report and Written Opinion for International Application No. PCT/US2022/036410, dated Nov. 16, 2022, 10 pages.

International Search Report and Written Opinion for International Application No. PCT/US2023/060662, dated on Apr. 4, 2023, 9 pages.

Isin, E.M., et al.; "Use of radiolabeled compounds in drug metabolism and pharmacokinetic studies," Chemical Research in Toxicology; 25(3):532-442 (2012).

Kaufman, M.S., et al.; "Negative-ion Chemical lonization of Amphetamine Derivatives," Journal of Mass Spectrometry; 31(8):913-920 (Aug. 1996).

Kim, S.Y., et al.; "Method development for simultaneous determination of amphetamine type stimulants and cannabinoids in urine using GC-MS," Microchemical Journal; 110:326-333 (2013).

Lim, H.K., et al.; "Stereoselective disposition: enantioselective quantitation of 3,4-(methylenedioxy) methamphetamine and three of its metabolites by gas chromatography/electron capture negative ion chemical ionization mass spectrometry," Biol Mass Spectrom.; 22(7):403-411 (Jul. 1993); doi: 10.1002/bms.1200220707.

Palenicek, T., et al.; "Emerging toxicity of 5,6-methylenedioxy-2-aminoindane (MDAI): Pharmacokinetics, behaviour, thermoregulation and LD50 in rats," Prog Neuropsychopharmacol Biol Psychiatry.; 69:49-59 (2016).

Paterson, S., et al.; "Qualitative screening for drugs of abuse in hair using GC-MS," J Anal Toxicol.; 25(3):203-208 (Apr. 2001); doi: 10.1093/jat/25.3.203.

Paul, B.D., et al.; "Enantiomeric separation and quantitation of (+/−)-amphetamine, (+/−)-methamphetamine, (+/−)-MDA, (+/−)-MDMA, and (+/-)-MDEA in urine specimens by GC-EI-MS after derivatization with (R)-(−)- or (S)-(+)-alpha-methoxy-alpha-(trifluoromethy)phenylacetyl chloride (MTPA)," J Anal Toxicol.; 28(6):449-455 (Sep. 2004); doi: 10.1093/jat/28.6.449.

Pubchem SID 249924520: "3,4-Methylenedioxymethamphetamine-acetyl," Deposit Date: Apr. 28, 2015 [retrieved online Aug. 22, 2024] URL:https://pubchem.ncbi.nlm.nih.gov/substance/249924520, 6 pages.

Tran, K-V., et al.; "Dakin-West synthesis of beta-aryl ketones," J Org. Chem .; 71(17):6640-6643 (2006).

Versace, F., et al.; "Rapid sample pre-treatment prior to GC-MS and GC-MS/MS urinary toxicological screening," Talanta; 101:299-306 (2012).

* cited by examiner

PHENETHYLAMINE COMPOUNDS SALTS, POLYMORPHIC FORMS AND METHODS OF USE THEREOF

CROSS REFERENCE TO RELATED APPLICATIONS

This application is a continuation of U.S. patent application Ser. No. 18/176,441, filed Feb. 28, 2023, now U.S. U.S. Pat. No. 11,958,821, which is a continuation of U.S. patent application Ser. No. 17/989,673, filed on Nov. 17, 2022, which claims priority to and the benefit of U.S. Provisional Application No. 63/280,550, filed on Nov. 17, 2021, 63/280,552, filed on Nov. 17, 2021, 63/280,854, filed on Nov. 18, 2021, 63/280,960, filed on Nov. 18, 2021, 63/280,964, filed on Nov. 18, 2021, 63/282,591, filed on Nov. 23, 2021, 63/283,017, filed on Nov. 24, 2021, 63/283,024, filed on Nov. 24, 2021, 63/284,923, filed on Dec. 1, 2021, 63/284,927, filed on Dec. 1, 2021, 63/303,588, filed on Jan. 27, 2022, 63/304,176, filed on Jan. 28, 2022, 63/326,721, filed on Apr. 1, 2022, 63/326,735, filed on Apr. 1, 2022, 63/326,743, filed on Apr. 1, 2022, 63/326,797, filed on Apr. 1, 2022, 63/326,802, filed on Apr. 1, 2022, and 63/357,611, filed on Jun. 30, 2022, and PCT Application Nos. PCT/US2022/079411, filed on Nov. 7, 2022, PCT/US2022/079413, filed on Nov. 7, 2022, and PCT/US2022/079415, filed on Nov. 7, 2022, all of which are incorporated by reference herein in their entirety for all purposes.

BACKGROUND

Major depressive disorder and related neuropsychiatric diseases are among the leading causes of disability worldwide. Despite recent advances, there remains a need for new therapeutics to support treatment of debilitating neuropsychiatric diseases.

Recently, psychedelic compounds have received renewed interest for the treatment of depression and other disorders. For example, the Food and Drug Administration (FDA) recently approved the dissociative anesthetic ketamine for treatment-resistant depression, making it the first mechanistically distinct medicine to be introduced to psychiatry in nearly thirty years. Ketamine is a member of a class of compounds known as psychoplastogens. Psychoplastogens promote neuronal growth through a mechanism involving the activation of AMPA receptors, the tropomyosin receptor kinase B (TrkB), and the mammalian target of rapamycin (mTOR). As pyramidal neurons in the PFC exhibit top-down control over areas of the brain controlling motivation, fear, and reward, these effects support clinical development of psychoplastogenic compounds for their antidepressant, anxiolytic, and anti-addictive effects properties.

N-methyl-3,4-methylenedioxyamphetamine (MDMA), (R)-MDMA, (S)-MDMA, N-ethyl-3,4-methylenedioxyamphetamine hydrochloride (MDE), 5,6-methylenedioxy-2-aminoindane (MDAI), N-methyl-1,3-benzodioxolylbutanamine (MBDB), 5-Methoxy-2-aminoindane (MEAI), and 5,6-Dimethoxy-2-aminoindane are synthetic analogues of the psychedelic phenethylamine class of compounds. Solid forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane, and salts thereof having improved properties are disclosed herein.

SUMMARY

Disclosed herein are solid forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane, including salts, crystalline forms of the compounds and salts, as well as polymorphs of the solid forms.

The solid forms of (R)-MDMA and (S)-MDMA may have an enantiomeric excess of at least 70%, such as an enantiomeric excess of at least 90%, or at least 98%, or about 100%.

Also disclosed herein are methods for making the solid forms and methods for using the solid forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane. The solid forms made by the disclosed methods may have at least one improved property compared to known forms of the same compound. In some embodiments, the solid forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane are polymorphs of the free base forms. In other embodiments, the solid forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane are salt forms, such as a pharmaceutically acceptable salt. In some embodiments, the salt may be provided in a solid form. In some embodiments, the solid forms of these salts can be amorphous or crystalline. In one embodiment, the hydrochloride salt solid forms disclosed herein are crystalline forms that have an improved property relative to the amorphous forms. In one embodiment a crystalline form disclosed herein is a polymorph of the hydrochloride salt. In certain embodiments, a disclosed polymorph has an improved property over one or more other solid forms.

In any embodiments, the at least one improved property of the solid form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane, or salts thereof disclosed herein may comprise a physical property, chemical property, pharmacokinetic property, or a combination thereof. In some embodiments, the at least one improved property comprises a melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane and salts thereof.

The salt may be formed from an acid selected from fumaric acid, galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, ethanesulfonic acid 2-hydroxy, glutaric acid, L-aspartic acid, cinnamic acid, maleic acid, adipic acid, phosphoric acid, sebacic acid, ethanesulfonic acid, (+)-camphoric acid, glutamic acid, acetic acid, hydrochloric acid, or a combination thereof. In any embodiments, a stoichiometric ratio of acid to MDMA, (R)-MDMA, (S)-MDMA, MDE, S-MDE, R-MDE, MDAI, MBDB, S-MBDB, R-MBDB, MEAI, or 5,6-Dimethoxy-2-aminoindane is from about 0.4 to about 2.2, such as from about 0.5 to about 2, or from about 0.5, 1 or 2.

In any embodiments, the solid form may be a crystalline solid, a solvate such as a hydrate, or a combination thereof. The crystalline solid may be substantially a single form, such as a polymorph form. The solid form can be selected as described herein to have one or more desired properties, particularly improved properties, such as physical properties, chemical properties, pharmacokinetic properties, or a combination thereof. The one or more desired properties may comprise melting point, glass transition temperature, flowability, thermal stability, mechanical stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample and/or a previously known crystalline form.

Also disclosed herein are embodiments of a pharmaceutical composition, comprising a solid form of a disclosed compound or a salt thereof, and a pharmaceutically acceptable excipient.

A method for administering the solid form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane and salts thereof also is disclosed herein. In some embodiments, the method comprises administering to a subject an effective amount of a solid form MDMA, (R)-MDMA, (S)-MDMA, MDE, S-MDE, R-MDE, MDAI, MBDB, S-MBDB, R-MBDB, MEAI, or 5,6-Dimethoxy-2-aminoindane, salts thereof, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

The method may comprise further comprising administering an effective amount of an empathogenic agent and/or a 5-$HT_{2A}$ antagonist to the subject. The 5-$HT_{2A}$ antagonist may be selected from ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl) piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena, or a pharmaceutically acceptable salt, solvate, metabolite, deuterated analog, derivative, prodrug, or combinations thereof.

In any embodiments, administering the solid form of the compound comprises oral, parenteral, or topical administration. In certain embodiments, oral administration is used, but in other particular embodiments, administration is by injection, inhalation, intraocular, intravaginal, intrarectal or transdermal routes.

The foregoing and other objects and features of the present disclosure will become more apparent from the following detailed description, which proceeds with reference to the accompanying figures.

BRIEF DESCRIPTION OF THE FIGURES

FIG. 120 illustrates the frequency of SAPs after racemic MDE compared to vehicle and chlordiazepoxide control on the elevated zero maze.

FIG. 121 illustrates the frequency of SAPs after R-MDE compared to vehicle and chlordiazepoxide control on the elevated zero maze.

FIG. 122 illustrates the frequency of SAPs after S-MDE compared to vehicle and chlordiazepoxide control on the elevated zero maze.

FIG. 123 illustrates the frequency of stretched attend postures (SAPs) after racemic MBDB, R-MBDB, and S-MBDB compared to vehicle and chlordiazepoxide control on the elevated zero maze.

FIG. 124 illustrates the percentage of time spent in the open arms after MDAI compared to vehicle and chlordiazepoxide control on the elevated zero maze.

FIG. 125 illustrates the total open arm entries after MDAI compared to vehicle and chlordiazepoxide control on the elevated zero maze.

FIG. 126 illustrates the total line crossings after MDAI compared to vehicle and chlordiazepoxide control on the elevated zero maze.

FIG. 127 illustrates the frequency of HDIPS after MDAI compared to vehicle and chlordiazepoxide control on the elevated zero maze.

Figure 128:
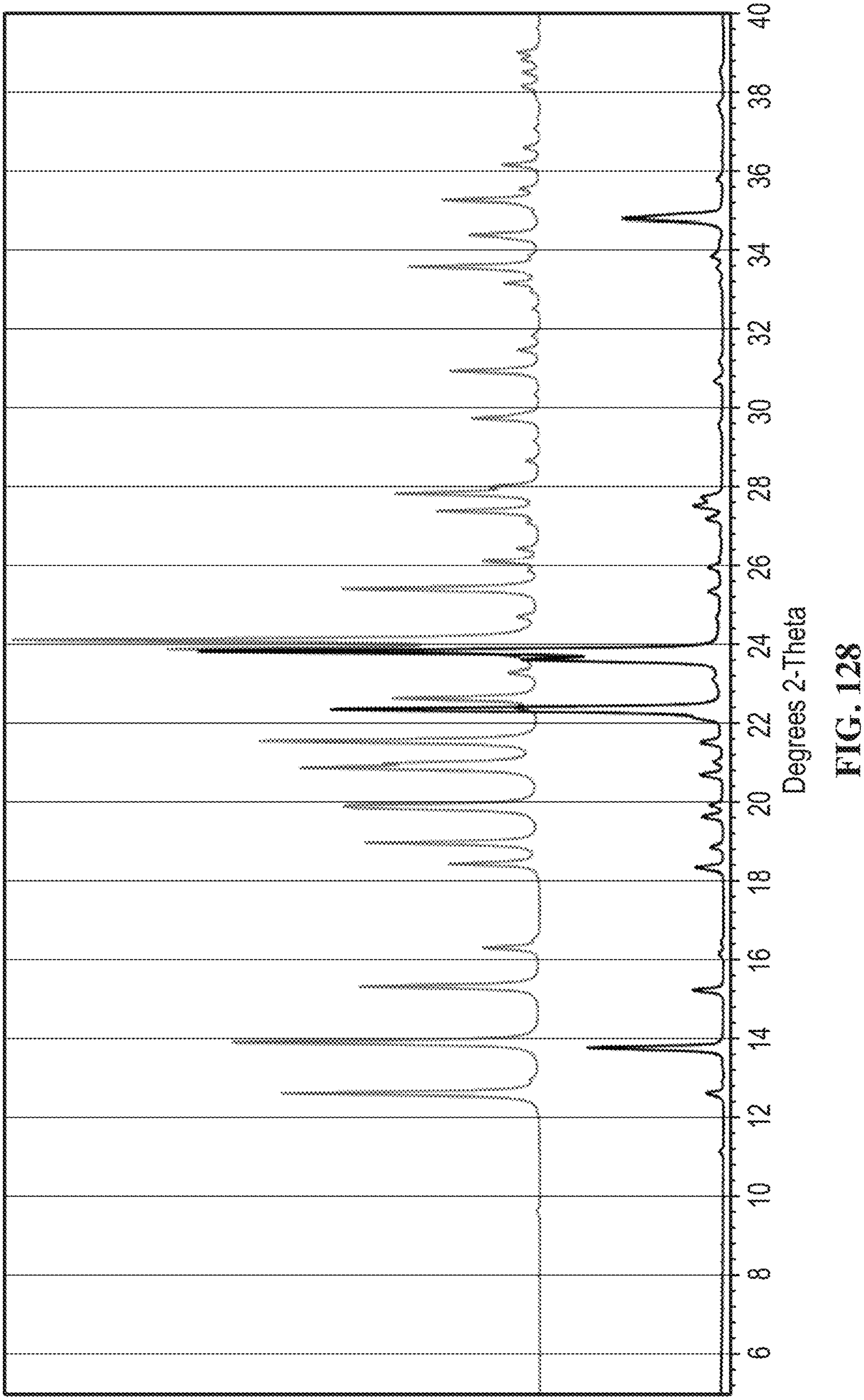

FIG. 128 provides an overlay plot of the XRPD diffractogram of MBDB Maleate Form 1 and the XRPD diffractogram calculated from a single crystal of MBDB Maleate Form 1.

DETAILED DESCRIPTION

Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods.

When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

"Administering" refers to any suitable mode of administration, including, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"3,4-methylenedioxymethamphetamine" refers to the racemic compound 1-(benzo[d][1,3]dioxol-5-yl)-N-methylpropan-2-amine. The compound may also be referred to as MDMA, or N-methyl-3,4-methylenedioxyamphetamine.

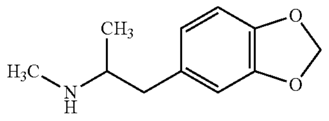

3,4-methylenedioxymethamphetamine

"(R)-3,4-methylenedioxymethamphetamine" refers to the compound (R)-1-(benzo[d][1,3]dioxol-5-yl)-N-methylpropan-2-amine. The compound may also be referred to as (R)-MDMA, or (R)—N-methyl-3,4-methylenedioxyamphetamine.

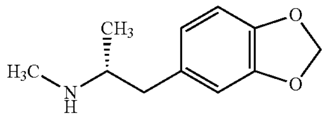

(R)-3,4-methylenedioxymethamphetamine

"(S)-3,4-methylenedioxymethamphetamine" refers to the compound(S)-1-(benzo[d][1,3]dioxol-5-yl)-N-methylpropan-2-amine. The compound may also be referred to as (S)-MDMA, or(S)—N-methyl-3,4-methylenedioxyamphetamine.

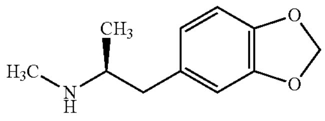

(S)-3,4-methylenedioxymethamphetamine

"N-ethyl-3,4-methylenedioxyamphetamine hydrochloride" refers to the compound

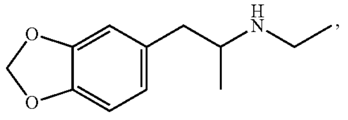

which also may be referred to as MDE or MDEA.

"N-ethyl-3,4-methylenedioxyamphetamine hydrochloride," "N-ethyl-3,4-methylenedioxyamphetamine HCl," and "MDE·HCl" each refer to the hydrochloric acid salt of N-ethyl-3,4-methylenedioxyamphetamine.

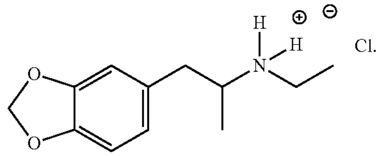

"(S)—N-ethyl-3,4-methylenedioxyamphetamine" refers to the compound

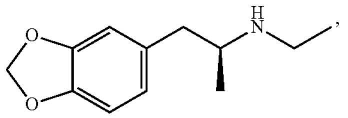

which also may be referred to as S-MDE or S-MDEA.

"5,6-methylenedioxy-2-aminoindane" refers to the compound:

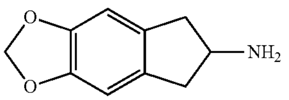 [SMILES: NC1Cc2cc3c(cc2C1)OCO3]

5,6-methylenedioxy-2-aminoindane which also may be referred to as, "MDAI."

"5,6-methylenedioxy-2-aminoindane hydrochloride" refers to the hydrochloric acid salt of 5,6-methylenedioxy-2-aminoindane:

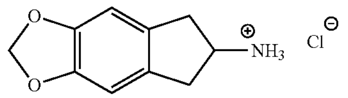 [SMILES: [NH3+]C1Cc2cc3c(cc2C1)OCO3 ; [Cl-]]

which also may be referred to herein as 5,6-methylenedioxy-2-aminoindane·HCl or MDAI·HCl, wherein the middle dot, "·", represents that the compound is the acid addition salt of 5,6-methylenedioxy-2-aminoindane.

"N-methyl-1,3-benzodioxolylbutanamine" refers to the compound

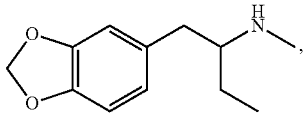

which also may be referred to as "MBDB" or "1-(benzo[d][1,3]dioxol-5-yl)-N-methylbutan-2-amine."

"N-methyl-1,3-benzodioxolylbutanamine hydrochloride" or "MBDB·HCl" refers to the hydrochloric acid salt of N-methyl-1,3-benzodioxolylbutanamine.

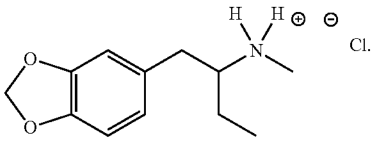

"5-Methoxy-2-aminoindane hydrochloride" as used herein refers to the racemic compound 5-methoxy-2,3-dihydro-$^{1}$H-inden-2-amine hydrochloride. The compound also may be referred to as 2-amino-5-methoxyindan hydrochloride, 5-methoxyindan-2-ylamine hydrochloride, MEAI HCl, or 5-MeO-AI HCl.

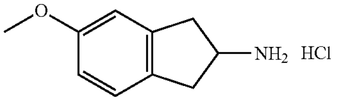

5-Methoxy-2-aminoindane hydrochloride

"5,6-Dimethoxy-2-aminoindane hydrochloride" as used herein refers to the compound 5,6-dimethoxy-2,3-dihydro-$^{1}$H-inden-2-amine hydrochloride. The compound also may be referred to as 5,6-dimethoxyindan-2-amine hydrochloride, 2-amino-5,6-dimethoxyindan hydrochloride, or 5,6-dimethoxyindan-2-ylamine hydrochloride.

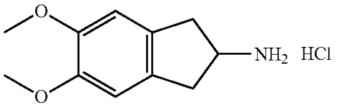

5,6-Dimethoxy-2-aminoindane hydrochloride

"Subject" refers to an animal, such as a mammal, including, but not limited to, primates (e.g., humans), cows, sheep, goats, horses, dogs, cats, rabbits, rats, mice and the like. In certain embodiments, the subject is a human subject.

"Therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the present disclosure can be used in combination with other pharmaceutically active compounds. The compounds of the present disclosure can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 mM. In some embodiments, the term "agonist" includes full agonists or partial agonists. "Full agonist" refers to a modulator that binds to and activates a receptor with the maximum response that an agonist can elicit at the receptor. “Partial agonist” refers to a modulator that binds to and activates a given receptor, but has partial efficacy, that is, less than the maximal response, at the receptor relative to a full agonist.

“Positive allosteric modulator” refers to a modulator that binds to a site distinct from the orthosteric binding site and enhances or amplifies the effect of an agonist.

“Antagonism” refers to the inactivation of a receptor or enzyme by a modulator, or antagonist. Antagonism of a receptor, for example, is when a molecule binds to the receptor and does not allow activity to occur.

“Antagonist” or “neutral antagonist” refers to a modulator that binds to a receptor or enzyme and blocks a biological response. An antagonist has no activity in the absence of an agonist or inverse agonist but can block the activity of either, causing no change in the biological response.

“Composition” refers to a product comprising the specified ingredients in the specified amounts, as well as any product, which results, directly or indirectly, from combination of the specified ingredients in the specified amounts. By “pharmaceutically acceptable” it is meant the carrier, diluent or excipient must be compatible with the other ingredients of the formulation.

“Pharmaceutically acceptable excipient” refers to a substance that aids the administration of an active agent to and absorption by a subject. Pharmaceutical excipients useful in the present disclosure include, but are not limited to, binders, fillers, disintegrants, lubricants, coatings, sweeteners, flavors and colors. One of skill in the art will recognize that other pharmaceutical excipients are useful in the present disclosure.

“Racemic” or “racemic mixture” refers to a compound which comprises equal proportions of the dextrorotatory and levorotatory forms of a compound or salt thereof, such that the racemic compound is not optically active.

“Enantiomeric excess” or “e.e.” refers to the degree to which a sample contains one enantiomer in greater amounts than the other. A racemic mixture has an e.e. of 0% (i.e., there is no excess of one enantiomer compared to another), while a single completely pure enantiomer has an e.e. of 100%. In some embodiments of the disclosed solid forms and/or salts of (R)-3,4-methylenedioxymethamphetamine, the compound is synthesized and/or purified to be in at least a 70% enantiomeric excess, at least a 75% enantiomeric excess, at least 80% enantiomeric excess, at least an 85% enantiomeric excess, at least a 90% enantiomeric excess, at least a 95% enantiomeric excess, at least a 97% enantiomeric excess, at least a 98% enantiomeric excess, at least a 99% enantiomeric excess, or even in greater than a 99% enantiomeric excess, such as in a substantially enantiopure form (substantially 100% enantiomeric excess), compared to the amount of the corresponding(S)-enantiomer. In some embodiments of the disclosed solid forms and/or salts of (S)-3,4-methylenedioxymethamphetamine, the compound is synthesized and/or purified to be in at least a 70% enantiomeric excess, at least a 75% enantiomeric excess, at least 80% enantiomeric excess, at least an 85% enantiomeric excess, at least a 90% enantiomeric excess, at least a 95% enantiomeric excess, at least a 97% enantiomeric excess, at least a 98% enantiomeric excess, at least a 99% enantiomeric excess, or even in greater than a 99% enantiomeric excess, such as in a substantially enantiopure form (substantially 100% enantiomeric excess), compared to the amount of the corresponding (R)-enantiomer.

Compounds

Disclosed herein are solid forms of MDMA, (R)-MDMA, (S)-MDMA, MDE, S-MDE, R-MDE, MDAI, MBDB, S-MBDB, R-MBDB, MEAI, and 5,6-Dimethoxy-2-aminoindane, salts thereof, and solid forms of these salts, e.g., with improved properties compared to amorphous forms or known solid forms of the molecule. The disclosed forms are useful to treat various disorders, such as brain disorders. Also disclosed are methods for making the solid forms of these compounds and methods of administering the same.

In some embodiments, the solid form of the compound is a crystalline form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane. In some embodiments, the solid form of MDMA, (R)-MDMA, (S)-MDMA, MDE, S-MDE, R-MDE, MDAI, MBDB, S-MBDB, R-MBDB, MEAI, and/or 5,6-Dimethoxy-2-aminoindane is a crystalline polymorph of MDMA, (R)-MDMA, (S)-MDMA, MDE, S-MDE, R-MDE, MDAI, MBDB, S-MBDB, R-MBDB, MEAI, and/or 5,6-Dimethoxy-2-aminoindane such as a polymorph of the free base compound or a polymorph of the salt. In some embodiments, the solid form of the compound is a salt of the compound. In some embodiments, the solid form of the compound is a crystalline salt form of the compound, such as an acid addition salt form. In some embodiments, the salt is a salt formed from galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D-glucoheptonic acid, glycolic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, 2-hydroxy ethanesulfonic acid, glutaric acid, L-aspartic acid, cinnamic acid, maleic acid, adipic acid, phosphoric acid, sebacic acid, ethanesulfonic acid, (+)-camphoric acid, glutamic acid, acetic acid, fumaric acid, gentisic acid, tartaric acid, malonic acid, xinafoic acid, hydrochloric acid, or a combination thereof. In some embodiments, the stoichiometric ratio of acid to free base is 1:1. In some embodiments, the stoichiometric ratio of acid to free base is 1:2. In some embodiments, the stoichiometric ratio of acid to free base is 2:1. In some embodiments, the solid form of the compound is a polymorph of the compound, such as a novel polymorph that is not previously known in the art.

Salts

In some embodiments, the solid form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane comprises a salt of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane. Suitable salts include pharmaceutically acceptable salts of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane. In some embodiments, the salt is provided as a solid form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane that is not, and does not comprise, a hydrochloride salt.

In some embodiments, the salt forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane may be formed from a suitable pharmaceutically acceptable acid, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like.

In other embodiments, the salt forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Additional information concerning pharmaceutically acceptable salts can be found in, for example, S. M. Berge, et al., "Pharmaceutical Salts," J. Pharm. Sci., 1977; 66:1-19 which is incorporated herein by reference.

In some embodiments, the disclosed salt forms may be formed using an acid from Table 1.

TABLE 1

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| Hydrochloric acid | carbonic acid |
| galactaric (mucic) acid | Fumaric acid |
| xinafoic acid | |

The acid salts of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane disclosed herein can have any suitable stoichiometric ratio of acid to free base. In one embodiment, the molar ratio of acid to MDMA, (R)-MDMA, (S)-MDMA, MDE, S-MDE, R-MDE, MDAI, MBDB, S-MBDB, R-MBDB, MEAI, or 5,6-Dimethoxy-2-aminoindane is from about 0.4 to about 2.2, such as forms wherein the salt has a stoichiometric ratio of acid to MDMA, (R)-MDMA, (S)-MDMA, MDE, S-MDE, R-MDE, MDAI, MBDB, S-MBDB, R-MBDB, MEAI, or 5,6-Dimethoxy-2-aminoindane of from about 0.5 to about 2, such as about 0.5, about 1 or about 2.

Solid Forms

Embodiments of the compounds of the present disclosure are in a solid form. The solid form may be a crystalline form or an amorphous form. In some embodiments, the solid form is a crystalline form, such as a polymorph. In some embodiments, the solid form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane is a salt. In certain embodiments, the solid form is a crystalline salt form of the compound. A solid form of a salt may be a crystalline form or an amorphous form. A person of ordinary skill in the art understands that solid forms of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane, such as crystalline forms including salt and non-salt crystalline forms, may exist in more than one crystal form. Such different forms are referred to as polymorphs. In some embodiments, the disclosed compounds are particular polymorphs of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane or salts thereof.

In some embodiments, the solid form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane or salts thereof disclosed herein is selected to be a crystalline form, such as a particular polymorph of a crystalline form of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane, e.g., that provides one or more desired properties. In one embodiment, the crystalline form offers advantages over the amorphous form of the molecule. In another embodiment, the disclosed polymorph offers improved properties as compared to another polymorph of MDMA, (R)-MDMA, (S)-MDMA, MDE, S-MDE, R-MDE, MDAI, MBDB, S-MBDB, R-MBDB, MEAI, or 5,6-Dimethoxy-2-aminoindane.

The MDMA, (R)-MDMA, (S)-MDMA, MDE, S-MDE, R-MDE, MDAI, MBDB, S-MBDB, R-MBDB, MEAI, or 5,6-Dimethoxy-2-aminoindane may be a salt or free base compound. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques as described herein and also are known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of a compound are described herein and are also known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

MDMA, (R)-MDMA, (S)-MDMA, MDE, (S)-MDE, (R)-MDE, MDAI, MBDB, (S)-MBDB, (R)-MBDB, MEAI, or 5,6-Dimethoxy-2-aminoindane and Salts and Solid Forms Thereof Solid Forms of MDMA Fumarate Form 1

Figure 1:
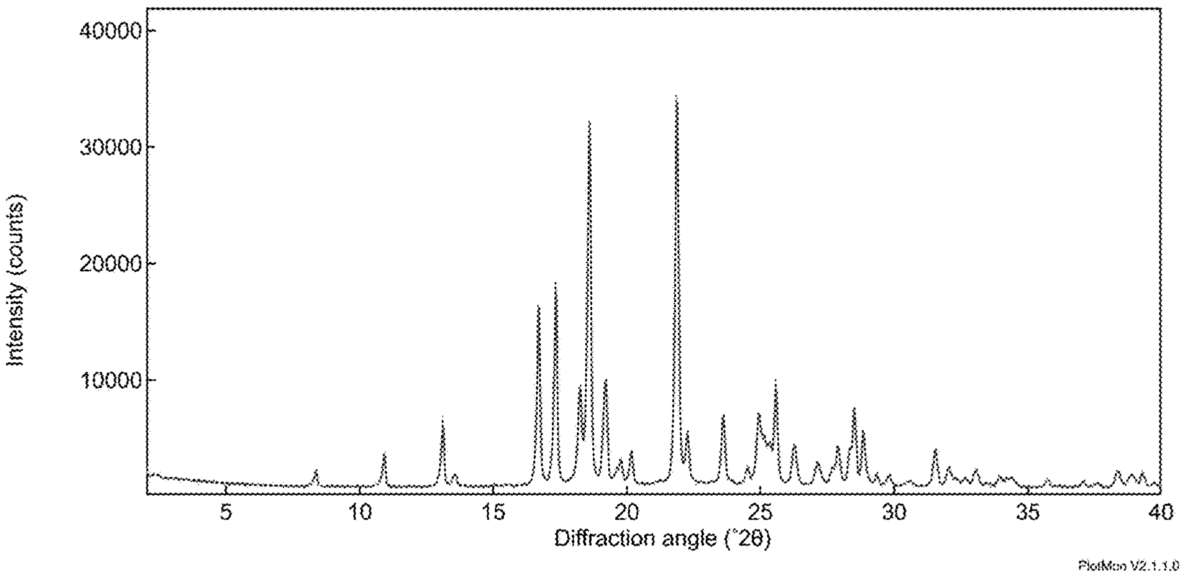
FIG. 1 provides an XRPD diffractogram of a sample comprising crystalline MDMA·fumarate.
Figure 44:
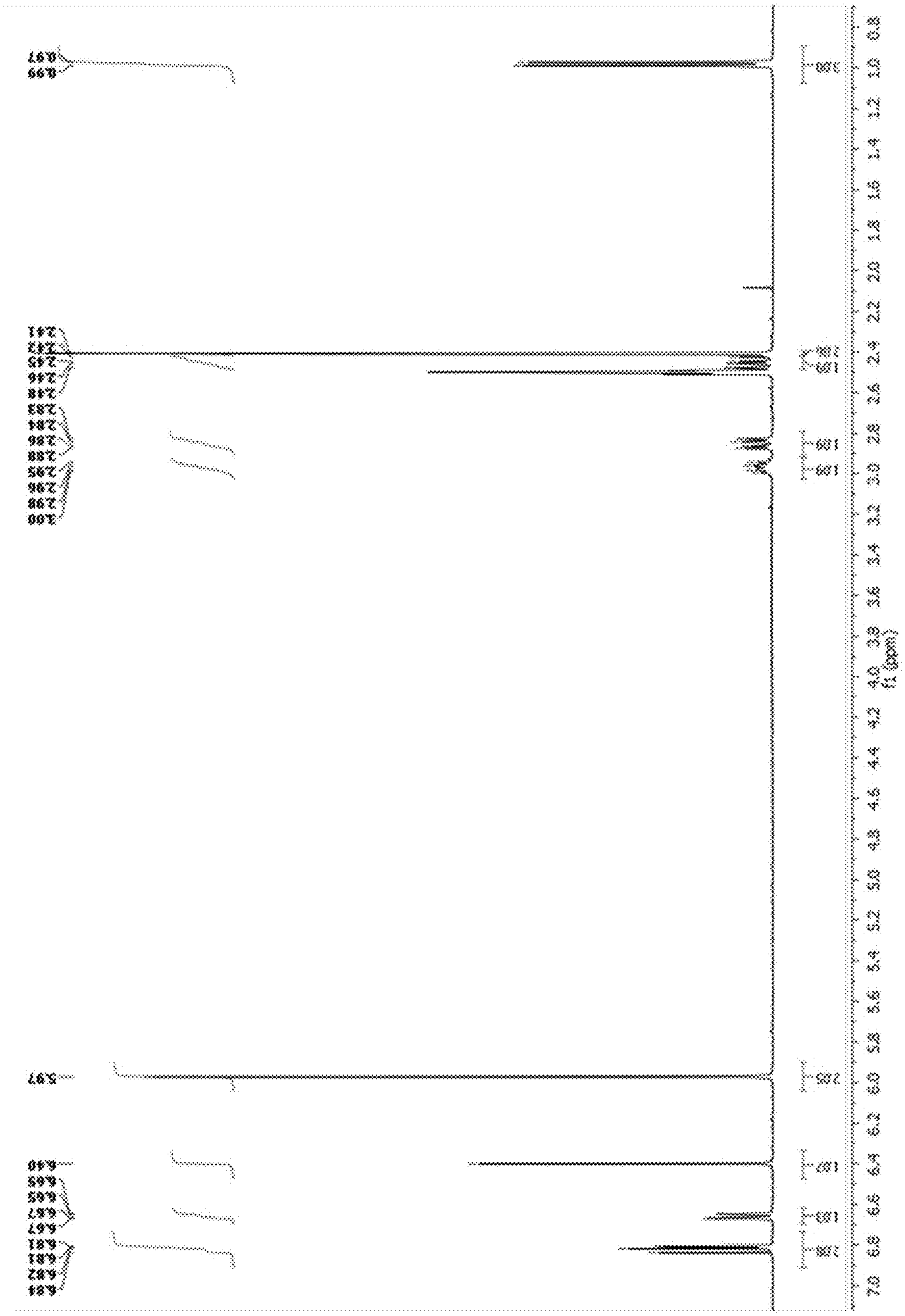
FIG. 44 provides a $^1$H NMR spectrum for MDMA fumarate Form 1.
Figure 45:
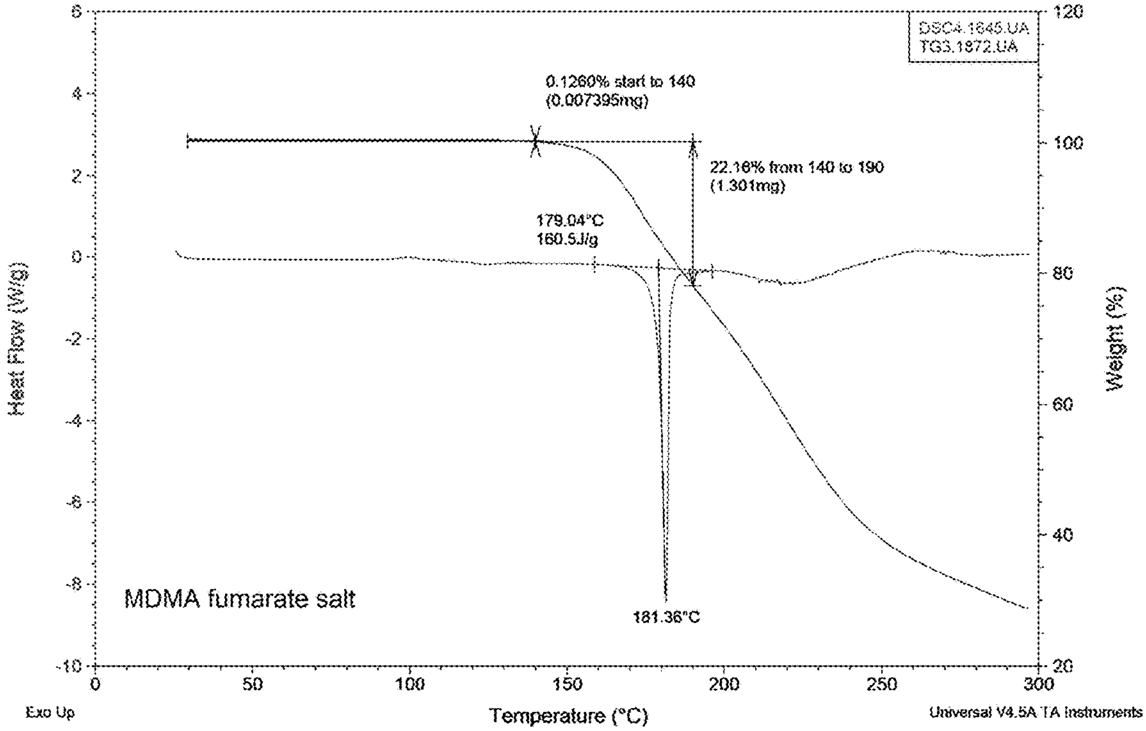
FIG. 45 provides TGA and DSC profiles for MDMA fumarate Form 1.

In some embodiments, the present disclosure provides solid forms of MDMA fumarate Form 1, e.g., crystalline forms of MDMA fumarate Form 1. In some embodiments, the MDMA fumarate Form 1 XRPD profile is substantially similar to that shown in FIG. 1. In some embodiments, the MDMA fumarate Form 1 $^1$H NMR spectrum is substantially similar to that shown in FIG. 44. In some embodiments, the MDMA fumarate Form 1 TGA profile is substantially similar to that shown in FIG. 45. In some embodiments, the MDMA fumarate Form 1 DSC profile is substantially similar to that shown in FIG. 45.

In some embodiments, the solid form of MDMA fumarate Form 1 is crystalline MDMA fumarate Form 1 characterized by two or more, or three or more XRPD signals selected from the group consisting of 17.3° 2θ, 18.6° 2θ, and 21.9° 2θ (±0.2° 2θ; ±0.1° 2θ; or ±0.0° 2θ; Cu Kα1 radiation). In some embodiments, the solid form of MDMA fumarate Form 1 is crystalline MDMA fumarate Form 1 characterized by XRPD signals at 17.3° 2θ, 18.6° 2θ, and 21.9° 2θ (±0.2° 2θ; =0.1° 2θ; or ±0.0° 2θ; Cu Kα1 radiation).

In some embodiments, the solid form of MDMA fumarate Form 1 is crystalline MDMA fumarate Form 1 characterized by two or more, or three or more XRPD signals selected from the group consisting of 16.7° 2θ, 17.3° 2θ, 18.6° 2θ, 19.2° 2θ, and 21.9° 2θ (±0.2° 2θ; ±0.1° 2θ; or ±0.0° 2θ; Cu Kα1 radiation). In some embodiments, the solid form of MDMA fumarate Form 1 is MDMA fumarate Form 1 characterized by XRPD signals at 16.7° 2θ, 17.3° 2θ, 18.6° 2θ, 19.2° 2θ, and 21.9° 2θ (±0.2° 2θ; ±0.1° 2θ; or ±0.0° 2θ; Cu Kα1 radiation).

In some embodiments, the solid form of MDMA fumarate Form 1 is crystalline MDMA fumarate Form 1 characterized by two or more, or three or more XRPD signals selected from the group consisting of 10.9° 2θ, 13.1° 2θ, and 16.7° 2θ (±0.2° 2θ; ±0.1° 2θ; or ±0.0° 2θ; Cu Kα1 radiation). In some embodiments, the solid form of MDMA fumarate Form 1 is crystalline MDMA fumarate Form 1 characterized by XRPD signals at 10.9° 2θ, 13.1° 2θ, and 16.7° 2θ (±0.2° 2θ; ±0.1° 2θ; or ±0.0° 2θ; Cu Kα1 radiation).

In some embodiments, the solid form of MDMA fumarate Form 1 is crystalline MDMA fumarate Form 1 characterized by two or more, or three or more XRPD signals selected from the group consisting of 10.9° 2θ, 13.1° 2θ, 16.7° 2θ, 17.3° 2θ, and 18.6° 2θ (±0.2° 2θ; ±0.1° 2θ; or ±0.0° 2θ; Cu Kα1 radiation). In some embodiments, the solid form of MDMA fumarate Form 1 is MDMA fumarate Form 1 characterized by XRPD signals at 10.9° 2θ, 13.1° 2θ, 16.7° 2θ, 17.3° 2θ, and 18.6° 2θ (±0.2° 2θ; ±0.1° 2θ; or ±0.0° 2θ; Cu Kα1 radiation).

In some embodiments, the crystalline MDMA fumarate Form 1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, or forty-six XRPD signals selected from those set forth in Table 2.

TABLE 2

XRPD Signals for MDMA fumarate Form 1

| Signal no. | Position | d-value | Relative |
|---|---|---|---|
| 1 | 8.4 | 10.6 | 6.4 |
| 2 | 10.9 | 8.1 | 10.5 |
| 3 | 13.1 | 6.8 | 18.2 |
| 4 | 13.6 | 6.5 | 5.4 |
| 5 | 16.7 | 5.3 | 47.9 |
| 6 | 17.3 | 5.1 | 52.1 |
| 7 | 18.3 | 4.9 | 27.9 |
| 8 | 18.6 | 4.8 | 93.3 |
| 9 | 19.2 | 4.6 | 29.5 |
| 10 | 19.6 | 4.5 | 7.1 |
| 11 | 19.8 | 4.5 | 9.4 |
| 12 | 20.2 | 4.4 | 11.3 |
| 13 | 21.9 | 4.1 | 100.0 |
| 14 | 22.3 | 4.0 | 15.9 |
| 15 | 23.6 | 3.8 | 20.6 |
| 16 | 24.5 | 3.6 | 7.4 |
| 17 | 24.9 | 3.6 | 21.1 |
| 18 | 24.9 | 3.6 | 21.1 |
| 19 | 25.2 | 3.5 | 15.5 |
| 20 | 25.4 | 3.5 | 13.6 |
| 21 | 25.6 | 3.5 | 27.9 |
| 22 | 26.3 | 3.4 | 13.0 |
| 23 | 27.1 | 3.3 | 8.5 |
| 24 | 27.7 | 3.2 | 7.0 |
| 25 | 27.9 | 3.2 | 12.7 |
| 26 | 28.3 | 3.1 | 12.3 |
| 27 | 28.5 | 3.1 | 22.4 |
| 28 | 28.8 | 3.1 | 16.6 |
| 29 | 29.4 | 3.0 | 5.5 |
| 30 | 29.8 | 3.0 | 5.4 |
| 31 | 30.5 | 2.9 | 3.8 |
| 32 | 31.5 | 2.8 | 11.9 |
| 33 | 32.1 | 2.8 | 7.3 |
| 34 | 32.3 | 2.8 | 4.7 |
| 35 | 32.7 | 2.7 | 4.6 |
| 36 | 33.1 | 2.7 | 6.8 |
| 37 | 33.5 | 2.7 | 3.4 |
| 38 | 33.9 | 2.6 | 5.0 |
| 39 | 34.2 | 2.6 | 4.4 |
| 40 | 34.4 | 2.6 | 4.7 |
| 41 | 35.7 | 2.5 | 4.2 |
| 42 | 37.1 | 2.4 | 4.0 |
| 43 | 37.6 | 2.4 | 3.3 |
| 44 | 38.4 | 2.3 | 6.5 |
| 45 | 38.9 | 2.3 | 5.4 |
| 46 | 39.3 | 2.3 | 6.1 |

Solid Forms of MDMA Maleate Form 1

Figure 2:
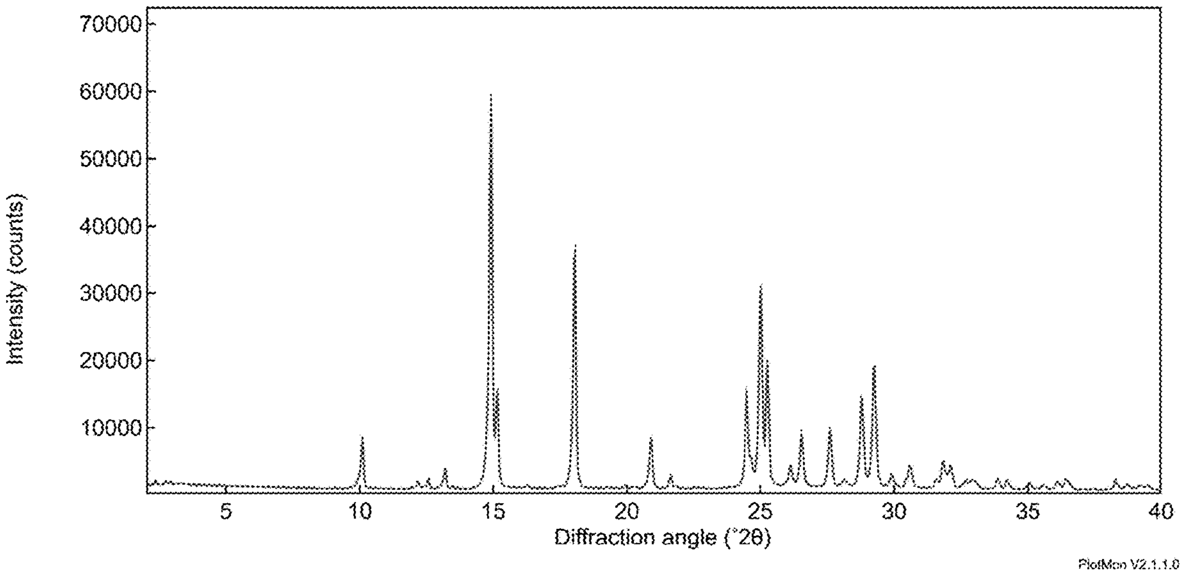
FIG. 2 provides an XRPD diffractogram of a sample comprising crystalline MDMA·maleate.
Figure 51:
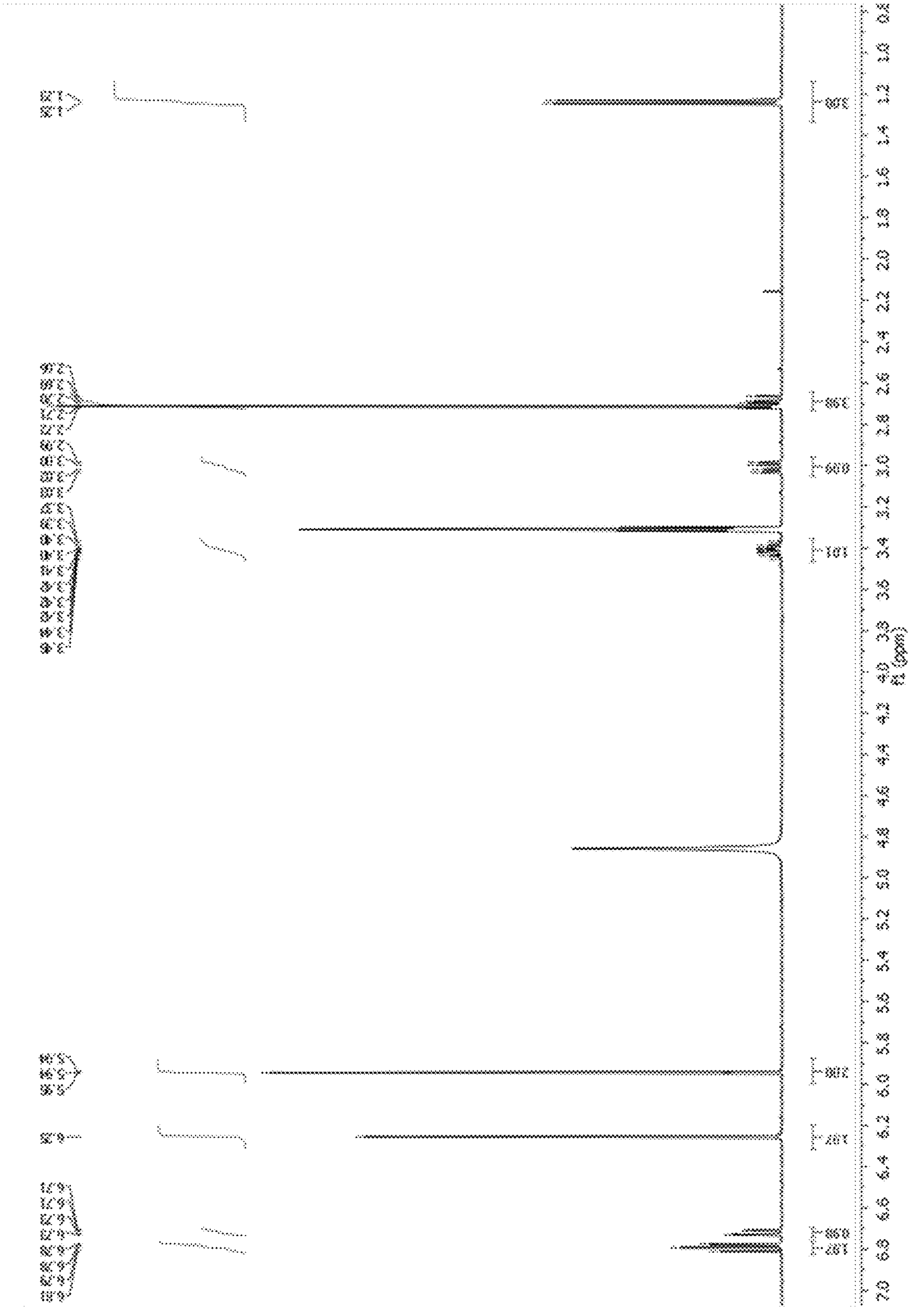
FIG. 51 provides a $^1$H NMR spectrum for MDMA maleate Form 1.

In some embodiments, the present disclosure provides solid forms of MDMA maleate Form 1, e.g., crystalline forms of MDMA maleate Form 1. In some embodiments, the MDMA maleate Form 1 XRPD profile is substantially similar to that shown in FIG. 2. In some embodiments, the MDMA maleate Form 1 $^1$H NMR spectrum is substantially similar to that shown in FIG. 51. In some embodiments, the MDMA maleate Form 1 TGA profile is substantially similar to that shown in FIG. 52. In some embodiments, the MDMA maleate Form 1 DSC profile is substantially similar to that shown in FIG. 52.

In some embodiments, the solid form of MDMA maleate Form 1 is crystalline MDMA maleate Form 1 characterized by two or more, or three or more XRPD signals selected from the group consisting of 14.9° 2θ, 18.1° 2θ, and 25.0° 2θ (±0.2° 2θ; ±0.1° 2θ; or ±0.0° 2θ; Cu Kα1 radiation). In some embodiments, the solid form of MDMA maleate Form 1 is crystalline MDMA maleate Form 1 characterized by XRPD signals at 14.9° 2θ, 18.1° 2θ, and 25.0° 2θ (±0.2° 2θ; ±0.1° 2θ; or ±0.0° 2θ; Cu Kα1 radiation).

In some embodiments, the solid form of MDMA maleate Form 1 is crystalline MDMA maleate Form 1 characterized by two or more, or three or more XRPD signals selected from the group consisting of 14.9° 2θ, 18.1° 2θ, 25.0° 2θ, 25.3° 2θ, and 29.2° 2θ (±0.2° 2θ; ±0.1° 2θ; or ±0.0° 2θ; Cu Kα1 radiation). In some embodiments, the solid form of MDMA maleate Form 1 is MDMA maleate Form 1 characterized by XRPD signals at 14.9° 2θ, 18.1° 2θ, 25.0° 2θ, 25.3° 2θ, and 29.2° 2θ (±0.2° 2θ; ±0.1° 2θ; or ±0.0° 2θ; Cu Kα1 radiation).

In some embodiments, the solid form of MDMA maleate Form 1 is crystalline MDMA maleate Form 1 characterized by two or more, or three or more XRPD signals selected from the group consisting of 10.1° 2θ, 14.9° 2θ, and 18.1° 2θ (±0.2° 2θ; ±0.1° 2θ; or ±0.0° 2θ; Cu Kα1 radiation). In some embodiments, the solid form of MDMA maleate Form 1 is crystalline MDMA maleate Form 1 characterized by XRPD signals at 10.1° 2θ, 14.9° 2θ, and 18.1° 2θ (±0.2° 2θ; ±0.1° 2θ; or ±0.0° 2θ; Cu Kα1 radiation).

In some embodiments, the solid form of MDMA maleate Form 1 is crystalline MDMA maleate Form 1 characterized by two or more, or three or more XRPD signals selected from the group consisting of 10.1° 2θ, 14.9° 2θ, 18.1° 2θ, 25.0° 2θ, and 28.8° 2θ (±0.2° 2θ; ±0.1° 2θ; or ±0.0° 2θ; Cu Kα1 radiation). In some embodiments, the solid form of MDMA maleate Form 1 is MDMA maleate Form 1 characterized by XRPD signals at 10.1° 2θ, 14.9° 2θ, 18.1° 2θ, 25.0° 2θ, and 28.8° 2θ (±0.2° 2θ; ±0.1° 2θ; or ±0.0° 2θ; Cu Kα1 radiation).

In some embodiments, the crystalline MDMA maleate Form 1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, or thirty-nine XRPD signals selected from those set forth in Table 3.

TABLE 3

XRPD Signals for MDMA maleate Form 1

| Signal no. | Position | d-value | Relative |
|---|---|---|---|
| 1 | 2.4 | 37.4 | 4.0 |
| 2 | 2.8 | 32.0 | 3.7 |
| 3 | 2.9 | 30.3 | 3.4 |
| 4 | 10.1 | 8.8 | 14.3 |
| 5 | 12.2 | 7.3 | 3.4 |
| 6 | 12.6 | 7.0 | 4.1 |
| 7 | 13.2 | 6.7 | 6.6 |
| 8 | 14.9 | 5.9 | 100.0 |
| 9 | 15.2 | 5.8 | 26.0 |
| 10 | 18.1 | 4.9 | 61.8 |
| 11 | 20.9 | 4.3 | 14.3 |
| 12 | 21.6 | 4.1 | 5.1 |
| 13 | 24.5 | 3.6 | 25.7 |
| 14 | 24.6 | 3.6 | 9.7 |
| 15 | 25.0 | 3.6 | 52.3 |
| 16 | 25.3 | 3.5 | 33.6 |
| 17 | 26.1 | 3.4 | 7.5 |
| 18 | 26.5 | 3.4 | 15.4 |
| 19 | 27.6 | 3.2 | 16.5 |
| 20 | 28.1 | 3.2 | 3.9 |
| 21 | 28.8 | 3.1 | 24.7 |
| 22 | 29.2 | 3.1 | 32.9 |
| 23 | 29.9 | 3.0 | 5.3 |
| 24 | 30.6 | 2.9 | 7.5 |
| 25 | 31.6 | 2.8 | 3.9 |

TABLE 3-continued

XRPD Signals for MDMA maleate Form 1

| Signal no. | Position | d-value | Relative |
|---|---|---|---|
| 26 | 31.8 | 2.8 | 8.7 |
| 27 | 32.1 | 2.8 | 7.7 |
| 28 | 32.7 | 2.7 | 3.9 |
| 29 | 32.9 | 2.7 | 3.8 |
| 30 | 33.9 | 2.6 | 4.1 |
| 31 | 34.2 | 2.6 | 3.9 |
| 32 | 35.0 | 2.6 | 3.3 |
| 33 | 35.6 | 2.5 | 2.5 |
| 34 | 36.1 | 2.5 | 3.4 |
| 35 | 36.5 | 2.5 | 4.0 |
| 36 | 38.3 | 2.4 | 3.9 |
| 37 | 38.8 | 2.3 | 2.9 |
| 38 | 39.2 | 2.3 | 2.7 |
| 39 | 39.5 | 2.3 | 2.6 |

Solid Forms of MDMA Phosphate

Figure 4:
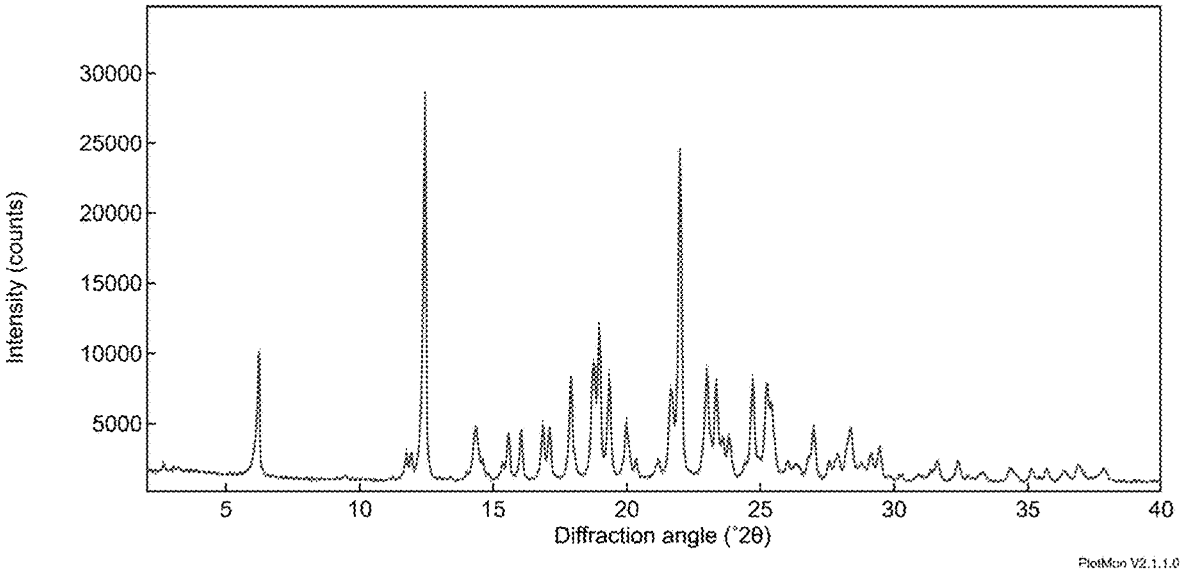
FIG. 4 provides an XRPD diffractogram of a sample comprising crystalline MDMA·phosphate.
Figure 47:
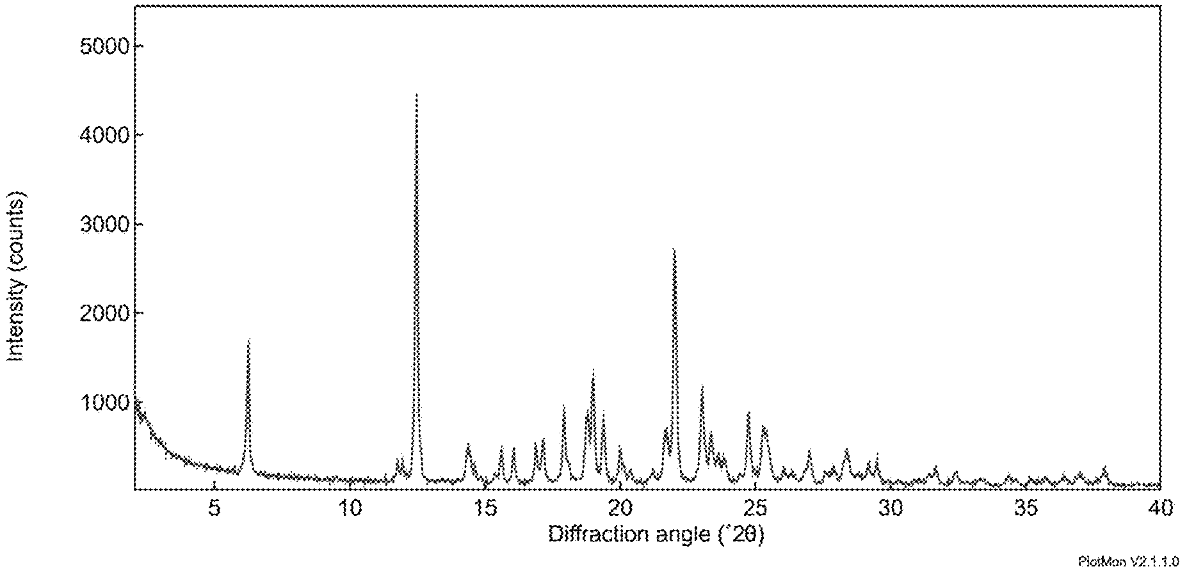
FIG. 47 provides an XRPD diffractogram of crystalline MDMA phosphate.
Figure 57:
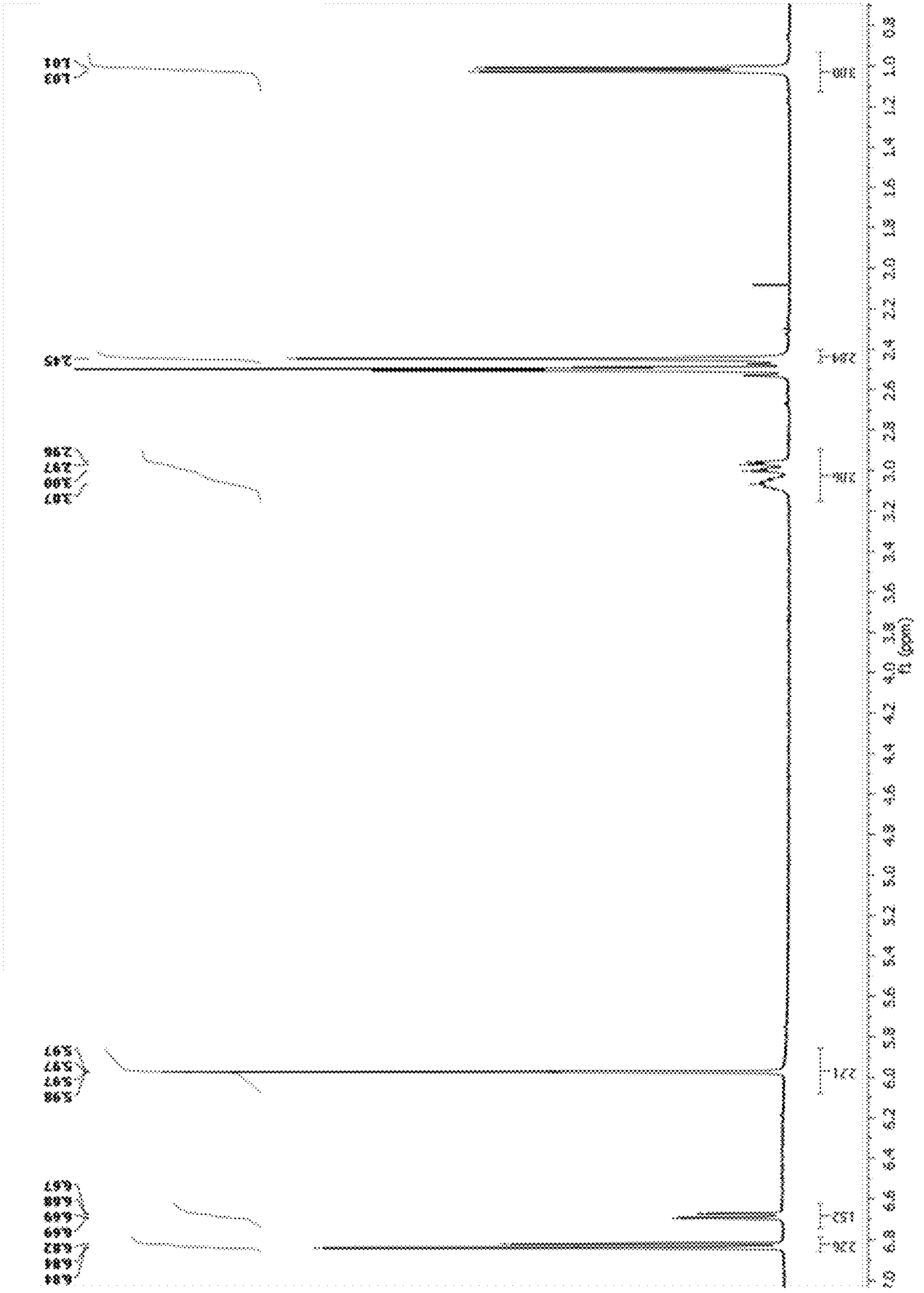
FIG. 57 provides a $^1$H NMR spectrum for MDMA phosphate.

In some embodiments, the present disclosure provides solid forms of MDMA phosphate, e.g., crystalline forms of MDMA phosphate. In some embodiments, the MDMA phosphate XRPD profile is substantially similar to that shown in any one of FIG. 4 or 47. In some embodiments, the MDMA phosphate $^1$H NMR spectrum is substantially similar to that shown in FIG. 57. In some embodiments, the MDMA phosphate TGA profile is substantially similar to that shown in FIG. 58. In some embodiments, the MDMA phosphate DSC profile is substantially similar to that shown in FIG. 58.

In some embodiments, the solid form of MDMA phosphate is crystalline MDMA phosphate characterized by two or more, or three or more XRPD signals selected from the group consisting of 12.4° 2θ, 19.0° 2θ, and 22.0° 2θ (±0.2° 2θ; ±0.1° 2θ; or ±0.0° 2θ; Cu Kα1 radiation). In some embodiments, the solid form of MDMA phosphate is crystalline MDMA phosphate characterized by XRPD signals at 12.4° 2θ, 19.0° 2θ, and 22.0° 2θ (±0.2° 2θ; ±0.1° 2θ; or ±0.0° 2θ; Cu Kα1 radiation).

In some embodiments, the solid form of MDMA phosphate is crystalline MDMA phosphate characterized by two or more, or three or more XRPD signals selected from the group consisting of 6.2° 2θ, 12.4° 2θ, 18.8° 2θ, 19.0° 2θ, and 22.0° 2θ (±0.2° 2θ; ±0.1° 2θ; or ±0.0° 2θ; Cu Kα1 radiation). In some embodiments, the solid form of MDMA phosphate is MDMA phosphate characterized by XRPD signals at 6.2° 2θ, 12.4° 2θ, 18.8° 2θ, 19.0° 2θ, and 22.0° 2θ (±0.2° 2θ; =0.1° 2θ; or ±0.0° 2θ; Cu Kα1 radiation).

In some embodiments, the solid form of MDMA phosphate is crystalline MDMA phosphate characterized by two or more, or three or more XRPD signals selected from the group consisting of 6.2° 2θ, 12.4° 2θ, and 22.0° 2θ (±0.2° 2θ; ±0.1° 2θ; or ±0.0° 2θ; Cu Kα1 radiation). In some embodiments, the solid form of MDMA phosphate is crystalline MDMA phosphate characterized by XRPD signals at 6.2° 2θ, 12.4° 2θ, and 22.0° 2θ (±0.2° 2θ; ±0.1° 2θ; or ±0.0° 2θ; Cu Kα1 radiation).

In some embodiments, the solid form of MDMA phosphate is crystalline MDMA phosphate characterized by two or more, or three or more XRPD signals selected from the group consisting of 6.2° 2θ, 12.4° 2θ, 17.9° 2θ, 19.3° 2θ, and 22.0° 2θ (±0.2° 2θ; ±0.1° 2θ; or ±0.0° 2θ; Cu Kα1 radiation). In some embodiments, the solid form of MDMA phosphate is MDMA phosphate characterized by XRPD signals at 6.2° 2θ, 12.4° 2θ, 17.9° 2θ, 19.3° 2θ, and 22.0° 2θ (±0.2° 2θ; =0.1° 2θ; or ±0.0° 2θ; Cu Kα1 radiation).

In some embodiments, the crystalline MDMA phosphate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty XRPD signals selected from those set forth in Table 4.

TABLE 4

| XRPD Signals for MDMA phosphate | | | |
|---|---|---|---|
| Signal no. | Position | d-value | Relative |
| 1 | 6.2 | 14.2 | 35.8 |
| 2 | 11.7 | 7.5 | 10.1 |
| 3 | 11.9 | 7.4 | 10.3 |
| 4 | 12.4 | 7.1 | 100.0 |
| 5 | 14.3 | 6.2 | 16.9 |
| 6 | 14.6 | 6.1 | 8.6 |
| 7 | 15.4 | 5.8 | 7.8 |
| 8 | 15.6 | 5.7 | 15.0 |
| 9 | 16.1 | 5.5 | 16.0 |
| 10 | 16.9 | 5.3 | 17.3 |
| 11 | 17.1 | 5.2 | 16.9 |
| 12 | 17.9 | 5.0 | 29.8 |
| 13 | 18.8 | 4.7 | 33.5 |
| 14 | 19.0 | 4.7 | 41.8 |
| 15 | 19.3 | 4.6 | 29.3 |
| 16 | 20.0 | 4.4 | 18.2 |
| 17 | 20.3 | 4.4 | 8.8 |
| 18 | 21.2 | 4.2 | 8.6 |
| 19 | 21.6 | 4.1 | 26.7 |
| 20 | 22.0 | 4.0 | 85.6 |
| 21 | 23.0 | 3.9 | 31.0 |
| 22 | 23.3 | 3.8 | 28.7 |
| 23 | 23.6 | 3.8 | 14.3 |
| 24 | 23.8 | 3.7 | 14.6 |
| 25 | 24.4 | 3.6 | 8.3 |
| 26 | 24.7 | 3.6 | 28.5 |
| 27 | 25.3 | 3.5 | 28.1 |
| 28 | 26.0 | 3.4 | 8.3 |
| 29 | 26.4 | 3.4 | 7.5 |
| 30 | 27.0 | 3.3 | 17.2 |
| 31 | 27.6 | 3.2 | 8.3 |
| 32 | 27.9 | 3.2 | 9.9 |
| 33 | 28.4 | 3.1 | 16.8 |
| 34 | 28.8 | 3.1 | 7.8 |
| 35 | 29.1 | 3.1 | 10.2 |
| 36 | 29.5 | 3.0 | 11.6 |
| 37 | 29.8 | 3.0 | 4.4 |
| 38 | 30.2 | 3.0 | 4.9 |
| 39 | 30.9 | 2.9 | 4.7 |
| 40 | 31.4 | 2.8 | 6.2 |
| 41 | 31.6 | 2.8 | 8.3 |
| 42 | 32.4 | 2.8 | 8.3 |
| 43 | 32.7 | 2.7 | 4.8 |
| 44 | 33.3 | 2.7 | 5.2 |
| 45 | 34.4 | 2.6 | 6.6 |
| 46 | 35.1 | 2.6 | 6.1 |
| 47 | 35.7 | 2.5 | 6.3 |
| 48 | 36.4 | 2.5 | 5.8 |
| 49 | 36.9 | 2.4 | 7.1 |
| 50 | 37.8 | 2.4 | 6.6 |

In some embodiments, the solid form of MDMA phosphate is crystalline MDMA phosphate characterized by two or more, or three or more XRPD signals selected from the group consisting of 6.3° 2θ, 12.5° 2θ, and 22.0° 2θ (±0.2° 2θ; ±0.1° 2θ; or ±0.0° 2θ; Cu Kα1 radiation). In some embodiments, the solid form of MDMA phosphate is crystalline MDMA phosphate characterized by XRPD signals at 6.3° 2θ, 12.5° 2θ, and 22.0° 2θ (±0.2° 2θ; ±0.1° 2θ; or ±0.0° 2θ; Cu Kα1 radiation).

In some embodiments, the solid form of MDMA phosphate is crystalline MDMA phosphate characterized by two or more, or three or more XRPD signals selected from the group consisting of 6.3° 2θ, 12.5° 2θ, 19.0° 2θ, 22.0° 2θ, and 23.0° 2θ (±0.2° 2θ; ±0.1° 2θ; or ±0.0° 2θ; Cu Kα1 radiation). In some embodiments, the solid form of MDMA phosphate is MDMA phosphate characterized by XRPD signals at 6.3° 2θ, 12.5° 2θ, 19.0° 2θ, 22.0° 2θ, and 23.0° 2θ (±0.2° 2θ; ±0.1° 2θ; or ±0.0° 2θ; Cu Kα1 radiation).

In some embodiments, the solid form of MDMA phosphate is crystalline MDMA phosphate characterized by two or more, or three or more XRPD signals selected from the group consisting of 6.3° 2θ, 12.5° 2θ, 17.9° 2θ, 19.4° 2θ, and 22.0° 2θ (±0.2° 2θ; ±0.1° 2θ; or ±0.0° 2θ; Cu Kα1 radiation). In some embodiments, the solid form of MDMA phosphate is MDMA phosphate characterized by XRPD signals at 6.3° 2θ, 12.5° 2θ, 17.9° 2θ, 19.4° 2θ, and 22.0° 2θ (±0.2° 2θ; ±0.1° 2θ; or ±0.0° 2θ; Cu Kα1 radiation).

In some embodiments, the crystalline MDMA phosphate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, or forty-nine XRPD signals selected from those set forth in Table 5.

TABLE 5

| XRPD Signals for MDMA phosphate | | | |
|---|---|---|---|
| Signal no. | Position | d-value | Relative |
| 1 | 6.3 | 14.1 | 37.5 |
| 2 | 11.8 | 7.5 | 7.6 |
| 3 | 11.9 | 7.4 | 7.9 |
| 4 | 12.5 | 7.1 | 100.0 |
| 5 | 14.4 | 6.2 | 12.0 |
| 6 | 14.6 | 6.1 | 6.7 |
| 7 | 15.4 | 5.8 | 4.7 |
| 8 | 15.6 | 5.7 | 10.9 |
| 9 | 16.1 | 5.5 | 11.0 |
| 10 | 16.9 | 5.3 | 11.8 |
| 11 | 17.2 | 5.2 | 13.4 |
| 12 | 17.9 | 4.9 | 20.3 |
| 13 | 18.8 | 4.7 | 19.8 |
| 14 | 19.0 | 4.7 | 29.5 |
| 15 | 19.4 | 4.6 | 18.3 |
| 16 | 20.0 | 4.4 | 10.7 |
| 17 | 20.1 | 4.4 | 7.5 |
| 18 | 20.4 | 4.4 | 5.7 |
| 19 | 21.2 | 4.2 | 5.7 |
| 20 | 21.7 | 4.1 | 15.7 |
| 21 | 22.0 | 4.0 | 60.8 |
| 22 | 23.0 | 3.9 | 25.2 |
| 23 | 23.3 | 3.8 | 15.1 |
| 24 | 23.6 | 3.8 | 9.7 |
| 25 | 23.8 | 3.7 | 9.2 |
| 26 | 24.4 | 3.6 | 4.7 |
| 27 | 24.8 | 3.6 | 20.1 |
| 28 | 25.3 | 3.5 | 16.6 |
| 29 | 25.4 | 3.5 | 15.1 |
| 30 | 26.0 | 3.4 | 5.9 |
| 31 | 26.4 | 3.4 | 5.0 |
| 32 | 27.0 | 3.3 | 10.2 |
| 33 | 27.6 | 3.2 | 5.3 |
| 34 | 27.9 | 3.2 | 6.2 |
| 35 | 28.4 | 3.1 | 10.8 |
| 36 | 28.8 | 3.1 | 4.6 |
| 37 | 29.2 | 3.1 | 7.0 |
| 38 | 29.5 | 3.0 | 7.9 |

TABLE 5-continued

| XRPD Signals for MDMA phosphate | | | |
|---|---|---|---|
| Signal no. | Position | d-value | Relative |
| 39 | 31.4 | 2.8 | 4.8 |
| 40 | 31.7 | 2.8 | 5.8 |
| 41 | 32.4 | 2.8 | 5.1 |
| 42 | 33.3 | 2.7 | 3.4 |
| 43 | 34.4 | 2.6 | 4.3 |
| 44 | 34.6 | 2.6 | 3.2 |
| 45 | 35.1 | 2.6 | 3.5 |
| 46 | 35.8 | 2.5 | 3.9 |
| 47 | 36.4 | 2.5 | 3.9 |
| 48 | 37.0 | 2.4 | 4.8 |
| 49 | 37.9 | 2.4 | 5.7 |

Solid Forms of MDMA Tartrate Form 1

Figure 5:
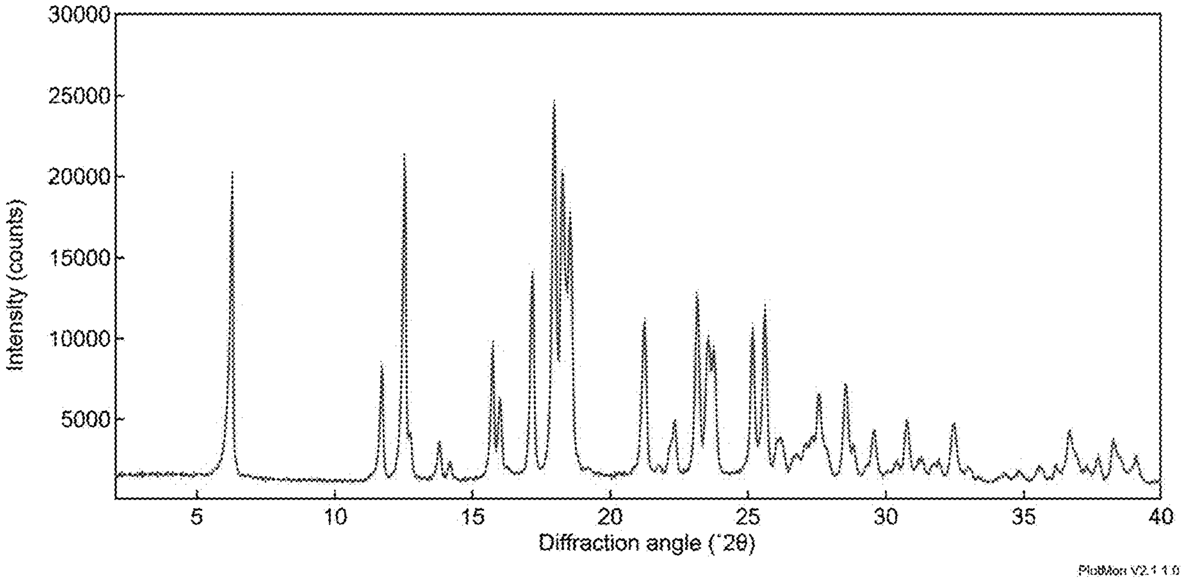
FIG. 5 provides an XRPD diffractogram of a sample comprising crystalline MDMA·L-tartrate.

In some embodiments, the present disclosure provides solid forms of MDMA tartrate Form 1, e.g., crystalline forms of MDMA tartrate Form 1. In some embodiments, the MDMA tartrate Form 1 XRPD profile is substantially similar to that shown in FIG. 5. In some embodiments, the MDMA tartrate Form 1 $^{1}$H NMR spectrum is substantially similar to that shown in FIG. 61. In some embodiments, the MDMA tartrate Form 1 TGA profile is substantially similar to that shown in FIG. 62. In some embodiments, the MDMA tartrate Form 1 DSC profile is substantially similar to that shown in FIG. 62.

In some embodiments, the solid form of MDMA tartrate Form 1 is crystalline MDMA tartrate Form 1 characterized by two or more, or three or more XRPD signals selected from the group consisting of 12.5° 2θ, 18.0° 2θ, and 18.3° 2θ (±0.2° 2θ; ±0.1° 2θ; or ±0.0° 2θ; Cu Kα1 radiation). In some embodiments, the solid form of MDMA tartrate Form 1 is crystalline MDMA tartrate Form 1 characterized by XRPD signals at 12.5° 2θ, 18.0° 2θ, and 18.3° 2θ (±0.2° 2θ; ±0.1° 2θ; or ±0.0° 2θ; Cu Kα1 radiation).

In some embodiments, the solid form of MDMA tartrate Form 1 is crystalline MDMA tartrate Form 1 characterized by two or more, or three or more XRPD signals selected from the group consisting of 6.3° 2θ, 12.5° 2θ, 18.0° 2θ, 18.3° 2θ, and 18.5° 2θ (±0.2° 2θ; ±0.1° 2θ; or ±0.0° 2θ; Cu Kα1 radiation). In some embodiments, the solid form of MDMA tartrate Form 1 is MDMA tartrate Form 1 characterized by XRPD signals at 6.3° 2θ, 12.5° 2θ, 18.0° 2θ, 18.3° 2θ, and 18.5° 2θ (±0.2° 2θ; ±0.1° 2θ; or ±0.0° 2θ; Cu Kα1 radiation).

In some embodiments, the solid form of MDMA tartrate Form 1 is crystalline MDMA tartrate Form 1 characterized by two or more, or three or more XRPD signals selected from the group consisting of 6.3° 2θ, 11.7° 2θ, and 12.5° 2θ (±0.2° 2θ; ±0.1° 2θ; or ±0.0° 2θ; Cu Kα1 radiation). In some embodiments, the solid form of MDMA tartrate Form 1 is crystalline MDMA tartrate Form 1 characterized by XRPD signals at 6.3° 2θ, 11.7° 2θ, and 12.5° 2θ (±0.2° 2θ; ±0.1° 2θ; or ±0.0° 2θ; Cu Kα1 radiation).

In some embodiments, the solid form of MDMA tartrate Form 1 is crystalline MDMA tartrate Form 1 characterized by two or more, or three or more XRPD signals selected from the group consisting of 6.3° 2θ, 11.7° 2θ, 12.5° 2θ, 17.2° 2θ, and 18.0° 2θ (±0.2° 2θ; ±0.1° 2θ; or ±0.0° 2θ; Cu Kα1 radiation). In some embodiments, the solid form of MDMA tartrate Form 1 is MDMA tartrate Form 1 characterized by XRPD signals at 6.3° 2θ, 11.7° 2θ, 12.5° 2θ, 17.2° 2θ, and 18.0° 2θ (±0.2° 2θ; ±0.1° 2θ; or ±0.0° 2θ; Cu Kα1 radiation).

In some embodiments, the crystalline MDMA tartrate Form 1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four XRPD signals selected from those set forth in Table 6.

TABLE 6

| XRPD Signals for MDMA tartrate Form 1 | | | |
|---|---|---|---|
| Signal no. | Position | d-value | Relative |
| 1 | 6.3 | 14.1 | 81.2 |
| 2 | 11.7 | 7.6 | 33.1 |
| 3 | 12.5 | 7.1 | 85.9 |
| 4 | 12.7 | 7.0 | 17.1 |
| 5 | 13.8 | 6.4 | 14.7 |
| 6 | 14.1 | 6.3 | 9.6 |
| 7 | 15.7 | 5.6 | 38.3 |
| 8 | 16.0 | 5.5 | 25.2 |
| 9 | 17.2 | 5.2 | 57.4 |
| 10 | 18.0 | 4.9 | 100.0 |
| 11 | 18.3 | 4.9 | 83.4 |
| 12 | 18.5 | 4.8 | 72.1 |
| 13 | 21.2 | 4.2 | 45.1 |
| 14 | 21.8 | 4.1 | 9.1 |
| 15 | 22.3 | 4.0 | 20.1 |
| 16 | 23.1 | 3.8 | 51.5 |
| 17 | 23.5 | 3.8 | 41.0 |
| 18 | 23.7 | 3.7 | 38.5 |
| 19 | 25.2 | 3.5 | 43.2 |
| 20 | 25.6 | 3.5 | 48.0 |
| 21 | 26.2 | 3.4 | 16.1 |
| 22 | 26.8 | 3.3 | 11.9 |
| 23 | 27.1 | 3.3 | 14.4 |
| 24 | 27.3 | 3.3 | 16.3 |
| 25 | 27.6 | 3.2 | 26.8 |
| 26 | 28.5 | 3.1 | 29.6 |
| 27 | 28.8 | 3.1 | 14.0 |
| 28 | 29.6 | 3.0 | 17.8 |
| 29 | 30.4 | 2.9 | 9.9 |
| 30 | 30.8 | 2.9 | 20.3 |
| 31 | 31.3 | 2.9 | 10.7 |
| 32 | 31.7 | 2.8 | 9.4 |
| 33 | 31.9 | 2.8 | 10.2 |
| 34 | 32.5 | 2.8 | 19.4 |
| 35 | 33.0 | 2.7 | 8.6 |
| 36 | 34.3 | 2.6 | 7.0 |
| 37 | 34.8 | 2.6 | 7.7 |
| 38 | 35.6 | 2.5 | 8.5 |
| 39 | 36.2 | 2.5 | 9.1 |
| 40 | 36.7 | 2.5 | 17.6 |
| 41 | 37.3 | 2.4 | 8.8 |
| 42 | 37.7 | 2.4 | 11.3 |
| 43 | 38.3 | 2.4 | 15.3 |
| 44 | 39.1 | 2.3 | 11.0 |

Solid Forms of MDMA Malate

Figure 6:
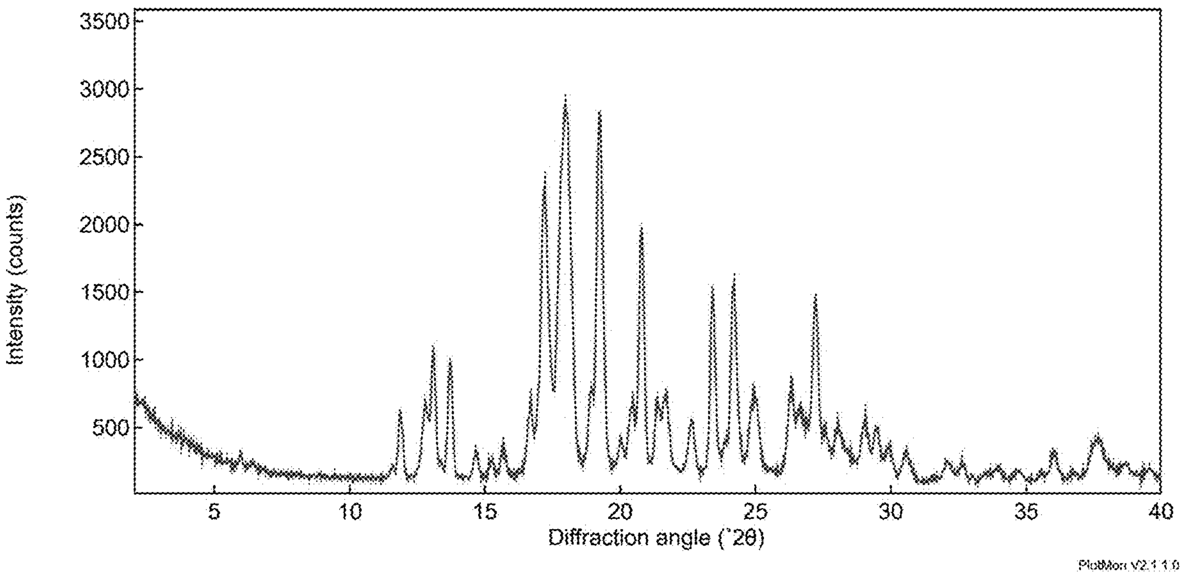
FIG. 6 provides an XRPD diffractogram of a sample comprising crystalline MDMA·L-malate.

In some embodiments, the present disclosure provides solid forms of MDMA malate, e.g., crystalline forms of MDMA malate. In some embodiments, the MDMA malate XRPD profile is substantially similar to that shown in FIG. 6. In some embodiments, the MDMA malate $^{1}$H NMR spectrum is substantially similar to that shown in FIG. 49. In some embodiments, the MDMA malate TGA profile is substantially similar to that shown in FIG. 50. In some embodiments, the MDMA malate DSC profile is substantially similar to that shown in FIG. 50.

In some embodiments, the solid form of MDMA malate is crystalline MDMA malate characterized by two or more, or three or more XRPD signals selected from the group consisting of 17.2° 2θ, 18.0° 2θ, and 19.2° 2θ (±0.2° 2θ; ±0.1° 2θ; or ±0.0° 2θ; Cu Kα1 radiation). In some embodiments, the solid form of MDMA malate is crystalline MDMA malate characterized by XRPD signals at 17.2° 2θ, 18.0° 2θ, and 19.2° 2θ (±0.2° 2θ; ±0.1° 2θ; or ±0.0° 2θ; Cu Kα1 radiation).

In some embodiments, the solid form of MDMA malate is crystalline MDMA malate characterized by two or more, or three or more XRPD signals selected from the group consisting of 17.2° 2θ, 18.0° 2θ, 19.2° 2θ, 20.8° 2θ, and 24.2° 2θ (±0.2° 2θ; ±0.1° 2θ; or ±0.0° 2θ; Cu Kα1 radiation). In some embodiments, the solid form of MDMA malate is MDMA malate characterized by XRPD signals at 17.2° 2θ, 18.0° 2θ, 19.2° 2θ, 20.8° 2θ, and 24.2° 2θ (±0.2° 2θ; ±0.1° 2θ; or ±0.0° 2θ; Cu Kα1 radiation).

In some embodiments, the solid form of MDMA malate is crystalline MDMA malate characterized by two or more, or three or more XRPD signals selected from the group consisting of 11.9° 2θ, 13.1° 2θ, and 13.7° 2θ (±0.2° 2θ; ±0.1° 2θ; or ±0.0° 2θ; Cu Kα1 radiation). In some embodiments, the solid form of MDMA malate is crystalline MDMA malate characterized by XRPD signals at 11.9° 2θ, 13.1° 2θ, and 13.7° 2θ (±0.2° 2θ; ±0.1° 2θ; or ±0.0° 2θ; Cu Kα1 radiation).

In some embodiments, the solid form of MDMA malate is crystalline MDMA malate characterized by two or more, or three or more XRPD signals selected from the group consisting of 11.9° 2θ, 13.1° 2θ, 13.7° 2θ, 17.2° 2θ, and 18.0° 2θ (±0.2° 2θ; ±0.1° 2θ; or ±0.0° 2θ; Cu Kα1 radiation). In some embodiments, the solid form of MDMA malate is MDMA malate characterized by XRPD signals at 11.9° 2θ, 13.1° 2θ, 13.7° 2θ, 17.2° 2θ, and 18.0° 2θ (±0.2° 2θ; ±0.1° 2θ; or ±0.0° 2θ; Cu Kα1 radiation).

In some embodiments, the crystalline MDMA malate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, or forty-five XRPD signals selected from those set forth in Table 7.

TABLE 7

XRPD Signals for MDMA malate

| Signal no. | Position | d-value | Relative |
|---|---|---|---|
| 1 | 6.0 | 14.8 | 11.3 |
| 2 | 11.6 | 7.6 | 7.8 |
| 3 | 11.9 | 7.5 | 21.6 |
| 4 | 12.8 | 6.9 | 23.9 |
| 5 | 13.1 | 6.8 | 36.9 |
| 6 | 13.7 | 6.5 | 34.3 |
| 7 | 14.7 | 6.0 | 11.9 |
| 8 | 15.1 | 5.9 | 8.7 |
| 9 | 15.3 | 5.8 | 9.3 |
| 10 | 15.7 | 5.7 | 12.9 |
| 11 | 16.7 | 5.3 | 25.0 |
| 12 | 17.2 | 5.1 | 80.2 |
| 13 | 18.0 | 4.9 | 100.0 |
| 14 | 18.9 | 4.7 | 27.7 |
| 15 | 19.2 | 4.6 | 97.8 |
| 16 | 20.0 | 4.4 | 14.6 |
| 17 | 20.5 | 4.3 | 24.9 |
| 18 | 20.8 | 4.3 | 68.0 |
| 19 | 21.4 | 4.2 | 24.2 |
| 20 | 21.7 | 4.1 | 25.8 |
| 21 | 22.6 | 3.9 | 19.5 |

TABLE 7-continued

XRPD Signals for MDMA malate

| Signal no. | Position | d-value | Relative |
|---|---|---|---|
| 22 | 23.4 | 3.8 | 51.9 |
| 23 | 24.2 | 3.7 | 54.9 |
| 24 | 24.9 | 3.6 | 26.6 |
| 25 | 26.3 | 3.4 | 28.9 |
| 26 | 26.7 | 3.3 | 23.1 |
| 27 | 27.2 | 3.3 | 50.3 |
| 28 | 27.6 | 3.2 | 17.4 |
| 29 | 28.0 | 3.2 | 18.9 |
| 30 | 29.1 | 3.1 | 20.9 |
| 31 | 29.4 | 3.0 | 17.5 |
| 32 | 30.0 | 3.0 | 12.6 |
| 33 | 30.6 | 2.9 | 12.1 |
| 34 | 32.0 | 2.8 | 8.7 |
| 35 | 32.6 | 2.7 | 9.2 |
| 36 | 33.0 | 2.7 | 5.3 |
| 37 | 33.5 | 2.7 | 6.2 |
| 38 | 34.0 | 2.6 | 7.8 |
| 39 | 34.7 | 2.6 | 6.6 |
| 40 | 35.6 | 2.5 | 6.4 |
| 41 | 36.0 | 2.5 | 11.4 |
| 42 | 36.7 | 2.4 | 6.4 |
| 43 | 37.7 | 2.4 | 15.0 |
| 44 | 38.7 | 2.3 | 8.3 |
| 45 | 39.6 | 2.3 | 7.7 |

Solid Forms of MDMA Galactarate (Mucate)

Figure 7:
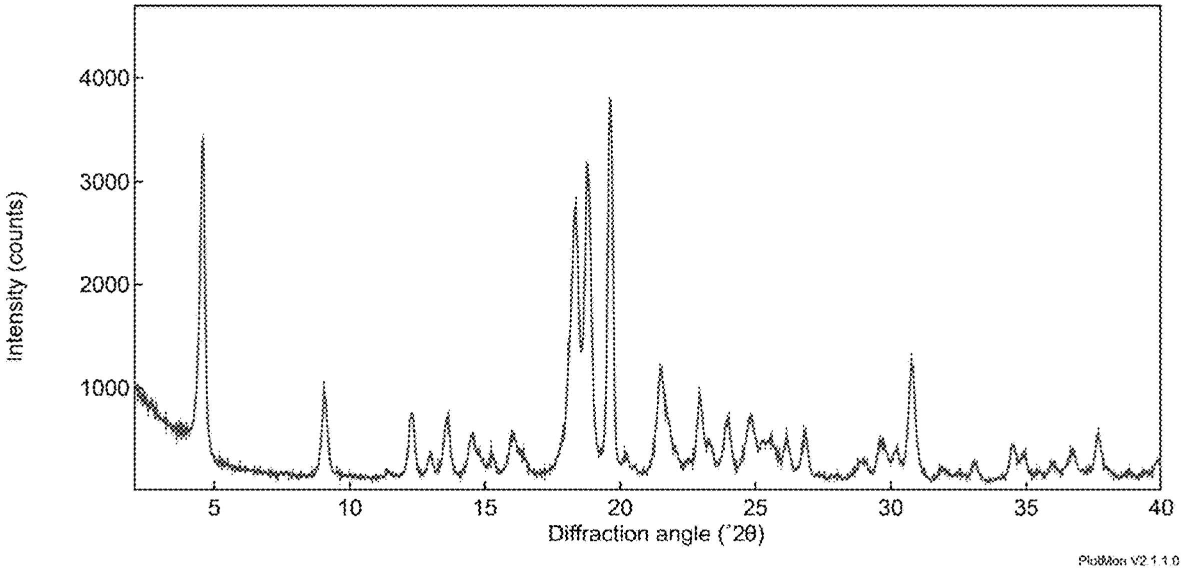
FIG. 7 provides an XRPD diffractogram of a sample comprising crystalline MDMA·galactarate (mucate).
Figure 46:
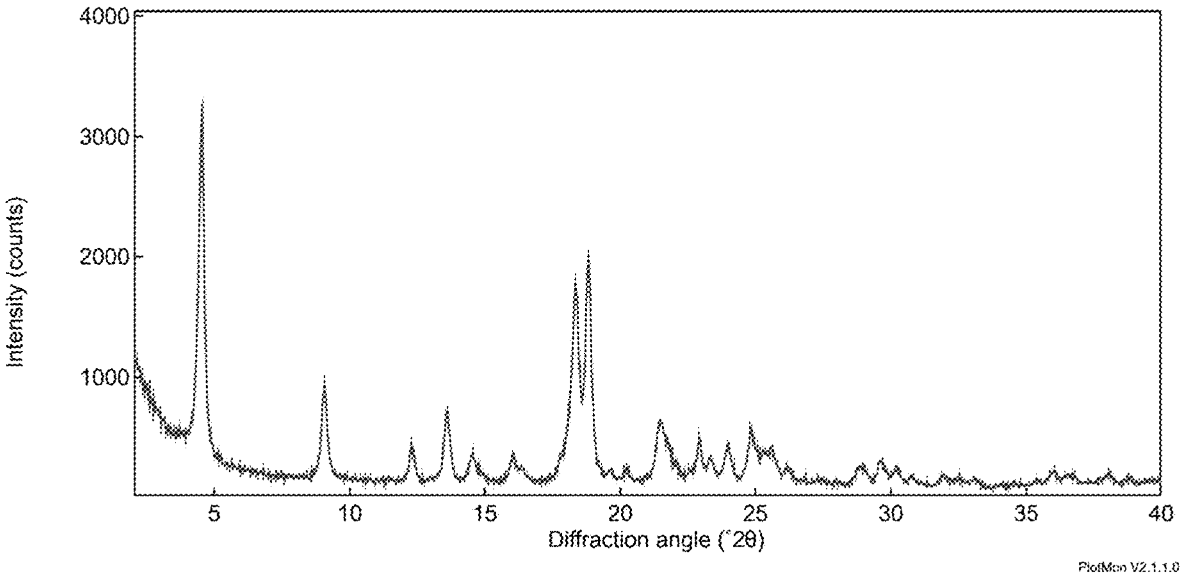
FIG. 46 provides an XRPD diffractogram of crystalline MDMA galactarate (mucate).
Figure 55:
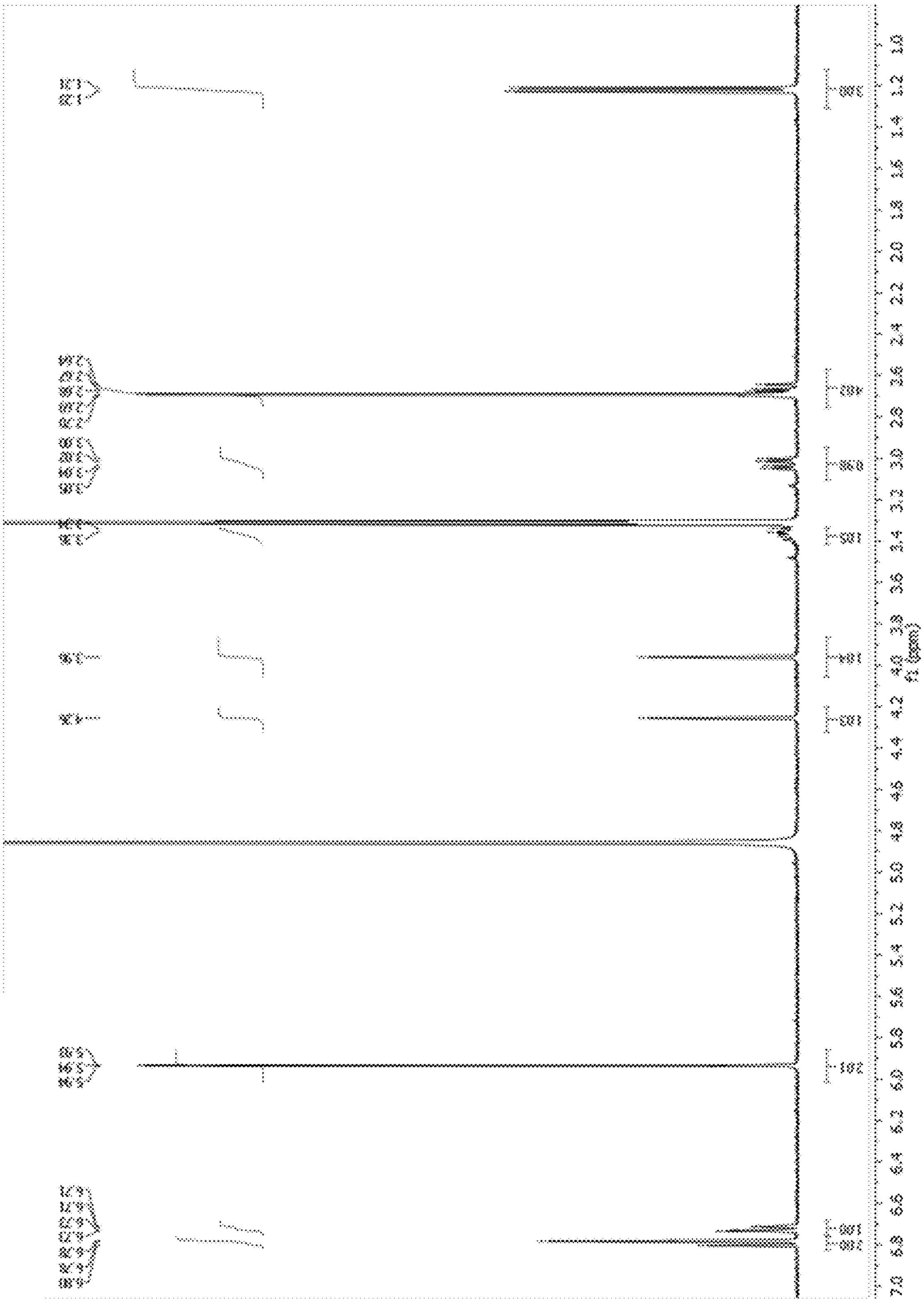
FIG. 55 provides a $^1$H NMR spectrum for MDMA galactarate (mucate).
Figure 56:
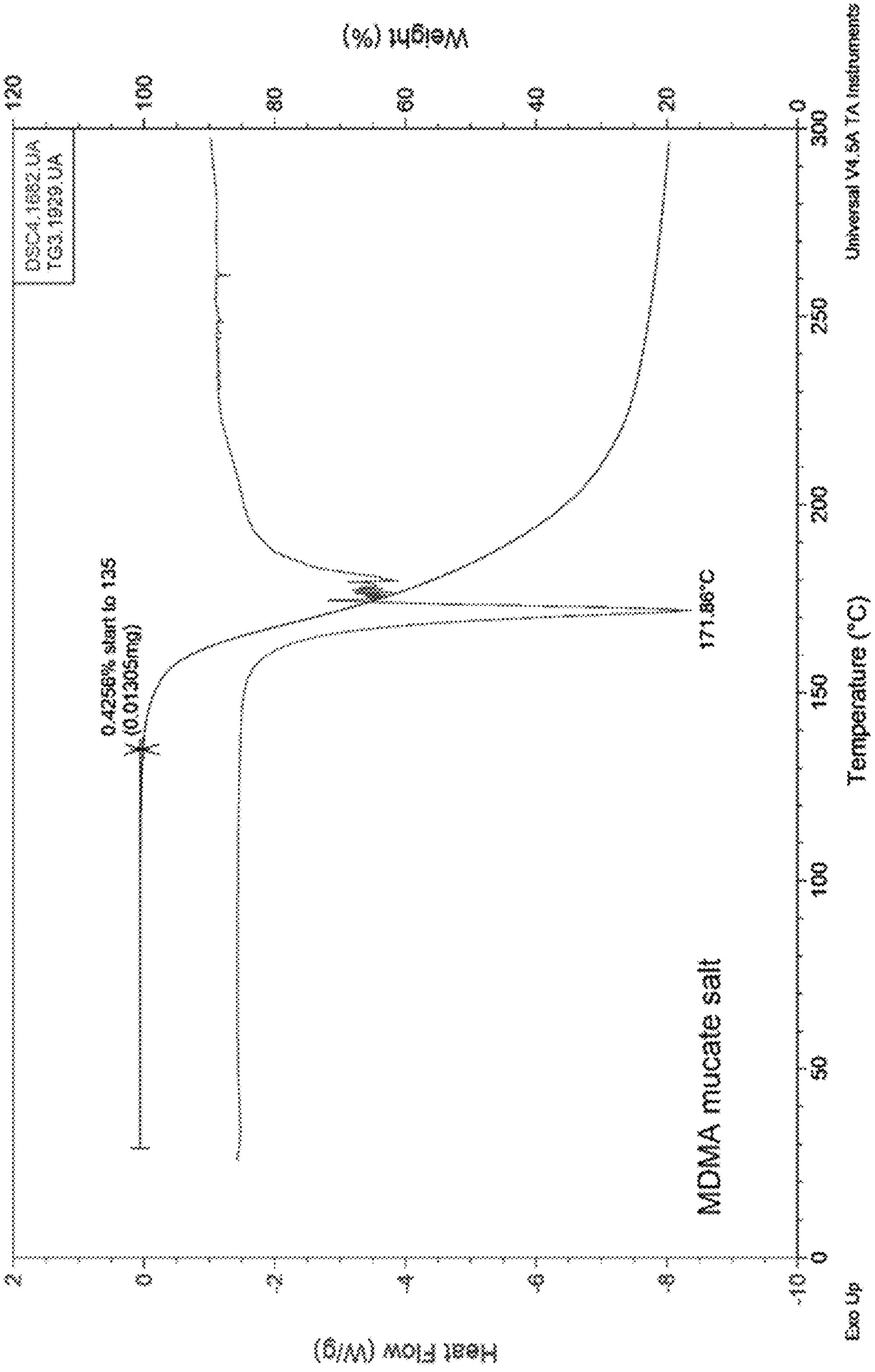
FIG. 56 provides TGA and DSC profiles for MDMA galactarate (mucate).

In some embodiments, the present disclosure provides solid forms of MDMA galactarate (mucate), e.g., crystalline forms of MDMA galactarate (mucate). In some embodiments, the MDMA galactarate (mucate) XRPD profile is substantially similar to that shown in any one of FIG. 7 or 46. In some embodiments, the MDMA galactarate (mucate) $^1$H NMR spectrum is substantially similar to that shown in FIG. 55. In some embodiments, the MDMA galactarate (mucate) TGA profile is substantially similar to that shown in FIG. 56. In some embodiments, the MDMA galactarate (mucate) DSC profile is substantially similar to that shown in FIG. 56.

In some embodiments, the solid form of MDMA galactarate (mucate) is crystalline MDMA galactarate (mucate) characterized by two or more, or three or more XRPD signals selected from the group consisting of 4.6° 2θ, 18.8° 2θ, and 19.6° 2θ (±0.2° 2θ; ±0.1° 2θ; or ±0.0° 2θ; Cu Kα1 radiation). In some embodiments, the solid form of MDMA galactarate (mucate) is crystalline MDMA galactarate (mucate) characterized by XRPD signals at 4.6° 2θ, 18.8° 2θ, and 19.6° 2θ (±0.2° 2θ; ±0.1° 2θ; or ±0.0° 2θ; Cu Kα1 radiation).

In some embodiments, the solid form of MDMA galactarate (mucate) is crystalline MDMA galactarate (mucate) characterized by two or more, or three or more XRPD signals selected from the group consisting of 4.6° 2θ, 18.4° 2θ, 18.8° 2θ, 19.6° 2θ, and 30.8° 2θ (±0.2° 2θ; ±0.1° 2θ; or ±0.0° 2θ; Cu Kα1 radiation). In some embodiments, the solid form of MDMA galactarate (mucate) is MDMA galactarate (mucate) characterized by XRPD signals at 4.6° 2θ, 18.4° 2θ, 18.8° 2θ, 19.6° 2θ, and 30.8° 2θ (±0.2° 2θ; ±0.1° 2θ; or ±0.0° 2θ; Cu Kα1 radiation).

In some embodiments, the solid form of MDMA galactarate (mucate) is crystalline MDMA galactarate (mucate) characterized by two or more, or three or more XRPD signals selected from the group consisting of 4.6° 2θ, 9.0° 2θ, and 13.6° 2θ (±0.2° 2θ; ±0.1° 2θ; or ±0.0° 2θ; Cu Kα1 radiation). In some embodiments, the solid form of MDMA galactarate (mucate) is crystalline MDMA galactarate (mucate) characterized by XRPD signals at 4.6° 2θ, 9.0° 2θ, and 13.6° 2θ (±0.2° 2θ; ±0.1° 2θ; or ±0.0° 2θ; Cu Kα1 radiation).

In some embodiments, the solid form of MDMA galactarate (mucate) is crystalline MDMA galactarate (mucate) characterized by two or more, or three or more XRPD signals selected from the group consisting of 4.6° 2θ, 9.0° 2θ, 13.6° 2θ, 18.4° 2θ, and 18.8° 2θ (±0.2° 2θ; ±0.1° 2θ; or ±0.0° 2θ; Cu Kα1 radiation). In some embodiments, the solid form of MDMA galactarate (mucate) is MDMA galactarate (mucate) characterized by XRPD signals at 4.6° 2θ, 9.0° 2θ, 13.6° 2θ, 18.4° 2θ, and 18.8° 2θ (±0.2° 2θ; ±0.1° 2θ; or ±0.0° 2θ; Cu Kα1 radiation).

In some embodiments, the crystalline MDMA galactarate (mucate) is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, or forty-one XRPD signals selected from those set forth in Table 8.

TABLE 8

XRPD Signals for MDMA galactarate (mucate)

| Signal no. | Position | d-value | Relative |
|---|---|---|---|
| 1 | 4.6 | 19.3 | 89.9 |
| 2 | 9.0 | 9.8 | 26.1 |
| 3 | 11.4 | 7.8 | 5.7 |
| 4 | 12.3 | 7.2 | 19.9 |
| 5 | 13.0 | 6.8 | 10.2 |
| 6 | 13.6 | 6.5 | 18.9 |
| 7 | 14.6 | 6.1 | 14.8 |
| 8 | 15.2 | 5.8 | 10.8 |
| 9 | 16.0 | 5.5 | 15.4 |
| 10 | 16.4 | 5.4 | 9.6 |
| 11 | 18.4 | 4.8 | 73.7 |
| 12 | 18.8 | 4.7 | 82.5 |
| 13 | 19.6 | 4.5 | 100.0 |
| 14 | 20.2 | 4.4 | 9.8 |
| 15 | 20.5 | 4.3 | 6.8 |
| 16 | 21.5 | 4.1 | 31.3 |
| 17 | 21.8 | 4.1 | 18.2 |
| 18 | 22.9 | 3.9 | 25.0 |
| 19 | 23.3 | 3.8 | 13.0 |
| 20 | 24.0 | 3.7 | 18.9 |
| 21 | 24.9 | 3.6 | 19.5 |
| 22 | 25.3 | 3.5 | 13.1 |
| 23 | 25.6 | 3.5 | 14.3 |
| 24 | 26.2 | 3.4 | 14.3 |
| 25 | 26.8 | 3.3 | 15.5 |
| 26 | 28.0 | 3.2 | 4.7 |
| 27 | 29.0 | 3.1 | 8.0 |
| 28 | 29.7 | 3.0 | 13.4 |
| 29 | 30.2 | 3.0 | 11.1 |
| 30 | 30.8 | 2.9 | 33.5 |
| 31 | 31.9 | 2.8 | 6.4 |
| 32 | 32.6 | 2.8 | 5.4 |
| 33 | 33.1 | 2.7 | 7.7 |
| 34 | 34.5 | 2.6 | 12.0 |
| 35 | 35.0 | 2.6 | 9.8 |
| 36 | 35.4 | 2.5 | 5.5 |
| 37 | 36.0 | 2.5 | 7.6 |
| 38 | 36.7 | 2.4 | 10.5 |
| 39 | 37.7 | 2.4 | 15.0 |
| 40 | 38.8 | 2.3 | 5.8 |
| 41 | 39.8 | 2.3 | 8.2 |

In some embodiments, the solid form of MDMA galactarate (mucate) is crystalline MDMA galactarate (mucate) characterized by two or more, or three or more XRPD signals selected from the group consisting of 4.6° 2θ, 18.3° 2θ, and 18.8° 2θ (±0.2° 2θ; ±0.1° 2θ; or ±0.0° 2θ; Cu Kα1 radiation). In some embodiments, the solid form of MDMA galactarate (mucate) is crystalline MDMA galactarate (mucate) characterized by XRPD signals at 4.6° 2θ, 18.3° 2θ, and 18.8° 2θ (±0.2° 2θ; ±0.1° 2θ; or ±0.0° 2θ; Cu Kα1 radiation).

In some embodiments, the solid form of MDMA galactarate (mucate) is crystalline MDMA galactarate (mucate) characterized by two or more, or three or more XRPD signals selected from the group consisting of 4.6° 2θ, 9.1° 2θ, 13.6° 2θ, 18.3° 2θ, and 18.8° 2θ (±0.2° 2θ; ±0.1° 2θ; or ±0.0° 2θ; Cu Kα1 radiation). In some embodiments, the solid form of MDMA galactarate (mucate) is MDMA galactarate (mucate) characterized by XRPD signals at 4.6° 2θ, 9.1° 2θ, 13.6° 2θ, 18.3° 2θ, and 18.8° 2θ (±0.2° 2θ; ±0.1° 2θ; or ±0.0° 2θ; Cu Kα1 radiation).

In some embodiments, the solid form of MDMA galactarate (mucate) is crystalline MDMA galactarate (mucate) characterized by two or more, or three or more XRPD signals selected from the group consisting of 4.6° 2θ, 9.1° 2θ, and 13.6° 2θ (±0.2° 2θ; ±0.1° 2θ; or ±0.0° 2θ; Cu Kα1 radiation). In some embodiments, the solid form of MDMA galactarate (mucate) is crystalline MDMA galactarate (mucate) characterized by XRPD signals at 4.6° 2θ, 9.1° 2θ, and 13.6° 2θ (±0.2° 2θ; ±0.1° 2θ; or ±0.0° 2θ; Cu Kα1 radiation).

In some embodiments, the crystalline MDMA galactarate (mucate) is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, or thirty-four XRPD signals selected from those set forth in Table 9.

TABLE 9

XRPD Signals for MDMA galactarate (mucate)

| Signal no. | Position | d-value | Relative |
|---|---|---|---|
| 1 | 4.6 | 19.4 | 100.0 |
| 2 | 9.1 | 9.8 | 29.4 |
| 3 | 12.3 | 7.2 | 13.9 |
| 4 | 13.6 | 6.5 | 22.4 |
| 5 | 14.6 | 6.1 | 12.1 |
| 6 | 16.0 | 5.5 | 11.5 |
| 7 | 16.3 | 5.4 | 8.1 |
| 8 | 18.3 | 4.8 | 54.8 |
| 9 | 18.8 | 4.7 | 61.6 |
| 10 | 19.7 | 4.5 | 7.3 |
| 11 | 20.2 | 4.4 | 7.9 |
| 12 | 21.5 | 4.1 | 19.7 |
| 13 | 21.7 | 4.1 | 15.4 |
| 14 | 22.0 | 4.0 | 9.7 |
| 15 | 22.9 | 3.9 | 15.7 |
| 16 | 23.3 | 3.8 | 10.5 |
| 17 | 24.0 | 3.7 | 14.0 |
| 18 | 24.9 | 3.6 | 17.4 |
| 19 | 25.3 | 3.5 | 12.2 |
| 20 | 25.6 | 3.5 | 13.2 |
| 21 | 26.2 | 3.4 | 8.4 |
| 22 | 29.0 | 3.1 | 8.2 |
| 23 | 29.6 | 3.0 | 9.5 |
| 24 | 30.2 | 3.0 | 8.0 |
| 25 | 30.8 | 2.9 | 5.8 |
| 26 | 31.9 | 2.8 | 6.1 |
| 27 | 32.5 | 2.8 | 5.7 |
| 28 | 33.1 | 2.7 | 5.3 |
| 29 | 36.1 | 2.5 | 7.6 |
| 30 | 36.6 | 2.5 | 6.1 |

TABLE 9-continued

| XRPD Signals for MDMA galactarate (mucate) | | | |
|---|---|---|---|
| Signal no. | Position | d-value | Relative |
| 31 | 36.7 | 2.4 | 6.2 |
| 32 | 36.8 | 2.4 | 6.0 |
| 33 | 38.1 | 2.4 | 7.1 |
| 34 | 38.8 | 2.3 | 5.5 |

Solid Forms of MDMA Succinate

Figure 8:
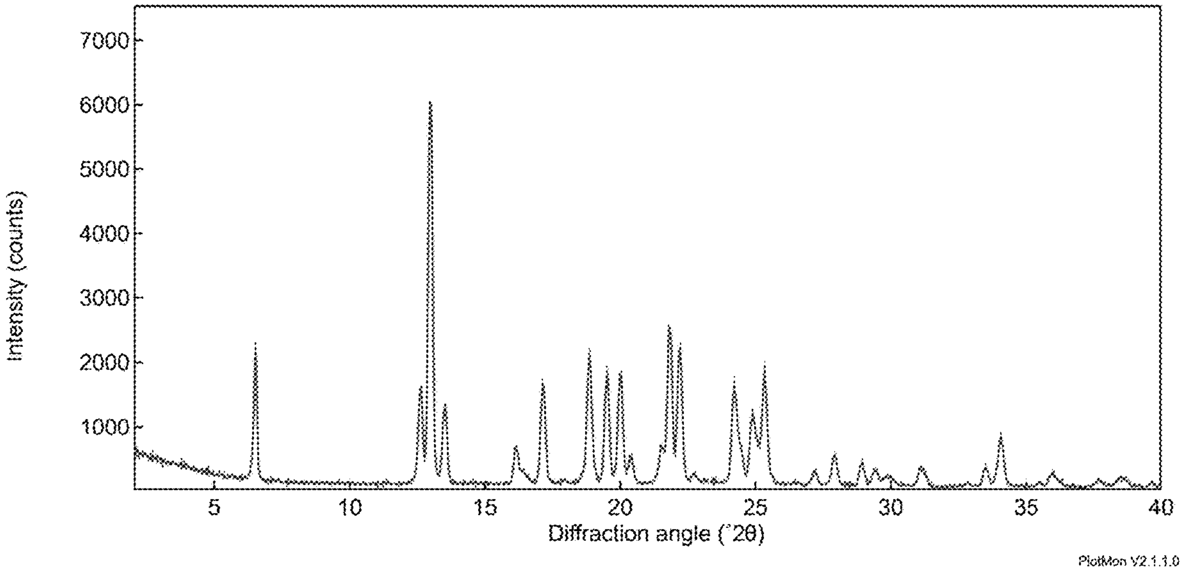
FIG. 8 provides an XRPD diffractogram of a sample comprising crystalline MDMA·succinate.
Figure 59:
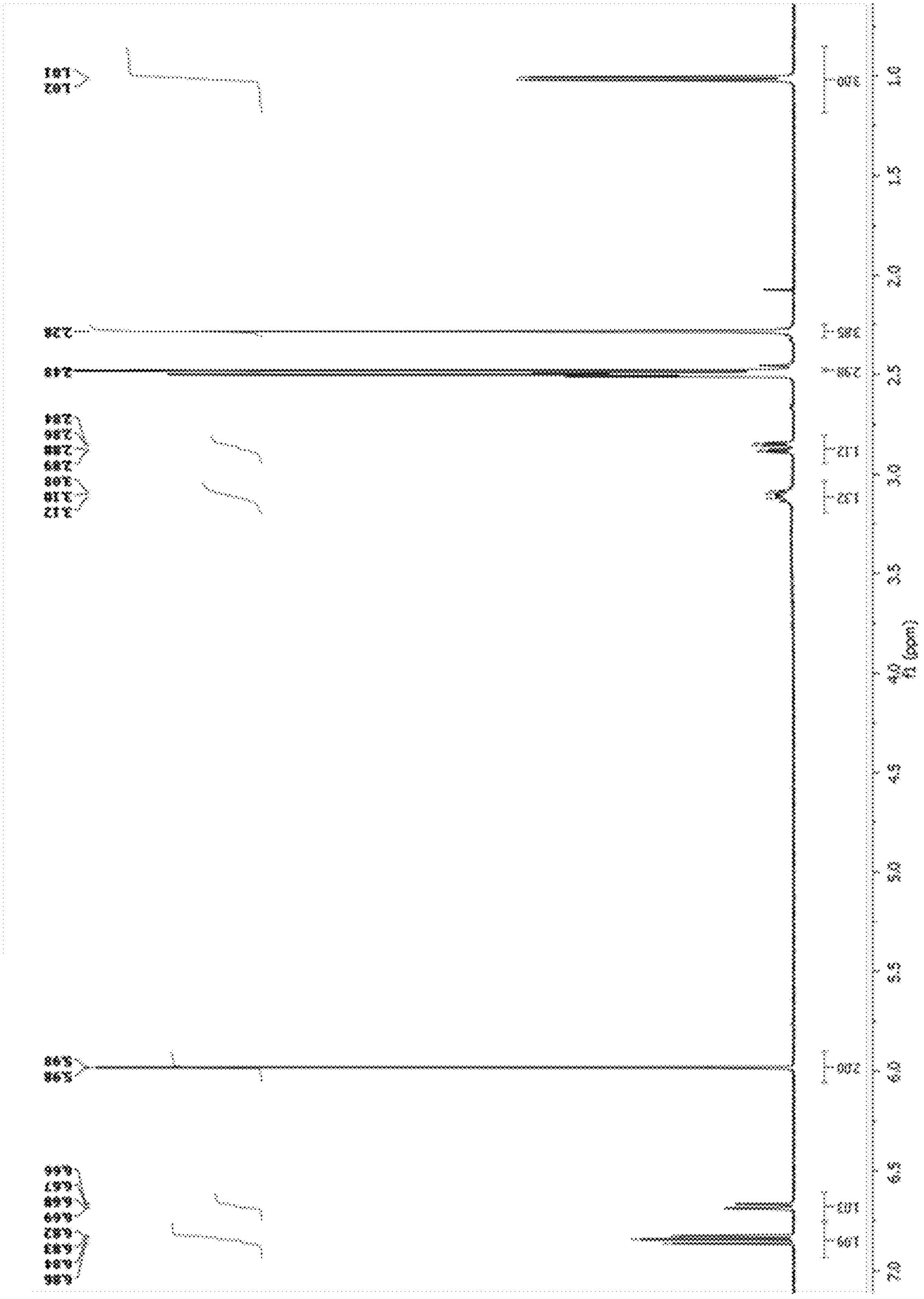
FIG. 59 provides a $^1$H NMR spectrum for MDMA succinate.

In some embodiments, the present disclosure provides solid forms of MDMA succinate, e.g., crystalline forms of MDMA succinate. In some embodiments, the MDMA succinate XRPD profile is substantially similar to that shown in FIG. 8. In some embodiments, the MDMA succinate $^1H$ NMR spectrum is substantially similar to that shown in FIG. 59. In some embodiments, the MDMA succinate TGA profile is substantially similar to that shown in FIG. 60. In some embodiments, the MDMA succinate DSC profile is substantially similar to that shown in FIG. 60.

In some embodiments, the solid form of MDMA succinate is crystalline MDMA succinate characterized by two or more, or three or more XRPD signals selected from the group consisting of 13.0° 2θ, 21.8° 2θ, and 22.2° 2θ (±0.2° 2θ; ±0.1° 2θ; or ±0.0° 2θ; Cu Kα1 radiation). In some embodiments, the solid form of MDMA succinate is crystalline MDMA succinate characterized by XRPD signals at 13.0° 2θ, 21.8° 2θ, and 22.2° 2θ (±0.2° 2θ; ±0.1° 2θ; or ±0.0° 2θ; Cu Kα1 radiation).

In some embodiments, the solid form of MDMA succinate is crystalline MDMA succinate characterized by two or more, or three or more XRPD signals selected from the group consisting of 6.5° 2θ, 13.0° 2θ, 18.9° 2θ, 21.8° 2θ, and 22.2° 2θ (±0.2° 2θ; ±0.1° 2θ; or ±0.0° 2θ; Cu Kα1 radiation). In some embodiments, the solid form of MDMA succinate is MDMA succinate characterized by XRPD signals at 6.5° 2θ, 13.0° 2θ, 18.9° 2θ, 21.8° 2θ, and 22.2° 2θ (±0.2° 2θ; ±0.1° 2θ; or ±0.0° 2θ; Cu Kα1 radiation).

In some embodiments, the solid form of MDMA succinate is crystalline MDMA succinate characterized by two or more, or three or more XRPD signals selected from the group consisting of 6.5° 2θ, 12.6° 2θ, and 13.0° 2θ (±0.2° 2θ; ±0.1° 2θ; or ±0.0° 2θ; Cu Kα1 radiation). In some embodiments, the solid form of MDMA succinate is crystalline MDMA succinate characterized by XRPD signals at 6.5° 2θ, 12.6° 2θ, and 13.0° 2θ (±0.2° 2θ; ±0.1° 2θ; or ±0.0° 2θ; Cu Kα1 radiation). In some embodiments, the solid form of MDMA succinate is crystalline MDMA succinate characterized by two or more, or three or more XRPD signals selected from the group consisting of 6.5° 2θ, 12.6° 2θ, 13.0° 2θ, 17.1° 2θ, and 18.9° 2θ (±0.2° 2θ; ±0.1° 2θ; or ±0.0° 2θ; Cu Kα1 radiation). In some embodiments, the solid form of MDMA succinate is MDMA succinate characterized by XRPD signals at 6.5° 2θ, 12.6° 2θ, 13.0° 2θ, 17.1° 2θ, and 18.9° 2θ (±0.2° 2θ; ±0.1° 2θ; or ±0.0° 2θ; Cu Kα1 radiation).

In some embodiments, the crystalline MDMA succinate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, or thirty XRPD signals selected from those set forth in Table 10.

TABLE 10

| XRPD Signals for MDMA succinate | | | |
|---|---|---|---|
| Signal no. | Position | d-value | Relative |
| 1 | 6.5 | 13.6 | 36.1 |
| 2 | 12.6 | 7.0 | 26.6 |
| 3 | 13.0 | 6.8 | 100.0 |
| 4 | 13.5 | 6.5 | 22.2 |
| 5 | 16.2 | 5.5 | 11.3 |
| 6 | 17.1 | 5.2 | 27.5 |
| 7 | 18.9 | 4.7 | 34.6 |
| 8 | 19.5 | 4.5 | 29.9 |
| 9 | 20.0 | 4.4 | 29.8 |
| 10 | 20.4 | 4.3 | 9.1 |
| 11 | 21.5 | 4.1 | 11.7 |
| 12 | 21.8 | 4.1 | 41.8 |
| 13 | 22.2 | 4.0 | 36.8 |
| 14 | 22.7 | 3.9 | 4.7 |
| 15 | 24.2 | 3.7 | 27.2 |
| 16 | 24.9 | 3.6 | 20.3 |
| 17 | 25.3 | 3.5 | 30.8 |
| 18 | 27.2 | 3.3 | 5.4 |
| 19 | 27.9 | 3.2 | 9.5 |
| 20 | 28.9 | 3.1 | 7.7 |
| 21 | 29.4 | 3.0 | 5.8 |
| 22 | 30.0 | 3.0 | 4.0 |
| 23 | 31.1 | 2.9 | 6.1 |
| 24 | 33.5 | 2.7 | 6.4 |
| 25 | 34.1 | 2.6 | 14.1 |
| 26 | 35.6 | 2.5 | 2.3 |
| 27 | 36.0 | 2.5 | 4.9 |
| 28 | 37.7 | 2.4 | 3.2 |
| 29 | 38.5 | 2.3 | 3.7 |
| 30 | 39.6 | 2.3 | 2.4 |

Solid Forms of MDMA Tosylate (Toluene Sulfonate)

Figure 9:
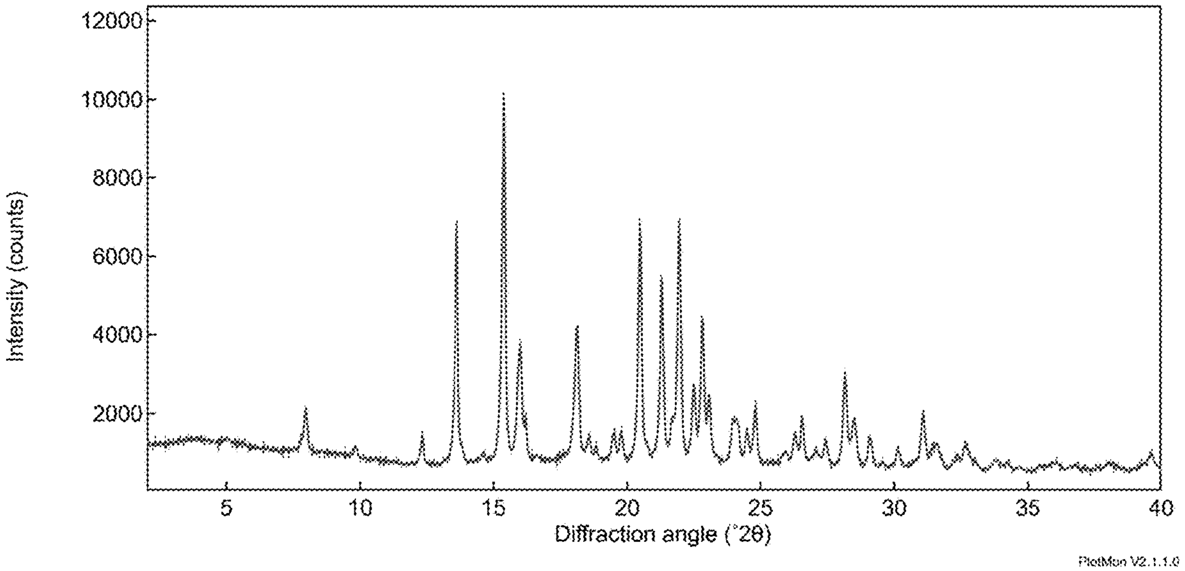
FIG. 9 provides an XRPD diffractogram of a sample comprising crystalline MDMA·toluenesulfonate (tosylate).
Figure 63:
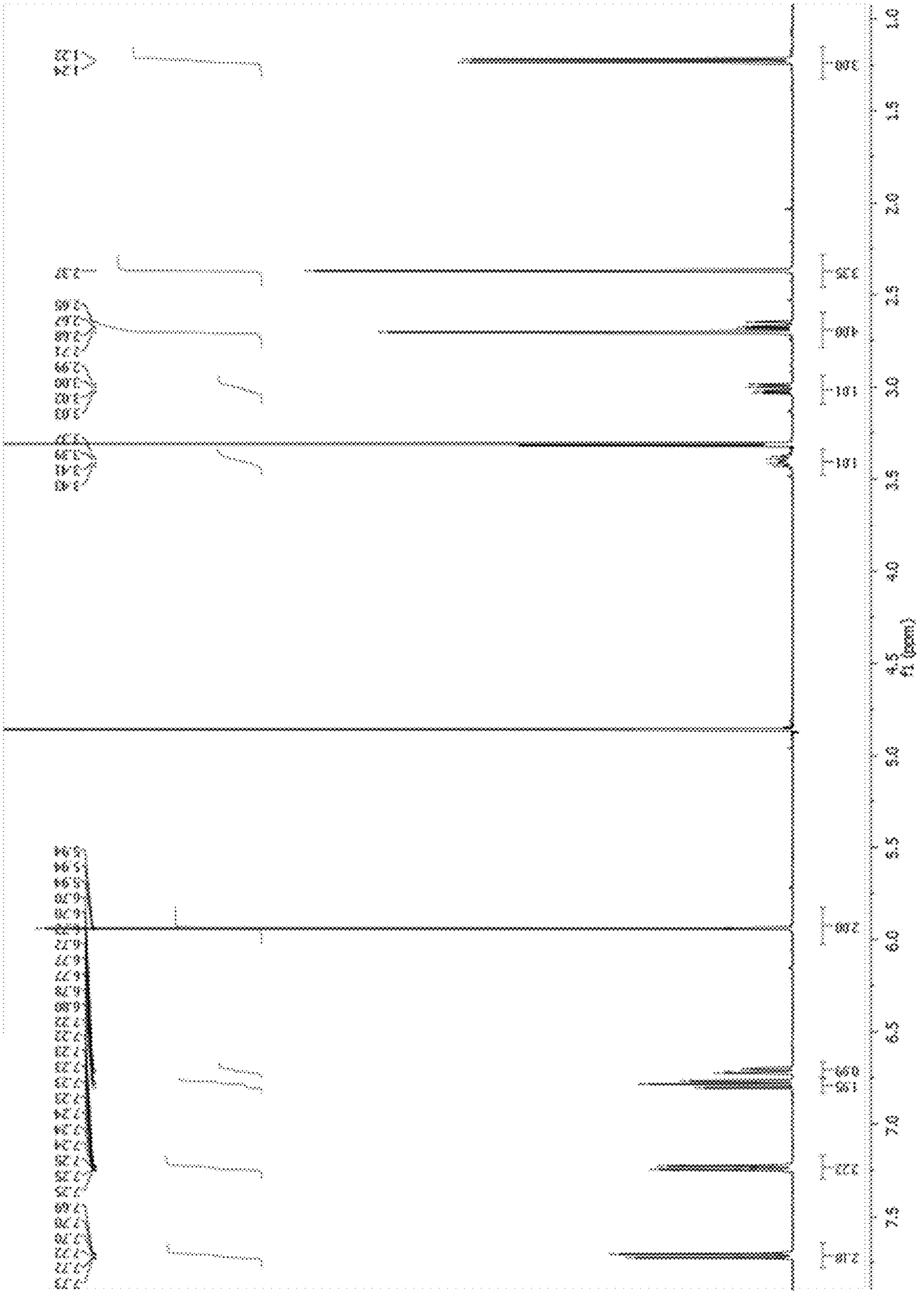
FIG. 63 provides a $^1$H NMR spectrum for MDMA tosylate (toluenesulfonate).
Figure 64:
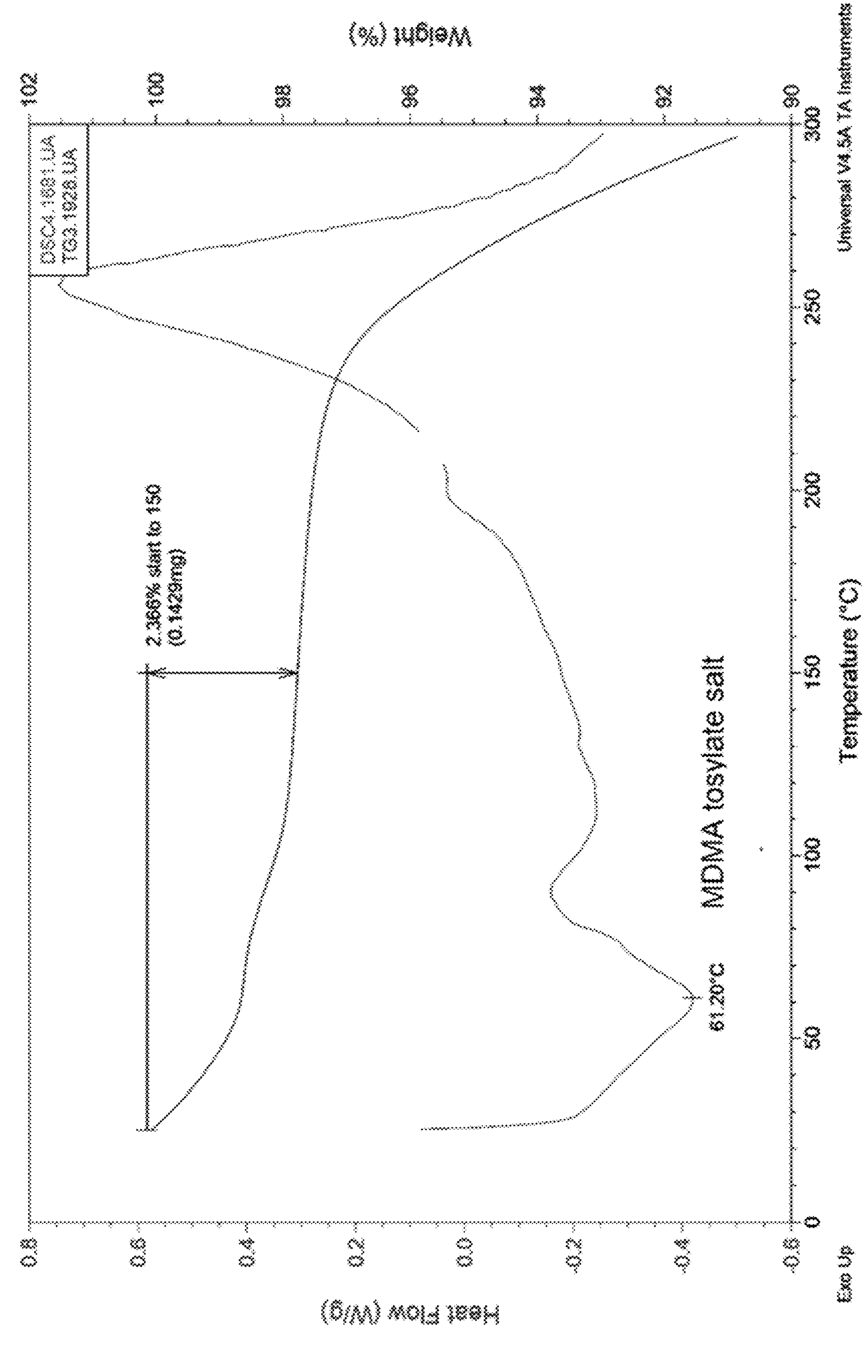
FIG. 64 provides TGA and DSC profiles for MDMA tosylate (toluenesulfonate).

In some embodiments, the present disclosure provides solid forms of MDMA tosylate, e.g., crystalline forms of MDMA tosylate. In some embodiments, the MDMA tosylate XRPD profile is substantially similar to that shown in FIG. 9. In some embodiments, the MDMA tosylate $^1H$ NMR spectrum is substantially similar to that shown in FIG. 63. In some embodiments, the MDMA tosylate TGA profile is substantially similar to that shown in FIG. 64. In some embodiments, the MDMA tosylate DSC profile is substantially similar to that shown in FIG. 64.

In some embodiments, the solid form of MDMA tosylate is crystalline MDMA tosylate characterized by two or more, or three or more XRPD signals selected from the group consisting of 15.4° 2θ, 20.5° 2θ, and 21.9° 2θ (±0.2° 2θ; ±0.1° 2θ; or ±0.0° 2θ; Cu Kα1 radiation). In some embodiments, the solid form of MDMA tosylate is crystalline MDMA tosylate characterized by XRPD signals at 15.4° 2θ, 20.5° 2θ, and 21.9° 2θ (±0.2° 2θ; ±0.1° 2θ; or ±0.0° 2θ; Cu Kα1 radiation).

In some embodiments, the solid form of MDMA tosylate is crystalline MDMA tosylate characterized by two or more, or three or more XRPD signals selected from the group consisting of 13.6° 2θ, 15.4° 2θ, 20.5° 2θ, 21.3° 2θ, and 21.9° 2θ (±0.2° 2θ; ±0.1° 2θ; or ±0.0° 2θ; Cu Kα1 radiation). In some embodiments, the solid form of MDMA tosylate is MDMA tosylate characterized by XRPD signals at 13.6° 2θ, 15.4° 2θ, 20.5° 2θ, 21.3° 2θ, and 21.9° 2θ (±0.2° 2θ; ±0.1° 2θ; or ±0.0° 2θ; Cu Kα1 radiation).

In some embodiments, the solid form of MDMA tosylate is crystalline MDMA tosylate characterized by two or more, or three or more XRPD signals selected from the group consisting of 8.0° 2θ, 12.3° 2θ, and 13.6° 2θ (±0.2° 2θ; ±0.1° 2θ; or ±0.0° 2θ; Cu Kα1 radiation). In some embodiments, the solid form of MDMA tosylate is crystalline MDMA tosylate characterized by XRPD signals at 8.0° 2θ, 12.3° 2θ, and 13.6° 2θ (±0.2° 2θ; ±0.1° 2θ; or ±0.0° 2θ; Cu Kα1 radiation).

In some embodiments, the solid form of MDMA tosylate is crystalline MDMA tosylate characterized by two or more, or three or more XRPD signals selected from the group consisting of 8.0° 2θ, 12.3° 2θ, 13.6° 2θ, 15.4° 2θ, and 20.5° 2θ (±0.2° 2θ; ±0.1° 2θ; or ±0.0° 2θ; Cu Kα1 radiation). In some embodiments, the solid form of MDMA tosylate is MDMA tosylate characterized by XRPD signals at 8.0° 2θ, 12.3° 2θ, 13.6° 2θ, 15.4° 2θ, and 20.5° 2θ (±0.2° 2θ; ±0.1° 2θ; or ±0.0° 2θ; Cu Kα1 radiation).

In some embodiments, the crystalline MDMA tosylate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, or forty-seven XRPD signals selected from those set forth in Table 11.

TABLE 11

XRPD Signals for MDMA tosylate

| Signal no. | Position | d-value | Relative |
|---|---|---|---|
| 1 | 8.0 | 11.1 | 21.2 |
| 2 | 9.8 | 9.0 | 11.6 |
| 3 | 12.3 | 7.2 | 14.5 |
| 4 | 13.6 | 6.5 | 67.1 |
| 5 | 14.7 | 6.0 | 9.9 |
| 6 | 15.4 | 5.8 | 100.0 |
| 7 | 16.0 | 5.5 | 37.1 |
| 8 | 16.2 | 5.5 | 19.1 |
| 9 | 18.1 | 4.9 | 42.1 |
| 10 | 18.6 | 4.8 | 14.4 |
| 11 | 18.8 | 4.7 | 12.0 |
| 12 | 19.5 | 4.5 | 15.3 |
| 13 | 19.8 | 4.5 | 15.3 |
| 14 | 20.5 | 4.3 | 68.1 |
| 15 | 21.3 | 4.2 | 54.0 |
| 16 | 21.7 | 4.1 | 19.0 |
| 17 | 21.9 | 4.1 | 67.2 |
| 18 | 22.5 | 4.0 | 27.3 |
| 19 | 22.8 | 3.9 | 43.8 |
| 20 | 23.1 | 3.9 | 24.8 |
| 21 | 24.0 | 3.7 | 18.8 |
| 22 | 24.5 | 3.6 | 15.8 |
| 23 | 24.8 | 3.6 | 21.6 |
| 24 | 25.9 | 3.4 | 10.5 |
| 25 | 26.3 | 3.4 | 14.6 |
| 26 | 26.6 | 3.4 | 19.3 |
| 27 | 27.1 | 3.3 | 10.8 |
| 28 | 27.4 | 3.3 | 13.1 |
| 29 | 28.2 | 3.2 | 29.9 |
| 30 | 28.5 | 3.1 | 18.9 |
| 31 | 29.1 | 3.1 | 14.1 |
| 32 | 29.6 | 3.0 | 7.9 |
| 33 | 30.1 | 3.0 | 11.1 |
| 34 | 31.1 | 2.9 | 20.0 |
| 35 | 31.6 | 2.8 | 12.5 |
| 36 | 32.4 | 2.8 | 9.3 |
| 37 | 32.6 | 2.7 | 12.4 |
| 38 | 33.0 | 2.7 | 8.3 |
| 39 | 33.8 | 2.7 | 8.3 |
| 40 | 34.3 | 2.6 | 7.6 |
| 41 | 34.7 | 2.6 | 6.4 |
| 42 | 35.5 | 2.5 | 6.8 |
| 43 | 36.1 | 2.5 | 7.9 |
| 44 | 36.7 | 2.4 | 6.9 |
| 45 | 37.6 | 2.4 | 6.5 |

TABLE 11-continued

XRPD Signals for MDMA tosylate

| Signal no. | Position | d-value | Relative |
|---|---|---|---|
| 46 | 38.1 | 2.4 | 7.3 |
| 47 | 39.6 | 2.3 | 9.8 |

Solid Forms of MDMA Fumarate Form 2

Figure 10:
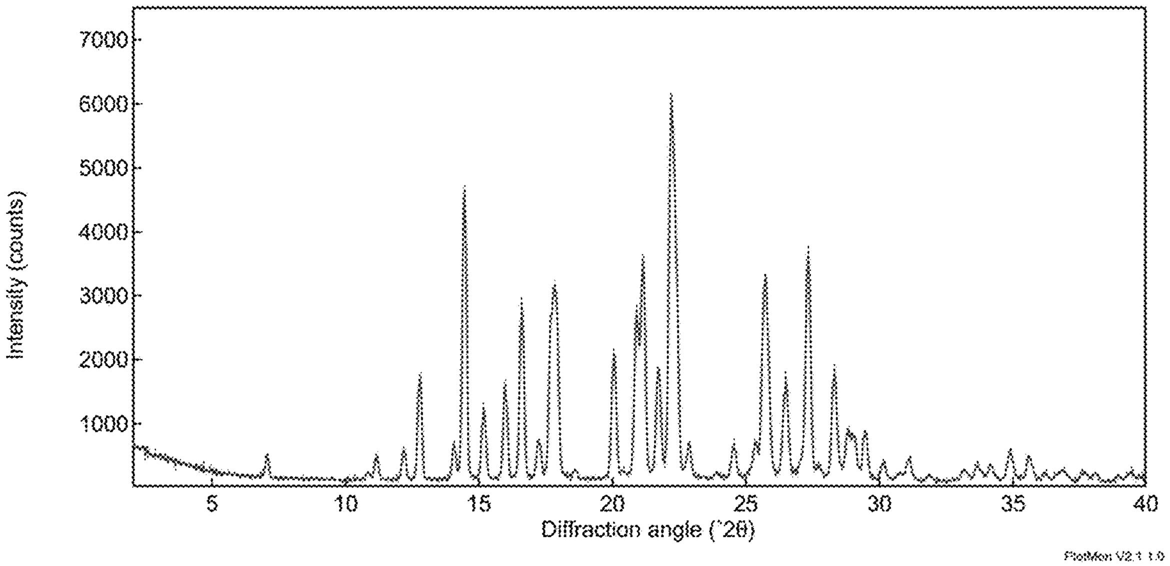
FIG. 10 provides an XRPD diffractogram of a sample comprising crystalline MDMA·fumarate Form 2.

In some embodiments, the present disclosure provides solid forms of MDMA fumarate Form 2, e.g., crystalline forms of MDMA fumarate Form 2. In some embodiments, a mixture of MDMA fumarate Forms 1 and 2 has an XRPD profile substantially similar to that shown in FIG. 10.

In some embodiments, the solid form of MDMA fumarate Form 2 is crystalline MDMA fumarate Form 2 characterized by two or more, or three or more XRPD signals selected from the group consisting of 14.5° 2θ, 22.2° 2θ, and 27.3° 2θ (±0.2° 2θ; ±0.1° 2θ; or ±0.0° 2θ; Cu Kα1 radiation). In some embodiments, the solid form of MDMA fumarate Form 2 is crystalline MDMA fumarate Form 2 characterized by XRPD signals at 14.5° 2θ, 22.2° 2θ, and 27.3° 2θ (±0.2° 2θ; ±0.1° 2θ; or ±0.0° 2θ; Cu Kα1 radiation).

In some embodiments, the solid form of MDMA fumarate Form 2 is crystalline MDMA fumarate Form 2 characterized by two or more, or three or more XRPD signals selected from the group consisting of 14.5° 2θ, 17.8° 2θ, 22.2° 2θ, 25.7° 2θ, and 27.3° 2θ (±0.2° 2θ; ±0.1° 2θ; or ±0.0° 2θ; Cu Kα1 radiation). In some embodiments, the solid form of MDMA fumarate Form 2 is MDMA fumarate Form 2 characterized by XRPD signals at 14.5° 2θ, 17.8° 2θ, 22.2° 2θ, 25.7° 2θ, and 27.3° 2θ (±0.2° 2θ; ±0.1° 2θ; or ±0.0° 2θ; Cu Kα1 radiation).

In some embodiments, the solid form of MDMA fumarate Form 2 is crystalline MDMA fumarate Form 2 characterized by two or more, or three or more XRPD signals selected from the group consisting of 12.2° 2θ, 12.8° 2θ, and 14.5° 2θ (±0.2° 2θ; ±0.1° 2θ; or ±0.0° 2θ; Cu Kα1 radiation). In some embodiments, the solid form of MDMA fumarate Form 2 is crystalline MDMA fumarate Form 2 characterized by XRPD signals at 12.2° 2θ, 12.8° 2θ, and 14.5° 2θ (±0.2° 2θ; ±0.1° 2θ; or ±0.0° 2θ; Cu Kα1 radiation).

In some embodiments, the solid form of MDMA fumarate Form 2 is crystalline MDMA fumarate Form 2 characterized by two or more, or three or more XRPD signals selected from the group consisting of 12.2° 2θ, 12.8° 2θ, 14.5° 2θ, 16.0° 2θ, and 16.6° 2θ (±0.2° 2θ; ±0.1° 2θ; or ±0.0° 2θ; Cu Kα1 radiation). In some embodiments, the solid form of MDMA fumarate Form 2 is MDMA fumarate Form 2 characterized by XRPD signals at 12.2° 2θ, 12.8° 2θ, 14.5° 2θ, 16.0° 2θ, and 16.6° 2θ (±0.2° 2θ; ±0.1° 2θ; or ±0.0° 2θ; Cu Kα1 radiation).

In some embodiments, the crystalline MDMA fumarate Form 2 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, or thirty-five XRPD signals selected from those set forth in Table 12.

TABLE 12

| XRPD Signals for MDMA fumarate Form 2 | | | |
|---|---|---|---|
| Signal no. | Position | d-value | Relative |
| 1 | 7.1 | 12.5 | 8.7 |
| 2 | 10.8 | 8.2 | 4.1 |
| 3 | 11.2 | 7.9 | 8.2 |
| 4 | 12.2 | 7.3 | 10.2 |
| 5 | 12.8 | 6.9 | 28.2 |
| 6 | 14.1 | 6.3 | 11.6 |
| 7 | 14.5 | 6.1 | 76.0 |
| 8 | 15.2 | 5.8 | 20.6 |
| 9 | 16.0 | 5.5 | 26.3 |
| 10 | 16.6 | 5.3 | 47.2 |
| 11 | 17.2 | 5.1 | 12.3 |
| 12 | 17.8 | 5.0 | 52.1 |
| 13 | 20.0 | 4.4 | 34.1 |
| 14 | 20.4 | 4.3 | 4.9 |
| 15 | 20.9 | 4.3 | 45.7 |
| 16 | 21.7 | 4.1 | 31.0 |
| 17 | 22.2 | 4.0 | 100.0 |
| 18 | 23.9 | 3.7 | 4.1 |
| 19 | 25.3 | 3.5 | 12.1 |
| 20 | 25.7 | 3.5 | 54.7 |
| 21 | 26.5 | 3.4 | 28.0 |
| 22 | 27.3 | 3.3 | 60.7 |
| 23 | 28.3 | 3.2 | 30.0 |
| 24 | 30.2 | 3.0 | 6.9 |
| 25 | 30.7 | 2.9 | 4.1 |
| 26 | 31.1 | 2.9 | 7.6 |
| 27 | 33.1 | 2.7 | 4.8 |
| 28 | 33.7 | 2.7 | 6.3 |
| 29 | 34.9 | 2.6 | 9.9 |
| 30 | 36.3 | 2.5 | 4.2 |
| 31 | 36.9 | 2.4 | 4.8 |
| 32 | 37.6 | 2.4 | 4.4 |
| 33 | 38.1 | 2.4 | 3.7 |
| 34 | 39.0 | 2.3 | 3.1 |
| 35 | 39.5 | 2.3 | 4.4 |

Solid Forms of MDMA Maleate Form 2

Figure 53:
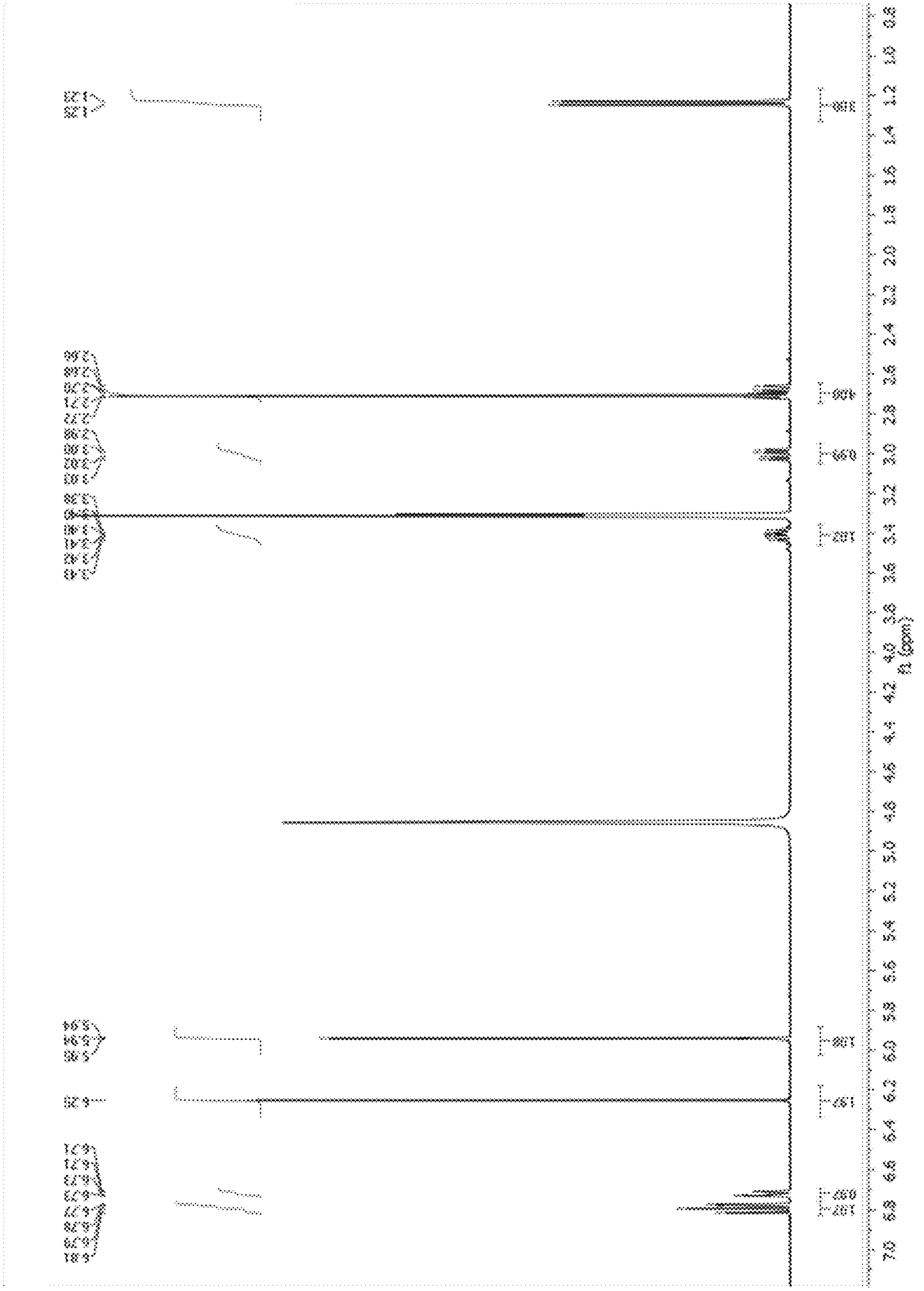
FIG. 53 provides a $^1$H NMR spectrum for MDMA maleate Form 2.
Figure 54:
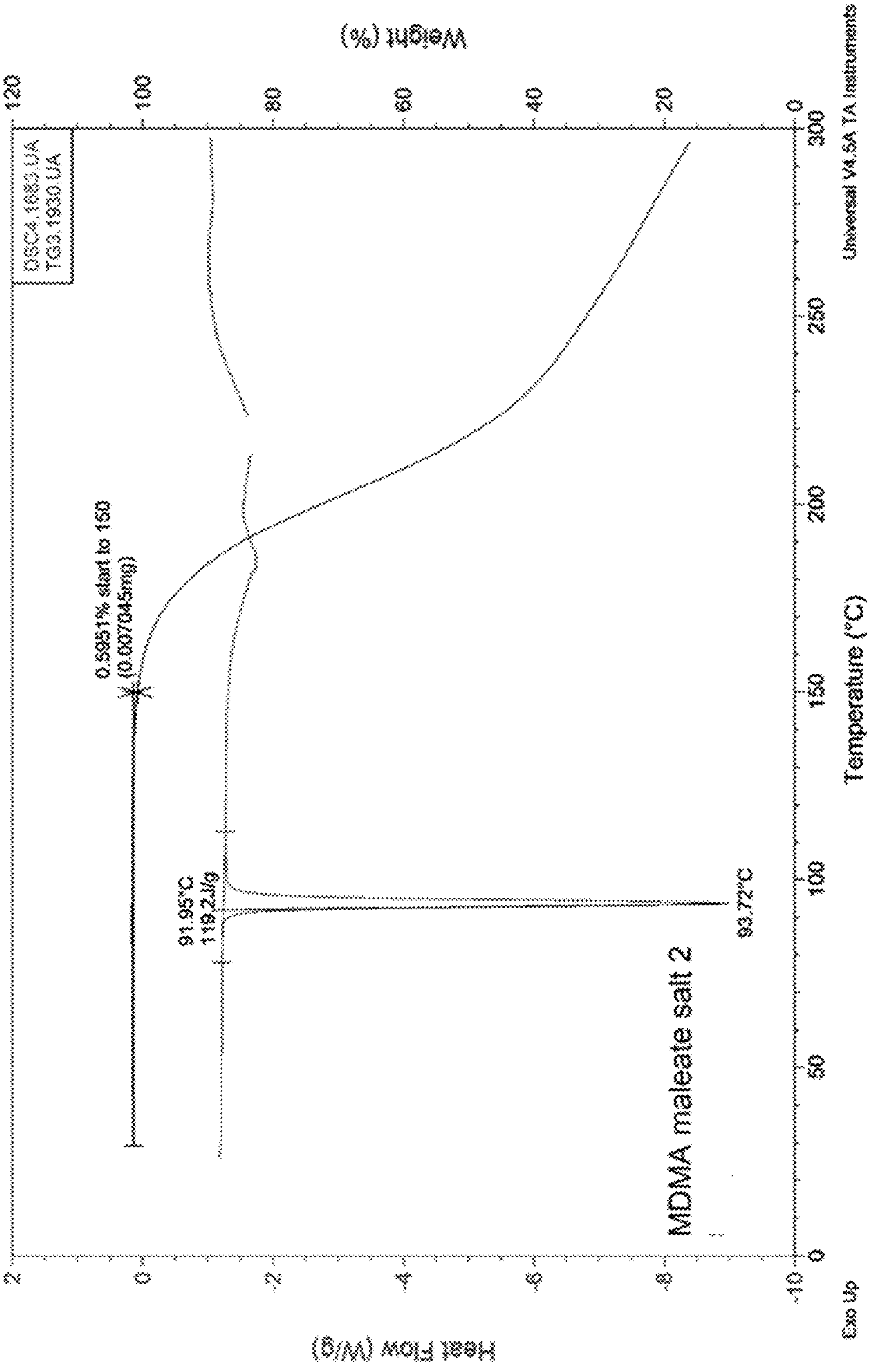
FIG. 54 provides TGA and DSC profiles for MDMA maleate Form 2.

In some embodiments, the present disclosure provides solid forms of MDMA maleate Form 2, e.g., crystalline forms of MDMA maleate Form 2. In some embodiments, the MDMA maleate Form 2 XRPD profile is substantially similar to that shown in FIG. 11. In some embodiments, the MDMA maleate Form 2 $^1$H NMR spectrum is substantially similar to that shown in FIG. 53. In some embodiments, the MDMA maleate Form 2 TGA profile is substantially similar to that shown in FIG. 54. In some embodiments, the MDMA maleate Form 2 DSC profile is substantially similar to that shown in FIG. 54.

In some embodiments, the solid form of MDMA maleate Form 2 is crystalline MDMA maleate Form 2 characterized by two or more, or three or more XRPD signals selected from the group consisting of 9.4° 2θ, 18.5° 2θ, and 26.8° 2θ (±0.2° 2θ; ±0.1° 2θ; or ±0.0° 2θ; Cu Kα1 radiation). In some embodiments, the solid form of MDMA maleate Form 2 is crystalline MDMA maleate Form 2 characterized by XRPD signals at 9.4° 2θ, 18.5° 2θ, and 26.8° 2θ (±0.2° 2θ; ±0.1° 2θ; or ±0.0° 2θ; Cu Kα1 radiation).

In some embodiments, the solid form of MDMA maleate Form 2 is crystalline MDMA maleate Form 2 characterized by two or more, or three or more XRPD signals selected from the group consisting of 9.4° 2θ, 15.6° 2θ, 15.9° 2θ, 18.5° 2θ, and 26.8° 2θ (±0.2° 2θ; ±0.1° 2θ; or ±0.0° 2θ; Cu Kα1 radiation). In some embodiments, the solid form of MDMA maleate Form 2 is MDMA maleate Form 2 characterized by XRPD signals at 9.4° 2θ, 15.6° 2θ, 15.9° 2θ, 18.5° 2θ, and 26.8° 2θ (±0.2° 2θ; ±0.1° 2θ; or ±0.0° 2θ; Cu Kα1 radiation).

In some embodiments, the solid form of MDMA maleate Form 2 is crystalline MDMA maleate Form 2 characterized by two or more, or three or more XRPD signals selected from the group consisting of 9.4° 2θ, 13.8° 2θ, and 14.8° 2θ (±0.2° 2θ; ±0.1° 2θ; or ±0.0° 2θ; Cu Kα1 radiation). In some embodiments, the solid form of MDMA maleate Form 2 is crystalline MDMA maleate Form 2 characterized by XRPD signals at 9.4° 2θ, 13.8° 2θ, and 14.8° 2θ (±0.2° 2θ; ±0.1° 2θ; or ±0.0° 2θ; Cu Kα1 radiation).

In some embodiments, the solid form of MDMA maleate Form 2 is crystalline MDMA maleate Form 2 characterized by two or more, or three or more XRPD signals selected from the group consisting of 9.4° 2θ, 13.8° 2θ, 14.8° 2θ, 18.5° 2θ, and 26.8° 2θ (±0.2° 2θ; ±0.1° 2θ; or ±0.0° 2θ; Cu Kα1 radiation). In some embodiments, the solid form of MDMA maleate Form 2 is MDMA maleate Form 2 characterized by XRPD signals at 9.4° 2θ, 13.8° 2θ, 14.8° 2θ, 18.5° 2θ, and 26.8° 2θ (±0.2° 2θ; ±0.1° 2θ; or ±0.0° 2θ; Cu Kα1 radiation).

In some embodiments, the crystalline MDMA maleate Form 2 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, or forty-one XRPD signals selected from those set forth in Table 13.

TABLE 13

| XRPD Signals for MDMA maleate Form 2 | | | |
|---|---|---|---|
| Signal no. | Position | d-value | Relative |
| 1 | 2.7 | 33.2 | 10.0 |
| 2 | 3.2 | 27.4 | 7.0 |
| 3 | 9.4 | 9.4 | 100.0 |
| 4 | 11.1 | 7.9 | 5.5 |
| 5 | 12.5 | 7.1 | 2.6 |
| 6 | 13.8 | 6.4 | 8.9 |
| 7 | 14.8 | 6.0 | 8.7 |
| 8 | 15.6 | 5.7 | 11.4 |
| 9 | 15.9 | 5.6 | 18.4 |
| 10 | 16.5 | 5.4 | 2.4 |
| 11 | 17.6 | 5.0 | 6.9 |
| 12 | 18.5 | 4.8 | 22.8 |
| 13 | 18.9 | 4.7 | 1.8 |
| 14 | 19.5 | 4.5 | 6.8 |
| 15 | 19.9 | 4.5 | 6.2 |
| 16 | 20.9 | 4.2 | 1.9 |
| 17 | 21.3 | 4.2 | 4.6 |
| 18 | 22.7 | 3.9 | 2.4 |
| 19 | 24.1 | 3.7 | 1.6 |
| 20 | 24.8 | 3.6 | 9.6 |
| 21 | 25.1 | 3.5 | 3.9 |
| 22 | 25.5 | 3.5 | 10.8 |
| 23 | 25.8 | 3.5 | 5.1 |
| 24 | 26.8 | 3.3 | 62.3 |
| 25 | 28.0 | 3.2 | 2.8 |
| 26 | 28.6 | 3.1 | 6.5 |
| 27 | 29.2 | 3.1 | 10.2 |
| 28 | 29.8 | 3.0 | 2.2 |
| 29 | 30.3 | 3.0 | 4.3 |
| 30 | 30.7 | 2.9 | 1.7 |
| 31 | 31.2 | 2.9 | 3.6 |
| 32 | 32.9 | 2.7 | 2.7 |
| 33 | 33.4 | 2.7 | 4.3 |
| 34 | 33.8 | 2.7 | 1.5 |
| 35 | 34.4 | 2.6 | 1.6 |
| 36 | 35.2 | 2.6 | 1.8 |
| 37 | 35.7 | 2.5 | 2.0 |

TABLE 13-continued

| XRPD Signals for MDMA maleate Form 2 | | | |
|---|---|---|---|
| Signal no. | Position | d-value | Relative |
| 38 | 37.1 | 2.4 | 1.9 |
| 39 | 37.9 | 2.4 | 2.0 |
| 40 | 38.9 | 2.3 | 1.5 |
| 41 | 39.4 | 2.3 | 1.6 |

Solid Forms of MDMA Tartrate Form 2

Figure 12:
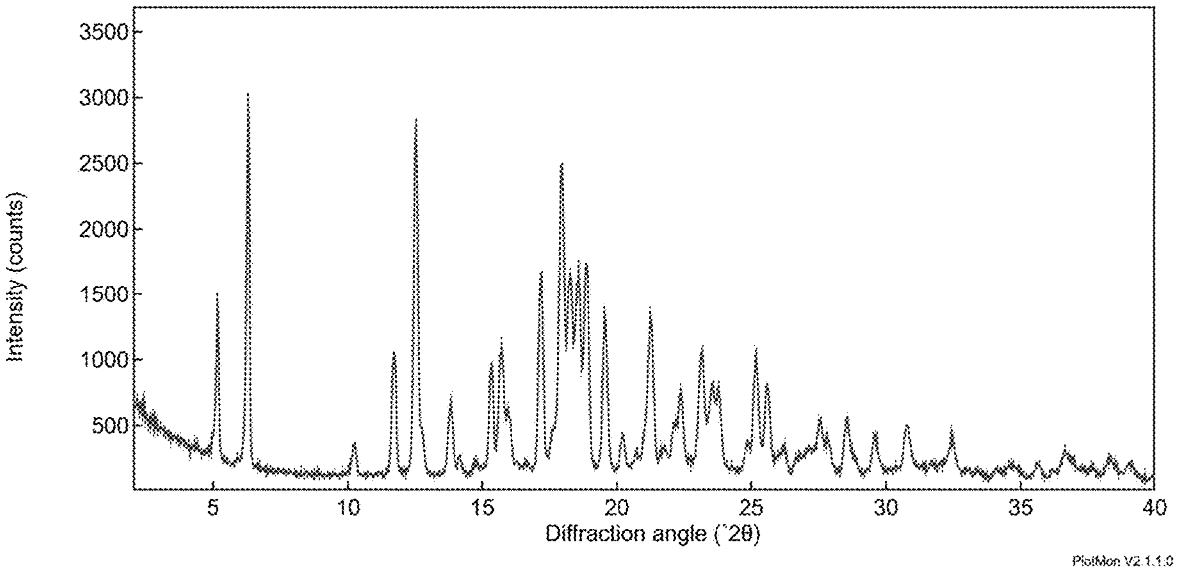
FIG. 12 provides an XRPD diffractogram of a sample comprising a mixture of crystalline MDMA·tartrate Form 1 and Form 2.

In some embodiments, the present disclosure provides solid forms of MDMA tartrate Form 2, e.g., crystalline forms of MDMA tartrate Form 2. In some embodiments, a mixture of MDMA tartrate Forms 1 and 2 has an XRPD profile substantially similar to that shown in FIG. 12.

In some embodiments, the solid form of MDMA tartrate Form 2 is crystalline MDMA tartrate Form 2 characterized by two or more, or three or more XRPD signals selected from the group consisting of 5.2° 2θ, 18.9° 2θ, and 19.5° 2θ (±0.2° 2θ; ±0.1° 2θ; or ±0.0° 2θ; Cu Kα1 radiation). In some embodiments, the solid form of MDMA tartrate Form 2 is crystalline MDMA tartrate Form 2 characterized by XRPD signals at 5.2° 2θ, 18.9° 2θ, and 19.5° 2θ (±0.2° 2θ; ±0.1° 2θ; or ±0.0° 2θ; Cu Kα1 radiation).

In some embodiments, the solid form of MDMA tartrate Form 2 is crystalline MDMA tartrate Form 2 characterized by two or more, or three or more XRPD signals selected from the group consisting of 5.2° 2θ, 11.7° 2θ, 15.4° 2θ, 18.9° 2θ, and 19.5° 2θ (±0.2° 2θ; ±0.1° 2θ; or ±0.0° 2θ; Cu Kα1 radiation). In some embodiments, the solid form of MDMA tartrate Form 2 is MDMA tartrate Form 2 characterized by XRPD signals at 5.2° 2θ, 11.7° 2θ, 15.4° 2θ, 18.9° 2θ, and 19.5° 2θ (±0.2° 2θ; ±0.1° 2θ; or ±0.0° 2θ; Cu Kα1 radiation).

In some embodiments, the solid form of MDMA tartrate Form 2 is crystalline MDMA tartrate Form 2 characterized by two or more, or three or more XRPD signals selected from the group consisting of 5.2° 2θ, 10.3° 2θ, and 11.7° 2θ (±0.2° 2θ; ±0.1° 2θ; or ±0.0° 2θ; Cu Kα1 radiation). In some embodiments, the solid form of MDMA tartrate Form 2 is crystalline MDMA tartrate Form 2 characterized by XRPD signals at 5.2° 2θ, 10.3° 2θ, and 11.7° 2θ (±0.2° 2θ; ±0.1° 2θ; or ±0.0° 2θ; Cu Kα1 radiation).

In some embodiments, the solid form of MDMA tartrate Form 2 is crystalline MDMA tartrate Form 2 characterized by two or more, or three or more XRPD signals selected from the group consisting of 5.2° 2θ, 10.3° 2θ, 11.7° 2θ, 15.4° 2θ, and 19.5° 2θ (±0.2° 2θ; ±0.1° 2θ; or ±0.0° 2θ; Cu Kα1 radiation). In some embodiments, the solid form of MDMA tartrate Form 2 is MDMA tartrate Form 2 characterized by XRPD signals at 5.2° 2θ, 10.3° 2θ, 11.7° 2θ, 15.4° 2θ, and 19.5° 2θ (±0.2° 2θ; ±0.1° 2θ; or ±0.0° 2θ; Cu Kα1 radiation).

In some embodiments, the crystalline MDMA tartrate Form 2 is characterized by one, two, three, four, five, six, seven, eight, nine, ten, or eleven XRPD signals selected from those set forth in Table 14.

TABLE 14

| XRPD Signals for MDMA tartrate Form 2 | | | |
|---|---|---|---|
| Signal no. | Position | d-value | Relative |
| 1 | 5.2 | 17.1 | 83.9 |
| 2 | 10.3 | 8.6 | 20.9 |
| 3 | 11.7 | 7.6 | 61.2 |
| 4 | 14.7 | 6.0 | 14.0 |
| 5 | 15.4 | 5.8 | 55.7 |
| 6 | 16.6 | 5.3 | 13.7 |
| 7 | 18.9 | 4.7 | 100.0 |
| 8 | 19.5 | 4.5 | 78.3 |
| 9 | 20.2 | 4.4 | 25.4 |
| 10 | 20.7 | 4.3 | 17.9 |
| 11 | 24.9 | 3.6 | 22.2 |

Solid Forms of MDMA HCl

Figure 48:
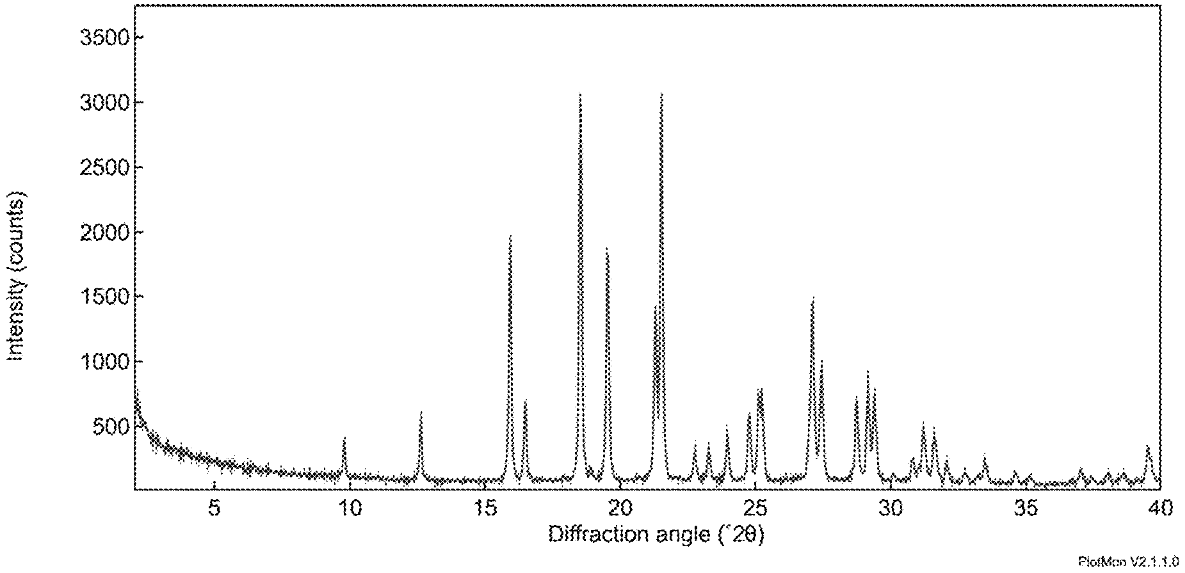
FIG. 48 provides an XRPD diffractogram of crystalline MDMA. HCl.
Figure 95:
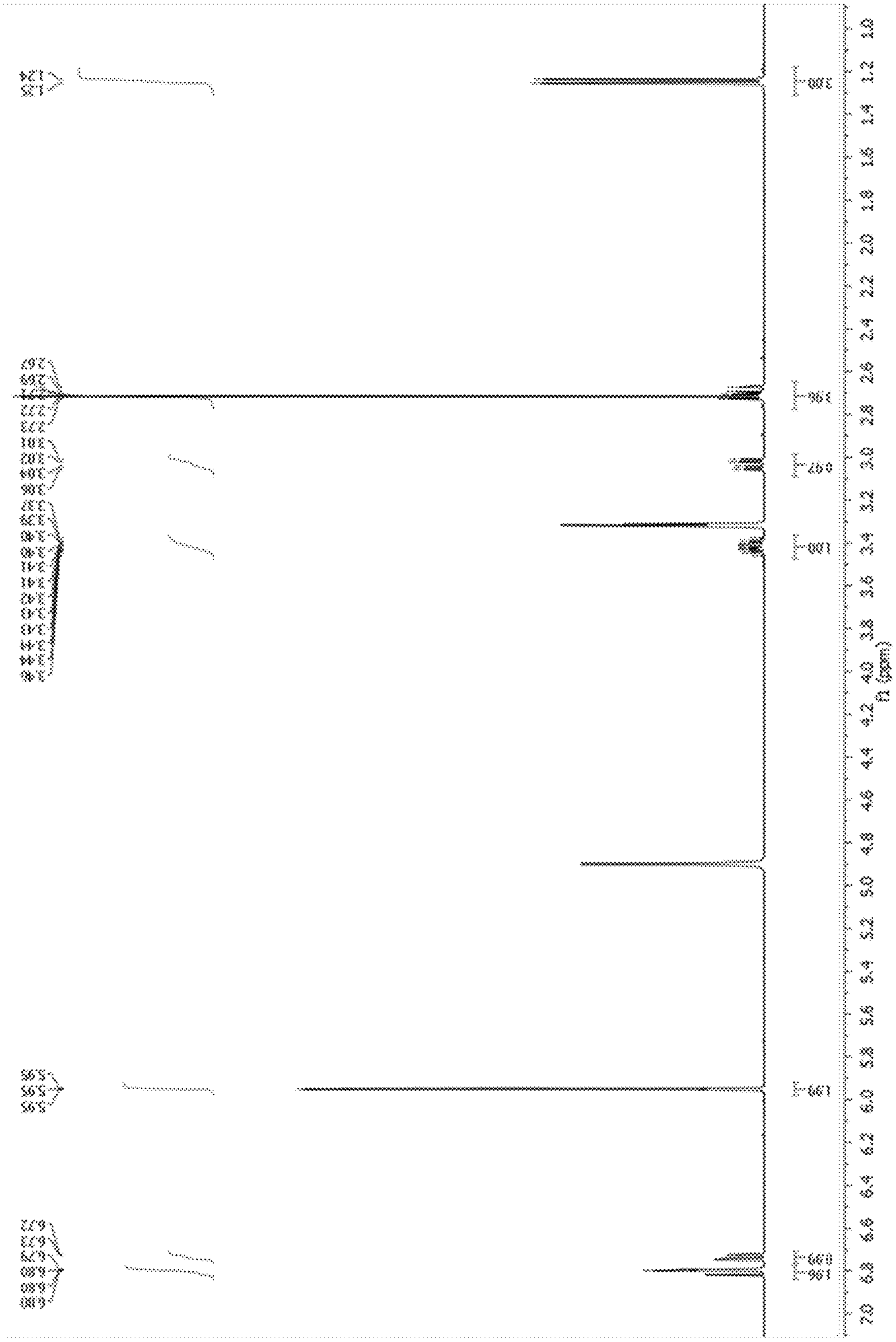
FIG. 95 provides a $^1$H NMR spectrum for MDMA HCl.

In some embodiments, the present disclosure provides solid forms of MDMA HCl, e.g., crystalline forms of MDMA HCl. In some embodiments, the MDMA HCl XRPD profile is substantially similar to that shown in FIG. 48. In some embodiments, the MDMA HCl $^1$H NMR spectrum is substantially similar to that shown in FIG. 95.

In some embodiments, the solid form of MDMA HCl is crystalline MDMA HCl characterized by two or more, or three or more XRPD signals selected from the group consisting of 15.9° 2θ, 18.5° 2θ, and 21.5° 2θ (±0.2° 2θ; ±0.1° 2θ; or ±0.0° 2θ; Cu Kα1 radiation). In some embodiments, the solid form of MDMA HCl is crystalline MDMA HCl characterized by XRPD signals at 15.9° 2θ, 18.5° 2θ, and 21.5° 2θ (±0.2° 2θ; ±0.1° 2θ; or ±0.0° 2θ; Cu Kα1 radiation).

In some embodiments, the solid form of MDMA HCl is crystalline MDMA HCl characterized by two or more, or three or more XRPD signals selected from the group consisting of 15.9° 2θ, 18.5° 2θ, 19.5° 2θ, 21.5° 2θ, and 27.1° 2θ (±0.2° 2θ; ±0.1° 2θ; or ±0.0° 2θ; Cu Kα1 radiation). In some embodiments, the solid form of MDMA HCl is MDMA HCl characterized by XRPD signals at 15.9° 2θ, 18.5° 2θ, 19.5° 2θ, 21.5° 2θ, and 27.1° 2θ (±0.2° 2θ; ±0.1° 2θ; or ±0.0° 2θ; Cu Kα1 radiation).

In some embodiments, the solid form of MDMA HCl is crystalline MDMA HCl characterized by two or more, or three or more XRPD signals selected from the group consisting of 9.8° 2θ, 12.6° 2θ, and 15.9° 2θ (±0.2° 2θ; ±0.1° 2θ; or ±0.0° 2θ; Cu Kα1 radiation). In some embodiments, the solid form of MDMA HCl is crystalline MDMA HCl characterized by XRPD signals at 9.8° 2θ, 12.6° 2θ, and 15.9° 2θ (±0.2° 2θ; ±0.1° 2θ; or ±0.0° 2θ; Cu Kα1 radiation).

In some embodiments, the solid form of MDMA HCl is crystalline MDMA HCl characterized by two or more, or three or more XRPD signals selected from the group consisting of 9.8° 2θ, 12.6° 2θ, 15.9° 2θ, 18.5° 2θ, and 19.5° 2θ (±0.2° 2θ; ±0.1° 2θ; or ±0.0° 2θ; Cu Kα1 radiation). In some embodiments, the solid form of MDMA HCl is MDMA HCl characterized by XRPD signals at 9.8° 2θ, 12.6° 2θ, 15.9° 2θ, 18.5° 2θ, and 19.5° 2θ (±0.2° 2θ; ±0.1° 2θ; or ±0.0° 2θ; Cu Kα1 radiation).

In some embodiments, the crystalline MDMA HCl is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, or thirty-six XRPD signals selected from those set forth in Table 15.

TABLE 15

| XRPD Signals for MDMA HCl | | | |
|---|---|---|---|
| Signal no. | Position | d-value | Relative |
| 1 | 9.8 | 9.0 | 13.1 |
| 2 | 12.6 | 7.0 | 18.3 |
| 3 | 15.9 | 5.6 | 63.4 |
| 4 | 16.5 | 5.4 | 22.6 |
| 5 | 18.5 | 4.8 | 100.0 |
| 6 | 18.9 | 4.7 | 6.5 |
| 7 | 19.5 | 4.5 | 60.6 |
| 8 | 21.3 | 4.2 | 46.5 |
| 9 | 21.5 | 4.1 | 99.8 |
| 10 | 22.8 | 3.9 | 10.6 |
| 11 | 23.3 | 3.8 | 11.5 |
| 12 | 23.9 | 3.7 | 14.9 |
| 13 | 24.8 | 3.6 | 19.8 |
| 14 | 25.1 | 3.5 | 24.0 |
| 15 | 25.2 | 3.5 | 24.2 |
| 16 | 27.1 | 3.3 | 48.0 |
| 17 | 27.5 | 3.2 | 32.2 |
| 18 | 28.7 | 3.1 | 23.4 |
| 19 | 29.2 | 3.1 | 28.5 |
| 20 | 29.4 | 3.0 | 24.5 |
| 21 | 30.1 | 3.0 | 4.6 |
| 22 | 30.8 | 2.9 | 8.3 |
| 23 | 31.2 | 2.9 | 16.3 |
| 24 | 31.6 | 2.8 | 14.9 |
| 25 | 32.1 | 2.8 | 7.5 |
| 26 | 32.7 | 2.7 | 5.4 |
| 27 | 33.3 | 2.7 | 4.3 |
| 28 | 33.5 | 2.7 | 8.1 |
| 29 | 34.6 | 2.6 | 5.2 |
| 30 | 35.2 | 2.6 | 4.2 |
| 31 | 37.0 | 2.4 | 6.0 |
| 32 | 37.4 | 2.4 | 3.9 |
| 33 | 38.0 | 2.4 | 4.9 |
| 34 | 38.6 | 2.3 | 4.8 |
| 35 | 39.1 | 2.3 | 3.5 |
| 36 | 39.5 | 2.3 | 11.2 |

Solid Forms of MDE HCl

Figure 108:
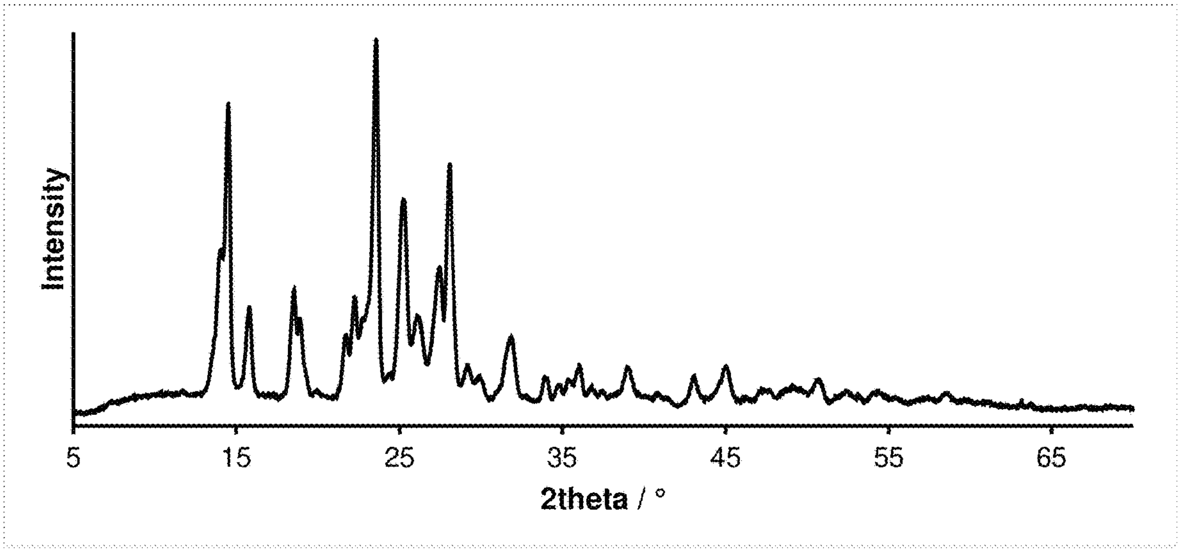
FIG. 108 provides an XRPD diffractogram of crystalline MDE HCl.

In some embodiments, the present disclosure provides solid forms of MDE HCl, e.g., crystalline forms of MDE HCl. In some embodiments, the MDE HCl XRPD profile is substantially similar to that shown in FIG. 17 or 108.

In some embodiments, the solid form of MDE HCl is crystalline MDE HCl characterized by XRPD signals at 15.6° 2θ and 21.6° 2θ (±0.2° 2θ; ±0.1° 2θ; or ±0.0° 2θ; Cu Kα1 radiation).

In some embodiments, the solid form of MDE HCl is crystalline MDE HCl characterized by two or more, or three or more XRPD signals selected from the group consisting of 15.6° 2θ, 21.6° 2θ, 22.1° 2θ, and 23.5° 2θ (±0.2° 2θ; ±0.1° 2θ; or ±0.0° 2θ; Cu Kα1 radiation). In some embodiments, the solid form of MDE HCl is MDE HCl characterized by XRPD signals at 15.6° 2θ, 21.6° 2θ, 22.1° 2θ, and 23.5° 2θ (±0.2° 2θ; ±0.1° 2θ; or ±0.0° 2θ; Cu Kα1 radiation).

In some embodiments, the solid form of MDE HCl is crystalline MDE HCl characterized by two or more, or three or more XRPD signals selected from the group consisting of 14.0° 2θ, 14.4° 2θ, and 23.5° 2θ (±0.2° 2θ; ±0.1° 2θ; or ±0.0° 2θ; Cu Kα1 radiation). In some embodiments, the solid form of MDE HCl is crystalline MDE HCl characterized by XRPD signals at 14.0° 2θ, 14.4° 2θ, and 23.5° 2θ (±0.2° 2θ; ±0.1° 2θ; or ±0.0° 2θ; Cu Kα1 radiation).

In some embodiments, the solid form of MDE HCl is crystalline MDE HCl characterized by two or more, or three or more XRPD signals selected from the group consisting of 14.0° 2θ, 14.4° 2θ, 23.5° 2θ, 24.9° 2θ, and 28.0° 2θ (±0.2° 2θ; ±0.1° 2θ; or ±0.0° 2θ; Cu Kα1 radiation). In some embodiments, the solid form of MDE HCl is MDE HCl characterized by XRPD signals at 14.0° 2θ, 14.4° 2θ, 23.5° 2θ, 24.9° 2θ, and 28.0° 2θ (±0.2° 2θ; ±0.1° 2θ; or ±0.0° 2θ; Cu Kα1 radiation).

In some embodiments, the crystalline MDE HCl is characterized by one, two, three, four, five, six, seven, eight, nine, ten, eleven, twelve, thirteen, fourteen, fifteen, or sixteen XRPD signals selected from those set forth in Table 16.

TABLE 16

| XRPD Signals for MDE HCl | | | |
|---|---|---|---|
| Signal no. | Position | d-value | Relative |
| 1 | 14.0 | 6.3 | 42.4 |
| 2 | 14.4 | 6.2 | 100.0 |
| 3 | 15.6 | 5.7 | 20.7 |
| 4 | 18.3 | 4.8 | 22.1 |
| 5 | 18.8 | 4.7 | 14.1 |
| 6 | 21.6 | 4.1 | 10.9 |
| 7 | 22.1 | 4.0 | 20.4 |
| 8 | 22.6 | 3.9 | 16.7 |
| 9 | 23.0 | 3.9 | 11.7 |
| 10 | 23.5 | 3.8 | 80.7 |
| 11 | 24.9 | 3.6 | 40.3 |
| 12 | 25.8 | 3.4 | 14.3 |
| 13 | 27.3 | 3.3 | 27.5 |
| 14 | 28.0 | 3.2 | 37.9 |
| 15 | 31.7 | 2.8 | 13.6 |
| 16 | 33.7 | 2.7 | 3.0 |

In some embodiments, the solid form of MDE HCl is crystalline MDE HCl characterized by two or more, or three or more XRPD signals selected from the group consisting of 14.1° 2θ, 14.5° 2θ, and 15.7° 2θ (±0.2° 2θ; ±0.1° 2θ; or ±0.0° 2θ; Cu Kα1 radiation). In some embodiments, the solid form of MDE HCl is crystalline MDE HCl characterized by XRPD signals at 14.1° 2θ, 14.5° 2θ, and 15.7° 2θ (±0.2° 2θ; ±0.1° 2θ; or ±0.0° 2θ; Cu Kα1 radiation).

In some embodiments, the solid form of MDE HCl is crystalline MDE HCl characterized by two or more, or three or more XRPD signals selected from the group consisting of 14.1° 2θ, 14.5° 2θ, 15.7° 2θ, 18.5° 2θ, and 18.9° 2θ (±0.2° 2θ; ±0.1° 2θ; or ±0.0° 2θ; Cu Kα1 radiation). In some embodiments, the solid form of MDE HCl is MDE HCl characterized by XRPD signals at 14.1° 2θ, 14.5° 2θ, 15.7° 2θ, 18.5° 2θ, and 18.9° 2θ (±0.2° 2θ; ±0.1° 2θ; or ±0.0° 2θ; Cu Kα1 radiation).

In some embodiments, the solid form of MDE HCl is crystalline MDE HCl characterized by two or more, or three or more XRPD signals selected from the group consisting of 14.5° 2θ, 23.5° 2θ, and 28.1° 2θ (±0.2° 2θ; ±0.1° 2θ; or ±0.0° 2θ; Cu Kα1 radiation). In some embodiments, the solid form of MDE HCl is crystalline MDE HCl characterized by XRPD signals at 14.5° 2θ, 23.5° 2θ, and 28.1° 2θ (±0.2° 2θ; ±0.1° 2θ; or ±0.0° 2θ; Cu Kα1 radiation).

In some embodiments, the solid form of MDE HCl is crystalline MDE HCl characterized by two or more, or three or more XRPD signals selected from the group consisting of 14.1° 2θ, 14.5° 2θ, 23.5° 2θ, 25.2° 2θ, and 28.1° 2θ (±0.2° 2θ; ±0.1° 2θ; or ±0.0° 2θ; Cu Kα1 radiation). In some embodiments, the solid form of MDE HCl is MDE HCl characterized by XRPD signals at 14.1° 2θ, 14.5° 2θ, 23.5° 2θ, 25.2° 2θ, and 28.1° 2θ (±0.2° 2θ; ±0.1° 2θ; or ±0.0° 2θ; Cu Kα1 radiation).

In some embodiments, the crystalline MDE HCl is characterized by one, two, three, four, five, six, seven, eight, nine, ten, eleven, twelve, thirteen, fourteen, fifteen, sixteen, or seventeen XRPD signals selected from those set forth in Table 17.

TABLE 17

XRPD Signals for MDE HCl

| Signal no. | Position | d-value | Relative |
|---|---|---|---|
| 1 | 14.1 | 6.3 | 45.2 |
| 2 | 14.5 | 6.1 | 71.2 |
| 3 | 15.7 | 5.6 | 25.8 |
| 4 | 18.5 | 4.8 | 27.5 |
| 5 | 18.9 | 4.7 | 21.8 |
| 6 | 21.7 | 4.1 | 13.4 |
| 7 | 22.2 | 4.0 | 29.2 |
| 8 | 23.1 | 3.9 | 25.1 |
| 9 | 23.5 | 3.8 | 100.0 |
| 10 | 25.2 | 3.5 | 62.9 |
| 11 | 26.1 | 3.4 | 19.5 |
| 12 | 27.3 | 3.3 | 39.0 |
| 13 | 28.1 | 3.2 | 63.5 |
| 14 | 31.5 | 2.8 | 10.4 |
| 15 | 31.9 | 2.8 | 16.6 |
| 16 | 36.0 | 2.5 | 11.5 |
| 17 | 39.0 | 2.3 | 11.5 |

Solid Forms of S-MDE Tosylate (Toluenesulfonate)

In some embodiments, the present disclosure provides solid forms of S-MDE tosylate, e.g., crystalline forms of S-MDE tosylate. In some embodiments, the S-MDE tosylate XRPD profile is substantially similar to that shown in FIG. 19.

In some embodiments, the solid form of S-MDE tosylate is crystalline S-MDE tosylate characterized by two or more, or three or more XRPD signals selected from the group consisting of 12.1° 2θ, 13.9° 2θ, and 15.1° 2θ (±0.2° 2θ; ±0.1° 2θ; or ±0.0° 2θ; Cu Kα1 radiation). In some embodiments, the solid form of S-MDE tosylate is crystalline S-MDE tosylate characterized by XRPD signals at 12.1° 2θ, 13.9° 2θ, and 15.1° 2θ (±0.2° 2θ; ±0.1° 2θ; or ±0.0° 2θ; Cu Kα1 radiation).

In some embodiments, the solid form of S-MDE tosylate is crystalline S-MDE tosylate characterized by two or more, or three or more XRPD signals selected from the group consisting of 12.1° 2θ, 13.9° 2θ, 15.1° 2θ, 15.6° 2θ, and 16.1° 2θ (±0.2° 2θ; ±0.1° 2θ; or ±0.0° 2θ; Cu Kα1 radiation). In some embodiments, the solid form of S-MDE tosylate is S-MDE tosylate characterized by XRPD signals at 12.1° 2θ, 13.9° 2θ, 15.1° 2θ, 15.6° 2θ, and 16.1° 2θ (±0.2° 2θ; ±0.1° 2θ; or ±0.0° 2θ; Cu Kα1 radiation).

In some embodiments, the solid form of S-MDE tosylate is crystalline S-MDE tosylate characterized by two or more, or three or more XRPD signals selected from the group consisting of 13.9° 2θ, 19.8° 2θ, and 21.8° 2θ (±0.2° 2θ; ±0.1° 2θ; or ±0.0° 2θ; Cu Kα1 radiation). In some embodiments, the solid form of S-MDE tosylate is crystalline S-MDE tosylate characterized by XRPD signals at 13.9° 2θ, 19.8° 2θ, and 21.8° 2θ (±0.2° 2θ; ±0.1° 2θ; or ±0.0° 2θ; Cu Kα1 radiation).

In some embodiments, the solid form of S-MDE tosylate is crystalline S-MDE tosylate characterized by two or more, or three or more XRPD signals selected from the group consisting of 13.9° 2θ, 19.8° 2θ, 21.8° 2θ, 24.3° 2θ, and 26.9° 2θ (±0.2° 2θ; ±0.1° 2θ; or ±0.0° 2θ; Cu Kα1 radiation). In some embodiments, the solid form of S-MDE tosylate is S-MDE tosylate characterized by XRPD signals at 13.9° 2θ, 19.8° 2θ, 21.8° 2θ, 24.3° 2θ, and 26.9° 2θ (±0.2° 2θ; ±0.1° 2θ; or ±0.0° 2θ; Cu Kα1 radiation).

In some embodiments, the crystalline S-MDE tosylate is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 18.

TABLE 18

XRPD Signals for S-MDE tosylate

| Signal no. | Position | d-value | Relative |
|---|---|---|---|
| 1 | 12.1 | 7.3 | 28.3 |
| 2 | 13.4 | 6.6 | 4.6 |
| 3 | 13.9 | 6.3 | 76.5 |
| 4 | 15.1 | 5.9 | 26.0 |
| 5 | 15.6 | 5.7 | 19.8 |
| 6 | 16.1 | 5.5 | 10.2 |
| 7 | 18.5 | 4.8 | 19.0 |
| 8 | 19.8 | 4.5 | 99.4 |
| 9 | 20.6 | 4.3 | 22.8 |
| 10 | 21.0 | 4.2 | 13.5 |
| 11 | 21.4 | 4.2 | 55.0 |
| 12 | 21.8 | 4.1 | 100.0 |
| 13 | 22.2 | 4.0 | 28.9 |
| 14 | 23.2 | 3.8 | 49.7 |
| 15 | 24.0 | 3.7 | 35.4 |
| 16 | 24.3 | 3.7 | 58.3 |
| 17 | 26.9 | 3.3 | 63.2 |
| 18 | 27.2 | 3.3 | 15.3 |
| 19 | 30.2 | 3.0 | 17.5 |
| 20 | 31.6 | 2.8 | 11.8 |

Solid Forms of MDAI HCl

In some embodiments, the present disclosure provides solid forms of MDAI HCl, e.g., crystalline forms of MDAI HCl. In some embodiments, the MDAI HCl XRPD profile is substantially similar to that shown in FIG. 22.

In some embodiments, the solid form of MDAI HCl is crystalline MDAI HCl characterized by two or more, or three or more XRPD signals selected from the group consisting of 16.9° 2θ, 23.6° 2θ, and 24.2° 2θ (±0.2° 2θ; ±0.1° 2θ; or ±0.0° 2θ; Cu Kα1 radiation). In some embodiments, the solid form of MDAI HCl is crystalline MDAI HCl characterized by XRPD signals at 16.9° 2θ, 23.6° 2θ, and 24.2° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 16.9° 2θ, 23.6° 2θ, 24.2° 2θ, 26.4° 2θ, and 27.2° 2θ (±0.2° 2θ; ±0.1° 2θ; or ±0.0° 2θ; Cu Kα1 radiation). In some embodiments, the solid form of MDAI HCl is MDAI HCl characterized by XRPD signals at 16.9° 2θ, 23.6° 2θ, 24.2° 2θ, 26.4° 2θ, and 27.2° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 24.2° 2θ, 27.2° 2θ, and 45.8° 2θ (±0.2° 2θ; ±0.1° 2θ; or ±0.0° 2θ; Cu Kα1 radiation). In some embodiments, the solid form of MDAI HCl is crystalline MDAI HCl characterized by XRPD signals at 24.2° 2θ, 27.2° 2θ, and 45.8° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 23.6° 2θ, 24.2° 2θ, 26.4° 2θ, 27.2° 2θ, and 45.8° 2θ (±0.2° 2θ; ±0.1° 2θ; or ±0.0° 2θ; Cu Kα1 radiation). In some embodiments, the solid form of MDAI HCl is MDAI HCl characterized by XRPD signals at 23.6 20, 24.2° 2θ, 26.4° 2θ, 27.2° 2θ, and 45.8° 2θ (±0.2° 2θ; ±0.1° 2θ; or ±0.0° 2θ; Cu Kα1 radiation).

In some embodiments, the crystalline MDAI HCl is characterized by one, two, three, four, five, six, seven, eight, nine, ten, eleven, twelve, or thirteen XRPD signals selected from those set forth in Table 19.

TABLE 19

XRPD Signals for MDAI HCl

| Signal no. | Position | d-value | Relative |
|---|---|---|---|
| 1 | 15.4 | 5.8 | 17.7 |
| 2 | 15.7 | 5.6 | 9.6 |
| 3 | 16.9 | 5.2 | 16.2 |
| 4 | 23.6 | 3.8 | 27.4 |
| 5 | 24.2 | 3.7 | 100.0 |
| 6 | 26.4 | 3.4 | 25.9 |
| 7 | 27.2 | 3.3 | 45.4 |
| 8 | 28.3 | 3.2 | 9.5 |
| 9 | 31.6 | 2.8 | 13.0 |
| 10 | 33.3 | 2.7 | 20.5 |
| 11 | 34.0 | 2.6 | 14.2 |
| 12 | 45.8 | 2.0 | 56.1 |
| 13 | 52.0 | 1.8 | 10.8 |

In some embodiments, the solid form of MDAI HCl is crystalline MDAI HCl characterized by two or more, or three or more XRPD signals selected from the group consisting of 16.8° 2θ, 23.2° 2θ, and 24.2° 2θ (±0.2° 2θ; ±0.1° 2θ; or ±0.0° 2θ; Cu Kα1 radiation). In some embodiments, the solid form of MDAI HCl is crystalline MDAI HCl (Pattern #1) characterized by XRPD signals at 16.8° 2θ, 23.2° 2θ, and 24.2° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 16.8° 2θ, 23.2° 2θ, 24.2° 2θ, 26.4° 2θ, and 27.1° 2θ (±0.2° 2θ; ±0.1° 2θ; or ±0.0° 2θ; Cu Kα1 radiation). In some embodiments, the solid form of MDAI HCl is crystalline MDAI HCl characterized by XRPD signals at 16.8° 2θ, 23.2° 2θ, 24.2° 2θ, 26.4° 2θ, and 27.1° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 24.2° 2θ, 45.8° 2θ, and 27.1° 2θ (±0.2° 2θ; ±0.1° 2θ; or ±0.0° 2θ; Cu Kα1 radiation). In some embodiments, the solid form of MDAI HCl is crystalline MDAI HCl (Pattern #1) characterized by XRPD signals at 24.2° 2θ, 45.8° 2θ, and 27.1° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 24.2° 2θ, 45.8° 2θ, 27.1° 2θ, 23.6° 2θ, and 26.4° 2θ (±0.2° 2θ; ±0.1° 2θ; or ±0.0° 2θ; Cu Kα1 radiation). In some embodiments, the solid form of MDAI HCl is crystalline MDAI HCl characterized by XRPD signals at 24.2° 2θ, 45.8° 2θ, 27.1° 2θ, 23.6° 2θ, and 26.4° 2θ (±0.2° 2θ; ±0.1° 2θ; or ±0.0° 2θ; Cu Kα1 radiation).

In some embodiments, the crystalline MDAI HCl is characterized by one, two, three, four, five, six, seven, eight, nine, ten, eleven, twelve, thirteen, fourteen, or fifteen XRPD signals selected from those set forth in Table 20.

TABLE 20

XRPD Signals for MDAI HCl

| Signal No. | Pos. [°2θ] | d-spacing [Å] | Rel. Int. [%] |
|---|---|---|---|
| 1 | 15.3 | 5.8 | 15.3 |
| 2 | 15.6 | 5.7 | 11.5 |
| 3 | 16.8 | 5.3 | 21.1 |
| 4 | 23.2 | 3.8 | 13.8 |
| 5 | 23.6 | 3.8 | 28.6 |
| 6 | 24.2 | 3.7 | 100.0 |
| 7 | 26.4 | 3.4 | 22.5 |
| 8 | 27.1 | 3.3 | 41.8 |
| 9 | 31.5 | 2.8 | 10.0 |
| 10 | 33.2 | 2.7 | 18.7 |
| 11 | 33.8 | 2.6 | 10.4 |
| 12 | 34.0 | 2.6 | 17.8 |
| 13 | 45.8 | 2.0 | 75.8 |
| 14 | 51.9 | 1.8 | 13.0 |
| 15 | 58.1 | 1.6 | 10.4 |

Solid Forms of MBDB Citrate

Figure 26:
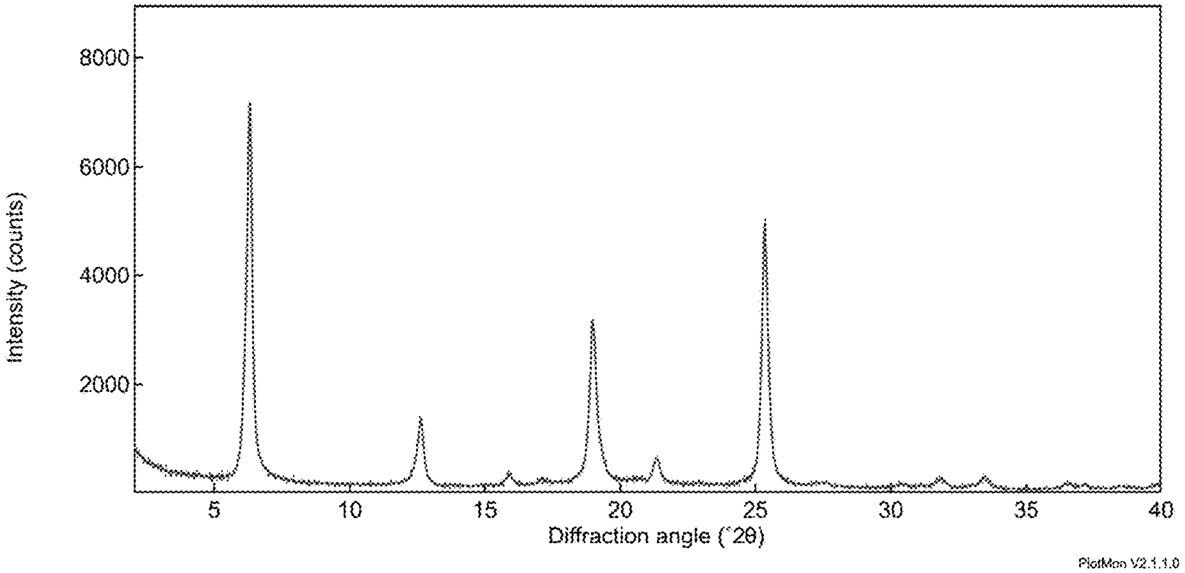
FIG. 26 provides an XRPD diffractogram of crystalline MBDB·citrate.
Figure 65:
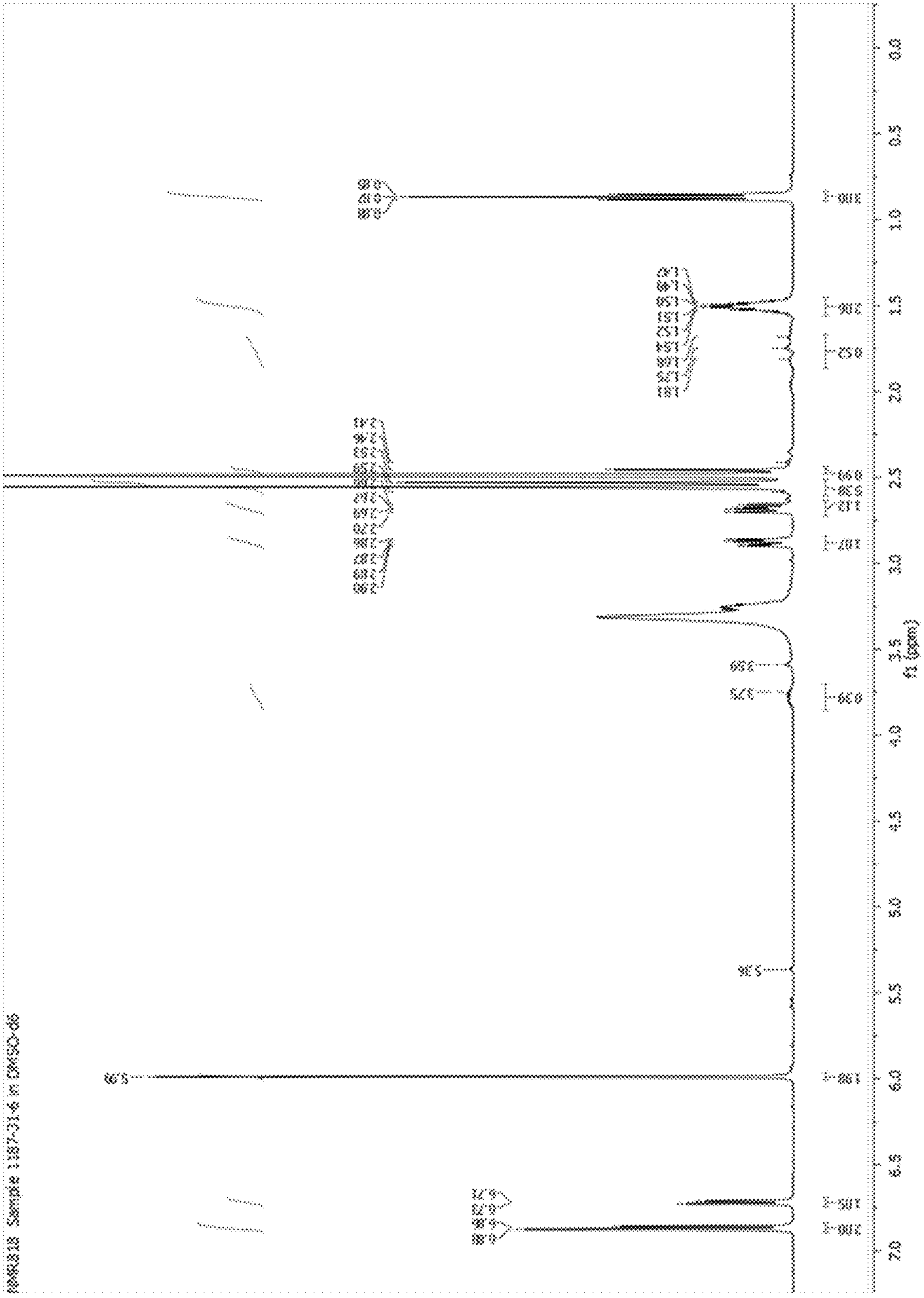
FIG. 65 provides a $^1$H NMR spectrum for MBDB citrate.
Figure 66:
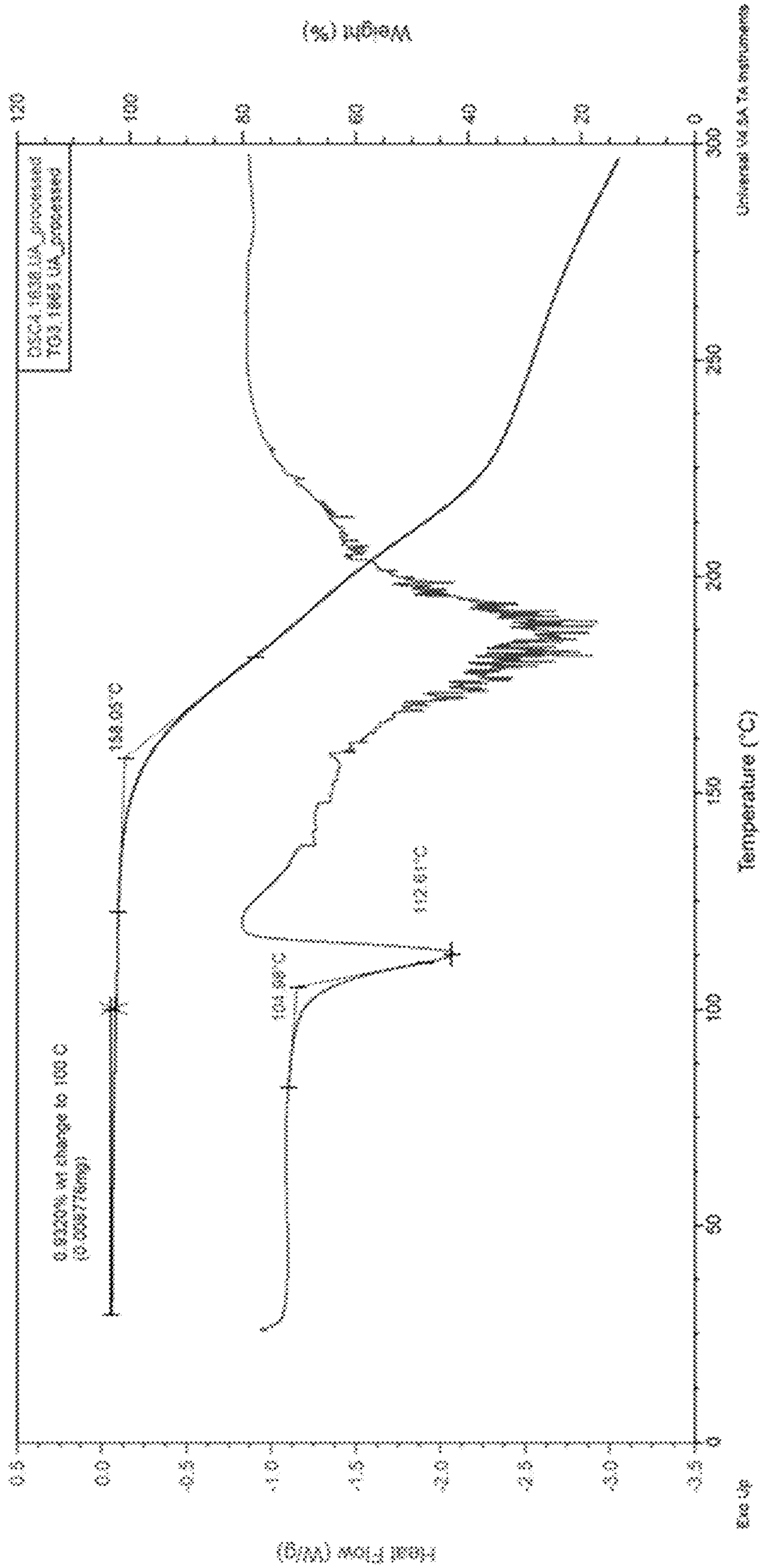
FIG. 66 provides TGA and DSC profiles for MBDB citrate.
Figure 84:
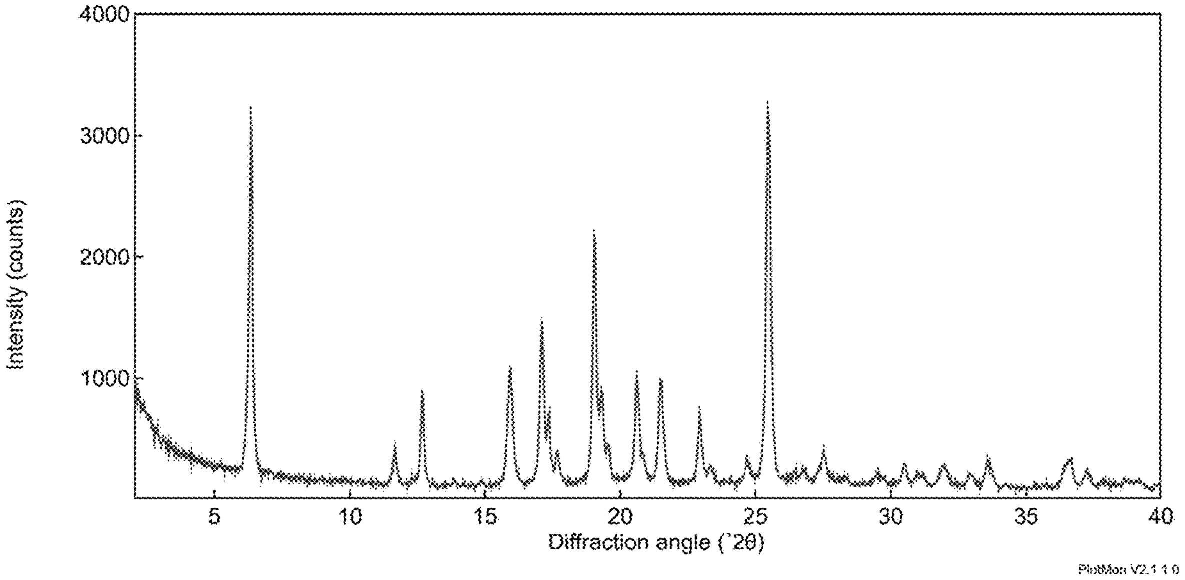
FIG. 84 provides an XRPD diffractogram of crystalline MBDB·citrate.

In some embodiments, the present disclosure provides solid forms of MBDB citrate, e.g., crystalline forms of MBDB citrate. In some embodiments, the MBDB citrate XRPD profile is substantially similar to that shown in any one of FIG. 26 or 84. In some embodiments, the MBDB citrate $^1$H NMR spectrum is substantially similar to that shown in FIG. 65. In some embodiments, the MBDB citrate TGA profile is substantially similar to that shown in FIG. 66. In some embodiments, the MBDB citrate DSC profile is substantially similar to that shown in FIG. 66.

In some embodiments, the solid form of MBDB citrate is crystalline MBDB citrate characterized by two or more, or three or more XRPD signals selected from the group consisting of 6.3° 2θ, 19.0° 2θ, and 25.4° 2θ (±0.2° 2θ; ±0.1° 2θ; or ±0.0° 2θ; Cu Kα1 radiation). In some embodiments, the solid form of MBDB citrate is crystalline MBDB citrate characterized by XRPD signals at 6.3° 2θ, 19.0° 2θ, and 25.4° 2θ (±0.2° 2θ; ±0.1° 2θ; or ±0.0° 2θ; Cu Kα1 radiation).

In some embodiments, the solid form of MBDB citrate is crystalline MBDB citrate characterized by two or more, or three or more XRPD signals selected from the group consisting of 6.3° 2θ, 12.6° 2θ, 19.0° 2θ, 21.4° 2θ, and 25.4° 2θ (±0.2° 2θ; ±0.1° 2θ; or ±0.0° 2θ; Cu Kα1 radiation). In some embodiments, the solid form of MBDB citrate is MBDB citrate characterized by XRPD signals at 6.3° 2θ, 12.6° 2θ, 19.0° 2θ, 21.4° 2θ, and 25.4° 2θ (±0.2° 2θ; ±0.1° 2θ; or ±0.0° 2θ; Cu Kα1 radiation).

In some embodiments, the solid form of MBDB citrate is crystalline MBDB citrate characterized by two or more, or three or more XRPD signals selected from the group consisting of 6.3° 2θ, 12.6° 2θ, and 19.0° 2θ (±0.2° 2θ; ±0.1° 2θ; or ±0.0° 2θ; Cu Kα1 radiation). In some embodiments, the solid form of MBDB citrate is crystalline MBDB citrate characterized by XRPD signals at 6.3° 2θ, 12.6° 2θ, and 19.0° 2θ (±0.2° 2θ; ±0.1° 2θ; or ±0.0° 2θ; Cu Kα1 radiation).

In some embodiments, the crystalline MBDB citrate is characterized by one, two, three, four, five, six, seven, eight, nine, ten, eleven, twelve, thirteen, fourteen, fifteen, sixteen, or seventeen XRPD signals selected from those set forth in Table 21.

TABLE 21

| XRPD Signals for MBDB citrate | | | |
|---|---|---|---|
| Signal no. | Position | d-value | Relative |
| 1 | 6.3 | 14.0 | 100.0 |
| 2 | 12.6 | 7.0 | 19.1 |
| 3 | 15.9 | 5.6 | 5.4 |
| 4 | 17.1 | 5.2 | 4.2 |
| 5 | 19.0 | 4.7 | 44.0 |
| 6 | 20.7 | 4.3 | 4.2 |
| 7 | 21.4 | 4.2 | 9.2 |
| 8 | 22.9 | 3.9 | 3.3 |
| 9 | 25.4 | 3.5 | 69.5 |
| 10 | 27.5 | 3.2 | 3.1 |
| 11 | 30.3 | 2.9 | 2.8 |
| 12 | 31.8 | 2.8 | 4.1 |
| 13 | 33.4 | 2.7 | 4.4 |
| 14 | 36.5 | 2.5 | 2.9 |
| 15 | 37.1 | 2.4 | 2.5 |
| 16 | 38.4 | 2.3 | 2.1 |
| 17 | 39.8 | 2.3 | 2.4 |

In some embodiments, the solid form of MBDB citrate is crystalline MBDB citrate characterized by two or more, or three or more XRPD signals selected from the group consisting of 6.3° 2θ, 19.0° 2θ, and 25.5° 2θ (±0.2° 2θ; ±0.1° 2θ; or ±0.0° 2θ; Cu Kα1 radiation). In some embodiments, the solid form of MBDB citrate is crystalline MBDB citrate characterized by XRPD signals at 6.3° 2θ, 19.0° 2θ, and 25.5° 2θ (±0.2° 2θ; ±0.1° 2θ; or ±0.0° 2θ; Cu Kα1 radiation).

In some embodiments, the solid form of MBDB citrate is crystalline MBDB citrate characterized by two or more, or three or more XRPD signals selected from the group consisting of 6.3° 2θ, 15.9° 2θ, 17.1° 2θ, 19.0° 2θ, and 25.5° 2θ (±0.2° 2θ; ±0.1° 2θ; or ±0.0° 2θ; Cu Kα1 radiation). In some embodiments, the solid form of MBDB citrate is MBDB citrate characterized by XRPD signals at 6.3° 2θ, 15.9° 2θ, 17.1° 2θ, 19.0° 2θ, and 25.5° 2θ (±0.2° 2θ; ±0.1° 2θ; or ±0.0° 2θ; Cu Kα1 radiation).

In some embodiments, the solid form of MBDB citrate is crystalline MBDB citrate characterized by two or more, or three or more XRPD signals selected from the group consisting of 6.3° 2θ, 11.7° 2θ, and 12.7° 2θ (±0.2° 2θ; ±0.1° 2θ; or ±0.0° 2θ; Cu Kα1 radiation). In some embodiments, the solid form of MBDB citrate is crystalline MBDB citrate characterized by XRPD signals at 6.3° 2θ, 11.7° 2θ, and 12.7° 2θ (±0.2° 2θ; ±0.1° 2θ; or ±0.0° 2θ; Cu Kα1 radiation).

In some embodiments, the solid form of MBDB citrate is crystalline MBDB citrate characterized by two or more, or three or more XRPD signals selected from the group consisting of 6.3° 2θ, 11.7° 2θ, 12.7° 2θ, 15.9° 2θ, and 17.1° 2θ (±0.2° 2θ; ±0.1° 2θ; or ±0.0° 2θ; Cu Kα1 radiation). In some embodiments, the solid form of MBDB citrate is MBDB citrate characterized by XRPD signals at 6.3° 2θ, 11.7° 2θ, 12.7° 2θ, 15.9° 2θ, and 17.1° 2θ (±0.2° 2θ; ±0.1° 2θ; or ±0.0° 2θ; Cu Kα1 radiation).

In some embodiments, the crystalline MBDB citrate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, or twenty-eight XRPD signals selected from those set forth in Table 22.

TABLE 22

| XRPD Signals for MBDB citrate | | | |
|---|---|---|---|
| Signal no. | Position | d-value | Relative |
| 1 | 6.3 | 13.9 | 98.2 |
| 2 | 11.7 | 7.6 | 13.3 |
| 3 | 12.7 | 7.0 | 27.5 |
| 4 | 15.9 | 5.6 | 33.5 |
| 5 | 17.1 | 5.2 | 45.1 |
| 6 | 17.4 | 5.1 | 21.5 |
| 7 | 17.7 | 5.0 | 12.2 |
| 8 | 19.0 | 4.7 | 67.2 |
| 9 | 19.3 | 4.6 | 28.2 |
| 10 | 19.6 | 4.5 | 14.4 |
| 11 | 20.6 | 4.3 | 31.4 |
| 12 | 20.8 | 4.3 | 12.5 |
| 13 | 21.5 | 4.1 | 30.4 |
| 14 | 22.9 | 3.9 | 22.0 |
| 15 | 23.3 | 3.8 | 8.9 |
| 16 | 24.7 | 3.6 | 11.1 |
| 17 | 25.5 | 3.5 | 100.0 |
| 18 | 26.5 | 3.4 | 7.4 |
| 19 | 26.7 | 3.3 | 7.9 |
| 20 | 27.5 | 3.2 | 12.8 |
| 21 | 29.5 | 3.0 | 7.5 |
| 22 | 30.5 | 2.9 | 9.3 |
| 23 | 31.0 | 2.9 | 7.5 |
| 24 | 32.0 | 2.8 | 9.1 |
| 25 | 32.9 | 2.7 | 6.7 |
| 26 | 33.6 | 2.7 | 10.5 |
| 27 | 36.6 | 2.5 | 10.4 |
| 28 | 37.3 | 2.4 | 7.7 |

Solid Forms of MBDB Fumarate

Figure 27:
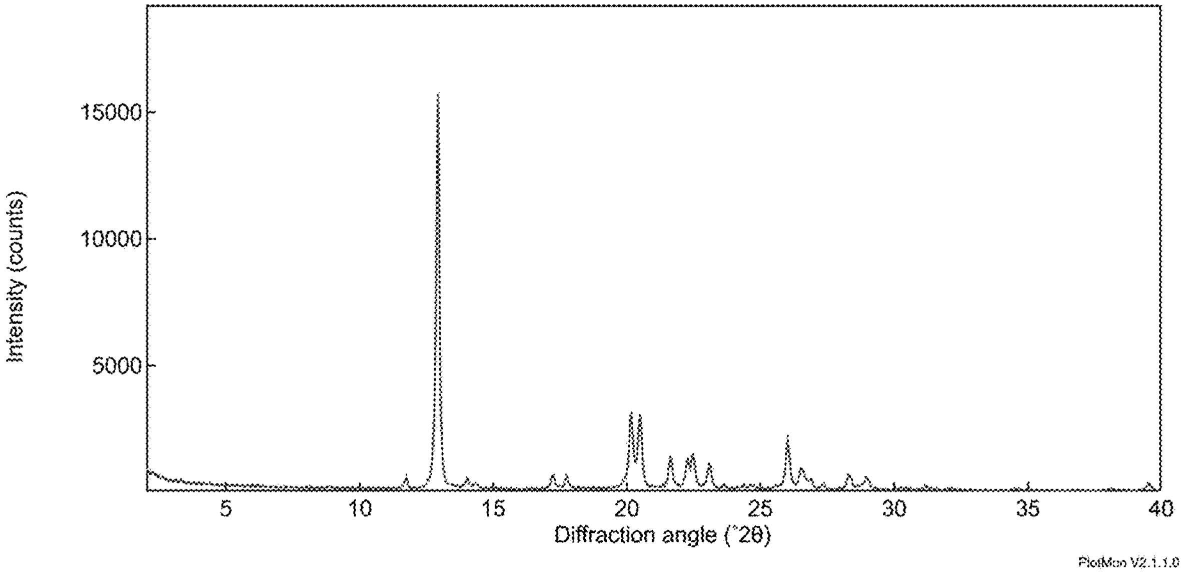
FIG. 27 provides an XRPD diffractogram of crystalline MBDB·fumarate.
Figure 67:
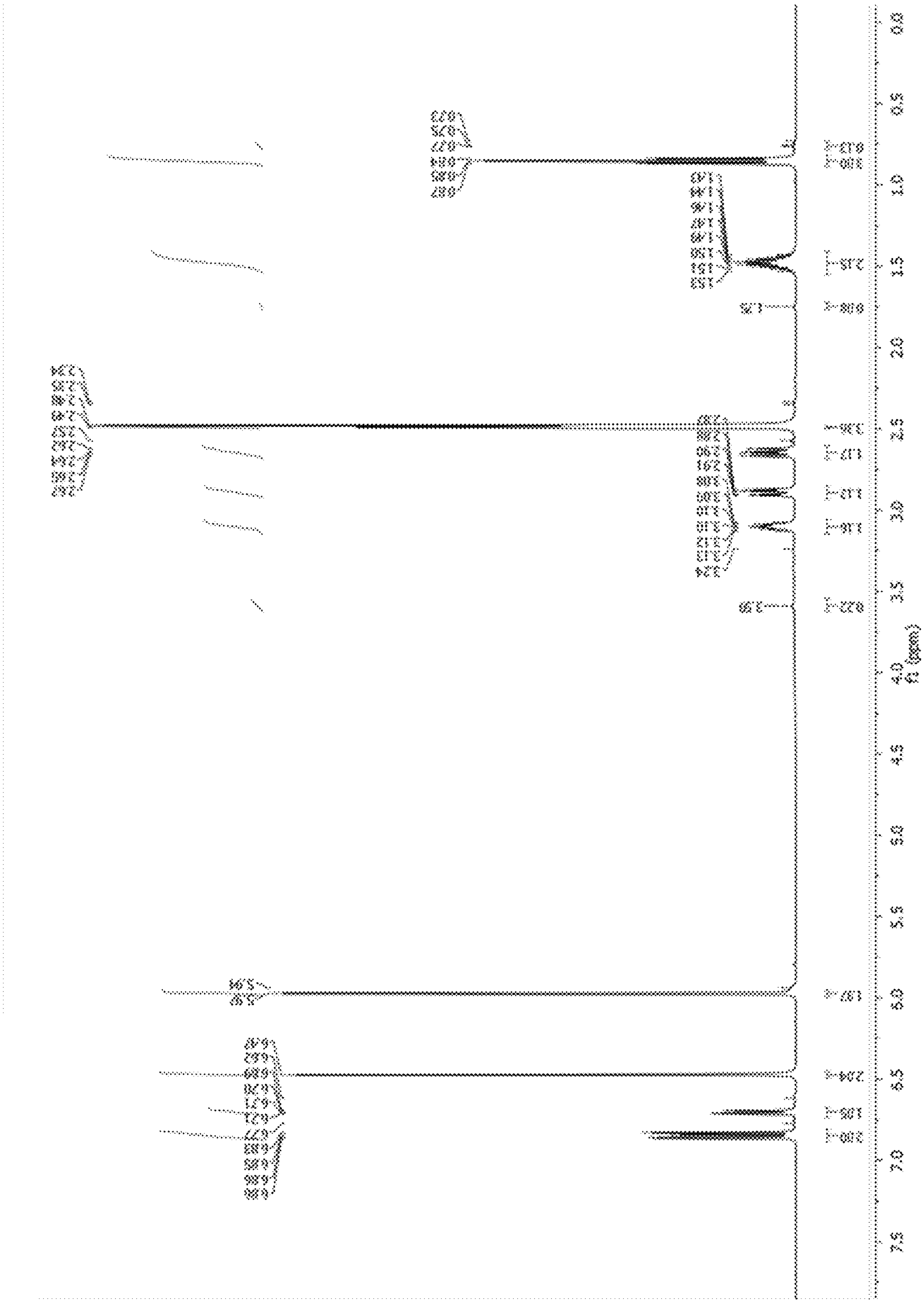
FIG. 67 provides a $^1$H NMR spectrum for MBDB fumarate.
Figure 68:
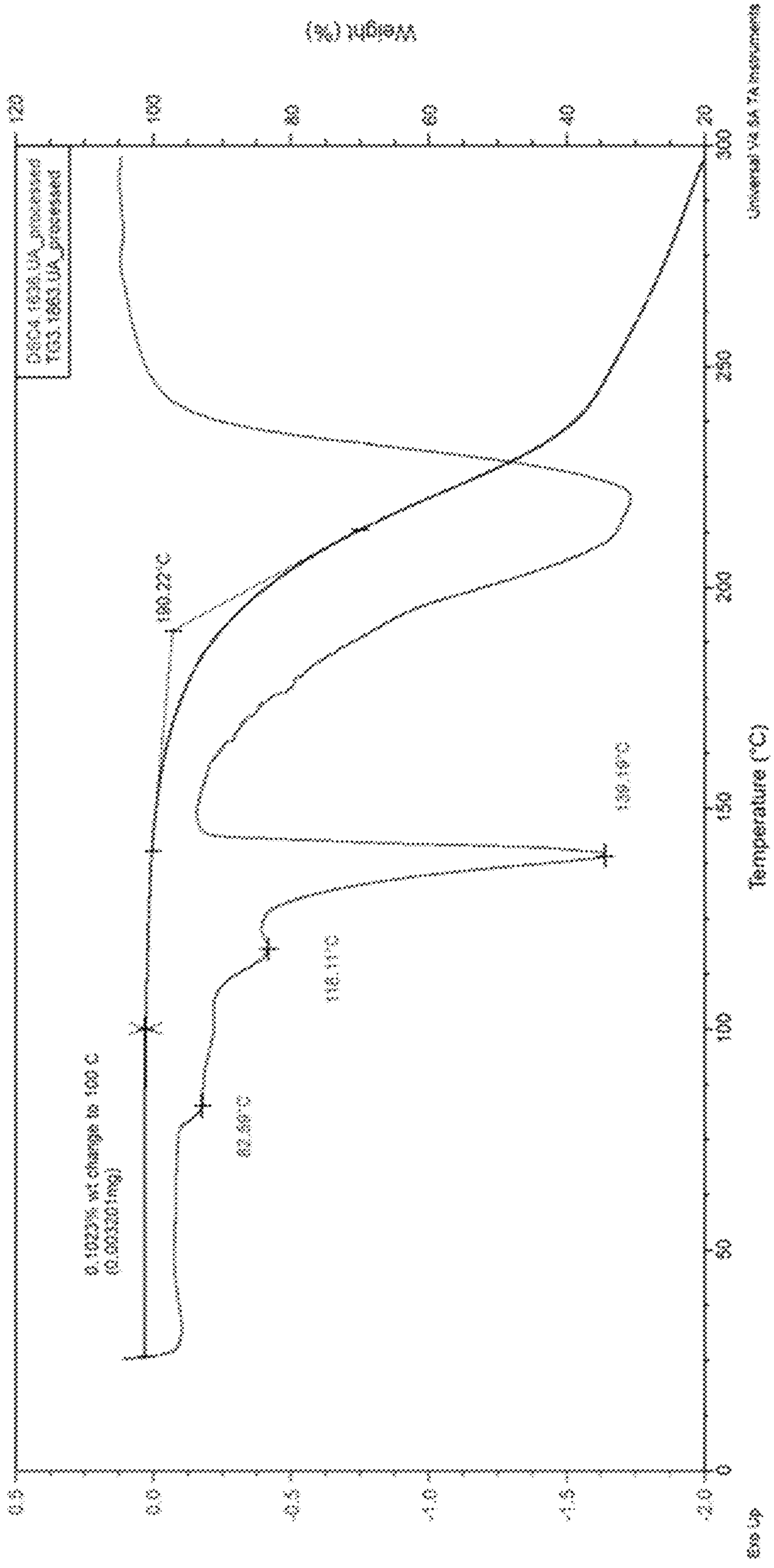
FIG. 68 provides TGA and DSC profiles for MBDB fumarate.
Figure 85:
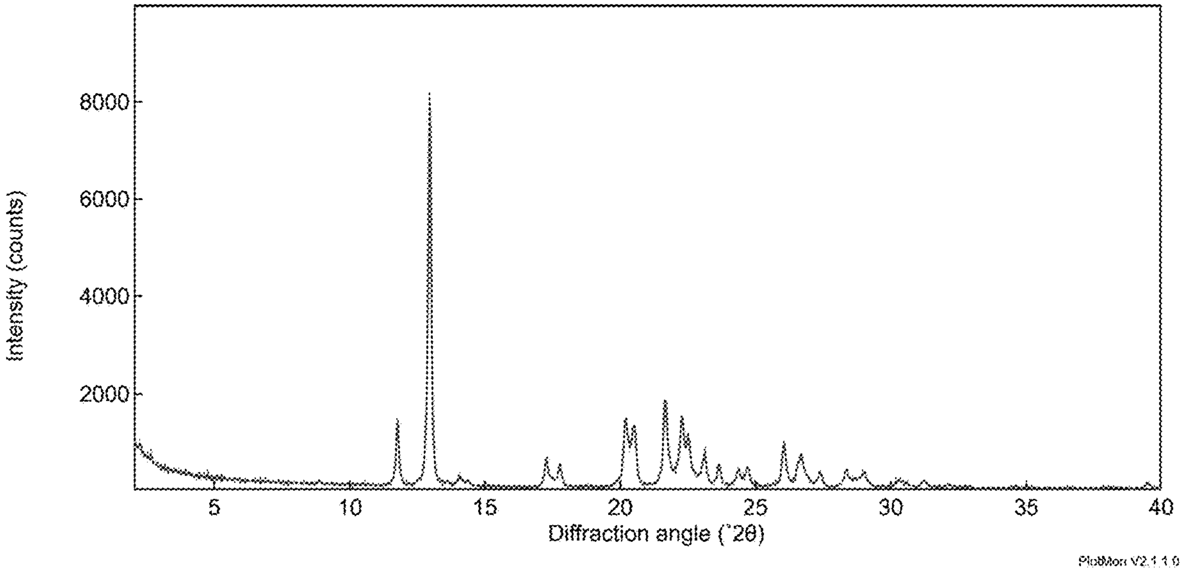
FIG. 85 provides an XRPD diffractogram of crystalline MBDB·fumarate.

In some embodiments, the present disclosure provides solid forms of MBDB fumarate, e.g., crystalline forms of MBDB fumarate. In some embodiments, the MBDB fumarate XRPD profile is substantially similar to that shown in any one of FIG. 27 or 85. In some embodiments, the MBDB fumarate $^{1}H$ NMR spectrum is substantially similar to that shown in FIG. 67. In some embodiments, the MBDB fumarate TGA profile is substantially similar to that shown in FIG. 68. In some embodiments, the MBDB fumarate DSC profile is substantially similar to that shown in FIG. 68.

In some embodiments, the solid form of MBDB fumarate is crystalline MBDB fumarate characterized by two or more, or three or more XRPD signals selected from the group consisting of 12.9° 2θ, 20.2° 2θ, and 20.5° 2θ (±0.2° 2θ; ±0.1° 2θ; or ±0.0° 2θ; Cu Kα1 radiation). In some embodiments, the solid form of MBDB fumarate is crystalline MBDB fumarate characterized by XRPD signals at 12.9° 2θ, 20.2° 2θ, and 20.5° 2θ (±0.2° 2θ; ±0.1° 2θ; or ±0.0° 2θ; Cu Kα1 radiation).

In some embodiments, the solid form of MBDB fumarate is crystalline MBDB fumarate characterized by two or more, or three or more XRPD signals selected from the group consisting of 12.9° 2θ, 20.2° 2θ, 20.5° 2θ, 22.5° 2θ, and 26.0° 2θ (±0.2° 2θ; ±0.1° 2θ; or ±0.0° 2θ; Cu Kα1 radiation). In some embodiments, the solid form of MBDB fumarate is MBDB fumarate characterized by XRPD signals at 12.9° 2θ, 20.2° 2θ, 20.5° 2θ, 22.5° 2θ, and 26.0° 2θ (±0.2° 2θ; ±0.1° 2θ; or ±0.0° 2θ; Cu Kα1 radiation).

In some embodiments, the solid form of MBDB fumarate is crystalline MBDB fumarate characterized by two or more, or three or more XRPD signals selected from the group consisting of 11.7° 2θ, 12.9° 2θ, 20.2° 2θ, 20.5° 2θ, and 26.0° 2θ (±0.2° 2θ; ±0.1° 2θ; or ±0.0° 2θ; Cu Kα1 radiation). In some embodiments, the solid form of MBDB fumarate is MBDB fumarate characterized by XRPD signals at 11.7° 2θ, 12.9° 2θ, 20.2° 2θ, 20.5° 2θ, and 26.0° 2θ (±0.2° 2θ; ±0.1° 2θ; or ±0.0° 2θ; Cu Kα1 radiation).

In some embodiments, the crystalline MBDB fumarate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, or twenty-seven XRPD signals selected from those set forth in Table 23.

TABLE 23

XRPD Signals for MBDB fumarate

| Signal no. | Position | d-value | Relative |
|---|---|---|---|
| 1 | 11.7 | 7.5 | 4.1 |
| 2 | 12.9 | 6.9 | 100.0 |
| 3 | 14.0 | 6.3 | 3.5 |
| 4 | 14.4 | 6.2 | 2.3 |
| 5 | 17.2 | 5.1 | 4.7 |
| 6 | 17.7 | 5.0 | 4.1 |
| 7 | 20.2 | 4.4 | 20.1 |
| 8 | 20.5 | 4.3 | 19.7 |
| 9 | 21.6 | 4.1 | 8.9 |
| 10 | 22.3 | 4.0 | 8.5 |
| 11 | 22.5 | 4.0 | 9.7 |
| 12 | 23.1 | 3.9 | 7.4 |
| 13 | 23.6 | 3.8 | 2.1 |
| 14 | 24.3 | 3.7 | 2.0 |
| 15 | 24.7 | 3.6 | 2.2 |
| 16 | 26.0 | 3.4 | 13.4 |
| 17 | 26.5 | 3.4 | 6.3 |
| 18 | 26.9 | 3.3 | 3.6 |
| 19 | 27.4 | 3.3 | 2.3 |
| 20 | 28.3 | 3.2 | 4.7 |
| 21 | 29.0 | 3.1 | 4.0 |
| 22 | 30.3 | 2.9 | 1.3 |
| 23 | 31.2 | 2.9 | 1.8 |
| 24 | 32.1 | 2.8 | 1.1 |
| 25 | 34.5 | 2.6 | 1.0 |
| 26 | 38.2 | 2.4 | 1.0 |
| 27 | 39.5 | 2.3 | 2.3 |

In some embodiments, the solid form of MBDB fumarate is crystalline MBDB fumarate characterized by two or more, or three or more XRPD signals selected from the group consisting of 12.9° 2θ, 21.6° 2θ, and 22.3° 2θ (±0.2° 2θ; ±0.1° 2θ; or ±0.0° 2θ; Cu Kα1 radiation). In some embodiments, the solid form of MBDB fumarate is crystalline MBDB fumarate characterized by XRPD signals at 12.9° 2θ, 21.6° 2θ, and 22.3° 2θ (±0.2° 2θ; ±0.1° 2θ; or ±0.0° 2θ; Cu Kα1 radiation).

In some embodiments, the solid form of MBDB fumarate is crystalline MBDB fumarate characterized by two or more, or three or more XRPD signals selected from the group consisting of 11.8° 2θ, 12.9° 2θ, 20.2° 2θ, 21.6° 2θ, and 22.3° 2θ (±0.2° 2θ; ±0.1° 2θ; or ±0.0° 2θ; Cu Kα1 radiation). In some embodiments, the solid form of MBDB fumarate is MBDB fumarate characterized by XRPD signals at 11.8° 2θ, 12.9° 2θ, 20.2° 2θ, 21.6° 2θ, and 22.3° 2θ (±0.2° 2θ; ±0.1° 2θ; or ±0.0° 2θ; Cu Kα1 radiation).

In some embodiments, the solid form of MBDB fumarate is crystalline MBDB fumarate characterized by two or more, or three or more XRPD signals selected from the group consisting of 11.8° 2θ, 12.9° 2θ, and 21.6° 2θ (±0.2° 2θ; ±0.1° 2θ; or ±0.0° 2θ; Cu Kα1 radiation). In some embodiments, the solid form of MBDB fumarate is crystalline MBDB fumarate characterized by XRPD signals at 11.8° 2θ, 12.9° 2θ, and 21.6° 2θ (±0.2° 2θ; ±0.1° 2θ; or ±0.0° 2θ; Cu Kα1 radiation).

In some embodiments, the solid form of MBDB fumarate is crystalline MBDB fumarate characterized by two or more, or three or more XRPD signals selected from the group consisting of 11.8° 2θ, 12.9° 2θ, 20.2° 2θ, 20.5° 2θ, and 21.6° 2θ (±0.2° 2θ; ±0.1° 2θ; or ±0.0° 2θ; Cu Kα1 radiation). In some embodiments, the solid form of MBDB fumarate is MBDB fumarate characterized by XRPD signals at 11.8° 2θ, 12.9° 2θ, 20.2° 2θ, 20.5° 2θ, and 21.6° 2θ (±0.2° 2θ; ±0.1° 2θ; or ±0.0° 2θ; Cu Kα1 radiation).

In some embodiments, the crystalline MBDB fumarate is characterized by one, two, three, four, five, six, seven, eight, nine, ten, eleven, twelve, thirteen, fourteen, fifteen, sixteen, seventeen, eighteen, nineteen, twenty, twenty-one, twenty-two, or twenty-three XRPD signals selected from those set forth in Table 24.

TABLE 24

XRPD Signals for MBDB fumarate

| Signal no. | Position | d-value | Relative |
|---|---|---|---|
| 1 | 11.8 | 7.5 | 17.8 |
| 2 | 12.9 | 6.8 | 100.0 |
| 3 | 14.1 | 6.3 | 4.0 |
| 4 | 17.3 | 5.1 | 8.3 |
| 5 | 17.8 | 5.0 | 6.9 |
| 6 | 20.2 | 4.4 | 18.8 |
| 7 | 20.5 | 4.3 | 16.9 |
| 8 | 21.6 | 4.1 | 23.2 |
| 9 | 22.3 | 4.0 | 19.2 |
| 10 | 22.5 | 4.0 | 14.4 |
| 11 | 23.1 | 3.8 | 9.9 |
| 12 | 23.6 | 3.8 | 6.8 |
| 13 | 24.4 | 3.7 | 5.8 |
| 14 | 24.7 | 3.6 | 6.1 |
| 15 | 26.1 | 3.4 | 12.3 |
| 16 | 26.7 | 3.3 | 9.4 |
| 17 | 27.4 | 3.3 | 5.1 |
| 18 | 28.4 | 3.1 | 5.5 |
| 19 | 29.0 | 3.1 | 4.9 |
| 20 | 30.3 | 2.9 | 3.2 |
| 21 | 31.2 | 2.9 | 2.7 |
| 22 | 32.2 | 2.8 | 1.9 |
| 23 | 39.5 | 2.3 | 2.2 |

Solid Forms of MBDB Galactarate (Mucate)

Figure 28:
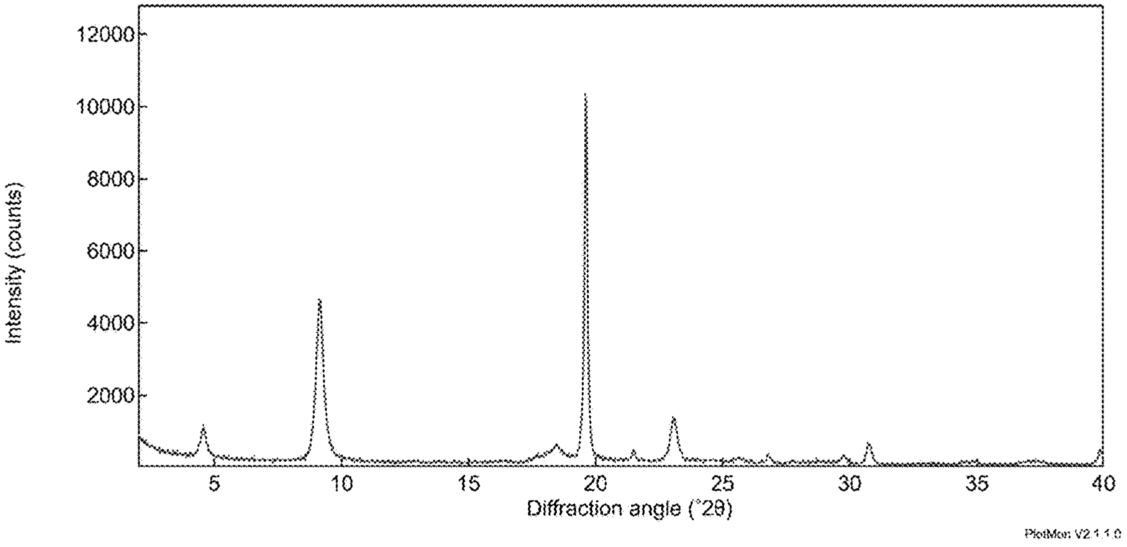
FIG. 28 provides an XRPD diffractogram of crystalline MBDB·galactarate.
Figure 69:
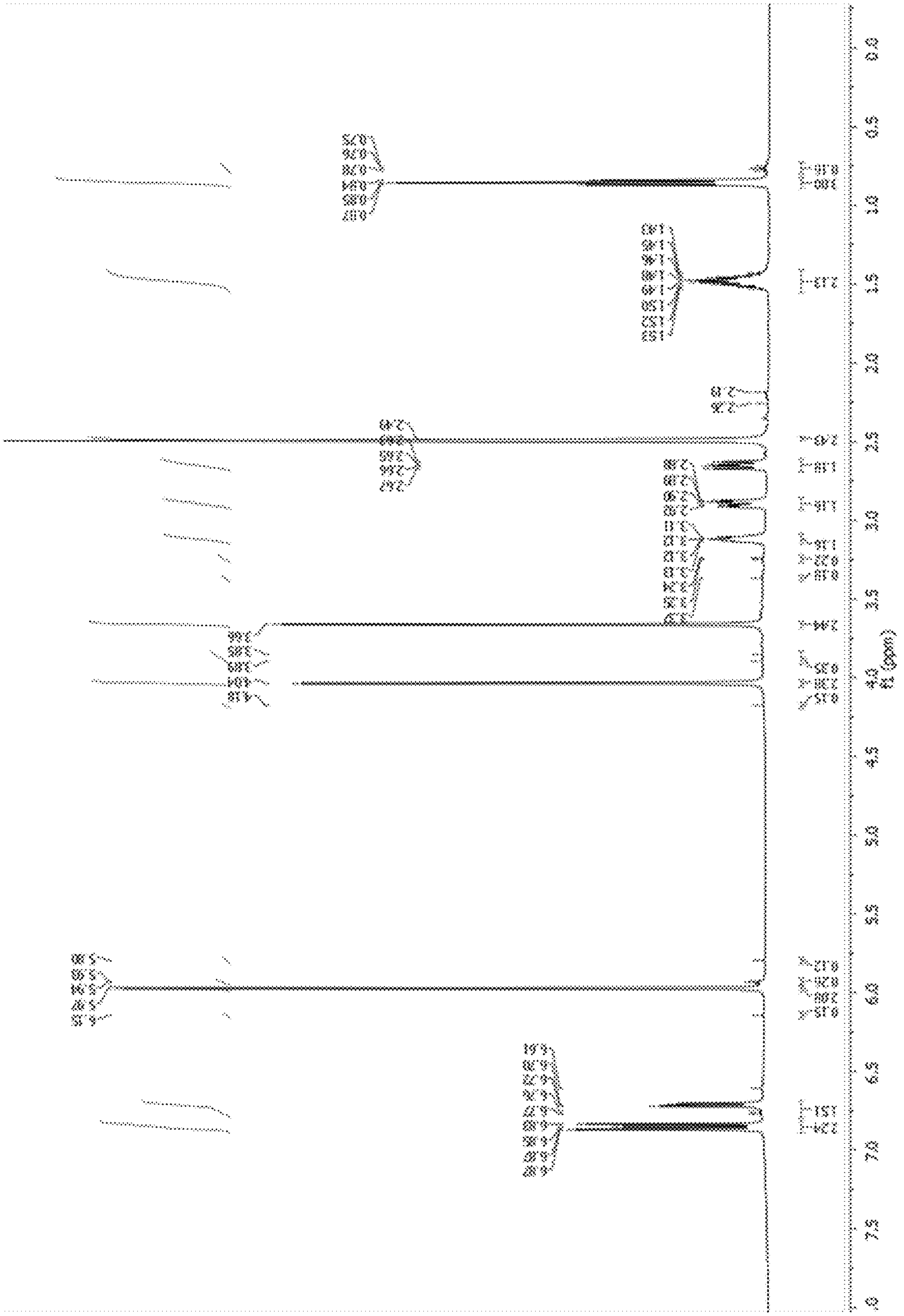
FIG. 69 provides a $^1$H NMR spectrum for MBDB galactarate (mucate).
Figure 70:
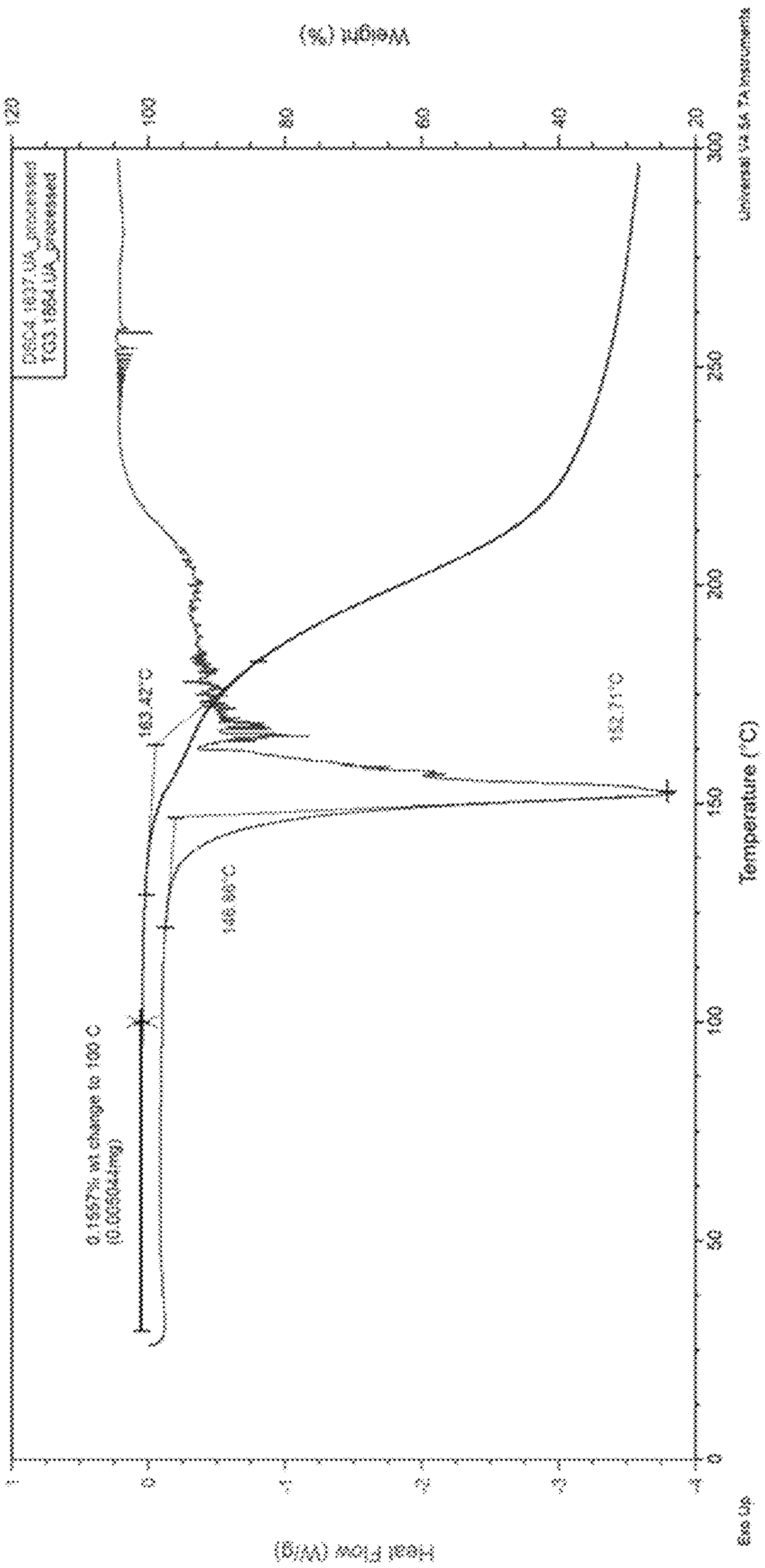
FIG. 70 provides TGA and DSC profiles for MBDB galactarate (mucate).
Figure 89:
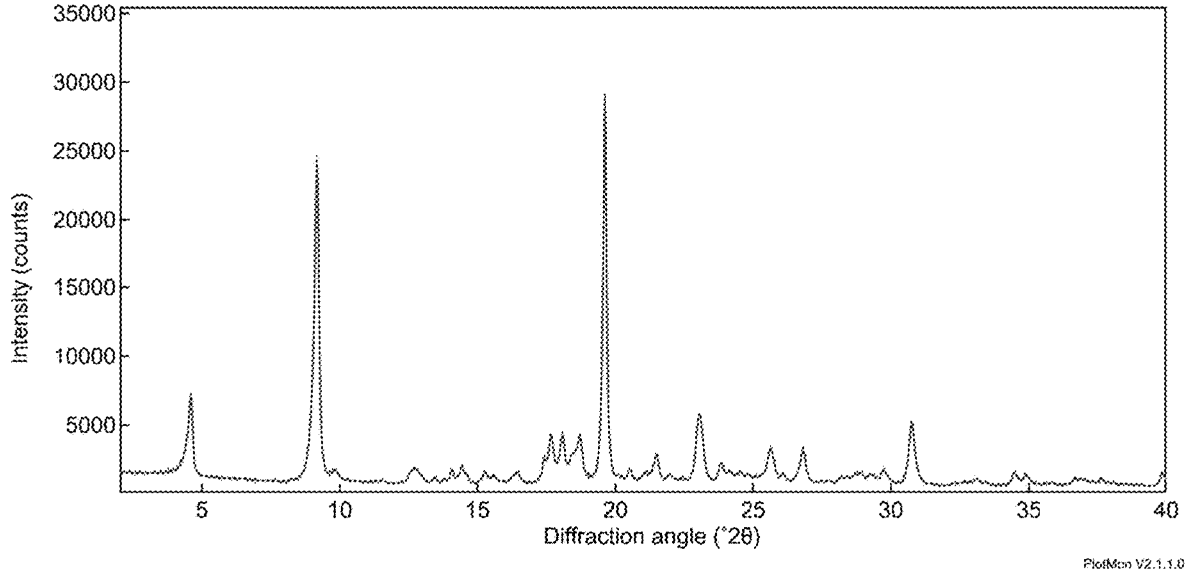
FIG. 89 provides an XRPD diffractogram of crystalline MBDB·galactarate (mucate).

In some embodiments, the present disclosure provides solid forms of MBDB galactarate (mucate), e.g., crystalline forms of MBDB galactarate. In some embodiments, the MBDB galactarate XRPD profile is substantially similar to that shown in any one of FIG. 28 or 89. In some embodiments, the MBDB galactarate $^1$H NMR spectrum is substantially similar to that shown in FIG. 69. In some embodiments, the MBDB galactarate TGA profile is substantially similar to that shown in FIG. 70. In some embodiments, the MBDB galactarate DSC profile is substantially similar to that shown in FIG. 70.

In some embodiments, the solid form of MBDB galactarate is crystalline MBDB galactarate characterized by two or more, or three or more XRPD signals selected from the group consisting of 9.2° 2θ, 19.6° 2θ, and 23.1° 2θ (±0.2° 2θ; ±0.1° 2θ; or ±0.0° 2θ; Cu Kα1 radiation). In some embodiments, the solid form of MBDB galactarate is crystalline MBDB galactarate characterized by XRPD signals at 9.2° 2θ, 19.6° 2θ, and 23.1° 2θ (±0.2° 2θ; ±0.1° 2θ; or ±0.0° 2θ; Cu Kα1 radiation).

In some embodiments, the solid form of MBDB galactarate is crystalline MBDB galactarate characterized by two or more, or three or more XRPD signals selected from the group consisting of 4.6° 2θ, 9.2° 2θ, 19.6° 2θ, 23.1° 2θ, and 30.7° 2θ (±0.2° 2θ; ±0.1° 2θ; or ±0.0° 2θ; Cu Kα1 radiation). In some embodiments, the solid form of MBDB galactarate is MBDB galactarate characterized by XRPD signals at 4.6° 2θ, 9.2° 2θ, 19.6° 2θ, 23.1° 2θ, and 30.7° 2θ (±0.2° 2θ; ±0.1° 2θ; or ±0.0° 2θ; Cu Kα1 radiation).

In some embodiments, the solid form of MBDB galactarate is crystalline MBDB galactarate characterized by two or more, or three or more XRPD signals selected from the group consisting of 4.6° 2θ, 9.2° 2θ, and 19.6° 2θ (±0.2° 2θ; ±0.1° 2θ; or ±0.0° 2θ; Cu Kα1 radiation). In some embodiments, the solid form of MBDB galactarate is crystalline MBDB galactarate characterized by XRPD signals at 4.6° 2θ, 9.2° 2θ, and 19.6° 2θ (±0.2° 2θ; ±0.1° 2θ; or ±0.0° 2θ; Cu Kα1 radiation).

In some embodiments, the solid form of MBDB galactarate is crystalline MBDB galactarate characterized by two or more, or three or more XRPD signals selected from the group consisting of 4.6° 2θ, 9.2° 2θ, 18.5° 2θ, 19.6° 2θ, and 23.1° 2θ (±0.2° 2θ; ±0.1° 2θ; or ±0.0° 2θ; Cu Kα1 radiation). In some embodiments, the solid form of MBDB galactarate is MBDB galactarate characterized by XRPD signals at 4.6° 2θ, 9.2° 2θ, 18.5° 2θ, 19.6° 2θ, and 23.1° 2θ (±0.2° 2θ; ±0.1° 2θ; or ±0.0° 2θ; Cu Kα1 radiation).

In some embodiments, the crystalline MBDB galactarate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four XRPD signals selected from those set forth in Table 25.

TABLE 25

XRPD Signals for MBDB galactarate

| Signal no. | Position | d-value | Relative |
|---|---|---|---|
| 1 | 4.6 | 19.3 | 11.0 |
| 2 | 9.2 | 9.7 | 44.9 |
| 3 | 12.7 | 7.0 | 1.9 |
| 4 | 13.8 | 6.4 | 2.0 |
| 5 | 14.4 | 6.1 | 2.0 |
| 6 | 15.3 | 5.8 | 1.9 |
| 7 | 16.4 | 5.4 | 1.8 |
| 8 | 17.7 | 5.0 | 3.1 |
| 9 | 18.1 | 4.9 | 4.3 |
| 10 | 18.5 | 4.8 | 6.4 |
| 11 | 19.6 | 4.5 | 100.0 |
| 12 | 21.5 | 4.1 | 4.7 |
| 13 | 23.1 | 3.9 | 13.4 |
| 14 | 23.9 | 3.7 | 2.5 |
| 15 | 25.6 | 3.5 | 2.9 |
| 16 | 26.8 | 3.3 | 3.7 |
| 17 | 27.8 | 3.2 | 2.0 |
| 18 | 29.7 | 3.0 | 3.4 |
| 19 | 30.7 | 2.9 | 6.7 |
| 20 | 34.5 | 2.6 | 1.9 |
| 21 | 34.8 | 2.6 | 1.8 |
| 22 | 36.7 | 2.4 | 1.6 |
| 23 | 37.3 | 2.4 | 2.2 |
| 24 | 39.9 | 2.3 | 4.8 |

In some embodiments, the solid form of MBDB galactarate is crystalline MBDB galactarate (mucate) characterized by two or more, or three or more XRPD signals selected from the group consisting of 4.6° 2θ, 9.2° 2θ, and 19.6° 2θ (±0.2° 2θ; ±0.1° 2θ; or ±0.0° 2θ; Cu Kα1 radiation). In some embodiments, the solid form of MBDB galactarate is crystalline MBDB galactarate characterized by XRPD signals at 4.6° 2θ, 9.2° 2θ, and 19.6° 2θ (±0.2° 2θ; ±0.1° 2θ; or ±0.0° 2θ; Cu Kα1 radiation).

In some embodiments, the solid form of MBDB galactarate is crystalline MBDB galactarate characterized by two or more, or three or more XRPD signals selected from the group consisting of 4.6° 2θ, 9.2° 2θ, 19.6° 2θ, 23.1° 2θ, and 30.7° 2θ (±0.2° 2θ; ±0.1° 2θ; or ±0.0° 2θ; Cu Kα1 radiation). In some embodiments, the solid form of MBDB galactarate is MBDB galactarate characterized by XRPD signals at 4.6° 2θ, 9.2° 2θ, 19.6° 2θ, 23.1° 2θ, and 30.7° 2θ (±0.2° 2θ; ±0.1° 2θ; or ±0.0° 2θ; Cu Kα1 radiation).

In some embodiments, the solid form of MBDB galactarate is crystalline MBDB galactarate characterized by two or more, or three or more XRPD signals selected from the group consisting of 4.6° 2θ, 9.2° 2θ, 17.7° 2θ, 18.1° 2θ, and 19.6° 2θ (±0.2° 2θ; ±0.1° 2θ; or ±0.0° 2θ; Cu Kα1 radiation). In some embodiments, the solid form of MBDB galactarate is MBDB galactarate characterized by XRPD signals at 4.6° 2θ, 9.2° 2θ, 17.7° 2θ, 18.1° 2θ, and 19.6° 2θ (±0.2° 2θ; ±0.1° 2θ; or ±0.0° 2θ; Cu Kα1 radiation).

In some embodiments, the crystalline MBDB galactarate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, or thirty-nine XRPD signals selected from those set forth in Table 26.

TABLE 26

XRPD Signals for MBDB galactarate

| Signal no. | Position | d-value | Relative |
|---|---|---|---|
| 1 | 4.6 | 19.2 | 25.0 |
| 2 | 9.2 | 9.7 | 84.5 |
| 3 | 9.8 | 9.0 | 6.3 |
| 4 | 12.7 | 7.0 | 6.6 |
| 5 | 13.4 | 6.6 | 4.4 |
| 6 | 14.0 | 6.3 | 6.3 |
| 7 | 14.4 | 6.1 | 7.2 |
| 8 | 15.3 | 5.8 | 5.9 |
| 9 | 15.6 | 5.7 | 4.9 |
| 10 | 16.5 | 5.4 | 5.7 |
| 11 | 17.4 | 5.1 | 9.5 |
| 12 | 17.7 | 5.0 | 15.2 |
| 13 | 18.1 | 4.9 | 15.4 |
| 14 | 18.7 | 4.7 | 14.9 |
| 15 | 19.6 | 4.5 | 100.0 |
| 16 | 20.5 | 4.3 | 6.2 |
| 17 | 21.1 | 4.2 | 5.7 |
| 18 | 21.5 | 4.1 | 10.4 |
| 19 | 22.0 | 4.0 | 5.0 |
| 20 | 23.1 | 3.9 | 20.3 |
| 21 | 23.8 | 3.7 | 7.8 |
| 22 | 24.1 | 3.7 | 5.9 |
| 23 | 24.5 | 3.6 | 5.8 |
| 24 | 24.8 | 3.6 | 5.2 |
| 25 | 25.6 | 3.5 | 11.9 |
| 26 | 26.1 | 3.4 | 5.3 |
| 27 | 26.8 | 3.3 | 11.5 |
| 28 | 28.2 | 3.2 | 4.3 |
| 29 | 28.5 | 3.1 | 4.5 |
| 30 | 29.0 | 3.1 | 5.5 |
| 31 | 29.4 | 3.0 | 5.1 |
| 32 | 29.7 | 3.0 | 6.4 |
| 33 | 30.7 | 2.9 | 18.3 |
| 34 | 33.1 | 2.7 | 4.0 |
| 35 | 34.5 | 2.6 | 5.6 |
| 36 | 34.9 | 2.6 | 5.2 |
| 37 | 36.7 | 2.5 | 4.4 |
| 38 | 37.6 | 2.4 | 4.2 |
| 39 | 39.8 | 2.3 | 5.6 |

Solid Forms of MBDB Maleate Form 1

Figure 29:
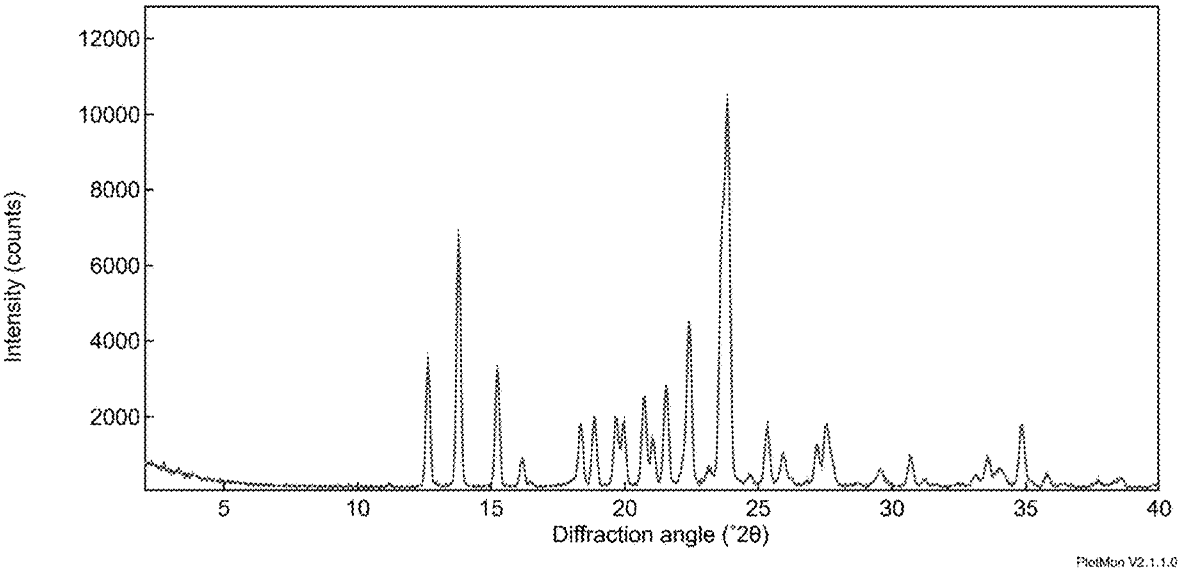
FIG. 29 provides an XRPD diffractogram of crystalline MBDB·maleate (Form 1).
Figure 71:
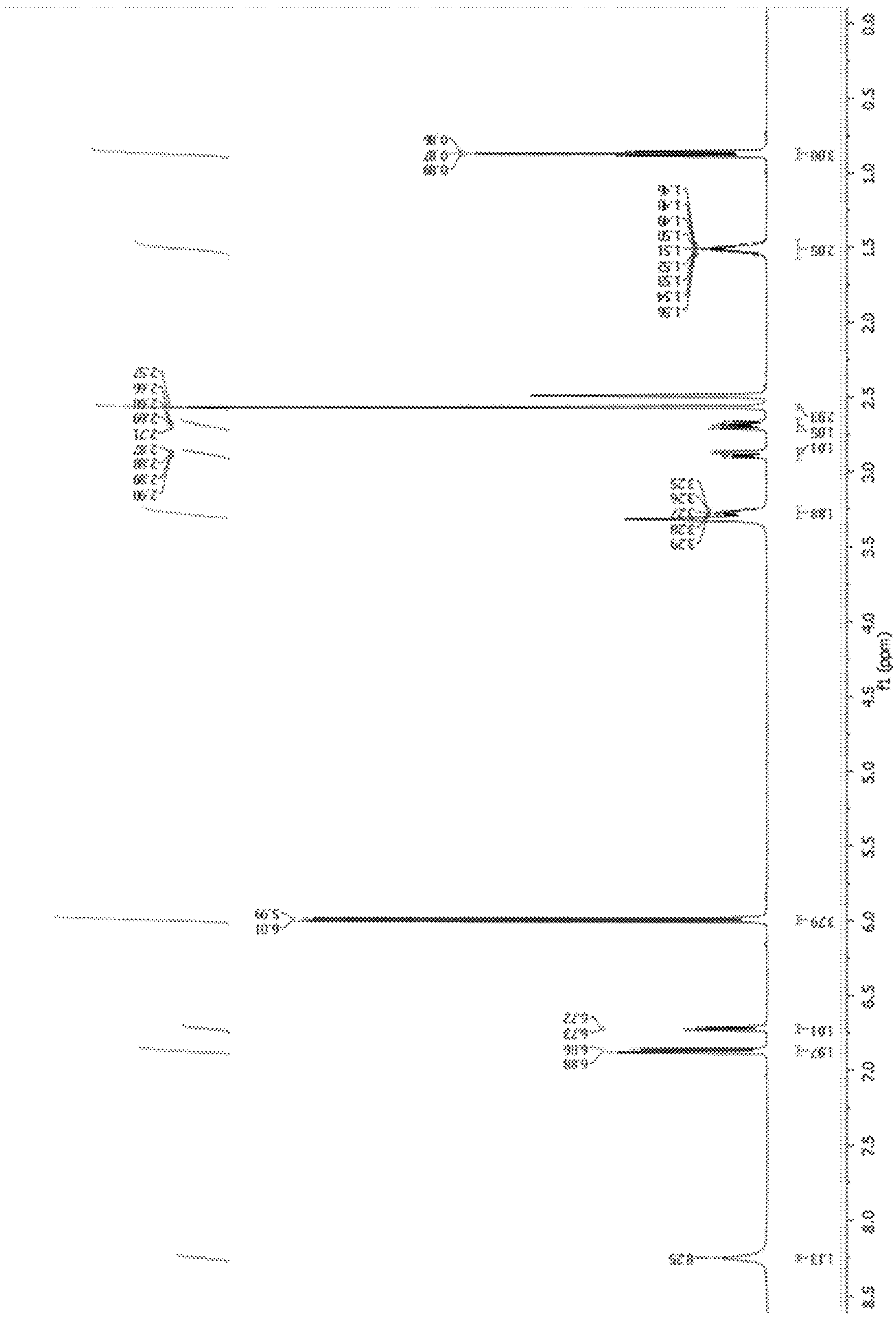
FIG. 71 provides a $^1$H NMR spectrum for MBDB maleate (Form 1).
Figure 72:
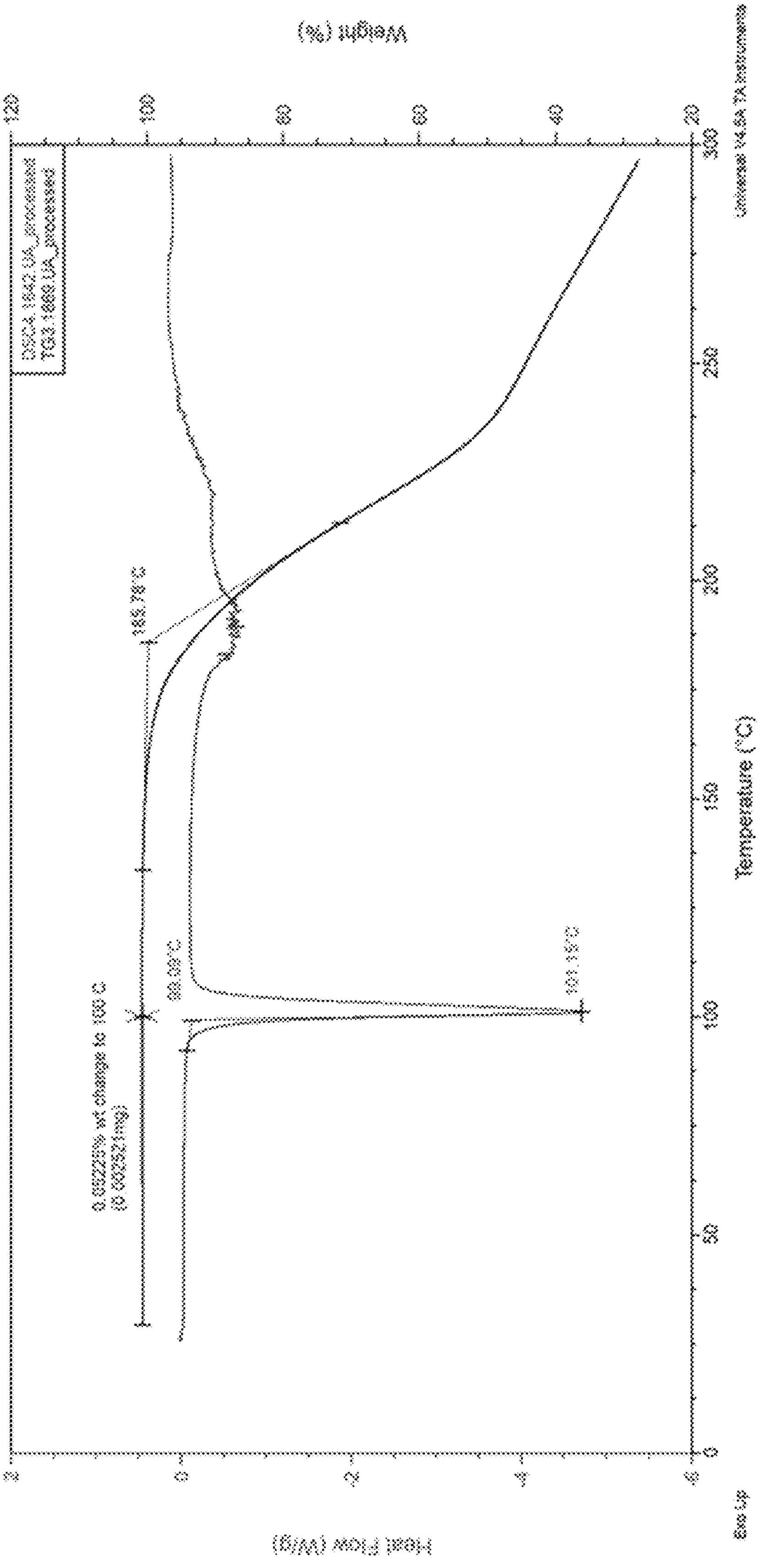
FIG. 72 provides TGA and DSC profiles for MBDB maleate (Form 1).
Figure 88:
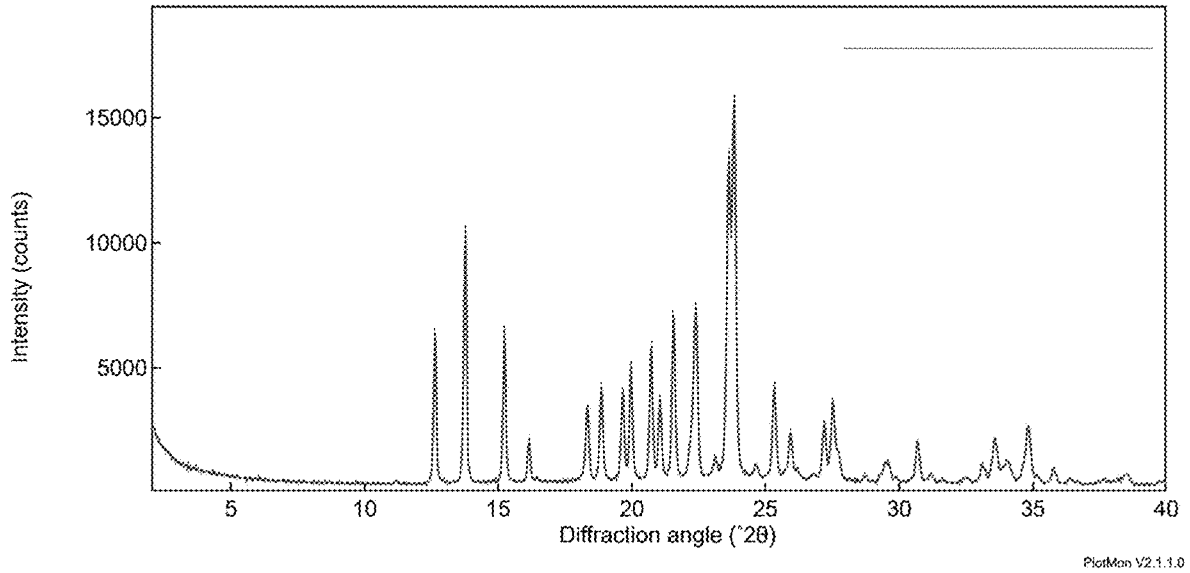
FIG. 88 provides an XRPD diffractogram of crystalline MBDB·maleate Form 1.

In some embodiments, the present disclosure provides solid forms of MBDB maleate Form 1, e.g., crystalline forms of MBDB maleate Form 1. In some embodiments, the MBDB maleate Form 1 XRPD profile is substantially similar to that shown in any one of FIG. 29 or 88. In some embodiments, the MBDB maleate Form 1 $^1$H NMR spectrum is substantially similar to that shown in FIG. 71. In some embodiments, the MBDB maleate Form 1 TGA profile is substantially similar to that shown in FIG. 72. In some embodiments, the MBDB maleate Form 1 DSC profile is substantially similar to that shown in FIG. 72.

In some embodiments, the solid form of MBDB maleate Form 1 is crystalline MBDB maleate Form 1 characterized by two or more, or three or more XRPD signals selected from the group consisting of 13.8° 2θ, 22.4° 2θ, and 23.8° 2θ (±0.2° 2θ; ±0.1° 2θ; or ±0.0° 2θ; Cu Kα1 radiation). In some embodiments, the solid form of MBDB maleate Form 1 is crystalline MBDB maleate Form 1 characterized by XRPD signals at 13.8° 2θ, 22.4° 2θ, and 23.8° 2θ (±0.2° 2θ; ±0.1° 2θ; or ±0.0° 2θ; Cu Kα1 radiation).

In some embodiments, the solid form of MBDB maleate Form 1 is crystalline MBDB maleate Form 1 characterized by two or more, or three or more XRPD signals selected from the group consisting of 12.6° 2θ, 13.8° 2θ, 15.2° 2θ, 22.4° 2θ, and 23.8° 2θ (±0.2° 2θ; ±0.1° 2θ; or ±0.0° 2θ; Cu Kα1 radiation). In some embodiments, the solid form of MBDB maleate Form 1 is MBDB maleate Form 1 characterized by XRPD signals at 12.6° 2θ, 13.8° 2θ, 15.2° 2θ, 22.4° 2θ, and 23.8° 2θ (±0.2° 2θ; ±0.1° 2θ; or ±0.0° 2θ; Cu Kα1 radiation).

In some embodiments, the solid form of MBDB maleate Form 1 is crystalline MBDB maleate Form 1 characterized by two or more, or three or more XRPD signals selected from the group consisting of 12.6° 2θ, 13.8° 2θ, and 15.2° 2θ (±0.2° 2θ; ±0.1° 2θ; or ±0.0° 2θ; Cu Kα1 radiation). In some embodiments, the solid form of MBDB maleate Form 1 is crystalline MBDB maleate Form 1 characterized by XRPD signals at 12.6° 2θ, 13.8° 2θ, and 15.2° 2θ (±0.2° 2θ; ±0.1° 2θ; or ±0.0° 2θ; Cu Kα1 radiation).

In some embodiments, the solid form of MBDB maleate Form 1 is crystalline MBDB maleate Form 1 characterized by two or more, or three or more XRPD signals selected from the group consisting of 12.6° 2θ, 13.8° 2θ, 15.2° 2θ, 16.2° 2θ, and 18.3° 2θ (±0.2° 2θ; ±0.1° 2θ; or ±0.0° 2θ; Cu Kα1 radiation). In some embodiments, the solid form of MBDB maleate Form 1 is MBDB maleate Form 1 characterized by XRPD signals at 12.6° 2θ, 13.8° 2θ, 15.2° 2θ, 16.2° 2θ, and 18.3° 2θ (±0.2° 2θ; ±0.1° 2θ; or ±0.0° 2θ; Cu Kα1 radiation).

In some embodiments, the crystalline MBDB maleate Form 1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, or thirty-four XRPD signals selected from those set forth in Table 27.

TABLE 27

XRPD Signals for MBDB maleate Form 1

| Signal no. | Position | d-value | Relative |
|---|---|---|---|
| 1 | 12.6 | 7.0 | 33.4 |
| 2 | 13.8 | 6.4 | 65.5 |
| 3 | 15.2 | 5.8 | 31.4 |
| 4 | 16.2 | 5.5 | 8.4 |
| 5 | 18.3 | 4.8 | 17.7 |
| 6 | 18.8 | 4.7 | 18.8 |
| 7 | 19.6 | 4.5 | 18.9 |
| 8 | 20.0 | 4.4 | 18.2 |
| 9 | 20.7 | 4.3 | 24.4 |
| 10 | 21.0 | 4.2 | 13.9 |
| 11 | 21.5 | 4.1 | 27.1 |
| 12 | 22.4 | 4.0 | 43.6 |
| 13 | 23.1 | 3.9 | 6.2 |
| 14 | 23.8 | 3.7 | 100.0 |
| 15 | 24.7 | 3.6 | 4.7 |
| 16 | 25.3 | 3.5 | 16.9 |
| 17 | 25.9 | 3.4 | 10.0 |
| 18 | 27.2 | 3.3 | 12.1 |
| 19 | 27.5 | 3.2 | 17.6 |
| 20 | 28.7 | 3.1 | 2.5 |
| 21 | 29.5 | 3.0 | 5.8 |
| 22 | 30.7 | 2.9 | 9.1 |
| 23 | 31.2 | 2.9 | 3.5 |
| 24 | 31.6 | 2.8 | 2.1 |
| 25 | 32.5 | 2.8 | 2.4 |
| 26 | 33.1 | 2.7 | 4.5 |
| 27 | 33.6 | 2.7 | 9.1 |
| 28 | 34.1 | 2.6 | 6.3 |
| 29 | 34.9 | 2.6 | 17.1 |
| 30 | 35.8 | 2.5 | 4.7 |
| 31 | 36.5 | 2.5 | 2.4 |
| 32 | 36.7 | 2.4 | 1.9 |
| 33 | 37.7 | 2.4 | 3.2 |
| 34 | 38.5 | 2.3 | 3.7 |

In some embodiments, the solid form of MBDB maleate Form 1 is crystalline MBDB maleate Form 1 characterized by two or more, or three or more XRPD signals selected from the group consisting of 13.8° 2θ, 23.6° 2θ, and 23.8° 2θ (±0.2° 2θ; ±0.1° 2θ; or ±0.0° 2θ; Cu Kα1 radiation). In some embodiments, the solid form of MBDB maleate Form 1 is crystalline MBDB maleate Form 1 characterized by XRPD signals at 13.8° 2θ, 23.6° 2θ, and 23.8° 2θ (±0.2° 2θ; ±0.1° 2θ; or ±0.0° 2θ; Cu Kα1 radiation).

In some embodiments, the solid form of MBDB maleate Form 1 is crystalline MBDB maleate Form 1 characterized by two or more, or three or more XRPD signals selected from the group consisting of 13.8° 2θ, 21.5° 2θ, 22.4° 2θ, 23.6° 2θ, and 23.8° 2θ (±0.2° 2θ; ±0.1° 2θ; or ±0.0° 2θ; Cu Kα1 radiation). In some embodiments, the solid form of MBDB maleate Form 1 is MBDB maleate Form 1 characterized by XRPD signals at 13.8° 2θ, 21.5° 2θ, 22.4° 2θ, 23.6° 2θ, and 23.8° 2θ (±0.2° 2θ; ±0.1° 2θ; or ±0.0° 2θ; Cu Kα1 radiation).

In some embodiments, the solid form of MBDB maleate Form 1 is crystalline MBDB maleate Form 1 characterized by two or more, or three or more XRPD signals selected from the group consisting of 12.6° 2θ, 13.8° 2θ, and 15.2° 2θ (±0.2° 2θ; ±0.1° 2θ; or ±0.0° 2θ; Cu Kα1 radiation). In some embodiments, the solid form of MBDB maleate Form 1 is crystalline MBDB maleate Form 1 characterized by XRPD signals at 12.6° 2θ, 13.8° 2θ, and 15.2° 2θ (±0.2° 2θ; ±0.1° 2θ; or ±0.0° 2θ; Cu Kα1 radiation).

In some embodiments, the solid form of MBDB maleate Form 1 is crystalline MBDB maleate Form 1 characterized by two or more, or three or more XRPD signals selected from the group consisting of 12.6° 2θ, 13.8° 2θ, and 15.2° 2θ, 16.2° 2θ, and 18.3° 2θ (±0.2° 2θ; ±0.1° 2θ; or ±0.0° 2θ;

Cu Kα1 radiation). In some embodiments, the solid form of MBDB maleate Form 1 is MBDB maleate Form 1 characterized by XRPD signals at 12.6° 2θ, 13.8° 2θ, and 15.2° 2θ, 16.2° 2θ, and 18.3° 2θ (±0.2° 2θ; ±0.1° 2θ; or ±0.0° 2θ; Cu Kα1 radiation).

In some embodiments, the crystalline MBDB maleate Form 1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, or thirty-five XRPD signals selected from those set forth in Table 28.

TABLE 28

XRPD Signals for MBDB maleate Form 1

| Signal no. | Position | d-value | Relative |
|---|---|---|---|
| 1 | 12.6 | 7.0 | 40.3 |
| 2 | 13.8 | 6.4 | 66.1 |
| 3 | 15.2 | 5.8 | 40.3 |
| 4 | 16.2 | 5.5 | 13.3 |
| 5 | 18.3 | 4.8 | 21.8 |
| 6 | 18.9 | 4.7 | 26.6 |
| 7 | 19.7 | 4.5 | 25.7 |
| 8 | 20.0 | 4.4 | 31.7 |
| 9 | 20.7 | 4.3 | 36.5 |
| 10 | 21.0 | 4.2 | 24.0 |
| 11 | 21.5 | 4.1 | 44.9 |
| 12 | 22.4 | 4.0 | 47.2 |
| 13 | 23.1 | 3.9 | 9.2 |
| 14 | 23.6 | 3.8 | 85.7 |
| 15 | 23.8 | 3.7 | 100.0 |
| 16 | 24.7 | 3.6 | 7.3 |
| 17 | 25.3 | 3.5 | 26.8 |
| 18 | 25.9 | 3.4 | 15.4 |
| 19 | 27.2 | 3.3 | 18.0 |
| 20 | 27.5 | 3.2 | 23.1 |
| 21 | 28.7 | 3.1 | 4.6 |
| 22 | 29.6 | 3.0 | 8.0 |
| 23 | 29.9 | 3.0 | 4.4 |
| 24 | 30.7 | 2.9 | 13.0 |
| 25 | 31.2 | 2.9 | 4.7 |
| 26 | 32.4 | 2.8 | 3.9 |
| 27 | 33.1 | 2.7 | 7.4 |
| 28 | 33.6 | 2.7 | 14.1 |
| 29 | 34.0 | 2.6 | 8.2 |
| 30 | 34.8 | 2.6 | 17.0 |
| 31 | 35.1 | 2.6 | 4.7 |
| 32 | 35.8 | 2.5 | 6.4 |
| 33 | 36.4 | 2.5 | 3.6 |
| 34 | 37.6 | 2.4 | 3.5 |
| 35 | 38.5 | 2.3 | 4.7 |

In some embodiments, the solid form of MBDB maleate Form 1 is crystalline MBDB maleate Form 1 characterized by two or more, or three or more XRPD signals selected from the group consisting of 12.6° 2θ, 13.9° 2θ, and 15.3° 2θ (±0.2° 2θ; ±0.1° 2θ; or ±0.0° 2θ; Cu Kα1 radiation). In some embodiments, the solid form of MBDB maleate Form 1 is crystalline MBDB maleate Form 1 characterized by XRPD signals at 12.6° 2θ, 13.9° 2θ, and 15.3° 2θ (±0.2° 2θ; ±0.1° 2θ; or ±0.0° 2θ; Cu Kα1 radiation).

In some embodiments, the solid form of MBDB maleate Form 1 is crystalline MBDB maleate Form 1 characterized by two or more, or three or more XRPD signals selected from the group consisting of 12.6° 2θ, 13.9° 2θ, 15.3° 2θ, 18.4° 2θ, and 19.0° 2θ (±0.2° 2θ; ±0.1° 2θ; or ±0.0° 2θ; Cu Kα1 radiation). In some embodiments, the solid form of MBDB maleate Form 1 is MBDB maleate Form 1 characterized by XRPD signals at 12.6° 2θ, 13.9° 2θ, 15.3° 2θ, 18.4° 2θ, and 19.0° 2θ (±0.2° 2θ; ±0.1° 2θ; or ±0.0° 2θ; Cu Kα1 radiation).

In some embodiments, the crystalline MBDB maleate Form 1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, or fifty-seven XRPD signals selected from those set forth in Table 28A.

TABLE 28A

XRPD Signals calculated from a single crystal of MBDB maleate Form 1

| Signal no. | Position | Relative |
|---|---|---|
| 1 | 9.6 | 0.7 |
| 2 | 11.3 | 0.2 |
| 3 | 12.6 | 49.1 |
| 4 | 13.0 | 2.0 |
| 5 | 13.9 | 58.1 |
| 6 | 15.3 | 34.4 |
| 7 | 16.3 | 11.0 |
| 8 | 16.3 | 11.0 |
| 9 | 16.5 | 1.4 |
| 10 | 18.4 | 17.4 |
| 11 | 19.0 | 33.3 |
| 12 | 19.9 | 36.2 |
| 13 | 19.9 | 37.4 |
| 14 | 20.9 | 45.5 |
| 15 | 21.0 | 29.9 |
| 16 | 21.6 | 53.4 |
| 17 | 22.4 | 4.8 |
| 18 | 22.6 | 28.1 |
| 19 | 23.3 | 6.2 |
| 20 | 23.9 | 70.7 |
| 21 | 24.1 | 100.0 |
| 22 | 24.7 | 4.4 |
| 23 | 25.4 | 37.8 |
| 24 | 25.9 | 2.5 |
| 25 | 26.1 | 11.0 |
| 26 | 26.4 | 4.6 |
| 27 | 27.1 | 2.8 |
| 28 | 27.4 | 19.9 |
| 29 | 27.8 | 27.6 |
| 30 | 28.0 | 9.7 |
| 31 | 28.7 | 2.7 |
| 32 | 29.2 | 1.4 |
| 33 | 29.7 | 13.1 |
| 34 | 30.3 | 1.0 |
| 35 | 30.9 | 17.3 |
| 36 | 31.5 | 4.3 |
| 37 | 31.8 | 1.8 |
| 38 | 32.5 | 1.7 |
| 39 | 33.0 | 1.9 |
| 40 | 33.2 | 7.0 |
| 41 | 33.6 | 25.0 |
| 42 | 33.9 | 2.2 |
| 43 | 34.3 | 6.6 |
| 44 | 34.4 | 13.6 |
| 45 | 34.9 | 1.6 |
| 46 | 35.3 | 18.6 |
| 47 | 35.5 | 4.0 |
| 48 | 36.2 | 7.3 |
| 49 | 36.6 | 3.1 |
| 50 | 37.1 | 1.2 |
| 51 | 37.4 | 0.5 |
| 52 | 37.9 | 1.2 |
| 53 | 38.1 | 3.6 |
| 54 | 38.5 | 3.4 |

TABLE 28A-continued

| XRPD Signals calculated from a single crystal of MBDB maleate Form 1 | | |
|---|---|---|
| Signal no. | Position | Relative |
| 55 | 38.8 | 3.9 |
| 56 | 39.0 | 4.5 |
| 57 | 39.6 | 0.6 |

Solid Forms of MBDB Phosphate

Figure 30:
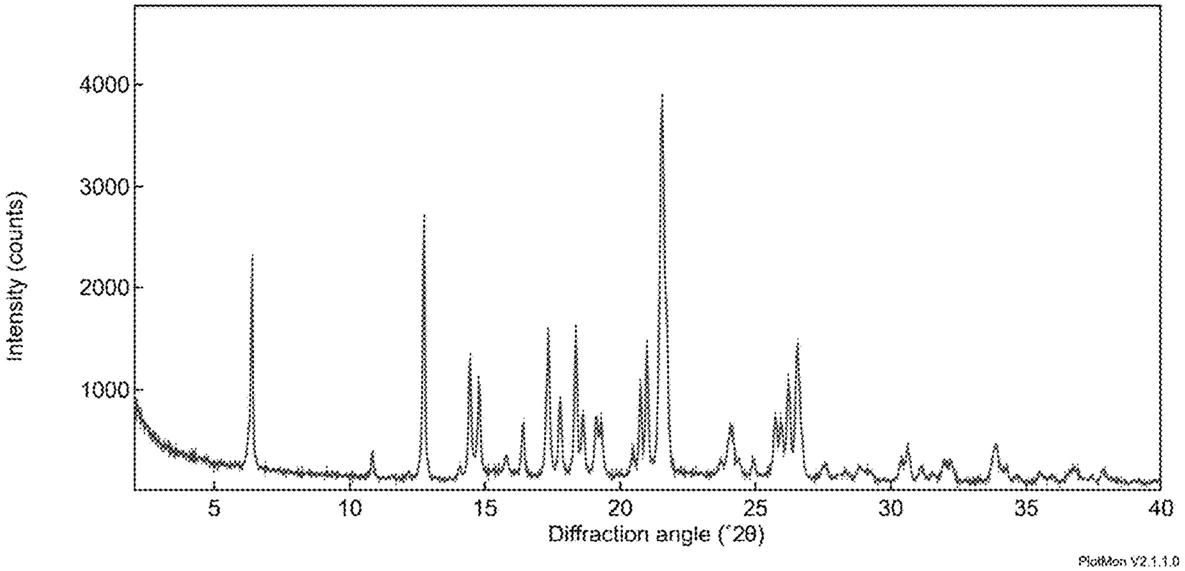
FIG. 30 provides an XRPD diffractogram of crystalline MBDB·phosphate.
Figure 75:
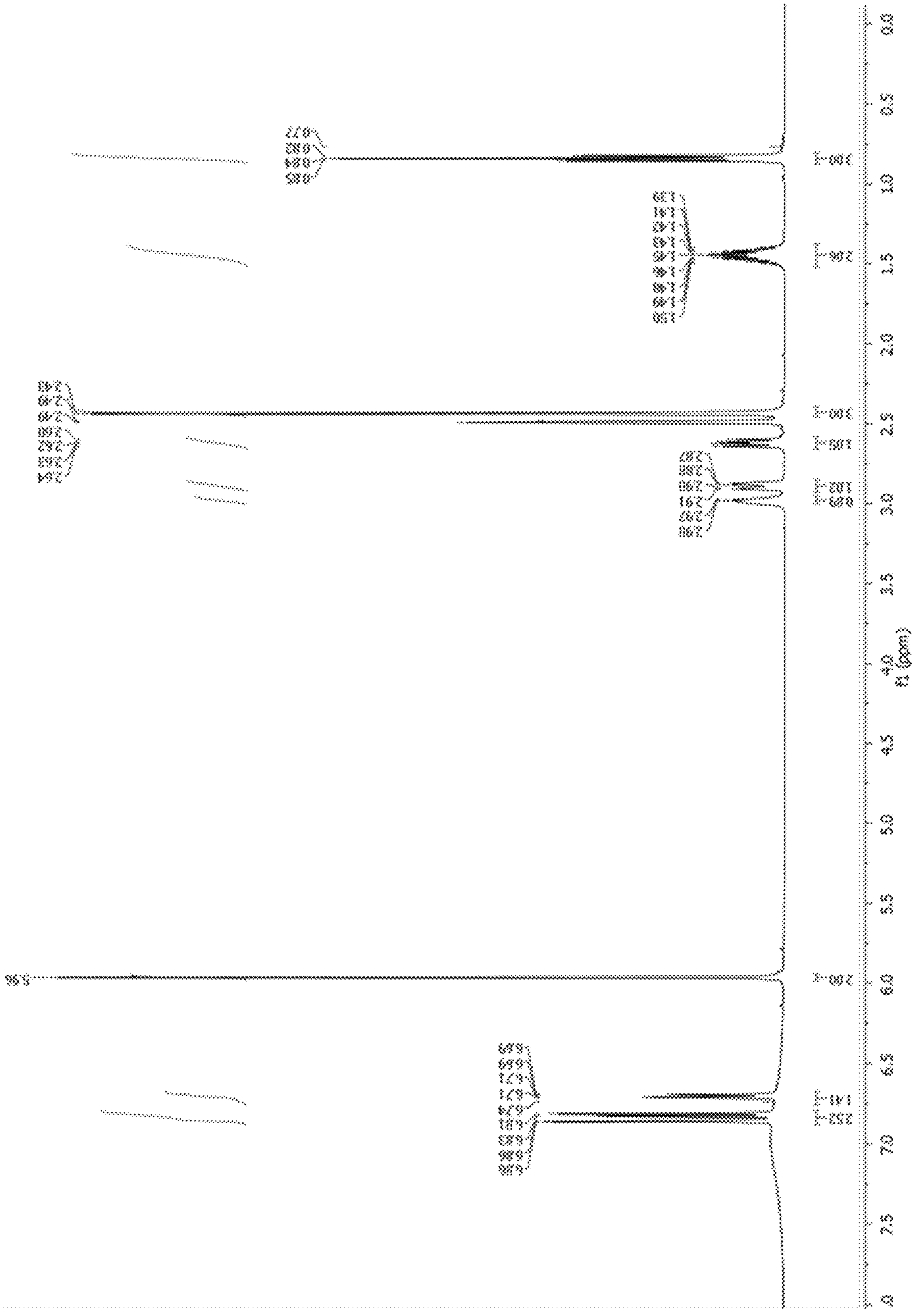
FIG. 75 provides a $^1$H NMR spectrum for MBDB phosphate.
Figure 76:
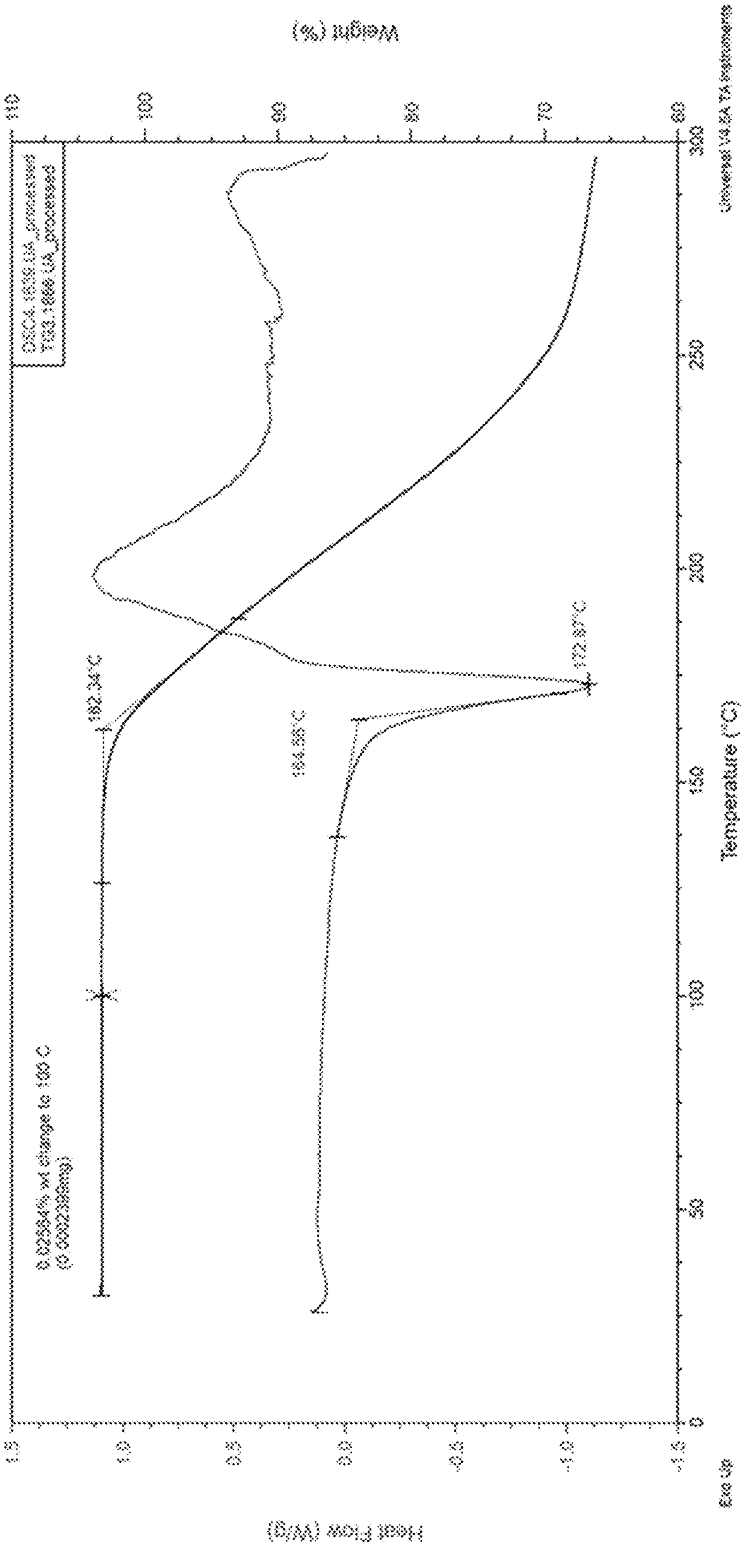
FIG. 76 provides TGA and DSC profiles for MBDB phosphate.

In some embodiments, the present disclosure provides solid forms of MBDB phosphate, e.g., crystalline forms of MBDB phosphate. In some embodiments, the MBDB phosphate XRPD profile is substantially similar to that shown in FIG. 30. In some embodiments, the MBDB phosphate $^{1}$H NMR spectrum is substantially similar to that shown in FIG. 75. In some embodiments, the MBDB phosphate TGA profile is substantially similar to that shown in FIG. 76. In some embodiments, the MBDB phosphate DSC profile is substantially similar to that shown in FIG. 76.

In some embodiments, the solid form of MBDB phosphate is crystalline MBDB phosphate characterized by two or more, or three or more XRPD signals selected from the group consisting of 6.4° 2θ, 12.7° 2θ, and 21.5° 2θ (±0.2° 2θ; ±0.1° 2θ; or ±0.0° 2θ; Cu Kα1 radiation). In some embodiments, the solid form of MBDB phosphate is crystalline MBDB phosphate characterized by XRPD signals at 6.4° 2θ, 12.7° 2θ, and 21.5° 2θ (±0.2° 2θ; ±0.1° 2θ; or ±0.0° 2θ; Cu Kα1 radiation).

In some embodiments, the solid form of MBDB phosphate is crystalline MBDB phosphate characterized by two or more, or three or more XRPD signals selected from the group consisting of 6.4° 2θ, 12.7° 2θ, 17.3° 2θ, 18.4° 2θ, and 21.5° 2θ (±0.2° 2θ; ±0.1° 2θ; or ±0.0° 2θ; Cu Kα1 radiation). In some embodiments, the solid form of MBDB phosphate is MBDB phosphate characterized by XRPD signals at 6.4° 2θ, 12.7° 2θ, 17.3° 2θ, 18.4° 2θ, and 21.5° 2θ (±0.2° 2θ; ±0.1° 2θ; or ±0.0° 2θ; Cu Kα1 radiation).

In some embodiments, the solid form of MBDB phosphate is crystalline MBDB phosphate characterized by two or more, or three or more XRPD signals selected from the group consisting of 6.4° 2θ, 12.7° 2θ, and 14.5° 2θ (±0.2° 2θ; ±0.1° 2θ; or ±0.0° 2θ; Cu Kα1 radiation). In some embodiments, the solid form of MBDB phosphate is crystalline MBDB phosphate characterized by XRPD signals at 6.4° 2θ, 12.7° 2θ, and 14.5° 2θ (±0.2° 2θ; ±0.1° 2θ; or ±0.0° 2θ; Cu Kα1 radiation).

In some embodiments, the solid form of MBDB phosphate is crystalline MBDB phosphate characterized by two or more, or three or more XRPD signals selected from the group consisting of 6.4° 2θ, 12.7° 2θ, 14.5° 2θ, 14.8° 2θ, and 17.3° 2θ (±0.2° 2θ; ±0.1° 2θ; or ±0.0° 2θ; Cu Kα1 radiation). In some embodiments, the solid form of MBDB phosphate is MBDB phosphate characterized by XRPD signals at 6.4° 2θ, 12.7° 2θ, 14.5° 2θ, 14.8° 2θ, and 17.3° 2θ (±0.2° 2θ; ±0.1° 2θ; or ±0.0° 2θ; Cu Kα1 radiation).

In some embodiments, the crystalline MBDB phosphate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four XRPD signals selected from those set forth in Table 29.

TABLE 29

| XRPD Signals for MBDB phosphate | | | |
|---|---|---|---|
| Signal no. | Position | d-value | Relative |
| 1 | 6.4 | 13.8 | 58.1 |
| 2 | 10.8 | 8.2 | 10.0 |
| 3 | 12.7 | 6.9 | 68.8 |
| 4 | 14.1 | 6.3 | 6.9 |
| 5 | 14.5 | 6.1 | 33.6 |
| 6 | 14.8 | 6.0 | 27.8 |
| 7 | 15.8 | 5.6 | 9.3 |
| 8 | 16.4 | 5.4 | 17.4 |
| 9 | 17.3 | 5.1 | 39.7 |
| 10 | 17.8 | 5.0 | 23.6 |
| 11 | 18.4 | 4.8 | 40.2 |
| 12 | 18.6 | 4.8 | 19.8 |
| 13 | 19.1 | 4.6 | 19.5 |
| 14 | 19.3 | 4.6 | 17.7 |
| 15 | 20.5 | 4.3 | 10.4 |
| 16 | 20.7 | 4.3 | 26.5 |
| 17 | 21.0 | 4.2 | 36.6 |
| 18 | 21.5 | 4.1 | 100.0 |
| 19 | 23.7 | 3.8 | 8.2 |
| 20 | 24.1 | 3.7 | 16.8 |
| 21 | 24.4 | 3.7 | 8.6 |
| 22 | 24.9 | 3.6 | 8.6 |
| 23 | 25.7 | 3.5 | 19.2 |
| 24 | 25.9 | 3.4 | 18.3 |
| 25 | 26.2 | 3.4 | 28.5 |
| 26 | 26.6 | 3.4 | 36.9 |
| 27 | 27.6 | 3.2 | 7.2 |
| 28 | 28.3 | 3.2 | 5.9 |
| 29 | 28.8 | 3.1 | 6.8 |
| 30 | 29.2 | 3.1 | 5.8 |
| 31 | 30.4 | 2.9 | 8.5 |
| 32 | 30.6 | 2.9 | 11.7 |
| 33 | 31.1 | 2.9 | 6.6 |
| 34 | 31.5 | 2.8 | 5.0 |
| 35 | 32.0 | 2.8 | 8.2 |
| 36 | 32.2 | 2.8 | 8.0 |
| 37 | 33.9 | 2.6 | 12.0 |
| 38 | 34.3 | 2.6 | 6.7 |
| 39 | 34.7 | 2.6 | 4.3 |
| 40 | 35.5 | 2.5 | 5.2 |
| 41 | 36.0 | 2.5 | 4.1 |
| 42 | 36.7 | 2.4 | 6.2 |
| 43 | 37.4 | 2.4 | 4.3 |
| 44 | 37.8 | 2.4 | 5.7 |

Solid Forms of MBDB Succinate Form 1

Figure 31:
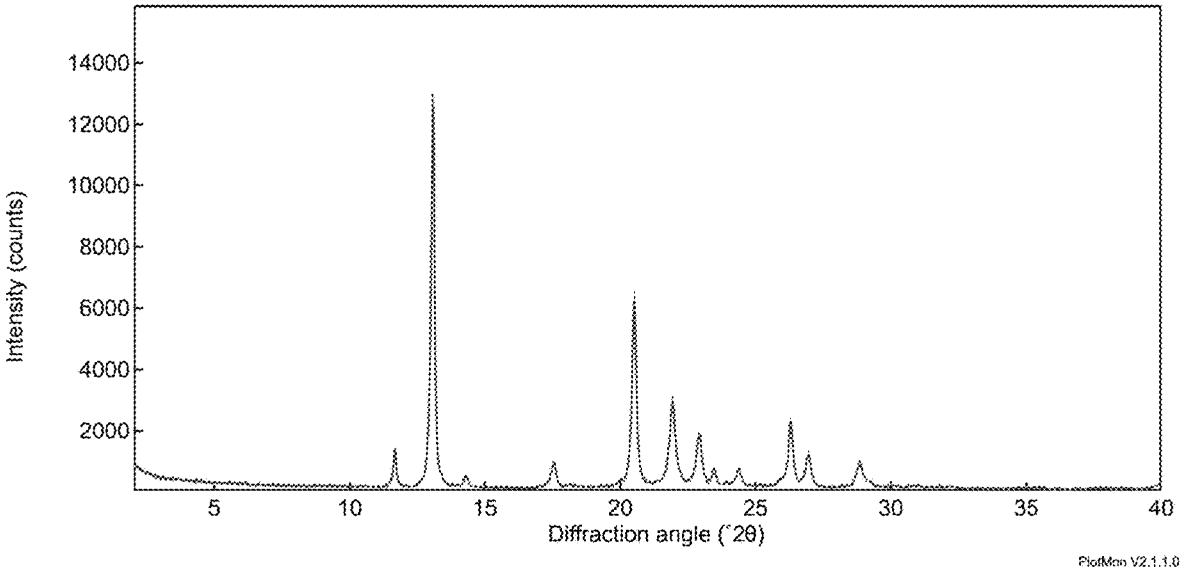
FIG. 31 provides an XRPD diffractogram of crystalline MBDB·succinate.
Figure 77:
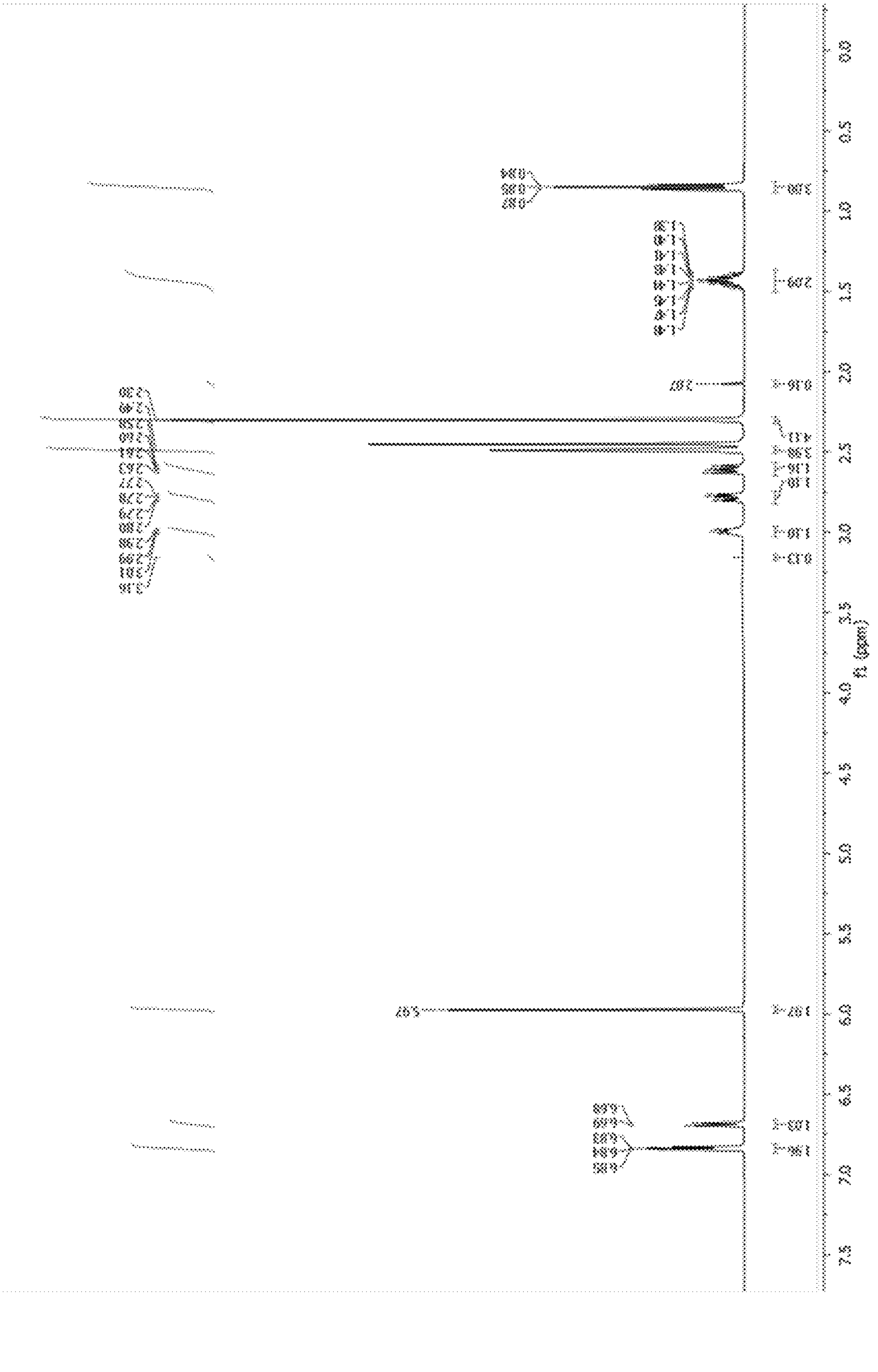
FIG. 77 provides a $^1$H NMR spectrum for MBDB succinate Form 1.
Figure 78:
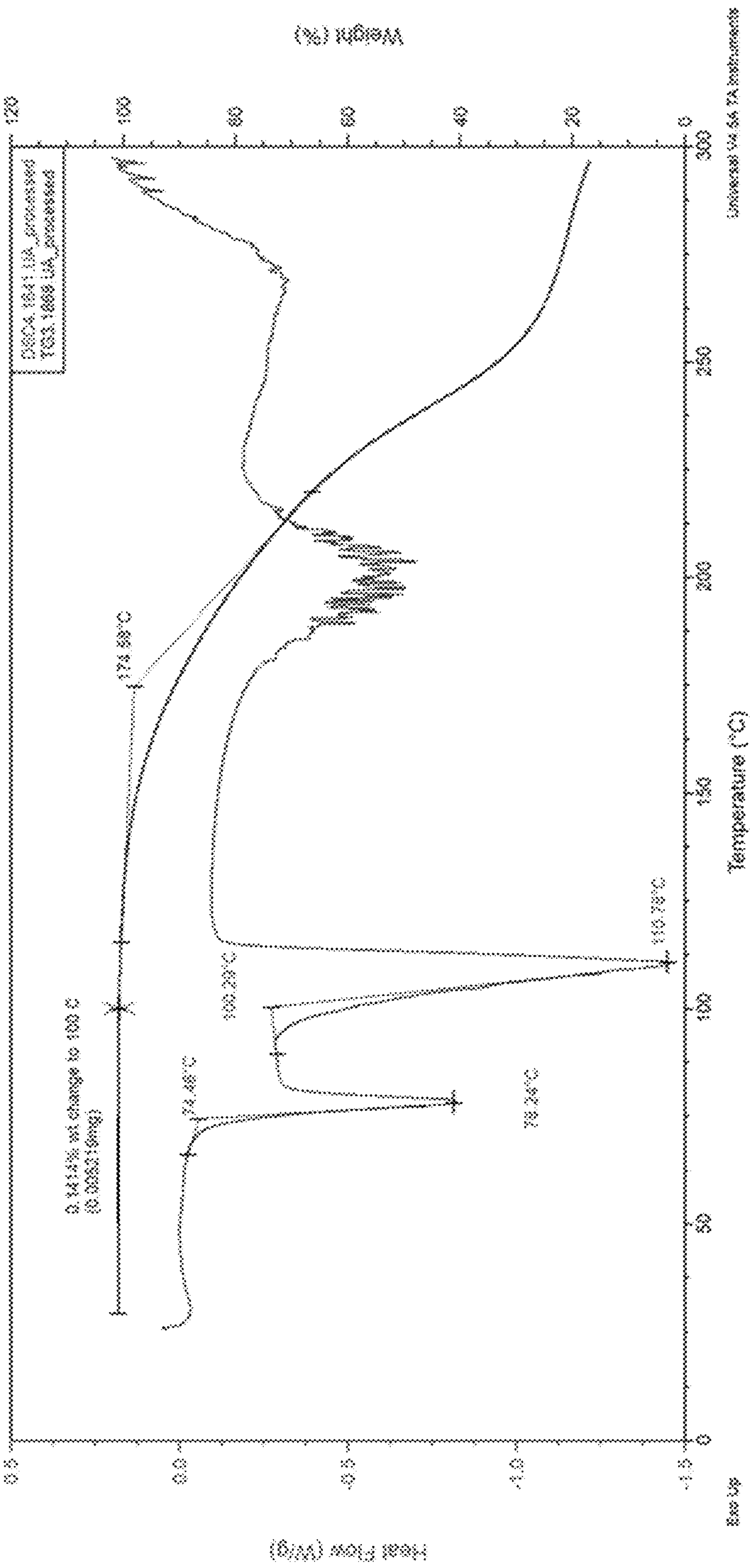
FIG. 78 provides TGA and DSC profiles for MBDB succinate Form 1.

In some embodiments, the present disclosure provides solid forms of MBDB succinate Form 1, e.g., crystalline forms of MBDB succinate Form 1. In some embodiments, the MBDB succinate Form 1 XRPD profile is substantially similar to that shown in FIG. 31. In some embodiments, the MBDB succinate Form 1 $^{1}$H NMR spectrum is substantially similar to that shown in FIG. 77. In some embodiments, the MBDB succinate Form 1 TGA profile is substantially similar to that shown in FIG. 78. In some embodiments, the MBDB succinate Form 1 DSC profile is substantially similar to that shown in FIG. 78.

In some embodiments, the solid form of MBDB succinate Form 1 is crystalline MBDB succinate Form 1 characterized by two or more, or three or more XRPD signals selected from the group consisting of 13.1° 2θ, 20.5° 2θ, and 21.9° 2θ (±0.2° 2θ; ±0.1° 2θ; or ±0.0° 2θ; Cu Kα1 radiation). In some embodiments, the solid form of MBDB succinate Form 1 is crystalline MBDB succinate Form 1 characterized by XRPD signals at 13.1° 2θ, 20.5° 2θ, and 21.9° 2θ (±0.2° 2θ; ±0.1° 2θ; or ±0.0° 2θ; Cu Kα1 radiation).

In some embodiments, the solid form of MBDB succinate Form 1 is crystalline MBDB succinate Form 1 characterized by two or more, or three or more XRPD signals selected from the group consisting of 13.1° 2θ, 20.5° 2θ, 21.9° 2θ, 22.9° 2θ, and 26.3° 2θ (±0.2° 2θ; =0.1° 2θ; or ±0.0° 2θ; Cu Kα1 radiation). In some embodiments, the solid form of MBDB succinate Form 1 is MBDB succinate Form 1 characterized by XRPD signals at 13.1° 2θ, 20.5° 2θ, 21.9° 2θ, 22.9° 2θ, and 26.3° 2θ (±0.2° 2θ; ±0.1° 2θ; or ±0.0° 2θ; Cu Kα1 radiation).

In some embodiments, the solid form of MBDB succinate Form 1 is crystalline MBDB succinate Form 1 characterized by two or more, or three or more XRPD signals selected from the group consisting of 11.7° 2θ, 13.1° 2θ, and 20.5° 2θ (±0.2° 2θ; ±0.1° 2θ; or ±0.0° 2θ; Cu Kα1 radiation). In some embodiments, the solid form of MBDB succinate Form 1 is crystalline MBDB succinate Form 1 characterized by XRPD signals at 11.7° 2θ, 13.1° 2θ, and 20.5° 2θ (±0.2° 2θ; ±0.1° 2θ; or ±0.0° 2θ; Cu Kα1 radiation).

In some embodiments, the solid form of MBDB succinate Form 1 is crystalline MBDB succinate Form 1 characterized by two or more, or three or more XRPD signals selected from the group consisting of 11.7° 2θ, 13.1° 2θ, 20.5° 2θ, 21.9° 2θ, and 22.9° 2θ (±0.2° 2θ; ±0.1° 2θ; or ±0.0° 2θ; Cu Kα1 radiation). In some embodiments, the solid form of MBDB succinate Form 1 is MBDB succinate Form 1 characterized by XRPD signals at 11.7° 2θ, 13.1° 2θ, 20.5° 2θ, 21.9° 2θ, and 22.9° 2θ (±0.2° 2θ; ±0.1° 2θ; or ±0.0° 2θ; Cu Kα1 radiation).

In some embodiments, the crystalline MBDB succinate Form 1 is characterized by one, two, three, four, five, six, seven, eight, nine, ten, eleven, or twelve XRPD signals selected from those set forth in Table 30.

TABLE 30

XRPD Signals for MBDB succinate Form 1

| Signal no. | Position | d-value | Relative |
|---|---|---|---|
| 1 | 11.7 | 7.6 | 10.9 |
| 2 | 13.1 | 6.8 | 100.0 |
| 3 | 14.3 | 6.2 | 4.3 |
| 4 | 17.5 | 5.1 | 7.6 |
| 5 | 20.5 | 4.3 | 49.4 |
| 6 | 21.9 | 4.1 | 23.4 |
| 7 | 22.9 | 3.9 | 14.8 |
| 8 | 23.5 | 3.8 | 6.0 |
| 9 | 24.4 | 3.7 | 5.8 |
| 10 | 26.3 | 3.4 | 18.5 |
| 11 | 27.0 | 3.3 | 9.9 |
| 12 | 28.8 | 3.1 | 7.4 |

Solid Forms of MBDB Sulfate

Figure 32:
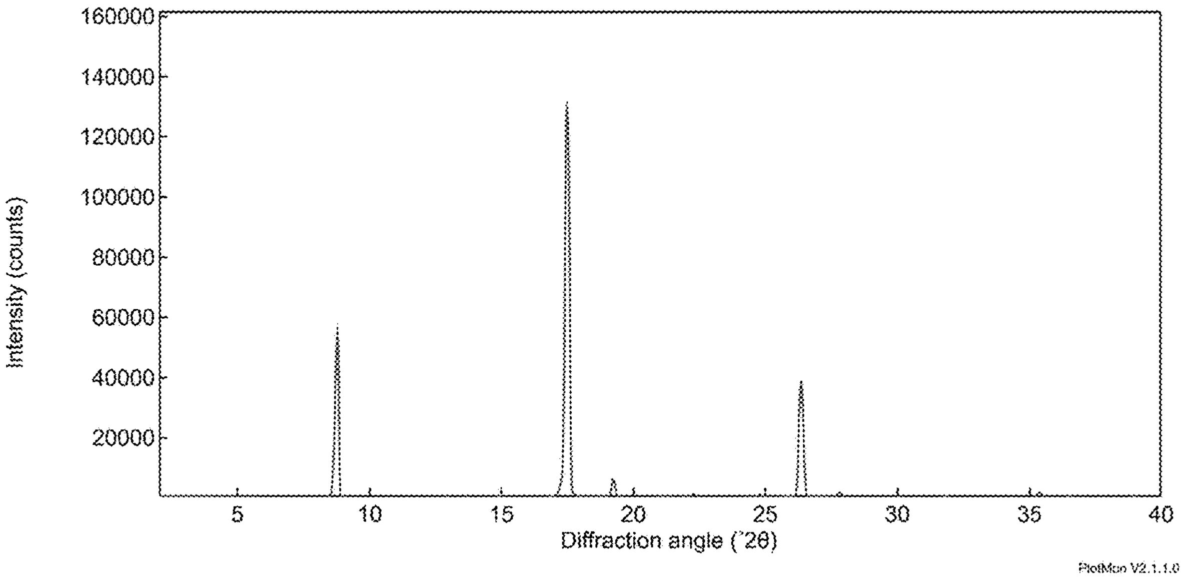
FIG. 32 provides an XRPD diffractogram of crystalline MBDB·sulfate.
Figure 81:
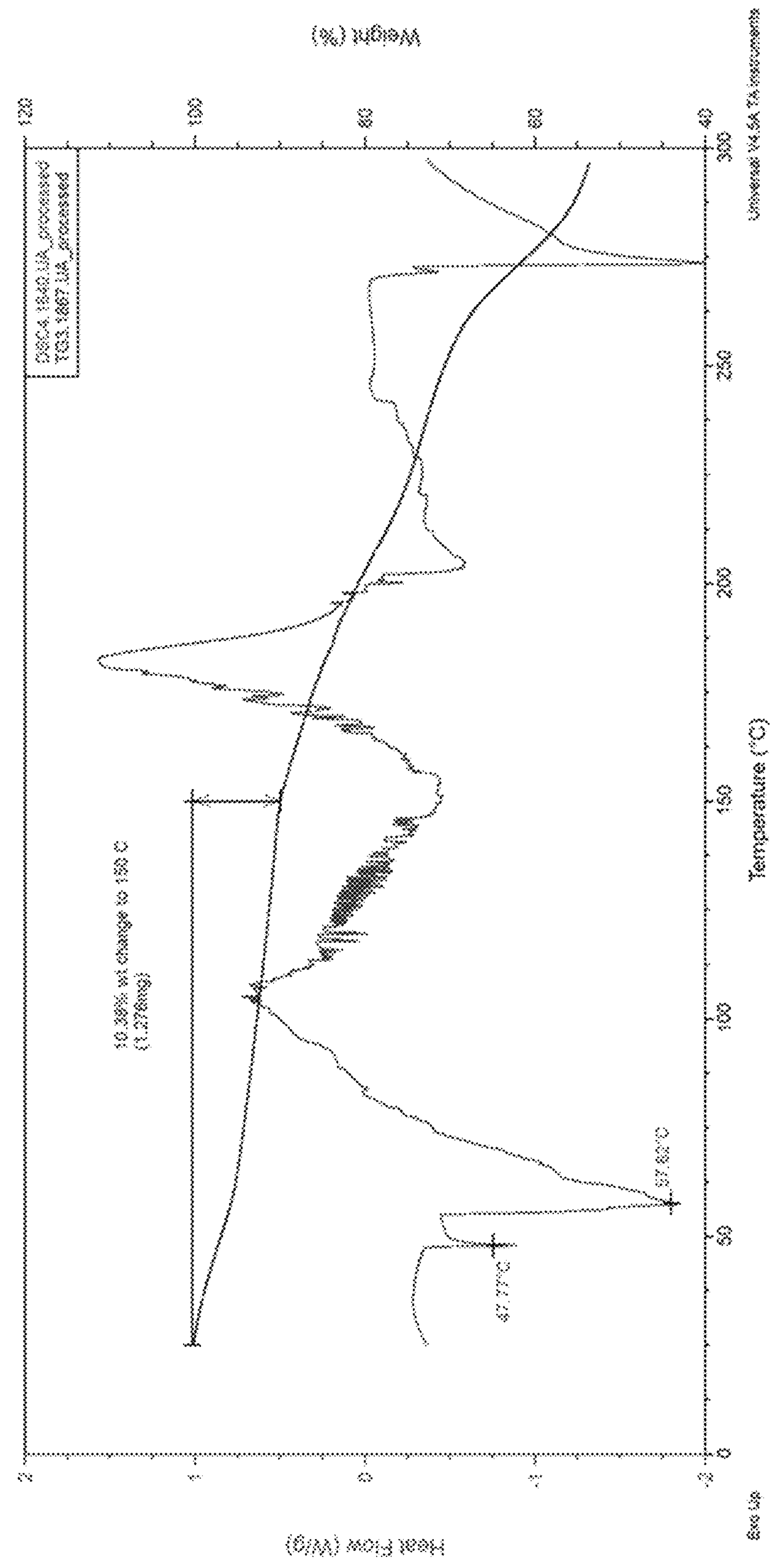
FIG. 81 provides TGA and DSC profiles for MBDB sulfate.

In some embodiments, the present disclosure provides solid forms of MBDB sulfate, e.g., crystalline forms of MBDB sulfate. In some embodiments, the MBDB sulfate XRPD profile is substantially similar to that shown in any one of FIG. 32 or 34. In some embodiments, the MBDB sulfate TGA profile is substantially similar to that shown in FIG. 81. In some embodiments, the MBDB sulfate DSC profile is substantially similar to that shown in FIG. 81.

In some embodiments, the solid form of MBDB sulfate is crystalline MBDB sulfate characterized by two or more, or three or more XRPD signals selected from the group consisting of 8.8° 2θ, 17.5° 2θ, and 26.4° 2θ (±0.2° 2θ; ±0.1° 2θ; or ±0.0° 2θ; Cu Kα1 radiation). In some embodiments, the solid form of MBDB sulfate is crystalline MBDB sulfate characterized by XRPD signals at 8.8° 2θ, 17.5° 2θ, and 26.4° 2θ (±0.2° 2θ; ±0.1° 2θ; or ±0.0° 2θ; Cu Kα1 radiation).

In some embodiments, the solid form of MBDB sulfate is crystalline MBDB sulfate characterized by two or more, or three or more XRPD signals selected from the group consisting of 8.8° 2θ, 13.7° 2θ, 17.5° 2θ, 21.0° 2θ, and 26.4° 2θ (±0.2° 2θ; ±0.1° 2θ; or ±0.0° 2θ; Cu Kα1 radiation). In some embodiments, the solid form of MBDB sulfate is MBDB sulfate characterized by XRPD signals at 8.8° 2θ, 13.7° 2θ, 17.5° 2θ, 21.0° 2θ, and 26.4° 2θ (±0.2° 2θ; ±0.1° 2θ; or ±0.0° 2θ; Cu Kα1 radiation).

In some embodiments, the solid form of MBDB sulfate is crystalline MBDB sulfate characterized by two or more, or three or more XRPD signals selected from the group consisting of 8.8° 2θ, 15.0° 2θ, 17.5° 2θ, 22.3° 2θ, and 26.4° 2θ (±0.2° 2θ; ±0.1° 2θ; or ±0.0° 2θ; Cu Kα1 radiation). In some embodiments, the solid form of MBDB sulfate is MBDB sulfate characterized by XRPD signals at 8.8° 2θ, 15.0° 2θ, 17.5° 2θ, 22.3° 2θ, and 26.4° 2θ (±0.2° 2θ; ±0.1° 2θ; or ±0.0° 2θ; Cu Kα1 radiation).

In some embodiments, the crystalline MBDB sulfate is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 31.

TABLE 31

XRPD Signals for MBDB sulfate

| Signal no. | Position | d-value | Relative |
|---|---|---|---|
| 1 | 8.8 | 10.1 | 38.7 |
| 2 | 12.9 | 6.9 | 6.1 |
| 3 | 13.7 | 6.5 | 6.1 |
| 4 | 15.0 | 5.9 | 5.8 |
| 5 | 17.5 | 5.1 | 100.0 |
| 6 | 18.7 | 4.8 | 6.0 |
| 7 | 19.2 | 4.6 | 1.1 |
| 8 | 21.0 | 4.2 | 6.1 |
| 9 | 21.3 | 4.2 | 6.0 |
| 10 | 21.9 | 4.1 | 6.0 |
| 11 | 22.3 | 4.0 | 5.1 |
| 12 | 24.8 | 3.6 | 5.4 |
| 13 | 26.4 | 3.4 | 25.3 |
| 14 | 27.0 | 3.3 | 5.7 |
| 15 | 27.8 | 3.2 | 4.9 |
| 16 | 30.1 | 3.0 | 6.0 |
| 17 | 31.8 | 2.8 | 5.9 |
| 18 | 35.4 | 2.5 | 5.0 |
| 19 | 36.5 | 2.5 | 6.0 |
| 20 | 39.0 | 2.3 | 6.0 |

In some embodiments, the solid form of MBDB sulfate is crystalline MBDB sulfate characterized by two or more, or three or more XRPD signals selected from the group consisting of 17.4° 2θ, 22.4° 2θ, and 24.9° 2θ (±0.2° 2θ; ±0.1° 2θ; or ±0.0° 2θ; Cu Kα1 radiation). In some embodiments, the solid form of MBDB sulfate is crystalline MBDB sulfate characterized by XRPD signals at 17.4° 2θ, 22.4° 2θ, and 24.9° 2θ (±0.2° 2θ; ±0.1° 2θ; or ±0.0° 2θ; Cu Kα1 radiation).

In some embodiments, the solid form of MBDB sulfate is crystalline MBDB sulfate characterized by two or more, or three or more XRPD signals selected from the group consisting of 17.4° 2θ, 18.9° 2θ, 21.5° 2θ, 22.4° 2θ, and 24.9° 2θ (±0.2° 2θ; ±0.1° 2θ; or ±0.0° 2θ; Cu Kα1 radiation). In some embodiments, the solid form of MBDB sulfate is MBDB sulfate characterized by XRPD signals at 17.4° 2θ, 18.9° 2θ, 21.5° 2θ, 22.4° 2θ, and 24.9° 2θ (±0.2° 2θ; ±0.1° 2θ; or ±0.0° 2θ; Cu Kα1 radiation).

In some embodiments, the solid form of MBDB sulfate is crystalline MBDB sulfate characterized by two or more, or three or more XRPD signals selected from the group consisting of 8.8° 2θ, 17.4° 2θ, and 18.9° 2θ (±0.2° 2θ; ±0.1° 2θ; or ±0.0° 2θ; Cu Kα1 radiation). In some embodiments, the solid form of MBDB sulfate is crystalline MBDB sulfate characterized by XRPD signals at 8.8° 2θ, 17.4° 2θ, and 18.9° 2θ (±0.2° 2θ; ±0.1° 2θ; or ±0.0° 2θ; Cu Kα1 radiation).

In some embodiments, the solid form of MBDB sulfate is crystalline MBDB sulfate characterized by two or more, or three or more XRPD signals selected from the group consisting of 8.8° 2θ, 17.4° 2θ, 18.9° 2θ, 21.1° 2θ, and 22.4° 2θ (±0.2° 2θ; ±0.1° 2θ; or ±0.0° 2θ; Cu Kα1 radiation). In some embodiments, the solid form of MBDB sulfate is MBDB sulfate characterized by XRPD signals at 8.8° 2θ, 17.4° 2θ, 18.9° 2θ, 21.1° 2θ, and 22.4° 2θ (±0.2° 2θ; ±0.1° 2θ; or ±0.0° 2θ; Cu Kα1 radiation).

In some embodiments, the crystalline MBDB sulfate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 32.

TABLE 32

Calculated single crystal XRPD Signals for MBDB sulfate

| Signal no. | Position | Relative |
|---|---|---|
| 1 | 8.8 | 19.8 |
| 2 | 10.9 | 6.7 |
| 3 | 12.5 | 4.1 |
| 4 | 12.9 | 12.2 |
| 5 | 13.0 | 12.1 |
| 6 | 13.6 | 15.4 |
| 7 | 15.1 | 14.3 |
| 8 | 17.4 | 100.0 |
| 9 | 17.7 | 37.8 |
| 10 | 18.9 | 52.6 |
| 11 | 19.1 | 9.6 |
| 12 | 19.4 | 29.7 |
| 13 | 19.5 | 10.5 |
| 14 | 20.1 | 6.7 |
| 15 | 21.1 | 38.5 |
| 16 | 21.3 | 6.8 |
| 17 | 21.5 | 44.8 |
| 18 | 22.2 | 11.8 |
| 19 | 22.4 | 69.5 |
| 20 | 24.4 | 11.7 |
| 21 | 24.9 | 56.8 |
| 22 | 25.1 | 36.1 |
| 23 | 25.9 | 2.5 |
| 24 | 26.1 | 26.5 |
| 25 | 26.3 | 3.0 |
| 26 | 26.5 | 3.3 |
| 27 | 26.7 | 17.7 |
| 28 | 27.1 | 1.6 |
| 29 | 27.3 | 6.9 |
| 30 | 27.5 | 30.3 |
| 31 | 28.0 | 10.2 |

TABLE 32-continued

Calculated single crystal XRPD Signals for MBDB sulfate

| Signal no. | Position | Relative |
|---|---|---|
| 32 | 28.1 | 9.9 |
| 33 | 28.4 | 2.6 |
| 34 | 28.9 | 5.6 |
| 35 | 29.4 | 5.9 |
| 36 | 29.7 | 7.7 |
| 37 | 30.1 | 7.1 |
| 38 | 30.4 | 5.0 |
| 39 | 30.9 | 3.5 |
| 40 | 31.5 | 1.6 |
| 41 | 32.0 | 17.7 |
| 42 | 32.2 | 4.4 |
| 43 | 32.7 | 0.4 |
| 44 | 32.9 | 0.5 |
| 45 | 33.2 | 0.3 |
| 46 | 33.8 | 2.0 |
| 47 | 34.2 | 1.6 |
| 48 | 34.7 | 2.0 |
| 49 | 35.2 | 0.6 |
| 50 | 35.7 | 5.7 |
| 51 | 35.9 | 2.7 |
| 52 | 36.0 | 3.7 |
| 53 | 36.5 | 7.1 |
| 54 | 37.0 | 6.5 |
| 55 | 37.1 | 4.1 |
| 56 | 37.3 | 3.6 |
| 57 | 37.4 | 1.3 |
| 58 | 37.6 | 1.3 |
| 59 | 38.0 | 0.7 |
| 60 | 38.2 | 1.9 |
| 61 | 38.5 | 1.4 |
| 62 | 38.7 | 0.7 |
| 63 | 39.1 | 3.9 |
| 64 | 39.3 | 3.3 |
| 65 | 39.7 | 2.0 |
| 66 | 39.9 | 3.3 |

Solid Forms of MBDB Tartrate

Figure 33:
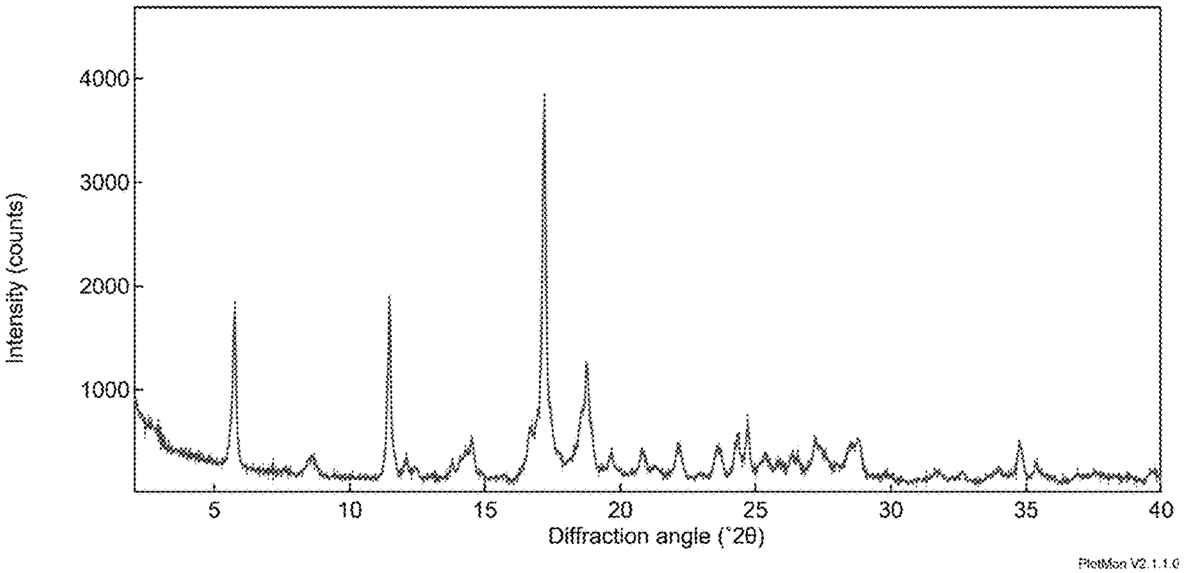
FIG. 33 provides an XRPD diffractogram of crystalline MBDB·tartrate.

In some embodiments, the present disclosure provides solid forms of MBDB tartrate, e.g., crystalline forms of MBDB tartrate. In some embodiments, the MBDB tartrate XRPD profile is substantially similar to FIG. 33.

In some embodiments, the solid form of MBDB tartrate is crystalline MBDB tartrate characterized by two or more, or three or more XRPD signals selected from the group consisting of 5.8° 2θ, 11.5° 2θ, and 17.2° 2θ (±0.2° 2θ; ±0.1° 2θ; or ±0.0° 2θ; Cu Kα1 radiation). In some embodiments, the solid form of MBDB tartrate is crystalline MBDB tartrate characterized by XRPD signals at 5.8° 2θ, 11.5° 2θ, and 17.2° 2θ (±0.2° 2θ; ±0.1° 2θ; or ±0.0° 2θ; Cu Kα1 radiation).

In some embodiments, the solid form of MBDB tartrate is crystalline MBDB tartrate characterized by two or more, or three or more XRPD signals selected from the group consisting of 5.8° 2θ, 11.5° 2θ, 17.2° 2θ, 18.7° 2θ, and 24.7° 2θ (±0.2° 2θ; ±0.1° 2θ; or ±0.0° 2θ; Cu Kα1 radiation). In some embodiments, the solid form of MBDB tartrate is MBDB tartrate characterized by XRPD signals at 5.8° 2θ, 11.5° 2θ, 17.2° 2θ, 18.7° 2θ, and 24.7° 2θ (±0.2° 2θ; ±0.1° 2θ; or ±0.0° 2θ; Cu Kα1 radiation).

In some embodiments, the solid form of MBDB tartrate is crystalline MBDB tartrate characterized by two or more, or three or more XRPD signals selected from the group consisting of 5.8° 2θ, 8.6° 2θ, 11.5° 2θ, 17.2° 2θ, and 18.7° 2θ (±0.2° 2θ; ±0.1° 2θ; or ±0.0° 2θ; Cu Kα1 radiation). In some embodiments, the solid form of MBDB tartrate is MBDB tartrate characterized by XRPD signals at 5.8° 2θ, 8.6° 2θ, 11.5° 2θ, 17.2° 2θ, and 18.7° 2θ (±0.2° 2θ; ±0.1° 2θ; or ±0.0° 2θ; Cu Kα1 radiation).

In some embodiments, the crystalline MBDB tartrate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, or twenty-eight XRPD signals selected from those set forth in Table 33.

TABLE 33

XRPD Signals for MBDB tartrate

| Signal no. | Position | d-value | Relative |
|---|---|---|---|
| 1 | 5.8 | 15.3 | 47.1 |
| 2 | 8.6 | 10.3 | 9.5 |
| 3 | 11.5 | 7.7 | 48.4 |
| 4 | 12.1 | 7.3 | 9.8 |
| 5 | 12.4 | 7.1 | 6.9 |
| 6 | 13.8 | 6.4 | 8.7 |
| 7 | 14.5 | 6.1 | 14.0 |
| 8 | 16.7 | 5.3 | 17.0 |
| 9 | 17.2 | 5.2 | 100.0 |
| 10 | 18.7 | 4.7 | 33.2 |
| 11 | 19.7 | 4.5 | 11.0 |
| 12 | 20.8 | 4.3 | 11.4 |
| 13 | 21.3 | 4.2 | 7.5 |
| 14 | 22.2 | 4.0 | 12.4 |
| 15 | 23.6 | 3.8 | 12.2 |
| 16 | 24.4 | 3.7 | 15.4 |
| 17 | 24.7 | 3.6 | 18.3 |
| 18 | 25.4 | 3.5 | 10.9 |
| 19 | 25.9 | 3.4 | 8.3 |
| 20 | 26.4 | 3.4 | 10.3 |
| 21 | 27.2 | 3.3 | 14.1 |
| 22 | 28.6 | 3.1 | 12.8 |
| 23 | 28.8 | 3.1 | 14.1 |
| 24 | 31.8 | 2.8 | 5.8 |
| 25 | 32.6 | 2.7 | 5.7 |
| 26 | 34.0 | 2.6 | 6.7 |
| 27 | 34.7 | 2.6 | 13.1 |
| 28 | 35.4 | 2.5 | 7.7 |

Solid Forms of MBDB Malonate

Figure 35:
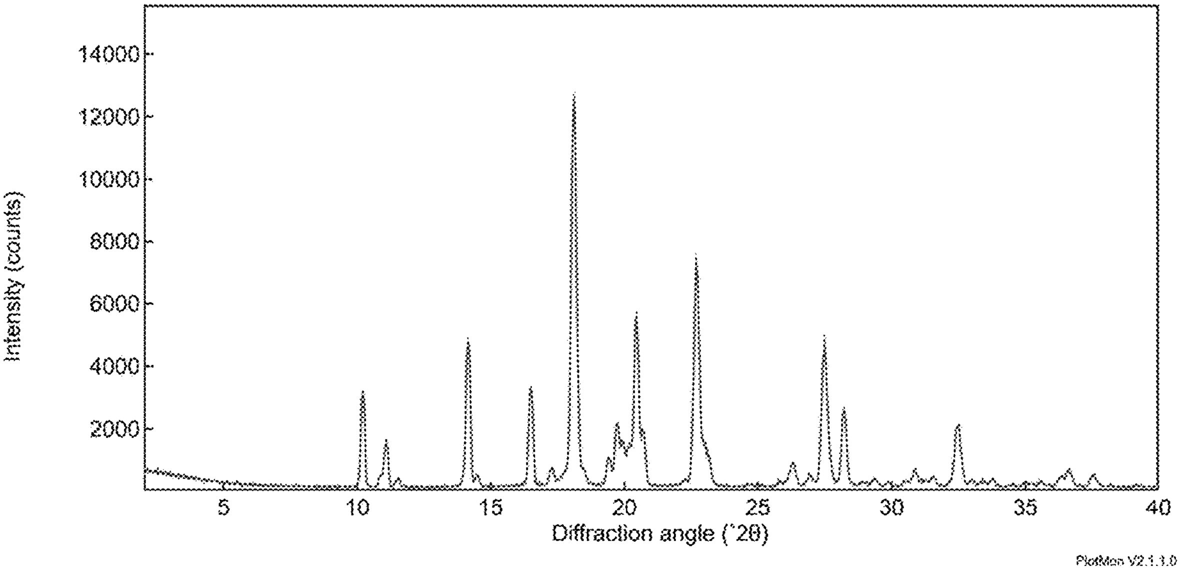
FIG. 35 provides an XRPD diffractogram of crystalline MBDB·malonate.
Figure 73:
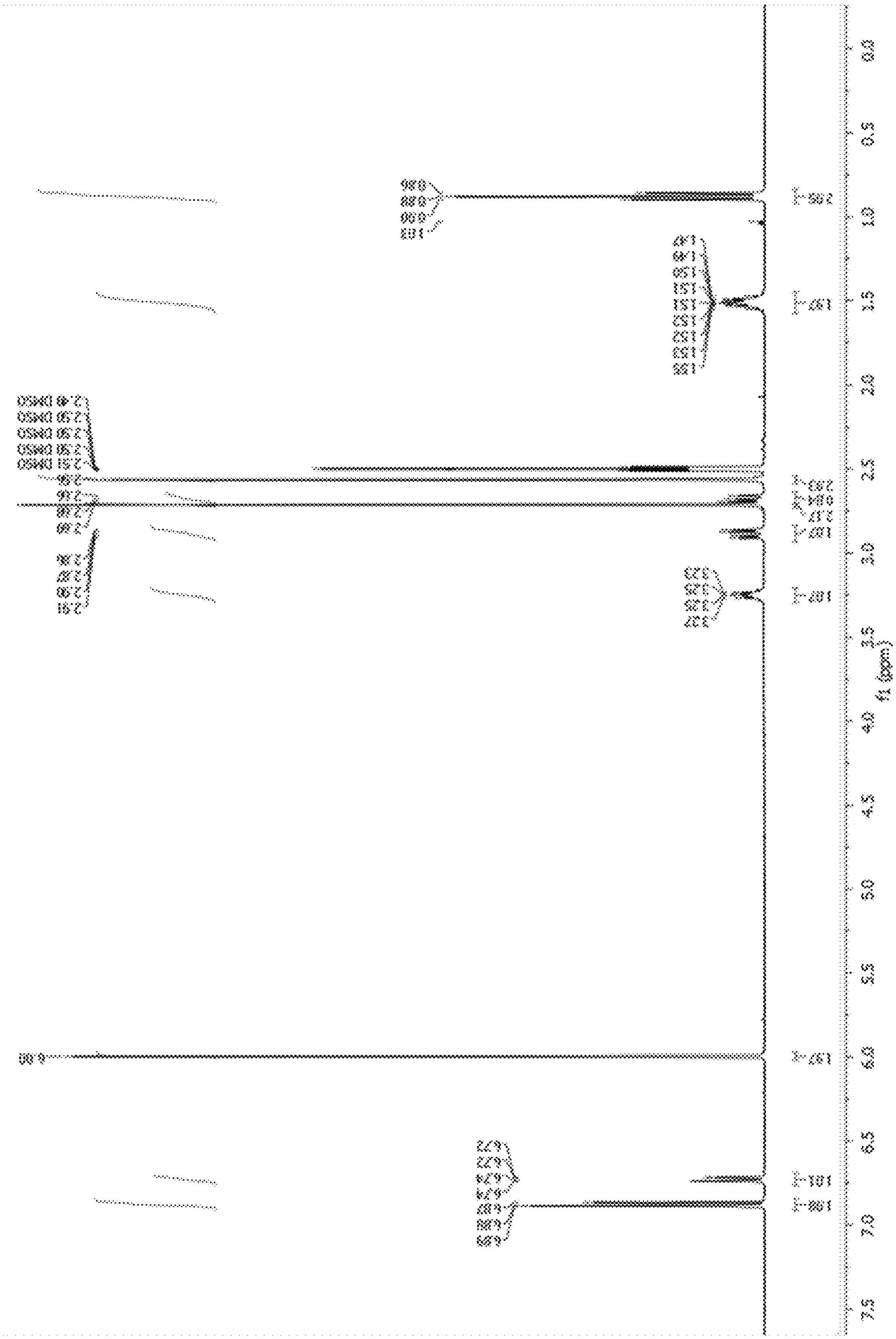
FIG. 73 provides a $^1$H NMR spectrum for MBDB malonate.
Figure 74:
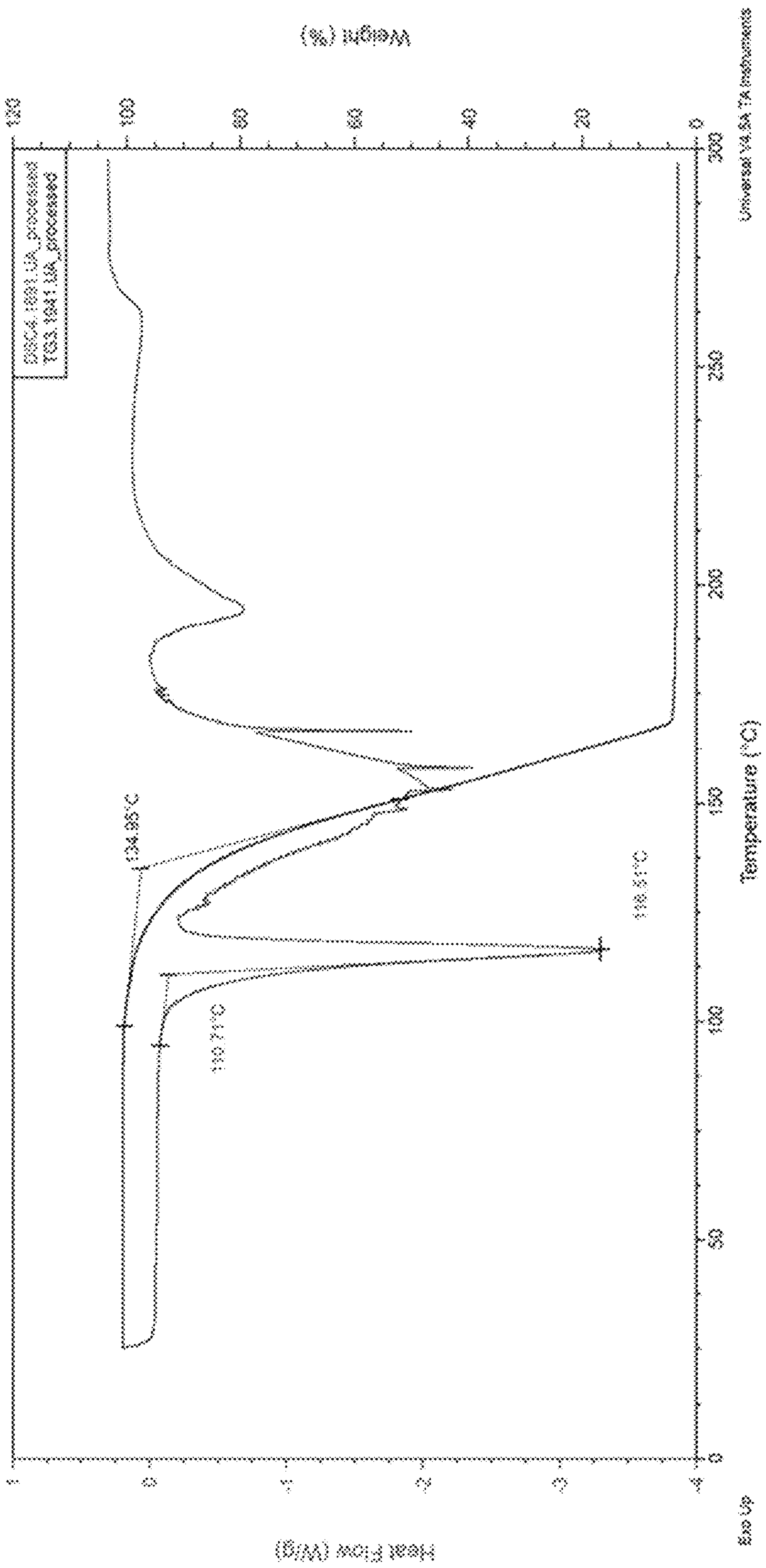
FIG. 74 provides TGA and DSC profiles for MBDB malonate.

In some embodiments, the present disclosure provides solid forms of MBDB malonate, e.g., crystalline forms of MBDB malonate. In some embodiments, the MBDB malonate XRPD profile is substantially similar to FIG. 35. In some embodiments, the MBDB malonate $^1$H NMR spectrum is substantially similar to that shown in FIG. 73. In some embodiments, the MBDB malonate TGA profile is substantially similar to that shown in FIG. 74. In some embodiments, the MBDB malonate DSC profile is substantially similar to that shown in FIG. 74.

In some embodiments, the solid form of MBDB malonate is crystalline MBDB malonate characterized by two or more, or three or more XRPD signals selected from the group consisting of 18.1° 2θ, 20.4° 2θ, and 22.7° 2θ (±0.2° 2θ; ±0.1° 2θ; or ±0.0° 2θ; Cu Kα1 radiation). In some embodiments, the solid form of MBDB malonate is crystalline MBDB malonate characterized by XRPD signals at 18.1° 2θ, 20.4° 2θ, and 22.7° 2θ (±0.2° 2θ; ±0.1° 2θ; or ±0.0° 2θ; Cu Kα1 radiation).

In some embodiments, the solid form of MBDB malonate is crystalline MBDB malonate characterized by two or more, or three or more XRPD signals selected from the group consisting of 14.2° 2θ, 18.1° 2θ, 20.4° 2θ, 22.7° 2θ, and 27.5° 2θ (±0.2° 2θ; ±0.1° 2θ; or ±0.0° 2θ; Cu Kα1 radiation). In some embodiments, the solid form of MBDB malonate is MBDB malonate characterized by XRPD signals at 14.2° 2θ, 18.1° 2θ, 20.4° 2θ, 22.7° 2θ, and 27.5° 2θ (±0.2° 2θ; ±0.1° 2θ; or ±0.0° 2θ; Cu Kα1 radiation).

In some embodiments, the solid form of MBDB malonate is crystalline MBDB malonate characterized by two or more, or three or more XRPD signals selected from the group consisting of 10.2° 2θ, 14.2° 2θ, and 16.5° 2θ (±0.2° 2θ; ±0.1° 2θ; or ±0.0° 2θ; Cu Kα1 radiation). In some embodiments, the solid form of MBDB malonate is crystalline MBDB malonate characterized by XRPD signals at 10.2° 2θ, 14.2° 2θ, and 16.5° 2θ (±0.2° 2θ; ±0.1° 2θ; or ±0.0° 2θ; Cu Kα1 radiation).

In some embodiments, the solid form of MBDB malonate is crystalline MBDB malonate characterized by two or more, or three or more XRPD signals selected from the group consisting of 10.2° 2θ, 14.2° 2θ, 16.5° 2θ, 18.1° 2θ, and 22.7° 2θ (±0.2° 2θ; ±0.1° 2θ; or ±0.0° 2θ; Cu Kα1 radiation). In some embodiments, the solid form of MBDB malonate is MBDB malonate characterized by XRPD signals at 10.2° 2θ, 14.2° 2θ, 16.5° 2θ, 18.1° 2θ, and 22.7° 2θ (±0.2° 2θ; ±0.1° 2θ; or ±0.0° 2θ; Cu Kα1 radiation).

In some embodiments, the crystalline MBDB malonate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, or thirty-seven XRPD signals selected from those set forth in Table 34.

TABLE 34

XRPD Signals for MBDB malonate

| Signal no. | Position | d-value | Relative |
|---|---|---|---|
| 1 | 10.2 | 8.7 | 25.4 |
| 2 | 11.1 | 8.0 | 12.9 |
| 3 | 11.5 | 7.7 | 3.5 |
| 4 | 14.2 | 6.3 | 38.3 |
| 5 | 14.5 | 6.1 | 4.4 |
| 6 | 16.5 | 5.4 | 26.5 |
| 7 | 17.3 | 5.1 | 6.3 |
| 8 | 18.1 | 4.9 | 100.0 |
| 9 | 19.4 | 4.6 | 8.8 |
| 10 | 19.7 | 4.5 | 17.6 |
| 11 | 19.9 | 4.5 | 12.9 |
| 12 | 20.2 | 4.4 | 12.3 |
| 13 | 20.4 | 4.3 | 44.8 |
| 14 | 20.7 | 4.3 | 16.1 |
| 15 | 22.7 | 3.9 | 58.7 |
| 16 | 25.8 | 3.4 | 2.8 |
| 17 | 26.3 | 3.4 | 7.6 |
| 18 | 26.9 | 3.3 | 4.5 |
| 19 | 27.5 | 3.2 | 37.7 |
| 20 | 28.2 | 3.2 | 21.2 |
| 21 | 29.0 | 3.1 | 2.6 |
| 22 | 29.3 | 3.0 | 3.5 |
| 23 | 29.9 | 3.0 | 2.6 |
| 24 | 30.6 | 2.9 | 2.8 |
| 25 | 30.9 | 2.9 | 5.8 |
| 26 | 31.2 | 2.9 | 3.1 |
| 27 | 31.5 | 2.8 | 3.9 |
| 28 | 32.5 | 2.8 | 17.2 |
| 29 | 33.0 | 2.7 | 3.0 |
| 30 | 33.4 | 2.7 | 3.0 |
| 31 | 33.8 | 2.7 | 3.4 |
| 32 | 34.5 | 2.6 | 2.2 |
| 33 | 35.0 | 2.6 | 2.6 |
| 34 | 35.6 | 2.5 | 2.8 |
| 35 | 36.4 | 2.5 | 4.1 |
| 36 | 36.7 | 2.5 | 5.7 |
| 37 | 37.6 | 2.4 | 4.4 |

Solid Forms of MBDB Succinate Form 2

Figure 36:
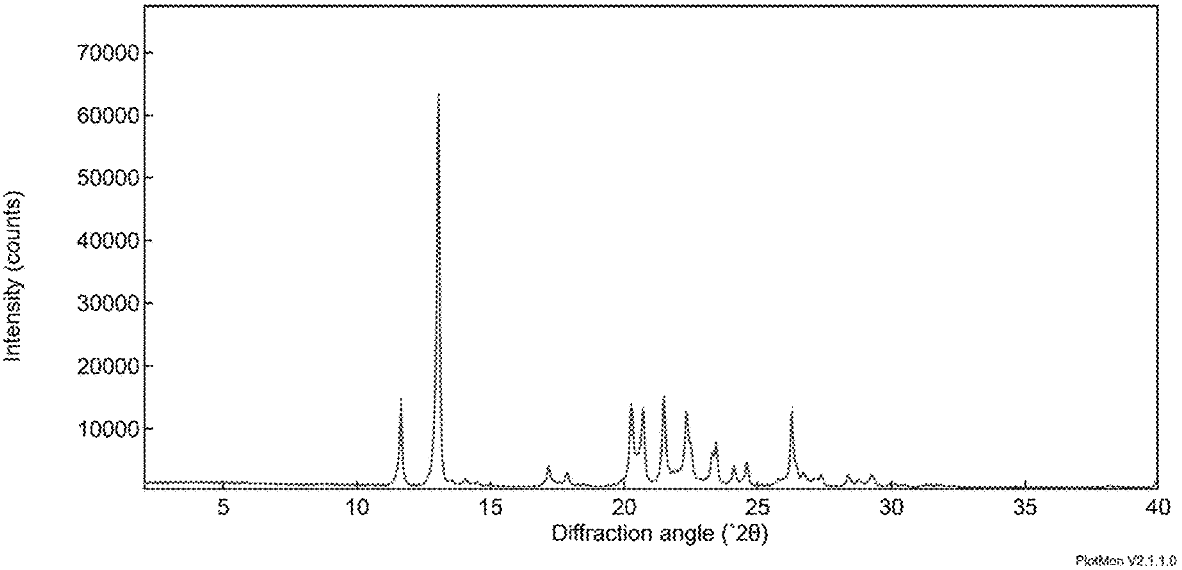
FIG. 36 provides an XRPD diffractogram of crystalline MBDB·succinate (form 2).
Figure 79:
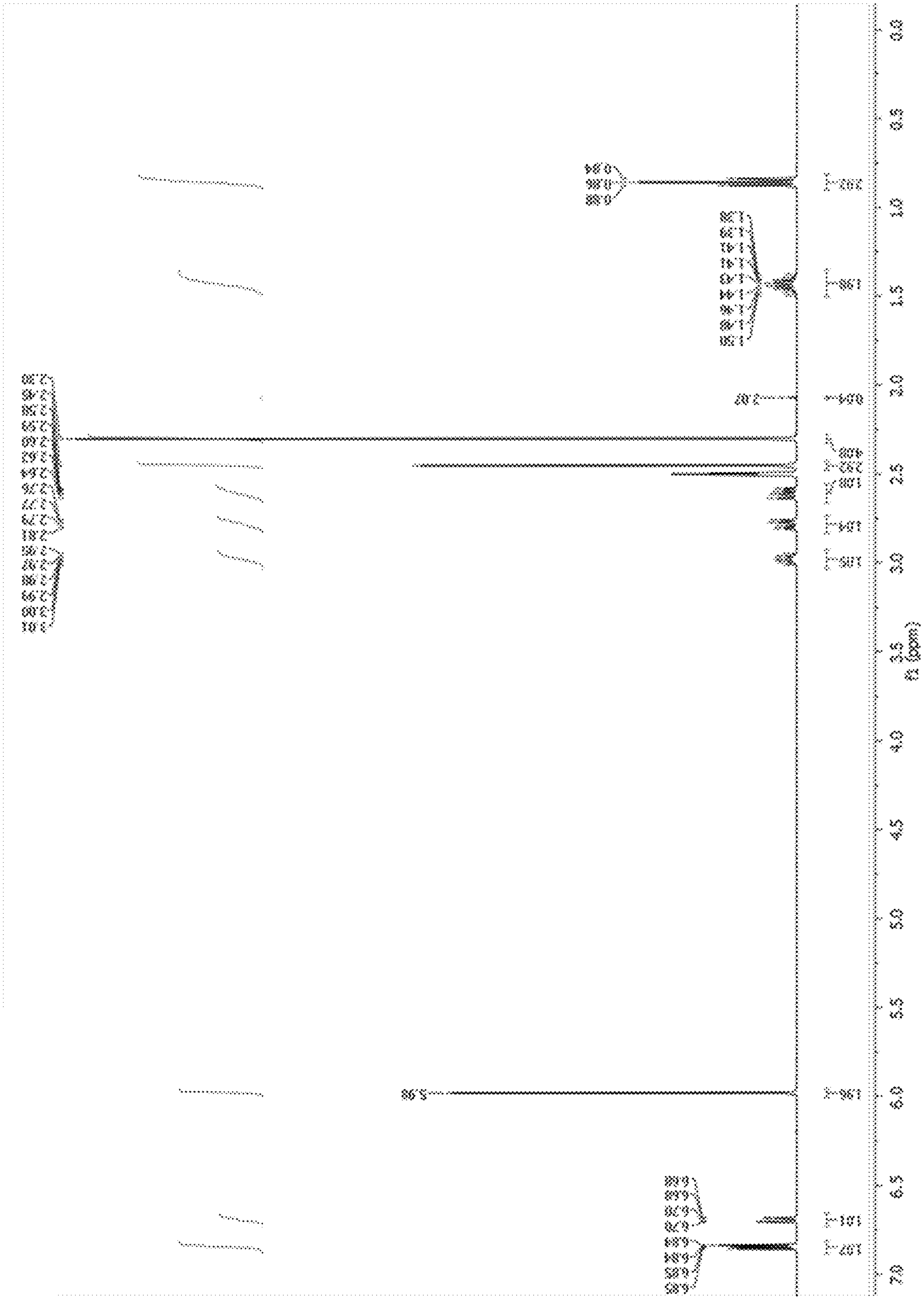
FIG. 79 provides a $^1$H NMR spectrum for MBDB succinate Form 2.
Figure 80:
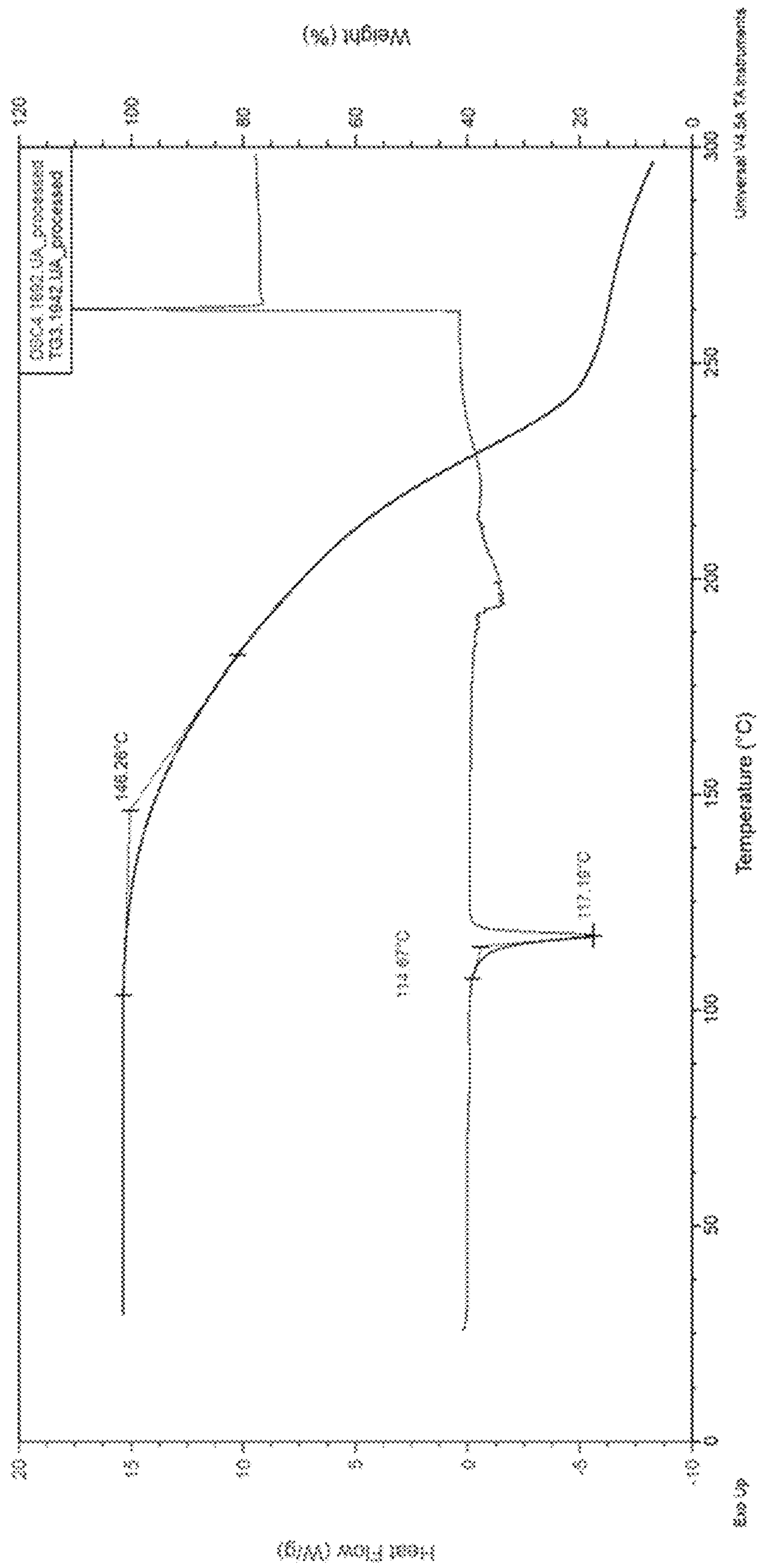
FIG. 80 provides TGA and DSC profiles for MBDB succinate Form 2.

In some embodiments, the present disclosure provides solid forms of MBDB succinate Form 2, e.g., crystalline forms of MBDB succinate Form 2. In some embodiments, the MBDB succinate Form 2 XRPD profile is substantially similar to that shown in FIG. 36. In some embodiments, the MBDB succinate Form 2 $^1$H NMR spectrum is substantially similar to that shown in FIG. 79. In some embodiments, the MBDB succinate Form 2 TGA profile is substantially similar to that shown in FIG. 80. In some embodiments, the MBDB succinate Form 2 DSC profile is substantially similar to that shown in FIG. 80.

In some embodiments, the solid form of MBDB succinate Form 2 is crystalline MBDB succinate Form 2 characterized by two or more, or three or more XRPD signals selected from the group consisting of 13.0° 2θ, 20.3° 2θ, and 21.5° 2θ (±0.2° 2θ; ±0.1° 2θ; or ±0.0° 2θ; Cu Kα1 radiation). In some embodiments, the solid form of MBDB succinate Form 2 is crystalline MBDB succinate Form 2 characterized by XRPD signals at 13.0° 2θ, 20.3° 2θ, and 21.5° 2θ (±0.2° 2θ; ±0.1° 2θ; or ±0.0° 2θ; Cu Kα1 radiation).

In some embodiments, the solid form of MBDB succinate Form 2 is crystalline MBDB succinate Form 2 characterized by two or more, or three or more XRPD signals selected from the group consisting of 11.6° 2θ, 13.0° 2θ, 20.3° 2θ, 20.7° 2θ, and 21.5° 2θ (±0.2° 2θ; ±0.1° 2θ; or ±0.0° 2θ; Cu Kα1 radiation). In some embodiments, the solid form of MBDB succinate Form 2 is MBDB succinate Form 2 characterized by XRPD signals at 11.6° 2θ, 13.0° 2θ, 20.3° 2θ, 20.7° 2θ, and 21.5° 2θ (±0.2° 2θ; ±0.1° 2θ; or ±0.0° 2θ; Cu Kα1 radiation).

In some embodiments, the solid form of MBDB succinate Form 2 is crystalline MBDB succinate Form 2 characterized by two or more, or three or more XRPD signals selected from the group consisting of 11.6° 2θ, 13.0° 2θ, and 21.5° 2θ (±0.2° 2θ; ±0.1° 2θ; or ±0.0° 2θ; Cu Kα1 radiation). In some embodiments, the solid form of MBDB succinate Form 2 is crystalline MBDB succinate Form 2 characterized by XRPD signals at 11.6° 2θ, 13.0° 2θ, and 21.5° 2θ (±0.2° 2θ; ±0.1° 2θ; or ±0.0° 2θ; Cu Kα1 radiation).

In some embodiments, the crystalline MBDB succinate Form 2 is characterized by one, two, three, four, five, six, seven, eight, nine, ten, eleven, twelve, thirteen, fourteen, fifteen, sixteen, seventeen, or eighteen XRPD signals selected from those set forth in Table 35.

TABLE 35

XRPD Signals for MBDB succinate Form 2

| Signal no. | Position | d-value | Relative |
|---|---|---|---|
| 1 | 11.6 | 7.6 | 21.9 |
| 2 | 13.0 | 6.8 | 100.0 |
| 3 | 17.2 | 5.2 | 6.3 |
| 4 | 17.9 | 5.0 | 4.7 |
| 5 | 20.3 | 4.4 | 22.0 |
| 6 | 20.7 | 4.3 | 20.7 |
| 7 | 21.5 | 4.1 | 23.5 |
| 8 | 22.3 | 4.0 | 20.4 |
| 9 | 23.3 | 3.8 | 9.7 |
| 10 | 23.4 | 3.8 | 12.5 |
| 11 | 24.1 | 3.7 | 6.2 |
| 12 | 24.6 | 3.6 | 7.3 |
| 13 | 26.3 | 3.4 | 19.7 |
| 14 | 26.7 | 3.3 | 4.9 |
| 15 | 27.4 | 3.3 | 4.5 |
| 16 | 28.4 | 3.1 | 4.1 |
| 17 | 28.8 | 3.1 | 2.8 |
| 18 | 29.3 | 3.1 | 4.4 |

Solid Forms of MBDB Tosylate (Toluenesulfonate)

Figure 37:
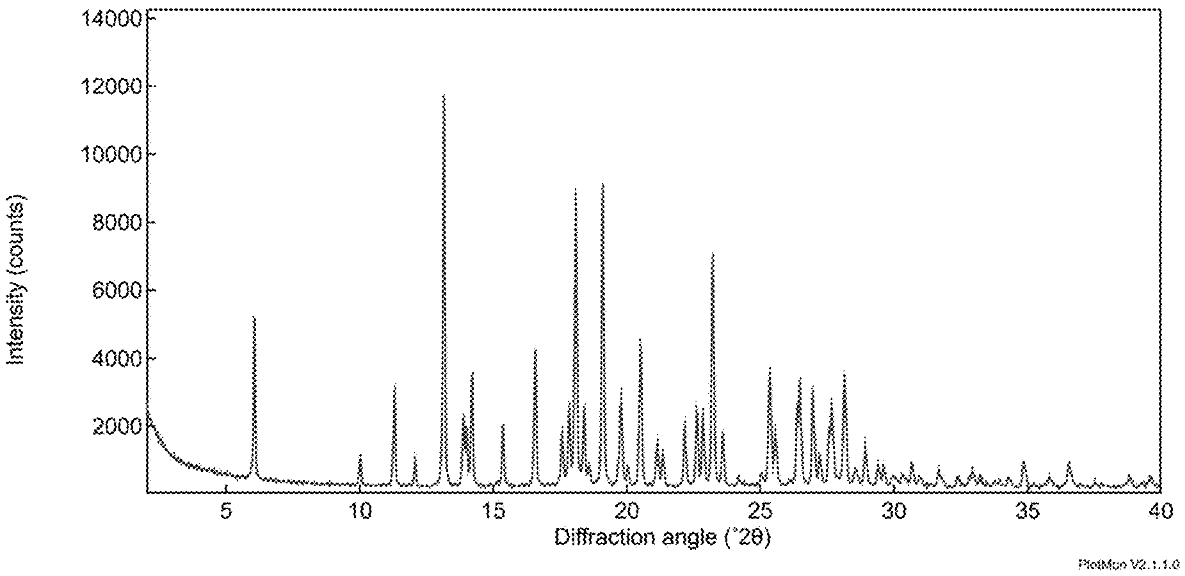
FIG. 37 provides an XRPD diffractogram of crystalline MBDB·tosylate.
Figure 82:
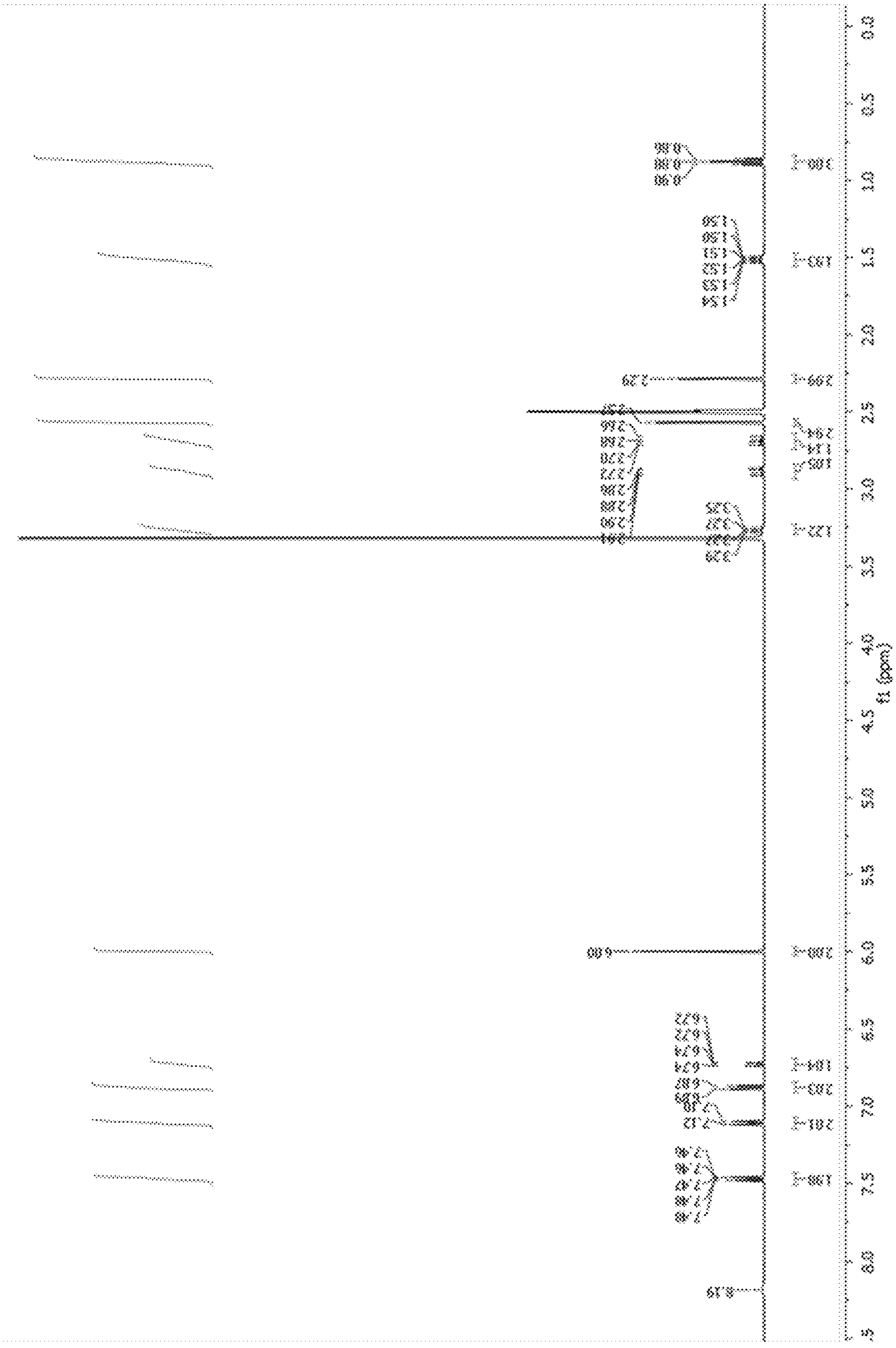
FIG. 82 provides a $^1$H NMR spectrum for MBDB tosylate (toluenesulfonate).
Figure 83:
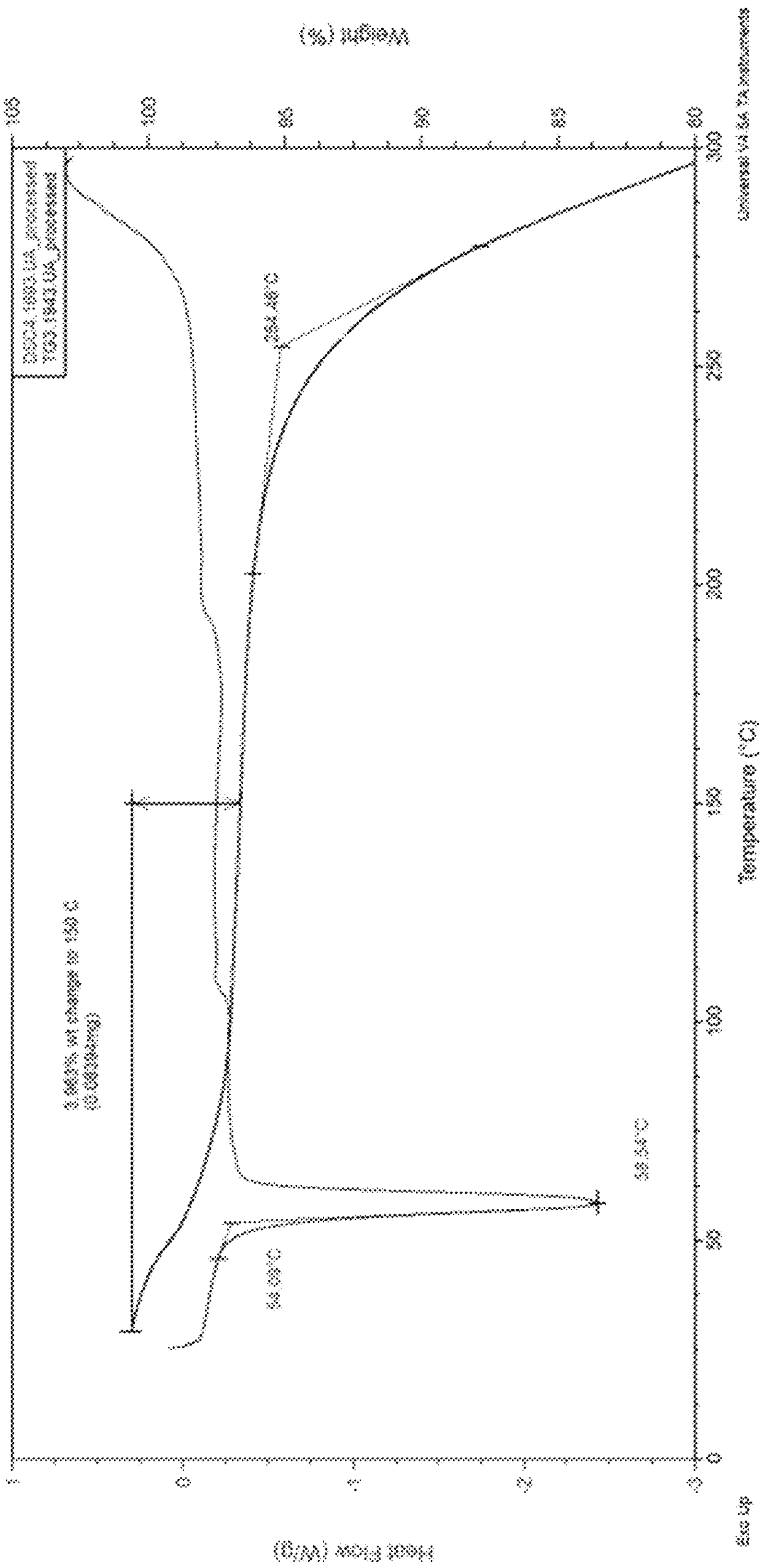
FIG. 83 provides TGA and DSC profiles for MBDB tosylate (toluenesulfonate).

In some embodiments, the present disclosure provides solid forms of MBDB tosylate, e.g., crystalline forms of MBDB tosylate. In some embodiments, the MBDB tosylate XRPD profile is substantially similar to FIG. 37. In some embodiments, the MBDB tosylate $^1$H NMR spectrum is substantially similar to that shown in FIG. 82. In some embodiments, the MBDB tosylate TGA profile is substantially similar to that shown in FIG. 83. In some embodiments, the MBDB tosylate DSC profile is substantially similar to that shown in FIG. 83.

In some embodiments, the solid form of MBDB tosylate is crystalline MBDB tosylate characterized by two or more, or three or more XRPD signals selected from the group consisting of 13.1° 2θ, 18.1° 2θ, and 19.1° 2θ (±0.2° 2θ; ±0.1° 2θ; or ±0.0° 2θ; Cu Kα1 radiation). In some embodiments, the solid form of MBDB tosylate is crystalline MBDB tosylate characterized by XRPD signals at 13.1° 2θ, 18.1° 2θ, and 19.1° 2θ (±0.2° 2θ; ±0.1° 2θ; or ±0.0° 2θ; Cu Kα1 radiation).

In some embodiments, the solid form of MBDB tosylate is crystalline MBDB tosylate characterized by two or more, or three or more XRPD signals selected from the group consisting of 6.1° 2θ, 13.1° 2θ, 18.1° 2θ, 19.1° 2θ, and 23.2° 2θ (±0.2° 2θ; ±0.1° 2θ; or ±0.0° 2θ; Cu Kα1 radiation). In some embodiments, the solid form of MBDB tosylate is MBDB tosylate characterized by XRPD signals at 6.1° 2θ, 13.1° 2θ, 18.1° 2θ, 19.1° 2θ, and 23.2° 2θ (±0.2° 2θ; ±0.1° 2θ; or ±0.0° 2θ; Cu Kα1 radiation).

In some embodiments, the solid form of MBDB tosylate is crystalline MBDB tosylate characterized by two or more, or three or more XRPD signals selected from the group consisting of 6.1° 2θ, 11.3° 2θ, and 13.1° 2θ (±0.2° 2θ; ±0.1° 2θ; or ±0.0° 2θ; Cu Kα1 radiation). In some embodiments, the solid form of MBDB tosylate is crystalline MBDB tosylate characterized by XRPD signals at 6.1° 2θ, 11.3° 2θ, and 13.1° 2θ (±0.2° 2θ; ±0.1° 2θ; or ±0.0° 2θ; Cu Kα1 radiation).

In some embodiments, the solid form of MBDB tosylate is crystalline MBDB tosylate characterized by two or more, or three or more XRPD signals selected from the group consisting of 6.1° 2θ, 10.0° 2θ, 11.3° 2θ, 12.1° 2θ, and 13.1° 2θ (±0.2° 2θ; ±0.1° 2θ; or ±0.0° 2θ; Cu Kα1 radiation). In some embodiments, the solid form of MBDB tosylate is MBDB tosylate characterized by XRPD signals at 6.1° 2θ, 10.0° 2θ, 11.3° 2θ, 12.1° 2θ, and 13.1° 2θ (±0.2° 2θ; ±0.1° 2θ; or ±0.0° 2θ; Cu Kα1 radiation).

In some embodiments, the crystalline MBDB tosylate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, or sixty-three XRPD signals selected from those set forth in Table 36.

TABLE 36

| XRPD Signals for MBDB tosylate | | | |
|---|---|---|---|
| Signal no. | Position | d-value | Relative |
| 1 | 6.1 | 14.6 | 44.8 |
| 2 | 10.0 | 8.8 | 9.9 |
| 3 | 11.3 | 7.8 | 26.4 |
| 4 | 12.1 | 7.3 | 8.8 |
| 5 | 13.1 | 6.7 | 100.0 |
| 6 | 13.9 | 6.4 | 20.0 |
| 7 | 14.0 | 6.3 | 17.0 |
| 8 | 14.2 | 6.2 | 30.3 |
| 9 | 15.4 | 5.8 | 17.6 |
| 10 | 16.6 | 5.3 | 37.2 |
| 11 | 17.6 | 5.0 | 15.8 |
| 12 | 17.8 | 5.0 | 21.6 |
| 13 | 18.1 | 4.9 | 75.9 |
| 14 | 18.4 | 4.8 | 21.4 |
| 15 | 18.6 | 4.8 | 7.6 |
| 16 | 19.1 | 4.6 | 77.5 |
| 17 | 19.8 | 4.5 | 24.8 |
| 18 | 20.0 | 4.4 | 7.1 |
| 19 | 20.5 | 4.3 | 38.1 |
| 20 | 21.1 | 4.2 | 13.4 |
| 21 | 21.3 | 4.2 | 10.6 |
| 22 | 22.2 | 4.0 | 17.5 |
| 23 | 22.6 | 3.9 | 21.6 |
| 24 | 22.8 | 3.9 | 20.5 |
| 25 | 23.2 | 3.8 | 59.8 |
| 26 | 23.6 | 3.8 | 15.6 |
| 27 | 24.2 | 3.7 | 4.7 |
| 28 | 25.0 | 3.6 | 5.6 |
| 29 | 25.4 | 3.5 | 30.8 |
| 30 | 25.6 | 3.5 | 15.7 |
| 31 | 26.1 | 3.4 | 3.9 |
| 32 | 26.4 | 3.4 | 21.4 |
| 33 | 26.5 | 3.4 | 28.7 |
| 34 | 27.0 | 3.3 | 25.5 |
| 35 | 27.2 | 3.3 | 10.4 |
| 36 | 27.6 | 3.2 | 17.1 |
| 37 | 27.7 | 3.2 | 22.9 |
| 38 | 28.1 | 3.2 | 30.6 |
| 39 | 28.6 | 3.1 | 6.7 |
| 40 | 28.9 | 3.1 | 12.4 |
| 41 | 29.4 | 3.0 | 7.8 |
| 42 | 29.6 | 3.0 | 7.5 |
| 43 | 30.0 | 3.0 | 4.8 |
| 44 | 30.3 | 2.9 | 5.4 |
| 45 | 30.7 | 2.9 | 8.4 |
| 46 | 31.0 | 2.9 | 4.7 |
| 47 | 31.7 | 2.8 | 6.5 |
| 48 | 32.4 | 2.8 | 4.8 |
| 49 | 32.9 | 2.7 | 6.8 |
| 50 | 33.2 | 2.7 | 4.9 |
| 51 | 33.4 | 2.7 | 3.3 |
| 52 | 33.7 | 2.7 | 3.6 |
| 53 | 33.9 | 2.6 | 3.9 |
| 54 | 34.3 | 2.6 | 4.7 |
| 55 | 34.8 | 2.6 | 8.7 |
| 56 | 35.2 | 2.5 | 2.9 |
| 57 | 35.8 | 2.5 | 4.8 |
| 58 | 36.6 | 2.5 | 8.2 |
| 59 | 37.5 | 2.4 | 3.5 |
| 60 | 38.8 | 2.3 | 4.9 |
| 61 | 39.4 | 2.3 | 3.1 |
| 62 | 39.6 | 2.3 | 4.6 |
| 63 | 39.6 | 2.3 | 4.5 |

Solid Forms of MBDB HCl Form A

Figure 86:
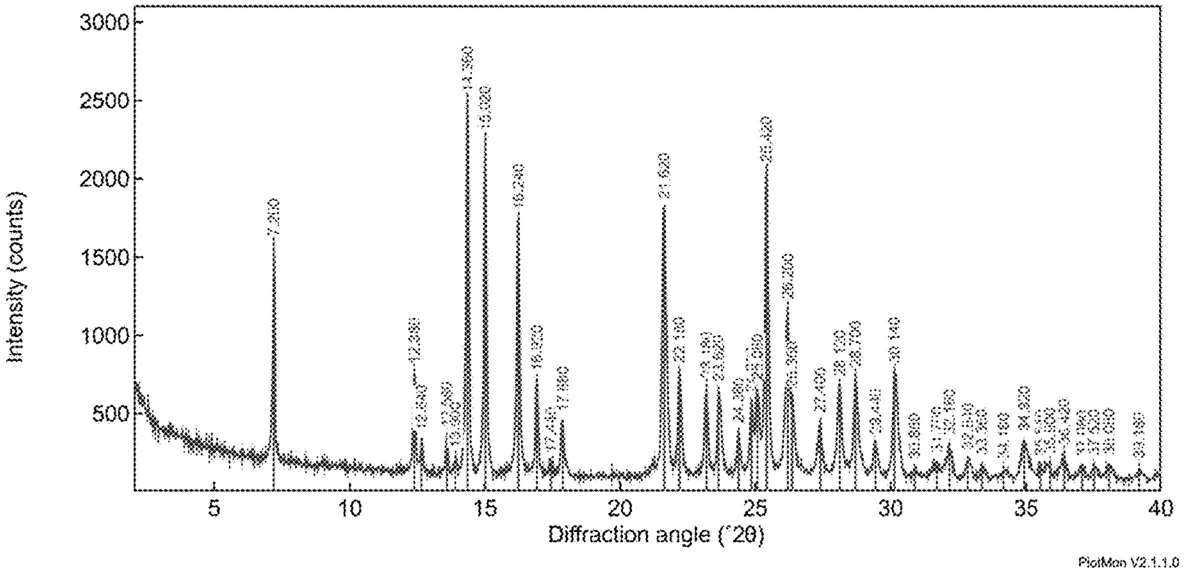
FIG. 86 provides an XRPD diffractogram of crystalline MBDB·HCl Form A.
Figure 90:
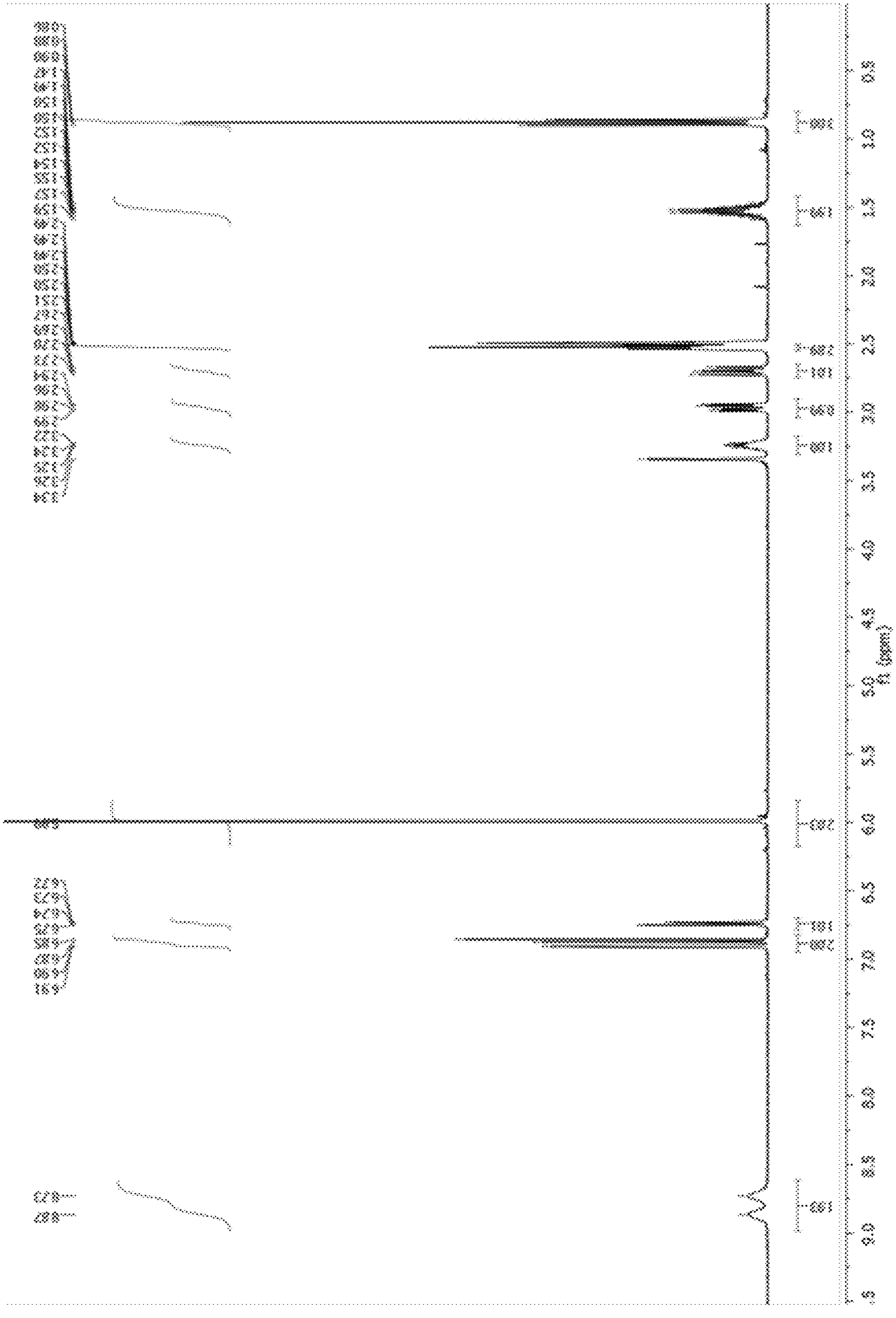
FIG. 90 provides a $^1$H NMR spectrum for MBDB HCl Form A.
Figure 91:
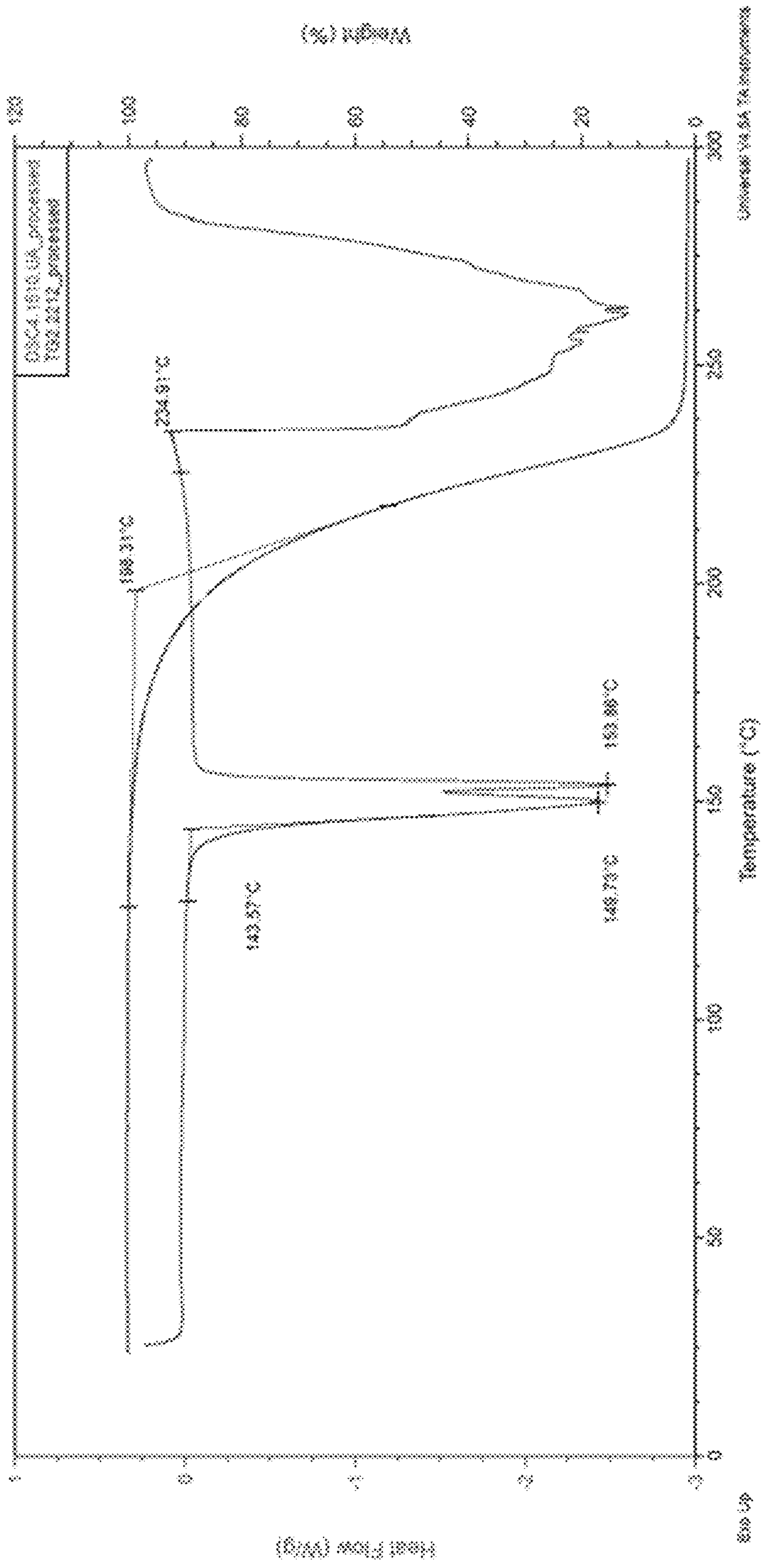
FIG. 91 provides TGA and DSC profiles for MBDB HCl Form A.
Figure 92:
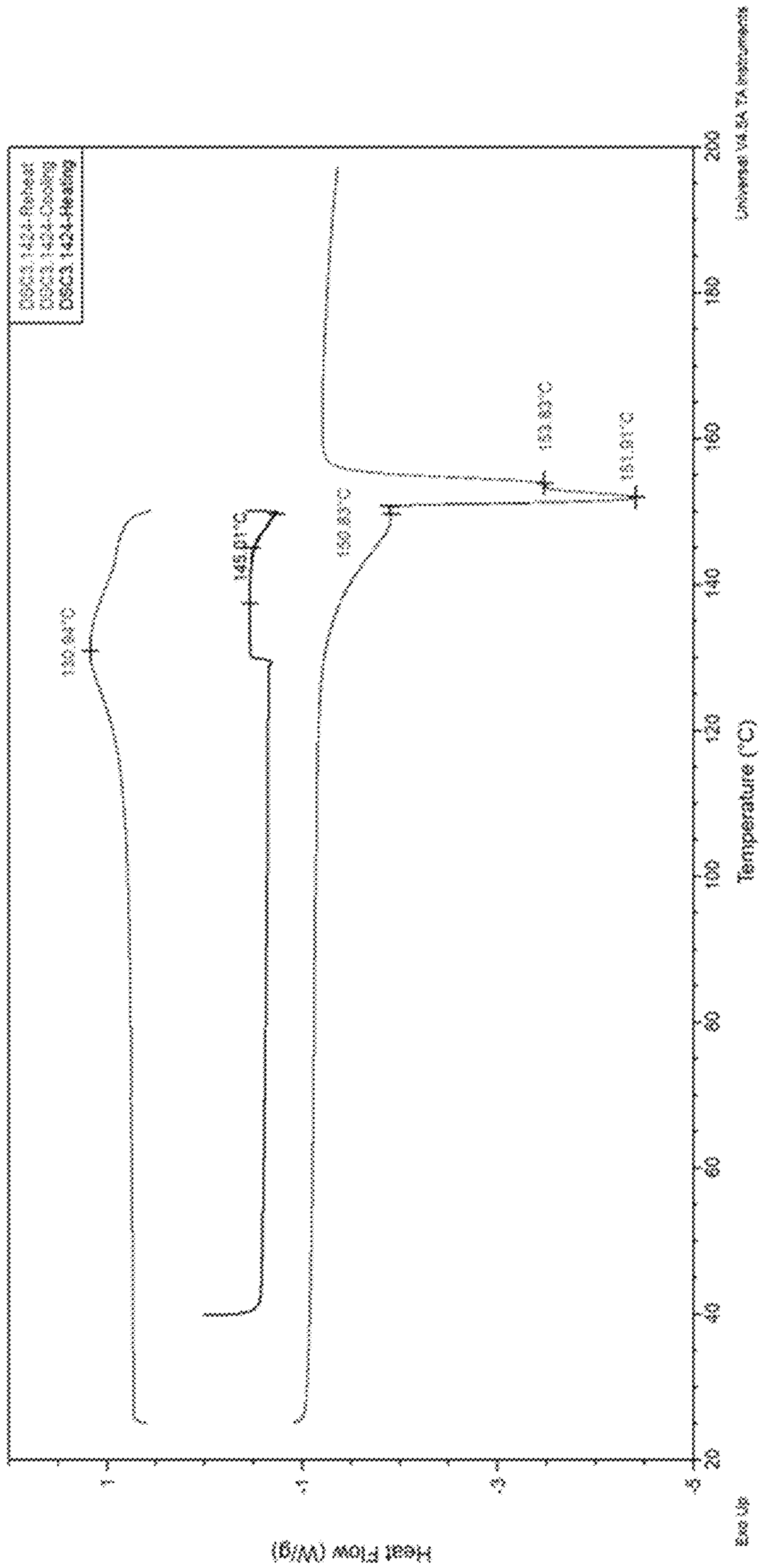
FIG. 92 provides a cyclic DSC profile for MBDB HCl Form A

In some embodiments, the present disclosure provides solid forms of MBDB HCl Form A, e.g., crystalline forms of MBDB HCl Form A. In some embodiments, the MBDB HCl Form A XRPD profile is substantially similar to that shown in any one of FIG. 38 or 86. In some embodiments, the MBDB HCl Form A $^1$H NMR spectrum is substantially similar to that shown in FIG. 90. In some embodiments, the MBDB HCl Form A TGA profile is substantially similar to that shown in FIG. 91. In some embodiments, the MBDB HCl Form A DSC profile is substantially similar to that shown in FIG. 91.

In some embodiments, the solid form of MBDB HCl Form A is crystalline MBDB HCl Form A characterized by two or more, or three or more XRPD signals selected from the group consisting of 14.3° 2θ, 14.9° 2θ, and 25.4° 2θ (±0.2° 2θ; ±0.1° 2θ; or ±0.0° 2θ; Cu Kα1 radiation). In some embodiments, the solid form of MBDB HCl Form A is crystalline MBDB HCl Form A characterized by XRPD signals at 14.3° 2θ, 14.9° 2θ, and 25.4° 2θ (±0.2° 2θ; ±0.1° 2θ; or ±0.0° 2θ; Cu Kα1 radiation).

In some embodiments, the solid form of MBDB HCl Form A is crystalline MBDB HCl Form A characterized by two or more, or three or more XRPD signals selected from the group consisting of 7.1° 2θ, 14.3° 2θ, 14.9° 2θ, 25.4° 2θ, and 26.1° 2θ (±0.2° 2θ; ±0.1° 2θ; or ±0.0° 2θ; Cu Kα1 radiation). In some embodiments, the solid form of MBDB HCl Form A is MBDB HCl Form A characterized by XRPD signals at 7.1° 2θ, 14.3° 2θ, 14.9° 2θ, 25.4° 2θ, and 26.1° 2θ (±0.2° 2θ; ±0.1° 2θ; or ±0.0° 2θ; Cu Kα1 radiation).

In some embodiments, the solid form of MBDB HCl Form A is crystalline MBDB HCl Form A characterized by two or more, or three or more XRPD signals selected from the group consisting of 7.1° 2θ, 12.3° 2θ, and 14.3° 2θ (±0.2° 2θ; ±0.1° 2θ; or ±0.0° 2θ; Cu Kα1 radiation). In some embodiments, the solid form of MBDB HCl Form A is crystalline MBDB HCl Form A characterized by XRPD signals at 7.1° 2θ, 12.3° 2θ, and 14.3° 2θ (±0.2° 2θ; ±0.1° 2θ; or ±0.0° 2θ; Cu Kα1 radiation).

In some embodiments, the solid form of MBDB HCl Form A is crystalline MBDB HCl Form A characterized by two or more, or three or more XRPD signals selected from the group consisting of 7.1° 2θ, 12.3° 2θ, 14.3° 2θ, 14.9° 2θ, and 16.2° 2θ (±0.2° 2θ; ±0.1° 2θ; or ±0.0° 2θ; Cu Kα1 radiation). In some embodiments, the solid form of MBDB HCl Form A is MBDB HCl Form A characterized by XRPD signals at 7.1° 2θ, 12.3° 2θ, 14.3° 2θ, 14.9° 2θ, and 16.2° 2θ (±0.2° 2θ; ±0.1° 2θ; or ±0.0° 2θ; Cu Kα1 radiation).

In some embodiments, the crystalline MBDB HCl Form A is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, or thirty XRPD signals selected from those set forth in Table 37.

TABLE 37

| XRPD Signals for MBDB HCl Form A | | | |
|---|---|---|---|
| Signal no. | Position | d-value | Relative |
| 1 | 7.1 | 12.4 | 66.6 |
| 2 | 12.3 | 7.2 | 35.6 |
| 3 | 13.5 | 6.6 | 17.8 |
| 4 | 14.3 | 6.2 | 91.5 |
| 5 | 14.9 | 5.9 | 100.0 |
| 6 | 16.2 | 5.5 | 26.9 |
| 7 | 16.9 | 5.3 | 25.5 |
| 8 | 17.8 | 5.0 | 21.8 |
| 9 | 21.5 | 4.1 | 42.1 |
| 10 | 22.1 | 4.0 | 32.6 |
| 11 | 23.1 | 3.9 | 20.2 |
| 12 | 23.5 | 3.8 | 26.7 |
| 13 | 24.4 | 3.7 | 18.4 |
| 14 | 24.8 | 3.6 | 29.0 |
| 15 | 25.0 | 3.6 | 32.9 |
| 16 | 25.4 | 3.5 | 82.2 |

TABLE 37-continued

XRPD Signals for MBDB HCl Form A

| Signal no. | Position | d-value | Relative |
|---|---|---|---|
| 17 | 26.1 | 3.4 | 44.9 |
| 18 | 27.4 | 3.3 | 19.6 |
| 19 | 27.9 | 3.2 | 18.8 |
| 20 | 28.7 | 3.1 | 22.2 |
| 21 | 29.3 | 3.0 | 11.2 |
| 22 | 30.0 | 3.0 | 28.4 |
| 23 | 32.2 | 2.8 | 10.4 |
| 24 | 32.7 | 2.7 | 10.3 |
| 25 | 33.3 | 2.7 | 9.2 |
| 26 | 34.1 | 2.6 | 8.7 |
| 27 | 35.2 | 2.5 | 10.1 |
| 28 | 36.1 | 2.5 | 9.9 |
| 29 | 36.9 | 2.4 | 8.3 |
| 30 | 37.5 | 2.4 | 9.3 |

In some embodiments, the solid form of MBDB HCl Form A is crystalline MBDB HCl Form A characterized by two or more, or three or more XRPD signals selected from the group consisting of 14.4° 2θ, 15.0° 2θ, and 25.4° 2θ (±0.2° 2θ; ±0.1° 2θ; or ±0.0° 2θ; Cu Kα1 radiation). In some embodiments, the solid form of MBDB HCl Form A is crystalline MBDB HCl Form A characterized by XRPD signals at 14.4° 2θ, 15.0° 2θ, and 25.4° 2θ (±0.2° 2θ; ±0.1° 2θ; or ±0.0° 2θ; Cu Kα1 radiation).

In some embodiments, the solid form of MBDB HCl Form A is crystalline MBDB HCl Form A characterized by two or more, or three or more XRPD signals selected from the group consisting of 14.4° 2θ, 15.0° 2θ, 16.2° 2θ, 21.6° 2θ, and 25.4° 2θ (±0.2° 2θ; ±0.1° 2θ; or ±0.0° 2θ; Cu Kα1 radiation). In some embodiments, the solid form of MBDB HCl Form A is MBDB HCl Form A characterized by XRPD signals at 14.4° 2θ, 15.0° 2θ, 16.2° 2θ, 21.6° 2θ, and 25.4° 2θ (±0.2° 2θ; ±0.1° 2θ; or ±0.0° 2θ; Cu Kα1 radiation).

In some embodiments, the solid form of MBDB HCl Form A is crystalline MBDB HCl Form A characterized by two or more, or three or more XRPD signals selected from the group consisting of 7.2° 2θ, 12.4° 2θ, and 14.4° 2θ (±0.2° 2θ; ±0.1° 2θ; or ±0.0° 2θ; Cu Kα1 radiation). In some embodiments, the solid form of MBDB HCl Form A is crystalline MBDB HCl Form A characterized by XRPD signals at 7.2° 2θ, 12.4° 2θ, and 14.4° 2θ (±0.2° 2θ; ±0.1° 2θ; or ±0.0° 2θ; Cu Kα1 radiation).

In some embodiments, the solid form of MBDB HCl Form A is crystalline MBDB HCl Form A characterized by two or more, or three or more XRPD signals selected from the group consisting of 7.2° 2θ, 12.4° 2θ, 14.4° 2θ, 15.0° 2θ, and 16.2° 2θ (±0.2° 2θ; ±0.1° 2θ; or ±0.0° 2θ; Cu Kα1 radiation). In some embodiments, the solid form of MBDB HCl Form A is MBDB HCl Form A characterized by XRPD signals at 7.2° 2θ, 12.4° 2θ, 14.4° 2θ, 15.0° 2θ, and 16.2° 2θ (±0.2° 2θ; ±0.1° 2θ; or ±0.0° 2θ; Cu Kα1 radiation).

In some embodiments, the crystalline MBDB HCl Form A is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, or forty XRPD signals selected from those set forth in Table 38.

TABLE 38

XRPD Signals for MBDB HCl Form A

| Signal no. | Position | d-value | Relative |
|---|---|---|---|
| 1 | 7.2 | 12.3 | 63.2 |
| 2 | 12.4 | 7.1 | 30.6 |
| 3 | 12.6 | 7.0 | 13.5 |
| 4 | 13.6 | 6.5 | 14.3 |
| 5 | 13.9 | 6.4 | 9.1 |
| 6 | 14.4 | 6.2 | 100.0 |
| 7 | 15.0 | 5.9 | 90.0 |
| 8 | 16.2 | 5.5 | 69.9 |
| 9 | 16.9 | 5.2 | 28.8 |
| 10 | 17.4 | 5.1 | 7.8 |
| 11 | 17.9 | 5.0 | 18.2 |
| 12 | 21.6 | 4.1 | 72.7 |
| 13 | 22.2 | 4.0 | 30.8 |
| 14 | 23.2 | 3.8 | 27.0 |
| 15 | 23.6 | 3.8 | 26.2 |
| 16 | 24.4 | 3.7 | 15.3 |
| 17 | 24.9 | 3.6 | 23.3 |
| 18 | 25.1 | 3.6 | 26.5 |
| 19 | 25.4 | 3.5 | 82.0 |
| 20 | 26.2 | 3.4 | 47.1 |
| 21 | 26.4 | 3.4 | 24.6 |
| 22 | 27.4 | 3.3 | 17.9 |
| 23 | 28.1 | 3.2 | 27.4 |
| 24 | 28.7 | 3.1 | 29.8 |
| 25 | 29.4 | 3.0 | 12.6 |
| 26 | 30.1 | 3.0 | 30.8 |
| 27 | 30.9 | 2.9 | 6.2 |
| 28 | 31.7 | 2.8 | 7.9 |
| 29 | 32.2 | 2.8 | 12.4 |
| 30 | 32.8 | 2.7 | 8.7 |
| 31 | 33.4 | 2.7 | 7.3 |
| 32 | 34.2 | 2.6 | 6.2 |
| 33 | 34.9 | 2.6 | 13.3 |
| 34 | 35.5 | 2.5 | 7.1 |
| 35 | 35.9 | 2.5 | 7.5 |
| 36 | 36.4 | 2.5 | 9.9 |
| 37 | 37.1 | 2.4 | 7.0 |
| 38 | 37.5 | 2.4 | 7.2 |
| 39 | 38.1 | 2.4 | 7.3 |
| 40 | 39.2 | 2.3 | 6.4 |

Solid Forms of MBDB HCl Form B

Figure 87:
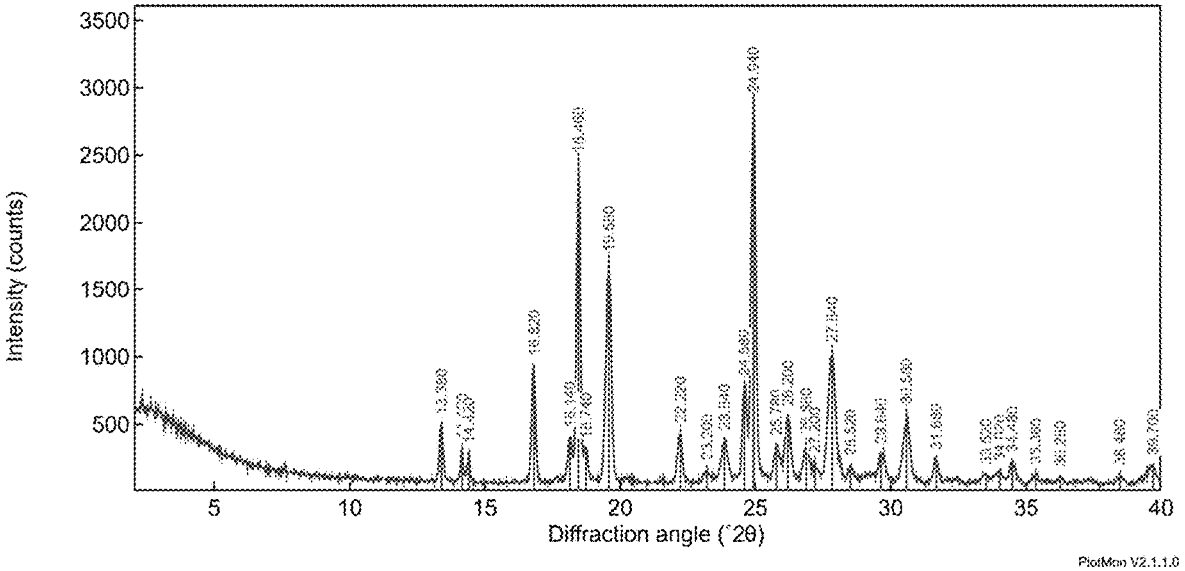
FIG. 87 provides an XRPD diffractogram of crystalline MBDB·HCl Form B.
Figure 93:
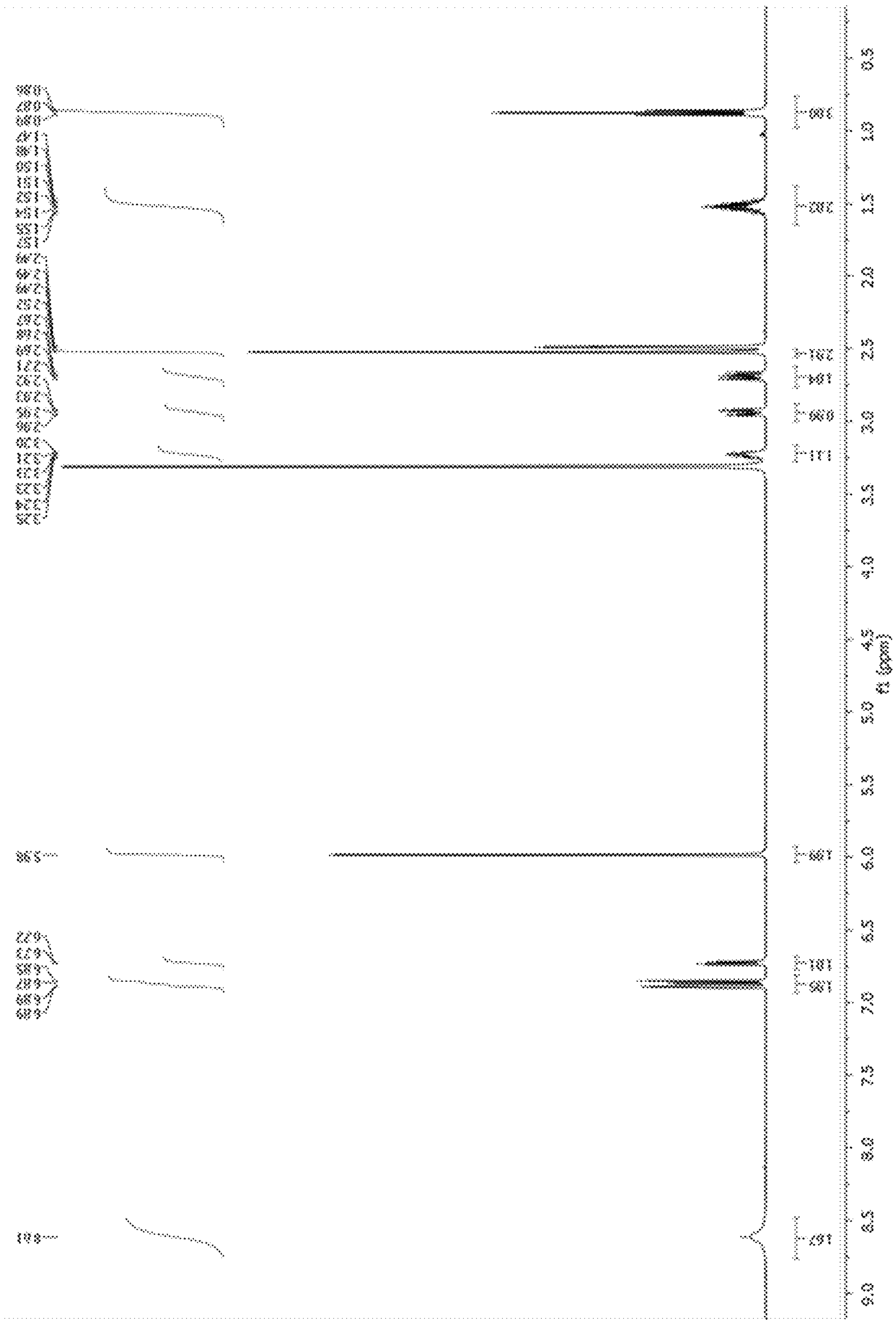
FIG. 93 provides a $^1$H NMR spectrum for MBDB HCl Form B.
Figure 94:
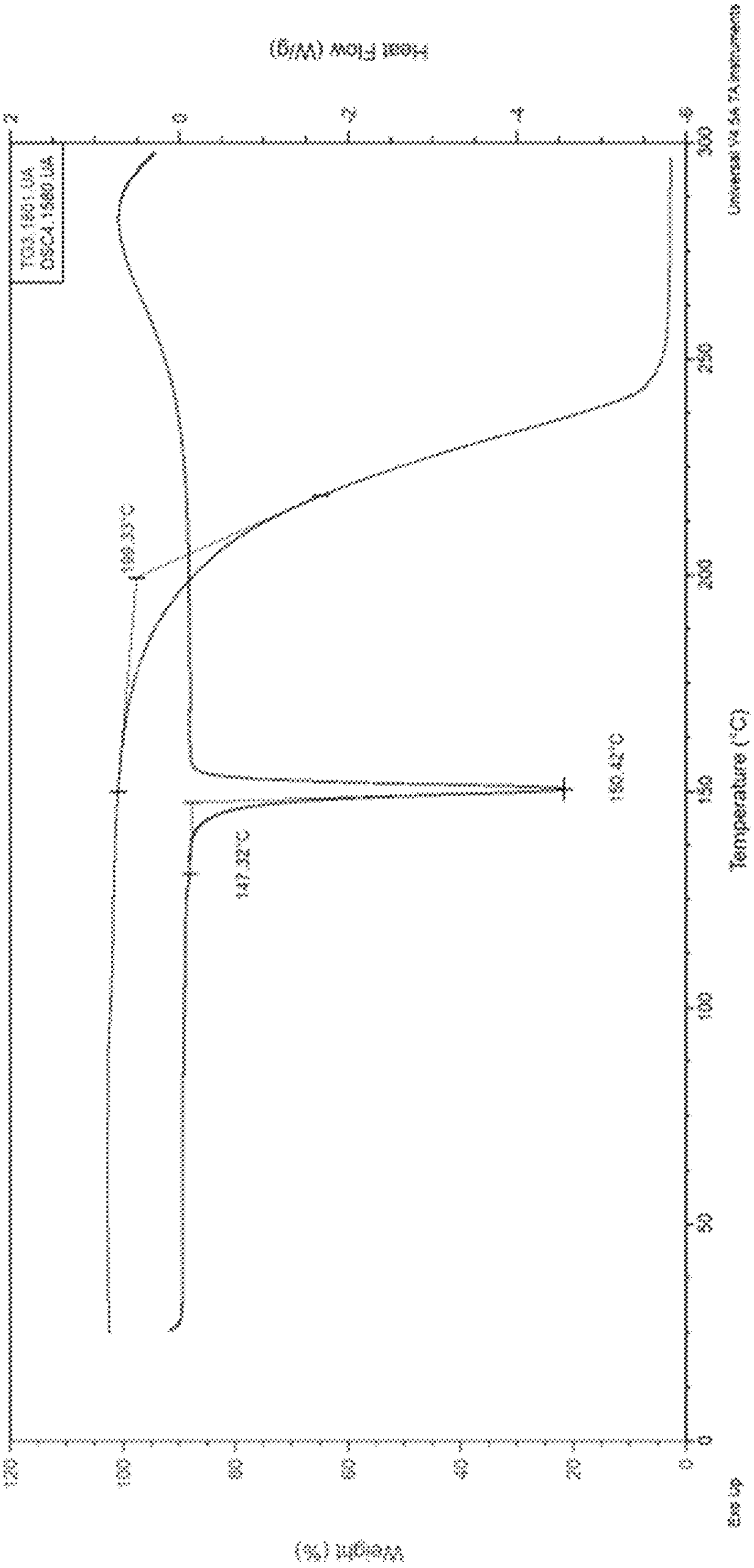
FIG. 94 provides TGA and DSC profiles for MBDB HCl Form B.

In some embodiments, the present disclosure provides solid forms of MBDB HCl Form B, e.g., crystalline forms of MBDB HCl Form B. In some embodiments, the MBDB HCl Form B XRPD profile is substantially similar to that shown in any one of FIG. 39 or 87. In some embodiments, the MBDB HCl Form B $^{1}H$ NMR spectrum is substantially similar to that shown in FIG. 93. In some embodiments, the MBDB HCl Form B TGA profile is substantially similar to that shown in FIG. 94. In some embodiments, the MBDB HCl Form B DSC profile is substantially similar to that shown in FIG. 94.

In some embodiments, the solid form of MBDB HCl Form B is crystalline MBDB HCl Form B characterized by two or more, or three or more XRPD signals selected from the group consisting of 19.7° 2θ, 25.0° 2θ, and 30.7° 2θ (±0.2° 2θ; ±0.1° 2θ; or ±0.0° 2θ; Cu Kα1 radiation). In some embodiments, the solid form of MBDB HCl Form B is crystalline MBDB HCl Form B characterized by XRPD signals at 19.7° 2θ, 25.0° 2θ, and 30.7° 2θ (±0.2° 2θ; ±0.1° 2θ; or ±0.0° 2θ; Cu Kα1 radiation).

In some embodiments, the solid form of MBDB HCl Form B is crystalline MBDB HCl Form B characterized by two or more, or three or more XRPD signals selected from the group consisting of 7.6° 2θ, 18.5° 2θ, 19.7° 2θ, 25.0° 2θ, and 30.7° 2θ (±0.2° 2θ; ±0.1° 2θ; or ±0.0° 2θ; Cu Kα1 radiation). In some embodiments, the solid form of MBDB HCl Form B is MBDB HCl Form B characterized by XRPD signals at 7.6° 2θ, 18.5° 2θ, 19.7° 2θ, 25.0° 2θ, and 30.7° 2θ (±0.2° 2θ; ±0.1° 2θ; or ±0.0° 2θ; Cu Kα1 radiation).

In some embodiments, the solid form of MBDB HCl Form B is crystalline MBDB HCl Form B characterized by two or more, or three or more XRPD signals selected from the group consisting of 7.6° 2θ, 13.3° 2θ, and 14.2° 2θ (±0.2° 2θ; ±0.1° 2θ; or ±0.0° 2θ; Cu Kα1 radiation). In some embodiments, the solid form of MBDB HCl Form B is crystalline MBDB HCl Form B characterized by XRPD signals at 7.6° 2θ, 13.3° 2θ, and 14.2° 2θ (±0.2° 2θ; ±0.1° 2θ; or ±0.0° 2θ; Cu Kα1 radiation).

In some embodiments, the solid form of MBDB HCl Form B is crystalline MBDB HCl Form B characterized by two or more, or three or more XRPD signals selected from the group consisting of 7.6° 2θ, 13.3° 2θ, 14.2° 2θ, 18.5° 2θ, and 19.7° 2θ (±0.2° 2θ; ±0.1° 2θ; or ±0.0° 2θ; Cu Kα1 radiation). In some embodiments, the solid form of MBDB HCl Form B is MBDB HCl Form B characterized by XRPD signals at 7.6° 2θ, 13.3° 2θ, 14.2° 2θ, 18.5° 2θ, and 19.7° 2θ (±0.2° 2θ; ±0.1° 2θ; or ±0.0° 2θ; Cu Kα1 radiation).

In some embodiments, the crystalline MBDB HCl Form B is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four XRPD signals selected from those set forth in Table 39.

TABLE 39

XRPD Signals for MBDB HCl Form B

| Signal no. | Position | d-value | Relative |
|---|---|---|---|
| 1 | 7.6 | 11.7 | 40.3 |
| 2 | 13.3 | 6.6 | 17.7 |
| 3 | 14.2 | 6.3 | 17.1 |
| 4 | 16.8 | 5.3 | 6.9 |
| 5 | 17.6 | 5.0 | 6.0 |
| 6 | 18.5 | 4.8 | 64.4 |
| 7 | 19.7 | 4.5 | 68.1 |
| 8 | 22.2 | 4.0 | 5.4 |
| 9 | 23.4 | 3.8 | 7.7 |
| 10 | 23.8 | 3.7 | 6.9 |
| 11 | 24.8 | 3.6 | 25.1 |
| 12 | 25.0 | 3.6 | 100.0 |
| 13 | 25.9 | 3.4 | 6.4 |
| 14 | 26.3 | 3.4 | 13.9 |
| 15 | 27.9 | 3.2 | 11.3 |
| 16 | 28.6 | 3.1 | 5.6 |
| 17 | 29.5 | 3.0 | 10.5 |
| 18 | 29.7 | 3.0 | 6.9 |
| 19 | 30.7 | 2.9 | 76.0 |
| 20 | 31.7 | 2.8 | 7.2 |
| 21 | 32.1 | 2.8 | 5.0 |
| 22 | 32.6 | 2.7 | 6.9 |
| 23 | 33.6 | 2.7 | 7.3 |
| 24 | 34.5 | 2.6 | 4.6 |

In some embodiments, the solid form of MBDB HCl Form B is crystalline MBDB HCl Form B characterized by two or more, or three or more XRPD signals selected from the group consisting of 18.5° 2θ, 19.6° 2θ, and 24.9° 2θ (±0.2° 2θ; ±0.1° 2θ; or ±0.0° 2θ; Cu Kα1 radiation). In some embodiments, the solid form of MBDB HCl Form B is crystalline MBDB HCl Form B characterized by XRPD signals at 18.5° 2θ, 19.6° 2θ, and 24.9° 2θ (±0.2° 2θ; ±0.1° 2θ; or ±0.0° 2θ; Cu Kα1 radiation).

In some embodiments, the solid form of MBDB HCl Form B is crystalline MBDB HCl Form B characterized by two or more, or three or more XRPD signals selected from the group consisting of 16.8° 2θ, 18.5° 2θ, 19.6° 2θ, 24.9° 2θ, and 27.8° 2θ (±0.2° 2θ; ±0.1° 2θ; or ±0.0° 2θ; Cu Kα1 radiation). In some embodiments, the solid form of MBDB HCl Form B is MBDB HCl Form B characterized by XRPD signals at 16.8° 2θ, 18.5° 2θ, 19.6° 2θ, 24.9° 2θ, and 27.8° 2θ (±0.2° 2θ; ±0.1° 2θ; or ±0.0° 2θ; Cu Kα1 radiation).

In some embodiments, the solid form of MBDB HCl Form B is crystalline MBDB HCl Form B characterized by two or more, or three or more XRPD signals selected from the group consisting of 13.4° 2θ, 14.2° 2θ, and 16.8° 2θ (±0.2° 2θ; ±0.1° 2θ; or ±0.0° 2θ; Cu Kα1 radiation). In some embodiments, the solid form of MBDB HCl Form B is crystalline MBDB HCl Form B characterized by XRPD signals at 13.4° 2θ, 14.2° 2θ, and 16.8° 2θ (±0.2° 2θ; ±0.1° 2θ; or ±0.0° 2θ; Cu Kα1 radiation).

In some embodiments, the solid form of MBDB HCl Form B is crystalline MBDB HCl Form B characterized by two or more, or three or more XRPD signals selected from the group consisting of 13.4° 2θ, 14.2° 2θ, 16.8° 2θ, 18.5° 2θ, and 19.6° 2θ (±0.2° 2θ; ±0.1° 2θ; or ±0.0° 2θ; Cu Kα1 radiation). In some embodiments, the solid form of MBDB HCl Form B is MBDB HCl Form B characterized by XRPD signals at 13.4° 2θ, 14.2° 2θ, 16.8° 2θ, 18.5° 2θ, and 19.6° 2θ (±0.2° 2θ; ±0.1° 2θ; or ±0.0° 2θ; Cu Kα1 radiation).

In some embodiments, the crystalline MBDB HCl Form B is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, or twenty-nine XRPD signals selected from those set forth in Table 40.

TABLE 40

XRPD Signals for MBDB HCl Form B

| Signal no. | Position | d-value | Relative |
|---|---|---|---|
| 1 | 13.4 | 6.6 | 17.5 |
| 2 | 14.2 | 6.3 | 11.2 |
| 3 | 14.4 | 6.1 | 10.1 |
| 4 | 16.8 | 5.3 | 32.5 |
| 5 | 18.1 | 4.9 | 14.2 |
| 6 | 18.5 | 4.8 | 84.6 |
| 7 | 18.7 | 4.7 | 11.4 |
| 8 | 19.6 | 4.5 | 59.3 |
| 9 | 22.2 | 4.0 | 15.5 |
| 10 | 23.2 | 3.8 | 6.0 |
| 11 | 23.8 | 3.7 | 13.5 |
| 12 | 24.6 | 3.6 | 27.5 |
| 13 | 24.9 | 3.6 | 100.0 |
| 14 | 25.8 | 3.5 | 12.2 |
| 15 | 26.2 | 3.4 | 19.6 |
| 16 | 26.9 | 3.3 | 12.6 |
| 17 | 27.2 | 3.3 | 7.7 |
| 18 | 27.8 | 3.2 | 35.8 |
| 19 | 28.5 | 3.1 | 7.1 |
| 20 | 29.6 | 3.0 | 10.1 |
| 21 | 30.6 | 2.9 | 20.2 |
| 22 | 31.7 | 2.8 | 8.6 |
| 23 | 33.5 | 2.7 | 4.8 |
| 24 | 34.0 | 2.6 | 5.8 |
| 25 | 34.5 | 2.6 | 7.9 |
| 26 | 35.4 | 2.5 | 4.9 |
| 27 | 36.3 | 2.5 | 4.2 |
| 28 | 38.5 | 2.3 | 4.6 |
| 29 | 39.7 | 2.3 | 7.2 |

Solid Forms of MEAI HCl

In some embodiments, the present disclosure provides solid forms of MEAI HCl, e.g., crystalline forms of MEAI HCl. In some embodiments, the MEAI HCl XRPD profile is substantially similar to that shown in FIG. 40.

In some embodiments, the solid form of MEAI HCl is crystalline MEAI HCl characterized by two or more, or three or more XRPD signals selected from the group consisting of 21.6° 2θ, 21.7° 2θ, and 32.7° 2θ (±0.2° 2θ; ±0.1° 2θ; or ±0.0° 2θ; Cu Kα1 radiation). In some embodiments, the solid form of MEAI HCl is crystalline MEAI HCl characterized by XRPD signals at 21.6° 2θ, 21.7° 2θ, and 32.7° 2θ (±0.2° 2θ; ±0.1° 2θ; or ±0.0° 2θ; Cu Kα1 radiation).

In some embodiments, the solid form of MEAI HCl is crystalline MEAI HCl characterized by two or more, or three or more XRPD signals selected from the group consisting of 21.6° 2θ, 21.7° 2θ, 24.5° 2θ, 32.7° 2θ, and 32.8° 2θ (±0.2° 2θ; ±0.1° 2θ; or ±0.0° 2θ; Cu Kα1 radiation). In some embodiments, the solid form of MEAI HCl is MEAI HCl characterized by XRPD signals at 21.6° 2θ, 21.7° 2θ, 24.5° 2θ, 32.7° 2θ, and 32.8° 2θ (±0.2° 2θ; ±0.1° 2θ; or ±0.0° 2θ; Cu Kα1 radiation).

In some embodiments, the solid form of MEAI HCl is crystalline MEAI HCl characterized by two or more, or three or more XRPD signals selected from the group consisting of 14.9° 2θ, 18.2° 2θ, and 24.0° 2θ (±0.2° 2θ; ±0.1° 2θ; or ±0.0° 2θ; Cu Kα1 radiation). In some embodiments, the solid form of MEAI HCl is crystalline MEAI HCl characterized by XRPD signals at 14.9° 2θ, 18.2° 2θ, and 24.0° 2θ (±0.2° 2θ; ±0.1° 2θ; or ±0.0° 2θ; Cu Kα1 radiation).

In some embodiments, the solid form of MEAI HCl is crystalline MEAI HCl characterized by two or more, or three or more XRPD signals selected from the group consisting of 14.9° 2θ, 18.2° 2θ, 24.0° 2θ, 24.5° 2θ, and 25.5° 2θ (±0.2° 2θ; ±0.1° 2θ; or ±0.0° 2θ; Cu Kα1 radiation). In some embodiments, the solid form of MEAI HCl is MEAI HCl characterized by XRPD signals at 21.6° 2θ, 21.7° 2θ, 24.5° 2θ, 32.7° 2θ, and 32.8° 2θ (±0.2° 2θ; ±0.1° 2θ; or ±0.0° 2θ; Cu Kα1 radiation).

In some embodiments, the crystalline MEAI HCl is characterized by one, two, three, four, five, six, seven, eight, nine, ten, eleven, twelve, thirteen, fourteen, fifteen, or sixteen XRPD signals selected from those set forth in Table 41.

TABLE 41

XRPD Signals for MEAI HCl

| Signal no. | Position | d-value | Relative |
|---|---|---|---|
| 1 | 10.7 | 8.3 | 19.5 |
| 2 | 10.8 | 8.2 | 16.7 |
| 3 | 14.9 | 6.0 | 12.4 |
| 4 | 18.2 | 4.9 | 17.5 |
| 5 | 18.8 | 4.7 | 9.0 |
| 6 | 20.0 | 4.4 | 23.4 |
| 7 | 20.3 | 4.4 | 16.9 |
| 8 | 21.6 | 4.1 | 100.0 |
| 9 | 21.7 | 4.1 | 73.3 |
| 10 | 24.0 | 3.7 | 20.0 |
| 11 | 24.5 | 3.6 | 48.5 |
| 12 | 25.5 | 3.5 | 11.8 |
| 13 | 25.7 | 3.5 | 17.5 |
| 14 | 29.9 | 3.0 | 12.9 |
| 15 | 32.7 | 2.7 | 54.4 |
| 16 | 32.8 | 2.7 | 30.5 |

Solid Forms of 5,6-dimethoxy-2-aminoindane HCl

In some embodiments, the present disclosure provides solid forms of 5,6-dimethoxy-2-aminoindane HCl, e.g., crystalline forms of 5,6-dimethoxy-2-aminoindane HCl. In some embodiments, the 5,6-dimethoxy-2-aminoindane HCl XRPD profile is substantially similar to that shown in FIG. 42.

In some embodiments, the solid form of 5,6-dimethoxy-2-aminoindane HCl is crystalline 5,6-dimethoxy-2-aminoindane HCl characterized by two or more, or three or more XRPD signals selected from the group consisting of 11.7° 2θ, 18.2° 2θ, and 18.9° 2θ (±0.2° 2θ; ±0.1° 2θ; or ±0.0° 2θ; Cu Kα1 radiation). In some embodiments, the solid form of 5,6-dimethoxy-2-aminoindane HCl is crystalline 5,6-dimethoxy-2-aminoindane HCl characterized by XRPD signals at 11.7° 2θ, 18.2° 2θ, and 18.9° 2θ (±0.2° 2θ; ±0.1° 2θ; or ±0.0° 2θ; Cu Kα1 radiation).

In some embodiments, the solid form of 5,6-dimethoxy-2-aminoindane HCl is crystalline 5,6-dimethoxy-2-aminoindane HCl characterized by two or more, or three or more XRPD signals selected from the group consisting of 11.7° 2θ, 18.2° 2θ, 18.9° 2θ, 23.0° 2θ, and 23.5° 2θ (±0.2° 2θ; ±0.1° 2θ; or ±0.0° 2θ; Cu Kα1 radiation). In some embodiments, the solid form of 5,6-dimethoxy-2-aminoindane HCl is 5,6-dimethoxy-2-aminoindane HCl characterized by XRPD signals at 11.7° 2θ, 18.2° 2θ, 18.9° 2θ, 23.0° 2θ, and 23.5° 2θ (±0.2° 2θ; ±0.1° 2θ; or ±0.0° 2θ; Cu Kα1 radiation).

In some embodiments, the solid form of 5,6-dimethoxy-2-aminoindane HCl is crystalline 5,6-dimethoxy-2-aminoindane HCl characterized by two or more, or three or more XRPD signals selected from the group consisting of 11.7° 2θ, 27.3° 2θ, and 27.5° 2θ (±0.2° 2θ; ±0.1° 2θ; or ±0.0° 2θ; Cu Kα1 radiation). In some embodiments, the solid form of 5,6-dimethoxy-2-aminoindane HCl is crystalline 5,6-dimethoxy-2-aminoindane HCl characterized by XRPD signals at 11.7° 2θ, 27.3° 2θ, and 27.5° 2θ (±0.2° 2θ; ±0.1° 2θ; or ±0.0° 2θ; Cu Kα1 radiation).

In some embodiments, the solid form of 5,6-dimethoxy-2-aminoindane HCl is crystalline 5,6-dimethoxy-2-aminoindane HCl characterized by two or more, or three or more XRPD signals selected from the group consisting of 9.0° 2θ, 9.1° 2θ, 11.7° 2θ, 27.3° 2θ, and 27.5° 2θ (±0.2° 2θ; ±0.1° 2θ; or ±0.0° 2θ; Cu Kα1 radiation). In some embodiments, the solid form of 5,6-dimethoxy-2-aminoindane HCl is 5,6-dimethoxy-2-aminoindane HCl characterized by XRPD signals at 9.0° 2θ, 9.1° 2θ, 11.7° 2θ, 27.3° 2θ, and 27.5° 2θ (±0.2° 2θ; ±0.1° 2θ; or ±0.0° 2θ; Cu Kα1 radiation).

In some embodiments, the crystalline 5,6-dimethoxy-2-aminoindane HCl is characterized by one, two, three, four, five, six, seven, eight, nine, ten, eleven, twelve, thirteen, fourteen, fifteen, sixteen, seventeen, or eighteen XRPD signals selected from those set forth in Table 42.

TABLE 42

XRPD Signals for 5,6-dimethoxy-2-aminoindane HCl

| Signal no. | Position | d-value | Relative |
|---|---|---|---|
| 1 | 9.0 | 9.8 | 49.3 |
| 2 | 9.1 | 9.7 | 68.6 |
| 3 | 11.6 | 7.6 | 30.4 |
| 4 | 11.7 | 7.5 | 93.2 |
| 5 | 18.2 | 4.9 | 16.5 |
| 6 | 18.9 | 4.7 | 23.1 |
| 7 | 23.0 | 3.9 | 20.1 |
| 8 | 23.5 | 3.8 | 16.2 |
| 9 | 25.3 | 3.5 | 14.5 |
| 10 | 25.9 | 3.4 | 9.2 |
| 11 | 27.3 | 3.3 | 83.3 |
| 12 | 27.5 | 3.2 | 100.0 |
| 13 | 30.4 | 2.9 | 15.4 |
| 14 | 30.9 | 2.9 | 15.1 |
| 15 | 36.8 | 2.4 | 9.1 |
| 16 | 39.2 | 2.3 | 17.5 |

TABLE 42-continued

| XRPD Signals for 5,6-dimethoxy-2-aminoindane HCl | | | |
|---|---|---|---|
| Signal no. | Position | d-value | Relative |
| 17 | 42.4 | 2.1 | 10.0 |
| 18 | 48.6 | 1.9 | 9.7 |

Solid Forms of MBDB Maleate Form 2

Figure 98:
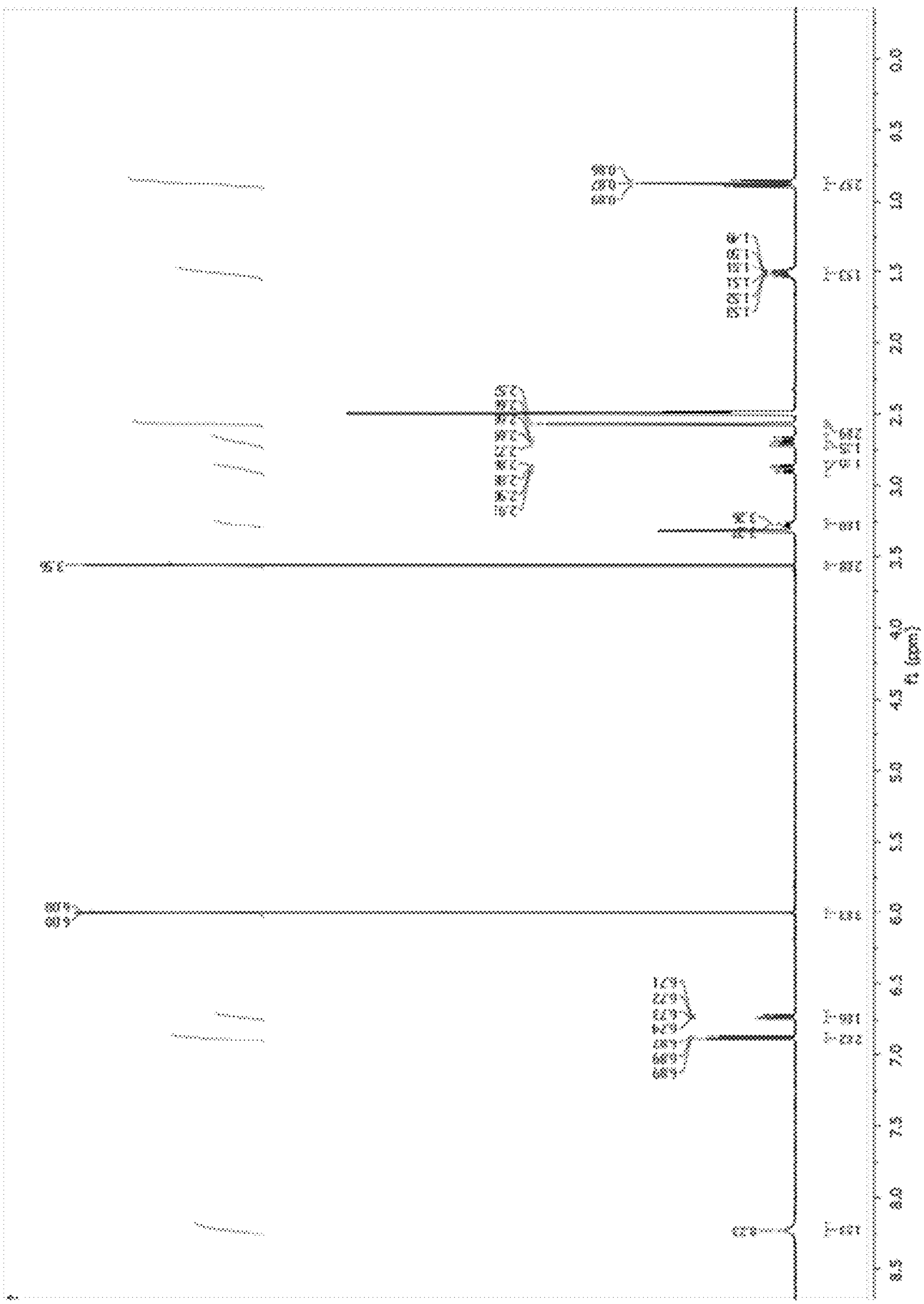
FIG. 98 provides a $^1$H NMR spectrum for MBDB maleate (Form 2).

In some embodiments, the present disclosure provides solid forms of MBDB maleate Form 2, e.g., crystalline forms of MBDB maleate Form 2. In some embodiments, the MBDB maleate Form 2 XRPD profile is substantially similar to that shown in FIG. 96. In some embodiments, the MBDB maleate Form 2 $^1$H NMR spectrum is substantially similar to that shown in FIG. 98. In some embodiments, the MBDB maleate Form 2 TGA profile is substantially similar to that shown in FIG. 100. In some embodiments, the MBDB maleate Form 2 DSC profile is substantially similar to that shown in FIG. 100.

In some embodiments, the solid form of MBDB maleate Form 2 is crystalline MBDB maleate Form 2 characterized by two or more, or three or more XRPD signals selected from the group consisting of 19.3° 2θ, 23.7° 2θ, and 24.2° 2θ (±0.2° 2θ; ±0.1° 2θ; or ±0.0° 2θ; Cu Kα1 radiation). In some embodiments, the solid form of MBDB maleate Form 2 is MBDB maleate Form 2 characterized by XRPD signals at 19.3° 2θ, 23.7° 2θ, and 24.2° 2θ (±0.2° 2θ; ±0.1° 2θ; or ±0.0° 2θ; Cu Kα1 radiation).

In some embodiments, the solid form of MBDB maleate Form 2 is crystalline MBDB maleate Form 2 characterized by two or more, or three or more XRPD signals selected from the group consisting of 14.5° 2θ, 15.3° 2θ, 19.3° 2θ, 23.7° 2θ, and 24.2° 2θ (±0.2° 2θ; ±0.1° 2θ; or ±0.0° 2θ; Cu Kα1 radiation). In some embodiments, the solid form of MBDB maleate Form 2 is MBDB maleate Form 2 characterized by XRPD signals at 14.5° 2θ, 15.3° 2θ, 19.3° 2θ, 23.7° 2θ, and 24.2° 2θ (±0.2° 2θ; ±0.1° 2θ; or ±0.0° 2θ; Cu Kα1 radiation).

In some embodiments, the solid form of MBDB maleate Form 2 is crystalline MBDB maleate Form 2 characterized by two or more, or three or more XRPD signals selected from the group consisting of 9.7° 2θ, 11.8° 2θ, and 14.5° 2θ (±0.2° 2θ; ±0.1° 2θ; or ±0.0° 2θ; Cu Kα1 radiation). In some embodiments, the solid form of MBDB maleate Form 2 is MBDB maleate Form 2 characterized by XRPD signals at 9.7° 2θ, 11.8° 2θ, and 14.5° 2θ (±0.2° 2θ; ±0.1° 2θ; or ±0.0° 2θ; Cu Kα1 radiation).

In some embodiments, the solid form of MBDB maleate Form 2 is crystalline MBDB maleate Form 2 characterized by two or more, or three or more XRPD signals selected from the group consisting of 9.7° 2θ, 11.8° 2θ, 14.5° 2θ, 15.3° 2θ, and 19.3° 2θ (±0.2° 2θ; ±0.1° 2θ; or ±0.0° 2θ; Cu Kα1 radiation). In some embodiments, the solid form of MBDB maleate Form 2 is MBDB maleate Form 2 characterized by XRPD signals at 9.7° 2θ, 11.8° 2θ, 14.5° 2θ, 15.3° 2θ, and 19.3° 2θ (±0.2° 2θ; ±0.1° 2θ; or ±0.0° 2θ; Cu Kα1 radiation).

In some embodiments, the crystalline MBDB maleate Form 2 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, or thirty-two XRPD signals selected from those set forth in Table 42A.

TABLE 42A

| XRPD Signals for MBDB maleate Form 2 | | | |
|---|---|---|---|
| Signal no. | Position | d-value | Relative |
| 1 | 4.8 | 18.3 | 3.6 |
| 2 | 5.7 | 15.5 | 1.1 |
| 3 | 9.7 | 9.1 | 7.1 |
| 4 | 11.4 | 7.8 | 0.9 |
| 5 | 11.8 | 7.5 | 7.4 |
| 6 | 14.5 | 6.1 | 22.7 |
| 7 | 15.3 | 5.8 | 20.4 |
| 8 | 17.1 | 5.2 | 2.0 |
| 9 | 18.8 | 4.7 | 5.4 |
| 10 | 19.3 | 4.6 | 82.1 |
| 11 | 20.0 | 4.4 | 4.4 |
| 12 | 21.2 | 4.2 | 3.4 |
| 13 | 21.7 | 4.1 | 13.6 |
| 14 | 22.2 | 4.0 | 2.4 |
| 15 | 22.9 | 3.9 | 3.3 |
| 16 | 23.0 | 3.9 | 4.7 |
| 17 | 23.7 | 3.8 | 67.1 |
| 18 | 24.2 | 3.7 | 100.0 |
| 19 | 24.7 | 3.6 | 2.4 |
| 20 | 25.2 | 3.5 | 9.8 |
| 21 | 26.6 | 3.4 | 6.2 |
| 22 | 27.1 | 3.3 | 2.0 |
| 23 | 28.3 | 3.2 | 11.5 |
| 24 | 28.9 | 3.1 | 4.1 |
| 25 | 29.1 | 3.1 | 40.0 |
| 26 | 30.8 | 2.9 | 4.7 |
| 27 | 31.6 | 2.8 | 4.0 |
| 28 | 32.8 | 2.7 | 1.8 |
| 29 | 33.0 | 2.7 | 15.6 |
| 30 | 34.9 | 2.6 | 2.6 |
| 31 | 37.9 | 2.4 | 2.3 |
| 32 | 39.2 | 2.3 | 2.2 |

Solid Forms of MBDB Maleate Form 3

Figure 97:
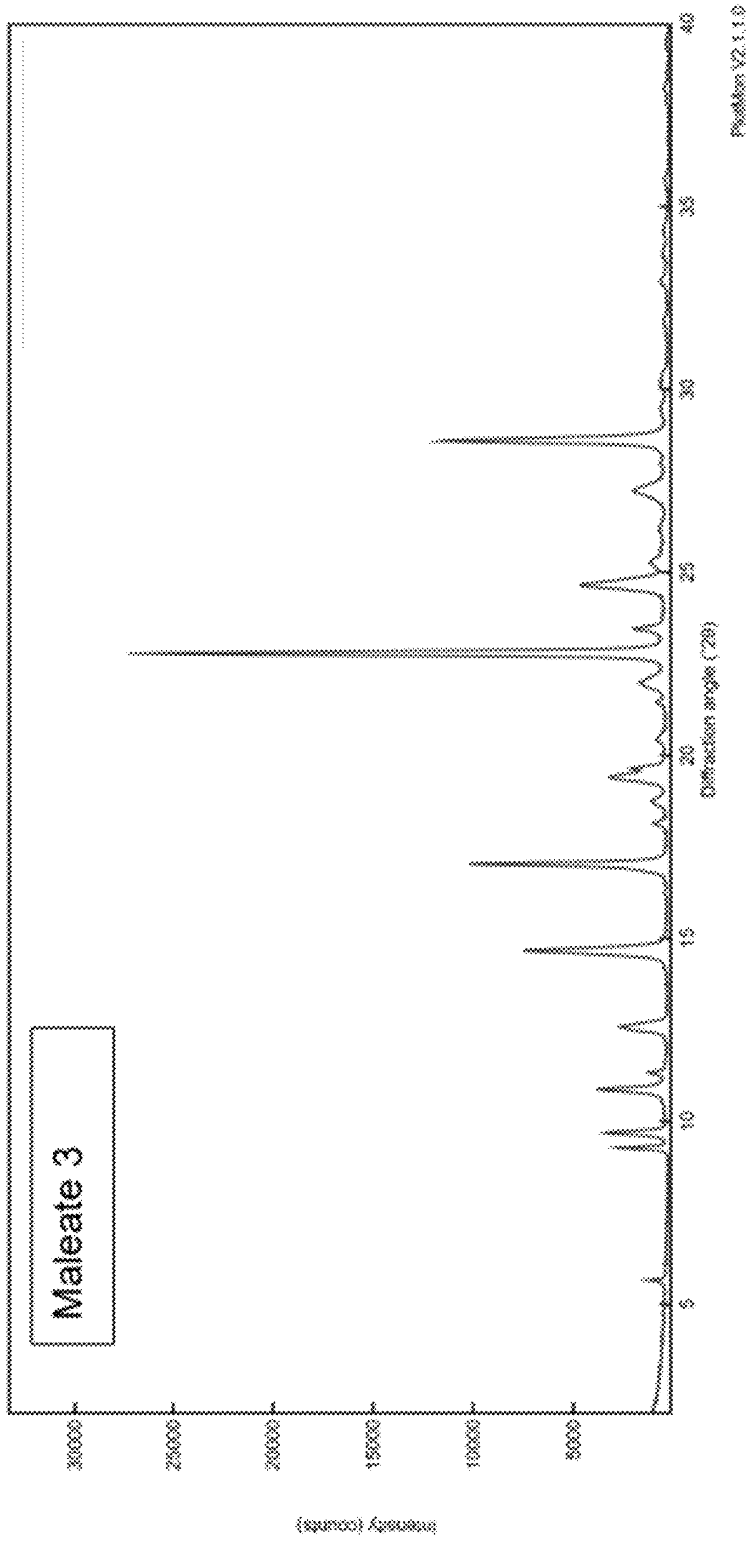
FIG. 97 provides an XRPD diffractogram of crystalline MBDB·maleate Form 3.
Figure 99:
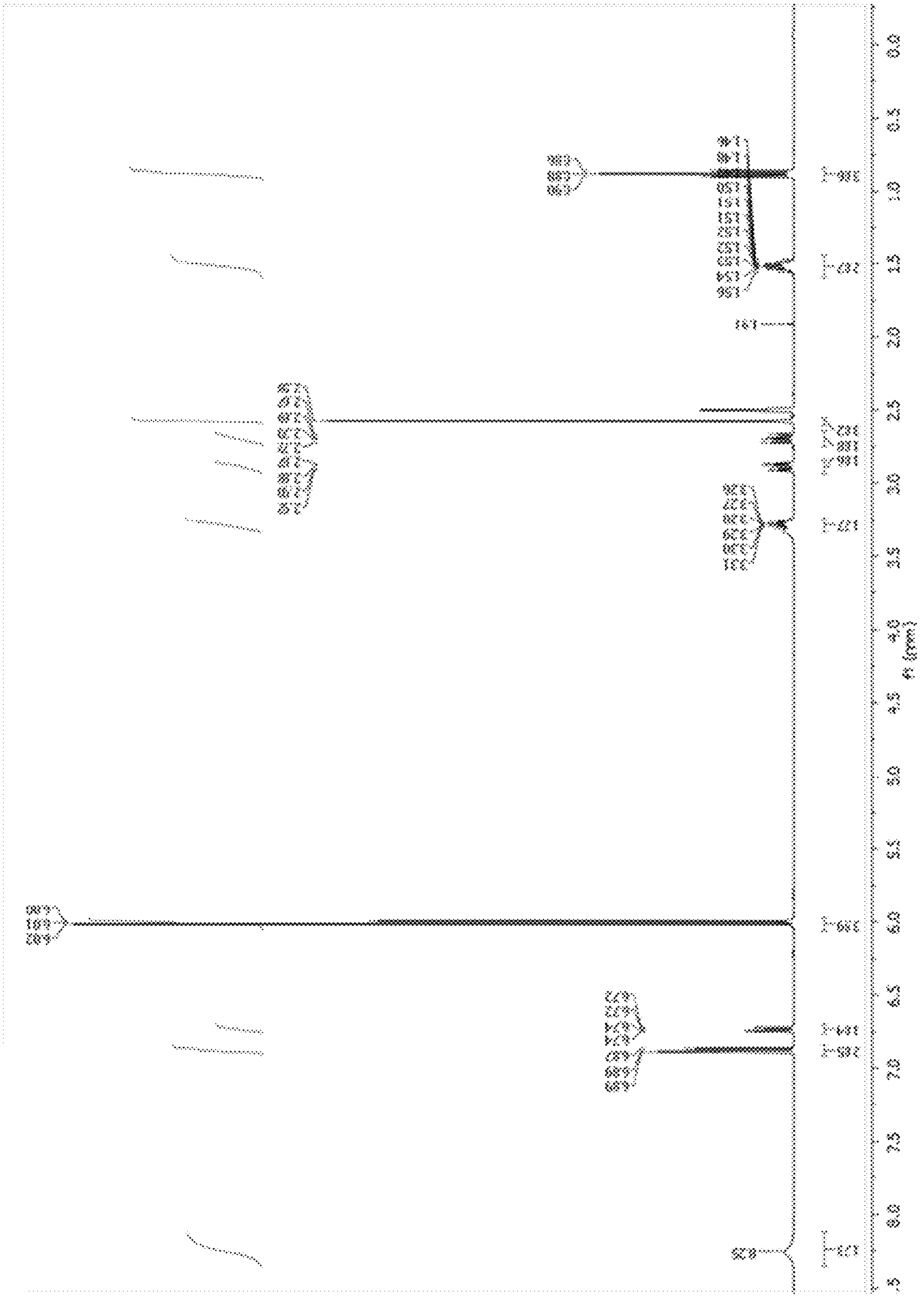
FIG. 99 provides a $^1$H NMR spectrum for MBDB maleate (Form 3).

In some embodiments, the present disclosure provides solid forms of MBDB maleate Form 3, e.g., crystalline forms of MBDB maleate Form 3. In some embodiments, the MBDB maleate Form 3 XRPD profile is substantially similar to that shown in FIG. 97. In some embodiments, the MBDB maleate Form 3 $^1$H NMR spectrum is substantially similar to that shown in FIG. 99. In some embodiments, the MBDB maleate Form 3 TGA profile is substantially similar to that shown in FIG. 101. In some embodiments, the MBDB maleate Form 3 DSC profile is substantially similar to that shown in FIG. 101.

In some embodiments, the solid form of MBDB maleate Form 3 is crystalline MBDB maleate Form 3 characterized by two or more, or three or more XRPD signals selected from the group consisting of 17.0° 2θ, 22.8° 2θ, and 28.6° 2θ (±0.2° 2θ; ±0.1° 2θ; or ±0.0° 2θ; Cu Kα1 radiation). In some embodiments, the solid form of MBDB maleate Form 3 is MBDB maleate Form 3 characterized by XRPD signals at 17.0° 2θ, 22.8° 2θ, and 28.6° 2θ (±0.2° 2θ; ±0.1° 2θ; or ±0.0° 2θ; Cu Kα1 radiation).

In some embodiments, the solid form of MBDB maleate Form 3 is crystalline MBDB maleate Form 3 characterized by two or more, or three or more XRPD signals selected from the group consisting of 9.7 20, 10.9° 2θ, 17.0° 2θ, 22.8° 2θ, and 28.6° 2θ (±0.2° 2θ; ±0.1° 2θ; or ±0.0° 2θ; Cu Kα1 radiation). In some embodiments, the solid form of MBDB maleate Form 3 is MBDB maleate Form 3 characterized by XRPD signals at 9.7 20, 10.9° 2θ, 17.0° 2θ, 22.8° 2θ, and 28.6° 2θ (±0.2° 2θ; ±0.1° 2θ; or ±0.0° 2θ; Cu Kα1 radiation).

In some embodiments, the solid form of MBDB maleate Form 3 is crystalline MBDB maleate Form 3 characterized by two or more, or three or more XRPD signals selected from the group consisting of 9.3° 2θ, 9.7° 2θ, and 10.9° 2θ (±0.2° 2θ; ±0.1° 2θ; or ±0.0° 2θ; Cu Kα1 radiation). In some embodiments, the solid form of MBDB maleate Form 3 is MBDB maleate Form 3 characterized by XRPD signals at 9.3° 2θ, 9.7° 2θ, and 10.9° 2θ (±0.2° 2θ; ±0.1° 2θ; or ±0.0° 2θ; Cu Kα1 radiation).

In some embodiments, the solid form of MBDB maleate Form 3 is crystalline MBDB maleate Form 3 characterized by two or more, or three or more XRPD signals selected from the group consisting of 9.3° 2θ, 9.7° 2θ, 10.9° 2θ, 14.7° 2θ, and 17.0° 2θ (±0.2° 2θ; ±0.1° 2θ; or ±0.0° 2θ; Cu Kα1 radiation). In some embodiments, the solid form of MBDB maleate Form 3 is MBDB maleate Form 3 characterized by XRPD signals at 9.3° 2θ, 9.7° 2θ, 10.9° 2θ, 14.7° 2θ, and 17.0° 2θ (±0.2° 2θ; ±0.1° 2θ; or ±0.0° 2θ; Cu Kα1 radiation).

In some embodiments, the crystalline MBDB maleate Form 3 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, or thirty-five XRPD signals selected from those set forth in Table 42B.

TABLE 42B

XRPD Signals for MBDB maleate Form 3

| Signal no. | Position | d-value | Relative |
|---|---|---|---|
| 1 | 5.7 | 15.6 | 4.8 |
| 2 | 9.3 | 9.5 | 10.7 |
| 3 | 9.7 | 9.1 | 12.9 |
| 4 | 10.9 | 8.1 | 14.2 |
| 5 | 11.3 | 7.8 | 4.8 |
| 6 | 12.6 | 7.0 | 10.1 |
| 7 | 14.7 | 6.0 | 27.8 |
| 8 | 17.0 | 5.2 | 37.8 |
| 9 | 18.1 | 4.9 | 3.9 |
| 10 | 18.7 | 4.7 | 4.1 |
| 11 | 19.4 | 4.6 | 11.9 |
| 12 | 19.6 | 4.5 | 8.0 |
| 13 | 20.4 | 4.3 | 3.2 |
| 14 | 21.4 | 4.1 | 3.1 |
| 15 | 22.0 | 4.0 | 6.4 |
| 16 | 22.8 | 3.9 | 100.0 |
| 17 | 23.5 | 3.8 | 7.5 |
| 18 | 24.6 | 3.6 | 17.3 |
| 19 | 25.3 | 3.5 | 4.4 |
| 20 | 25.6 | 3.5 | 2.5 |
| 21 | 26.1 | 3.4 | 2.7 |
| 22 | 27.2 | 3.3 | 7.4 |
| 23 | 28.0 | 3.2 | 2.5 |
| 24 | 28.6 | 3.1 | 43.5 |
| 25 | 29.5 | 3.0 | 2.4 |
| 26 | 30.1 | 3.0 | 2.4 |
| 27 | 30.4 | 2.9 | 2.2 |
| 28 | 31.9 | 2.8 | 1.8 |
| 29 | 33.0 | 2.7 | 2.5 |
| 30 | 33.8 | 2.7 | 2.0 |
| 31 | 34.3 | 2.6 | 1.9 |
| 32 | 35.8 | 2.5 | 1.7 |
| 33 | 37.9 | 2.4 | 1.4 |
| 34 | 38.2 | 2.4 | 1.8 |
| 35 | 39.5 | 2.3 | 1.4 |

Solid Forms of (R)-MDE HCl

Figure 102:
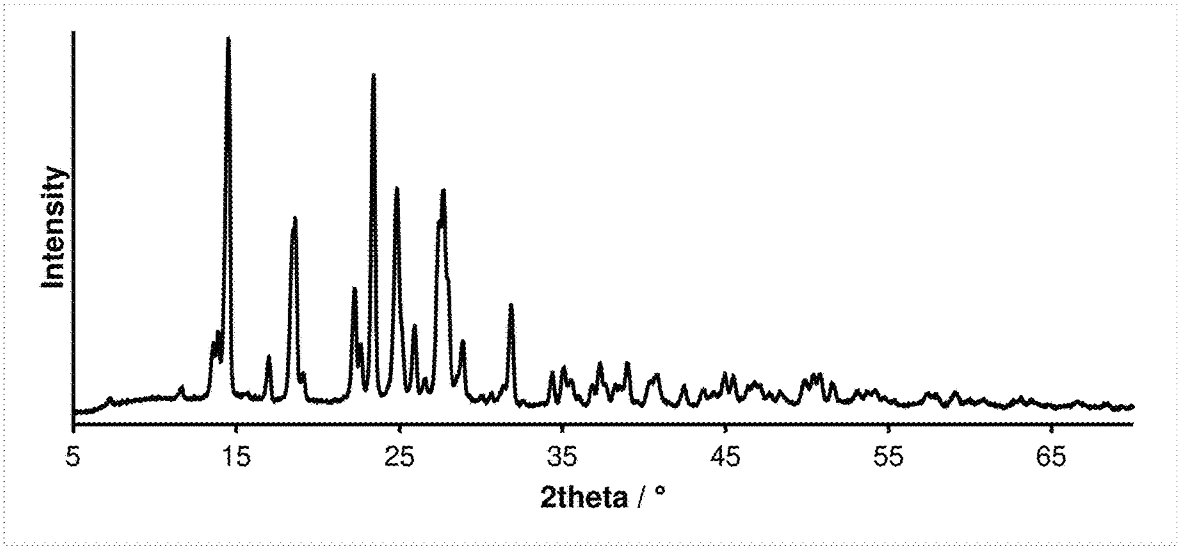
FIG. 102 provides an XRPD diffractogram of crystalline (R)-MDE HCl.

In some embodiments, the present disclosure provides solid forms of (R)-MDE HCl, e.g., crystalline forms of (R)-MDE HCl. In some embodiments, the (R)-MDE HCl XRPD profile is substantially similar to that shown in FIG. 102.

In some embodiments, the solid form of (R)-MDE HCl is crystalline (R)-MDE HCl characterized by two or more, or three or more XRPD signals selected from the group consisting of 14.5° 2θ, 17.0° 2θ, and 22.2° 2θ (±0.2° 2θ; ±0.1° 2θ; or ±0.0° 2θ; Cu Kα1 radiation). In some embodiments, the solid form of (R)-MDE HCl is crystalline (R)-MDE HCl characterized by XRPD signals at 14.5° 2θ, 17.0° 2θ, and 22.2° 2θ (±0.2° 2θ; ±0.1° 2θ; or ±0.0° 2θ; Cu Kα1 radiation).

In some embodiments, the solid form of (R)-MDE HCl is crystalline (R)-MDE HCl characterized by two or more, or three or more XRPD signals selected from the group consisting of 14.5° 2θ, 17.0° 2θ, 22.2° 2θ, 22.6° 2θ, and 23.4° 2θ (±0.2° 2θ; ±0.1° 2θ; or ±0.0° 2θ; Cu Kα1 radiation). In some embodiments, the solid form of (R)-MDE HCl is (R)-MDE HCl characterized by XRPD signals at 14.5° 2θ, 17.0° 2θ, 22.2° 2θ, 22.6° 2θ, and 23.4° 2θ (±0.2° 2θ; ±0.1° 2θ; or ±0.0° 2θ; Cu Kα1 radiation).

In some embodiments, the solid form of (R)-MDE HCl is crystalline (R)-MDE HCl characterized by two or more, or three or more XRPD signals selected from the group consisting of 14.5° 2θ, 23.4° 2θ, and 24.8° 2θ (±0.2° 2θ; ±0.1° 2θ; or ±0.0° 2θ; Cu Kα1 radiation). In some embodiments, the solid form of (R)-MDE HCl is crystalline (R)-MDE HCl characterized by XRPD signals at 14.5° 2θ, 23.4° 2θ, and 24.8° 2θ (±0.2° 2θ; ±0.1° 2θ; or ±0.0° 2θ; Cu Kα1 radiation).

In some embodiments, the solid form of (R)-MDE HCl is crystalline (R)-MDE HCl characterized by two or more, or three or more XRPD signals selected from the group consisting of 14.5° 2θ, 23.4° 2θ, 24.8° 2θ, 27.4° 2θ, and 27.7° 2θ (±0.2° 2θ; ±0.1° 2θ; or ±0.0° 2θ; Cu Kα1 radiation). In some embodiments, the solid form of (R)-MDE HCl is (R)-MDE HCl characterized by XRPD signals at 14.5° 2θ, 23.4° 2θ, 24.8° 2θ, 27.4° 2θ, and 27.7° 2θ (±0.2° 2θ; ±0.1° 2θ; or ±0.0° 2θ; Cu Kα1 radiation).

In some embodiments, the crystalline (R)-MDE HCl is characterized by one, two, three, four, five, six, seven, eight, nine, ten, eleven, twelve, thirteen, fourteen, fifteen, sixteen, or seventeen XRPD signals selected from those set forth in Table 58.

TABLE 58

XRPD Signals for (R)-MDE HCl

| Signal no. | Position | d-value | Relative |
|---|---|---|---|
| 1 | 13.6 | 6.5 | 11.6 |
| 2 | 13.9 | 6.4 | 19.5 |
| 3 | 14.5 | 6.1 | 100.0 |
| 4 | 17.0 | 5.2 | 11.9 |
| 5 | 18.4 | 4.8 | 41.7 |
| 6 | 18.6 | 4.8 | 35.9 |
| 7 | 22.2 | 4.0 | 32.1 |
| 8 | 22.6 | 3.9 | 15.0 |
| 9 | 23.4 | 3.8 | 95.5 |
| 10 | 24.8 | 3.6 | 61.6 |
| 11 | 25.2 | 3.5 | 10.1 |
| 12 | 25.9 | 3.4 | 21.5 |
| 13 | 27.4 | 3.3 | 45.9 |
| 14 | 27.7 | 3.2 | 53.0 |
| 15 | 28.0 | 3.2 | 28.4 |
| 16 | 28.8 | 3.1 | 17.3 |
| 17 | 31.8 | 2.8 | 28.2 |

Solid Forms of (S)-MDE HCl

Figure 103:
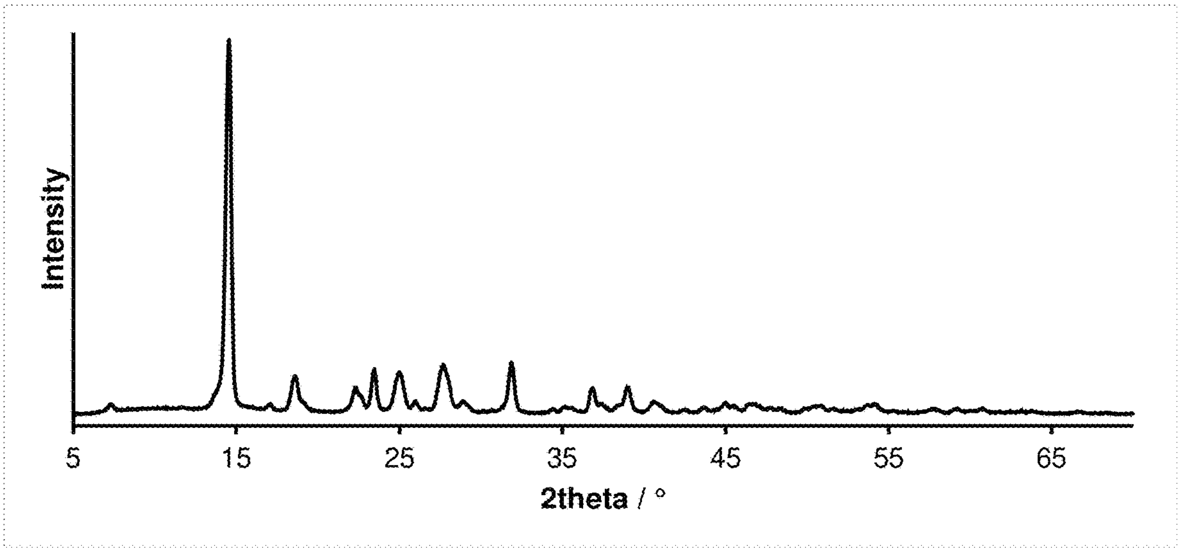
FIG. 103 provides an XRPD diffractogram of crystalline (S)-MDE HCl.

In some embodiments, the present disclosure provides solid forms of (S)-MDE HCl, e.g., crystalline forms of (S)-MDE HCl. In some embodiments, the (S)-MDE HCl XRPD profile is substantially similar to that shown in FIG. 103.

In some embodiments, the solid form of (S)-MDE HCl is crystalline(S)-MDE HCl characterized by two or more, or three or more XRPD signals selected from the group consisting of 14.5° 2θ, 23.4° 2θ, and 25.0° 2θ (±0.2° 2θ; ±0.1° 2θ; or ±0.0° 2θ; Cu Kα1 radiation). In some embodiments, the solid form of (S)-MDE HCl is crystalline(S)-MDE HCl characterized by XRPD signals at 14.5° 2θ, 23.4° 2θ, and 25.0° 2θ (±0.2° 2θ; ±0.1° 2θ; or ±0.0° 2θ; Cu Kα1 radiation).

In some embodiments, the solid form of (S)-MDE HCl is crystalline(S)-MDE HCl characterized by two or more, or three or more XRPD signals selected from the group consisting of 14.5° 2θ, 27.6° 2θ, and 31.8° 2θ (±0.2° 2θ; ±0.1° 2θ; or ±0.0° 2θ; Cu Kα1 radiation). In some embodiments, the solid form of (S)-MDE HCl is crystalline(S)-MDE HCl characterized by XRPD signals at 14.5° 2θ, 27.6° 2θ, and 31.8° 2θ (±0.2° 2θ; ±0.1° 2θ; or ±0.0° 2θ; Cu Kα1 radiation).

In some embodiments, the solid form of (S)-MDE HCl is crystalline(S)-MDE HCl characterized by two or more, or three or more XRPD signals selected from the group consisting of 14.5° 2θ, 23.4° 2θ, 25.0° 2θ, 27.6° 2θ, and 31.8° 2θ (±0.2° 2θ; ±0.1° 2θ; or ±0.0° 2θ; Cu Kα1 radiation). In some embodiments, the solid form of (S)-MDE HCl is (S)-MDE HCl characterized by XRPD signals at 14.5° 2θ, 23.4° 2θ, 25.0° 2θ, 27.6° 2θ, and 31.8° 2θ (±0.2° 2θ; ±0.1° 2θ; or ±0.0° 2θ; Cu Kα1 radiation).

In some embodiments, the crystalline(S)-MDE HCl is characterized by one, two, three, four, or five XRPD signals selected from those set forth in Table 59.

TABLE 59

XRPD Signals for (S)-MDE HCl

| Signal no. | Position | d-value | Relative |
|---|---|---|---|
| 1 | 14.5 | 6.1 | 100.0 |
| 2 | 23.4 | 3.8 | 11.0 |
| 3 | 25.0 | 3.6 | 10.3 |
| 4 | 27.6 | 3.2 | 11.5 |
| 5 | 31.8 | 2.8 | 13.2 |

Solid Forms of (R)-MBDB HCl

Figure 104:
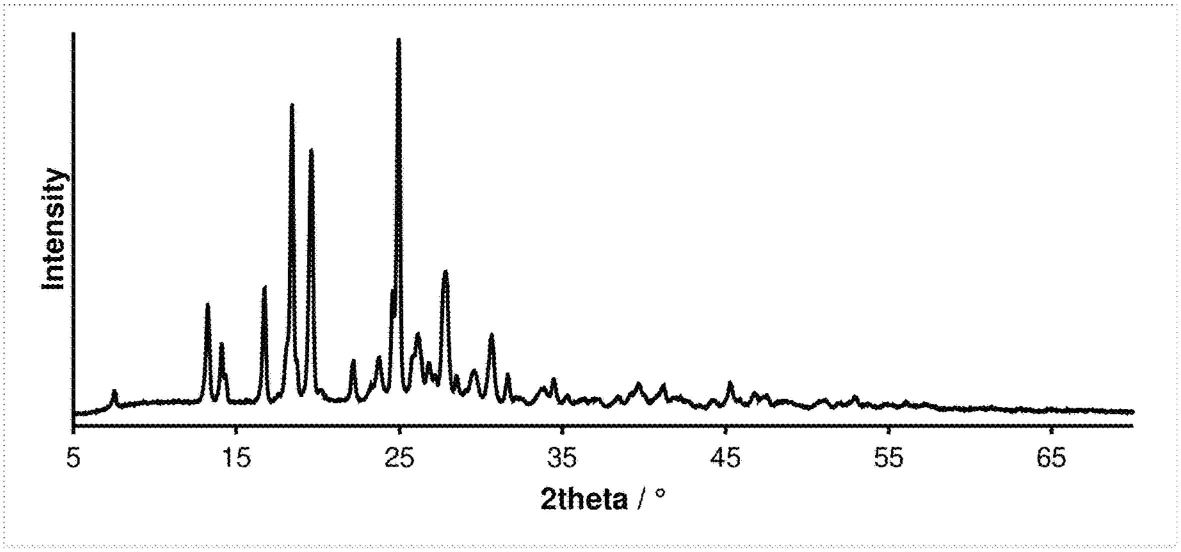
FIG. 104 provides an XRPD diffractogram of crystalline (R)-MBDB HCl.

In some embodiments, the present disclosure provides solid forms of (R)-MBDB HCl, e.g., crystalline forms of (R)-MBDB HCl. In some embodiments, the (R)-MBDB HCl XRPD profile is substantially similar to that shown in FIG. 104.

In some embodiments, the solid form of (R)-MBDB HCl is crystalline (R)-MBDB HCl characterized by two or more, or three or more XRPD signals selected from the group consisting of 13.2° 2θ, 14.1° 2θ, and 16.7° 2θ (±0.2° 2θ; ±0.1° 2θ; or ±0.0° 2θ; Cu Kα1 radiation). In some embodiments, the solid form of (R)-MBDB HCl is crystalline (R)-MBDB HCl characterized by XRPD signals at 13.2° 2θ, 14.1° 2θ, and 16.7° 2θ (±0.2° 2θ; ±0.1° 2θ; or ±0.0° 2θ; Cu Kα1 radiation).

In some embodiments, the solid form of (R)-MBDB HCl is crystalline (R)-MBDB HCl characterized by two or more, or three or more XRPD signals selected from the group consisting of 13.2° 2θ, 14.1° 2θ, 16.7° 2θ, 19.6° 2θ, and 24.9° 2θ (±0.2° 2θ; ±0.1° 2θ; or ±0.0° 2θ; Cu Kα1 radiation). In some embodiments, the solid form of (R)-MBDB HCl is (R)-MBDB HCl characterized by XRPD signals at 13.2° 2θ, 14.1° 2θ, 16.7° 2θ, 19.6° 2θ, and 24.9° 2θ (±0.2° 2θ; ±0.1° 2θ; or ±0.0° 2θ; Cu Kα1 radiation).

In some embodiments, the solid form of (R)-MBDB HCl is crystalline (R)-MBDB HCl characterized by two or more, or three or more XRPD signals selected from the group consisting of 18.4° 2θ, 19.6° 2θ, and 24.9° 2θ (±0.2° 2θ; ±0.1° 2θ; or ±0.0° 2θ; Cu Kα1 radiation). In some embodiments, the solid form of (R)-MBDB HCl is crystalline (R)-MBDB HCl characterized by XRPD signals at 18.4° 2θ, 19.6° 2θ, and 24.9° 2θ (±0.2° 2θ; ±0.1° 2θ; or ±0.0° 2θ; Cu Kα1 radiation).

In some embodiments, the solid form of (R)-MBDB HCl is crystalline (R)-MBDB HCl characterized by two or more, or three or more XRPD signals selected from the group consisting of 16.7° 2θ, 18.4° 2θ, 19.6° 2θ, 24.9° 2θ, and 27.9° 2θ (±0.2° 2θ; ±0.1° 2θ; or ±0.0° 2θ; Cu Kα1 radiation). In some embodiments, the solid form of (R)-MBDB HCl is (R)-MBDB HCl characterized by XRPD signals at 16.7° 2θ, 18.4° 2θ, 19.6° 2θ, 24.9° 2θ, and 27.9° 2θ (±0.2° 2θ; ±0.1° 2θ; or ±0.0° 2θ; Cu Kα1 radiation).

In some embodiments, the crystalline (R)-MBDB HCl is characterized by one, two, three, four, five, six, seven, eight, nine, ten, eleven, twelve, or thirteen XRPD signals selected from those set forth in Table 60.

TABLE 60

XRPD Signals for (R)-MBDB HCl

| Signal no. | Position | d-value | Relative |
|---|---|---|---|
| 1 | 13.2 | 6.7 | 25.4 |
| 2 | 14.1 | 6.3 | 14.4 |
| 3 | 16.7 | 5.3 | 29.2 |
| 4 | 18.4 | 4.8 | 81.7 |
| 5 | 19.6 | 4.5 | 66.0 |
| 6 | 22.1 | 4.0 | 10.5 |
| 7 | 23.7 | 3.8 | 11.5 |
| 8 | 24.6 | 3.6 | 26.2 |
| 9 | 24.9 | 3.6 | 100.0 |
| 10 | 26.1 | 3.4 | 15.4 |
| 11 | 27.6 | 3.2 | 23.5 |
| 12 | 27.9 | 3.2 | 27.6 |
| 13 | 30.6 | 2.9 | 17.2 |

Solid Forms of (S)-MBDB HCl

Figure 105:
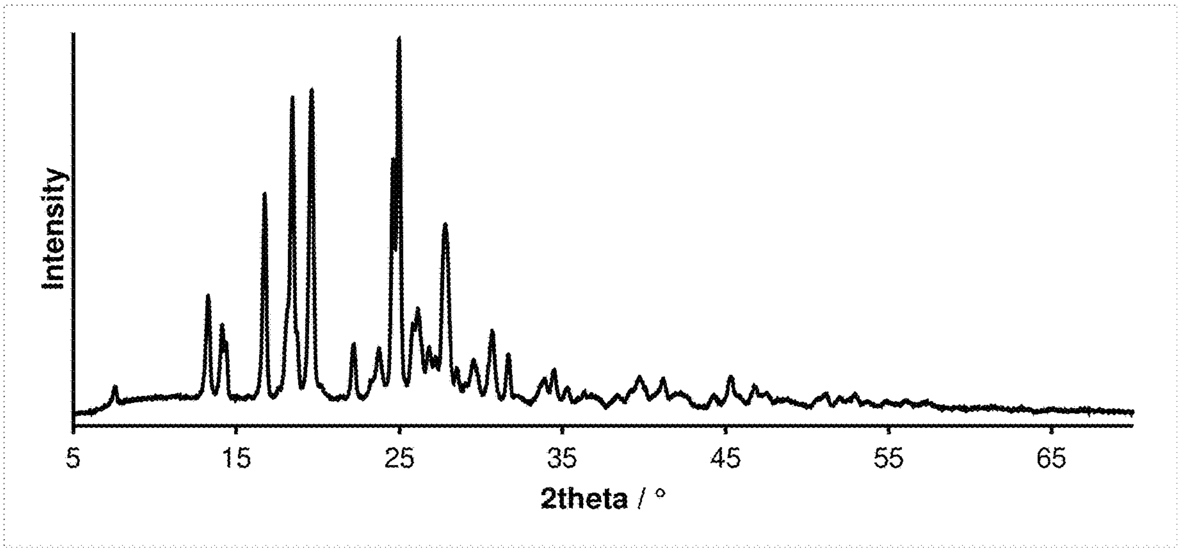
FIG. 105 provides an XRPD diffractogram of crystalline (S)-MBDB HCl.

In some embodiments, the present disclosure provides solid forms of (S)-MBDB HCl, e.g., crystalline forms of (S)-MBDB HCl. In some embodiments, the (S)-MBDB HCl XRPD profile is substantially similar to that shown in FIG. 105.

In some embodiments, the solid form of (S)-MBDB HCl is crystalline(S)-MBDB HCl characterized by two or more, or three or more XRPD signals selected from the group consisting of 13.3° 2θ, 16.7° 2θ, and 19.6° 2θ (±0.2° 2θ; ±0.1° 2θ; or ±0.0° 2θ; Cu Kα1 radiation). In some embodiments, the solid form of (S)-MBDB HCl is crystalline(S)-MBDB HCl characterized by XRPD signals at 13.3° 2θ, 16.7° 2θ, and 19.6° 2θ (±0.2° 2θ; ±0.1° 2θ; or ±0.0° 2θ; Cu Kα1 radiation).

In some embodiments, the solid form of (S)-MBDB HCl is crystalline(S)-MBDB HCl characterized by two or more, or three or more XRPD signals selected from the group consisting of 13.3° 2θ, 16.7° 2θ, 19.6° 2θ, 22.2° 2θ, and 24.6° 2θ (±0.2° 2θ; ±0.1° 2θ; or ±0.0° 2θ; Cu Kα1 radiation). In some embodiments, the solid form of (S)-MBDB HCl is (S)-MBDB HCl characterized by XRPD signals at 13.3° 2θ, 16.7° 2θ, 19.6° 2θ, 22.2° 2θ, and 24.6° 2θ (±0.2° 2θ; ±0.1° 2θ; or ±0.0° 2θ; Cu Kα1 radiation).

In some embodiments, the solid form of (S)-MBDB HCl is crystalline(S)-MBDB HCl characterized by two or more, or three or more XRPD signals selected from the group consisting of 18.4° 2θ, 19.6° 2θ, and 24.9° 2θ (±0.2° 2θ; ±0.1° 2θ; or ±0.0° 2θ; Cu Kα1 radiation). In some embodiments, the solid form of (S)-MBDB HCl is crystalline(S)-MBDB HCl characterized by XRPD signals at 18.4° 2θ, 19.6° 2θ, and 24.9° 2θ (±0.2° 2θ; ±0.1° 2θ; or ±0.0° 2θ; Cu Kα1 radiation).

In some embodiments, the solid form of (S)-MBDB HCl is crystalline(S)-MBDB HCl characterized by two or more, or three or more XRPD signals selected from the group consisting of 16.7° 2θ, 18.4° 2θ, 19.6° 2θ, 24.6° 2θ, and 24.9° 2θ (±0.2° 2θ; ±0.1° 2θ; or ±0.0° 2θ; Cu Kα1 radiation). In some embodiments, the solid form of (S)-MBDB HCl is (S)-MBDB HCl characterized by XRPD signals at 16.7° 2θ, 18.4° 2θ, 19.6° 2θ, 24.6° 2θ, and 24.9° 2θ (±0.2° 2θ; ±0.1° 2θ; or ±0.0° 2θ; Cu Kα1 radiation).

In some embodiments, the crystalline(S)-MBDB HCl is characterized by one, two, three, four, five, six, seven, eight, nine, ten, eleven, twelve, thirteen, fourteen, fifteen, sixteen, seventeen, eighteen, or nineteen XRPD signals selected from those set forth in Table 61.

TABLE 61

XRPD Signals for (S)-MBDB HCl

| Signal no. | Position | d-value | Relative |
|---|---|---|---|
| 1 | 13.3 | 6.7 | 27.8 |
| 2 | 14.1 | 6.3 | 18.2 |
| 3 | 14.4 | 6.1 | 10.9 |
| 4 | 16.7 | 5.3 | 54.0 |
| 5 | 18.1 | 4.9 | 17.3 |
| 6 | 18.4 | 4.8 | 82.4 |
| 7 | 18.7 | 4.7 | 10.6 |
| 8 | 19.6 | 4.5 | 85.3 |
| 9 | 22.2 | 4.0 | 14.3 |
| 10 | 23.7 | 3.8 | 13.1 |
| 11 | 24.6 | 3.6 | 62.7 |
| 12 | 24.9 | 3.6 | 100.0 |
| 13 | 25.7 | 3.5 | 15.2 |
| 14 | 26.1 | 3.4 | 20.7 |
| 15 | 26.8 | 3.3 | 13.2 |
| 16 | 27.8 | 3.2 | 49.1 |
| 17 | 29.6 | 3.0 | 10.2 |
| 18 | 30.7 | 2.9 | 18.1 |
| 19 | 31.7 | 2.8 | 13.8 |

Solid Forms of MBDB HCl Form A

Figure 106:
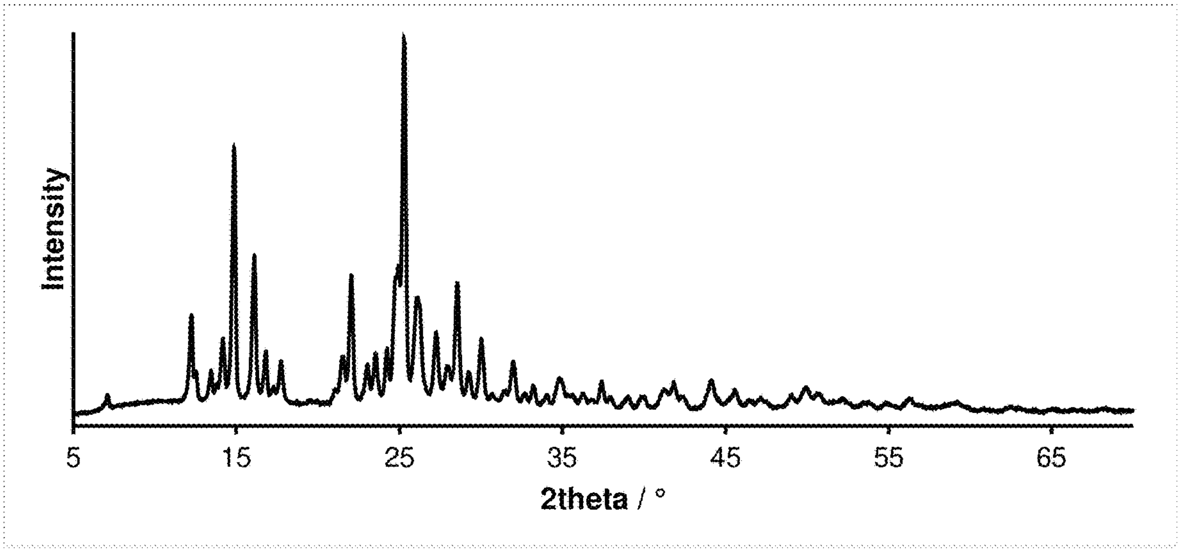
FIG. 106 provides an XRPD diffractogram of crystalline MBDB HCl.

In some embodiments, the present disclosure provides solid forms of MBDB HCl Form A, e.g., crystalline forms of MBDB HCl Form A. In some embodiments, the MBDB HCl Form A XRPD profile is substantially similar to that shown in FIG. 106. In some embodiments, the solid form of MBDB HCl Form A is crystalline MBDB HCl Form A characterized by two or more, or three or more XRPD signals selected from the group consisting of 14.2° 2θ, 14.8° 2θ, and 16.1° 2θ (±0.2° 2θ; ±0.1° 2θ; or ±0.0° 2θ; Cu Kα1 radiation). In some embodiments, the solid form of MBDB HCl Form A is crystalline MBDB HCl Form A characterized by XRPD signals at 14.2° 2θ, 14.8° 2θ, and 16.1° 2θ (±0.2° 2θ; ±0.1° 2θ; or ±0.0° 2θ; Cu Kα1 radiation).

In some embodiments, the solid form of MBDB HCl Form A is crystalline MBDB HCl Form A characterized by two or more, or three or more XRPD signals selected from the group consisting of 14.2° 2θ, 14.8° 2θ, and 16.1° 2θ, 16.8° 2θ, and 17.7° 2θ (±0.2° 2θ; ±0.1° 2θ; or ±0.0° 2θ; Cu Kα1 radiation). In some embodiments, the solid form of MBDB HCl Form A is MBDB HCl Form A characterized by XRPD signals at 14.2° 2θ, 14.8° 2θ, and 16.1° 2θ, 16.8° 2θ, and 17.7° 2θ (±0.2° 2θ; ±0.1° 2θ; or ±0.0° 2θ; Cu Kα1 radiation).

In some embodiments, the crystalline MBDB HCl Form A is characterized by one, two, three, four, five, six, seven, eight, nine, ten, eleven, twelve, thirteen, fourteen, fifteen, sixteen, seventeen, eighteen, or nineteen XRPD signals selected from those set forth in Table 62.

TABLE 62

XRPD Signals for MBDB HCl Form A

| Signal no. | Position | d-value | Relative |
|---|---|---|---|
| 1 | 12.2 | 7.2 | 23.7 |
| 2 | 14.2 | 6.2 | 15.8 |
| 3 | 14.8 | 6.0 | 65.7 |
| 4 | 16.1 | 5.5 | 38.8 |
| 5 | 16.8 | 5.3 | 12.5 |
| 6 | 17.7 | 5.0 | 10.2 |
| 7 | 21.5 | 4.1 | 12.0 |
| 8 | 22.0 | 4.0 | 33.4 |
| 9 | 23.0 | 3.9 | 9.9 |
| 10 | 23.5 | 3.8 | 12.8 |
| 11 | 24.2 | 3.7 | 14.2 |
| 12 | 24.8 | 3.6 | 33.9 |
| 13 | 25.3 | 3.5 | 100.0 |
| 14 | 26.0 | 3.4 | 22.7 |
| 15 | 26.2 | 3.4 | 12.1 |
| 16 | 27.2 | 3.3 | 18.6 |
| 17 | 28.5 | 3.1 | 32.8 |
| 18 | 30.0 | 3.0 | 17.2 |
| 19 | 32.0 | 2.8 | 11.9 |

Solid Forms of MDAI HCl

Figure 107:
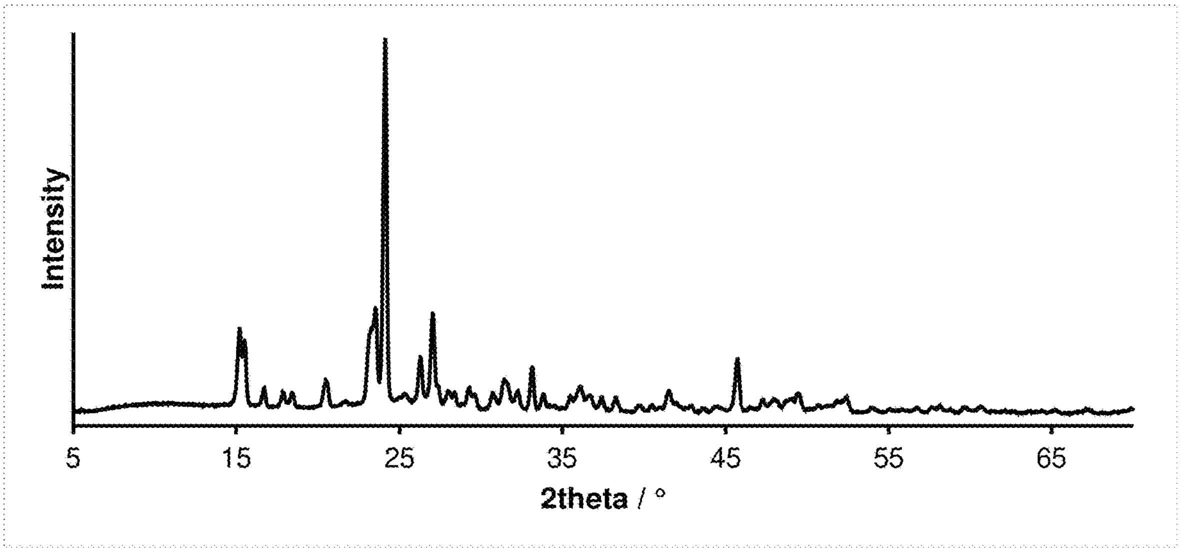
FIG. 107 provides an XRPD diffractogram of crystalline MDAI HCl.

In some embodiments, the present disclosure provides solid forms of MDAI HCl, e.g., crystalline forms of MDAI HCl. In some embodiments, the MDAI HCl XRPD profile is substantially similar to that shown in FIG. 107.

In some embodiments, the solid form of MDAI HCl is crystalline MDAI HCl characterized by two or more, or three or more XRPD signals selected from the group consisting of 15.2° 2θ, 15.5° 2θ, and 24.1° 2θ (±0.2° 2θ; ±0.1° 2θ; or ±0.0° 2θ; Cu Kα1 radiation). In some embodiments, the solid form of MDAI HCl is crystalline MDAI HCl characterized by XRPD signals at 15.2° 2θ, 15.5° 2θ, and 24.1° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 15.2° 2θ, 15.5° 2θ, 24.1° 2θ, 26.2° 2θ, and 27.0° 2θ (±0.2° 2θ; ±0.1° 2θ; or ±0.0° 2θ; Cu Kα1 radiation). In some embodiments, the solid form of MDAI HCl is MDAI HCl characterized by XRPD signals at 15.2° 2θ, 15.5° 2θ, 24.1° 2θ, 26.2° 2θ, and 27.0° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 23.5° 2θ, 24.1° 2θ, and 27.0° 2θ (±0.2° 2θ; ±0.1° 2θ; or ±0.0° 2θ; Cu Kα1 radiation). In some embodiments, the solid form of MDAI HCl is crystalline MDAI HCl characterized by XRPD signals at 23.5° 2θ, 24.1° 2θ, and 27.0° 2θ (±0.2° 2θ; ±0.1° 2θ; or ±0.0° 2θ; Cu Kα1 radiation).

In some embodiments, the solid form of MDAI HCl is crystalline MDAI HCl characterized by two or more, or three or more XRPD signals selected from the group consisting of 15.2° 2θ, 23.2° 2θ, 23.5° 2θ, 24.1° 2θ, and 27.0°

2θ (±0.2° 2θ; ±0.1° 2θ; or ±0.0° 2θ; Cu Kα1 radiation). In some embodiments, the solid form of MDAI HCl is MDAI HCl characterized by XRPD signals at 15.2° 2θ, 23.2° 2θ, 23.5° 2θ, 24.1° 2θ, and 27.0° 2θ (±0.2° 2θ; ±0.1° 2θ; or ±0.0° 2θ; Cu Kα1 radiation).

In some embodiments, the crystalline MDAI HCl is characterized by one, two, three, four, five, six, seven, eight, or nine XRPD signals selected from those set forth in Table 63.

TABLE 63

XRPD Signals for MDAI HCl

| Signal no. | Position | d-value | Relative |
|---|---|---|---|
| 1 | 15.2 | 5.8 | 20.0 |
| 2 | 15.5 | 5.7 | 15.8 |
| 3 | 23.2 | 3.8 | 18.0 |
| 4 | 23.5 | 3.8 | 23.3 |
| 5 | 24.1 | 3.7 | 100.0 |
| 6 | 26.2 | 3.4 | 13.6 |
| 7 | 27.0 | 3.3 | 26.6 |
| 8 | 33.1 | 2.7 | 11.8 |
| 9 | 45.7 | 2.0 | 15.7 |

Solid Forms of MDMA Hemifumarate Form A

Figure 116:
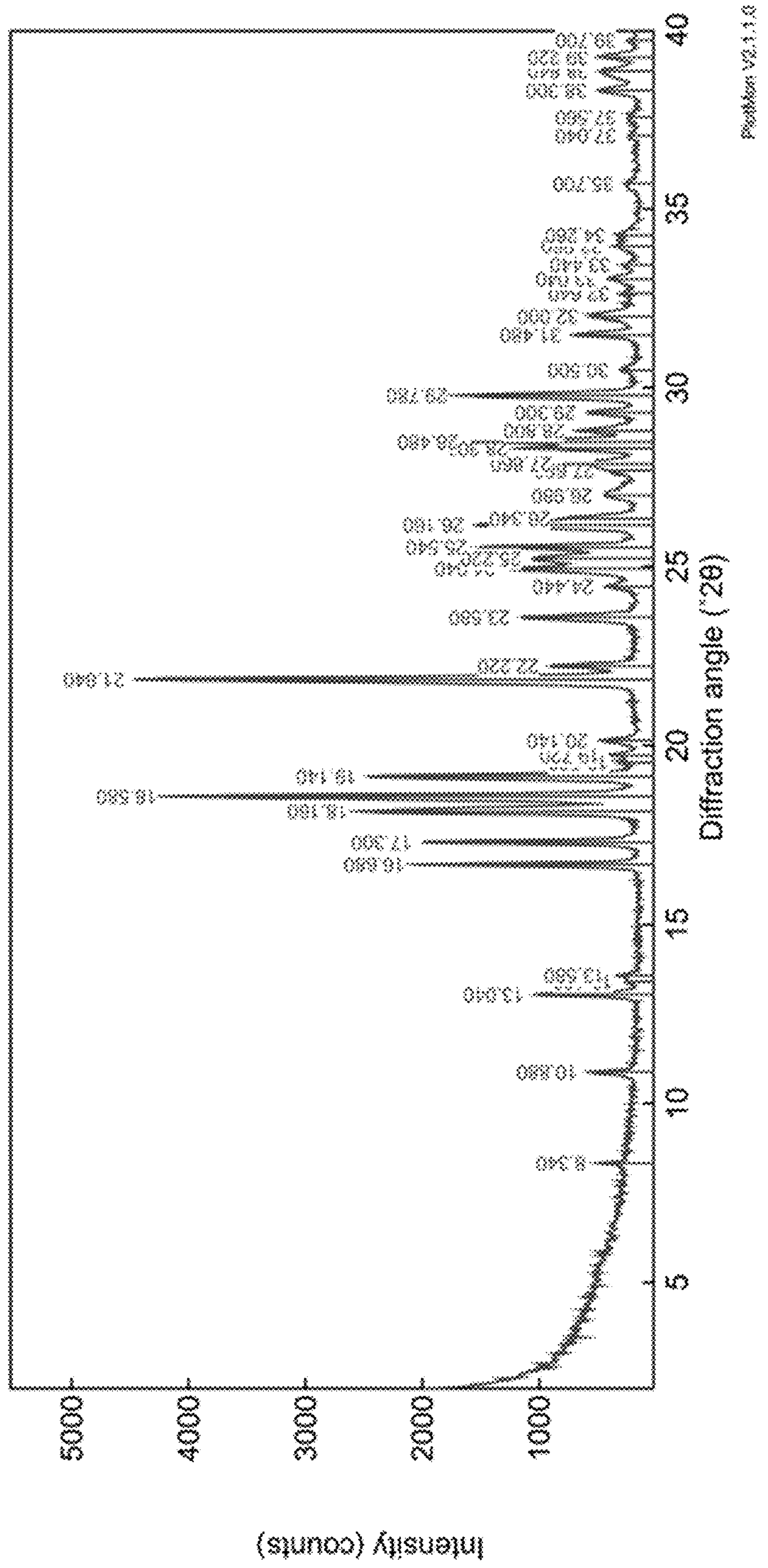
FIG. 116 provides an XRPD diffractogram of crystalline MDMA hemifumarate Form A.

In some embodiments, the present disclosure provides solid forms of MDMA hemifumarate Form A, e.g., crystalline forms of MDMA hemifumarate Form A. In some embodiments, the MDMA hemifumarate Form A XRPD profile is substantially similar to that shown in FIG. 116.

In some embodiments, the solid form of MDMA hemifumarate Form A is crystalline MDMA hemifumarate Form A characterized by two or more, or three or more XRPD signals selected from the group consisting of 18.2° 2θ, 18.6° 2θ, 21.8° 2θ (±0.2° 2θ; ±0.1° 2θ; or ±0.0° 2θ; Cu Kα1 radiation). In some embodiments, the solid form of MDMA hemifumarate Form A is crystalline MDMA hemifumarate Form A characterized by XRPD signals at 18.2° 2θ, 18.6° 2θ, 21.8° 2θ (±0.2° 2θ; ±0.1° 2θ; or ±0.0° 2θ; Cu Kα1 radiation).

In some embodiments, the solid form of MDMA hemifumarate Form A is crystalline MDMA hemifumarate Form A characterized by two or more, or three or more XRPD signals selected from the group consisting of 16.7° 2θ, 18.2° 2θ, 18.6° 2θ, 19.1° 2θ, 21.8° 2θ (±0.2° 2θ; ±0.1° 2θ; or ±0.0° 2θ; Cu Kα1 radiation). In some embodiments, the solid form of MDMA hemifumarate Form A is MDMA hemifumarate Form A characterized by XRPD signals at 16.7° 2θ, 18.2° 2θ, 18.6° 2θ, 19.1° 2θ, 21.8° 2θ (±0.2° 2θ; ±0.1° 2θ; or ±0.0° 2θ; Cu Kα1 radiation).

In some embodiments, the solid form of MDMA hemifumarate Form A is crystalline MDMA hemifumarate Form A characterized by two or more, or three or more XRPD signals selected from the group consisting of 8.3° 2θ, 10.9° 2θ, and 13.0° 2θ (±0.2° 2θ; ±0.1° 2θ; or ±0.0° 2θ; Cu Kα1 radiation). In some embodiments, the solid form of MDMA hemifumarate Form A is crystalline MDMA hemifumarate Form A characterized by XRPD signals at 8.3° 2θ, 10.9° 2θ, and 13.0° 2θ (±0.2° 2θ; ±0.1° 2θ; or ±0.0° 2θ; Cu Kα1 radiation).

In some embodiments, the solid form of MDMA hemifumarate Form A is crystalline MDMA hemifumarate Form A characterized by two or more, or three or more XRPD signals selected from the group consisting of 8.3° 2θ, 10.9° 2θ, 13.0° 2θ, 16.7° 2θ, and 17.3° 2θ (±0.2° 2θ; ±0.1° 2θ; or ±0.0° 2θ; Cu Kα1 radiation). In some embodiments, the solid form of MDMA hemifumarate Form A is MDMA hemifumarate Form A characterized by XRPD signals at 8.3° 2θ, 10.9° 2θ, 13.0° 2θ, 16.7° 2θ, and 17.3° 2θ (±0.2° 2θ; ±0.1° 2θ; or ±0.0° 2θ; Cu Kα1 radiation).

In some embodiments, the crystalline MDMA hemifumarate Form A is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, or forty-five XRPD signals selected from those set forth in Table 64.

TABLE 64

XRPD Signals for MDMA Hemifumarate Form A

| Signal No. | Position | d-value | Relative |
|---|---|---|---|
| 1 | 8.3 | 10.6 | 11.3 |
| 2 | 10.9 | 8.1 | 12.9 |
| 3 | 13.0 | 6.8 | 23.1 |
| 4 | 13.4 | 6.6 | 6.0 |
| 5 | 13.6 | 6.5 | 7.6 |
| 6 | 16.7 | 5.3 | 46.1 |
| 7 | 17.3 | 5.1 | 44.7 |
| 8 | 18.2 | 4.9 | 56.9 |
| 9 | 18.6 | 4.8 | 93.7 |
| 10 | 19.1 | 4.6 | 55.3 |
| 11 | 19.5 | 4.5 | 6.9 |
| 12 | 19.7 | 4.5 | 8.5 |
| 13 | 20.1 | 4.4 | 10.9 |
| 14 | 21.8 | 4.1 | 100.0 |
| 15 | 22.2 | 4.0 | 20.4 |
| 16 | 23.6 | 3.8 | 25.9 |
| 17 | 24.4 | 3.6 | 9.8 |
| 18 | 24.9 | 3.6 | 28.7 |
| 19 | 25.2 | 3.5 | 23.7 |
| 20 | 25.5 | 3.5 | 34.2 |
| 21 | 26.2 | 3.4 | 34.7 |
| 22 | 26.3 | 3.4 | 18.2 |
| 23 | 27.0 | 3.3 | 10.0 |
| 24 | 27.7 | 3.2 | 9.6 |
| 25 | 27.9 | 3.2 | 17.9 |
| 26 | 28.3 | 3.2 | 26.3 |
| 27 | 28.5 | 3.1 | 35.8 |
| 28 | 28.8 | 3.1 | 15.5 |
| 29 | 29.3 | 3.0 | 13.2 |
| 30 | 29.8 | 3.0 | 37.9 |
| 31 | 30.5 | 2.9 | 6.9 |
| 32 | 31.5 | 2.8 | 16.0 |
| 33 | 32.0 | 2.8 | 12.7 |
| 34 | 32.6 | 2.7 | 6.8 |
| 35 | 33.0 | 2.7 | 9.3 |
| 36 | 33.4 | 2.7 | 6.6 |
| 37 | 34.0 | 2.6 | 8.2 |
| 38 | 34.3 | 2.6 | 7.5 |
| 39 | 35.7 | 2.5 | 5.9 |
| 40 | 37.0 | 2.4 | 5.5 |
| 41 | 37.6 | 2.4 | 5.5 |
| 42 | 38.3 | 2.4 | 11.1 |
| 43 | 38.8 | 2.3 | 10.8 |
| 44 | 39.2 | 2.3 | 10.8 |
| 45 | 39.7 | 2.3 | 5.4 |

Figure 115:
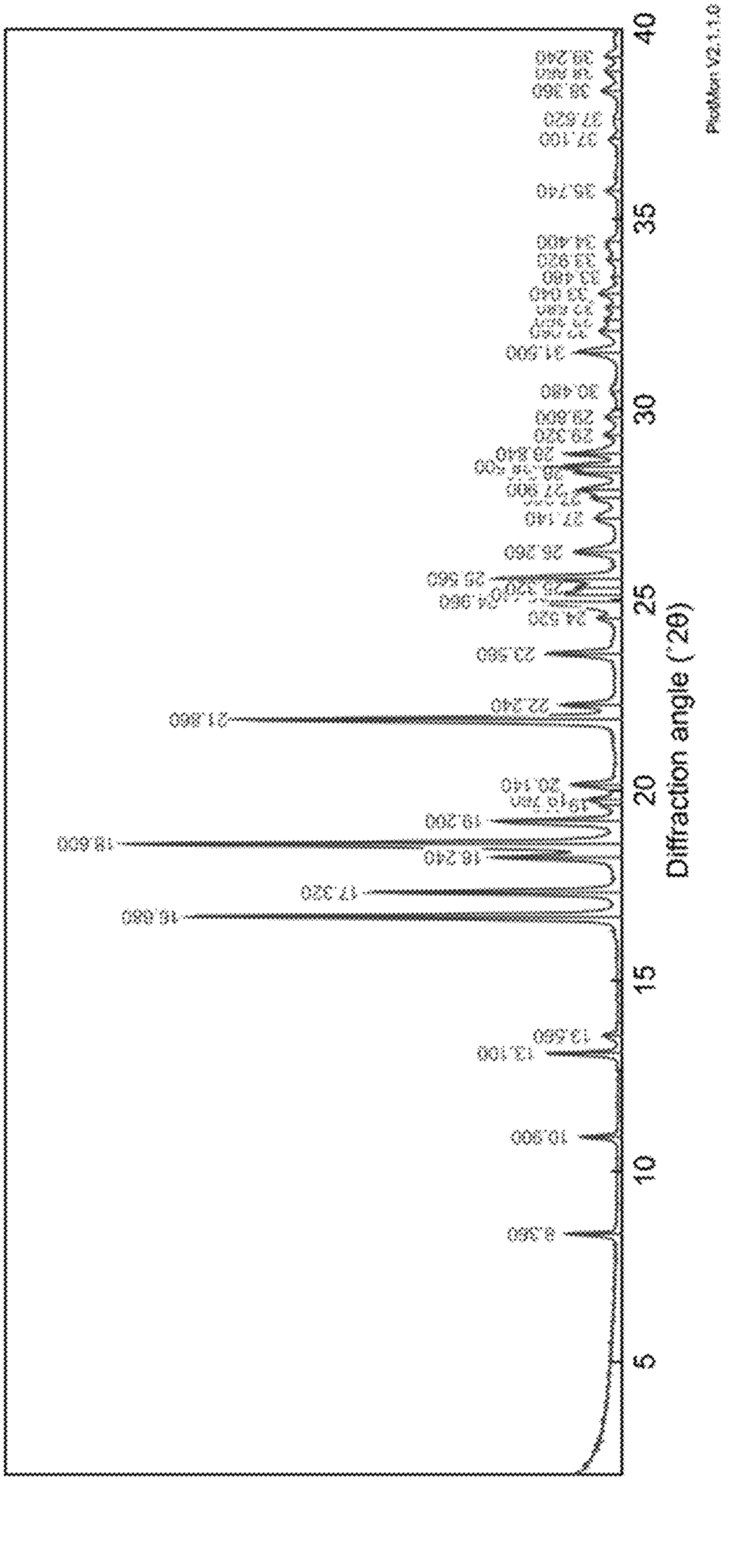
FIG. 115 provides an XRPD diffractogram of crystalline MDMA hemifumarate Form A.

In some embodiments, the present disclosure provides solid forms of MDMA hemifumarate Form A, e.g., crystalline forms of MDMA hemifumarate Form A. In some embodiments, the MDMA hemifumarate Form A XRPD profile is substantially similar to that shown in FIG. 115.

In some embodiments, the solid form of MDMA hemifumarate Form A is crystalline MDMA hemifumarate Form A characterized by two or more, or three or more XRPD signals selected from the group consisting of 16.7° 2θ, 18.6° 2θ, and 21.9° 2θ (±0.2° 2θ; ±0.1° 2θ; or ±0.0° 2θ; Cu Kα1 radiation). In some embodiments, the solid form of MDMA hemifumarate Form A is crystalline MDMA hemifumarate Form A characterized by XRPD signals at 16.7° 2θ, 18.6° 2θ, and 21.9° 2θ (±0.2° 2θ; =0.1° 2θ; or ±0.0° 2θ; Cu Kα1 radiation).

In some embodiments, the solid form of MDMA hemifumarate Form A is crystalline MDMA hemifumarate Form A characterized by two or more, or three or more XRPD signals selected from the group consisting of 16.7° 2θ, 17.3° 2θ, 18.2° 2θ, 18.6° 2θ, 21.9° 2θ (±0.2° 2θ; ±0.1° 2θ; or ±0.0° 2θ; Cu Kα1 radiation). In some embodiments, the solid form of MDMA hemifumarate Form A is MDMA hemifumarate Form A characterized by XRPD signals at 16.7° 2θ, 17.3° 2θ, 18.2° 2θ, 18.6° 2θ, 21.9° 2θ (±0.2° 2θ; ±0.1° 2θ; or ±0.0° 2θ; Cu Kα1 radiation).

In some embodiments, the solid form of MDMA hemifumarate Form A is crystalline MDMA hemifumarate Form A characterized by two or more, or three or more XRPD signals selected from the group consisting of 8.4° 2θ, 10.9° 2θ, and 13.1° 2θ (±0.2° 2θ; ±0.1° 2θ; or ±0.0° 2θ; Cu Kα1 radiation). In some embodiments, the solid form of MDMA hemifumarate Form A is crystalline MDMA hemifumarate Form A characterized by XRPD signals at 8.4° 2θ, 10.9° 2θ, and 13.1° 2θ (±0.2° 2θ; ±0.1° 2θ; or ±0.0° 2θ; Cu Kα1 radiation). In some embodiments, the solid form of MDMA hemifumarate Form A is crystalline MDMA hemifumarate Form A characterized by two or more, or three or more XRPD signals selected from the group consisting of 8.4° 2θ, 10.9° 2θ, 13.1° 2θ, 16.7° 2θ, and 17.3° 2θ (±0.2° 2θ; ±0.1° 2θ; or ±0.0° 2θ; Cu Kα1 radiation). In some embodiments, the solid form of MDMA hemifumarate Form A is MDMA hemifumarate Form A characterized by XRPD signals at 8.4° 2θ, 10.9° 2θ, 13.1° 2θ, 16.7° 2θ, and 17.3° 2θ (±0.2° 2θ; ±0.1° 2θ; or ±0.0° 2θ; Cu Kα1 radiation).

In some embodiments, the crystalline MDMA hemifumarate Form A is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four XRPD signals selected from those set forth in Table 65.

TABLE 65

XRPD Signals for MDMA Hemifumarate Form A

| Signal No. | Position | d-value | Relative |
|---|---|---|---|
| 1 | 8.4 | 10.6 | 11.7 |
| 2 | 10.9 | 8.1 | 8.8 |
| 3 | 13.1 | 6.8 | 15.6 |
| 4 | 13.6 | 6.5 | 4.3 |
| 5 | 16.7 | 5.3 | 87.1 |
| 6 | 17.3 | 5.1 | 51.0 |
| 7 | 18.2 | 4.9 | 26.2 |
| 8 | 18.6 | 4.8 | 100.0 |
| 9 | 19.2 | 4.6 | 26.1 |
| 10 | 19.6 | 4.5 | 4.7 |
| 11 | 19.8 | 4.5 | 8.9 |
| 12 | 20.1 | 4.4 | 10.8 |
| 13 | 21.9 | 4.1 | 77.5 |
| 14 | 22.2 | 4.0 | 12.9 |
| 15 | 23.6 | 3.8 | 15.8 |
| 16 | 24.5 | 3.6 | 5.4 |
| 17 | 25.0 | 3.6 | 23.2 |
| 18 | 25.1 | 3.5 | 12.9 |
| 19 | 25.3 | 3.5 | 9.9 |
| 20 | 25.6 | 3.5 | 25.7 |

TABLE 65-continued

XRPD Signals for MDMA Hemifumarate Form A

| Signal No. | Position | d-value | Relative |
|---|---|---|---|
| 21 | 26.3 | 3.4 | 10.2 |
| 22 | 27.1 | 3.3 | 6.0 |
| 23 | 27.7 | 3.2 | 6.5 |
| 24 | 27.9 | 3.2 | 9.8 |
| 25 | 28.3 | 3.1 | 9.9 |
| 26 | 28.5 | 3.1 | 16.2 |
| 27 | 28.8 | 3.1 | 11.9 |
| 28 | 29.3 | 3.0 | 4.1 |
| 29 | 29.8 | 3.0 | 3.9 |
| 30 | 30.5 | 2.9 | 2.8 |
| 31 | 31.5 | 2.8 | 9.8 |
| 32 | 32.1 | 2.8 | 5.0 |
| 33 | 32.4 | 2.8 | 4.1 |
| 34 | 32.7 | 2.7 | 3.8 |
| 35 | 33.0 | 2.7 | 5.1 |
| 36 | 33.5 | 2.7 | 2.5 |
| 37 | 33.9 | 2.6 | 3.6 |
| 38 | 34.4 | 2.6 | 3.6 |
| 39 | 35.7 | 2.5 | 3.7 |
| 40 | 37.1 | 2.4 | 3.1 |
| 41 | 37.6 | 2.4 | 2.2 |
| 42 | 38.4 | 2.3 | 4.6 |
| 43 | 38.9 | 2.3 | 4.0 |
| 44 | 39.2 | 2.3 | 3.9 |

Solid Forms of MDMA Freebase

Figure 3:
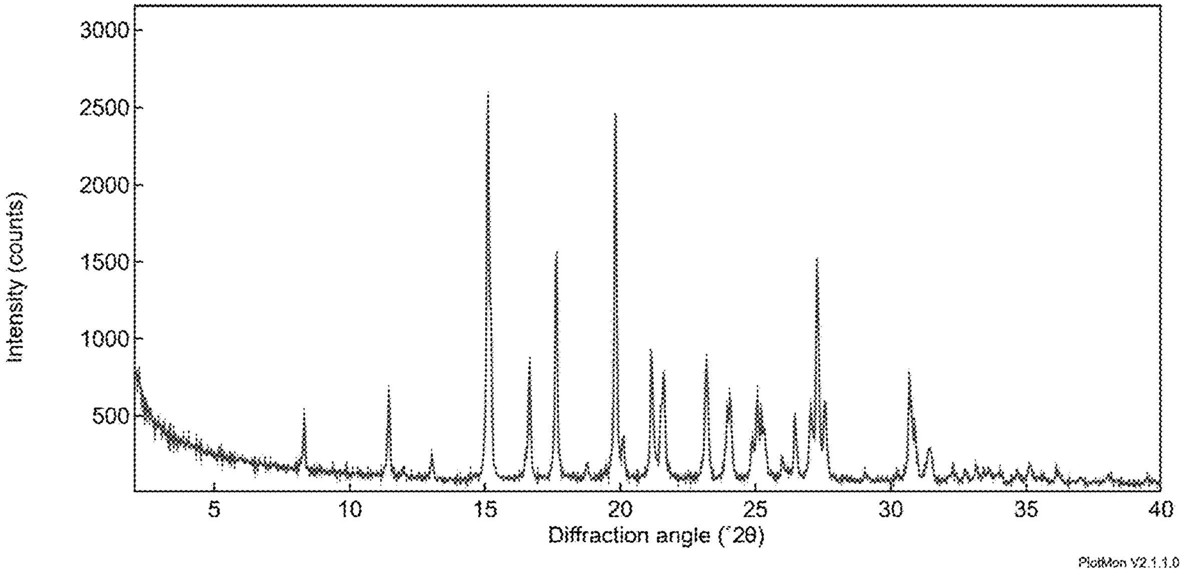
FIG. 3 provides an XRPD diffractogram of a sample comprising crystalline MDMA freebase.

In some embodiments, the present disclosure provides solid forms of MDMA freebase, e.g., crystalline forms of MDMA freebase. In some embodiments, the MDMA freebase XRPD profile is substantially similar to that shown in FIG. 3.

In some embodiments, the solid form of MDMA freebase is crystalline MDMA freebase characterized by two or more, or three or more XRPD signals selected from the group consisting of 15.1° 2θ, 19.8° 2θ, and 17.6° 2θ (±0.2° 2θ; ±0.1° 2θ; or ±0.0° 2θ; Cu Kα1 radiation). In some embodiments, the solid form of MDMA freebase is crystalline MDMA freebase characterized by XRPD signals at 15.1° 2θ, 19.8° 2θ, and 17.6° 2θ (±0.2° 2θ; ±0.1° 2θ; or ±0.0° 2θ; Cu Kα1 radiation).

In some embodiments, the solid form of MDMA freebase is crystalline MDMA freebase characterized by two or more, or three or more XRPD signals selected from the group consisting of 15.1° 2θ, 19.8° 2θ, 17.6, 27.3° 2θ, and 21.1° 2θ (±0.2° 2θ; ±0.1° 2θ; or ±0.0° 2θ; Cu Kα1 radiation). In some embodiments, the solid form of MDMA freebase is MDMA freebase characterized by XRPD signals at 15.1° 2θ, 19.8° 2θ, 17.6, 27.3° 2θ, and 21.1° 2θ (±0.2° 2θ; ±0.1° 2θ; or ±0.0° 2θ; Cu Kα1 radiation).

In some embodiments, the solid form of MDMA freebase is crystalline MDMA freebase characterized by two or more, or three or more XRPD signals selected from the group consisting of 8.3° 2θ, 11.4° 2θ, and 15.1° 2θ (±0.2° 2θ; ±0.1° 2θ; or ±0.0° 2θ; Cu Kα1 radiation). In some embodiments, the solid form of MDMA freebase is crystalline MDMA freebase characterized by XRPD signals at 8.3° 2θ, 11.4° 2θ, and 15.1° 2θ (±0.2° 2θ; ±0.1° 2θ; or ±0.0° 2θ; Cu Kα1 radiation).

In some embodiments, the solid form of MDMA freebase is crystalline MDMA freebase characterized by two or more, or three or more XRPD signals selected from the group consisting of 8.3° 2θ, 11.4° 2θ, 15.1° 2θ, 16.7° 2θ, 17.6° 2θ (±0.2° 2θ; ±0.1° 2θ; or ±0.0° 2θ; Cu Kα1 radiation). In some embodiments, the solid form of MDMA freebase is MDMA freebase characterized by XRPD signals at 8.3° 2θ, 11.4° 2θ, 15.1° 2θ, 16.7° 2θ, 17.6° 2θ (±0.2° 2θ; ±0.1° 2θ; or ±0.0° 2θ; Cu Kα1 radiation).

In some embodiments, the crystalline MDMA freebase is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, or thirty-nine XRPD signals selected from those set forth in Table 66.

TABLE 66

XRPD Signals for MDMA Freebase

| Signal No. | Position | d-value | Relative |
|---|---|---|---|
| 1 | 8.3 | 10.6 | 19.3 |
| 2 | 11.4 | 7.7 | 25.2 |
| 3 | 12.0 | 7.4 | 7.0 |
| 4 | 13.0 | 6.8 | 9.8 |
| 5 | 15.1 | 5.9 | 100.0 |
| 6 | 16.7 | 5.3 | 32.9 |
| 7 | 17.6 | 5.0 | 59.6 |
| 8 | 18.8 | 4.7 | 7.7 |
| 9 | 19.8 | 4.5 | 94.7 |
| 10 | 20.1 | 4.4 | 14.2 |
| 11 | 21.1 | 4.2 | 34.7 |
| 12 | 21.6 | 4.1 | 29.9 |
| 13 | 23.2 | 3.8 | 33.5 |
| 14 | 23.9 | 3.7 | 21.2 |
| 15 | 24.0 | 3.7 | 24.5 |
| 16 | 24.0 | 3.7 | 24.5 |
| 17 | 24.9 | 3.6 | 14.3 |
| 18 | 25.1 | 3.6 | 24.9 |
| 19 | 25.2 | 3.5 | 20.7 |
| 20 | 25.3 | 3.5 | 16.6 |
| 21 | 26.0 | 3.4 | 9.3 |
| 22 | 26.5 | 3.4 | 19.2 |
| 23 | 27.0 | 3.3 | 21.8 |
| 24 | 27.3 | 3.3 | 58.1 |
| 25 | 27.6 | 3.2 | 23.3 |
| 26 | 29.0 | 3.1 | 5.7 |
| 27 | 30.7 | 2.9 | 29.4 |
| 28 | 30.9 | 2.9 | 15.5 |
| 29 | 31.4 | 2.8 | 11.5 |
| 30 | 32.3 | 2.8 | 7.5 |
| 31 | 32.7 | 2.7 | 6.2 |
| 32 | 33.1 | 2.7 | 7.3 |
| 33 | 33.6 | 2.7 | 6.3 |
| 34 | 34.0 | 2.6 | 5.8 |
| 35 | 34.7 | 2.6 | 6.0 |
| 36 | 35.1 | 2.6 | 7.5 |
| 37 | 36.1 | 2.5 | 6.5 |
| 38 | 37.0 | 2.4 | 4.0 |
| 39 | 38.1 | 2.4 | 5.2 |

Solid Forms of (S)-MDMA HCl

In some embodiments, the present disclosure provides solid forms of (S)-MDMA HCl, e.g., crystalline forms of (S)-MDMA HCl. In some embodiments, the (S)-MDMA HCl profile is substantially similar to that shown in FIGS. 13 and 14.

In some embodiments, the solid form of (S)-MDMA HCl is crystalline(S)-MDMA HCl characterized by two or more, or three or more XRPD signals selected from the group consisting of 15.7° 2θ, 17.4° 2θ, and 20.6° 2θ (±0.2° 2θ; ±0.1° 2θ; or ±0.0° 2θ; Cu Kα1 radiation). In some embodiments, the solid form of (S)-MDMA HCl is crystalline(S)-MDMA HCl characterized by XRPD signals at 15.7° 2θ, 17.4° 2θ, and 20.6° 2θ (±0.2° 2θ; ±0.1° 2θ; or ±0.0° 2θ; Cu Kα1 radiation).

In some embodiments, the solid form of (S)-MDMA HCl is crystalline(S)-MDMA HCl characterized by two or more, or three or more XRPD signals selected from the group consisting of 15.7° 2θ, 17.4° 2θ, 20.6° 2θ, 24.7° 2θ, and 29.1° 2θ (±0.2° 2θ; ±0.1° 2θ; or ±0.0° 2θ; Cu Kα1 radiation). In some embodiments, the solid form of (S)-MDMA HCl is (S)-MDMA HCl characterized by XRPD signals at 15.7° 2θ, 17.4° 2θ, 20.6° 2θ, 24.7° 2θ, and 29.1° 2θ (±0.2° 2θ; ±0.1° 2θ; or ±0.0° 2θ; Cu Kα1 radiation).

In some embodiments, the solid form of (S)-MDMA HCl is crystalline(S)-MDMA HCl characterized by two or more, or three or more XRPD signals selected from the group consisting of 7.9° 2θ, 14.0° 2θ, and 15.7° 2θ (±0.2° 2θ; ±0.1° 2θ; or ±0.0° 2θ; Cu Kα1 radiation). In some embodiments, the solid form of (S)-MDMA HCl is crystalline(S)-MDMA HCl characterized by XRPD signals at 7.9° 2θ, 14.0° 2θ, and 15.7° 2θ (±0.2° 2θ; ±0.1° 2θ; or ±0.0° 2θ; Cu Kα1 radiation).

In some embodiments, the solid form of (S)-MDMA HCl is crystalline(S)-MDMA HCl characterized by two or more, or three or more XRPD signals selected from the group consisting of 7.9° 2θ, 14.0° 2θ, 15.7° 2θ, 19.6° 2θ, and 20.6° 2θ (±0.2° 2θ; ±0.1° 2θ; or ±0.0° 2θ; Cu Kα1 radiation). In some embodiments, the solid form of (S)-MDMA HCl is (S)-MDMA HCl characterized by XRPD signals at 7.9° 2θ, 14.0° 2θ, 15.7° 2θ, 19.6° 2θ, and 20.6° 2θ (±0.2° 2θ; ±0.1° 2θ; or ±0.0° 2θ; Cu Kα1 radiation).

In some embodiments, the crystalline(S)-MDMA HCl is characterized by one, two, three, four, five, six, seven, eight, nine, ten, eleven, twelve, thirteen, fourteen, fifteen, sixteen, seventeen, eighteen, or nineteen XRPD signals selected from those set forth in Table 67A.

TABLE 67A

XRPD Signals for (S)-MDMA HCl

| Signal No. | Position | d-value | Relative |
|---|---|---|---|
| 1 | 7.9 | 11.2 | 11.6 |
| 2 | 14.0 | 6.3 | 14.5 |
| 3 | 15.7 | 5.6 | 100.0 |
| 4 | 17.1 | 5.2 | 13.2 |
| 5 | 17.4 | 5.1 | 63.4 |
| 6 | 19.6 | 4.5 | 22.9 |
| 7 | 20.6 | 4.3 | 30.8 |
| 8 | 23.4 | 3.8 | 13.9 |
| 9 | 24.7 | 3.6 | 84.0 |
| 10 | 26.0 | 3.4 | 17.8 |
| 11 | 26.3 | 3.4 | 12.0 |
| 12 | 26.8 | 3.3 | 17.1 |
| 13 | 29.1 | 3.1 | 25.1 |
| 14 | 30.4 | 2.9 | 14.4 |
| 15 | 30.6 | 2.9 | 13.8 |
| 16 | 32.6 | 2.7 | 11.3 |
| 17 | 33.2 | 2.7 | 11.0 |
| 18 | 37.8 | 2.4 | 17.1 |
| 19 | 38.3 | 2.4 | 16.6 |

Solid Forms of (R)-MDMA HCl

In some embodiments, the present disclosure provides solid forms of (R)-MDMA HCl, e.g., crystalline forms of (R)-MDMA HCl. In some embodiments, the (R)-MDMA HCl profile is substantially similar to that shown in FIGS. 15 and/or 16.

In some embodiments, the solid form of (R)-MDMA HCl is crystalline (R)-MDMA HCl characterized by two or more, or three or more XRPD signals selected from the group consisting of 15.7° 2θ, 17.4° 2θ, and 20.6° 2θ (±0.2° 2θ; ±0.1° 2θ; or ±0.0° 2θ; Cu Kα1 radiation). In some embodiments, the solid form of (R)-MDMA HCl is crystalline (R)-MDMA HCl characterized by XRPD signals at 15.7° 2θ, 17.4° 2θ, and 20.6° 2θ (±0.2° 2θ; ±0.1° 2θ; or ±0.0° 2θ; Cu Kα1 radiation).

In some embodiments, the solid form of (R)-MDMA HCl is crystalline (R)-MDMA HCl characterized by two or more, or three or more XRPD signals selected from the group consisting of 15.7° 2θ, 17.4° 2θ, 20.6° 2θ, 24.7° 2θ, and 29.1° 2θ (±0.2° 2θ; ±0.1° 2θ; or ±0.0° 2θ; Cu Kα1 radiation). In some embodiments, the solid form of (R)-MDMA HCl is (R)-MDMA HCl characterized by XRPD signals at 15.7° 2θ, 17.4° 2θ, 20.6° 2θ, 24.7° 2θ, and 29.1° 2θ (±0.2° 2θ; ±0.1° 2θ; or ±0.0° 2θ; Cu Kα1 radiation).

In some embodiments, the solid form of (R)-MDMA HCl is crystalline (R)-MDMA HCl characterized by two or more, or three or more XRPD signals selected from the group consisting of 7.9° 2θ, 14.0° 2θ, and 15.7° 2θ (±0.2° 2θ; ±0.1° 2θ; or ±0.0° 2θ; Cu Kα1 radiation). In some embodiments, the solid form of (R)-MDMA HCl is crystalline (R)-MDMA HCl characterized by XRPD signals at 7.9° 2θ, 14.0° 2θ, and 15.7° 2θ (±0.2° 2θ; ±0.1° 2θ; or ±0.0° 2θ; Cu Kα1 radiation).

In some embodiments, the solid form of (R)-MDMA HCl is crystalline (R)-MDMA HCl characterized by two or more, or three or more XRPD signals selected from the group consisting of 7.9° 2θ, 14.0° 2θ, 15.7° 2θ, 19.6° 2θ, and 20.6° 2θ (±0.2° 2θ; ±0.1° 2θ; or ±0.0° 2θ; Cu Kα1 radiation). In some embodiments, the solid form of (R)-MDMA HCl is (R)-MDMA HCl characterized by XRPD signals at 7.9° 2θ, 14.0° 2θ, 15.7° 2θ, 19.6° 2θ, and 20.6° 2θ (±0.2° 2θ; ±0.1° 2θ; or ±0.0° 2θ; Cu Kα1 radiation).

In some embodiments, the crystalline (R)-MDMA HCl is characterized by one, two, three, four, five, six, seven, eight, nine, ten, eleven, twelve, thirteen, fourteen, fifteen, sixteen, seventeen, eighteen, or nineteen XRPD signals selected from those set forth in Table 67B.

TABLE 67B

XRPD Signals for (R)-MDMA HCl

| Signal No. | Position | d-value | Relative |
|---|---|---|---|
| 1 | 7.9 | 11.3 | 11.4 |
| 2 | 14.0 | 6.3 | 13.7 |
| 3 | 15.7 | 5.6 | 100.0 |
| 4 | 17.0 | 5.2 | 12.1 |
| 5 | 17.4 | 5.1 | 68.1 |
| 6 | 19.6 | 4.5 | 21.4 |
| 7 | 20.6 | 4.3 | 32.5 |
| 8 | 23.4 | 3.8 | 15.8 |
| 9 | 24.7 | 3.6 | 91.1 |
| 10 | 26.0 | 3.4 | 20.1 |
| 11 | 26.3 | 3.4 | 12.6 |
| 12 | 26.8 | 3.3 | 18.0 |
| 13 | 29.1 | 3.1 | 26.2 |
| 14 | 30.4 | 2.9 | 14.9 |
| 15 | 30.6 | 2.9 | 16.1 |
| 16 | 32.6 | 2.7 | 11.6 |
| 17 | 33.2 | 2.7 | 9.9 |
| 18 | 37.8 | 2.4 | 16.8 |
| 19 | 38.2 | 2.4 | 18.1 |

Pharmaceutical Compositions and Formulations

In some embodiments, the present disclosure provides a pharmaceutical composition comprising one or more of the disclosed solid forms of MDMA, (R)-MDMA, (S)-MDMA, MDE, MDAI, MBDB, MEAI, 5,6-Dimethoxy-2-aminoindane, or salts thereof, and a pharmaceutically acceptable excipient. Such compositions are suitable for administration to a subject, such as a human subject.

The presently disclosed pharmaceutical compositions can be prepared in a wide variety of oral, parenteral, such as intravenous, and topical dosage forms. Oral preparations include tablets, pills, powder, capsules, lozenges, cachets, slurries, suspensions, etc., suitable for ingestion by the patient. The compositions of the present disclosure can also be administered as solutions, orally or parenterally, such as by injection, that is, intravenously, intramuscularly, intracutaneously, subcutaneously, intraduodenally, or intraperitoneally. Also, the compositions described herein can be administered by inhalation, for example, intranasally. Additionally, the compositions of the present disclosure can be administered transdermally. The compositions of the present disclosure can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present disclosure also provides pharmaceutical compositions including a pharmaceutically acceptable carrier or excipient and the solid form of the compounds of the present disclosure.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% to 70% or 10% to 70% of the compounds of the present disclosure.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen.

If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present disclosure are dispersed homogeneously therein, as by stirring. The molten homogeneous mixture is then poured into convenient sized molds, allowed to cool, and thereby to solidify.

Liquid form preparations include solutions and suspensions, for example, water or water/propylene glycol suspensions.

Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include suspensions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present disclosure in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the present disclosure can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present disclosure can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the pharmaceutical compositions of the present disclosure can be formulated for parenteral administration, such as intravenous (IV) administration or administration into a body cavity or lumen of an organ. The formulations for administration will commonly comprise a solution or suspension of the compositions of the present disclosure dissolved or suspended in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions or suspensions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present disclosure in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present disclosure can be delivered by the use of liposomes which fuse with the cellular membrane or are endocytosed, for example, by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, Am. J. Hosp. Pharm. 46:1576-1587, 1989).

Administration

The compositions of the present disclosure can be administered by any suitable means, including oral, parenteral and topical methods. Transdermal administration methods, by a topical route, can be formulated as applicator sticks, suspensions, creams, ointments, pastes, jellies, paints, powders, and aerosols.

The pharmaceutical preparation is preferably in unit dosage form. In such form the preparation is subdivided into unit doses containing appropriate quantities of the compounds of the present disclosure. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present disclosure can be present in any suitable amount, and can depend on various factors including, but not limited to, weight and age of the subject, state of the disease, and the like as is known to those of ordinary skill in the art.

The (R)-MDMA or(S)-MDMA forms administered herein typically are administered to provide between about 50 mg and about 200 mg, or between about 80 mg and 120 mg.

The MDMA forms administered herein typically are administered to provide between about 50 mg and about 200 mg, or between about 80 mg and 120 mg.

Suitable dosage ranges for the N-ethyl-3,4-methylenedioxyamphetamine hydrochloride forms disclosed herein are administered in about 10 mg to about 300 mg or about 100 mg to about 180 mg or about 120 mg or about 150 mg or about 160 mg. Suitable dosages for the N-ethyl-3,4-methylenedioxyamphetamine hydrochloride forms disclosed herein include about 1 mg, 5, 10, 20, 30, 40, 50, 60, 70, 80, 90, 100, 200, 300, or 400 mg.

Suitable dosage ranges for the MDAI HCl forms disclosed herein include from about 10 mg to about 500 mg or about 60 mg to about 180 mg or about 160 mg to about 300 mg. Suitable dosages for the MDAI HCl forms disclosed herein include about 5 mg, 10, 20, 30, 40, 50, 60, 70, 80, 90, 100, 110, 120, 130, 140, 150, 160, 170, 180, 190, 200, 300, 400, or 500 mg.

Suitable dosage ranges for the N-methyl-1,3-benzodioxolylbutanamine hydrochloride forms disclosed herein are administered in about 10 mg to about 500 mg or about 150 mg to about 250 mg or about 180 mg or about 210 mg or about 250 mg.

Suitable dosages ranges for the MBDB salt and solid forms disclosed herein are administered in about 10 mg to about 500 mg or from about 150 mg to about 250 mg or about 180 mg or about 210 mg or about 250 mg.

Suitable dosage ranges for the (S)—N-ethyl-3,4-methylenedioxyamphetamine salts and solid forms disclosed herein are administered in about 10 mg to about 300 mg or about 100 mg to about 180 mg or about 120 mg or about 150 mg or about 160 mg. Suitable dosages for the (S)—N-ethyl-3,4-methylenedioxyamphetamine salts and solid forms disclosed herein include about 1 mg, 5, 10, 20, 30, 40, 50, 60, 70, 80, 90, 100, 200, 300, 400, 500, 600, 700, 800, 900 or 1000 mg.

Suitable dosage ranges for the 5-methoxy-2-aminoindane hydrochloride forms disclosed herein and the 5,6-dimethoxy-2-aminoindane hydrochloride forms disclosed herein include from about 10 mg to about 500 mg. Suitable dosages include those from about 1 mg per kg to about 5 mg per kg, such as from about 1.6 mg per kg to about 4.8 mg per kg or about 99.2 mg to about 297.6 mg. In one embodiment suitable dosages range from about 60 mg to about 180 mg or from about 160 mg to about 300 mg. Suitable dosages for the 5-methoxy-2-aminoindane hydrochloride forms disclosed herein and the 5,6-dimethoxy-2-aminoindane hydrochloride forms disclosed herein include about 1 mg, 5, 10, 20, 30, 40, 50, 60, 70, 80, 90, 100, 110, 120, 130, 140, 150, 160, 170, 180, 190, 200, 300, 400, or 500 mg.

The compounds disclosed herein can be administered at any suitable frequency, interval and duration. For example, the compounds can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with a second active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present disclosure and the active agent can each be administered once a day, or two, three, or more times per day so as to provide the preferred dosage level per day.

In some embodiments, co-administration can be accomplished by co-formulation, such as by preparing a single pharmaceutical composition including both the compound of the present disclosure and a second active agent. In other embodiments, the compound of the present disclosure and the second active agent can be formulated separately.

The disclosed compounds and the second active agent can be present in the compositions of the present disclosure in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present disclosure and the second active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present disclosure and the active agent are suitable in the compositions and methods disclosed herein.

Methods of Treatment

The solid forms of the present disclosure can be used for increasing neuronal plasticity. The compounds of the present disclosure can also be used to treat any brain disease. The solid forms of the present disclosure can also be used for increasing at least one of translation, transcription or secretion of neurotrophic factors.

In some embodiments, a compound of the present disclosure is used to treat neurological diseases. In some embodiments, the methods described herein are for treating a disease or disorder that is a brain disease or disorder. In some embodiments, the methods described herein are for increasing at least one of translation, transcription or secretion of neurotrophic factors. In some embodiments, the compounds have, for example, anti-addictive properties, antidepressant properties, anxiolytic properties, or a combination thereof. In some embodiments, the compositions provided herein have, for example, anti-addictive properties, antidepressant properties, anxiolytic properties, or a combination thereof. In some embodiments, the neurological disease is a neuropsychiatric disease. In some embodiments, the brain disorder is a neuropsychiatric disease. In some embodiments, the methods described herein are for treating a disease or disorder that is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder for example alcohol abuse, opiate addition, or abuse), depression, and anxiety.

In some embodiments, the brain disease, disorder, or neurological disease is a neurodegenerative disorder, Alzheimer's disease or Parkinson's disease. In some embodiments, the neurological disease is a psychological disorder. In some embodiments, the brain disease or disorder is psychological disorder, depression, addiction, anxiety, or a post-traumatic stress disorder. In some embodiments, the brain disorder is depression. In some embodiments, the brain disorder is addiction. In some embodiments, the brain disorder comprises treatment resistant depression, suicidal ideation, major depressive disorder, bipolar disorder, schizophrenia, stroke, traumatic brain injury or substance use disorder and/or anxiety. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the methods described herein are for treating a disease or disorder that is a neurological disease. For example, a compound provided herein can exhibit, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is selected from migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, hypoxic brain injury, chronic traumatic encephalopathy (CTE), traumatic brain injury, dementia, and addiction (e.g., substance use disorder). In some embodiments, the neurological disease is a migraine or cluster headache. In some embodiments, the neurological disease is a neurodegenerative disorder, dementia, Alzheimer's disease, or Parkinson's disease. In some embodiments, the neurological disease is dementia. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety.

In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, the methods described herein are for increasing neuronal plasticity and has, for example, anti-addictive properties, antidepressant properties, anxiolytic properties, or a combination thereof. In some embodiments, decreased neuronal plasticity is associated with a neuropsychiatric disease.

In some embodiments, a compound of the present disclosure is used for increasing neuronal plasticity. In some embodiments, the compounds described herein are used for treating a brain disorder. In some embodiments, the compounds described herein are used for increasing at least one of translation, transcription, or secretion of neurotrophic factors.

In some embodiments, the present disclosure provides a method of treating a disease, including administering to a subject in need thereof, a therapeutically effective amount of a compound of the present disclosure. In some embodiments, the disease is a musculoskeletal pain disorder including fibromyalgia, muscle pain, joint stiffness, osteoarthritis, rheumatoid arthritis, and muscle cramps. In some embodiments, the present disclosure provides a method of treating a disease of women's reproductive health including premenstrual dysphoric disorder (PMDD), premenstrual syndrome (PMS), post-partum depression, and menopause.

Diseases of particular interest include depression and related conditions. Accordingly, in some embodiments, the disease or disorder treated herein is depression or a disease or disorder related to depression. In some embodiments, the depression is major depressive disorder, persistent depressive disorder, bipolar disorder, treatment resistant depression (TRD), postpartum depression, premenstrual dysphoric disorder, or seasonal affective disorder. In some embodiments, the disease or disorder is post-traumatic stress disorder. In some embodiments, the disease or disorder is fibromyalgia. In some embodiments, the disease or disorder related to depression is anxiety. In some embodiments, methods of treating depression or a disease or disorder related to depression comprise treating the symptoms associated with the depression or the disease or disorder related to depression.

In yet another aspect, also provided herein are methods of treating fibromyalgia or a disease or disorder related to chronic widespread pain, fatigue or hypersensitivity, wherein the methods comprise administering to the subject a therapeutically effective amount of a solid form described herein.

Described herein are methods of treating depression or a disease or disorder related to depression in a subject in need thereof, the method comprising administering to the subject a psychedelic and a serotonin receptor modulator, wherein the serotonin receptor modulator is administered at most about 3 hours prior to the administration or release of the psychedelic. In some embodiments, the depression is major depressive disorder, persistent depressive disorder, bipolar disorder, treatment resistant depression (TRD), postpartum depression, premenstrual dysphoric disorder, or seasonal affective disorder. In some embodiments, the disease or disorder related to depression is anxiety. In some embodiments, methods of treating depression or a disease or disorder related to depression comprise treating the symptoms associated with the depression or the disease or disorder related to depression.

In some embodiments, the solid forms of the present disclosure have activity as 5-$HT_{2A}$ modulators. In some embodiments, the compounds of the present disclosure elicit a biological response by activating the 5-$HT_{2A}$ receptor (by way of example, through allosteric modulation or modulation of a biological target that activates the 5-$HT_{2A}$ receptor).

$5-HT_{2A}$ agonism has been correlated with the promotion of neural plasticity (Ly et al., 2018). $5-HT_{2A}$ antagonists abrogate the neuritogenesis and spinogenesis effects of hallucinogenic compounds with $5-HT_{2A}$ agonist activity, for example, DMT, LSD, and DOI. In some embodiments, the compounds of the present disclosure function as $5-HT_{2A}$ modulators and promote neural plasticity (e.g., cortical structural plasticity). In some embodiments, the compounds of the present disclosure are selective $5-HT_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the $5-HT_{2A}$ modulators (e.g., $5-HT_{2A}$ agonists) are non-hallucinogenic or are administered at a dose that is non-hallucinogenic. In some embodiments, non-hallucinogenic $5-HT_{2A}$ modulators (e.g., $5-HT_{2A}$ agonists) are used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds and combinations of compounds described herein is compared to the hallucinogenic potential assessed in vitro of hallucinogenic homologs. In some embodiments, the compounds described herein elicit less hallucinogenic potential in vitro than the hallucinogenic homologs.

In some embodiments, the presently disclosed compound forms function as serotonin receptor modulators, such as modulators of serotonin receptor 2A ($5-HT_{2A}$ modulators, e.g., $5-HT_{2A}$ agonists), and are used to treat a brain disorder. The presently disclosed compounds can function as $5-HT_{2A}$ agonists alone, or in combination with a second therapeutic agent that also is a $5-HT_{2A}$ modulator. In such cases the second therapeutic agent can be an agonist or an antagonist. In some instances, it may be helpful to administer a $5-HT_{2A}$ antagonist in combination with a compound of the present disclosure to mitigate undesirable effects of $5-HT_{2A}$ agonism, such as potential hallucinogenic effects. Thus, in some embodiments of combination therapy with the presently disclosed compounds, the second therapeutic agent is a serotonin receptor modulator. Serotonin receptor modulators, including $5-HT_{2A}$ antagonists, useful as second therapeutic agents for combination therapy as described herein are known to those of skill in the art and include, without limitation, ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl) piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena, or a pharmaceutically acceptable salt, solvate, metabolite, deuterated analog, derivative, prodrug, or combinations thereof.

In some embodiments, the serotonin receptor modulator for combination with the presently disclosed compounds is selected from glemanserin (MDL-11,939), eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, volinanserin (MDL-100,907), pimavanserin (ACO-103), pruvanserin, nelotanserin, lorcaserin, flibanserin, roluperiodone or a pharmaceutically acceptable salt, solvate, metabolite, deuterated analog, derivative, prodrug, or combinations thereof.

In certain embodiments the serotonin receptor modulator is selected from the group consisting of altanserin, blonanserin, eplivanserin, glemanserin, volinanserin, ketanserin, ritanserin, pimavanserin, nelotanserin, pruvanserin, and flibanserin. In one embodiment, the serotonin receptor modulator is selected from the group consisting of eplivanserin, volinanserin, ketanserin, ritanserin, pimavanserin, nelotanserin, pruvanserin, flibanserin, olanzapine, quetiapine, and risperidone.

In some embodiments, the serotonin receptor modulator is ketanserin or a pharmaceutically acceptable salt, solvate, metabolite, deuterated analog, derivative, or prodrug thereof. In some embodiments, the serotonin receptor modulator is pimavanserin or a pharmaceutically acceptable salt, solvate, metabolite, deuterated analog, derivative, or prodrug thereof. In some embodiments, the serotonin receptor modulator is eplivanserin or a pharmaceutically acceptable salt, solvate, metabolite, deuterated analog, derivative, or prodrug thereof. In some embodiments, the serotonin receptor modulator is flibanserin or a pharmaceutically acceptable salt, solvate, metabolite, deuterated analog, derivative, or prodrug thereof. In some embodiments, the serotonin receptor modulator is roluperiodone or a pharmaceutically acceptable salt, solvate, metabolite, deuterated analog, derivative, or prodrug thereof. In some embodiments, the serotonin receptor modulator is administered prior to a compound disclosed herein, such as about three hours prior to the administration or release of a compound disclosed herein. In some embodiments, the serotonin receptor modulator is administered at about one or about three hours prior to the administration or release of a presently disclosed compound. In some embodiments, the serotonin receptor modulator is administered at most about one hour prior to the administration or release presently disclosed compound. Thus, in some embodiments of combination therapy with the presently disclosed compounds, the second therapeutic agent is a serotonin receptor modulator.

In some embodiments the second therapeutic agent serotonin receptor modulator is provided at a dose of from about 10 mg to about 350 mg. In some embodiments, the serotonin receptor modulator is provided at a dose of from about 20 mg to about 200 mg. In some embodiments, the serotonin receptor modulator is provided at a dose of from about 10 mg to about 100 mg. In certain such embodiments, the compound of the present disclosure is provided at a dose of from about 10 mg to about 100 mg, or from about 20 to about 200 mg, or from about 15 to about 300 mg, and the serotonin receptor modulator is provided at a dose of about 10 mg to about 100 mg.

In some embodiments, non-hallucinogenic 5-$HT_{2A}$ modulators (e.g., 5-$HT_{2A}$ agonists) are used to treat neurological diseases. In some embodiments, the solid forms of the present disclosure act as non-hallucinogenic 5-$HT_{2A}$ modulators (e.g., 5-$HT_{2A}$ agonists) that are used to treat neurological diseases. In some embodiments, the neurological diseases comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, the solid forms of this disclosure act as non-hallucinogenic 5-$HT_{2A}$ modulators (e.g., 5-$HT_{2A}$ agonists) that are used for increasing neuronal plasticity. In some embodiments, the solid forms of this disclosure act as non-hallucinogenic 5-$HT_{2A}$ modulators (e.g., 5-$HT_{2A}$ agonists) that are used for treating a brain disorder. In some embodiments, the solid forms of this disclosure act as non-hallucinogenic 5-$HT_{2A}$ modulators (e.g., 5-$HT_{2A}$ agonists) that are used for increasing at least one of translation, transcription, or secretion of neurotrophic factors.

In some embodiments, the present forms are used as 5-$HT_{2A}$ modulators (e.g., 5-$HT_{2A}$ agonists) for increasing neuronal plasticity. In some embodiments, the present forms are used as 5-$HT_{2A}$ modulators (e.g., 5-$HT_{2A}$ agonists) to treat a brain disorder. In some embodiments, the compound forms are used as 5-$HT_{2A}$ modulators (e.g., 5-$HT_{2A}$ agonists) to increase at least one of translation, transcription, or secretion of neurotrophic factors.

In some embodiments the presently disclosed compounds are given to patients in a low dose that is lower than would produce noticeable psychedelic effects but high enough to provide a therapeutic benefit. This dose range is predicted to be between 200 ug (micrograms) and 2 mg.

Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with one or more of the disclosed compounds can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present disclosure provides methods for increasing neuronal plasticity, comprising contacting a neuronal cell with a compound of the present disclosure. In some embodiments, increasing neuronal plasticity improves a brain disorder described herein.

In some embodiments, a compound of the present disclosure is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present disclosure is a phenotypic assay, a dendritogenesis assay, a spinogenesis assay, a synaptogenesis assay, a Sholl analysis, a concentration-response experiment, a 5-$HT_{2A}$ agonist assay, a 5-$HT_{2A}$ antagonist assay, a 5-$HT_{2A}$ binding assay, or a 5-$HT_{2A}$ blocking experiment (e.g., ketanserin blocking experiments). In some embodiments, the experiment or assay to determine the hallucinogenic potential of any compound of the present disclosure is a mouse head-twitch response (HTR) assay.

In some embodiments, the present disclosure provides a method for increasing neuronal plasticity, comprising contacting a neuronal cell with a compound disclosed herein.

Methods of Treating a Brain Disorder

In some embodiments, the present disclosure provides a method of treating a disease, including administering to a subject in need thereof, a therapeutically effective amount of a solid form of the present disclosure. In some embodiments the disease is a brain disorder. By way of example and not limitation, brain disorders include, for example, migraines, addiction (e.g., substance use disorder), depression, and anxiety. Such disorders also may be considered neuropsychiatric disorders or neurological disorders. In some embodiments, neurological disorders that can be treated relate to other disease conditions. In some embodiments, the disease is a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause.

In some embodiments, the present disclosure provides a method of treating a brain disorder, including administering to a subject in need thereof, a therapeutically effective amount of a compound of the present disclosure. In some embodiments, the present disclosure provides a method of treating a brain disorder with combination therapy, including administering to a subject in need thereof, a therapeutically effective amount of a compound of the present disclosure and at least one additional therapeutic agent.

In some embodiments, 5-$HT_{2A}$ modulators (e.g., 5-$HT_{2A}$ agonists) are used to treat a brain disorder. In some embodiments, the brain disorders comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound of the present disclosure is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder), depression, and anxiety.

In some embodiments, the present disclosure provides a method of treating a brain disorder, comprising administering to a subject in need thereof a therapeutically effective amount of a compound disclosed herein.

In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the method further comprises administering one or more additional therapeutic agent that is lithium, olanzapine (Zyprexa), quetiapine (Seroquel), risperidone (Risperdal), ariprazole (Abilify), ziprasidone (Geodon), clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In certain embodiments of the method for treating a brain disorder with a solid form disclosed herein, a second therapeutic agent that is an empathogenic agent is administered. Examples of suitable empathogenic agents for use in combination with the present solid forms include phenethylamines, such as 3,4-methylene-dioxymethamphetamine (MDMA), N-ethyl-3,4-methylenedioxyamphetamine (MDE; MDEA), solid forms and analogs thereof. Other suitable empathogenic agents for use in combination with the presently disclosed solid forms include, without limitation, N-Allyl-3,4-methylenedioxy-amphetamine (MDAL)
N-Butyl-3,4-methylenedioxyamphetamine (MDBU)
N-Benzyl-3,4-methylenedioxyamphetamine (MDBZ)
N-Cyclopropylmethyl-3,4-methylenedioxyamphetamine (MDCPM)
N,N-Dimethyl-3,4-methylenedioxyamphetamine (MDDM)
N-(2-Hydroxyethyl)-3,4-methylenedioxy amphetamine (MDHOET)
N-Isopropyl-3,4-methylenedioxyamphetamine (MDIP)
N-Methyl-3,4-ethylenedioxyamphetamine (MDMC)
N-Methoxy-3,4-methylenedioxyamphetamine (MDMEO)
N-(2-Methoxyethyl)-3,4-methylenedioxyamphetamine (MDMEOET)
alpha, alpha,N-Trimethyl-3,4-methylenedioxyphenethylamine (MDMP; 3,4-Methylenedioxy-N-methylphentermine)
N-Hydroxy-3,4-methylenedioxyamphetamine (MDOH)
3,4-Methylenedioxyphenethylamine (MDPEA)
alpha, alpha-Dimethyl-3,4-methylenedioxyphenethylamine (MDPH; 3,4-methylenedioxyphentermine)
N-Propargyl-3,4-methylenedioxyamphetamine (MDPL)
Methylenedioxy-2-aminoindane (MDAI)
1,3-Benzodioxolyl-N-methylbutanamine (MBDB)
N-methyl-1,3-benzodioxolylbutanamine (MBDB)
3,4-methylenedioxy-N-methyl-α-ethylphenylethylamine
3,4-Methylenedioxyamphetamine (MDA)
Methylone (also known as 3,4-methylenedioxy-N-methylcathinone)
Ethylone (also known as 3,4-methylenedioxy-N-ethylcathinone)
GHB (also known as Gamma Hydroxybutyrate or sodium oxybate)
N-Propyl-3,4-methylenedioxyamphetamine (MDPR), and the like.

In some embodiments, the compounds of the present disclosure are used in combination with the standard of care therapy for a neurological disease described herein. Non-limiting examples of the standard of care therapies, may include, for example, lithium, olanzapine, quetiapine, risperidone, ariprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline. Additional examples of standard of care therapeutics are known to those of ordinary skill in the art.

Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-$HT_{2A}$ modulators (e.g., 5-$HT_{2A}$ agonists) are used to increase at least one of translation, transcription, or secretion of neurotrophic factors. In some embodiments, a compound of the present disclosure is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present disclosure provides a method for increasing at least one of translation, transcription or secretion of neurotrophic factors, comprising contacting a neuronal cell with a compound disclosed herein.

Combination Therapy

In particular embodiments of treating the disorders described above, combination therapy is used as described herein. In such therapy a form of MDMA, S-MDMA, R-MDMA, MDAI, MDE, R-MDE, S-MDE, MBDB, R-MBDB, S-MBDB, 5, methoxy-2-aminoindane, or 5,6-dimethoxy-2-aminoindane described herein is administered in combination with a serotonin receptor modulator. Serotonin receptor modulators useful as second therapeutic agents for combination therapy as described herein are known to those of skill in the art and include, glemanserin (MDL-11,939), eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, volinanserin (MDL-100,907), pimavanserin (ACO-103), pruvanserin, nelotanserin, lorcaserin, flibanserin, roluperiodone or a pharmaceutically acceptable salt, solvate, metabolite, deuterated analog, derivative, prodrug, or combinations thereof.

In particular embodiments of treating the disorders described above, combination therapy is used as described herein. In such therapy a form of any one of the compounds as described herein is administered in combination with a serotonin receptor modulator. Serotonin receptor modulators useful as second therapeutic agents for combination therapy as described herein are known to those of skill in the art and include, glemanserin (MDL-11,939), eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, volinanserin (MDL-100,907), pimavanserin (ACO-103), pruvanserin, nelotanserin, lorcaserin, flibanserin, roluperiodone or a pharmaceutically acceptable salt, solvate, metabolite, deuterated analog, derivative, prodrug, or combinations thereof.

In some embodiments, the serotonin receptor modulator comprises ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl) piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena, or a pharmaceutically acceptable salt, solvate, metabolite, deuterated analog, derivative, prodrug, or combinations thereof. In certain embodiments the serotonin receptor modulator is selected from the group consisting of altanserin, blonanserin, eplivanserin, glemanserin, volinanserin, ketanserin, ritanserin, pimavanserin, nelotanserin, pruvanserin, and flibanserin. In one embodiment, the serotonin receptor modulator is selected from the group consisting of serotonin receptor modulator is selected from the group consisting of eplivanserin, volinanserin, ketanserin, ritanserin, pimavanserin, nelotanserin, pruvanserin, flibanserin, olanzapine, quetiapine, and risperidone.

In some embodiments, the serotonin receptor modulator for use with the psychedelic MDMA is eplivanserin and, wherein the eplivanserin is administered in about 1 mg to about 40 mg, or about 5 mg to about 10 mg, and the MDMA is administered between about 50 mg and about 200 mg, or between about 80 mg and 120 mg.

In some embodiments, the serotonin receptor modulator is volinanserin and the psychedelic is MDMA, wherein the volinanserin is administered in about 1 mg to about 60 mg, or about 5 mg to about 20 mg, and the MDMA is administered between about 50 mg and about 200 mg, or between about 80 mg and 120 mg.

In some embodiments, the serotonin receptor modulator for use with the psychedelic MDMA is ketanserin, wherein the ketanserin is administered in about 10 mg to about 80 mg, about 30 mg to about 50 mg, or about 40 mg and the MDMA is administered between about 50 mg and about 200 mg, or between about 80 mg and 120 mg.

In some embodiments, the serotonin receptor modulator for use with the psychedelic MDMA is ritanserin, wherein the ritanserin is administered in about 1 mg to about 40 mg, or about 2.5 mg to about 10 mg, and the MDMA is administered between about 50 mg and about 200 mg, or between about 80 mg and 120 mg.

In some embodiments, the serotonin receptor modulator is pimavanserin and the psychedelic is MDMA, wherein the pimavanserin is administered in about 1 mg to about 60 mg, or about 17 mg to about 34 mg, and the MDMA is administered between about 50 mg and about 200 mg, or between about 80 mg and 120 mg.

In some embodiments, the serotonin receptor modulator for use with the psychedelic MDMA is nelotanserin, wherein the nelotanserin is administered in about 1 mg to about 80 mg, or about 40 mg to about 80 mg, and the MDMA is administered between about 50 mg and about 200 mg, or between about 80 mg and 120 mg.

In some embodiments, the serotonin receptor modulator for use with the psychedelic MDMA is pruvanserin, wherein the pruvanserin is administered in about 1 mg to about 40 mg, or about 3 mg to about 10 mg, and the MDMA is administered between about 50 mg and about 200 mg, or between about 80 mg and 120 mg.

In some embodiments, the serotonin receptor modulator for use with the psychedelic MDMA is flibanserin, wherein the flibanserin is administered in about 10 mg to about 200 mg, or about 80 mg to about 120 mg, or about 100 mg and the MDMA is administered between about 50 mg and about 200 mg, or between about 80 mg and 120 mg.

In some embodiments, the serotonin receptor modulator for use with the MDMA salts and solid forms disclosed herein, including those described in Table Ex3, is eplivanserin, wherein the eplivanserin is administered in about 1 mg to about 40 mg, or about 5 mg to about 10 mg, and the MDMA salts and solid forms disclosed herein, including those described in Table Ex3, are administered between about 50 mg and about 200 mg, or between about 80 mg and 120 mg.

In some embodiments, the serotonin receptor modulator for use with the MDMA salts and solid forms disclosed herein, including those described in Table Ex3, is volinanserin, wherein the volinanserin is administered in about 1 mg to about 60 mg, or about 5 mg to about 20 mg, and the MDMA salts and solid forms disclosed herein, including those described in Table Ex3, are administered between about 50 mg and about 200 mg, or between about 80 mg and 120 mg.

In some embodiments, the serotonin receptor modulator for use with the MDMA salts and solid forms disclosed herein, including those described in Table Ex3 is ketanserin, wherein the ketanserin is administered in about 10 mg to about 80 mg, about 30 mg to about 50 mg, or about 40 mg and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is ritanserin, wherein the ritanserin is administered in about 1 mg to about 40 mg, or about 2.5 mg to about 10 mg, and the MDMA salts and solid forms disclosed herein, including those described in Table Ex3 are administered between about 50 mg and about 200 mg, or between about 80 mg and 120 mg.

In some embodiments, the serotonin receptor modulator is pimavanserin and the MDMA salts and solid forms disclosed herein, including those described in Table Ex3, wherein the pimavanserin is administered in about 1 mg to about 60 mg, or about 17 mg to about 34 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is nelotanserin, wherein the nelotanserin is administered in about 1 mg to about 80 mg, or about 40 mg to about 80 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is pruvanserin, wherein the pruvanserin is administered in about 1 mg to about 40 mg, or about 3 mg to about 10 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is flibanserin, wherein the flibanserin is administered in about 10 mg to about 200 mg, or about 80 mg to about 120 mg, or about 100 mg and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is olanzapine, wherein the olanzapine is administered in about 2.5 mg to about 30 mg, or about 5 mg or about 10 mg, or about 20 mg or about 25 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is quetiapine, wherein the quetiapine is administered in about 25 mg to about 800 mg, or about 50 mg to about 100 mg, or about 150 mg or about 200 mg or about 250 mg or about 300 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is an extended-release of quetiapine, wherein the extended-release of quetiapine is administered in about 50 mg to about 300 mg, or about 50 mg or about 100 mg or about 200 mg, or about 300 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA salts and solid forms disclosed herein, including those described in Table Ex3 is an extended-release of risperidone including (RISPERDAL CONSTA), wherein the extended-release of risperidone is administered in about 12.5 mg, or about 25 mg, or about 37.5 mg, or about 50 mg, and the MDMA salts and solid forms disclosed herein, including those described in Table Ex3 are administered between about 50 mg and about 200 mg, or between about 80 mg and 120 mg.

In some embodiments, the serotonin receptor modulator for use with the MDMA hemifumarate Form A is eplivanserin, wherein the eplivanserin is administered in about 1 mg to about 40 mg, or about 5 mg to about 10 mg, and the MDMA hemifumarate Form A is administered between about 50 mg and about 200 mg, or between about 80 mg and 120 mg.

In some embodiments, the serotonin receptor modulator for use with the MDMA hemifumarate Form A is volinanserin, wherein the volinanserin is administered in about 1 mg to about 60 mg, or about 5 mg to about 20 mg, and the MDMA hemifumarate Form A is administered between about 50 mg and about 200 mg, or between about 80 mg and 120 mg.

In some embodiments, the serotonin receptor modulator for use with the MDMA hemifumarate Form A is ketanserin, wherein the ketanserin is administered in about 10 mg to about 80 mg, about 30 mg to about 50 mg, or about 40 mg and the MDMA hemifumarate Form A is administered between about 50 mg and about 200 mg, or between about 80 mg and 120 mg.

In some embodiments, the serotonin receptor modulator for use with the MDMA hemifumarate Form A is ritanserin, wherein the ritanserin is administered in about 1 mg to about 40 mg, or about 2.5 mg to about 10 mg, and the MDMA hemifumarate Form A is administered between about 50 mg and about 200 mg, or between about 80 mg and 120 mg.

In some embodiments, the serotonin receptor modulator is pimavanserin and the MDMA hemifumarate Form A wherein the pimavanserin is administered in about 1 mg to about 60 mg, or about 17 mg to about 34 mg, and the MDMA hemifumarate Form A is administered between about 50 mg and about 200 mg, or between about 80 mg and 120 mg.

In some embodiments, the serotonin receptor modulator for use with the MDMA hemifumarate Form A is nelotanserin, wherein the nelotanserin is administered in about 1 mg to about 80 mg, or about 40 mg to about 80 mg, and the MDMA hemifumarate Form A is administered between about 50 mg and about 200 mg, or between about 80 mg and 120 mg.

In some embodiments, the serotonin receptor modulator for use with the MDMA hemifumarate Form A is pruvanserin, wherein the pruvanserin is administered in about 1 mg to about 40 mg, or about 3 mg to about 10 mg, and the MDMA hemifumarate Form A is administered between about 50 mg and about 200 mg, or between about 80 mg and 120 mg.

In some embodiments, the serotonin receptor modulator for use with the MDMA hemifumarate Form A is flibanserin, wherein the flibanserin is administered in about 10 mg to about 200 mg, or about 80 mg to about 120 mg, or about 100 mg and the MDMA hemifumarate Form A is administered between about 50 mg and about 200 mg, or between about 80 mg and 120 mg.

In some embodiments, the serotonin receptor modulator for use with the MDMA hemifumarate Form A is olanzapine, wherein the olanzapine is administered in about 2.5 mg to about 30 mg, or about 5 mg or about 10 mg, or about 20 mg or about 25 mg, and the MDMA hemifumarate Form A is administered between about 50 mg and about 200 mg, or between about 80 mg and 120 mg.

In some embodiments, the serotonin receptor modulator for use with the MDMA hemifumarate Form A is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the MDMA hemifumarate Form A is administered between about 50 mg and about 200 mg, or between about 80 mg and 120 mg.

In some embodiments, the serotonin receptor modulator for use with the MDMA hemifumarate Form A is quetiapine, wherein the quetiapine is administered in about 25 mg to about 800 mg, or about 50 mg to about 100 mg, or about 150 mg or about 200 mg or about 250 mg or about 300 mg, and the MDMA hemifumarate Form A is administered between about 50 mg and about 200 mg, or between about 80 mg and 120 mg.

In some embodiments, the serotonin receptor modulator for use with the MDMA hemifumarate Form A is an extended-release of quetiapine, wherein the extended-release of quetiapine is administered in about 50 mg to about 300 mg, or about 50 mg or about 100 mg or about 200 mg, or about 300 mg, and the MDMA hemifumarate Form A is administered between about 50 mg and about 200 mg, or between about 80 mg and 120 mg.

In some embodiments, the serotonin receptor modulator for use with the MDMA hemifumarate Form A is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the MDMA hemifumarate Form A is administered between about 50 mg and about 200 mg, or between about 80 mg and 120 mg.

In some embodiments, the serotonin receptor modulator for use with the MDMA hemifumarate Form A is an extended-release of risperidone including (RISPERDAL CONSTA), wherein the extended-release of risperidone is administered in about 12.5 mg, or about 25 mg, or about 37.5 mg, or about 50 mg, and the MDMA hemifumarate Form A is administered between about 50 mg and about 200 mg, or between about 80 mg and 120 mg.

In certain embodiments, such as those described above a MDMA form disclosed herein, including those described in Table Ex3 is co-administered with a serotonin receptor modulator in the same or in separate compositions. In one embodiment, the serotonin receptor modulator is administered prior to the MDMA form disclosed herein, including those described in Table Ex3. In one embodiment, the MDMA form disclosed herein, including those described in Table Ex3 is administered in a modified release formulation such that the subject is effectively pretreated with serotonin receptor modulator prior to release of an effective amount of the MDMA. In some embodiments the serotonin receptor modulator is part of a single fixed dose formulation that releases serotonin receptor modulator first followed by the MDMA on two different release profiles. In another embodiment the serotonin receptor modulator is administered first as a single dosage and after a length of time, the MDMA form disclosed herein, including those described in Table Ex3 is administered as a second dosage separate from the first dosage. Thus, in some embodiments, the serotonin receptor modulator is administered or released from a composition provided herein prior to the administration and/or release of the psychedelic. This allows pretreatment to attenuate activation of the serotonin receptor by the psychedelic.

In some embodiments, the serotonin receptor modulator is eplivanserin and the psychedelic is MDMA, wherein the eplivanserin is administered to pretreat at least 15 minutes prior to the administration of MDMA. In some embodiments, the serotonin receptor modulator is eplivanserin and the psychedelic is MDMA, wherein the eplivanserin is administered to pretreat between at least 30 minutes prior and 360 minutes prior to the release or administration of the MDMA. In some embodiments, the serotonin receptor modulator is eplivanserin and the psychedelic is MDMA, wherein the eplivanserin is administered to pretreat between at least 60 minutes prior and 360 minutes prior to the release or administration the MDMA. In some embodiments, the serotonin receptor modulator is eplivanserin and the psychedelic is MDMA, wherein the eplivanserin is administered to pretreat at between least 90 minutes and 240 minutes prior to the MDMA. In some embodiments, the serotonin receptor modulator is eplivanserin and the psychedelic is MDMA, wherein the eplivanserin is administered to pretreat at least 120 minutes prior to the MDMA.

In some embodiments, the serotonin receptor modulator is eplivanserin and the psychedelic is MDMA, wherein the eplivanserin is administered to pretreat at least 150 minutes prior to the MDMA. In some embodiments, the serotonin receptor modulator is eplivanserin and the psychedelic is MDMA, wherein the eplivanserin is administered to pretreat at least 180 minutes prior to the MDMA. In some embodiments, the serotonin receptor modulator is eplivanserin and the psychedelic is MDMA, wherein the eplivanserin is administered to pretreat at least 210 minutes prior to the MDMA. In some embodiments, the serotonin receptor modulator is eplivanserin and the psychedelic is MDMA, wherein the eplivanserin is administered to pretreat at least 240 minutes prior to the MDMA.

In some embodiments, the serotonin receptor modulator is eplivanserin and the psychedelic is MDMA, wherein the eplivanserin is administered to pretreat at least 270 minutes prior to MDMA. In some embodiments, the serotonin receptor modulator is eplivanserin and the psychedelic is MDMA, wherein the eplivanserin is administered to pretreat at least 300 minutes prior to the MDMA. In some embodiments, the serotonin receptor modulator is eplivanserin and the psychedelic is MDMA, wherein the eplivanserin is administered to pretreat at least 330 minutes prior to the MDMA. In some embodiments, the serotonin receptor modulator is eplivanserin and the psychedelic is MDMA, wherein the eplivanserin is administered to pretreat at least 360 minutes prior to the MDMA.

In some preferred embodiments, the serotonin receptor modulator is eplivanserin and the psychedelic is MDMA, wherein eplivanserin is administered to pretreat between about 60 minutes and about 180 minutes prior to the administration of MDMA.

In some embodiments, the serotonin receptor modulator is volinanserin and the psychedelic is MDMA, wherein the volinanserin is administered to pretreat a subject between at least 15 minutes and 360 minutes prior to the administration or release of MDMA. In some embodiments, the serotonin receptor modulator is volinanserin and the psychedelic is MDMA, wherein the volinanserin is administered to pretreat between at least 30 minutes and 360 minutes prior to the administration or release of MDMA. In some embodiments, the serotonin receptor modulator is volinanserin and the psychedelic is MDMA, wherein the volinanserin is administered to pretreat between at least 60 minutes and 240 minutes prior to the administration or release of MDMA. In some embodiments, the serotonin receptor modulator is volinanserin and the psychedelic is MDMA, wherein the volinanserin is administered to pretreat at least 90 minutes prior to MDMA. In some embodiments, the serotonin receptor modulator is volinanserin and the psychedelic is MDMA, wherein the volinanserin is administered to pretreat at least 120 minutes prior to the MDMA.

In some embodiments, the serotonin receptor modulator is volinanserin and the psychedelic is MDMA, wherein the volinanserin is administered to pretreat at least 150 minutes prior to the MDMA. In some embodiments, the serotonin receptor modulator is volinanserin and the psychedelic is MDMA, wherein the volinanserin is administered to pretreat between about 15 minutes and about 150 minutes prior to the MDMA. In some embodiments, the serotonin receptor modulator is volinanserin and the psychedelic is MDMA, wherein the volinanserin is administered to pretreat at least 180 minutes prior to the MDMA. In some embodiments, the serotonin receptor modulator is volinanserin and the psychedelic is MDMA, wherein the volinanserin is administered to pretreat at least 210 minutes prior to the MDMA. In some embodiments, the serotonin receptor modulator is volinanserin and the psychedelic is MDMA, wherein the volinanserin is administered to pretreat at least 240 minutes prior to the MDMA. In some embodiments, the serotonin receptor modulator is volinanserin and the psychedelic is MDMA, wherein the volinanserin is administered to pretreat at least 270 minutes prior to the MDMA. In some embodiments, the serotonin receptor modulator is volinanserin and the psychedelic is MDMA, wherein the volinanserin is administered to pretreat at least 300 minutes prior to the MDMA. In some embodiments, the serotonin receptor modulator is volinanserin and the psychedelic is MDMA, wherein the volinanserin is administered to pretreat at least 330 minutes prior to the MDMA. In some embodiments, the serotonin receptor modulator is volinanserin and the psychedelic is MDMA, wherein the volinanserin is administered to pretreat at least 360 minutes prior to the MDMA. In some preferred embodiments, the serotonin receptor modulator is volinanserin and the psychedelic is MDMA, wherein volinanserin is administered to pretreat between about 60 minutes and about 180 minutes prior to the administration of MDMA.

In some embodiments, the serotonin receptor modulator is ketanserin and the psychedelic is MDMA, wherein the ketanserin is administered to pretreat at least 15 minutes prior to the administration of MDMA. In some embodiments, the serotonin receptor modulator is ketanserin and the psychedelic is MDMA, wherein the ketanserin is administered to pretreat between at least 30 minutes and 360 minutes prior to the administration or release MDMA. In some embodiments, the serotonin receptor modulator is ketanserin and the psychedelic is MDMA, wherein the ketanserin is administered to pretreat between at least 60 minutes and 240 minutes prior to the administration or release of MDMA. In some embodiments, the serotonin receptor modulator is ketanserin and the psychedelic is MDMA, wherein the ketanserin is administered to pretreat at least 90 minutes prior to the MDMA. In some embodiments, the serotonin receptor modulator is ketanserin and the psychedelic is MDMA, wherein the ketanserin is administered to pretreat at least 120 minutes prior to the MDMA. In some embodiments, the serotonin receptor modulator is ketanserin and the psychedelic is MDMA, wherein the ketanserin is administered to pretreat at least 150 minutes prior to the MDMA. In some embodiments, the serotonin receptor modulator is ketanserin and the psychedelic is MDMA, wherein the ketanserin is administered to pretreat between about 15 minutes and about 150 minutes prior to the MDMA. In some embodiments, the serotonin receptor modulator is ketanserin and the psychedelic is MDMA, wherein the ketanserin is administered to pretreat at least 180 minutes prior to the MDMA. In some embodiments, the serotonin receptor modulator is ketanserin and the psychedelic is MDMA, wherein the ketanserin is administered to pretreat at least 210 minutes prior to the MDMA. In some embodiments, the serotonin receptor modulator is ketanserin and the psychedelic is MDMA, wherein the ketanserin is administered to pretreat at least 240 minutes prior to the MDMA. In some embodiments, the serotonin receptor modulator is ketanserin and the psychedelic is MDMA, wherein the ketanserin is administered to pretreat at least 270 minutes prior to the MDMA. In some embodiments, the serotonin receptor modulator is ketanserin and the psychedelic is MDMA, wherein the ketanserin is administered to pretreat at least 300 minutes prior to the MDMA. In some embodiments, the serotonin receptor modulator is ketanserin and the psychedelic is MDMA, wherein the ketanserin is administered to pretreat at least 330 minutes prior to the MDMA. In some embodiments, the serotonin receptor modulator is ketanserin and the psychedelic is MDMA, wherein the ketanserin is administered to pretreat at least 360 minutes prior to the MDMA. In some preferred embodiments, the serotonin receptor modulator is ketanserin and the psychedelic is MDMA, wherein ketanserin is administered to pretreat between about 60 minutes and about 180 minutes prior to the administration of MDMA.

In some embodiments, the serotonin receptor modulator is ritanserin and the psychedelic is MDMA, wherein the ritanserin is administered to pretreat at least 15 minutes prior to the administration of MDMA. In some embodiments, the serotonin receptor modulator is ritanserin and the psychedelic is MDMA, wherein the ritanserin is administered to pretreat at least 30 minutes prior to the MDMA. In some embodiments, the serotonin receptor modulator is ritanserin and the psychedelic is MDMA, wherein the ritanserin is administered to pretreat between at least 60 minutes and 240 minutes prior to the administration or release of MDMA. In some embodiments, the serotonin receptor modulator is ritanserin and the psychedelic is MDMA, wherein the ritanserin is administered to pretreat at least 90 minutes prior to the MDMA. In some embodiments, the serotonin receptor modulator is ritanserin and the psychedelic is MDMA, wherein the ritanserin is administered to pretreat at least 120 minutes prior to the MDMA. In some embodiments, the serotonin receptor modulator is ritanserin and the psychedelic is MDMA, wherein the ritanserin is administered to pretreat at least 150 minutes prior to the MDMA. In some embodiments, the serotonin receptor modulator is ritanserin and the psychedelic is MDMA, wherein the ritanserin is administered to pretreat between about 15 minutes and about 150 minutes prior to the MDMA. In some embodiments, the serotonin receptor modulator is ritanserin and the psychedelic is MDMA, wherein the ritanserin is administered to pretreat at least 180 minutes prior to the MDMA. In some embodiments, the serotonin receptor modulator is ritanserin and the psychedelic is MDMA, wherein the ritanserin is administered to pretreat at least 210 minutes prior to the MDMA. In some embodiments, the serotonin receptor modulator is ritanserin and the psychedelic is MDMA, wherein the ritanserin is administered to pretreat at least 240 minutes prior to the MDMA. In some embodiments, the serotonin receptor modulator is ritanserin and the psychedelic is MDMA, wherein the ritanserin is administered to pretreat at least 270 minutes prior to the MDMA. In some embodiments, the serotonin receptor modulator is ritanserin and the psychedelic is MDMA, wherein the ritanserin is administered to pretreat at least 300 minutes prior to the MDMA. In some embodiments, the serotonin receptor modulator is ritanserin and the psychedelic is MDMA, wherein the ritanserin is administered to pretreat at least 330 minutes prior to the MDMA. In some embodiments, the serotonin receptor modulator is ritanserin and the psychedelic is MDMA, wherein the ritanserin is administered to pretreat at least 360 minutes prior to the MDMA. In some preferred embodiments, the serotonin receptor modulator is ritanserin and the psychedelic is MDMA, wherein ritanserin is administered to pretreat between about 60 minutes and about 180 minutes prior to the administration of MDMA.

In some embodiments, the serotonin receptor modulator is pimavanserin and the psychedelic is MDMA, wherein the pimavanserin is administered to pretreat at least 15 minutes prior to the administration of MDMA. In some embodiments, the serotonin receptor modulator is pimavanserin and the psychedelic is MDMA, wherein the pimavanserin is administered to pretreat at least 30 minutes prior to the MDMA. In some embodiments, the serotonin receptor modulator is pimavanserin and the psychedelic is MDMA, wherein the pimavanserin is administered to pretreat between at least 60 minutes and 240 minutes prior to the administration or release of MDMA. In some embodiments, the serotonin receptor modulator is pimavanserin and the psychedelic is MDMA, wherein the pimavanserin is administered to pretreat at least 90 minutes prior to the MDMA. In some embodiments, the serotonin receptor modulator is pimavanserin and the psychedelic is MDMA, wherein the pimavanserin is administered to pretreat at least 120 minutes prior to the MDMA. In some embodiments, the serotonin receptor modulator is pimavanserin and the psychedelic is MDMA, wherein the pimavanserin is administered to pretreat at least 150 minutes prior to the MDMA. In some embodiments, the serotonin receptor modulator is pimavanserin and the psychedelic is MDMA, wherein the pimavanserin is administered to pretreat between about 15 minutes and about 150 minutes prior to the MDMA. In some embodiments, the serotonin receptor modulator is pimavanserin and the psychedelic is MDMA, wherein the pimavanserin is administered to pretreat at least 180 minutes prior to the MDMA. In some embodiments, the serotonin receptor modulator is pimavanserin and the psychedelic is MDMA, wherein the pimavanserin is administered to pretreat at least 210 minutes prior to the MDMA. In some embodiments, the serotonin receptor modulator is pimavanserin and the psychedelic is MDMA, wherein the pimavanserin is administered to pretreat at least 240 minutes prior to the MDMA. In some embodiments, the serotonin receptor modulator is pimavanserin and the psychedelic is MDMA, wherein the pimavanserin is administered to pretreat at least 270 minutes prior to the MDMA. In some embodiments, the serotonin receptor modulator is pimavanserin and the psychedelic is MDMA, wherein the pimavanserin is administered to pretreat at least 300 minutes prior to the MDMA. In some embodiments, the serotonin receptor modulator is pimavanserin and the psychedelic is MDMA, wherein the pimavanserin is administered to pretreat at least 330 minutes prior to the MDMA. In some embodiments, the serotonin receptor modulator is pimavanserin and the psychedelic is MDMA, wherein the pimavanserin is administered to pretreat at least 360 minutes prior to the MDMA. In some preferred embodiments, the serotonin receptor modulator is pimavanserin and the psychedelic is MDMA, wherein pimavanserin is administered to pretreat between about 60 minutes and about 180 minutes prior to the administration of MDMA.

In some embodiments, the serotonin receptor modulator is nelotanserin and the psychedelic is MDMA, wherein the nelotanserin is administered to pretreat at least 15 minutes prior to the administration of MDMA. In some embodiments, the serotonin receptor modulator is nelotanserin and the psychedelic is MDMA, wherein the nelotanserin is administered to pretreat at least 30 minutes prior to the MDMA. In some embodiments, the serotonin receptor modulator is nelotanserin and the psychedelic is MDMA, wherein the nelotanserin is administered to pretreat between at least 60 minutes and 240 minutes prior to the administration or release of MDMA. In some embodiments, the serotonin receptor modulator is nelotanserin and the psychedelic is MDMA, wherein the nelotanserin is administered to pretreat at least 90 minutes prior to the MDMA. In some embodiments, the serotonin receptor modulator is nelotanserin and the psychedelic is MDMA, wherein the nelotanserin is administered to pretreat at least 120 minutes prior to the MDMA.

In some embodiments, the serotonin receptor modulator is nelotanserin and the psychedelic is MDMA, wherein the nelotanserin is administered to pretreat at least 150 minutes prior to the MDMA. In some embodiments, the serotonin receptor modulator is nelotanserin and the psychedelic is MDMA, wherein the nelotanserin is administered to pretreat between about 15 minutes and about 150 minutes prior to the MDMA. In some embodiments, the serotonin receptor modulator is nelotanserin and the psychedelic is MDMA, wherein the nelotanserin is administered to pretreat at least 180 minutes prior to the MDMA. In some embodiments, the serotonin receptor modulator is nelotanserin and the psychedelic is MDMA, wherein the nelotanserin is administered to pretreat at least 210 minutes prior to the MDMA. In some embodiments, the serotonin receptor modulator is nelotanserin and the psychedelic is MDMA, wherein the nelotanserin is administered to pretreat at least 240 minutes prior to the MDMA. In some embodiments, the serotonin receptor modulator is nelotanserin and the psychedelic is MDMA, wherein the nelotanserin is administered to pretreat at least 270 minutes prior to the MDMA.

In some embodiments, the serotonin receptor modulator is nelotanserin and the psychedelic is MDMA, wherein the nelotanserin is administered to pretreat at least 300 minutes prior to the MDMA. In some embodiments, the serotonin receptor modulator is nelotanserin and the psychedelic is MDMA, wherein the nelotanserin is administered to pretreat at least 330 minutes prior to the MDMA. In some embodiments, the serotonin receptor modulator is nelotanserin and the psychedelic is MDMA, wherein the nelotanserin is administered to pretreat at least 360 minutes prior to the MDMA. In some preferred embodiments, the serotonin receptor modulator is nelotanserin and the psychedelic is MDMA, wherein nelotanserin is administered to pretreat between about 60 minutes and about 180 minutes prior to the administration of MDMA.

In some embodiments, the serotonin receptor modulator is pruvanserin and the psychedelic is MDMA, wherein the pruvanserin is administered to pretreat at least 15 minutes prior to the administration of MDMA. In some embodiments, the serotonin receptor modulator is pruvanserin and the psychedelic is MDMA, wherein the pruvanserin is administered to pretreat at least 30 minutes prior to the MDMA. In some embodiments, the serotonin receptor modulator is pruvanserin and the psychedelic is MDMA, wherein the pruvanserin is administered to pretreat between at least 60 minutes and 240 minutes prior to the administration or release of MDMA. In some embodiments, the serotonin receptor modulator is pruvanserin and the psychedelic is MDMA, wherein the pruvanserin is administered to pretreat at least 90 minutes prior to the MDMA. In some embodiments, the serotonin receptor modulator is pruvanserin and the psychedelic is MDMA, wherein the pruvanserin is administered to pretreat at least 120 minutes prior to the MDMA. In some embodiments, the serotonin receptor modulator is pruvanserin and the psychedelic is MDMA, wherein the pruvanserin is administered to pretreat at least 150 minutes prior to the MDMA. In some embodiments, the serotonin receptor modulator is pruvanserin and the psychedelic is MDMA, wherein the pruvanserin is administered to pretreat between about 15 minutes and about 150 minutes prior to the MDMA. In some embodiments, the serotonin receptor modulator is pruvanserin and the psychedelic is MDMA, wherein the pruvanserin is administered to pretreat at least 180 minutes prior to the MDMA. In some embodiments, the serotonin receptor modulator is pruvanserin and the psychedelic is MDMA, wherein the pruvanserin is administered to pretreat at least 210 minutes prior to the MDMA.

In some embodiments, the serotonin receptor modulator is pruvanserin and the psychedelic is MDMA, wherein the pruvanserin is administered to pretreat at least 240 minutes prior to the MDMA. In some embodiments, the serotonin receptor modulator is pruvanserin and the psychedelic is MDMA, wherein the pruvanserin is administered to pretreat at least 270 minutes prior to the MDMA. In some embodiments, the serotonin receptor modulator is pruvanserin and the psychedelic is MDMA, wherein the pruvanserin is administered to pretreat at least 300 minutes prior to the MDMA. In some embodiments, the serotonin receptor modulator is pruvanserin and the psychedelic is MDMA, wherein the pruvanserin is administered to pretreat at least 330 minutes prior to the MDMA. In some embodiments, the serotonin receptor modulator is pruvanserin and the psychedelic is MDMA, wherein the pruvanserin is administered to pretreat at least 360 minutes prior to the MDMA. In some preferred embodiments, the serotonin receptor modulator is pruvanserin and the psychedelic is MDMA, wherein pruvanserin is administered to pretreat between about 60 minutes and about 180 minutes prior to the administration of MDMA.

In some embodiments, the serotonin receptor modulator is eplivanserin and the psychedelic is MDMA, wherein the eplivanserin is administered to pretreat at least 15 minutes prior to the administration of the MDMA form disclosed herein, including those described in Table Ex3. In some embodiments, the serotonin receptor modulator is eplivanserin and the psychedelic is MDMA, wherein the eplivanserin is administered to pretreat between at least 30 minutes prior and 360 minutes prior to the release or administration of the MDMA form disclosed herein, including those described in Table Ex3. In some embodiments, the serotonin receptor modulator is eplivanserin and the psychedelic is MDMA, wherein the eplivanserin is administered to pretreat between at least 60 minutes prior and 360 minutes prior to the release or administration the MDMA form disclosed herein, including those described in Table Ex3. In some embodiments, the serotonin receptor modulator is eplivanserin and the psychedelic is MDMA, wherein the eplivanserin is administered to pretreat at between least 90 minutes and 240 minutes prior to the MDMA form disclosed herein, including those described in Table Ex3. In some embodiments, the serotonin receptor modulator is eplivanserin and the psychedelic is MDMA, wherein the eplivanserin is administered to pretreat at least 120 minutes prior to the MDMA form disclosed herein, including those described in Table Ex3.

In some embodiments, the serotonin receptor modulator is eplivanserin and the psychedelic is MDMA, wherein the eplivanserin is administered to pretreat at least 150 minutes prior to the MDMA form disclosed herein, including those described in Table Ex3. In some embodiments, the serotonin receptor modulator is eplivanserin and the psychedelic is MDMA, wherein the eplivanserin is administered to pretreat between about 15 minutes and about 150 minutes prior to the MDMA form disclosed herein, including those described in Table Ex3. In some embodiments, the serotonin receptor modulator is eplivanserin and the psychedelic is MDMA, wherein the eplivanserin is administered to pretreat at least 180 minutes prior to the MDMA form disclosed herein, including those described in Table Ex3. In some embodiments, the serotonin receptor modulator is eplivanserin and the psychedelic is MDMA, wherein the eplivanserin is administered to pretreat at least 210 minutes prior to the MDMA form disclosed herein, including those described in Table Ex3. In some embodiments, the serotonin receptor modulator is eplivanserin and the psychedelic is MDMA, wherein the eplivanserin is administered to pretreat at least 240 minutes prior to the MDMA form disclosed herein, including those described in Table Ex3.

In some embodiments, the serotonin receptor modulator is eplivanserin and the psychedelic is MDMA, wherein the eplivanserin is administered to pretreat at least 270 minutes prior to the MDMA form disclosed herein, including those described in Table Ex3. In some embodiments, the serotonin receptor modulator is eplivanserin and the psychedelic is MDMA, wherein the eplivanserin is administered to pretreat at least 300 minutes prior to the MDMA form disclosed herein, including those described in Table Ex3. In some embodiments, the serotonin receptor modulator is eplivanserin and the psychedelic is MDMA, wherein the eplivanserin is administered to pretreat at least 330 minutes prior to the MDMA form disclosed herein, including those described in Table Ex3. In some embodiments, the serotonin receptor modulator is eplivanserin and the psychedelic is MDMA, wherein the eplivanserin is administered to pretreat at least 360 minutes prior to the MDMA form disclosed herein, including those described in Table Ex3.

In some preferred embodiments, the serotonin receptor modulator is eplivanserin and the psychedelic is MDMA, wherein eplivanserin is administered to pretreat between about 60 minutes and about 180 minutes prior to the administration of the MDMA form disclosed herein, including those described in Table Ex3.

In some embodiments, the serotonin receptor modulator is volinanserin and the psychedelic is MDMA, wherein the volinanserin is administered to pretreat a subject between at least 15 minutes and 360 minutes prior to the administration or release of the MDMA form disclosed herein, including those described in Table Ex3. In some embodiments, the serotonin receptor modulator is volinanserin and the psychedelic is MDMA, wherein the volinanserin is administered to pretreat between at least 30 minutes and 360 minutes prior to the administration or release of the MDMA form disclosed herein, including those described in Table Ex3. In some embodiments, the serotonin receptor modulator is volinanserin and the psychedelic is MDMA, wherein the volinanserin is administered to pretreat between at least 60 minutes and 240 minutes prior to the administration or release of the MDMA form disclosed herein, including those described in Table Ex3. In some embodiments, the serotonin receptor modulator is volinanserin and the psychedelic is MDMA, wherein the volinanserin is administered to pretreat at least 90 minutes prior to the MDMA form disclosed herein, including those described in Table Ex3. In some embodiments, the serotonin receptor modulator is volinanserin and the psychedelic is MDMA, wherein the volinanserin is administered to pretreat at least 120 minutes prior to the MDMA form disclosed herein, including those described in Table Ex3.

In some embodiments, the serotonin receptor modulator is volinanserin and the psychedelic is MDMA, wherein the volinanserin is administered to pretreat at least 150 minutes prior to the MDMA form disclosed herein, including those described in Table Ex3. In some embodiments, the serotonin receptor modulator is volinanserin and the psychedelic is MDMA, wherein the volinanserin is administered to pretreat between about 15 minutes and about 150 minutes prior to the MDMA form disclosed herein, including those described in Table Ex3. In some embodiments, the serotonin receptor modulator is volinanserin and the psychedelic is MDMA, wherein the volinanserin is administered to pretreat at least 180 minutes prior to the MDMA form disclosed herein, including those described in Table Ex3. In some embodiments, the serotonin receptor modulator is volinanserin and the psychedelic is MDMA, wherein the volinanserin is administered to pretreat at least 210 minutes prior to the MDMA form disclosed herein, including those described in Table Ex3. In some embodiments, the serotonin receptor modulator is volinanserin and the psychedelic is MDMA, wherein the volinanserin is administered to pretreat at least 240 minutes prior to the MDMA form disclosed herein, including those described in Table Ex3. In some embodiments, the serotonin receptor modulator is volinanserin and the psychedelic is MDMA, wherein the volinanserin is administered to pretreat at least 270 minutes prior to the MDMA form disclosed herein, including those described in Table Ex3. In some embodiments, the serotonin receptor modulator is volinanserin and the psychedelic is MDMA, wherein the volinanserin is administered to pretreat at least 300 minutes prior to the MDMA form disclosed herein, including those described in Table Ex3. In some embodiments, the serotonin receptor modulator is volinanserin and the psychedelic is MDMA, wherein the volinanserin is administered to pretreat at least 330 minutes prior to the MDMA form disclosed herein, including those described in Table Ex3. In some embodiments, the serotonin receptor modulator is volinanserin and the psychedelic is MDMA, wherein the volinanserin is administered to pretreat at least 360 minutes prior to the MDMA form disclosed herein, including those described in Table Ex3. In some preferred embodiments, the serotonin receptor modulator is volinanserin and the psychedelic is MDMA, wherein volinanserin is administered to pretreat between about 60 minutes and about 180 minutes prior to the administration of the MDMA form disclosed herein, including those described in Table Ex3.

In some embodiments, the serotonin receptor modulator is ketanserin and the psychedelic is MDMA, wherein the ketanserin is administered to pretreat at least 15 minutes prior to the administration of the MDMA form disclosed herein, including those described in Table Ex3. In some embodiments, the serotonin receptor modulator is ketanserin and the psychedelic is MDMA, wherein the ketanserin is administered to pretreat between at least 30 minutes and 360 minutes prior to the administration or release the MDMA form disclosed herein, including those described in Table Ex3. In some embodiments, the serotonin receptor modulator is ketanserin and the psychedelic is MDMA, wherein the ketanserin is administered to pretreat between at least 60 minutes and 240 minutes prior to the administration or release of the MDMA form disclosed herein, including those described in Table Ex3. In some embodiments, the serotonin receptor modulator is ketanserin and the psychedelic is MDMA, wherein the ketanserin is administered to pretreat at least 90 minutes prior to the MDMA form disclosed herein, including those described in Table Ex3. In some embodiments, the serotonin receptor modulator is ketanserin and the psychedelic is MDMA, wherein the ketanserin is administered to pretreat at least 120 minutes prior to the MDMA form disclosed herein, including those described in Table Ex3. In some embodiments, the serotonin receptor modulator is ketanserin and the psychedelic is MDMA, wherein the ketanserin is administered to pretreat at least 150 minutes prior to the MDMA form disclosed herein, including those described in Table Ex3. In some embodiments, the serotonin receptor modulator is ketanserin and the psychedelic is MDMA, wherein the ketanserin is administered to pretreat between about 15 minutes and about 150 minutes prior to the MDMA form disclosed herein, including those described in Table Ex3. In some embodiments, the serotonin receptor modulator is ketanserin and the psychedelic is MDMA, wherein the ketanserin is administered to pretreat at least 180 minutes prior to the MDMA form disclosed herein, including those described in Table Ex3. In some embodiments, the serotonin receptor modulator is ketanserin and the psychedelic is MDMA, wherein the ketanserin is administered to pretreat at least 210 minutes prior to the MDMA form disclosed herein, including those described in Table Ex3. In some embodiments, the serotonin receptor modulator is ketanserin and the psychedelic is MDMA, wherein the ketanserin is administered to pretreat at least 240 minutes prior to the MDMA form disclosed herein, including those described in Table Ex3. In some embodiments, the serotonin receptor modulator is ketanserin and the psychedelic is MDMA, wherein the ketanserin is administered to pretreat at least 270 minutes prior to the MDMA form disclosed herein, including those described in Table Ex3. In some embodiments, the serotonin receptor modulator is ketanserin and the psychedelic is MDMA, wherein the ketanserin is administered to pretreat at least 300 minutes prior to the MDMA form disclosed herein, including those described in Table Ex3. In some embodiments, the serotonin receptor modulator is ketanserin and the psychedelic is MDMA, wherein the ketanserin is administered to pretreat at least 330 minutes prior to the MDMA form disclosed herein, including those described in Table Ex3. In some embodiments, the serotonin receptor modulator is ketanserin and the psychedelic is MDMA, wherein the ketanserin is administered to pretreat at least 360 minutes prior to the MDMA form disclosed herein, including those described in Table Ex3. In some preferred embodiments, the serotonin receptor modulator is ketanserin and the psychedelic is MDMA, wherein ketanserin is administered to pretreat between about 60 minutes and about 180 minutes prior to the administration of the MDMA form disclosed herein, including those described in Table Ex3.

In some embodiments, the serotonin receptor modulator is ritanserin and the psychedelic is MDMA, wherein the ritanserin is administered to pretreat at least 15 minutes prior to the administration of the MDMA form disclosed herein, including those described in Table Ex3. In some embodiments, the serotonin receptor modulator is ritanserin and the psychedelic is MDMA, wherein the ritanserin is administered to pretreat at least 30 minutes prior to the MDMA form disclosed herein, including those described in Table Ex3. In some embodiments, the serotonin receptor modulator is ritanserin and the psychedelic is MDMA, wherein the ritanserin is administered to pretreat between at least 60 minutes and 240 minutes prior to the administration or release of the MDMA form disclosed herein, including those described in Table Ex3. In some embodiments, the serotonin receptor modulator is ritanserin and the psychedelic is MDMA, wherein the ritanserin is administered to pretreat at least 90 minutes prior to the MDMA form disclosed herein, including those described in Table Ex3. In some embodiments, the serotonin receptor modulator is ritanserin and the psychedelic is MDMA, wherein the ritanserin is administered to pretreat at least 120 minutes prior to the MDMA form disclosed herein, including those described in Table Ex3. In some embodiments, the serotonin receptor modulator is ritanserin and the psychedelic is MDMA, wherein the ritanserin is administered to pretreat at least 150 minutes prior to the MDMA form disclosed herein, including those described in Table Ex3. In some embodiments, the serotonin receptor modulator is ritanserin and the psychedelic is MDMA, wherein the ritanserin is administered to pretreat between about 15 minutes and about 150 minutes prior to the MDMA form disclosed herein, including those described in Table Ex3. In some embodiments, the serotonin receptor modulator is ritanserin and the psychedelic is MDMA, wherein the ritanserin is administered to pretreat at least 180 minutes prior to the MDMA form disclosed herein, including those described in Table Ex3. In some embodiments, the serotonin receptor modulator is ritanserin and the psychedelic is MDMA, wherein the ritanserin is administered to pretreat at least 210 minutes prior to the MDMA form disclosed herein, including those described in Table Ex3. In some embodiments, the serotonin receptor modulator is ritanserin and the psychedelic is MDMA, wherein the ritanserin is administered to pretreat at least 240 minutes prior to the MDMA form disclosed herein, including those described in Table Ex3. In some embodiments, the serotonin receptor modulator is ritanserin and the psychedelic is MDMA, wherein the ritanserin is administered to pretreat at least 270 minutes prior to the MDMA form disclosed herein, including those described in Table Ex3. In some embodiments, the serotonin receptor modulator is ritanserin and the psychedelic is MDMA, wherein the ritanserin is administered to pretreat at least 300 minutes prior to the MDMA form disclosed herein, including those described in Table Ex3. In some embodiments, the serotonin receptor modulator is ritanserin and the psychedelic is MDMA, wherein the ritanserin is administered to pretreat at least 330 minutes prior to the MDMA form disclosed herein, including those described in Table Ex3. In some embodiments, the serotonin receptor modulator is ritanserin and the psychedelic is MDMA, wherein the ritanserin is administered to pretreat at least 360 minutes prior to the MDMA form disclosed herein, including those described in Table Ex3. In some preferred embodiments, the serotonin receptor modulator is ritanserin and the psychedelic is MDMA, wherein ritanserin is administered to pretreat between about 60 minutes and about 180 minutes prior to the administration of the MDMA form disclosed herein, including those described in Table Ex3.

In some embodiments, the serotonin receptor modulator is pimavanserin and the psychedelic is MDMA, wherein the pimavanserin is administered to pretreat at least 15 minutes prior to the administration of the MDMA form disclosed herein, including those described in Table Ex3. In some embodiments, the serotonin receptor modulator is pimavanserin and the psychedelic is MDMA, wherein the pimavanserin is administered to pretreat at least 30 minutes prior to the MDMA form disclosed herein, including those described in Table Ex3. In some embodiments, the serotonin receptor modulator is pimavanserin and the psychedelic is MDMA, wherein the pimavanserin is administered to pretreat between at least 60 minutes and 240 minutes prior to the administration or release of the MDMA form disclosed herein, including those described in Table Ex3. In some embodiments, the serotonin receptor modulator is pimavanserin and the psychedelic is MDMA, wherein the pimavanserin is administered to pretreat at least 90 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 120 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 150 minutes prior to the MDMA form disclosed herein, including those described in Table Ex3. In some embodiments, the serotonin receptor modulator is pimavanserin and the psychedelic is MDMA, wherein the pimavanserin is administered to pretreat between about 15 minutes and about 150 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 180 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 210 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 240 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 270 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 300 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 330 minutes prior to the MDMA form disclosed herein, including those described in Table Ex3. In some embodiments, the serotonin receptor modulator is pimavanserin and the psychedelic is MDMA, wherein the pimavanserin is administered to pretreat at least 360 minutes prior to the MDMA form disclosed herein, including those described in Table Ex3. In some preferred embodiments, the serotonin receptor modulator is pimavanserin and the psychedelic is MDMA, wherein pimavanserin is administered to pretreat between about 60 minutes and about 180 minutes prior to the administration of the MDMA form disclosed herein, including those described in Table Ex3.

In some embodiments, the serotonin receptor modulator is nelotanserin and the psychedelic is MDMA, wherein the nelotanserin is administered to pretreat at least 15 minutes prior to the administration of the MDMA form disclosed herein, including those described in Table Ex3. In some embodiments, the serotonin receptor modulator is nelotanserin and the psychedelic is MDMA, wherein the nelotanserin is administered to pretreat at least 30 minutes prior to the MDMA form disclosed herein, including those described in Table Ex3. In some embodiments, the serotonin receptor modulator is nelotanserin and the psychedelic is MDMA, wherein the nelotanserin is administered to pretreat between at least 60 minutes and 240 minutes prior to the administration or release of the MDMA form disclosed herein, including those described in Table Ex3. In some embodiments, the serotonin receptor modulator is nelotanserin and the psychedelic is MDMA, wherein the nelotanserin is administered to pretreat at least 90 minutes prior to the MDMA form disclosed herein, including those described in Table Ex3. In some embodiments, the serotonin receptor modulator is nelotanserin and the psychedelic is MDMA, wherein the nelotanserin is administered to pretreat at least 120 minutes prior to the MDMA form disclosed herein, including those described in Table Ex3.

In some embodiments, the serotonin receptor modulator is nelotanserin and the psychedelic is MDMA, wherein the nelotanserin is administered to pretreat at least 150 minutes prior to the MDMA form disclosed herein, including those described in Table Ex3. In some embodiments, the serotonin receptor modulator is nelotanserin and the psychedelic is MDMA, wherein the nelotanserin is administered to pretreat between about 15 minutes and about 150 minutes prior to the MDMA form disclosed herein, including those described in Table Ex3. In some embodiments, the serotonin receptor modulator is nelotanserin and the psychedelic is MDMA, wherein the nelotanserin is administered to pretreat at least 180 minutes prior to the MDMA form disclosed herein, including those described in Table Ex3. In some embodiments, the serotonin receptor modulator is nelotanserin and the psychedelic is MDMA, wherein the nelotanserin is administered to pretreat at least 210 minutes prior to the MDMA form disclosed herein, including those described in Table Ex3. In some embodiments, the serotonin receptor modulator is nelotanserin and the psychedelic is MDMA, wherein the nelotanserin is administered to pretreat at least 240 minutes prior to the MDMA form disclosed herein, including those described in Table Ex3. In some embodiments, the serotonin receptor modulator is nelotanserin and the psychedelic is MDMA, wherein the nelotanserin is administered to pretreat at least 270 minutes prior to the MDMA form disclosed herein, including those described in Table Ex3.

In some embodiments, the serotonin receptor modulator is nelotanserin and the psychedelic is MDMA, wherein the nelotanserin is administered to pretreat at least 300 minutes prior to the MDMA form disclosed herein, including those described in Table Ex3. In some embodiments, the serotonin receptor modulator is nelotanserin and the psychedelic is MDMA, wherein the nelotanserin is administered to pretreat at least 330 minutes prior to the MDMA form disclosed herein, including those described in Table Ex3. In some embodiments, the serotonin receptor modulator is nelotanserin and the psychedelic is MDMA, wherein the nelotanserin is administered to pretreat at least 360 minutes prior to the MDMA form disclosed herein, including those described in Table Ex3. In some preferred embodiments, the serotonin receptor modulator is nelotanserin and the psychedelic is MDMA, wherein nelotanserin is administered to pretreat between about 60 minutes and about 180 minutes prior to the administration of the MDMA form disclosed herein, including those described in Table Ex3.

In some embodiments, the serotonin receptor modulator is pruvanserin and the psychedelic is MDMA, wherein the pruvanserin is administered to pretreat at least 15 minutes prior to the administration of the MDMA form disclosed herein, including those described in Table Ex3. In some embodiments, the serotonin receptor modulator is pruvanserin and the psychedelic is MDMA, wherein the pruvanserin is administered to pretreat at least 30 minutes prior to the MDMA form disclosed herein, including those described in Table Ex3. In some embodiments, the serotonin receptor modulator is pruvanserin and the psychedelic is MDMA, wherein the pruvanserin is administered to pretreat between at least 60 minutes and 240 minutes prior to the administration or release of the MDMA form disclosed herein, including those described in Table Ex3. In some embodiments, the serotonin receptor modulator is pruvanserin and the psychedelic is MDMA, wherein the pruvanserin is administered to pretreat at least 90 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 120 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 150 minutes prior to the MDMA form disclosed herein, including those described in Table Ex3. In some embodiments, the serotonin receptor modulator is pruvanserin and the psychedelic is MDMA, wherein the pruvanserin is administered to pretreat between about 15 minutes and about 150 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 180 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 210 minutes prior to the MDMA form disclosed herein, including those described in Table Ex3.

In some embodiments, the serotonin receptor modulator is pruvanserin and the psychedelic is MDMA, wherein the pruvanserin is administered to pretreat at least 240 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 270 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 300 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 330 minutes prior to the MDMA form disclosed herein, including those described in Table Ex3. In some embodiments, the serotonin receptor modulator is pruvanserin and the psychedelic is MDMA, wherein the pruvanserin is administered to pretreat at least 360 minutes prior to the MDMA form disclosed herein, including those described in Table Ex3. In some preferred embodiments, the serotonin receptor modulator is pruvanserin and the psychedelic is MDMA, wherein pruvanserin is administered to pretreat between about 60 minutes and about 180 minutes prior to the administration of the MDMA form disclosed herein, including those described in Table Ex3.

In some embodiments, the serotonin receptor modulator is flibanserin and the psychedelic is (R)-MDMA, wherein the flibanserin is administered to pretreat at least 15 minutes prior to the administration of the (R)-MDMA form disclosed herein, including those described in Table Ex9. In some embodiments, the serotonin receptor modulator is flibanserin and the psychedelic is (R)-MDMA, wherein the flibanserin is administered to pretreat at least 30 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat between at least 60 minutes and 240 minutes prior to the administration or release of the (R)-MDMA form disclosed herein, including those described in Table Ex9. In some embodiments, the serotonin receptor modulator is flibanserin and the psychedelic is (R)-MDMA, wherein the flibanserin is administered to pretreat at least 90 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 120 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 150 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat between about 15 minutes and about 150 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 180 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 210 minutes prior to the (R)-MDMA form disclosed herein, including those described in Table Ex9.

In some embodiments, the serotonin receptor modulator is flibanserin and the psychedelic is (R)-MDMA, wherein the flibanserin is administered to pretreat at least 240 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 270 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 300 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 330 minutes prior to the (R)-MDMA form disclosed herein, including those described in Table Ex9. In some embodiments, the serotonin receptor modulator is flibanserin and the psychedelic is (R)-MDMA, wherein the flibanserin is administered to pretreat at least 360 minutes prior to the (R)-MDMA form disclosed herein, including those described in Table Ex9. In some preferred embodiments, the serotonin receptor modulator is flibanserin and the psychedelic is (R)-MDMA, wherein flibanserin is administered to pretreat between about 60 minutes and about 180 minutes prior to the administration of the (R)-MDMA form disclosed herein, including those described in Table Ex9.

In some embodiments, the serotonin receptor modulator is olanzapine and the psychedelic is (R)-MDMA, wherein the olanzapine is administered to pretreat at least 15 minutes prior to the administration of the (R)-MDMA form disclosed herein, including those described in Table Ex9. In some embodiments, the serotonin receptor modulator is olanzapine and the psychedelic is (R)-MDMA, wherein the olanzapine is administered to pretreat at least 30 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat between at least 60 minutes and 240 minutes prior to the administration or release of the (R)-MDMA form disclosed herein, including those described in Table Ex9. In some embodiments, the serotonin receptor modulator is olanzapine and the psychedelic is (R)-MDMA, wherein the olanzapine is administered to pretreat at least 90 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 120 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 150 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat between about 15 minutes and about 150 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 180 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 210 minutes prior to the (R)-MDMA form disclosed herein, including those described in Table Ex9.

In some embodiments, the serotonin receptor modulator is olanzapine and the psychedelic is (R)-MDMA, wherein the olanzapine is administered to pretreat at least 240 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 270 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 300 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 330 minutes prior to the (R)-MDMA form disclosed herein, including those described in Table Ex9. In some embodiments, the serotonin receptor modulator is olanzapine and the psychedelic is (R)-MDMA, wherein the olanzapine is administered to pretreat at least 360 minutes prior to the (R)-MDMA form disclosed herein, including those described in Table Ex9. In some preferred embodiments, the serotonin receptor modulator is olanzapine and the psychedelic is (R)-MDMA, wherein olanzapine is administered to pretreat between about 60 minutes and about 180 minutes prior to the administration of the (R)-MDMA form disclosed herein, including those described in Table Ex9.

In some embodiments, the serotonin receptor modulator is quetiapine and the psychedelic is (R)-MDMA, wherein the quetiapine is administered to pretreat at least 15 minutes prior to the administration of the (R)-MDMA form disclosed herein, including those described in Table Ex9. In some embodiments, the serotonin receptor modulator is quetiapine and the psychedelic is (R)-MDMA, wherein the quetiapine is administered to pretreat at least 30 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat between at least 60 minutes and 240 minutes prior to the administration or release of the (R)-MDMA form disclosed herein, including those described in Table Ex9. In some embodiments, the serotonin receptor modulator is quetiapine and the psychedelic is (R)-MDMA, wherein the quetiapine is administered to pretreat at least 90 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 120 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 150 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat between about 15 minutes and about 150 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 180 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 210 minutes prior to the (R)-MDMA form disclosed herein, including those described in Table Ex9.

In some embodiments, the serotonin receptor modulator is quetiapine and the psychedelic is (R)-MDMA, wherein the quetiapine is administered to pretreat at least 240 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 270 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 300 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 330 minutes prior to the (R)-MDMA form disclosed herein, including those described in Table Ex9. In some embodiments, the serotonin receptor modulator is quetiapine and the psychedelic is (R)-MDMA, wherein the quetiapine is administered to pretreat at least 360 minutes prior to the (R)-MDMA form disclosed herein, including those described in Table Ex9. In some preferred embodiments, the serotonin receptor modulator is quetiapine and the psychedelic is (R)-MDMA, wherein quetiapine is administered to pretreat between about 60 minutes and about 180 minutes prior to the administration of the (R)-MDMA form disclosed herein, including those described in Table Ex9.

In some embodiments, the serotonin receptor modulator is risperidone and the psychedelic is (R)-MDMA, wherein the risperidone is administered to pretreat at least 15 minutes prior to the administration of the (R)-MDMA form disclosed herein, including those described in Table Ex9. In some embodiments, the serotonin receptor modulator is risperidone and the psychedelic is (R)-MDMA, wherein the risperidone is administered to pretreat at least 30 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat between at least 60 minutes and 240 minutes prior to the administration or release of the (R)-MDMA form disclosed herein, including those described in Table Ex9. In some embodiments, the serotonin receptor modulator is risperidone and the psychedelic is (R)-MDMA, wherein the risperidone is administered to pretreat at least 90 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 120 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 150 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat between about 15 minutes and about 150 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 180 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 210 minutes prior to the (R)-MDMA form disclosed herein, including those described in Table Ex9.

In some embodiments, the serotonin receptor modulator is risperidone and the psychedelic is (R)-MDMA, wherein the risperidone is administered to pretreat at least 240 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 270 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 300 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 330 minutes prior to the (R)-MDMA form disclosed herein, including those described in Table Ex9. In some embodiments, the serotonin receptor modulator is risperidone and the psychedelic is (R)-MDMA, wherein the risperidone is administered to pretreat at least 360 minutes prior to the (R)-MDMA form disclosed herein, including those described in Table Ex9. In some preferred embodiments, the serotonin receptor modulator is risperidone and the psychedelic is (R)-MDMA, wherein risperidone is administered to pretreat between about 60 minutes and about 180 minutes prior to the administration of the (R)-MDMA form disclosed herein, including those described in Table Ex9.

In some embodiments, the serotonin receptor modulator is flibanserin and the psychedelic is (S)-MDMA, wherein the flibanserin is administered to pretreat at least 15 minutes prior to the administration of the (S)-MDMA form disclosed herein, including those described in Table Ex8. In some embodiments, the serotonin receptor modulator is flibanserin and the psychedelic is (S)-MDMA, wherein the flibanserin is administered to pretreat at least 30 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat between at least 60 minutes and 240 minutes prior to the administration or release of the (S)-MDMA form disclosed herein, including those described in Table Ex8. In some embodiments, the serotonin receptor modulator is flibanserin and the psychedelic is (S)-MDMA, wherein the flibanserin is administered to pretreat at least 90 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 120 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 150 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat between about 15 minutes and about 150 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 180 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 210 minutes prior to the (S)-MDMA form disclosed herein, including those described in Table Ex8.

In some embodiments, the serotonin receptor modulator is flibanserin and the psychedelic is (S)-MDMA, wherein the flibanserin is administered to pretreat at least 240 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 270 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 300 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 330 minutes prior to the (S)-MDMA form disclosed herein, including those described in Table Ex8. In some embodiments, the serotonin receptor modulator is flibanserin and the psychedelic is (S)-MDMA, wherein the flibanserin is administered to pretreat at least 360 minutes prior to the (S)-MDMA form disclosed herein, including those described in Table Ex8. In some preferred embodiments, the serotonin receptor modulator is flibanserin and the psychedelic is (S)-MDMA, wherein flibanserin is administered to pretreat between about 60 minutes and about 180 minutes prior to the administration of the (S)-MDMA form disclosed herein, including those described in Table Ex8.

In some embodiments, the serotonin receptor modulator is olanzapine and the psychedelic is (S)-MDMA, wherein the olanzapine is administered to pretreat at least 15 minutes prior to the administration of the (S)-MDMA form disclosed herein, including those described in Table Ex8. In some embodiments, the serotonin receptor modulator is olanzapine and the psychedelic is (S)-MDMA, wherein the olanzapine is administered to pretreat at least 30 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat between at least 60 minutes and 240 minutes prior to the administration or release of the (S)-MDMA form disclosed herein, including those described in Table Ex8. In some embodiments, the serotonin receptor modulator is olanzapine and the psychedelic is (S)-MDMA, wherein the olanzapine is administered to pretreat at least 90 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 120 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 150 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat between about 15 minutes and about 150 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 180 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 210 minutes prior to the (S)-MDMA form disclosed herein, including those described in Table Ex8.

In some embodiments, the serotonin receptor modulator is olanzapine and the psychedelic is (S)-MDMA, wherein the olanzapine is administered to pretreat at least 240 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 270 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 300 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 330 minutes prior to the (S)-MDMA form disclosed herein, including those described in Table Ex8. In some embodiments, the serotonin receptor modulator is olanzapine and the psychedelic is (S)-MDMA, wherein the olanzapine is administered to pretreat at least 360 minutes prior to the (S)-MDMA form disclosed herein, including those described in Table Ex8. In some preferred embodiments, the serotonin receptor modulator is olanzapine and the psychedelic is (S)-MDMA, wherein olanzapine is administered to pretreat between about 60 minutes and about 180 minutes prior to the administration of the (S)-MDMA form disclosed herein, including those described in Table Ex8.

In some embodiments, the serotonin receptor modulator is quetiapine and the psychedelic is (S)-MDMA, wherein the quetiapine is administered to pretreat at least 15 minutes prior to the administration of the (S)-MDMA form disclosed herein, including those described in Table Ex8. In some embodiments, the serotonin receptor modulator is quetiapine and the psychedelic is (S)-MDMA, wherein the quetiapine is administered to pretreat at least 30 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat between at least 60 minutes and 240 minutes prior to the administration or release of the (S)-MDMA form disclosed herein, including those described in Table Ex8. In some embodiments, the serotonin receptor modulator is quetiapine and the psychedelic is (S)-MDMA, wherein the quetiapine is administered to pretreat at least 90 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 120 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 150 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat between about 15 minutes and about 150 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 180 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 210 minutes prior to the (S)-MDMA form disclosed herein, including those described in Table Ex8.

In some embodiments, the serotonin receptor modulator is quetiapine and the psychedelic is (S)-MDMA, wherein the quetiapine is administered to pretreat at least 240 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 270 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 300 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 330 minutes prior to the (S)-MDMA form disclosed herein, including those described in Table Ex8. In some embodiments, the serotonin receptor modulator is quetiapine and the psychedelic is (S)-MDMA, wherein the quetiapine is administered to pretreat at least 360 minutes prior to the (S)-MDMA form disclosed herein, including those described in Table Ex8. In some preferred embodiments, the serotonin receptor modulator is quetiapine and the psychedelic is (S)-MDMA, wherein quetiapine is administered to pretreat between about 60 minutes and about 180 minutes prior to the administration of the (S)-MDMA form disclosed herein, including those described in Table Ex8.

In some embodiments, the serotonin receptor modulator is risperidone and the psychedelic is (S)-MDMA, wherein the risperidone is administered to pretreat at least 15 minutes prior to the administration of the (S)-MDMA form disclosed herein, including those described in Table Ex8. In some embodiments, the serotonin receptor modulator is risperidone and the psychedelic is (S)-MDMA, wherein the risperidone is administered to pretreat at least 30 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat between at least 60 minutes and 240 minutes prior to the administration or release of the (S)-MDMA form disclosed herein, including those described in Table Ex8. In some embodiments, the serotonin receptor modulator is risperidone and the psychedelic is (S)-MDMA, wherein the risperidone is administered to pretreat at least 90 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 120 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 150 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat between about 15 minutes and about 150 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 180 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 210 minutes prior to the (S)-MDMA form disclosed herein, including those described in Table Ex8.

In some embodiments, the serotonin receptor modulator is risperidone and the psychedelic is (S)-MDMA, wherein the risperidone is administered to pretreat at least 240 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 270 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 300 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 330 minutes prior to the (S)-MDMA form disclosed herein, including those described in Table Ex8. In some embodiments, the serotonin receptor modulator is risperidone and the psychedelic is (S)-MDMA, wherein the risperidone is administered to pretreat at least 360 minutes prior to the (S)-MDMA form disclosed herein, including those described in Table Ex8. In some preferred embodiments, the serotonin receptor modulator is risperidone and the psychedelic is (S)-MDMA, wherein risperidone is administered to pretreat between about 60 minutes and about 180 minutes prior to the administration of the (S)-MDMA form disclosed herein, including those described in Table Ex8.

In some embodiments, the serotonin receptor modulator is flibanserin and the psychedelic is N-ethyl-3,4-methylenedioxyamphetamine, wherein the flibanserin is administered to pretreat at least 15 minutes prior to the administration of the N-ethyl-3,4-methylenedioxyamphetamine. HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 30 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat between at least 60 minutes and 240 minutes prior to the administration or release of the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 90 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 120 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 150 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat between about 15 minutes and about 150 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 180 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 210 minutes prior to the N-ethyl-3,4-methylenedioxyamphetamine·HCl forms disclosed herein, including those described in Table Ex10.

In some embodiments, the serotonin receptor modulator is flibanserin and the psychedelic is N-ethyl-3,4-methylenedioxyamphetamine, wherein the flibanserin is administered to pretreat at least 240 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 270 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 300 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 330 minutes prior to the N-ethyl-3,4-methylenedioxyamphetamine·HCl forms disclosed herein, including those described in Table Ex10. In some embodiments, the serotonin receptor modulator is flibanserin and the psychedelic is N-ethyl-3,4-methylenedioxyamphetamine, wherein the flibanserin is administered to pretreat at least 360 minutes prior to the N-ethyl-3,4-methylenedioxyamphetamine·HCl forms disclosed herein, including those described in Table Ex10. In some preferred embodiments, the serotonin receptor modulator is flibanserin and the psychedelic is N-ethyl-3,4-methylenedioxyamphetamine, wherein flibanserin is administered to pretreat between about 60 minutes and about 180 minutes prior to the administration of the N-ethyl-3,4-methylenedioxyamphetamine·HCl forms disclosed herein, including those described in Table Ex10.

In some embodiments, the serotonin receptor modulator is olanzapine and the psychedelic is N-ethyl-3,4-methylenedioxyamphetamine, wherein the olanzapine is administered to pretreat at least 15 minutes prior to the administration of the N-ethyl-3,4-methylenedioxyamphetamine. HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 30 minutes prior to the N-ethyl-3,4-methylenedioxyamphetamine. HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat between at least 60 minutes and 240 minutes prior to the administration or release of the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 90 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 120 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 150 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat between about 15 minutes and about 150 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 180 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 210 minutes prior to the N-ethyl-3,4-methylenedioxyamphetamine·HCl forms disclosed herein, including those described in Table Ex10.

In some embodiments, the serotonin receptor modulator is olanzapine and the psychedelic is N-ethyl-3,4-methylenedioxyamphetamine, wherein the olanzapine is administered to pretreat at least 240 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 270 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 300 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 330 minutes prior to the N-ethyl-3,4-methylenedioxyamphetamine·HCl forms disclosed herein, including those described in Table Ex10. In some embodiments, the serotonin receptor modulator is olanzapine and the psychedelic is N-ethyl-3,4-methylenedioxyamphetamine, wherein the olanzapine is administered to pretreat at least 360 minutes prior to the N-ethyl-3,4-methylenedioxyamphetamine. HCl forms disclosed herein, including those described in Table Ex10. In some preferred embodiments, the serotonin receptor modulator is olanzapine and the psychedelic is N-ethyl-3,4-methylenedioxyamphetamine, wherein olanzapine is administered to pretreat between about 60 minutes and about 180 minutes prior to the administration of the N-ethyl-3,4-methylenedioxyamphetamine·HCl forms disclosed herein, including those described in Table Ex10.

In some embodiments, the serotonin receptor modulator is quetiapine and the psychedelic is N-ethyl-3,4-methylenedioxyamphetamine, wherein the quetiapine is administered to pretreat at least 15 minutes prior to the administration of the N-ethyl-3,4-methylenedioxyamphetamine. HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 30 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat between at least 60 minutes and 240 minutes prior to the administration or release of the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 90 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 120 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 150 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat between about 15 minutes and about 150 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 180 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 210 minutes prior to the N-ethyl-3,4-methylenedioxyamphetamine·HCl forms disclosed herein, including those described in Table Ex10.

In some embodiments, the serotonin receptor modulator is quetiapine and the psychedelic is N-ethyl-3,4-methylenedioxyamphetamine, wherein the quetiapine is administered to pretreat at least 240 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 270 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 300 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 330 minutes prior to the N-ethyl-3,4-methylenedioxyamphetamine·HCl forms disclosed herein, including those described in Table Ex10. In some embodiments, the serotonin receptor modulator is quetiapine and the psychedelic is N-ethyl-3,4-methylenedioxyamphetamine, wherein the quetiapine is administered to pretreat at least 360 minutes prior to the N-ethyl-3,4-methylenedioxyamphetamine·HCl forms disclosed herein, including those described in Table Ex10. In some preferred embodiments, the serotonin receptor modulator is quetiapine and the psychedelic is N-ethyl-3,4-methylenedioxyamphetamine, wherein quetiapine is administered to pretreat between about 60 minutes and about 180 minutes prior to the administration of the N-ethyl-3,4-methylenedioxyamphetamine·HCl forms disclosed herein, including those described in Table Ex10.

In some embodiments, the serotonin receptor modulator is risperidone and the psychedelic is N-ethyl-3,4-methylenedioxyamphetamine, wherein the risperidone is administered to pretreat at least 15 minutes prior to the administration of the N-ethyl-3,4-methylenedioxyamphetamine. HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 30 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat between at least 60 minutes and 240 minutes prior to the administration or release of the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 90 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 120 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 150 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat between about 15 minutes and about 150 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 180 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 210 minutes prior to the N-ethyl-3,4-methylenedioxyamphetamine·HCl forms disclosed herein, including those described in Table Ex10.

In some embodiments, the serotonin receptor modulator is risperidone and the psychedelic is N-ethyl-3,4-methylenedioxyamphetamine, wherein the risperidone is administered to pretreat at least 240 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 270 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 300 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 330 minutes prior to the N-ethyl-3,4-methylenedioxyamphetamine·HCl forms disclosed herein, including those described in Table Ex10. In some embodiments, the serotonin receptor modulator is risperidone and the psychedelic is N-ethyl-3,4-methylenedioxyamphetamine, wherein the risperidone is administered to pretreat at least 360 minutes prior to the N-ethyl-3,4-methylenedioxyamphetamine·HCl forms disclosed herein, including those described in Table Ex10. In some preferred embodiments, the serotonin receptor modulator is risperidone and the psychedelic is N-ethyl-3,4-methylenedioxyamphetamine, wherein risperidone is administered to pretreat between about 60 minutes and about 180 minutes prior to the administration of the N-ethyl-3,4-methylenedioxyamphetamine·HCl forms disclosed herein, including those described in Table Ex10.

In some embodiments, the serotonin receptor modulator is flibanserin and the psychedelic is (S)—N-ethyl-3,4-methylenedioxyamphetamine, wherein the flibanserin is administered to pretreat at least 15 minutes prior to the administration of the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 30 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 90 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 120 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 150 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 180 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 210 minutes prior to the (S)—N-ethyl-3,4-methylenedioxyamphetamine form disclosed herein, including those described in Table Ex11.

In some embodiments, the serotonin receptor modulator is flibanserin and the psychedelic is (S)—N-ethyl-3,4-methylenedioxyamphetamine, wherein the flibanserin is administered to pretreat at least 240 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 270 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 300 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 330 minutes prior to the (S)—N-ethyl-3,4-methylenedioxyamphetamine form disclosed herein, including those described in Table Ex11. In some embodiments, the serotonin receptor modulator is flibanserin and the psychedelic is (S)—N-ethyl-3,4-methylenedioxyamphetamine, wherein the flibanserin is administered to pretreat at least 360 minutes prior to the (S)—N-ethyl-3,4-methylenedioxyamphetamine form disclosed herein, including those described in Table Ex11. In some preferred embodiments, the serotonin receptor modulator is flibanserin and the psychedelic is (S)—N-ethyl-3,4-methylenedioxyamphetamine, wherein flibanserin is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is olanzapine and the psychedelic is (S)—N-ethyl-3,4-methylenedioxyamphetamine, wherein the olanzapine is administered to pretreat at least 15 minutes prior to the administration of the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 30 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 90 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 120 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 150 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 180 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 210 minutes prior to the (S)—N-ethyl-3,4-methylenedioxyamphetamine form disclosed herein, including those described in Table Ex11.

In some embodiments, the serotonin receptor modulator is olanzapine and the psychedelic is (S)—N-ethyl-3,4-methylenedioxyamphetamine, wherein the olanzapine is administered to pretreat at least 240 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 270 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 300 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 330 minutes prior to the (S)—N-ethyl-3,4-methylenedioxyamphetamine form disclosed herein, including those described in Table Ex11. In some embodiments, the serotonin receptor modulator is olanzapine and the psychedelic is (S)—N-ethyl-3,4-methylenedioxyamphetamine, wherein the olanzapine is administered to pretreat at least 360 minutes prior to the (S)—N-ethyl-3,4-methylenedioxyamphetamine form disclosed herein, including those described in Table Ex11. In some preferred embodiments, the serotonin receptor modulator is olanzapine and the psychedelic is (S)—N-ethyl-3,4-methylenedioxyamphetamine, wherein olanzapine is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is quetiapine and the psychedelic is (S)—N-ethyl-3,4-methylenedioxyamphetamine, wherein the quetiapine is administered to pretreat at least 15 minutes prior to the administration of the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 30 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 90 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 120 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 150 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 180 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 210 minutes prior to the (S)—N-ethyl-3,4-methylenedioxyamphetamine form disclosed herein, including those described in Table Ex11.

In some embodiments, the serotonin receptor modulator is quetiapine and the psychedelic is (S)—N-ethyl-3,4-methylenedioxyamphetamine, wherein the quetiapine is administered to pretreat at least 240 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 270 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 300 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 330 minutes prior to the (S)—N-ethyl-3,4-methylenedioxyamphetamine form disclosed herein, including those described in Table Ex11. In some embodiments, the serotonin receptor modulator is quetiapine and the psychedelic is (S)—N-ethyl-3,4-methylenedioxyamphetamine, wherein the quetiapine is administered to pretreat at least 360 minutes prior to the (S)—N-ethyl-3,4-methylenedioxyamphetamine form disclosed herein, including those described in Table Ex11. In some preferred embodiments, the serotonin receptor modulator is quetiapine and the psychedelic is (S)—N-ethyl-3,4-methylenedioxyamphetamine, wherein quetiapine is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is risperidone and the psychedelic is (S)—N-ethyl-3,4-methylenedioxyamphetamine, wherein the risperidone is administered to pretreat at least 15 minutes prior to the administration of the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 30 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 90 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 120 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 150 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 180 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 210 minutes prior to the (S)—N-ethyl-3,4-methylenedioxyamphetamine form disclosed herein, including those described in Table Ex11.

In some embodiments, the serotonin receptor modulator is risperidone and the psychedelic is (S)—N-ethyl-3,4-methylenedioxyamphetamine, wherein the risperidone is administered to pretreat at least 240 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 270 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 300 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 330 minutes prior to the (S)—N-ethyl-3,4-methylenedioxyamphetamine form disclosed herein, including those described in Table Ex11. In some embodiments, the serotonin receptor modulator is risperidone and the psychedelic is (S)—N-ethyl-3,4-methylenedioxyamphetamine, wherein the risperidone is administered to pretreat at least 360 minutes prior to the (S)—N-ethyl-3,4-methylenedioxyamphetamine form disclosed herein, including those described in Table Ex11. In some preferred embodiments, the serotonin receptor modulator is risperidone and the psychedelic is (S)—N-ethyl-3,4-methylenedioxyamphetamine, wherein risperidone is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is flibanserin and the psychedelic is MDAI, wherein the flibanserin is administered to pretreat at least 15 minutes prior to the administration of the MDAI HCl forms disclosed herein, including those described in Table Ex12. In some embodiments, the serotonin receptor modulator is flibanserin and the psychedelic is MDAI, wherein the flibanserin is administered to pretreat at least 30 minutes prior to the MDAI HCl forms disclosed herein, including those described in Table Ex12. In some embodiments, the serotonin receptor modulator is flibanserin and the psychedelic is MDAI, wherein the flibanserin is administered to pretreat between at least 60 minutes and 240 minutes prior to the administration or release of the MDAI HCl forms disclosed herein, including those described in Table Ex12. In some embodiments, the serotonin receptor modulator is flibanserin and the psychedelic is MDAI, wherein the flibanserin is administered to pretreat at least 90 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 120 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 150 minutes prior to the MDAI HCl forms disclosed herein, including those described in Table Ex12. In some embodiments, the serotonin receptor modulator is flibanserin and the psychedelic is MDAI, wherein the flibanserin is administered to pretreat between about 15 minutes and about 150 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 180 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 210 minutes prior to the MDAI HCl forms disclosed herein, including those described in Table Ex12.

In some embodiments, the serotonin receptor modulator is flibanserin and the psychedelic is MDAI, wherein the flibanserin is administered to pretreat at least 240 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 270 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 300 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 330 minutes prior to the MDAI HCl forms disclosed herein, including those described in Table Ex12. In some embodiments, the serotonin receptor modulator is flibanserin and the psychedelic is MDAI, wherein the flibanserin is administered to pretreat at least 360 minutes prior to the MDAI HCl forms disclosed herein, including those described in Table Ex12. In some preferred embodiments, the serotonin receptor modulator is flibanserin and the psychedelic is MDAI, wherein flibanserin is administered to pretreat between about 60 minutes and about 180 minutes prior to the administration of the MDAI HCl forms disclosed herein, including those described in Table Ex12.

In some embodiments, the serotonin receptor modulator is olanzapine and the psychedelic is MDAI, wherein the olanzapine is administered to pretreat at least 15 minutes prior to the administration of the MDAI HCl forms disclosed herein, including those described in Table Ex12. In some embodiments, the serotonin receptor modulator is olanzapine and the psychedelic is MDAI, wherein the olanzapine is administered to pretreat at least 30 minutes prior to the MDAI HCl forms disclosed herein, including those described in Table Ex12. In some embodiments, the serotonin receptor modulator is olanzapine and the psychedelic is MDAI, wherein the olanzapine is administered to pretreat between at least 60 minutes and 240 minutes prior to the administration or release of the MDAI HCl forms disclosed herein, including those described in Table Ex12. In some embodiments, the serotonin receptor modulator is olanzapine and the psychedelic is MDAI, wherein the olanzapine is administered to pretreat at least 90 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 120 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 150 minutes prior to the MDAI HCl forms disclosed herein, including those described in Table Ex12. In some embodiments, the serotonin receptor modulator is olanzapine and the psychedelic is MDAI, wherein the olanzapine is administered to pretreat between about 15 minutes and about 150 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 180 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 210 minutes prior to the MDAI HCl forms disclosed herein, including those described in Table Ex12.

In some embodiments, the serotonin receptor modulator is olanzapine and the psychedelic is MDAI, wherein the olanzapine is administered to pretreat at least 240 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 270 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 300 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 330 minutes prior to the MDAI HCl forms disclosed herein, including those described in Table Ex12. In some embodiments, the serotonin receptor modulator is olanzapine and the psychedelic is MDAI, wherein the olanzapine is administered to pretreat at least 360 minutes prior to the MDAI HCl forms disclosed herein, including those described in Table Ex12. In some preferred embodiments, the serotonin receptor modulator is olanzapine and the psychedelic is MDAI, wherein olanzapine is administered to pretreat between about 60 minutes and about 180 minutes prior to the administration of the MDAI HCl forms disclosed herein, including those described in Table Ex12.

In some embodiments, the serotonin receptor modulator is quetiapine and the psychedelic is MDAI, wherein the quetiapine is administered to pretreat at least 15 minutes prior to the administration of the MDAI HCl forms disclosed herein, including those described in Table Ex12. In some embodiments, the serotonin receptor modulator is quetiapine and the psychedelic is MDAI, wherein the quetiapine is administered to pretreat at least 30 minutes prior to the MDAI HCl forms disclosed herein, including those described in Table Ex12. In some embodiments, the serotonin receptor modulator is quetiapine and the psychedelic is MDAI, wherein the quetiapine is administered to pretreat between at least 60 minutes and 240 minutes prior to the administration or release of the MDAI HCl forms disclosed herein, including those described in Table Ex12. In some embodiments, the serotonin receptor modulator is quetiapine and the psychedelic is MDAI, wherein the quetiapine is administered to pretreat at least 90 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 120 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 150 minutes prior to the MDAI HCl forms disclosed herein, including those described in Table Ex12. In some embodiments, the serotonin receptor modulator is quetiapine and the psychedelic is MDAI, wherein the quetiapine is administered to pretreat between about 15 minutes and about 150 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 180 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 210 minutes prior to the MDAI HCl forms disclosed herein, including those described in Table Ex12.

In some embodiments, the serotonin receptor modulator is quetiapine and the psychedelic is MDAI, wherein the quetiapine is administered to pretreat at least 240 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 270 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 300 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 330 minutes prior to the MDAI HCl forms disclosed herein, including those described in Table Ex12. In some embodiments, the serotonin receptor modulator is quetiapine and the psychedelic is MDAI, wherein the quetiapine is administered to pretreat at least 360 minutes prior to the MDAI HCl forms disclosed herein, including those described in Table Ex12. In some preferred embodiments, the serotonin receptor modulator is quetiapine and the psychedelic is MDAI, wherein quetiapine is administered to pretreat between about 60 minutes and about 180 minutes prior to the administration of the MDAI HCl forms disclosed herein, including those described in Table Ex12.

In some embodiments, the serotonin receptor modulator is risperidone and the psychedelic is MDAI, wherein the risperidone is administered to pretreat at least 15 minutes prior to the administration of the MDAI HCl forms disclosed herein, including those described in Table Ex12. In some embodiments, the serotonin receptor modulator is risperidone and the psychedelic is MDAI, wherein the risperidone is administered to pretreat at least 30 minutes prior to the MDAI HCl forms disclosed herein, including those described in Table Ex12. In some embodiments, the serotonin receptor modulator is risperidone and the psychedelic is MDAI, wherein the risperidone is administered to pretreat between at least 60 minutes and 240 minutes prior to the administration or release of the MDAI HCl forms disclosed herein, including those described in Table Ex12. In some embodiments, the serotonin receptor modulator is risperidone and the psychedelic is MDAI, wherein the risperidone is administered to pretreat at least 90 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 120 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 150 minutes prior to the MDAI HCl forms disclosed herein, including those described in Table Ex12. In some embodiments, the serotonin receptor modulator is risperidone and the psychedelic is MDAI, wherein the risperidone is administered to pretreat between about 15 minutes and about 150 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 180 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 210 minutes prior to the MDAI HCl forms disclosed herein, including those described in Table Ex12.

In some embodiments, the serotonin receptor modulator is risperidone and the psychedelic is MDAI, wherein the risperidone is administered to pretreat at least 240 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 270 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 300 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 330 minutes prior to the MDAI HCl forms disclosed herein, including those described in Table Ex12. In some embodiments, the serotonin receptor modulator is risperidone and the psychedelic is MDAI, wherein the risperidone is administered to pretreat at least 360 minutes prior to the MDAI HCl forms disclosed herein, including those described in Table Ex12. In some preferred embodiments, the serotonin receptor modulator is risperidone and the psychedelic is MDAI, wherein risperidone is administered to pretreat between about 60 minutes and about 180 minutes prior to the administration of the MDAI HCl forms disclosed herein, including those described in Table Ex12.

In some embodiments, the serotonin receptor modulator is flibanserin and the psychedelic is MBDB, wherein the flibanserin is administered to pretreat at least 15 minutes prior to the administration of the MBDB forms disclosed herein, including those described in Example 5. In some embodiments, the serotonin receptor modulator is flibanserin and the psychedelic is MBDB, wherein the flibanserin is administered to pretreat at least 30 minutes prior to the MBDB forms disclosed herein, including those described in Example 5. In some embodiments, the serotonin receptor modulator is flibanserin and the psychedelic is MBDB, wherein the flibanserin is administered to pretreat between at least 60 minutes and 240 minutes prior to the administration or release of the MBDB forms disclosed herein, including those described in Example 5. In some embodiments, the serotonin receptor modulator is flibanserin and the psychedelic is MBDB, wherein the flibanserin is administered to pretreat at least 90 minutes prior to the MBDB forms disclosed herein, including those described in Example 5. In some embodiments, the serotonin receptor modulator is flibanserin and the psychedelic is MBDB, wherein the flibanserin is administered to pretreat at least 120 minutes prior to the MBDB forms disclosed herein, including those described in Example 5. In some embodiments, the serotonin receptor modulator is flibanserin and the psychedelic is MBDB, wherein the flibanserin is administered to pretreat at least 150 minutes prior to the MBDB forms disclosed herein, including those described in Example 5. In some embodiments, the serotonin receptor modulator is flibanserin and the psychedelic is MBDB, wherein the flibanserin is administered to pretreat between about 15 minutes and about 150 minutes prior to the MBDB forms disclosed herein, including those described in Example 5. In some embodiments, the serotonin receptor modulator is flibanserin and the psychedelic is MBDB, wherein the flibanserin is administered to pretreat at least 180 minutes prior to the MBDB forms disclosed herein, including those described in Example 5. In some embodiments, the serotonin receptor modulator is flibanserin and the psychedelic is MBDB, wherein the flibanserin is administered to pretreat at least 210 minutes prior to the MBDB forms disclosed herein, including those described in Example 5.

In some embodiments, the serotonin receptor modulator is flibanserin and the psychedelic is MBDB, wherein the flibanserin is administered to pretreat at least 240 minutes prior to the MBDB forms disclosed herein, including those described in Example 5. In some embodiments, the serotonin receptor modulator is flibanserin and the psychedelic is MBDB, wherein the flibanserin is administered to pretreat at least 270 minutes prior to the MBDB forms disclosed herein, including those described in Example 5. In some embodiments, the serotonin receptor modulator is flibanserin and the psychedelic is MBDB, wherein the flibanserin is administered to pretreat at least 300 minutes prior to the MBDB forms disclosed herein, including those described in Example 5. In some embodiments, the serotonin receptor modulator is flibanserin and the psychedelic is MBDB, wherein the flibanserin is administered to pretreat at least 330 minutes prior to the MBDB forms disclosed herein, including those described in Example 5. In some embodiments, the serotonin receptor modulator is flibanserin and the psychedelic is MBDB, wherein the flibanserin is administered to pretreat at least 360 minutes prior to the MBDB forms disclosed herein, including those described in Example 5. In some preferred embodiments, the serotonin receptor modulator is flibanserin and the psychedelic is MBDB, wherein flibanserin is administered to pretreat between about 60 minutes and about 180 minutes prior to the administration of the MBDB forms disclosed herein, including those described in Example 5.

In some embodiments, the serotonin receptor modulator is olanzapine and the psychedelic is MBDB, wherein the olanzapine is administered to pretreat at least 15 minutes prior to the administration of the MBDB forms disclosed herein, including those described in Example 5. In some embodiments, the serotonin receptor modulator is olanzapine and the psychedelic is MBDB, wherein the olanzapine is administered to pretreat at least 30 minutes prior to the MBDB forms disclosed herein, including those described in Example 5. In some embodiments, the serotonin receptor modulator is olanzapine and the psychedelic is MBDB, wherein the olanzapine is administered to pretreat between at least 60 minutes and 240 minutes prior to the administration or release of the MBDB forms disclosed herein, including those described in Example 5. In some embodiments, the serotonin receptor modulator is olanzapine and the psychedelic is MBDB, wherein the olanzapine is administered to pretreat at least 90 minutes prior to the MBDB forms disclosed herein, including those described in Example 5. In some embodiments, the serotonin receptor modulator is olanzapine and the psychedelic is MBDB, wherein the olanzapine is administered to pretreat at least 120 minutes prior to the MBDB forms disclosed herein, including those described in Example 5. In some embodiments, the serotonin receptor modulator is olanzapine and the psychedelic is MBDB, wherein the olanzapine is administered to pretreat at least 150 minutes prior to the MBDB forms disclosed herein, including those described in Example 5. In some embodiments, the serotonin receptor modulator is olanzapine and the psychedelic is MBDB, wherein the olanzapine is administered to pretreat between about 15 minutes and about 150 minutes prior to the MBDB forms disclosed herein, including those described in Example 5. In some embodiments, the serotonin receptor modulator is olanzapine and the psychedelic is MBDB, wherein the olanzapine is administered to pretreat at least 180 minutes prior to the MBDB forms disclosed herein, including those described in Example 5. In some embodiments, the serotonin receptor modulator is olanzapine and the psychedelic is MBDB, wherein the olanzapine is administered to pretreat at least 210 minutes prior to the MBDB forms disclosed herein, including those described in Example 5.

In some embodiments, the serotonin receptor modulator is olanzapine and the psychedelic is MBDB, wherein the olanzapine is administered to pretreat at least 240 minutes prior to the MBDB forms disclosed herein, including those described in Example 5. In some embodiments, the serotonin receptor modulator is olanzapine and the psychedelic is MBDB, wherein the olanzapine is administered to pretreat at least 270 minutes prior to the MBDB forms disclosed herein, including those described in Example 5. In some embodiments, the serotonin receptor modulator is olanzapine and the psychedelic is MBDB, wherein the olanzapine is administered to pretreat at least 300 minutes prior to the MBDB forms disclosed herein, including those described in Example 5. In some embodiments, the serotonin receptor modulator is olanzapine and the psychedelic is MBDB, wherein the olanzapine is administered to pretreat at least 330 minutes prior to the MBDB forms disclosed herein, including those described in Example 5. In some embodiments, the serotonin receptor modulator is olanzapine and the psychedelic is MBDB, wherein the olanzapine is administered to pretreat at least 360 minutes prior to the MBDB forms disclosed herein, including those described in Example 5. In some preferred embodiments, the serotonin receptor modulator is olanzapine and the psychedelic is MBDB, wherein olanzapine is administered to pretreat between about 60 minutes and about 180 minutes prior to the administration of the MBDB forms disclosed herein, including those described in Example 5.

In some embodiments, the serotonin receptor modulator is quetiapine and the psychedelic is MBDB, wherein the quetiapine is administered to pretreat at least 15 minutes prior to the administration of the MBDB forms disclosed herein, including those described in Example 5. In some embodiments, the serotonin receptor modulator is quetiapine and the psychedelic is MBDB, wherein the quetiapine is administered to pretreat at least 30 minutes prior to the MBDB forms disclosed herein, including those described in Example 5. In some embodiments, the serotonin receptor modulator is quetiapine and the psychedelic is MBDB, wherein the quetiapine is administered to pretreat between at least 60 minutes and 240 minutes prior to the administration or release of the MBDB forms disclosed herein, including those described in Example 5. In some embodiments, the serotonin receptor modulator is quetiapine and the psychedelic is MBDB, wherein the quetiapine is administered to pretreat at least 90 minutes prior to the MBDB forms disclosed herein, including those described in Example 5. In some embodiments, the serotonin receptor modulator is quetiapine and the psychedelic is MBDB, wherein the quetiapine is administered to pretreat at least 120 minutes prior to the MBDB forms disclosed herein, including those described in Example 5. In some embodiments, the serotonin receptor modulator is quetiapine and the psychedelic is MBDB, wherein the quetiapine is administered to pretreat at least 150 minutes prior to the MBDB forms disclosed herein, including those described in Example 5. In some embodiments, the serotonin receptor modulator is quetiapine and the psychedelic is MBDB, wherein the quetiapine is administered to pretreat between about 15 minutes and about 150 minutes prior to the MBDB forms disclosed herein, including those described in Example 5. In some embodiments, the serotonin receptor modulator is quetiapine and the psychedelic is MBDB, wherein the quetiapine is administered to pretreat at least 180 minutes prior to the MBDB forms disclosed herein, including those described in Example 5. In some embodiments, the serotonin receptor modulator is quetiapine and the psychedelic is MBDB, wherein the quetiapine is administered to pretreat at least 210 minutes prior to the MBDB forms disclosed herein, including those described in Example 5.

In some embodiments, the serotonin receptor modulator is quetiapine and the psychedelic is MBDB, wherein the quetiapine is administered to pretreat at least 240 minutes prior to the MBDB forms disclosed herein, including those described in Example 5. In some embodiments, the serotonin receptor modulator is quetiapine and the psychedelic is MBDB, wherein the quetiapine is administered to pretreat at least 270 minutes prior to the MBDB forms disclosed herein, including those described in Example 5. In some embodiments, the serotonin receptor modulator is quetiapine and the psychedelic is MBDB, wherein the quetiapine is administered to pretreat at least 300 minutes prior to the MBDB forms disclosed herein, including those described in Example 5. In some embodiments, the serotonin receptor modulator is quetiapine and the psychedelic is MBDB, wherein the quetiapine is administered to pretreat at least 330 minutes prior to the MBDB forms disclosed herein, including those described in Example 5. In some embodiments, the serotonin receptor modulator is quetiapine and the psychedelic is MBDB, wherein the quetiapine is administered to pretreat at least 360 minutes prior to the MBDB forms disclosed herein, including those described in Example 5. In some preferred embodiments, the serotonin receptor modulator is quetiapine and the psychedelic is MBDB, wherein quetiapine is administered to pretreat between about 60 minutes and about 180 minutes prior to the administration of the MBDB forms disclosed herein, including those described in Example 5.

In some embodiments, the serotonin receptor modulator is risperidone and the psychedelic is MBDB, wherein the risperidone is administered to pretreat at least 15 minutes prior to the administration of the MBDB forms disclosed herein, including those described in Example 5. In some embodiments, the serotonin receptor modulator is risperidone and the psychedelic is MBDB, wherein the risperidone is administered to pretreat at least 30 minutes prior to the MBDB forms disclosed herein, including those described in Example 5. In some embodiments, the serotonin receptor modulator is risperidone and the psychedelic is MBDB, wherein the risperidone is administered to pretreat between at least 60 minutes and 240 minutes prior to the administration or release of the MBDB forms disclosed herein, including those described in Example 5. In some embodiments, the serotonin receptor modulator is risperidone and the psychedelic is MBDB, wherein the risperidone is administered to pretreat at least 90 minutes prior to the MBDB forms disclosed herein, including those described in Example 5. In some embodiments, the serotonin receptor modulator is risperidone and the psychedelic is MBDB, wherein the risperidone is administered to pretreat at least 120 minutes prior to the MBDB forms disclosed herein, including those described in Example 5. In some embodiments, the serotonin receptor modulator is risperidone and the psychedelic is MBDB, wherein the risperidone is administered to pretreat at least 150 minutes prior to the MBDB forms disclosed herein, including those described in Example 5. In some embodiments, the serotonin receptor modulator is risperidone and the psychedelic is MBDB, wherein the risperidone is administered to pretreat between about 15 minutes and about 150 minutes prior to the MBDB forms disclosed herein, including those described in Example 5. In some embodiments, the serotonin receptor modulator is risperidone and the psychedelic is MBDB, wherein the risperidone is administered to pretreat at least 180 minutes prior to the MBDB forms disclosed herein, including those described in Example 5. In some embodiments, the serotonin receptor modulator is risperidone and the psychedelic is MBDB, wherein the risperidone is administered to pretreat at least 210 minutes prior to the MBDB forms disclosed herein, including those described in Example 5.

In some embodiments, the serotonin receptor modulator is risperidone and the psychedelic is MBDB, wherein the risperidone is administered to pretreat at least 240 minutes prior to the MBDB forms disclosed herein, including those described in Example 5. In some embodiments, the serotonin receptor modulator is risperidone and the psychedelic is MBDB, wherein the risperidone is administered to pretreat at least 270 minutes prior to the MBDB forms disclosed herein, including those described in Example 5. In some embodiments, the serotonin receptor modulator is risperidone and the psychedelic is MBDB, wherein the risperidone is administered to pretreat at least 300 minutes prior to the MBDB forms disclosed herein, including those described in Example 5. In some embodiments, the serotonin receptor modulator is risperidone and the psychedelic is MBDB, wherein the risperidone is administered to pretreat at least 330 minutes prior to the MBDB forms disclosed herein, including those described in Example 5. In some embodiments, the serotonin receptor modulator is risperidone and the psychedelic is MBDB, wherein the risperidone is administered to pretreat at least 360 minutes prior to the MBDB forms disclosed herein, including those described in Example 5. In some preferred embodiments, the serotonin receptor modulator is risperidone and the psychedelic is MBDB, wherein risperidone is administered to pretreat between about 60 minutes and about 180 minutes prior to the administration of the MBDB forms disclosed herein, including those described in Example 5.

In some embodiments, the serotonin receptor modulator is flibanserin and the psychedelic is MBDB, wherein the flibanserin is administered to pretreat at least 15 minutes prior to the administration of the MBDB HCl form disclosed herein, including those described in Table Ex13. In some embodiments, the serotonin receptor modulator is flibanserin and the psychedelic is MBDB, wherein the flibanserin is administered to pretreat at least 30 minutes prior to the MBDB HCl form disclosed herein, including those described in Table Ex13. In some embodiments, the serotonin receptor modulator is flibanserin and the psychedelic is MBDB, wherein the flibanserin is administered to pretreat between at least 60 minutes and 240 minutes prior to the administration or release of the MBDB HCl form disclosed herein, including those described in Table Ex13. In some embodiments, the serotonin receptor modulator is flibanserin and the psychedelic is MBDB, wherein the flibanserin is administered to pretreat at least 90 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 120 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 150 minutes prior to the MBDB HCl form disclosed herein, including those described in Table Ex13. In some embodiments, the serotonin receptor modulator is flibanserin and the psychedelic is MBDB, wherein the flibanserin is administered to pretreat between about 15 minutes and about 150 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 180 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 210 minutes prior to the MBDB HCl form disclosed herein, including those described in Table Ex13.

In some embodiments, the serotonin receptor modulator is flibanserin and the psychedelic is MBDB, wherein the flibanserin is administered to pretreat at least 240 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 270 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 300 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 330 minutes prior to the MBDB HCl form disclosed herein, including those described in Table Ex13. In some embodiments, the serotonin receptor modulator is flibanserin and the psychedelic is MBDB, wherein the flibanserin is administered to pretreat at least 360 minutes prior to the MBDB HCl form disclosed herein, including those described in Table Ex13. In some preferred embodiments, the serotonin receptor modulator is flibanserin and the psychedelic is MBDB, wherein flibanserin is administered to pretreat between about 60 minutes and about 180 minutes prior to the administration of the MBDB HCl form disclosed herein, including those described in Table Ex13.

In some embodiments, the serotonin receptor modulator is olanzapine and the psychedelic is MBDB, wherein the olanzapine is administered to pretreat at least 15 minutes prior to the administration of the MBDB HCl form disclosed herein, including those described in Table Ex13. In some embodiments, the serotonin receptor modulator is olanzapine and the psychedelic is MBDB, wherein the olanzapine is administered to pretreat at least 30 minutes prior to the MBDB HCl form disclosed herein, including those described in Table Ex13. In some embodiments, the serotonin receptor modulator is olanzapine and the psychedelic is MBDB, wherein the olanzapine is administered to pretreat between at least 60 minutes and 240 minutes prior to the administration or release of the MBDB HCl form disclosed herein, including those described in Table Ex13. In some embodiments, the serotonin receptor modulator is olanzapine and the psychedelic is MBDB, wherein the olanzapine is administered to pretreat at least 90 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 120 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 150 minutes prior to the MBDB HCl form disclosed herein, including those described in Table Ex13. In some embodiments, the serotonin receptor modulator is olanzapine and the psychedelic is MBDB, wherein the olanzapine is administered to pretreat between about 15 minutes and about 150 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 180 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 210 minutes prior to the MBDB HCl form disclosed herein, including those described in Table Ex13.

In some embodiments, the serotonin receptor modulator is olanzapine and the psychedelic is MBDB, wherein the olanzapine is administered to pretreat at least 240 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 270 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 300 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 330 minutes prior to the MBDB HCl form disclosed herein, including those described in Table Ex13. In some embodiments, the serotonin receptor modulator is olanzapine and the psychedelic is MBDB, wherein the olanzapine is administered to pretreat at least 360 minutes prior to the MBDB HCl form disclosed herein, including those described in Table Ex13. In some preferred embodiments, the serotonin receptor modulator is olanzapine and the psychedelic is MBDB, wherein olanzapine is administered to pretreat between about 60 minutes and about 180 minutes prior to the administration of the MBDB HCl form disclosed herein, including those described in Table Ex13.

In some embodiments, the serotonin receptor modulator is quetiapine and the psychedelic is MBDB, wherein the quetiapine is administered to pretreat at least 15 minutes prior to the administration of the MBDB HCl form disclosed herein, including those described in Table Ex13. In some embodiments, the serotonin receptor modulator is quetiapine and the psychedelic is MBDB, wherein the quetiapine is administered to pretreat at least 30 minutes prior to the MBDB HCl form disclosed herein, including those described in Table Ex13. In some embodiments, the serotonin receptor modulator is quetiapine and the psychedelic is MBDB, wherein the quetiapine is administered to pretreat between at least 60 minutes and 240 minutes prior to the administration or release of the MBDB HCl form disclosed herein, including those described in Table Ex13. In some embodiments, the serotonin receptor modulator is quetiapine and the psychedelic is MBDB, wherein the quetiapine is administered to pretreat at least 90 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 120 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 150 minutes prior to the MBDB HCl form disclosed herein, including those described in Table Ex13. In some embodiments, the serotonin receptor modulator is quetiapine and the psychedelic is MBDB, wherein the quetiapine is administered to pretreat between about 15 minutes and about 150 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 180 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 210 minutes prior to the MBDB HCl form disclosed herein, including those described in Table Ex13.

In some embodiments, the serotonin receptor modulator is quetiapine and the psychedelic is MBDB, wherein the quetiapine is administered to pretreat at least 240 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 270 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 300 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 330 minutes prior to the MBDB HCl form disclosed herein, including those described in Table Ex13. In some embodiments, the serotonin receptor modulator is quetiapine and the psychedelic is MBDB, wherein the quetiapine is administered to pretreat at least 360 minutes prior to the MBDB HCl form disclosed herein, including those described in Table Ex13. In some preferred embodiments, the serotonin receptor modulator is quetiapine and the psychedelic is MBDB, wherein quetiapine is administered to pretreat between about 60 minutes and about 180 minutes prior to the administration of the MBDB HCl form disclosed herein, including those described in Table Ex13.

In some embodiments, the serotonin receptor modulator is risperidone and the psychedelic is MBDB, wherein the risperidone is administered to pretreat at least 15 minutes prior to the administration of the MBDB HCl form disclosed herein, including those described in Table Ex13. In some embodiments, the serotonin receptor modulator is risperidone and the psychedelic is MBDB, wherein the risperidone is administered to pretreat at least 30 minutes prior to the MBDB HCl form disclosed herein, including those described in Table Ex13. In some embodiments, the serotonin receptor modulator is risperidone and the psychedelic is MBDB, wherein the risperidone is administered to pretreat between at least 60 minutes and 240 minutes prior to the administration or release of the MBDB HCl form disclosed herein, including those described in Table Ex13. In some embodiments, the serotonin receptor modulator is risperidone and the psychedelic is MBDB, wherein the risperidone is administered to pretreat at least 90 minutes prior to the MBDB HCl form disclosed herein, including those described in Table Ex13. In some embodiments, the serotonin receptor modulator is risperidone and the psychedelic is MBDB, wherein the risperidone is administered to pretreat at least 120 minutes prior to the MBDB HCl form disclosed herein, including those described in Table Ex13. In some embodiments, the serotonin receptor modulator is risperidone and the psychedelic is MBDB, wherein the risperidone is administered to pretreat at least 150 minutes prior to the MBDB HCl form disclosed herein, including those described in Table Ex13. In some embodiments, the serotonin receptor modulator is risperidone and the psychedelic is MBDB, wherein the risperidone is administered to pretreat between about 15 minutes and about 150 minutes prior to the MBDB HCl form disclosed herein, including those described in Table Ex13. In some embodiments, the serotonin receptor modulator is risperidone and the psychedelic is MBDB, wherein the risperidone is administered to pretreat at least 180 minutes prior to the MBDB HCl form disclosed herein, including those described in Table Ex13. In some embodiments, the serotonin receptor modulator is risperidone and the psychedelic is MBDB, wherein the risperidone is administered to pretreat at least 210 minutes prior to the MBDB HCl form disclosed herein, including those described in Table Ex13.

In some embodiments, the serotonin receptor modulator is risperidone and the psychedelic is MBDB, wherein the risperidone is administered to pretreat at least 240 minutes prior to the MBDB HCl form disclosed herein, including those described in Table Ex13. In some embodiments, the serotonin receptor modulator is risperidone and the psychedelic is MBDB, wherein the risperidone is administered to pretreat at least 270 minutes prior to the MBDB HCl form disclosed herein, including those described in Table Ex13. In some embodiments, the serotonin receptor modulator is risperidone and the psychedelic is MBDB, wherein the risperidone is administered to pretreat at least 300 minutes prior to the MBDB HCl form disclosed herein, including those described in Table Ex13. In some embodiments, the serotonin receptor modulator is risperidone and the psychedelic is MBDB, wherein the risperidone is administered to pretreat at least 330 minutes prior to the MBDB HCl form disclosed herein, including those described in Table Ex13. In some embodiments, the serotonin receptor modulator is risperidone and the psychedelic is MBDB, wherein the risperidone is administered to pretreat at least 360 minutes prior to the MBDB HCl form disclosed herein, including those described in Table Ex13. In some preferred embodiments, the serotonin receptor modulator is risperidone and the psychedelic is MBDB, wherein risperidone is administered to pretreat between about 60 minutes and about 180 minutes prior to the administration of the MBDB HCl form disclosed herein, including those described in Table Ex13.

In some embodiments, the serotonin receptor modulator is flibanserin and the psychedelic is 5,6-dimethoxy-2-aminoindane, wherein the flibanserin is administered to pretreat at least 15 minutes prior to the administration of the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 30 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat between at least 60 minutes and 240 minutes prior to the administration or release of the 5,6-dimethoxy- 2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 90 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 120 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 150 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 180 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 210 minutes prior to the 5,6-dimethoxy-2-aminoindane hydrochloride form disclosed herein, including those described in Table Ex15.

In some embodiments, the serotonin receptor modulator is flibanserin and the psychedelic is 5,6-dimethoxy-2-aminoindane, wherein the flibanserin is administered to pretreat at least 240 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 270 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 300 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 330 minutes prior to the 5,6-dimethoxy-2-aminoindane hydrochloride form disclosed herein, including those described in Table Ex15. In some embodiments, the serotonin receptor modulator is flibanserin and the psychedelic is 5,6-dimethoxy-2-aminoindane, wherein the flibanserin is administered to pretreat at least 360 minutes prior to the 5,6-dimethoxy-2-aminoindane hydrochloride form disclosed herein, including those described in Table Ex15. In some preferred embodiments, the serotonin receptor modulator is flibanserin and the psychedelic is 5,6-dimethoxy-2-aminoindane, wherein flibanserin is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is olanzapine and the psychedelic is 5,6-dimethoxy-2-aminoindane, wherein the olanzapine is administered to pretreat at least 15 minutes prior to the administration of the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 30 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 90 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 120 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 150 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 180 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 210 minutes prior to the 5,6-dimethoxy-2-aminoindane hydrochloride form disclosed herein, including those described in Table Ex15.

In some embodiments, the serotonin receptor modulator is olanzapine and the psychedelic is 5,6-dimethoxy-2-aminoindane, wherein the olanzapine is administered to pretreat at least 240 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 270 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 300 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 330 minutes prior to the 5,6-dimethoxy-2-aminoindane hydrochloride form disclosed herein, including those described in Table Ex15. In some embodiments, the serotonin receptor modulator is olanzapine and the psychedelic is 5,6-dimethoxy-2-aminoindane, wherein the olanzapine is administered to pretreat at least 360 minutes prior to the 5,6-dimethoxy-2-aminoindane hydrochloride form disclosed herein, including those described in Table Ex15. In some preferred embodiments, the serotonin receptor modulator is olanzapine and the psychedelic is 5,6-dimethoxy-2-aminoindane, wherein olanzapine is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is quetiapine and the psychedelic is 5,6-dimethoxy-2-aminoindane, wherein the quetiapine is administered to pretreat at least 15 minutes prior to the administration of the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 30 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 90 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 120 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 150 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 180 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 210 minutes prior to the 5,6-dimethoxy-2-aminoindane hydrochloride form disclosed herein, including those described in Table Ex15.

In some embodiments, the serotonin receptor modulator is quetiapine and the psychedelic is 5,6-dimethoxy-2-aminoindane, wherein the quetiapine is administered to pretreat at least 240 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 270 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 300 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 330 minutes prior to the 5,6-dimethoxy-2-aminoindane hydrochloride form disclosed herein, including those described in Table Ex15. In some embodiments, the serotonin receptor modulator is quetiapine and the psychedelic is 5,6-dimethoxy-2-aminoindane, wherein the quetiapine is administered to pretreat at least 360 minutes prior to the 5,6-dimethoxy-2-aminoindane hydrochloride form disclosed herein, including those described in Table Ex15. In some preferred embodiments, the serotonin receptor modulator is quetiapine and the psychedelic is 5,6-dimethoxy-2-aminoindane, wherein quetiapine is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is risperidone and the psychedelic is 5,6-dimethoxy-2-aminoindane, wherein the risperidone is administered to pretreat at least 15 minutes prior to the administration of the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 30 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 90 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 120 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 150 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 180 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 210 minutes prior to the 5,6-dimethoxy-2-aminoindane hydrochloride form disclosed herein, including those described in Table Ex15.

In some embodiments, the serotonin receptor modulator is risperidone and the psychedelic is 5,6-dimethoxy-2-aminoindane, wherein the risperidone is administered to pretreat at least 240 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 270 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 300 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 330 minutes prior to the 5,6-dimethoxy-2-aminoindane hydrochloride form disclosed herein, including those described in Table Ex15. In some embodiments, the serotonin receptor modulator is risperidone and the psychedelic is 5,6-dimethoxy-2-aminoindane, wherein the risperidone is administered to pretreat at least 360 minutes prior to the 5,6-dimethoxy-2-aminoindane hydrochloride form disclosed herein, including those described in Table Ex15. In some preferred embodiments, the serotonin receptor modulator is risperidone and the psychedelic is 5,6-dimethoxy-2-aminoindane, wherein risperidone is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is flibanserin and the psychedelic is 5-methoxy-2-aminoindane, wherein the flibanserin is administered to pretreat at least 15 minutes prior to the administration of the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 30 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 90 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 120 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 150 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat between about 15 minutes and about 150 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 180 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 210 minutes prior to the 5-methoxy-2-aminoindane hydrochloride form disclosed herein, including those described in Table Ex14.

In some embodiments, the serotonin receptor modulator is flibanserin and the psychedelic is 5-methoxy-2-aminoindane, wherein the flibanserin is administered to pretreat at least 240 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 270 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 300 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 330 minutes prior to the 5-methoxy-2-aminoindane hydrochloride form disclosed herein, including those described in Table Ex14. In some embodiments, the serotonin receptor modulator is flibanserin and the psychedelic is 5-methoxy-2-aminoindane, wherein the flibanserin is administered to pretreat at least 360 minutes prior to the 5-methoxy-2-aminoindane hydrochloride form disclosed herein, including those described in Table Ex14. In some preferred embodiments, the serotonin receptor modulator is flibanserin and the psychedelic is 5-methoxy-2-aminoindane, wherein flibanserin is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is olanzapine and the psychedelic is 5-methoxy-2-aminoindane, wherein the olanzapine is administered to pretreat at least 15 minutes prior to the administration of the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 30 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 90 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 120 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 150 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat between about 15 minutes and about 150 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 180 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 210 minutes prior to the 5-methoxy-2-aminoindane hydrochloride form disclosed herein, including those described in Table Ex14.

In some embodiments, the serotonin receptor modulator is olanzapine and the psychedelic is 5-methoxy-2-aminoindane, wherein the olanzapine is administered to pretreat at least 240 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 270 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 300 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 330 minutes prior to the 5-methoxy-2-aminoindane hydrochloride form disclosed herein, including those described in Table Ex14. In some embodiments, the serotonin receptor modulator is olanzapine and the psychedelic is 5-methoxy-2-aminoindane, wherein the olanzapine is administered to pretreat at least 360 minutes prior to the 5-methoxy-2-aminoindane hydrochloride form disclosed herein, including those described in Table Ex14. In some preferred embodiments, the serotonin receptor modulator is olanzapine and the psychedelic is 5-methoxy-2-aminoindane, wherein olanzapine is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is quetiapine and the psychedelic is 5-methoxy-2-aminoindane, wherein the quetiapine is administered to pretreat at least 15 minutes prior to the administration of the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 30 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 90 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 120 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 150 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat between about 15 minutes and about 150 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 180 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 210 minutes prior to the 5-methoxy-2-aminoindane hydrochloride form disclosed herein, including those described in Table Ex14.

In some embodiments, the serotonin receptor modulator is quetiapine and the psychedelic is 5-methoxy-2-aminoindane, wherein the quetiapine is administered to pretreat at least 240 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 270 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 300 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 330 minutes prior to the 5-methoxy-2-aminoindane hydrochloride form disclosed herein, including those described in Table Ex14. In some embodiments, the serotonin receptor modulator is quetiapine and the psychedelic is 5-methoxy-2-aminoindane, wherein the quetiapine is administered to pretreat at least 360 minutes prior to the 5-methoxy-2-aminoindane hydrochloride form disclosed herein, including those described in Table Ex14. In some preferred embodiments, the serotonin receptor modulator is quetiapine and the psychedelic is 5-methoxy-2-aminoindane, wherein quetiapine is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is risperidone and the psychedelic is 5-methoxy-2-aminoindane, wherein the risperidone is administered to pretreat at least 15 minutes prior to the administration of the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 30 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 90 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 120 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 150 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat between about 15 minutes and about 150 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 180 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 210 minutes prior to the 5-methoxy-2-aminoindane hydrochloride form disclosed herein, including those described in Table Ex14.

In some embodiments, the serotonin receptor modulator is risperidone and the psychedelic is 5-methoxy-2-aminoindane, wherein the risperidone is administered to pretreat at least 240 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 270 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 300 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 330 minutes prior to the 5-methoxy-2-aminoindane hydrochloride form disclosed herein, including those described in Table Ex14. In some embodiments, the serotonin receptor modulator is risperidone and the psychedelic is 5-methoxy-2-aminoindane, wherein the risperidone is administered to pretreat at least 360 minutes prior to the 5-methoxy-2-aminoindane hydrochloride form disclosed herein, including those described in Table Ex14. In some preferred embodiments, the serotonin receptor modulator is risperidone and the psychedelic is 5-methoxy-2-aminoindane, wherein risperidone is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is flibanserin and the psychedelic is MDMA, wherein the flibanserin is administered to pretreat at least 15 minutes prior to the administration of the MDMA form disclosed herein, including those described in Table Ex3. In some embodiments, the serotonin receptor modulator is flibanserin and the psychedelic is MDMA, wherein the flibanserin is administered to pretreat at least 30 minutes prior to the MDMA form disclosed herein, including those described in Table Ex3. In some embodiments, the serotonin receptor modulator is flibanserin and the psychedelic is MDMA, wherein the flibanserin is administered to pretreat between at least 60 minutes and 240 minutes prior to the administration or release of the MDMA form disclosed herein, including those described in Table Ex3. In some embodiments, the serotonin receptor modulator is flibanserin and the psychedelic is MDMA, wherein the flibanserin is administered to pretreat at least 90 minutes prior to the MDMA form disclosed herein, including those described in Table Ex3. In some embodiments, the serotonin receptor modulator is flibanserin and the psychedelic is MDMA, wherein the flibanserin is administered to pretreat at least 120 minutes prior to the MDMA form disclosed herein, including those described in Table Ex3. In some embodiments, the serotonin receptor modulator is flibanserin and the psychedelic is MDMA, wherein the flibanserin is administered to pretreat at least 150 minutes prior to the MDMA form disclosed herein, including those described in Table Ex3. In some embodiments, the serotonin receptor modulator is flibanserin and the psychedelic is MDMA, wherein the flibanserin is administered to pretreat between about 15 minutes and about 150 minutes prior to the MDMA form disclosed herein, including those described in Table Ex3. In some embodiments, the serotonin receptor modulator is flibanserin and the psychedelic is MDMA, wherein the flibanserin is administered to pretreat at least 180 minutes prior to the MDMA form disclosed herein, including those described in Table Ex3. In some embodiments, the serotonin receptor modulator is flibanserin and the psychedelic is MDMA, wherein the flibanserin is administered to pretreat at least 210 minutes prior to the MDMA form disclosed herein, including those described in Table Ex3.

In some embodiments, the serotonin receptor modulator is flibanserin and the psychedelic is MDMA, wherein the flibanserin is administered to pretreat at least 240 minutes prior to the MDMA form disclosed herein, including those described in Table Ex3. In some embodiments, the serotonin receptor modulator is flibanserin and the psychedelic is MDMA, wherein the flibanserin is administered to pretreat at least 270 minutes prior to the MDMA form disclosed herein, including those described in Table Ex3. In some embodiments, the serotonin receptor modulator is flibanserin and the psychedelic is MDMA, wherein the flibanserin is administered to pretreat at least 300 minutes prior to the MDMA form disclosed herein, including those described in Table Ex3. In some embodiments, the serotonin receptor modulator is flibanserin and the psychedelic is MDMA, wherein the flibanserin is administered to pretreat at least 330 minutes prior to the MDMA form disclosed herein, including those described in Table Ex3. In some embodiments, the serotonin receptor modulator is flibanserin and the psychedelic is MDMA, wherein the flibanserin is administered to pretreat at least 360 minutes prior to the MDMA form disclosed herein, including those described in Table Ex3. In some preferred embodiments, the serotonin receptor modulator is flibanserin and the psychedelic is MDMA, wherein flibanserin is administered to pretreat between about 60 minutes and about 180 minutes prior to the administration of the MDMA form disclosed herein, including those described in Table Ex3.

In some embodiments, the serotonin receptor modulator is olanzapine and the psychedelic is MDMA, wherein the olanzapine is administered to pretreat at least 15 minutes prior to the administration of the MDMA form disclosed herein, including those described in Table Ex3. In some embodiments, the serotonin receptor modulator is olanzapine and the psychedelic is MDMA, wherein the olanzapine is administered to pretreat at least 30 minutes prior to the MDMA form disclosed herein, including those described in Table Ex3. In some embodiments, the serotonin receptor modulator is olanzapine and the psychedelic is MDMA, wherein the olanzapine is administered to pretreat between at least 60 minutes and 240 minutes prior to the administration or release of the MDMA form disclosed herein, including those described in Table Ex3. In some embodiments, the serotonin receptor modulator is olanzapine and the psychedelic is MDMA, wherein the olanzapine is administered to pretreat at least 90 minutes prior to the MDMA form disclosed herein, including those described in Table Ex3. In some embodiments, the serotonin receptor modulator is olanzapine and the psychedelic is MDMA, wherein the olanzapine is administered to pretreat at least 120 minutes prior to the MDMA form disclosed herein, including those described in Table Ex3. In some embodiments, the serotonin receptor modulator is olanzapine and the psychedelic is MDMA, wherein the olanzapine is administered to pretreat at least 150 minutes prior to the MDMA form disclosed herein, including those described in Table Ex3. In some embodiments, the serotonin receptor modulator is olanzapine and the psychedelic is MDMA, wherein the olanzapine is administered to pretreat between about 15 minutes and about 150 minutes prior to the MDMA form disclosed herein, including those described in Table Ex3. In some embodiments, the serotonin receptor modulator is olanzapine and the psychedelic is MDMA, wherein the olanzapine is administered to pretreat at least 180 minutes prior to the MDMA form disclosed herein, including those described in Table Ex3. In some embodiments, the serotonin receptor modulator is olanzapine and the psychedelic is MDMA, wherein the olanzapine is administered to pretreat at least 210 minutes prior to the MDMA form disclosed herein, including those described in Table Ex3.

In some embodiments, the serotonin receptor modulator is olanzapine and the psychedelic is MDMA, wherein the olanzapine is administered to pretreat at least 240 minutes prior to the MDMA form disclosed herein, including those described in Table Ex3. In some embodiments, the serotonin receptor modulator is olanzapine and the psychedelic is MDMA, wherein the olanzapine is administered to pretreat at least 270 minutes prior to the MDMA form disclosed herein, including those described in Table Ex3. In some embodiments, the serotonin receptor modulator is olanzapine and the psychedelic is MDMA, wherein the olanzapine is administered to pretreat at least 300 minutes prior to the MDMA form disclosed herein, including those described in Table Ex3. In some embodiments, the serotonin receptor modulator is olanzapine and the psychedelic is MDMA, wherein the olanzapine is administered to pretreat at least 330 minutes prior to the MDMA form disclosed herein, including those described in Table Ex3. In some embodiments, the serotonin receptor modulator is olanzapine and the psychedelic is MDMA, wherein the olanzapine is administered to pretreat at least 360 minutes prior to the MDMA form disclosed herein, including those described in Table Ex3. In some preferred embodiments, the serotonin receptor modulator is olanzapine and the psychedelic is MDMA, wherein olanzapine is administered to pretreat between about 60 minutes and about 180 minutes prior to the administration of the MDMA form disclosed herein, including those described in Table Ex3.

In some embodiments, the serotonin receptor modulator is quetiapine and the psychedelic is MDMA, wherein the quetiapine is administered to pretreat at least 15 minutes prior to the administration of the MDMA form disclosed herein, including those described in Table Ex3. In some embodiments, the serotonin receptor modulator is quetiapine and the psychedelic is MDMA, wherein the quetiapine is administered to pretreat at least 30 minutes prior to the MDMA form disclosed herein, including those described in Table Ex3. In some embodiments, the serotonin receptor modulator is quetiapine and the psychedelic is MDMA, wherein the quetiapine is administered to pretreat between at least 60 minutes and 240 minutes prior to the administration or release of the MDMA form disclosed herein, including those described in Table Ex3. In some embodiments, the serotonin receptor modulator is quetiapine and the psychedelic is MDMA, wherein the quetiapine is administered to pretreat at least 90 minutes prior to the MDMA form disclosed herein, including those described in Table Ex3. In some embodiments, the serotonin receptor modulator is quetiapine and the psychedelic is MDMA, wherein the quetiapine is administered to pretreat at least 120 minutes prior to the MDMA form disclosed herein, including those described in Table Ex3. In some embodiments, the serotonin receptor modulator is quetiapine and the psychedelic is MDMA, wherein the quetiapine is administered to pretreat at least 150 minutes prior to the MDMA form disclosed herein, including those described in Table Ex3. In some embodiments, the serotonin receptor modulator is quetiapine and the psychedelic is MDMA, wherein the quetiapine is administered to pretreat between about 15 minutes and about 150 minutes prior to the MDMA form disclosed herein, including those described in Table Ex3. In some embodiments, the serotonin receptor modulator is quetiapine and the psychedelic is MDMA, wherein the quetiapine is administered to pretreat at least 180 minutes prior to the MDMA form disclosed herein, including those described in Table Ex3. In some embodiments, the serotonin receptor modulator is quetiapine and the psychedelic is MDMA, wherein the quetiapine is administered to pretreat at least 210 minutes prior to the MDMA form disclosed herein, including those described in Table Ex3.

In some embodiments, the serotonin receptor modulator is quetiapine and the psychedelic is MDMA, wherein the quetiapine is administered to pretreat at least 240 minutes prior to the MDMA form disclosed herein, including those described in Table Ex3. In some embodiments, the serotonin receptor modulator is quetiapine and the psychedelic is MDMA, wherein the quetiapine is administered to pretreat at least 270 minutes prior to the MDMA form disclosed herein, including those described in Table Ex3. In some embodiments, the serotonin receptor modulator is quetiapine and the psychedelic is MDMA, wherein the quetiapine is administered to pretreat at least 300 minutes prior to the MDMA form disclosed herein, including those described in Table Ex3. In some embodiments, the serotonin receptor modulator is quetiapine and the psychedelic is MDMA, wherein the quetiapine is administered to pretreat at least 330 minutes prior to the MDMA form disclosed herein, including those described in Table Ex3. In some embodiments, the serotonin receptor modulator is quetiapine and the psychedelic is MDMA, wherein the quetiapine is administered to pretreat at least 360 minutes prior to the MDMA form disclosed herein, including those described in Table Ex3. In some preferred embodiments, the serotonin receptor modulator is quetiapine and the psychedelic is MDMA, wherein quetiapine is administered to pretreat between about 60 minutes and about 180 minutes prior to the administration of the MDMA form disclosed herein, including those described in Table Ex3.

In some embodiments, the serotonin receptor modulator is risperidone and the psychedelic is MDMA, wherein the risperidone is administered to pretreat at least 15 minutes prior to the administration of the MDMA form disclosed herein, including those described in Table Ex3. In some embodiments, the serotonin receptor modulator is risperidone and the psychedelic is MDMA, wherein the risperidone is administered to pretreat at least 30 minutes prior to the MDMA form disclosed herein, including those described in Table Ex3. In some embodiments, the serotonin receptor modulator is risperidone and the psychedelic is MDMA, wherein the risperidone is administered to pretreat between at least 60 minutes and 240 minutes prior to the administration or release of the MDMA form disclosed herein, including those described in Table Ex3. In some embodiments, the serotonin receptor modulator is risperidone and the psychedelic is MDMA, wherein the risperidone is administered to pretreat at least 90 minutes prior to the MDMA form disclosed herein, including those described in Table Ex3. In some embodiments, the serotonin receptor modulator is risperidone and the psychedelic is MDMA, wherein the risperidone is administered to pretreat at least 120 minutes prior to the MDMA form disclosed herein, including those described in Table Ex3. In some embodiments, the serotonin receptor modulator is risperidone and the psychedelic is MDMA, wherein the risperidone is administered to pretreat at least 150 minutes prior to the MDMA form disclosed herein, including those described in Table Ex3. In some embodiments, the serotonin receptor modulator is risperidone and the psychedelic is MDMA, wherein the risperidone is administered to pretreat between about 15 minutes and about 150 minutes prior to the MDMA form disclosed herein, including those described in Table Ex3. In some embodiments, the serotonin receptor modulator is risperidone and the psychedelic is MDMA, wherein the risperidone is administered to pretreat at least 180 minutes prior to the MDMA form disclosed herein, including those described in Table Ex3. In some embodiments, the serotonin receptor modulator is risperidone and the psychedelic is MDMA, wherein the risperidone is administered to pretreat at least 210 minutes prior to the MDMA form disclosed herein, including those described in Table Ex3.

In some embodiments, the serotonin receptor modulator is risperidone and the psychedelic is MDMA, wherein the risperidone is administered to pretreat at least 240 minutes prior to the MDMA form disclosed herein, including those described in Table Ex3. In some embodiments, the serotonin receptor modulator is risperidone and the psychedelic is MDMA, wherein the risperidone is administered to pretreat at least 270 minutes prior to the MDMA form disclosed herein, including those described in Table Ex3. In some embodiments, the serotonin receptor modulator is risperidone and the psychedelic is MDMA, wherein the risperidone is administered to pretreat at least 300 minutes prior to the MDMA form disclosed herein, including those described in Table Ex3. In some embodiments, the serotonin receptor modulator is risperidone and the psychedelic is MDMA, wherein the risperidone is administered to pretreat at least 330 minutes prior to the MDMA form disclosed herein, including those described in Table Ex3. In some embodiments, the serotonin receptor modulator is risperidone and the psychedelic is MDMA, wherein the risperidone is administered to pretreat at least 360 minutes prior to the MDMA form disclosed herein, including those described in Table Ex3. In some preferred embodiments, the serotonin receptor modulator is risperidone and the psychedelic is MDMA, wherein risperidone is administered to pretreat between about 60 minutes and about 180 minutes prior to the administration of the MDMA form disclosed herein, including those described in Table Ex3.

In some embodiments, the serotonin receptor modulator is eplivanserin and the psychedelic is MDMA hemifumarate Form A, wherein the eplivanserin is administered to pretreat at least 15 minutes prior to the administration of the MDMA hemifumarate Form A. In some embodiments, the serotonin receptor modulator is eplivanserin and the psychedelic is MDMA hemifumarate Form A, wherein the eplivanserin is administered to pretreat between at least 30 minutes prior and 360 minutes prior to the release or administration of the MDMA hemifumarate Form A. In some embodiments, the serotonin receptor modulator is eplivanserin and the psychedelic is MDMA hemifumarate Form A, wherein the eplivanserin is administered to pretreat between at least 60 minutes prior and 360 minutes prior to the release or administration of the MDMA hemifumarate Form A. In some embodiments, the serotonin receptor modulator is eplivanserin and the psychedelic is MDMA hemifumarate Form A, wherein the eplivanserin is administered to pretreat between at least 90 minutes and 240 minutes prior to the MDMA hemifumarate Form A. In some embodiments, the serotonin receptor modulator is eplivanserin and the psychedelic is MDMA hemifumarate Form A, wherein the eplivanserin is administered to pretreat at least 120 minutes prior to the MDMA hemifumarate Form A.

In some embodiments, the serotonin receptor modulator is eplivanserin and the psychedelic is MDMA hemifumarate Form A, wherein the eplivanserin is administered to pretreat at least 150 minutes prior to the MDMA hemifumarate Form A. In some embodiments, the serotonin receptor modulator is eplivanserin and the psychedelic is MDMA hemifumarate Form A, wherein the eplivanserin is administered to pretreat between about 15 minutes and about 150 minutes prior to the MDMA hemifumarate Form A. In some embodiments, the serotonin receptor modulator is eplivanserin and the psychedelic is MDMA hemifumarate Form A, wherein the eplivanserin is administered to pretreat at least 180 minutes prior to the MDMA hemifumarate Form A. In some embodiments, the serotonin receptor modulator is eplivanserin and the psychedelic is MDMA hemifumarate Form A, wherein the eplivanserin is administered to pretreat at least 210 minutes prior to the MDMA hemifumarate Form A. In some embodiments, the serotonin receptor modulator is eplivanserin and the psychedelic is MDMA hemifumarate Form A, wherein the eplivanserin is administered to pretreat at least 240 minutes prior to the MDMA hemifumarate Form A.

In some embodiments, the serotonin receptor modulator is eplivanserin and the psychedelic is MDMA hemifumarate Form A, wherein the eplivanserin is administered to pretreat at least 270 minutes prior to MDMA hemifumarate Form A. In some embodiments, the serotonin receptor modulator is eplivanserin and the psychedelic is MDMA hemifumarate Form A, wherein the eplivanserin is administered to pretreat at least 300 minutes prior to the MDMA hemifumarate Form A. In some embodiments, the serotonin receptor modulator is eplivanserin and the psychedelic is MDMA hemifumarate Form A, wherein the eplivanserin is administered to pretreat at least 330 minutes prior to the MDMA hemifumarate Form A. In some embodiments, the serotonin receptor modulator is eplivanserin and the psychedelic is MDMA hemifumarate Form A, wherein the eplivanserin is administered to pretreat at least 360 minutes prior to the MDMA hemifumarate Form A.

In some preferred embodiments, the serotonin receptor modulator is eplivanserin and the psychedelic is MDMA hemifumarate Form A, wherein eplivanserin is administered to pretreat between about 60 minutes and about 180 minutes prior to the administration of the MDMA hemifumarate Form A.

In some embodiments, the serotonin receptor modulator is volinanserin and the psychedelic is MDMA hemifumarate Form A, wherein the volinanserin is administered to pretreat a subject between at least 15 minutes and 360 minutes prior to the administration or release of the MDMA hemifumarate Form A. In some embodiments, the serotonin receptor modulator is volinanserin and the psychedelic is MDMA hemifumarate Form A, wherein the volinanserin is administered to pretreat between at least 30 minutes and 360 minutes prior to the administration or release of the MDMA hemifumarate Form A. In some embodiments, the serotonin receptor modulator is volinanserin and the psychedelic is MDMA hemifumarate Form A, wherein the volinanserin is administered to pretreat between at least 60 minutes and 240 minutes prior to the administration or release of the MDMA hemifumarate Form A. In some embodiments, the serotonin receptor modulator is volinanserin and the psychedelic is MDMA hemifumarate Form A, wherein the volinanserin is administered to pretreat at least 90 minutes prior to the MDMA hemifumarate Form A. In some embodiments, the serotonin receptor modulator is volinanserin and the psychedelic is MDMA hemifumarate Form A, wherein the volinanserin is administered to pretreat at least 120 minutes prior to the MDMA hemifumarate Form A.

In some embodiments, the serotonin receptor modulator is volinanserin and the psychedelic is MDMA hemifumarate Form A, wherein the volinanserin is administered to pretreat at least 150 minutes prior to the MDMA hemifumarate Form A. In some embodiments, the serotonin receptor modulator is volinanserin and the psychedelic is MDMA hemifumarate Form A, wherein the volinanserin is administered to pretreat between about 15 minutes and about 150 minutes prior to the MDMA hemifumarate Form A. In some embodiments, the serotonin receptor modulator is volinanserin and the psychedelic is MDMA hemifumarate Form A, wherein the volinanserin is administered to pretreat at least 180 minutes prior to the MDMA hemifumarate Form A. In some embodiments, the serotonin receptor modulator is volinanserin and the psychedelic is MDMA hemifumarate Form A, wherein the volinanserin is administered to pretreat at least 210 minutes prior to the MDMA hemifumarate Form A. In some embodiments, the serotonin receptor modulator is volinanserin and the psychedelic is MDMA hemifumarate Form A, wherein the volinanserin is administered to pretreat at least 240 minutes prior to the MDMA hemifumarate Form A. In some embodiments, the serotonin receptor modulator is volinanserin and the psychedelic is MDMA hemifumarate Form A, wherein the volinanserin is administered to pretreat at least 270 minutes prior to the MDMA hemifumarate Form A. In some embodiments, the serotonin receptor modulator is volinanserin and the psychedelic is MDMA hemifumarate Form A, wherein the volinanserin is administered to pretreat at least 300 minutes prior to the MDMA hemifumarate Form A. In some embodiments, the serotonin receptor modulator is volinanserin and the psychedelic is MDMA hemifumarate Form A, wherein the volinanserin is administered to pretreat at least 330 minutes prior to the MDMA hemifumarate Form A. In some embodiments, the serotonin receptor modulator is volinanserin and the psychedelic is MDMA hemifumarate Form A, wherein the volinanserin is administered to pretreat at least 360 minutes prior to the MDMA hemifumarate Form A. In some preferred embodiments, the serotonin receptor modulator is volinanserin and the psychedelic is MDMA hemifumarate Form A, wherein volinanserin is administered to pretreat between about 60 minutes and about 180 minutes prior to the administration of the MDMA hemifumarate Form A.

In some embodiments, the serotonin receptor modulator is ketanserin and the psychedelic is MDMA hemifumarate Form A, wherein the ketanserin is administered to pretreat at least 15 minutes prior to the administration of the MDMA hemifumarate Form A. In some embodiments, the serotonin receptor modulator is ketanserin and the psychedelic is MDMA hemifumarate Form A, wherein the ketanserin is administered to pretreat between at least 30 minutes and 360 minutes prior to the administration or release of the MDMA hemifumarate Form A. In some embodiments, the serotonin receptor modulator is ketanserin and the psychedelic is MDMA hemifumarate Form A, wherein the ketanserin is administered to pretreat between at least 60 minutes and 240 minutes prior to the administration or release of the MDMA hemifumarate Form A. In some embodiments, the serotonin receptor modulator is ketanserin and the psychedelic is MDMA hemifumarate Form A, wherein the ketanserin is administered to pretreat at least 90 minutes prior to the MDMA hemifumarate Form A. In some embodiments, the serotonin receptor modulator is ketanserin and the psychedelic is MDMA hemifumarate Form A, wherein the ketanserin is administered to pretreat at least 120 minutes prior to the MDMA hemifumarate Form A. In some embodiments, the serotonin receptor modulator is ketanserin and the psychedelic is MDMA hemifumarate Form A, wherein the ketanserin is administered to pretreat at least 150 minutes prior to the MDMA hemifumarate Form A. In some embodiments, the serotonin receptor modulator is ketanserin and the psychedelic is MDMA hemifumarate Form A, wherein the ketanserin is administered to pretreat between about 15 minutes and about 150 minutes prior to the MDMA hemifumarate Form A. In some embodiments, the serotonin receptor modulator is ketanserin and the psychedelic is MDMA hemifumarate Form A, wherein the ketanserin is administered to pretreat at least 180 minutes prior to the MDMA hemifumarate Form A. In some embodiments, the serotonin receptor modulator is ketanserin and the psychedelic is MDMA hemifumarate Form A, wherein the ketanserin is administered to pretreat at least 210 minutes prior to the MDMA hemifumarate Form A. In some embodiments, the serotonin receptor modulator is ketanserin and the psychedelic is MDMA hemifumarate Form A, wherein the ketanserin is administered to pretreat at least 240 minutes prior to the MDMA hemifumarate Form A. In some embodiments, the serotonin receptor modulator is ketanserin and the psychedelic is MDMA hemifumarate Form A, wherein the ketanserin is administered to pretreat at least 270 minutes prior to the MDMA hemifumarate Form A. In some embodiments, the serotonin receptor modulator is ketanserin and the psychedelic is MDMA hemifumarate Form A, wherein the ketanserin is administered to pretreat at least 300 minutes prior to the MDMA hemifumarate Form A. In some embodiments, the serotonin receptor modulator is ketanserin and the psychedelic is MDMA hemifumarate Form A, wherein the ketanserin is administered to pretreat at least 330 minutes prior to the MDMA hemifumarate Form A. In some embodiments, the serotonin receptor modulator is ketanserin and the psychedelic is MDMA hemifumarate Form A, wherein the ketanserin is administered to pretreat at least 360 minutes prior to the MDMA hemifumarate Form A. In some preferred embodiments, the serotonin receptor modulator is ketanserin and the psychedelic is MDMA hemifumarate Form A, wherein ketanserin is administered to pretreat between about 60 minutes and about 180 minutes prior to the administration of the MDMA hemifumarate Form A.

In some embodiments, the serotonin receptor modulator is ritanserin and the psychedelic is MDMA hemifumarate Form A, wherein the ritanserin is administered to pretreat at least 15 minutes prior to the administration of the MDMA hemifumarate Form A. In some embodiments, the serotonin receptor modulator is ritanserin and the psychedelic is MDMA hemifumarate Form A, wherein the ritanserin is administered to pretreat at least 30 minutes prior to the MDMA hemifumarate Form A. In some embodiments, the serotonin receptor modulator is ritanserin and the psychedelic is MDMA hemifumarate Form A, wherein the ritanserin is administered to pretreat between at least 60 minutes and 240 minutes prior to the administration or release of the MDMA hemifumarate Form A. In some embodiments, the serotonin receptor modulator is ritanserin and the psychedelic is MDMA hemifumarate Form A, wherein the ritanserin is administered to pretreat at least 90 minutes prior to the MDMA hemifumarate Form A. In some embodiments, the serotonin receptor modulator is ritanserin and the psychedelic is MDMA hemifumarate Form A, wherein the ritanserin is administered to pretreat at least 120 minutes prior to the MDMA hemifumarate Form A. In some embodiments, the serotonin receptor modulator is ritanserin and the psychedelic is MDMA hemifumarate Form A, wherein the ritanserin is administered to pretreat at least 150 minutes prior to the MDMA hemifumarate Form A. In some embodiments, the serotonin receptor modulator is ritanserin and the psychedelic is MDMA hemifumarate Form A, wherein the ritanserin is administered to pretreat between about 15 minutes and about 150 minutes prior to the MDMA hemifumarate Form A. In some embodiments, the serotonin receptor modulator is ritanserin and the psychedelic is MDMA hemifumarate Form A, wherein the ritanserin is administered to pretreat at least 180 minutes prior to the MDMA hemifumarate Form A. In some embodiments, the serotonin receptor modulator is ritanserin and the psychedelic is MDMA hemifumarate Form A, wherein the ritanserin is administered to pretreat at least 210 minutes prior to the MDMA hemifumarate Form A. In some embodiments, the serotonin receptor modulator is ritanserin and the psychedelic is MDMA hemifumarate Form A, wherein the ritanserin is administered to pretreat at least 240 minutes prior to the MDMA hemifumarate Form A. In some embodiments, the serotonin receptor modulator is ritanserin and the psychedelic is MDMA hemifumarate Form A, wherein the ritanserin is administered to pretreat at least 270 minutes prior to the MDMA hemifumarate Form A. In some embodiments, the serotonin receptor modulator is ritanserin and the psychedelic is MDMA hemifumarate Form A, wherein the ritanserin is administered to pretreat at least 300 minutes prior to the MDMA hemifumarate Form A. In some embodiments, the serotonin receptor modulator is ritanserin and the psychedelic is MDMA hemifumarate Form A, wherein the ritanserin is administered to pretreat at least 330 minutes prior to the MDMA hemifumarate Form A. In some embodiments, the serotonin receptor modulator is ritanserin and the psychedelic is MDMA hemifumarate Form A, wherein the ritanserin is administered to pretreat at least 360 minutes prior to the MDMA hemifumarate Form A. In some preferred embodiments, the serotonin receptor modulator is ritanserin and the psychedelic is MDMA hemifumarate Form A, wherein ritanserin is administered to pretreat between about 60 minutes and about 180 minutes prior to the administration of the MDMA hemifumarate Form A.

In some embodiments, the serotonin receptor modulator is pimavanserin and the psychedelic is MDMA hemifumarate Form A, wherein the pimavanserin is administered to pretreat at least 15 minutes prior to the administration of the MDMA hemifumarate Form A. In some embodiments, the serotonin receptor modulator is pimavanserin and the psychedelic is MDMA hemifumarate Form A, wherein the pimavanserin is administered to pretreat at least 30 minutes prior to the MDMA hemifumarate Form A. In some embodiments, the serotonin receptor modulator is pimavanserin and the psychedelic is MDMA hemifumarate Form A, wherein the pimavanserin is administered to pretreat between at least 60 minutes and 240 minutes prior to the administration or release of the MDMA hemifumarate Form A. In some embodiments, the serotonin receptor modulator is pimavanserin and the psychedelic is MDMA hemifumarate Form A, wherein the pimavanserin is administered to pretreat at least 90 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 120 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 150 minutes prior to the MDMA hemifumarate Form A. In some embodiments, the serotonin receptor modulator is pimavanserin and the psychedelic is MDMA hemifumarate Form A, wherein the pimavanserin is administered to pretreat between about 15 minutes and about 150 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 180 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 210 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 240 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 270 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 300 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 330 minutes prior to the MDMA hemifumarate Form A. In some embodiments, the serotonin receptor modulator is pimavanserin and the psychedelic is MDMA hemifumarate Form A, wherein the pimavanserin is administered to pretreat at least 360 minutes prior to the MDMA hemifumarate Form A. In some preferred embodiments, the serotonin receptor modulator is pimavanserin and the psychedelic is MDMA hemifumarate Form A, wherein pimavanserin is administered to pretreat between about 60 minutes and about 180 minutes prior to the administration of the MDMA hemifumarate Form A.

In some embodiments, the serotonin receptor modulator is nelotanserin and the psychedelic is MDMA hemifumarate Form A, wherein the nelotanserin is administered to pretreat at least 15 minutes prior to the administration of the MDMA hemifumarate Form A. In some embodiments, the serotonin receptor modulator is nelotanserin and the psychedelic is MDMA hemifumarate Form A, wherein the nelotanserin is administered to pretreat at least 30 minutes prior to the MDMA hemifumarate Form A. In some embodiments, the serotonin receptor modulator is nelotanserin and the psychedelic is MDMA hemifumarate Form A, wherein the nelotanserin is administered to pretreat between at least 60 minutes and 240 minutes prior to the administration or release of the MDMA hemifumarate Form A. In some embodiments, the serotonin receptor modulator is nelotanserin and the psychedelic is MDMA hemifumarate Form A, wherein the nelotanserin is administered to pretreat at least 90 minutes prior to the MDMA hemifumarate Form A. In some embodiments, the serotonin receptor modulator is nelotanserin and the psychedelic is MDMA hemifumarate Form A, wherein the nelotanserin is administered to pretreat at least 120 minutes prior to the MDMA hemifumarate Form A.

In some embodiments, the serotonin receptor modulator is nelotanserin and the psychedelic is MDMA hemifumarate Form A, wherein the nelotanserin is administered to pretreat at least 150 minutes prior to the MDMA hemifumarate Form A. In some embodiments, the serotonin receptor modulator is nelotanserin and the psychedelic is MDMA hemifumarate Form A, wherein the nelotanserin is administered to pretreat between about 15 minutes and about 150 minutes prior to the MDMA hemifumarate Form A. In some embodiments, the serotonin receptor modulator is nelotanserin and the psychedelic is MDMA hemifumarate Form A, wherein the nelotanserin is administered to pretreat at least 180 minutes prior to the MDMA hemifumarate Form A. In some embodiments, the serotonin receptor modulator is nelotanserin and the psychedelic is MDMA hemifumarate Form A, wherein the nelotanserin is administered to pretreat at least 210 minutes prior to the MDMA hemifumarate Form A. In some embodiments, the serotonin receptor modulator is nelotanserin and the psychedelic is MDMA hemifumarate Form A, wherein the nelotanserin is administered to pretreat at least 240 minutes prior to the MDMA hemifumarate Form A. In some embodiments, the serotonin receptor modulator is nelotanserin and the psychedelic is MDMA hemifumarate Form A, wherein the nelotanserin is administered to pretreat at least 270 minutes prior to the MDMA hemifumarate Form A.

In some embodiments, the serotonin receptor modulator is nelotanserin and the psychedelic is MDMA hemifumarate Form A, wherein the nelotanserin is administered to pretreat at least 300 minutes prior to the MDMA hemifumarate Form A. In some embodiments, the serotonin receptor modulator is nelotanserin and the psychedelic is MDMA hemifumarate Form A, wherein the nelotanserin is administered to pretreat at least 330 minutes prior to the MDMA hemifumarate Form A. In some embodiments, the serotonin receptor modulator is nelotanserin and the psychedelic is MDMA hemifumarate Form A, wherein the nelotanserin is administered to pretreat at least 360 minutes prior to the MDMA hemifumarate Form A. In some preferred embodiments, the serotonin receptor modulator is nelotanserin and the psychedelic is MDMA hemifumarate Form A, wherein nelotanserin is administered to pretreat between about 60 minutes and about 180 minutes prior to the administration of the MDMA hemifumarate Form A.

In some embodiments, the serotonin receptor modulator is pruvanserin and the psychedelic is MDMA hemifumarate Form A, wherein the pruvanserin is administered to pretreat at least 15 minutes prior to the administration of the MDMA hemifumarate Form A. In some embodiments, the serotonin receptor modulator is pruvanserin and the psychedelic is MDMA hemifumarate Form A, wherein the pruvanserin is administered to pretreat at least 30 minutes prior to the MDMA hemifumarate Form A. In some embodiments, the serotonin receptor modulator is pruvanserin and the psychedelic is MDMA hemifumarate Form A, wherein the pruvanserin is administered to pretreat between at least 60 minutes and 240 minutes prior to the administration or release of the MDMA hemifumarate Form A. In some embodiments, the serotonin receptor modulator is pruvanserin and the psychedelic is MDMA hemifumarate Form A, wherein the pruvanserin is administered to pretreat at least 90 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 120 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 150 minutes prior to the MDMA hemifumarate Form A. In some embodiments, the serotonin receptor modulator is pruvanserin and the psychedelic is MDMA hemifumarate Form A, wherein the pruvanserin is administered to pretreat between about 15 minutes and about 150 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 180 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 210 minutes prior to the MDMA hemifumarate Form A.

In some embodiments, the serotonin receptor modulator is pruvanserin and the psychedelic is MDMA hemifumarate Form A, wherein the pruvanserin is administered to pretreat at least 240 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 270 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 300 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 330 minutes prior to the MDMA hemifumarate Form A. In some embodiments, the serotonin receptor modulator is pruvanserin and the psychedelic is MDMA hemifumarate Form A, wherein the pruvanserin is administered to pretreat at least 360 minutes prior to the MDMA hemifumarate Form A. In some preferred embodiments, the serotonin receptor modulator is pruvanserin and the psychedelic is MDMA hemifumarate Form A, wherein pruvanserin is administered to pretreat between about 60 minutes and about 180 minutes prior to the administration of the MDMA hemifumarate Form A.

In some embodiments, the serotonin receptor modulator is flibanserin and the psychedelic is MDMA hemifumarate Form A, wherein the flibanserin is administered to pretreat at least 15 minutes prior to the administration of the MDMA hemifumarate Form A. In some embodiments, the serotonin receptor modulator is flibanserin and the psychedelic is MDMA hemifumarate Form A, wherein the flibanserin is administered to pretreat at least 30 minutes prior to the MDMA hemifumarate Form A. In some embodiments, the serotonin receptor modulator is flibanserin and the psychedelic is MDMA hemifumarate Form A, wherein the flibanserin is administered to pretreat between at least 60 minutes and 240 minutes prior to the administration or release of the MDMA hemifumarate Form A. In some embodiments, the serotonin receptor modulator is flibanserin and the psychedelic is MDMA hemifumarate Form A, wherein the flibanserin is administered to pretreat at least 90 minutes prior to the MDMA hemifumarate Form A. In some embodiments, the serotonin receptor modulator is flibanserin and the psychedelic is MDMA hemifumarate Form A, wherein the flibanserin is administered to pretreat at least 120 minutes prior to the MDMA hemifumarate Form A. In some embodiments, the serotonin receptor modulator is flibanserin and the psychedelic is MDMA hemifumarate Form A, wherein the flibanserin is administered to pretreat at least 150 minutes prior to the MDMA hemifumarate Form A. In some embodiments, the serotonin receptor modulator is flibanserin and the psychedelic is MDMA hemifumarate Form A, wherein the flibanserin is administered to pretreat between about 15 minutes and about 150 minutes prior to the MDMA hemifumarate Form A. In some embodiments, the serotonin receptor modulator is flibanserin and the psychedelic is MDMA hemifumarate Form A, wherein the flibanserin is administered to pretreat at least 180 minutes prior to the MDMA hemifumarate Form A. In some embodiments, the serotonin receptor modulator is flibanserin and the psychedelic is MDMA hemifumarate Form A, wherein the flibanserin is administered to pretreat at least 210 minutes prior to the MDMA hemifumarate Form A.

In some embodiments, the serotonin receptor modulator is flibanserin and the psychedelic is MDMA hemifumarate Form A, wherein the flibanserin is administered to pretreat at least 240 minutes prior to the MDMA hemifumarate Form A. In some embodiments, the serotonin receptor modulator is flibanserin and the psychedelic is MDMA hemifumarate Form A, wherein the flibanserin is administered to pretreat at least 270 minutes prior to the MDMA hemifumarate Form A. In some embodiments, the serotonin receptor modulator is flibanserin and the psychedelic is MDMA hemifumarate Form A, wherein the flibanserin is administered to pretreat at least 300 minutes prior to the MDMA hemifumarate Form A. In some embodiments, the serotonin receptor modulator is flibanserin and the psychedelic is MDMA hemifumarate Form A, wherein the flibanserin is administered to pretreat at least 330 minutes prior to the MDMA hemifumarate Form A. In some embodiments, the serotonin receptor modulator is flibanserin and the psychedelic is MDMA hemifumarate Form A, wherein the flibanserin is administered to pretreat at least 360 minutes prior to the MDMA hemifumarate Form A. In some preferred embodiments, the serotonin receptor modulator is flibanserin and the psychedelic is MDMA hemifumarate Form A, wherein flibanserin is administered to pretreat between about 60 minutes and about 180 minutes prior to the administration of the MDMA hemifumarate Form A.

In some embodiments, the serotonin receptor modulator is olanzapine and the psychedelic is MDMA hemifumarate Form A, wherein the olanzapine is administered to pretreat at least 15 minutes prior to the administration of the MDMA hemifumarate Form A. In some embodiments, the serotonin receptor modulator is olanzapine and the psychedelic is MDMA hemifumarate Form A, wherein the olanzapine is administered to pretreat at least 30 minutes prior to the MDMA hemifumarate Form A. In some embodiments, the serotonin receptor modulator is olanzapine and the psychedelic is MDMA hemifumarate Form A, wherein the olanzapine is administered to pretreat between at least 60 minutes and 240 minutes prior to the administration or release of the MDMA hemifumarate Form A. In some embodiments, the serotonin receptor modulator is olanzapine and the psychedelic is MDMA hemifumarate Form A, wherein the olanzapine is administered to pretreat at least 90 minutes prior to the MDMA hemifumarate Form A. In some embodiments, the serotonin receptor modulator is olanzapine and the psychedelic is MDMA hemifumarate Form A, wherein the olanzapine is administered to pretreat at least 120 minutes prior to the MDMA hemifumarate Form A. In some embodiments, the serotonin receptor modulator is olanzapine and the psychedelic is MDMA hemifumarate Form A, wherein the olanzapine is administered to pretreat at least 150 minutes prior to the MDMA hemifumarate Form A. In some embodiments, the serotonin receptor modulator is olanzapine and the psychedelic is MDMA hemifumarate Form A, wherein the olanzapine is administered to pretreat between about 15 minutes and about 150 minutes prior to the MDMA hemifumarate Form A. In some embodiments, the serotonin receptor modulator is olanzapine and the psychedelic is MDMA hemifumarate Form A, wherein the olanzapine is administered to pretreat at least 180 minutes prior to the MDMA hemifumarate Form A. In some embodiments, the serotonin receptor modulator is olanzapine and the psychedelic is MDMA hemifumarate Form A, wherein the olanzapine is administered to pretreat at least 210 minutes prior to the MDMA hemifumarate Form A.

In some embodiments, the serotonin receptor modulator is olanzapine and the psychedelic is MDMA hemifumarate Form A, wherein the olanzapine is administered to pretreat at least 240 minutes prior to the MDMA hemifumarate Form A. In some embodiments, the serotonin receptor modulator is olanzapine and the psychedelic is MDMA hemifumarate Form A, wherein the olanzapine is administered to pretreat at least 270 minutes prior to the MDMA hemifumarate Form A. In some embodiments, the serotonin receptor modulator is olanzapine and the psychedelic is MDMA hemifumarate Form A, wherein the olanzapine is administered to pretreat at least 300 minutes prior to the MDMA hemifumarate Form A. In some embodiments, the serotonin receptor modulator is olanzapine and the psychedelic is MDMA hemifumarate Form A, wherein the olanzapine is administered to pretreat at least 330 minutes prior to the MDMA hemifumarate Form A. In some embodiments, the serotonin receptor modulator is olanzapine and the psychedelic is MDMA hemifumarate Form A, wherein the olanzapine is administered to pretreat at least 360 minutes prior to the MDMA hemifumarate Form A. In some preferred embodiments, the serotonin receptor modulator is olanzapine and the psychedelic is MDMA hemifumarate Form A, wherein olanzapine is administered to pretreat between about 60 minutes and about 180 minutes prior to the administration of the MDMA hemifumarate Form A.

In some embodiments, the serotonin receptor modulator is risperidone and the psychedelic is MDMA hemifumarate Form A, wherein the risperidone is administered to pretreat at least 15 minutes prior to the administration of the MDMA hemifumarate Form A. In some embodiments, the serotonin receptor modulator is risperidone and the psychedelic is MDMA hemifumarate Form A, wherein the risperidone is administered to pretreat at least 30 minutes prior to the MDMA hemifumarate Form A. In some embodiments, the serotonin receptor modulator is risperidone and the psychedelic is MDMA hemifumarate Form A, wherein the risperidone is administered to pretreat between at least 60 minutes and 240 minutes prior to the administration or release of the MDMA hemifumarate Form A. In some embodiments, the serotonin receptor modulator is risperidone and the psychedelic is MDMA hemifumarate Form A, wherein the risperidone is administered to pretreat at least 90 minutes prior to the MDMA hemifumarate Form A. In some embodiments, the serotonin receptor modulator is risperidone and the psychedelic is MDMA hemifumarate Form A, wherein the risperidone is administered to pretreat at least 120 minutes prior to the MDMA hemifumarate Form A. In some embodiments, the serotonin receptor modulator is risperidone and the psychedelic is MDMA hemifumarate Form A, wherein the risperidone is administered to pretreat at least 150 minutes prior to the MDMA hemifumarate Form A. In some embodiments, the serotonin receptor modulator is risperidone and the psychedelic is MDMA hemifumarate Form A, wherein the risperidone is administered to pretreat between about 15 minutes and about 150 minutes prior to the MDMA hemifumarate Form A. In some embodiments, the serotonin receptor modulator is risperidone and the psychedelic is MDMA hemifumarate Form A, wherein the risperidone is administered to pretreat at least 180 minutes prior to the MDMA hemifumarate Form A. In some embodiments, the serotonin receptor modulator is risperidone and the psychedelic is MDMA hemifumarate Form A, wherein the risperidone is administered to pretreat at least 210 minutes prior to the MDMA hemifumarate Form A.

In some embodiments, the serotonin receptor modulator is risperidone and the psychedelic is MDMA hemifumarate Form A, wherein the risperidone is administered to pretreat at least 240 minutes prior to the MDMA hemifumarate Form A. In some embodiments, the serotonin receptor modulator is risperidone and the psychedelic is MDMA hemifumarate Form A, wherein the risperidone is administered to pretreat at least 270 minutes prior to the MDMA hemifumarate Form A. In some embodiments, the serotonin receptor modulator is risperidone and the psychedelic is MDMA hemifumarate Form A, wherein the risperidone is administered to pretreat at least 300 minutes prior to the MDMA hemifumarate Form A. In some embodiments, the serotonin receptor modulator is risperidone and the psychedelic is MDMA hemifumarate Form A, wherein the risperidone is administered to pretreat at least 330 minutes prior to the MDMA hemifumarate Form A. In some embodiments, the serotonin receptor modulator is risperidone and the psychedelic is MDMA hemifumarate Form A, wherein the risperidone is administered to pretreat at least 360 minutes prior to the MDMA hemifumarate Form A. In some preferred embodiments, the serotonin receptor modulator is risperidone and the psychedelic is MDMA hemifumarate Form A, wherein risperidone is administered to pretreat between about 60 minutes and about 180 minutes prior to the administration of the MDMA hemifumarate Form A.

In some embodiments, the serotonin receptor modulator is quetiapine and the psychedelic is MDMA hemifumarate Form A, wherein the quetiapine is administered to pretreat at least 15 minutes prior to the administration of the MDMA hemifumarate Form A. In some embodiments, the serotonin receptor modulator is quetiapine and the psychedelic is MDMA hemifumarate Form A, wherein the quetiapine is administered to pretreat at least 30 minutes prior to the MDMA hemifumarate Form A. In some embodiments, the serotonin receptor modulator is quetiapine and the psychedelic is MDMA hemifumarate Form A, wherein the quetiapine is administered to pretreat between at least 60 minutes and 240 minutes prior to the administration or release of the MDMA hemifumarate Form A. In some embodiments, the serotonin receptor modulator is quetiapine and the psychedelic is MDMA hemifumarate Form A, wherein the quetiapine is administered to pretreat at least 90 minutes prior to the MDMA hemifumarate Form A. In some embodiments, the serotonin receptor modulator is quetiapine and the psychedelic is MDMA hemifumarate Form A, wherein the quetiapine is administered to pretreat at least 120 minutes prior to the MDMA hemifumarate Form A. In some embodiments, the serotonin receptor modulator is quetiapine and the psychedelic is MDMA hemifumarate Form A, wherein the quetiapine is administered to pretreat at least 150 minutes prior to the MDMA hemifumarate Form A. In some embodiments, the serotonin receptor modulator is quetiapine and the psychedelic is MDMA hemifumarate Form A, wherein the quetiapine is administered to pretreat between about 15 minutes and about 150 minutes prior to the MDMA hemifumarate Form A. In some embodiments, the serotonin receptor modulator is quetiapine and the psychedelic is MDMA hemifumarate Form A, wherein the quetiapine is administered to pretreat at least 180 minutes prior to the MDMA hemifumarate Form A. In some embodiments, the serotonin receptor modulator is quetiapine and the psychedelic is MDMA hemifumarate Form A, wherein the quetiapine is administered to pretreat at least 210 minutes prior to the MDMA hemifumarate Form A.

In some embodiments, the serotonin receptor modulator is quetiapine and the psychedelic is MDMA hemifumarate Form A, wherein the quetiapine is administered to pretreat at least 240 minutes prior to the MDMA hemifumarate Form A. In some embodiments, the serotonin receptor modulator is quetiapine and the psychedelic is MDMA hemifumarate Form A, wherein the quetiapine is administered to pretreat at least 270 minutes prior to the MDMA hemifumarate Form A. In some embodiments, the serotonin receptor modulator is quetiapine and the psychedelic is MDMA hemifumarate Form A, wherein the quetiapine is administered to pretreat at least 300 minutes prior to the MDMA hemifumarate Form A. In some embodiments, the serotonin receptor modulator is quetiapine and the psychedelic is MDMA hemifumarate Form A, wherein the quetiapine is administered to pretreat at least 330 minutes prior to the MDMA hemifumarate Form A. In some embodiments, the serotonin receptor modulator is quetiapine and the psychedelic is MDMA hemifumarate Form A, wherein the quetiapine is administered to pretreat at least 360 minutes prior to the MDMA hemifumarate Form A. In some preferred embodiments, the serotonin receptor modulator is quetiapine and the psychedelic is MDMA hemifumarate Form A, wherein quetiapine is administered to pretreat between about 60 minutes and about 180 minutes prior to the administration of the MDMA hemifumarate Form A.

In certain embodiments, such as those described above a MDMA form disclosed herein, including those described in Table Ex3 is co-administered with a serotonin receptor modulator in the same or in separate compositions. In one embodiment, the serotonin receptor modulator is administered after the MDMA form disclosed herein, including those described in Table Ex3. In one embodiment, the MDMA form disclosed herein, including those described in Table Ex3 is administered in a modified release formulation such that the subject is effectively post-treated with serotonin receptor modulator post to release of an effective amount of the MDMA form disclosed herein, including those described in Table Ex3. In some embodiments, the serotonin receptor modulator is part of a single fixed dose formulation that releases the MDMA form disclosed herein, including those described in Table Ex3 first followed by serotonin receptor modulator on two different release profiles. In another embodiment, the MDMA form disclosed herein, including those described in Table Ex3 is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the psychedelic. This allows post-treatment to attenuate activation of the serotonin receptor by the psychedelic.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post to the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the psychedelic.

In a preferred embodiment, the serotonin receptor modulator is administered at about 1 hour to about 3 hours post to the administration of the psychedelic.

In some embodiments, the serotonin receptor modulator is eplivanserin and the psychedelic is MDMA, wherein the eplivanserin is administered to post-treat at least 15 minutes post to the administration of the MDMA form disclosed herein, including those described in Table Ex3. In some embodiments, the serotonin receptor modulator is eplivanserin and the psychedelic is MDMA, wherein the eplivanserin is administered to post-treat between at least 30 minutes post and 360 minutes post to the release or administration of the MDMA form disclosed herein, including those described in Table Ex3. In some embodiments, the serotonin receptor modulator is eplivanserin and the psychedelic is MDMA, wherein the eplivanserin is administered to post-treat between at least 60 minutes post and 360 minutes post to the release or administration the MDMA form disclosed herein, including those described in Table Ex3. In some embodiments, the serotonin receptor modulator is eplivanserin and the psychedelic is MDMA, wherein the eplivanserin is administered to post-treat at between least 90 minutes and 240 minutes post to the MDMA form disclosed herein, including those described in Table Ex3. In some embodiments, the serotonin receptor modulator is eplivanserin and the psychedelic is MDMA, wherein the eplivanserin is administered to post-treat at least 120 minutes post to the MDMA form disclosed herein, including those described in Table Ex3.

In some embodiments, the serotonin receptor modulator is eplivanserin and the psychedelic is MDMA, wherein the eplivanserin is administered to post-treat at least 150 minutes post to the MDMA form disclosed herein, including those described in Table Ex3. In some embodiments, the serotonin receptor modulator is eplivanserin and the psychedelic is MDMA, wherein the eplivanserin is administered to post-treat between about 15 minutes and about 150 minutes post to the MDMA form disclosed herein, including those described in Table Ex3. In some embodiments, the serotonin receptor modulator is eplivanserin and the psychedelic is MDMA, wherein the eplivanserin is administered to post-treat at least 180 minutes post to the MDMA form disclosed herein, including those described in Table Ex3. In some embodiments, the serotonin receptor modulator is eplivanserin and the psychedelic is MDMA, wherein the eplivanserin is administered to post-treat at least 210 minutes post to the MDMA form disclosed herein, including those described in Table Ex3. In some embodiments, the serotonin receptor modulator is eplivanserin and the psychedelic is MDMA, wherein the eplivanserin is administered to post-treat at least 240 minutes post to the MDMA form disclosed herein, including those described in Table Ex3.

In some embodiments, the serotonin receptor modulator is eplivanserin and the psychedelic is MDMA, wherein the eplivanserin is administered to post-treat at least 270 minutes post to the MDMA form disclosed herein, including those described in Table Ex3. In some embodiments, the serotonin receptor modulator is eplivanserin and the psychedelic is MDMA, wherein the eplivanserin is administered to post-treat at least 300 minutes post to the MDMA form disclosed herein, including those described in Table Ex3. In some embodiments, the serotonin receptor modulator is eplivanserin and the psychedelic is MDMA, wherein the eplivanserin is administered to post-treat at least 330 minutes post to the MDMA form disclosed herein, including those described in Table Ex3. In some embodiments, the serotonin receptor modulator is eplivanserin and the psychedelic is MDMA, wherein the eplivanserin is administered to post-treat at least 360 minutes post to the MDMA form disclosed herein, including those described in Table Ex3.

In some preferred embodiments, the serotonin receptor modulator is eplivanserin and the psychedelic is MDMA, wherein eplivanserin is administered to post-treat between about 60 minutes and about 180 minutes post to the administration of the MDMA form disclosed herein, including those described in Table Ex3.

In some embodiments, the serotonin receptor modulator is volinanserin and the psychedelic is MDMA, wherein the volinanserin is administered to post-treat a subject between at least 15 minutes and 360 minutes post to the administration or release of the MDMA form disclosed herein, including those described in Table Ex3. In some embodiments, the serotonin receptor modulator is volinanserin and the psychedelic is MDMA, wherein the volinanserin is administered to post-treat between at least 30 minutes and 360 minutes post to the administration or release of the MDMA form disclosed herein, including those described in Table Ex3. In some embodiments, the serotonin receptor modulator is volinanserin and the psychedelic is MDMA, wherein the volinanserin is administered to post-treat between at least 60 minutes and 240 minutes post to the administration or release of the MDMA form disclosed herein, including those described in Table Ex3. In some embodiments, the serotonin receptor modulator is volinanserin and the psychedelic is MDMA, wherein the volinanserin is administered to post-treat at least 90 minutes post to the MDMA form disclosed herein, including those described in Table Ex3. In some embodiments, the serotonin receptor modulator is volinanserin and the psychedelic is MDMA, wherein the volinanserin is administered to post-treat at least 120 minutes post to the MDMA form disclosed herein, including those described in Table Ex3.

In some embodiments, the serotonin receptor modulator is volinanserin and the psychedelic is MDMA, wherein the volinanserin is administered to post-treat at least 150 minutes post to the MDMA form disclosed herein, including those described in Table Ex3. In some embodiments, the serotonin receptor modulator is volinanserin and the psychedelic is MDMA, wherein the volinanserin is administered to post-treat between about 15 minutes and about 150 minutes post to the MDMA form disclosed herein, including those described in Table Ex3. In some embodiments, the serotonin receptor modulator is volinanserin and the psychedelic is MDMA, wherein the volinanserin is administered to post-treat at least 180 minutes post to the MDMA form disclosed herein, including those described in Table Ex3. In some embodiments, the serotonin receptor modulator is volinanserin and the psychedelic is MDMA, wherein the volinanserin is administered to post-treat at least 210 minutes post to the MDMA form disclosed herein, including those described in Table Ex3. In some embodiments, the serotonin receptor modulator is volinanserin and the psychedelic is MDMA, wherein the volinanserin is administered to post-treat at least 240 minutes post to the MDMA form disclosed herein, including those described in Table Ex3. In some embodiments, the serotonin receptor modulator is volinanserin and the psychedelic is MDMA, wherein the volinanserin is administered to post-treat at least 270 minutes post to the MDMA form disclosed herein, including those described in Table Ex3. In some embodiments, the serotonin receptor modulator is volinanserin and the psychedelic is MDMA, wherein the volinanserin is administered to post-treat at least 300 minutes post to the MDMA form disclosed herein, including those described in Table Ex3. In some embodiments, the serotonin receptor modulator is volinanserin and the psychedelic is MDMA, wherein the volinanserin is administered to post-treat at least 330 minutes post to the MDMA form disclosed herein, including those described in Table Ex3. In some embodiments, the serotonin receptor modulator is volinanserin and the psychedelic is MDMA, wherein the volinanserin is administered to post-treat at least 360 minutes post to the MDMA form disclosed herein, including those described in Table Ex3. In some preferred embodiments, the serotonin receptor modulator is volinanserin and the psychedelic is MDMA, wherein volinanserin is administered to post-treat between about 60 minutes and about 180 minutes post to the administration of the MDMA form disclosed herein, including those described in Table Ex3.

In some embodiments, the serotonin receptor modulator is ketanserin and the psychedelic is MDMA, wherein the ketanserin is administered to post-treat at least 15 minutes post to the administration of the MDMA form disclosed herein, including those described in Table Ex3. In some embodiments, the serotonin receptor modulator is ketanserin and the psychedelic is MDMA, wherein the ketanserin is administered to post-treat between at least 30 minutes and 360 minutes post to the administration or release of the MDMA form disclosed herein, including those described in Table Ex3. In some embodiments, the serotonin receptor modulator is ketanserin and the psychedelic is MDMA, wherein the ketanserin is administered to post-treat between at least 60 minutes and 240 minutes post to the administration or release of the MDMA form disclosed herein, including those described in Table Ex3. In some embodiments, the serotonin receptor modulator is ketanserin and the psychedelic is MDMA, wherein the ketanserin is administered to post-treat at least 90 minutes post to the MDMA form disclosed herein, including those described in Table Ex3. In some embodiments, the serotonin receptor modulator is ketanserin and the psychedelic is MDMA, wherein the ketanserin is administered to post-treat at least 120 minutes post to the MDMA form disclosed herein, including those described in Table Ex3. In some embodiments, the serotonin receptor modulator is ketanserin and the psychedelic is MDMA, wherein the ketanserin is administered to post-treat at least 150 minutes post to the MDMA form disclosed herein, including those described in Table Ex3. In some embodiments, the serotonin receptor modulator is ketanserin and the psychedelic is MDMA, wherein the ketanserin is administered to post-treat between about 15 minutes and about 150 minutes post to the MDMA form disclosed herein, including those described in Table Ex3. In some embodiments, the serotonin receptor modulator is ketanserin and the psychedelic is MDMA, wherein the ketanserin is administered to post-treat at least 180 minutes post to the MDMA form disclosed herein, including those described in Table Ex3. In some embodiments, the serotonin receptor modulator is ketanserin and the psychedelic is MDMA, wherein the ketanserin is administered to post-treat at least 210 minutes post to the MDMA form disclosed herein, including those described in Table Ex3. In some embodiments, the serotonin receptor modulator is ketanserin and the psychedelic is MDMA, wherein the ketanserin is administered to post-treat at least 240 minutes post to the MDMA form disclosed herein, including those described in Table Ex3. In some embodiments, the serotonin receptor modulator is ketanserin and the psychedelic is MDMA, wherein the ketanserin is administered to post-treat at least 270 minutes post to the MDMA form disclosed herein, including those described in Table Ex3. In some embodiments, the serotonin receptor modulator is ketanserin and the psychedelic is MDMA, wherein the ketanserin is administered to post-treat at least 300 minutes post to the MDMA form disclosed herein, including those described in Table Ex3. In some embodiments, the serotonin receptor modulator is ketanserin and the psychedelic is MDMA, wherein the ketanserin is administered to post-treat at least 330 minutes post to the MDMA form disclosed herein, including those described in Table Ex3. In some embodiments, the serotonin receptor modulator is ketanserin and the psychedelic is MDMA, wherein the ketanserin is administered to post-treat at least 360 minutes post to the MDMA form disclosed herein, including those described in Table Ex3. In some preferred embodiments, the serotonin receptor modulator is ketanserin and the psychedelic is MDMA, wherein ketanserin is administered to post-treat between about 60 minutes and about 180 minutes post to the administration of the MDMA form disclosed herein, including those described in Table Ex3.

In some embodiments, the serotonin receptor modulator is ritanserin and the psychedelic is MDMA, wherein the ritanserin is administered to post-treat at least 15 minutes post to the administration of the MDMA form disclosed herein, including those described in Table Ex3. In some embodiments, the serotonin receptor modulator is ritanserin and the psychedelic is MDMA, wherein the ritanserin is administered to post-treat at least 30 minutes post to the MDMA form disclosed herein, including those described in Table Ex3. In some embodiments, the serotonin receptor modulator is ritanserin and the psychedelic is MDMA, wherein the ritanserin is administered to post-treat between at least 60 minutes and 240 minutes post to the administration or release of the MDMA form disclosed herein, including those described in Table Ex3. In some embodiments, the serotonin receptor modulator is ritanserin and the psychedelic is MDMA, wherein the ritanserin is administered to post-treat at least 90 minutes post to the MDMA form disclosed herein, including those described in Table Ex3. In some embodiments, the serotonin receptor modulator is ritanserin and the psychedelic is MDMA, wherein the ritanserin is administered to post-treat at least 120 minutes post to the MDMA form disclosed herein, including those described in Table Ex3. In some embodiments, the serotonin receptor modulator is ritanserin and the psychedelic is MDMA, wherein the ritanserin is administered to post-treat at least 150 minutes post to the MDMA form disclosed herein, including those described in Table Ex3. In some embodiments, the serotonin receptor modulator is ritanserin and the psychedelic is MDMA, wherein the ritanserin is administered to post-treat between about 15 minutes and about 150 minutes post to the MDMA form disclosed herein, including those described in Table Ex3. In some embodiments, the serotonin receptor modulator is ritanserin and the psychedelic is MDMA, wherein the ritanserin is administered to post-treat at least 180 minutes post to the MDMA form disclosed herein, including those described in Table Ex3. In some embodiments, the serotonin receptor modulator is ritanserin and the psychedelic is MDMA, wherein the ritanserin is administered to post-treat at least 210 minutes post to the MDMA form disclosed herein, including those described in Table Ex3. In some embodiments, the serotonin receptor modulator is ritanserin and the psychedelic is MDMA, wherein the ritanserin is administered to post-treat at least 240 minutes post to the MDMA form disclosed herein, including those described in Table Ex3. In some embodiments, the serotonin receptor modulator is ritanserin and the psychedelic is MDMA, wherein the ritanserin is administered to post-treat at least 270 minutes post to the MDMA form disclosed herein, including those described in Table Ex3. In some embodiments, the serotonin receptor modulator is ritanserin and the psychedelic is MDMA, wherein the ritanserin is administered to post-treat at least 300 minutes post to the MDMA form disclosed herein, including those described in Table Ex3. In some embodiments, the serotonin receptor modulator is ritanserin and the psychedelic is MDMA, wherein the ritanserin is administered to post-treat at least 330 minutes post to the MDMA form disclosed herein, including those described in Table Ex3. In some embodiments, the serotonin receptor modulator is ritanserin and the psychedelic is MDMA, wherein the ritanserin is administered to post-treat at least 360 minutes post to the MDMA form disclosed herein, including those described in Table Ex3. In some preferred embodiments, the serotonin receptor modulator is ritanserin and the psychedelic is MDMA, wherein ritanserin is administered to post-treat between about 60 minutes and about 180 minutes post to the administration of the MDMA form disclosed herein, including those described in Table Ex3.

In some embodiments, the serotonin receptor modulator is pimavanserin and the psychedelic is MDMA, wherein the pimavanserin is administered to post-treat at least 15 minutes post to the administration of the MDMA form disclosed herein, including those described in Table Ex3. In some embodiments, the serotonin receptor modulator is pimavanserin and the psychedelic is MDMA, wherein the pimavanserin is administered to post-treat at least 30 minutes post to the MDMA form disclosed herein, including those described in Table Ex3. In some embodiments, the serotonin receptor modulator is pimavanserin and the psychedelic is MDMA, wherein the pimavanserin is administered to post-treat between at least 60 minutes and 240 minutes post to the administration or release of the MDMA form disclosed herein, including those described in Table Ex3. In some embodiments, the serotonin receptor modulator is pimavanserin and the psychedelic is MDMA, wherein the pimavanserin is administered to post-treat at least 90 minutes post to the MDMA form disclosed herein, including those described in Table Ex3. In some embodiments, the serotonin receptor modulator is pimavanserin and the psychedelic is MDMA, wherein the pimavanserin is administered to post-treat at least 120 minutes post to the MDMA form disclosed herein, including those described in Table Ex3. In some embodiments, the serotonin receptor modulator is pimavanserin and the psychedelic is MDMA, wherein the pimavanserin is administered to post-treat at least 150 minutes post to the MDMA form disclosed herein, including those described in Table Ex3. In some embodiments, the serotonin receptor modulator is pimavanserin and the psychedelic is MDMA, wherein the pimavanserin is administered to post-treat between about 15 minutes and about 150 minutes post to the MDMA form disclosed herein, including those described in Table Ex3. In some embodiments, the serotonin receptor modulator is pimavanserin and the psychedelic is MDMA, wherein the pimavanserin is administered to post-treat at least 180 minutes post to the MDMA form disclosed herein, including those described in Table Ex3. In some embodiments, the serotonin receptor modulator is pimavanserin and the psychedelic is MDMA, wherein the pimavanserin is administered to post-treat at least 210 minutes post to the MDMA form disclosed herein, including those described in Table Ex3. In some embodiments, the serotonin receptor modulator is pimavanserin and the psychedelic is MDMA, wherein the pimavanserin is administered to post-treat at least 240 minutes post to the MDMA form disclosed herein, including those described in Table Ex3. In some embodiments, the serotonin receptor modulator is pimavanserin and the psychedelic is MDMA, wherein the pimavanserin is administered to post-treat at least 270 minutes post to the MDMA form disclosed herein, including those described in Table Ex3. In some embodiments, the serotonin receptor modulator is pimavanserin and the psychedelic is MDMA, wherein the pimavanserin is administered to post-treat at least 300 minutes post to the MDMA form disclosed herein, including those described in Table Ex3. In some embodiments, the serotonin receptor modulator is pimavanserin and the psychedelic is MDMA, wherein the pimavanserin is administered to post-treat at least 330 minutes post to the MDMA form disclosed herein, including those described in Table Ex3. In some embodiments, the serotonin receptor modulator is pimavanserin and the psychedelic is MDMA, wherein the pimavanserin is administered to post-treat at least 360 minutes post to the MDMA form disclosed herein, including those described in Table Ex3. In some preferred embodiments, the serotonin receptor modulator is pimavanserin and the psychedelic is MDMA, wherein pimavanserin is administered to post-treat between about 60 minutes and about 180 minutes post to the administration of the MDMA form disclosed herein, including those described in Table Ex3.

In some embodiments, the serotonin receptor modulator is nelotanserin and the psychedelic is MDMA, wherein the nelotanserin is administered to post-treat at least 15 minutes post to the administration of the MDMA form disclosed herein, including those described in Table Ex3. In some embodiments, the serotonin receptor modulator is nelotanserin and the psychedelic is MDMA, wherein the nelotanserin is administered to post-treat at least 30 minutes post to the MDMA form disclosed herein, including those described in Table Ex3. In some embodiments, the serotonin receptor modulator is nelotanserin and the psychedelic is MDMA, wherein the nelotanserin is administered to post-treat between at least 60 minutes and 240 minutes post to the administration or release of the MDMA form disclosed herein, including those described in Table Ex3. In some embodiments, the serotonin receptor modulator is nelotanserin and the psychedelic is MDMA, wherein the nelotanserin is administered to post-treat at least 90 minutes post to the MDMA form disclosed herein, including those described in Table Ex3. In some embodiments, the serotonin receptor modulator is nelotanserin and the psychedelic is MDMA, wherein the nelotanserin is administered to post-treat at least 120 minutes post to the MDMA form disclosed herein, including those described in Table Ex3.

In some embodiments, the serotonin receptor modulator is nelotanserin and the psychedelic is MDMA, wherein the nelotanserin is administered to post-treat at least 150 minutes post to the MDMA form disclosed herein, including those described in Table Ex3. In some embodiments, the serotonin receptor modulator is nelotanserin and the psychedelic is MDMA, wherein the nelotanserin is administered to post-treat between about 15 minutes and about 150 minutes post to the MDMA form disclosed herein, including those described in Table Ex3. In some embodiments, the serotonin receptor modulator is nelotanserin and the psychedelic is MDMA, wherein the nelotanserin is administered to post-treat at least 180 minutes post to the MDMA form disclosed herein, including those described in Table Ex3. In some embodiments, the serotonin receptor modulator is nelotanserin and the psychedelic is MDMA, wherein the nelotanserin is administered to post-treat at least 210 minutes post to the MDMA form disclosed herein, including those described in Table Ex3. In some embodiments, the serotonin receptor modulator is nelotanserin and the psychedelic is MDMA, wherein the nelotanserin is administered to post-treat at least 240 minutes post to the MDMA form disclosed herein, including those described in Table Ex3. In some embodiments, the serotonin receptor modulator is nelotanserin and the psychedelic is MDMA, wherein the nelotanserin is administered to post-treat at least 270 minutes post to the MDMA form disclosed herein, including those described in Table Ex3.

In some embodiments, the serotonin receptor modulator is nelotanserin and the psychedelic is MDMA, wherein the nelotanserin is administered to post-treat at least 300 minutes post to the MDMA form disclosed herein, including those described in Table Ex3. In some embodiments, the serotonin receptor modulator is nelotanserin and the psychedelic is MDMA, wherein the nelotanserin is administered to post-treat at least 330 minutes post to the MDMA form disclosed herein, including those described in Table Ex3. In some embodiments, the serotonin receptor modulator is nelotanserin and the psychedelic is MDMA, wherein the nelotanserin is administered to post-treat at least 360 minutes post to the MDMA form disclosed herein, including those described in Table Ex3. In some preferred embodiments, the serotonin receptor modulator is nelotanserin and the psychedelic is MDMA, wherein nelotanserin is administered to post-treat between about 60 minutes and about 180 minutes post to the administration of the MDMA form disclosed herein, including those described in Table Ex3.

In some embodiments, the serotonin receptor modulator is pruvanserin and the psychedelic is MDMA, wherein the pruvanserin is administered to post-treat at least 15 minutes post to the administration of the MDMA form disclosed herein, including those described in Table Ex3. In some embodiments, the serotonin receptor modulator is pruvanserin and the psychedelic is MDMA, wherein the pruvanserin is administered to post-treat at least 30 minutes post to the MDMA form disclosed herein, including those described in Table Ex3. In some embodiments, the serotonin receptor modulator is pruvanserin and the psychedelic is MDMA, wherein the pruvanserin is administered to post-treat between at least 60 minutes and 240 minutes post to the administration or release of the MDMA form disclosed herein, including those described in Table Ex3. In some embodiments, the serotonin receptor modulator is pruvanserin and the psychedelic is MDMA, wherein the pruvanserin is administered to post-treat at least 90 minutes post to the MDMA form disclosed herein, including those described in Table Ex3. In some embodiments, the serotonin receptor modulator is pruvanserin and the psychedelic is MDMA, wherein the pruvanserin is administered to post-treat at least 120 minutes post to the MDMA form disclosed herein, including those described in Table Ex3. In some embodiments, the serotonin receptor modulator is pruvanserin and the psychedelic is MDMA, wherein the pruvanserin is administered to post-treat at least 150 minutes post to the MDMA form disclosed herein, including those described in Table Ex3. In some embodiments, the serotonin receptor modulator is pruvanserin and the psychedelic is MDMA, wherein the pruvanserin is administered to post-treat between about 15 minutes and about 150 minutes post to the MDMA form disclosed herein, including those described in Table Ex3. In some embodiments, the serotonin receptor modulator is pruvanserin and the psychedelic is MDMA, wherein the pruvanserin is administered to post-treat at least 180 minutes post to the MDMA form disclosed herein, including those described in Table Ex3. In some embodiments, the serotonin receptor modulator is pruvanserin and the psychedelic is MDMA, wherein the pruvanserin is administered to post-treat at least 210 minutes post to the MDMA form disclosed herein, including those described in Table Ex3.

In some embodiments, the serotonin receptor modulator is pruvanserin and the psychedelic is MDMA, wherein the pruvanserin is administered to post-treat at least 240 minutes post to the MDMA form disclosed herein, including those described in Table Ex3. In some embodiments, the serotonin receptor modulator is pruvanserin and the psychedelic is MDMA, wherein the pruvanserin is administered to post-treat at least 270 minutes post to the MDMA form disclosed herein, including those described in Table Ex3. In some embodiments, the serotonin receptor modulator is pruvanserin and the psychedelic is MDMA, wherein the pruvanserin is administered to post-treat at least 300 minutes post to the MDMA form disclosed herein, including those described in Table Ex3. In some embodiments, the serotonin receptor modulator is pruvanserin and the psychedelic is MDMA, wherein the pruvanserin is administered to post-treat at least 330 minutes post to the MDMA form disclosed herein, including those described in Table Ex3. In some embodiments, the serotonin receptor modulator is pruvanserin and the psychedelic is MDMA, wherein the pruvanserin is administered to post-treat at least 360 minutes post to the MDMA form disclosed herein, including those described in Table Ex3. In some preferred embodiments, the serotonin receptor modulator is pruvanserin and the psychedelic is MDMA, wherein pruvanserin is administered to post-treat between about 60 minutes and about 180 minutes post to the administration of the MDMA form disclosed herein, including those described in Table Ex3.

In some embodiments, the serotonin receptor modulator is flibanserin, wherein the flibanserin is administered to post-treat at least 15 minutes post to the administration of the MDMA form disclosed herein, including those described in Table Ex3. In some embodiments, the serotonin receptor modulator is flibanserin, wherein the flibanserin is administered to post-treat at least 30 minutes post to the MDMA form disclosed herein, including those described in Table Ex3. In some embodiments, the serotonin receptor modulator is flibanserin, wherein the flibanserin is administered to post-treat between at least 60 minutes and 240 minutes post to the administration or release of the MDMA form disclosed herein, including those described in Table Ex3. In some embodiments, the serotonin receptor modulator is flibanserin, wherein the flibanserin is administered to post-treat at least 90 minutes post to the MDMA form disclosed herein, including those described in Table Ex3. In some embodiments, the serotonin receptor modulator is flibanserin, wherein the flibanserin is administered to post-treat at least 120 minutes post to the MDMA form disclosed herein, including those described in Table Ex3. In some embodiments, the serotonin receptor modulator is flibanserin, wherein the flibanserin is administered to post-treat at least 150 minutes post to the MDMA form disclosed herein, including those described in Table Ex3. In some embodiments, the serotonin receptor modulator is flibanserin, wherein the flibanserin is administered to post-treat between about 15 minutes and about 150 minutes post to the MDMA form disclosed herein, including those described in Table Ex3. In some embodiments, the serotonin receptor modulator is flibanserin, wherein the flibanserin is administered to post-treat at least 180 minutes post to the MDMA form disclosed herein, including those described in Table Ex3. In some embodiments, the serotonin receptor modulator is flibanserin, wherein the flibanserin is administered to post-treat at least 210 minutes post to the MDMA form disclosed herein, including those described in Table Ex3.

In some embodiments, the serotonin receptor modulator is flibanserin, wherein the flibanserin is administered to post-treat at least 240 minutes post to the MDMA form disclosed herein, including those described in Table Ex3. In some embodiments, the serotonin receptor modulator is flibanserinserin, wherein the flibanserin is administered to post-treat at least 270 minutes post to the MDMA form disclosed herein, including those described in Table Ex3. In some embodiments, the serotonin receptor modulator is flibanserin, wherein the flibanserin is administered to post-treat at least 300 minutes post to the MDMA form disclosed herein, including those described in Table Ex3. In some embodiments, the serotonin receptor modulator is flibanserin, wherein the flibanserin is administered to post-treat at least 330 minutes post to the MDMA form disclosed herein, including those described in Table Ex3. In some embodiments, the serotonin receptor modulator is flibanserin, wherein the flibanserin is administered to post-treat at least 360 minutes post to the MDMA form disclosed herein, including those described in Table Ex3. In some preferred embodiments, the serotonin receptor modulator is flibanserin, wherein flibanserin is administered to post-treat between about 60 minutes and about 180 minutes post to the administration of the MDMA form disclosed herein, including those described in Table Ex3.

In some embodiments, the serotonin receptor modulator is olanzapine, wherein the olanzapine is administered to post-treat at least 15 minutes post to the administration of the MDMA form disclosed herein, including those described in Table Ex3. In some embodiments, the serotonin receptor modulator is olanzapine, wherein the olanzapine is administered to post-treat at least 30 minutes post to the MDMA form disclosed herein, including those described in Table Ex3. In some embodiments, the serotonin receptor modulator is olanzapine, wherein the olanzapine is administered to post-treat between at least 60 minutes and 240 minutes post to the administration or release of the MDMA form disclosed herein, including those described in Table Ex3. In some embodiments, the serotonin receptor modulator is olanzapine, wherein the olanzapine is administered to post-treat at least 90 minutes post to the MDMA form disclosed herein, including those described in Table Ex3. In some embodiments, the serotonin receptor modulator is olanzapine, wherein the olanzapine is administered to post-treat at least 120 minutes post to the MDMA form disclosed herein, including those described in Table Ex3. In some embodiments, the serotonin receptor modulator is olanzapine, wherein the olanzapine is administered to post-treat at least 150 minutes post to the MDMA form disclosed herein, including those described in Table Ex3. In some embodiments, the serotonin receptor modulator is olanzapine, wherein the olanzapine is administered to post-treat between about 15 minutes and about 150 minutes post to the MDMA form disclosed herein, including those described in Table Ex3. In some embodiments, the serotonin receptor modulator is olanzapine, wherein the olanzapine is administered to post-treat at least 180 minutes post to the MDMA form disclosed herein, including those described in Table Ex3. In some embodiments, the serotonin receptor modulator is olanzapine, wherein the olanzapine is administered to post-treat at least 210 minutes post to the MDMA form disclosed herein, including those described in Table Ex3.

In some embodiments, the serotonin receptor modulator is olanzapine, wherein the olanzapine is administered to post-treat at least 240 minutes post to the MDMA form disclosed herein, including those described in Table Ex3. In some embodiments, the serotonin receptor modulator is olanzapine, wherein the olanzapine is administered to post-treat at least 270 minutes post to the MDMA form disclosed herein, including those described in Table Ex3. In some embodiments, the serotonin receptor modulator is olanzapine, wherein the olanzapine is administered to post-treat at least 300 minutes post to the MDMA form disclosed herein, including those described in Table Ex3. In some embodiments, the serotonin receptor modulator is olanzapine, wherein the olanzapine is administered to post-treat at least 330 minutes post to the MDMA form disclosed herein, including those described in Table Ex3. In some embodiments, the serotonin receptor modulator is olanzapine, wherein the olanzapine is administered to post-treat at least 360 minutes post to the MDMA form disclosed herein, including those described in Table Ex3. In some preferred embodiments, the serotonin receptor modulator is olanzapine, wherein olanzapine is administered to post-treat between about 60 minutes and about 180 minutes post to the administration of the MDMA form disclosed herein, including those described in Table Ex3.

In some embodiments, the serotonin receptor modulator is quetiapine, wherein the quetiapine is administered to post-treat at least 15 minutes post to the administration of the MDMA form disclosed herein, including those described in Table Ex3. In some embodiments, the serotonin receptor modulator is quetiapine, wherein the quetiapine is administered to post-treat at least 30 minutes post to the MDMA form disclosed herein, including those described in Table Ex3. In some embodiments, the serotonin receptor modulator is quetiapine, wherein the quetiapine is administered to post-treat between at least 60 minutes and 240 minutes post to the administration or release of the MDMA form disclosed herein, including those described in Table Ex3. In some embodiments, the serotonin receptor modulator is quetiapine, wherein the quetiapine is administered to post-treat at least 90 minutes post to the MDMA form disclosed herein, including those described in Table Ex3. In some embodiments, the serotonin receptor modulator is quetiapine, wherein the quetiapine is administered to post-treat at least 120 minutes post to the MDMA form disclosed herein, including those described in Table Ex3. In some embodiments, the serotonin receptor modulator is quetiapine, wherein the quetiapine is administered to post-treat at least 150 minutes post to the MDMA form disclosed herein, including those described in Table Ex3. In some embodiments, the serotonin receptor modulator is quetiapine, wherein the quetiapine is administered to post-treat between about 15 minutes and about 150 minutes post to the MDMA form disclosed herein, including those described in Table Ex3. In some embodiments, the serotonin receptor modulator is quetiapine, wherein the quetiapine is administered to post-treat at least 180 minutes post to the MDMA form disclosed herein, including those described in Table Ex3. In some embodiments, the serotonin receptor modulator is quetiapine, wherein the quetiapine is administered to post-treat at least 210 minutes post to the MDMA form disclosed herein, including those described in Table Ex3.

In some embodiments, the serotonin receptor modulator is quetiapine, wherein the quetiapine is administered to post-treat at least 240 minutes post to the MDMA form disclosed herein, including those described in Table Ex3. In some embodiments, the serotonin receptor modulator is quetiapine, wherein the quetiapine is administered to post-treat at least 270 minutes post to the MDMA form disclosed herein, including those described in Table Ex3. In some embodiments, the serotonin receptor modulator is quetiapine, wherein the quetiapine is administered to post-treat at least 300 minutes post to the MDMA form disclosed herein, including those described in Table Ex3. In some embodiments, the serotonin receptor modulator is quetiapine, wherein the quetiapine is administered to post-treat at least 330 minutes post to the MDMA form disclosed herein, including those described in Table Ex3. In some embodiments, the serotonin receptor modulator is quetiapine, wherein the quetiapine is administered to post-treat at least 360 minutes post to the MDMA form disclosed herein, including those described in Table Ex3. In some preferred embodiments, the serotonin receptor modulator is quetiapine, wherein quetiapine is administered to post-treat between about 60 minutes and about 180 minutes post to the administration of the MDMA form disclosed herein, including those described in Table Ex3.

In some embodiments, the serotonin receptor modulator is risperidone, wherein the risperidone is administered to post-treat at least 15 minutes post to the administration of the MDMA form disclosed herein, including those described in Table Ex3. In some embodiments, the serotonin receptor modulator is risperidone, wherein the risperidone is administered to post-treat at least 30 minutes post to the MDMA form disclosed herein, including those described in Table Ex3. In some embodiments, the serotonin receptor modulator is risperidone, wherein the risperidone is administered to post-treat between at least 60 minutes and 240 minutes post to the administration or release of the MDMA form disclosed herein, including those described in Table Ex3. In some embodiments, the serotonin receptor modulator is risperidone, wherein the risperidone is administered to post-treat at least 90 minutes post to the MDMA form disclosed herein, including those described in Table Ex3. In some embodiments, the serotonin receptor modulator is risperidone, wherein the risperidone is administered to post-treat at least 120 minutes post to the MDMA form disclosed herein, including those described in Table Ex3. In some embodiments, the serotonin receptor modulator is risperidone, wherein the risperidone is administered to post-treat at least 150 minutes post to the MDMA form disclosed herein, including those described in Table Ex3. In some embodiments, the serotonin receptor modulator is risperidone, wherein the risperidone is administered to post-treat between about 15 minutes and about 150 minutes post to the MDMA form disclosed herein, including those described in Table Ex3. In some embodiments, the serotonin receptor modulator is risperidone, wherein the risperidone is administered to post-treat at least 180 minutes post to the MDMA form disclosed herein, including those described in Table Ex3. In some embodiments, the serotonin receptor modulator is risperidone, wherein the risperidone is administered to post-treat at least 210 minutes post to the MDMA form disclosed herein, including those described in Table Ex3.

In some embodiments, the serotonin receptor modulator is risperidone, wherein the risperidone is administered to post-treat at least 240 minutes post to the MDMA form disclosed herein, including those described in Table Ex3. In some embodiments, the serotonin receptor modulator is risperidone, wherein the risperidone is administered to post-treat at least 270 minutes post to the MDMA form disclosed herein, including those described in Table Ex3. In some embodiments, the serotonin receptor modulator is risperidone, wherein the risperidone is administered to post-treat at least 300 minutes post to the MDMA form disclosed herein, including those described in Table Ex3. In some embodiments, the serotonin receptor modulator is risperidone, wherein the risperidone is administered to post-treat at least 330 minutes post to the MDMA form disclosed herein, including those described in Table Ex3. In some embodiments, the serotonin receptor modulator is risperidone, wherein the risperidone is administered to post-treat at least 360 minutes post to the MDMA form disclosed herein, including those described in Table Ex3. In some preferred embodiments, the serotonin receptor modulator is risperidone, wherein risperidone is administered to post-treat between about 60 minutes and about 180 minutes post to the administration of the MDMA form disclosed herein, including those described in Table Ex3.

In some embodiments, the serotonin receptor modulator is eplivanserin and the psychedelic is MDMA hemifumarate Form A, wherein the eplivanserin is administered to post-treat at least 15 minutes after the administration of the MDMA hemifumarate Form A. In some embodiments, the serotonin receptor modulator is eplivanserin and the psychedelic is MDMA hemifumarate Form A, wherein the eplivanserin is administered to post-treat between at least 30 minutes after and 360 minutes after the release or administration of the MDMA hemifumarate Form A. In some embodiments, the serotonin receptor modulator is eplivanserin and the psychedelic is MDMA hemifumarate Form A, wherein the eplivanserin is administered to post-treat between at least 60 minutes after and 360 minutes after the release or administration of the MDMA hemifumarate Form A. In some embodiments, the serotonin receptor modulator is eplivanserin and the psychedelic is MDMA hemifumarate Form A, wherein the eplivanserin is administered to post-treat between at least 90 minutes and 240 minutes after the MDMA hemifumarate Form A. In some embodiments, the serotonin receptor modulator is eplivanserin and the psychedelic is MDMA hemifumarate Form A, wherein the eplivanserin is administered to post-treat at least 120 minutes after the MDMA hemifumarate Form A.

In some embodiments, the serotonin receptor modulator is eplivanserin and the psychedelic is MDMA hemifumarate Form A, wherein the eplivanserin is administered to post-treat at least 150 minutes after the MDMA hemifumarate Form A. In some embodiments, the serotonin receptor modulator is eplivanserin and the psychedelic is MDMA hemifumarate Form A, wherein the eplivanserin is administered to post-treat between about 15 minutes and about 150 minutes after the MDMA hemifumarate Form A. In some embodiments, the serotonin receptor modulator is eplivanserin and the psychedelic is MDMA hemifumarate Form A, wherein the eplivanserin is administered to post-treat at least 180 minutes after the MDMA hemifumarate Form A. In some embodiments, the serotonin receptor modulator is eplivanserin and the psychedelic is MDMA hemifumarate Form A, wherein the eplivanserin is administered to post-treat at least 210 minutes after the MDMA hemifumarate Form A. In some embodiments, the serotonin receptor modulator is eplivanserin and the psychedelic is MDMA hemifumarate Form A, wherein the eplivanserin is administered to post-treat at least 240 minutes after the MDMA hemifumarate Form A.

In some embodiments, the serotonin receptor modulator is eplivanserin and the psychedelic is MDMA hemifumarate Form A, wherein the eplivanserin is administered to post-treat at least 270 minutes after the MDMA hemifumarate Form A. In some embodiments, the serotonin receptor modulator is eplivanserin and the psychedelic is MDMA hemifumarate Form A, wherein the eplivanserin is administered to post-treat at least 300 minutes after the MDMA hemifumarate Form A. In some embodiments, the serotonin receptor modulator is eplivanserin and the psychedelic is MDMA hemifumarate Form A, wherein the eplivanserin is administered to post-treat at least 330 minutes after the MDMA hemifumarate Form A. In some embodiments, the serotonin receptor modulator is eplivanserin and the psychedelic is MDMA hemifumarate Form A, wherein the eplivanserin is administered to post-treat at least 360 minutes after the MDMA hemifumarate Form A.

In some preferred embodiments, the serotonin receptor modulator is eplivanserin and the psychedelic is MDMA hemifumarate Form A, wherein eplivanserin is administered to post-treat between about 60 minutes and about 180 minutes after the administration of the MDMA hemifumarate Form A.

In some embodiments, the serotonin receptor modulator is volinanserin and the psychedelic is MDMA hemifumarate Form A, wherein the volinanserin is administered to post-treat a subject between at least 15 minutes and 360 minutes after the administration or release of the MDMA hemifumarate Form A. In some embodiments, the serotonin receptor modulator is volinanserin and the psychedelic is MDMA hemifumarate Form A, wherein the volinanserin is administered to post-treat between at least 30 minutes and 360 minutes after the administration or release of the MDMA hemifumarate Form A. In some embodiments, the serotonin receptor modulator is volinanserin and the psychedelic is MDMA hemifumarate Form A, wherein the volinanserin is administered to post-treat between at least 60 minutes and 240 minutes after the administration or release of the MDMA hemifumarate Form A. In some embodiments, the serotonin receptor modulator is volinanserin and the psychedelic is MDMA hemifumarate Form A, wherein the volinanserin is administered to post-treat at least 90 minutes after MDMA hemifumarate Form A. In some embodiments, the serotonin receptor modulator is volinanserin and the psychedelic is MDMA hemifumarate Form A, wherein the volinanserin is administered to post-treat at least 120 minutes after the MDMA hemifumarate Form A.

In some embodiments, the serotonin receptor modulator is volinanserin and the psychedelic is MDMA hemifumarate Form A, wherein the volinanserin is administered to post-treat at least 150 minutes after the MDMA hemifumarate Form A. In some embodiments, the serotonin receptor modulator is volinanserin and the psychedelic is MDMA hemifumarate Form A, wherein the volinanserin is administered to post-treat between about 15 minutes and about 150 minutes after the MDMA hemifumarate Form A. In some embodiments, the serotonin receptor modulator is volinanserin and the psychedelic is MDMA hemifumarate Form A, wherein the volinanserin is administered to post-treat at least 180 minutes after the MDMA hemifumarate Form A. In some embodiments, the serotonin receptor modulator is volinanserin and the psychedelic is MDMA hemifumarate Form A, wherein the volinanserin is administered to post-treat at least 210 minutes after the MDMA hemifumarate Form A. In some embodiments, the serotonin receptor modulator is volinanserin and the psychedelic is MDMA hemifumarate Form A, wherein the volinanserin is administered to post-treat at least 240 minutes after the MDMA hemifumarate Form A. In some embodiments, the serotonin receptor modulator is volinanserin and the psychedelic is MDMA hemifumarate Form A, wherein the volinanserin is administered to post-treat at least 270 minutes after the MDMA hemifumarate Form A. In some embodiments, the serotonin receptor modulator is volinanserin and the psychedelic is MDMA hemifumarate Form A, wherein the volinanserin is administered to post-treat at least 300 minutes after the MDMA hemifumarate Form A. In some embodiments, the serotonin receptor modulator is volinanserin and the psychedelic is MDMA hemifumarate Form A, wherein the volinanserin is administered to post-treat at least 330 minutes after the MDMA hemifumarate Form A. In some embodiments, the serotonin receptor modulator is volinanserin and the psychedelic is MDMA hemifumarate Form A, wherein the volinanserin is administered to post-treat at least 360 minutes after the MDMA hemifumarate Form A. In some preferred embodiments, the serotonin receptor modulator is volinanserin and the psychedelic is MDMA hemifumarate Form A, wherein volinanserin is administered to post-treat between about 60 minutes and about 180 minutes after the administration of the MDMA hemifumarate Form A.

In some embodiments, the serotonin receptor modulator is ketanserin and the psychedelic is MDMA hemifumarate Form A, wherein the ketanserin is administered to post-treat at least 15 minutes after the administration of the MDMA hemifumarate Form A. In some embodiments, the serotonin receptor modulator is ketanserin and the psychedelic is MDMA hemifumarate Form A, wherein the ketanserin is administered to post-treat between at least 30 minutes and 360 minutes after the administration or release of the MDMA hemifumarate Form A. In some embodiments, the serotonin receptor modulator is ketanserin and the psychedelic is MDMA hemifumarate Form A, wherein the ketanserin is administered to post-treat between at least 60 minutes and 240 minutes after the administration or release of the MDMA hemifumarate Form A. In some embodiments, the serotonin receptor modulator is ketanserin and the psychedelic is MDMA hemifumarate Form A, wherein the ketanserin is administered to post-treat at least 90 minutes after the MDMA hemifumarate Form A. In some embodiments, the serotonin receptor modulator is ketanserin and the psychedelic is MDMA hemifumarate Form A, wherein the ketanserin is administered to post-treat at least 120 minutes after the MDMA hemifumarate Form A. In some embodiments, the serotonin receptor modulator is ketanserin and the psychedelic is MDMA hemifumarate Form A, wherein the ketanserin is administered to post-treat at least 150 minutes after the MDMA hemifumarate Form A. In some embodiments, the serotonin receptor modulator is ketanserin and the psychedelic is MDMA hemifumarate Form A, wherein the ketanserin is administered to post-treat between about 15 minutes and about 150 minutes after the MDMA hemifumarate Form A. In some embodiments, the serotonin receptor modulator is ketanserin and the psychedelic is MDMA hemifumarate Form A, wherein the ketanserin is administered to post-treat at least 180 minutes after the MDMA hemifumarate Form A. In some embodiments, the serotonin receptor modulator is ketanserin and the psychedelic is MDMA hemifumarate Form A, wherein the ketanserin is administered to post-treat at least 210 minutes after the MDMA hemifumarate Form A. In some embodiments, the serotonin receptor modulator is ketanserin and the psychedelic is MDMA hemifumarate Form A, wherein the ketanserin is administered to post-treat at least 240 minutes after the MDMA hemifumarate Form A. In some embodiments, the serotonin receptor modulator is ketanserin and the psychedelic is MDMA hemifumarate Form A, wherein the ketanserin is administered to post-treat at least 270 minutes after the MDMA hemifumarate Form A. In some embodiments, the serotonin receptor modulator is ketanserin and the psychedelic is MDMA hemifumarate Form A, wherein the ketanserin is administered to post-treat at least 300 minutes after the MDMA hemifumarate Form A. In some embodiments, the serotonin receptor modulator is ketanserin and the psychedelic is MDMA hemifumarate Form A, wherein the ketanserin is administered to post-treat at least 330 minutes after the MDMA hemifumarate Form A. In some embodiments, the serotonin receptor modulator is ketanserin and the psychedelic is MDMA hemifumarate Form A, wherein the ketanserin is administered to post-treat at least 360 minutes after the MDMA hemifumarate Form A. In some preferred embodiments, the serotonin receptor modulator is ketanserin and the psychedelic is MDMA hemifumarate Form A, wherein ketanserin is administered to post-treat between about 60 minutes and about 180 minutes after the administration of the MDMA hemifumarate Form A.

In some embodiments, the serotonin receptor modulator is ritanserin and the psychedelic is MDMA hemifumarate Form A, wherein the ritanserin is administered to post-treat at least 15 minutes after the administration of the MDMA hemifumarate Form A. In some embodiments, the serotonin receptor modulator is ritanserin and the psychedelic is MDMA hemifumarate Form A, wherein the ritanserin is administered to post-treat at least 30 minutes after the MDMA hemifumarate Form A. In some embodiments, the serotonin receptor modulator is ritanserin and the psychedelic is MDMA hemifumarate Form A, wherein the ritanserin is administered to post-treat between at least 60 minutes and 240 minutes after the administration or release of the MDMA hemifumarate Form A. In some embodiments, the serotonin receptor modulator is ritanserin and the psychedelic is MDMA hemifumarate Form A, wherein the ritanserin is administered to post-treat at least 90 minutes after the MDMA hemifumarate Form A. In some embodiments, the serotonin receptor modulator is ritanserin and the psychedelic is MDMA hemifumarate Form A, wherein the ritanserin is administered to post-treat at least 120 minutes after the MDMA hemifumarate Form A. In some embodiments, the serotonin receptor modulator is ritanserin and the psychedelic is MDMA hemifumarate Form A, wherein the ritanserin is administered to post-treat at least 150 minutes after the MDMA hemifumarate Form A. In some embodiments, the serotonin receptor modulator is ritanserin and the psychedelic is MDMA hemifumarate Form A, wherein the ritanserin is administered to post-treat between about 15 minutes and about 150 minutes after the MDMA hemifumarate Form A. In some embodiments, the serotonin receptor modulator is ritanserin and the psychedelic is MDMA hemifumarate Form A, wherein the ritanserin is administered to post-treat at least 180 minutes after the MDMA hemifumarate Form A. In some embodiments, the serotonin receptor modulator is ritanserin and the psychedelic is MDMA hemifumarate Form A, wherein the ritanserin is administered to post-treat at least 210 minutes after the MDMA hemifumarate Form A. In some embodiments, the serotonin receptor modulator is ritanserin and the psychedelic is MDMA hemifumarate Form A, wherein the ritanserin is administered to post-treat at least 240 minutes after the MDMA hemifumarate Form A. In some embodiments, the serotonin receptor modulator is ritanserin and the psychedelic is MDMA hemifumarate Form A, wherein the ritanserin is administered to post-treat at least 270 minutes after the MDMA hemifumarate Form A. In some embodiments, the serotonin receptor modulator is ritanserin and the psychedelic is MDMA hemifumarate Form A, wherein the ritanserin is administered to post-treat at least 300 minutes after the MDMA hemifumarate Form A. In some embodiments, the serotonin receptor modulator is ritanserin and the psychedelic is MDMA hemifumarate Form A, wherein the ritanserin is administered to post-treat at least 330 minutes after the MDMA hemifumarate Form A. In some embodiments, the serotonin receptor modulator is ritanserin and the psychedelic is MDMA hemifumarate Form A, wherein the ritanserin is administered to post-treat at least 360 minutes after the MDMA hemifumarate Form A. In some preferred embodiments, the serotonin receptor modulator is ritanserin and the psychedelic is MDMA hemifumarate Form A, wherein ritanserin is administered to post-treat between about 60 minutes and about 180 minutes after the administration of the MDMA hemifumarate Form A.

In some embodiments, the serotonin receptor modulator is pimavanserin and the psychedelic is MDMA hemifumarate Form A, wherein the pimavanserin is administered to post-treat at least 15 minutes after the administration of the MDMA hemifumarate Form A. In some embodiments, the serotonin receptor modulator is pimavanserin and the psychedelic is MDMA hemifumarate Form A, wherein the pimavanserin is administered to post-treat at least 30 minutes after the MDMA hemifumarate Form A. In some embodiments, the serotonin receptor modulator is pimavanserin and the psychedelic is MDMA hemifumarate Form A, wherein the pimavanserin is administered to post-treat between at least 60 minutes and 240 minutes after the administration or release of the MDMA hemifumarate Form A. In some embodiments, the serotonin receptor modulator is pimavanserin and the psychedelic is MDMA hemifumarate Form A, wherein the pimavanserin is administered to post-treat at least 90 minutes after the MDMA hemifumarate Form A. In some embodiments, the serotonin receptor modulator is pimavanserin and the psychedelic is MDMA hemifumarate Form A, wherein the pimavanserin is administered to post-treat at least 120 minutes after the MDMA hemifumarate Form A. In some embodiments, the serotonin receptor modulator is pimavanserin and the psychedelic is MDMA hemifumarate Form A, wherein the pimavanserin is administered to post-treat at least 150 minutes after the MDMA hemifumarate Form A. In some embodiments, the serotonin receptor modulator is pimavanserin and the psychedelic is MDMA hemifumarate Form A, wherein the pimavanserin is administered to post-treat between about 15 minutes and about 150 minutes after the MDMA hemifumarate Form A. In some embodiments, the serotonin receptor modulator is pimavanserin and the psychedelic is MDMA hemifumarate Form A, wherein the pimavanserin is administered to post-treat at least 180 minutes after the MDMA hemifumarate Form A. In some embodiments, the serotonin receptor modulator is pimavanserin and the psychedelic is MDMA hemifumarate Form A, wherein the pimavanserin is administered to post-treat at least 210 minutes after the MDMA hemifumarate Form A. In some embodiments, the serotonin receptor modulator is pimavanserin and the psychedelic is MDMA hemifumarate Form A, wherein the pimavanserin is administered to post-treat at least 240 minutes after the MDMA hemifumarate Form A. In some embodiments, the serotonin receptor modulator is pimavanserin and the psychedelic is MDMA hemifumarate Form A, wherein the pimavanserin is administered to post-treat at least 270 minutes after the MDMA hemifumarate Form A. In some embodiments, the serotonin receptor modulator is pimavanserin and the psychedelic is MDMA hemifumarate Form A, wherein the pimavanserin is administered to post-treat at least 300 minutes after the MDMA hemifumarate Form A. In some embodiments, the serotonin receptor modulator is pimavanserin and the psychedelic is MDMA hemifumarate Form A, wherein the pimavanserin is administered to post-treat at least 330 minutes after the MDMA hemifumarate Form A. In some embodiments, the serotonin receptor modulator is pimavanserin and the psychedelic is MDMA hemifumarate Form A, wherein the pimavanserin is administered to post-treat at least 360 minutes after the MDMA hemifumarate Form A. In some preferred embodiments, the serotonin receptor modulator is pimavanserin and the psychedelic is MDMA hemifumarate Form A, wherein pimavanserin is administered to post-treat between about 60 minutes and about 180 minutes after the administration of the MDMA hemifumarate Form A.

In some embodiments, the serotonin receptor modulator is nelotanserin and the psychedelic is MDMA hemifumarate Form A, wherein the nelotanserin is administered to post-treat at least 15 minutes after the administration of the MDMA hemifumarate Form A. In some embodiments, the serotonin receptor modulator is nelotanserin and the psychedelic is MDMA hemifumarate Form A, wherein the nelotanserin is administered to post-treat at least 30 minutes after the MDMA hemifumarate Form A. In some embodiments, the serotonin receptor modulator is nelotanserin and the psychedelic is MDMA hemifumarate Form A, wherein the nelotanserin is administered to post-treat between at least 60 minutes and 240 minutes after the administration or release of the MDMA hemifumarate Form A. In some embodiments, the serotonin receptor modulator is nelotanserin and the psychedelic is MDMA hemifumarate Form A, wherein the nelotanserin is administered to post-treat at least 90 minutes after the MDMA hemifumarate Form A. In some embodiments, the serotonin receptor modulator is nelotanserin and the psychedelic is MDMA hemifumarate Form A, wherein the nelotanserin is administered to post-treat at least 120 minutes after the MDMA hemifumarate Form A.

In some embodiments, the serotonin receptor modulator is nelotanserin and the psychedelic is MDMA hemifumarate Form A, wherein the nelotanserin is administered to post-treat at least 150 minutes after the MDMA hemifumarate Form A. In some embodiments, the serotonin receptor modulator is nelotanserin and the psychedelic is MDMA hemifumarate Form A, wherein the nelotanserin is administered to post-treat between about 15 minutes and about 150 minutes after the MDMA hemifumarate Form A. In some embodiments, the serotonin receptor modulator is nelotanserin and the psychedelic is MDMA hemifumarate Form A, wherein the nelotanserin is administered to post-treat at least 180 minutes after the MDMA hemifumarate Form A. In some embodiments, the serotonin receptor modulator is nelotanserin and the psychedelic is MDMA hemifumarate Form A, wherein the nelotanserin is administered to post-treat at least 210 minutes after the MDMA hemifumarate Form A. In some embodiments, the serotonin receptor modulator is nelotanserin and the psychedelic is MDMA hemifumarate Form A, wherein the nelotanserin is administered to post-treat at least 240 minutes after the MDMA hemifumarate Form A. In some embodiments, the serotonin receptor modulator is nelotanserin and the psychedelic is MDMA hemifumarate Form A, wherein the nelotanserin is administered to post-treat at least 270 minutes after the MDMA hemifumarate Form A.

In some embodiments, the serotonin receptor modulator is nelotanserin and the psychedelic is MDMA hemifumarate Form A, wherein the nelotanserin is administered to post-treat at least 300 minutes after the MDMA hemifumarate Form A. In some embodiments, the serotonin receptor modulator is nelotanserin and the psychedelic is MDMA hemifumarate Form A, wherein the nelotanserin is administered to post-treat at least 330 minutes after the MDMA hemifumarate Form A. In some embodiments, the serotonin receptor modulator is nelotanserin and the psychedelic is MDMA hemifumarate Form A, wherein the nelotanserin is administered to post-treat at least 360 minutes after the MDMA hemifumarate Form A. In some preferred embodiments, the serotonin receptor modulator is nelotanserin and the psychedelic is MDMA hemifumarate Form A, wherein nelotanserin is administered to post-treat between about 60 minutes and about 180 minutes after the administration of the MDMA hemifumarate Form A.

In some embodiments, the serotonin receptor modulator is pruvanserin and the psychedelic is MDMA hemifumarate Form A, wherein the pruvanserin is administered to post-treat at least 15 minutes after the administration of the MDMA hemifumarate Form A. In some embodiments, the serotonin receptor modulator is pruvanserin and the psychedelic is MDMA hemifumarate Form A, wherein the pruvanserin is administered to post-treat at least 30 minutes after the MDMA hemifumarate Form A. In some embodiments, the serotonin receptor modulator is pruvanserin and the psychedelic is MDMA hemifumarate Form A, wherein the pruvanserin is administered to post-treat between at least 60 minutes and 240 minutes after the administration or release of the MDMA hemifumarate Form A. In some embodiments, the serotonin receptor modulator is pruvanserin and the psychedelic is MDMA hemifumarate Form A, wherein the pruvanserin is administered to post-treat at least 90 minutes after the MDMA hemifumarate Form A. In some embodiments, the serotonin receptor modulator is pruvanserin and the psychedelic is MDMA hemifumarate Form A, wherein the pruvanserin is administered to post-treat at least 120 minutes after the MDMA hemifumarate Form A. In some embodiments, the serotonin receptor modulator is pruvanserin and the psychedelic is MDMA hemifumarate Form A, wherein the pruvanserin is administered to post-treat at least 150 minutes after the MDMA hemifumarate Form A. In some embodiments, the serotonin receptor modulator is pruvanserin and the psychedelic is MDMA hemifumarate Form A, wherein the pruvanserin is administered to post-treat between about 15 minutes and about 150 minutes after the MDMA hemifumarate Form A. In some embodiments, the serotonin receptor modulator is pruvanserin and the psychedelic is MDMA hemifumarate Form A, wherein the pruvanserin is administered to post-treat at least 180 minutes after the MDMA hemifumarate Form A. In some embodiments, the serotonin receptor modulator is pruvanserin and the psychedelic is MDMA hemifumarate Form A, wherein the pruvanserin is administered to post-treat at least 210 minutes after the MDMA hemifumarate Form A.

In some embodiments, the serotonin receptor modulator is pruvanserin and the psychedelic is MDMA hemifumarate Form A, wherein the pruvanserin is administered to post-treat at least 240 minutes after the MDMA hemifumarate Form A. In some embodiments, the serotonin receptor modulator is pruvanserin and the psychedelic is MDMA hemifumarate Form A, wherein the pruvanserin is administered to post-treat at least 270 minutes after the MDMA hemifumarate Form A. In some embodiments, the serotonin receptor modulator is pruvanserin and the psychedelic is MDMA hemifumarate Form A, wherein the pruvanserin is administered to post-treat at least 300 minutes after the MDMA hemifumarate Form A. In some embodiments, the serotonin receptor modulator is pruvanserin and the psychedelic is MDMA hemifumarate Form A, wherein the pruvanserin is administered to post-treat at least 330 minutes after the MDMA hemifumarate Form A. In some embodiments, the serotonin receptor modulator is pruvanserin and the psychedelic is MDMA hemifumarate Form A, wherein the pruvanserin is administered to post-treat at least 360 minutes after the MDMA hemifumarate Form A. In some preferred embodiments, the serotonin receptor modulator is pruvanserin and the psychedelic is MDMA hemifumarate Form A, wherein pruvanserin is administered to post-treat between about 60 minutes and about 180 minutes after the administration of the MDMA hemifumarate Form A.

In some embodiments, the serotonin receptor modulator is flibanserin, wherein the flibanserin is administered to post-treat at least 15 minutes post to the administration of the MDMA hemifumarate Form A. In some embodiments, the serotonin receptor modulator is flibanserin, wherein the flibanserin is administered to post-treat at least 30 minutes post to the MDMA hemifumarate Form A. In some embodiments, the serotonin receptor modulator is flibanserin, wherein the flibanserin is administered to post-treat between at least 60 minutes and 240 minutes post to the administration or release of the MDMA hemifumarate Form A. In some embodiments, the serotonin receptor modulator is flibanserin, wherein the flibanserin is administered to post-treat at least 90 minutes post to the MDMA hemifumarate Form A. In some embodiments, the serotonin receptor modulator is flibanserin, wherein the flibanserin is administered to post-treat at least 120 minutes post to the MDMA hemifumarate Form A. In some embodiments, the serotonin receptor modulator is flibanserin, wherein the flibanserin is administered to post-treat at least 150 minutes post to the MDMA hemifumarate Form A. In some embodiments, the serotonin receptor modulator is flibanserin, wherein the flibanserin is administered to post-treat between about 15 minutes and about 150 minutes post to the MDMA hemifumarate Form A. In some embodiments, the serotonin receptor modulator is flibanserin, wherein the flibanserin is administered to post-treat at least 180 minutes post to the MDMA hemifumarate Form A. In some embodiments, the serotonin receptor modulator is flibanserin, wherein the flibanserin is administered to post-treat at least 210 minutes post to the MDMA hemifumarate Form A.

In some embodiments, the serotonin receptor modulator is flibanserin, wherein the flibanserin is administered to post-treat at least 240 minutes post to the MDMA hemifumarate Form A. In some embodiments, the serotonin receptor modulator is flibanserin, wherein the flibanserin is administered to post-treat at least 270 minutes post to the MDMA hemifumarate Form A. In some embodiments, the serotonin receptor modulator is flibanserin, wherein the flibanserin is administered to post-treat at least 300 minutes post to the MDMA hemifumarate Form A. In some embodiments, the serotonin receptor modulator is flibanserin, wherein the flibanserin is administered to post-treat at least 330 minutes post to the MDMA hemifumarate Form A. In some embodiments, the serotonin receptor modulator is flibanserin, wherein the flibanserin is administered to post-treat at least 360 minutes post to the MDMA hemifumarate Form A. In some preferred embodiments, the serotonin receptor modulator is flibanserin, wherein flibanserin is administered to post-treat between about 60 minutes and about 180 minutes post to the administration of the MDMA hemifumarate Form A.

In some embodiments, the serotonin receptor modulator is olanzapine, wherein the olanzapine is administered to post-treat at least 15 minutes post to the administration of the MDMA hemifumarate Form A. In some embodiments, the serotonin receptor modulator is olanzapine, wherein the olanzapine is administered to post-treat at least 30 minutes post to the MDMA hemifumarate Form A. In some embodiments, the serotonin receptor modulator is olanzapine, wherein the olanzapine is administered to post-treat between at least 60 minutes and 240 minutes post to the administration or release of the MDMA hemifumarate Form A. In some embodiments, the serotonin receptor modulator is olanzapine, wherein the olanzapine is administered to post-treat at least 90 minutes post to the MDMA hemifumarate Form A. In some embodiments, the serotonin receptor modulator is olanzapine, wherein the olanzapine is administered to post-treat at least 120 minutes post to the MDMA hemifumarate Form A. In some embodiments, the serotonin receptor modulator is olanzapine, wherein the olanzapine is administered to post-treat at least 150 minutes post to the MDMA hemifumarate Form A. In some embodiments, the serotonin receptor modulator is olanzapine, wherein the olanzapine is administered to post-treat between about 15 minutes and about 150 minutes post to the MDMA hemifumarate Form A. In some embodiments, the serotonin receptor modulator is olanzapine, wherein the olanzapine is administered to post-treat at least 180 minutes post to the MDMA hemifumarate Form A. In some embodiments, the serotonin receptor modulator is olanzapine, wherein the olanzapine is administered to post-treat at least 210 minutes post to the MDMA hemifumarate Form A.

In some embodiments, the serotonin receptor modulator is olanzapine, wherein the olanzapine is administered to post-treat at least 240 minutes post to the MDMA hemifumarate Form A. In some embodiments, the serotonin receptor modulator is olanzapine, wherein the olanzapine is administered to post-treat at least 270 minutes post to the MDMA hemifumarate Form A. In some embodiments, the serotonin receptor modulator is olanzapine, wherein the olanzapine is administered to post-treat at least 300 minutes post to the MDMA hemifumarate Form A. In some embodiments, the serotonin receptor modulator is olanzapine, wherein the olanzapine is administered to post-treat at least 330 minutes post to the MDMA hemifumarate Form A. In some embodiments, the serotonin receptor modulator is olanzapine, wherein the olanzapine is administered to post-treat at least 360 minutes post to the MDMA hemifumarate Form A. In some preferred embodiments, the serotonin receptor modulator is olanzapine, wherein olanzapine is administered to post-treat between about 60 minutes and about 180 minutes post to the administration of the MDMA hemifumarate Form A.

In some embodiments, the serotonin receptor modulator is quetiapine, wherein the quetiapine is administered to post-treat at least 15 minutes post to the administration of the MDMA hemifumarate Form A. In some embodiments, the serotonin receptor modulator is quetiapine, wherein the quetiapine is administered to post-treat at least 30 minutes post to the MDMA hemifumarate Form A. In some embodiments, the serotonin receptor modulator is quetiapine, wherein the quetiapine is administered to post-treat between at least 60 minutes and 240 minutes post to the administration or release of the MDMA hemifumarate Form A. In some embodiments, the serotonin receptor modulator is quetiapine, wherein the quetiapine is administered to post-treat at least 90 minutes post to the MDMA hemifumarate Form A. In some embodiments, the serotonin receptor modulator is quetiapine, wherein the quetiapine is administered to post-treat at least 120 minutes post to the MDMA hemifumarate Form A. In some embodiments, the serotonin receptor modulator is quetiapine, wherein the quetiapine is administered to post-treat at least 150 minutes post to the MDMA hemifumarate Form A. In some embodiments, the serotonin receptor modulator is quetiapine, wherein the quetiapine is administered to post-treat between about 15 minutes and about 150 minutes post to the MDMA hemifumarate Form A. In some embodiments, the serotonin receptor modulator is quetiapine, wherein the quetiapine is administered to post-treat at least 180 minutes post to the MDMA hemifumarate Form A. In some embodiments, the serotonin receptor modulator is quetiapine, wherein the quetiapine is administered to post-treat at least 210 minutes post to the MDMA hemifumarate Form A.

In some embodiments, the serotonin receptor modulator is quetiapine, wherein the quetiapine is administered to post-treat at least 240 minutes post to the MDMA hemifumarate Form A. In some embodiments, the serotonin receptor modulator is quetiapine, wherein the quetiapine is administered to post-treat at least 270 minutes post to the MDMA hemifumarate Form A. In some embodiments, the serotonin receptor modulator is quetiapine, wherein the quetiapine is administered to post-treat at least 300 minutes post to the MDMA hemifumarate Form A. In some embodiments, the serotonin receptor modulator is quetiapine, wherein the quetiapine is administered to post-treat at least 330 minutes post to the MDMA hemifumarate Form A. In some embodiments, the serotonin receptor modulator is quetiapine, wherein the quetiapine is administered to post-treat at least 360 minutes post to the MDMA hemifumarate Form A. In some preferred embodiments, the serotonin receptor modulator is quetiapine, wherein quetiapine is administered to post-treat between about 60 minutes and about 180 minutes post to the administration of the MDMA hemifumarate Form A.

In some embodiments, the serotonin receptor modulator is risperidone, wherein the risperidone is administered to post-treat at least 15 minutes post to the administration of the MDMA hemifumarate Form A. In some embodiments, the serotonin receptor modulator is risperidone, wherein the risperidone is administered to post-treat at least 30 minutes post to the MDMA hemifumarate Form A. In some embodiments, the serotonin receptor modulator is risperidone, wherein the risperidone is administered to post-treat between at least 60 minutes and 240 minutes post to the administration or release of the MDMA hemifumarate Form A. In some embodiments, the serotonin receptor modulator is risperidone, wherein the risperidone is administered to post-treat at least 90 minutes post to the MDMA hemifumarate Form A. In some embodiments, the serotonin receptor modulator is risperidone, wherein the risperidone is administered to post-treat at least 120 minutes post to the MDMA hemifumarate Form A. In some embodiments, the serotonin receptor modulator is risperidone, wherein the risperidone is administered to post-treat at least 150 minutes post to the MDMA hemifumarate Form A. In some embodiments, the serotonin receptor modulator is risperidone, wherein the risperidone is administered to post-treat between about 15 minutes and about 150 minutes post to the MDMA hemifumarate Form A. In some embodiments, the serotonin receptor modulator is risperidone, wherein the risperidone is administered to post-treat at least 180 minutes post to the MDMA hemifumarate Form A. In some embodiments, the serotonin receptor modulator is risperidone, wherein the risperidone is administered to post-treat at least 210 minutes post to the MDMA hemifumarate Form A.

In some embodiments, the serotonin receptor modulator is risperidone, wherein the risperidone is administered to post-treat at least 240 minutes post to the MDMA hemifumarate Form A. In some embodiments, the serotonin receptor modulator is risperidone, wherein the risperidone is administered to post-treat at least 270 minutes post to the MDMA hemifumarate Form A. In some embodiments, the serotonin receptor modulator is risperidone, wherein the risperidone is administered to post-treat at least 300 minutes post to the MDMA hemifumarate Form A. In some embodiments, the serotonin receptor modulator is risperidone, wherein the risperidone is administered to post-treat at least 330 minutes post to the MDMA hemifumarate Form A. In some embodiments, the serotonin receptor modulator is risperidone, wherein the risperidone is administered to post-treat at least 360 minutes post to the MDMA hemifumarate Form A. In some preferred embodiments, the serotonin receptor modulator is risperidone, wherein risperidone is administered to post-treat between about 60 minutes and about 180 minutes post to the administration of the MDMA hemifumarate Form A.

In some embodiments, the serotonin receptor modulator for use with the psychedelic (R)-MDMA is eplivanserin and, wherein the eplivanserin is administered in about 1 mg to about 40 mg, or about 5 mg to about 10 mg, and the (R)-MDMA is administered between about 50 mg and about 200 mg, or between about 80 mg and 120 mg.

In some embodiments, the serotonin receptor modulator is volinanserin and the psychedelic is (R)-MDMA, wherein the volinanserin is administered in about 1 mg to about 60 mg, or about 5 mg to about 20 mg, and the (R)-MDMA is administered between about 50 mg and about 200 mg, or between about 80 mg and 120 mg.

In some embodiments, the serotonin receptor modulator for use with the psychedelic (R)-MDMA is ketanserin, wherein the ketanserin is administered in about 10 mg to about 80 mg, about 30 mg to about 50 mg, or about 40 mg and the (R)-MDMA is administered between about 50 mg and about 200 mg, or between about 80 mg and 120 mg.

In some embodiments, the serotonin receptor modulator for use with the psychedelic (R)-MDMA is ritanserin, wherein the ritanserin is administered in about 1 mg to about 40 mg, or about 2.5 mg to about 10 mg, and the (R)-MDMA is administered between about 50 mg and about 200 mg, or between about 80 mg and 120 mg.

In some embodiments, the serotonin receptor modulator is pimavanserin and the psychedelic is (R)-MDMA, wherein the pimavanserin is administered in about 1 mg to about 60 mg, or about 17 mg to about 34 mg, and the (R)-MDMA is administered between about 50 mg and about 200 mg, or between about 80 mg and 120 mg.

In some embodiments, the serotonin receptor modulator for use with the psychedelic (R)-MDMA is nelotanserin, wherein the nelotanserin is administered in about 1 mg to about 80 mg, or about 40 mg to about 80 mg, and the (R)-MDMA is administered between about 50 mg and about 200 mg, or between about 80 mg and 120 mg.

In some embodiments, the serotonin receptor modulator for use with the psychedelic (R)-MDMA is pruvanserin, wherein the pruvanserin is administered in about 1 mg to about 40 mg, or about 3 mg to about 10 mg, and the (R)-MDMA is administered between about 50 mg and about 200 mg, or between about 80 mg and 120 mg.

In some embodiments, the serotonin receptor modulator for use with the psychedelic (R)-MDMA is flibanserin, wherein the flibanserin is administered in about 10 mg to about 200 mg, or about 80 mg to about 120 mg, or about 100 mg and the (R)-MDMA is administered between about 50 mg and about 200 mg, or between about 80 mg and 120 mg.

In certain embodiments, such as those described above a disclosed (R)-MDMA form is co-administered with a serotonin receptor modulator in the same or in separate compositions. In one embodiment, the (R)-MDMA is administered in a modified release formulation such that the subject is effectively pretreated with serotonin receptor modulator prior to release of an effective amount of the psychedelic. Thus, in some embodiments, the serotonin receptor modulator is administered or released from a composition provided herein prior to the administration and/or release of the psychedelic. This allows pretreatment to attenuate activation of the serotonin receptor by the psychedelic.

In some embodiments, the serotonin receptor modulator is eplivanserin and the psychedelic is (R)-MDMA, wherein the eplivanserin is administered to pretreat at least 15 minutes prior to the administration of (R)-MDMA. In some embodiments, the serotonin receptor modulator is eplivanserin and the psychedelic is (R)-MDMA, wherein the eplivanserin is administered to pretreat between at least 30 minutes prior and 360 minutes prior to the release or administration of the (R)-MDMA. In some embodiments, the serotonin receptor modulator is eplivanserin and the psychedelic is (R)-MDMA, wherein the eplivanserin is administered to pretreat between at least 60 minutes prior and 360 minutes prior to the release or administration the (R)-MDMA. In some embodiments, the serotonin receptor modulator is eplivanserin and the psychedelic is (R)-MDMA, wherein the eplivanserin is administered to pretreat between at least 90 minutes and 240 minutes prior to the (R)-MDMA. In some embodiments, the serotonin receptor modulator is eplivanserin and the psychedelic is (R)-MDMA, wherein the eplivanserin is administered to pretreat at least 120 minutes prior to the (R)-MDMA.

In some embodiments, the serotonin receptor modulator is eplivanserin and the psychedelic is (R)-MDMA, wherein the eplivanserin is administered to pretreat at least 150 minutes prior to the (R)-MDMA. In some embodiments, the serotonin receptor modulator is eplivanserin and the psychedelic is (R)-MDMA, wherein the eplivanserin is administered to pretreat at least 180 minutes prior to the (R)-MDMA. In some embodiments, the serotonin receptor modulator is eplivanserin and the psychedelic is (R)-MDMA, wherein the eplivanserin is administered to pretreat at least 210 minutes prior to the (R)-MDMA. In some embodiments, the serotonin receptor modulator is eplivanserin and the psychedelic is (R)-MDMA, wherein the eplivanserin is administered to pretreat at least 240 minutes prior to the (R)-MDMA.

In some embodiments, the serotonin receptor modulator is eplivanserin and the psychedelic is (R)-MDMA, wherein the eplivanserin is administered to pretreat at least 270 minutes prior to (R)-MDMA. In some embodiments, the serotonin receptor modulator is eplivanserin and the psychedelic is (R)-MDMA, wherein the eplivanserin is administered to pretreat at least 300 minutes prior to the (R)-MDMA. In some embodiments, the serotonin receptor modulator is eplivanserin and the psychedelic is (R)-MDMA, wherein the eplivanserin is administered to pretreat at least 330 minutes prior to the (R)-MDMA. In some embodiments, the serotonin receptor modulator is eplivanserin and the psychedelic is (R)-MDMA, wherein the eplivanserin is administered to pretreat at least 360 minutes prior to the (R)-MDMA.

In some preferred embodiments, the serotonin receptor modulator is eplivanserin and the psychedelic is (R)-MDMA, wherein eplivanserin is administered to pretreat between about 60 minutes and about 180 minutes prior to the administration of (R)-MDMA.

In some embodiments, the serotonin receptor modulator is volinanserin and the psychedelic is (R)-MDMA, wherein the volinanserin is administered to pretreat a subject between at least 15 minutes and 360 minutes prior to the administration or release of (R)-MDMA. In some embodiments, the serotonin receptor modulator is volinanserin and the psychedelic is (R)-MDMA, wherein the volinanserin is administered to pretreat between at least 30 minutes and 360 minutes prior to the administration or release of (R)-MDMA. In some embodiments, the serotonin receptor modulator is volinanserin and the psychedelic is (R)-MDMA, wherein the volinanserin is administered to pretreat between at least 60 minutes and 240 minutes prior to the administration or release of (R)-MDMA. In some embodiments, the serotonin receptor modulator is volinanserin and the psychedelic is (R)-MDMA, wherein the volinanserin is administered to pretreat at least 90 minutes prior to (R)-MDMA. In some embodiments, the serotonin receptor modulator is volinanserin and the psychedelic is (R)-MDMA, wherein the volinanserin is administered to pretreat at least 120 minutes prior to the (R)-MDMA.

In some embodiments, the serotonin receptor modulator is volinanserin and the psychedelic is (R)-MDMA, wherein the volinanserin is administered to pretreat at least 150 minutes prior to the (R)-MDMA. In some embodiments, the serotonin receptor modulator is volinanserin and the psychedelic is (R)-MDMA, wherein the volinanserin is administered to pretreat between about 15 minutes and about 150 minutes prior to the (R)-MDMA. In some embodiments, the serotonin receptor modulator is volinanserin and the psychedelic is (R)-MDMA, wherein the volinanserin is administered to pretreat at least 180 minutes prior to the (R)-MDMA. In some embodiments, the serotonin receptor modulator is volinanserin and the psychedelic is (R)-MDMA, wherein the volinanserin is administered to pretreat at least 210 minutes prior to the (R)-MDMA. In some embodiments, the serotonin receptor modulator is volinanserin and the psychedelic is (R)-MDMA, wherein the volinanserin is administered to pretreat at least 240 minutes prior to the (R)-MDMA. In some embodiments, the serotonin receptor modulator is volinanserin and the psychedelic is (R)-MDMA, wherein the volinanserin is administered to pretreat at least 270 minutes prior to the (R)-MDMA. In some embodiments, the serotonin receptor modulator is volinanserin and the psychedelic is (R)-MDMA, wherein the volinanserin is administered to pretreat at least 300 minutes prior to the (R)-MDMA. In some embodiments, the serotonin receptor modulator is volinanserin and the psychedelic is (R)-MDMA, wherein the volinanserin is administered to pretreat at least 330 minutes prior to the (R)-MDMA. In some embodiments, the serotonin receptor modulator is volinanserin and the psychedelic is (R)-MDMA, wherein the volinanserin is administered to pretreat at least 360 minutes prior to the (R)-MDMA. In some preferred embodiments, the serotonin receptor modulator is volinanserin and the psychedelic is (R)-MDMA, wherein volinanserin is administered to pretreat between about 60 minutes and about 180 minutes prior to the administration of (R)-MDMA.

In some embodiments, the serotonin receptor modulator is ketanserin and the psychedelic is (R)-MDMA, wherein the ketanserin is administered to pretreat at least 15 minutes prior to the administration of (R)-MDMA. In some embodiments, the serotonin receptor modulator is ketanserin and the psychedelic is (R)-MDMA, wherein the ketanserin is administered to pretreat between at least 30 minutes and 360 minutes prior to the administration or release (R)-MDMA. In some embodiments, the serotonin receptor modulator is ketanserin and the psychedelic is (R)-MDMA, wherein the ketanserin is administered to pretreat between at least 60 minutes and 240 minutes prior to the administration or release of (R)-MDMA. In some embodiments, the serotonin receptor modulator is ketanserin and the psychedelic is (R)-MDMA, wherein the ketanserin is administered to pretreat at least 90 minutes prior to the (R)-MDMA. In some embodiments, the serotonin receptor modulator is ketanserin and the psychedelic is (R)-MDMA, wherein the ketanserin is administered to pretreat at least 120 minutes prior to the (R)-MDMA. In some embodiments, the serotonin receptor modulator is ketanserin and the psychedelic is (R)-MDMA, wherein the ketanserin is administered to pretreat at least 150 minutes prior to the (R)-MDMA. In some embodiments, the serotonin receptor modulator is ketanserin and the psychedelic is (R)-MDMA, wherein the ketanserin is administered to pretreat between about 15 minutes and about 150 minutes prior to the (R)-MDMA. In some embodiments, the serotonin receptor modulator is ketanserin and the psychedelic is (R)-MDMA, wherein the ketanserin is administered to pretreat at least 180 minutes prior to the (R)-MDMA. In some embodiments, the serotonin receptor modulator is ketanserin and the psychedelic is (R)-MDMA, wherein the ketanserin is administered to pretreat at least 210 minutes prior to the (R)-MDMA. In some embodiments, the serotonin receptor modulator is ketanserin and the psychedelic is (R)-MDMA, wherein the ketanserin is administered to pretreat at least 240 minutes prior to the (R)-MDMA. In some embodiments, the serotonin receptor modulator is ketanserin and the psychedelic is (R)-MDMA, wherein the ketanserin is administered to pretreat at least 270 minutes prior to the (R)-MDMA. In some embodiments, the serotonin receptor modulator is ketanserin and the psychedelic is (R)-MDMA, wherein the ketanserin is administered to pretreat at least 300 minutes prior to the (R)-MDMA. In some embodiments, the serotonin receptor modulator is ketanserin and the psychedelic is (R)-MDMA, wherein the ketanserin is administered to pretreat at least 330 minutes prior to the (R)-MDMA. In some embodiments, the serotonin receptor modulator is ketanserin and the psychedelic is (R)-MDMA, wherein the ketanserin is administered to pretreat at least 360 minutes prior to the (R)-MDMA. In some preferred embodiments, the serotonin receptor modulator is ketanserin and the psychedelic is (R)-MDMA, wherein ketanserin is administered to pretreat between about 60 minutes and about 180 minutes prior to the administration of (R)-MDMA.

In some embodiments, the serotonin receptor modulator is ritanserin and the psychedelic is (R)-MDMA, wherein the ritanserin is administered to pretreat at least 15 minutes prior to the administration of (R)-MDMA. In some embodiments, the serotonin receptor modulator is ritanserin and the psychedelic is (R)-MDMA, wherein the ritanserin is administered to pretreat at least 30 minutes prior to the (R)-MDMA. In some embodiments, the serotonin receptor modulator is ritanserin and the psychedelic is (R)-MDMA, wherein the ritanserin is administered to pretreat between at least 60 minutes and 240 minutes prior to the administration or release of (R)-MDMA. In some embodiments, the serotonin receptor modulator is ritanserin and the psychedelic is (R)-MDMA, wherein the ritanserin is administered to pretreat at least 90 minutes prior to the (R)-MDMA. In some embodiments, the serotonin receptor modulator is ritanserin and the psychedelic is (R)-MDMA, wherein the ritanserin is administered to pretreat at least 120 minutes prior to the (R)-MDMA. In some embodiments, the serotonin receptor modulator is ritanserin and the psychedelic is (R)-MDMA, wherein the ritanserin is administered to pretreat at least 150 minutes prior to the (R)-MDMA. In some embodiments, the serotonin receptor modulator is ritanserin and the psychedelic is (R)-MDMA, wherein the ritanserin is administered to pretreat between about 15 minutes and about 150 minutes prior to the (R)-MDMA. In some embodiments, the serotonin receptor modulator is ritanserin and the psychedelic is (R)-MDMA, wherein the ritanserin is administered to pretreat at least 180 minutes prior to the (R)-MDMA. In some embodiments, the serotonin receptor modulator is ritanserin and the psychedelic is (R)-MDMA, wherein the ritanserin is administered to pretreat at least 210 minutes prior to the (R)-MDMA. In some embodiments, the serotonin receptor modulator is ritanserin and the psychedelic is (R)-MDMA, wherein the ritanserin is administered to pretreat at least 240 minutes prior to the (R)-MDMA. In some embodiments, the serotonin receptor modulator is ritanserin and the psychedelic is (R)-MDMA, wherein the ritanserin is administered to pretreat at least 270 minutes prior to the (R)-MDMA. In some embodiments, the serotonin receptor modulator is ritanserin and the psychedelic is (R)-MDMA, wherein the ritanserin is administered to pretreat at least 300 minutes prior to the (R)-MDMA. In some embodiments, the serotonin receptor modulator is ritanserin and the psychedelic is (R)-MDMA, wherein the ritanserin is administered to pretreat at least 330 minutes prior to the (R)-MDMA. In some embodiments, the serotonin receptor modulator is ritanserin and the psychedelic is (R)-MDMA, wherein the ritanserin is administered to pretreat at least 360 minutes prior to the (R)-MDMA. In some preferred embodiments, the serotonin receptor modulator is ritanserin and the psychedelic is (R)-MDMA, wherein ritanserin is administered to pretreat between about 60 minutes and about 180 minutes prior to the administration of (R)-MDMA.

In some embodiments, the serotonin receptor modulator is pimavanserin and the psychedelic is (R)-MDMA, wherein the pimavanserin is administered to pretreat at least 15 minutes prior to the administration of (R)-MDMA. In some embodiments, the serotonin receptor modulator is pimavanserin and the psychedelic is (R)-MDMA, wherein the pimavanserin is administered to pretreat at least 30 minutes prior to the (R)-MDMA. In some embodiments, the serotonin receptor modulator is pimavanserin and the psychedelic is (R)-MDMA, wherein the pimavanserin is administered to pretreat between at least 60 minutes and 240 minutes prior to the administration or release of (R)-MDMA. In some embodiments, the serotonin receptor modulator is pimavanserin and the psychedelic is (R)-MDMA, wherein the pimavanserin is administered to pretreat at least 90 minutes prior to the (R)-MDMA. In some embodiments, the serotonin receptor modulator is pimavanserin and the psychedelic is (R)-MDMA, wherein the pimavanserin is administered to pretreat at least 120 minutes prior to the (R)-MDMA. In some embodiments, the serotonin receptor modulator is pimavanserin and the psychedelic is (R)-MDMA, wherein the pimavanserin is administered to pretreat at least 150 minutes prior to the (R)-MDMA. In some embodiments, the serotonin receptor modulator is pimavanserin and the psychedelic is (R)-MDMA, wherein the pimavanserin is administered to pretreat between about 15 minutes and about 150 minutes prior to the (R)-MDMA. In some embodiments, the serotonin receptor modulator is pimavanserin and the psychedelic is (R)-MDMA, wherein the pimavanserin is administered to pretreat at least 180 minutes prior to the (R)-MDMA. In some embodiments, the serotonin receptor modulator is pimavanserin and the psychedelic is (R)-MDMA, wherein the pimavanserin is administered to pretreat at least 210 minutes prior to the (R)-MDMA. In some embodiments, the serotonin receptor modulator is pimavanserin and the psychedelic is (R)-MDMA, wherein the pimavanserin is administered to pretreat at least 240 minutes prior to the (R)-MDMA. In some embodiments, the serotonin receptor modulator is pimavanserin and the psychedelic is (R)-MDMA, wherein the pimavanserin is administered to pretreat at least 270 minutes prior to the (R)-MDMA. In some embodiments, the serotonin receptor modulator is pimavanserin and the psychedelic is (R)-MDMA, wherein the pimavanserin is administered to pretreat at least 300 minutes prior to the (R)-MDMA. In some embodiments, the serotonin receptor modulator is pimavanserin and the psychedelic is (R)-MDMA, wherein the pimavanserin is administered to pretreat at least 330 minutes prior to the (R)-MDMA. In some embodiments, the serotonin receptor modulator is pimavanserin and the psychedelic is (R)-MDMA, wherein the pimavanserin is administered to pretreat at least 360 minutes prior to the (R)-MDMA. In some preferred embodiments, the serotonin receptor modulator is pimavanserin and the psychedelic is (R)-MDMA, wherein pimavanserin is administered to pretreat between about 60 minutes and about 180 minutes prior to the administration of (R)-MDMA.

In some embodiments, the serotonin receptor modulator is nelotanserin and the psychedelic is (R)-MDMA, wherein the nelotanserin is administered to pretreat at least 15 minutes prior to the administration of (R)-MDMA. In some embodiments, the serotonin receptor modulator is nelotanserin and the psychedelic is (R)-MDMA, wherein the nelotanserin is administered to pretreat at least 30 minutes prior to the (R)-MDMA. In some embodiments, the serotonin receptor modulator is nelotanserin and the psychedelic is (R)-MDMA, wherein the nelotanserin is administered to pretreat between at least 60 minutes and 240 minutes prior to the administration or release of (R)-MDMA. In some embodiments, the serotonin receptor modulator is nelotanserin and the psychedelic is (R)-MDMA, wherein the nelotanserin is administered to pretreat at least 90 minutes prior to the (R)-MDMA. In some embodiments, the serotonin receptor modulator is nelotanserin and the psychedelic is (R)-MDMA, wherein the nelotanserin is administered to pretreat at least 120 minutes prior to the (R)-MDMA.

In some embodiments, the serotonin receptor modulator is nelotanserin and the psychedelic is (R)-MDMA, wherein the nelotanserin is administered to pretreat at least 150 minutes prior to the (R)-MDMA. In some embodiments, the serotonin receptor modulator is nelotanserin and the psychedelic is (R)-MDMA, wherein the nelotanserin is administered to pretreat between about 15 minutes and about 150 minutes prior to the (R)-MDMA. In some embodiments, the serotonin receptor modulator is nelotanserin and the psychedelic is (R)-MDMA, wherein the nelotanserin is administered to pretreat at least 180 minutes prior to the (R)-MDMA. In some embodiments, the serotonin receptor modulator is nelotanserin and the psychedelic is (R)-MDMA, wherein the nelotanserin is administered to pretreat at least 210 minutes prior to the (R)-MDMA. In some embodiments, the serotonin receptor modulator is nelotanserin and the psychedelic is (R)-MDMA, wherein the nelotanserin is administered to pretreat at least 240 minutes prior to the (R)-MDMA. In some embodiments, the serotonin receptor modulator is nelotanserin and the psychedelic is (R)-MDMA, wherein the nelotanserin is administered to pretreat at least 270 minutes prior to the (R)-MDMA.

In some embodiments, the serotonin receptor modulator is nelotanserin and the psychedelic is (R)-MDMA, wherein the nelotanserin is administered to pretreat at least 300 minutes prior to the (R)-MDMA. In some embodiments, the serotonin receptor modulator is nelotanserin and the psychedelic is (R)-MDMA, wherein the nelotanserin is administered to pretreat at least 330 minutes prior to the (R)-MDMA. In some embodiments, the serotonin receptor modulator is nelotanserin and the psychedelic is (R)-MDMA, wherein the nelotanserin is administered to pretreat at least 360 minutes prior to the (R)-MDMA. In some preferred embodiments, the serotonin receptor modulator is nelotanserin and the psychedelic is (R)-MDMA, wherein nelotanserin is administered to pretreat between about 60 minutes and about 180 minutes prior to the administration of (R)-MDMA.

In some embodiments, the serotonin receptor modulator is pruvanserin and the psychedelic is (R)-MDMA, wherein the pruvanserin is administered to pretreat at least 15 minutes prior to the administration of (R)-MDMA. In some embodiments, the serotonin receptor modulator is pruvanserin and the psychedelic is (R)-MDMA, wherein the pruvanserin is administered to pretreat at least 30 minutes prior to the (R)-MDMA. In some embodiments, the serotonin receptor modulator is pruvanserin and the psychedelic is (R)-MDMA, wherein the pruvanserin is administered to pretreat between at least 60 minutes and 240 minutes prior to the administration or release of (R)-MDMA. In some embodiments, the serotonin receptor modulator is pruvanserin and the psychedelic is (R)-MDMA, wherein the pruvanserin is administered to pretreat at least 90 minutes prior to the (R)-MDMA. In some embodiments, the serotonin receptor modulator is pruvanserin and the psychedelic is (R)-MDMA, wherein the pruvanserin is administered to pretreat at least 120 minutes prior to the (R)-MDMA. In some embodiments, the serotonin receptor modulator is pruvanserin and the psychedelic is (R)-MDMA, wherein the pruvanserin is administered to pretreat at least 150 minutes prior to the (R)-MDMA. In some embodiments, the serotonin receptor modulator is pruvanserin and the psychedelic is (R)-MDMA, wherein the pruvanserin is administered to pretreat between about 15 minutes and about 150 minutes prior to the (R)-MDMA. In some embodiments, the serotonin receptor modulator is pruvanserin and the psychedelic is (R)-MDMA, wherein the pruvanserin is administered to pretreat at least 180 minutes prior to the (R)-MDMA. In some embodiments, the serotonin receptor modulator is pruvanserin and the psychedelic is (R)-MDMA, wherein the pruvanserin is administered to pretreat at least 210 minutes prior to the (R)-MDMA.

In some embodiments, the serotonin receptor modulator is pruvanserin and the psychedelic is (R)-MDMA, wherein the pruvanserin is administered to pretreat at least 240 minutes prior to the (R)-MDMA. In some embodiments, the serotonin receptor modulator is pruvanserin and the psychedelic is (R)-MDMA, wherein the pruvanserin is administered to pretreat at least 270 minutes prior to the (R)-MDMA. In some embodiments, the serotonin receptor modulator is pruvanserin and the psychedelic is (R)-MDMA, wherein the pruvanserin is administered to pretreat at least 300 minutes prior to the (R)-MDMA. In some embodiments, the serotonin receptor modulator is pruvanserin and the psychedelic is (R)-MDMA, wherein the pruvanserin is administered to pretreat at least 330 minutes prior to the (R)-MDMA. In some embodiments, the serotonin receptor modulator is pruvanserin and the psychedelic is (R)-MDMA, wherein the pruvanserin is administered to pretreat at least 360 minutes prior to the (R)-MDMA. In some preferred embodiments, the serotonin receptor modulator is pruvanserin and the psychedelic is (R)-MDMA, wherein pruvanserin is administered to pretreat between about 60 minutes and about 180 minutes prior to the administration of (R)-MDMA.

In some embodiments, the serotonin receptor modulator for use with the (R)-MDMA salts and solid forms disclosed herein, including those described in Table Ex9 is eplivanserin and, wherein the eplivanserin is administered in about 1 mg to about 40 mg, or about 5 mg to about 10 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator is volinanserin and the (R)-MDMA salts and solid forms disclosed herein, including those described in Table Ex9, wherein the volinanserin is administered in about 1 mg to about 60 mg, or about 5 mg to about 20 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is ketanserin, wherein the ketanserin is administered in about 10 mg to about 80 mg, about 30 mg to about 50 mg, or about 40 mg and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is ritanserin, wherein the ritanserin is administered in about 1 mg to about 40 mg, or about 2.5 mg to about 10 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator is pimavanserin and the (R)-MDMA salts and solid forms disclosed herein, including those described in Table Ex9, wherein the pimavanserin is administered in about 1 mg to about 60 mg, or about 17 mg to about 34 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is nelotanserin, wherein the nelotanserin is administered in about 1 mg to about 80 mg, or about 40 mg to about 80 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is pruvanserin, wherein the pruvanserin is administered in about 1 mg to about 40 mg, or about 3 mg to about 10 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is flibanserin, wherein the flibanserin is administered in about 10 mg to about 200 mg, or about 80 mg to about 120 mg, or about 100 mg and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is olanzapine, wherein the olanzapine is administered in about 2.5 mg to about 30 mg, or about 5 mg or about 10 mg, or about 20 mg or about 25 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is quetiapine, wherein the quetiapine is administered in about 25 mg to about 800 mg, or about 50 mg to about 100 mg, or about 150 mg or about 200 mg or about 250 mg or about 300 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is an extended-release of quetiapine, wherein the extended-release of quetiapine is administered in about 50 mg to about 300 mg, or about 50 mg or about 100 mg or about 200 mg, or about 300 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the (R)-MDMA salts and solid forms disclosed herein, including those described in Table Ex9 are administered between about 50 mg and about 200 mg, or between about 80 mg and 120 mg.

In some embodiments, the serotonin receptor modulator for use with the (R)-MDMA salts and solid forms disclosed herein, including those described in Table Ex9 is an extended-release of risperidone including (RISPERDAL CONSTA), wherein the extended-release of risperidone is administered in about 12.5 mg, or about 25 mg, or about 37.5 mg, or about 50 mg, and the (R)-MDMA salts and solid forms disclosed herein, including those described in Table Ex9 are administered between about 50 mg and about 200 mg, or between about 80 mg and 120 mg.

In certain embodiments, such as those described above a (R)-MDMA form disclosed herein, including those described in Table Ex9 is co-administered with a serotonin receptor modulator in the same or in separate compositions. In one embodiment, the serotonin receptor modulator is administered prior to the (R)-MDMA form disclosed herein, including those described in Table Ex9. In one embodiment, the (R)-MDMA form disclosed herein, including those described in Table Ex9 is administered in a modified release formulation such that the subject is effectively pretreated with serotonin receptor modulator prior to release of an effective amount of the (R)-MDMA. In some embodiments the serotonin receptor modulator is part of a single fixed dose formulation that releases serotonin receptor modulator first followed by the (R)-MDMA on two different release profiles. In another embodiment the serotonin receptor modulator is administered first as a single dosage and after a length of time, the (R)-MDMA form disclosed herein, including those described in Table Ex9 is administered as a second dosage separate from the first dosage. Thus, in some embodiments, the serotonin receptor modulator is administered or released from a composition provided herein prior to the administration and/or release of the psychedelic. This allows pretreatment to attenuate activation of the serotonin receptor by the psychedelic.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is (R)-MDMA, wherein the eplivanserin is administered to pretreat at least 15 minutes prior to the administration of the (R)-MDMA form disclosed herein, including those described in Table Ex9. In some embodiments, the serotonin receptor modulator is eplivanserin and the psychedelic is (R)-MDMA, wherein the eplivanserin is administered to pretreat between at least 30 minutes prior and 360 minutes prior to the release or administration of the (R)-MDMA form disclosed herein, including those described in Table Ex9. In some embodiments, the serotonin receptor modulator is eplivanserin and the psychedelic is (R)-MDMA, wherein the eplivanserin is administered to pretreat between at least 60 minutes prior and 360 minutes prior to the release or administration of the (R)-MDMA form disclosed herein, including those described in Table Ex9. In some embodiments, the serotonin receptor modulator is eplivanserin and the psychedelic is (R)-MDMA, wherein the eplivanserin is administered to pretreat between at least 90 minutes and 240 minutes prior to the (R)-MDMA form disclosed herein, including those described in Table Ex9. In some embodiments, the serotonin receptor modulator is eplivanserin and the psychedelic is (R)-MDMA, wherein the eplivanserin is administered to pretreat at least 120 minutes prior to the (R)-MDMA form disclosed herein, including those described in Table Ex9.

In some embodiments, the serotonin receptor modulator is eplivanserin and the psychedelic is (R)-MDMA, wherein the eplivanserin is administered to pretreat at least 150 minutes prior to the (R)-MDMA form disclosed herein, including those described in Table Ex9. In some embodiments, the serotonin receptor modulator is eplivanserin and the psychedelic is (R)-MDMA, wherein the eplivanserin is administered to pretreat at least 180 minutes prior to the (R)-MDMA form disclosed herein, including those described in Table Ex9. In some embodiments, the serotonin receptor modulator is eplivanserin and the psychedelic is (R)-MDMA, wherein the eplivanserin is administered to pretreat at least 210 minutes prior to the (R)-MDMA form disclosed herein, including those described in Table Ex9. In some embodiments, the serotonin receptor modulator is eplivanserin and the psychedelic is (R)-MDMA, wherein the eplivanserin is administered to pretreat at least 240 minutes prior to the (R)-MDMA form disclosed herein, including those described in Table Ex9.

In some embodiments, the serotonin receptor modulator is eplivanserin and the psychedelic is (R)-MDMA, wherein the eplivanserin is administered to pretreat at least 270 minutes prior to the (R)-MDMA form disclosed herein, including those described in Table Ex9. In some embodiments, the serotonin receptor modulator is eplivanserin and the psychedelic is (R)-MDMA, wherein the eplivanserin is administered to pretreat at least 300 minutes prior to the (R)-MDMA form disclosed herein, including those described in Table Ex9. In some embodiments, the serotonin receptor modulator is eplivanserin and the psychedelic is (R)-MDMA, wherein the eplivanserin is administered to pretreat at least 330 minutes prior to the (R)-MDMA form disclosed herein, including those described in Table Ex9. In some embodiments, the serotonin receptor modulator is eplivanserin and the psychedelic is (R)-MDMA, wherein the eplivanserin is administered to pretreat at least 360 minutes prior to the (R)-MDMA form disclosed herein, including those described in Table Ex9.

In some preferred embodiments, the serotonin receptor modulator is eplivanserin and the psychedelic is (R)-MDMA, wherein eplivanserin is administered to pretreat between about 60 minutes and about 180 minutes prior to the administration of the (R)-MDMA form disclosed herein, including those described in Table Ex9.

In some embodiments, the serotonin receptor modulator is volinanserin and the psychedelic is (R)-MDMA, wherein the volinanserin is administered to pretreat a subject between at least 15 minutes and 360 minutes prior to the administration or release of the (R)-MDMA form disclosed herein, including those described in Table Ex9. In some embodiments, the serotonin receptor modulator is volinanserin and the psychedelic is (R)-MDMA, wherein the volinanserin is administered to pretreat between at least 30 minutes and 360 minutes prior to the administration or release of the (R)-MDMA form disclosed herein, including those described in Table Ex9. In some embodiments, the serotonin receptor modulator is volinanserin and the psychedelic is (R)-MDMA, wherein the volinanserin is administered to pretreat between at least 60 minutes and 240 minutes prior to the administration or release of the (R)-MDMA form disclosed herein, including those described in Table Ex9. In some embodiments, the serotonin receptor modulator is volinanserin and the psychedelic is (R)-MDMA, wherein the volinanserin is administered to pretreat at least 90 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 120 minutes prior to the (R)-MDMA form disclosed herein, including those described in Table Ex9.

In some embodiments, the serotonin receptor modulator is volinanserin and the psychedelic is (R)-MDMA, wherein the volinanserin is administered to pretreat at least 150 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat between about 15 minutes and about 150 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 180 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 210 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 240 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 270 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 300 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 330 minutes prior to the (R)-MDMA form disclosed herein, including those described in Table Ex9. In some embodiments, the serotonin receptor modulator is volinanserin and the psychedelic is (R)-MDMA, wherein the volinanserin is administered to pretreat at least 360 minutes prior to the (R)-MDMA form disclosed herein, including those described in Table Ex9. In some preferred embodiments, the serotonin receptor modulator is volinanserin and the psychedelic is (R)-MDMA, wherein volinanserin is administered to pretreat between about 60 minutes and about 180 minutes prior to the administration of the (R)-MDMA form disclosed herein, including those described in Table Ex9.

In some embodiments, the serotonin receptor modulator is ketanserin and the psychedelic is (R)-MDMA, wherein the ketanserin is administered to pretreat at least 15 minutes prior to the administration of the (R)-MDMA form disclosed herein, including those described in Table Ex9. In some embodiments, the serotonin receptor modulator is ketanserin and the psychedelic is (R)-MDMA, wherein the ketanserin is administered to pretreat between at least 30 minutes and 360 minutes prior to the administration or release of the (R)-MDMA form disclosed herein, including those described in Table Ex9. In some embodiments, the serotonin receptor modulator is ketanserin and the psychedelic is (R)-MDMA, wherein the ketanserin is administered to pretreat between at least 60 minutes and 240 minutes prior to the administration or release of the (R)-MDMA form disclosed herein, including those described in Table Ex9. In some embodiments, the serotonin receptor modulator is ketanserin and the psychedelic is (R)-MDMA, wherein the ketanserin is administered to pretreat at least 90 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 120 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 150 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat between about 15 minutes and about 150 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 180 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 210 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 240 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 270 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 300 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 330 minutes prior to the (R)-MDMA form disclosed herein, including those described in Table Ex9. In some embodiments, the serotonin receptor modulator is ketanserin and the psychedelic is (R)-MDMA, wherein the ketanserin is administered to pretreat at least 360 minutes prior to the (R)-MDMA form disclosed herein, including those described in Table Ex9. In some preferred embodiments, the serotonin receptor modulator is ketanserin and the psychedelic is (R)-MDMA, wherein ketanserin is administered to pretreat between about 60 minutes and about 180 minutes prior to the administration of the (R)-MDMA form disclosed herein, including those described in Table Ex9.

In some embodiments, the serotonin receptor modulator is ritanserin and the psychedelic is (R)-MDMA, wherein the ritanserin is administered to pretreat at least 15 minutes prior to the administration of the (R)-MDMA form disclosed herein, including those described in Table Ex9. In some embodiments, the serotonin receptor modulator is ritanserin and the psychedelic is (R)-MDMA, wherein the ritanserin is administered to pretreat at least 30 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat between at least 60 minutes and 240 minutes prior to the administration or release of the (R)-MDMA form disclosed herein, including those described in Table Ex9. In some embodiments, the serotonin receptor modulator is ritanserin and the psychedelic is (R)-MDMA, wherein the ritanserin is administered to pretreat at least 90 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 120 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 150 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat between about 15 minutes and about 150 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 180 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 210 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 240 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 270 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 300 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 330 minutes prior to the (R)-MDMA form disclosed herein, including those described in Table Ex9. In some embodiments, the serotonin receptor modulator is ritanserin and the psychedelic is (R)-MDMA, wherein the ritanserin is administered to pretreat at least 360 minutes prior to the (R)-MDMA form disclosed herein, including those described in Table Ex9. In some preferred embodiments, the serotonin receptor modulator is ritanserin and the psychedelic is (R)-MDMA, wherein ritanserin is administered to pretreat between about 60 minutes and about 180 minutes prior to the administration of the (R)-MDMA form disclosed herein, including those described in Table Ex9.

In some embodiments, the serotonin receptor modulator is pimavanserin and the psychedelic is (R)-MDMA, wherein the pimavanserin is administered to pretreat at least 15 minutes prior to the administration of the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 30 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat between at least 60 minutes and 240 minutes prior to the administration or release of the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 90 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 120 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 150 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat between about 15 minutes and about 150 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 180 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 210 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 240 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 270 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 300 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 330 minutes prior to the (R)-MDMA form disclosed herein, including those described in Table Ex9. In some embodiments, the serotonin receptor modulator is pimavanserin and the psychedelic is (R)-MDMA, wherein the pimavanserin is administered to pretreat at least 360 minutes prior to the (R)-MDMA form disclosed herein, including those described in Table Ex9. In some preferred embodiments, the serotonin receptor modulator is pimavanserin and the psychedelic is (R)-MDMA, wherein pimavanserin is administered to pretreat between about 60 minutes and about 180 minutes prior to the administration of the (R)-MDMA form disclosed herein, including those described in Table Ex9.

In some embodiments, the serotonin receptor modulator is nelotanserin and the psychedelic is (R)-MDMA, wherein the nelotanserin is administered to pretreat at least 15 minutes prior to the administration of the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 30 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat between at least 60 minutes and 240 minutes prior to the administration or release of the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 90 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 120 minutes prior to the (R)-MDMA form disclosed herein, including those described in Table Ex9.

In some embodiments, the serotonin receptor modulator is nelotanserin and the psychedelic is (R)-MDMA, wherein the nelotanserin is administered to pretreat at least 150 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat between about 15 minutes and about 150 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 180 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 210 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 240 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 270 minutes prior to the (R)-MDMA form disclosed herein, including those described in Table Ex9.

In some embodiments, the serotonin receptor modulator is nelotanserin and the psychedelic is (R)-MDMA, wherein the nelotanserin is administered to pretreat at least 300 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 330 minutes prior to the (R)-MDMA form disclosed herein, including those described in Table Ex9. In some embodiments, the serotonin receptor modulator is nelotanserin and the psychedelic is (R)-MDMA, wherein the nelotanserin is administered to pretreat at least 360 minutes prior to the (R)-MDMA form disclosed herein, including those described in Table Ex9. In some preferred embodiments, the serotonin receptor modulator is nelotanserin and the psychedelic is (R)-MDMA, wherein nelotanserin is administered to pretreat between about 60 minutes and about 180 minutes prior to the administration of the (R)-MDMA form disclosed herein, including those described in Table Ex9.

In some embodiments, the serotonin receptor modulator is pruvanserin and the psychedelic is (R)-MDMA, wherein the pruvanserin is administered to pretreat at least 15 minutes prior to the administration of the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 30 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat between at least 60 minutes and 240 minutes prior to the administration or release of the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 90 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 120 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 150 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat between about 15 minutes and about 150 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 180 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 210 minutes prior to the (R)-MDMA form disclosed herein, including those described in Table Ex9.

In some embodiments, the serotonin receptor modulator is pruvanserin and the psychedelic is (R)-MDMA, wherein the pruvanserin is administered to pretreat at least 240 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 270 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 300 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 330 minutes prior to the (R)-MDMA form disclosed herein, including those described in Table Ex9. In some embodiments, the serotonin receptor modulator is pruvanserin and the psychedelic is (R)-MDMA, wherein the pruvanserin is administered to pretreat at least 360 minutes prior to the (R)-MDMA form disclosed herein, including those described in Table Ex9. In some preferred embodiments, the serotonin receptor modulator is pruvanserin and the psychedelic is (R)-MDMA, wherein pruvanserin is administered to pretreat between about 60 minutes and about 180 minutes prior to the administration of the (R)-MDMA form disclosed herein, including those described in Table Ex9.

In certain embodiments, such as those described above a (R)-MDMA form disclosed herein, including those described in Table Ex9 is co-administered with a serotonin receptor modulator in the same or in separate compositions. In one embodiment, the serotonin receptor modulator is administered after the (R)-MDMA form disclosed herein, including those described in Table Ex9. In one embodiment, the (R)-MDMA form disclosed herein, including those described in Table Ex9 is administered in a modified release formulation such that the subject is effectively post-treated with serotonin receptor modulator post to release of an effective amount of the (R)-MDMA. In some embodiments, the serotonin receptor modulator is part of a single fixed dose formulation that releases the (R)-MDMA first followed by serotonin receptor modulator on two different release profiles. In another embodiment, the (R)-MDMA form disclosed herein, including those described in Table Ex9 is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the psychedelic. This allows post-treatment to attenuate activation of the serotonin receptor by the psychedelic.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours after the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours after the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour after the release of the psychedelic.

In a preferred embodiment, the serotonin receptor modulator is administered at about 1 hour to about 3 hours after the administration of the psychedelic.

In some embodiments, the serotonin receptor modulator is eplivanserin and the psychedelic is (R)-MDMA, wherein the eplivanserin is administered to post-treat at least 15 minutes after the administration of the (R)-MDMA form disclosed herein, including those described in Table Ex9. In some embodiments, the serotonin receptor modulator is eplivanserin and the psychedelic is (R)-MDMA, wherein the eplivanserin is administered to post-treat between at least 30 minutes after and 360 minutes after the release or administration of the (R)-MDMA form disclosed herein, including those described in Table Ex9. In some embodiments, the serotonin receptor modulator is eplivanserin and the psychedelic is (R)-MDMA, wherein the eplivanserin is administered to post-treat between at least 60 minutes after and 360 minutes after the release or administration of the (R)-MDMA form disclosed herein, including those described in Table Ex9. In some embodiments, the serotonin receptor modulator is eplivanserin and the psychedelic is (R)-MDMA, wherein the eplivanserin is administered to post-treat between at least 90 minutes and 240 minutes after the (R)-MDMA form disclosed herein, including those described in Table Ex9. In some embodiments, the serotonin receptor modulator is eplivanserin and the psychedelic is (R)-MDMA, wherein the eplivanserin is administered to post-treat at least 120 minutes after the (R)-MDMA form disclosed herein, including those described in Table Ex9.

In some embodiments, the serotonin receptor modulator is eplivanserin and the psychedelic is (R)-MDMA, wherein the eplivanserin is administered to post-treat at least 150 minutes after the (R)-MDMA form disclosed herein, including those described in Table Ex9. In some embodiments, the serotonin receptor modulator is eplivanserin and the psychedelic is (R)-MDMA, wherein the eplivanserin is administered to post-treat at least 180 minutes after the (R)-MDMA form disclosed herein, including those described in Table Ex9. In some embodiments, the serotonin receptor modulator is eplivanserin and the psychedelic is (R)-MDMA, wherein the eplivanserin is administered to post-treat at least 210 minutes after the (R)-MDMA form disclosed herein, including those described in Table Ex9. In some embodiments, the serotonin receptor modulator is eplivanserin and the psychedelic is (R)-MDMA, wherein the eplivanserin is administered to post-treat at least 240 minutes after the (R)-MDMA form disclosed herein, including those described in Table Ex9.

In some embodiments, the serotonin receptor modulator is eplivanserin and the psychedelic is (R)-MDMA, wherein the eplivanserin is administered to post-treat at least 270 minutes after the (R)-MDMA form disclosed herein, including those described in Table Ex9. In some embodiments, the serotonin receptor modulator is eplivanserin and the psychedelic is (R)-MDMA, wherein the eplivanserin is administered to post-treat at least 300 minutes after the (R)-MDMA form disclosed herein, including those described in Table Ex9. In some embodiments, the serotonin receptor modulator is eplivanserin and the psychedelic is (R)-MDMA, wherein the eplivanserin is administered to post-treat at least 330 minutes after the (R)-MDMA form disclosed herein, including those described in Table Ex9. In some embodiments, the serotonin receptor modulator is eplivanserin and the psychedelic is (R)-MDMA, wherein the eplivanserin is administered to post-treat at least 360 minutes after the (R)-MDMA form disclosed herein, including those described in Table Ex9.

In some preferred embodiments, the serotonin receptor modulator is eplivanserin and the psychedelic is (R)-MDMA, wherein eplivanserin is administered to post-treat between about 60 minutes and about 180 minutes after the administration of the (R)-MDMA form disclosed herein, including those described in Table Ex9.

In some embodiments, the serotonin receptor modulator is volinanserin and the psychedelic is (R)-MDMA, wherein the volinanserin is administered to post-treat a subject between at least 15 minutes and 360 minutes after the administration or release of the (R)-MDMA form disclosed herein, including those described in Table Ex9. In some embodiments, the serotonin receptor modulator is volinanserin and the psychedelic is (R)-MDMA, wherein the volinanserin is administered to post-treat between at least 30 minutes and 360 minutes after the administration or release of the (R)-MDMA form disclosed herein, including those described in Table Ex9. In some embodiments, the serotonin receptor modulator is volinanserin and the psychedelic is (R)-MDMA, wherein the volinanserin is administered to post-treat between at least 60 minutes and 240 minutes after the administration or release of the (R)-MDMA form disclosed herein, including those described in Table Ex9. In some embodiments, the serotonin receptor modulator is volinanserin and the psychedelic is (R)-MDMA, wherein the volinanserin is administered to post-treat at least 90 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 120 minutes after the (R)-MDMA form disclosed herein, including those described in Table Ex9.

In some embodiments, the serotonin receptor modulator is volinanserin and the psychedelic is (R)-MDMA, wherein the volinanserin is administered to post-treat at least 150 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat between about 15 minutes and about 150 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 180 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 210 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 240 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 270 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 300 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 330 minutes after the (R)-MDMA form disclosed herein, including those described in Table Ex9. In some embodiments, the serotonin receptor modulator is volinanserin and the psychedelic is (R)-MDMA, wherein the volinanserin is administered to post-treat at least 360 minutes after the (R)-MDMA form disclosed herein, including those described in Table Ex9. In some preferred embodiments, the serotonin receptor modulator is volinanserin and the psychedelic is (R)-MDMA, wherein volinanserin is administered to post-treat between about 60 minutes and about 180 minutes after the administration of the (R)-MDMA form disclosed herein, including those described in Table Ex9.

In some embodiments, the serotonin receptor modulator is ketanserin and the psychedelic is (R)-MDMA, wherein the ketanserin is administered to post-treat at least 15 minutes after the administration of the (R)-MDMA form disclosed herein, including those described in Table Ex9. In some embodiments, the serotonin receptor modulator is ketanserin and the psychedelic is (R)-MDMA, wherein the ketanserin is administered to post-treat between at least 30 minutes and 360 minutes after the administration or release of the (R)-MDMA form disclosed herein, including those described in Table Ex9. In some embodiments, the serotonin receptor modulator is ketanserin and the psychedelic is (R)-MDMA, wherein the ketanserin is administered to post-treat between at least 60 minutes and 240 minutes after the administration or release of the (R)-MDMA form disclosed herein, including those described in Table Ex9. In some embodiments, the serotonin receptor modulator is ketanserin and the psychedelic is (R)-MDMA, wherein the ketanserin is administered to post-treat at least 90 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 120 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 150 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat between about 15 minutes and about 150 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 180 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 210 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 240 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 270 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 300 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 330 minutes after the (R)-MDMA form disclosed herein, including those described in Table Ex9. In some embodiments, the serotonin receptor modulator is ketanserin and the psychedelic is (R)-MDMA, wherein the ketanserin is administered to post-treat at least 360 minutes after the (R)-MDMA form disclosed herein, including those described in Table Ex9. In some preferred embodiments, the serotonin receptor modulator is ketanserin and the psychedelic is (R)-MDMA, wherein ketanserin is administered to post-treat between about 60 minutes and about 180 minutes after the administration of the (R)-MDMA form disclosed herein, including those described in Table Ex9.

In some embodiments, the serotonin receptor modulator is ritanserin and the psychedelic is (R)-MDMA, wherein the ritanserin is administered to post-treat at least 15 minutes after the administration of the (R)-MDMA form disclosed herein, including those described in Table Ex9. In some embodiments, the serotonin receptor modulator is ritanserin and the psychedelic is (R)-MDMA, wherein the ritanserin is administered to post-treat at least 30 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat between at least 60 minutes and 240 minutes after the administration or release of the (R)-MDMA form disclosed herein, including those described in Table Ex9. In some embodiments, the serotonin receptor modulator is ritanserin and the psychedelic is (R)-MDMA, wherein the ritanserin is administered to post-treat at least 90 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 120 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 150 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat between about 15 minutes and about 150 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 180 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 210 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 240 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 270 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 300 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 330 minutes after the (R)-MDMA form disclosed herein, including those described in Table Ex9. In some embodiments, the serotonin receptor modulator is ritanserin and the psychedelic is (R)-MDMA, wherein the ritanserin is administered to post-treat at least 360 minutes after the (R)-MDMA form disclosed herein, including those described in Table Ex9. In some preferred embodiments, the serotonin receptor modulator is ritanserin and the psychedelic is (R)-MDMA, wherein ritanserin is administered to post-treat between about 60 minutes and about 180 minutes after the administration of the (R)-MDMA form disclosed herein, including those described in Table Ex9.

In some embodiments, the serotonin receptor modulator is pimavanserin and the psychedelic is (R)-MDMA, wherein the pimavanserin is administered to post-treat at least 15 minutes after the administration of the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 30 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat between at least 60 minutes and 240 minutes after the administration or release of the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 90 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 120 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 150 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat between about 15 minutes and about 150 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 180 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 210 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 240 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 270 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 300 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 330 minutes after the (R)-MDMA form disclosed herein, including those described in Table Ex9. In some embodiments, the serotonin receptor modulator is pimavanserin and the psychedelic is (R)-MDMA, wherein the pimavanserin is administered to post-treat at least 360 minutes after the (R)-MDMA form disclosed herein, including those described in Table Ex9. In some preferred embodiments, the serotonin receptor modulator is pimavanserin and the psychedelic is (R)-MDMA, wherein pimavanserin is administered to post-treat between about 60 minutes and about 180 minutes after the administration of the (R)-MDMA form disclosed herein, including those described in Table Ex9.

In some embodiments, the serotonin receptor modulator is nelotanserin and the psychedelic is (R)-MDMA, wherein the nelotanserin is administered to post-treat at least 15 minutes after the administration of the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 30 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat between at least 60 minutes and 240 minutes after the administration or release of the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 90 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 120 minutes after the (R)-MDMA form disclosed herein, including those described in Table Ex9.

In some embodiments, the serotonin receptor modulator is nelotanserin and the psychedelic is (R)-MDMA, wherein the nelotanserin is administered to post-treat at least 150 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat between about 15 minutes and about 150 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 180 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 210 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 240 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 270 minutes after the (R)-MDMA form disclosed herein, including those described in Table Ex9.

In some embodiments, the serotonin receptor modulator is nelotanserin and the psychedelic is (R)-MDMA, wherein the nelotanserin is administered to post-treat at least 300 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 330 minutes after the (R)-MDMA form disclosed herein, including those described in Table Ex9. In some embodiments, the serotonin receptor modulator is nelotanserin and the psychedelic is (R)-MDMA, wherein the nelotanserin is administered to post-treat at least 360 minutes after the (R)-MDMA form disclosed herein, including those described in Table Ex9. In some preferred embodiments, the serotonin receptor modulator is nelotanserin and the psychedelic is (R)-MDMA, wherein nelotanserin is administered to post-treat between about 60 minutes and about 180 minutes after the administration of the (R)-MDMA form disclosed herein, including those described in Table Ex9.

In some embodiments, the serotonin receptor modulator is pruvanserin and the psychedelic is (R)-MDMA, wherein the pruvanserin is administered to post-treat at least 15 minutes after the administration of the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 30 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat between at least 60 minutes and 240 minutes after the administration or release of the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 90 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 120 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 150 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat between about 15 minutes and about 150 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 180 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 210 minutes after the (R)-MDMA form disclosed herein, including those described in Table Ex9.

In some embodiments, the serotonin receptor modulator is pruvanserin and the psychedelic is (R)-MDMA, wherein the pruvanserin is administered to post-treat at least 240 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 270 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 300 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 330 minutes after the (R)-MDMA form disclosed herein, including those described in Table Ex9. In some embodiments, the serotonin receptor modulator is pruvanserin and the psychedelic is (R)-MDMA, wherein the pruvanserin is administered to post-treat at least 360 minutes after the (R)-MDMA form disclosed herein, including those described in Table Ex9. In some preferred embodiments, the serotonin receptor modulator is pruvanserin and the psychedelic is (R)-MDMA, wherein pruvanserin is administered to post-treat between about 60 minutes and about 180 minutes after the administration of the (R)-MDMA form disclosed herein, including those described in Table Ex9.

In some embodiments, the serotonin receptor modulator is flibanserin, wherein the flibanserin is administered to post-treat at least 15 minutes post to the administration of the (R)-MDMA form disclosed herein, including those described in Table Ex9. In some embodiments, the serotonin receptor modulator is flibanserin, wherein the flibanserin is administered to post-treat at least 30 minutes post to the (R)-MDMA form disclosed herein, including those described in Table Ex9. In some embodiments, the serotonin receptor modulator is flibanserin, wherein the flibanserin is administered to post-treat between at least 60 minutes and 240 minutes post to the administration or release of the (R)-MDMA form disclosed herein, including those described in Table Ex9. In some embodiments, the serotonin receptor modulator is flibanserin, wherein the flibanserin is administered to post-treat at least 90 minutes post to the (R)-MDMA form disclosed herein, including those described in Table Ex9. In some embodiments, the serotonin receptor modulator is flibanserin, wherein the flibanserin is administered to post-treat at least 120 minutes post to the (R)-MDMA form disclosed herein, including those described in Table Ex9. In some embodiments, the serotonin receptor modulator is flibanserin, wherein the flibanserin is administered to post-treat at least 150 minutes post to the (R)-MDMA form disclosed herein, including those described in Table Ex9. In some embodiments, the serotonin receptor modulator is flibanserin, wherein the flibanserin is administered to post-treat between about 15 minutes and about 150 minutes post to the (R)-MDMA form disclosed herein, including those described in Table Ex9. In some embodiments, the serotonin receptor modulator is flibanserin, wherein the flibanserin is administered to post-treat at least 180 minutes post to the (R)-MDMA form disclosed herein, including those described in Table Ex9. In some embodiments, the serotonin receptor modulator is flibanserin, wherein the flibanserin is administered to post-treat at least 210 minutes post to the (R)-MDMA form disclosed herein, including those described in Table Ex9.

In some embodiments, the serotonin receptor modulator is flibanserin, wherein the flibanserin is administered to post-treat at least 240 minutes post to the (R)-MDMA form disclosed herein, including those described in Table Ex9. In some embodiments, the serotonin receptor modulator is flibanserin, wherein the flibanserin is administered to post-treat at least 270 minutes post to the (R)-MDMA form disclosed herein, including those described in Table Ex9. In some embodiments, the serotonin receptor modulator is flibanserin, wherein the flibanserin is administered to post-treat at least 300 minutes post to the (R)-MDMA form disclosed herein, including those described in Table Ex9. In some embodiments, the serotonin receptor modulator is flibanserin, wherein the flibanserin is administered to post-treat at least 330 minutes post to the (R)-MDMA form disclosed herein, including those described in Table Ex9. In some embodiments, the serotonin receptor modulator is flibanserin, wherein the flibanserin is administered to post-treat at least 360 minutes post to the (R)-MDMA form disclosed herein, including those described in Table Ex9. In some preferred embodiments, the serotonin receptor modulator is flibanserin, wherein flibanserin is administered to post-treat between about 60 minutes and about 180 minutes post to the administration of the (R)-MDMA form disclosed herein, including those described in Table Ex9.

In some embodiments, the serotonin receptor modulator is olanzapine, wherein the olanzapine is administered to post-treat at least 15 minutes post to the administration of the (R)-MDMA form disclosed herein, including those described in Table Ex9. In some embodiments, the serotonin receptor modulator is olanzapine, wherein the olanzapine is administered to post-treat at least 30 minutes post to the (R)-MDMA form disclosed herein, including those described in Table Ex9. In some embodiments, the serotonin receptor modulator is olanzapine, wherein the olanzapine is administered to post-treat between at least 60 minutes and 240 minutes post to the administration or release of the (R)-MDMA form disclosed herein, including those described in Table Ex9. In some embodiments, the serotonin receptor modulator is olanzapine, wherein the olanzapine is administered to post-treat at least 90 minutes post to the (R)-MDMA form disclosed herein, including those described in Table Ex9. In some embodiments, the serotonin receptor modulator is olanzapine, wherein the olanzapine is administered to post-treat at least 120 minutes post to the (R)-MDMA form disclosed herein, including those described in Table Ex9. In some embodiments, the serotonin receptor modulator is olanzapine, wherein the olanzapine is administered to post-treat at least 150 minutes post to the (R)-MDMA form disclosed herein, including those described in Table Ex9. In some embodiments, the serotonin receptor modulator is olanzapine, wherein the olanzapine is administered to post-treat between about 15 minutes and about 150 minutes post to the (R)-MDMA form disclosed herein, including those described in Table Ex9. In some embodiments, the serotonin receptor modulator is olanzapine, wherein the olanzapine is administered to post-treat at least 180 minutes post to the (R)-MDMA form disclosed herein, including those described in Table Ex9. In some embodiments, the serotonin receptor modulator is olanzapine, wherein the olanzapine is administered to post-treat at least 210 minutes post to the (R)-MDMA form disclosed herein, including those described in Table Ex9.

In some embodiments, the serotonin receptor modulator is olanzapine, wherein the olanzapine is administered to post-treat at least 240 minutes post to the (R)-MDMA form disclosed herein, including those described in Table Ex9. In some embodiments, the serotonin receptor modulator is olanzapine, wherein the olanzapine is administered to post-treat at least 270 minutes post to the (R)-MDMA form disclosed herein, including those described in Table Ex9. In some embodiments, the serotonin receptor modulator is olanzapine, wherein the olanzapine is administered to post-treat at least 300 minutes post to the (R)-MDMA form disclosed herein, including those described in Table Ex9. In some embodiments, the serotonin receptor modulator is olanzapine, wherein the olanzapine is administered to post-treat at least 330 minutes post to the (R)-MDMA form disclosed herein, including those described in Table Ex9. In some embodiments, the serotonin receptor modulator is olanzapine, wherein the olanzapine is administered to post-treat at least 360 minutes post to the (R)-MDMA form disclosed herein, including those described in Table Ex9. In some preferred embodiments, the serotonin receptor modulator is olanzapine, wherein olanzapine is administered to post-treat between about 60 minutes and about 180 minutes post to the administration of the (R)-MDMA form disclosed herein, including those described in Table Ex9.

In some embodiments, the serotonin receptor modulator is quetiapine, wherein the quetiapine is administered to post-treat at least 15 minutes post to the administration of the (R)-MDMA form disclosed herein, including those described in Table Ex9. In some embodiments, the serotonin receptor modulator is quetiapine, wherein the quetiapine is administered to post-treat at least 30 minutes post to the (R)-MDMA form disclosed herein, including those described in Table Ex9. In some embodiments, the serotonin receptor modulator is quetiapine, wherein the quetiapine is administered to post-treat between at least 60 minutes and 240 minutes post to the administration or release of the (R)-MDMA form disclosed herein, including those described in Table Ex9. In some embodiments, the serotonin receptor modulator is quetiapine, wherein the quetiapine is administered to post-treat at least 90 minutes post to the (R)-MDMA form disclosed herein, including those described in Table Ex9. In some embodiments, the serotonin receptor modulator is quetiapine, wherein the quetiapine is administered to post-treat at least 120 minutes post to the (R)-MDMA form disclosed herein, including those described in Table Ex9. In some embodiments, the serotonin receptor modulator is quetiapine, wherein the quetiapine is administered to post-treat at least 150 minutes post to the (R)-MDMA form disclosed herein, including those described in Table Ex9. In some embodiments, the serotonin receptor modulator is quetiapine, wherein the quetiapine is administered to post-treat between about 15 minutes and about 150 minutes post to the (R)-MDMA form disclosed herein, including those described in Table Ex9. In some embodiments, the serotonin receptor modulator is quetiapine, wherein the quetiapine is administered to post-treat at least 180 minutes post to the (R)-MDMA form disclosed herein, including those described in Table Ex9. In some embodiments, the serotonin receptor modulator is quetiapine, wherein the quetiapine is administered to post-treat at least 210 minutes post to the (R)-MDMA form disclosed herein, including those described in Table Ex9.

In some embodiments, the serotonin receptor modulator is quetiapine, wherein the quetiapine is administered to post-treat at least 240 minutes post to the (R)-MDMA form disclosed herein, including those described in Table Ex9. In some embodiments, the serotonin receptor modulator is quetiapine, wherein the quetiapine is administered to post-treat at least 270 minutes post to the (R)-MDMA form disclosed herein, including those described in Table Ex9. In some embodiments, the serotonin receptor modulator is quetiapine, wherein the quetiapine is administered to post-treat at least 300 minutes post to the (R)-MDMA form disclosed herein, including those described in Table Ex9. In some embodiments, the serotonin receptor modulator is quetiapine, wherein the quetiapine is administered to post-treat at least 330 minutes post to the (R)-MDMA form disclosed herein, including those described in Table Ex9. In some embodiments, the serotonin receptor modulator is quetiapine, wherein the quetiapine is administered to post-treat at least 360 minutes post to the (R)-MDMA form disclosed herein, including those described in Table Ex9. In some preferred embodiments, the serotonin receptor modulator is quetiapine, wherein quetiapine is administered to post-treat between about 60 minutes and about 180 minutes post to the administration of the (R)-MDMA form disclosed herein, including those described in Table Ex9.

In some embodiments, the serotonin receptor modulator is risperidone, wherein the risperidone is administered to post-treat at least 15 minutes post to the administration of the (R)-MDMA form disclosed herein, including those described in Table Ex9. In some embodiments, the serotonin receptor modulator is risperidone, wherein the risperidone is administered to post-treat at least 30 minutes post to the (R)-MDMA form disclosed herein, including those described in Table Ex9. In some embodiments, the serotonin receptor modulator is risperidone, wherein the risperidone is administered to post-treat between at least 60 minutes and 240 minutes post to the administration or release of the (R)-MDMA form disclosed herein, including those described in Table Ex9. In some embodiments, the serotonin receptor modulator is risperidone, wherein the risperidone is administered to post-treat at least 90 minutes post to the (R)-MDMA form disclosed herein, including those described in Table Ex9. In some embodiments, the serotonin receptor modulator is risperidone, wherein the risperidone is administered to post-treat at least 120 minutes post to the (R)-MDMA form disclosed herein, including those described in Table Ex9. In some embodiments, the serotonin receptor modulator is risperidone, wherein the risperidone is administered to post-treat at least 150 minutes post to the (R)-MDMA form disclosed herein, including those described in Table Ex9. In some embodiments, the serotonin receptor modulator is risperidone, wherein the risperidone is administered to post-treat between about 15 minutes and about 150 minutes post to the (R)-MDMA form disclosed herein, including those described in Table Ex9. In some embodiments, the serotonin receptor modulator is risperidone, wherein the risperidone is administered to post-treat at least 180 minutes post to the (R)-MDMA form disclosed herein, including those described in Table Ex9. In some embodiments, the serotonin receptor modulator is risperidone, wherein the risperidone is administered to post-treat at least 210 minutes post to the (R)-MDMA form disclosed herein, including those described in Table Ex9.

In some embodiments, the serotonin receptor modulator is risperidone, wherein the risperidone is administered to post-treat at least 240 minutes post to the (R)-MDMA form disclosed herein, including those described in Table Ex9. In some embodiments, the serotonin receptor modulator is risperidone, wherein the risperidone is administered to post-treat at least 270 minutes post to the (R)-MDMA form disclosed herein, including those described in Table Ex9. In some embodiments, the serotonin receptor modulator is risperidone, wherein the risperidone is administered to post-treat at least 300 minutes post to the (R)-MDMA form disclosed herein, including those described in Table Ex9. In some embodiments, the serotonin receptor modulator is risperidone, wherein the risperidone is administered to post-treat at least 330 minutes post to the (R)-MDMA form disclosed herein, including those described in Table Ex9. In some embodiments, the serotonin receptor modulator is risperidone, wherein the risperidone is administered to post-treat at least 360 minutes post to the (R)-MDMA form disclosed herein, including those described in Table Ex9. In some preferred embodiments, the serotonin receptor modulator is risperidone, wherein risperidone is administered to post-treat between about 60 minutes and about 180 minutes post to the administration of the (R)-MDMA form disclosed herein, including those described in Table Ex9.

In some embodiments, the serotonin receptor modulator for use with the psychedelic(S)-MDMA is eplivanserin and, wherein the eplivanserin is administered in about 1 mg to about 40 mg, or about 5 mg to about 10 mg, and the (S)-MDMA is administered between about 50 mg and about 200 mg, or between about 80 mg and 120 mg.

In some embodiments, the serotonin receptor modulator is volinanserin and the psychedelic is (S)-MDMA, wherein the volinanserin is administered in about 1 mg to about 60 mg, or about 5 mg to about 20 mg, and the (S)-MDMA is administered between about 50 mg and about 200 mg, or between about 80 mg and 120 mg.

In some embodiments, the serotonin receptor modulator for use with the psychedelic(S)-MDMA is ketanserin, wherein the ketanserin is administered in about 10 mg to about 80 mg, about 30 mg to about 50 mg, or about 40 mg and the (S)-MDMA is administered between about 50 mg and about 200 mg, or between about 80 mg and 120 mg.

In some embodiments, the serotonin receptor modulator for use with the psychedelic(S)-MDMA is ritanserin, wherein the ritanserin is administered in about 1 mg to about 40 mg, or about 2.5 mg to about 10 mg, and the (S)-MDMA is administered between about 50 mg and about 200 mg, or between about 80 mg and 120 mg.

In some embodiments, the serotonin receptor modulator is pimavanserin and the psychedelic is (S)-MDMA, wherein the pimavanserin is administered in about 1 mg to about 60 mg, or about 17 mg to about 34 mg, and the (S)-MDMA is administered between about 50 mg and about 200 mg, or between about 80 mg and 120 mg.

In some embodiments, the serotonin receptor modulator for use with the psychedelic(S)-MDMA is nelotanserin, wherein the nelotanserin is administered in about 1 mg to about 80 mg, or about 40 mg to about 80 mg, and the (S)-MDMA is administered between about 50 mg and about 200 mg, or between about 80 mg and 120 mg.

In some embodiments, the serotonin receptor modulator for use with the psychedelic(S)-MDMA is pruvanserin, wherein the pruvanserin is administered in about 1 mg to about 40 mg, or about 3 mg to about 10 mg, and the (S)-MDMA is administered between about 50 mg and about 200 mg, or between about 80 mg and 120 mg.

In some embodiments, the serotonin receptor modulator for use with the psychedelic(S)-MDMA is flibanserin, wherein the flibanserin is administered in about 10 mg to about 200 mg, or about 80 mg to about 120 mg, or about 100 mg and the (S)-MDMA is administered between about 50 mg and about 200 mg, or between about 80 mg and 120 mg.

In certain embodiments, such as those described above a disclosed(S)-MDMA form is co-administered with a serotonin receptor modulator in the same or in separate compositions. In one embodiment, the (S)-MDMA is administered in a modified release formulation such that the subject is effectively pretreated with serotonin receptor modulator prior to release of an effective amount of the psychedelic. Thus, in some embodiments, the serotonin receptor modulator is administered or released from a composition provided herein prior to the administration and/or release of the psychedelic. This allows pretreatment to attenuate activation of the serotonin receptor by the psychedelic.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is (S)-MDMA, wherein the eplivanserin is administered to pretreat at least 15 minutes prior to the administration of (S)-MDMA. In some embodiments, the serotonin receptor modulator is eplivanserin and the psychedelic is (S)-MDMA, wherein the eplivanserin is administered to pretreat between at least 30 minutes prior and 360 minutes prior to the release or administration of the (S)-MDMA. In some embodiments, the serotonin receptor modulator is eplivanserin and the psychedelic is (S)-MDMA, wherein the eplivanserin is administered to pretreat between at least 60 minutes prior and 360 minutes prior to the release or administration the(S)-MDMA. In some embodiments, the serotonin receptor modulator is eplivanserin and the psychedelic is (S)-MDMA, wherein the eplivanserin is administered to pretreat between at least 90 minutes and 240 minutes prior to the (S)-MDMA. In some embodiments, the serotonin receptor modulator is eplivanserin and the psychedelic is (S)-MDMA, wherein the eplivanserin is administered to pretreat at least 120 minutes prior to the (S)-MDMA.

In some embodiments, the serotonin receptor modulator is eplivanserin and the psychedelic is (S)-MDMA, wherein the eplivanserin is administered to pretreat at least 150 minutes prior to the (S)-MDMA. In some embodiments, the serotonin receptor modulator is eplivanserin and the psychedelic is (S)-MDMA, wherein the eplivanserin is administered to pretreat at least 180 minutes prior to the (S)-MDMA. In some embodiments, the serotonin receptor modulator is eplivanserin and the psychedelic is (S)-MDMA, wherein the eplivanserin is administered to pretreat at least 210 minutes prior to the (S)-MDMA. In some embodiments, the serotonin receptor modulator is eplivanserin and the psychedelic is (S)-MDMA, wherein the eplivanserin is administered to pretreat at least 240 minutes prior to the (S)-MDMA.

In some embodiments, the serotonin receptor modulator is eplivanserin and the psychedelic is (S)-MDMA, wherein the eplivanserin is administered to pretreat at least 270 minutes prior to(S)-MDMA. In some embodiments, the serotonin receptor modulator is eplivanserin and the psychedelic is (S)-MDMA, wherein the eplivanserin is administered to pretreat at least 300 minutes prior to the (S)-MDMA. In some embodiments, the serotonin receptor modulator is eplivanserin and the psychedelic is (S)-MDMA, wherein the eplivanserin is administered to pretreat at least 330 minutes prior to the (S)-MDMA. In some embodiments, the serotonin receptor modulator is eplivanserin and the psychedelic is (S)-MDMA, wherein the eplivanserin is administered to pretreat at least 360 minutes prior to the (S)-MDMA.

In some preferred embodiments, the serotonin receptor modulator is eplivanserin and the psychedelic is (S)-MDMA, wherein eplivanserin is administered to pretreat between about 60 minutes and about 180 minutes prior to the administration of (S)-MDMA.

In some embodiments, the serotonin receptor modulator is volinanserin and the psychedelic is (S)-MDMA, wherein the volinanserin is administered to pretreat a subject between at least 15 minutes and 360 minutes prior to the administration or release of (S)-MDMA. In some embodiments, the serotonin receptor modulator is volinanserin and the psychedelic is (S)-MDMA, wherein the volinanserin is administered to pretreat between at least 30 minutes and 360 minutes prior to the administration or release of (S)-MDMA. In some embodiments, the serotonin receptor modulator is volinanserin and the psychedelic is (S)-MDMA, wherein the volinanserin is administered to pretreat between at least 60 minutes and 240 minutes prior to the administration or release of (S)-MDMA. In some embodiments, the serotonin receptor modulator is volinanserin and the psychedelic is (S)-MDMA, wherein the volinanserin is administered to pretreat at least 90 minutes prior to(S)-MDMA. In some embodiments, the serotonin receptor modulator is volinanserin and the psychedelic is (S)-MDMA, wherein the volinanserin is administered to pretreat at least 120 minutes prior to the (S)-MDMA.

In some embodiments, the serotonin receptor modulator is volinanserin and the psychedelic is (S)-MDMA, wherein the volinanserin is administered to pretreat at least 150 minutes prior to the (S)-MDMA. In some embodiments, the serotonin receptor modulator is volinanserin and the psychedelic is (S)-MDMA, wherein the volinanserin is administered to pretreat between about 15 minutes and about 150 minutes prior to the (S)-MDMA. In some embodiments, the serotonin receptor modulator is volinanserin and the psychedelic is (S)-MDMA, wherein the volinanserin is administered to pretreat at least 180 minutes prior to the (S)-MDMA. In some embodiments, the serotonin receptor modulator is volinanserin and the psychedelic is (S)-MDMA, wherein the volinanserin is administered to pretreat at least 210 minutes prior to the (S)-MDMA. In some embodiments, the serotonin receptor modulator is volinanserin and the psychedelic is (S)-MDMA, wherein the volinanserin is administered to pretreat at least 240 minutes prior to the (S)-MDMA. In some embodiments, the serotonin receptor modulator is volinanserin and the psychedelic is (S)-MDMA, wherein the volinanserin is administered to pretreat at least 270 minutes prior to the (S)-MDMA. In some embodiments, the serotonin receptor modulator is volinanserin and the psychedelic is (S)-MDMA, wherein the volinanserin is administered to pretreat at least 300 minutes prior to the (S)-MDMA. In some embodiments, the serotonin receptor modulator is volinanserin and the psychedelic is (S)-MDMA, wherein the volinanserin is administered to pretreat at least 330 minutes prior to the (S)-MDMA. In some embodiments, the serotonin receptor modulator is volinanserin and the psychedelic is (S)-MDMA, wherein the volinanserin is administered to pretreat at least 360 minutes prior to the (S)-MDMA. In some preferred embodiments, the serotonin receptor modulator is volinanserin and the psychedelic is (S)-MDMA, wherein volinanserin is administered to pretreat between about 60 minutes and about 180 minutes prior to the administration of (S)-MDMA.

In some embodiments, the serotonin receptor modulator is ketanserin and the psychedelic is (S)-MDMA, wherein the ketanserin is administered to pretreat at least 15 minutes prior to the administration of (S)-MDMA. In some embodiments, the serotonin receptor modulator is ketanserin and the psychedelic is (S)-MDMA, wherein the ketanserin is administered to pretreat between at least 30 minutes and 360 minutes prior to the administration or release(S)-MDMA. In some embodiments, the serotonin receptor modulator is ketanserin and the psychedelic is (S)-MDMA, wherein the ketanserin is administered to pretreat between at least 60 minutes and 240 minutes prior to the administration or release of (S)-MDMA. In some embodiments, the serotonin receptor modulator is ketanserin and the psychedelic is (S)-MDMA, wherein the ketanserin is administered to pretreat at least 90 minutes prior to the (S)-MDMA. In some embodiments, the serotonin receptor modulator is ketanserin and the psychedelic is (S)-MDMA, wherein the ketanserin is administered to pretreat at least 120 minutes prior to the (S)-MDMA. In some embodiments, the serotonin receptor modulator is ketanserin and the psychedelic is (S)-MDMA, wherein the ketanserin is administered to pretreat at least 150 minutes prior to the (S)-MDMA. In some embodiments, the serotonin receptor modulator is ketanserin and the psychedelic is (S)-MDMA, wherein the ketanserin is administered to pretreat between about 15 minutes and about 150 minutes prior to the (S)-MDMA. In some embodiments, the serotonin receptor modulator is ketanserin and the psychedelic is (S)-MDMA, wherein the ketanserin is administered to pretreat at least 180 minutes prior to the (S)-MDMA. In some embodiments, the serotonin receptor modulator is ketanserin and the psychedelic is (S)-MDMA, wherein the ketanserin is administered to pretreat at least 210 minutes prior to the (S)-MDMA. In some embodiments, the serotonin receptor modulator is ketanserin and the psychedelic is (S)-MDMA, wherein the ketanserin is administered to pretreat at least 240 minutes prior to the (S)-MDMA. In some embodiments, the serotonin receptor modulator is ketanserin and the psychedelic is (S)-MDMA, wherein the ketanserin is administered to pretreat at least 270 minutes prior to the (S)-MDMA. In some embodiments, the serotonin receptor modulator is ketanserin and the psychedelic is (S)-MDMA, wherein the ketanserin is administered to pretreat at least 300 minutes prior to the (S)-MDMA. In some embodiments, the serotonin receptor modulator is ketanserin and the psychedelic is (S)-MDMA, wherein the ketanserin is administered to pretreat at least 330 minutes prior to the (S)-MDMA. In some embodiments, the serotonin receptor modulator is ketanserin and the psychedelic is (S)-MDMA, wherein the ketanserin is administered to pretreat at least 360 minutes prior to the (S)-MDMA. In some preferred embodiments, the serotonin receptor modulator is ketanserin and the psychedelic is (S)-MDMA, wherein ketanserin is administered to pretreat between about 60 minutes and about 180 minutes prior to the administration of (S)-MDMA.

In some embodiments, the serotonin receptor modulator is ritanserin and the psychedelic is (S)-MDMA, wherein the ritanserin is administered to pretreat at least 15 minutes prior to the administration of (S)-MDMA. In some embodiments, the serotonin receptor modulator is ritanserin and the psychedelic is (S)-MDMA, wherein the ritanserin is administered to pretreat at least 30 minutes prior to the (S)-MDMA. In some embodiments, the serotonin receptor modulator is ritanserin and the psychedelic is (S)-MDMA, wherein the ritanserin is administered to pretreat between at least 60 minutes and 240 minutes prior to the administration or release of (S)-MDMA. In some embodiments, the serotonin receptor modulator is ritanserin and the psychedelic is (S)-MDMA, wherein the ritanserin is administered to pretreat at least 90 minutes prior to the (S)-MDMA. In some embodiments, the serotonin receptor modulator is ritanserin and the psychedelic is (S)-MDMA, wherein the ritanserin is administered to pretreat at least 120 minutes prior to the (S)-MDMA. In some embodiments, the serotonin receptor modulator is ritanserin and the psychedelic is (S)-MDMA, wherein the ritanserin is administered to pretreat at least 150 minutes prior to the (S)-MDMA. In some embodiments, the serotonin receptor modulator is ritanserin and the psychedelic is (S)-MDMA, wherein the ritanserin is administered to pretreat between about 15 minutes and about 150 minutes prior to the (S)-MDMA. In some embodiments, the serotonin receptor modulator is ritanserin and the psychedelic is (S)-MDMA, wherein the ritanserin is administered to pretreat at least 180 minutes prior to the (S)-MDMA. In some embodiments, the serotonin receptor modulator is ritanserin and the psychedelic is (S)-MDMA, wherein the ritanserin is administered to pretreat at least 210 minutes prior to the (S)-MDMA. In some embodiments, the serotonin receptor modulator is ritanserin and the psychedelic is (S)-MDMA, wherein the ritanserin is administered to pretreat at least 240 minutes prior to the (S)-MDMA. In some embodiments, the serotonin receptor modulator is ritanserin and the psychedelic is (S)-MDMA, wherein the ritanserin is administered to pretreat at least 270 minutes prior to the (S)-MDMA. In some embodiments, the serotonin receptor modulator is ritanserin and the psychedelic is (S)-MDMA, wherein the ritanserin is administered to pretreat at least 300 minutes prior to the (S)-MDMA. In some embodiments, the serotonin receptor modulator is ritanserin and the psychedelic is (S)-MDMA, wherein the ritanserin is administered to pretreat at least 330 minutes prior to the (S)-MDMA. In some embodiments, the serotonin receptor modulator is ritanserin and the psychedelic is (S)-MDMA, wherein the ritanserin is administered to pretreat at least 360 minutes prior to the (S)-MDMA. In some preferred embodiments, the serotonin receptor modulator is ritanserin and the psychedelic is (S)-MDMA, wherein ritanserin is administered to pretreat between about 60 minutes and about 180 minutes prior to the administration of (S)-MDMA.

In some embodiments, the serotonin receptor modulator is pimavanserin and the psychedelic is (S)-MDMA, wherein the pimavanserin is administered to pretreat at least 15 minutes prior to the administration of (S)-MDMA. In some embodiments, the serotonin receptor modulator is pimavanserin and the psychedelic is (S)-MDMA, wherein the pimavanserin is administered to pretreat at least 30 minutes prior to the (S)-MDMA. In some embodiments, the serotonin receptor modulator is pimavanserin and the psychedelic is (S)-MDMA, wherein the pimavanserin is administered to pretreat between at least 60 minutes and 240 minutes prior to the administration or release of (S)-MDMA. In some embodiments, the serotonin receptor modulator is pimavanserin and the psychedelic is (S)-MDMA, wherein the pimavanserin is administered to pretreat at least 90 minutes prior to the (S)-MDMA. In some embodiments, the serotonin receptor modulator is pimavanserin and the psychedelic is (S)-MDMA, wherein the pimavanserin is administered to pretreat at least 120 minutes prior to the (S)-MDMA. In some embodiments, the serotonin receptor modulator is pimavanserin and the psychedelic is (S)-MDMA, wherein the pimavanserin is administered to pretreat at least 150 minutes prior to the (S)-MDMA. In some embodiments, the serotonin receptor modulator is pimavanserin and the psychedelic is (S)-MDMA, wherein the pimavanserin is administered to pretreat between about 15 minutes and about 150 minutes prior to the (S)-MDMA. In some embodiments, the serotonin receptor modulator is pimavanserin and the psychedelic is (S)-MDMA, wherein the pimavanserin is administered to pretreat at least 180 minutes prior to the (S)-MDMA. In some embodiments, the serotonin receptor modulator is pimavanserin and the psychedelic is (S)-MDMA, wherein the pimavanserin is administered to pretreat at least 210 minutes prior to the (S)-MDMA. In some embodiments, the serotonin receptor modulator is pimavanserin and the psychedelic is (S)-MDMA, wherein the pimavanserin is administered to pretreat at least 240 minutes prior to the (S)-MDMA. In some embodiments, the serotonin receptor modulator is pimavanserin and the psychedelic is (S)-MDMA, wherein the pimavanserin is administered to pretreat at least 270 minutes prior to the (S)-MDMA. In some embodiments, the serotonin receptor modulator is pimavanserin and the psychedelic is (S)-MDMA, wherein the pimavanserin is administered to pretreat at least 300 minutes prior to the (S)-MDMA. In some embodiments, the serotonin receptor modulator is pimavanserin and the psychedelic is (S)-MDMA, wherein the pimavanserin is administered to pretreat at least 330 minutes prior to the (S)-MDMA. In some embodiments, the serotonin receptor modulator is pimavanserin and the psychedelic is (S)-MDMA, wherein the pimavanserin is administered to pretreat at least 360 minutes prior to the (S)-MDMA. In some preferred embodiments, the serotonin receptor modulator is pimavanserin and the psychedelic is (S)-MDMA, wherein pimavanserin is administered to pretreat between about 60 minutes and about 180 minutes prior to the administration of (S)-MDMA.

In some embodiments, the serotonin receptor modulator is nelotanserin and the psychedelic is (S)-MDMA, wherein the nelotanserin is administered to pretreat at least 15 minutes prior to the administration of (S)-MDMA. In some embodiments, the serotonin receptor modulator is nelotanserin and the psychedelic is (S)-MDMA, wherein the nelotanserin is administered to pretreat at least 30 minutes prior to the (S)-MDMA. In some embodiments, the serotonin receptor modulator is nelotanserin and the psychedelic is (S)-MDMA, wherein the nelotanserin is administered to pretreat between at least 60 minutes and 240 minutes prior to the administration or release of (S)-MDMA. In some embodiments, the serotonin receptor modulator is nelotanserin and the psychedelic is (S)-MDMA, wherein the nelotanserin is administered to pretreat at least 90 minutes prior to the (S)-MDMA. In some embodiments, the serotonin receptor modulator is nelotanserin and the psychedelic is (S)-MDMA, wherein the nelotanserin is administered to pretreat at least 120 minutes prior to the (S)-MDMA.

In some embodiments, the serotonin receptor modulator is nelotanserin and the psychedelic is (S)-MDMA, wherein the nelotanserin is administered to pretreat at least 150 minutes prior to the (S)-MDMA. In some embodiments, the serotonin receptor modulator is nelotanserin and the psychedelic is (S)-MDMA, wherein the nelotanserin is administered to pretreat between about 15 minutes and about 150 minutes prior to the (S)-MDMA. In some embodiments, the serotonin receptor modulator is nelotanserin and the psychedelic is (S)-MDMA, wherein the nelotanserin is administered to pretreat at least 180 minutes prior to the (S)-MDMA. In some embodiments, the serotonin receptor modulator is nelotanserin and the psychedelic is (S)-MDMA, wherein the nelotanserin is administered to pretreat at least 210 minutes prior to the (S)-MDMA. In some embodiments, the serotonin receptor modulator is nelotanserin and the psychedelic is (S)-MDMA, wherein the nelotanserin is administered to pretreat at least 240 minutes prior to the (S)-MDMA. In some embodiments, the serotonin receptor modulator is nelotanserin and the psychedelic is (S)-MDMA, wherein the nelotanserin is administered to pretreat at least 270 minutes prior to the (S)-MDMA.

In some embodiments, the serotonin receptor modulator is nelotanserin and the psychedelic is (S)-MDMA, wherein the nelotanserin is administered to pretreat at least 300 minutes prior to the (S)-MDMA. In some embodiments, the serotonin receptor modulator is nelotanserin and the psychedelic is (S)-MDMA, wherein the nelotanserin is administered to pretreat at least 330 minutes prior to the (S)-MDMA. In some embodiments, the serotonin receptor modulator is nelotanserin and the psychedelic is (S)-MDMA, wherein the nelotanserin is administered to pretreat at least 360 minutes prior to the (S)-MDMA. In some preferred embodiments, the serotonin receptor modulator is nelotanserin and the psychedelic is (S)-MDMA, wherein nelotanserin is administered to pretreat between about 60 minutes and about 180 minutes prior to the administration of (S)-MDMA.

In some embodiments, the serotonin receptor modulator is pruvanserin and the psychedelic is (S)-MDMA, wherein the pruvanserin is administered to pretreat at least 15 minutes prior to the administration of (S)-MDMA. In some embodiments, the serotonin receptor modulator is pruvanserin and the psychedelic is (S)-MDMA, wherein the pruvanserin is administered to pretreat at least 30 minutes prior to the (S)-MDMA. In some embodiments, the serotonin receptor modulator is pruvanserin and the psychedelic is (S)-MDMA, wherein the pruvanserin is administered to pretreat between at least 60 minutes and 240 minutes prior to the administration or release of (S)-MDMA. In some embodiments, the serotonin receptor modulator is pruvanserin and the psychedelic is (S)-MDMA, wherein the pruvanserin is administered to pretreat at least 90 minutes prior to the (S)-MDMA. In some embodiments, the serotonin receptor modulator is pruvanserin and the psychedelic is (S)-MDMA, wherein the pruvanserin is administered to pretreat at least 120 minutes prior to the (S)-MDMA. In some embodiments, the serotonin receptor modulator is pruvanserin and the psychedelic is (S)-MDMA, wherein the pruvanserin is administered to pretreat at least 150 minutes prior to the (S)-MDMA. In some embodiments, the serotonin receptor modulator is pruvanserin and the psychedelic is (S)-MDMA, wherein the pruvanserin is administered to pretreat between about 15 minutes and about 150 minutes prior to the(S)-MDMA. In some embodiments, the serotonin receptor modulator is pruvanserin and the psychedelic is (S)-MDMA, wherein the pruvanserin is administered to pretreat at least 180 minutes prior to the (S)-MDMA. In some embodiments, the serotonin receptor modulator is pruvanserin and the psychedelic is (S)-MDMA, wherein the pruvanserin is administered to pretreat at least 210 minutes prior to the (S)-MDMA.

In some embodiments, the serotonin receptor modulator is pruvanserin and the psychedelic is (S)-MDMA, wherein the pruvanserin is administered to pretreat at least 240 minutes prior to the (S)-MDMA. In some embodiments, the serotonin receptor modulator is pruvanserin and the psychedelic is (S)-MDMA, wherein the pruvanserin is administered to pretreat at least 270 minutes prior to the (S)-MDMA. In some embodiments, the serotonin receptor modulator is pruvanserin and the psychedelic is (S)-MDMA, wherein the pruvanserin is administered to pretreat at least 300 minutes prior to the (S)-MDMA. In some embodiments, the serotonin receptor modulator is pruvanserin and the psychedelic is (S)-MDMA, wherein the pruvanserin is administered to pretreat at least 330 minutes prior to the (S)-MDMA. In some embodiments, the serotonin receptor modulator is pruvanserin and the psychedelic is (S)-MDMA, wherein the pruvanserin is administered to pretreat at least 360 minutes prior to the (S)-MDMA. In some preferred embodiments, the serotonin receptor modulator is pruvanserin and the psychedelic is (S)-MDMA, wherein pruvanserin is administered to pretreat between about 60 minutes and about 180 minutes prior to the administration of (S)-MDMA.

In some embodiments, the serotonin receptor modulator for use with the (S)-MDMA salts and solid forms disclosed herein, including those described in Table Ex8 is eplivanserin and, wherein the eplivanserin is administered in about 1 mg to about 40 mg, or about 5 mg to about 10 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator is volinanserin and the (S)-MDMA salts and solid forms disclosed herein, including those described in Table Ex8, wherein the volinanserin is administered in about 1 mg to about 60 mg, or about 5 mg to about 20 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is ketanserin, wherein the ketanserin is administered in about 10 mg to about 80 mg, about 30 mg to about 50 mg, or about 40 mg and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is ritanserin, wherein the ritanserin is administered in about 1 mg to about 40 mg, or about 2.5 mg to about 10 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator is pimavanserin and the (S)-MDMA salts and solid forms disclosed herein, including those described in Table Ex8, wherein the pimavanserin is administered in about 1 mg to about 60 mg, or about 17 mg to about 34 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is nelotanserin, wherein the nelotanserin is administered in about 1 mg to about 80 mg, or about 40 mg to about 80 mg, and the(S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is pruvanserin, wherein the pruvanserin is administered in about 1 mg to about 40 mg, or about 3 mg to about 10 mg, and the(S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is flibanserin, wherein the flibanserin is administered in about 10 mg to about 200 mg, or about 80 mg to about 120 mg, or about 100 mg and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is olanzapine, wherein the olanzapine is administered in about 2.5 mg to about 30 mg, or about 5 mg or about 10 mg, or about 20 mg or about 25 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is quetiapine, wherein the quetiapine is administered in about 25 mg to about 800 mg, or about 50 mg to about 100 mg, or about 150 mg or about 200 mg or about 250 mg or about 300 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is an extended-release of quetiapine, wherein the extended-release of quetiapine is administered in about 50 mg to about 300 mg, or about 50 mg or about 100 mg or about 200 mg, or about 300 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the (S)-MDMA salts and solid forms disclosed herein, including those described in Table Ex8 are administered between about 50 mg and about 200 mg, or between about 80 mg and 120 mg.

In some embodiments, the serotonin receptor modulator for use with the (S)-MDMA salts and solid forms disclosed herein, including those described in Table Ex8 is an extended-release of risperidone including (RISPERDAL CONSTA), wherein the extended-release of risperidone is administered in about 12.5 mg, or about 25 mg, or about 37.5 mg, or about 50 mg, and the (S)-MDMA salts and solid forms disclosed herein, including those described in Table Ex8 are administered between about 50 mg and about 200 mg, or between about 80 mg and 120 mg.

In certain embodiments, such as those described above a(S)-MDMA form disclosed herein, including those described in Table Ex8 is co-administered with a serotonin receptor modulator in the same or in separate compositions. In one embodiment, the serotonin receptor modulator is administered prior to the (S)-MDMA form disclosed herein, including those described in Table Ex8. In one embodiment, the (S)-MDMA form disclosed herein, including those described in Table Ex8 is administered in a modified release formulation such that the subject is effectively pretreated with serotonin receptor modulator prior to release of an effective amount of the (S)-MDMA. In some embodiments the serotonin receptor modulator is part of a single fixed dose formulation that releases serotonin receptor modulator first followed by the (S)-MDMA on two different release profiles. In another embodiment the serotonin receptor modulator is administered first as a single dosage and after a length of time, the (S)-MDMA form disclosed herein, including those described in Table Ex8 is administered as a second dosage separate from the first dosage. Thus, in some embodiments, the serotonin receptor modulator is administered or released from a composition provided herein prior to the administration and/or release of the psychedelic. This allows pretreatment to attenuate activation of the serotonin receptor by the psychedelic.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is (S)-MDMA, wherein the eplivanserin is administered to pretreat at least 15 minutes prior to the administration of the (S)-MDMA form disclosed herein, including those described in Table Ex8. In some embodiments, the serotonin receptor modulator is eplivanserin and the psychedelic is (S)-MDMA, wherein the eplivanserin is administered to pretreat between at least 30 minutes prior and 360 minutes prior to the release or administration of the (S)-MDMA form disclosed herein, including those described in Table Ex8. In some embodiments, the serotonin receptor modulator is eplivanserin and the psychedelic is (S)-MDMA, wherein the eplivanserin is administered to pretreat between at least 60 minutes prior and 360 minutes prior to the release or administration of the (S)-MDMA form disclosed herein, including those described in Table Ex8. In some embodiments, the serotonin receptor modulator is eplivanserin and the psychedelic is (S)-MDMA, wherein the eplivanserin is administered to pretreat between at least 90 minutes and 240 minutes prior to the (S)-MDMA form disclosed herein, including those described in Table Ex8. In some embodiments, the serotonin receptor modulator is eplivanserin and the psychedelic is (S)-MDMA, wherein the eplivanserin is administered to pretreat at least 120 minutes prior to the (S)-MDMA form disclosed herein, including those described in Table Ex8.

In some embodiments, the serotonin receptor modulator is eplivanserin and the psychedelic is (S)-MDMA, wherein the eplivanserin is administered to pretreat at least 150 minutes prior to the (S)-MDMA form disclosed herein, including those described in Table Ex8. In some embodiments, the serotonin receptor modulator is eplivanserin and the psychedelic is (S)-MDMA, wherein the eplivanserin is administered to pretreat at least 180 minutes prior to the (S)-MDMA form disclosed herein, including those described in Table Ex8. In some embodiments, the serotonin receptor modulator is eplivanserin and the psychedelic is (S)-MDMA, wherein the eplivanserin is administered to pretreat at least 210 minutes prior to the (S)-MDMA form disclosed herein, including those described in Table Ex8. In some embodiments, the serotonin receptor modulator is eplivanserin and the psychedelic is (S)-MDMA, wherein the eplivanserin is administered to pretreat at least 240 minutes prior to the (S)-MDMA form disclosed herein, including those described in Table Ex8.

In some embodiments, the serotonin receptor modulator is eplivanserin and the psychedelic is (S)-MDMA, wherein the eplivanserin is administered to pretreat at least 270 minutes prior to(S)-MDMA. In some embodiments, the serotonin receptor modulator is eplivanserin and the psychedelic is (S)-MDMA, wherein the eplivanserin is administered to pretreat at least 300 minutes prior to the (S)-MDMA form disclosed herein, including those described in Table Ex8. In some embodiments, the serotonin receptor modulator is eplivanserin and the psychedelic is (S)-MDMA, wherein the eplivanserin is administered to pretreat at least 330 minutes prior to the (S)-MDMA form disclosed herein, including those described in Table Ex8. In some embodiments, the serotonin receptor modulator is eplivanserin and the psychedelic is (S)-MDMA, wherein the eplivanserin is administered to pretreat at least 360 minutes prior to the(S)-MDMA form disclosed herein, including those described in Table Ex8.

In some preferred embodiments, the serotonin receptor modulator is eplivanserin and the psychedelic is (S)-MDMA, wherein eplivanserin is administered to pretreat between about 60 minutes and about 180 minutes prior to the administration of the (S)-MDMA form disclosed herein, including those described in Table Ex8.

In some embodiments, the serotonin receptor modulator is volinanserin and the psychedelic is (S)-MDMA, wherein the volinanserin is administered to pretreat a subject between at least 15 minutes and 360 minutes prior to the administration or release of the (S)-MDMA form disclosed herein, including those described in Table Ex8. In some embodiments, the serotonin receptor modulator is volinanserin and the psychedelic is (S)-MDMA, wherein the volinanserin is administered to pretreat between at least 30 minutes and 360 minutes prior to the administration or release of the (S)-MDMA form disclosed herein, including those described in Table Ex8. In some embodiments, the serotonin receptor modulator is volinanserin and the psychedelic is (S)-MDMA, wherein the volinanserin is administered to pretreat between at least 60 minutes and 240 minutes prior to the administration or release of the (S)-MDMA form disclosed herein, including those described in Table Ex8. In some embodiments, the serotonin receptor modulator is volinanserin and the psychedelic is (S)-MDMA, wherein the volinanserin is administered to pretreat at least 90 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat at least 120 minutes prior to the (S)-MDMA form disclosed herein, including those described in Table Ex8.

In some embodiments, the serotonin receptor modulator is volinanserin and the psychedelic is (S)-MDMA, wherein the volinanserin is administered to pretreat at least 150 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat between about 15 minutes and about 150 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat at least 180 minutes prior to the(S)-MDMA form disclosed herein, including those described in Table Ex8. In some embodiments, the serotonin receptor modulator is volinanserin and the psychedelic is (S)-MDMA, wherein the volinanserin is administered to pretreat at least 210 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat at least 240 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat at least 270 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat at least 300 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat at least 330 minutes prior to the (S)-MDMA form disclosed herein, including those described in Table Ex8. In some embodiments, the serotonin receptor modulator is volinanserin and the psychedelic is (S)-MDMA, wherein the volinanserin is administered to pretreat at least 360 minutes prior to the(S)-MDMA form disclosed herein, including those described in Table Ex8. In some preferred embodiments, the serotonin receptor modulator is volinanserin and the psychedelic is (S)-MDMA, wherein volinanserin is administered to pretreat between about 60 minutes and about 180 minutes prior to the administration of the (S)-MDMA form disclosed herein, including those described in Table Ex8.

In some embodiments, the serotonin receptor modulator is ketanserin and the psychedelic is (S)-MDMA, wherein the ketanserin is administered to pretreat at least 15 minutes prior to the administration of the (S)-MDMA form disclosed herein, including those described in Table Ex8. In some embodiments, the serotonin receptor modulator is ketanserin and the psychedelic is (S)-MDMA, wherein the ketanserin is administered to pretreat between at least 30 minutes and 360 minutes prior to the administration or release of the (S)-MDMA form disclosed herein, including those described in Table Ex8. In some embodiments, the serotonin receptor modulator is ketanserin and the psychedelic is (S)-MDMA, wherein the ketanserin is administered to pretreat between at least 60 minutes and 240 minutes prior to the administration or release of the (S)-MDMA form disclosed herein, including those described in Table Ex8. In some embodiments, the serotonin receptor modulator is ketanserin and the psychedelic is (S)-MDMA, wherein the ketanserin is administered to pretreat at least 90 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 120 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 150 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat between about 15 minutes and about 150 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 180 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 210 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 240 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 270 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 300 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 330 minutes prior to the (S)-MDMA form disclosed herein, including those described in Table Ex8. In some embodiments, the serotonin receptor modulator is ketanserin and the psychedelic is (S)-MDMA, wherein the ketanserin is administered to pretreat at least 360 minutes prior to the (S)-MDMA form disclosed herein, including those described in Table Ex8. In some preferred embodiments, the serotonin receptor modulator is ketanserin and the psychedelic is (S)-MDMA, wherein ketanserin is administered to pretreat between about 60 minutes and about 180 minutes prior to the administration of the (S)-MDMA form disclosed herein, including those described in Table Ex8.

In some embodiments, the serotonin receptor modulator is ritanserin and the psychedelic is (S)-MDMA, wherein the ritanserin is administered to pretreat at least 15 minutes prior to the administration of the (S)-MDMA form disclosed herein, including those described in Table Ex8. In some embodiments, the serotonin receptor modulator is ritanserin and the psychedelic is (S)-MDMA, wherein the ritanserin is administered to pretreat at least 30 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat between at least 60 minutes and 240 minutes prior to the administration or release of the (S)-MDMA form disclosed herein, including those described in Table Ex8. In some embodiments, the serotonin receptor modulator is ritanserin and the psychedelic is (S)-MDMA, wherein the ritanserin is administered to pretreat at least 90 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 120 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 150 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat between about 15 minutes and about 150 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 180 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 210 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 240 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 270 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 300 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 330 minutes prior to the (S)-MDMA form disclosed herein, including those described in Table Ex8. In some embodiments, the serotonin receptor modulator is ritanserin and the psychedelic is (S)-MDMA, wherein the ritanserin is administered to pretreat at least 360 minutes prior to the (S)-MDMA form disclosed herein, including those described in Table Ex8. In some preferred embodiments, the serotonin receptor modulator is ritanserin and the psychedelic is (S)-MDMA, wherein ritanserin is administered to pretreat between about 60 minutes and about 180 minutes prior to the administration of the (S)-MDMA form disclosed herein, including those described in Table Ex8.

In some embodiments, the serotonin receptor modulator is pimavanserin and the psychedelic is (S)-MDMA, wherein the pimavanserin is administered to pretreat at least 15 minutes prior to the administration of the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 30 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat between at least 60 minutes and 240 minutes prior to the administration or release of the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 90 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 120 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 150 minutes prior to the(S)-MDMA form disclosed herein, including those described in Table Ex8. In some embodiments, the serotonin receptor modulator is pimavanserin and the psychedelic is (S)-MDMA, wherein the pimavanserin is administered to pretreat between about 15 minutes and about 150 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 180 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 210 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 240 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 270 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 300 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 330 minutes prior to the (S)-MDMA form disclosed herein, including those described in Table Ex8. In some embodiments, the serotonin receptor modulator is pimavanserin and the psychedelic is (S)-MDMA, wherein the pimavanserin is administered to pretreat at least 360 minutes prior to the(S)-MDMA form disclosed herein, including those described in Table Ex8. In some preferred embodiments, the serotonin receptor modulator is pimavanserin and the psychedelic is (S)-MDMA, wherein pimavanserin is administered to pretreat between about 60 minutes and about 180 minutes prior to the administration of the (S)-MDMA form disclosed herein, including those described in Table Ex8.

In some embodiments, the serotonin receptor modulator is nelotanserin and the psychedelic is (S)-MDMA, wherein the nelotanserin is administered to pretreat at least 15 minutes prior to the administration of the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 30 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat between at least 60 minutes and 240 minutes prior to the administration or release of the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 90 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 120 minutes prior to the (S)-MDMA form disclosed herein, including those described in Table Ex8.

In some embodiments, the serotonin receptor modulator is nelotanserin and the psychedelic is (S)-MDMA, wherein the nelotanserin is administered to pretreat at least 150 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat between about 15 minutes and about 150 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 180 minutes prior to the(S)-MDMA form disclosed herein, including those described in Table Ex8. In some embodiments, the serotonin receptor modulator is nelotanserin and the psychedelic is (S)-MDMA, wherein the nelotanserin is administered to pretreat at least 210 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 240 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 270 minutes prior to the (S)-MDMA form disclosed herein, including those described in Table Ex8.

In some embodiments, the serotonin receptor modulator is nelotanserin and the psychedelic is (S)-MDMA, wherein the nelotanserin is administered to pretreat at least 300 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 330 minutes prior to the (S)-MDMA form disclosed herein, including those described in Table Ex8. In some embodiments, the serotonin receptor modulator is nelotanserin and the psychedelic is (S)-MDMA, wherein the nelotanserin is administered to pretreat at least 360 minutes prior to the (S)-MDMA form disclosed herein, including those described in Table Ex8. In some preferred embodiments, the serotonin receptor modulator is nelotanserin and the psychedelic is (S)-MDMA, wherein nelotanserin is administered to pretreat between about 60 minutes and about 180 minutes prior to the administration of the (S)-MDMA form disclosed herein, including those described in Table Ex8.

In some embodiments, the serotonin receptor modulator is pruvanserin and the psychedelic is (S)-MDMA, wherein the pruvanserin is administered to pretreat at least 15 minutes prior to the administration of the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 30 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat between at least 60 minutes and 240 minutes prior to the administration or release of the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 90 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 120 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 150 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat between about 15 minutes and about 150 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 180 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 210 minutes prior to the (S)-MDMA form disclosed herein, including those described in Table Ex8.

In some embodiments, the serotonin receptor modulator is pruvanserin and the psychedelic is (S)-MDMA, wherein the pruvanserin is administered to pretreat at least 240 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 270 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 300 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 330 minutes prior to the (S)-MDMA form disclosed herein, including those described in Table Ex8. In some embodiments, the serotonin receptor modulator is pruvanserin and the psychedelic is (S)-MDMA, wherein the pruvanserin is administered to pretreat at least 360 minutes prior to the (S)-MDMA form disclosed herein, including those described in Table Ex8. In some preferred embodiments, the serotonin receptor modulator is pruvanserin and the psychedelic is (S)-MDMA, wherein pruvanserin is administered to pretreat between about 60 minutes and about 180 minutes prior to the administration of the (S)-MDMA form disclosed herein, including those described in Table Ex8.

In certain embodiments, such as those described above a(S)-MDMA form disclosed herein, including those described in Table Ex8 is co-administered with a serotonin receptor modulator in the same or in separate compositions. In certain embodiments, such as those described above a(S)-MDMA form disclosed herein, including those described in Table Ex8 is co-administered with a serotonin receptor modulator in the same or in separate compositions. In one embodiment, the serotonin receptor modulator is administered after the (S)-MDMA form disclosed herein, including those described in Table Ex8. In one embodiment, the (S)-MDMA form disclosed herein, including those described in Table Ex8 is administered in a modified release formulation such that the subject is effectively post-treated with serotonin receptor modulator post to release of an effective amount of the (S)-MDMA. In some embodiments, the serotonin receptor modulator is part of a single fixed dose formulation that releases the (S)-MDMA first followed by serotonin receptor modulator on two different release profiles. In another embodiment, the (S)-MDMA form disclosed herein, including those described in Table Ex8 is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the psychedelic. This allows post-treatment to attenuate activation of the serotonin receptor by the psychedelic.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours after the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours after the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour after the release of the psychedelic.

In a preferred embodiment, the serotonin receptor modulator is administered at about 1 hour to about 3 hours after the administration of the psychedelic.

In some embodiments, the serotonin receptor modulator is eplivanserin and the psychedelic is (S)-MDMA, wherein the eplivanserin is administered to post-treat at least 15 minutes after the administration of the (S)-MDMA form disclosed herein, including those described in Table Ex8. In some embodiments, the serotonin receptor modulator is eplivanserin and the psychedelic is (S)-MDMA, wherein the eplivanserin is administered to post-treat between at least 30 minutes after and 360 minutes after the release or administration of the (S)-MDMA form disclosed herein, including those described in Table Ex8. In some embodiments, the serotonin receptor modulator is eplivanserin and the psychedelic is (S)-MDMA, wherein the eplivanserin is administered to post-treat between at least 60 minutes after and 360 minutes after the release or administration of the (S)-MDMA form disclosed herein, including those described in Table Ex8. In some embodiments, the serotonin receptor modulator is eplivanserin and the psychedelic is (S)-MDMA, wherein the eplivanserin is administered to post-treat between at least 90 minutes and 240 minutes after the (S)-MDMA form disclosed herein, including those described in Table Ex8. In some embodiments, the serotonin receptor modulator is eplivanserin and the psychedelic is (S)-MDMA, wherein the eplivanserin is administered to post-treat at least 120 minutes after the (S)-MDMA form disclosed herein, including those described in Table Ex8.

In some embodiments, the serotonin receptor modulator is eplivanserin and the psychedelic is (S)-MDMA, wherein the eplivanserin is administered to post-treat at least 150 minutes after the (S)-MDMA form disclosed herein, including those described in Table Ex8. In some embodiments, the serotonin receptor modulator is eplivanserin and the psychedelic is (S)-MDMA, wherein the eplivanserin is administered to post-treat at least 180 minutes after the (S)-MDMA form disclosed herein, including those described in Table Ex8. In some embodiments, the serotonin receptor modulator is eplivanserin and the psychedelic is (S)-MDMA, wherein the eplivanserin is administered to post-treat at least 210 minutes after the (S)-MDMA form disclosed herein, including those described in Table Ex8. In some embodiments, the serotonin receptor modulator is eplivanserin and the psychedelic is (S)-MDMA, wherein the eplivanserin is administered to post-treat at least 240 minutes after the (S)-MDMA form disclosed herein, including those described in Table Ex8.

In some embodiments, the serotonin receptor modulator is eplivanserin and the psychedelic is (S)-MDMA, wherein the eplivanserin is administered to post-treat at least 270 minutes after the (S)-MDMA form disclosed herein, including those described in Table Ex8. In some embodiments, the serotonin receptor modulator is eplivanserin and the psychedelic is (S)-MDMA, wherein the eplivanserin is administered to post-treat at least 300 minutes after the (S)-MDMA form disclosed herein, including those described in Table Ex8. In some embodiments, the serotonin receptor modulator is eplivanserin and the psychedelic is (S)-MDMA, wherein the eplivanserin is administered to post-treat at least 330 minutes after the (S)-MDMA form disclosed herein, including those described in Table Ex8. In some embodiments, the serotonin receptor modulator is eplivanserin and the psychedelic is (S)-MDMA, wherein the eplivanserin is administered to post-treat at least 360 minutes after the (S)-MDMA form disclosed herein, including those described in Table Ex8.

In some preferred embodiments, the serotonin receptor modulator is eplivanserin and the psychedelic is (S)-MDMA, wherein eplivanserin is administered to post-treat between about 60 minutes and about 180 minutes after the administration of the (S)-MDMA form disclosed herein, including those described in Table Ex8.

In some embodiments, the serotonin receptor modulator is volinanserin and the psychedelic is (S)-MDMA, wherein the volinanserin is administered to post-treat a subject between at least 15 minutes and 360 minutes after the administration or release of the (S)-MDMA form disclosed herein, including those described in Table Ex8. In some embodiments, the serotonin receptor modulator is volinanserin and the psychedelic is (S)-MDMA, wherein the volinanserin is administered to post-treat between at least 30 minutes and 360 minutes after the administration or release of the (S)-MDMA form disclosed herein, including those described in Table Ex8. In some embodiments, the serotonin receptor modulator is volinanserin and the psychedelic is (S)-MDMA, wherein the volinanserin is administered to post-treat between at least 60 minutes and 240 minutes after the administration or release of the (S)-MDMA form disclosed herein, including those described in Table Ex8. In some embodiments, the serotonin receptor modulator is volinanserin and the psychedelic is (S)-MDMA, wherein the volinanserin is administered to post-treat at least 90 minutes after(S)-MDMA. In some embodiments, the serotonin receptor modulator is volinanserin and the psychedelic is (S)-MDMA, wherein the volinanserin is administered to post-treat at least 120 minutes after the (S)-MDMA form disclosed herein, including those described in Table Ex8.

In some embodiments, the serotonin receptor modulator is volinanserin and the psychedelic is (S)-MDMA, wherein the volinanserin is administered to post-treat at least 150 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat between about 15 minutes and about 150 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat at least 180 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat at least 210 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat at least 240 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat at least 270 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat at least 300 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat at least 330 minutes after the (S)-MDMA form disclosed herein, including those described in Table Ex8. In some embodiments, the serotonin receptor modulator is volinanserin and the psychedelic is (S)-MDMA, wherein the volinanserin is administered to post-treat at least 360 minutes after the (S)-MDMA form disclosed herein, including those described in Table Ex8. In some preferred embodiments, the serotonin receptor modulator is volinanserin and the psychedelic is (S)-MDMA, wherein volinanserin is administered to post-treat between about 60 minutes and about 180 minutes after the administration of the (R)-MDMA form.

In some embodiments, the serotonin receptor modulator is ketanserin and the psychedelic is (S)-MDMA, wherein the ketanserin is administered to post-treat at least 15 minutes after the administration of the (S)-MDMA form disclosed herein, including those described in Table Ex8. In some embodiments, the serotonin receptor modulator is ketanserin and the psychedelic is (S)-MDMA, wherein the ketanserin is administered to post-treat between at least 30 minutes and 360 minutes after the administration or release of the (S)-MDMA form disclosed herein, including those described in Table Ex8. In some embodiments, the serotonin receptor modulator is ketanserin and the psychedelic is (S)-MDMA, wherein the ketanserin is administered to post-treat between at least 60 minutes and 240 minutes after the administration or release of the (S)-MDMA form disclosed herein, including those described in Table Ex8. In some embodiments, the serotonin receptor modulator is ketanserin and the psychedelic is (S)-MDMA, wherein the ketanserin is administered to post-treat at least 90 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 120 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 150 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat between about 15 minutes and about 150 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 180 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 210 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 240 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 270 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 300 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 330 minutes after the (S)-MDMA form disclosed herein, including those described in Table Ex8. In some embodiments, the serotonin receptor modulator is ketanserin and the psychedelic is (S)-MDMA, wherein the ketanserin is administered to post-treat at least 360 minutes after the (S)-MDMA form disclosed herein, including those described in Table Ex8. In some preferred embodiments, the serotonin receptor modulator is ketanserin and the psychedelic is (S)-MDMA, wherein ketanserin is administered to post-treat between about 60 minutes and about 180 minutes after the administration of the (S)-MDMA form disclosed herein, including those described in Table Ex8.

In some embodiments, the serotonin receptor modulator is ritanserin and the psychedelic is (S)-MDMA, wherein the ritanserin is administered to post-treat at least 15 minutes after the administration of the (S)-MDMA form disclosed herein, including those described in Table Ex8. In some embodiments, the serotonin receptor modulator is ritanserin and the psychedelic is (S)-MDMA, wherein the ritanserin is administered to post-treat at least 30 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat between at least 60 minutes and 240 minutes after the administration or release of the (S)-MDMA form disclosed herein, including those described in Table Ex8. In some embodiments, the serotonin receptor modulator is ritanserin and the psychedelic is (S)-MDMA, wherein the ritanserin is administered to post-treat at least 90 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 120 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 150 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat between about 15 minutes and about 150 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 180 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 210 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 240 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 270 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 300 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 330 minutes after the (S)-MDMA form disclosed herein, including those described in Table Ex8. In some embodiments, the serotonin receptor modulator is ritanserin and the psychedelic is (S)-MDMA, wherein the ritanserin is administered to post-treat at least 360 minutes after the (S)-MDMA form disclosed herein, including those described in Table Ex8. In some preferred embodiments, the serotonin receptor modulator is ritanserin and the psychedelic is (S)-MDMA, wherein ritanserin is administered to post-treat between about 60 minutes and about 180 minutes after the administration of the (S)-MDMA form disclosed herein, including those described in Table Ex8.

In some embodiments, the serotonin receptor modulator is pimavanserin and the psychedelic is (S)-MDMA, wherein the pimavanserin is administered to post-treat at least 15 minutes after the administration of the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 30 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat between at least 60 minutes and 240 minutes after the administration or release of the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 90 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 120 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 150 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat between about 15 minutes and about 150 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 180 minutes after the(S)-MDMA form disclosed herein, including those described in Table Ex8. In some embodiments, the serotonin receptor modulator is pimavanserin and the psychedelic is (S)-MDMA, wherein the pimavanserin is administered to post-treat at least 210 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 240 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 270 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 300 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 330 minutes after the (S)-MDMA form disclosed herein, including those described in Table Ex8. In some embodiments, the serotonin receptor modulator is pimavanserin and the psychedelic is (S)-MDMA, wherein the pimavanserin is administered to post-treat at least 360 minutes after the (S)-MDMA form disclosed herein, including those described in Table Ex8. In some preferred embodiments, the serotonin receptor modulator is pimavanserin and the psychedelic is (S)-MDMA, wherein pimavanserin is administered to post-treat between about 60 minutes and about 180 minutes after the administration of the (S)-MDMA form disclosed herein, including those described in Table Ex8.

In some embodiments, the serotonin receptor modulator is nelotanserin and the psychedelic is (S)-MDMA, wherein the nelotanserin is administered to post-treat at least 15 minutes after the administration of the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 30 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat between at least 60 minutes and 240 minutes after the administration or release of the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 90 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 120 minutes after the (S)-MDMA form disclosed herein, including those described in Table Ex8.

In some embodiments, the serotonin receptor modulator is nelotanserin and the psychedelic is (S)-MDMA, wherein the nelotanserin is administered to post-treat at least 150 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat between about 15 minutes and about 150 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 180 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 210 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 240 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 270 minutes after the (S)-MDMA form disclosed herein, including those described in Table Ex8.

In some embodiments, the serotonin receptor modulator is nelotanserin and the psychedelic is (S)-MDMA, wherein the nelotanserin is administered to post-treat at least 300 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 330 minutes after the (S)-MDMA form disclosed herein, including those described in Table Ex8. In some embodiments, the serotonin receptor modulator is nelotanserin and the psychedelic is (S)-MDMA, wherein the nelotanserin is administered to post-treat at least 360 minutes after the (S)-MDMA form disclosed herein, including those described in Table Ex8. In some preferred embodiments, the serotonin receptor modulator is nelotanserin and the psychedelic is (S)-MDMA, wherein nelotanserin is administered to post-treat between about 60 minutes and about 180 minutes after the administration of the (S)-MDMA form disclosed herein, including those described in Table Ex8.

In some embodiments, the serotonin receptor modulator is pruvanserin and the psychedelic is (S)-MDMA, wherein the pruvanserin is administered to post-treat at least 15 minutes after the administration of the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 30 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat between at least 60 minutes and 240 minutes after the administration or release of the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 90 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 120 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 150 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat between about 15 minutes and about 150 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 180 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 210 minutes after the (S)-MDMA form disclosed herein, including those described in Table Ex8.

In some embodiments, the serotonin receptor modulator is pruvanserin and the psychedelic is (S)-MDMA, wherein the pruvanserin is administered to post-treat at least 240 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 270 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 300 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 330 minutes after the (S)-MDMA form disclosed herein, including those described in Table Ex8. In some embodiments, the serotonin receptor modulator is pruvanserin and the psychedelic is (S)-MDMA, wherein the pruvanserin is administered to post-treat at least 360 minutes after the (S)-MDMA form disclosed herein, including those described in Table Ex8. In some preferred embodiments, the serotonin receptor modulator is pruvanserin and the psychedelic is (S)-MDMA, wherein pruvanserin is administered to post-treat between about 60 minutes and about 180 minutes after the administration of the (S)-MDMA form disclosed herein, including those described in Table Ex8.

In some embodiments, the serotonin receptor modulator is flibanserin, wherein the flibanserin is administered to post-treat at least 15 minutes post to the administration of the (S)-MDMA form disclosed herein, including those described in Table Ex8. In some embodiments, the serotonin receptor modulator is flibanserin, wherein the flibanserin is administered to post-treat at least 30 minutes post to the (S)-MDMA form disclosed herein, including those described in Table Ex8. In some embodiments, the serotonin receptor modulator is flibanserin, wherein the flibanserin is administered to post-treat between at least 60 minutes and 240 minutes post to the administration or release of the (S)-MDMA form disclosed herein, including those described in Table Ex8. In some embodiments, the serotonin receptor modulator is flibanserin, wherein the flibanserin is administered to post-treat at least 90 minutes post to the (S)-MDMA form disclosed herein, including those described in Table Ex8. In some embodiments, the serotonin receptor modulator is flibanserin, wherein the flibanserin is administered to post-treat at least 120 minutes post to the (S)-MDMA form disclosed herein, including those described in Table Ex8. In some embodiments, the serotonin receptor modulator is flibanserin, wherein the flibanserin is administered to post-treat at least 150 minutes post to the (S)-MDMA form disclosed herein, including those described in Table Ex8. In some embodiments, the serotonin receptor modulator is flibanserin, wherein the flibanserin is administered to post-treat between about 15 minutes and about 150 minutes post to the (S)-MDMA form disclosed herein, including those described in Table Ex8. In some embodiments, the serotonin receptor modulator is flibanserin, wherein the flibanserin is administered to post-treat at least 180 minutes post to the (S)-MDMA form disclosed herein, including those described in Table Ex8. In some embodiments, the serotonin receptor modulator is flibanserin, wherein the flibanserin is administered to post-treat at least 210 minutes post to the (S)-MDMA form disclosed herein, including those described in Table Ex8.

In some embodiments, the serotonin receptor modulator is flibanserin, wherein the flibanserin is administered to post-treat at least 240 minutes post to the (S)-MDMA form disclosed herein, including those described in Table Ex8. In some embodiments, the serotonin receptor modulator is flibanserin, wherein the flibanserin is administered to post-treat at least 270 minutes post to the (S)-MDMA form disclosed herein, including those described in Table Ex8. In some embodiments, the serotonin receptor modulator is flibanserin, wherein the flibanserin is administered to post-treat at least 300 minutes post to the (S)-MDMA form disclosed herein, including those described in Table Ex8. In some embodiments, the serotonin receptor modulator is flibanserin, wherein the flibanserin is administered to post-treat at least 330 minutes post to the (S)-MDMA form disclosed herein, including those described in Table Ex8. In some embodiments, the serotonin receptor modulator is flibanserin, wherein the flibanserin is administered to post-treat at least 360 minutes post to the (S)-MDMA form disclosed herein, including those described in Table Ex8. In some preferred embodiments, the serotonin receptor modulator is flibanserin, wherein flibanserin is administered to post-treat between about 60 minutes and about 180 minutes post to the administration of the (S)-MDMA form disclosed herein, including those described in Table Ex8.

In some embodiments, the serotonin receptor modulator is olanzapine, wherein the olanzapine is administered to post-treat at least 15 minutes post to the administration of the (S)-MDMA form disclosed herein, including those described in Table Ex8. In some embodiments, the serotonin receptor modulator is olanzapine, wherein the olanzapine is administered to post-treat at least 30 minutes post to the (S)-MDMA form disclosed herein, including those described in Table Ex8. In some embodiments, the serotonin receptor modulator is olanzapine, wherein the olanzapine is administered to post-treat between at least 60 minutes and 240 minutes post to the administration or release of the (S)-MDMA form disclosed herein, including those described in Table Ex8. In some embodiments, the serotonin receptor modulator is olanzapine, wherein the olanzapine is administered to post-treat at least 90 minutes post to the (S)-MDMA form disclosed herein, including those described in Table Ex8. In some embodiments, the serotonin receptor modulator is olanzapine, wherein the olanzapine is administered to post-treat at least 120 minutes post to the (S)-MDMA form disclosed herein, including those described in Table Ex8. In some embodiments, the serotonin receptor modulator is olanzapine, wherein the olanzapine is administered to post-treat at least 150 minutes post to the (S)-MDMA form disclosed herein, including those described in Table Ex8. In some embodiments, the serotonin receptor modulator is olanzapine, wherein the olanzapine is administered to post-treat between about 15 minutes and about 150 minutes post to the (S)-MDMA form disclosed herein, including those described in Table Ex8. In some embodiments, the serotonin receptor modulator is olanzapine, wherein the olanzapine is administered to post-treat at least 180 minutes post to the (S)-MDMA form disclosed herein, including those described in Table Ex8. In some embodiments, the serotonin receptor modulator is olanzapine, wherein the olanzapine is administered to post-treat at least 210 minutes post to the (S)-MDMA form disclosed herein, including those described in Table Ex8.

In some embodiments, the serotonin receptor modulator is olanzapine, wherein the olanzapine is administered to post-treat at least 240 minutes post to the (S)-MDMA form disclosed herein, including those described in Table Ex8. In some embodiments, the serotonin receptor modulator is olanzapine, wherein the olanzapine is administered to post-treat at least 270 minutes post to the (S)-MDMA form disclosed herein, including those described in Table Ex8. In some embodiments, the serotonin receptor modulator is olanzapine, wherein the olanzapine is administered to post-treat at least 300 minutes post to the (S)-MDMA form disclosed herein, including those described in Table Ex8. In some embodiments, the serotonin receptor modulator is olanzapine, wherein the olanzapine is administered to post-treat at least 330 minutes post to the (S)-MDMA form disclosed herein, including those described in Table Ex8. In some embodiments, the serotonin receptor modulator is olanzapine, wherein the olanzapine is administered to post-treat at least 360 minutes post to the (S)-MDMA form disclosed herein, including those described in Table Ex8. In some preferred embodiments, the serotonin receptor modulator is olanzapine, wherein olanzapine is administered to post-treat between about 60 minutes and about 180 minutes post to the administration of the (S)-MDMA form disclosed herein, including those described in Table Ex8.

In some embodiments, the serotonin receptor modulator is quetiapine, wherein the quetiapine is administered to post-treat at least 15 minutes post to the administration of the (S)-MDMA form disclosed herein, including those described in Table Ex8. In some embodiments, the serotonin receptor modulator is quetiapine, wherein the quetiapine is administered to post-treat at least 30 minutes post to the (S)-MDMA form disclosed herein, including those described in Table Ex8. In some embodiments, the serotonin receptor modulator is quetiapine, wherein the quetiapine is administered to post-treat between at least 60 minutes and 240 minutes post to the administration or release of the (S)-MDMA form disclosed herein, including those described in Table Ex8. In some embodiments, the serotonin receptor modulator is quetiapine, wherein the quetiapine is administered to post-treat at least 90 minutes post to the (S)-MDMA form disclosed herein, including those described in Table Ex8. In some embodiments, the serotonin receptor modulator is quetiapine, wherein the quetiapine is administered to post-treat at least 120 minutes post to the (S)-MDMA form disclosed herein, including those described in Table Ex8. In some embodiments, the serotonin receptor modulator is quetiapine, wherein the quetiapine is administered to post-treat at least 150 minutes post to the (S)-MDMA form disclosed herein, including those described in Table Ex8. In some embodiments, the serotonin receptor modulator is quetiapine, wherein the quetiapine is administered to post-treat between about 15 minutes and about 150 minutes post to the (S)-MDMA form disclosed herein, including those described in Table Ex8. In some embodiments, the serotonin receptor modulator is quetiapine, wherein the quetiapine is administered to post-treat at least 180 minutes post to the (S)-MDMA form disclosed herein, including those described in Table Ex8. In some embodiments, the serotonin receptor modulator is quetiapine, wherein the quetiapine is administered to post-treat at least 210 minutes post to the (S)-MDMA form disclosed herein, including those described in Table Ex8.

In some embodiments, the serotonin receptor modulator is quetiapine, wherein the quetiapine is administered to post-treat at least 240 minutes post to the (S)-MDMA form disclosed herein, including those described in Table Ex8. In some embodiments, the serotonin receptor modulator is quetiapine, wherein the quetiapine is administered to post-treat at least 270 minutes post to the (S)-MDMA form disclosed herein, including those described in Table Ex8. In some embodiments, the serotonin receptor modulator is quetiapine, wherein the quetiapine is administered to post-treat at least 300 minutes post to the (S)-MDMA form disclosed herein, including those described in Table Ex8. In some embodiments, the serotonin receptor modulator is quetiapine, wherein the quetiapine is administered to post-treat at least 330 minutes post to the (S)-MDMA form disclosed herein, including those described in Table Ex8. In some embodiments, the serotonin receptor modulator is quetiapine, wherein the quetiapine is administered to post-treat at least 360 minutes post to the (S)-MDMA form disclosed herein, including those described in Table Ex8. In some preferred embodiments, the serotonin receptor modulator is quetiapine, wherein quetiapine is administered to post-treat between about 60 minutes and about 180 minutes post to the administration of the (S)-MDMA form disclosed herein, including those described in Table Ex8.

In some embodiments, the serotonin receptor modulator is risperidone, wherein the risperidone is administered to post-treat at least 15 minutes post to the administration of the (S)-MDMA form disclosed herein, including those described in Table Ex8. In some embodiments, the serotonin receptor modulator is risperidone, wherein the risperidone is administered to post-treat at least 30 minutes post to the (S)-MDMA form disclosed herein, including those described in Table Ex8. In some embodiments, the serotonin receptor modulator is risperidone, wherein the risperidone is administered to post-treat between at least 60 minutes and 240 minutes post to the administration or release of the (S)-MDMA form disclosed herein, including those described in Table Ex8. In some embodiments, the serotonin receptor modulator is risperidone, wherein the risperidone is administered to post-treat at least 90 minutes post to the (S)-MDMA form disclosed herein, including those described in Table Ex8. In some embodiments, the serotonin receptor modulator is risperidone, wherein the risperidone is administered to post-treat at least 120 minutes post to the (S)-MDMA form disclosed herein, including those described in Table Ex8. In some embodiments, the serotonin receptor modulator is risperidone, wherein the risperidone is administered to post-treat at least 150 minutes post to the (S)-MDMA form disclosed herein, including those described in Table Ex8. In some embodiments, the serotonin receptor modulator is risperidone, wherein the risperidone is administered to post-treat between about 15 minutes and about 150 minutes post to the (S)-MDMA form disclosed herein, including those described in Table Ex8. In some embodiments, the serotonin receptor modulator is risperidone, wherein the risperidone is administered to post-treat at least 180 minutes post to the (S)-MDMA form disclosed herein, including those described in Table Ex8. In some embodiments, the serotonin receptor modulator is risperidone, wherein the risperidone is administered to post-treat at least 210 minutes post to the (S)-MDMA form disclosed herein, including those described in Table Ex8.

In some embodiments, the serotonin receptor modulator is risperidone, wherein the risperidone is administered to post-treat at least 240 minutes post to the (S)-MDMA form disclosed herein, including those described in Table Ex8. In some embodiments, the serotonin receptor modulator is risperidone, wherein the risperidone is administered to post-treat at least 270 minutes post to the (S)-MDMA form disclosed herein, including those described in Table Ex8. In some embodiments, the serotonin receptor modulator is risperidone, wherein the risperidone is administered to post-treat at least 300 minutes post to the (S)-MDMA form disclosed herein, including those described in Table Ex8. In some embodiments, the serotonin receptor modulator is risperidone, wherein the risperidone is administered to post-treat at least 330 minutes post to the (S)-MDMA form disclosed herein, including those described in Table Ex8. In some embodiments, the serotonin receptor modulator is risperidone, wherein the risperidone is administered to post-treat at least 360 minutes post to the (S)-MDMA form disclosed herein, including those described in Table Ex8. In some preferred embodiments, the serotonin receptor modulator is risperidone, wherein risperidone is administered to post-treat between about 60 minutes and about 180 minutes post to the administration of the (S)-MDMA form disclosed herein, including those described in Table Ex8.

In some embodiments, the serotonin receptor modulator for use with N-ethyl-3,4-methylenedioxyamphetamine·HCl forms disclosed herein, including those described in Table Ex10 is eplivanserin, wherein the eplivanserin is administered in about 1 mg to about 40 mg, or about 5 mg to about 10 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine·HCl forms disclosed herein, including those described in Table Ex10 is volinanserin, wherein the volinanserin is administered in about 1 mg to about 60 mg, or about 5 mg to about 20 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the with N-ethyl-3,4-methylenedioxyamphetamine·HCl forms disclosed herein, including those described in Table Ex10 is ketanserin, wherein the ketanserin is administered in about 10 mg to about 80 mg, about 30 mg to about 50 mg, or about 40 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine·HCl forms disclosed herein, including those described in Table Ex10 is ritanserin, wherein the ritanserin is administered in about 1 mg to about 40 mg, or about 2.5 mg to about 10 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine·HCl forms disclosed herein, including those described in Table Ex10 is pimavanserin, wherein the pimavanserin is administered in about 1 mg to about 60 mg, or about 17 mg to about 34 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine·HCl forms disclosed herein, including those described in Table Ex10 is nelotanserin, wherein the nelotanserin is administered in about 1 mg to about 80 mg, or about 40 mg to about 80 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine·HCl forms disclosed herein, including those described in Table Ex10 is pruvanserin, wherein the pruvanserin is administered in about 1 mg to about 40 mg, or about 3 mg to about 10 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine·HCl forms disclosed herein, including those described in Table Ex10 is flibanserin, wherein the flibanserin is administered in about 10 mg to about 200 mg, or about 80 mg to about 120 mg, or about 100 mg and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine HCl forms disclosed herein, including those described in Table Ex10 is olanzapine, wherein the olanzapine is administered in about 2.5 mg to about 30 mg, or about 5 mg or about 10 mg, or about 20 mg or about 25 mg, and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine HCl forms disclosed herein, including those described in Table Ex10 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine HCl forms disclosed herein, including those described in Table Ex10 is quetiapine, wherein the quetiapine is administered in about 25 mg to about 800 mg, or about 50 mg to about 100 mg, or about 150 mg or about 200 mg or about 250 mg or about 300 mg, and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine HCl forms disclosed herein, including those described in Table Ex10 is an extended-release of quetiapine, wherein the extended-release of quetiapine is administered in about 50 mg to about 300 mg, or about 50 mg or about 100 mg or about 200 mg, or about 300 mg, and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine HCl forms disclosed herein, including those described in Table Ex10 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In some embodiments, the serotonin receptor modulator for use with the N-ethyl-3,4-methylenedioxyamphetamine HCl forms disclosed herein, including those described in Table Ex10 is an extended-release of risperidone including (RISPERDAL CONSTA), wherein the extended-release of risperidone is administered in about 12.5 mg, or about 25 mg, or about 37.5 mg, or about 50 mg, and the N-ethyl-3,4-methylenedioxyamphetamine HCl forms disclosed herein, including those described in Table Ex10 are administered in about 10 mg to about 300 mg or about 100 mg to about 180 mg or about 120 mg or about 150 mg or about 160 mg.

In certain embodiments, such as those described above a N-ethyl-3,4-methylenedioxyamphetamine·HCl form disclosed herein, including those described in Table Ex10 is co-administered with a serotonin receptor modulator in the same or in separate compositions. In one embodiment, the serotonin receptor modulator is administered prior to the N-ethyl-3,4-methylenedioxyamphetamine·HCl form disclosed herein, including those described in Table Ex10. In one embodiment, the N-ethyl-3,4-methylenedioxyamphetamine·HCl form disclosed herein, including those described in Table Ex10 is administered in a modified release formulation such that the subject is effectively pretreated with serotonin receptor modulator prior to release of an effective amount of the N-ethyl-3,4-methylenedioxyamphetamine·HCl. In some embodiments the serotonin receptor modulator is part of a single fixed dose formulation that releases serotonin receptor modulator first followed by N-ethyl-3,4-methylenedioxyamphetamine·HCl on two different release profiles. In another embodiment the serotonin receptor modulator is administered first as a single dosage and after a length of time, N-ethyl-3,4-methylenedioxyamphetamine. HCl is administered as a second dosage separate from the first dosage. Thus, in some embodiments, the serotonin receptor modulator is administered or released from a composition provided herein prior to the administration and/or release of the N-ethyl-3,4-methylenedioxyamphetamine·HCl form disclosed herein, including those described in Table Ex10. This allows pretreatment to attenuate activation of the serotonin receptor by the N-ethyl-3,4-methylenedioxyamphetamine·HCl form disclosed herein, including those described in Table Ex10.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the N-ethyl-3,4-methylenedioxyamphetamine. HCl form disclosed herein, including those described in Table Ex10. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of N-ethyl-3,4-methylenedioxyamphetamine·HCl form disclosed herein, including those described in Table Ex10. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the N-ethyl-3,4-methylenedioxyamphetamine·HCl form disclosed herein, including those described in Table Ex10.

In a preferred embodiment, the serotonin receptor modulator is administered at about 1 hour to about 3 hours prior to the administration of the N-ethyl-3,4-methylenedioxyamphetamine·HCl form disclosed herein, including those described in Table Ex10.

In some embodiments, the serotonin receptor modulator is eplivanserin, wherein the eplivanserin is administered to pretreat at least 15 minutes prior to the administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat between at least 30 minutes prior and 360 minutes prior to the release or administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat between at least 60 minutes prior and 360 minutes prior to the release or administration the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat between at least 90 minutes and 240 minutes prior to the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat at least 120 minutes prior to the N-ethyl-3,4-methylenedioxyamphetamine·HCl form disclosed herein, including those described in Table Ex10.

In some embodiments, the serotonin receptor modulator is eplivanserin, wherein the eplivanserin is administered to pretreat at least 150 minutes prior to the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat at least 180 minutes prior to the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat at least 210 minutes prior to the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat at least 240 minutes prior to the N-ethyl-3,4-methylenedioxyamphetamine·HCl form disclosed herein, including those described in Table Ex10.

In some embodiments, the serotonin receptor modulator is eplivanserin, wherein the eplivanserin is administered to pretreat at least 270 minutes prior to the N-ethyl-3,4- methylenedioxyamphetamine·HCl form disclosed herein, including those described in Table Ex10. In some embodiments, the serotonin receptor modulator is eplivanserin, wherein the eplivanserin is administered to pretreat at least 300 minutes prior to the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat at least 330 minutes prior to the N-ethyl-3,4-methylenedioxyamphetamine·HCl form disclosed herein, including those described in Table Ex10. In some embodiments, the serotonin receptor modulator is eplivanserin, wherein the eplivanserin is administered to pretreat at least 360 minutes prior to administration or release of the N-ethyl-3,4-methylenedioxyamphetamine·HCl form disclosed herein, including those described in Table Ex10.

In some preferred embodiments, the serotonin receptor modulator is eplivanserin, wherein eplivanserin is administered to pretreat between about 60 minutes and about 180 minutes prior to the administration or release of the N-ethyl-3,4-methylenedioxyamphetamine·HCl form disclosed herein, including those described in Table Ex10.

In some embodiments, the serotonin receptor modulator is volinanserin, wherein the volinanserin is administered to pretreat a subject between at least 15 minutes and 360 minutes prior to the administration or release of the N-ethyl-3,4-methylenedioxyamphetamine·HCl form disclosed herein, including those described in Table Ex10. In some embodiments, the serotonin receptor modulator is volinanserin, wherein the volinanserin is administered to pretreat between at least 30 minutes and 360 minutes prior to the administration or release of the N-ethyl-3,4-methylenedioxyamphetamine·HCl form disclosed herein, including those described in Table Ex10. In some embodiments, the serotonin receptor modulator is volinanserin, wherein the volinanserin is administered to pretreat between at least 60 minutes and 240 minutes prior to the administration or release of the N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 90 minutes prior to N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 120 minutes prior to the N-ethyl-3,4-methylenedioxyamphetamine·HCl form disclosed herein, including those described in Table Ex10.

In some embodiments, the serotonin receptor modulator is volinanserin, wherein the volinanserin is administered to pretreat at least 150 minutes prior to the N-ethyl-3,4-methylenedioxyamphetamine·HCl form disclosed herein, including those described in Table Ex10. In some embodiments, the serotonin receptor modulator is volinanserin, wherein the volinanserin is administered to pretreat between about 15 minutes and about 150 minutes prior to the N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 180 minutes prior to the N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 210 minutes prior to the N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 240 minutes prior to the N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 270 minutes prior to the N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 300 minutes prior to the N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 330 minutes prior to N-ethyl-3,4-methylenedioxyamphetamine·HCl form disclosed herein, including those described in Table Ex10. In some embodiments, the serotonin receptor modulator is volinanserin, wherein the volinanserin is administered to pretreat at least 360 minutes prior to the N-ethyl-3,4-methylenedioxyamphetamine·HCl form disclosed herein, including those described in Table Ex10. In some preferred embodiments, the serotonin receptor modulator is volinanserin, wherein volinanserin is administered to pretreat between about 60 minutes and about 180 minutes prior to the administration of the N-ethyl-3,4-methylenedioxyamphetamine·HCl form disclosed herein, including those described in Table Ex10.

In some embodiments, the serotonin receptor modulator is ketanserin, wherein the ketanserin is administered to pretreat at least 15 minutes prior to the administration of the N-ethyl-3,4-methylenedioxyamphetamine·HCl form disclosed herein, including those described in Table Ex10. In some embodiments, the serotonin receptor modulator is ketanserin, wherein the ketanserin is administered to pretreat between at least 30 minutes and 360 minutes prior to the administration or release of the N-ethyl-3,4-methylenedioxyamphetamine·HCl form disclosed herein, including those described in Table Ex10. In some embodiments, the serotonin receptor modulator is ketanserin, wherein the ketanserin is administered to pretreat between at least 60 minutes and 240 minutes prior to the administration or release of the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 90 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 120 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 150 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat between about 15 minutes and about 150 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 180 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 210 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 240 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 270 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 300 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 330 minutes prior to the N-ethyl-3,4-methylenedioxyamphetamine·HCl form disclosed herein, including those described in Table Ex10. In some embodiments, the serotonin receptor modulator is ketanserin, wherein the ketanserin is administered to pretreat at least 360 minutes prior to the N-ethyl-3,4-methylenedioxyamphetamine·HCl form disclosed herein, including those described in Table Ex10. In some preferred embodiments, the serotonin receptor modulator is ketanserin, wherein ketanserin is administered to pretreat between about 60 minutes and about 180 minutes prior to the administration of the N-ethyl-3,4-methylenedioxyamphetamine·HCl form disclosed herein, including those described in Table Ex10.

In some embodiments, the serotonin receptor modulator is ritanserin, wherein the ritanserin is administered to pretreat at least 15 minutes prior to the administration of the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 30 minutes prior to the N-ethyl-3,4-methylenedioxyamphetamine·HCl form disclosed herein, including those described in Table Ex10. In some embodiments, the serotonin receptor modulator is ritanserin wherein the ritanserin is administered to pretreat between at least 60 minutes and 240 minutes prior to the administration or release of the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 90 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 120 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 150 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat between about 15 minutes and about 150 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 180 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 210 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 240 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 270 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 300 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 330 minutes prior to the N-ethyl-3,4-methylenedioxyamphetamine·HCl form disclosed herein, including those described in Table Ex10. In some embodiments, the serotonin receptor modulator is ritanserin, wherein the ritanserin is administered to pretreat at least 360 minutes prior to the N-ethyl-3,4-methylenedioxyamphetamine·HCl form disclosed herein, including those described in Table Ex10. In some preferred embodiments, the serotonin receptor modulator is ritanserin, wherein ritanserin is administered to pretreat between about 60 minutes and about 180 minutes prior to the administration of the N-ethyl-3,4-methylenedioxyamphetamine·HCl form disclosed herein, including those described in Table Ex10.

In some embodiments, the serotonin receptor modulator is pimavanserin, wherein the pimavanserin is administered to pretreat at least 15 minutes prior to the administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 30 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat between at least 60 minutes and 240 minutes prior to the administration or release of the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 90 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 120 minutes prior to the N-ethyl-3,4-methylenedioxyamphetamine. HCl form disclosed herein, including those described in Table Ex10. In some embodiments, the serotonin receptor modulator is pimavanserin, wherein the pimavanserin is administered to pretreat at least 150 minutes prior to the N-ethyl-3,4-methylenedioxyamphetamine. HCl form disclosed herein, including those described in Table Ex10. In some embodiments, the serotonin receptor modulator is pimavanserin, wherein the pimavanserin is administered to pretreat between about 15 minutes and about 150 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 180 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 210 minutes prior to the N-ethyl-3,4-methylenedioxyamphetamine. HCl form disclosed herein, including those described in Table Ex10. In some embodiments, the serotonin receptor modulator is pimavanserin, wherein the pimavanserin is administered to pretreat at least 240 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 270 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 300 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 330 minutes prior to the N-ethyl-3,4-methylenedioxyamphetamine·HCl form disclosed herein, including those described in Table Ex10. In some embodiments, the serotonin receptor modulator is pimavanserin, wherein the pimavanserin is administered to pretreat at least 360 minutes prior to the N-ethyl-3,4-methylenedioxyamphetamine·HCl form disclosed herein, including those described in Table Ex10. In some preferred embodiments, the serotonin receptor modulator is pimavanserin, wherein pimavanserin is administered to pretreat between about 60 minutes and about 180 minutes prior to the administration of the N-ethyl-3,4-methylenedioxyamphetamine·HCl form disclosed herein, including those described in Table Ex10.

In some embodiments, the serotonin receptor modulator is nelotanserin, wherein the nelotanserin is administered to pretreat at least 15 minutes prior to the administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 30 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat between at least 60 minutes and 240 minutes prior to the administration or release of the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 90 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 120 minutes prior to the N-ethyl-3,4-methylenedioxyamphetamine·HCl form disclosed herein, including those described in Table Ex10.

In some embodiments, the serotonin receptor modulator is nelotanserin, wherein the nelotanserin is administered to pretreat at least 150 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat between about 15 minutes and about 150 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 180 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 210 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 240 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 270 minutes prior to the N-ethyl-3,4-methylenedioxyamphetamine·HCl form disclosed herein, including those described in Table Ex10.

In some embodiments, the serotonin receptor modulator is nelotanserin, wherein the nelotanserin is administered to pretreat at least 300 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 330 minutes prior to the N-ethyl-3,4-methylenedioxyamphetamine·HCl form disclosed herein, including those described in Table Ex10. In some embodiments, the serotonin receptor modulator is nelotanserin, wherein the nelotanserin is administered to pretreat at least 360 minutes prior to the N-ethyl-3,4- methylenedioxyamphetamine·HCl form disclosed herein, including those described in Table Ex10. In some preferred embodiments, the serotonin receptor modulator is nelotanserin, wherein nelotanserin is administered to pretreat between about 60 minutes and about 180 minutes prior to the administration of the N-ethyl-3,4-methylenedioxyamphetamine·HCl form disclosed herein, including those described in Table Ex10.

In some embodiments, the serotonin receptor modulator is pruvanserin, wherein the pruvanserin is administered to pretreat at least 15 minutes prior to the administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 30 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat between at least 60 minutes and 240 minutes prior to the administration or release of the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 90 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 120 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 150 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat between about 15 minutes and about 150 minutes prior to the N-ethyl-3,4-methylenedioxyamphetamine. HCl form disclosed herein, including those described in Table Ex10. In some embodiments, the serotonin receptor modulator is pruvanserin, wherein the pruvanserin is administered to pretreat at least 180 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 210 minutes prior to the N-ethyl-3,4-methylenedioxyamphetamine·HCl form disclosed herein, including those described in Table Ex10.

In some embodiments, the serotonin receptor modulator is pruvanserin, wherein the pruvanserin is administered to pretreat at least 240 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 270 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 300 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 330 minutes prior to the N-ethyl-3,4-methylenedioxyamphetamine·HCl form disclosed herein, including those described in Table Ex10. In some embodiments, the serotonin receptor modulator is pruvanserin, wherein the pruvanserin is administered to pretreat at least 360 minutes prior to the N-ethyl-3,4-methylenedioxyamphetamine·HCl form disclosed herein, including those described in Table Ex10. In some preferred embodiments, the serotonin receptor modulator is pruvanserin, wherein pruvanserin is administered to pretreat between about 60 minutes and about 180 minutes prior to the administration of the N-ethyl-3,4-methylenedioxyamphetamine·HCl form disclosed herein, including those described in Table Ex10.

In some embodiments, the serotonin receptor modulator is co-administered with the N-ethyl-3,4-methylenedioxyamphetamine·HCl form disclosed herein, including those described in Table Ex10 in the same or separate compositions. In one embodiment, the serotonin receptor modulator is administered after the N-ethyl-3,4-methylenedioxyamphetamine·HCl form disclosed herein, including those described in Table Ex10. In one embodiment, the N-ethyl-3,4-methylenedioxyamphetamine·HCl form disclosed herein, including those described in Table Ex10 is administered in a modified release formulation such that the subject is effectively post-treated with serotonin receptor modulator after release of an effective amount of the N-ethyl-3,4-methylenedioxyamphetamine·HCl form disclosed herein, including those described in Table Ex10. In some embodiments, the serotonin receptor modulator is part of a single fixed dose formulation that releases N-ethyl-3,4-methylenedioxyamphetamine·HCl form disclosed herein, including those described in Table Ex10 first followed by serotonin receptor modulator on two different release profiles. In another embodiment, the N-ethyl-3,4-methylenedioxyamphetamine·HCl form disclosed herein, including those described in Table Ex10 is administered first as a single dosage and, after a length of time, serotonin receptor modulator is administered as a second dosage separate from the first dosage. Thus, in some embodiments, the serotonin receptor modulator is administered or released from a composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post release of the N-ethyl-3,4-methylenedioxyamphetamine·HCl form disclosed herein, including those described in Table Ex10. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post release of N-ethyl-3,4-methylenedioxyamphetamine·HCl form disclosed herein, including those described in Table Ex10. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post release of the N-ethyl-3,4-methylenedioxyamphetamine. HCl form disclosed herein, including those described in Table Ex10.

In a preferred embodiment, the serotonin receptor modulator is administered at about 1 hour to about 3 hours post administration of the N-ethyl-3,4-methylenedioxyamphetamine. HCl form disclosed herein, including those described in Table Ex10.

In some embodiments, the serotonin receptor modulator is eplivanserin, wherein the eplivanserin is administered to post-treat at least 15 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat between at least 30 minutes prior and 360 minutes post release or administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat between at least 60 minutes prior and 360 minutes post release or administration the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat between at least 90 minutes and 240 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat at least 120 minutes post administration of the N-ethyl-3,4-methylenedioxyamphetamine·HCl form disclosed herein, including those described in Table Ex10.

In some embodiments, the serotonin receptor modulator is eplivanserin, wherein the eplivanserin is administered to post-treat at least 150 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat at least 180 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat at least 210 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat at least 240 minutes post administration of the N-ethyl-3,4-methylenedioxyamphetamine·HCl form disclosed herein, including those described in Table Ex10.

In some embodiments, the serotonin receptor modulator is eplivanserin, wherein the eplivanserin is administered to post-treat at least 270 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat at least 300 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat at least 330 minutes post administration of the N-ethyl-3,4-methylenedioxyamphetamine·HCl form disclosed herein, including those described in Table Ex10. In some embodiments, the serotonin receptor modulator is eplivanserin, wherein the eplivanserin is administered to post-treat at least 360 minutes post administration or release of the N-ethyl-3,4-methylenedioxyamphetamine·HCl form disclosed herein, including those described in Table Ex10.

In some preferred embodiments, the serotonin receptor modulator is eplivanserin, wherein eplivanserin is administered to post-treat between about 60 minutes and about 180 minutes post administration or release of the N-ethyl-3,4-methylenedioxyamphetamine. HCl form disclosed herein, including those described in Table Ex10.

In some embodiments, the serotonin receptor modulator is volinanserin, wherein the volinanserin is administered to post-treat a subject between at least 15 minutes and 360 minutes post administration or release of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat between at least 30 minutes and 360 minutes post administration or release of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat between at least 60 minutes and 240 minutes post administration or release of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 90 minutes post administration of N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 120 minutes post administration of the N-ethyl-3,4-methylenedioxyamphetamine·HCl form disclosed herein, including those described in Table Ex10.

In some embodiments, the serotonin receptor modulator is volinanserin, wherein the volinanserin is administered to post-treat at least 150 minutes post administration of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat between about 15 minutes and about 150 minutes post administration of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 180 minutes post administration of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 210 minutes post administration of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 240 minutes post administration of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 270 minutes post administration of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 300 minutes post administration of the N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 330 minutes post administration of N-ethyl-3,4-methylenedioxyamphetamine·HCl form disclosed herein, including those described in Table Ex10. In some embodiments, the serotonin receptor modulator is volinanserin, wherein the volinanserin is administered to post-treat at least 360 minutes post administration of the N-ethyl-3,4-methylenedioxyamphetamine·HCl form disclosed herein, including those described in Table Ex10. In some preferred embodiments, the serotonin receptor modulator is volinanserin, wherein volinanserin is administered to post-treat between about 60 minutes and about 180 minutes post administration of the N-ethyl-3,4-methylenedioxyamphetamine·HCl form disclosed herein, including those described in Table Ex10.

In some embodiments, the serotonin receptor modulator is ketanserin, wherein the ketanserin is administered to post-treat at least 15 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat between at least 30 minutes and 360 minutes post administration or release of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat between at least 60 minutes and 240 minutes post administration or release of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 90 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 120 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 150 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat between about 15 minutes and about 150 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 180 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 210 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 240 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 270 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 300 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 330 minutes post administration of the N-ethyl-3,4-methylenedioxyamphetamine·HCl form disclosed herein, including those described in Table Ex10. In some embodiments, the serotonin receptor modulator is ketanserin, wherein the ketanserin is administered to post-treat at least 360 minutes post administration of the N-ethyl-3,4-methylenedioxyamphetamine·HCl form disclosed herein, including those described in Table Ex10. In some preferred embodiments, the serotonin receptor modulator is ketanserin, wherein ketanserin is administered to post-treat between about 60 minutes and about 180 minutes post administration of the N-ethyl-3,4-methylenedioxyamphetamine. HCl form disclosed herein, including those described in Table Ex10.

In some embodiments, the serotonin receptor modulator is ritanserin, wherein the ritanserin is administered to post-treat at least 15 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 30 minutes post administration of the N-ethyl-3,4-methylenedioxyamphetamine·HCl form disclosed herein, including those described in Table Ex10. In some embodiments, the serotonin receptor modulator is ritanserin wherein the ritanserin is administered to post-treat between at least 60 minutes and 240 minutes post administration or release of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 90 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 120 minutes post administration of the N-ethyl-3,4- methylenedioxyamphetamine·HCl form disclosed herein, including those described in Table Ex10. In some embodiments, the serotonin receptor modulator is ritanserin, wherein the ritanserin is administered to post-treat at least 150 minutes post administration of the N-ethyl-3,4-methylenedioxyamphetamine. HCl form disclosed herein, including those described in Table Ex10. In some embodiments, the serotonin receptor modulator is ritanserin, wherein the ritanserin is administered to post-treat between about 15 minutes and about 150 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 180 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 210 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 240 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 270 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 300 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 330 minutes post administration of the N-ethyl-3,4-methylenedioxyamphetamine·HCl form disclosed herein, including those described in Table Ex10. In some embodiments, the serotonin receptor modulator is ritanserin, wherein the ritanserin is administered to post-treat at least 360 minutes post administration of the N-ethyl-3,4-methylenedioxyamphetamine·HCl form disclosed herein, including those described in Table Ex10. In some preferred embodiments, the serotonin receptor modulator is ritanserin, wherein ritanserin is administered to post-treat between about 60 minutes and about 180 minutes post administration of the N-ethyl-3,4-methylenedioxyamphetamine. HCl form disclosed herein, including those described in Table Ex10.

In some embodiments, the serotonin receptor modulator is pimavanserin, wherein the pimavanserin is administered to post-treat at least 15 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 30 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat between at least 60 minutes and 240 minutes post administration or release of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 90 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 120 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 150 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat between about 15 minutes and about 150 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 180 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 210 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 240 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 270 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 300 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 330 minutes post administration of the N-ethyl-3,4-methylenedioxyamphetamine·HCl form disclosed herein, including those described in Table Ex10. In some embodiments, the serotonin receptor modulator is pimavanserin, wherein the pimavanserin is administered to post-treat at least 360 minutes post administration of the N-ethyl-3,4-methylenedioxyamphetamine·HCl form disclosed herein, including those described in Table Ex10. In some preferred embodiments, the serotonin receptor modulator is pimavanserin, wherein pimavanserin is administered to post-treat between about 60 minutes and about 180 minutes post administration of the N-ethyl-3,4-methylenedioxyamphetamine·HCl form disclosed herein, including those described in Table Ex10.

In some embodiments, the serotonin receptor modulator is nelotanserin, wherein the nelotanserin is administered to post-treat at least 15 minutes post the administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 30 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat between at least 60 minutes and 240 minutes post administration or release of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 90 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 120 minutes post administration of the N-ethyl-3,4-methylenedioxyamphetamine·HCl form disclosed herein, including those described in Table Ex10.

In some embodiments, the serotonin receptor modulator is nelotanserin, wherein the nelotanserin is administered to post-treat at least 150 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat between about 15 minutes and about 150 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 180 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 210 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 240 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 270 minutes post administration of the N-ethyl-3,4-methylenedioxyamphetamine·HCl form disclosed herein, including those described in Table Ex10.

In some embodiments, the serotonin receptor modulator is nelotanserin, wherein the nelotanserin is administered to post-treat at least 300 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 330 minutes post administration of the N-ethyl-3,4-methylenedioxyamphetamine·HCl form disclosed herein, including those described in Table Ex10. In some embodiments, the serotonin receptor modulator is nelotanserin, wherein the nelotanserin is administered to post-treat at least 360 minutes post administration of the N-ethyl-3,4-methylenedioxyamphetamine·HCl form disclosed herein, including those described in Table Ex10. In some preferred embodiments, the serotonin receptor modulator is nelotanserin, wherein nelotanserin is administered to post-treat between about 60 minutes and about 180 minutes post administration of the N-ethyl-3,4-methylenedioxyamphetamine·HCl form disclosed herein, including those described in Table Ex10.

In some embodiments, the serotonin receptor modulator is pruvanserin, wherein the pruvanserin is administered to post-treat at least 15 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 30 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat between at least 60 minutes and 240 minutes post the administration or release of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 90 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 120 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 150 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat between about 15 minutes and about 150 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 180 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 210 minutes post administration of the N-ethyl-3,4-methylenedioxyamphetamine·HCl form disclosed herein, including those described in Table Ex10.

In some embodiments, the serotonin receptor modulator is pruvanserin, wherein the pruvanserin is administered to post-treat at least 240 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 270 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 300 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 330 minutes post administration of the N-ethyl-3,4-methylenedioxyamphetamine·HCl form disclosed herein, including those described in Table Ex10. In some embodiments, the serotonin receptor modulator is pruvanserin, wherein the pruvanserin is administered to post-treat at least 360 minutes post administration of the N-ethyl-3,4-methylenedioxyamphetamine·HCl form disclosed herein, including those described in Table Ex10. In some preferred embodiments, the serotonin receptor modulator is pruvanserin, wherein pruvanserin is administered to post-treat between about 60 minutes and about 180 minutes post administration of the N-ethyl-3,4-methylenedioxyamphetamine·HCl form disclosed herein, including those described in Table Ex10.

In some embodiments, the serotonin receptor modulator is flibanserin, wherein the flibanserin is administered to post-treat at least 15 minutes post to the administration of the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 30 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat between at least 60 minutes and 240 minutes post to the administration or release of the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 90 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 120 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 150 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat between about 15 minutes and about 150 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 180 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 210 minutes post to the N-ethyl-3,4-methylenedioxyamphetamine HCl form disclosed herein, including those described in Table Ex10.

In some embodiments, the serotonin receptor modulator is flibanserin, wherein the flibanserin is administered to post-treat at least 240 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 270 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 300 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 330 minutes post to the N-ethyl-3,4-methylenedioxyamphetamine HCl form disclosed herein, including those described in Table Ex10. In some embodiments, the serotonin receptor modulator is flibanserin, wherein the flibanserin is administered to post-treat at least 360 minutes post to the N-ethyl-3,4-methylenedioxyamphetamine HCl form disclosed herein, including those described in Table Ex10. In some preferred embodiments, the serotonin receptor modulator is flibanserin, wherein flibanserin is administered to post-treat between about 60 minutes and about 180 minutes post to the administration of the N-ethyl-3,4-methylenedioxyamphetamine HCl form disclosed herein, including those described in Table Ex10.

In some embodiments, the serotonin receptor modulator is olanzapine, wherein the olanzapine is administered to post-treat at least 15 minutes post to the administration of the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 30 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat between at least 60 minutes and 240 minutes post to the administration or release of the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 90 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 120 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 150 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat between about 15 minutes and about 150 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 180 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 210 minutes post to the N-ethyl-3,4-methylenedioxyamphetamine HCl form disclosed herein, including those described in Table Ex10.

In some embodiments, the serotonin receptor modulator is olanzapine, wherein the olanzapine is administered to post-treat at least 240 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 270 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 300 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 330 minutes post to the N-ethyl-3,4-methylenedioxyamphetamine HCl form disclosed herein, including those described in Table Ex10. In some embodiments, the serotonin receptor modulator is olanzapine, wherein the olanzapine is administered to post-treat at least 360 minutes post to the N-ethyl-3,4-methylenedioxyamphetamine HCl form disclosed herein, including those described in Table Ex10. In some preferred embodiments, the serotonin receptor modulator is olanzapine, wherein olanzapine is administered to post-treat between about 60 minutes and about 180 minutes post to the administration of the N-ethyl-3,4-methylenedioxyamphetamine HCl form disclosed herein, including those described in Table Ex10.

In some embodiments, the serotonin receptor modulator is quetiapine, wherein the quetiapine is administered to post-treat at least 15 minutes post to the administration of the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 30 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat between at least 60 minutes and 240 minutes post to the administration or release of the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 90 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 120 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 150 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat between about 15 minutes and about 150 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 180 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 210 minutes post to the N-ethyl-3,4-methylenedioxyamphetamine HCl form disclosed herein, including those described in Table Ex10.

In some embodiments, the serotonin receptor modulator is quetiapine, wherein the quetiapine is administered to post-treat at least 240 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 270 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 300 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 330 minutes post to the N-ethyl-3,4-methylenedioxyamphetamine HCl form disclosed herein, including those described in Table Ex10. In some embodiments, the serotonin receptor modulator is quetiapine, wherein the quetiapine is administered to post-treat at least 360 minutes post to the N-ethyl-3,4-methylenedioxyamphetamine HCl form disclosed herein, including those described in Table Ex10. In some preferred embodiments, the serotonin receptor modulator is quetiapine, wherein quetiapine is administered to post-treat between about 60 minutes and about 180 minutes post to the administration of the N-ethyl-3,4-methylenedioxyamphetamine HCl form disclosed herein, including those described in Table Ex10.

In some embodiments, the serotonin receptor modulator is risperidone, wherein the risperidone is administered to post-treat at least 15 minutes post to the administration of the N-ethyl-3,4-methylenedioxyamphetamine HCl form disclosed herein, including those described in Table Ex10. In some embodiments, the serotonin receptor modulator is risperidone, wherein the risperidone is administered to post-treat at least 30 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat between at least 60 minutes and 240 minutes post to the administration or release of the N-ethyl-3,4-methylenedioxyamphetamine HCl form disclosed herein, including those described in Table Ex10. In some embodiments, the serotonin receptor modulator is risperidone, wherein the risperidone is administered to post-treat at least 90 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 120 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 150 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat between about 15 minutes and about 150 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 180 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 210 minutes post to the N-ethyl-3,4-methylenedioxyamphetamine HCl form disclosed herein, including those described in Table Ex10.

In some embodiments, the serotonin receptor modulator is risperidone, wherein the risperidone is administered to post-treat at least 240 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 270 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 300 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 330 minutes post to the N-ethyl-3,4-methylenedioxyamphetamine HCl form disclosed herein, including those described in Table Ex10. In some embodiments, the serotonin receptor modulator is risperidone, wherein the risperidone is administered to post-treat at least 360 minutes post to the N-ethyl-3,4-methylenedioxyamphetamine HCl form disclosed herein, including those described in Table Ex10. In some preferred embodiments, the serotonin receptor modulator is risperidone, wherein risperidone is administered to post-treat between about 60 minutes and about 180 minutes post to the administration of the N-ethyl-3,4-methylenedioxyamphetamine HCl form disclosed herein, including those described in Table Ex10.

In some embodiments, the serotonin receptor modulator for use with the (S)—N-ethyl-3,4-methylenedioxyamphetamine salts and solid forms disclosed herein, including those described in Table Ex11 is eplivanserin, wherein the eplivanserin is administered in about 1 mg to about 40 mg, or about 5 mg to about 10 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is volinanserin, wherein the volinanserin is administered in about 1 mg to about 60 mg, or about 5 mg to about 20 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is ketanserin, wherein the ketanserin is administered in about 10 mg to about 80 mg, about 30 mg to about 50 mg, or about 40 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is ritanserin, wherein the ritanserin is administered in about 1 mg to about 40 mg, or about 2.5 mg to about 10 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is pimavanserin, wherein the pimavanserin is administered in about 1 mg to about 60 mg, or about 17 mg to about 34 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is nelotanserin, wherein the nelotanserin is administered in about 1 mg to about 80 mg, or about 40 mg to about 80 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is pruvanserin, wherein the pruvanserin is administered in about 1 mg to about 40 mg, or about 3 mg to about 10 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is flibanserin, wherein the flibanserin is administered in about 10 mg to about 200 mg, or about 80 mg to about 120 mg, or about 100 mg and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is olanzapine, wherein the olanzapine is administered in about 2.5 mg to about 30 mg, or about 5 mg or about 10 mg, or about 20 mg or about 25 mg, and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is quetiapine, wherein the quetiapine is administered in about 25 mg to about 800 mg, or about 50 mg to about 100 mg, or about 150 mg or about 200 mg or about 250 mg or about 300 mg, and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is an extended-release of quetiapine, wherein the extended-release of quetiapine is administered in about 50 mg to about 300 mg, or about 50 mg or about 100 mg or about 200 mg, or about 300 mg, and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In some embodiments, the serotonin receptor modulator for use with the (S)—N-ethyl-3,4-methylenedioxyamphetamine salts and solid forms disclosed herein, including those described in Table Ex11 is an extended-release of risperidone including (RISPERDAL CONSTA), wherein the extended-release of risperidone is administered in about 12.5 mg, or about 25 mg, or about 37.5 mg, or about 50 mg, and the (S)—N-ethyl-3,4-methylenedioxyamphetamine salts and solid forms disclosed herein, including those described in Table Ex11 are administered in about 10 mg to about 300 mg or about 100 mg to about 180 mg or about 120 mg or about 150 mg or about 160 mg.

In certain embodiments, such as those described above a(S)—N-ethyl-3,4-methylenedioxyamphetamine form disclosed herein, including those described in Table Ex11 is co-administered with a serotonin receptor modulator in the same or in separate compositions. In one embodiment, the serotonin receptor modulator is administered prior to the (S)—N-ethyl-3,4-methylenedioxyamphetamine form disclosed herein, including those described in Table Ex11. In one embodiment, the (S)—N-ethyl-3,4-methylenedioxyamphetamine form disclosed herein, including those described in Table Ex11 is administered in a modified release formulation such that the subject is effectively pretreated with serotonin receptor modulator prior to release of an effective amount of the (S)—N-ethyl-3,4-methylenedioxyamphetamine. In some embodiments the serotonin receptor modulator is part of a single fixed dose formulation that releases serotonin receptor modulator first followed by the (S)—N-ethyl-3,4-methylenedioxyamphetamine on two different release profiles. In another embodiment the serotonin receptor modulator is administered first as a single dosage and after a length of time, the (S)—N-ethyl-3,4-methylenedioxyamphetamine form disclosed herein, including those described in Table Ex11 is administered as a second dosage separate from the first dosage. Thus, in some embodiments, the serotonin receptor modulator is administered or released from a composition provided herein prior to the administration and/or release of the (S)—N-ethyl-3,4-methylenedioxyamphetamine form disclosed herein, including those described in Table Ex11. This allows pretreatment to attenuate activation of the serotonin receptor by the (S)—N-ethyl-3,4-methylenedioxyamphetamine form disclosed herein, including those described in Table Ex11.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the (S)—N-ethyl-3,4-methylenedioxyamphetamine form disclosed herein, including those described in Table Ex11. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of (S)—N-ethyl-3,4-methylenedioxyamphetamine form disclosed herein, including those described in Table Ex11. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the (S)—N-ethyl-3,4-methylenedioxyamphetamine form disclosed herein, including those described in Table Ex11.

In a preferred embodiment, the serotonin receptor modulator is administered at about 1 hour to about 3 hours prior to the administration of the (S)—N-ethyl-3,4-methylenedioxyamphetamine form disclosed herein, including those described in Table Ex11.

In some embodiments, the serotonin receptor modulator is eplivanserin, wherein the eplivanserin is administered to pretreat at least 15 minutes prior to the administration of the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat between at least 30 minutes prior and 360 minutes prior to the release or administration of the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat between at least 60 minutes prior and 360 minutes prior to the release or administration the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat between at least 90 minutes and 240 minutes prior to the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat at least 120 minutes prior to the (S)—N-ethyl-3,4-methylenedioxyamphetamine form disclosed herein, including those described in Table Ex11.

In some embodiments, the serotonin receptor modulator is eplivanserin, wherein the eplivanserin is administered to pretreat at least 150 minutes prior to the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat at least 180 minutes prior to the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat at least 210 minutes prior to the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat at least 240 minutes prior to the (S)—N-ethyl-3,4-methylenedioxyamphetamine form disclosed herein, including those described in Table Ex11.

In some embodiments, the serotonin receptor modulator is eplivanserin, wherein the eplivanserin is administered to pretreat at least 270 minutes prior to the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat at least 300 minutes prior to the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat at least 330 minutes prior to the (S)—N-ethyl-3,4-methylenedioxyamphetamine form disclosed herein, including those described in Table Ex11. In some embodiments, the serotonin receptor modulator is eplivanserin, wherein the eplivanserin is administered to pretreat at least 360 minutes prior to administration or release of the (S)—N-ethyl-3,4-methylenedioxyamphetamine form disclosed herein, including those described in Table Ex11.

In some preferred embodiments, the serotonin receptor modulator is eplivanserin, wherein eplivanserin is administered to pretreat between about 60 minutes and about 180 minutes prior to the administration or release of the (S)—N-ethyl-3,4-methylenedioxyamphetamine form disclosed herein, including those described in Table Ex11.

In some embodiments, the serotonin receptor modulator is volinanserin, wherein the volinanserin is administered to pretreat a subject between at least 15 minutes and 360 minutes prior to the administration or release of the (S)—N-ethyl-3,4-methylenedioxyamphetamine form disclosed herein, including those described in Table Ex11. In some embodiments, the serotonin receptor modulator is volinanserin, wherein the volinanserin is administered to pretreat between at least 30 minutes and 360 minutes prior to the administration or release of the (S)—N-ethyl-3,4-methylenedioxyamphetamine form disclosed herein, including those described in Table Ex11. In some embodiments, the serotonin receptor modulator is volinanserin, wherein the volinanserin is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 90 minutes prior to(S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 120 minutes prior to the (S)—N-ethyl-3,4-methylenedioxyamphetamine form disclosed herein, including those described in Table Ex11.

In some embodiments, the serotonin receptor modulator is volinanserin, wherein the volinanserin is administered to pretreat at least 150 minutes prior to the (S)—N-ethyl-3,4-methylenedioxyamphetamine form disclosed herein, including those described in Table Ex11. In some embodiments, the serotonin receptor modulator is volinanserin, wherein the volinanserin is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 180 minutes prior to the (S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 210 minutes prior to the (S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 240 minutes prior to the (S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 270 minutes prior to the (S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 300 minutes prior to the (S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 330 minutes prior to(S)—N-ethyl-3,4-methylenedioxyamphetamine form disclosed herein, including those described in Table Ex11. In some embodiments, the serotonin receptor modulator is volinanserin, wherein the volinanserin is administered to pretreat at least 360 minutes prior to the (S)—N-ethyl-3,4-methylenedioxyamphetamine form disclosed herein, including those described in Table Ex11. In some preferred embodiments, the serotonin receptor modulator is volinanserin, wherein volinanserin is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is ketanserin, wherein the ketanserin is administered to pretreat at least 15 minutes prior to the administration of the (S)—N-ethyl-3,4-methylenedioxyamphetamine form disclosed herein, including those described in Table Ex11. In some embodiments, the serotonin receptor modulator is ketanserin, wherein the ketanserin is administered to pretreat between at least 30 minutes and 360 minutes prior to the administration or release of the (S)—N-ethyl-3,4-methylenedioxyamphetamine form disclosed herein, including those described in Table Ex11. In some embodiments, the serotonin receptor modulator is ketanserin, wherein the ketanserin is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 90 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 120 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 150 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 180 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 210 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 240 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 270 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 300 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 330 minutes prior to the (S)—N-ethyl-3,4-methylenedioxyamphetamine form disclosed herein, including those described in Table Ex11. In some embodiments, the serotonin receptor modulator is ketanserin, wherein the ketanserin is administered to pretreat at least 360 minutes prior to the (S)—N-ethyl-3,4-methylenedioxyamphetamine form disclosed herein, including those described in Table Ex11. In some preferred embodiments, the serotonin receptor modulator is ketanserin, wherein ketanserin is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is ritanserin, wherein the ritanserin is administered to pretreat at least 15 minutes prior to the administration of the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 30 minutes prior to the (S)—N-ethyl-3,4-methylenedioxyamphetamine form disclosed herein, including those described in Table Ex11. In some embodiments, the serotonin receptor modulator is ritanserin wherein the ritanserin is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 90 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 120 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 150 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 180 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 210 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 240 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 270 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 300 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 330 minutes prior to the (S)—N-ethyl-3,4-methylenedioxyamphetamine form disclosed herein, including those described in Table Ex11. In some embodiments, the serotonin receptor modulator is ritanserin, wherein the ritanserin is administered to pretreat at least 360 minutes prior to the (S)—N-ethyl-3,4-methylenedioxyamphetamine form disclosed herein, including those described in Table Ex11. In some preferred embodiments, the serotonin receptor modulator is ritanserin, wherein ritanserin is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is pimavanserin, wherein the pimavanserin is administered to pretreat at least 15 minutes prior to the administration of the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 30 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 90 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 120 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 150 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 180 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 210 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 240 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 270 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 300 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 330 minutes prior to the (S)—N-ethyl-3,4-methylenedioxyamphetamine form disclosed herein, including those described in Table Ex11. In some embodiments, the serotonin receptor modulator is pimavanserin, wherein the pimavanserin is administered to pretreat at least 360 minutes prior to the (S)—N-ethyl-3,4-methylenedioxyamphetamine form disclosed herein, including those described in Table Ex11. In some preferred embodiments, the serotonin receptor modulator is pimavanserin, wherein pimavanserin is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is nelotanserin, wherein the nelotanserin is administered to pretreat at least 15 minutes prior to the administration of the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 30 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 90 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 120 minutes prior to the (S)—N-ethyl-3,4-methylenedioxyamphetamine form disclosed herein, including those described in Table Ex11.

In some embodiments, the serotonin receptor modulator is nelotanserin, wherein the nelotanserin is administered to pretreat at least 150 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 180 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 210 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 240 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 270 minutes prior to the (S)—N-ethyl-3,4-methylenedioxyamphetamine form disclosed herein, including those described in Table Ex11.

In some embodiments, the serotonin receptor modulator is nelotanserin, wherein the nelotanserin is administered to pretreat at least 300 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 330 minutes prior to the (S)—N-ethyl-3,4-methylenedioxyamphetamine form disclosed herein, including those described in Table Ex11. In some embodiments, the serotonin receptor modulator is nelotanserin, wherein the nelotanserin is administered to pretreat at least 360 minutes prior to the (S)—N-ethyl-3,4-methylenedioxyamphetamine form disclosed herein, including those described in Table Ex11. In some preferred embodiments, the serotonin receptor modulator is nelotanserin, wherein nelotanserin is administered to pretreat between about 60 minutes and about 180 minutes prior to the administration of the (S)—N-ethyl-3,4-methylenedioxyamphetamine form disclosed herein, including those described in Table Ex11.

In some embodiments, the serotonin receptor modulator is pruvanserin, wherein the pruvanserin is administered to pretreat at least 15 minutes prior to the administration of the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 30 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat between at least 60 minutes and 240 minutes prior to the administration or release of the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 90 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 120 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 150 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat between about 15 minutes and about 150 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 180 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 210 minutes prior to the (S)—N-ethyl-3,4-methylenedioxyamphetamine form disclosed herein, including those described in Table Ex11.

In some embodiments, the serotonin receptor modulator is pruvanserin, wherein the pruvanserin is administered to pretreat at least 240 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 270 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 300 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 330 minutes prior to the (S)—N-ethyl-3,4-methylenedioxyamphetamine form disclosed herein, including those described in Table Ex11. In some embodiments, the serotonin receptor modulator is pruvanserin, wherein the pruvanserin is administered to pretreat at least 360 minutes prior to the (S)—N-ethyl-3,4-methylenedioxyamphetamine form disclosed herein, including those described in Table Ex11. In some preferred embodiments, the serotonin receptor modulator is pruvanserin, wherein pruvanserin is administered to pretreat between about 60 minutes and about 180 minutes prior to the administration of the (S)—N-ethyl-3,4-methylenedioxyamphetamine form disclosed herein, including those described in Table Ex11.

In certain embodiments, such as those described above a(S)—N-ethyl-3,4-methylenedioxyamphetamine form disclosed herein, including those described in Table Ex11 is co-administered with a serotonin receptor modulator in the same or in separate compositions. In one embodiment, the serotonin receptor modulator is administered after the (S)—N-ethyl-3,4-methylenedioxyamphetamine form disclosed herein, including those described in Table Ex11. In one embodiment, the (S)—N-ethyl-3,4-methylenedioxyamphetamine form disclosed herein, including those described in Table Ex11 is administered in a modified release formulation such that the subject is effectively post-treated with serotonin receptor modulator post to release of an effective amount of the (S)—N-ethyl-3,4-methylenedioxyamphetamine. In some embodiments, the serotonin receptor modulator is part of a single fixed dose formulation that releases the (S)—N-ethyl-3,4-methylenedioxyamphetamine first followed by serotonin receptor modulator on two different release profiles. In another embodiment, the (S)—N-ethyl-3,4-methylenedioxyamphetamine form disclosed herein, including those described in Table Ex11 is administered first as a single dosage and, after a length of time, serotonin receptor modulator is administered as a second dosage separate from the first dosage. Thus, in some embodiments, the serotonin receptor modulator is administered or released from a composition provided herein post to the administration and/or release of the (S)—N-ethyl-3,4-methylenedioxyamphetamine form disclosed herein, including those described in Table Ex11. This allows post-treatment to attenuate activation of the serotonin receptor by the (S)—N-ethyl-3,4-methylenedioxyamphetamine form disclosed herein, including those described in Table Ex11.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post to the release of the (S)—N-ethyl-3,4-methylenedioxyamphetamine form disclosed herein, including those described in Table Ex11. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of (S)—N-ethyl-3,4-methylenedioxyamphetamine form disclosed herein, including those described in Table Ex11. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the (S)—N-ethyl-3,4-methylenedioxyamphetamine form disclosed herein, including those described in Table Ex11.

In a preferred embodiment, the serotonin receptor modulator is administered at about 1 hour to about 3 hours post to the administration of the (S)—N-ethyl-3,4-methylenedioxyamphetamine form disclosed herein, including those described in Table Ex11.

In some embodiments, the serotonin receptor modulator is eplivanserin, wherein the eplivanserin is administered to post-treat at least 15 minutes post to the administration of the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat between at least 30 minutes post and 360 minutes post to the release or administration of the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat between at least 60 minutes post and 360 minutes post to the release or administration the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat between at least 90 minutes and 240 minutes post to the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat at least 120 minutes post to the (S)—N-ethyl-3,4-methylenedioxyamphetamine form disclosed herein, including those described in Table Ex11.

In some embodiments, the serotonin receptor modulator is eplivanserin, wherein the eplivanserin is administered to post-treat at least 150 minutes post to the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat at least 180 minutes post to the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat at least 210 minutes post to the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat at least 240 minutes post to the (S)—N-ethyl-3,4-methylenedioxyamphetamine form disclosed herein, including those described in Table Ex11.

In some embodiments, the serotonin receptor modulator is eplivanserin, wherein the eplivanserin is administered to post-treat at least 270 minutes post to the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat at least 300 minutes post to the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat at least 330 minutes post to the (S)—N-ethyl-3,4-methylenedioxyamphetamine form disclosed herein, including those described in Table Ex11. In some embodiments, the serotonin receptor modulator is eplivanserin, wherein the eplivanserin is administered to post-treat at least 360 minutes post to administration or release of the (S)—N-ethyl-3,4-methylenedioxyamphetamine form disclosed herein, including those described in Table Ex11.

In some preferred embodiments, the serotonin receptor modulator is eplivanserin, wherein eplivanserin is administered to post-treat between about 60 minutes and about 180 minutes post to the administration or release of the (S)—N-ethyl-3,4-methylenedioxyamphetamine form disclosed herein, including those described in Table Ex11.

In some embodiments, the serotonin receptor modulator is volinanserin, wherein the volinanserin is administered to post-treat a subject between at least 15 minutes and 360 minutes post to the administration or release of the (S)—N-ethyl-3,4-methylenedioxyamphetamine form disclosed herein, including those described in Table Ex11. In some embodiments, the serotonin receptor modulator is volinanserin, wherein the volinanserin is administered to post-treat between at least 30 minutes and 360 minutes post to the administration or release of the (S)—N-ethyl-3,4-methylenedioxyamphetamine form disclosed herein, including those described in Table Ex11. In some embodiments, the serotonin receptor modulator is volinanserin, wherein the volinanserin is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 90 minutes post to(S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 120 minutes post to the (S)—N-ethyl-3,4-methylenedioxyamphetamine form disclosed herein, including those described in Table Ex11.

In some embodiments, the serotonin receptor modulator is volinanserin, wherein the volinanserin is administered to post-treat at least 150 minutes post to the (S)—N-ethyl-3,4-methylenedioxyamphetamine form disclosed herein, including those described in Table Ex11. In some embodiments, the serotonin receptor modulator is volinanserin, wherein the volinanserin is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 180 minutes post to the (S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 210 minutes post to the (S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 240 minutes post to the (S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 270 minutes post to the (S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 300 minutes post to the (S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 330 minutes post to(S)—N-ethyl-3,4-methylenedioxyamphetamine form disclosed herein, including those described in Table Ex11. In some embodiments, the serotonin receptor modulator is volinanserin, wherein the volinanserin is administered to post-treat at least 360 minutes post to the (S)—N-ethyl-3,4-methylenedioxyamphetamine form disclosed herein, including those described in Table Ex11. In some preferred embodiments, the serotonin receptor modulator is volinanserin, wherein volinanserin is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is ketanserin, wherein the ketanserin is administered to post-treat at least 15 minutes post to the administration of the (S)—N-ethyl-3,4-methylenedioxyamphetamine form disclosed herein, including those described in Table Ex11. In some embodiments, the serotonin receptor modulator is ketanserin, wherein the ketanserin is administered to post-treat between at least 30 minutes and 360 minutes post to the administration or release of the (S)—N-ethyl-3,4-methylenedioxyamphetamine form disclosed herein, including those described in Table Ex11. In some embodiments, the serotonin receptor modulator is ketanserin, wherein the ketanserin is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 90 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 120 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 150 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 180 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 210 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 240 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 270 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 300 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 330 minutes post to the (S)—N-ethyl-3,4-methylenedioxyamphetamine form disclosed herein, including those described in Table Ex11. In some embodiments, the serotonin receptor modulator is ketanserin, wherein the ketanserin is administered to post-treat at least 360 minutes post to the (S)—N-ethyl-3,4-methylenedioxyamphetamine form disclosed herein, including those described in Table Ex11. In some preferred embodiments, the serotonin receptor modulator is ketanserin, wherein ketanserin is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is ritanserin, wherein the ritanserin is administered to post-treat at least 15 minutes post to the administration of the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 30 minutes post to the (S)—N-ethyl-3,4-methylenedioxyamphetamine form disclosed herein, including those described in Table Ex11. In some embodiments, the serotonin receptor modulator is ritanserin wherein the ritanserin is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 90 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 120 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 150 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 180 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 210 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 240 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 270 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 300 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 330 minutes post to the (S)—N-ethyl-3,4-methylenedioxyamphetamine form disclosed herein, including those described in Table Ex11. In some embodiments, the serotonin receptor modulator is ritanserin, wherein the ritanserin is administered to post-treat at least 360 minutes post to the (S)—N-ethyl-3,4-methylenedioxyamphetamine form disclosed herein, including those described in Table Ex11. In some preferred embodiments, the serotonin receptor modulator is ritanserin, wherein ritanserin is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is pimavanserin, wherein the pimavanserin is administered to post-treat at least 15 minutes post to the administration of the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 30 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 90 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 120 minutes post to the(S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 150 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 180 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 210 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 240 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 270 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 300 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 330 minutes post to the (S)—N-ethyl-3,4-methylenedioxyamphetamine form disclosed herein, including those described in Table Ex11. In some embodiments, the serotonin receptor modulator is pimavanserin, wherein the pimavanserin is administered to post-treat at least 360 minutes post to the (S)—N-ethyl-3,4-methylenedioxyamphetamine form disclosed herein, including those described in Table Ex11. In some preferred embodiments, the serotonin receptor modulator is pimavanserin, wherein pimavanserin is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is nelotanserin, wherein the nelotanserin is administered to post-treat at least 15 minutes post to the administration of the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 30 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 90 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 120 minutes post to the (S)—N-ethyl-3,4-methylenedioxyamphetamine form disclosed herein, including those described in Table Ex11.

In some embodiments, the serotonin receptor modulator is nelotanserin, wherein the nelotanserin is administered to post-treat at least 150 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 180 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 210 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 240 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 270 minutes post to the (S)—N-ethyl-3,4-methylenedioxyamphetamine form disclosed herein, including those described in Table Ex11.

In some embodiments, the serotonin receptor modulator is nelotanserin, wherein the nelotanserin is administered to post-treat at least 300 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 330 minutes post to the (S)—N-ethyl-3,4-methylenedioxyamphetamine form disclosed herein, including those described in Table Ex11. In some embodiments, the serotonin receptor modulator is nelotanserin, wherein the nelotanserin is administered to post-treat at least 360 minutes post to the (S)—N-ethyl-3,4-methylenedioxyamphetamine form disclosed herein, including those described in Table Ex11. In some preferred embodiments, the serotonin receptor modulator is nelotanserin, wherein nelotanserin is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is pruvanserin, wherein the pruvanserin is administered to post-treat at least 15 minutes post to the administration of the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 30 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 90 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 120 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 150 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 180 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 210 minutes post to the (S)—N-ethyl-3,4-methylenedioxyamphetamine form disclosed herein, including those described in Table Ex11.

In some embodiments, the serotonin receptor modulator is pruvanserin, wherein the pruvanserin is administered to post-treat at least 240 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 270 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 300 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 330 minutes post to the (S)—N-ethyl-3,4-methylenedioxyamphetamine form disclosed herein, including those described in Table Ex11. In some embodiments, the serotonin receptor modulator is pruvanserin, wherein the pruvanserin is administered to post-treat at least 360 minutes post to the (S)—N-ethyl-3,4-methylenedioxyamphetamine form disclosed herein, including those described in Table Ex11. In some preferred embodiments, the serotonin receptor modulator is pruvanserin, wherein pruvanserin is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is flibanserin, wherein the flibanserin is administered to post-treat at least 15 minutes post to the administration of the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 30 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 90 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 120 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 150 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 180 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 210 minutes post to the (S)—N-ethyl-3,4-methylenedioxyamphetamine form disclosed herein, including those described in Table Ex11.

In some embodiments, the serotonin receptor modulator is flibanserin, wherein the flibanserin is administered to post-treat at least 240 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 270 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 300 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 330 minutes post to the (S)—N-ethyl-3,4-methylenedioxyamphetamine form disclosed herein, including those described in Table Ex11. In some embodiments, the serotonin receptor modulator is flibanserin, wherein the flibanserin is administered to post-treat at least 360 minutes post to the (S)—N-ethyl-3,4-methylenedioxyamphetamine form disclosed herein, including those described in Table Ex11. In some preferred embodiments, the serotonin receptor modulator is flibanserin, wherein flibanserin is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is olanzapine, wherein the olanzapine is administered to post-treat at least 15 minutes post to the administration of the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 30 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 90 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 120 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 150 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 180 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 210 minutes post to the (S)—N-ethyl-3,4-methylenedioxyamphetamine form disclosed herein, including those described in Table Ex11.

In some embodiments, the serotonin receptor modulator is olanzapine, wherein the olanzapine is administered to post-treat at least 240 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 270 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 300 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 330 minutes post to the (S)—N-ethyl-3,4-methylenedioxyamphetamine form disclosed herein, including those described in Table Ex11. In some embodiments, the serotonin receptor modulator is olanzapine, wherein the olanzapine is administered to post-treat at least 360 minutes post to the (S)—N-ethyl-3,4-methylenedioxyamphetamine form disclosed herein, including those described in Table Ex11. In some preferred embodiments, the serotonin receptor modulator is olanzapine, wherein olanzapine is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is quetiapine, wherein the quetiapine is administered to post-treat at least 15 minutes post to the administration of the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 30 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 90 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 120 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 150 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 180 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 210 minutes post to the (S)—N-ethyl-3,4-methylenedioxyamphetamine form disclosed herein, including those described in Table Ex11.

In some embodiments, the serotonin receptor modulator is quetiapine, wherein the quetiapine is administered to post-treat at least 240 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 270 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 300 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 330 minutes post to the (S)—N-ethyl-3,4-methylenedioxyamphetamine form disclosed herein, including those described in Table Ex11. In some embodiments, the serotonin receptor modulator is quetiapine, wherein the quetiapine is administered to post-treat at least 360 minutes post to the (S)—N-ethyl-3,4-methylenedioxyamphetamine form disclosed herein, including those described in Table Ex11. In some preferred embodiments, the serotonin receptor modulator is quetiapine, wherein quetiapine is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator is risperidone, wherein the risperidone is administered to post-treat at least 15 minutes post to the administration of the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 30 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat between at least 60 minutes and 240 minutes post to the administration or release of the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 90 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 120 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 150 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat between about 15 minutes and about 150 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 180 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 210 minutes post to the (S)—N-ethyl-3,4-methylenedioxyamphetamine form disclosed herein, including those described in Table Ex11.

In some embodiments, the serotonin receptor modulator is risperidone, wherein the risperidone is administered to post-treat at least 240 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 270 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 300 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 330 minutes post to the (S)—N-ethyl-3,4-methylenedioxyamphetamine form disclosed herein, including those described in Table Ex11. In some embodiments, the serotonin receptor modulator is risperidone, wherein the risperidone is administered to post-treat at least 360 minutes post to the (S)—N-ethyl-3,4-methylenedioxyamphetamine form disclosed herein, including those described in Table Ex11. In some preferred embodiments, the serotonin receptor modulator is risperidone, wherein risperidone is administered to post-treat between about 60 minutes and about 180 minutes post to the administration of the (S)—N-ethyl-3,4-methylenedioxyamphetamine form disclosed herein, including those described in Table Ex11.

In some embodiments, the serotonin receptor modulator for use with the MDAI HCl forms disclosed herein, including those described in Table Ex12 is eplivanserin and, wherein the eplivanserin is administered in about 1 mg to about 40 mg, or about 5 mg to about 10 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator is volinanserin and the MDAI HCl forms disclosed herein, including those described in Table Ex12, wherein the volinanserin is administered in about 1 mg to about 60 mg, or about 5 mg to about 20 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is ketanserin, wherein the ketanserin is administered in about 10 mg to about 80 mg, about 30 mg to about 50 mg, or about 40 mg and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is ritanserin, wherein the ritanserin is administered in about 1 mg to about 40 mg, or about 2.5 mg to about 10 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator is pimavanserin and the MDAI HCl forms disclosed herein, including those described in Table Ex12, wherein the pimavanserin is administered in about 1 mg to about 60 mg, or about 17 mg to about 34 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is nelotanserin, wherein the nelotanserin is administered in about 1 mg to about 80 mg, or about 40 mg to about 80 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is pruvanserin, wherein the pruvanserin is administered in about 1 mg to about 40 mg, or about 3 mg to about 10 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is flibanserin, wherein the flibanserin is administered in about 10 mg to about 200 mg, or about 80 mg to about 120 mg, or about 100 mg and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is olanzapine, wherein the olanzapine is administered in about 2.5 mg to about 30 mg, or about 5 mg or about 10 mg, or about 20 mg or about 25 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is quetiapine, wherein the quetiapine is administered in about 25 mg to about 800 mg, or about 50 mg to about 100 mg, or about 150 mg or about 200 mg or about 250 mg or about 300 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is an extended-release of quetiapine, wherein the extended-release of quetiapine is administered in about 50 mg to about 300 mg, or about 50 mg or about 100 mg or about 200 mg, or about 300 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In some embodiments, the serotonin receptor modulator for use with the MDAI HCl forms disclosed herein, including those described in Table Ex12 is an extended-release of risperidone including (RISPERDAL CONSTA), wherein the extended-release of risperidone is administered in about 12.5 mg, or about 25 mg, or about 37.5 mg, or about 50 mg, and the MDAI HCl forms disclosed herein, including those described in Table Ex12 are administered in about 40 mg to about 300 mg or about 60 mg to about 180 mg or about 60 mg or about 80 mg or about 100 mg or about 180 mg.

In certain embodiments, such as those described above a MDAI. HCl form disclosed herein, including those described in Table Ex12 is co-administered with a serotonin receptor modulator in the same or in separate compositions. In one embodiment, the serotonin receptor modulator is administered prior to the MDAI HCl form disclosed herein, including those described in Table Ex12. In one embodiment, the MDAI HCl form disclosed herein, including those described in Table Ex12 is administered in a modified release formulation such that the subject is effectively pretreated with serotonin receptor modulator prior to release of an effective amount of the MDAI HCl. In some embodiments the serotonin receptor modulator is part of a single fixed dose formulation that releases serotonin receptor modulator first followed by the MDAI HCl on two different release profiles. In another embodiment the serotonin receptor modulator is administered first as a single dosage and after a length of time, the MDAI HCl form disclosed herein, including those described in Table Ex12 is administered as a second dosage separate from the first dosage. Thus, in some embodiments, the serotonin receptor modulator is administered or released from a composition provided herein prior to the administration and/or release of the MDAI HCl form disclosed herein, including those described in Table Ex12. This allows pretreatment to attenuate activation of the serotonin receptor by the MDAI HCl form.

In some embodiments, the serotonin receptor modulator is eplivanserin and the psychedelic is MDAI HCl, wherein the eplivanserin is administered to pretreat at least 15 minutes prior to the administration of the MDAI HCl form disclosed herein, including those described in Table Ex12. In some embodiments, the serotonin receptor modulator is eplivanserin and the psychedelic is MDAI HCl, wherein the eplivanserin is administered to pretreat between at least 30 minutes prior and 360 minutes prior to the release or administration of the MDAI HCl form disclosed herein, including those described in Table Ex12. In some embodiments, the serotonin receptor modulator is eplivanserin and the psychedelic is MDAI HCl, wherein the eplivanserin is administered to pretreat between at least 60 minutes prior and 360 minutes prior to the release or administration of the MDAI HCl form disclosed herein, including those described in Table Ex12. In some embodiments, the serotonin receptor modulator is eplivanserin and the psychedelic is MDAI HCl, wherein the eplivanserin is administered to pretreat between at least 90 minutes and 240 minutes prior to the MDAI HCl form disclosed herein, including those described in Table Ex12. In some embodiments, the serotonin receptor modulator is eplivanserin and the psychedelic is MDAI HCl, wherein the eplivanserin is administered to pretreat at least 120 minutes prior to the MDAI HCl form disclosed herein, including those described in Table Ex12.

In some embodiments, the serotonin receptor modulator is eplivanserin and the psychedelic is MDAI HCl, wherein the eplivanserin is administered to pretreat at least 150 minutes prior to the MDAI HCl form disclosed herein, including those described in Table Ex12. In some embodiments, the serotonin receptor modulator is eplivanserin and the psychedelic is MDAI HCl, wherein the eplivanserin is administered to pretreat at least 180 minutes prior to the MDAI HCl form disclosed herein, including those described in Table Ex12. In some embodiments, the serotonin receptor modulator is eplivanserin and the psychedelic is MDAI HCl, wherein the eplivanserin is administered to pretreat at least 210 minutes prior to the MDAI HCl form disclosed herein, including those described in Table Ex12. In some embodiments, the serotonin receptor modulator is eplivanserin and the psychedelic is MDAI HCl, wherein the eplivanserin is administered to pretreat at least 240 minutes prior to the MDAI HCl form disclosed herein, including those described in Table Ex12.

In some embodiments, the serotonin receptor modulator is eplivanserin and the psychedelic is MDAI HCl, wherein the eplivanserin is administered to pretreat at least 270 minutes prior to MDAI HCl. In some embodiments, the serotonin receptor modulator is eplivanserin and the psychedelic is MDAI HCl, wherein the eplivanserin is administered to pretreat at least 300 minutes prior to the MDAI HCl form disclosed herein, including those described in Table Ex12. In some embodiments, the serotonin receptor modulator is eplivanserin and the psychedelic is MDAI HCl, wherein the eplivanserin is administered to pretreat at least 330 minutes prior to the MDAI HCl form disclosed herein, including those described in Table Ex12. In some embodiments, the serotonin receptor modulator is eplivanserin and the psychedelic is MDAI HCl, wherein the eplivanserin is administered to pretreat at least 360 minutes prior to the MDAI HCl form disclosed herein, including those described in Table Ex12.

In some preferred embodiments, the serotonin receptor modulator is eplivanserin and the psychedelic is MDAI HCl, wherein eplivanserin is administered to pretreat between about 60 minutes and about 180 minutes prior to the administration of the MDAI HCl form disclosed herein, including those described in Table Ex12.

In some embodiments, the serotonin receptor modulator is volinanserin and the psychedelic is MDAI HCl, wherein the volinanserin is administered to pretreat a subject between at least 15 minutes and 360 minutes prior to the administration or release of the MDAI HCl form disclosed herein, including those described in Table Ex12. In some embodiments, the serotonin receptor modulator is volinanserin and the psychedelic is MDAI HCl, wherein the volinanserin is administered to pretreat between at least 30 minutes and 360 minutes prior to the administration or release of the MDAI HCl form disclosed herein, including those described in Table Ex12. In some embodiments, the serotonin receptor modulator is volinanserin and the psychedelic is MDAI HCl, wherein the volinanserin is administered to pretreat between at least 60 minutes and 240 minutes prior to the administration or release of the MDAI HCl form disclosed herein, including those described in Table Ex12. In some embodiments, the serotonin receptor modulator is volinanserin and the psychedelic is MDAI HCl, wherein the volinanserin is administered to pretreat at least 90 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 120 minutes prior to the MDAI HCl form disclosed herein, including those described in Table Ex12.

In some embodiments, the serotonin receptor modulator is volinanserin and the psychedelic is MDAI HCl, wherein the volinanserin is administered to pretreat at least 150 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat between about 15 minutes and about 150 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 180 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 210 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 240 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 270 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 300 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 330 minutes prior to the MDAI HCl form disclosed herein, including those described in Table Ex12. In some embodiments, the serotonin receptor modulator is volinanserin and the psychedelic is MDAI HCl, wherein the volinanserin is administered to pretreat at least 360 minutes prior to the MDAI HCl form disclosed herein, including those described in Table Ex12. In some preferred embodiments, the serotonin receptor modulator is volinanserin and the psychedelic is MDAI HCl, wherein volinanserin is administered to pretreat between about 60 minutes and about 180 minutes prior to the administration of the MDAI HCl form disclosed herein, including those described in Table Ex12.

In some embodiments, the serotonin receptor modulator is ketanserin and the psychedelic is MDAI HCl, wherein the ketanserin is administered to pretreat at least 15 minutes prior to the administration of the MDAI HCl form disclosed herein, including those described in Table Ex12. In some embodiments, the serotonin receptor modulator is ketanserin and the psychedelic is MDAI HCl, wherein the ketanserin is administered to pretreat between at least 30 minutes and 360 minutes prior to the administration or release of the MDAI HCl form disclosed herein, including those described in Table Ex12. In some embodiments, the serotonin receptor modulator is ketanserin and the psychedelic is MDAI HCl, wherein the ketanserin is administered to pretreat between at least 60 minutes and 240 minutes prior to the administration or release of the MDAI HCl form disclosed herein, including those described in Table Ex12. In some embodiments, the serotonin receptor modulator is ketanserin and the psychedelic is MDAI HCl, wherein the ketanserin is administered to pretreat at least 90 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 120 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 150 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat between about 15 minutes and about 150 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 180 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 210 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 240 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 270 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 300 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 330 minutes prior to the MDAI HCl form disclosed herein, including those described in Table Ex12. In some embodiments, the serotonin receptor modulator is ketanserin and the psychedelic is MDAI HCl, wherein the ketanserin is administered to pretreat at least 360 minutes prior to the MDAI HCl form disclosed herein, including those described in Table Ex12. In some preferred embodiments, the serotonin receptor modulator is ketanserin and the psychedelic is MDAI HCl, wherein ketanserin is administered to pretreat between about 60 minutes and about 180 minutes prior to the administration of the MDAI HCl form disclosed herein, including those described in Table Ex12.

In some embodiments, the serotonin receptor modulator is ritanserin and the psychedelic is MDAI HCl, wherein the ritanserin is administered to pretreat at least 15 minutes prior to the administration of the MDAI HCl form disclosed herein, including those described in Table Ex12. In some embodiments, the serotonin receptor modulator is ritanserin and the psychedelic is MDAI HCl, wherein the ritanserin is administered to pretreat at least 30 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat between at least 60 minutes and 240 minutes prior to the administration or release of the MDAI HCl form disclosed herein, including those described in Table Ex12. In some embodiments, the serotonin receptor modulator is ritanserin and the psychedelic is MDAI HCl, wherein the ritanserin is administered to pretreat at least 90 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 120 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 150 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat between about 15 minutes and about 150 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 180 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 210 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 240 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 270 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 300 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 330 minutes prior to the MDAI HCl form disclosed herein, including those described in Table Ex12. In some embodiments, the serotonin receptor modulator is ritanserin and the psychedelic is MDAI HCl, wherein the ritanserin is administered to pretreat at least 360 minutes prior to the MDAI HCl form disclosed herein, including those described in Table Ex12. In some preferred embodiments, the serotonin receptor modulator is ritanserin and the psychedelic is MDAI HCl, wherein ritanserin is administered to pretreat between about 60 minutes and about 180 minutes prior to the administration of the MDAI HCl form disclosed herein, including those described in Table Ex12.

In some embodiments, the serotonin receptor modulator is pimavanserin and the psychedelic is MDAI HCl, wherein the pimavanserin is administered to pretreat at least 15 minutes prior to the administration of the MDAI HCl form disclosed herein, including those described in Table Ex12. In some embodiments, the serotonin receptor modulator is pimavanserin and the psychedelic is MDAI HCl, wherein the pimavanserin is administered to pretreat at least 30 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat between at least 60 minutes and 240 minutes prior to the administration or release of the MDAI HCl form disclosed herein, including those described in Table Ex12. In some embodiments, the serotonin receptor modulator is pimavanserin and the psychedelic is MDAI HCl, wherein the pimavanserin is administered to pretreat at least 90 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 120 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 150 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat between about 15 minutes and about 150 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 180 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 210 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 240 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 270 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 300 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 330 minutes prior to the MDAI HCl form disclosed herein, including those described in Table Ex12. In some embodiments, the serotonin receptor modulator is pimavanserin and the psychedelic is MDAI HCl, wherein the pimavanserin is administered to pretreat at least 360 minutes prior to the MDAI HCl form disclosed herein, including those described in Table Ex12. In some preferred embodiments, the serotonin receptor modulator is pimavanserin and the psychedelic is MDAI HCl, wherein pimavanserin is administered to pretreat between about 60 minutes and about 180 minutes prior to the administration of the MDAI HCl form disclosed herein, including those described in Table Ex12.

In some embodiments, the serotonin receptor modulator is nelotanserin and the psychedelic is MDAI HCl, wherein the nelotanserin is administered to pretreat at least 15 minutes prior to the administration of the MDAI HCl form disclosed herein, including those described in Table Ex12. In some embodiments, the serotonin receptor modulator is nelotanserin and the psychedelic is MDAI HCl, wherein the nelotanserin is administered to pretreat at least 30 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat between at least 60 minutes and 240 minutes prior to the administration or release of the MDAI HCl form disclosed herein, including those described in Table Ex12. In some embodiments, the serotonin receptor modulator is nelotanserin and the psychedelic is MDAI HCl, wherein the nelotanserin is administered to pretreat at least 90 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat at least 120 minutes prior to the MDAI HCl form disclosed herein, including those described in Table Ex12.

In some embodiments, the serotonin receptor modulator is nelotanserin and the psychedelic is MDAI HCl, wherein the nelotanserin is administered to pretreat at least 150 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat between about 15 minutes and about 150 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat at least 180 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat at least 210 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat at least 240 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat at least 270 minutes prior to the MDAI HCl form disclosed herein, including those described in Table Ex12.

In some embodiments, the serotonin receptor modulator is nelotanserin and the psychedelic is MDAI HCl, wherein the nelotanserin is administered to pretreat at least 300 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat at least 330 minutes prior to the MDAI HCl form disclosed herein, including those described in Table Ex12. In some embodiments, the serotonin receptor modulator is nelotanserin and the psychedelic is MDAI HCl, wherein the nelotanserin is administered to pretreat at least 360 minutes prior to the MDAI HCl form disclosed herein, including those described in Table Ex12. In some preferred embodiments, the serotonin receptor modulator is nelotanserin and the psychedelic is MDAI HCl, wherein nelotanserin is administered to pretreat between about 60 minutes and about 180 minutes prior to the administration of the MDAI HCl form disclosed herein, including those described in Table Ex12.

In some embodiments, the serotonin receptor modulator is pruvanserin and the psychedelic is MDAI HCl, wherein the pruvanserin is administered to pretreat at least 15 minutes prior to the administration of the MDAI HCl form disclosed herein, including those described in Table Ex12. In some embodiments, the serotonin receptor modulator is pruvanserin and the psychedelic is MDAI HCl, wherein the pruvanserin is administered to pretreat at least 30 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat between at least 60 minutes and 240 minutes prior to the administration or release of the MDAI HCl form disclosed herein, including those described in Table Ex12. In some embodiments, the serotonin receptor modulator is pruvanserin and the psychedelic is MDAI HCl, wherein the pruvanserin is administered to pretreat at least 90 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 120 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 150 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat between about 15 minutes and about 150 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 180 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 210 minutes prior to the MDAI HCl form disclosed herein, including those described in Table Ex12.

In some embodiments, the serotonin receptor modulator is pruvanserin and the psychedelic is MDAI HCl, wherein the pruvanserin is administered to pretreat at least 240 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 270 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 300 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 330 minutes prior to the MDAI HCl form disclosed herein, including those described in Table Ex12. In some embodiments, the serotonin receptor modulator is pruvanserin and the psychedelic is MDAI HCl, wherein the pruvanserin is administered to pretreat at least 360 minutes prior to the MDAI HCl form disclosed herein, including those described in Table Ex12. In some preferred embodiments, the serotonin receptor modulator is pruvanserin and the psychedelic is MDAI HCl, wherein pruvanserin is administered to pretreat between about 60 minutes and about 180 minutes prior to the administration of the MDAI HCl form disclosed herein, including those described in Table Ex12.

In certain embodiments, such as those described above a MDAI HCl form disclosed herein, including those described in Table Ex12 is co-administered with a serotonin receptor modulator in the same or in separate compositions. In one embodiment, the serotonin receptor modulator is administered after the MDAI HCl form disclosed herein, including those described in Table Ex12. In one embodiment, the MDAI HCl form disclosed herein, including those described in Table Ex12 is administered in a modified release formulation such that the subject is effectively post-treated with serotonin receptor modulator post to release of an effective amount of the MDAI HCl. In some embodiments, the serotonin receptor modulator is part of a single fixed dose formulation that releases the MDAI HCl first followed by serotonin receptor modulator on two different release profiles. In another embodiment, the MDAI HCl form disclosed herein, including those described in Table Ex12 is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the MDAI HCl form disclosed herein, including those described in Table Ex12. This allows post-treatment to attenuate activation of the serotonin receptor by the MDAI HCl form disclosed herein, including those described in Table Ex12.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours after the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours after the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour after the release of the psychedelic.

In a preferred embodiment, the serotonin receptor modulator is administered at about 1 hour to about 3 hours after the administration of the psychedelic.

In some embodiments, the serotonin receptor modulator is eplivanserin and the psychedelic is MDAI HCl, wherein the eplivanserin is administered to post-treat at least 15 minutes after the administration of the MDAI HCl form disclosed herein, including those described in Table Ex12. In some embodiments, the serotonin receptor modulator is eplivanserin and the psychedelic is MDAI HCl, wherein the eplivanserin is administered to post-treat between at least 30 minutes after and 360 minutes after the release or administration of the MDAI HCl form disclosed herein, including those described in Table Ex12. In some embodiments, the serotonin receptor modulator is eplivanserin and the psychedelic is MDAI HCl, wherein the eplivanserin is administered to post-treat between at least 60 minutes after and 360 minutes after the release or administration of the MDAI HCl form disclosed herein, including those described in Table Ex12. In some embodiments, the serotonin receptor modulator is eplivanserin and the psychedelic is MDAI HCl, wherein the eplivanserin is administered to post-treat between at least 90 minutes and 240 minutes after the MDAI HCl form disclosed herein, including those described in Table Ex12. In some embodiments, the serotonin receptor modulator is eplivanserin and the psychedelic is MDAI HCl, wherein the eplivanserin is administered to post-treat at least 120 minutes after the MDAI HCl form disclosed herein, including those described in Table Ex12.

In some embodiments, the serotonin receptor modulator is eplivanserin and the psychedelic is MDAI HCl, wherein the eplivanserin is administered to post-treat at least 150 minutes after the MDAI HCl form disclosed herein, including those described in Table Ex12. In some embodiments, the serotonin receptor modulator is eplivanserin and the psychedelic is MDAI HCl, wherein the eplivanserin is administered to post-treat at least 180 minutes after the MDAI HCl form disclosed herein, including those described in Table Ex12. In some embodiments, the serotonin receptor modulator is eplivanserin and the psychedelic is MDAI HCl, wherein the eplivanserin is administered to post-treat at least 210 minutes after the MDAI HCl form disclosed herein, including those described in Table Ex12. In some embodiments, the serotonin receptor modulator is eplivanserin and the psychedelic is MDAI HCl, wherein the eplivanserin is administered to post-treat at least 240 minutes after the MDAI HCl form disclosed herein, including those described in Table Ex12.

In some embodiments, the serotonin receptor modulator is eplivanserin and the psychedelic is MDAI HCl, wherein the eplivanserin is administered to post-treat at least 270 minutes after the MDAI HCl form disclosed herein, including those described in Table Ex12. In some embodiments, the serotonin receptor modulator is eplivanserin and the psychedelic is MDAI HCl, wherein the eplivanserin is administered to post-treat at least 300 minutes after the MDAI HCl form disclosed herein, including those described in Table Ex12. In some embodiments, the serotonin receptor modulator is eplivanserin and the psychedelic is MDAI HCl, wherein the eplivanserin is administered to post-treat at least 330 minutes after the MDAI HCl form disclosed herein, including those described in Table Ex12. In some embodiments, the serotonin receptor modulator is eplivanserin and the psychedelic is MDAI HCl, wherein the eplivanserin is administered to post-treat at least 360 minutes after the MDAI HCl form disclosed herein, including those described in Table Ex12.

In some preferred embodiments, the serotonin receptor modulator is eplivanserin and the psychedelic is MDAI HCl, wherein eplivanserin is administered to post-treat between about 60 minutes and about 180 minutes after the administration of the MDAI HCl form disclosed herein, including those described in Table Ex12.

In some embodiments, the serotonin receptor modulator is volinanserin and the psychedelic is MDAI HCl, wherein the volinanserin is administered to post-treat a subject between at least 15 minutes and 360 minutes after the administration or release of the MDAI HCl form disclosed herein, including those described in Table Ex12. In some embodiments, the serotonin receptor modulator is volinanserin and the psychedelic is MDAI HCl, wherein the volinanserin is administered to post-treat between at least 30 minutes and 360 minutes after the administration or release of the MDAI HCl form disclosed herein, including those described in Table Ex12. In some embodiments, the serotonin receptor modulator is volinanserin and the psychedelic is MDAI HCl, wherein the volinanserin is administered to post-treat between at least 60 minutes and 240 minutes after the administration or release of the MDAI HCl form disclosed herein, including those described in Table Ex12. In some embodiments, the serotonin receptor modulator is volinanserin and the psychedelic is MDAI HCl, wherein the volinanserin is administered to post-treat at least 90 minutes after MDAI HCl. In some embodiments, the serotonin receptor modulator is volinanserin and the psychedelic is MDAI HCl, wherein the volinanserin is administered to post-treat at least 120 minutes after the MDAI HCl form disclosed herein, including those described in Table Ex12.

In some embodiments, the serotonin receptor modulator is volinanserin and the psychedelic is MDAI HCl, wherein the volinanserin is administered to post-treat at least 150 minutes after the MDAI HCl form disclosed herein, including those described in Table Ex12. In some embodiments, the serotonin receptor modulator is volinanserin and the psychedelic is MDAI HCl, wherein the volinanserin is administered to post-treat between about 15 minutes and about 150 minutes after the MDAI HCl form disclosed herein, including those described in Table Ex12. In some embodiments, the serotonin receptor modulator is volinanserin and the psychedelic is MDAI HCl, wherein the volinanserin is administered to post-treat at least 180 minutes after the MDAI HCl form disclosed herein, including those described in Table Ex12. In some embodiments, the serotonin receptor modulator is volinanserin and the psychedelic is MDAI HCl, wherein the volinanserin is administered to post-treat at least 210 minutes after the MDAI HCl form disclosed herein, including those described in Table Ex12. In some embodiments, the serotonin receptor modulator is volinanserin and the psychedelic is MDAI HCl, wherein the volinanserin is administered to post-treat at least 240 minutes after the MDAI HCl form disclosed herein, including those described in Table Ex12. In some embodiments, the serotonin receptor modulator is volinanserin and the psychedelic is MDAI HCl, wherein the volinanserin is administered to post-treat at least 270 minutes after the MDAI HCl form disclosed herein, including those described in Table Ex12. In some embodiments, the serotonin receptor modulator is volinanserin and the psychedelic is MDAI HCl, wherein the volinanserin is administered to post-treat at least 300 minutes after the MDAI HCl form disclosed herein, including those described in Table Ex12. In some embodiments, the serotonin receptor modulator is volinanserin and the psychedelic is MDAI HCl, wherein the volinanserin is administered to post-treat at least 330 minutes after the MDAI HCl form disclosed herein, including those described in Table Ex12. In some embodiments, the serotonin receptor modulator is volinanserin and the psychedelic is MDAI HCl, wherein the volinanserin is administered to post-treat at least 360 minutes after the MDAI HCl form disclosed herein, including those described in Table Ex12. In some preferred embodiments, the serotonin receptor modulator is volinanserin and the psychedelic is MDAI HCl, wherein volinanserin is administered to post-treat between about 60 minutes and about 180 minutes after the administration of the (R)-MDMA form.

In some embodiments, the serotonin receptor modulator is ketanserin and the psychedelic is MDAI HCl, wherein the ketanserin is administered to post-treat at least 15 minutes after the administration of the MDAI HCl form disclosed herein, including those described in Table Ex12. In some embodiments, the serotonin receptor modulator is ketanserin and the psychedelic is MDAI HCl, wherein the ketanserin is administered to post-treat between at least 30 minutes and 360 minutes after the administration or release of the MDAI HCl form disclosed herein, including those described in Table Ex12. In some embodiments, the serotonin receptor modulator is ketanserin and the psychedelic is MDAI HCl, wherein the ketanserin is administered to post-treat between at least 60 minutes and 240 minutes after the administration or release of the MDAI HCl form disclosed herein, including those described in Table Ex12. In some embodiments, the serotonin receptor modulator is ketanserin and the psychedelic is MDAI HCl, wherein the ketanserin is administered to post-treat at least 90 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 120 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 150 minutes after the MDAI HCl form disclosed herein, including those described in Table Ex12. In some embodiments, the serotonin receptor modulator is ketanserin and the psychedelic is MDAI HCl, wherein the ketanserin is administered to post-treat between about 15 minutes and about 150 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 180 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 210 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 240 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 270 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 300 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 330 minutes after the MDAI HCl form disclosed herein, including those described in Table Ex12. In some embodiments, the serotonin receptor modulator is ketanserin and the psychedelic is MDAI HCl, wherein the ketanserin is administered to post-treat at least 360 minutes after the MDAI HCl form disclosed herein, including those described in Table Ex12. In some preferred embodiments, the serotonin receptor modulator is ketanserin and the psychedelic is MDAI HCl, wherein ketanserin is administered to post-treat between about 60 minutes and about 180 minutes after the administration of the MDAI HCl form disclosed herein, including those described in Table Ex12.

In some embodiments, the serotonin receptor modulator is ritanserin and the psychedelic is MDAI HCl, wherein the ritanserin is administered to post-treat at least 15 minutes after the administration of the MDAI HCl form disclosed herein, including those described in Table Ex12. In some embodiments, the serotonin receptor modulator is ritanserin and the psychedelic is MDAI HCl, wherein the ritanserin is administered to post-treat at least 30 minutes after the MDAI HCl form disclosed herein, including those described in Table Ex12. In some embodiments, the serotonin receptor modulator is ritanserin and the psychedelic is MDAI HCl, wherein the ritanserin is administered to post-treat between at least 60 minutes and 240 minutes after the administration or release of the MDAI HCl form disclosed herein, including those described in Table Ex12. In some embodiments, the serotonin receptor modulator is ritanserin and the psychedelic is MDAI HCl, wherein the ritanserin is administered to post-treat at least 90 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 120 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 150 minutes after the MDAI HCl form disclosed herein, including those described in Table Ex12. In some embodiments, the serotonin receptor modulator is ritanserin and the psychedelic is MDAI HCl, wherein the ritanserin is administered to post-treat between about 15 minutes and about 150 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 180 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 210 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 240 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 270 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 300 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 330 minutes after the MDAI HCl form disclosed herein, including those described in Table Ex12. In some embodiments, the serotonin receptor modulator is ritanserin and the psychedelic is MDAI HCl, wherein the ritanserin is administered to post-treat at least 360 minutes after the MDAI HCl form disclosed herein, including those described in Table Ex12. In some preferred embodiments, the serotonin receptor modulator is ritanserin and the psychedelic is MDAI HCl, wherein ritanserin is administered to post-treat between about 60 minutes and about 180 minutes after the administration of the MDAI HCl form disclosed herein, including those described in Table Ex12.

In some embodiments, the serotonin receptor modulator is pimavanserin and the psychedelic is MDAI HCl, wherein the pimavanserin is administered to post-treat at least 15 minutes after the administration of the MDAI HCl form disclosed herein, including those described in Table Ex12. In some embodiments, the serotonin receptor modulator is pimavanserin and the psychedelic is MDAI HCl, wherein the pimavanserin is administered to post-treat at least 30 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat between at least 60 minutes and 240 minutes after the administration or release of the MDAI HCl form disclosed herein, including those described in Table Ex12. In some embodiments, the serotonin receptor modulator is pimavanserin and the psychedelic is MDAI HCl, wherein the pimavanserin is administered to post-treat at least 90 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 120 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 150 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat between about 15 minutes and about 150 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 180 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 210 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 240 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 270 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 300 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 330 minutes after the MDAI HCl form disclosed herein, including those described in Table Ex12. In some embodiments, the serotonin receptor modulator is pimavanserin and the psychedelic is MDAI HCl, wherein the pimavanserin is administered to post-treat at least 360 minutes after the MDAI HCl form disclosed herein, including those described in Table Ex12. In some preferred embodiments, the serotonin receptor modulator is pimavanserin and the psychedelic is MDAI HCl, wherein pimavanserin is administered to post-treat between about 60 minutes and about 180 minutes after the administration of the MDAI HCl form disclosed herein, including those described in Table Ex12.

In some embodiments, the serotonin receptor modulator is nelotanserin and the psychedelic is MDAI HCl, wherein the nelotanserin is administered to post-treat at least 15 minutes after the administration of the MDAI HCl form disclosed herein, including those described in Table Ex12. In some embodiments, the serotonin receptor modulator is nelotanserin and the psychedelic is MDAI HCl, wherein the nelotanserin is administered to post-treat at least 30 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat between at least 60 minutes and 240 minutes after the administration or release of the MDAI HCl form disclosed herein, including those described in Table Ex12. In some embodiments, the serotonin receptor modulator is nelotanserin and the psychedelic is MDAI HCl, wherein the nelotanserin is administered to post-treat at least 90 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat at least 120 minutes after the MDAI HCl form disclosed herein, including those described in Table Ex12.

In some embodiments, the serotonin receptor modulator is nelotanserin and the psychedelic is MDAI HCl, wherein the nelotanserin is administered to post-treat at least 150 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat between about 15 minutes and about 150 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat at least 180 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat at least 210 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat at least 240 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat at least 270 minutes after the MDAI HCl form disclosed herein, including those described in Table Ex12.

In some embodiments, the serotonin receptor modulator is nelotanserin and the psychedelic is MDAI HCl, wherein the nelotanserin is administered to post-treat at least 300 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat at least 330 minutes after the MDAI HCl form disclosed herein, including those described in Table Ex12. In some embodiments, the serotonin receptor modulator is nelotanserin and the psychedelic is MDAI HCl, wherein the nelotanserin is administered to post-treat at least 360 minutes after the MDAI HCl form disclosed herein, including those described in Table Ex12. In some preferred embodiments, the serotonin receptor modulator is nelotanserin and the psychedelic is MDAI HCl, wherein nelotanserin is administered to post-treat between about 60 minutes and about 180 minutes after the administration of the MDAI HCl form disclosed herein, including those described in Table Ex12.

In some embodiments, the serotonin receptor modulator is pruvanserin and the psychedelic is MDAI HCl, wherein the pruvanserin is administered to post-treat at least 15 minutes after the administration of the MDAI HCl form disclosed herein, including those described in Table Ex12. In some embodiments, the serotonin receptor modulator is pruvanserin and the psychedelic is MDAI HCl, wherein the pruvanserin is administered to post-treat at least 30 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat between at least 60 minutes and 240 minutes after the administration or release of the MDAI HCl form disclosed herein, including those described in Table Ex12. In some embodiments, the serotonin receptor modulator is pruvanserin and the psychedelic is MDAI HCl, wherein the pruvanserin is administered to post-treat at least 90 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 120 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 150 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat between about 15 minutes and about 150 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 180 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 210 minutes after the MDAI HCl form disclosed herein, including those described in Table Ex12.

In some embodiments, the serotonin receptor modulator is pruvanserin and the psychedelic is MDAI HCl, wherein the pruvanserin is administered to post-treat at least 240 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 270 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 300 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 330 minutes after the MDAI HCl form disclosed herein, including those described in Table Ex12. In some embodiments, the serotonin receptor modulator is pruvanserin and the psychedelic is MDAI HCl, wherein the pruvanserin is administered to post-treat at least 360 minutes after the MDAI HCl form disclosed herein, including those described in Table Ex12. In some preferred embodiments, the serotonin receptor modulator is pruvanserin and the psychedelic is MDAI HCl, wherein pruvanserin is administered to post-treat between about 60 minutes and about 180 minutes after the administration of the MDAI HCl form disclosed herein, including those described in Table Ex12.

In some embodiments, the serotonin receptor modulator is flibanserin, wherein the flibanserin is administered to post-treat at least 15 minutes post to the administration of the MDAI HCl form disclosed herein, including those described in Table Ex12. In some embodiments, the serotonin receptor modulator is flibanserin, wherein the flibanserin is administered to post-treat at least 30 minutes post to the MDAI HCl form disclosed herein, including those described in Table Ex12. In some embodiments, the serotonin receptor modulator is flibanserin, wherein the flibanserin is administered to post-treat between at least 60 minutes and 240 minutes post to the administration or release of the MDAI HCl form disclosed herein, including those described in Table Ex12. In some embodiments, the serotonin receptor modulator is flibanserin, wherein the flibanserin is administered to post-treat at least 90 minutes post to the MDAI HCl form disclosed herein, including those described in Table Ex12. In some embodiments, the serotonin receptor modulator is flibanserin, wherein the flibanserin is administered to post-treat at least 120 minutes post to the MDAI HCl form disclosed herein, including those described in Table Ex12. In some embodiments, the serotonin receptor modulator is flibanserin, wherein the flibanserin is administered to post-treat at least 150 minutes post to the MDAI HCl form disclosed herein, including those described in Table Ex12. In some embodiments, the serotonin receptor modulator is flibanserin, wherein the flibanserin is administered to post-treat between about 15 minutes and about 150 minutes post to the MDAI HCl form disclosed herein, including those described in Table Ex12. In some embodiments, the serotonin receptor modulator is flibanserin, wherein the flibanserin is administered to post-treat at least 180 minutes post to the MDAI HCl form disclosed herein, including those described in Table Ex12. In some embodiments, the serotonin receptor modulator is flibanserin, wherein the flibanserin is administered to post-treat at least 210 minutes post to the MDAI HCl form disclosed herein, including those described in Table Ex12.

In some embodiments, the serotonin receptor modulator is flibanserin, wherein the flibanserin is administered to post-treat at least 240 minutes post to the MDAI HCl form disclosed herein, including those described in Table Ex12. In some embodiments, the serotonin receptor modulator is flibanserin, wherein the flibanserin is administered to post-treat at least 270 minutes post to the MDAI HCl form disclosed herein, including those described in Table Ex12. In some embodiments, the serotonin receptor modulator is flibanserin, wherein the flibanserin is administered to post-treat at least 300 minutes post to the MDAI HCl form disclosed herein, including those described in Table Ex12. In some embodiments, the serotonin receptor modulator is flibanserin, wherein the flibanserin is administered to post-treat at least 330 minutes post to the MDAI HCl form disclosed herein, including those described in Table Ex12. In some embodiments, the serotonin receptor modulator is flibanserin, wherein the flibanserin is administered to post-treat at least 360 minutes post to the MDAI HCl form disclosed herein, including those described in Table Ex12. In some preferred embodiments, the serotonin receptor modulator is flibanserin, wherein flibanserin is administered to post-treat between about 60 minutes and about 180 minutes post to the administration of the MDAI HCl form disclosed herein, including those described in Table Ex12.

In some embodiments, the serotonin receptor modulator is olanzapine, wherein the olanzapine is administered to post-treat at least 15 minutes post to the administration of the MDAI HCl form disclosed herein, including those described in Table Ex12. In some embodiments, the serotonin receptor modulator is olanzapine, wherein the olanzapine is administered to post-treat at least 30 minutes post to the MDAI HCl form disclosed herein, including those described in Table Ex12. In some embodiments, the serotonin receptor modulator is olanzapine, wherein the olanzapine is administered to post-treat between at least 60 minutes and 240 minutes post to the administration or release of the MDAI HCl form disclosed herein, including those described in Table Ex12. In some embodiments, the serotonin receptor modulator is olanzapine, wherein the olanzapine is administered to post-treat at least 90 minutes post to the MDAI HCl form disclosed herein, including those described in Table Ex12. In some embodiments, the serotonin receptor modulator is olanzapine, wherein the olanzapine is administered to post-treat at least 120 minutes post to the MDAI HCl form disclosed herein, including those described in Table Ex12. In some embodiments, the serotonin receptor modulator is olanzapine, wherein the olanzapine is administered to post-treat at least 150 minutes post to the MDAI HCl form disclosed herein, including those described in Table Ex12. In some embodiments, the serotonin receptor modulator is olanzapine, wherein the olanzapine is administered to post-treat between about 15 minutes and about 150 minutes post to the MDAI HCl form disclosed herein, including those described in Table Ex12. In some embodiments, the serotonin receptor modulator is olanzapine, wherein the olanzapine is administered to post-treat at least 180 minutes post to the MDAI HCl form disclosed herein, including those described in Table Ex12. In some embodiments, the serotonin receptor modulator is olanzapine, wherein the olanzapine is administered to post-treat at least 210 minutes post to the MDAI HCl form disclosed herein, including those described in Table Ex12.

In some embodiments, the serotonin receptor modulator is olanzapine, wherein the olanzapine is administered to post-treat at least 240 minutes post to the MDAI HCl form disclosed herein, including those described in Table Ex12. In some embodiments, the serotonin receptor modulator is olanzapine, wherein the olanzapine is administered to post-treat at least 270 minutes post to the MDAI HCl form disclosed herein, including those described in Table Ex12. In some embodiments, the serotonin receptor modulator is olanzapine, wherein the olanzapine is administered to post-treat at least 300 minutes post to the MDAI HCl form disclosed herein, including those described in Table Ex12. In some embodiments, the serotonin receptor modulator is olanzapine, wherein the olanzapine is administered to post-treat at least 330 minutes post to the MDAI HCl form disclosed herein, including those described in Table Ex12. In some embodiments, the serotonin receptor modulator is olanzapine, wherein the olanzapine is administered to post-treat at least 360 minutes post to the MDAI HCl form disclosed herein, including those described in Table Ex12. In some preferred embodiments, the serotonin receptor modulator is olanzapine, wherein olanzapine is administered to post-treat between about 60 minutes and about 180 minutes post to the administration of the MDAI HCl form disclosed herein, including those described in Table Ex12.

In some embodiments, the serotonin receptor modulator is quetiapine, wherein the quetiapine is administered to post-treat at least 15 minutes post to the administration of the MDAI HCl form disclosed herein, including those described in Table Ex12. In some embodiments, the serotonin receptor modulator is quetiapine, wherein the quetiapine is administered to post-treat at least 30 minutes post to the MDAI HCl form disclosed herein, including those described in Table Ex12. In some embodiments, the serotonin receptor modulator is quetiapine, wherein the quetiapine is administered to post-treat between at least 60 minutes and 240 minutes post to the administration or release of the MDAI HCl form disclosed herein, including those described in Table Ex12. In some embodiments, the serotonin receptor modulator is quetiapine, wherein the quetiapine is administered to post-treat at least 90 minutes post to the MDAI HCl form disclosed herein, including those described in Table Ex12. In some embodiments, the serotonin receptor modulator is quetiapine, wherein the quetiapine is administered to post-treat at least 120 minutes post to the MDAI HCl form disclosed herein, including those described in Table Ex12. In some embodiments, the serotonin receptor modulator is quetiapine, wherein the quetiapine is administered to post-treat at least 150 minutes post to the MDAI HCl form disclosed herein, including those described in Table Ex12. In some embodiments, the serotonin receptor modulator is quetiapine, wherein the quetiapine is administered to post-treat between about 15 minutes and about 150 minutes post to the MDAI HCl form disclosed herein, including those described in Table Ex12. In some embodiments, the serotonin receptor modulator is quetiapine, wherein the quetiapine is administered to post-treat at least 180 minutes post to the MDAI HCl form disclosed herein, including those described in Table Ex12. In some embodiments, the serotonin receptor modulator is quetiapine, wherein the quetiapine is administered to post-treat at least 210 minutes post to the MDAI HCl form disclosed herein, including those described in Table Ex12.

In some embodiments, the serotonin receptor modulator is quetiapine, wherein the quetiapine is administered to post-treat at least 240 minutes post to the MDAI HCl form disclosed herein, including those described in Table Ex12. In some embodiments, the serotonin receptor modulator is quetiapine, wherein the quetiapine is administered to post-treat at least 270 minutes post to the MDAI HCl form disclosed herein, including those described in Table Ex12. In some embodiments, the serotonin receptor modulator is quetiapine, wherein the quetiapine is administered to post-treat at least 300 minutes post to the MDAI HCl form disclosed herein, including those described in Table Ex12. In some embodiments, the serotonin receptor modulator is quetiapine, wherein the quetiapine is administered to post-treat at least 330 minutes post to the MDAI HCl form disclosed herein, including those described in Table Ex12. In some embodiments, the serotonin receptor modulator is quetiapine, wherein the quetiapine is administered to post-treat at least 360 minutes post to the MDAI HCl form disclosed herein, including those described in Table Ex12. In some preferred embodiments, the serotonin receptor modulator is quetiapine, wherein quetiapine is administered to post-treat between about 60 minutes and about 180 minutes post to the administration of the MDAI HCl form disclosed herein, including those described in Table Ex12.

In some embodiments, the serotonin receptor modulator is risperidone, wherein the risperidone is administered to post-treat at least 15 minutes post to the administration of the MDAI HCl form disclosed herein, including those described in Table Ex12. In some embodiments, the serotonin receptor modulator is risperidone, wherein the risperidone is administered to post-treat at least 30 minutes post to the MDAI HCl form disclosed herein, including those described in Table Ex12. In some embodiments, the serotonin receptor modulator is risperidone, wherein the risperidone is administered to post-treat between at least 60 minutes and 240 minutes post to the administration or release of the MDAI HCl form disclosed herein, including those described in Table Ex12. In some embodiments, the serotonin receptor modulator is risperidone, wherein the risperidone is administered to post-treat at least 90 minutes post to the MDAI HCl form disclosed herein, including those described in Table Ex12. In some embodiments, the serotonin receptor modulator is risperidone, wherein the risperidone is administered to post-treat at least 120 minutes post to the MDAI HCl form disclosed herein, including those described in Table Ex12. In some embodiments, the serotonin receptor modulator is risperidone, wherein the risperidone is administered to post-treat at least 150 minutes post to the MDAI HCl form disclosed herein, including those described in Table Ex12. In some embodiments, the serotonin receptor modulator is risperidone, wherein the risperidone is administered to post-treat between about 15 minutes and about 150 minutes post to the MDAI HCl form disclosed herein, including those described in Table Ex12. In some embodiments, the serotonin receptor modulator is risperidone, wherein the risperidone is administered to post-treat at least 180 minutes post to the MDAI HCl form disclosed herein, including those described in Table Ex12. In some embodiments, the serotonin receptor modulator is risperidone, wherein the risperidone is administered to post-treat at least 210 minutes post to the MDAI HCl form disclosed herein, including those described in Table Ex12.

In some embodiments, the serotonin receptor modulator is risperidone, wherein the risperidone is administered to post-treat at least 240 minutes post to the MDAI HCl form disclosed herein, including those described in Table Ex12. In some embodiments, the serotonin receptor modulator is risperidone, wherein the risperidone is administered to post-treat at least 270 minutes post to the MDAI HCl form disclosed herein, including those described in Table Ex12. In some embodiments, the serotonin receptor modulator is risperidone, wherein the risperidone is administered to post-treat at least 300 minutes post to the MDAI HCl form disclosed herein, including those described in Table Ex12. In some embodiments, the serotonin receptor modulator is risperidone, wherein the risperidone is administered to post-treat at least 330 minutes post to the MDAI HCl form disclosed herein, including those described in Table Ex12. In some embodiments, the serotonin receptor modulator is risperidone, wherein the risperidone is administered to post-treat at least 360 minutes post to the MDAI HCl form disclosed herein, including those described in Table Ex12. In some preferred embodiments, the serotonin receptor modulator is risperidone, wherein risperidone is administered to post-treat between about 60 minutes and about 180 minutes post to the administration of the MDAI HCl form disclosed herein, including those described in Table Ex12.

In some embodiments, the serotonin receptor modulator for use with the 5,6-dimethoxy-2-aminoindane hydrochloride forms disclosed herein, including those described in Table Ex15 is eplivanserin, wherein the eplivanserin is administered in about 1 mg to about 40 mg, or about 5 mg to about 10 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5,6-dimethoxy-2-aminoindane hydrochloride forms disclosed herein, including those described in Table Ex15 is volinanserin, wherein the volinanserin is administered in about 1 mg to about 60 mg, or about 5 mg to about 20 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg. In some embodiments, the serotonin receptor modulator for use with the 5,6-dimethoxy-2-aminoindane hydrochloride forms disclosed herein, including those described in Table Ex15 is ketanserin, wherein the ketanserin is administered in about 10 mg to about 80 mg, about 30 mg to about 50 mg, or about 40 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg. In some embodiments, the serotonin receptor modulator for use with the 5,6-dimethoxy-2-aminoindane hydrochloride forms disclosed herein, including those described in Table Ex15 is ritanserin, wherein the ritanserin is administered in about 1 mg to about 40 mg, or about 2.5 mg to about 10 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg. In some embodiments, the serotonin receptor modulator for use with the 5,6-dimethoxy-2-aminoindane hydrochloride forms disclosed herein, including those described in Table Ex15 is pimavanserin, wherein the pimavanserin is administered in about 1 mg to about 60 mg, or about 17 mg to about 34 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg. In some embodiments, the serotonin receptor modulator for use with the 5,6-dimethoxy-2-aminoindane hydrochloride forms disclosed herein, including those described in Table Ex15 is nelotanserin, wherein the nelotanserin is administered in about 1 mg to about 80 mg, or about 40 mg to about 80 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg. In some embodiments, the serotonin receptor modulator for use with the 5,6-dimethoxy-2-aminoindane hydrochloride forms disclosed herein, including those described in Table Ex15 is pruvanserin, wherein the pruvanserin is administered in about 1 mg to about 40 mg, or about 3 mg to about 10 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg. In some embodiments, the serotonin receptor modulator for use with the 5,6-dimethoxy-2-aminoindane hydrochloride forms disclosed herein, including those described in Table Ex15 is flibanserin, wherein the flibanserin is administered in about 10 mg to about 200 mg, or about 80 mg to about 120 mg, or about 100 mg and 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg. In some embodiments, the serotonin receptor modulator for use with the 5,6-dimethoxy-2-aminoindane hydrochloride forms disclosed herein, including those described in Table Ex15 is olanzapine, wherein the olanzapine is administered in about 2.5 mg to about 30 mg, or about 5 mg or about 10 mg, or about 20 mg or about 25 mg, and the 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5,6-dimethoxy-2-aminoindane hydrochloride solid forms disclosed herein, including those described in Table Ex15 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5,6-dimethoxy-2-aminoindane hydrochloride solid forms disclosed herein, including those described in Table Ex15 is quetiapine, wherein the quetiapine is administered in about 25 mg to about 800 mg, or about 50 mg to about 100 mg, or about 150 mg or about 200 mg or about 250 mg or about 300 mg, and the 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5,6-dimethoxy-2-aminoindane hydrochloride solid forms disclosed herein, including those described in Table Ex15 is an extended-release of quetiapine, wherein the extended-release of quetiapine is administered in about 50 mg to about 300 mg, or about 50 mg or about 100 mg or about 200 mg, or about 300 mg, and the 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5,6-dimethoxy-2-aminoindane hydrochloride solid forms disclosed herein, including those described in Table Ex15 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5,6-dimethoxy-2-aminoindane hydrochloride solid forms disclosed herein, including those described in Table Ex15 is an extended-release of risperidone including (RISPERDAL CONSTA), wherein the extended-release of risperidone is administered in about 12.5 mg, or about 25 mg, or about 37.5 mg, or about 50 mg, and the 5,6-dimethoxy-2-aminoindane hydrochloride forms disclosed herein, including those described in Table Ex15 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In certain embodiments, such as those described above a 5,6-dimethoxy-2-aminoindane hydrochloride form disclosed herein, including those described in Table Ex15 is co-administered with a serotonin receptor modulator in the same or in separate compositions. In one embodiment, the serotonin receptor modulator is administered prior to the 5,6-dimethoxy-2-aminoindane hydrochloride form disclosed herein, including those described in Table Ex15. In one embodiment, the 5,6-dimethoxy-2-aminoindane hydrochloride form disclosed herein, including those described in Table Ex15 is administered in a modified release formulation such that the subject is effectively pretreated with serotonin receptor modulator prior to release of an effective amount of 5,6-dimethoxy-2-aminoindane hydrochloride. In some embodiments the serotonin receptor modulator is part of a single fixed dose formulation that releases serotonin receptor modulator first followed by 5,6-dimethoxy-2-aminoindane hydrochloride on two different release profiles. In another embodiment the serotonin receptor modulator is administered first as a single dosage and after a length of time, the 5,6-dimethoxy-2-aminoindane hydrochloride form disclosed herein, including those described in Table Ex15 is administered as a second dosage separate from the first dosage. Thus, in some embodiments, the serotonin receptor modulator is administered or released from a composition provided herein prior to the administration and/or release of the 5,6-dimethoxy-2-aminoindane hydrochloride form disclosed herein, including those described in Table Ex15. This allows pretreatment to attenuate activation of the serotonin receptor by the 5,6-dimethoxy-2-aminoindane hydrochloride form disclosed herein, including those described in Table Ex15.

In some embodiments, the serotonin receptor modulator is eplivanserin and the psychedelic is 5,6-dimethoxy-2-aminoindane hydrochloride, wherein the eplivanserin is administered to pretreat at least 15 minutes prior to the administration of the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat between at least 30 minutes prior and 360 minutes prior to the release or administration of the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat between at least 60 minutes prior and 360 minutes prior to the release or administration of the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat between at least 90 minutes and 240 minutes prior to the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat at least 120 minutes prior to the 5,6-dimethoxy-2-aminoindane hydrochloride form disclosed herein, including those described in Table Ex15.

In some embodiments, the serotonin receptor modulator is eplivanserin and the psychedelic is 5,6-dimethoxy-2-aminoindane hydrochloride, wherein the eplivanserin is administered to pretreat at least 150 minutes prior to the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat at least 180 minutes prior to the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat at least 210 minutes prior to the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat at least 240 minutes prior to the 5,6-dimethoxy-2-aminoindane hydrochloride form disclosed herein, including those described in Table Ex15.

In some embodiments, the serotonin receptor modulator is eplivanserin and the psychedelic is 5,6-dimethoxy-2-aminoindane hydrochloride, wherein the eplivanserin is administered to pretreat at least 270 minutes prior to the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat at least 300 minutes prior to the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat at least 330 minutes prior to the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to pretreat at least 360 minutes prior to the 5,6-dimethoxy-2-aminoindane hydrochloride form disclosed herein, including those described in Table Ex15.

In some preferred embodiments, the serotonin receptor modulator is eplivanserin and the psychedelic is 5,6-dimethoxy-2-aminoindane hydrochloride, wherein eplivanserin is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is volinanserin and the psychedelic is 5,6-dimethoxy-2-aminoindane hydrochloride, wherein the volinanserin is administered to pretreat a subject between at least 15 minutes and 360 minutes prior to the administration or release of the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat between at least 30 minutes and 360 minutes prior to the administration or release of the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 90 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 120 minutes prior to the 5,6-dimethoxy-2-aminoindane hydrochloride form disclosed herein, including those described in Table Ex15.

In some embodiments, the serotonin receptor modulator is volinanserin and the psychedelic is 5,6-dimethoxy-2-aminoindane hydrochloride, wherein the volinanserin is administered to pretreat at least 150 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 180 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 210 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 240 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 270 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 300 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 330 minutes prior to the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to pretreat at least 360 minutes prior to the 5,6-dimethoxy-2-aminoindane hydrochloride form disclosed herein, including those described in Table Ex15. In some preferred embodiments, the serotonin receptor modulator is volinanserin and the psychedelic is 5,6-dimethoxy-2-aminoindane hydrochloride, wherein volinanserin is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is ketanserin and the psychedelic is 5,6-dimethoxy-2-aminoindane hydrochloride, wherein the ketanserin is administered to pretreat at least 15 minutes prior to the administration of the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat between at least 30 minutes and 360 minutes prior to the administration or release of the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 90 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 120 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 150 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 180 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 210 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 240 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 270 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 300 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 330 minutes prior to the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to pretreat at least 360 minutes prior to the 5,6-dimethoxy-2-aminoindane hydrochloride form disclosed herein, including those described in Table Ex15. In some preferred embodiments, the serotonin receptor modulator is ketanserin and the psychedelic is 5,6-dimethoxy-2-aminoindane hydrochloride, wherein ketanserin is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is ritanserin and the psychedelic is 5,6-dimethoxy-2-aminoindane hydrochloride, wherein the ritanserin is administered to pretreat at least 15 minutes prior to the administration of the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 30 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 90 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 120 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 150 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 180 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 210 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 240 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 270 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 300 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 330 minutes prior to the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to pretreat at least 360 minutes prior to the 5,6-dimethoxy-2-aminoindane hydrochloride form disclosed herein, including those described in Table Ex15. In some preferred embodiments, the serotonin receptor modulator is ritanserin and the psychedelic is 5,6-dimethoxy-2-aminoindane hydrochloride, wherein ritanserin is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is pimavanserin and the psychedelic is 5,6-dimethoxy-2-aminoindane hydrochloride, wherein the pimavanserin is administered to pretreat at least 15 minutes prior to the administration of the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 30 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 90 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 120 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 150 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 180 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 210 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 240 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 270 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 300 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 330 minutes prior to the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to pretreat at least 360 minutes prior to the 5,6-dimethoxy-2-aminoindane hydrochloride form disclosed herein, including those described in Table Ex15. In some preferred embodiments, the serotonin receptor modulator is pimavanserin and the psychedelic is 5,6-dimethoxy-2-aminoindane hydrochloride, wherein pimavanserin is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is nelotanserin and the psychedelic is 5,6-dimethoxy-2-aminoindane hydrochloride, wherein the nelotanserin is administered to pretreat at least 15 minutes prior to the administration of the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 30 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 90 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 120 minutes prior to the 5,6-dimethoxy-2-aminoindane hydrochloride form disclosed herein, including those described in Table Ex15.

In some embodiments, the serotonin receptor modulator is nelotanserin and the psychedelic is 5,6-dimethoxy-2-aminoindane hydrochloride, wherein the nelotanserin is administered to pretreat at least 150 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 180 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 210 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 240 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 270 minutes prior to the 5,6-dimethoxy-2-aminoindane hydrochloride form disclosed herein, including those described in Table Ex15.

In some embodiments, the serotonin receptor modulator is nelotanserin and the psychedelic is 5,6-dimethoxy-2-aminoindane hydrochloride, wherein the nelotanserin is administered to pretreat at least 300 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 330 minutes prior to the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to pretreat at least 360 minutes prior to the 5,6-dimethoxy-2-aminoindane hydrochloride form disclosed herein, including those described in Table Ex15. In some preferred embodiments, the serotonin receptor modulator is nelotanserin and the psychedelic is 5,6-dimethoxy-2-aminoindane hydrochloride, wherein nelotanserin is administered to pretreat between about 60 minutes and about 180 minutes prior to the administration of the 5,6-dimethoxy-2-aminoindane hydrochloride form disclosed herein, including those described in Table Ex15.

In some embodiments, the serotonin receptor modulator is pruvanserin and the psychedelic is 5,6-dimethoxy-2-aminoindane hydrochloride, wherein the pruvanserin is administered to pretreat at least 15 minutes prior to the administration of the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 30 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat between at least 60 minutes and 240 minutes prior to the administration or release of the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 90 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 120 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 150 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat between about 15 minutes and about 150 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 180 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 210 minutes prior to the 5,6-dimethoxy-2-aminoindane hydrochloride form disclosed herein, including those described in Table Ex15.

In some embodiments, the serotonin receptor modulator is pruvanserin and the psychedelic is 5,6-dimethoxy-2-aminoindane hydrochloride, wherein the pruvanserin is administered to pretreat at least 240 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 270 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 300 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 330 minutes prior to the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to pretreat at least 360 minutes prior to the 5,6-dimethoxy-2-aminoindane hydrochloride form disclosed herein, including those described in Table Ex15. In some preferred embodiments, the serotonin receptor modulator is pruvanserin and the psychedelic is 5,6-dimethoxy-2-aminoindane hydrochloride, wherein pruvanserin is administered to pretreat between about 60 minutes and about 180 minutes prior to the administration of the 5,6-dimethoxy-2-aminoindane hydrochloride form disclosed herein, including those described in Table Ex15.

In certain embodiments, such as those described above a 5,6-dimethoxy-2-aminoindane hydrochloride form disclosed herein, including those described in Table Ex15 is co-administered with a serotonin receptor modulator in the same or in separate compositions. In one embodiment, the serotonin receptor modulator is administered after the 5,6-dimethoxy-2-aminoindane hydrochloride form disclosed herein, including those described in Table Ex15. In one embodiment, the 5,6-dimethoxy-2-aminoindane hydrochloride form disclosed herein, including those described in Table Ex15 is administered in a modified release formulation such that the subject is effectively post-treated with serotonin receptor modulator post to release of an effective amount of the 5,6-dimethoxy-2-aminoindane hydrochloride. In some embodiments, the serotonin receptor modulator is part of a single fixed dose formulation that releases the 5,6-dimethoxy-2-aminoindane hydrochloride first followed by serotonin receptor modulator on two different release profiles. In another embodiment, the 5,6-dimethoxy-2-aminoindane hydrochloride form disclosed herein, including those described in Table Ex15 is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the 5,6-dimethoxy-2-aminoindane hydrochloride form disclosed herein, including those described in Table Ex15. This allows post-treatment to attenuate activation of the serotonin receptor by the 5,6-dimethoxy-2-aminoindane hydrochloride form disclosed herein, including those described in Table Ex15.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours after the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours after the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour after the release of the psychedelic.

In a preferred embodiment, the serotonin receptor modulator is administered at about 1 hour to about 3 hours after the administration of the psychedelic.

In some embodiments, the serotonin receptor modulator is eplivanserin and the psychedelic is 5,6-dimethoxy-2-aminoindane hydrochloride, wherein the eplivanserin is administered to post-treat at least 15 minutes after the administration of the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat between at least 30 minutes after and 360 minutes after the release or administration of the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat between at least 60 minutes after and 360 minutes after the release or administration of the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat between at least 90 minutes and 240 minutes after the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat at least 120 minutes after the 5,6-dimethoxy-2-aminoindane hydrochloride form disclosed herein, including those described in Table Ex15.

In some embodiments, the serotonin receptor modulator is eplivanserin and the psychedelic is 5,6-dimethoxy-2-aminoindane hydrochloride, wherein the eplivanserin is administered to post-treat at least 150 minutes after the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat at least 180 minutes after the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat at least 210 minutes after the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat at least 240 minutes after the 5,6-dimethoxy-2-aminoindane hydrochloride form disclosed herein, including those described in Table Ex15.

In some embodiments, the serotonin receptor modulator is eplivanserin and the psychedelic is 5,6-dimethoxy-2-aminoindane hydrochloride, wherein the eplivanserin is administered to post-treat at least 270 minutes after the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat at least 300 minutes after the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat at least 330 minutes after the 5,6-dimethoxy-2-aminoindane hydrochloride form disclosed herein, including those described in Table Ex15. In some embodiments, the serotonin receptor modulator is eplivanserin and the psychedelic is 5,6-dimethoxy-2-aminoindane hydrochloride, wherein the eplivanserin is administered to post-treat at least 360 minutes after the 5,6-dimethoxy-2-aminoindane hydrochloride form disclosed herein, including those described in Table Ex15.

In some preferred embodiments, the serotonin receptor modulator is eplivanserin and the psychedelic is 5,6-dimethoxy-2-aminoindane hydrochloride, wherein eplivanserin is administered to post-treat between about 60 minutes and about 180 minutes after the administration of the 5,6-dimethoxy-2-aminoindane hydrochloride form disclosed herein, including those described in Table Ex15.

In some embodiments, the serotonin receptor modulator is volinanserin and the psychedelic is 5,6-dimethoxy-2-aminoindane hydrochloride, wherein the volinanserin is administered to post-treat a subject between at least 15 minutes and 360 minutes after the administration or release of the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat between at least 30 minutes and 360 minutes after the administration or release of the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat between at least 60 minutes and 240 minutes after the administration or release of the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 90 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 120 minutes after the 5,6-dimethoxy-2-aminoindane hydrochloride form disclosed herein, including those described in Table Ex15.

In some embodiments, the serotonin receptor modulator is volinanserin and the psychedelic is 5,6-dimethoxy-2-aminoindane hydrochloride, wherein the volinanserin is administered to post-treat at least 150 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat between about 15 minutes and about 150 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 180 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 210 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 240 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 270 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 300 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 330 minutes after the 5,6-dimethoxy-2-aminoindane hydrochloride form disclosed herein, including those described in Table Ex15. In some embodiments, the serotonin receptor modulator is volinanserin and the psychedelic is 5,6-dimethoxy-2-aminoindane hydrochloride, wherein the volinanserin is administered to post-treat at least 360 minutes after the 5,6-dimethoxy-2-aminoindane hydrochloride form disclosed herein, including those described in Table Ex15. In some preferred embodiments, the serotonin receptor modulator is volinanserin and the psychedelic is 5,6-dimethoxy-2-aminoindane hydrochloride, wherein volinanserin is administered to post-treat between about 60 minutes and about 180 minutes after the administration of the (R)-MDMA form.

In some embodiments, the serotonin receptor modulator is ketanserin and the psychedelic is 5,6-dimethoxy-2-aminoindane hydrochloride, wherein the ketanserin is administered to post-treat at least 15 minutes after the administration of the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat between at least 30 minutes and 360 minutes after the administration or release of the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat between at least 60 minutes and 240 minutes after the administration or release of the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 90 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 120 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 150 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat between about 15 minutes and about 150 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 180 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 210 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 240 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 270 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 300 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 330 minutes after the 5,6-dimethoxy-2-aminoindane hydrochloride form disclosed herein, including those described in Table Ex15. In some embodiments, the serotonin receptor modulator is ketanserin and the psychedelic is 5,6-dimethoxy-2-aminoindane hydrochloride, wherein the ketanserin is administered to post-treat at least 360 minutes after the 5,6-dimethoxy-2-aminoindane hydrochloride form disclosed herein, including those described in Table Ex15. In some preferred embodiments, the serotonin receptor modulator is ketanserin and the psychedelic is 5,6-dimethoxy-2-aminoindane hydrochloride, wherein ketanserin is administered to post-treat between about 60 minutes and about 180 minutes after the administration of the 5,6-dimethoxy-2-aminoindane hydrochloride form disclosed herein, including those described in Table Ex15.

In some embodiments, the serotonin receptor modulator is ritanserin and the psychedelic is 5,6-dimethoxy-2-aminoindane hydrochloride, wherein the ritanserin is administered to post-treat at least 15 minutes after the administration of the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 30 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat between at least 60 minutes and 240 minutes after the administration or release of the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 90 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 120 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 150 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat between about 15 minutes and about 150 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 180 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 210 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 240 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 270 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 300 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 330 minutes after the 5,6-dimethoxy-2-aminoindane hydrochloride form disclosed herein, including those described in Table Ex15. In some embodiments, the serotonin receptor modulator is ritanserin and the psychedelic is 5,6-dimethoxy-2-aminoindane hydrochloride, wherein the ritanserin is administered to post-treat at least 360 minutes after the 5,6-dimethoxy-2-aminoindane hydrochloride form disclosed herein, including those described in Table Ex15. In some preferred embodiments, the serotonin receptor modulator is ritanserin and the psychedelic is 5,6-dimethoxy-2-aminoindane hydrochloride, wherein ritanserin is administered to post-treat between about 60 minutes and about 180 minutes after the administration of the 5,6-dimethoxy-2-aminoindane hydrochloride form disclosed herein, including those described in Table Ex15.

In some embodiments, the serotonin receptor modulator is pimavanserin and the psychedelic is 5,6-dimethoxy-2-aminoindane hydrochloride, wherein the pimavanserin is administered to post-treat at least 15 minutes after the administration of the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 30 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat between at least 60 minutes and 240 minutes after the administration or release of the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 90 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 120 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 150 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat between about 15 minutes and about 150 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 180 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 210 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 240 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 270 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 300 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 330 minutes after the 5,6-dimethoxy-2-aminoindane hydrochloride form disclosed herein, including those described in Table Ex15. In some embodiments, the serotonin receptor modulator is pimavanserin and the psychedelic is 5,6-dimethoxy-2-aminoindane hydrochloride, wherein the pimavanserin is administered to post-treat at least 360 minutes after the 5,6-dimethoxy-2-aminoindane hydrochloride form disclosed herein, including those described in Table Ex15. In some preferred embodiments, the serotonin receptor modulator is pimavanserin and the psychedelic is 5,6-dimethoxy-2-aminoindane hydrochloride, wherein pimavanserin is administered to post-treat between about 60 minutes and about 180 minutes after the administration of the 5,6-dimethoxy-2-aminoindane hydrochloride form disclosed herein, including those described in Table Ex15.

In some embodiments, the serotonin receptor modulator is nelotanserin and the psychedelic is 5,6-dimethoxy-2-aminoindane hydrochloride, wherein the nelotanserin is administered to post-treat at least 15 minutes after the administration of the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 30 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat between at least 60 minutes and 240 minutes after the administration or release of the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 90 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 120 minutes after the 5,6-dimethoxy-2-aminoindane hydrochloride form disclosed herein, including those described in Table Ex15.

In some embodiments, the serotonin receptor modulator is nelotanserin and the psychedelic is 5,6-dimethoxy-2-aminoindane hydrochloride, wherein the nelotanserin is administered to post-treat at least 150 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat between about 15 minutes and about 150 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 180 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 210 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 240 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 270 minutes after the 5,6-dimethoxy-2-aminoindane hydrochloride form disclosed herein, including those described in Table Ex15.

In some embodiments, the serotonin receptor modulator is nelotanserin and the psychedelic is 5,6-dimethoxy-2-aminoindane hydrochloride, wherein the nelotanserin is administered to post-treat at least 300 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 330 minutes after the 5,6-dimethoxy-2-aminoindane hydrochloride form disclosed herein, including those described in Table Ex15. In some embodiments, the serotonin receptor modulator is nelotanserin and the psychedelic is 5,6-dimethoxy-2-aminoindane hydrochloride, wherein the nelotanserin is administered to post-treat at least 360 minutes after the 5,6-dimethoxy-2-aminoindane hydrochloride form disclosed herein, including those described in Table Ex15. In some preferred embodiments, the serotonin receptor modulator is nelotanserin and the psychedelic is 5,6-dimethoxy-2-aminoindane hydrochloride, wherein nelotanserin is administered to post-treat between about 60 minutes and about 180 minutes after the administration of the 5,6-dimethoxy-2-aminoindane hydrochloride form disclosed herein, including those described in Table Ex15.

In some embodiments, the serotonin receptor modulator is pruvanserin and the psychedelic is 5,6-dimethoxy-2-aminoindane hydrochloride, wherein the pruvanserin is administered to post-treat at least 15 minutes after the administration of the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 30 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat between at least 60 minutes and 240 minutes after the administration or release of the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 90 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 120 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 150 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat between about 15 minutes and about 150 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 180 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 210 minutes after the 5,6-dimethoxy-2-aminoindane hydrochloride form disclosed herein, including those described in Table Ex15.

In some embodiments, the serotonin receptor modulator is pruvanserin and the psychedelic is 5,6-dimethoxy-2-aminoindane hydrochloride, wherein the pruvanserin is administered to post-treat at least 240 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 270 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 300 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 330 minutes after the 5,6-dimethoxy-2-aminoindane hydrochloride form disclosed herein, including those described in Table Ex15. In some embodiments, the serotonin receptor modulator is pruvanserin and the psychedelic is 5,6-dimethoxy-2-aminoindane hydrochloride, wherein the pruvanserin is administered to post-treat at least 360 minutes after the 5,6-dimethoxy-2-aminoindane hydrochloride form disclosed herein, including those described in Table Ex15. In some preferred embodiments, the serotonin receptor modulator is pruvanserin and the psychedelic is 5,6-dimethoxy-2-aminoindane hydrochloride, wherein pruvanserin is administered to post-treat between about 60 minutes and about 180 minutes after the administration of the 5,6-dimethoxy-2-aminoindane hydrochloride form disclosed herein, including those described in Table Ex15.

In some embodiments, the serotonin receptor modulator is flibanserin, wherein the flibanserin is administered to post-treat at least 15 minutes post to the administration of the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 30 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat between at least 60 minutes and 240 minutes post to the administration or release of the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 90 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 120 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 150 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat between about 15 minutes and about 150 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 180 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 210 minutes post to the 5,6-dimethoxy-2-aminoindane hydrochloride form disclosed herein, including those described in Table Ex15.

In some embodiments, the serotonin receptor modulator is flibanserin, wherein the flibanserin is administered to post-treat at least 240 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 270 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 300 minutes post to the 5,6-dimethoxy-2- aminoindane hydrochloride form disclosed herein, including those described in Table Ex15. In some embodiments, the serotonin receptor modulator is flibanserin, wherein the flibanserin is administered to post-treat at least 330 minutes post to the 5,6-dimethoxy-2-aminoindane hydrochloride form disclosed herein, including those described in Table Ex15. In some embodiments, the serotonin receptor modulator is flibanserin, wherein the flibanserin is administered to post-treat at least 360 minutes post to the 5,6-dimethoxy-2-aminoindane hydrochloride form disclosed herein, including those described in Table Ex15. In some preferred embodiments, the serotonin receptor modulator is flibanserin, wherein flibanserin is administered to post-treat between about 60 minutes and about 180 minutes post to the administration of the 5,6-dimethoxy-2-aminoindane hydrochloride form disclosed herein, including those described in Table Ex15.

In some embodiments, the serotonin receptor modulator is olanzapine, wherein the olanzapine is administered to post-treat at least 15 minutes post to the administration of the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 30 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat between at least 60 minutes and 240 minutes post to the administration or release of the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 90 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 120 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 150 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat between about 15 minutes and about 150 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 180 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 210 minutes post to the 5,6-dimethoxy-2-aminoindane hydrochloride form disclosed herein, including those described in Table Ex15.

In some embodiments, the serotonin receptor modulator is olanzapine, wherein the olanzapine is administered to post-treat at least 240 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 270 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 300 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 330 minutes post to the 5,6-dimethoxy-2-aminoindane hydrochloride form disclosed herein, including those described in Table Ex15. In some embodiments, the serotonin receptor modulator is olanzapine, wherein the olanzapine is administered to post-treat at least 360 minutes post to the 5,6-dimethoxy-2-aminoindane hydrochloride form disclosed herein, including those described in Table Ex15. In some preferred embodiments, the serotonin receptor modulator is olanzapine, wherein olanzapine is administered to post-treat between about 60 minutes and about 180 minutes post to the administration of the 5,6-dimethoxy-2-aminoindane hydrochloride form disclosed herein, including those described in Table Ex15.

In some embodiments, the serotonin receptor modulator is quetiapine, wherein the quetiapine is administered to post-treat at least 15 minutes post to the administration of the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 30 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat between at least 60 minutes and 240 minutes post to the administration or release of the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 90 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 120 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 150 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat between about 15 minutes and about 150 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 180 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 210 minutes post to the 5,6-dimethoxy-2-aminoindane hydrochloride form disclosed herein, including those described in Table Ex15.

In some embodiments, the serotonin receptor modulator is quetiapine, wherein the quetiapine is administered to post-treat at least 240 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 270 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 300 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 330 minutes post to the 5,6-dimethoxy-2-aminoindane hydrochloride form disclosed herein, including those described in Table Ex15. In some embodiments, the serotonin receptor modulator is quetiapine, wherein the quetiapine is administered to post-treat at least 360 minutes post to the 5,6-dimethoxy-2-aminoindane hydrochloride form disclosed herein, including those described in Table Ex15. In some preferred embodiments, the serotonin receptor modulator is quetiapine, wherein quetiapine is administered to post-treat between about 60 minutes and about 180 minutes post to the administration of the 5,6-dimethoxy-2-aminoindane hydrochloride form disclosed herein, including those described in Table Ex15.

In some embodiments, the serotonin receptor modulator is risperidone, wherein the risperidone is administered to post-treat at least 15 minutes post to the administration of the 5,6-dimethoxy-2-aminoindane hydrochloride form disclosed herein, including those described in Table Ex15. In some embodiments, the serotonin receptor modulator is risperidone, wherein the risperidone is administered to post-treat at least 30 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat between at least 60 minutes and 240 minutes post to the administration or release of the 5,6-dimethoxy-2-aminoindane hydrochloride form disclosed herein, including those described in Table Ex15. In some embodiments, the serotonin receptor modulator is risperidone, wherein the risperidone is administered to post-treat at least 90 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 120 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 150 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat between about 15 minutes and about 150 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 180 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 210 minutes post to the 5,6-dimethoxy-2-aminoindane hydrochloride form disclosed herein, including those described in Table Ex15.

In some embodiments, the serotonin receptor modulator is risperidone, wherein the risperidone is administered to post-treat at least 240 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 270 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 300 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 330 minutes post to the 5,6-dimethoxy-2-aminoindane hydrochloride form disclosed herein, including those described in Table Ex15. In some embodiments, the serotonin receptor modulator is risperidone, wherein the risperidone is administered to post-treat at least 360 minutes post to the 5,6-dimethoxy-2-aminoindane hydrochloride form disclosed herein, including those described in Table Ex15. In some preferred embodiments, the serotonin receptor modulator is risperidone, wherein risperidone is administered to post-treat between about 60 minutes and about 180 minutes post to the administration of the 5,6-dimethoxy-2-aminoindane hydrochloride form disclosed herein, including those described in Table Ex15.

In some embodiments, the serotonin receptor modulator for use with an MBDB form. disclosed herein, including those described in Example 5 is eplivanserin, wherein the eplivanserin is administered in about 1 mg to about 40 mg, or about 5 mg to about 10 mg, and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is volinanserin, wherein the volinanserin is administered in about 1 mg to about 60 mg, or about 5 mg to about 20 mg and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is ketanserin, wherein the ketanserin is administered in about 10 mg to about 80 mg, about 30 mg to about 50 mg, or about 40 mg and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is ritanserin, wherein the ritanserin is administered in about 1 mg to about 40 mg, or about 2.5 mg to about 10 mg and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is pimavanserin, wherein the pimavanserin is administered in about 1 mg to about 60 mg, or about 17 mg to about 34 mg and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is nelotanserin, wherein the nelotanserin is administered in about 1 mg to about 80 mg, or about 40 mg to about 80 mg and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is pruvanserin, wherein the pruvanserin is administered in about 1 mg to about 40 mg, or about 3 mg to about 10 mg and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is flibanserin, wherein the flibanserin is administered in about 10 mg to about 200 mg, or about 80 mg to about 120 mg, or about 100 mg and MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is olanzapine, wherein the olanzapine is administered in about 2.5 mg to about 30 mg, or about 5 mg or about 10 mg, or about 20 mg or about 25 mg, and the MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is quetiapine, wherein the quetiapine is administered in about 25 mg to about 800 mg, or about 50 mg to about 100 mg, or about 150 mg or about 200 mg or about 250 mg or about 300 mg, and the MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is an extended-release of quetiapine, wherein the extended-release of quetiapine is administered in about 50 mg to about 300 mg, or about 50 mg or about 100 mg or about 200 mg, or about 300 mg, and the MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the MBDB salt and solid forms disclosed herein, including those described in Example 5 are administered in about 10 mg to about 500 mg or about 150 mg to about 250 mg or about 180 mg or about 210 mg or about 250 mg.

In some embodiments, the serotonin receptor modulator for use with an MBDB form disclosed herein, including those described in Example 5 is an extended-release of risperidone including (RISPERDAL CONSTA), wherein the extended-release of risperidone is administered in about 12.5 mg, or about 25 mg, or about 37.5 mg, or about 50 mg, and the MBDB salt and solid forms disclosed herein, including those described in Example 5 are administered in about 10 mg to about 500 mg or about 150 mg to about 250 mg or about 180 mg or about 210 mg or about 250 mg.

In certain embodiments, such as those described above a MBDB form disclosed herein, including those described in Example 5 is co-administered with a serotonin receptor modulator in the same or in separate compositions. In one embodiment, the serotonin receptor modulator is administered prior to the MBDB form disclosed herein, including those described in Example 5. In one embodiment, the MBDB form disclosed herein, including those described in Example 5 is administered in a modified release formulation such that the subject is effectively pretreated with serotonin receptor modulator prior to release of an effective amount of MBDB. In some embodiments the serotonin receptor modulator is part of a single fixed dose formulation that releases serotonin receptor modulator first followed by MBDB on two different release profiles. In another embodiment the serotonin receptor modulator is administered first as a single dosage and after a length of time, the MBDB form disclosed herein, including those described in Example 5 is administered as a second dosage separate from the first dosage. Thus, in some embodiments, the serotonin receptor modulator is administered or released from a composition provided herein prior to the administration and/or release of the MBDB form disclosed herein, including those described in Example 5. This allows pretreatment to attenuate activation of the serotonin receptor by the MBDB.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the MBDB form disclosed herein, including those described in Example 5. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of MBDB form disclosed herein, including those described in Example 5. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the MBDB form disclosed herein, including those described in Example 5.

In a preferred embodiment, the serotonin receptor modulator is administered at about 1 hour to about 3 hours prior to the administration of the MBDB form disclosed herein, including those described in Example 5.

In some embodiments, the serotonin receptor modulator is eplivanserin, wherein the eplivanserin is administered to pretreat at least 15 minutes prior to the administration of the MBDB form disclosed herein, including those described in Example 5. In some embodiments, the serotonin receptor modulator is eplivanserin, wherein the eplivanserin is administered to pretreat between at least 30 minutes prior and 360 minutes prior to the release or administration of the MBDB form disclosed herein, including those described in Example 5. In some embodiments, the serotonin receptor modulator is eplivanserin, wherein the eplivanserin is administered to pretreat between at least 60 minutes prior and 360 minutes prior to the release or administration the MBDB form disclosed herein, including those described in Example 5. In some embodiments, the serotonin receptor modulator is eplivanserin, wherein the eplivanserin is administered to pretreat between at least 90 minutes and 240 minutes prior to the MBDB form disclosed herein, including those described in Example 5. In some embodiments, the serotonin receptor modulator is eplivanserin, wherein the eplivanserin is administered to pretreat at least 120 minutes prior to the MBDB form disclosed herein, including those described in Example 5.

In some embodiments, the serotonin receptor modulator is eplivanserin, wherein the eplivanserin is administered to pretreat at least 150 minutes prior to the MBDB form disclosed herein, including those described in Example 5. In some embodiments, the serotonin receptor modulator is eplivanserin, wherein the eplivanserin is administered to pretreat at least 180 minutes prior to the MBDB form disclosed herein, including those described in Example 5. In some embodiments, the serotonin receptor modulator is eplivanserin, wherein the eplivanserin is administered to pretreat at least 210 minutes prior to the MBDB form disclosed herein, including those described in Example 5. In some embodiments, the serotonin receptor modulator is eplivanserin, wherein the eplivanserin is administered to pretreat at least 240 minutes prior to the MBDB form disclosed herein, including those described in Example 5.

In some embodiments, the serotonin receptor modulator is eplivanserin, wherein the eplivanserin is administered to pretreat at least 270 minutes prior to the MBDB form disclosed herein, including those described in Example 5. In some embodiments, the serotonin receptor modulator is eplivanserin, wherein the eplivanserin is administered to pretreat at least 300 minutes prior to the MBDB form disclosed herein, including those described in Example 5. In some embodiments, the serotonin receptor modulator is eplivanserin, wherein the eplivanserin is administered to pretreat at least 330 minutes prior to the MBDB form disclosed herein, including those described in Example 5. In some embodiments, the serotonin receptor modulator is eplivanserin, wherein the eplivanserin is administered to pretreat at least 360 minutes prior to administration or release of the MBDB form disclosed herein, including those described in Example 5.

In some preferred embodiments, the serotonin receptor modulator is eplivanserin, wherein eplivanserin is administered to pretreat between about 60 minutes and about 180 minutes prior to the administration or release of the MBDB form disclosed herein, including those described in Example 5.

In some embodiments, the serotonin receptor modulator is volinanserin, wherein the volinanserin is administered to pretreat a subject between at least 15 minutes and 360 minutes prior to the administration or release of the MBDB form disclosed herein, including those described in Example 5. In some embodiments, the serotonin receptor modulator is volinanserin, wherein the volinanserin is administered to pretreat between at least 30 minutes and 360 minutes prior to the administration or release of the MBDB form disclosed herein, including those described in Example 5. In some embodiments, the serotonin receptor modulator is volinanserin, wherein the volinanserin is administered to pretreat between at least 60 minutes and 240 minutes prior to the administration or release of the MBDB form disclosed herein, including those described in Example 5. In some embodiments, the serotonin receptor modulator is volinanserin, wherein the volinanserin is administered to pretreat at least 90 minutes prior to MBDB form disclosed herein, including those described in Example 5. In some embodiments, the serotonin receptor modulator is volinanserin, wherein the volinanserin is administered to pretreat at least 120 minutes prior to the MBDB form disclosed herein, including those described in Example 5.

In some embodiments, the serotonin receptor modulator is volinanserin, wherein the volinanserin is administered to pretreat at least 150 minutes prior to the MBDB form disclosed herein, including those described in Example 5. In some embodiments, the serotonin receptor modulator is volinanserin, wherein the volinanserin is administered to pretreat between about 15 minutes and about 150 minutes prior to the MBDB form disclosed herein, including those described in Example 5. In some embodiments, the serotonin receptor modulator is volinanserin, wherein the volinanserin is administered to pretreat at least 180 minutes prior to the MBDB form disclosed herein, including those described in Example 5. In some embodiments, the serotonin receptor modulator is volinanserin, wherein the volinanserin is administered to pretreat at least 210 minutes prior to the MBDB form disclosed herein, including those described in Example 5. In some embodiments, the serotonin receptor modulator is volinanserin, wherein the volinanserin is administered to pretreat at least 240 minutes prior to the MBDB form disclosed herein, including those described in Example 5. In some embodiments, the serotonin receptor modulator is volinanserin, wherein the volinanserin is administered to pretreat at least 270 minutes prior to the MBDB form disclosed herein, including those described in Example 5. In some embodiments, the serotonin receptor modulator is volinanserin, wherein the volinanserin is administered to pretreat at least 300 minutes prior to the MBDB form disclosed herein, including those described in Example 5. In some embodiments, the serotonin receptor modulator is volinanserin, wherein the volinanserin is administered to pretreat at least 330 minutes prior to MBDB form disclosed herein, including those described in Example 5. In some embodiments, the serotonin receptor modulator is volinanserin, wherein the volinanserin is administered to pretreat at least 360 minutes prior to the MBDB form disclosed herein, including those described in Example 5. In some preferred embodiments, the serotonin receptor modulator is volinanserin, wherein volinanserin is administered to pretreat between about 60 minutes and about 180 minutes prior to the administration of the MBDB form disclosed herein, including those described in Example 5.

In some embodiments, the serotonin receptor modulator is ketanserin, wherein the ketanserin is administered to pretreat at least 15 minutes prior to the administration of the MBDB form disclosed herein, including those described in Example 5. In some embodiments, the serotonin receptor modulator is ketanserin, wherein the ketanserin is administered to pretreat between at least 30 minutes and 360 minutes prior to the administration or release of the MBDB form disclosed herein, including those described in Example 5. In some embodiments, the serotonin receptor modulator is ketanserin, wherein the ketanserin is administered to pretreat between at least 60 minutes and 240 minutes prior to the administration or release of the MBDB form disclosed herein, including those described in Example 5. In some embodiments, the serotonin receptor modulator is ketanserin, wherein the ketanserin is administered to pretreat at least 90 minutes prior to the MBDB form disclosed herein, including those described in Example 5. In some embodiments, the serotonin receptor modulator is ketanserin, wherein the ketanserin is administered to pretreat at least 120 minutes prior to the MBDB form disclosed herein, including those described in Example 5. In some embodiments, the serotonin receptor modulator is ketanserin, wherein the ketanserin is administered to pretreat at least 150 minutes prior to the MBDB form disclosed herein, including those described in Example 5. In some embodiments, the serotonin receptor modulator is ketanserin, wherein the ketanserin is administered to pretreat between about 15 minutes and about 150 minutes prior to the MBDB form disclosed herein, including those described in Example 5. In some embodiments, the serotonin receptor modulator is ketanserin, wherein the ketanserin is administered to pretreat at least 180 minutes prior to the MBDB form disclosed herein, including those described in Example 5. In some embodiments, the serotonin receptor modulator is ketanserin, wherein the ketanserin is administered to pretreat at least 210 minutes prior to the MBDB form disclosed herein, including those described in Example 5. In some embodiments, the serotonin receptor modulator is ketanserin, wherein the ketanserin is administered to pretreat at least 240 minutes prior to the MBDB form disclosed herein, including those described in Example 5. In some embodiments, the serotonin receptor modulator is ketanserin, wherein the ketanserin is administered to pretreat at least 270 minutes prior to the MBDB form disclosed herein, including those described in Example 5. In some embodiments, the serotonin receptor modulator is ketanserin, wherein the ketanserin is administered to pretreat at least 300 minutes prior to the MBDB form disclosed herein, including those described in Example 5. In some embodiments, the serotonin receptor modulator is ketanserin, wherein the ketanserin is administered to pretreat at least 330 minutes prior to the MBDB form disclosed herein, including those described in Example 5. In some embodiments, the serotonin receptor modulator is ketanserin, wherein the ketanserin is administered to pretreat at least 360 minutes prior to the MBDB form disclosed herein, including those described in Example 5. In some preferred embodiments, the serotonin receptor modulator is ketanserin, wherein ketanserin is administered to pretreat between about 60 minutes and about 180 minutes prior to the administration of the MBDB form disclosed herein, including those described in Example 5.

In some embodiments, the serotonin receptor modulator is ritanserin, wherein the ritanserin is administered to pretreat at least 15 minutes prior to the administration of the MBDB form disclosed herein, including those described in Example 5. In some embodiments, the serotonin receptor modulator is ritanserin, wherein the ritanserin is administered to pretreat at least 30 minutes prior to the MBDB form disclosed herein, including those described in Example 5. In some embodiments, the serotonin receptor modulator is ritanserin wherein the ritanserin is administered to pretreat between at least 60 minutes and 240 minutes prior to the administration or release of the MBDB form disclosed herein, including those described in Example 5. In some embodiments, the serotonin receptor modulator is ritanserin, wherein the ritanserin is administered to pretreat at least 90 minutes prior to the MBDB form disclosed herein, including those described in Example 5. In some embodiments, the serotonin receptor modulator is ritanserin, wherein the ritanserin is administered to pretreat at least 120 minutes prior to the MBDB form disclosed herein, including those described in Example 5. In some embodiments, the serotonin receptor modulator is ritanserin, wherein the ritanserin is administered to pretreat at least 150 minutes prior to the MBDB form disclosed herein, including those described in Example 5. In some embodiments, the serotonin receptor modulator is ritanserin, wherein the ritanserin is administered to pretreat between about 15 minutes and about 150 minutes prior to the MBDB form disclosed herein, including those described in Example 5. In some embodiments, the serotonin receptor modulator is ritanserin, wherein the ritanserin is administered to pretreat at least 180 minutes prior to the MBDB form disclosed herein, including those described in Example 5. In some embodiments, the serotonin receptor modulator is ritanserin, wherein the ritanserin is administered to pretreat at least 210 minutes prior to the MBDB form disclosed herein, including those described in Example 5. In some embodiments, the serotonin receptor modulator is ritanserin, wherein the ritanserin is administered to pretreat at least 240 minutes prior to the MBDB form disclosed herein, including those described in Example 5. In some embodiments, the serotonin receptor modulator is ritanserin, wherein the ritanserin is administered to pretreat at least 270 minutes prior to the MBDB form disclosed herein, including those described in Example 5. In some embodiments, the serotonin receptor modulator is ritanserin, wherein the ritanserin is administered to pretreat at least 300 minutes prior to the MBDB form disclosed herein, including those described in Example 5. In some embodiments, the serotonin receptor modulator is ritanserin, wherein the ritanserin is administered to pretreat at least 330 minutes prior to the MBDB form disclosed herein, including those described in Example 5. In some embodiments, the serotonin receptor modulator is ritanserin, wherein the ritanserin is administered to pretreat at least 360 minutes prior to the MBDB form disclosed herein, including those described in Example 5. In some preferred embodiments, the serotonin receptor modulator is ritanserin, wherein ritanserin is administered to pretreat between about 60 minutes and about 180 minutes prior to the administration of the MBDB form disclosed herein, including those described in Example 5.

In some embodiments, the serotonin receptor modulator is pimavanserin, wherein the pimavanserin is administered to pretreat at least 15 minutes prior to the administration of the MBDB form disclosed herein, including those described in Example 5. In some embodiments, the serotonin receptor modulator is pimavanserin, wherein the pimavanserin is administered to pretreat at least 30 minutes prior to the MBDB form disclosed herein, including those described in Example 5. In some embodiments, the serotonin receptor modulator is pimavanserin, wherein the pimavanserin is administered to pretreat between at least 60 minutes and 240 minutes prior to the administration or release of the MBDB form disclosed herein, including those described in Example 5. In some embodiments, the serotonin receptor modulator is pimavanserin, wherein the pimavanserin is administered to pretreat at least 90 minutes prior to the MBDB form disclosed herein, including those described in Example 5. In some embodiments, the serotonin receptor modulator is pimavanserin, wherein the pimavanserin is administered to pretreat at least 120 minutes prior to the MBDB form disclosed herein, including those described in Example 5. In some embodiments, the serotonin receptor modulator is pimavanserin, wherein the pimavanserin is administered to pretreat at least 150 minutes prior to the MBDB form disclosed herein, including those described in Example 5. In some embodiments, the serotonin receptor modulator is pimavanserin, wherein the pimavanserin is administered to pretreat between about 15 minutes and about 150 minutes prior to the MBDB form disclosed herein, including those described in Example 5. In some embodiments, the serotonin receptor modulator is pimavanserin, wherein the pimavanserin is administered to pretreat at least 180 minutes prior to the MBDB form disclosed herein, including those described in Example 5. In some embodiments, the serotonin receptor modulator is pimavanserin, wherein the pimavanserin is administered to pretreat at least 210 minutes prior to the MBDB form disclosed herein, including those described in Example 5. In some embodiments, the serotonin receptor modulator is pimavanserin, wherein the pimavanserin is administered to pretreat at least 240 minutes prior to the MBDB form disclosed herein, including those described in Example 5. In some embodiments, the serotonin receptor modulator is pimavanserin, wherein the pimavanserin is administered to pretreat at least 270 minutes prior to the MBDB form disclosed herein, including those described in Example 5. In some embodiments, the serotonin receptor modulator is pimavanserin, wherein the pimavanserin is administered to pretreat at least 300 minutes prior to the MBDB form disclosed herein, including those described in Example 5. In some embodiments, the serotonin receptor modulator is pimavanserin, wherein the pimavanserin is administered to pretreat at least 330 minutes prior to the MBDB form disclosed herein, including those described in Example 5. In some embodiments, the serotonin receptor modulator is pimavanserin, wherein the pimavanserin is administered to pretreat at least 360 minutes prior to the MBDB form disclosed herein, including those described in Example 5. In some preferred embodiments, the serotonin receptor modulator is pimavanserin, wherein pimavanserin is administered to pretreat between about 60 minutes and about 180 minutes prior to the administration of the MBDB form disclosed herein, including those described in Example 5.

In some embodiments, the serotonin receptor modulator is nelotanserin, wherein the nelotanserin is administered to pretreat at least 15 minutes prior to the administration of the MBDB form disclosed herein, including those described in Example 5. In some embodiments, the serotonin receptor modulator is nelotanserin, wherein the nelotanserin is administered to pretreat at least 30 minutes prior to the MBDB form disclosed herein, including those described in Example 5. In some embodiments, the serotonin receptor modulator is nelotanserin, wherein the nelotanserin is administered to pretreat between at least 60 minutes and 240 minutes prior to the administration or release of the MBDB form disclosed herein, including those described in Example 5. In some embodiments, the serotonin receptor modulator is nelotanserin, wherein the nelotanserin is administered to pretreat at least 90 minutes prior to the MBDB form disclosed herein, including those described in Example 5. In some embodiments, the serotonin receptor modulator is nelotanserin, wherein the nelotanserin is administered to pretreat at least 120 minutes prior to the MBDB form disclosed herein, including those described in Example 5.

In some embodiments, the serotonin receptor modulator is nelotanserin, wherein the nelotanserin is administered to pretreat at least 150 minutes prior to the MBDB form disclosed herein, including those described in Example 5. In some embodiments, the serotonin receptor modulator is nelotanserin, wherein the nelotanserin is administered to pretreat between about 15 minutes and about 150 minutes prior to the MBDB form disclosed herein, including those described in Example 5. In some embodiments, the serotonin receptor modulator is nelotanserin, wherein the nelotanserin is administered to pretreat at least 180 minutes prior to the MBDB form disclosed herein, including those described in Example 5. In some embodiments, the serotonin receptor modulator is nelotanserin, wherein the nelotanserin is administered to pretreat at least 210 minutes prior to the MBDB form disclosed herein, including those described in Example 5. In some embodiments, the serotonin receptor modulator is nelotanserin, wherein the nelotanserin is administered to pretreat at least 240 minutes prior to the MBDB form disclosed herein, including those described in Example 5. In some embodiments, the serotonin receptor modulator is nelotanserin, wherein the nelotanserin is administered to pretreat at least 270 minutes prior to the MBDB form disclosed herein, including those described in Example 5.

In some embodiments, the serotonin receptor modulator is nelotanserin, wherein the nelotanserin is administered to pretreat at least 300 minutes prior to the MBDB form disclosed herein, including those described in Example 5. In some embodiments, the serotonin receptor modulator is nelotanserin, wherein the nelotanserin is administered to pretreat at least 330 minutes prior to the MBDB form disclosed herein, including those described in Example 5. In some embodiments, the serotonin receptor modulator is nelotanserin, wherein the nelotanserin is administered to pretreat at least 360 minutes prior to the MBDB form disclosed herein, including those described in Example 5. In some preferred embodiments, the serotonin receptor modulator is nelotanserin, wherein nelotanserin is administered to pretreat between about 60 minutes and about 180 minutes prior to the administration of the MBDB form disclosed herein, including those described in Example 5.

In some embodiments, the serotonin receptor modulator is pruvanserin, wherein the pruvanserin is administered to pretreat at least 15 minutes prior to the administration of the MBDB form disclosed herein, including those described in Example 5. In some embodiments, the serotonin receptor modulator is pruvanserin, wherein the pruvanserin is administered to pretreat at least 30 minutes prior to the MBDB form disclosed herein, including those described in Example 5. In some embodiments, the serotonin receptor modulator is pruvanserin, wherein the pruvanserin is administered to pretreat between at least 60 minutes and 240 minutes prior to the administration or release of the MBDB form disclosed herein, including those described in Example 5. In some embodiments, the serotonin receptor modulator is pruvanserin, wherein the pruvanserin is administered to pretreat at least 90 minutes prior to the MBDB form disclosed herein, including those described in Example 5. In some embodiments, the serotonin receptor modulator is pruvanserin, wherein the pruvanserin is administered to pretreat at least 120 minutes prior to the MBDB form disclosed herein, including those described in Example 5. In some embodiments, the serotonin receptor modulator is pruvanserin, wherein the pruvanserin is administered to pretreat at least 150 minutes prior to the MBDB form disclosed herein, including those described in Example 5. In some embodiments, the serotonin receptor modulator is pruvanserin, wherein the pruvanserin is administered to pretreat between about 15 minutes and about 150 minutes prior to the MBDB form disclosed herein, including those described in Example 5. In some embodiments, the serotonin receptor modulator is pruvanserin, wherein the pruvanserin is administered to pretreat at least 180 minutes prior to the MBDB form disclosed herein, including those described in Example 5. In some embodiments, the serotonin receptor modulator is pruvanserin, wherein the pruvanserin is administered to pretreat at least 210 minutes prior to the MBDB form disclosed herein, including those described in Example 5.

In some embodiments, the serotonin receptor modulator is pruvanserin, wherein the pruvanserin is administered to pretreat at least 240 minutes prior to the MBDB form disclosed herein, including those described in Example 5. In some embodiments, the serotonin receptor modulator is pruvanserin, wherein the pruvanserin is administered to pretreat at least 270 minutes prior to the MBDB form disclosed herein, including those described in Example 5. In some embodiments, the serotonin receptor modulator is pruvanserin, wherein the pruvanserin is administered to pretreat at least 300 minutes prior to the MBDB form disclosed herein, including those described in Example 5. In some embodiments, the serotonin receptor modulator is pruvanserin, wherein the pruvanserin is administered to pretreat at least 330 minutes prior to the MBDB form disclosed herein, including those described in Example 5. In some embodiments, the serotonin receptor modulator is pruvanserin, wherein the pruvanserin is administered to pretreat at least 360 minutes prior to the MBDB form disclosed herein, including those described in Example 5. In some preferred embodiments, the serotonin receptor modulator is pruvanserin, wherein pruvanserin is administered to pretreat between about 60 minutes and about 180 minutes prior to the administration of the MBDB form disclosed herein, including those described in Example 5.

In some embodiments, the serotonin receptor modulator is administered after a compound disclosed herein, such as from about one to about three hours post administration of a compound disclosed herein. In some embodiments, the serotonin receptor modulator is administered at most about one hour post to the presently disclosed compound.

In certain embodiments, such as those described above a MBDB form disclosed herein, including those described in Example 5 is co-administered with a serotonin receptor modulator in the same or in separate compositions. In one embodiment, the serotonin receptor modulator is administered after the MBDB form disclosed herein, including those described in Example 5. In one embodiment, the MBDB form disclosed herein, including those described in Example 5 is administered in a modified release formulation such that the subject is effectively post-treated with serotonin receptor modulator post to release of an effective amount of MBDB. In some embodiments, the serotonin receptor modulator is part of a single fixed dose formulation that releases MBDB first followed by serotonin receptor modulator on two different release profiles. In another embodiment, the MBDB form disclosed herein, including those described in Example 5 is administered first as a single dosage and, after a length of time, serotonin receptor modulator is administered as a second dosage separate from the first dosage. Thus, in some embodiments, the serotonin receptor modulator is administered or released from a composition provided herein post to the administration and/or release of the MBDB. This allows post-treatment to attenuate activation of the serotonin receptor by the MBDB.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post to the release of the MBDB form disclosed herein, including those described in Example 5. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of MBDB form disclosed herein, including those described in Example 5. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the MBDB form disclosed herein, including those described in Example 5.

In a preferred embodiment, the serotonin receptor modulator is administered at about 1 hour to about 3 hours post to the administration of the MBDB form disclosed herein, including those described in Example 5.

In some embodiments, the serotonin receptor modulator is eplivanserin, wherein the eplivanserin is administered to post-treat at least 15 minutes post to the administration of the MBDB form disclosed herein, including those described in Example 5. In some embodiments, the serotonin receptor modulator is eplivanserin, wherein the eplivanserin is administered to post-treat between at least 30 minutes post and 360 minutes post to the release or administration of the MBDB form disclosed herein, including those described in Example 5. In some embodiments, the serotonin receptor modulator is eplivanserin, wherein the eplivanserin is administered to post-treat between at least 60 minutes post and 360 minutes post to the release or administration the MBDB form disclosed herein, including those described in Example 5. In some embodiments, the serotonin receptor modulator is eplivanserin, wherein the eplivanserin is administered to post-treat between at least 90 minutes and 240 minutes post to the MBDB form disclosed herein, including those described in Example 5. In some embodiments, the serotonin receptor modulator is eplivanserin, wherein the eplivanserin is administered to post-treat at least 120 minutes post to the MBDB form disclosed herein, including those described in Example 5.

In some embodiments, the serotonin receptor modulator is eplivanserin, wherein the eplivanserin is administered to post-treat at least 150 minutes post to the MBDB form disclosed herein, including those described in Example 5. In some embodiments, the serotonin receptor modulator is eplivanserin, wherein the eplivanserin is administered to post-treat at least 180 minutes post to the MBDB form disclosed herein, including those described in Example 5. In some embodiments, the serotonin receptor modulator is eplivanserin, wherein the eplivanserin is administered to post-treat at least 210 minutes post to the MBDB form disclosed herein, including those described in Example 5. In some embodiments, the serotonin receptor modulator is eplivanserin, wherein the eplivanserin is administered to post-treat at least 240 minutes post to the MBDB form disclosed herein, including those described in Example 5.

In some embodiments, the serotonin receptor modulator is eplivanserin, wherein the eplivanserin is administered to post-treat at least 270 minutes post to the MBDB form disclosed herein, including those described in Example 5. In some embodiments, the serotonin receptor modulator is eplivanserin, wherein the eplivanserin is administered to post-treat at least 300 minutes post to the MBDB form disclosed herein, including those described in Example 5. In some embodiments, the serotonin receptor modulator is eplivanserin, wherein the eplivanserin is administered to post-treat at least 330 minutes post to the MBDB form disclosed herein, including those described in Example 5. In some embodiments, the serotonin receptor modulator is eplivanserin, wherein the eplivanserin is administered to post-treat at least 360 minutes post to administration or release of the MBDB form disclosed herein, including those described in Example 5.

In some preferred embodiments, the serotonin receptor modulator is eplivanserin, wherein eplivanserin is administered to post-treat between about 60 minutes and about 180 minutes post to the administration or release of the MBDB form disclosed herein, including those described in Example 5.

In some embodiments, the serotonin receptor modulator is volinanserin, wherein the volinanserin is administered to post-treat a subject between at least 15 minutes and 360 minutes post to the administration or release of the MBDB form disclosed herein, including those described in Example 5. In some embodiments, the serotonin receptor modulator is volinanserin, wherein the volinanserin is administered to post-treat between at least 30 minutes and 360 minutes post to the administration or release of the MBDB form disclosed herein, including those described in Example 5. In some embodiments, the serotonin receptor modulator is volinanserin, wherein the volinanserin is administered to post-treat between at least 60 minutes and 240 minutes post to the administration or release of the MBDB form disclosed herein, including those described in Example 5. In some embodiments, the serotonin receptor modulator is volinanserin, wherein the volinanserin is administered to post-treat at least 90 minutes post to MBDB form disclosed herein, including those described in Example 5. In some embodiments, the serotonin receptor modulator is volinanserin, wherein the volinanserin is administered to post-treat at least 120 minutes post to the MBDB form disclosed herein, including those described in Example 5.

In some embodiments, the serotonin receptor modulator is volinanserin, wherein the volinanserin is administered to post-treat at least 150 minutes post to the MBDB form disclosed herein, including those described in Example 5. In some embodiments, the serotonin receptor modulator is volinanserin, wherein the volinanserin is administered to post-treat between about 15 minutes and about 150 minutes post to the MBDB form disclosed herein, including those described in Example 5. In some embodiments, the serotonin receptor modulator is volinanserin, wherein the volinanserin is administered to post-treat at least 180 minutes post to the MBDB form disclosed herein, including those described in Example 5. In some embodiments, the serotonin receptor modulator is volinanserin, wherein the volinanserin is administered to post-treat at least 210 minutes post to the MBDB form disclosed herein, including those described in Example 5. In some embodiments, the serotonin receptor modulator is volinanserin, wherein the volinanserin is administered to post-treat at least 240 minutes post to the MBDB form disclosed herein, including those described in Example 5. In some embodiments, the serotonin receptor modulator is volinanserin, wherein the volinanserin is administered to post-treat at least 270 minutes post to the MBDB form disclosed herein, including those described in Example 5. In some embodiments, the serotonin receptor modulator is volinanserin, wherein the volinanserin is administered to post-treat at least 300 minutes post to the MBDB form disclosed herein, including those described in Example 5. In some embodiments, the serotonin receptor modulator is volinanserin, wherein the volinanserin is administered to post-treat at least 330 minutes post to MBDB form disclosed herein, including those described in Example 5. In some embodiments, the serotonin receptor modulator is volinanserin, wherein the volinanserin is administered to post-treat at least 360 minutes post to the MBDB form disclosed herein, including those described in Example 5. In some preferred embodiments, the serotonin receptor modulator is volinanserin, wherein volinanserin is administered to post-treat between about 60 minutes and about 180 minutes post to the administration of the MBDB form disclosed herein, including those described in Example 5.

In some embodiments, the serotonin receptor modulator is ketanserin, wherein the ketanserin is administered to post-treat at least 15 minutes post to the administration of the MBDB form disclosed herein, including those described in Example 5. In some embodiments, the serotonin receptor modulator is ketanserin, wherein the ketanserin is administered to post-treat between at least 30 minutes and 360 minutes post to the administration or release of the MBDB form disclosed herein, including those described in Example 5. In some embodiments, the serotonin receptor modulator is ketanserin, wherein the ketanserin is administered to post-treat between at least 60 minutes and 240 minutes post to the administration or release of the MBDB form disclosed herein, including those described in Example 5. In some embodiments, the serotonin receptor modulator is ketanserin, wherein the ketanserin is administered to post-treat at least 90 minutes post to the MBDB form disclosed herein, including those described in Example 5. In some embodiments, the serotonin receptor modulator is ketanserin, wherein the ketanserin is administered to post-treat at least 120 minutes post to the MBDB form disclosed herein, including those described in Example 5. In some embodiments, the serotonin receptor modulator is ketanserin, wherein the ketanserin is administered to post-treat at least 150 minutes post to the MBDB form disclosed herein, including those described in Example 5. In some embodiments, the serotonin receptor modulator is ketanserin, wherein the ketanserin is administered to post-treat between about 15 minutes and about 150 minutes post to the MBDB form disclosed herein, including those described in Example 5. In some embodiments, the serotonin receptor modulator is ketanserin, wherein the ketanserin is administered to post-treat at least 180 minutes post to the MBDB form disclosed herein, including those described in Example 5. In some embodiments, the serotonin receptor modulator is ketanserin, wherein the ketanserin is administered to post-treat at least 210 minutes post to the MBDB form disclosed herein, including those described in Example 5. In some embodiments, the serotonin receptor modulator is ketanserin, wherein the ketanserin is administered to post-treat at least 240 minutes post to the MBDB form disclosed herein, including those described in Example 5. In some embodiments, the serotonin receptor modulator is ketanserin, wherein the ketanserin is administered to post-treat at least 270 minutes post to the MBDB form disclosed herein, including those described in Example 5. In some embodiments, the serotonin receptor modulator is ketanserin, wherein the ketanserin is administered to post-treat at least 300 minutes post to the MBDB form disclosed herein, including those described in Example 5. In some embodiments, the serotonin receptor modulator is ketanserin, wherein the ketanserin is administered to post-treat at least 330 minutes post to the MBDB form disclosed herein, including those described in Example 5. In some embodiments, the serotonin receptor modulator is ketanserin, wherein the ketanserin is administered to post-treat at least 360 minutes post to the MBDB form disclosed herein, including those described in Example 5. In some preferred embodiments, the serotonin receptor modulator is ketanserin, wherein ketanserin is administered to post-treat between about 60 minutes and about 180 minutes post to the administration of the MBDB form disclosed herein, including those described in Example 5.

In some embodiments, the serotonin receptor modulator is ritanserin, wherein the ritanserin is administered to post-treat at least 15 minutes post to the administration of the MBDB form disclosed herein, including those described in Example 5. In some embodiments, the serotonin receptor modulator is ritanserin, wherein the ritanserin is administered to post-treat at least 30 minutes post to the MBDB form disclosed herein, including those described in Example 5. In some embodiments, the serotonin receptor modulator is ritanserin wherein the ritanserin is administered to post-treat between at least 60 minutes and 240 minutes post to the administration or release of the MBDB form disclosed herein, including those described in Example 5. In some embodiments, the serotonin receptor modulator is ritanserin, wherein the ritanserin is administered to post-treat at least 90 minutes post to the MBDB form disclosed herein, including those described in Example 5. In some embodiments, the serotonin receptor modulator is ritanserin, wherein the ritanserin is administered to post-treat at least 120 minutes post to the MBDB form disclosed herein, including those described in Example 5. In some embodiments, the serotonin receptor modulator is ritanserin, wherein the ritanserin is administered to post-treat at least 150 minutes post to the MBDB form disclosed herein, including those described in Example 5. In some embodiments, the serotonin receptor modulator is ritanserin, wherein the ritanserin is administered to post-treat between about 15 minutes and about 150 minutes post to the MBDB form disclosed herein, including those described in Example 5. In some embodiments, the serotonin receptor modulator is ritanserin, wherein the ritanserin is administered to post-treat at least 180 minutes post to the MBDB form disclosed herein, including those described in Example 5. In some embodiments, the serotonin receptor modulator is ritanserin, wherein the ritanserin is administered to post-treat at least 210 minutes post to the MBDB form disclosed herein, including those described in Example 5. In some embodiments, the serotonin receptor modulator is ritanserin, wherein the ritanserin is administered to post-treat at least 240 minutes post to the MBDB form disclosed herein, including those described in Example 5. In some embodiments, the serotonin receptor modulator is ritanserin, wherein the ritanserin is administered to post-treat at least 270 minutes post to the MBDB form disclosed herein, including those described in Example 5. In some embodiments, the serotonin receptor modulator is ritanserin, wherein the ritanserin is administered to post-treat at least 300 minutes post to the MBDB form disclosed herein, including those described in Example 5. In some embodiments, the serotonin receptor modulator is ritanserin, wherein the ritanserin is administered to post-treat at least 330 minutes post to the MBDB form disclosed herein, including those described in Example 5. In some embodiments, the serotonin receptor modulator is ritanserin, wherein the ritanserin is administered to post-treat at least 360 minutes post to the MBDB form disclosed herein, including those described in Example 5. In some preferred embodiments, the serotonin receptor modulator is ritanserin, wherein ritanserin is administered to post-treat between about 60 minutes and about 180 minutes post to the administration of the MBDB form disclosed herein, including those described in Example 5.

In some embodiments, the serotonin receptor modulator is pimavanserin, wherein the pimavanserin is administered to post-treat at least 15 minutes post to the administration of the MBDB form disclosed herein, including those described in Example 5. In some embodiments, the serotonin receptor modulator is pimavanserin, wherein the pimavanserin is administered to post-treat at least 30 minutes post to the MBDB form disclosed herein, including those described in Example 5. In some embodiments, the serotonin receptor modulator is pimavanserin, wherein the pimavanserin is administered to post-treat between at least 60 minutes and 240 minutes post to the administration or release of the MBDB form disclosed herein, including those described in Example 5. In some embodiments, the serotonin receptor modulator is pimavanserin, wherein the pimavanserin is administered to post-treat at least 90 minutes post to the MBDB form disclosed herein, including those described in Example 5. In some embodiments, the serotonin receptor modulator is pimavanserin, wherein the pimavanserin is administered to post-treat at least 120 minutes post to the MBDB form disclosed herein, including those described in Example 5. In some embodiments, the serotonin receptor modulator is pimavanserin, wherein the pimavanserin is administered to post-treat at least 150 minutes post to the MBDB form disclosed herein, including those described in Example 5. In some embodiments, the serotonin receptor modulator is pimavanserin, wherein the pimavanserin is administered to post-treat between about 15 minutes and about 150 minutes post to the MBDB form disclosed herein, including those described in Example 5. In some embodiments, the serotonin receptor modulator is pimavanserin, wherein the pimavanserin is administered to post-treat at least 180 minutes post to the MBDB form disclosed herein, including those described in Example 5. In some embodiments, the serotonin receptor modulator is pimavanserin, wherein the pimavanserin is administered to post-treat at least 210 minutes post to the MBDB form disclosed herein, including those described in Example 5. In some embodiments, the serotonin receptor modulator is pimavanserin, wherein the pimavanserin is administered to post-treat at least 240 minutes post to the MBDB form disclosed herein, including those described in Example 5. In some embodiments, the serotonin receptor modulator is pimavanserin, wherein the pimavanserin is administered to post-treat at least 270 minutes post to the MBDB form disclosed herein, including those described in Example 5. In some embodiments, the serotonin receptor modulator is pimavanserin, wherein the pimavanserin is administered to post-treat at least 300 minutes post to the MBDB form disclosed herein, including those described in Example 5. In some embodiments, the serotonin receptor modulator is pimavanserin, wherein the pimavanserin is administered to post-treat at least 330 minutes post to the MBDB form disclosed herein, including those described in Example 5. In some embodiments, the serotonin receptor modulator is pimavanserin, wherein the pimavanserin is administered to post-treat at least 360 minutes post to the MBDB form disclosed herein, including those described in Example 5. In some preferred embodiments, the serotonin receptor modulator is pimavanserin, wherein pimavanserin is administered to post-treat between about 60 minutes and about 180 minutes post to the administration of the MBDB form disclosed herein, including those described in Example 5.

In some embodiments, the serotonin receptor modulator is nelotanserin, wherein the nelotanserin is administered to post-treat at least 15 minutes post to the administration of the MBDB form disclosed herein, including those described in Example 5. In some embodiments, the serotonin receptor modulator is nelotanserin, wherein the nelotanserin is administered to post-treat at least 30 minutes post to the MBDB form disclosed herein, including those described in Example 5. In some embodiments, the serotonin receptor modulator is nelotanserin, wherein the nelotanserin is administered to post-treat between at least 60 minutes and 240 minutes post to the administration or release of the MBDB form disclosed herein, including those described in Example 5. In some embodiments, the serotonin receptor modulator is nelotanserin, wherein the nelotanserin is administered to post-treat at least 90 minutes post to the MBDB form disclosed herein, including those described in Example 5. In some embodiments, the serotonin receptor modulator is nelotanserin, wherein the nelotanserin is administered to post-treat at least 120 minutes post to the MBDB form disclosed herein, including those described in Example 5.

In some embodiments, the serotonin receptor modulator is nelotanserin, wherein the nelotanserin is administered to post-treat at least 150 minutes post to the MBDB form disclosed herein, including those described in Example 5. In some embodiments, the serotonin receptor modulator is nelotanserin, wherein the nelotanserin is administered to post-treat between about 15 minutes and about 150 minutes post to the MBDB form disclosed herein, including those described in Example 5. In some embodiments, the serotonin receptor modulator is nelotanserin, wherein the nelotanserin is administered to post-treat at least 180 minutes post to the MBDB form disclosed herein, including those described in Example 5. In some embodiments, the serotonin receptor modulator is nelotanserin, wherein the nelotanserin is administered to post-treat at least 210 minutes post to the MBDB form disclosed herein, including those described in Example 5. In some embodiments, the serotonin receptor modulator is nelotanserin, wherein the nelotanserin is administered to post-treat at least 240 minutes post to the MBDB form disclosed herein, including those described in Example 5. In some embodiments, the serotonin receptor modulator is nelotanserin, wherein the nelotanserin is administered to post-treat at least 270 minutes post to the MBDB form disclosed herein, including those described in Example 5.

In some embodiments, the serotonin receptor modulator is nelotanserin, wherein the nelotanserin is administered to post-treat at least 300 minutes post to the MBDB form disclosed herein, including those described in Example 5. In some embodiments, the serotonin receptor modulator is nelotanserin, wherein the nelotanserin is administered to post-treat at least 330 minutes post to the MBDB form disclosed herein, including those described in Example 5. In some embodiments, the serotonin receptor modulator is nelotanserin, wherein the nelotanserin is administered to post-treat at least 360 minutes post to the MBDB form disclosed herein, including those described in Example 5. In some preferred embodiments, the serotonin receptor modulator is nelotanserin, wherein nelotanserin is administered to post-treat between about 60 minutes and about 180 minutes post to the administration of the MBDB form disclosed herein, including those described in Example 5.

In some embodiments, the serotonin receptor modulator is pruvanserin, wherein the pruvanserin is administered to post-treat at least 15 minutes post to the administration of the MBDB form disclosed herein, including those described in Example 5. In some embodiments, the serotonin receptor modulator is pruvanserin, wherein the pruvanserin is administered to post-treat at least 30 minutes post to the MBDB form disclosed herein, including those described in Example 5. In some embodiments, the serotonin receptor modulator is pruvanserin, wherein the pruvanserin is administered to post-treat between at least 60 minutes and 240 minutes post to the administration or release of the MBDB form disclosed herein, including those described in Example 5. In some embodiments, the serotonin receptor modulator is pruvanserin, wherein the pruvanserin is administered to post-treat at least 90 minutes post to the MBDB form disclosed herein, including those described in Example 5. In some embodiments, the serotonin receptor modulator is pruvanserin, wherein the pruvanserin is administered to post-treat at least 120 minutes post to the MBDB form disclosed herein, including those described in Example 5. In some embodiments, the serotonin receptor modulator is pruvanserin, wherein the pruvanserin is administered to post-treat at least 150 minutes post to the MBDB form disclosed herein, including those described in Example 5. In some embodiments, the serotonin receptor modulator is pruvanserin, wherein the pruvanserin is administered to post-treat between about 15 minutes and about 150 minutes post to the MBDB form disclosed herein, including those described in Example 5. In some embodiments, the serotonin receptor modulator is pruvanserin, wherein the pruvanserin is administered to post-treat at least 180 minutes post to the MBDB form disclosed herein, including those described in Example 5. In some embodiments, the serotonin receptor modulator is pruvanserin, wherein the pruvanserin is administered to post-treat at least 210 minutes post to the MBDB form disclosed herein, including those described in Example 5.

In some embodiments, the serotonin receptor modulator is pruvanserin, wherein the pruvanserin is administered to post-treat at least 240 minutes post to the MBDB form disclosed herein, including those described in Example 5. In some embodiments, the serotonin receptor modulator is pruvanserin, wherein the pruvanserin is administered to post-treat at least 270 minutes post to the MBDB form disclosed herein, including those described in Example 5. In some embodiments, the serotonin receptor modulator is pruvanserin, wherein the pruvanserin is administered to post-treat at least 300 minutes post to the MBDB form disclosed herein, including those described in Example 5. In some embodiments, the serotonin receptor modulator is pruvanserin, wherein the pruvanserin is administered to post-treat at least 330 minutes post to the MBDB form disclosed herein, including those described in Example 5. In some embodiments, the serotonin receptor modulator is pruvanserin, wherein the pruvanserin is administered to post-treat at least 360 minutes post to the MBDB form disclosed herein, including those described in Example 5. In some preferred embodiments, the serotonin receptor modulator is pruvanserin, wherein pruvanserin is administered to post-treat between about 60 minutes and about 180 minutes post to the administration of the MBDB form disclosed herein, including those described in Example 5.

In some embodiments, the serotonin receptor modulator is flibanserin, wherein the flibanserin is administered to post-treat at least 15 minutes post to the administration of the MBDB form disclosed herein, including those described in Example 5. In some embodiments, the serotonin receptor modulator is flibanserin, wherein the flibanserin is administered to post-treat at least 30 minutes post to the MBDB form disclosed herein, including those described in Example 5. In some embodiments, the serotonin receptor modulator is flibanserin, wherein the flibanserin is administered to post-treat between at least 60 minutes and 240 minutes post to the administration or release of the MBDB form disclosed herein, including those described in Example 5. In some embodiments, the serotonin receptor modulator is flibanserin, wherein the flibanserin is administered to post-treat at least 90 minutes post to the MBDB form disclosed herein, including those described in Example 5. In some embodiments, the serotonin receptor modulator is flibanserin, wherein the flibanserin is administered to post-treat at least 120 minutes post to the MBDB form disclosed herein, including those described in Example 5. In some embodiments, the serotonin receptor modulator is flibanserin, wherein the flibanserin is administered to post-treat at least 150 minutes post to the MBDB form disclosed herein, including those described in Example 5. In some embodiments, the serotonin receptor modulator is flibanserin, wherein the flibanserin is administered to post-treat between about 15 minutes and about 150 minutes post to the MBDB form disclosed herein, including those described in Example 5. In some embodiments, the serotonin receptor modulator is flibanserin, wherein the flibanserin is administered to post-treat at least 180 minutes post to the MBDB form disclosed herein, including those described in Example 5. In some embodiments, the serotonin receptor modulator is flibanserin, wherein the flibanserin is administered to post-treat at least 210 minutes post to the MBDB form disclosed herein, including those described in Example 5.

In some embodiments, the serotonin receptor modulator is flibanserin, wherein the flibanserin is administered to post-treat at least 240 minutes post to the MBDB form disclosed herein, including those described in Example 5. In some embodiments, the serotonin receptor modulator is flibanserin, wherein the flibanserin is administered to post-treat at least 270 minutes post to the MBDB form disclosed herein, including those described in Example 5. In some embodiments, the serotonin receptor modulator is flibanserin, wherein the flibanserin is administered to post-treat at least 300 minutes post to the MBDB form disclosed herein, including those described in Example 5. In some embodiments, the serotonin receptor modulator is flibanserin, wherein the flibanserin is administered to post-treat at least 330 minutes post to the MBDB form disclosed herein, including those described in Example 5. In some embodiments, the serotonin receptor modulator is flibanserin, wherein the flibanserin is administered to post-treat at least 360 minutes post to the MBDB form disclosed herein, including those described in Example 5. In some preferred embodiments, the serotonin receptor modulator is flibanserin, wherein flibanserin is administered to post-treat between about 60 minutes and about 180 minutes post to the administration of the MBDB form disclosed herein, including those described in Example 5.

In some embodiments, the serotonin receptor modulator is olanzapine, wherein the olanzapine is administered to post-treat at least 15 minutes post to the administration of the MBDB form disclosed herein, including those described in Example 5. In some embodiments, the serotonin receptor modulator is olanzapine, wherein the olanzapine is administered to post-treat at least 30 minutes post to the MBDB form disclosed herein, including those described in Example 5. In some embodiments, the serotonin receptor modulator is olanzapine, wherein the olanzapine is administered to post-treat between at least 60 minutes and 240 minutes post to the administration or release of the MBDB form disclosed herein, including those described in Example 5. In some embodiments, the serotonin receptor modulator is olanzapine, wherein the olanzapine is administered to post-treat at least 90 minutes post to the MBDB form disclosed herein, including those described in Example 5. In some embodiments, the serotonin receptor modulator is olanzapine, wherein the olanzapine is administered to post-treat at least 120 minutes post to the MBDB form disclosed herein, including those described in Example 5. In some embodiments, the serotonin receptor modulator is olanzapine, wherein the olanzapine is administered to post-treat at least 150 minutes post to the MBDB form disclosed herein, including those described in Example 5. In some embodiments, the serotonin receptor modulator is olanzapine, wherein the olanzapine is administered to post-treat between about 15 minutes and about 150 minutes post to the MBDB form disclosed herein, including those described in Example 5. In some embodiments, the serotonin receptor modulator is olanzapine, wherein the olanzapine is administered to post-treat at least 180 minutes post to the MBDB form disclosed herein, including those described in Example 5. In some embodiments, the serotonin receptor modulator is olanzapine, wherein the olanzapine is administered to post-treat at least 210 minutes post to the MBDB form disclosed herein, including those described in Example 5.

In some embodiments, the serotonin receptor modulator is olanzapine, wherein the olanzapine is administered to post-treat at least 240 minutes post to the MBDB form disclosed herein, including those described in Example 5. In some embodiments, the serotonin receptor modulator is olanzapine, wherein the olanzapine is administered to post-treat at least 270 minutes post to the MBDB form disclosed herein, including those described in Example 5. In some embodiments, the serotonin receptor modulator is olanzapine, wherein the olanzapine is administered to post-treat at least 300 minutes post to the MBDB form disclosed herein, including those described in Example 5. In some embodiments, the serotonin receptor modulator is olanzapine, wherein the olanzapine is administered to post-treat at least 330 minutes post to the MBDB form disclosed herein, including those described in Example 5. In some embodiments, the serotonin receptor modulator is olanzapine, wherein the olanzapine is administered to post-treat at least 360 minutes post to the MBDB form disclosed herein, including those described in Example 5. In some preferred embodiments, the serotonin receptor modulator is olanzapine, wherein olanzapine is administered to post-treat between about 60 minutes and about 180 minutes post to the administration of the MBDB form disclosed herein, including those described in Example 5.

In some embodiments, the serotonin receptor modulator is quetiapine, wherein the quetiapine is administered to post-treat at least 15 minutes post to the administration of the MBDB form disclosed herein, including those described in Example 5. In some embodiments, the serotonin receptor modulator is quetiapine, wherein the quetiapine is administered to post-treat at least 30 minutes post to the MBDB form disclosed herein, including those described in Example 5. In some embodiments, the serotonin receptor modulator is quetiapine, wherein the quetiapine is administered to post-treat between at least 60 minutes and 240 minutes post to the administration or release of the MBDB form disclosed herein, including those described in Example 5. In some embodiments, the serotonin receptor modulator is quetiapine, wherein the quetiapine is administered to post-treat at least 90 minutes post to the MBDB form disclosed herein, including those described in Example 5. In some embodiments, the serotonin receptor modulator is quetiapine, wherein the quetiapine is administered to post-treat at least 120 minutes post to the MBDB form disclosed herein, including those described in Example 5. In some embodiments, the serotonin receptor modulator is quetiapine, wherein the quetiapine is administered to post-treat at least 150 minutes post to the MBDB form disclosed herein, including those described in Example 5. In some embodiments, the serotonin receptor modulator is quetiapine, wherein the quetiapine is administered to post-treat between about 15 minutes and about 150 minutes post to the MBDB form disclosed herein, including those described in Example 5. In some embodiments, the serotonin receptor modulator is quetiapine, wherein the quetiapine is administered to post-treat at least 180 minutes post to the MBDB form disclosed herein, including those described in Example 5. In some embodiments, the serotonin receptor modulator is quetiapine, wherein the quetiapine is administered to post-treat at least 210 minutes post to the MBDB form disclosed herein, including those described in Example 5.

In some embodiments, the serotonin receptor modulator is quetiapine, wherein the quetiapine is administered to post-treat at least 240 minutes post to the MBDB form disclosed herein, including those described in Example 5. In some embodiments, the serotonin receptor modulator is quetiapine, wherein the quetiapine is administered to post-treat at least 270 minutes post to the MBDB form disclosed herein, including those described in Example 5. In some embodiments, the serotonin receptor modulator is quetiapine, wherein the quetiapine is administered to post-treat at least 300 minutes post to the MBDB form disclosed herein, including those described in Example 5. In some embodiments, the serotonin receptor modulator is quetiapine, wherein the quetiapine is administered to post-treat at least 330 minutes post to the MBDB form disclosed herein, including those described in Example 5. In some embodiments, the serotonin receptor modulator is quetiapine, wherein the quetiapine is administered to post-treat at least 360 minutes post to the MBDB form disclosed herein, including those described in Example 5. In some preferred embodiments, the serotonin receptor modulator is quetiapine, wherein quetiapine is administered to post-treat between about 60 minutes and about 180 minutes post to the administration of the MBDB form disclosed herein, including those described in Example 5.

In some embodiments, the serotonin receptor modulator is risperidone, wherein the risperidone is administered to post-treat at least 15 minutes post to the administration of the MBDB form disclosed herein, including those described in Example 5. In some embodiments, the serotonin receptor modulator is risperidone, wherein the risperidone is administered to post-treat at least 30 minutes post to the MBDB form disclosed herein, including those described in Example 5. In some embodiments, the serotonin receptor modulator is risperidone, wherein the risperidone is administered to post-treat between at least 60 minutes and 240 minutes post to the administration or release of the MBDB form disclosed herein, including those described in Example 5. In some embodiments, the serotonin receptor modulator is risperidone, wherein the risperidone is administered to post-treat at least 90 minutes post to the MBDB form disclosed herein, including those described in Example 5. In some embodiments, the serotonin receptor modulator is risperidone, wherein the risperidone is administered to post-treat at least 120 minutes post to the MBDB form disclosed herein, including those described in Example 5. In some embodiments, the serotonin receptor modulator is risperidone, wherein the risperidone is administered to post-treat at least 150 minutes post to the MBDB form disclosed herein, including those described in Example 5. In some embodiments, the serotonin receptor modulator is risperidone, wherein the risperidone is administered to post-treat between about 15 minutes and about 150 minutes post to the MBDB form disclosed herein, including those described in Example 5. In some embodiments, the serotonin receptor modulator is risperidone, wherein the risperidone is administered to post-treat at least 180 minutes post to the MBDB form disclosed herein, including those described in Example 5. In some embodiments, the serotonin receptor modulator is risperidone, wherein the risperidone is administered to post-treat at least 210 minutes post to the MBDB form disclosed herein, including those described in Example 5.

In some embodiments, the serotonin receptor modulator is risperidone, wherein the risperidone is administered to post-treat at least 240 minutes post to the MBDB form disclosed herein, including those described in Example 5. In some embodiments, the serotonin receptor modulator is risperidone, wherein the risperidone is administered to post-treat at least 270 minutes post to the MBDB form disclosed herein, including those described in Example 5. In some embodiments, the serotonin receptor modulator is risperidone, wherein the risperidone is administered to post-treat at least 300 minutes post to the MBDB form disclosed herein, including those described in Example 5. In some embodiments, the serotonin receptor modulator is risperidone, wherein the risperidone is administered to post-treat at least 330 minutes post to the MBDB form disclosed herein, including those described in Example 5. In some embodiments, the serotonin receptor modulator is risperidone, wherein the risperidone is administered to post-treat at least 360 minutes post to the MBDB form disclosed herein, including those described in Example 5. In some preferred embodiments, the serotonin receptor modulator is risperidone, wherein risperidone is administered to post-treat between about 60 minutes and about 180 minutes post to the administration of the MBDB form disclosed herein, including those described in Example 5. In some embodiments, the serotonin receptor modulator for use with the 5-methoxy-2-aminoindane hydrochloride forms disclosed herein, including those described in Table Ex14 is eplivanserin, wherein the eplivanserin is administered in about 1 mg to about 40 mg, or about 5 mg to about 10 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is volinanserin, wherein the volinanserin is administered in about 1 mg to about 60 mg, or about 5 mg to about 20 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is ketanserin, wherein the ketanserin is administered in about 10 mg to about 80 mg, about 30 mg to about 50 mg, or about 40 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is ritanserin, wherein the ritanserin is administered in about 1 mg to about 40 mg, or about 2.5 mg to about 10 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is pimavanserin, wherein the pimavanserin is administered in about 1 mg to about 60 mg, or about 17 mg to about 34 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is nelotanserin, wherein the nelotanserin is administered in about 1 mg to about 80 mg, or about 40 mg to about 80 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is pruvanserin, wherein the pruvanserin is administered in about 1 mg to about 40 mg, or about 3 mg to about 10 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is flibanserin, wherein the flibanserin is administered in about 10 mg to about 200 mg, or about 80 mg to about 120 mg, or about 100 mg and 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride forms disclosed herein, including those described in Table Ex14 is olanzapine, wherein the olanzapine is administered in about 2.5 mg to about 30 mg, or about 5 mg or about 10 mg, or about 20 mg or about 25 mg, and the 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride solid forms disclosed herein, including those described in Table Ex14 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride solid forms disclosed herein, including those described in Table Ex14 is quetiapine, wherein the quetiapine is administered in about 25 mg to about 800 mg, or about 50 mg to about 100 mg, or about 150 mg or about 200 mg or about 250 mg or about 300 mg, and the 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride solid forms disclosed herein, including those described in Table Ex14 is an extended-release of quetiapine, wherein the extended-release of quetiapine is administered in about 50 mg to about 300 mg, or about 50 mg or about 100 mg or about 200 mg, or about 300 mg, and the 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride solid forms disclosed herein, including those described in Table Ex14 is risperidone, wherein the risperidone is administered in about 0.5 mg to about 20 mg or about. 5 mg, or about 1 mg, or about 2 mg, or about 3 mg or about 4 mg or about 5 mg or about 7.5 mg or about 10 mg or about 16 mg, and the 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In some embodiments, the serotonin receptor modulator for use with the 5-methoxy-2-aminoindane hydrochloride solid forms disclosed herein, including those described in Table Ex14 is an extended-release of risperidone including (RISPERDAL CONSTA), wherein the extended-release of risperidone is administered in about 12.5 mg, or about 25 mg, or about 37.5 mg, or about 50 mg, and the 5-methoxy-2-aminoindane hydrochloride forms disclosed herein, including those described in Table Ex14 are administered in about 20 mg to about 300 mg or about 60 mg to about 180 mg or about 160 mg to about 300 mg or about 1.6 mg per kg to about 4.8 mg per kg or about 99.2 mg to about 297.6 mg.

In certain embodiments, such as those described above a 5-methoxy-2-aminoindane hydrochloride form disclosed herein, including those described in Table Ex14 is co-administered with a serotonin receptor modulator in the same or in separate compositions. In one embodiment, the serotonin receptor modulator is administered prior to the 5-methoxy-2-aminoindane hydrochloride form disclosed herein, including those described in Table Ex14. In one embodiment, the 5-methoxy-2-aminoindane hydrochloride form disclosed herein, including those described in Table Ex14 is administered in a modified release formulation such that the subject is effectively pretreated with serotonin receptor modulator prior to release of an effective amount of 5-methoxy-2-aminoindane hydrochloride. In some embodiments the serotonin receptor modulator is part of a single fixed dose formulation that releases serotonin receptor modulator first followed by 5-methoxy-2-aminoindane hydrochloride on two different release profiles. In another embodiment the serotonin receptor modulator is administered first as a single dosage and after a length of time, the 5-methoxy-2-aminoindane hydrochloride form disclosed herein, including those described in Table Ex14 is administered as a second dosage separate from the first dosage.

Thus, in some embodiments, the serotonin receptor modulator is administered or released from a composition provided herein prior to the administration and/or release of the 5-methoxy-2-aminoindane hydrochloride form disclosed herein, including those described in Table Ex14. This allows pretreatment to attenuate activation of the serotonin receptor by the 5-methoxy-2-aminoindane hydrochloride form disclosed herein, including those described in Table Ex14.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the psychedelic. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin and the psychedelic is 5-methoxy-2-aminoindane hydrochloride, wherein the eplivanserin is administered to pretreat at least 15 minutes prior to the administration of the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat between at least 30 minutes prior and 360 minutes prior to the release or administration of the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat between at least 60 minutes prior and 360 minutes prior to the release or administration of the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat between at least 90 minutes and 240 minutes prior to the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat at least 120 minutes prior to the 5-methoxy-2-aminoindane hydrochloride form disclosed herein, including those described in Table Ex14.

In some embodiments, the serotonin receptor modulator is eplivanserin and the psychedelic is 5-methoxy-2-aminoindane hydrochloride, wherein the eplivanserin is administered to pretreat at least 150 minutes prior to the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat at least 180 minutes prior to the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat at least 210 minutes prior to the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat at least 240 minutes prior to the 5-methoxy-2-aminoindane hydrochloride form disclosed herein, including those described in Table Ex14.

In some embodiments, the serotonin receptor modulator is eplivanserin and the psychedelic is 5-methoxy-2-aminoindane hydrochloride, wherein the eplivanserin is administered to pretreat at least 270 minutes prior to the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat at least 300 minutes prior to the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat at least 330 minutes prior to the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to pretreat at least 360 minutes prior to the 5-methoxy-2-aminoindane hydrochloride form disclosed herein, including those described in Table Ex14.

In some preferred embodiments, the serotonin receptor modulator is eplivanserin and the psychedelic is 5-methoxy-2-aminoindane hydrochloride, wherein eplivanserin is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is volinanserin and the psychedelic is 5-methoxy-2-aminoindane hydrochloride, wherein the volinanserin is administered to pretreat a subject between at least 15 minutes and 360 minutes prior to the administration or release of the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat between at least 30 minutes and 360 minutes prior to the administration or release of the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 90 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 120 minutes prior to the 5-methoxy-2-aminoindane hydrochloride form disclosed herein, including those described in Table Ex14.

In some embodiments, the serotonin receptor modulator is volinanserin and the psychedelic is 5-methoxy-2-aminoindane hydrochloride, wherein the volinanserin is administered to pretreat at least 150 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat between about 15 minutes and about 150 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 180 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 210 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 240 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 270 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 300 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 330 minutes prior to the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to pretreat at least 360 minutes prior to the 5-methoxy-2-aminoindane hydrochloride form disclosed herein, including those described in Table Ex14. In some preferred embodiments, the serotonin receptor modulator is volinanserin and the psychedelic is 5-methoxy-2-aminoindane hydrochloride, wherein volinanserin is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is ketanserin and the psychedelic is 5-methoxy-2-aminoindane hydrochloride, wherein the ketanserin is administered to pretreat at least 15 minutes prior to the administration of the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat between at least 30 minutes and 360 minutes prior to the administration or release of the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 90 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 120 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 150 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat between about 15 minutes and about 150 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 180 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 210 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 240 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 270 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 300 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 330 minutes prior to the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to pretreat at least 360 minutes prior to the 5-methoxy-2-aminoindane hydrochloride form disclosed herein, including those described in Table Ex14. In some preferred embodiments, the serotonin receptor modulator is ketanserin and the psychedelic is 5-methoxy-2-aminoindane hydrochloride, wherein ketanserin is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is ritanserin and the psychedelic is 5-methoxy-2-aminoindane hydrochloride, wherein the ritanserin is administered to pretreat at least 15 minutes prior to the administration of the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 30 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 90 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 120 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 150 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat between about 15 minutes and about 150 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 180 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 210 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 240 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 270 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 300 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 330 minutes prior to the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to pretreat at least 360 minutes prior to the 5-methoxy-2-aminoindane hydrochloride form disclosed herein, including those described in Table Ex14. In some preferred embodiments, the serotonin receptor modulator is ritanserin and the psychedelic is 5-methoxy-2-aminoindane hydrochloride, wherein ritanserin is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is pimavanserin and the psychedelic is 5-methoxy-2-aminoindane hydrochloride, wherein the pimavanserin is administered to pretreat at least 15 minutes prior to the administration of the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 30 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 90 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 120 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 150 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat between about 15 minutes and about 150 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 180 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 210 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 240 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 270 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 300 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 330 minutes prior to the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to pretreat at least 360 minutes prior to the 5-methoxy-2-aminoindane hydrochloride form disclosed herein, including those described in Table Ex14. In some preferred embodiments, the serotonin receptor modulator is pimavanserin and the psychedelic is 5-methoxy-2-aminoindane hydrochloride, wherein pimavanserin is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is nelotanserin and the psychedelic is 5-methoxy-2-aminoindane hydrochloride, wherein the nelotanserin is administered to pretreat at least 15 minutes prior to the administration of the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 30 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 90 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 120 minutes prior to the 5-methoxy-2-aminoindane hydrochloride form disclosed herein, including those described in Table Ex14.

In some embodiments, the serotonin receptor modulator is nelotanserin and the psychedelic is 5-methoxy-2-aminoindane hydrochloride, wherein the nelotanserin is administered to pretreat at least 150 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat between about 15 minutes and about 150 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 180 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 210 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 240 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 270 minutes prior to the 5-methoxy-2-aminoindane hydrochloride form disclosed herein, including those described in Table Ex14.

In some embodiments, the serotonin receptor modulator is nelotanserin and the psychedelic is 5-methoxy-2-aminoindane hydrochloride, wherein the nelotanserin is administered to pretreat at least 300 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 330 minutes prior to the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to pretreat at least 360 minutes prior to the 5-methoxy-2-aminoindane hydrochloride form disclosed herein, including those described in Table Ex14. In some preferred embodiments, the serotonin receptor modulator is nelotanserin and the psychedelic is 5-methoxy-2-aminoindane hydrochloride, wherein nelotanserin is administered to pretreat between about 60 minutes and about 180 minutes prior to the administration of the 5-methoxy-2-aminoindane hydrochloride form disclosed herein, including those described in Table Ex14.

In some embodiments, the serotonin receptor modulator is pruvanserin and the psychedelic is 5-methoxy-2-aminoindane hydrochloride, wherein the pruvanserin is administered to pretreat at least 15 minutes prior to the administration of the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 30 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat between at least 60 minutes and 240 minutes prior to the administration or release of the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 90 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 120 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 150 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat between about 15 minutes and about 150 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 180 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 210 minutes prior to the 5-methoxy-2-aminoindane hydrochloride form disclosed herein, including those described in Table Ex14.

In some embodiments, the serotonin receptor modulator is pruvanserin and the psychedelic is 5-methoxy-2-aminoindane hydrochloride, wherein the pruvanserin is administered to pretreat at least 240 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 270 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 300 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 330 minutes prior to the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to pretreat at least 360 minutes prior to the 5-methoxy-2-aminoindane hydrochloride form disclosed herein, including those described in Table Ex14. In some preferred embodiments, the serotonin receptor modulator is pruvanserin and the psychedelic is 5-methoxy-2-aminoindane hydrochloride, wherein pruvanserin is administered to pretreat between about 60 minutes and about 180 minutes prior to the administration of the 5-methoxy-2-aminoindane hydrochloride form disclosed herein, including those described in Table Ex14.

In certain embodiments, such as those described above a 5-methoxy-2-aminoindane hydrochloride form disclosed herein, including those described in Table Ex14 is co-administered with a serotonin receptor modulator in the same or in separate compositions. In one embodiment, the serotonin receptor modulator is administered after the 5-methoxy-2-aminoindane hydrochloride form disclosed herein, including those described in Table Ex14. In one embodiment, the 5-methoxy-2-aminoindane hydrochloride form disclosed herein, including those described in Table Ex14 is administered in a modified release formulation such that the subject is effectively post-treated with serotonin receptor modulator post to release of an effective amount of the 5-methoxy-2-aminoindane hydrochloride. In some embodiments, the serotonin receptor modulator is part of a single fixed dose formulation that releases the 5-methoxy-2-aminoindane hydrochloride first followed by serotonin receptor modulator on two different release profiles. In another embodiment, the 5-methoxy-2-aminoindane hydrochloride form disclosed herein, including those described in Table Ex14 is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the 5-methoxy-2-aminoindane hydrochloride form disclosed herein, including those described in Table Ex14. This allows post-treatment to attenuate activation of the serotonin receptor by the 5-methoxy-2-aminoindane hydrochloride form disclosed herein, including those described in Table Ex14.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours after the release of the psychedelic. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours after the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour after the release of the psychedelic.

In a preferred embodiment, the serotonin receptor modulator is administered at about 1 hour to about 3 hours after the administration of the psychedelic.

In some embodiments, the serotonin receptor modulator is eplivanserin and the psychedelic is 5-methoxy-2-aminoindane hydrochloride, wherein the eplivanserin is administered to post-treat at least 15 minutes after the administration of the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat between at least 30 minutes after and 360 minutes after the release or administration of the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat between at least 60 minutes after and 360 minutes after the release or administration of the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat between at least 90 minutes and 240 minutes after the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat at least 120 minutes after the 5-methoxy-2-aminoindane hydrochloride form disclosed herein, including those described in Table Ex14.

In some embodiments, the serotonin receptor modulator is eplivanserin and the psychedelic is 5-methoxy-2-aminoindane hydrochloride, wherein the eplivanserin is administered to post-treat at least 150 minutes after the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat at least 180 minutes after the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat at least 210 minutes after the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat at least 240 minutes after the 5-methoxy-2-aminoindane hydrochloride form disclosed herein, including those described in Table Ex14.

In some embodiments, the serotonin receptor modulator is eplivanserin and the psychedelic is 5-methoxy-2-aminoindane hydrochloride, wherein the eplivanserin is administered to post-treat at least 270 minutes after the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat at least 300 minutes after the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat at least 330 minutes after the 5-methoxy-2-aminoindane hydrochloride form disclosed herein, including those described in Table Ex14. In some embodiments, the serotonin receptor modulator is eplivanserin and the psychedelic is 5-methoxy-2-aminoindane hydrochloride, wherein the eplivanserin is administered to post-treat at least 360 minutes after the 5-methoxy-2-aminoindane hydrochloride form disclosed herein, including those described in Table Ex14.

In some preferred embodiments, the serotonin receptor modulator is eplivanserin and the psychedelic is 5-methoxy-2-aminoindane hydrochloride, wherein eplivanserin is administered to post-treat between about 60 minutes and about 180 minutes after the administration of the 5-methoxy-2-aminoindane hydrochloride form disclosed herein, including those described in Table Ex14.

In some embodiments, the serotonin receptor modulator is volinanserin and the psychedelic is 5-methoxy-2-aminoindane hydrochloride, wherein the volinanserin is administered to post-treat a subject between at least 15 minutes and 360 minutes after the administration or release of the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat between at least 30 minutes and 360 minutes after the administration or release of the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat between at least 60 minutes and 240 minutes after the administration or release of the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 90 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 120 minutes after the 5-methoxy-2-aminoindane hydrochloride form disclosed herein, including those described in Table Ex14.

In some embodiments, the serotonin receptor modulator is volinanserin and the psychedelic is 5-methoxy-2-aminoindane hydrochloride, wherein the volinanserin is administered to post-treat at least 150 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat between about 15 minutes and about 150 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 180 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 210 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 240 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 270 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 300 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 330 minutes after the 5-methoxy-2-aminoindane hydrochloride form disclosed herein, including those described in Table Ex14. In some embodiments, the serotonin receptor modulator is volinanserin and the psychedelic is 5-methoxy-2-aminoindane hydrochloride, wherein the volinanserin is administered to post-treat at least 360 minutes after the 5-methoxy-2-aminoindane hydrochloride form disclosed herein, including those described in Table Ex14. In some preferred embodiments, the serotonin receptor modulator is volinanserin and the psychedelic is 5-methoxy-2-aminoindane hydrochloride, wherein volinanserin is administered to post-treat between about 60 minutes and about 180 minutes after the administration of the (R)-MDMA form.

In some embodiments, the serotonin receptor modulator is ketanserin and the psychedelic is 5-methoxy-2-aminoindane hydrochloride, wherein the ketanserin is administered to post-treat at least 15 minutes after the administration of the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat between at least 30 minutes and 360 minutes after the administration or release of the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat between at least 60 minutes and 240 minutes after the administration or release of the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 90 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 120 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 150 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat between about 15 minutes and about 150 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 180 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 210 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 240 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 270 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 300 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 330 minutes after the 5-methoxy-2-aminoindane hydrochloride form disclosed herein, including those described in Table Ex14. In some embodiments, the serotonin receptor modulator is ketanserin and the psychedelic is 5-methoxy-2-aminoindane hydrochloride, wherein the ketanserin is administered to post-treat at least 360 minutes after the 5-methoxy-2-aminoindane hydrochloride form disclosed herein, including those described in Table Ex14. In some preferred embodiments, the serotonin receptor modulator is ketanserin and the psychedelic is 5-methoxy-2-aminoindane hydrochloride, wherein ketanserin is administered to post-treat between about 60 minutes and about 180 minutes after the administration of the 5-methoxy-2-aminoindane hydrochloride form disclosed herein, including those described in Table Ex14.

In some embodiments, the serotonin receptor modulator is ritanserin and the psychedelic is 5-methoxy-2-aminoindane hydrochloride, wherein the ritanserin is administered to post-treat at least 15 minutes after the administration of the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 30 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat between at least 60 minutes and 240 minutes after the administration or release of the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 90 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 120 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 150 minutes after the 5-methoxy- 2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat between about 15 minutes and about 150 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 180 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 210 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 240 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 270 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 300 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 330 minutes after the 5-methoxy-2-aminoindane hydrochloride form disclosed herein, including those described in Table Ex14. In some embodiments, the serotonin receptor modulator is ritanserin and the psychedelic is 5-methoxy-2-aminoindane hydrochloride, wherein the ritanserin is administered to post-treat at least 360 minutes after the 5-methoxy-2-aminoindane hydrochloride form disclosed herein, including those described in Table Ex14. In some preferred embodiments, the serotonin receptor modulator is ritanserin and the psychedelic is 5-methoxy-2-aminoindane hydrochloride, wherein ritanserin is administered to post-treat between about 60 minutes and about 180 minutes after the administration of the 5-methoxy-2-aminoindane hydrochloride form disclosed herein, including those described in Table Ex14.

In some embodiments, the serotonin receptor modulator is pimavanserin and the psychedelic is 5-methoxy-2-aminoindane hydrochloride, wherein the pimavanserin is administered to post-treat at least 15 minutes after the administration of the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 30 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat between at least 60 minutes and 240 minutes after the administration or release of the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 90 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 120 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 150 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat between about 15 minutes and about 150 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 180 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 210 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 240 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 270 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 300 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 330 minutes after the 5-methoxy-2-aminoindane hydrochloride form disclosed herein, including those described in Table Ex14. In some embodiments, the serotonin receptor modulator is pimavanserin and the psychedelic is 5-methoxy-2-aminoindane hydrochloride, wherein the pimavanserin is administered to post-treat at least 360 minutes after the 5-methoxy-2-aminoindane hydrochloride form disclosed herein, including those described in Table Ex14. In some preferred embodiments, the serotonin receptor modulator is pimavanserin and the psychedelic is 5-methoxy-2-aminoindane hydrochloride, wherein pimavanserin is administered to post-treat between about 60 minutes and about 180 minutes after the administration of the 5-methoxy-2-aminoindane hydrochloride form disclosed herein, including those described in Table Ex14.

In some embodiments, the serotonin receptor modulator is nelotanserin and the psychedelic is 5-methoxy-2-aminoindane hydrochloride, wherein the nelotanserin is administered to post-treat at least 15 minutes after the administration of the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 30 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat between at least 60 minutes and 240 minutes after the administration or release of the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 90 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 120 minutes after the 5-methoxy-2-aminoindane hydrochloride form disclosed herein, including those described in Table Ex14.

In some embodiments, the serotonin receptor modulator is nelotanserin and the psychedelic is 5-methoxy-2-aminoindane hydrochloride, wherein the nelotanserin is administered to post-treat at least 150 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat between about 15 minutes and about 150 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 180 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 210 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 240 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 270 minutes after the 5-methoxy-2-aminoindane hydrochloride form disclosed herein, including those described in Table Ex14.

In some embodiments, the serotonin receptor modulator is nelotanserin and the psychedelic is 5-methoxy-2-aminoindane hydrochloride, wherein the nelotanserin is administered to post-treat at least 300 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 330 minutes after the 5-methoxy-2-aminoindane hydrochloride form disclosed herein, including those described in Table Ex14. In some embodiments, the serotonin receptor modulator is nelotanserin and the psychedelic is 5-methoxy-2-aminoindane hydrochloride, wherein the nelotanserin is administered to post-treat at least 360 minutes after the 5-methoxy-2-aminoindane hydrochloride form disclosed herein, including those described in Table Ex14. In some preferred embodiments, the serotonin receptor modulator is nelotanserin and the psychedelic is 5-methoxy-2-aminoindane hydrochloride, wherein nelotanserin is administered to post-treat between about 60 minutes and about 180 minutes after the administration of the 5-methoxy-2-aminoindane hydrochloride form disclosed herein, including those described in Table Ex14.

In some embodiments, the serotonin receptor modulator is pruvanserin and the psychedelic is 5-methoxy-2-aminoindane hydrochloride, wherein the pruvanserin is administered to post-treat at least 15 minutes after the administration of the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 30 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat between at least 60 minutes and 240 minutes after the administration or release of the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 90 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 120 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 150 minutes after the 5-methoxy-2-aminoindane hydrochloride form disclosed herein, including those described in Table Ex14. In some embodiments, the serotonin receptor modulator is pruvanserin and the psychedelic is 5-methoxy-2- aminoindane hydrochloride, wherein the pruvanserin is administered to post-treat between about 15 minutes and about 150 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 180 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 210 minutes after the 5-methoxy-2-aminoindane hydrochloride form disclosed herein, including those described in Table Ex14.

In some embodiments, the serotonin receptor modulator is pruvanserin and the psychedelic is 5-methoxy-2-aminoindane hydrochloride, wherein the pruvanserin is administered to post-treat at least 240 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 270 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 300 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 330 minutes after the 5-methoxy-2-aminoindane hydrochloride form disclosed herein, including those described in Table Ex14. In some embodiments, the serotonin receptor modulator is pruvanserin and the psychedelic is 5-methoxy-2-aminoindane hydrochloride, wherein the pruvanserin is administered to post-treat at least 360 minutes after the 5-methoxy-2-aminoindane hydrochloride form disclosed herein, including those described in Table Ex14. In some preferred embodiments, the serotonin receptor modulator is pruvanserin and the psychedelic is 5-methoxy-2-aminoindane hydrochloride, wherein pruvanserin is administered to post-treat between about 60 minutes and about 180 minutes after the administration of the 5-methoxy-2-aminoindane hydrochloride form disclosed herein, including those described in Table Ex14.

In some embodiments, the serotonin receptor modulator is flibanserin, wherein the flibanserin is administered to post-treat at least 15 minutes post to the administration of the 5-methoxy-2-aminoindane hydrochloride form disclosed herein, including those described in Table Ex14. In some embodiments, the serotonin receptor modulator is flibanserin, wherein the flibanserin is administered to post-treat at least 30 minutes post to the 5-methoxy-2-aminoindane hydrochloride form disclosed herein, including those described in Table Ex14. In some embodiments, the serotonin receptor modulator is flibanserin, wherein the flibanserin is administered to post-treat between at least 60 minutes and 240 minutes post to the administration or release of the 5-methoxy-2-aminoindane hydrochloride form disclosed herein, including those described in Table Ex14. In some embodiments, the serotonin receptor modulator is flibanserin, wherein the flibanserin is administered to post-treat at least 90 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 120 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 150 minutes post to the 5-methoxy-2-aminoindane hydrochloride form disclosed herein, including those described in Table Ex14. In some embodiments, the serotonin receptor modulator is flibanserin, wherein the flibanserin is administered to post-treat between about 15 minutes and about 150 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 180 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 210 minutes post to the 5-methoxy-2-aminoindane hydrochloride form disclosed herein, including those described in Table Ex14.

In some embodiments, the serotonin receptor modulator is flibanserin, wherein the flibanserin is administered to post-treat at least 240 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 270 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 300 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 330 minutes post to the 5-methoxy-2-aminoindane hydrochloride form disclosed herein, including those described in Table Ex14. In some embodiments, the serotonin receptor modulator is flibanserin, wherein the flibanserin is administered to post-treat at least 360 minutes post to the 5-methoxy-2-aminoindane hydrochloride form disclosed herein, including those described in Table Ex14. In some preferred embodiments, the serotonin receptor modulator is flibanserin, wherein flibanserin is administered to post-treat between about 60 minutes and about 180 minutes post to the administration of the 5-methoxy-2-aminoindane hydrochloride form disclosed herein, including those described in Table Ex14.

In some embodiments, the serotonin receptor modulator is olanzapine, wherein the olanzapine is administered to post-treat at least 15 minutes post to the administration of the 5-methoxy-2-aminoindane hydrochloride form disclosed herein, including those described in Table Ex14. In some embodiments, the serotonin receptor modulator is olanzapine, wherein the olanzapine is administered to post-treat at least 30 minutes post to the 5-methoxy-2-aminoindane hydrochloride form disclosed herein, including those described in Table Ex14. In some embodiments, the serotonin receptor modulator is olanzapine, wherein the olanzapine is administered to post-treat between at least 60 minutes and 240 minutes post to the administration or release of the 5-methoxy-2-aminoindane hydrochloride form disclosed herein, including those described in Table Ex14. In some embodiments, the serotonin receptor modulator is olanzapine, wherein the olanzapine is administered to post-treat at least 90 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 120 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 150 minutes post to the 5-methoxy-2-aminoindane hydrochloride form disclosed herein, including those described in Table Ex14. In some embodiments, the serotonin receptor modulator is olanzapine, wherein the olanzapine is administered to post-treat between about 15 minutes and about 150 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 180 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 210 minutes post to the 5-methoxy-2-aminoindane hydrochloride form disclosed herein, including those described in Table Ex14.

In some embodiments, the serotonin receptor modulator is olanzapine, wherein the olanzapine is administered to post-treat at least 240 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 270 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 300 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 330 minutes post to the 5-methoxy-2-aminoindane hydrochloride form disclosed herein, including those described in Table Ex14. In some embodiments, the serotonin receptor modulator is olanzapine, wherein the olanzapine is administered to post-treat at least 360 minutes post to the 5-methoxy-2-aminoindane hydrochloride form disclosed herein, including those described in Table Ex14. In some preferred embodiments, the serotonin receptor modulator is olanzapine, wherein olanzapine is administered to post-treat between about 60 minutes and about 180 minutes post to the administration of the 5-methoxy-2-aminoindane hydrochloride form disclosed herein, including those described in Table Ex14.

In some embodiments, the serotonin receptor modulator is quetiapine, wherein the quetiapine is administered to post-treat at least 15 minutes post to the administration of the 5-methoxy-2-aminoindane hydrochloride form disclosed herein, including those described in Table Ex14. In some embodiments, the serotonin receptor modulator is quetiapine, wherein the quetiapine is administered to post-treat at least 30 minutes post to the 5-methoxy-2-aminoindane hydrochloride form disclosed herein, including those described in Table Ex14. In some embodiments, the serotonin receptor modulator is quetiapine, wherein the quetiapine is administered to post-treat between at least 60 minutes and 240 minutes post to the administration or release of the 5-methoxy-2-aminoindane hydrochloride form disclosed herein, including those described in Table Ex14. In some embodiments, the serotonin receptor modulator is quetiapine, wherein the quetiapine is administered to post-treat at least 90 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 120 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 150 minutes post to the 5-methoxy-2-aminoindane hydrochloride form disclosed herein, including those described in Table Ex14. In some embodiments, the serotonin receptor modulator is quetiapine, wherein the quetiapine is administered to post-treat between about 15 minutes and about 150 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 180 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 210 minutes post to the 5-methoxy-2-aminoindane hydrochloride form disclosed herein, including those described in Table Ex14.

In some embodiments, the serotonin receptor modulator is quetiapine, wherein the quetiapine is administered to post-treat at least 240 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 270 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 300 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 330 minutes post to the 5-methoxy-2-aminoindane hydrochloride form disclosed herein, including those described in Table Ex14. In some embodiments, the serotonin receptor modulator is quetiapine, wherein the quetiapine is administered to post-treat at least 360 minutes post to the 5-methoxy-2-aminoindane hydrochloride form disclosed herein, including those described in Table Ex14. In some preferred embodiments, the serotonin receptor modulator is quetiapine, wherein quetiapine is administered to post-treat between about 60 minutes and about 180 minutes post to the administration of the 5-methoxy-2-aminoindane hydrochloride form disclosed herein, including those described in Table Ex14.

In some embodiments, the serotonin receptor modulator is risperidone, wherein the risperidone is administered to post-treat at least 15 minutes post to the administration of the 5-methoxy-2-aminoindane hydrochloride form disclosed herein, including those described in Table Ex14. In some embodiments, the serotonin receptor modulator is risperidone, wherein the risperidone is administered to post-treat at least 30 minutes post to the 5-methoxy-2-aminoindane hydrochloride form disclosed herein, including those described in Table Ex14. In some embodiments, the serotonin receptor modulator is risperidone, wherein the risperidone is administered to post-treat between at least 60 minutes and 240 minutes post to the administration or release of the 5-methoxy-2-aminoindane hydrochloride form disclosed herein, including those described in Table Ex14. In some embodiments, the serotonin receptor modulator is risperidone, wherein the risperidone is administered to post-treat at least 90 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 120 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 150 minutes post to the 5-methoxy-2-aminoindane hydrochloride form disclosed herein, including those described in Table Ex14. In some embodiments, the serotonin receptor modulator is risperidone, wherein the risperidone is administered to post-treat between about 15 minutes and about 150 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 180 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 210 minutes post to the 5-methoxy-2-aminoindane hydrochloride form disclosed herein, including those described in Table Ex14.

In some embodiments, the serotonin receptor modulator is risperidone, wherein the risperidone is administered to post-treat at least 240 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 270 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 300 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 330 minutes post to the 5-methoxy-2-aminoindane hydrochloride form disclosed herein, including those described in Table Ex14. In some embodiments, the serotonin receptor modulator is risperidone, wherein the risperidone is administered to post-treat at least 360 minutes post to the 5-methoxy-2-aminoindane hydrochloride form disclosed herein, including those described in Table Ex14. In some preferred embodiments, the serotonin receptor modulator is risperidone, wherein risperidone is administered to post-treat between about 60 minutes and about 180 minutes post to the administration of the 5-methoxy-2-aminoindane hydrochloride form disclosed herein, including those described in Table Ex14.

In some embodiments, the serotonin receptor modulator for use with the MBDB hydrochloride forms disclosed herein, including those described in Table Ex13 is eplivanserin, wherein the eplivanserin is administered in about 1 mg to about 40 mg, or about 5 mg to about 10 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with MBDB hydrochloride is volinanserin, wherein the volinanserin is administered in about 1 mg to about 60 mg, or about 5 mg to about 20 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride is ketanserin, wherein the ketanserin is administered in about 10 mg to about 80 mg, about 30 mg to about 50 mg, or about 40 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride is ritanserin, wherein the ritanserin is administered in about 1 mg to about 40 mg, or about 2.5 mg to about 10 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride is pimavanserin, wherein the pimavanserin is administered in about 1 mg to about 60 mg, or about 17 mg to about 34 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride is nelotanserin, wherein the nelotanserin is administered in about 1 mg to about 80 mg, or about 40 mg to about 80 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride is pruvanserin, wherein the pruvanserin is administered in about 1 mg to about 40 mg, or about 3 mg to about 10 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride is flibanserin, wherein the flibanserin is administered in about 10 mg to about 200 mg, or about 80 mg to about 120 mg, or about 100 mg and MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride forms disclosed herein, including those described in Table Ex13 is olanzapine, wherein the olanzapine is administered in about 2.5 mg to about 30 mg, or about 5 mg or about 10 mg, or about 20 mg or about 25 mg, and the MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride forms disclosed herein, including those described in Table Ex13 is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride forms disclosed herein, including those described in Table Ex13 is quetiapine, wherein the quetiapine is administered in about 25 mg to about 800 mg, or about 50 mg to about 100 mg, or about 150 mg or about 200 mg or about 250 mg or about 300 mg, and the MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride forms disclosed herein, including those described in Table Ex13 is an extended-release of quetiapine, wherein the extended-release of quetiapine is administered in about 50 mg to about 300 mg, or about 50 mg or about 100 mg or about 200 mg, or about 300 mg, and the MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride forms disclosed herein, including those described in Table Ex13 is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the MBDB hydrochloride forms disclosed herein, including those described in Table Ex13 are administered in about 10 mg to about 500 mg or about 150 mg to about 250 mg or about 180 mg or about 210 mg or about 250 mg.

In some embodiments, the serotonin receptor modulator for use with the MBDB hydrochloride forms disclosed herein, including those described in Table Ex13 is an extended-release of risperidone including (RISPERDAL CONSTA), wherein the extended-release of risperidone is administered in about 12.5 mg, or about 25 mg, or about 37.5 mg, or about 50 mg, and the MBDB hydrochloride forms disclosed herein, including those described in Table Ex13 are administered in about 10 mg to about 500 mg or about 150 mg to about 250 mg or about 180 mg or about 210 mg or about 250 mg.

In certain embodiments, such as those described above a MBDB HCl form disclosed herein, including those described in Table Ex13 is co-administered with a serotonin receptor modulator in the same or in separate compositions. In one embodiment, the serotonin receptor modulator is administered prior to the MBDB HCl form disclosed herein, including those described in Table Ex13. In one embodiment, the MBDB HCl form disclosed herein, including those described in Table Ex13 is administered in a modified release formulation such that the subject is effectively pretreated with serotonin receptor modulator prior to release of an effective amount of MBDB. In some embodiments the serotonin receptor modulator is part of a single fixed dose formulation that releases serotonin receptor modulator first followed by MBDB on two different release profiles. In another embodiment the serotonin receptor modulator is administered first as a single dosage and after a length of time, the MBDB HCl form disclosed herein, including those described in Table Ex13 is administered as a second dosage separate from the first dosage. Thus, in some embodiments, the serotonin receptor modulator is administered or released from a composition provided herein prior to the administration and/or release of the MBDB. This allows pretreatment to attenuate activation of the serotonin receptor by the MBDB.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the MBDB HCl form disclosed herein, including those described in Table Ex13. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of MBDB HCl form disclosed herein, including those described in Table Ex13. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the MBDB HCl form disclosed herein, including those described in Table Ex13.

In a preferred embodiment, the serotonin receptor modulator is administered at about 1 hour to about 3 hours prior to the administration of the MBDB HCl form disclosed herein, including those described in Table Ex13.

In some embodiments, the serotonin receptor modulator is eplivanserin, wherein the eplivanserin is administered to pretreat at least 15 minutes prior to the administration of the MBDB HCl form disclosed herein, including those described in Table Ex13. In some embodiments, the serotonin receptor modulator is eplivanserin, wherein the eplivanserin is administered to pretreat between at least 30 minutes prior and 360 minutes prior to the release or administration of the MBDB HCl form disclosed herein, including those described in Table Ex13. In some embodiments, the serotonin receptor modulator is eplivanserin, wherein the eplivanserin is administered to pretreat between at least 60 minutes prior and 360 minutes prior to the release or administration the MBDB HCl form disclosed herein, including those described in Table Ex13. In some embodiments, the serotonin receptor modulator is eplivanserin, wherein the eplivanserin is administered to pretreat between at least 90 minutes and 240 minutes prior to the MBDB HCl form disclosed herein, including those described in Table Ex13. In some embodiments, the serotonin receptor modulator is eplivanserin, wherein the eplivanserin is administered to pretreat at least 120 minutes prior to the MBDB HCl form disclosed herein, including those described in Table Ex13.

In some embodiments, the serotonin receptor modulator is eplivanserin, wherein the eplivanserin is administered to pretreat at least 150 minutes prior to the MBDB HCl form disclosed herein, including those described in Table Ex13. In some embodiments, the serotonin receptor modulator is eplivanserin, wherein the eplivanserin is administered to pretreat at least 180 minutes prior to the MBDB HCl form disclosed herein, including those described in Table Ex13. In some embodiments, the serotonin receptor modulator is eplivanserin, wherein the eplivanserin is administered to pretreat at least 210 minutes prior to the MBDB HCl form disclosed herein, including those described in Table Ex13. In some embodiments, the serotonin receptor modulator is eplivanserin, wherein the eplivanserin is administered to pretreat at least 240 minutes prior to the MBDB HCl form disclosed herein, including those described in Table Ex13.

In some embodiments, the serotonin receptor modulator is eplivanserin, wherein the eplivanserin is administered to pretreat at least 270 minutes prior to the MBDB HCl form disclosed herein, including those described in Table Ex13. In some embodiments, the serotonin receptor modulator is eplivanserin, wherein the eplivanserin is administered to pretreat at least 300 minutes prior to the MBDB HCl form disclosed herein, including those described in Table Ex13. In some embodiments, the serotonin receptor modulator is eplivanserin, wherein the eplivanserin is administered to pretreat at least 330 minutes prior to the MBDB HCl form disclosed herein, including those described in Table Ex13. In some embodiments, the serotonin receptor modulator is eplivanserin, wherein the eplivanserin is administered to pretreat at least 360 minutes prior to administration or release of the MBDB HCl form disclosed herein, including those described in Table Ex13.

In some preferred embodiments, the serotonin receptor modulator is eplivanserin, wherein eplivanserin is administered to pretreat between about 60 minutes and about 180 minutes prior to the administration or release of the MBDB HCl form disclosed herein, including those described in Table Ex13.

In some embodiments, the serotonin receptor modulator is volinanserin, wherein the volinanserin is administered to pretreat a subject between at least 15 minutes and 360 minutes prior to the administration or release of the MBDB HCl form disclosed herein, including those described in Table Ex13. In some embodiments, the serotonin receptor modulator is volinanserin, wherein the volinanserin is administered to pretreat between at least 30 minutes and 360 minutes prior to the administration or release of the MBDB HCl form disclosed herein, including those described in Table Ex13. In some embodiments, the serotonin receptor modulator is volinanserin, wherein the volinanserin is administered to pretreat between at least 60 minutes and 240 minutes prior to the administration or release of the MBDB HCl form disclosed herein, including those described in Table Ex13. In some embodiments, the serotonin receptor modulator is volinanserin, wherein the volinanserin is administered to pretreat at least 90 minutes prior to MBDB HCl form disclosed herein, including those described in Table Ex13. In some embodiments, the serotonin receptor modulator is volinanserin, wherein the volinanserin is administered to pretreat at least 120 minutes prior to the MBDB HCl form disclosed herein, including those described in Table Ex13.

In some embodiments, the serotonin receptor modulator is volinanserin, wherein the volinanserin is administered to pretreat at least 150 minutes prior to the MBDB HCl form disclosed herein, including those described in Table Ex13. In some embodiments, the serotonin receptor modulator is volinanserin, wherein the volinanserin is administered to pretreat between about 15 minutes and about 150 minutes prior to the MBDB HCl form disclosed herein, including those described in Table Ex13. In some embodiments, the serotonin receptor modulator is volinanserin, wherein the volinanserin is administered to pretreat at least 180 minutes prior to the MBDB HCl form disclosed herein, including those described in Table Ex13. In some embodiments, the serotonin receptor modulator is volinanserin, wherein the volinanserin is administered to pretreat at least 210 minutes prior to the MBDB HCl form disclosed herein, including those described in Table Ex13. In some embodiments, the serotonin receptor modulator is volinanserin, wherein the volinanserin is administered to pretreat at least 240 minutes prior to the MBDB HCl form disclosed herein, including those described in Table Ex13. In some embodiments, the serotonin receptor modulator is volinanserin, wherein the volinanserin is administered to pretreat at least 270 minutes prior to the MBDB HCl form disclosed herein, including those described in Table Ex13. In some embodiments, the serotonin receptor modulator is volinanserin, wherein the volinanserin is administered to pretreat at least 300 minutes prior to the MBDB HCl form disclosed herein, including those described in Table Ex13. In some embodiments, the serotonin receptor modulator is volinanserin, wherein the volinanserin is administered to pretreat at least 330 minutes prior to MBDB HCl form disclosed herein, including those described in Table Ex13. In some embodiments, the serotonin receptor modulator is volinanserin, wherein the volinanserin is administered to pretreat at least 360 minutes prior to the MBDB HCl form disclosed herein, including those described in Table Ex13. In some preferred embodiments, the serotonin receptor modulator is volinanserin, wherein volinanserin is administered to pretreat between about 60 minutes and about 180 minutes prior to the administration of the MBDB HCl form disclosed herein, including those described in Table Ex13.

In some embodiments, the serotonin receptor modulator is ketanserin, wherein the ketanserin is administered to pretreat at least 15 minutes prior to the administration of the MBDB HCl form disclosed herein, including those described in Table Ex13. In some embodiments, the serotonin receptor modulator is ketanserin, wherein the ketanserin is administered to pretreat between at least 30 minutes and 360 minutes prior to the administration or release of the MBDB HCl form disclosed herein, including those described in Table Ex13. In some embodiments, the serotonin receptor modulator is ketanserin, wherein the ketanserin is administered to pretreat between at least 60 minutes and 240 minutes prior to the administration or release of the MBDB HCl form disclosed herein, including those described in Table Ex13. In some embodiments, the serotonin receptor modulator is ketanserin, wherein the ketanserin is administered to pretreat at least 90 minutes prior to the MBDB HCl form disclosed herein, including those described in Table Ex13. In some embodiments, the serotonin receptor modulator is ketanserin, wherein the ketanserin is administered to pretreat at least 120 minutes prior to the MBDB HCl form disclosed herein, including those described in Table Ex13. In some embodiments, the serotonin receptor modulator is ketanserin, wherein the ketanserin is administered to pretreat at least 150 minutes prior to the MBDB HCl form disclosed herein, including those described in Table Ex13. In some embodiments, the serotonin receptor modulator is ketanserin, wherein the ketanserin is administered to pretreat between about 15 minutes and about 150 minutes prior to the MBDB HCl form disclosed herein, including those described in Table Ex13. In some embodiments, the serotonin receptor modulator is ketanserin, wherein the ketanserin is administered to pretreat at least 180 minutes prior to the MBDB HCl form disclosed herein, including those described in Table Ex13. In some embodiments, the serotonin receptor modulator is ketanserin, wherein the ketanserin is administered to pretreat at least 210 minutes prior to the MBDB HCl form disclosed herein, including those described in Table Ex13. In some embodiments, the serotonin receptor modulator is ketanserin, wherein the ketanserin is administered to pretreat at least 240 minutes prior to the MBDB HCl form disclosed herein, including those described in Table Ex13. In some embodiments, the serotonin receptor modulator is ketanserin, wherein the ketanserin is administered to pretreat at least 270 minutes prior to the MBDB HCl form disclosed herein, including those described in Table Ex13. In some embodiments, the serotonin receptor modulator is ketanserin, wherein the ketanserin is administered to pretreat at least 300 minutes prior to the MBDB HCl form disclosed herein, including those described in Table Ex13. In some embodiments, the serotonin receptor modulator is ketanserin, wherein the ketanserin is administered to pretreat at least 330 minutes prior to the MBDB HCl form disclosed herein, including those described in Table Ex13. In some embodiments, the serotonin receptor modulator is ketanserin, wherein the ketanserin is administered to pretreat at least 360 minutes prior to the MBDB HCl form disclosed herein, including those described in Table Ex13. In some preferred embodiments, the serotonin receptor modulator is ketanserin, wherein ketanserin is administered to pretreat between about 60 minutes and about 180 minutes prior to the administration of the MBDB HCl form disclosed herein, including those described in Table Ex13.

In some embodiments, the serotonin receptor modulator is ritanserin, wherein the ritanserin is administered to pretreat at least 15 minutes prior to the administration of the MBDB HCl form disclosed herein, including those described in Table Ex13. In some embodiments, the serotonin receptor modulator is ritanserin, wherein the ritanserin is administered to pretreat at least 30 minutes prior to the MBDB HCl form disclosed herein, including those described in Table Ex13. In some embodiments, the serotonin receptor modulator is ritanserin wherein the ritanserin is administered to pretreat between at least 60 minutes and 240 minutes prior to the administration or release of the MBDB HCl form disclosed herein, including those described in Table Ex13. In some embodiments, the serotonin receptor modulator is ritanserin, wherein the ritanserin is administered to pretreat at least 90 minutes prior to the MBDB HCl form disclosed herein, including those described in Table Ex13. In some embodiments, the serotonin receptor modulator is ritanserin, wherein the ritanserin is administered to pretreat at least 120 minutes prior to the MBDB HCl form disclosed herein, including those described in Table Ex13. In some embodiments, the serotonin receptor modulator is ritanserin, wherein the ritanserin is administered to pretreat at least 150 minutes prior to the MBDB HCl form disclosed herein, including those described in Table Ex13. In some embodiments, the serotonin receptor modulator is ritanserin, wherein the ritanserin is administered to pretreat between about 15 minutes and about 150 minutes prior to the MBDB HCl form disclosed herein, including those described in Table Ex13. In some embodiments, the serotonin receptor modulator is ritanserin, wherein the ritanserin is administered to pretreat at least 180 minutes prior to the MBDB HCl form disclosed herein, including those described in Table Ex13. In some embodiments, the serotonin receptor modulator is ritanserin, wherein the ritanserin is administered to pretreat at least 210 minutes prior to the MBDB HCl form disclosed herein, including those described in Table Ex13. In some embodiments, the serotonin receptor modulator is ritanserin, wherein the ritanserin is administered to pretreat at least 240 minutes prior to the MBDB HCl form disclosed herein, including those described in Table Ex13. In some embodiments, the serotonin receptor modulator is ritanserin, wherein the ritanserin is administered to pretreat at least 270 minutes prior to the MBDB HCl form disclosed herein, including those described in Table Ex13. In some embodiments, the serotonin receptor modulator is ritanserin, wherein the ritanserin is administered to pretreat at least 300 minutes prior to the MBDB HCl form disclosed herein, including those described in Table Ex13. In some embodiments, the serotonin receptor modulator is ritanserin, wherein the ritanserin is administered to pretreat at least 330 minutes prior to the MBDB HCl form disclosed herein, including those described in Table Ex13. In some embodiments, the serotonin receptor modulator is ritanserin, wherein the ritanserin is administered to pretreat at least 360 minutes prior to the MBDB HCl form disclosed herein, including those described in Table Ex13. In some preferred embodiments, the serotonin receptor modulator is ritanserin, wherein ritanserin is administered to pretreat between about 60 minutes and about 180 minutes prior to the administration of the MBDB HCl form disclosed herein, including those described in Table Ex13.

In some embodiments, the serotonin receptor modulator is pimavanserin, wherein the pimavanserin is administered to pretreat at least 15 minutes prior to the administration of the MBDB HCl form disclosed herein, including those described in Table Ex13. In some embodiments, the serotonin receptor modulator is pimavanserin, wherein the pimavanserin is administered to pretreat at least 30 minutes prior to the MBDB HCl form disclosed herein, including those described in Table Ex13. In some embodiments, the serotonin receptor modulator is pimavanserin, wherein the pimavanserin is administered to pretreat between at least 60 minutes and 240 minutes prior to the administration or release of the MBDB HCl form disclosed herein, including those described in Table Ex13. In some embodiments, the serotonin receptor modulator is pimavanserin, wherein the pimavanserin is administered to pretreat at least 90 minutes prior to the MBDB HCl form disclosed herein, including those described in Table Ex13. In some embodiments, the serotonin receptor modulator is pimavanserin, wherein the pimavanserin is administered to pretreat at least 120 minutes prior to the MBDB HCl form disclosed herein, including those described in Table Ex13. In some embodiments, the serotonin receptor modulator is pimavanserin, wherein the pimavanserin is administered to pretreat at least 150 minutes prior to the MBDB HCl form disclosed herein, including those described in Table Ex13. In some embodiments, the serotonin receptor modulator is pimavanserin, wherein the pimavanserin is administered to pretreat between about 15 minutes and about 150 minutes prior to the MBDB HCl form disclosed herein, including those described in Table Ex13. In some embodiments, the serotonin receptor modulator is pimavanserin, wherein the pimavanserin is administered to pretreat at least 180 minutes prior to the MBDB HCl form disclosed herein, including those described in Table Ex13. In some embodiments, the serotonin receptor modulator is pimavanserin, wherein the pimavanserin is administered to pretreat at least 210 minutes prior to the MBDB HCl form disclosed herein, including those described in Table Ex13. In some embodiments, the serotonin receptor modulator is pimavanserin, wherein the pimavanserin is administered to pretreat at least 240 minutes prior to the MBDB HCl form disclosed herein, including those described in Table Ex13. In some embodiments, the serotonin receptor modulator is pimavanserin, wherein the pimavanserin is administered to pretreat at least 270 minutes prior to the MBDB HCl form disclosed herein, including those described in Table Ex13. In some embodiments, the serotonin receptor modulator is pimavanserin, wherein the pimavanserin is administered to pretreat at least 300 minutes prior to the MBDB HCl form disclosed herein, including those described in Table Ex13. In some embodiments, the serotonin receptor modulator is pimavanserin, wherein the pimavanserin is administered to pretreat at least 330 minutes prior to the MBDB HCl form disclosed herein, including those described in Table Ex13. In some embodiments, the serotonin receptor modulator is pimavanserin, wherein the pimavanserin is administered to pretreat at least 360 minutes prior to the MBDB HCl form disclosed herein, including those described in Table Ex13. In some preferred embodiments, the serotonin receptor modulator is pimavanserin, wherein pimavanserin is administered to pretreat between about 60 minutes and about 180 minutes prior to the administration of the MBDB HCl form disclosed herein, including those described in Table Ex13.

In some embodiments, the serotonin receptor modulator is nelotanserin, wherein the nelotanserin is administered to pretreat at least 15 minutes prior to the administration of the MBDB HCl form disclosed herein, including those described in Table Ex13. In some embodiments, the serotonin receptor modulator is nelotanserin, wherein the nelotanserin is administered to pretreat at least 30 minutes prior to the MBDB HCl form disclosed herein, including those described in Table Ex13. In some embodiments, the serotonin receptor modulator is nelotanserin, wherein the nelotanserin is administered to pretreat between at least 60 minutes and 240 minutes prior to the administration or release of the MBDB HCl form disclosed herein, including those described in Table Ex13. In some embodiments, the serotonin receptor modulator is nelotanserin, wherein the nelotanserin is administered to pretreat at least 90 minutes prior to the MBDB HCl form disclosed herein, including those described in Table Ex13. In some embodiments, the serotonin receptor modulator is nelotanserin, wherein the nelotanserin is administered to pretreat at least 120 minutes prior to the MBDB HCl form disclosed herein, including those described in Table Ex13.

In some embodiments, the serotonin receptor modulator is nelotanserin, wherein the nelotanserin is administered to pretreat at least 150 minutes prior to the MBDB HCl form disclosed herein, including those described in Table Ex13. In some embodiments, the serotonin receptor modulator is nelotanserin, wherein the nelotanserin is administered to pretreat between about 15 minutes and about 150 minutes prior to the MBDB HCl form disclosed herein, including those described in Table Ex13. In some embodiments, the serotonin receptor modulator is nelotanserin, wherein the nelotanserin is administered to pretreat at least 180 minutes prior to the MBDB HCl form disclosed herein, including those described in Table Ex13. In some embodiments, the serotonin receptor modulator is nelotanserin, wherein the nelotanserin is administered to pretreat at least 210 minutes prior to the MBDB HCl form disclosed herein, including those described in Table Ex13. In some embodiments, the serotonin receptor modulator is nelotanserin, wherein the nelotanserin is administered to pretreat at least 240 minutes prior to the MBDB HCl form disclosed herein, including those described in Table Ex13. In some embodiments, the serotonin receptor modulator is nelotanserin, wherein the nelotanserin is administered to pretreat at least 270 minutes prior to the MBDB HCl form disclosed herein, including those described in Table Ex13.

In some embodiments, the serotonin receptor modulator is nelotanserin, wherein the nelotanserin is administered to pretreat at least 300 minutes prior to the MBDB HCl form disclosed herein, including those described in Table Ex13. In some embodiments, the serotonin receptor modulator is nelotanserin, wherein the nelotanserin is administered to pretreat at least 330 minutes prior to the MBDB HCl form disclosed herein, including those described in Table Ex13. In some embodiments, the serotonin receptor modulator is nelotanserin, wherein the nelotanserin is administered to pretreat at least 360 minutes prior to the MBDB HCl form disclosed herein, including those described in Table Ex13. In some preferred embodiments, the serotonin receptor modulator is nelotanserin, wherein nelotanserin is administered to pretreat between about 60 minutes and about 180 minutes prior to the administration of the MBDB HCl form disclosed herein, including those described in Table Ex13.

In some embodiments, the serotonin receptor modulator is pruvanserin, wherein the pruvanserin is administered to pretreat at least 15 minutes prior to the administration of the MBDB HCl form disclosed herein, including those described in Table Ex13. In some embodiments, the serotonin receptor modulator is pruvanserin, wherein the pruvanserin is administered to pretreat at least 30 minutes prior to the MBDB HCl form disclosed herein, including those described in Table Ex13. In some embodiments, the serotonin receptor modulator is pruvanserin, wherein the pruvanserin is administered to pretreat between at least 60 minutes and 240 minutes prior to the administration or release of the MBDB HCl form disclosed herein, including those described in Table Ex13. In some embodiments, the serotonin receptor modulator is pruvanserin, wherein the pruvanserin is administered to pretreat at least 90 minutes prior to the MBDB HCl form disclosed herein, including those described in Table Ex13. In some embodiments, the serotonin receptor modulator is pruvanserin, wherein the pruvanserin is administered to pretreat at least 120 minutes prior to the MBDB HCl form disclosed herein, including those described in Table Ex13. In some embodiments, the serotonin receptor modulator is pruvanserin, wherein the pruvanserin is administered to pretreat at least 150 minutes prior to the MBDB HCl form disclosed herein, including those described in Table Ex13. In some embodiments, the serotonin receptor modulator is pruvanserin, wherein the pruvanserin is administered to pretreat between about 15 minutes and about 150 minutes prior to the MBDB HCl form disclosed herein, including those described in Table Ex13. In some embodiments, the serotonin receptor modulator is pruvanserin, wherein the pruvanserin is administered to pretreat at least 180 minutes prior to the MBDB HCl form disclosed herein, including those described in Table Ex13. In some embodiments, the serotonin receptor modulator is pruvanserin, wherein the pruvanserin is administered to pretreat at least 210 minutes prior to the MBDB HCl form disclosed herein, including those described in Table Ex13.

In some embodiments, the serotonin receptor modulator is pruvanserin, wherein the pruvanserin is administered to pretreat at least 240 minutes prior to the MBDB HCl form disclosed herein, including those described in Table Ex13. In some embodiments, the serotonin receptor modulator is pruvanserin, wherein the pruvanserin is administered to pretreat at least 270 minutes prior to the MBDB HCl form disclosed herein, including those described in Table Ex13. In some embodiments, the serotonin receptor modulator is pruvanserin, wherein the pruvanserin is administered to pretreat at least 300 minutes prior to the MBDB HCl form disclosed herein, including those described in Table Ex13. In some embodiments, the serotonin receptor modulator is pruvanserin, wherein the pruvanserin is administered to pretreat at least 330 minutes prior to the MBDB HCl form disclosed herein, including those described in Table Ex13. In some embodiments, the serotonin receptor modulator is pruvanserin, wherein the pruvanserin is administered to pretreat at least 360 minutes prior to the MBDB HCl form disclosed herein, including those described in Table Ex13. In some preferred embodiments, the serotonin receptor modulator is pruvanserin, wherein pruvanserin is administered to pretreat between about 60 minutes and about 180 minutes prior to the administration of the MBDB HCl form disclosed herein, including those described in Table Ex13.

In some embodiments, the serotonin receptor modulator is administered after a compound disclosed herein, such as from about one to about three hours post administration of a compound disclosed herein. In some embodiments, the serotonin receptor modulator is administered at most about one hour post to the presently disclosed compound.

In certain embodiments, such as those described above a MBDB HCl form disclosed herein, including those described in Table Ex13 is co-administered with a serotonin receptor modulator in the same or in separate compositions. In one embodiment, the serotonin receptor modulator is administered after the MBDB HCl form disclosed herein, including those described in Table Ex13. In one embodiment, the MBDB HCl form disclosed herein, including those described in Table Ex13 is administered in a modified release formulation such that the subject is effectively post-treated with serotonin receptor modulator post to release of an effective amount of MBDB. In some embodiments, the serotonin receptor modulator is part of a single fixed dose formulation that releases MBDB first followed by serotonin receptor modulator on two different release profiles. In another embodiment, the MBDB HCl form disclosed herein, including those described in Table Ex13 is administered first as a single dosage and, after a length of time, serotonin receptor modulator is administered as a second dosage separate from the first dosage. Thus, in some embodiments, the serotonin receptor modulator is administered or released from a composition provided herein post to the administration and/or release of the MBDB HCl form disclosed herein, including those described in Table Ex13. This allows post-treatment to attenuate activation of the serotonin receptor by the MBDB.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours post to the release of the MBDB HCl form disclosed herein, including those described in Table Ex13. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours post to the release of MBDB HCl form disclosed herein, including those described in Table Ex13. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour post to the release of the MBDB HCl form disclosed herein, including those described in Table Ex13.

In a preferred embodiment, the serotonin receptor modulator is administered at about 1 hour to about 3 hours post to the administration of the MBDB HCl form disclosed herein, including those described in Table Ex13.

In some embodiments, the serotonin receptor modulator is eplivanserin, wherein the eplivanserin is administered to post-treat at least 15 minutes post to the administration of the MBDB HCl form disclosed herein, including those described in Table Ex13. In some embodiments, the serotonin receptor modulator is eplivanserin, wherein the eplivanserin is administered to post-treat between at least 30 minutes post and 360 minutes post to the release or administration of the MBDB HCl form disclosed herein, including those described in Table Ex13. In some embodiments, the serotonin receptor modulator is eplivanserin, wherein the eplivanserin is administered to post-treat between at least 60 minutes post and 360 minutes post to the release or administration the MBDB HCl form disclosed herein, including those described in Table Ex13. In some embodiments, the serotonin receptor modulator is eplivanserin, wherein the eplivanserin is administered to post-treat between at least 90 minutes and 240 minutes post to the MBDB HCl form disclosed herein, including those described in Table Ex13. In some embodiments, the serotonin receptor modulator is eplivanserin, wherein the eplivanserin is administered to post-treat at least 120 minutes post to the MBDB HCl form disclosed herein, including those described in Table Ex13.

In some embodiments, the serotonin receptor modulator is eplivanserin, wherein the eplivanserin is administered to post-treat at least 150 minutes post to the MBDB HCl form disclosed herein, including those described in Table Ex13. In some embodiments, the serotonin receptor modulator is eplivanserin, wherein the eplivanserin is administered to post-treat at least 180 minutes post to the MBDB HCl form disclosed herein, including those described in Table Ex13. In some embodiments, the serotonin receptor modulator is eplivanserin, wherein the eplivanserin is administered to post-treat at least 210 minutes post to the MBDB HCl form disclosed herein, including those described in Table Ex13. In some embodiments, the serotonin receptor modulator is eplivanserin, wherein the eplivanserin is administered to post-treat at least 240 minutes post to the MBDB HCl form disclosed herein, including those described in Table Ex13.

In some embodiments, the serotonin receptor modulator is eplivanserin, wherein the eplivanserin is administered to post-treat at least 270 minutes post to the MBDB HCl form disclosed herein, including those described in Table Ex13. In some embodiments, the serotonin receptor modulator is eplivanserin, wherein the eplivanserin is administered to post-treat at least 300 minutes post to the MBDB HCl form disclosed herein, including those described in Table Ex13. In some embodiments, the serotonin receptor modulator is eplivanserin, wherein the eplivanserin is administered to post-treat at least 330 minutes post to the MBDB HCl form disclosed herein, including those described in Table Ex13. In some embodiments, the serotonin receptor modulator is eplivanserin, wherein the eplivanserin is administered to post-treat at least 360 minutes post to administration or release of the MBDB HCl form disclosed herein, including those described in Table Ex13.

In some preferred embodiments, the serotonin receptor modulator is eplivanserin, wherein eplivanserin is administered to post-treat between about 60 minutes and about 180 minutes post to the administration or release of the MBDB HCl form disclosed herein, including those described in Table Ex13.

In some embodiments, the serotonin receptor modulator is volinanserin, wherein the volinanserin is administered to post-treat a subject between at least 15 minutes and 360 minutes post to the administration or release of the MBDB HCl form disclosed herein, including those described in Table Ex13. In some embodiments, the serotonin receptor modulator is volinanserin, wherein the volinanserin is administered to post-treat between at least 30 minutes and 360 minutes post to the administration or release of the MBDB HCl form disclosed herein, including those described in Table Ex13. In some embodiments, the serotonin receptor modulator is volinanserin, wherein the volinanserin is administered to post-treat between at least 60 minutes and 240 minutes post to the administration or release of the MBDB HCl form disclosed herein, including those described in Table Ex13. In some embodiments, the serotonin receptor modulator is volinanserin, wherein the volinanserin is administered to post-treat at least 90 minutes post to MBDB HCl form disclosed herein, including those described in Table Ex13. In some embodiments, the serotonin receptor modulator is volinanserin, wherein the volinanserin is administered to post-treat at least 120 minutes post to the MBDB HCl form disclosed herein, including those described in Table Ex13.

In some embodiments, the serotonin receptor modulator is volinanserin, wherein the volinanserin is administered to post-treat at least 150 minutes post to the MBDB HCl form disclosed herein, including those described in Table Ex13. In some embodiments, the serotonin receptor modulator is volinanserin, wherein the volinanserin is administered to post-treat between about 15 minutes and about 150 minutes post to the MBDB HCl form disclosed herein, including those described in Table Ex13. In some embodiments, the serotonin receptor modulator is volinanserin, wherein the volinanserin is administered to post-treat at least 180 minutes post to the MBDB HCl form disclosed herein, including those described in Table Ex13. In some embodiments, the serotonin receptor modulator is volinanserin, wherein the volinanserin is administered to post-treat at least 210 minutes post to the MBDB HCl form disclosed herein, including those described in Table Ex13. In some embodiments, the serotonin receptor modulator is volinanserin, wherein the volinanserin is administered to post-treat at least 240 minutes post to the MBDB HCl form disclosed herein, including those described in Table Ex13. In some embodiments, the serotonin receptor modulator is volinanserin, wherein the volinanserin is administered to post-treat at least 270 minutes post to the MBDB HCl form disclosed herein, including those described in Table Ex13. In some embodiments, the serotonin receptor modulator is volinanserin, wherein the volinanserin is administered to post-treat at least 300 minutes post to the MBDB HCl form disclosed herein, including those described in Table Ex13. In some embodiments, the serotonin receptor modulator is volinanserin, wherein the volinanserin is administered to post-treat at least 330 minutes post to MBDB HCl form disclosed herein, including those described in Table Ex13. In some embodiments, the serotonin receptor modulator is volinanserin, wherein the volinanserin is administered to post-treat at least 360 minutes post to the MBDB HCl form disclosed herein, including those described in Table Ex13. In some preferred embodiments, the serotonin receptor modulator is volinanserin, wherein volinanserin is administered to post-treat between about 60 minutes and about 180 minutes post to the administration of the MBDB HCl form disclosed herein, including those described in Table Ex13.

In some embodiments, the serotonin receptor modulator is ketanserin, wherein the ketanserin is administered to post-treat at least 15 minutes post to the administration of the MBDB HCl form disclosed herein, including those described in Table Ex13. In some embodiments, the serotonin receptor modulator is ketanserin, wherein the ketanserin is administered to post-treat between at least 30 minutes and 360 minutes post to the administration or release of the MBDB HCl form disclosed herein, including those described in Table Ex13. In some embodiments, the serotonin receptor modulator is ketanserin, wherein the ketanserin is administered to post-treat between at least 60 minutes and 240 minutes post to the administration or release of the MBDB HCl form disclosed herein, including those described in Table Ex13. In some embodiments, the serotonin receptor modulator is ketanserin, wherein the ketanserin is administered to post-treat at least 90 minutes post to the MBDB HCl form disclosed herein, including those described in Table Ex13. In some embodiments, the serotonin receptor modulator is ketanserin, wherein the ketanserin is administered to post-treat at least 120 minutes post to the MBDB HCl form disclosed herein, including those described in Table Ex13. In some embodiments, the serotonin receptor modulator is ketanserin, wherein the ketanserin is administered to post-treat at least 150 minutes post to the MBDB HCl form disclosed herein, including those described in Table Ex13. In some embodiments, the serotonin receptor modulator is ketanserin, wherein the ketanserin is administered to post-treat between about 15 minutes and about 150 minutes post to the MBDB HCl form disclosed herein, including those described in Table Ex13. In some embodiments, the serotonin receptor modulator is ketanserin, wherein the ketanserin is administered to post-treat at least 180 minutes post to the MBDB HCl form disclosed herein, including those described in Table Ex13. In some embodiments, the serotonin receptor modulator is ketanserin, wherein the ketanserin is administered to post-treat at least 210 minutes post to the MBDB HCl form disclosed herein, including those described in Table Ex13. In some embodiments, the serotonin receptor modulator is ketanserin, wherein the ketanserin is administered to post-treat at least 240 minutes post to the MBDB HCl form disclosed herein, including those described in Table Ex13. In some embodiments, the serotonin receptor modulator is ketanserin, wherein the ketanserin is administered to post-treat at least 270 minutes post to the MBDB HCl form disclosed herein, including those described in Table Ex13. In some embodiments, the serotonin receptor modulator is ketanserin, wherein the ketanserin is administered to post-treat at least 300 minutes post to the MBDB HCl form disclosed herein, including those described in Table Ex13. In some embodiments, the serotonin receptor modulator is ketanserin, wherein the ketanserin is administered to post-treat at least 330 minutes post to the MBDB HCl form disclosed herein, including those described in Table Ex13. In some embodiments, the serotonin receptor modulator is ketanserin, wherein the ketanserin is administered to post-treat at least 360 minutes post to the MBDB HCl form disclosed herein, including those described in Table Ex13. In some preferred embodiments, the serotonin receptor modulator is ketanserin, wherein ketanserin is administered to post-treat between about 60 minutes and about 180 minutes post to the administration of the MBDB HCl form disclosed herein, including those described in Table Ex13.

In some embodiments, the serotonin receptor modulator is ritanserin, wherein the ritanserin is administered to post-treat at least 15 minutes post to the administration of the MBDB HCl form disclosed herein, including those described in Table Ex13. In some embodiments, the serotonin receptor modulator is ritanserin, wherein the ritanserin is administered to post-treat at least 30 minutes post to the MBDB HCl form disclosed herein, including those described in Table Ex13. In some embodiments, the serotonin receptor modulator is ritanserin wherein the ritanserin is administered to post-treat between at least 60 minutes and 240 minutes post to the administration or release of the MBDB HCl form disclosed herein, including those described in Table Ex13. In some embodiments, the serotonin receptor modulator is ritanserin, wherein the ritanserin is administered to post-treat at least 90 minutes post to the MBDB HCl form disclosed herein, including those described in Table Ex13. In some embodiments, the serotonin receptor modulator is ritanserin, wherein the ritanserin is administered to post-treat at least 120 minutes post to the MBDB HCl form disclosed herein, including those described in Table Ex13. In some embodiments, the serotonin receptor modulator is ritanserin, wherein the ritanserin is administered to post-treat at least 150 minutes post to the MBDB HCl form disclosed herein, including those described in Table Ex13. In some embodiments, the serotonin receptor modulator is ritanserin, wherein the ritanserin is administered to post-treat between about 15 minutes and about 150 minutes post to the MBDB HCl form disclosed herein, including those described in Table Ex13. In some embodiments, the serotonin receptor modulator is ritanserin, wherein the ritanserin is administered to post-treat at least 180 minutes post to the MBDB HCl form disclosed herein, including those described in Table Ex13. In some embodiments, the serotonin receptor modulator is ritanserin, wherein the ritanserin is administered to post-treat at least 210 minutes post to the MBDB HCl form disclosed herein, including those described in Table Ex13. In some embodiments, the serotonin receptor modulator is ritanserin, wherein the ritanserin is administered to post-treat at least 240 minutes post to the MBDB HCl form disclosed herein, including those described in Table Ex13. In some embodiments, the serotonin receptor modulator is ritanserin, wherein the ritanserin is administered to post-treat at least 270 minutes post to the MBDB HCl form disclosed herein, including those described in Table Ex13. In some embodiments, the serotonin receptor modulator is ritanserin, wherein the ritanserin is administered to post-treat at least 300 minutes post to the MBDB HCl form disclosed herein, including those described in Table Ex13. In some embodiments, the serotonin receptor modulator is ritanserin, wherein the ritanserin is administered to post-treat at least 330 minutes post to the MBDB HCl form disclosed herein, including those described in Table Ex13. In some embodiments, the serotonin receptor modulator is ritanserin, wherein the ritanserin is administered to post-treat at least 360 minutes post to the MBDB HCl form disclosed herein, including those described in Table Ex13. In some preferred embodiments, the serotonin receptor modulator is ritanserin, wherein ritanserin is administered to post-treat between about 60 minutes and about 180 minutes post to the administration of the MBDB HCl form disclosed herein, including those described in Table Ex13.

In some embodiments, the serotonin receptor modulator is pimavanserin, wherein the pimavanserin is administered to post-treat at least 15 minutes post to the administration of the MBDB HCl form disclosed herein, including those described in Table Ex13. In some embodiments, the serotonin receptor modulator is pimavanserin, wherein the pimavanserin is administered to post-treat at least 30 minutes post to the MBDB HCl form disclosed herein, including those described in Table Ex13. In some embodiments, the serotonin receptor modulator is pimavanserin, wherein the pimavanserin is administered to post-treat between at least 60 minutes and 240 minutes post to the administration or release of the MBDB HCl form disclosed herein, including those described in Table Ex13. In some embodiments, the serotonin receptor modulator is pimavanserin, wherein the pimavanserin is administered to post-treat at least 90 minutes post to the MBDB HCl form disclosed herein, including those described in Table Ex13. In some embodiments, the serotonin receptor modulator is pimavanserin, wherein the pimavanserin is administered to post-treat at least 120 minutes post to the MBDB HCl form disclosed herein, including those described in Table Ex13. In some embodiments, the serotonin receptor modulator is pimavanserin, wherein the pimavanserin is administered to post-treat at least 150 minutes post to the MBDB HCl form disclosed herein, including those described in Table Ex13. In some embodiments, the serotonin receptor modulator is pimavanserin, wherein the pimavanserin is administered to post-treat between about 15 minutes and about 150 minutes post to the MBDB HCl form disclosed herein, including those described in Table Ex13. In some embodiments, the serotonin receptor modulator is pimavanserin, wherein the pimavanserin is administered to post-treat at least 180 minutes post to the MBDB HCl form disclosed herein, including those described in Table Ex13. In some embodiments, the serotonin receptor modulator is pimavanserin, wherein the pimavanserin is administered to post-treat at least 210 minutes post to the MBDB HCl form disclosed herein, including those described in Table Ex13. In some embodiments, the serotonin receptor modulator is pimavanserin, wherein the pimavanserin is administered to post-treat at least 240 minutes post to the MBDB HCl form disclosed herein, including those described in Table Ex13. In some embodiments, the serotonin receptor modulator is pimavanserin, wherein the pimavanserin is administered to post-treat at least 270 minutes post to the MBDB HCl form disclosed herein, including those described in Table Ex13. In some embodiments, the serotonin receptor modulator is pimavanserin, wherein the pimavanserin is administered to post-treat at least 300 minutes post to the MBDB HCl form disclosed herein, including those described in Table Ex13. In some embodiments, the serotonin receptor modulator is pimavanserin, wherein the pimavanserin is administered to post-treat at least 330 minutes post to the MBDB HCl form disclosed herein, including those described in Table Ex13. In some embodiments, the serotonin receptor modulator is pimavanserin, wherein the pimavanserin is administered to post-treat at least 360 minutes post to the MBDB HCl form disclosed herein, including those described in Table Ex13. In some preferred embodiments, the serotonin receptor modulator is pimavanserin, wherein pimavanserin is administered to post-treat between about 60 minutes and about 180 minutes post to the administration of the MBDB HCl form disclosed herein, including those described in Table Ex13.

In some embodiments, the serotonin receptor modulator is nelotanserin, wherein the nelotanserin is administered to post-treat at least 15 minutes post to the administration of the MBDB HCl form disclosed herein, including those described in Table Ex13. In some embodiments, the serotonin receptor modulator is nelotanserin, wherein the nelotanserin is administered to post-treat at least 30 minutes post to the MBDB HCl form disclosed herein, including those described in Table Ex13. In some embodiments, the serotonin receptor modulator is nelotanserin, wherein the nelotanserin is administered to post-treat between at least 60 minutes and 240 minutes post to the administration or release of the MBDB HCl form disclosed herein, including those described in Table Ex13. In some embodiments, the serotonin receptor modulator is nelotanserin, wherein the nelotanserin is administered to post-treat at least 90 minutes post to the MBDB HCl form disclosed herein, including those described in Table Ex13. In some embodiments, the serotonin receptor modulator is nelotanserin, wherein the nelotanserin is administered to post-treat at least 120 minutes post to the MBDB HCl form disclosed herein, including those described in Table Ex13.

In some embodiments, the serotonin receptor modulator is nelotanserin, wherein the nelotanserin is administered to post-treat at least 150 minutes post to the MBDB HCl form disclosed herein, including those described in Table Ex13. In some embodiments, the serotonin receptor modulator is nelotanserin, wherein the nelotanserin is administered to post-treat between about 15 minutes and about 150 minutes post to the MBDB HCl form disclosed herein, including those described in Table Ex13. In some embodiments, the serotonin receptor modulator is nelotanserin, wherein the nelotanserin is administered to post-treat at least 180 minutes post to the MBDB HCl form disclosed herein, including those described in Table Ex13. In some embodiments, the serotonin receptor modulator is nelotanserin, wherein the nelotanserin is administered to post-treat at least 210 minutes post to the MBDB HCl form disclosed herein, including those described in Table Ex13. In some embodiments, the serotonin receptor modulator is nelotanserin, wherein the nelotanserin is administered to post-treat at least 240 minutes post to the MBDB HCl form disclosed herein, including those described in Table Ex13. In some embodiments, the serotonin receptor modulator is nelotanserin, wherein the nelotanserin is administered to post-treat at least 270 minutes post to the MBDB HCl form disclosed herein, including those described in Table Ex13.

In some embodiments, the serotonin receptor modulator is nelotanserin, wherein the nelotanserin is administered to post-treat at least 300 minutes post to the MBDB HCl form disclosed herein, including those described in Table Ex13. In some embodiments, the serotonin receptor modulator is nelotanserin, wherein the nelotanserin is administered to post-treat at least 330 minutes post to the MBDB HCl form disclosed herein, including those described in Table Ex13. In some embodiments, the serotonin receptor modulator is nelotanserin, wherein the nelotanserin is administered to post-treat at least 360 minutes post to the MBDB HCl form disclosed herein, including those described in Table Ex13. In some preferred embodiments, the serotonin receptor modulator is nelotanserin, wherein nelotanserin is administered to post-treat between about 60 minutes and about 180 minutes post to the administration of the MBDB HCl form disclosed herein, including those described in Table Ex13.

In some embodiments, the serotonin receptor modulator is pruvanserin, wherein the pruvanserin is administered to post-treat at least 15 minutes post to the administration of the MBDB HCl form disclosed herein, including those described in Table Ex13. In some embodiments, the serotonin receptor modulator is pruvanserin, wherein the pruvanserin is administered to post-treat at least 30 minutes post to the MBDB HCl form disclosed herein, including those described in Table Ex13. In some embodiments, the serotonin receptor modulator is pruvanserin, wherein the pruvanserin is administered to post-treat between at least 60 minutes and 240 minutes post to the administration or release of the MBDB HCl form disclosed herein, including those described in Table Ex13. In some embodiments, the serotonin receptor modulator is pruvanserin, wherein the pruvanserin is administered to post-treat at least 90 minutes post to the MBDB HCl form disclosed herein, including those described in Table Ex13. In some embodiments, the serotonin receptor modulator is pruvanserin, wherein the pruvanserin is administered to post-treat at least 120 minutes post to the MBDB HCl form disclosed herein, including those described in Table Ex13. In some embodiments, the serotonin receptor modulator is pruvanserin, wherein the pruvanserin is administered to post-treat at least 150 minutes post to the MBDB HCl form disclosed herein, including those described in Table Ex13. In some embodiments, the serotonin receptor modulator is pruvanserin, wherein the pruvanserin is administered to post-treat between about 15 minutes and about 150 minutes post to the MBDB HCl form disclosed herein, including those described in Table Ex13. In some embodiments, the serotonin receptor modulator is pruvanserin, wherein the pruvanserin is administered to post-treat at least 180 minutes post to the MBDB HCl form disclosed herein, including those described in Table Ex13. In some embodiments, the serotonin receptor modulator is pruvanserin, wherein the pruvanserin is administered to post-treat at least 210 minutes post to the MBDB HCl form disclosed herein, including those described in Table Ex13.

In some embodiments, the serotonin receptor modulator is pruvanserin, wherein the pruvanserin is administered to post-treat at least 240 minutes post to the MBDB HCl form disclosed herein, including those described in Table Ex13. In some embodiments, the serotonin receptor modulator is pruvanserin, wherein the pruvanserin is administered to post-treat at least 270 minutes post to the MBDB HCl form disclosed herein, including those described in Table Ex13. In some embodiments, the serotonin receptor modulator is pruvanserin, wherein the pruvanserin is administered to post-treat at least 300 minutes post to the MBDB HCl form disclosed herein, including those described in Table Ex13. In some embodiments, the serotonin receptor modulator is pruvanserin, wherein the pruvanserin is administered to post-treat at least 330 minutes post to the MBDB HCl form disclosed herein, including those described in Table Ex13. In some embodiments, the serotonin receptor modulator is pruvanserin, wherein the pruvanserin is administered to post-treat at least 360 minutes post to the MBDB HCl form disclosed herein, including those described in Table Ex13. In some preferred embodiments, the serotonin receptor modulator is pruvanserin, wherein pruvanserin is administered to post-treat between about 60 minutes and about 180 minutes post to the administration of the MBDB HCl form disclosed herein, including those described in Table Ex13.

In some embodiments, the serotonin receptor modulator is flibanserin, wherein the flibanserin is administered to post-treat at least 15 minutes post to the administration of the MBDB HCl form disclosed herein, including those described in Table Ex13. In some embodiments, the serotonin receptor modulator is flibanserin, wherein the flibanserin is administered to post-treat at least 30 minutes post to the MBDB HCl form disclosed herein, including those described in Table Ex13. In some embodiments, the serotonin receptor modulator is flibanserin, wherein the flibanserin is administered to post-treat between at least 60 minutes and 240 minutes post to the administration or release of the MBDB HCl form disclosed herein, including those described in Table Ex13. In some embodiments, the serotonin receptor modulator is flibanserin, wherein the flibanserin is administered to post-treat at least 90 minutes post to the MBDB HCl form disclosed herein, including those described in Table Ex13. In some embodiments, the serotonin receptor modulator is flibanserin, wherein the flibanserin is administered to post-treat at least 120 minutes post to the MBDB HCl form disclosed herein, including those described in Table Ex13. In some embodiments, the serotonin receptor modulator is flibanserin, wherein the flibanserin is administered to post-treat at least 150 minutes post to the MBDB HCl form disclosed herein, including those described in Table Ex13. In some embodiments, the serotonin receptor modulator is flibanserin, wherein the flibanserin is administered to post-treat between about 15 minutes and about 150 minutes post to the MBDB HCl form disclosed herein, including those described in Table Ex13. In some embodiments, the serotonin receptor modulator is flibanserin, wherein the flibanserin is administered to post-treat at least 180 minutes post to the MBDB HCl form disclosed herein, including those described in Table Ex13. In some embodiments, the serotonin receptor modulator is flibanserin, wherein the flibanserin is administered to post-treat at least 210 minutes post to the MBDB HCl form disclosed herein, including those described in Table Ex13.

In some embodiments, the serotonin receptor modulator is flibanserin, wherein the flibanserin is administered to post-treat at least 240 minutes post to the MBDB HCl form disclosed herein, including those described in Table Ex13. In some embodiments, the serotonin receptor modulator is flibanserin, wherein the flibanserin is administered to post-treat at least 270 minutes post to the MBDB HCl form disclosed herein, including those described in Table Ex13. In some embodiments, the serotonin receptor modulator is flibanserin, wherein the flibanserin is administered to post-treat at least 300 minutes post to the MBDB HCl form disclosed herein, including those described in Table Ex13. In some embodiments, the serotonin receptor modulator is flibanserin, wherein the flibanserin is administered to post-treat at least 330 minutes post to the MBDB HCl form disclosed herein, including those described in Table Ex13. In some embodiments, the serotonin receptor modulator is flibanserin, wherein the flibanserin is administered to post-treat at least 360 minutes post to the MBDB HCl form disclosed herein, including those described in Table Ex13. In some preferred embodiments, the serotonin receptor modulator is flibanserin, wherein flibanserin is administered to post-treat between about 60 minutes and about 180 minutes post to the administration of the MBDB HCl form disclosed herein, including those described in Table Ex13.

In some embodiments, the serotonin receptor modulator is olanzapine, wherein the olanzapine is administered to post-treat at least 15 minutes post to the administration of the MBDB HCl form disclosed herein, including those described in Table Ex13. In some embodiments, the serotonin receptor modulator is olanzapine, wherein the olanzapine is administered to post-treat at least 30 minutes post to the MBDB HCl form disclosed herein, including those described in Table Ex13. In some embodiments, the serotonin receptor modulator is olanzapine, wherein the olanzapine is administered to post-treat between at least 60 minutes and 240 minutes post to the administration or release of the MBDB HCl form disclosed herein, including those described in Table Ex13. In some embodiments, the serotonin receptor modulator is olanzapine, wherein the olanzapine is administered to post-treat at least 90 minutes post to the MBDB HCl form disclosed herein, including those described in Table Ex13. In some embodiments, the serotonin receptor modulator is olanzapine, wherein the olanzapine is administered to post-treat at least 120 minutes post to the MBDB HCl form disclosed herein, including those described in Table Ex13. In some embodiments, the serotonin receptor modulator is olanzapine, wherein the olanzapine is administered to post-treat at least 150 minutes post to the MBDB HCl form disclosed herein, including those described in Table Ex13. In some embodiments, the serotonin receptor modulator is olanzapine, wherein the olanzapine is administered to post-treat between about 15 minutes and about 150 minutes post to the MBDB HCl form disclosed herein, including those described in Table Ex13. In some embodiments, the serotonin receptor modulator is olanzapine, wherein the olanzapine is administered to post-treat at least 180 minutes post to the MBDB HCl form disclosed herein, including those described in Table Ex13. In some embodiments, the serotonin receptor modulator is olanzapine, wherein the olanzapine is administered to post-treat at least 210 minutes post to the MBDB HCl form disclosed herein, including those described in Table Ex13.

In some embodiments, the serotonin receptor modulator is olanzapine, wherein the olanzapine is administered to post-treat at least 240 minutes post to the MBDB HCl form disclosed herein, including those described in Table Ex13. In some embodiments, the serotonin receptor modulator is olanzapine, wherein the olanzapine is administered to post-treat at least 270 minutes post to the MBDB HCl form disclosed herein, including those described in Table Ex13. In some embodiments, the serotonin receptor modulator is olanzapine, wherein the olanzapine is administered to post-treat at least 300 minutes post to the MBDB HCl form disclosed herein, including those described in Table Ex13. In some embodiments, the serotonin receptor modulator is olanzapine, wherein the olanzapine is administered to post-treat at least 330 minutes post to the MBDB HCl form disclosed herein, including those described in Table Ex13. In some embodiments, the serotonin receptor modulator is olanzapine, wherein the olanzapine is administered to post-treat at least 360 minutes post to the MBDB HCl form disclosed herein, including those described in Table Ex13. In some preferred embodiments, the serotonin receptor modulator is olanzapine, wherein olanzapine is administered to post-treat between about 60 minutes and about 180 minutes post to the administration of the MBDB HCl form disclosed herein, including those described in Table Ex13.

In some embodiments, the serotonin receptor modulator is quetiapine, wherein the quetiapine is administered to post-treat at least 15 minutes post to the administration of the MBDB HCl form disclosed herein, including those described in Table Ex13. In some embodiments, the serotonin receptor modulator is quetiapine, wherein the quetiapine is administered to post-treat at least 30 minutes post to the MBDB HCl form disclosed herein, including those described in Table Ex13. In some embodiments, the serotonin receptor modulator is quetiapine, wherein the quetiapine is administered to post-treat between at least 60 minutes and 240 minutes post to the administration or release of the MBDB HCl form disclosed herein, including those described in Table Ex13. In some embodiments, the serotonin receptor modulator is quetiapine, wherein the quetiapine is administered to post-treat at least 90 minutes post to the MBDB HCl form disclosed herein, including those described in Table Ex13. In some embodiments, the serotonin receptor modulator is quetiapine, wherein the quetiapine is administered to post-treat at least 120 minutes post to the MBDB HCl form disclosed herein, including those described in Table Ex13. In some embodiments, the serotonin receptor modulator is quetiapine, wherein the quetiapine is administered to post-treat at least 150 minutes post to the MBDB HCl form disclosed herein, including those described in Table Ex13. In some embodiments, the serotonin receptor modulator is quetiapine, wherein the quetiapine is administered to post-treat between about 15 minutes and about 150 minutes post to the MBDB HCl form disclosed herein, including those described in Table Ex13. In some embodiments, the serotonin receptor modulator is quetiapine, wherein the quetiapine is administered to post-treat at least 180 minutes post to the MBDB HCl form disclosed herein, including those described in Table Ex13. In some embodiments, the serotonin receptor modulator is quetiapine, wherein the quetiapine is administered to post-treat at least 210 minutes post to the MBDB HCl form disclosed herein, including those described in Table Ex13.

In some embodiments, the serotonin receptor modulator is quetiapine, wherein the quetiapine is administered to post-treat at least 240 minutes post to the MBDB HCl form disclosed herein, including those described in Table Ex13. In some embodiments, the serotonin receptor modulator is quetiapine, wherein the quetiapine is administered to post-treat at least 270 minutes post to the MBDB HCl form disclosed herein, including those described in Table Ex13. In some embodiments, the serotonin receptor modulator is quetiapine, wherein the quetiapine is administered to post-treat at least 300 minutes post to the MBDB HCl form disclosed herein, including those described in Table Ex13. In some embodiments, the serotonin receptor modulator is quetiapine, wherein the quetiapine is administered to post-treat at least 330 minutes post to the MBDB HCl form disclosed herein, including those described in Table Ex13. In some embodiments, the serotonin receptor modulator is quetiapine, wherein the quetiapine is administered to post-treat at least 360 minutes post to the MBDB HCl form disclosed herein, including those described in Table Ex13. In some preferred embodiments, the serotonin receptor modulator is quetiapine, wherein quetiapine is administered to post-treat between about 60 minutes and about 180 minutes post to the administration of the MBDB HCl form disclosed herein, including those described in Table Ex13.

In some embodiments, the serotonin receptor modulator is risperidone, wherein the risperidone is administered to post-treat at least 15 minutes post to the administration of the MBDB HCl form disclosed herein, including those described in Table Ex13. In some embodiments, the serotonin receptor modulator is risperidone, wherein the risperidone is administered to post-treat at least 30 minutes post to the MBDB HCl form disclosed herein, including those described in Table Ex13. In some embodiments, the serotonin receptor modulator is risperidone, wherein the risperidone is administered to post-treat between at least 60 minutes and 240 minutes post to the administration or release of the MBDB HCl form disclosed herein, including those described in Table Ex13. In some embodiments, the serotonin receptor modulator is risperidone, wherein the risperidone is administered to post-treat at least 90 minutes post to the MBDB HCl form disclosed herein, including those described in Table Ex13. In some embodiments, the serotonin receptor modulator is risperidone, wherein the risperidone is administered to post-treat at least 120 minutes post to the MBDB HCl form disclosed herein, including those described in Table Ex13. In some embodiments, the serotonin receptor modulator is risperidone, wherein the risperidone is administered to post-treat at least 150 minutes post to the MBDB HCl form disclosed herein, including those described in Table Ex13. In some embodiments, the serotonin receptor modulator is risperidone, wherein the risperidone is administered to post-treat between about 15 minutes and about 150 minutes post to the MBDB HCl form disclosed herein, including those described in Table Ex13. In some embodiments, the serotonin receptor modulator is risperidone, wherein the risperidone is administered to post-treat at least 180 minutes post to the MBDB HCl form disclosed herein, including those described in Table Ex13. In some embodiments, the serotonin receptor modulator is risperidone, wherein the risperidone is administered to post-treat at least 210 minutes post to the MBDB HCl form disclosed herein, including those described in Table Ex13.

In some embodiments, the serotonin receptor modulator is risperidone, wherein the risperidone is administered to post-treat at least 240 minutes post to the MBDB HCl form disclosed herein, including those described in Table Ex13. In some embodiments, the serotonin receptor modulator is risperidone, wherein the risperidone is administered to post-treat at least 270 minutes post to the MBDB HCl form disclosed herein, including those described in Table Ex13. In some embodiments, the serotonin receptor modulator is risperidone, wherein the risperidone is administered to post-treat at least 300 minutes post to the MBDB HCl form disclosed herein, including those described in Table Ex13. In some embodiments, the serotonin receptor modulator is risperidone, wherein the risperidone is administered to post-treat at least 330 minutes post to the MBDB HCl form disclosed herein, including those described in Table Ex13. In some embodiments, the serotonin receptor modulator is risperidone, wherein the risperidone is administered to post-treat at least 360 minutes post to the MBDB HCl form disclosed herein, including those described in Table Ex13. In some preferred embodiments, the serotonin receptor modulator is risperidone, wherein risperidone is administered to post-treat between about 60 minutes and about 180 minutes post to the administration of the MBDB HCl form disclosed herein, including those described in Table Ex13.

In yet another aspect, also provided herein are methods of treating a disease or disorder, wherein the methods comprise administering to the subject a therapeutically effective amount of an MBDB hydrochloride form described herein. In some embodiments, the methods further comprise administering to the subject a serotonin receptor modulator, wherein the serotonin receptor modulator is administered at most about 3 hours prior or post to the administration or release of the MBDB hydrochloride form, such as from about 1 hour to about 3 hours prior or post to administration or release of the MBDB hydrochloride. In some embodiments, the disease or disorder is depression or a disease or disorder related to depression. In some embodiments, the disease or disorder is post-traumatic stress disorder. In some embodiments, the disease or disorder is fibromyalgia.

In yet another aspect, also provided herein are methods of treating fibromyalgia or a disease or disorder related to chronic widespread pain, fatigue or hypersensitivity, wherein the methods comprise administering to the subject a therapeutically effective amount of an MBDB hydrochloride form described herein. In some embodiments, the methods further comprise administering to the subject a serotonin receptor modulator, wherein the serotonin receptor modulator is administered at most about 3 hours prior or post to the administration of the MBDB hydrochloride, such as from about 1 hour prior or post to about 3 hours prior or post to administration or release of the MBDB hydrochloride.

In some embodiments, the present MBDB forms act as non-hallucinogenic $5\text{-}HT_{2A}$ modulators (e.g., $5\text{-}HT_{2A}$ agonists) that are used to treat neurological diseases. In some embodiments, the neurological diseases comprise decreased neural plasticity, decreased cortical structural plasticity, decreased $5\text{-}HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, the present MBDB forms act as non-hallucinogenic $5\text{-}HT_{2A}$ modulators (e.g., $5\text{-}HT_{2A}$ agonists) that are used for increasing neuronal plasticity. In some embodiments, the present MBDB forms act as non-hallucinogenic $5\text{-}HT_{2A}$ modulators (e.g., $5\text{-}HT_{2A}$ agonists) that are used for treating a brain disorder. In some embodiments, the present MBDB forms act as non-hallucinogenic $5\text{-}HT_{2A}$ modulators (e.g., $5\text{-}HT_{2A}$ agonists) that are used for increasing at least one of translation, transcription, or secretion of neurotrophic factors.

EXAMPLES

Example 1

General Experimental Procedures

X-Ray Powder Diffraction (XRPD)

A Rigaku SmartLab X-Ray Diffractometer was configured in Bragg-Brentano reflection geometry equipped with a beam stop and knife edge to reduce incident beam and air scatter. Data collection parameters are shown in the following table.

PXRD Data Collection Parameters

PXRD Data Collection Parameters

| Parameter | Value |
|---|---|
| Geometry | Bragg-Brentano |
| Tube Anode | Cu |
| Tube Type | Long Fine Focus |
| Tube Voltage (kV) | 40 |
| Tube Current (mA) | 44 |
| Detector | D/teX Ultra 250 (RX1, RX3)<br>HyPix-3000 (XR4) |
| Monochromator | Ni foil Cu Kβ Filter |
| Incident Slit (°) | ⅓ |
| Receiving Slit 1 (mm) | 18 |
| Receiving Slit 2 (mm) | Open/20 |
| Start Angle 2θ (°) | 2 |
| End Angle 2θ (°) | 40 |
| Step Size (°) | 0.02 |
| Scan Speed (°/min) | 6 |
| Spinning (rpm) | 11 |
| Sample Holder | Low-background Si |

Differential Scanning Calorimetry (DSC)

DSC analyses were carried out using a TA Instruments Q2500 Discovery Series instrument. The instrument temperature calibration was performed using indium. The DSC cell was kept under a nitrogen purge of ~50 mL per minute during each analysis. The sample was placed in a standard, crimped, aluminum pan and was heated from approximately 25° C. to 350° C. at a rate of 10° C. per minute.

Thermogravimetric (TG) Analysis

The TG analysis was carried out using a TA Instruments Q5500 Discovery Series instrument. The instrument balance was calibrated using class M weights and the temperature calibration was performed using alumel. The nitrogen purge was ~40 mL per minute at the balance and ~60 mL per minute at the furnace. Each sample was placed into a pre-tared platinum pan and heated from approximately 25° C. to 350° C. at a rate of 10° C. per minute.

Dynamic Vapor Sorption (DVS) Analysis

DVS analysis was carried out using a TA Instruments Q5000 Dynamic Vapor Sorption analyzer. The instrument was calibrated with standard weights and a sodium bromide standard for humidity. Approximately 5-25 mg of sample was loaded into a metal-coated quartz pan for analysis. The sample was analyzed at 25° C. with a maximum equilibration time of one hour in 10% relative humidity (RH) steps from 5 to 95% RH (adsorption cycle) and from 95 to 5% RH (desorption cycle). The movement from one step to the next occurred either after satisfying the equilibrium criterion of 0.01% weight change or, if the equilibrium criterion was not met, after one hour. The percent weight change values were calculated using Microsoft Excel®.

Optical Microscopy

Optical microscopy experiments were carried out on a Leica DM 2500 P compound microscope. Images were captured using a PAXcam3 camera or a QImaging MicroPublisher 3.3 RTV camera. Magnification is displayed on each image.

Scanning Electron Microscopy (SEM)

SEM images were collected using a Phenom XL Desktop SEM equipped with a $CeB_6$ electron source. Phenom User Interface version 1.4 was used to acquire and save the images. Detailed image parameters are recorded in the footer of each image.

Nuclear Magnetic Resonance (NMR) Spectroscopy

The $^1H$ NMR spectra were acquired on a Bruker Avance II 400 spectrometer. Samples were prepared by dissolving material in an appropriate NMR solvent. The solutions were filtered and placed into individual 5-mm NMR tubes for subsequent spectral acquisition. The temperature controlled (295K) $^1H$ NMR spectra acquired on the Avance II 400 utilized a 5-mm cryoprobe operating at an observing frequency of 400.18 MHz.

Ion Chromatography (IC)

Ion chromatography analysis was carried out at Intertech Pharmaceutical Services. The data was acquired on an Agilent 1100 HPLC with a Shimadzu conductivity detector and a polymeric anion exchange resin column. The mobile phase was a sodium carbonate/sodium hydrogen carbonate solution. Each sample was dissolved in water at a concentration of 2 mg/mL and injected using a liquid pump and autosampler. The results are in w/w %. Prior to analysis, the system was calibrated using standards prepared from NIST traceable standard solutions.

Cyclic DSC

The cycling DSC analysis was carried out using a TA Instruments Q2000 instrument. The instrument temperature calibration was performed using indium. The heating profile used for the analysis included the following steps:

Ramp 10° C./min to 130° C.
Isothermal for 1 min
Ramp 1° C./min to 150° C.
Isothermal for 5 min
Ramp 10° C./min to 25° C.
Isothermal for 1 min
Ramp 10° C./min to 200° C.

Chiral HPLC Methods

As will be appreciated by those of skill in the art, MDEA exists as two mirror image compounds, enantiomers. The enantiomers are (R)—N-ethyl-3,4-methylenedioxyamphetamine and (S)—N-ethyl-3,4-methylenedioxyamphetamine. (S)—N-ethyl-3,4-methylenedioxyamphetamine can be isolated from a racemic mixture of the two isomers as described herein to provide a compound that is substantially enantiomerically pure. For example, using chiral HPLC as described herein, the two enantiomers can be separated to greater than a ratio of 85:15 (S)-MDEA:(R)-MDEA, such as 90:10 (S)-MDEA:(R)-MDEA, such as 95:5, 97:3, 98:2, 99:1 or greater. Thus, in certain embodiments the disclosed salts, solid forms and salts thereof are substantially pure(S)-MDEA. In other embodiments, the disclosed salts solid forms and salts thereof are optically active (meaning they have more(S)-MDEA than (R)-MDEA, such as in a ratio of from about 85:15, 90:10, 95:5, 97:3, 98:2 or about 99:1. As used herein, when a compound is referred to as an(S) or (R) isomer (such as(S)—N-ethyl-3,4-methylenedioxyamphetamine, or(S)-MDEA), that means it is in an optically active form, i.e. it contains more of that enantiomer than the other.

As will be appreciated by those of skill in the art, 3,4-methylenedioxymethamphetamine exists as two mirror image compounds, referred to as enantiomers. The enantiomers are (R)-3,4-methylenedioxymethamphetamine ((R)-MDMA) and (S)-3,4-methylenedioxymethamphetamine ((S)-MDMA). (R)-MDMA and (S)-MDMA can be isolated from a racemic mixture of the two isomers to provide a compound that is substantially enantiomerically pure. For example, using chiral HPLC as described herein, the two enantiomers can be separated to greater than a ratio of 85:15 (R)-MDMA:(S)-MDMA, such as 90:10 (R)-MDMA:(S)-MDMA, such as 95:5, 97:3, 98:2, 99:1 or greater. Thus, in certain embodiments the disclosed salts, solid forms and salts thereof are substantially pure (R)-MDMA (i.e., an enantiomeric excess of about 100%). In other embodiments, the disclosed salts solid forms and salts thereof are optically active (meaning they have more (R)-MDMA than(S)-MDMA, such as in a ratio of from about 85:15, 90:10, 95:5, 97:3, 98:2 or about 99:1. That is, the disclosed salts, solid forms and salts thereof of (R)-MDMA have an enantiomeric excess of from at least 70%, at least 80%, at least 90%, at least 94%, at least 96%, at least 98%, or at least 99% enantiomeric excess. For example, using chiral HPLC as described herein, the two enantiomers can be separated to greater than a ratio of 85:15 (S)-MDMA:(R)-MDMA, such as 90:10 (S)-MDMA:(R)-MDMA, such as 95:5, 97:3, 98:2, 99:1 or greater. Thus, in certain embodiments the disclosed salts, solid forms and salts thereof are substantially pure(S)-MDMA (i.e., an enantiomeric excess of about 100%). In other embodiments, the disclosed salts solid forms and salts thereof are optically active (meaning they have more(S)-MDMA than (R)-MDMA, such as in a ratio of from about 85:15, 90:10, 95:5, 97:3, 98:2 or about 99:1. That is, the disclosed salts, solid forms and salts thereof of (S)-MDMA have an enantiomeric excess of from at least 70%, at least 80%, at least 90%, at least 94%, at least 96%, at least 98%, or at least 99% enantiomeric excess.

Exemplary conditions useful to separate (R)-MDMA and (S)-MDMA or (R)-MDEA and (S)-MDEA into the purified optically active compositions described above are described in Protocols 1 and 2 below:

Protocol-1:

HPLC: Waters 2695 Alliance

Diode array detector (210-400 nm)

Column: Phenomenex Lux Amylose-2; 5 micron, 4.6×250 mm

Mobil phase (isocratic): 20% acetonitrile, 40% aqueous, 20 mM monobasic potassium phosphate buffer Flow rate: 0.5 ml/min Injection volume: 3 μL Concentration: approx 5 mg/ml Detection: UV at 254 nm Run Time: 30 minutes Protocol-2:

Column: Daicel Chemical Industries, Chiralcel OJ, 4.6×250 mm

Mobile phase: 1:1 Methanol Ethanol 0.1% diethylamine (isocratic)

Flow rate: 0.5 ml/min

Run time: 15 minutes

Temperature: room temperature

Detection: Water 996 PDA

HPLC: Waters 2690 Separations Module

Example 2

General Salt Screen Procedure

The solid forms disclosed herein are characterized to evaluate their physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the free base is a solvate or hydrate, and to evaluate thermal stability. DVS data is used to evaluate hygroscopicity of the free base and if hydrates can be formed at high relative humidity. About 10 to 15 solvents are selected from the list below, based on their properties (polarity, dielectric constant and dipole moment).

TABLE Ex2-1

| Solvents | |
|---|---|
| acetic acid | n-heptane |
| Acetone | n-hexane |
| Acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | Methanol |
| Chlorobenzene | methoxybenzene (anisole) |
| Chloroform | methyl acetate |
| di(ethylene glycol) | methyl ethyl ketone (2-butanone) |
| Dichloromethane | methyl isobutyl ketone |
| diethyl ether | Nitromethane |
| Diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | Perfluorohexane |
| 1,4-dioxane | propyl acetate |
| 1,2-ethanediol (ethylene glycol) | 1,1,2,2-tetrachloroethane |
| Ethanol | Tetrahydrofuran |
| Ethanolamine | Toluene |
| 2-ethoxyethanol (Cellusolve) | 1,1,1-trichloroethane |
| ethyl acetate | 2,2,2-trifluoroethanol |
| ethyl formate | Water |
| formic acid | o-xylene (1,2-dimethylbenzene) |
| Glycerol | p-xylene (1,4-dimethylbenzene) |

The information obtained is used for designing the subsequent salt screen. The salt screen is performed by reacting the free base with pharmaceutically acceptable acids under various conditions in attempts to generate crystalline salts. Pharmaceutically acceptable acids that may be used are listed below. Specific acids are selected based on the pKa of the free base, and typically 15 to 20 acids are selected. Experiments are performed using 0.5 molar equivalent, 1 molar equivalent and/or 2 molar equivalents of the acid.

TABLE Ex2-2

| Exemplary Acids | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| Hydrochloric acid | carbonic acid |
| galactaric (mucic) acid | Fumaric acid |

In some embodiments, hydrochloric acid is not used.

Solvent systems for the salt crystallization experiments are selected based on the solubility of the free base and the selected acid. Solvents are used as a single solvent or as solvent mixtures, some containing water. The techniques that are used for salt crystallization are chosen based on the solvent selected and properties of the free base. The following techniques (or combination of techniques) may be used for salt crystallization:

Free base and acid are dissolved in a solvent or mixture of solvents, and the solvents are evaporated at different rates (slow evaporation or fast evaporation) and at different temperatures (ambient or elevated).

Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).

Free base and acid are dissolved in a solvent or mixture of solvents, and an antisolvent is added to precipitate the salt. The solids formed will be recovered by filtration and dried (air dried or vacuum dried).

Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment can be also performed in solvent systems where the solvents are not miscible.

Free base and acid are milled together (by mechanical milling or by mortar and pestle), with a drop of solvent, or without any solvent.

Free base and acid are melted together, and cooled to various temperatures using various cooling rates.

If an amorphous form of a salt is obtained, the amorphous salt will be exposed to elevated humidity, or elevated temperature (or combination of both), or solvent vapors at various temperatures to form crystalline salts.

The stoichiometric ratio of acid to (R)-3,4-methylenedioxymethamphetamine is confirmed by $^1$H NMR, HPLC, or both as is known to those of ordinary skill in the art.

The salts obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on salts that are hydrated. DVS analysis is performed to evaluate hygroscopicity of the salt and if hydrated form is present.

Example 3

MDMA Salt Screen

MDMA freebase was mixed with various acids under various conditions in to generate crystalline salts as listed in Table Ex3. All samples were produced using 1 molar equivalent of acid (unless noted otherwise).

TABLE Ex3

Salt screen samples generated and analyzed

| Acid | Conditions[a] | XRPD Result[b] |
|---|---|---|
| L-aspartic | SL, ACN, RT, 7 days | aspartic acid |
| | SL, DMSO, RT, 7 days | aspartic acid |
| | SL, water, 50° C., 3 days; NS. E, RT | aspartic acid + NC |
| Benzenesulfonic | C, acetone, RT→–15° C.; NS. Add hexanes added until turbid. C, RT →–15° C.; NS. E, RT; oil. Added 1 mL $Et_2O$, dissolved. C, RT→–15° C.; NS. E, RT; clear oil | — |
| | C, ACN, RT →–15° C.; NS. Hexanes added until turbid. C, RT→ –15° C.; NS. E, RT; brown oil. | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |
| Citric | C, acetone, RT→–15° C.; NS. Hexanes added until turbid, cool to –15° C.; NS. E, RT. | NC |
| | SL, ACN, RT →–15° C.; NS. Hexanes added until turbid. C, RT→ –15° C.; NS. E, RT, dried in vacuum desiccator | NC |
| | E, EtOH, RT; oil. Hexanes added until turbid. C, RT→ –15° C.; NS. E, RT; oil. Added 1 mL $Et_2O$; dissolved. C, RT→ –15° C.; NS. E, RT; clear oil. | — |
| Ethanesulfonic | C, acetone, RT→–15° C.; NS. Add hexanes added until turbid. C, RT →–15° C.; NS. E, RT; oil. Added 1 mL $Et_2O$, dissolved. C, RT→–15° C.; NS. E, RT; clear oil | — |
| | C, ACN, RT →–15° C.; NS. Hexanes added until turbid. C, RT→ –15° C.; NS. E, RT; brown oil. | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |
| Fumaric | P, acetone, RT | Fumarate 1 (FIG. 1) |
| | SL, ACN, RT, 7 days | Fumarate 1 + 2 (FIG. 10) |
| Gentisic | C, acetone, RT→–15° C.; NS. Hexanes added until turbid. C, RT→ –15° C.; NS. E, RT | NC |
| | C, ACN, RT →–15° C.; NS. Hexanes added until turbid. C, RT→ –15° C.; NS. E, RT; brown oil. | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT | NC |
| D-gluconic | SL, ACN, RT, 7 days | NC |
| | C, acetone, RT→–15° C.; NS. Hexanes added until turbid. C, RT→ –15° C.; NS. E, RT; oil. Added 1 mL Et2O, dissolved. C, RT→ –15° C.; NS. E, RT | NC |
| | E, EtOH, RT; oil. Hexanes added until turbid. C, RT→ 15° C.; NS. E, RT | NC |
| Glutamic | SL, ACN, RT, 7 days | glutamic acid |
| | SL, DMSO, RT, 7 days | glutamic acid |
| | SL, water, 50° C., 3 days; NS. E, RT | glutamic acid + NC |
| Glycolic | C, acetone, RT→–15° C.; NS. Add hexanes added until turbid. C, RT →–15° C.; NS. E, RT; oil. Added 1 mL $Et_2O$, dissolved. C, RT→–15° C.; NS. E, RT; clear oil | — |
| | C, ACN, RT →–15° C.; NS. Hexanes added until turbid. C, RT→ –15° C.; NS. E, RT; brown oil. | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |
| 1-hydroxy-2-napthoic | C, acetone, RT→–15° C.; NS. Hexanes added until turbid. C, RT→ –15° C.; NS. E, RT; tacky solid. Dried in vac. desiccator. | NC |
| | C, ACN, RT →–15° C.; NS. Hexanes added until turbid. C, RT→ –15° C.; NS. E, RT; brown oil. | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |
| D,L-lactic | C, acetone, RT→–15° C.; NS. Add hexanes added until turbid. C, RT →–15° C.; NS. E, RT; oil. Added 1 mL $Et_2O$, dissolved. C, RT→–15° C.; NS. E, RT; clear oil | — |
| | C, ACN, RT →–15° C.; NS. Hexanes added until turbid. C, RT→ –15° C.; NS. E, RT; brown oil. | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |
| L-malic | C, acetone, RT→–15° C.; NS. Hexanes added until turbid. C, RT→ –15° C.; NS. E, RT; tacky solid. Added 1 mL $Et_2O$, SL, RT | Malate 1 + NC |
| | C, ACN, RT →–15° C. | Malate 1 (FIG. 6) |
| Maleic | C, acetone, RT→–15° C. | Maleate 1 (FIG. 2) |
| | C, ACN, RT →–15° C. | Maleate 2 (FIG. 11) |
| Malonic | C, acetone, RT→–15° C. | Free base (FIG. 3) |
| | C, ACN, RT→–15° C.; NS. Hexanes added until turbid. C, RT→ –15° C.; NS. E, RT; oil. Added 1 mL $Et_2O$; dissolved. C, RT→ –15° C.; NS. E, RT; clear oil | — |
| Methanesulfonic | C, acetone, RT→–15° C.; NS. Add hexanes added until turbid. C, RT →–15° C.; NS. E, RT; oil. Added 1 mL $Et_2O$, dissolved. C, RT→–15° C.; NS. E, RT; clear oil | — |
| | C, ACN, RT→–15° C.; NS. Hexanes added until turbid. C, RT→ –15° C.; NS. E, RT; oil. Added 1 mL $Et_2O$; dissolved. C, RT→ –15° C.; NS. E, RT; clear oil | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |
| Mucic (galacteric) | SL, ACN, RT, 7 days | Mucate 1 + acid (FIG. 7) |
| | Lyophilization, DMSO, RT | Mucate 1 + acid |
| | SL, ACN, RT (½ eq. acid), 7 days | Mucate 1 (FIG. 46) |
| Phosphoric | P, acetone, RT | Phosphate 1 (FIG. 4) |
| | SL, ACN, RT, 7 days | Phosphate 1 |
| | SL, EtOH, RT, 7 days | Phosphate 1 (FIG. 47) |
| Sulfuric | C, acetone, RT→–15° C.; NS. Add hexanes added until turbid. C, RT →–15° C.; NS. E, RT; oil. Added 1 mL $Et_2O$, dissolved. C, RT→–15° C.; NS. E, RT; clear oil | — |
| | C, ACN, RT→–15° C.; NS. Hexanes added until turbid. C, RT→ –15° C.; NS. E, RT; oil. Added 1 mL $Et_2O$; dissolved. C, RT→ –15° C.; NS. E, RT; clear oil | — |

TABLE Ex3-continued

| Salt screen samples generated and analyzed | | |
|---|---|---|
| Acid | Conditions[a] | XRPD Result[b] |
| Succinic | C, ACN, RT→–15° C. | Succinate 1 (FIG. 8) |
| | C, acetone, RT→–15° C.; NS | — |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |
| L-tartaric | P, acetone, RT | Tartrate 1 (FIG. 5) |
| | SL, ACN, RT, 7 days | Tartrate 1 + 2 (FIG. 12) |
| p-toluenesulfonic | C, acetone, RT→–15° C.; NS. Add hexanes added until turbid. C, RT →–15° C.; NS. E, RT; oil. Added 1 mL $Et_2O$, dissolved. C, RT→–15° C.; NS. E, RT; clear oil | — |
| | C, ACN, RT→–15° C.; NS. Hexanes added until turbid. C, RT → –15° C.; NS. E, RT; oil. Added 1 mL $Et_2O$. SL, RT, 1 day | Tosylate 1 (FIG. 9) |
| | E, EtOH, RT; oil. . Hexanes added until turbid. C, RT→ –15° C.; NS. E, RT; oil. Added 1 mL $Et_2O$, dissolved. C, RT→ –15° C.; NS, E, RT; clear oil. | — |

[a]ACN = acetonitrile; C = cool; DMSO = dimethylsulfoxide; E = evaporation; $Et_2O$ = diethyl ether; EtOH = ethanol; IS = insufficient solids; NS = no solid; P = precipitation; SE = slow evaporation; SL = slurry; RT = room temperature

[b]The acid name or "acid" indicate the XRPD pattern contains the crystalline acids. NC = non-crystalline A small amount of each salt was placed in a glass vial and exposed to 75% relative humidity for 24 hours. None of the salts showed evidence of hygroscopicity under these conditions. That is, the solids remained free flowing.

Example 4

Characterization of MDMA Salts

All materials having a unique X-ray powder diffraction (XRPD) pattern were characterized by differential scanning calorimetry (DSC), thermogravimetric analysis (TG), and $^1H$ nuclear magnetic resonance (NMR) spectroscopy. The hygroscopicity of each salt at 75% RH was also evaluated. The water solubility of each salt was estimated by adding water in aliquots to weighed portions of solid at room temperature while sonicating. Whether dissolution had occurred was judged by visual inspection after addition of each solvent aliquot. Solubility numbers were calculated by dividing the weight of the sample by the total amount of solvent used to dissolve the sample. The actual solubilities may be greater than the numbers calculated because of the use of solvent aliquots that were too large or because of slow dissolution rates.

| Salt | Stoichiometry (API:acid) | Solvation state | Melt point (° C.) | Hygroscopic at 75% RH?[a] | Approximate water solubility (mg/mL) |
|---|---|---|---|---|---|
| Fumarate | 2:1 | Unsolvated | 181 | No | 11 |
| Malate | 1:1 | Unsolvated | 77 | No | Not tested |
| Maleate Form 1 | 1:1 | Unsolvated | 104 | No | 19 |
| Maleate Form 2 | 1:1 | Unsolvated | 94 | No | 10 |
| Galactarate (Mucate) | 2:1 | Unsolvated | 172 | No | 10 |
| Phosphate | 1:2[c] | Unsolvated | 186 | No | 12 |
| Succinate | 1:1 | Unsolvated | 92 | No | 10 |
| Tartrate | 1:1 | Unsolvated | 117 | No | 14 |
| Tosylate | 1:1 | Possible hydrate | No event by DSC | No | Not tested |
| n/a (free base) | n/a | Unsolvated | 78 | Not tested | Not tested |

[a]Visual assessment after exposure to 75% RH (room temp) for 24 hours b. Solubility was determined by visual assessment

[c]Stoichiometry determined by ion chromatography

Estimated Solubilities of MDMA Hemi-Fumarate Salt

| Solvent | Solubility (mg/mL) |
|---|---|
| acetone | <1 |
| acetonitrile (ACN) | <1 |
| dichloromethane (DCM) | <1 |
| diethyl ether ($Et_2O$) | <1 |
| 1,4-dioxane | <1 |
| ethanol (EtOH) | 4 |
| ethyl acetate (EtOAc) | <1 |
| methanol (MeOH) | 47 |
| 2-propanol (IPA) | <1 |
| tetrahydrofuran (THF) | <1 |
| water | 260 |
| 1:1 MeOH:chloroform ($CHCl_3$) | 35 |
| 95:5 acetone: water | 2 |
| 95:5 ACN:water | 4 |
| 95:5 dioxane:water | 6 |
| 95:5 EtOH:water | 15 |
| 95:5 IPA:water | 5 |
| 95:5 THF:water | 14 |

Crystalline salts were obtained from eight different acids in the salt screen. The fumarate, mucate, and phosphate salts were chosen for scale-up since they were unsolvated, had a melting point above 170° C., showed no evidence of hygroscopicity at 75% RH, and had approximate water solubilities around 10 mg/mL. The phosphate salt needed further characterization to determine the stoichiometry and extent of proton transfer so it was removed from consideration. The hemifumarate was selected based on its anhydrate designation, slightly higher melting point, and acceptable solubility and handling properties.

Example 4.1

Polymorph Screen of MDMA Hemi-Fumarate

Samples of MDMA hemi-fumarate was mixed with various solvents under various conditions in attempts to generate crystalline materials. Only one crystalline form was identified, designated as form A. Attempts to make non-crystalline material via lyophilization and melt-quench were also carried out, but those experiments produced form A. The experiments are summarized in Table Ex4-1.

TABLE Ex4-1

Polymorph Screen of MDMA Hemi-Fumarate

| Method | Solvent | Conditions [a] | Results |
|---|---|---|---|
| Cooling | EtOH | 60° C. → RT | A |
| | ACN | 60° C. → RT | A |
| | IPA | 60° C. → RT | A |
| | 95:5 EtOH:water | 60° C. → RT | A |
| | 95:5 acetone:water | 60° C. → RT | A |
| | 95:5 ACN:water | 60° C. → RT | A |
| | 95:5 1,4-dioxane:water | 60° C. → RT | A |
| | 95:5 IPA: water | 60° C. → 2° C. | A |
| | 1,4-dioxane | 60° C. → 2° C.; NS. E, RT; oil. Added 1 mL hexanes, cool to −15° C.; NS. E, RT; oil. Added 1 mL $Et_2O$, cool to −15° C.; NS. E, RT; oil. | Oil |
| Antisolvent Precipitation | MeOH | AS: acetone, RT; NS. C, RT → −15° C. | A |
| | | AS: $Et_2O$, RT | A |
| | | AS: EtOAc, RT | A |
| | | AS: IPA, RT | A |
| | | AS: THF, RT; NS. C, RT → −15° C.; NS. E, RT; oil. Added 1 mL hexanes, cool to −15° C.; NS. E, RT; oil. Added 1 mL $Et_2O$, cool to −15° C.; NS. E, RT; oil | Oil |
| | 95:5 EtOH: water | AS: acetone, RT | A |
| | | AS: ACN, RT | A |
| | | AS: heptane, RT | A |
| | | AS: IPA, RT → 2° C. | A |
| Antisolvent Precipitation | water | AS: acetone, RT→−15° C. | A |
| | | AS: ACN, RT→−15° C.; NS, FE | A |
| | | AS: 1,4-dioxane, RT→−15° C.; NS. E, RT; oil. Added 1 mL hexanes, cool to −15° C., NS. E, RT; oil. Added 1 mL $Et_2O$, cool to −15° C., NS. E, RT | Oil |
| | | AS:IPA; NS. Cool to → 2° C. | A |
| Slurry | Acetone | 55° C. | A |
| | | RT, magnetic stirring, 5 d | A |
| | ACN | RT, magnetic stirring, 5 d | A |
| | DCM | RT, magnetic stirring, 5 d | A |
| | $Et_2O$ | RT, magnetic stirring, 5 d | A |
| | 1,4-dioxane | RT, magnetic stirring, 5 d | A |
| | EtOH | RT, magnetic stirring, 5 d | A |
| | EtOAc | RT, magnetic stirring, 5 d | A |
| | MeOH | RT, magnetic stirring, 5 d | A |
| | IPA | RT, magnetic stirring, 5 d | A |
| | THF | RT, magnetic stirring, 5 d | A |
| | 1:1 MeOH:$CHCl_3$ | RT, magnetic stirring, 5 d | A |
| | 95:5 acetone:water | RT, magnetic stirring, 5 d | A |
| | 95:5 ACN:water | RT, magnetic stirring, 5 d | A |
| | 95:5 1,4-dioxane:water | RT, magnetic stirring, 5 d | A |
| | 95:5 EtOH:water | RT, magnetic stirring, 5 d | A |
| | 95:5 IPA:water | RT, magnetic stirring, 5 d | A |
| | 95:5 THF:water | RT, magnetic stirring, 5 d | A |
| Lyophilization | Water | Upon completion of lyophilization, placed in 60° C. oven for 2 hours | A |
| | | Analyzed upon removal from lyophilizer | A |
| Evaporation | EtOH | Open vial, RT | A |
| | MeOH | Open vial, RT | A |
| | 1:1 MeOH:$CHCl_3$ | Open vial, RT | A |
| | 95:5 acetone:water | Open vial, RT | A |
| | 95:5 ACN:water | Open vial, RT | A |
| | 95:5 EtOH:water | Open vial, RT | A |
| | 95:5 IPA:water | Open vial, RT | A |
| | 95:5 THF:water | Open vial, RT; oil. Added 1 mL, hexanes, cool to −15° C.; NS. E, RT; oil. Added 1 mL $Et_2O$, cool to −15° C. | A |
| Melt-quench | n/a | n/a | A |

[a] E = evaporation;
$Et_2O$ = diethyl ether;
NS = no solids;
RT = room temperature One crystalline form of MDMA hemi-fumarate was identified, designated as form A. It is unsolvated, slightly hygroscopic, and melts around 183° C.

TABLE Ex4-2

Figure 109:
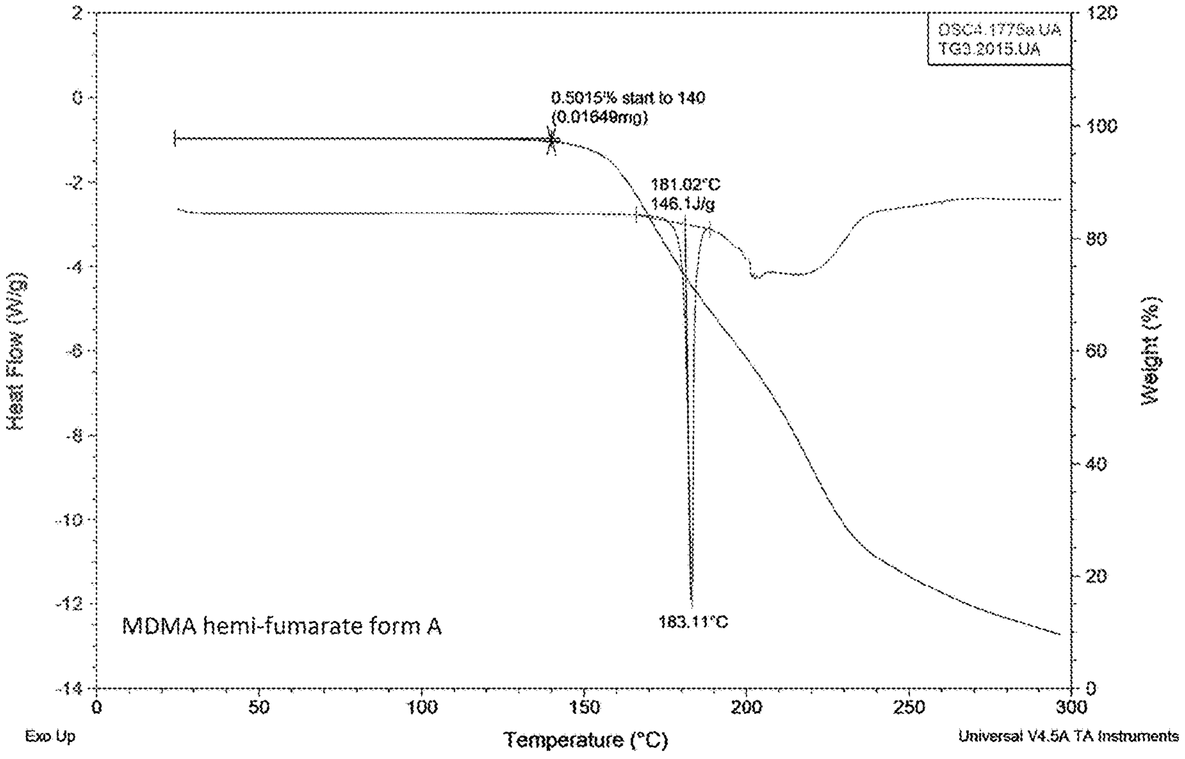
FIG. 109 provides TGA and DSC profiles for crystalline MDMA hemifumarate Form A.
Figure 110:
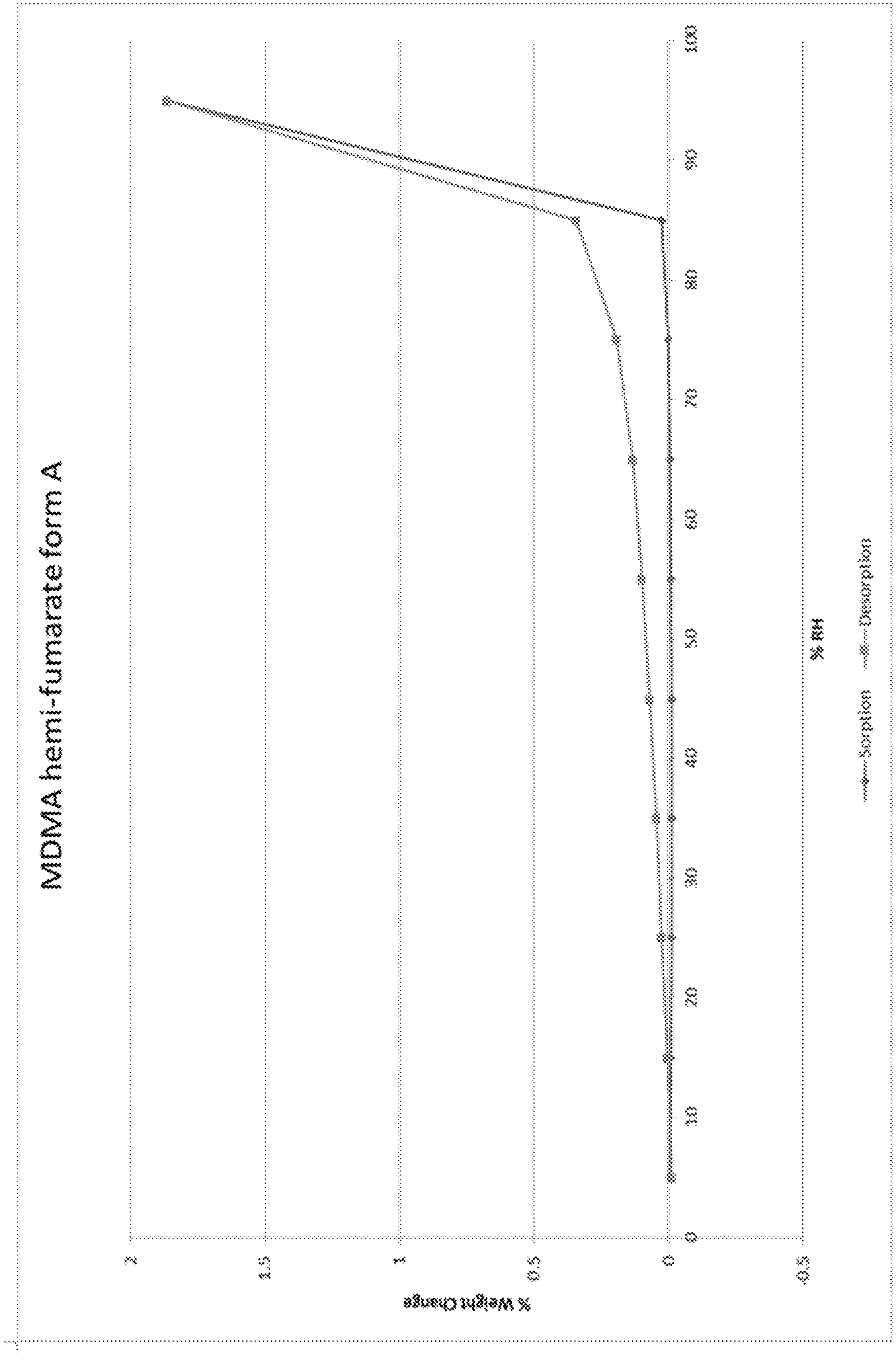
FIG. 110 provides a DVS spectrum of crystalline MDMA hemifumarate Form A.
Figure 111:
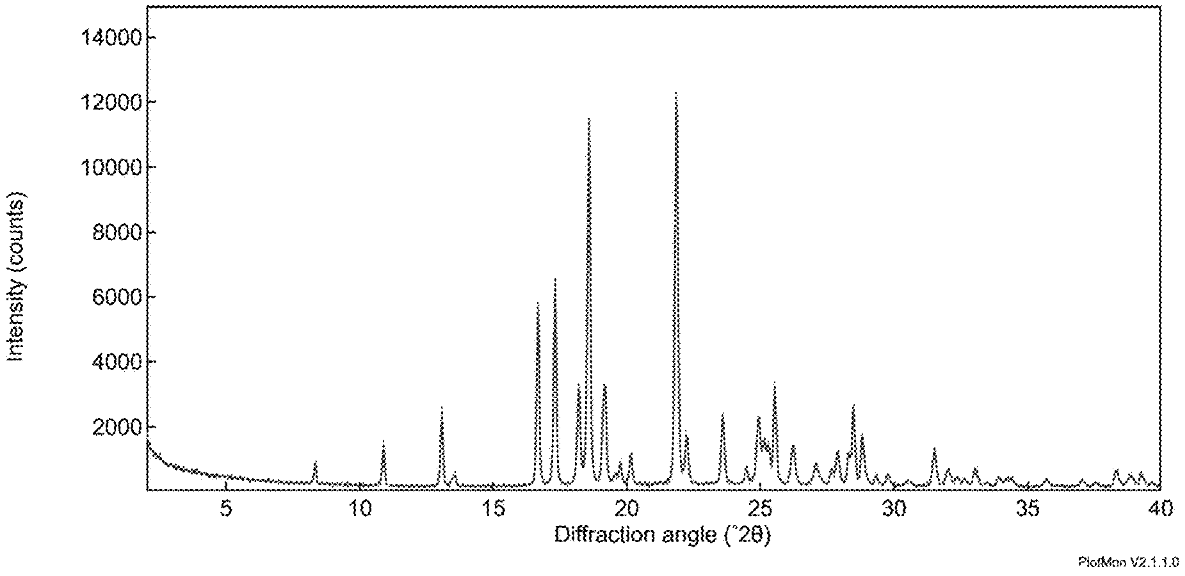
FIG. 111 provides a post-DVS XRPD diffractogram of crystalline MDMA hemifumarate Form A.
Figure 112:
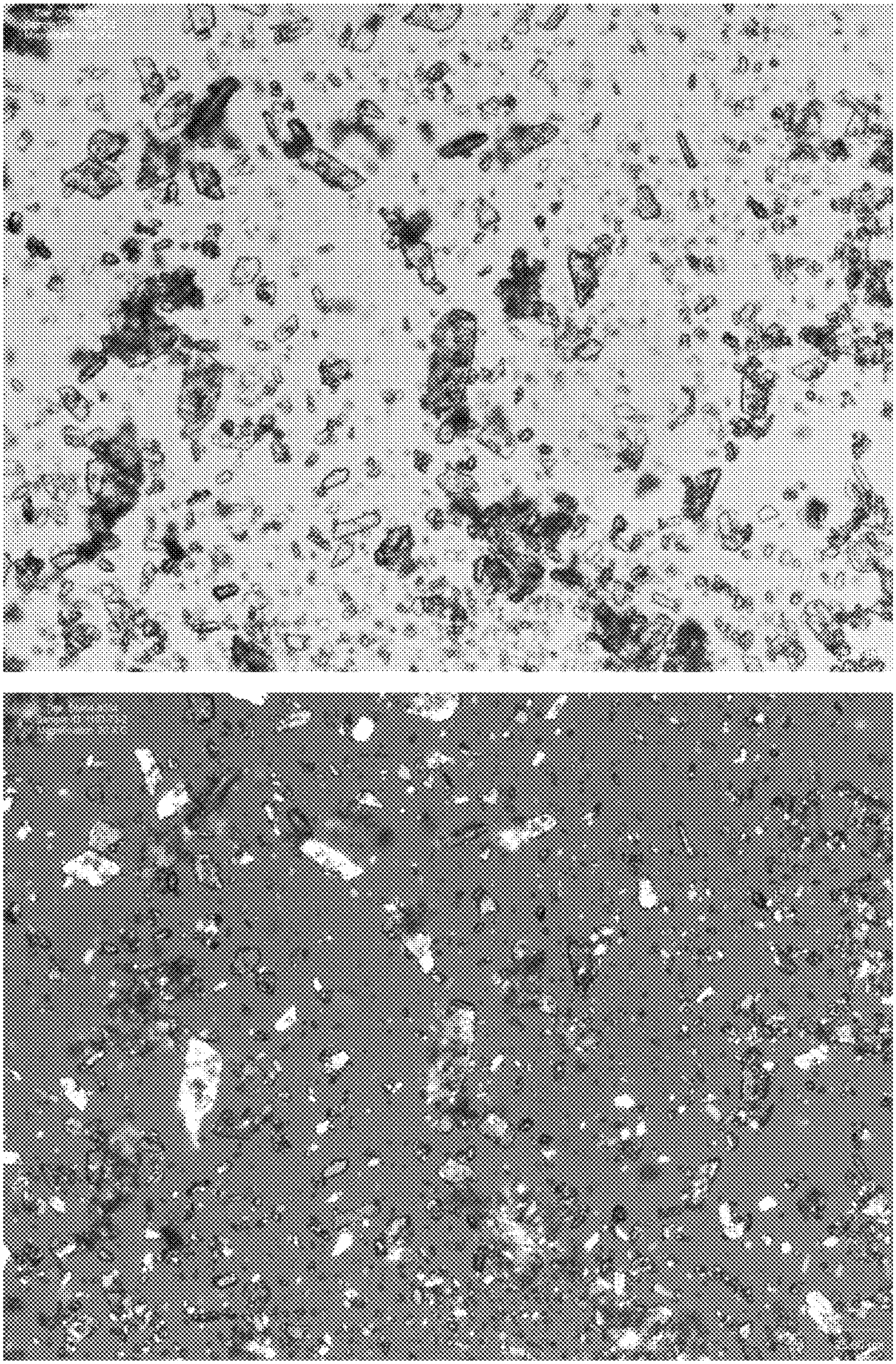
FIG. 112 provides an optical microscopy (OM) of crystalline MDMA hemifumarate Form A.
Figure 113:
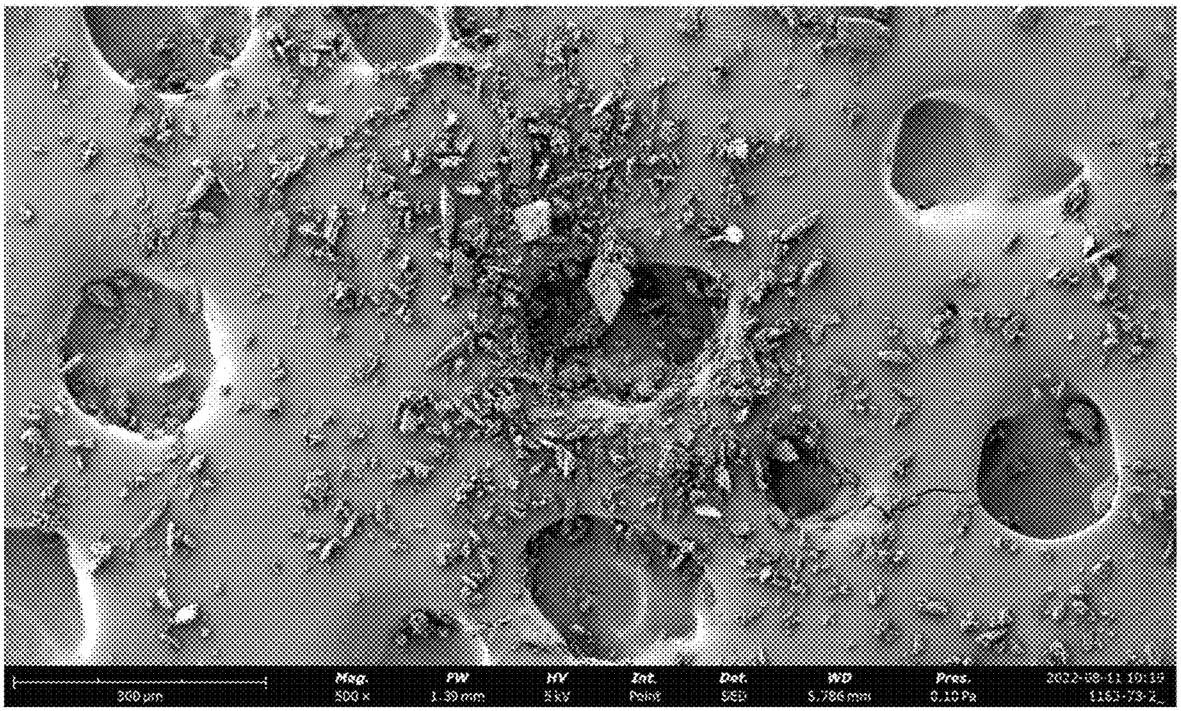
FIG. 113 provides an scanning electron microscope image of crystalline MDMA hemifumarate Form A.
Figure 114:
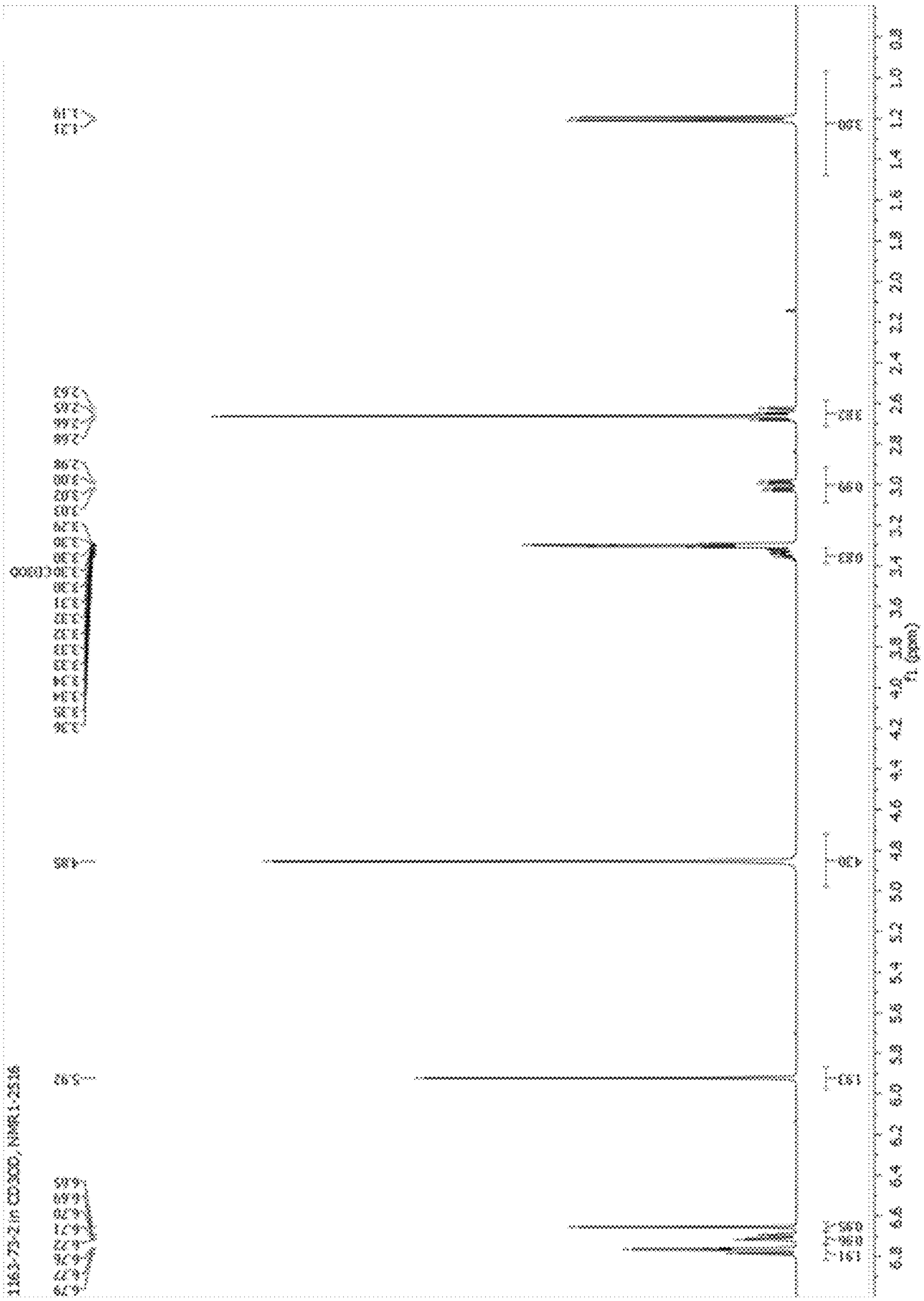
FIG. 114 provides $^1$H NMR of crystalline MDMA hemifumarate Form A.

| Characterization of MDMA Hemi-Fumarate | | |
|---|---|---|
| Test | Figures | Results[a] |
| DSC | FIG. 109 | Endo 183.1° C. |
| TG | FIG. 109 | 0.5% start to 140° C. |
| DVS | FIG. 110 | Slightly hygroscopic |
| Post-DVS XRPD | FIG. 111 | Unchanged |
| OM | FIG. 112 | Birefringent plates, irregulars |
| SEM | FIG. 113 | Plates and irregular shaped particles |
| NMR ($CD_3OD$) | FIG. 114 | Consistent with 2:1 API:acid |

Preparation of MDMA Freebase

Dissolved 2.11 g of MDMA HCl in 50 mL of water and placed in a 500 mL separatory funnel. Added 1 equivalent of aqueous sodium hydroxide (10.94 mL of 1N NaOH). The freebase precipitated as an immiscible oil and was extracted using dichloromethane (4×50 mL). The dichloromethane layers were combined and dried over magnesium sulfate. The dichloromethane was allowed to evaporated to give 1.78 g of freebase as a light tan oil.

Preparation of MDMA Hemi-Fumarate Form A

Dissolved 1.78 g of MDMA freebase in 35 mL of acetone. Dissolved 1.07 g of fumaric acid in 100 mL of acetone. The fumaric acid solution was slowly added to the solution of freebase, producing a precipitate. The white slurry was stirred magnetically at room temperature overnight. The slurry was vacuum filtered and the resulting white solid was dried in a vacuum desiccator at room temperature to give 1.91 g of hemi-fumarate salt form A.

Example 5

MBDB Salt Screen

The free base was prepared by adding 12.340 mL of 1N NaOH to a solution of 3.005 g of MBDB HCl in ~89.0 mL water (cloudy, then oiling observed). Approximately 40.0 mL of DCM was added to extract, followed by washing of the aqueous layer with DCM two more times with ~40.0 mL each time. The organic phase was isolated, dried with MgSO4 and vacuum filtered. Evaporation with a stream of air and vacuum drying overnight yielded the free base MBDB as a clear oil, 2.43 g recovered.

The salts in Table Ex5 were prepared from MBDB free base (API).

TABLE Ex5

| Salt formed | Procedure | $^1$H NMR consistent with salt form | XRPD |
|---|---|---|---|
| Citric acid | 23.3 mg of citric acid was added to 0.5 mL of a ~50 mg/mL MBDB free base solution in isopropanol at room temperature resulting in a mostly clear solution with a few undissolved solids. After stirring 1 day a white suspension was observed. White solids were recovered after centrifugation of the sample and removal of the supernatant. | Peak overlap between MBDB and counterion but total integration generally consistent with ~1:1 salt; no organic solvents present | FIG. 26 |
| Fumaric acid | 14.2 mg of citric acid was added to 0.5 mL of a ~50 mg/mL MBDB free base solution in ispropanol at room temperature resulting in a mostly clear solution with a few undissolved solids. After stirring 1 day a white suspension was observed. White solids were recovered after centrifugation of the sample and removal of the supernatant. | Consistent with ~1:1 salt; trace THF present | FIG. 27 |
| Galactaric acid | 25.4 mg of galactaric (mucic) acid was added to 0.5 mL of ~50 mg/mL MBDB free base solution in ispropanol at 50° C. resulting in a turbid solution. The sample was left to stir at 50° C. for 2 days resulting in a white suspension. White solids were recovered after centrifugation and removal of the supernatant. | Consistent with ~1:1 salt; no organic solvents present | FIG. 28 |
| Maleic acid | 14.2 mg of maleic acid was added to 0.5 mL of ~50 mg/mL MBDB free base solution in acetone at room temperature resulting in a clear solution. After 3 days of stirring no precipitation was observed so the sample was placed in the freezer. A clear solution with some solids was observed after 6 days in the freezer. The sample was uncapped, covered with aluminum foil with a small pin hole for slow evaporation at room temperature resulting in off-white solids and yellow gel. 2.0 mL of DEE was added and the sample was allowed to stir at room temperature. Sample was placed in the freezer resulting in a mixture of white and off-white solids. | Peak overlap between MBDB and counterion but total integration generally consistent with ~1:1 salt; no organic solvents present | FIG. 29 |
| Phosphoric acid | 8.30 μL of phosphoric acid was added to 0.5 mL of ~50 mg/mL MBDB free base solution in acetone. Instant precipitation was observed forming a white suspension. After 1 day of stirring at room temperature a white suspension was observed. Solids were isolated using centrifugation resulting in white solids. | Generally consistent with API structure; trace acetone present | FIG. 30 |

TABLE Ex5-continued

| Salt formed | Procedure | $^1$H NMR consistent with salt form | XRPD |
|---|---|---|---|
| Succinic acid Form 1 | 14.4 mg of succinic acid was added to 0.5 mL of ~50 mg/mL MBDB free base solution in acetone resulting in a clear solution. After 1 day of stirring at room temperature a white suspension was observed. Solids were isolated using centrifugation resulting in white solids. | Consistent with ~1:1 salt; trace acetone present | FIG. 31 |
| Sulfuric acid | 6.81 μL of sulfuric acid was added to 0.5 mL of ~50 mg/mL MBDB free base solution in acetone. Instantaneous precipitation was observed followed by redissolution. The sample was allowed to stir at overnight at room temperature and resulted in a clear solution. The sample was transferred to the fridge for additional stirring for 4 days. No precipitation was observed so the sample was placed in the freezer for 4 days. The sample remained a clear solution. The cap to the vial was removed and the sample was covered with aluminum foil with a small pin hole to allow for slow evaporation at room temperature. After 6 days a mixture of off-white and brown solids was observed. | | FIG. 32 |
| Tartaric acid | 18.2 mg of L-tartaric acid was contacted with 0.5 mL of ~50 mg/mL MBDB free base solution in acetone resulting in a mostly clear solution with a few undissolved solids. The sample was allowed to stir at room temperature for 1 day resulting in a white suspension. White solids were recovered after centrifugation and removal of the supernatant. | | FIG. 33 |
| Malonic acid | 13.1 mg of malonic acid was added to 0.5 mL of ~50 mg/mL MBDB free base solution in acetonitrile at room temperature resulting in a clear solution. The sample remained a clear solution after 4 days of stirring. 1.0 mL of di-isopropyl ether was added dropwise resulting in a turbid solution that was stirred at room temperature for 5 days. An additional 0.5 mL of di-isopropyl ether was added to the resulting clear solution and the sample was allowed to stir at room temperature for an additional 5 days. White solids were isolated from the resulting white suspension via centrifugation and decanting the liquid phase. | | FIG. 35 |
| Succinic acid Form 2 | 14.3 mg of succinic acid was added to 0.5 mL of ~50 mg/mL MBDB free base solution in acetonitrile resulting in a clear solution with a few undissolved solids. The sample was left to stir at room temperature for 2 days resulting in a white suspension. After centrifugation and removal of the supernatant, white solids were recovered. | | FIG. 36 |
| Toluene sulfonic acid | 21.1 mg of p-toluenesulfonic acid was added to 0.5 mL of ~50 mg/mL MBDB free base in isopropanol resulting in a mostly clear solution with a few undissolved solids. A clear solution remained after 2 days of stirring at room temperature. The sample was moved to the freezer to stir for 6 days resulting in a clear solution with gel-like particles. A turbid solution resulted from adding 0.5 mL of di-isopropyl ether. The sample was stirred at room temperature for 5 days resulting in a clear solution with a small amount of white solids. An additional 1.0 mL of di-isopropyl ether was added resulting in a turbid solution with solids. | | FIG. 37 |

TABLE Ex5-continued

| Salt formed | Procedure | $^1H$ NMR consistent with salt form | XRPD |
|---|---|---|---|
| | Sample was placed in the freezer and allowed to stir. White solids were recovered after centrifugation and removal of the supernatant. | | |

FB = free base;
sol'n = solution;
EtOH = ethanol;
$H_2O$ = water;
IPA = isopropanol;
DEE = diethyl ether;
EtOAc = ethyl acetate;
MeOH = methanol;
THF = tetrahydrofuran;
ACN = acetonitrile;
MTBE = methyl tert-butyl ether;
SL = slurry;
E = evaporation;
P = precipitation;
NS = no solids;
RT = room/ambient temperature;
ET = elevated temperature;
pp'd = precipitated;
d = day(s);
sol'n = solution;
DMSO = dimethyl sulfoxide TABLE Ex5-2

| Acid | Conditions[a] | PXRD Result[b] |
|---|---|---|
| L-aspartic | API dissolved in acetone, aspartic acid added, stirred, RT 6 d. White solids | Acid |
| | API dissolved in THF, aspartic acid added, stirred, RT, 6 d. White solids. | Acid |
| | API dissolved in ACN, aspartic acid acid and 10.0 uL $H_2O$ added, stirred, RT, 2 d. White solids. | Acid |
| Benzenesulfonic | API dissolved in acetone, benzenesulfonic acid added, stirred, RT → −25° C., clear soln. SE, clear slight yellow gel. Added DEE, stirred, RT, clear soln w/off-white gel. FE, clear gel. Dried under vacuum at 40° C., light yellow clear gel. | — |
| | API dissolved in THF, benzenesulfonic acid added, stirred, RT → −25° C., clear soln. SE, clear gel. Added IPE, stirred, RT, clear soln w/clear gel. FE, clear light yellow gel. Dried under vacuum at 40° C., light yellow clear gel. | — |
| | API dissolved in ACN, benzenesulfonic acid added, stirred, RT → −25° C., clear soln. SE, clear gel. Added MTBE, stirred, RT → −25° C., clear gel. FE, clear gel. Dried under vacuum at 50° C., clear gel. | — |
| Citric | API dissolved in THF, citric acid added, stirred, RT → 5° C. White solids. | Citrate 1; LC (FIG. 26) |
| | API dissolved in IPA, citric acid added, stirred, RT, 1 d. White solids. | Citrate 1 (FIG. 84) |
| | API dissolved in acetone, citric acid added, stirred, RT → −25° C., 6 d. White solids. | Citrate 1; LC |
| Ethanesulfonic | API dissolved in acetone, ethanesulfonic acid soln added, stirred, RT → −25° C., clear soln. SE, clear slight yellow gel. Added MTBE, stirred, RT, clear soln w/clear gel. FE, clear light brown gel. Dried under vacuum at 40° C., brown clear gel. | — |
| | API dissolved in THF, ethanesulfonic acid soln added, stirred, RT → −25° C., clear soln. SE, clear yellow oil. Added DEE, stirred, RT, clear soln w/brown oil. FE, brown gel. Dried under vacuum at 40° C., black gel. | — |
| | API dissolved in ACN, ethanesulfonic acid added, stirred, 50° C. → −25° C., clear soln. SE, brown/orange gel. Added IPE, stirred, RT → −25° C., light brown gel. FE, clear orange/yellow gel. Dried under vacuum at 50° C., clear orange/brown gel. | — |
| Fumaric | API dissolved in THF, fumaric acid added, stirred, RT, 1 d. White solids. | Fumarate 1 (FIG. 27) |
| | API dissolved in IPA, fumaric acid added, stirred, RT, 1 d. White solids. | Fumarate 1 (FIG. 85) |
| | API dissolved in THF, fumaric acid added, stirred, RT, 1 d. Light yellow/off-white solids. | Fumarate 1 |
| | API dissolved in acetone, fumaric acid and 10.0 uL $H_2O$ added, stirred, RT, 2 d. White solids. | Fumarate 1 |

TABLE Ex5-2-continued

| Acid | Conditions[a] | PXRD Result[b] |
|---|---|---|
| Galactaric (Mucic) | API dissolved in THF, galactaric acid added, stirred, RT, 6 d. White solids. | Galactarate 1 + acid (FIG. 28) |
| | API dissolved in ACN, galactaric acid added, stirred, RT, 1 d. White solids. | Galactarate 1 + acid |
| | API dissolved in acetone, galactaric acid added, stirred, 50° C., 2 d. White solids. | Galactarate 1 + acid (FIG. 89) |
| Gentisic | API dissolved in ACN, gentisic acid soln added, stirred, RT, clear soln. Added MTBE, stirred, RT → 5° C., clear soln. FE, clear brown/orange gel. Dried under vacuum at 40° C., brown/orange gel. | — |
| | API dissolved in IPA, gentisic acid soln added, stirred, RT, clear soln. Added hexanes, stirred, RT, clear soln w/off-white gel. FE, clear gel. Dried under vacuum at 40° C., clear gel. | — |
| | API dissolved in acetone, gentisic acid added, stirred, RT → −25° C., clear light brown soln. SE, brown/orange gel. Added IPE, stirred, RT → −25° C., brown/orange gel. FE, clear orange/brown gel. Dried under vacuum at 50° C., clear brown gel. | — |
| D-gluconic | API dissolved in THF, D-gluconic acid soln added, stirred, RT → −25° C., turbid soln w/oil. FE, clear gel. Added DEE, stirred, RT → −25° C., off-white gel. FE, off-white gel. | — |
| | API dissolved in ACN, D-gluconic acid soln added, stirred, RT, turbid soln w/off-white gel. FE, light yellow clear gel. Dried under vacuum at 40° C., yellow clear gel. | — |
| | API dissolved in IPA, D-gluconic acid added, stirred, RT → −25° C., clear light yellow soln. Added IPE, stirred, RT → −25° C., off-white gel. FE, clear yellow gel. Dried under vacuum at 50° C., clear yellow/orange gel. | — |
| L-glutamic | API dissolved in acetone, L-glutamic acid added, stirred, RT, 6 d. White solids. | Acid |
| | API dissolved in THF, L-glutamic acid added, stirred, RT, 6 d. White solids. | Acid |
| | API dissolved in ACN, L-glutamic acid added, stirred, RT, 2 d. White solids. | Acid |
| Glycolic | API dissolved in ACN, glycolic acid added, stirred, RT, clear soln. Added DEE, stirred, RT, clear soln w/small amt of gel. FE, clear gel. Dried under vacuum at 40° C., light yellow clear gel. | — |
| | API dissolved in IPA, glycolic acid added, stirred, RT, clear soln. Added IPE, stirred, RT → 5° C., clear soln. FE, clear/off-white gel. Dried under vacuum at 40° C., clear gel. | — |
| | API dissolved in THF, glycolic acid and 10.0 uL $H_2O$ added, stirred, RT → −25° C., clear yellow/green soln. Added MTBE, stirred, RT → −25° C., clear light yellow gel. FE, clear yellow gel. Dried under vacuum at 50° C., clear yellow/orange gel. | — |
| D-lactic | API dissolved in ACN, D-lactic acid added, stirred, RT, clear soln. Added MTBE, stirred, RT → 5° C., clear soln. FE, clear gel. Dried under vacuum at 40° C., clear gel. | — |
| | API dissolved in IPA, D-lactic acid added, stirred, RT, clear soln. Added IPE, stirred, RT → 5° C., clear soln. FE, clear gel. Dried under vacuum at 40° C., clear gel. | — |
| | API dissolved in THF, D-lactic acid added, stirred, RT → −25° C., clear yellow/green soln. Added DEE, stirred, RT → −25° C., clear yellow soln. FE, clear yellow gel. Dried under vacuum at 50° C., clear yellow/orange gel. | — |
| L-lactic | API dissolved in ACN, L-lactic acid added, stirred, RT, clear soln. Added DEE, stirred, RT → 5° C., clear soln. FE, clear gel. Dried under vacuum at 40° C., clear gel. | — |
| | API dissolved in IPA, L-lactic acid added, stirred, RT, clear soln. Added hexanes, stirred, RT, clear soln w/small amt of gel. FE, clear gel. Dried under vacuum at 40° C., clear gel. | — |
| | API dissolved in acetone, L-lactic acid added, stirred, RT → −25° C., clear soln. SE, clear gel. Added IPE, stirred, RT → −25° C., clear gel. FE, clear gel. Dried under vacuum at 50° C., clear gel. | — |
| Maleic | API dissolved in ACN, maleic acid soln added, stirred, RT, clear soln. Added IPE, stirred, RT, 5 d. White solids. | Maleate 1 (FIG. 29) |
| | API dissolved in IPA, maleic acid soln added, stirred, RT, clear soln. Added hexanes, stirred, RT, 5 d. White solids. | Maleate 1 |
| | API dissolved in acetone, maleic acid added, stirred, RT → −25° C., clear soln & small amt of white solids. SE, mix of off-white solids & yellow gel. Added DEE, stirred, RT → −25° C., mix of white & off-white solids. | Maleate 1 (FIG. 88) |
| L-malic | API dissolved in ACN, L-malic acid added, stirred, RT, clear soln. Added DEE, stirred, RT, clear soln w/off-white gel. FE, clear gel. Dried under vacuum at 40° C., light yellow clear gel. | — |

TABLE Ex5-2-continued

| Acid | Conditions[a] | PXRD Result[b] |
|---|---|---|
| | API dissolved in IPA, L-malic acid added, stirred, RT, clear soln. Added IPE, stirred, RT, clear soln w/off-white gel. FE, clear gel. Dried under vacuum at 40° C., clear gel. | — |
| | API dissolved in THF, L-malic acid added, stirred, RT → −25° C., clear yellow/green soln. Added MTBE, stirred, RT → −25° C., yellow gel. FE, clear yellow gel. Dried under vacuum at 50° C., clear yellow gel. | — |
| Malonic | API dissolved in ACN, malonic acid soln added, stirred, RT, clear soln. Added IPE, stirred, RT, 10 d. White solids. | Malonate 1 (FIG. 35) |
| | API dissolved in IPA, malonic acid soln added, stirred, RT, clear soln. Added DEE, stirred, RT, clear soln w/small amt of gel. FE, clear gel. Dried under vacuum at 40° C., clear gel. | — |
| | API dissolved in THF, malonic acid added, stirred, RT → −25° C., clear yellow/green soln. Added MTBE, stirred, RT → −25° C., clear light yellow gel. FE, clear yellow gel. Dried under vacuum at 50° C., clear yellow gel. | — |
| Methanesulfonic | API dissolved in acetone, methanesulfonic acid soln added, stirred, RT → −25° C., clear soln. SE, clear soln. Added DEE, stirred, RT, clear soln w/clear gel. FE, clear light yellow gel. Dried under vacuum at 40° C., light yellow clear gel. | — |
| | API dissolved in ACN, methanesulfonic acid soln added, stirred, RT, clear soln. Added IPE, stirred, RT, clear soln. FE, clear gel. Dried under vacuum at 40° C., clear gel. | — |
| | API dissolved in IPA, methanesulfonic acid and 10.0 uL $H_2O$ added, stirred, RT → −25° C., clear light yellow soln. Added MTBE, stirred, RT → −25° C., clear gel. FE, clear light brown gel. Dried under vacuum at 50° C., clear brown gel. | — |
| 1-hydroxy, 2-napthoic | API dissolved in acetone, 1-hydroxy, 2-naphthoic added, stirred, RT → −25° C., clear light brown soln. SE, brown gel. Added MTBE, stirred, RT, clear light brown soln w/light brown film. FE, brown gel. Dried under vacuum at 40° C., yellow/orange gel. | — |
| | API dissolved in IPA, 1-hydroxy, 2-naphthoic added, stirred, RT, clear light brown soln w/small amt of film. Added DEE, stirred, RT → 5° C., clear light brown soln w/small amt of brown film. FE, brown gel. Dried under vacuum at 40° C., brown gel. | — |
| Phosphoric | API dissolved in acetone, phosphoric acid soln added, stirred, RT, 1 d. White solids. | Phosphate 1 (FIG. 30) |
| | API dissolved in THF, phosphoric acid soln added, stirred, RT −25° C., turbid soln w/off-white gel. FE, clear brown/yellow gel. Added DEE, stirred, RT → −25° C., yellow/orange gel. FE, yellow/brown tacky gel-like solids. Dried under vacuum at 50° C., yellow/orange tacky gel. | — |
| | API dissolved in IPA, phosphoric acid added, stirred, RT, 2 d. White solids. | Phosphate 1 |
| Succinic | API dissolved in acetone, succinic acid added, stirred, RT → 5° C., 1 d. White solids. | Succinate 1 (FIG. 31) |
| | API dissolved in THF, succinic acid added, stirred, RT → −25° C., clear light yellow soln. SE, yellow gel. Added IPE, stirred, RT, clear soln w/yellow gel. FE, light yellow tacky gel/solids. Dried under vacuum at 40° C., yellow/orange tacky solids. | Succinate 2 + Succinate 1 + peaks + NC |
| | API dissolved in ACN, succinic acid added, stirred, RT, 2 d. White solids. | Succinate 2 (FIG. 36) |
| Sulfuric | API dissolved in acetone, sulfuric acid soln added, stirred, RT −25° C., clear soln. SE, mix of off-white & brown solids | Sulfate 1 (PO) (FIG. 32) |
| | API dissolved in ACN, sulfuric acid soln added, stirred, RT, clear soln. Added IPE, stirred, RT, clear soln w/clear gel. FE, clear gel. Dried under vacuum at 40° C., light black clear gel. | — |
| | API dissolved in THF, sulfuric acid and 10.0 uL $H_2O$ added, stirred, RT → −25° C., clear yellow soln. Added DEE, stirred, RT → −25° C., brown/orange oil. FE, clear orange/brown gel. Dried under vacuum at 50° C., black gel. | — |
| L-tartaric | API dissolved in acetone, L-tartaric acid added, stirred, RT, 1 d. White solids. | Tartrate 1; LC (FIG. 33) |
| | API dissolved in IPA, L-tartaric acid added, stirred, RT, 3 d. White solids. | Tartrate 1; LC |
| Toluenesulfonic | API dissolved in acetone, p-toluenesulfonic acid added, stirred, RT → −25° C., clear soln. SE, clear gel. Added DEE, stirred, RT, clear soln w/clear gel. FE, clear light yellow gel. Dried under vacuum at 40° C., clear gel. | — |
| | API dissolved in THF, p-toluenesulfonic acid added, stirred, RT → −25° C., clear soln. SE, clear slight yellow gel. Added MTBE, stirred, RT, clear soln w/light brown gel. FE, clear light brown gel. Dried under vacuum at 40° C., yellow/orange gel. | — |

TABLE Ex5-2-continued

| Acid | Conditions[a] | PXRD Result[b] |
|---|---|---|
| | API dissolved in IPA, p-toluenesulfonic acid added, stirred, RT → −25° C., clear soln w/gel-like particles. Added IPE, stirred, RT → −25° C., white solids. | Tosylate 1 (FIG. 37) |

[a]API = active pharmaceutical ingredient;
RT = room temperature;
d = day(s);
THF = tetrahydrofuran;
ACN = acetonitrile;
SE = slow evaporation;
DEE = diethyl ether;
FE = fast evaporation;
IPE = isopropyl ether;
MTBE = methyl tert-butyl ether;
IPA = isopropanol;
soln = solution;
w/= with;
amt = amount
[b]acid = PXRD pattern contained peaks matching a reference pattern for the acid used in the reaction;
LC = low crystallinity;
NC = non-crystalline MBDB HCl was crystallized by dissolving MBDB HCl in ACN at 70° C. The sample was cooled to RT yielding a clear solution. The sample was cooled to −25° C. (clear soln). MTBE was added and the sample returned to −25° C. After 3 days, white solids were collected and analyzed by XRPD, yielding the diffractogram provided in FIG. 38.

The MBDB free base was dissolved in IPA, 1N HCl in DEE was added. Stirring at room temperature for 1 day yielded white crystalline solids. Analysis of this material by XRPD yielded the diffractogram provided in FIG. 39.

Example 6

Characterization of MBDB Salts

| Salt | Stoichiometry[b] | Solvation State[c] | Thermal (° C.)[d] | Physical Stability [e] | Hygroscopic?[f] | Water solubility[g] |
|---|---|---|---|---|---|---|
| Citrate 1 | 1:1 | Unsolvated | 105 | Tacky solids | — | >62 |
| Fumarate 1 | 1:1 | Unsolvated | 83 | No change | — | 21 |
| Galactarate 1 [a] | 1:1 | Unsolvated | 147 | No change | — | <1 |
| Maleate 1 | 1:1 | Unsolvated | 99 | No change | Slightly hygroscopic | >68 |
| Malonate 1 | 1:1 | Unsolvated | 111 | No change | — | — |
| Phosphate 1 | 1:1.7 | Unsolvated | 165 | No change | Hygroscopic | 26 |
| Succinate 1 | 1:1 | Unsolvated | 78 | Tacky solids | — | >30 |
| Succinate 2 | 1:1 | Unsolvated | 115 | No change | Moderately hygroscopic | >27 |
| Sulfate 1[h] | 1:1 | Unsolvated | Continuous weight loss | Deliquesced | — | — |
| Tosylate 1 | 1:1 | Potential hydrate/ solvate | 4.0% loss to 150 | No change | — | — |

[a]Residual acid present based on PXRD analysis. Galactaraic acid is also known as mucic acid.
[b]Stoichiometry is API:acid molar ratio and was determined by NMR or IC
[c]Solvation state determined by the weight loss observed in TGA
[d]Lowest major endothermic event reported as melting point
[e] Physical stability assessed at 40° C./75% RH overnight.
[f]Hygroscopicity determined based on moisture uptake at 95% observed during DVS analysis
[g]Solubility determined based on a visual assessment after addition of water to weighed amounts of the salt. Solubility reported in mg/mL solvent.

Several crystalline hits were observed during the screen including potential salts with citric, fumaric, galactaric, maleic, malonic, phosphoric, succinic, sulfuric, and toluenesulfonic acids. Initial characterization data narrowed the salts to Maleate 1, Succinate 2, and Phosphate 1. Phosphate 1 exhibited minor unidentified peaks in the NMR and was removed from consideration. Succinate salt preparations were not consistent, resulting in different forms or mixtures of forms, and Succinate 2 exhibited possible hydrate formation at high RH conditions, therefore, it was advanced. Maleate 1 salt was selected based on its anhydrate designation, ease of preparation, high aqueous solubility, and minimal water sorption over RH range.

Estimated Solubilities of Maleate 1

| Solvent | Solubility (mg/mL) |
|---|---|
| acetone | >60 |
| acetonitrile (ACN) | 31 |
| chloroform ($CHCl_3$) | >60 |

-continued

| Solvent | Solubility (mg/mL) |
|---|---|
| dichloromethane (DCM) | >62 |
| 1,4-dioxane | 6 |

-continued

| Solvent | Solubility (mg/mL) |
|---|---|
| dimethylformamide (DMF) | >66 |
| dimethyl sulfoxide (DMSO) | >62 |
| ethyl acetate (EtOAc) | 3 |
| ethanol (EtOH) | >60 |
| methyl ethyl ketone (MEK) | 2 |
| methanol (MeOH) | >64 |
| methyl t-butyl ether (MTBE) | <1 |
| isopropanol (IPA) | 8 |
| tetrahydrofuran (THF) | 33 |
| toluene | <1 |
| water | >62 |

Example 6.1

Polymorph Screen of MBDB Maleate

| Crystallization Method[a] | Solvent[b] | Conditions[c, d] | PXRD Result |
|---|---|---|---|
| Slurry | 1:2 Acetone/methyl-cyclohexane | Slurried RT, 15 days, white solids. | Maleate 1 |
| | 1:1 ACN/MTBE | Slurried RT, 15 days, white solids. | Maleate 1 |
| | 1:2 Chloroform/DEE | Slurried RT, 15 days, white solids. | Maleate 1 |
| | Dioxane | Slurried RT, 15 days, white solids. | Maleate 1 |
| | EtOAc | Slurried RT, 15 days, white solids. | Maleate 1 |
| | 1 · 2 EtOH/heptane | Slurried RT, 15 days, white solids. | Maleate 1 |
| | IPA | Slurried RT, 15 days, white solids. | Maleate 1 |
| | 1.2 MeOH/IPE | Slurried RT, 15 days, white solids. | Maleate 1 |
| | MEK | Slurried RT, 15 days, white solids. | Maleate 1 |
| | 1:2 THF/hexane | Slurried RT, 15 days, white solids. | Maleate 1 |
| | iProAc | Slurried at 52° C., 9 days, white solids. | Maleate 1 |
| | MIBK | Slurried at 52° C., 9 days, white solids. | Maleate 1 |
| | Toluene | Slurried at 52° C., 9 days, white solids. | Maleate 1 |
| Antisolvent Addition | Acetone/IPE | IPE added dropwise to API/acetone soln until turbid, stirred, RT, 1 day. White solids. | Maleate 1 |
| | EtOH/MTBE | EtOH/API soln added to MTBE, stirred, RT, white solids. | Maleate 1 |
| | MeOH/DEE | MeOH/API soln added to DEE, stirred, RT, white solids. | Maleate 1 |
| | $H_2O$/Dioxane | $H_2O$/API soln added to dioxane, stirred, RT → −25° C., partially froze, clear soln. FE, mix of brown/orange gel & off-white gel-like solids. Discontinued. | — |
| | $CHCl_3$/EtOAc | $CHCl_3$/API soln added to EtOAc, stirred, RT → −25° C., clear soln. FE, mix of light tan and white solids. | Maleate 3 |
| | DCM/Heptane | DCM/API soln added to heptane, stirred, RT, white solids. | Maleate 1 |
| | THF/MTBE | THF/API soln added to DEE, stirred, RT, white solids. | Maleate 1 + minor |
| | DMSO/MTBE | DMSO/API soln added to MTBE, stirred, RT → −25° C., clear soln. FE, solids remained in soln. Discontinued. | — |
| | DMF/DEE | DMF/API soln added to DEE, stirred, RT, white solids. | Maleate 1 |
| FE | 92:8 ACN/water | Dissolved at ~50 mg/mL. Evaporated from uncapped vial at RT. White solids | Maleate 1 |
| | 84:16 IPA/water | Dissolved at ~50 mg/mL. Evaporated from uncapped vial at RT. White solids. | Maleate 1 |
| | 1-PrOH/heptane | Evaporated from uncapped vial at RT. White solids. | Maleate 1 |
| | Acetone | Evaporated from uncapped vial at RT, clear gel. Added DEE, stirred, RT, 2 d. White solids. | Maleate 1 |
| | $CHCl_3$ | Evaporated from uncapped vial at RT, white gel. Added IPE, stirred, RT, 2 d. White solids. | Maleate 1 |
| SE | DCM | Capped, clear soln. Removed cap, FE, white gel. Added IPE, stirred, RT, 1 d. White solids. | Maleate 1 |
| | EtOH | Parafilmed, clear gel. Added MTBE, stirred, RT, 2 d. White solids. | Maleate 1 |
| | THF | Parafilmed, clear gel. Added DEE, stirred, RT, 2 d. White solids. | Maleate 1 |
| Cooling | Dioxane | Dissolved at 70° C. → −25° C., white solids. | Maleate 2 |
| | | Dissolved at 70° C. and crash cool to freezer, white solids. Immobile plug. Warmed to RT. White mobile suspension. Seeded with 1208-86-4. Stirred at RT for 4 days. White solids. | Maleate 1 |
| | IPA | Dissolved at 70° C. → −25° C., white solids. | Maleate 1 |
| | iPrOAc | Dissolved at 70° C. → −25° C., agg of white solids. | Maleate 1 + Maleate 3 |
| | 2:1 ACN/Heptane | Crash cool 59° C. → −25° C., clear soln. Added addition heptane until just turbid, stirred, RT, 7 d. White solids. | Maleate 1 |
| Lyophilization | $H_2O$ | Clear gel. dried at RT, remained clear gel. 40° C./75% RH stress. Tan gel. Discontinued. | — |
| VD | EtOH | Hexane as antisolvent, RT, visible plates. Single crystal collected. | Maleate 1 |
| | THF | IPE as antisolvent. RT, 53 d, white solids. | Maleate 1 |
| | ACN | DEE as antisolvent, RT, small amt of solids. FE, white & clear gel. Added MTBE, stirred, RT, 4 d, white solids. | Maleate 1 |

-continued

| Crystallization Method[a] | Solvent[b] | Conditions[c, d] | PXRD Result |
|---|---|---|---|
| | $CHCl_3$ | MTBE as antisolvent, RT, 17 d. White agg solids. | Maleate 1 |
| RH Stress | 40° C./75% RH | 50 d. Free-flowing white solids. | Maleate 1 |
| Rotary evaporation | Acetone | Clear gel. Dried under vacuum, 22 d. White slightly tacky solids. | Maleate 1 + Maleate 3 |
| Milling | N/A | 100% power, 30 min. Light yellow/off-white solids. | Maleate 1 |

[a]FE = fast evaporation;
SE = slow evaporation;
VD = vapor diffusion;
RH = relative humidity
[b]ACN = acetonitrile;
MTBE = methyl tert-butyl ether;
DEE = diethyl ether;
EtOAc = ethyl acetate;
EtOH = ethanol;
IPA = isopropanol;
MeOH = methanol;
IPE = isopropyl ether;
MEK = methyl ethyl ketone;
THF = tetrahydrofuran;
IPrOAc = isopropyl acetate;
MIBK = methyl isobutyl ketone;
DCM = dichloromethane;
DMSO = dimethyl sulfoxide;
DMF = dimethylformamide;
1-PrOH = 1-propanol;
RH = relative humidity
[c]RT = room temperature;
API = active pharmaceutical ingredient;
soln = solution;
FE = fast evaporation;
d = day(s);
agg = agglomerate(s)

Salt Formation Experiments with MBDB Free Base and Maleic Acid

| Solvent[a] | Conditions[b] | PXRD Result |
|---|---|---|
| ACN | Slurry w/FB arid 1 equivalent of acid, stirred, RT → −25° C., 4 d. Added DEE until turbid, stirred, RT, 1 d. White solids. | Maleate 1 |
| EtOAc | Slurry w/FB and 0.5 equivalent of acid, stirred, RT, 2 d. White solids. | Maleate 1 |
| | Slurry w/FB and 0.75 equivalent of acid, stirred, RT 2 d. White solids. | Maleate 1 + Maleate 3 |
| | Slurry w/FB and 1 equivalent of acid, stirred, RT 2 d. White solids. | Maleate 1 |
| | Slurry w/FB and 2 equivalents of acid, stirred, RT → −25° C., 4 d. Added MTBE until turbid, stirred, RT, 1 d. Sample turned to an oil. Discontinued. | — |
| | Slurry w/FB and 5 equivalents of acid, stirred, RT 2 d. White solids. | Maleic acid |
| EtOH | Slurry w/FB and 1 equivalent of acid, stirred, RT → −25° C., 4 d. Added IPE until turbid, stirred, RT, 1 d. White solids. | Maleate 1 |
| THF | Slurry w/FB and 1 equivalent of acid, stirred, RT → −25° C., 4 d. White suspension at −25° C., clear soln at RT. Added DEE until turbid (some oiling observed), stirred, RT, 1 d. Off-white solids. | Maleate 1 |

Figure 96:
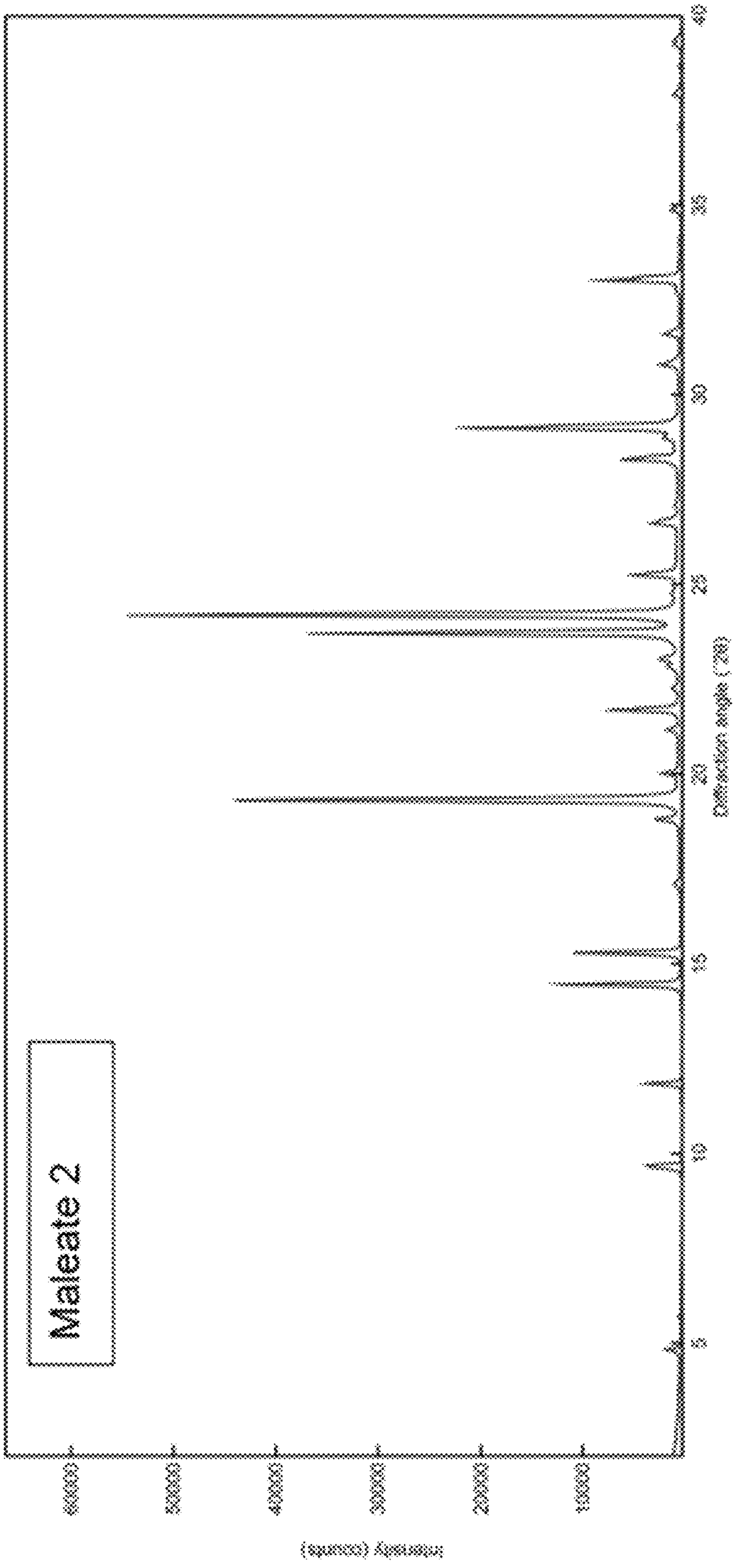
FIG. 96 provides an XRPD diffractogram of crystalline MBDB·maleate Form 2.
Figure 100:
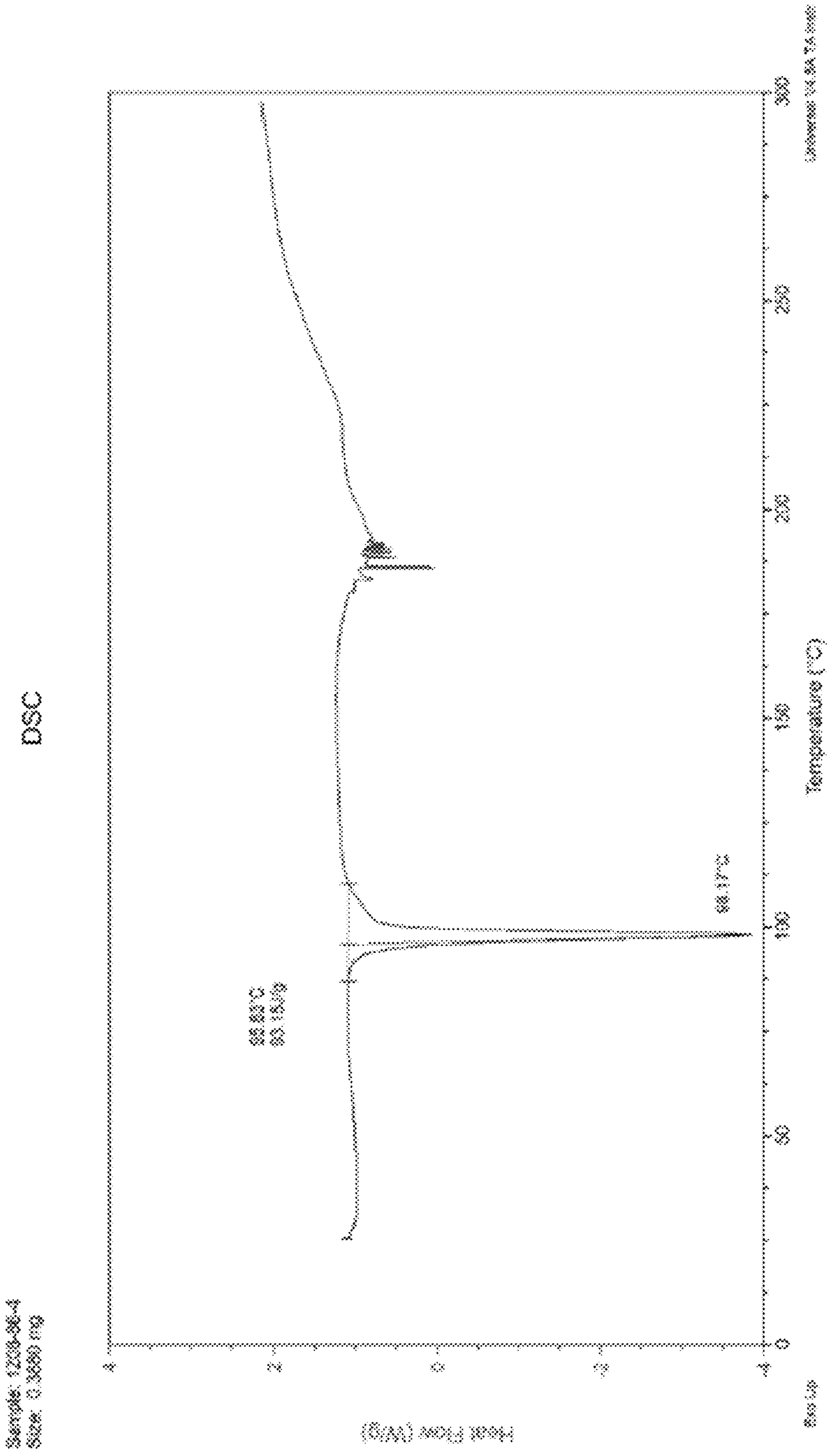
FIG. 100 provides TGA and DSC profiles for MBDB maleate (Form 2).
Figure 101:
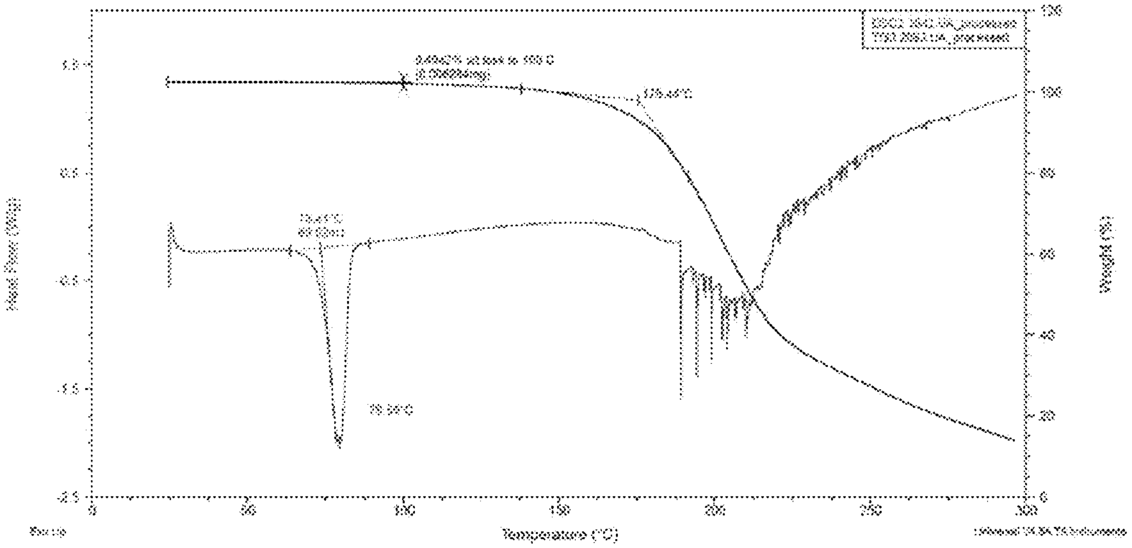
FIG. 101 provides TGA and DSC profiles for MBDB maleate (Form 3).

[a]ACN = acetonitrile;
EtOAc = ethyl acetate;
EtOH = ethanol;
THF = tetrahydrofuran
[b]w/= with;
FB = free base;
d = day(s);
RT = room temperature;
MTBE = methyl tert-butyl ether;
IPE = isopropyl ether;
DEE = diethyl ether During the screen, a single crystal Maleate 1 of sufficient size and quality was obtained from a vapor diffusion experiment with ethanol and hexane. The crystal structure is reported elsewhere but the data confirmed the anhydrous/unsolved nature of the material. MBDB Maleate 1 was exposed to 40° C./75% RH for 50 days and no change was observed by PXRD indicating the material is physically stable under those conditions. Maleate 1 was also ball milled and the recovered solids were consistent with the starting material indicating the material was stable under mechanical stressing. Two new crystalline forms of MBDB Maleate were observed during the screening designated as MBDB Maleate 2 and MBDB Maleate 3 (FIG. 96, 97). Additional characterization of these samples was conducted to better understand the nature of the materials produced, as shown below. MBDB Maleate 2 was generated once from a cooling crystallization from dioxane. The proton nuclear magnetic resonance (NMR) spectrum was consistent with a monomaleate salt of MBDB and contained residual dioxane. Only a limited amount of material was recovered so the only additional characterization that could be completed was differential scanning calorimetry (DSC). The DSC thermogram appears consistent with an anhydrous/unsolvated form with a likely melt at 96° C. (FIG. 100). The melting point and heat of fusion of Maleate 2 were both lower than Maleate 1 (FIG. 72) suggesting that Maleate 2 and Maleate 1 are likely monotropically related with Maleate 1 being more stable than Maleate 2. An attempt was made to reproduce Maleate 2 using the same conditions and seeds of Maleate 2. PXRD analysis of the recovered solids however was consistent with Maleate 1. MBDB Maleate 3 was isolated from an evaporation experiment involving chloroform and ethyl acetate. NMR analysis of the material was consistent with a mono-maleate salt of MBDB. Thermal analysis was consistent with an anhydrous/unsolvated material with a likely melting point of 73° C. (FIG. 101). The DSC showed a lower melting onset and heat of fusion compared to Maleate 1 and Maleate 2 suggesting that Maleate 3 is metastable to these forms. No additional characterization was completed on this sample due to the limited amount of material that was recovered. Maleate 3 was isolated as a mixture with Maleate 1 from several additional experiments involving different crystallization techniques and solvent systems. A sample that was found to be a mixture of Maleate 3 and Maleate 1 was dried at 46° C. overnight to remove solvent and PXRD analysis of the recovered solids was consistent with Maleate 1 indicating that Maleate 3 is metastable under these conditions Characterization of Selected Materials

| Sample | Analytical Technique[a] | Results[c] |
|---|---|---|
| Maleate 2 | PXRD | Maleate 2 |
| | $^{1}H$ NMR | Consistent with the chemical structure contains 0.3 mols of dioxane per mol of salt |
| | DSC | Single endotherm with onset of 96 and peak at 98° C. |
| Maleate 1 + Maleate 3 | $^{1}H$ NMR | Consistent with chemical structure; contains 4 mols iPrOAc per mol of salt |
| | PXRD[b] | Maleate 1 |
| Maleic acid | $^{1}H$ NMR | Inconsistent with starting material. Maleic acid:ethyl acetate:API ratio of ~ 1:0.3:0.1 |
| Maleate 3 | $^{1}H$ NMR | Consistent with the chemical structure |
| | DSC | Single endotherm with onset of 73 and peak of 80° C. |
| | TGA | 0.4% weight loss to 100° C. |

MBDB Maleate Interconversion Slurry

| Conditions | PXRD Result |
|---|---|
| Saturated solution of MBDB Maleate 1 in isopropanol filtered into mixture of Maleate 1 and Maleate 3. Saturated solution transferred to vial containing seeds of Maleate 2. Slurried 5 days. | Maleate 1 |

CONCLUSIONS

A polymorph screen of MBDB Maleate was conducted. MBDB Maleate 1 was used as the starting material for recrystallization experiments covering a wide range of conditions, crystallization techniques, and conditions. Two new forms, MBDB Maleate 2 and MBDB Maleate 3, were isolated during the screen. Limited characterization of the two forms was conducted due to the small amounts of material recovered. Both samples appear to be anhydrous/unsolvated forms with lower apparent melting points and heats of fusion suggestive that these forms are metastable with respect to MBDB Maleate 1. Maleate 3 was observed to convert to Maleate 1 while drying at 46° C. An interconversion slurry at room temperature using Maleate 3 and Maleate 1 with seeds of Maleate 2 resulted in Maleate 1. The results of the polymorph screen suggest that Maleate 1 is the stable form

Example 7

General Polymorph Screen Procedure

The active pharmaceutical ingredient (API), which may be a free base or a salt, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the API is a solvate or hydrate, and to evaluate thermal stability. DVS data is used to evaluate hygroscopicity of the API and if hydrates can be formed at high relative humidity. About 10 to 15 solvents may be selected from Table 42, based on their properties (polarity, dielectric constant and dipole moment).

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).

API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.

API is exposed to elevated humidity (or elevated temperature, or combination thereof), or to solvent vapors for extended period of days.

Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).

API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50 (TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45° 2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuKα radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 $Kmin^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005° 2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 8

(S)-MDMA HCl

Powder X-ray diffraction analysis was performed on free flowing powder samples of (S)-MDMA HCl. Samples were placed in a Si zero background holder, and a preliminary scan in the 2θ range of 5-120° was performed to determine the extent of the crystallinity, and the appropriate settings to use for the full scan. The parameters used were as follows.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2theta range: 5-70°, step size=0.0334°, 0.5 s step-1.

Figure 13:
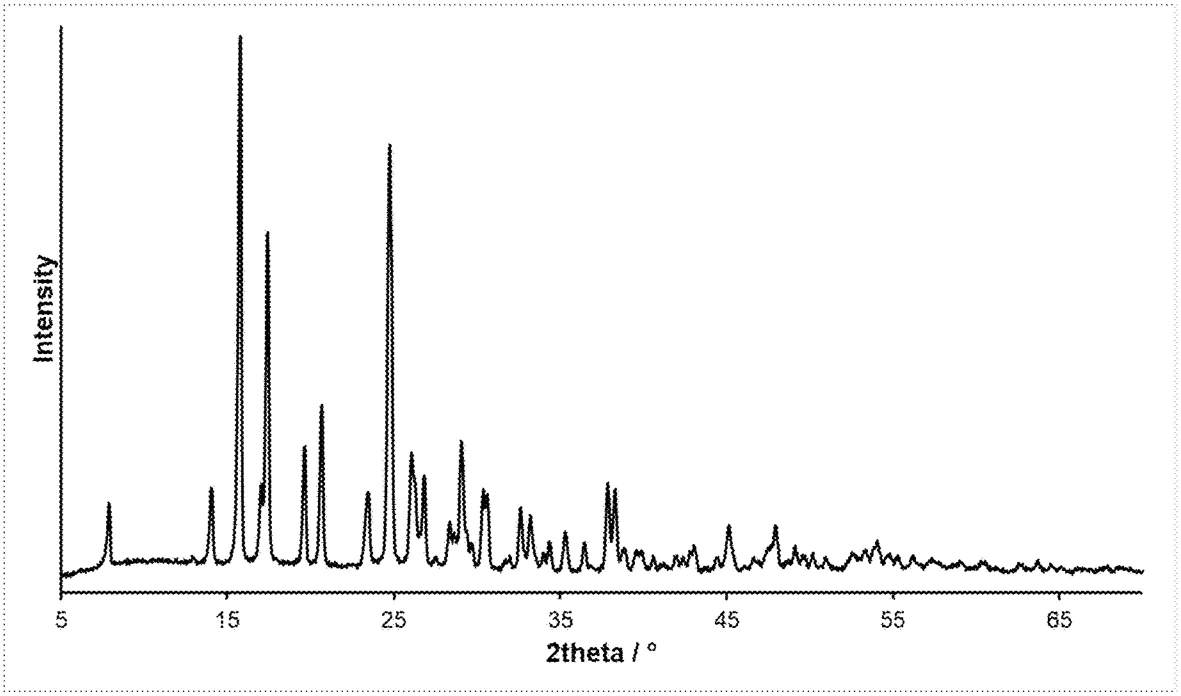
FIG. 13 is a plot of intensity versus 2theta, illustrating a stacked X-ray diffractogram plot of an exemplary solid form of (S)-3,4-methylenedioxymethamphetamine, crystalline (S)-3,4-methylenedioxymethamphetamine hydrochloride, with the data normalized to 10,000 counts.
Figure 14:
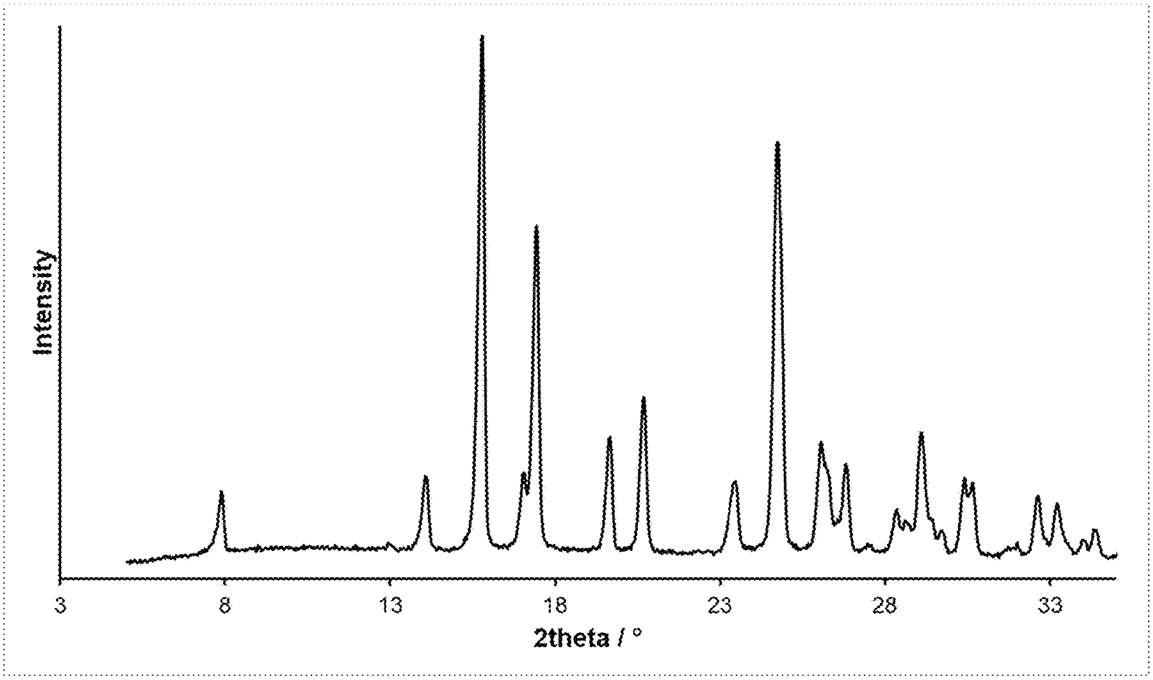
FIG. 14 is a plot of intensity versus 2theta, illustrating an expanded view of the 2theta region from 3° to 33° of the plot in FIG. 13.

A stacked diffractogram plot of the samples is provided in FIG. 13, and FIG. 14 provides an expanded view of the 2theta region from 3° to 33°.

The solid form of crystalline(S)-MDMA HCl analyzed is listed in Table Ex8.

TABLE Ex8

| Solid form of (S)-MDMA HCl | FIG. 13 |
|---|---|

Example 9

(R)-MDMA HCl

Powder X-ray diffraction analysis was performed on free flowing powder samples of (R)-MDMA HCl. Samples were placed in a Si zero background holder, and a preliminary scan in the 2θ range of 5-120° was performed to determine the extent of the crystallinity, and the appropriate settings to use for the full scan. The parameters used were as follows.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2theta range: 5-70°, step size=0.0334°, 0.5 s step-1

Figure 15:
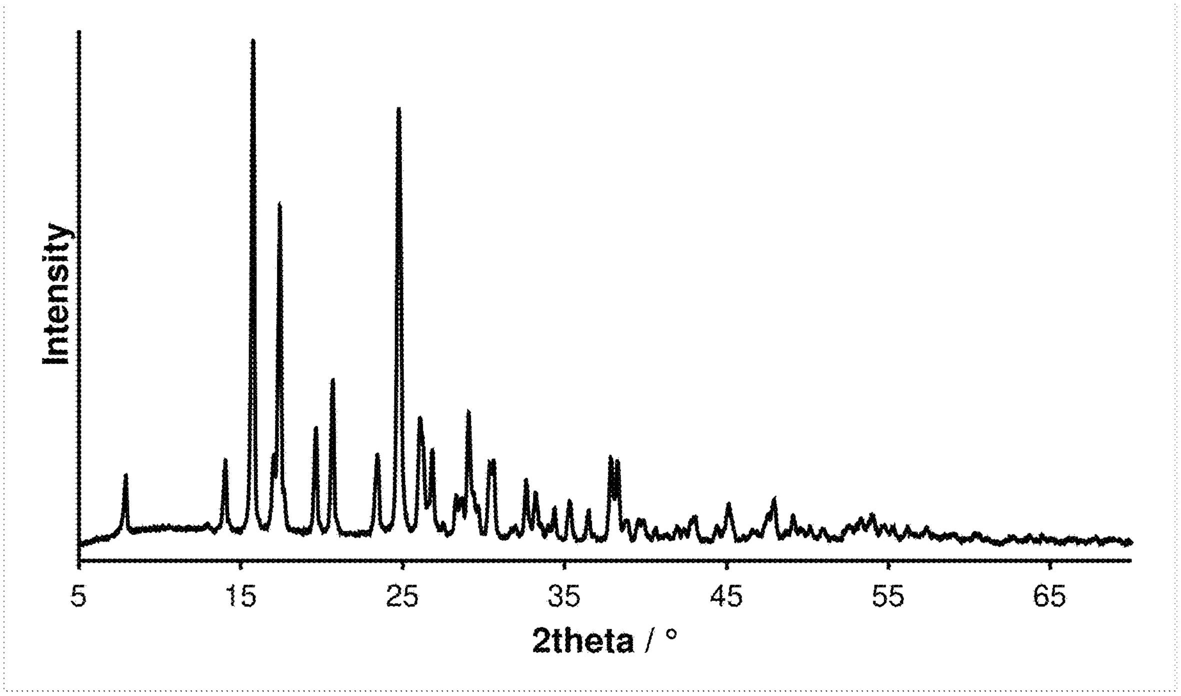
FIG. 15 is a plot of intensity versus 2theta, illustrating a stacked X-ray diffractogram plot of an exemplary solid form of (R)-3,4-methylenedioxymethamphetamine, crystalline (R)-3,4-methylenedioxymethamphetamine hydrochloride, with the data normalized to 10,000 counts.
Figure 16:
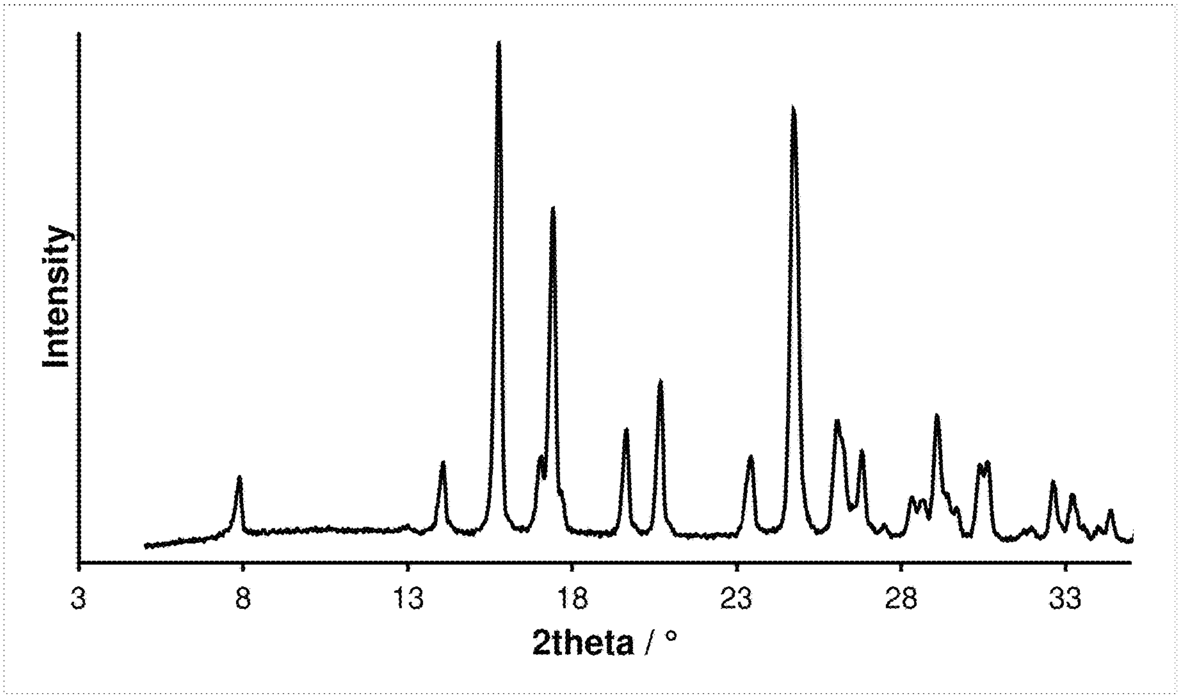
FIG. 16 is a plot of intensity versus 2theta, illustrating an expanded view of the 2theta region from 3° to 33° of the plot in FIG. 15.

A stacked diffractogram plot of the samples is provided in FIG. 15, and FIG. 16 provides an expanded view of the 2theta region from 3° to 33°. The solid form of crystalline (R)-MDMA HCl analyzed is listed in Table Ex9.

TABLE Ex9

| | |
|---|---|
| Solid form of R-MDMA HCl | FIG. 15 |

Example 10

N-ethyl-3,4-methylenedioxyamphetamine·hydrochloride

This example describes the characterization of an N-ethyl-3,4-methylenedioxyamphetamine hydrochloride salt and a crystalline solid form thereof. Samples transferred to a Si zero background holder.

A preliminary scan in the 2θ range of 5-120° was performed to determine the extent of the crystallinity, and the appropriate settings to use for the full scan.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2theta range: 5-70°, step size=0.0334°, 0.5 s step-1.

Figure 17:
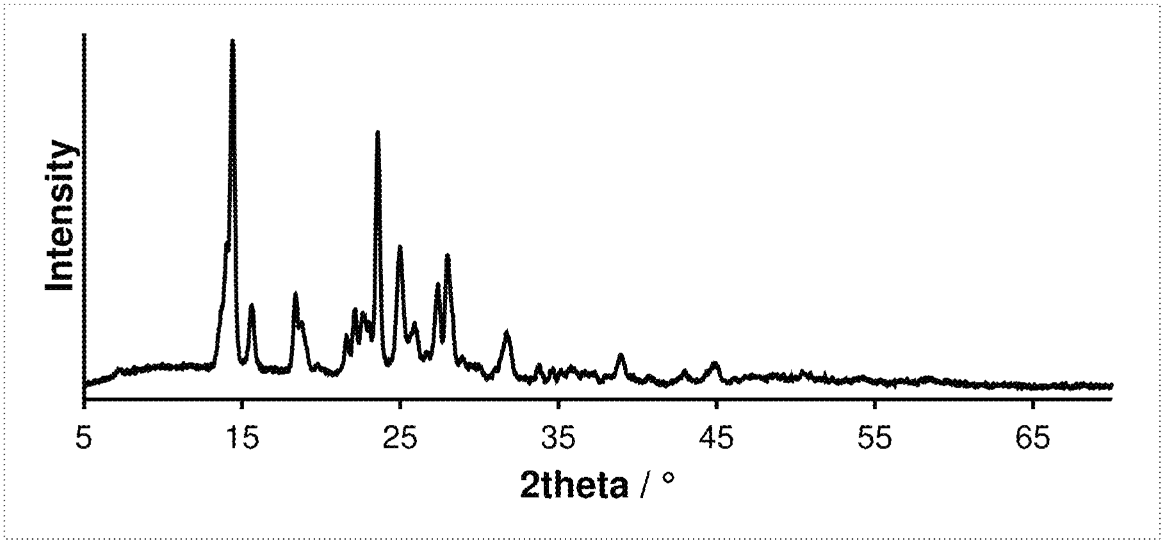
FIG. 17 provides an XRPD diffractogram of N-ethyl-3, 4-methylenedioxyamphetamine hydrochloride.
Figure 18:
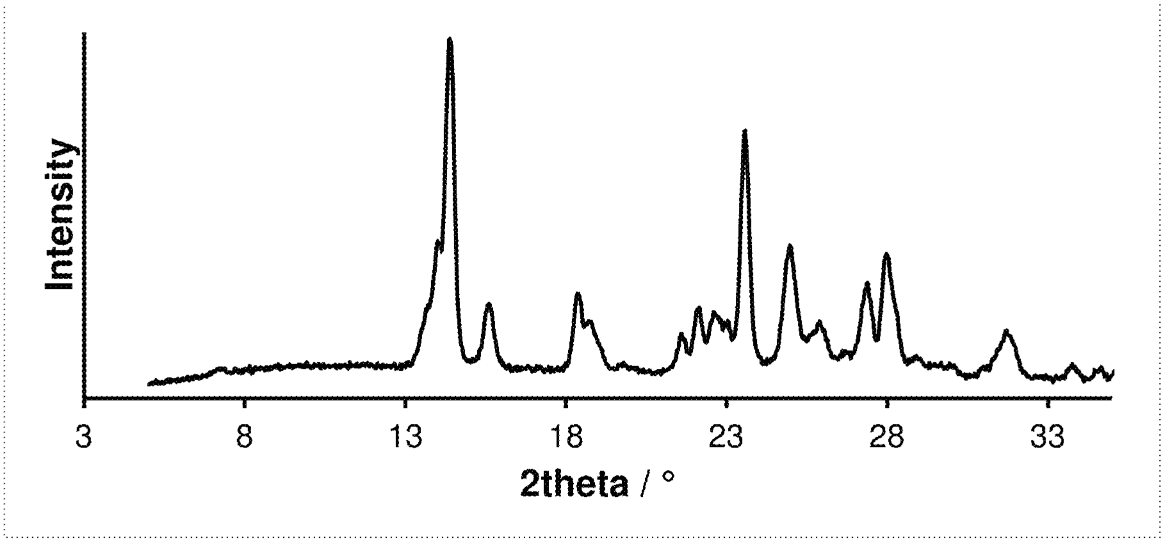
FIG. 18. provides an expanded section of the XRPD diffractogram provided in FIG. 17.

An XRPD diffractogram is provided in FIGS. 17 and 18, illustrating the crystallinity of the N-ethyl-3,4-methylenedioxyamphetamine hydrochloride salt. With reference to FIGS. 17 and 18, the data are normalised to 10000 counts.

The solid form of crystalline N-ethyl-3,4-methylenedioxyamphetamine HCl analyzed is listed in Table Ex10.

TABLE Ex10

| | |
|---|---|
| Solid form of N-ethyl-3,4-methylenedioxyamphetamine HCl | FIG. 17 |

Example 11

(S)—N-ethyl-3,4-methylenedioxyamphetamine·tosylate

This example describes the characterization of an(S)—N-ethyl-3,4-methylenedioxyamphetamine tosylate salt and a crystalline solid form thereof.

Samples transferred to a Si zero background holder.

A preliminary scan in the 2θ range of 5-120° was performed to determine the extent of the crystallinity, and the appropriate settings to use for the full scan.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2theta range: 5-70°, step size=0.0334°, 0.5 s step-1.

Figure 19:
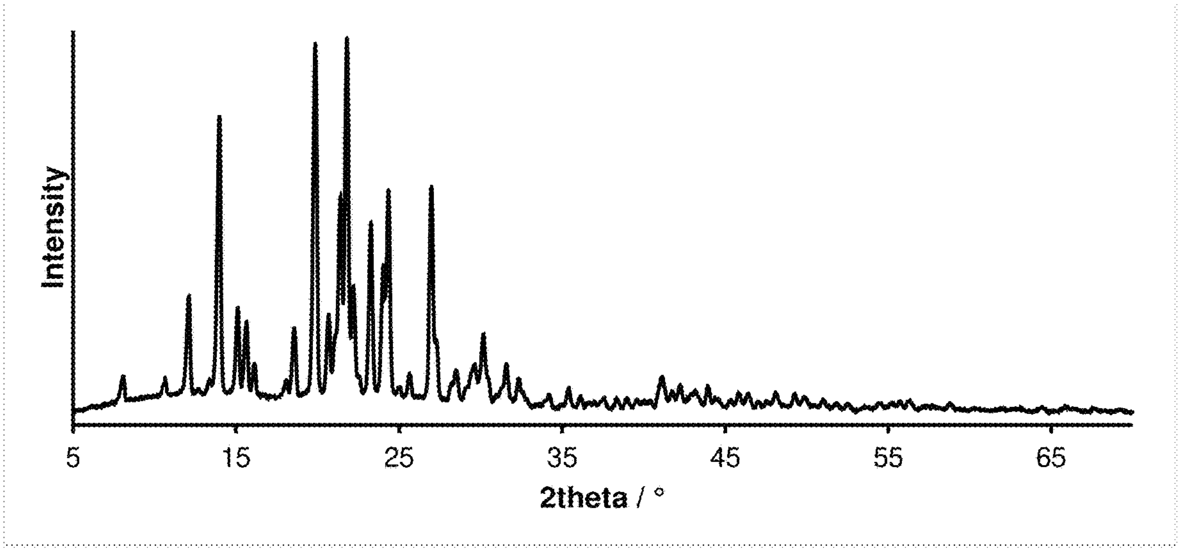
FIG. 19 provides an XRPD diffractogram of S-MDE tosylate.
Figure 20:
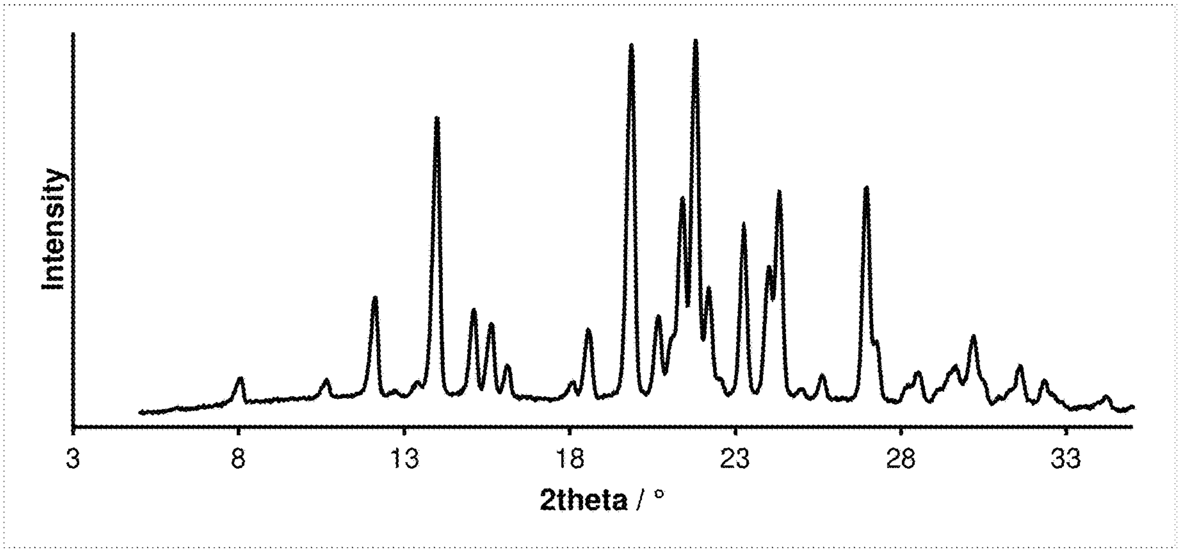
FIG. 20 provides an expanded section of the XRPD diffractogram provided in FIG. 19.
Figure 21:
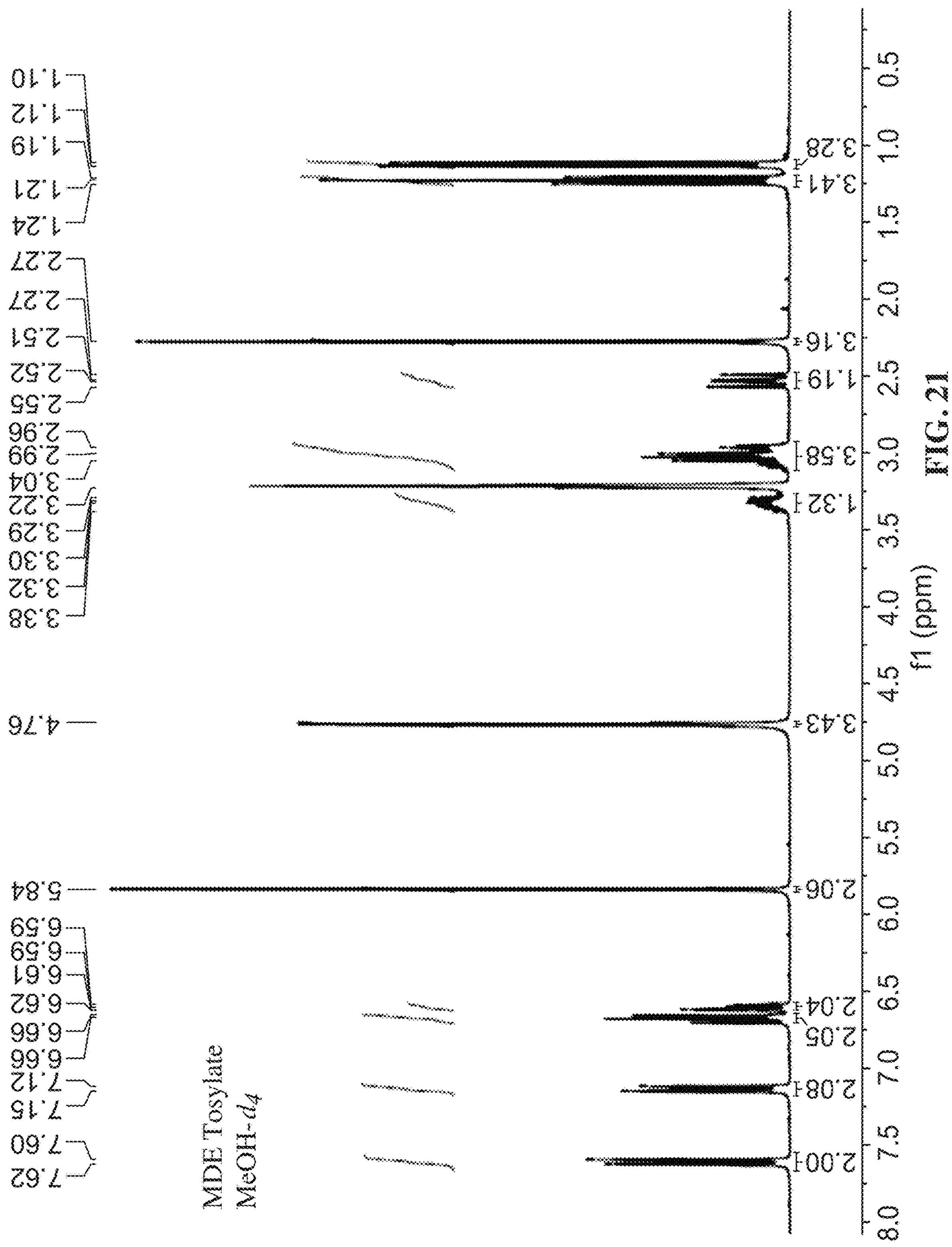
FIG. 21 provides a $^1$H NMR spectrum of the S-MDE tosylate salt in $d_4$-methanol.

An XRPD diffractogram is provided in FIGS. 19 and 20, illustrating the crystallinity of the (S)—N-ethyl-3,4-methylenedioxyamphetamine tosylate salt. With reference to FIGS. 19 and 20, the data are normalised to 10000 counts. A $^{1}H$ NMR spectrum is provided as FIG. 21, confirming the identity and stoichiometry of the tosylate salt.

The solid form of crystalline(S)—N-ethyl-3,4-methylenedioxyamphetamine tosylate analyzed is listed in Table Ex11.

TABLE Ex11

| | |
|---|---|
| Solid form of (S)-N-ethyl-3,4-methylenedioxyamphetamine tosylate | FIG. 19 |

Example 12

5,6-methylenedioxy-2-aminoindane hydrochloride

Powder X-ray diffraction analysis was performed on free flowing powder samples of 5,6-methylenedioxy-2-aminoindane hydrochloride. Samples were placed in a Si zero background holder, and a preliminary scan in the 2θ range of 5-120° was performed to determine the extent of the crystallinity, and the appropriate settings to use for the full scan. The parameters used were as follows.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2theta range: 5-70°, step size=0.0334°, 0.5 s step-1.

Stacked diffractogram plots of various samples of 5,6-methylenedioxy-2-aminoindane hydrochloride are provided in FIGS. 22 and 24, and FIGS. 23 and 25 provide expanded views of the 2theta region from 3° to 33°.

The solid forms of crystalline MDAI HCl analyzed are listed in Table Ex12.

TABLE Ex12

Figure 22:
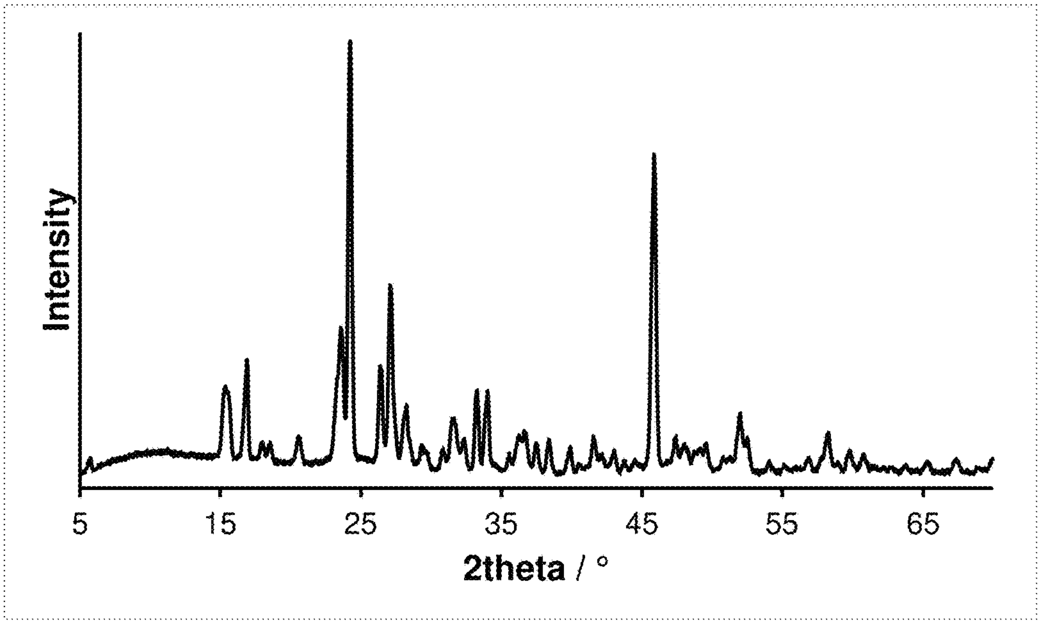
FIG. 22 is a plot of intensity versus 2theta, illustrating a stacked X-ray diffractogram plot of a first exemplary solid form of 5,6-methylenedioxy-2-aminoindane hydrochloride, crystalline 5,6-methylenedioxy-2-aminoindane hydrochloride, with the data normalized to 10,000 counts.
Figure 23:
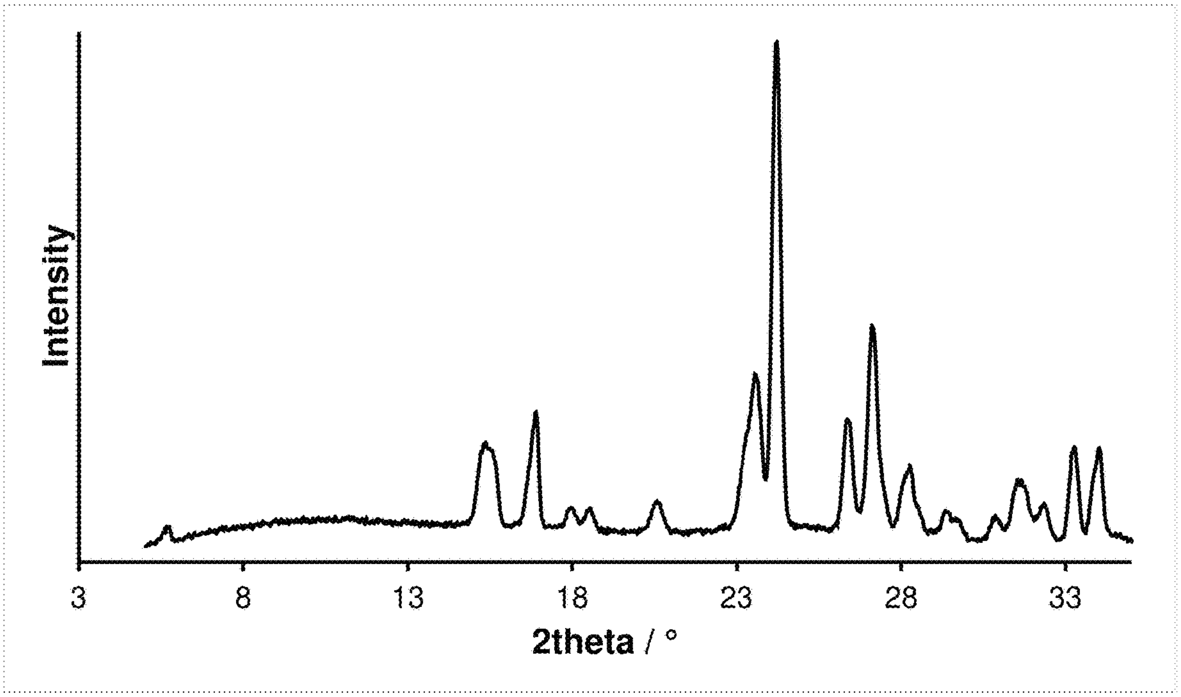
FIG. 23 is a plot of intensity versus 2theta, illustrating an expanded view of the 2theta region from 3° to 33° of the plot in FIG. 22.
Figure 24:
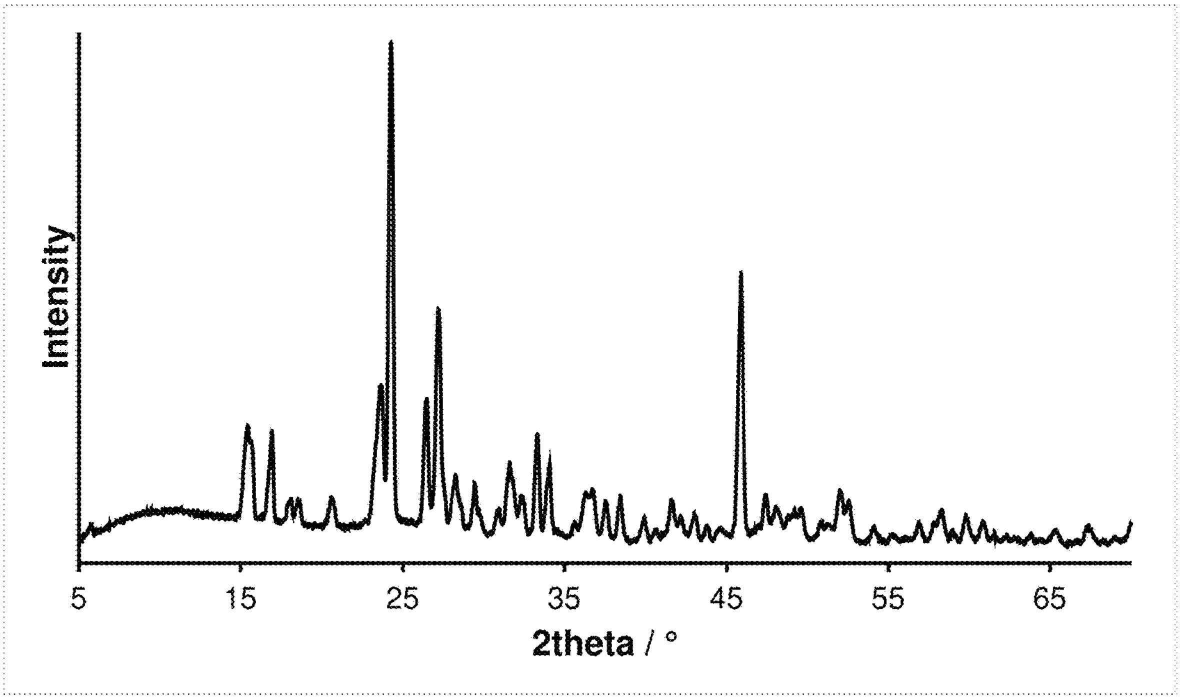
FIG. 24 is a plot of intensity versus 2theta, illustrating a stacked X-ray diffractogram plot of a second exemplary solid form of 5,6-methylenedioxy-2-aminoindane hydrochloride, crystalline 5,6-methylenedioxy-2-aminoindane hydrochloride, with the data normalized to 10,000 counts.
Figure 25:
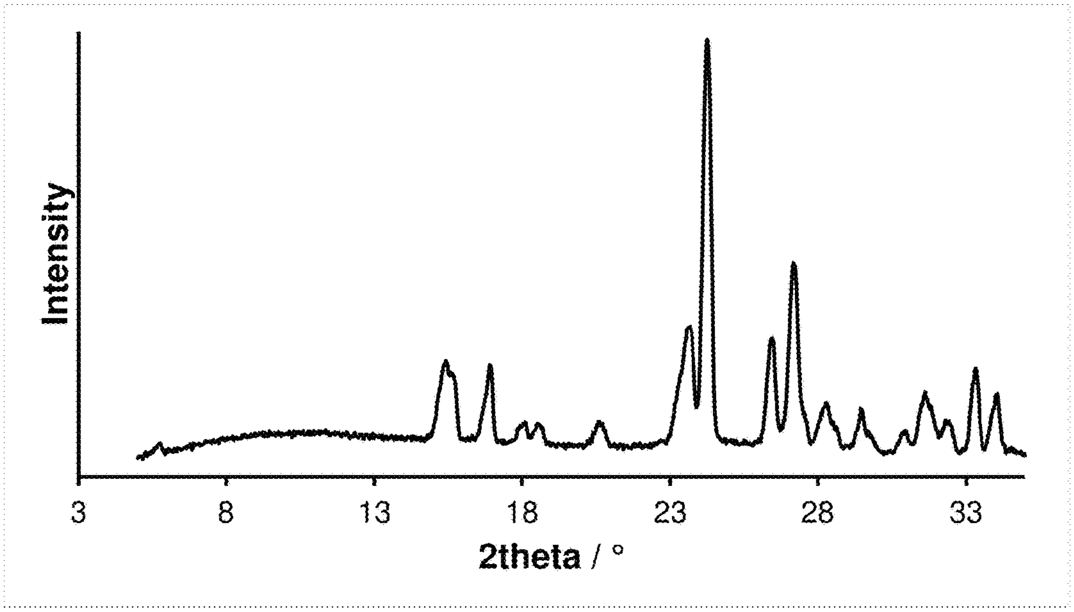
FIG. 25 is a plot of intensity versus 2theta, illustrating an expanded view of the 2theta region from 3° to 33° of the plot in FIG. 24.

| | |
|---|---|
| Solid form of MDAI HCl | FIG. 22 |
| Solid form of MDAI HCl | FIG. 24 |

Example 13

Preparation of MBDB HCl Solid Forms

Solid and crystalline forms thereof obtained from the polymorph screening experiments of MBDB HCl are summarized in Table Ex13.

MBDB HCl Form A 30.3 mg of MBDB HCl was weighed into a scintillation vial. Added approximately 3.0 mL of ACN dropwise and heated the system to 70° C. Clear solution was obtained and hot-filtered into a new clean pre-warmed vial. Heat was turned off and the sample was allowed to slowly cool to RT where the solution remained clear. Sample was placed in a freezer at ~−25° C. for 2 days resulting in a clear solution. Added approximately 3.0 mL of MTBE dropwise and returned the sample to the freezer for 3 days. White solids were observed to have formed and were isolated by decanting the liquid phase.

MBDB HCl Form B

Approximately 21.0 mg of MBDB freebase was dissolved by adding 0.5 mL of IPA and stirring at RT. 55.3 μL of 1N HCl in DEE was added and the sample was stirred at RT. After stirring overnight at RT, white solids were observed to have formed and were isolated via filtration.

TABLE Ex13

Figure 38:
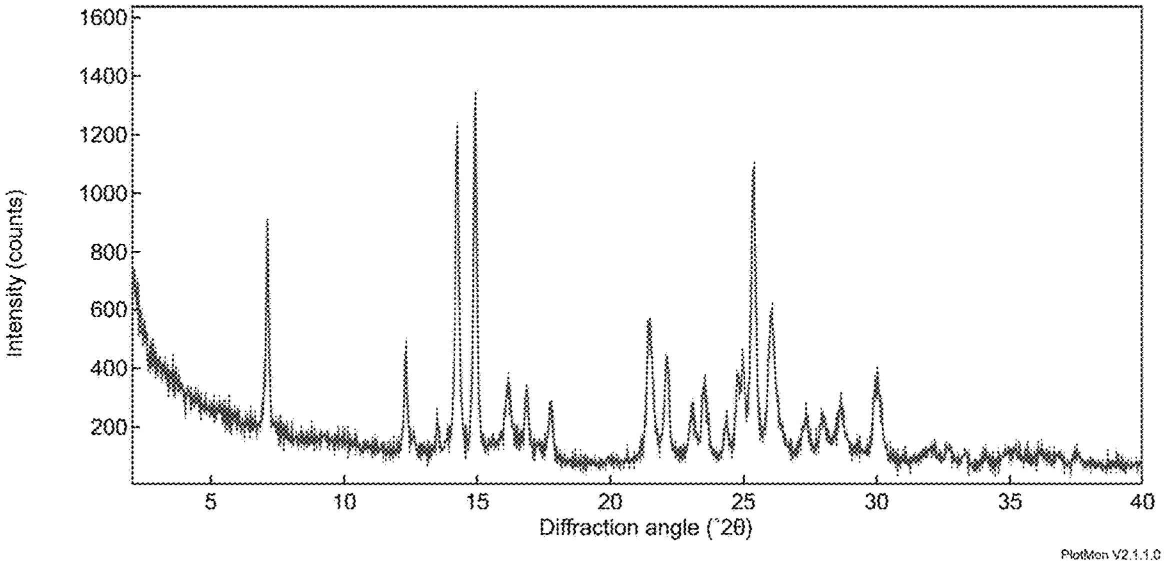
FIG. 38 provides an XRPD diffractogram of a sample comprising crystalline MBDB·HCl form A.
Figure 39:
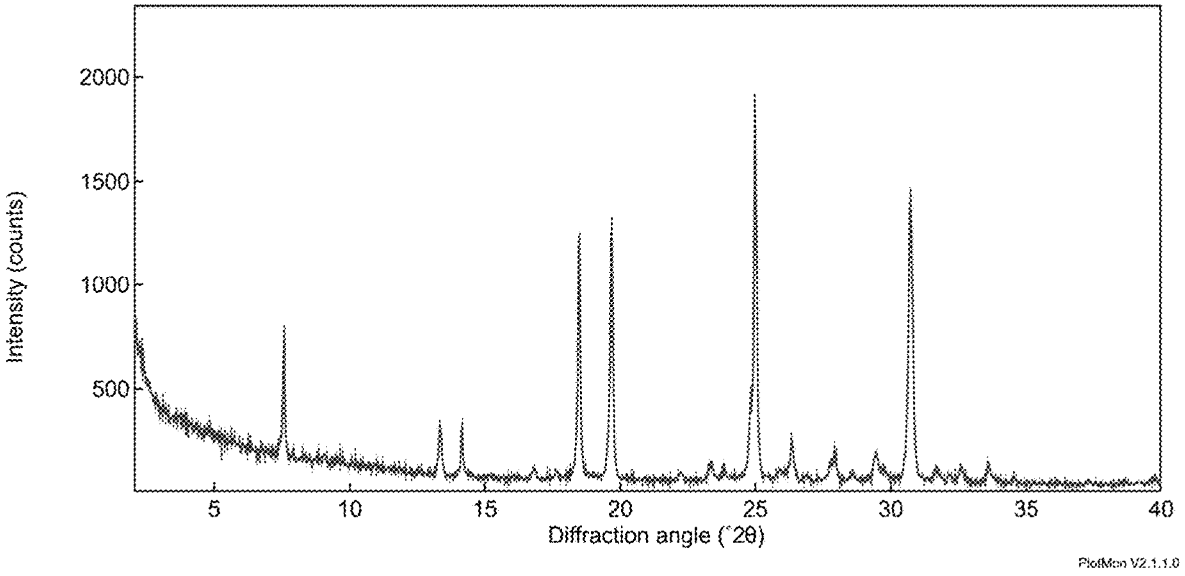
FIG. 39 provides an XRPD diffractogram of a sample comprising crystalline MBDB·HCl form B.

| | |
|---|---|
| MBDB HCl Form A | FIG. 38 |
| MBDB HCl Form B | FIG. 39 |

Estimated Solubilities of MBDB HCl

| Solvent | Solubility (mg/mL) |
|---|---|
| Acetone | 1 |
| ACN | 2 |
| EtOH | 15 |
| THF | <1 |
| Water | >62 |

Example 14

MEAI HCl

Powder X-ray diffraction analysis was performed on free-flowing powder samples of 5-methoxy-2-aminoindane hydrochloride. Samples were placed in a Si zero background holder, and a preliminary scan in the 2θ range of 5-120° was performed to determine the extent of the crystallinity, and the appropriate settings to use for the full scan. The parameters used were as follows.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2theta range: 5-70°, step size=0.0334°, 0.5 s step-1.

Figure 40:
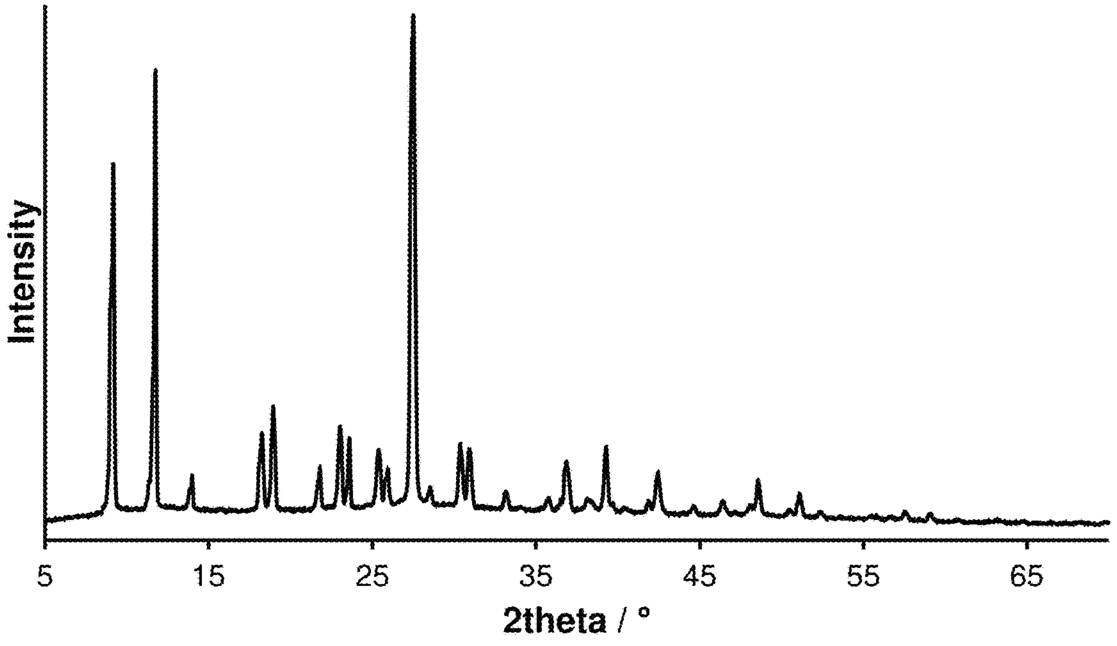
FIG. 40 is a plot of intensity versus 2theta, illustrating a stacked X-ray diffractogram plot of an exemplary solid form of 5-methoxy-2-aminoindane hydrochloride, crystalline 5-methoxy-2-aminoindane hydrochloride, with the data normalized to 10,000 counts.
Figure 41:
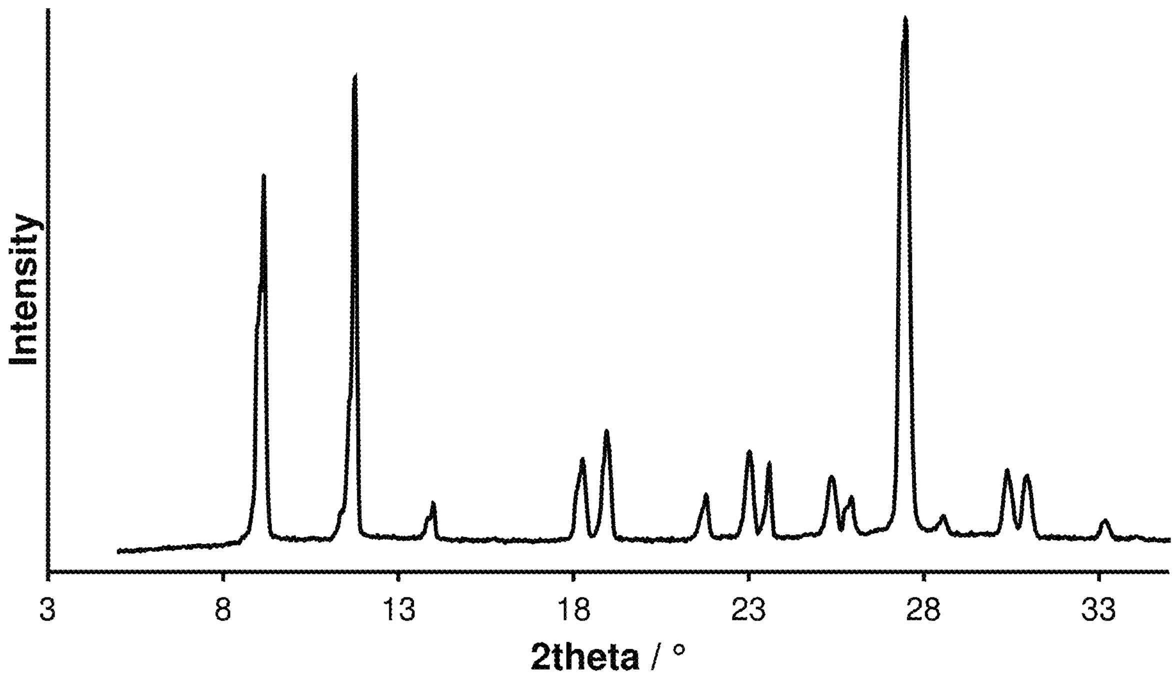
FIG. 41 is a plot of intensity versus 2theta, illustrating an expanded view of the 2theta region from 3° to 33° of the plot in FIG. 40.

A stacked diffractogram plot of the samples is provided in FIG. 40, and FIG. 41 provides an expanded view of the 2theta region from 3° to 33°.

The solid form of crystalline MEAI HCl analyzed is listed in Table Ex14.

TABLE Ex14

| | |
|---|---|
| Solid form of MEAI HCl | FIG. 40 |

Example 15

5,6-dimethoxy-2-aminoindane HCl

Powder X-ray diffraction analysis was performed on free-flowing powder samples of 5,6-dimethoxy-2-aminoindane hydrochloride. Samples were placed in a Si zero background holder, and a preliminary scan in the 2θ range of 5-120° was performed to determine the extent of the crystallinity, and the appropriate settings to use for the full scan. The parameters used were as follows.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2theta range: 5-70°, step size=0.0334°, 0.5 s step-1.

Figure 42:
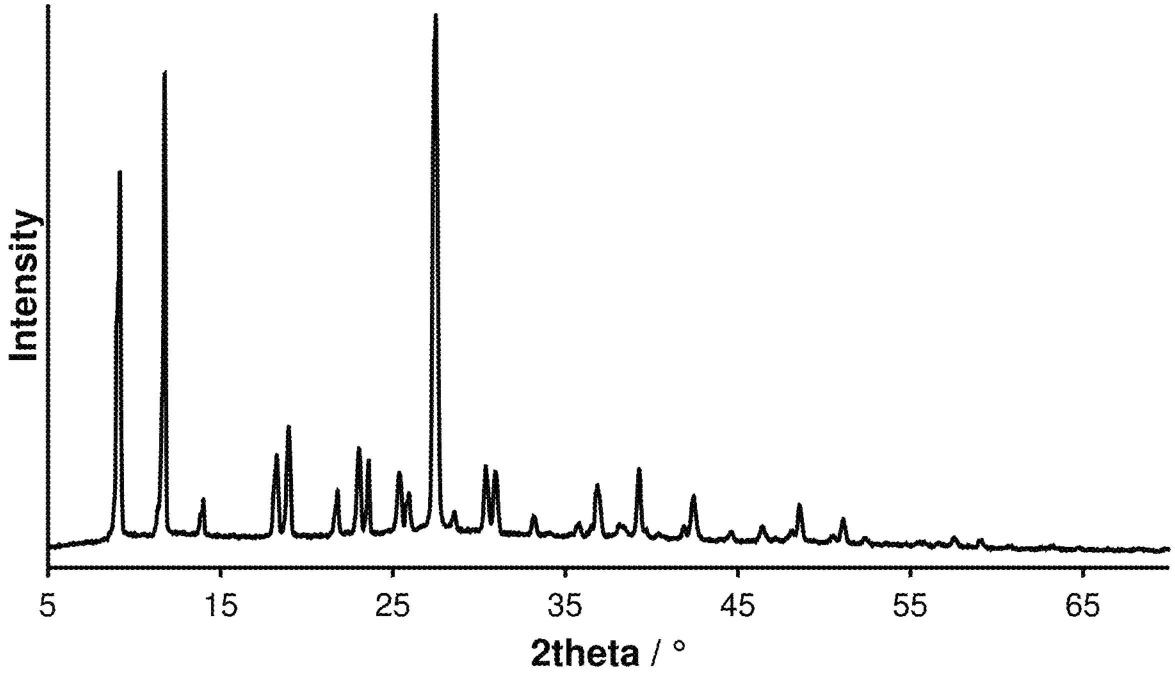
FIG. 42 is a plot of intensity versus 2theta, illustrating a stacked X-ray diffractogram plot of an exemplary solid form of 5,6-dimethoxy-2-aminoindane hydrochloride, crystalline 5,6-dimethoxy-2-aminoindane hydrochloride, with the data normalized to 10,000 counts.
Figure 43:
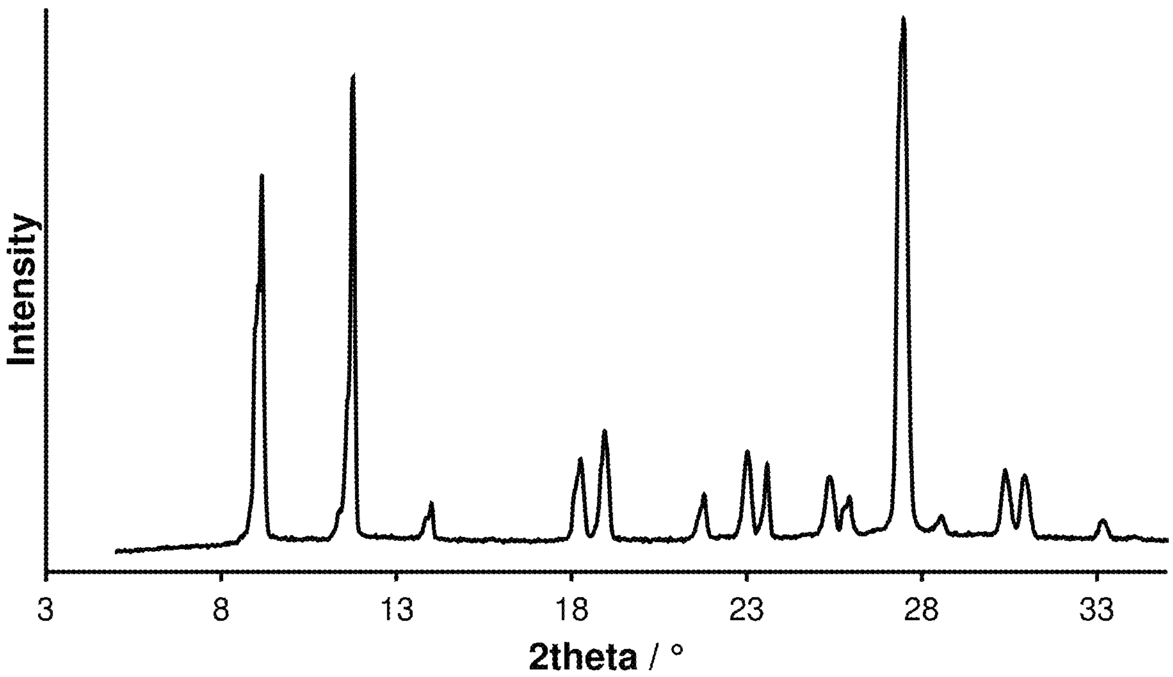
FIG. 43 is a plot of intensity versus 2theta, illustrating an expanded view of the 2theta region from 3° to 33° of the plot in FIG. 42.

A stacked diffractogram plot of the samples is provided in FIG. 42, and FIG. 43 provides an expanded view of the 2theta region from 3° to 33°.

The solid form of crystalline 5,6-dimethoxy-2-aminoindane HCl analyzed is listed in Table Ex15.

TABLE Ex15

| | |
|---|---|
| Solid form of 5,6-dimethoxy-2-aminoindane HCl | FIG. 42 |

Example 16

Scale Up and Characterization of MBDB Maleate Form 1

MBDB Maleate Form 1 was prepared at larger scale by adding a stoichiometric amount of maleic acid to a solution of MBDB free base in acetonitrile at room temperature. Additional IPE was added to the resulting clear solution and the sample was seeded with a small amount of Maleate 1 in an attempt to control the solid form produced. This process produced larger agglomerates composed of primary particles that were generally smaller than 20 μm in size.

The sample was initially characterized by PXRD, $^1H$ NMR, and thermal analysis. The characterization data was consistent with an unsolvated mono-maleate salt with a likely melting point around 99° C. The data generated for the scale up was consistent with the characterization data compiled for the screening sample.

DVS analysis of the material indicated the sample was slightly hygroscopic picking up 0.6% weight at 95% RH. The weight gain was reversibly lost during the desorption profile with no significant hysteresis observed. The post-DVS PXRD indicated no form change during the analysis.

Estimated Solubilities of MBDB Maleate Form 1

| Solvent | Solubility (mg/mL) |
|---|---|
| Acetone | >60 |
| acetonitrile (ACN) | 31 |
| chloroform ($CHCl_3$) | >60 |
| dichloromethane (DCM) | >62 |
| 1,4-dioxane | 6 |
| dimethylformamide (DMF) | >66 |
| dimethylsulfoxide (DMSO) | >62 |
| ethyl acetate (EtOAc) | 3 |
| ethanol (EtOH) | >60 |
| methyl ethyl ketone (MEK) | 2 |
| methanol (MeOH) | >64 |
| methyl t-butyl ether (MTBE) | <1 |
| isopropanol (IPA) | 8 |
| tetrahydrofuran (THF) | 33 |
| Toluene | <1 |
| Water | >62 |

Example 17

Scale Up and Characterization of MBDB Phosphate Form 1

To scale up MBDB Phosphate Form 1, MBDB free base oil was dissolved in acetone before adding a stoichiometric amount of phosphoric acid along with a small amount of seeds of MBDB Phosphate Form 1. After overnight stirring, the sample was isolated, and analyzed by PXRD to confirm that the targeted solid form was produced. The sample was composed mostly of agglomerates consisting of small primary particles (<10 μm).

Initial characterization of MBDB Phosphate 1 consisted of $^1H$ NMR and thermal analysis. The results were generally consistent with the small-scale results and showed an unsolvated form with a likely melt at 158° C. A gradual weight loss of 1.8% was observed upon heating that was not observed in the screening sample and could be due in part to residual moisture. The $^1H$ NMR spectrum was consistent with the structure of the compound with a few additional minor unknown peaks suggesting some potential minor impurities. While a mono-phosphate salt was expected based on the presence of a single ionizable functional group in the structure of MBDB, IC analysis of the material indicated a 1:1.7 API:acid molar ratio. The reason for the higher phosphate content was not investigated during the screen.

MBDB Phosphate Form 1 is hygroscopic on the basis of the DVS experiment conducted. The sample picked up 8.5% weight upon equilibration at 95% RH. The weight gained during the sorption step was reversibly lost during the desorption step with little hysteresis observed. PXRD analysis of the post-DVS solids indicated no form change.

Example 18

Scale Up and Characterization of MBDB Succinate Form 2

Scale up of MBDB Succinate Form 2 was conducted by adding a stoichiometric amount of succinic acid to a solution of MBDB free base oil dissolved in acetonitrile at room temperature. After the acid addition was completed, a small amount of MBDB Succinate Form 2 was added as seed to direct crystallization to the targeted form. The solids produced using this method were agglomerates and rod-shaped primary particles that were generally less than 20 μm in size.

PXRD analysis of the sample was consistent with the results seen at small scale. The MBDB Succinate Form 2 produced was consistent with a 1:1 salt with trace acetonitrile present by $^1H$ NMR spectroscopy. Thermal analysis was consistent with an unsolvated form with a likely melt at 114° C. A small broad endotherm was observed at 92° C. that was not observed in the screening sample. The nature of this peak was not determined.

DVS analysis indicated the succinate salt was moderately hygroscopic with a 2.7% weight gain upon equilibration at 95% RH. The weight gain was reversible upon exposure to lower relative humidities with no significant hysteresis observed. The post-DVS PXRD indicated no form change during the analysis.

| Salt | MBDB Maleate Form1 | MBDB Phosphate Form 1 | MBDB Succinate Form 2 |
|---|---|---|---|
| Crystallization Behavior | Consistently prepared from 3 small scale experiments. Successfully scaled using seeds. | Prepared 2 of 3 times from small scale experiments (gel observed in other experiment). Successfully scaled using seeds (some sticky solids observed initially). Greater than stoichiometric phosphate content observed | Two forms observed from three experiments at small scale. Successfully scaled using seeds. |
| Thermal | Anhydrous/unsolvated. Likely melt at 99° C. | Anhydrous/unsolvated (minor consistent weight loss observed in scale up sample). Likely melt at 165° C. | Anhydrous/unsolvated. Likely melt at 114° C. |
| DVS | 0.6% wt gain at 95% RH | 8.5% wt gain at 95% RH | 2.7% wt gain at 95% RH |
| Physical Stability | No visible change after 1 day at 40° C./75% RH | No visible change after 1 day at 40° C./75% RH | No visible change after 1 day at 40° C./75% RH |
| Particle Properties | Agglomerates and small plates | Agglomerates and tiny particles | Agglomerates and small rods/needles |
| Aqueous solubility estimate | >68 mg/mL | 26 (some gel-like particles observed) | >27 mg/mL |

Example 19

Single Crystal Characterization of MBDB·Sulfate

This example describes the structural characterization of crystalline MBDB·sulfate. The MBDB sulfate (for which an XRPD diffractogram is provided in FIG. 32), was examined by optical microscopy and a single crystal was mounted and the structure was solved.

Single Crystal Growth

With reference to the procedure outlined in Example 5, to a solution containing 0.5 mL of acetone and 25 mg of MBDB free base was added molar equivalent of sulfuric acid (6.81 μL) was added. Initially aprecipitate was observed, but the solids quickly dissolved, leaving a clear solution. The sample was cooled in a freezer to approximately −20° C. for 4 days, during which time nocrystallization occurred. The sample was warmed to room temperature, uncapped, and the opening of the vial was covered with aluminum foil having 1 pinhole. The vial was and placed into an ambient fume hood at ambient temperature to allow for evaporation to dryness, resulting in a mixture of off-white and brown solids. The sample was examined by optical microscopy revealing single crystals of sufficient size and quality for structural analysis.

Single Crystal X-Ray Structure Determination

A colorless plate shaped crystal with formula $C_{12}H_{18}NO_2 \cdot HO_4S$ having approximate dimensions of 0.32×0.29×0.12 mm was mounted on a Mitegen micromesh mount in a random orientation. Preliminary examination and data collection were performed using Mo Kα radiation (λ=0.71073 Å) on Bruker AXS D8 Quest CMOS diffractometer equipped with a fixed chi stage, a sealed tube X-ray tube with a curved graphite crystal for monochromatization, a PhotonII detector and an Oxford Cryosystems low temperature device. The initial unit cell was determined and data were collected using Apex4 at a temperature of 150 K (Apex4 v2022.10-RC10 (Bruker, 2022)). Frames were integrated using SAINT (Bruker (2020). Apex3 v2019.11-0, Saint V8.40B, Bruker Nano Inc., Madison (WI), USA). A total of 27,889 reflections were collected, of which 5,427 were unique. Cell constants for data collection were obtained from least-squares refinement using 9,937 reflections between 2.5168 and 33.1501°. The monoclinic cell parameters and calculated volume are a=10.3588 (14) Å, b=10.0109 (12) Å, c=14.2151 (16) Å, β=104.708 (5°) and V=1425.8 (3) $Å^3$. For Z=4 and a formula weight of 305.34 the calculated density is 1.422 $g/cm^3$. The linear absorption coefficient is 0.251/mm for Mo Kα radiation. Scaling and a multi-scan absorption correction using SADABS was applied Krause, L., Herbst-Irmer, R., Sheldrick G. M. & Stalke D. (2015). *J. Appl. Cryst.* 48, 3-10. Transmission coefficients ranged from 0.6917 to 0.7465. Intensities of equivalent reflections were not averaged during data processing.

The space group was determined by the program XPREP as embedded in SHELXTL (Bruker AXS (2003). SHELXTL (Version 6.14), Bruker AXS Inc., Madison (WI), USA). Systematic absences and intensity statistics indicated the space group P21/c (#14). The structure was solved by dual methods using SHELXT and refined by full matrix least squares against $F^2$ with all reflections using SHELXL-2018 and the graphical user interface ShelXl (Sheldrick G. M. (2015). "Crystal structure refinement with SHELXL", *Acta Cryst.*, C71, 3-8; Sheldrick G. M. (2015). "SHELXT—Integrated space-group and crystal-structure determination", *Acta Cryst.* A71, 3-8; *SHELXL*2018/3 (Sheldrick, 2015, 2018); Hübschle, C. B., Sheldrick, G. M. and Dittrich, B. (2011). *J. Appl. Cryst.*, 44, 1281-1284).

Additional atoms were located in succeeding difference Fourier syntheses. The structure was refined using full-matrix least-squares where the function minimized was Σw $(|Fo|^2-|Fc|^2)^2$ and the weight w is defined as $w=1/[\sigma^2(Fo^2)+(0.0455P)^2+0.3604P]$ where $P=(Fo^2+2Fc^2)/3$.

Scattering factors were taken from the International Tables for Crystallography (Vol C Tables 4.2.6.8 and 6.1.1.4). A total of 5,427 independent reflections were used in the refinements. 4,581 reflections with F2>2σ (F2) were used in the calculation of R1.

H atoms attached to carbon atoms were positioned geometrically and constrained to ride on their parent atoms. C—H bond distances were constrained to 0.95 Å for aromatic C—H moieties, and to 1.00, 0.99 and 0.98 Å for aliphatic C—H, $CH_2$ and $CH_3$ moieties, respectively. Positions of N and O bound H-atoms were freely refined. $U_{iso}$(H) values were set to a multiple of $U_{eq}$(C/N/O) with 1.5 for OH and $CH_3$, and 1.2 for N—H, C—H and $CH_2$ units, respectively.

The final cycle of refinement included 192 variable parameters and zero restraints and converged (the largest parameter shift was 0.001 times its standard uncertainty) with unweighted and weighted agreement factors of:

$$R1=\sum|F_o|-|F_c|/\sum|F_o|=0.0320$$

$$wR^2=\{\sum[w(F_o{}^2-F_c{}^2)^2]/\sum[w(F_o{}^2)^2]\}^{0.5}=0.0917$$

The goodness-of-fit parameter was 1.038. The highest peak in the final difference Fourier map had a height of 0.405 e/$Å^3$. The minimum negative peak had a height of −0.374 e/$Å^3$ (both located nearby the bromine atom).

Crystal Data and Data Collection Parameters are Given in Table Ex19.

TABLE Ex19

| Experimental Details | |
|---|---|
| **Crystal data** | |
| Chemical formula | $C_{12}H_{18}NO_2$•$HO_4S$ |
| Mr | 305.34 |
| Crystal system, space group | Monoclinic, $P_{21/c}$ |
| Temperature (K) | 150 |
| a, b, c (Å) | 10.3588 (14), 10.0109 (12), 14.2151 (16) |
| (°) | 104.708 (5) |
| V ($Å^3$) | 1425.8 (3) |
| Z | 4 |
| F(000) | 648 |
| Dx (Mg $m^{-3}$) | 1.422 |
| Radiation type | Mo Kα |
| No. of reflections for cell measurement | 9937 |
| range (°) for cell measurement | 2.5-33.2 |
| ($mm^{-1}$) | 0.25 |
| Crystal shape | Plate |
| Color | Colorless |
| Crystal size (mm) | 0.32 × 0.29 × 0.12 |
| **Data collection** | |
| Diffractometer | Bruker AXS D8 Quest diffractometer with PhotonII charge-integrating pixel array detector (CPAD) |
| Radiation source | fine focus sealed tube X-ray source |
| Monochromator | Triumph curved graphite crystal |
| Detector resolution (pixels $mm^{-1}$) | 7.4074 |
| Scan method | ω and phi scans |
| Absorption correction[3] | Multi-scan |
| Tmin, Tmax | 0.692, 0.747 |
| No. of measured, independent and observed [I > 2σ(I)] reflections | 27889, 5427, 4581 |
| Rint | 0.036 |
| θ values (°) | θmax = 33.2, θmin = 2.5 |
| (sin θ/λ)max ($Å^{-1}$) | 0.770 |
| Range of h, k, l | h = −15→15, k = −15→14, l = −21→16 |
| **Refinement** | |
| Refinement on | $F^2$ |
| $R[F^2 > 2\sigma(F^2)]$, $wR(F^2)$, S | 0.032, 0.092, 1.04 |
| No. of reflections | 5427 |
| No. of parameters | 192 |
| No. of restraints | 0 |
| H-atom treatment | H atoms treated by a mixture of independent and constrained refinement |
| Weighting scheme | $w = 1/[\sigma^2(Fo^2) + (0.0455\ P)^2 + 0.3604\ P]$ where $P = (Fo^2 + 2Fc^2)/3$. |
| (Δ/σ)max | 0.001 |
| Δρmax, Δρmin (e $Å^{-3}$) | 0.41, −0.37 |

Unit cell parameters for MBDB sulfate are provided in Table Ex19. The structure was determined to be an unsolvated mono-sulfate salt (1:1 MBDB:sulfuric acid).

TABLE Ex19

Unit cell parameters of MBDB sulfate

| crystal system, space group | Monoclinic, P21/c |
|---|---|
| data collection temperature (K) | 150 |
| a (Å) | 10.3588 (14) |
| b (Å) | 10.0109 (12) |
| c (Å) | 14.2151 (16) |
| α (°) | 90 |
| β (°) | 104.708 (5) |
| γ (°) | 90 |
| volume ($Å^3$) | 1425.8 (3) |
| Z | 4 |

Figure 34:
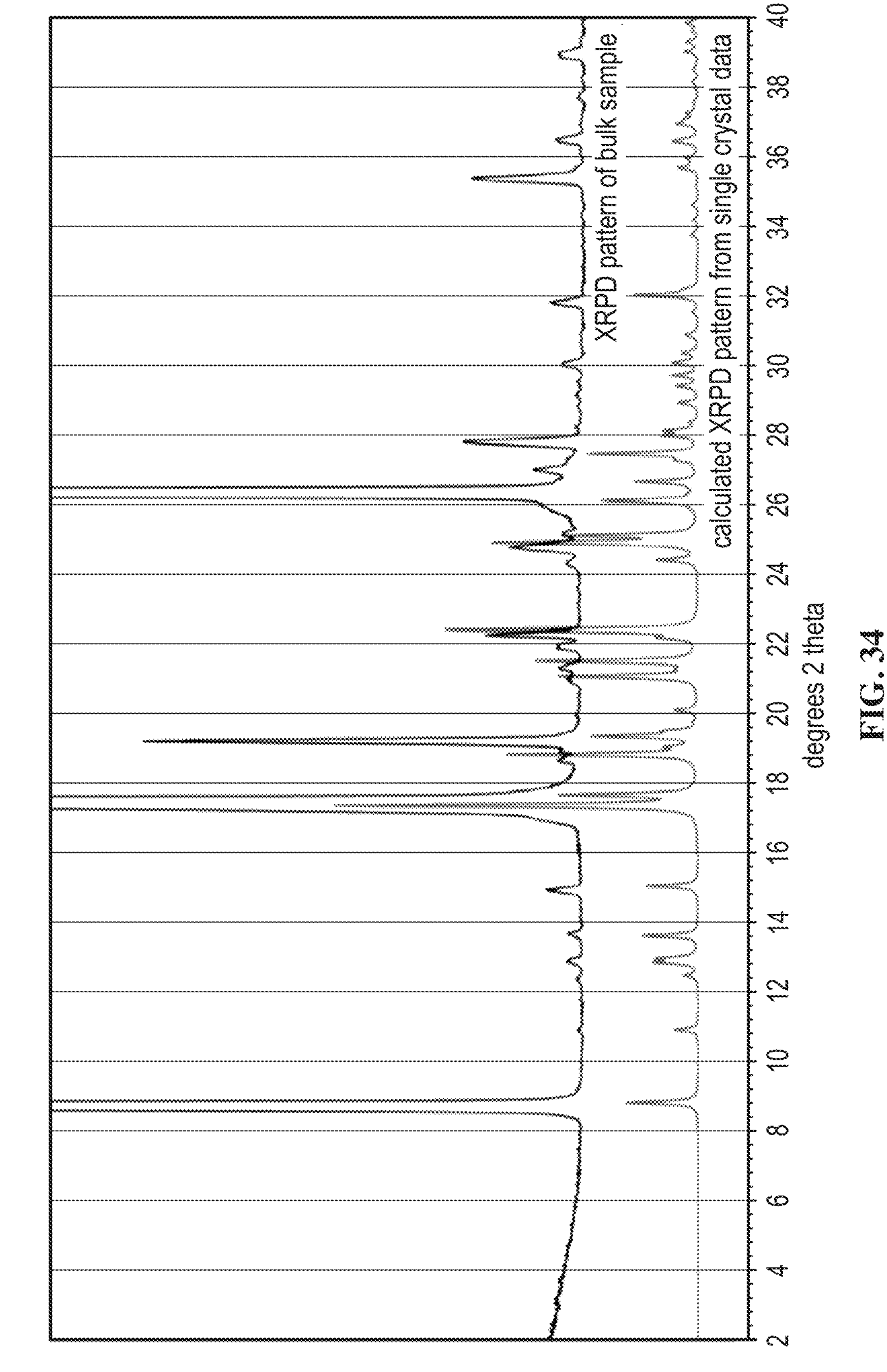
FIG. 34 provides an XRPD pattern calculated (bottom trace) from the single-crystal data is overlaid with a pattern obtained from the bulk material in FIG. 32.

An XRPD pattern calculated from the single-crystal data is overlaid with a pattern obtained from the bulk material (FIG. 32) in FIG. 34. The observed peak shifting is due to the temperature difference at which the single crystal and X-ray powder diffraction data were collected. Otherwise, the XRPD pattern of the bulk matches the calculated pattern from the single crystal data (Table 32).

X-Ray Powder Diffraction (XRPD)

The Rigaku Smart-Lab X-ray diffraction system was configured for reflection Bragg-Brentano geometry using a line source X-ray beam. The X-ray source is a Cu Long Fine Focus tube that was operated at 40 kV and 44 mA. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ.

Example 20

Single Crystal Characterization of MBDB·Maleate Form 1

This example describes the structural characterization of crystalline MBDB·maleate Form 1. The MBDB maleate Form 1 (for which an XRPD diffractogram is provided in FIG. 29), was examined by optical microscopy and a single crystal was mounted and the structure was solved.

Single Crystal Growth

With reference to the procedure outlined in Example 5, to a solution containing 0.5 mL of ethanol was used to dissolve 25.7 mg of MBDB Maleate Form 1 at room temperature. The solution was filtered using a 0.45 μm syringe filter into a new clean 1-dram vial. The vial was placed uncapped into a larger scintillation vial containing a larger volume of hexanes. The scintillation vial was capped and the sample was left at RT for vapor diffusion. Solids were observed to form over time and the solids were examined by optical microscopy and appeared to contain large single crystal plates of sufficient size and quality for analysis.

Single Crystal X-Ray Structure Determination

A colourless plate shaped crystal with formula $C_{12}H_{18}NO_2{\cdot}C_4H_3O_4$ having approximate dimensions of 0.040×0.200×0.270 mm was mounted on a Mitegen micro-mesh mount in a random orientation. Data were collected from a shock-cooled single crystal at 150 (2) K on a Bruker AXS D8 Quest four circle diffractometer with an I-mu-S microsource X-ray tube using a laterally graded multilayer (Goebel) mirror as monochromator and a PhotonIII_C14 charge-integrating and photon counting pixel array detector. The diffractometer used CuKα radiation (λ=1.54178 Å).

The crystal under investigation was found to be non-merohedrally twinned. The orientation matrices for the two components were identified using the program Cell_Now (Sheldrick, G. M. (2008). CELL_NOW. Version 2008/4. Göttingen, Germany) with the two components being related by a 180° rotation around the reciprocal a-axis. The data were integrated with SAINT V8.40B (Bruker, SAINT, V8.40B, Bruker AXS Inc., Madison, Wisconsin, USA) and a multi-scan absorption correction using TWINABS 2012/1 was applied (Krause, L., Herbst-Irmer, R., Sheldrick G. M. & Stalke D. (2015). *J. Appl. Cryst.* 48, 3-10. Sheldrick, G. M. (2012). TWINABS. Ver. 2012/1), resulting in the following statistics.

6163 data (1417 unique) involve domain 1 only, mean I/sigma 21.9

6144 data (1421 unique) involve domain 2 only, mean I/sigma 15.0 1743 data (504 unique) involve 2 domains, mean I/sigma 30.1

The exact twin matrix identified by the integration program was found to be:

| | | |
|---|---|---|
| 0.99990 | 0.00042 | 0.40866 |
| 0.00089 | −1.00000 | −0.00013 |
| 0.00047 | 0.00024 | −0.99990 |

The structure was solved by dual methods with SHELXT (Sheldrick G. M. (2015) *Acta Cryst.* A71, 3-8). using all non-overlapping reflections of both components and refined by full-matrix least-squares methods against $F^2$ using SHELXL-2018/3 (Sheldrick G. M. (2015) *Acta Cryst.* C71, 3-8) using the hklf 5 routine with all reflections of both components (including overlapping reflections), resulting in a BASF value of 0.333 (1). The $R_{int}$ value given is for all reflections and is based on agreement between observed single and composite intensities and those calculated from refined unique intensities and twin fractions (TWINABS).

All non-hydrogen atoms were refined with anisotropic displacement parameters. Carbon bound hydrogen atoms and ammonium $NH_2^+$ H atoms were refined isotropically on calculated positions using a riding model. Methyl $CH_3$ were allowed to rotate but not to tip to best fit the experimental electron density. The carboxylic acid H atom position was freely refined. $U_{iso}$ values were constrained to 1.5 times the $U_{eq}$ of their pivot atoms for methyl and hydroxyl groups and 1.2 times for all other hydrogen atoms.

TABLE Ex20-1

Crystal data and structure refinement for MBDB maleate Form 1

| Parameter | Value |
|---|---|
| Empirical formula | $C_{16}H_{21}NO_6$ |
| Moiety formula | $C_{12}H_{18}NO_2{\bullet}C_4H_3O_4$ |
| Formula weight | 323.34 |
| Temperature [K] | 150(2) |
| Crystal system | monoclinic |
| Space group (number) | $P2_1$ (4) |
| a [Å] | 8.0802(5) |
| b [Å] | 10.8638(6) |
| c [Å] | 9.4467(5) |
| α [°] | 90 |
| β [°] | 103.810(2) |
| γ [°] | 90 |
| Volume [Å$^3$] | 805.28(8) |
| Z | 2 |
| $\rho_{calc}$ [gcm$^{-3}$] | 1.333 |
| μ [mm$^{-1}$] | 0.857 |
| F(000) | 344 |
| Crystal size [mm$^3$] | 0.040 × 0.200 × 0.270 |
| Crystal colour | colourless |
| Crystal shape | plate |
| Radiation | CuK$_\alpha$ (λ = 1.54178 Å) |
| 2θ range [°] | 9.64 to 158.87 (0.78 Å) |

TABLE Ex20-1-continued

| Crystal data and structure refinement for MBDB maleate Form 1 | |
|---|---|
| Parameter | Value |
| Index ranges | $-10 \le h \le 10$<br>$-13 \le k \le 13$<br>$-11 \le l \le 11$ |
| Reflections collected | 14031 |
| Independent reflections | 5513<br>$R_{int} = 0.0326$<br>$R_{sigma} = 0.0319$ |
| Completeness to θ = 67.679° | 99.3% |
| Data/Restraints/Parameters | 5513/1/214 |
| Goodness-of-fit on $F^2$ | 1.056 |
| Final R indexes [I ≥ 2σ(I)] | $R_1 = 0.0333$<br>$wR_2 = 0.0845$ |
| Final R indexes [all data] | $R_1 = 0.0352$<br>$wR_2 = 0.0858$ |
| Largest peak/hole [$eÅ^{-3}$] | 0.16/−0.15 |
| Flack X parameter | 0.28(8) |

TABLE Ex20-2

| Unit cell parameters of MBDB maleate Form 1 | |
|---|---|
| Parameter | Value |
| Crystal system, space group | Monoclinic |
| Space group (number) | $P2_1$ (4) |
| Data collection temperature (K) | 150(2) |
| a (Å) | 8.0802(5) |
| b (Å) | 10.8638(6) |
| c (Å) | 9.4467(5) |
| α [°] | 90 |
| β [°] | 103.810(2) |
| γ [°] | 90 |
| volume ($Å^3$) | 805.28(8) |
| Z | 2 |

A Rigaku SmartLab X-Ray Diffractometer was configured in Bragg-Brentano reflection geometry equipped with a beam stop and knife edge to reduce incident beam and air scatter. Data collection parameters are shown in the following table.

| PXRD Data Collection Parameters | | | |
|---|---|---|---|
| Parameter | Value | Parameter | Value |
| Geometry | Bragg-Brentano | Receiving Slit 1 (mm) | 18 |
| Tube Anode | Cu | Receiving Slit 2 (mm) | 20 |
| Tube Type | Long Fine Focus | Start Angle 2θ (°) | 2 |
| Tube Voltage (kV) | 40 | End Angle 2θ (°) | 40 |
| Tube Current (mA) | 45 | Step Size (°) | 0.02 |
| Detector | HyPix-3000 (XR4) | Scan Speed (°/min) | 6 |
| Monochromator | Ni foil Cu Kβ Filter | Spinning (rpm) | 11 |
| Incident Slit (°) | ⅓ | Sample Holder | Low-background Si |

An XRPD pattern calculated from the single-crystal data is overlaid with a pattern obtained from the bulk material (FIG. 29) in FIG. 128. The observed peak shifting is due to the temperature difference at which the single crystal and X-ray powder diffraction data were collected. Otherwise, the XRPD pattern of the bulk matches the calculated pattern from the single crystal data (Table 28A).

Example 21

Preparation of MBDB Maleate Form 2

MBDB maleate Form 1 (35.5 mg) was dissolved in 0.5 mL of dioxane at 70° C. The resulting clear solution was hot-filtered using a 0.45 μm nylon syringe filter. The heat was turned off and the sample was allowed to slowly cool to RT. After 1 day the sample remained a solution and the sample was moved to the fridge for further cooling. After 8 days of storage in the fridge, the sample was transferred into a freezer. During storage in the freezer, white solids formed. The solids were isolated via centrifugation and decanting of the clear liquid layer.

Example 22

Preparation of MBDB Maleate Form 3

MBDB Maleate Form 1 (30.1 mg) was dissolved in 0.5 mL of chloroform and briefly sonicated to generate a clear solution. The clear solution was filtered using a 0.45 μm nylon syringe filter directly into 3.0 mL of ethyl acetate with stirring. The solution remained clear. An additional 4.5 mL of ethyl acetate was added and the sample was left to stir at RT. After 13 days of stirring the sample remained a clear solution and was moved to the freezer. After 9 days of equilibration in the freezer the sample remained a clear solution. The sample was uncapped at room temperature for fast evaporation. After 1 week, light tan and white solids were observed to have formed.

In view of the many possible embodiments to which the principles of the present disclosure may be applied, it should be recognized that the illustrated embodiments are only preferred examples and should not be taken as limiting the scope of the present disclosure. Rather, the scope is defined by the following claims. We therefore claim as our invention all that comes within the scope and spirit of these claims.

Example 23

Zeromaze Study with Racemic MDE, R-MDE, and S-MDE

Background

The rat zero-maze model is a refined alternative to the plus-maze, the most widely used animal model of anxiety, and consists of an elevated annular platform, divided equally into four quadrants. Two opposite quadrants are enclosed by Perspex walls on both the inner and the outer edges of the platform, while the remaining two opposite quadrants are open being enclosed only by a Perspex "lip". Animals will show a preference for the closed areas, and avoidance of the open sections is assumed to stem from a rodent's natural aversion to open, exposed spaces. A reduction in the amount of activity on the open areas is considered to reflect an increase in anxiety. The ethologically-based behavior, stretched attend postures (SAP) from closed to open quadrants, is assessed as an index of anxiety. Increase in SAPs is indicative of an anxiogenic effect and decreases in SAPs is indicative of an anxiolytic effect.

Shepherd, J K; Grewel, S S; Fletcher, A; Bill, D J; Dourish, C T (1994) Behavioural and pharmacological validation of the elevated "zero-maze" as an animal model of anxiety. Psychopharmacol., 116:56-64.

Animals

Male Sprague-Dawley 200-250 g (Envigo UK) rats were used. Animals were group-housed (5 per cage; cage size: 40×40×20 cm) in a temperature-controlled environment (22±2° C.), under a 12 h light-dark cycle (lights on: 08:00 hours) for one week prior to testing. Food and water were freely available. Number of animals per group=5. Animals were moved into the experimental room 16-24 hours before testing.

Apparatus

The elevated 0-maze comprises a black Perspex annular platform (105 cm diameter, 10 cm width) elevated to 65 cm above ground level, divided equally into four quadrants. Two opposite quadrants are enclosed by clear red Perspex walls (27 cm high) on both the inner and outer edges of the platform, while the remaining two opposite quadrants are surrounded only by a Perspex "lip" (1 cm high) which serves as a tactile guide to animals on these open areas.

Procedure

Subjects were weighed and tail marked before being injected. After a specified pre-treatment time, subjects were placed in a closed quadrant and a 5-min test period were recorded on videotape for subsequent analysis. The maze was cleaned with 5% methanol/water solution and dried thoroughly between test sessions. Behavioural measures comprise percentage time spent on the open areas (% TO) and frequency of stretched attend postures (SAP) from closed to open quadrants. Animals are scored as being in the open area when all four paws were in an open quadrant and in the closed area only when all four paws have passed over the open-closed divide. All testing were carried out between 9.00 and 16.00 hours.

Formulation:

IP: Rac-MDE (tosylate salt with 54.6% free base content) was formulated in Vehicle 1 (Saline) for injection to concentrations of 0.5, 1, 2, 3 and 6 mg/mL to provide doses of 2.5, 5, 10, 15 and 30 mg/kg when administered ip in 5 mL/kg dosing volumes.

IP: R-MDE (tosylate salt with 54.6% free base content) was formulated in Vehicle 1 (Saline) for injection to concentrations of 0.5, 1, 3 and 6 mg/mL to provide doses of 2.5, 5, 10, 15 and 30 mg/kg when administered ip in 5 mL/kg dosing volumes.

IP: S-MDE (tosylate salt with 54.6% free base content) was formulated in Vehicle 1 (Saline) for injection to concentrations of 0.5, 1, 2, 3 and 6 mg/mL to provide doses of 2.5, 5, 10, 15 and 30 mg/kg when administered ip in 5 mL/kg dosing volumes.

Chlordiazepoxide was formulated in Vehicle 1 (saline) to a concentration of 1.2 mg/mL to provide a dose of 6 mg/kg when administered ip in 5 mL/kg dosing volumes.

Effect of Administration of Rac-MDE and Chlordiazepoxide on Behavior in a Rat 0-Maze Study 35 male Sprague-Dawley rats in treatment groups of 5, were intraperitoneally dosed with either Vehicle 1 (saline) or Rac-MDE at 1 of 5 dose levels (2.5, 5, 10, 15 & 30 mg/kg) or chlordiazepoxide (6 mg/kg) in 5 mL/kg injection volumes. Thirty min later at T=0, rats were individually placed in a closed arm of the zero-maze and behavior was assessed by a "blind" observer using remote video monitoring over the subsequent 5 min. The animal was then removed and the maze carefully wiped with 5% methanol/water solution before the next test was begun.

TABLE

Synopsis of testing schedule Rac-MDE and chlordiazepoxide in the rat elevated zero maze model of anxiety.

| n | Rat Strain & sex | 0.5 Pretest in Veh 1 5 mL/kg ip | T = 0 Zero-maze |
|---|---|---|---|
| 5 | Male SD | Vehicle 1 | Test |
| 5 | Male SD | Rac-MDE 2.5 mg/kg | Test |
| 5 | Male SD | Rac-MDE 5 mg/kg | Test |
| 5 | Male SD | Rac-MDE 10 mg/kg | Test |
| 5 | Male SD | Rac-MDE 15 mg/kg | Test |
| 5 | Male SD | Rac-MDE 30 mg/kg | Test |
| 5 | Male SD | CDP 6 mg/kg | Test |

Effect of Administration of R-MDE and Chlordiazepoxide on Behavior in a Rat 0-Maze Study 35 male Sprague-Dawley rats in treatment groups of 5, were intraperitoneally dosed with either Vehicle 1 (saline) or R-MDE at 1 of 5 dose levels (2.5, 5, 10, 15 & 30 mg/kg) or chlordiazepoxide (6 mg/kg) in 5 mL/kg injection volumes. Thirty min later at T=0, rats were individually placed in a closed arm of the zero-maze and behavior was assessed by a "blind" observer using remote video monitoring over the subsequent 5 min. The animal was then removed and the maze carefully wiped with 5% methanol/water solution before the next test was begun.

TABLE

Synopsis of testing schedule R-MDE and chlordiazepoxide in the rat elevated zero maze model of anxiety.

| n | Rat Strain & sex | 0.5 Pretest in Veh 1 5 mL/kg ip | T = 0 Zero-maze |
|---|---|---|---|
| 5 | Male SD | Vehicle 1 | Test |
| 5 | Male SD | R-MDE 2.5 mg/kg | Test |
| 5 | Male SD | R-MDE 5 mg/kg | Test |
| 5 | Male SD | R-MDE 10 mg/kg | Test |
| 5 | Male SD | R-MDE 15 mg/kg | Test |
| 5 | Male SD | R-MDE 30 mg/kg | Test |
| 5 | Male SD | CDP 6 mg/kg | Test |

Effect of Administration of S-MDE and Chlordiazepoxide on Behavior in a Rat 0-Maze Study 35 male Sprague-Dawley rats in treatment groups of 5, were intraperitoneally dosed with either Vehicle 1 (saline) or S-MDE at 1 of 5 dose levels (2.5, 5, 15 & 30 mg/kg) or chlordiazepoxide (6 mg/kg) in 5 mL/kg injection volumes. Thirty min later at T=0, rats were individually placed in a closed arm of the zero-maze and behavior assessed by a "blind" observer using remote video monitoring over the subsequent 5 min. The animal was then removed and the maze carefully wiped with 5% methanol/water solution before the next test was begun.

TABLE

Synopsis of testing schedule S-MDE and chlordiazepoxide in the rat elevated zero maze model of anxiety.

| n | Rat Strain & sex | 0.5 Pretest in Veh 1 5 mL/kg ip | T = 0 Zero-maze |
|---|---|---|---|
| 5 | Male SD | Vehicle 1 | Test |
| 5 | Male SD | S-MDE 2.5 mg/kg | Test |
| 5 | Male SD | S-MDE 5 mg/kg | Test |
| 5 | Male SD | S-MDE 10 mg/kg | Test |
| 5 | Male SD | S-MDE 15 mg/kg | Test |
| 5 | Male SD | S-MDE 30 mg/kg* | Test |
| 5 | Male SD | CDP 6 mg/kg | Test |

Statistical Analysis

Data was analyzed with Statistica software (Statsoft USA version 10.0). All data is expressed as means±SEM. Data was analyzed by 1 way ANOVA and Dunnett's or Newman-Keuls test. Statistical significance in all analyses will be assumed when $P<0.05$.

MDE Discussion

Figure 120:
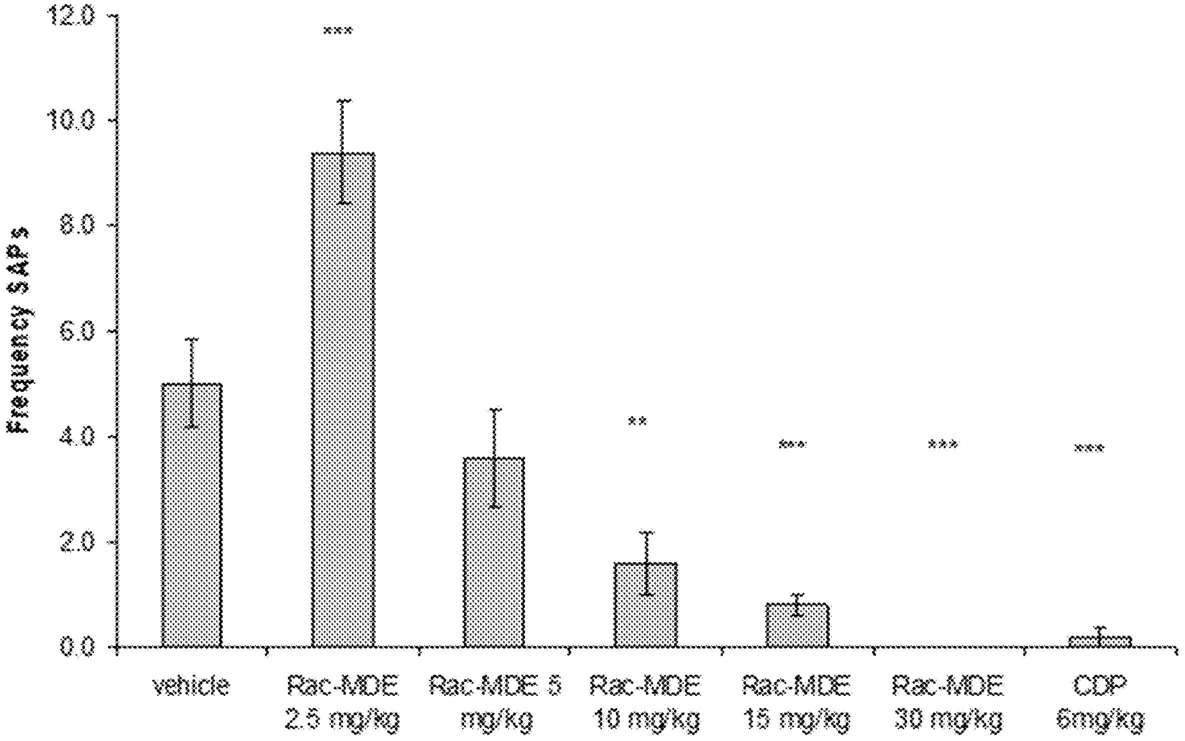
Figure 121:
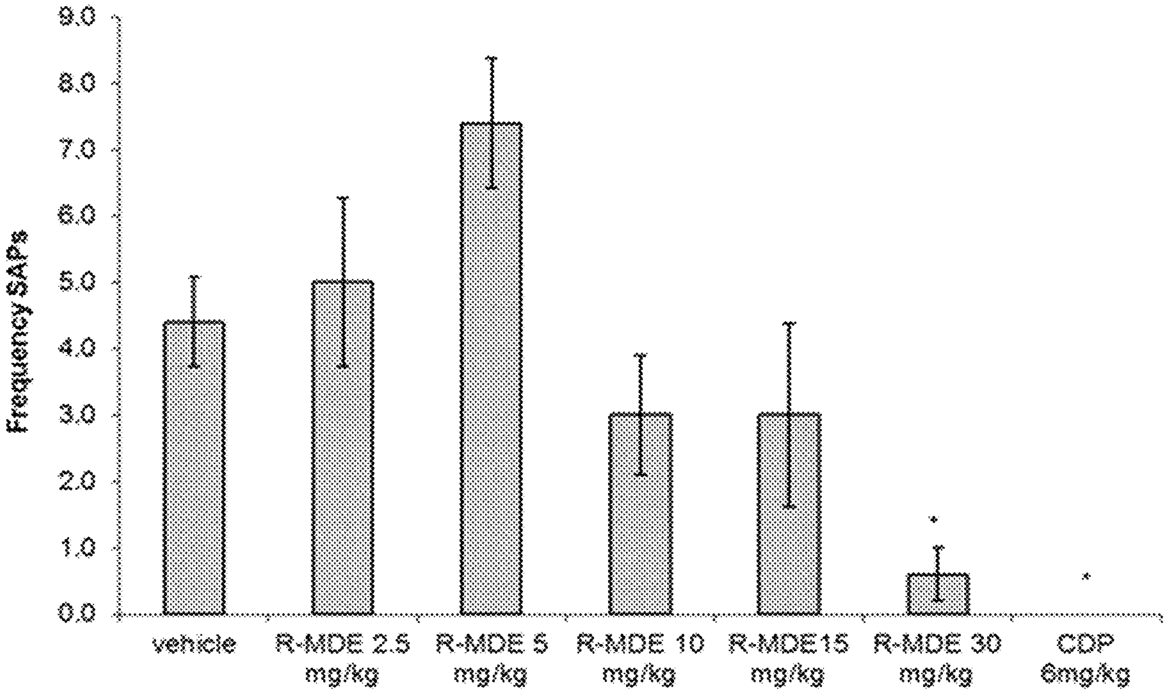
Figure 122:
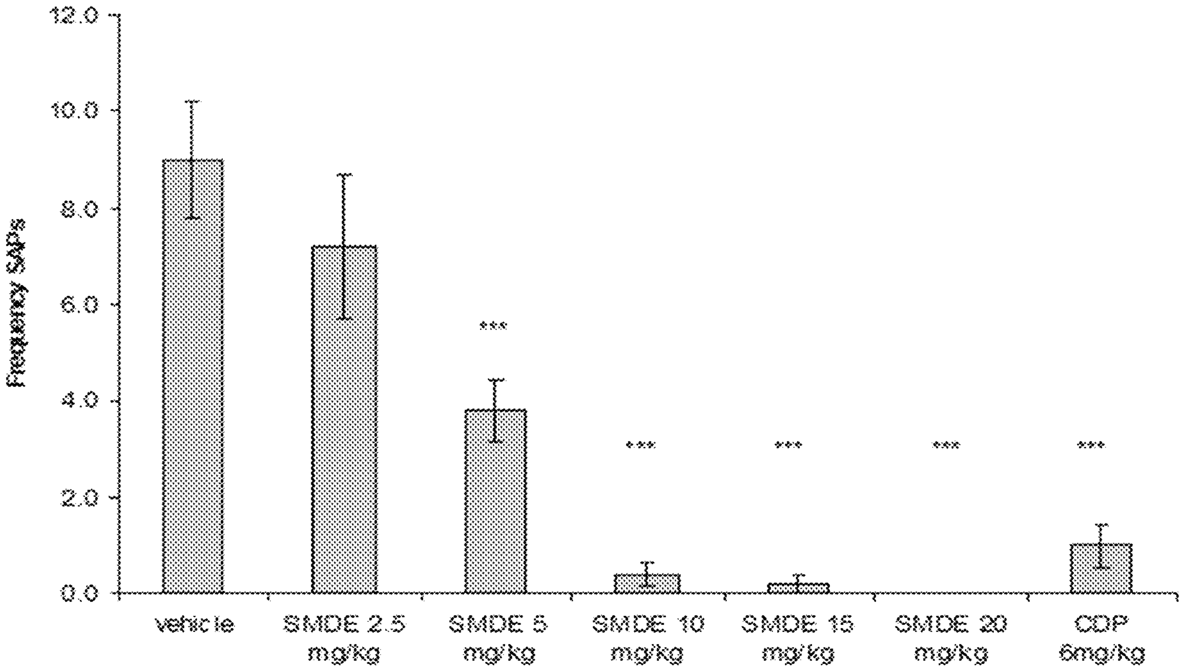

The results show that the highest dose of racemic MDE, R-MDE, and S-MDE decreased the frequency of SAPs as effectively as the benzodiazepine chlordiazepoxide (FIGS. 120-122). This shows that at a sufficient dose, racemic MDE, R-MDE, and S-MDE are all effective anxiolytics and supports their development in these indications. However, there were some unexpected findings that R-MDE and S-MDE showed are surprisingly not equivalent in regard to side effects that further inform dose selection for their therapeutic use in humans.

Figure 117:
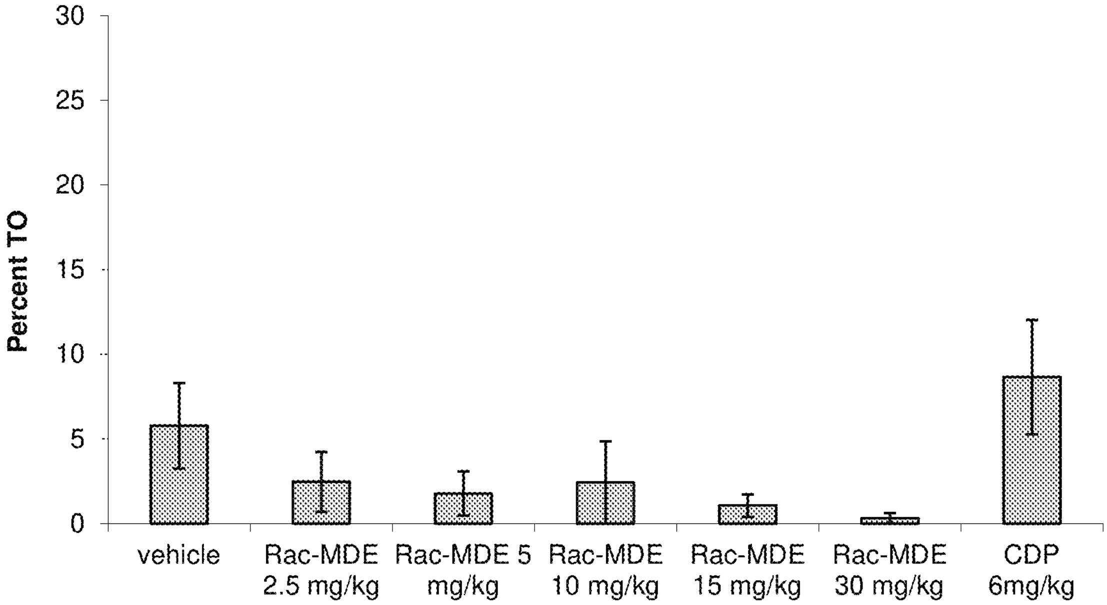
FIG. 117 illustrates the percentage of time spent in the open arms after racemic MDE compared to vehicle and chlordiazepoxide control on the elevated zero maze.
Figure 118:
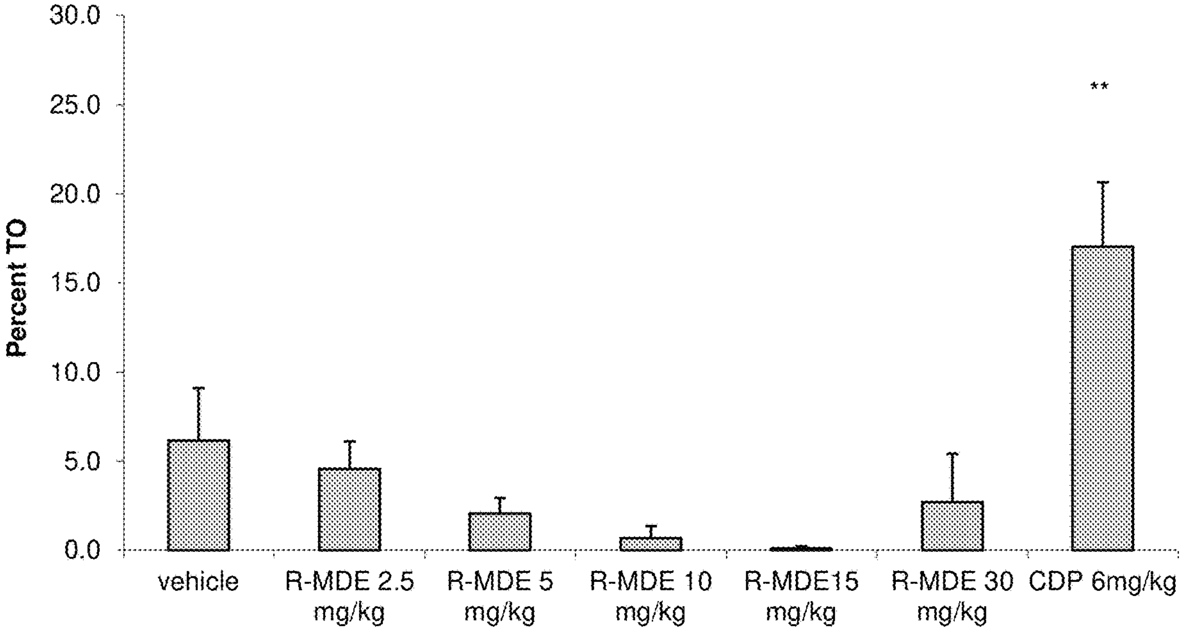
FIG. 118 illustrates the percentage of time spent in the open arms after R-MDE compared to vehicle and chlordiazepoxide control on the elevated zero maze.
Figure 119:
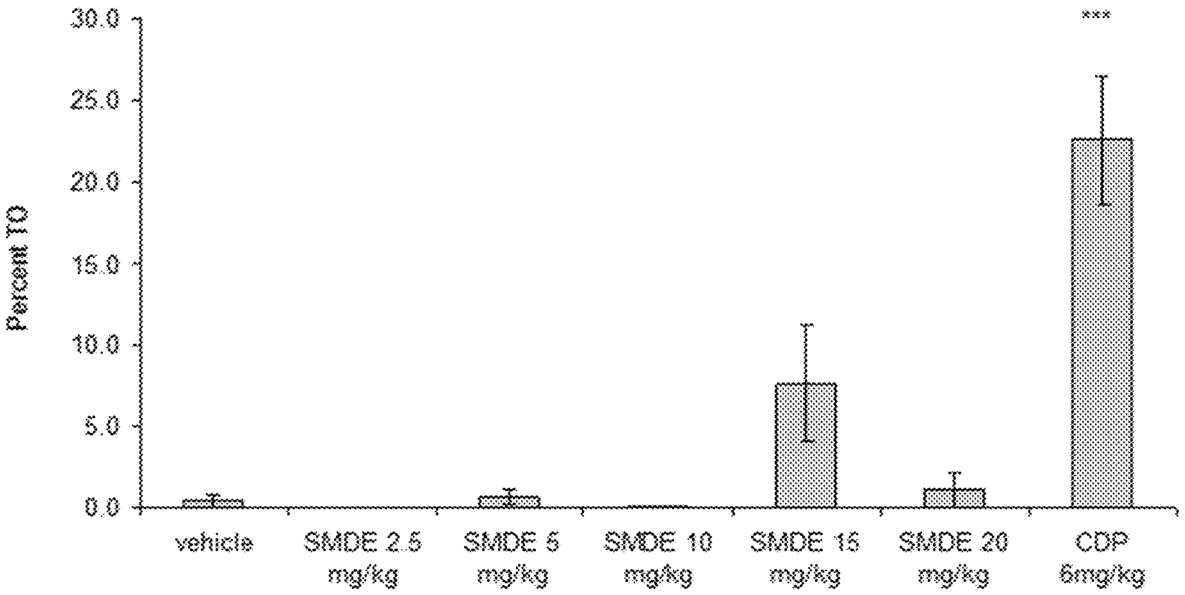
FIG. 119 illustrates the percentage of time spent in the open arms after S-MDE compared to vehicle and chlordiazepoxide control on the elevated zero maze.

First, for the percentage of time spent in the open arms, while racemic MDE, R MDE, and S MDE did not show significant changes when compared to placebo, the control CDP showed a significant increase in time in the open arms for the R MDE group and S MDE group only which indicated the experiment was underpowered. However, while racemic MDE and R MDE both trended towards reduced time in the open arms (an anxiogenic effect), S MDE showed a large numerical increase in time in the open arms at the 15 mg/kg dose level (an anxiolytic effect) (FIGS. 117-119). This was especially important since racemic MDE and R MDE did not increase time in the open arms at any dose when compared to placebo and only S MDE resulted in an increase in time in the open arms.

Since no form of MDE reached significance over vehicle on the percentage of time in the open arms (% TO) measure (although S-MDE showed a large numerical improvement), we then evaluated SAPs as the primary measure (Shepherd 1994). Shepherd describes using SAPs in cases where the % TO measure does not reach significance.

In the SAP analysis the positive control CDP did show a significant reduction in SAPs as shown in FIGS. 120-122. For racemic MDE, the lowest dose tested (2.5 mg/kg) showed a significant increase in SAPs (FIG. 120). This indicated that this low dose of MDE had an anxiogenic effect. In contrast, as the dose increased the anxiogenic effect switched to an anxiolytic effect. The 5 mg/kg dose did not show any difference from placebo and the 10 mg/kg, 15 mg/kg and 30 mg/kg doses showed a dose dependent decrease in SAPs and a significant anxiolytic effect. Similarly, R MDE showed an increase in the number of SAPs at the 2.5 mg/kg dose which trended towards significance indicating an anxiogenic effect (FIG. 121). In contrast to racemic MDE, R MDE also showed an increase in SAPs at the 5 mg/kg dose range as well which trended toward significance indicating an anxiogenic effect at this dose as well. The 10 mg/kg and 15 mg/kg doses were not significantly different from placebo and numerically had similar numbers of SAPs to placebo. Only the 30 mg/kg dose showed a significant reduction in SAPs. This indicates that R MDE has a stronger anxiogenic effect than racemic MDE that persists at higher dosages. This suggests that R MDE has a much lower therapeutic index than racemic MDE.

In contrast to racemic MDE and R MDE, S MDE did not increase the number of SAPs beyond placebo at any dose (FIG. 122). S MDE showed a dose dependent decrease in SAPs and 5 mg/kg, 10 mg/kg, 15 mg/kg and 20 mg/kg all significantly decreased the number of SAPs. This indicates that S MDE has a greater therapeutic index than racemic MDE and a much greater therapeutic index than R MDE. Since racemic MDE is comprised of equal amounts of S-MDE and R-MDE, this indicates that the anxiogenic side effects seen with lower doses of racemic MDE are due to the anxiogenic effects of R-MDE. This surprising result shows that S-MDE does not have the anxiogenic side effects seen with racemic MDE and R-MDE The data shows that while racemic MDE, S-MDE and R-MDE all have anxiolytic effects as effective as chlordiazepoxide at the high dose level, racemic MDE and R-MDE show anxiogenic effects at lower doses, an effect not seen with S-MDE. There are several critical implications of this finding. The first is that patients treated with racemic MDE or R-MDE must receive a dose high enough to reach the anxiolytic threshold since lower doses may cause anxiety as a side effect and result in worsening of the disorder being treated. This could have especially severe implications for anxiety disorders or depressive disorders including post-traumatic stress disorder, generalized anxiety disorder, panic disorder, major depressive disorder, or treatment resistant depression. All of these indications are associated with an increased level of anxiety. In these cases, a drug-induced increase in anxiety due to improper dosing of racemic MDE or R-MDE could have severe side effects on patients and worsen their underlying disorder. The data presented herein show that patients treated with a racemic MDE or R-MDE must be carefully titrated to avoid the anxiogenic effects and to reach the anxiolytic effect level. The data show that in some embodiments a Risk Evaluation and Mitigation Strategy (REMS) program should be utilized so that patients treated with racemic MDE or R-MDE should undergo an initial dose titration to determine the effective range specific to that patient. This dose titrating protocol would decrease the side effects related to underdosing racemic MDE or R-MDE.

The data also inform Phase 2 and Phase 3 clinical trial design. Clinical trials for neurological and psychiatric disorders often include one or more low dose arms to show a dose dependent effect of the full dose on the disease of interest. However, this data shows that racemic and R-MDE should only be dosed at the full effective dose and a low dose arm should not be included as a comparator as this may lead to harmful side effects on the patients. This data shows that studies of racemic and R-MDE should only use inactive matched placebo or a different standard of care therapeutic as a control. In clinical trials MDE should only be dosed at its effective dose range to avoid harmful side effects to the patients. This would be especially critical in clinical studies of anxiety disorders or depression including post-traumatic stress disorder, generalized anxiety disorder, panic disorder, major depressive disorder, or treatment resistant depression where increased anxiety could worsen the underlying disorder and lead to potentially devastating effects on the patients.

The data show that there is an advantage of S-MDE which is anxiolytic without any anxiogenic effects. In some embodiments, a clinician treating a patient with S-MDE does not need to utilize a specific dose titration protocol to reduce anxiogenic effects. In some embodiments clinical studies of S-MDE have a greater safety margin and are able to use lower doses in different arms of the study to demonstrate a dose dependent effect on the disease of interest. In some embodiments, S-MDE allows greater flexibility in clinical trial design including the safe use of a low dose active comparator to reduce expectancy bias. In some embodiments, S-MDE would be preferred to racemic MDE or R-MDE to treat patients with anxiety or depressive disorders including post-traumatic stress disorder, generalized anxiety disorder, panic disorder, major depressive disorder, or treatment resistant depression. In some embodiments S-MDE is a safer alternative to racemic MDE or R-MDE for the treatment of neurological and psychiatric disorders.

Example 24: MDE Dose Titration Risk Evaluation and Mitigation Strategy (REMS) Protocol General Information on MDE Treatment Session Initial MDE dosing and subsequent dosing adjustments must be done under the supervision of a qualified healthcare professional in a clinic or inpatient setting. The patient must remain under supervision of the healthcare professional for at least 6 hours and up to approximately 24 hours after the final MDE dose adjustment. The patient will be assessed periodically during the session for anxiety and other effects of MDE. Dose adjustments within a MDE treatment session will be based on changes from baseline levels of anxiety. Postdose anxiety measurement timing and duration of observation after dosing are based on the following information reported by (https://psychonautwiki.org/wiki/MDEA/Summary):

Duration of Effects of MDE

| Effects | Time After Dose |
|---|---|
| Onset | 20 min-60 min |
| Coming Up | 15 min-30 min |
| Peak | 90 min-120 min |
| Coming Down | 60 min-120 min |
| Normal After Effects | 12 hours-48 hours |
| Total Duration | 3 hours-6 hours |

MDE dosing is based on the following information reported by the following databases (https://erowid.org/chemicals/mde/mde_dose.shtml) and (https://psychonautwiki.org/wiki/MDEA/Summary):

MDE Dosages

| Drug Activity Level | Oral MDE Dose |
|---|---|
| Threshold | 30 mg-70 mg |
| Light | 70 mg-120 mg |
| Common | 120 mg-180 mg |
| Strong | 180 mg-225 mg |
| Very Strong | ≥225 mg |

Predose Assessment

The patient's baseline level of anxiety will be measured and recorded.

Initial MDE Dosing

The patient will receive an initial single oral dose of MDE in the range of approximately 120 mg-180 mg based on oral doses reported as producing moderate effects (https://psychonautwiki.org/wiki/MDEA/Summary)

Postdose Assessment

Change from baseline anxiety level will be measured at approximately 1 to 2 hours after dosing based on reported time to achieve peak effects (https://psychonautwiki.org/wiki/MDEA/Summary).

MDE Dose Adjustment

MDE effects have been maintained by taking a larger initial dose followed by smaller doses (50 mg to 75 mg p.o.) (PiHKAL 1991). Accordingly, the dose of MDE will be adjusted based on change from baseline in anxiety as follows:

MDE Dose Adjustment

| Change from Baseline Anxiety | MDE Dose Adjustment |
|---|---|
| Increased | Increase dose 30%-50% and reassess anxiety in approximately 1 hour |
| No Change | Increase dose 30%-50% and reassess anxiety in approximately 1 hour |
| Decreased | Maintain dose if therapeutic effect achieved or Increase to a maximum of 225 mg total dose to optimize therapeutic effect |

MDE Discontinuation

The patient will be observed for at least 6 hours after final MDE dose is administered. The patient may be confined to the inpatient unit for prolonged observation up to approximately 24 hours after last MDE dose if indicated based on persistent effects.

Anxiety that appears after the final MDE titration dose is administered can be managed with an appropriate anxiolytic agent. If this is necessary, the patient must remain under observation and undergo periodic reassessment until the supervising healthcare professional determines the patient can be discharged from care.

Example 25: A Double-Blind, Randomized, Placebo-Controlled Clinical Trial of MDE-Assisted Psychotherapy in PTSD A multicenter, randomized, double-blind, placebo-controlled trial is conducted to assess the efficacy and safety of MDE-assisted psychotherapy versus psychotherapy with placebo control in participants diagnosed with at least moderate post-traumatic stress disorder (PTSD).

Rationale

PTSD is a debilitating and often times chronic disorder associated with profound mental, physical, occupational, and functional impairment. PTSD can develop due to exposure to a traumatic event or persistent or recurring threats to an individual. Studies indicate that approximately 10% of individuals exposed to a traumatic event eventually go on to be diagnosed with PTSD (American Psychiatric Association. *Diagnostic and statistical manual of mental disorders*, $5^{th}$ edition, 2013). PTSD is a complex psychiatric disorder characterized by symptom heterogeneity including avoidance of trauma-related material, emotional blunting and distancing, hyper-vigilance, hyper-arousal, persistent negative alterations in mood, persistent alterations in cognition, disturbing thoughts, disruptions in sleep and/or dreams, and physical or mental distress. Symptoms can be severe and long lasting. Although this symptom heterogeneity may suggest a wide spectrum of separate disturbances, emotional dysregulation is considered to be a core component of this disorder. Particularly germane to the pathogenesis and progression of PTSD, emotional dysregulation in affected individuals is believed to give rise to observable and measurable features such as presence of hypervigilance and attentional biases, enhanced startle response, hyper-arousal, apathetic feeling or emotional numbness, irritability, enhanced memories associated with traumatic events, difficulty in discerning danger versus safety, a generalization of fear, and avoidance of reminders of trauma. Emotional dysregulation may be defined and also measured by elevated emotional reactivity based on abnormal detection or appraisal of emotional triggers involving bottom-up sensory detection and neuronal processing. Biochemical alterations found in individuals diagnosed with PTSD suggest abnormalities in the hypothalamic-pituitary-adrenal (HPA) axis. The HPA axis is known to regulate reactions to stress and controls significant aspects of the neuroendocrine system impacting many homeostatic systems in the body. In a typical flight-or-flight response in a healthy individual, catecholamine and cortisol levels detected in urine rise after exposure to a stressor. In PTSD, many individuals show a low secretion of cortisol and high secretion of catecholamine in response to a stressor indicating a change in catecholamine to cortisol ratio in the urine. More evidence that the HPA axis is impacted in PTSD is found in elevated levels of catecholamines and corticotropin-releasing factor in the brain of many affected individuals.

The initiation and/or maintenance of emotional dysregulation in PTSD may be due to abnormalities in top-down control of emotional responses indicating that cognitive influences and higher order representations may impinge on information and emotional processing. Certainly, some aspects of abnormalities in neuronal processing in PTSD occur either implicitly (e.g., unconsciously) or explicitly (e.g., consciously) indicating involvement of distinct cognitive processes. Exaggerated responses in the amygdala and insular cortex have been demonstrated in meta-analyses in PTSD pathology, as have decreases in activity in other brain regions including the anterior cingulate cortex and aspects the prefrontal cortex including the ventromedial prefrontal cortex. In addition to changes in patterns of neuronal activity in individuals with PTSD, several neuroanatomical changes in PTSD have also been demonstrated. A reduction of total brain volume, intracranial volume, and the volumes in regions such as the hippocampus (particularly localized to the CA3 and dentate gyrus regions), insular cortex, and anterior cingulate cortex have been indicated in occurring in some individuals with PTSD through meta-analyses of structural MRI studies. Animal studies have shown that severe chronic stress leads to atrophy of apical dendrites in the CA3 region of the hippocampus, reduced hippocampus neurogenesis, and elevated granule cell death in the dentate gyrus due to elevated levels of glucocorticoids (Gould E. and Tanapat. (1999). *Stress and hippocampal neurogenesis*. Biol. Psychiatry 46, 1472-1479.) Connections between brain areas such as the amygdala, hippocampus, prefrontal cortex, and hypothalamus can facilitate activation of the HPA axis to illustrate interactions between brain regions with structural changes and affected biochemical regulatory systems in PTSD.

MDE is a synthetic analog of the psychedelic phenethylamine class of compounds known to act as a mixed reuptake inhibitor/releasing agent of serotonin, norepinephrine, and dopamine and administration of MDE can produce acute modulations of neurotransmission. MDE administration also has indirect effects on neurohormone release. MDE can function as a psychoplastogen promoting neuronal growth, modulating neuronal connectivity, and regulating neuronal plasticity through longer term neuronal changes. The combined neurobiological effects of MDE administration on individuals reduce fear of emotional injury or distress, enhance introspection and communication, and increase empathetic feelings and compassion. Additionally, MDE may serve to enhance fear extinction. These combined effects may yield acute and longer-term productive psychological states to enhance behavioral or cognitive-behavioral therapies. MDE administration may enhance neuronal function at the biochemical and cellular levels to generate or restore favorable neural network pathways and connectivity to increase behavioral or cognitive-behavioral therapy productiveness.

Study Design

This multicenter, randomized, double-blind, placebo-controlled trial is conducted at various sites in the United States with IRB approval from each study site. A flexible dose of MDE hydrochloride salt or placebo, followed by a supplemental half-dose unless contraindicated by patient's previous response or medical history, is also administered during the Treatment Period with psychotherapy in at least 3 blinded monthly Experimental Sessions. The Supplemental Dose extends the duration of drug effects on the participants during an Experimental Session. MDE test groups are further subdivided into specific groups receiving only racemic MDE hydrochloride salt, S-MDE hydrochloride salt, or R-MDE hydrochloride salt. An optional Risk Evaluation and Mitigation Strategy (REMS) Protocol may be implemented for the racemic MDE, R-MDE, and placebo-groups. The Treatment Period lasts for approximately 12 weeks. During the Treatment Period, each Experimental Session is followed by three Intervening Sessions of non-drug psychotherapy. Each Experimental Session involves an overnight stay. The Primary Outcome measure, the change in Clinician Administered PTSD Scale for DSM-5 (CAPS-5), is determined by a blinded Independent Rater (IR) pool multiple times throughout the study. The study consists of separate periods for each participant. Initially, prospective participants undergo a Screening Period involving an initial eligibility assessment, a medical history intake, informed consent, and enrollment of eligible participants. Next, a Preparation Period is undertaken for enrolled participants involving medication tapering and clinical baseline assessments to confirm each participant meets enrollment criteria. As part of the Preparation Period, a detailed assessment of co-morbidities to PTSD is recorded. Participants may remain on prescribed courses of selective serotonin reuptake inhibitor (SSRI) or serotonin and norepinephrine reuptake inhibitor (SNRI) treatment. Dosages and/or frequency of administration of a prescribed SSRI or SNRI may be adjusted to fit within study parameters. Participants may be required to taper a prescribed course of medication in order to maintain eligibility within the study. The Treatment Period consists of three monthly Experimental Sessions and associated Intervening Sessions of integrative behavioral psychotherapy. The Treatment Period lasts approximately 12 weeks. Following the Treatment Period is a Follow-up Period and Study Conclusion. During the Follow-up Period and Study Conclusion, participants complete 4 weeks with no study visits, followed by a Study Conclusion visit.

Screening Period - from initial consent to beginning of enrollment (approx. 4 weeks)

| Study Visit | | Visit Timing | Description |
|---|---|---|---|
| Screening | Screening | Several visits taking place 5-30 days after initial phone call screen | Informed consent obtained and assessment measures of pre-study medications, complete personal and family medical history and all assessed screening measures undertaken. These measures may include any of: PTSD checklist for DSM-5 (PCL-5), Columbia-Suicide Severity Rating Scale (C-SSRS), Montgomery-Asberg Depression Rating Scale (MADRS), Hamilton Depression Rating Scale (HAM-D), Hamilton |

-continued

| Screening Period - from initial consent to beginning of enrollment (approx. 4 weeks) | | | |
|---|---|---|---|
| Study Visit | | Visit Timing | Description |
| | | | Anxiety Rating Scale (HAM-A), General Anxiety Disorder-7 (GAD-7), Beck Anxiety Inventory (BAI), Impact of Events Scale (IES), State-Trait Anxiety Inventory (STAI), Edinburgh Postnatal Depression Scale (EPDS), Clinical Global Impressions Scale (CGI-I), Epworth Sleepiness Scale (ESS), and Pittsburgh Sleep Quality Scale. Medical providers are contacted and medical records and laboratory results are obtained. All results and records are reviewed along with interview notes. If eligible, results of Life Events Checklist for DSM-5 (LEC-5) and Structured Clinical Interview for DSM-5 Personality Questionnaire (SCID-5-SPQ) are forwarded to IR. |
| | IR Screening | 2-10 days after initial eligibility determined during Screening Period | Initial eligibility after PCL-5 and initial eligibility are reviewed. Next, IR conducts a since last visit C-SSRS, SCID-5-PD, Dissociative Disorders Interview Schedule (DDIS), and/or International Neuropsychiatric Interview (MINI). Results of IR assessment confirmed over Preparatory Period. |
| Enrollment | Enrollment | 1-14 days after IR Screening | Prior to enrollment, all screening measures are reviewed and any clarification needed with participant is completed by telephone interview. If enrolled, and if it has been determined to taper an ongoing medication, begin a tapering treatment plan of at least 5 half-lives plus at least 5 days for stabilization. Begin collection of Adverse Events (AE). |

| Preparation Period (between 1-12 weeks) | | | |
|---|---|---|---|
| Study Visit | | Visit Timing | Description |
| Preparatory Period | Preparatory Session 1 | Undertaken 0-14 days post-enrollment | Schedule visit timing according to medication tapering needs. Schedule calls in between visits for safety concerns, tapering questions, or other issues related to medical history. Confirm enrollment. |
| | Preparatory Session 2 | Undertaken 2-21 days following Preparation Session 1 | Schedule upcoming visits if medication tapering is not needed or is already completed. If still tapering, schedule additional telephone call for continuing assessment of readiness to enter study. |
| | Taper follow-up | 0-7 days following end of medication taper | Schedule baseline CAPS-5. |
| Baseline and Enrollment Confirmation | Baseline Assessments | Following Preparatory Session 2 | Complete CAPS-5, Sheehan Disability Score (SDS), and Dissociative Subtype of PTSD Scale (DSPS) by IR via in-person or telemedicine appointment. Scores forwarded to therapy monitoring team. Resumption of tapered medicine in symptom management requires. Withdrawal of participants not meeting eligibility criteria at this point. |
| | Preparatory Session 3 | 1-7 days following baseline CAPS-5 | Participants complete baseline self-report metrics and schedule Experimental Session 1. |

The Treatment Period schedule follows the Screening Period and the Preparatory Period

| Treatment Period (lasts approximately 12 weeks) | | | |
|---|---|---|---|
| Study Visit | | Visit Timing | Description |
| Treatment 1 | Randomization | 0-10 days following Baseline assessments | Complete following verification participant is still enrolled and Experimental Session 1 is scheduled. Double-blind randomization. |
| | Experimental Session 1 | 8 hours plus overnight observation | Patient's weight is determined for dosage calculation. Baseline STAI assessment. Dose is 100-200 mg p.o. Placebo administered in placebo group at same time interval. |
| | | Optional. Following anxiety assessment 0.75-2 hours after first dose administration | REMS Protocol: Only considered for administration of racemic MDE and R-MDE treatment groups and associated placebo controls. Underdosing of racemic MDE or R-MDE may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 225 mg. Placebo administered in placebo group at same time interval. If anxiety is decreased, no REMS protocol dose is given at this time. |
| | | 2-2.5 hours after first dose administration | Supplemental Dose: Supplemental half-dose of 50-100 mg administered 2 to 2.5 hours following initial dose administration unless contraindicated. If initial plus REMS protocol doses total a cumulative dose of 225 mg, no Supplemental Dose is given. If initial plus any REMS protocol dose is less than 225 mg, Supplemental Dose is administered 2 to 2.5 hours following initial dose administration. Placebo administered in placebo group at same time intervals. |
| | Intervening Session 1A | Morning following Experimental Session 1 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 1B | 3 to 14 days following Experimental Session 1 | Behavioral or cognitive-behavioral therapy session lasting 60-120 minutes. CAPS-5 assessment. |
| | Intervening Session 1C | 18-34 days following Experimental Session 1 | Behavioral or cognitive-behavioral therapy session lasting 60-120 minutes. Assessments include LEC-5, HAM-A, C-SSRS and CAPS-5. |
| Treatment 2 | Experimental Session 2 | 8 hours plus overnight observation. 19-35 days following Experimental Session 1. | Patient's weight is determined for dosage calculation. Baseline STAI assessment. Dose is 100-200 mg p.o. Placebo administered in placebo group at same time interval. |
| | | Optional. Following anxiety assessment 0.75-2 hours after first dose administration | REMS Protocol: Only considered for administration of racemic MDE and R-MDE treatment groups and associated placebo controls. Underdosing of racemic MDE or R-MDE may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 225 mg. |

-continued

| Treatment Period (lasts approximately 12 weeks) | | | |
|---|---|---|---|
| | Study Visit | Visit Timing | Description |
| | | | Placebo administered in placebo group at same time interval. If anxiety is decreased, no REMS protocol dose is given at this time. |
| | | 2-2.5 hours after first dose administration | Supplemental Dose: Supplemental half-dose of 50-100 mg administered 2 to 2.5 hours following initial dose administration unless contraindicated. If initial plus REMS protocol doses total a cumulative dose of 225 mg, no Supplemental Dose is given. If initial plus any REMS protocol dose is less than 225 mg, Supplemental Dose is administered 2 to 2.5 hours following initial dose administration. Placebo administered in placebo group at same time intervals. |
| | Intervening Session 2A | Morning following Experimental Session 2 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 2B | 3 to 14 days following Experimental Session 2 | Behavioral or cognitive-behavioral therapy session lasting 60-120 minutes. CAPS-5 assessment. |
| | Intervening Session 2C | 18-34 days following Experimental Session 2 | Behavioral or cognitive-behavioral therapy session lasting 60-120 minutes. Assessments include LEC-5, HAM-A, and C-SSRS and CAPS-5 . . . |
| Treatment 3 | Experimental Session 3 | 8 hours plus overnight observation. 19-35 days following Experimental Session 2. | Patient's weight is determined for dosage calculation. Baseline STAI assessment. Dose is 100-200 mg p.o. Placebo administered in placebo group at same time interval. |
| | | Optional. Following anxiety assessment 0.75-2 hours after first dose administration | REMS Protocol: Only considered for administration of racemic MDE and R-MDE treatment groups and associated placebo controls. Underdosing of racemic MDE or R-MDE may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 225 mg. Placebo administered in placebo group at same time interval. If anxiety is decreased, no REMS protocol dose is given at this time. |
| | | 2-2.5 hours after first dose administration | Supplemental Dose: Supplemental half-dose of 50-100 mg administered 2 to 2.5 hours following initial dose administration unless contraindicated. If initial plus REMS protocol doses total a cumulative dose of 250 mg, no Supplemental Dose is given. If initial plus any REMS protocol dose is less than 225 mg, Supplemental Dose is administered 2 to 2.5 hours following initial dose administration. Placebo administered in placebo group at same time intervals. |
| | Intervening Session 3A | Morning following Experimental Session 3 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |

-continued

| Treatment Period (lasts approximately 12 weeks) | | |
|---|---|---|
| Study Visit | Visit Timing | Description |
| Intervening Session 3B | 3 to 14 days following Experimental Session 3 | Behavioral or cognitive-behavioral therapy session lasting 60-120 minutes. CAPS-5 assessment. |
| Intervening Session 3C | 18-34 days following Experimental Session 3 | Behavioral or cognitive-behavioral therapy session lasting 60-120 minutes. Assessments include LEC-5, HAM-A, C-SSRS and CAPS-5. |

The Follow-up Period schedule and Study Conclusion follow the Screening Period and the Treatment Period.

| Follow-up Period and Study Conclusion | | |
|---|---|---|
| Study Visit | Visit Timing | Description |
| Follow-up Period | Occurs 2-10 days after Intervening Session 3C. | Occurs about 100-150 days following Baseline assessment. Complete self-reported assessments and patient safety measures. Create exit treatment plan for participant based on results. Final CAPS-5 assessment. Final SDS, HAM-D, and ESS assessments. |
| Study Conclusion | At time of unblinding of group. | Inform participants who finished study protocol of unblinding of groups. If a participant was in a placebo group, offer opportunity to enroll in a open-label safety extension study using either racemic MDE, S-MDE, or R-MDE. |

Dose Selection

This study compares the effects of three blinded Experimental Sessions of psychotherapy in combination with flexible doses of MDE or placebo administered as described below. Non-drug preparatory and intervening psychotherapy sessions are also included. Patient's weight is determined for dosage calculation. Initial dose is 100 mg unless this will result in a dosage of less than 1.5 mg/kg of patient weight. Initial dose thereby adjusted upward in 25 mg increments to deliver the lowest dose possible of at least 1.5 mg/kg of patient weight. Initial dose for Experimental Session 2 and 3 is cumulative dose calculated by adding the initial dose plus REMS protocol dose used the previous Experimental Session for each patient.

Randomization and Masking

Randomization occurs prior to the initiation of Experimental Session 1. Each participant is provided the next randomized number in a sequence by a blinded study monitor. Participants are then randomized, according to a computer-generated randomization schedule, 1:1:1:1 to racemic MDE, S-MDE, R-MDE, or placebo. The randomization schedule is prepared and implemented by an independent statistician. Participants, clinicians, and study teams are blinded to treatment allocation. Racemic MDE and R-MDE treatment groups may be subjected to anxiogenic effects due to underdosing of participants. As such, an optional dose titration schedule (REMS protocol) exists for racemic MDE and R-MDE treatment groups if a participant displays no change or a significant worsening of assessed anxiety symptomatology. Participants are assessed for general well-being and anxiety by a medical practitioner about

| Double-blinded treatment group | Experimental Session | Initial Dose | Optional (REMS) protocol: Dose Titration if underdosing occurs | Supplemental Dose (unless contraindicated) | Cumulative Dose |
|---|---|---|---|---|---|
| Racemic MDE | 1 | 100-200 mg | 30-100 mg | 50-100 mg | 100-225 mg |
| Racemic MDE | 2 | 100-200 mg | 30-100 mg | 50-100 mg | 100-225 mg |
| Racemic MDE | 3 | 100-200 mg | 30-100 mg | 50-100 mg | 100-225 mg |
| R-MDE | 1 | 100-200 mg | 30-100 mg | 50-100 mg | 100-225 mg |
| R-MDE | 2 | 100-200 mg | 30-100 mg | 50-100 mg | 100-225 mg |
| R-MDE | 3 | 100-200 mg | 30-100 mg | 50-100 mg | 100-225 mg |
| S-MDE | 1 | 100-200 mg | N/A | 50-100 mg | 100-225 mg |
| S-MDE | 2 | 100-200 mg | N/A | 50-100 mg | 100-225 mg |
| S-MDE | 3 | 100-200 mg | N/A | 50-100 mg | 100-225 mg |

0.75 hours after the first dose is administered. Assessments performed may include general assessments of physical and mental well-being, a structured clinical interview for DSM-5 (SCID-5) module Al, and/or a STAI assessment and may continue throughout the period of overnight observation.

Subjects then undergo three Intervening Sessions with the first session the morning after the initial dose administration. S-MDE treatment group or placebo group participants qualifying with a significant worsening of assessed anxiety symptomatology would undergo a placebo dose titration administration. Subjects would then undergo three Intervening Sessions with the first session the morning after the placebo dose titration administration. The pharmacist at each site, who prepares the treatments according to the randomization schedule, and an unblinded monitor, who performs drug accountability during the study, are unblinded. No other study personnel are unblinded until after formal locking of the study database. In the event of a medical emergency, the pharmacist is to reveal actual treatment contents to the primary investigator, who is to alert the Sponsor of the emergency. If the participant or study center personnel are unblinded, the subject is to be removed from the study.

Outcomes

The primary objective of this study is to evaluate the efficacy and safety of MDE treatment combined with psychotherapy to treat moderate to severe PTSD compared to identical psychotherapy combined with placebo treatment. MDE treatment is further subdivided into three separate treatment groups (racemic MDE, S-MDE, and R-MDE) with each treatment subgroup only receiving administration of the single assigned drug. Treatment outcomes are determined based on a change in CAPS-5 Total Severity.

Several secondary objectives are designed for this study. One is an evaluation of clinician-rated functional impairment of MDE treatment combined with psychotherapy to treat moderate to severe PTSD compared to identical psychotherapy combined with placebo treatment. MDE treatment is further subdivided into three separate treatment groups (racemic MDE, S-MDE, and R-MDE) with each treatment subgroup only receiving administration of the single assigned drug. Treatment outcomes are determined based on a change in SDS. Another secondary objective of this study is to evaluate clinician-rated depression of MDE treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in HAM-D. An additional secondary objective of this study is to evaluate sleep assessments of MDE treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in ESS. Co-morbidities present in participants with a strong positive response to MDE treatment are correlated. Co-morbidities present in participants with weak-to-no positive response to MDE treatment are correlated. Changes to presence or severity of co-morbidities from the Preparation Period to the Study Conclusion are recorded to determine if MDE treatment combined with psychotherapy in moderate to severe PTSD subjects affects co-morbid phenotypes not falling under the constellation of PTSD symptoms.

Participant Populations

Participants are recruited through referrals by other treatment providers or through print or internet advertisements. The Sponsor monitors demographics of individuals assessed for enrollment to encourage diversity and an unbiased representation of the total PTSD population. Participants must be 18 years of age or older, have a confirmed diagnosis of at least moderate PTSD according to PCL-5 at the Screening Period. Medical history intake must indicate a presence of PTSD symptoms for at least 6 months prior to the Screening Period. Participants may be enrolled in the study while remaining on a treatment regimen involving SSRI or SNRI treatment prescribed for PTSD. In some cases, enrolled participants currently taking an SSRI, an SNRI, or another medication are tapered off these medications and stabilized prior to baseline assessments. Participants with a confirmed personality disorder diagnosis are excluded from this study. Participants must be in good general physical health without one or more severe chronic conditions that could affect the safety or tolerability of MDE treatment.

Statistical Analysis

The change from baseline in CAPS-5, SDS, HAM-D, and ESS in participants is analyzed using a mixed effects model for repeated measures (MMRM) to obtain covariance parameter estimates. The model includes treatment center, treatment subtype, baseline assessments, assessment time point, and time point-by-treatment as explanatory variables. Treatment center is treated as a random effect; all other explanatory variables are treated as fixed effects. Model-based point estimates (e.g., least squares means, 95% confidence intervals, and p-values) are reported for each time point. With a sample size of 50 participants per treatment group, this study has 90% power to detect a significant treatment effect, using a two-sided test with an alpha value of 0.05. Additional participants may be enrolled with conditional power analysis conducted at a group-unblinded interim analysis time point for efficacy when 200 participants are enrolled and at least 60% of the blinded participants (N=120) have completed a final CAPS-5 assessment and reached Study Conclusion.

Results

The results may indicate that the primary objective is achieved. At the point of Study Conclusion, racemic MDE-treated, S-MDE-treated, and R-MDE-treated participants may demonstrate a significant mean reduction in CAPS-5 assessment compared to the placebo group.

The S-MDE-treated subgroup may achieve a significant mean reduction in CAPS-5 assessment with a lower total dosage of drug compared to the racemic MDE-treated subgroup. The R-MDE-treated subgroup may achieve a significant mean reduction in CAPS-5 assessment with a lower total dosage of drug compared to the racemic MDE-treated subgroup. Significant improvements in CAPS-5 assessments may be observed for racemic MDE-treated, S-MDE-treated, and R-MDE-treated participants at time points of Intervening Session 1C, Intervening Session 2C, Intervening Session 3C and Study Conclusion, compared to placebo-treated controls. Significant improvements in CAPS-5 assessments may be observed for S-MDE-treated participants at time points of Intervening Session 1C, Intervening Session 2C, Intervening Session 3C, compared to placebo-treated controls without a significant increase in adverse anxiogenic incidents in S-MDE-treated participants.

The results may indicate that the secondary objectives of this study are also achieved. At the point of Study Conclusion, racemic MDE-treated, S-MDE-treated, and R-MDEtreated participants may demonstrate a significant improvement in clinician-rated functional impairment score as measured by SDS compared to placebo-treated controls. At the point of Study Conclusion, racemic MDE-treated, S-MDE-treated, and R-MDE-treated participants may demonstrate a significant improvement depression as measured by HAM-D compared to placebo-treated controls. At the point of Study Conclusion, racemic MDE-treated, S-MDE-treated, and R-MDE-treated participants may demonstrate a significant improvement in lessening daytime sleepiness as measured by ESS. At the point of Study Conclusion, S-MDE-treated participants may demonstrate a significant improvement in clinician-rated functional impairment score, in depression, and in lessening daytime sleepiness compared to placebo-treated controls without a significant increase in adverse anxiogenic incidents in S-MDE-treated participants.

Example 26: Zeromaze Study with Racemic MBDB, R-MBDB and S-MBDB

Background

The rat zero-maze model is a refined alternative to the plus-maze, the most widely used animal model of anxiety, and consists of an elevated annular platform, divided equally into four quadrants. Two opposite quadrants are enclosed by Perspex walls on both the inner and the outer edges of the platform, while the remaining two opposite quadrants are open being enclosed only by a Perspex "lip". Animals will show a preference for the closed areas, and avoidance of the open sections is assumed to stem from a rodent's natural aversion to open, exposed spaces. A reduction in the amount of activity on the open areas is considered to reflect an increase in anxiety. The ethologically-based behavior stretched attend postures (SAP) from closed to open quadrants is assessed as an index of anxiety. Increase in SAPs is indicative of an anxiogenic effect and decreases in SAPs is indicative of an anxiolytic effect.

Shepherd, J K; Grewel, S S; Fletcher, A; Bill, DJ; Dourish, CT (1994) Behavioural and pharmacological validation of the elevated "zero-maze" as an animal model of anxiety. Psychopharmacol., 116:56-64.

Animals

Male Sprague-Dawley 200-250 g (Envigo UK) rats were used. Animals were group-housed (5 per cage; cage size: 40×40×20 cm) in a temperature-controlled environment (22±2° C.), under a 12 h light-dark cycle (lights on: 08:00 hours) for one week prior to testing. Food and water were freely available. Number of animals per group-5. Animals were moved into the experimental room 16-24 hours before testing.

Apparatus

The elevated 0-maze comprises a black Perspex annular platform (105 cm diameter, 10 cm width) elevated to 65 cm above ground level, divided equally into four quadrants. Two opposite quadrants are enclosed by clear red Perspex walls (27 cm high) on both the inner and outer edges of the platform, while the remaining two opposite quadrants are surrounded only by a Perspex "lip" (1 cm high) which serves as a tactile guide to animals on these open areas.

Procedure

Subjects were weighed and tail marked before being injected. After a specified pre-treatment time, subjects were placed in a closed quadrant and a 5-min test period were recorded on videotape for subsequent analysis. The maze was cleaned with 5% methanol/water solution and dried thoroughly between test sessions. Behavioural measures comprise percentage time spent on the open areas (% TO) and frequency of stretched attend postures (SAP) from closed to open quadrants. Since the control groups were all treated identically with the same vehicle these were combined to increase power. The Chlordiazepoxide groups were also treated identically with the same dose so these were also combined to increase power. Animals are scored as being in the open area when all four paws were in an open quadrant and in the closed area only when all four paws have passed over the open-closed divide. All testing were carried out between 9.00 and 16.00 hours.

Formulation:

IP: Rac-MBDB (tosylate salt with 54.6% free base content) was formulated in Vehicle 1 (Saline) for injection to concentrations of 0.5, 1, 2, 3 and 6 mg/mL to provide doses of 2.5, 5, 10, 15 and 30 mg/kg when administered ip in 5 mL/kg dosing volumes.

IP: R-MBDB (tosylate salt with 54.6% free base content) was formulated in Vehicle 1 (Saline) for injection to concentrations of 0.5, 1, 2, 3 and 6 mg/mL to provide doses of 2.5, 5, 10, 15 and 30 mg/kg when administered ip in 5 mL/kg dosing volumes IP: S-MBDB (tosylate salt with 54.6% free base content) was formulated in Vehicle 1 (Saline) for injection to concentrations of 0.5, 1, 3 and 6 mg/mL to provide doses of 2.5, 5, 15 and 30 mg/kg when administered ip in 5 mL/kg dosing volumes.

Chlordiazepoxide was formulated in Vehicle 1 (saline) to a concentration of 1.2 mg/mL to provide a dose of 6 mg/kg when administered ip in 5 mL/kg dosing volumes.

Effect of Administration of Rac-MBDB and Chlordiazepoxide on Behavior in a Rat 0-Maze Study 35 male Sprague-Dawley rats in treatment groups of 5, were intraperitoneally dosed with either Vehicle 1 (saline) or Rac-MBDB at 1 of 5 dose levels (2.5, 5, 10, 15 & 30 mg/kg) or chlordiazepoxide (6 mg/kg) in 5 mL/kg injection volumes. Thirty min later at T=0, rats were individually placed in a closed arm of the zero-maze and behavior assessed by a "blind" observer using remote video monitoring over the subsequent 5 min. The animals were then removed and the maze carefully wiped with 5% methanol/water solution before the next test was begun.

Synopsis of Testing Schedule Rac-MBDB and Chlordiazepoxide in the Rat Elevated Zero Maze Model of Anxiety.

| n | Rat Strain & sex | 0.5 Pretest in Veh 1 5 mL/kg ip | T = 0 Zero-maze |
|---|---|---|---|
| 5 | Male SD | Vehicle 1 | Test |
| 5 | Male SD | Rac-MBDB 2.5 mg/kg | Test |
| 5 | Male SD | Rac-MBDB 5 mg/kg | Test |
| 5 | Male SD | Rac-MBDB 10 mg/kg | Test |
| 5 | Male SD | Rac-MBDB 15 mg/kg | Test |
| 5 | Male SD | Rac-MBDB 30 mg/kg | Test |
| 5 | Male SD | CDP 6 mg/kg | Test |

Effect of Administration of R-MBDB and Chlordiazepoxide on Behavior in a Rat 0-Maze Study 35 male Sprague-Dawley rats in treatment groups of 5, were intraperitoneally dosed with either Vehicle 1 (saline) or R-MBDB at 1 of 5 dose levels (2.5, 5, 10, 15 & 30 mg/kg) or chlordiazepoxide (6 mg/kg) in 5 mL/kg injection volumes. Thirty min later at T=0, rats were individually placed in a closed arm of the zero-maze and behavior was assessed by a "blind" observer using remote video monitoring over the subsequent 5 min. The animal were then removed and the maze carefully wiped with 5% methanol/water solution before the next test was begun.

Synopsis of Testing Schedule R-MBDB and Chlordiazepoxide in the Rat Elevated Zero Maze Model of Anxiety.

| n | Rat Strain & sex | 0.5 Pretest in Veh 1 5 mL/kg ip | T = 0 Zero-maze |
|---|---|---|---|
| 5 | Male SD | Vehicle 1 | Test |
| 5 | Male SD | R-MBDB 2.5 mg/kg | Test |
| 5 | Male SD | R-MBDB 5 mg/kg | Test |
| 5 | Male SD | R-MBDB 10 mg/kg | Test |
| 5 | Male SD | R-MBDB 15 mg/kg | Test |
| 5 | Male SD | R-MBDB 30 mg/kg | Test |
| 5 | Male SD | CDP 6 mg/kg | Test |

Effect of Administration of S-MBDB and Chlordiazepoxide on Behavior in a Rat 0-Maze Study 35 male Sprague-Dawley rats in treatment groups of 5, were intraperitoneally dosed with either Vehicle 1 (saline) or S-MBDB at 1 of 5 dose levels (2.5, 5, 10, 15 & 30 mg/kg) or chlordiazepoxide (6 mg/kg) in 5 mL/kg injection volumes. Thirty min later at T=0, rats were individually placed in a closed arm of the zero-maze and behavior was assessed by a "blind" observer using remote video monitoring over the subsequent 5 min. The animals were then removed and the maze carefully wiped with 5% methanol/water solution before the next test was begun.

Synopsis of Testing Schedule S-MBDB and Chlordiazepoxide in the Rat Elevated Zero Maze Model of Anxiety.

| n | Rat Strain & sex | 0.5 Pretest in Veh 1 5 mL/kg ip | T = 0 Zero-maze |
|---|---|---|---|
| 5 | Male SD | Vehicle 1 | Test |
| 5 | Male SD | S-MBDB 2.5 mg/kg | Test |
| 5 | Male SD | S-MBDB 5 mg/kg | Test |
| 5 | Male SD | S-MBDB 10 mg/kg | Test |
| 5 | Male SD | S-MBDB 15 mg/kg | Test |
| 5 | Male SD | S-MBDB 30 mg/kg | Test |
| 5 | Male SD | CDP 6 mg/kg | Test |

Statistical Analysis

Drug Versus Vehicle Treatments

For each study, a 1-way ANOVA was conducted across vehicle, CDP, and drug treatment groups. Each group was compared to the vehicle group and a p-value for treatment determined by Fishers Least Significant Difference (LSD) test. This analysis was performed in GraphPad Prism (Version 9).

Results

The positive control CDP did not show significance over vehicle on the percentage of time in the open arms (% TO) measure so we could not use % TO in this experiment as a measure to examine the effects of MBDB. We then evaluated SAPs as the primary measure (Shepherd 1994). Shepherd describes using SAPs in cases where % TO does not show significance. In this analysis the positive control CDP did show a significant reduction in SAPs shown in FIG. 123 so this measure was expanded to the MBDB groups.

MBDB Discussion

Figure 123:
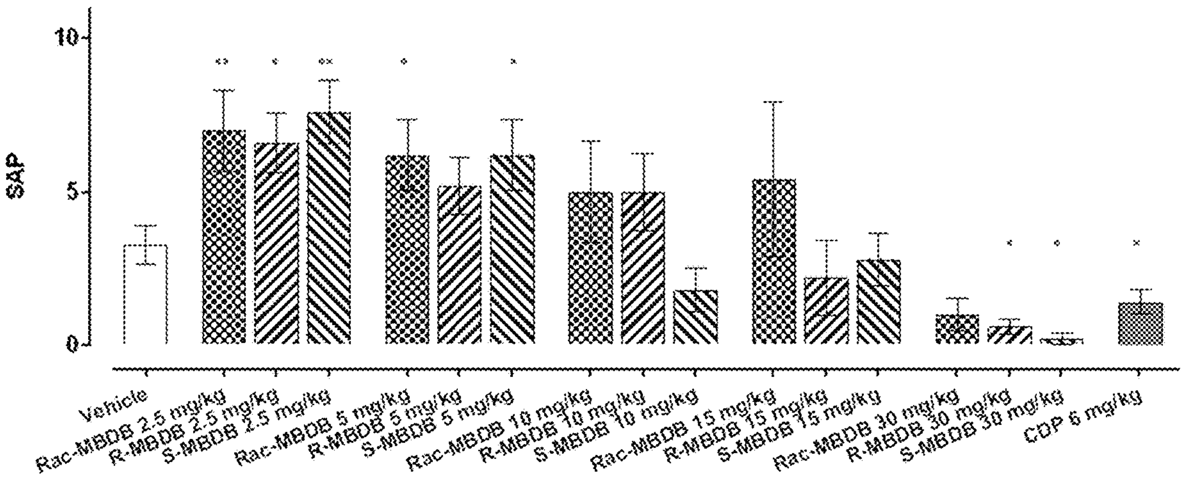

The results show that the 30 mg/kg dose S-MBDB, and R-MBDB both decreased the frequency of SAPs as effectively as the benzodiazepine chlordiazepoxide and racemic MBDB showed a trend toward significance (FIG. 123). This shows that at a sufficient dose, racemic MBDB, S-MBDB, and R-MBDB are each effective anxiolytics and supports their development in these indications. This is the first in vivo data showing MBDB is effective in these indications. However, there were some unexpected findings that show S-MBDB and R-MBDB are surprisingly not equivalent in regard to side effects that further inform dose selection for their therapeutic use in humans.

First, for all forms of MBDB, the lowest dose tested (2.5 mg/kg) showed a decrease SAPs vs placebo (FIG. 123). This indicates that this low dose of MBDB had an anxiogenic effect. This effect continued at the next dose level 5 mg/kg, for all three forms of MBDB and reached significance for both racemic MBDB and S-MBDB. This trend toward increased anxiety continued at 10 mg/kg for racemic MBDB and R-MBDB which produced a consistent level of SAPs similar to the 5 mg/kg, however, in contrast to racemic and R-MBDB, S-MBDB showed a rapid reduction in total SAPs at this dose level. This suggests that S-MBDB may have advantages over racemic MBDB and R MBDB. This effect continued at 15 mg/kg where both R MBDB and S MBDB showed a reduction in the number of SAPs compared to lower doses while racemic MBDB did not. However, the magnitude of the decrease in SAPs was not as great as chlordiazepoxide at this dose. Finally, at 30 mg/kg R MBDB and S MBDB both significantly reduced the number of SAPs, however the magnitude of the reduction was greatest with S MBDB, again providing support that S MBDB may me more effective at reducing anxiety at high doses and less likely to be anxiogenic at low doses than racemic MBDB and R MBDB. This data indicates that for MBDB, low doses can paradoxically increase anxiety and that this anxiogenic effect shifts to an anxiolytic effect at doses that are sufficiently high to induce a therapeutic effect.

There was an even stronger dose dependent anxiogenic effect observed with racemic-MBDB and R MBDB than with S MBDB. The data show that the lowest doses of MBDB induce an anxiogenic effect with this effect switching to an anxiolytic effect as the dose is increased. However, when considering the magnitude of the reduction in SAPs S-MBDB showed a switch to an anxiolytic effect at the 10 mg/kg range while R-MBDB showed this at 15 mg/kg and racemic MBDB only at 30 mg/kg. This suggests that S MBDB has a greater therapeutic index than racemic MBDB and R-MBDB and has a more reduced range of doses that could increase anxiety when compared to racemic MBDB and R-MBDB. Additionally, since the total reduction in SAPs was lowest with S-MBDB, it may have a greater overall therapeutic effect than racemic MBDB and R-MBDB. This indicates that the anxiogenic side effects seen with lower doses of racemic MBDB may be due to the increased anxiogenic effects of R-MBDB.

There are several critical implications of this finding. The first is that patients treated with any form of MBDB must receive a dose high enough to reach the anxiolytic threshold since lower doses may cause anxiety as a side effect and result in worsening of the disorder being treated and that this effect may be particularly severe with racemic MBDB and R-MBDB. This could have especially severe implications for anxiety disorders or depressive disorders including post-traumatic stress disorder, generalized anxiety disorder, panic disorder, major depressive disorder, or treatment resistant depression. All of these indications are associated with an increased level of anxiety as a major symptom. In these cases, a drug-induced increase in anxiety due to improper dosing of MBDB could have severe side effects on patients and worsen their underlying disorder. The data presented herein show that patients treated with a racemic MBDB or S-MBDB must be especially careful to titrate up to the therapeutic dose to avoid the anxiogenic effects and to reach the anxiolytic effect level. The data show that in some embodiments a Risk Evaluation and Mitigation Strategy (REMS) program should be utilized so that patients treated with MBDB should undergo an initial dose titration to determine the effective range specific to that patient. This dose titrating protocol would decrease the side effects related to underdosing MBDB.

The data also inform Phase 2 and Phase 3 clinical trial design. Clinical trials for neurological and psychiatric disorders often include one or more low dose arms to show a dose dependent effect of the full dose on the disease of interest. However, this data shows that MBDB should only be dosed at the full effective dose and a low dose arm should not be included as a comparator as this may lead to harmful side effects on the patients. This data shows that studies of MBDB should only use inactive matched placebo or a different standard of care therapeutic as a control. In clinical trials MBDB should only be dosed at its effective dose range to avoid harmful side effects to the patients. This would be especially critical in clinical studies of anxiety disorders or depression including post-traumatic stress disorder, generalized anxiety disorder, panic disorder, major depressive disorder, or treatment resistant depression where increased anxiety could worsen the underlying disorder and lead to potentially devastating effects on the patients.

The data show that there is an advantage of S-MBDB which has a greater therapeutic index and a lower range of doses that would produce anxiogenic side effects. In some embodiments, a clinician treating a patient with S-MBDB does not need to utilize a specific dose titration protocol to reduce anxiogenic effects. In some embodiments clinical studies of S-MBDB have a greater safety margin and are able to use lower doses in different arms of the study to demonstrate a dose dependent effect on the disease of interest. In some embodiments, S-MBDB allows greater flexibility in clinical trial design including the safe use of a low dose active comparator to reduce expectancy bias. In some embodiments, S-MBDB would be preferred to racemic MBDB or R-MBDB to treat patients with anxiety or depressive disorders including post-traumatic stress disorder, generalized anxiety disorder, panic disorder, major depressive disorder, or treatment resistant depression. In some embodiments S-MBDB is a safer alternative to racemic MBDB or R-MBDB for the treatment of neurological and psychiatric disorders.

Example 27: MBDB Dose Titration Risk Evaluation and Mitigation Strategy (REMS) Protocol General Information on MBDB Treatment Session Initial MBDB dosing and subsequent dosing adjustments must be done under the supervision of a qualified healthcare professional in a clinic or inpatient setting. The patient must remain under supervision of the healthcare professional for at least 6 hours and up to approximately 24 hours after the final MBDB dose adjustment. The patient will be assessed periodically during the session for anxiety and other effects of MBDB. Dose adjustments within a MBDB treatment session will be based on changes from baseline levels of anxiety. Postdose anxiety measurement timing and duration of observation after dosing are shown here as adapted from PiHKAL 1991:

Duration of Effects of MBDB

| Effects | Time After Dose |
|---|---|
| Onset | 20 min-30 min |
| Plateau | 60 min-90 min |
| Coming Down | ~90 min |
| Duration | 4 hours-6 hours |

MBDB dosing is shown here:

MBDB Dosages

| Drug Activity Level | Oral MBDB Dose |
|---|---|
| Threshold | 60 mg-120 mg |
| Light | 120 mg-150 mg |
| Common | 150 mg-250 mg |
| Strong | 250 mg-350 mg |
| Very Strong | ≥350 mg |

Predose Assessment

The patient's baseline level of anxiety will be measured and recorded.

Initial MBDB Dosing

The patient will receive an initial single oral dose of MBDB in the range of approximately 180 mg-210 mg based on oral doses reported as producing moderate effects (PiHKAL 1991).

Postdose Assessment

Change from baseline anxiety level will be measured at approximately 0.75 to 1 hours after dosing based on reported time to achieve peak effects (PiHKAL 1991).

MBDB Dose Adjustment

MBDB effects have been maintained by taking a larger initial dose followed by smaller doses (30 mg to 100 mg p.o.). Re-dose of one-third to one-half the initial dose usually prolongs duration (PiHKAL 1991). Accordingly, the dose of MBDB will be adjusted based on change from baseline in anxiety as follows:

MBDB Dose Adjustment

| Change from Baseline Anxiety | MBDB Dose Adjustment |
|---|---|
| Increased | Increase dose 30%-50% and reassess anxiety in approximately 1 hour |
| No Change | Increase dose 30%-50% and reassess anxiety in approximately 1 hour |
| Decreased | Maintain dose if therapeutic effect achieved or Increase to a maximum of 350 mg total dose to optimize therapeutic effect |

MBDB Discontinuation

The patient will be observed for at least 6 hours after final MBDB dose is administered.

The patient may be confined to the inpatient unit for prolonged observation up to approximately 24 hours after last MBDB dose if indicated based on persistent effects.

Anxiety that appears after the final MBDB titration dose is administered can be managed with an appropriate anxiolytic agent. If this is necessary, the patient must remain under observation and undergo periodic reassessment until the supervising healthcare professional determines the patient can be discharged from care.

Example 28: A Double-Blind, Randomized, Placebo-Controlled Clinical Trial of MBDB-Assisted Psychotherapy in PTSD A multicenter, randomized, double-blind, placebo-controlled trial is conducted to assess the efficacy and safety of MBDB-assisted psychotherapy versus psychotherapy with placebo control in participants diagnosed with at least moderate post-traumatic stress disorder (PTSD).

Rationale

PTSD is a debilitating and often times chronic disorder associated with profound mental, physical, occupational, and functional impairment. PTSD can develop due to exposure to a traumatic event or persistent or recurring threats to an individual. Studies indicate that approximately 10% of individuals exposed to a traumatic event eventually go on to be diagnosed with PTSD (American Psychiatric Association. *Diagnostic and statistical manual of mental disorders,* $5^{th}$ edition, 2013). PTSD is a complex psychiatric disorder characterized by symptom heterogeneity including avoidance of trauma-related material, emotional blunting and distancing, hyper-vigilance, hyper-arousal, persistent negative alterations in mood, persistent alterations in cognition, disturbing thoughts, disruptions in sleep and/or dreams, and physical or mental distress. Symptoms can be severe and long lasting. Although this symptom heterogeneity may suggest a wide spectrum of separate disturbances, emotional dysregulation is considered to be a core component of this disorder. Particularly germane to the pathogenesis and progression of PTSD, emotional dysregulation in affected individuals is believed to give rise to observable and measurable features such as presence of hypervigilance and attentional biases, enhanced startle response, hyper-arousal, apathetic feeling or emotional numbness, irritability, enhanced memories associated with traumatic events, difficulty in discerning danger versus safety, a generalization of fear, and avoidance of reminders of trauma. Emotional dysregulation may be defined and also measured by elevated emotional reactivity based on abnormal detection or appraisal of emotional triggers involving bottom-up sensory detection and neuronal processing. Biochemical alterations found in individuals diagnosed with PTSD suggest abnormalities in the hypothalamic-pituitary-adrenal (HPA) axis. The HPA axis is known to regulate reactions to stress and controls significant aspects of the neuroendocrine system impacting many homeostatic systems in the body. In a typical flight-or-flight response in a healthy individual, catecholamine and cortisol levels detected in urine rise after exposure to a stressor. In PTSD, many individuals show a low secretion of cortisol and high secretion of catecholamine in response to a stressor indicating a change in catecholamine to cortisol ratio in the urine. More evidence that the HPA axis is impacted in PTSD is found in elevated levels of catecholamines and corticotropin-releasing factor in the brain of many affected individuals.

The initiation and/or maintenance of emotional dysregulation in PTSD may be due to abnormalities in top-down control of emotional responses indicating that cognitive influences and higher order representations may impinge on information and emotional processing. Certainly, some aspects of abnormalities in neuronal processing in PTSD occur either implicitly (e.g., unconsciously) or explicitly (e.g., consciously) indicating involvement of distinct cognitive processes. Exaggerated responses in the amygdala and insular cortex have been demonstrated in meta-analyses in PTSD pathology, as have decreases in activity in other brain regions including the anterior cingulate cortex and aspects the prefrontal cortex including the ventromedial prefrontal cortex. In addition to changes in patterns of neuronal activity in individuals with PTSD, several neuroanatomical changes in PTSD have also been demonstrated. A reduction of total brain volume, intracranial volume, and the volumes in regions such as the hippocampus (particularly localized to the CA3 and dentate gyrus regions), insular cortex, and anterior cingulate cortex have been indicated in occurring in some individuals with PTSD through meta-analyses of structural MRI studies. Animal studies have shown that severe chronic stress leads to atrophy of apical dendrites in the CA3 region of the hippocampus, reduced hippocampus neurogenesis, and elevated granule cell death in the dentate gyrus due to elevated levels of glucocorticoids (Gould E. and Tanapat. (1999). Stress and hippocampal neurogenesis. Biol. Psychiatry 46, 1472-1479.) Connections between brain areas such as the amygdala, hippocampus, prefrontal cortex, and hypothalamus can facilitate activation of the HPA axis to illustrate interactions between brain regions with structural changes and affected biochemical regulatory systems in PTSD.

MBDB is a synthetic analog of the psychedelic phenethylamine class of compounds known to act as a mixed reuptake inhibitor/releasing agent of serotonin, norepinephrine, and dopamine and administration of MBDB can produce acute modulations of neurotransmission. MBDB administration also has indirect effects on neurohormone release. MBDB can function as a psychoplastogen promoting neuronal growth, modulating neuronal connectivity, and regulating neuronal plasticity through longer term neuronal changes. The combined neurobiological effects of MBDB administration on individuals reduce fear of emotional injury or distress, enhance introspection and communication, and increase empathetic feelings and compassion. Additionally, MBDB may serve to enhance fear extinction. These combined effects may yield acute and longer-term productive psychological states to enhance behavioral or cognitive-behavioral therapies. MBDB administration may enhance neuronal function at the biochemical and cellular levels to generate or restore favorable neural network pathways and connectivity to increase behavioral or cognitive-behavioral therapy productiveness.

Study Design

This multicenter, randomized, double-blind, placebo-controlled trial is conducted at various sites in the United States with IRB approval from each study site. A flexible dose of MBDB hydrochloride salt or placebo, followed by a supplemental half-dose unless contraindicated by patient's previous response or medical history, is also administered during the Treatment Period with psychotherapy in at least 3 blinded monthly Experimental Sessions. The Supplemental Dose extends the duration of drug effects on the participants during an Experimental Session. MBDB test groups are further subdivided into specific groups receiving only racemic MBDB hydrochloride salt, S-MBDB hydrochloride salt, or R-MBDB hydrochloride salt. An optional Risk Evaluation and Mitigation Strategy (REMS) Protocol may be implemented for the racemic MBDB, S-MBDB, R-MBDB, and placebo-groups. The Treatment Period lasts for approximately 12 weeks. During the Treatment Period, each Experimental Session is followed by three Intervening Sessions of non-drug psychotherapy. Each Experimental Session involves an overnight stay. The Primary Outcome measure, the change in Clinician Administered PTSD Scale for DSM-5 (CAPS-5), is determined by a blinded Independent Rater (IR) pool multiple times throughout the study. The study consists of separate periods for each participant. Initially, prospective participants undergo a Screening Period involving an initial eligibility assessment, a medical history intake, informed consent, and enrollment of eligible participants. Next, a Preparation Period is undertaken for enrolled participants involving medication tapering and clinical baseline assessments to confirm each participant meets enrollment criteria. As part of the Preparation Period, a detailed assessment of co-morbidities to PTSD is recorded. Participants may remain on prescribed courses of selective serotonin reuptake inhibitor (SSRI) or serotonin and norepinephrine reuptake inhibitor (SNRI) treatment. Dosages and/or frequency of administration of a prescribed SSRI or SNRI may be adjusted to fit within study parameters. Participants may be required to taper a prescribed course of medication in order to maintain eligibility within the study. The Treatment Period consists of three monthly Experimental Sessions and associated Intervening Sessions of integrative behavioral psychotherapy. The Treatment Period lasts approximately 12 weeks. Following the Treatment Period is a Follow-up Period and Study Conclusion. During the Follow-up Period and Study Conclusion, participants complete 4 weeks with no study visits, followed by a Study Conclusion visit.

| Screening Period - from initial consent to beginning of enrollment (approx. 4 weeks) | | | |
|---|---|---|---|
| Study Visit | | Visit Timing | Description |
| Screening | Screening | Several visits taking place 5-30 days after initial phone call screen | Informed consent obtained and assessment measures of pre-study medications, complete personal and family medical history and all assessed screening measures undertaken. These measures may include any of: PTSD checklist for DSM-5 (PCL-5), Columbia-Suicide Severity Rating Scale (C-SSRS), Montgomery-Asberg Depression Rating Scale (MADRS), Hamilton Depression Rating Scale (HAM-D), Hamilton Anxiety Rating Scale (HAM-A), General Anxiety Disorder-7 (GAD-7), Beck Anxiety Inventory (BAI), Impact of Events Scale (IES), State-Trait Anxiety Inventory (STAI), Edinburgh Postnatal Depression Scale (EPDS), Clinical Global Impressions Scale (CGI-I), Epworth Sleepiness Scale (ESS), and Pittsburgh Sleep Quality Scale. Medical providers are contacted and medical records and laboratory results are obtained. All results and records are reviewed along with interview notes. If eligible, results of Life Events Checklist for DSM-5 (LEC-5) and Structured Clinical Interview for DSM-5 Personality Questionnaire (SCID-5-SPQ) are forwarded to IR. |
| | IR Screening | 2-10 days after initial eligibility determined during Screening Period | Initial eligibility after PCL-5 and initial eligibility are reviewed. Next, IR conducts a since last visit C-SSRS, SCID-5-PD, Dissociative Disorders Interview Schedule (DDIS), and/or International Neuropsychiatric Interview (MINI). Results of IR assessment confirmed over Preparatory Period. |
| Enrollment | Enrollment | 1-14 days after IR Screening | Prior to enrollment, all screening measures are reviewed and any clarification needed with participant is completed by telephone interview. If enrolled, and if it has been determined to taper an ongoing medication, begin a tapering treatment plan of at least 5 half-lives plus at least 5 days for stabilization. Begin collection of Adverse Events (AE). |

| Preparation Period (between 1-12 weeks) | | | |
|---|---|---|---|
| Study Visit | | Visit Timing | Description |
| Preparatory Period | Preparatory Session 1 | Undertaken 0-14 days post-enrollment | Schedule visit timing according to medication tapering needs. Schedule calls in between visits for safety concerns, tapering questions, or other issues related to medical history. Confirm enrollment. |
| | Preparatory Session 2 | Undertaken 2-21 days following Preparation Session 1 | Schedule upcoming visits if medication tapering is not needed or is already completed. If still tapering, schedule additional telephone call for continuing assessment of readiness to enter study. |
| | Taper follow-up | 0-7 days following end of medication taper | Schedule baseline CAPS-5. |
| Baseline and Enrollment Confirmation | Baseline Assessments | Following Preparatory Session 2 | Complete CAPS-5, Sheehan Disability Score (SDS), and Dissociative Subtype of PTSD Scale (DSPS) by IR via in-person or telemedicine appointment. Scores forwarded to |

-continued

| Preparation Period (between 1-12 weeks) | | |
|---|---|---|
| Study Visit | Visit Timing | Description |
| | | therapy monitoring team. Resumption of tapered medicine in symptom management requires. Withdrawal of participants not meeting eligibility criteria at this point. |
| Preparatory Session 3 | 1-7 days following baseline CAPS-5 | Participants complete baseline self-report metrics and schedule Experimental Session 1. |

The Treatment Period schedule follows the Screening Period and the Preparatory Period

| Treatment Period (lasts approximately 12 weeks) | | | |
|---|---|---|---|
| | Study Visit | Visit Timing | Description |
| Treatment 1 | Randomization | 0-10 days following Baseline assessments | Complete following verification participant is still enrolled and Experimental Session 1 is scheduled. Double-blind randomization. |
| | Experimental Session 1 | 8 hours plus overnight observation | Patient's weight is determined for dosage calculation. Baseline STAI assessment. Dose is 180-210 mg p.o. Placebo administered in placebo group at same time interval. |
| | | Optional. Following anxiety assessment 0.75-2 hours after first dose administration | REMS Protocol: Considered for administration of racemic MBDB, R-MBDB, and S-MBDB treatment groups and associated placebo controls. Underdosing of racemic MBDB, R-MBDB, or S-MBDB may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 350 mg. Placebo administered in placebo group at same time interval. If anxiety is decreased, no REMS protocol dose is given at this time. |
| | | 1.5-2 hours after first dose administration | Supplemental Dose: Supplemental half-dose of 50-100 mg administered 1.5-2 hours following initial dose administration unless contraindicated. If initial plus REMS protocol doses total a cumulative dose of 350 mg, no Supplemental Dose is given. If initial plus any REMS protocol dose is less than 350 mg, Supplemental Dose is administered 1.5 to 2 hours following initial dose administration. Placebo administered in placebo group at same time intervals. |
| | Intervening Session 1A | Morning following Experimental Session 1 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 1B | 3 to 14 days following Experimental Session 1 | Behavioral or cognitive-behavioral therapy session lasting 60-120 minutes. CAPS-5 assessment. |
| | Intervening Session 1C | 18-34 days following Experimental Session 1 | Behavioral or cognitive-behavioral therapy session lasting 60-120 minutes. Assessments include LEC-5, HAM-A, C-SSRS and CAPS-5. |
| Treatment 2 | Experimental Session 2 | 8 hours plus overnight observation. | Patient's weight is determined for dosage calculation. Baseline STAI assessment. Dose is 180-210 mg p.o. Placebo |

-continued

| Treatment Period (lasts approximately 12 weeks) | | | |
|---|---|---|---|
| | Study Visit | Visit Timing | Description |
| | | 19-35 days following Experimental Session 1. | administered in placebo group at same time interval. |
| | | Optional. Following anxiety assessment 0.75-2 hours after first dose administration | REMS Protocol: Considered for administration of racemic MBDB, R-MBDB, and S-MBDB treatment groups and associated placebo controls. Underdosing of racemic MBDB, R-MBDB, or S-MBDB may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 350 mg. Placebo administered in placebo group at same time interval. If anxiety is decreased, no REMS protocol dose is given at this time. |
| | | 1.5-2 hours after first dose administration | Supplemental Dose: Supplemental half-dose of 50-100 mg administered 1.5 to 2 hours following initial dose administration unless contraindicated. If initial plus REMS protocol doses total a cumulative dose of 350 mg, no Supplemental Dose is given. If initial plus any REMS protocol dose is less than 350 mg, Supplemental Dose is administered 1.5 to 2 hours following initial dose administration. Placebo administered in placebo group at same time intervals. |
| | Intervening Session 2A | Morning following Experimental Session 2 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 2B | 3 to 14 days following Experimental Session 2 | Behavioral or cognitive-behavioral therapy session lasting 60-120 minutes. CAPS-5 assessment. |
| | Intervening Session 2C | 18-34 days following Experimental Session 2 | Behavioral or cognitive-behavioral therapy session lasting 60-120 minutes. Assessments include LEC-5, HAM-A, and C-SSRS and CAPS-5.. |
| Treatment 3 | Experimental Session 3 | 8 hours plus overnight observation. 19-35 days following Experimental Session 2. | Patient's weight is determined for dosage calculation. Baseline STAI assessment. Dose is 180-210 mg p.o. Placebo administered in placebo group at same time interval. |
| | | Optional. Following anxiety assessment 0.75-2 hours after first dose administration | REMS Protocol: Only considered for administration of racemic MBDB and S-MBDB treatment groups and associated placebo controls. Underdosing of racemic MBDB or S-MBDB may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 350 mg. Placebo administered in placebo group at same time interval. If anxiety is decreased, no REMS protocol dose is given at this time. |
| | | 1.5-2 hours after first dose administration | Supplemental Dose: Supplemental half-dose of 50-100 mg administered 1.5 to 2. hours following initial dose administration unless |

-continued

| Treatment Period (lasts approximately 12 weeks) | | |
|---|---|---|
| Study Visit | Visit Timing | Description |
| | | contraindicated. If initial plus REMS protocol doses total a cumulative dose of 350 mg, no Supplemental Dose is given. If initial plus any REMS protocol dose is less than 350 mg, Supplemental Dose is administered 2 to 2.5 hours following initial dose administration. Placebo administered in placebo group at same time intervals. |
| Intervening Session 3A | Morning following Experimental Session 3 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| Intervening Session 3B | 3 to 14 days following Experimental Session 3 | Behavioral or cognitive-behavioral therapy session lasting 60-120 minutes. CAPS-5 assessment. |
| Intervening Session 3C | 18-34 days following Experimental Session 3 | Behavioral or cognitive-behavioral therapy session lasting 60-120 minutes. Assessments include LEC-5, HAM-A, C-SSRS and CAPS-5. |

The Follow-up Period schedule and Study Conclusion follow the Screening Period and the Treatment Period.

| Follow-up Period and Study Conclusion | | |
|---|---|---|
| Study Visit | Visit Timing | Description |
| Follow-up Period | Occurs 2-10 days after Intervening Session 3C. | Occurs about 100-150 days following Baseline assessment. Complete self-reported assessments and patient safety measures. Create exit treatment plan for participant based on results. Final CAPS-5 assessment. Final SDS, HAM-D, and ESS assessments. |
| Study Conclusion | At time of unblinding of group. | Inform participants who finished study protocol of unblinding of groups. If a participant was in a placebo group, offer opportunity to enroll in a open-label safety extension study using either racemic MBDB, S-MBDB, or R-MBDB. |

Dose Selection

This study compares the effects of three blinded Experimental Sessions of psychotherapy in combination with flexible doses of MBDB or placebo administered as described below. Non-drug preparatory and intervening psychotherapy sessions are also included. Patient's weight is determined for dosage calculation. Initial dose is 180 mg unless this will result in a dosage of less than 1.5 mg/kg of patient weight. Initial dose thereby adjusted upward in 50 mg increments to deliver the lowest dose possible of at least 1.5 mg/kg of patient weight. Initial dose for Experimental Session 2 and 3 is cumulative dose calculated by adding the initial dose plus REMS protocol dose used the previous Experimental Session for each patient.

| Double-blinded treatment group | Experimental Session | Initial Dose | Optional (REMS) protocol: Dose Titration if underdosing occurs | Supplemental Dose (unless contraindicated) | Cumulative Dose |
|---|---|---|---|---|---|
| Racemic MBDB | 1 | 180-210 mg | 30-100 mg | 50-100 mg | 180-350 mg |
| Racemic MBDB | 2 | 180-210 mg | 30-100 mg | 50-100 mg | 180-350 mg |
| Racemic MBDB | 3 | 180-210 mg | 30-100 mg | 50-100 mg | 180-350 mg |
| S-MBDB | 1 | 180-210 mg | 30-100 mg | 50-100 mg | 180-350 mg |
| S-MBDB | 2 | 180-210 mg | 30-100 mg | 50-100 mg | 180-350 mg |
| S-MBDB | 3 | 180-210 mg | 30-100 mg | 50-100 mg | 180-350 mg |

-continued

| Double-blinded treatment group | Experimental Session | Initial Dose | Optional (REMS) protocol: Dose Titration if underdosing occurs | Supplemental Dose (unless contraindicated) | Cumulative Dose |
|---|---|---|---|---|---|
| R-MBDB | 1 | 180-210 mg | 30-100 mg | 50-100 mg | 180-350 mg |
| R-MBDB | 2 | 180-210 mg | 30-100 mg | 50-100 mg | 180-350 mg |
| R-MBDB | 3 | 180-210 mg | 30-100 mg | 50-100 mg | 180-350 mg |

Randomization and Masking

Randomization occurs prior to the initiation of Experimental Session 1. Each participant is provided the next randomized number in a sequence by a blinded study monitor. Participants are then randomized, according to a computer-generated randomization schedule, 1:1:1:1 to racemic MBDB, S-MBDB, R-MBDB, or placebo. The randomization schedule is prepared and implemented by an independent statistician. Participants, clinicians, and study teams are blinded to treatment allocation. Racemic MBDB, R-MBDB, and S-MBDB treatment groups may be subjected to anxiogenic effects due to underdosing of participants. As such, an optional dose titration schedule (REMS protocol) exists for racemic MBDB, R-MBDB, and S-MBDB treatment groups if a participant displays no change or a significant worsening of assessed anxiety symptomatology. Participants are assessed for general well-being and anxiety by a medical practitioner about 0.75 hours after the first dose is administered. Assessments performed may include general assessments of physical and mental well-being, a structured clinical interview for DSM-5 (SCID-5) module A1, and/or a STAI assessment and may continue throughout the period of overnight observation.

Subjects then undergo three Intervening Sessions with the first session the morning after the initial dose administration. MBDB treatment group or placebo group participants qualifying with a significant worsening of assessed anxiety symptomatology would undergo a placebo dose titration administration. Subjects would then undergo three Intervening Sessions with the first session the morning after the placebo dose titration administration. The pharmacist at each site, who prepares the treatments according to the randomization schedule, and an unblinded monitor, who performs drug accountability during the study, are unblinded. No other study personnel are unblinded until after formal locking of the study database. In the event of a medical emergency, the pharmacist is to reveal actual treatment contents to the primary investigator, who is to alert the Sponsor of the emergency. If the participant or study center personnel are unblinded, the subject is to be removed from the study.

Outcomes

The primary objective of this study is to evaluate the efficacy and safety of MBDB treatment combined with psychotherapy to treat moderate to severe PTSD compared to identical psychotherapy combined with placebo treatment. MBDB treatment is further subdivided into three separate treatment groups (racemic MBDB, S-MBDB, and R-MBDB) with each treatment subgroup only receiving administration of the single assigned drug. Treatment outcomes are determined based on a change in CAPS-5 Total Severity.

Several secondary objectives are designed for this study. One is an evaluation of clinician-rated functional impairment of MBDB treatment combined with psychotherapy to treat moderate to severe PTSD compared to identical psychotherapy combined with placebo treatment. MBDB treatment is further subdivided into three separate treatment groups (racemic MBDB, S-MBDB, and R-MBDB) with each treatment subgroup only receiving administration of the single assigned drug. Treatment outcomes are determined based on a change in SDS. Another secondary objective of this study is to evaluate clinician-rated depression of MBDB treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in HAM-D. An additional secondary objective of this study is to evaluate sleep assessments of MBDB treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in ESS. Co-morbidities present in participants with a strong positive response to MBDB treatment are correlated. Co-morbidities present in participants with weak-to-no positive response to MBDB treatment are correlated. Changes to presence or severity of co-morbidities from the Preparation Period to the Study Conclusion are recorded to determine if MBDB treatment combined with psychotherapy in moderate to severe PTSD subjects affects co-morbid phenotypes not falling under the constellation of PTSD symptoms.

Participant Populations

Participants are recruited through referrals by other treatment providers or through print or internet advertisements. The Sponsor monitors demographics of individuals assessed for enrollment to encourage diversity and an unbiased representation of the total PTSD population. Participants must be 18 years of age or older, have a confirmed diagnosis of at least moderate PTSD according to PCL-5 at the Screening Period. Medical history intake must indicate a presence of PTSD symptoms for at least 6 months prior to the Screening Period. Participants may be enrolled in the study while remaining on a treatment regimen involving SSRI or SNRI treatment prescribed for PTSD. In some cases, enrolled participants currently taking an SSRI, an SNRI, or another medication are tapered off these medications and stabilized prior to baseline assessments. Participants with a confirmed personality disorder diagnosis are excluded from this study. Participants must be in good general physical health without one or more severe chronic conditions that could affect the safety or tolerability of MBDB treatment.

Statistical Analysis

The change from baseline in CAPS-5, SDS, HAM-D, and ESS in participants is analyzed using a mixed effects model for repeated measures (MMRM) to obtain covariance parameter estimates. The model includes treatment center, treatment subtype, baseline assessments, assessment time point, and time point-by-treatment as explanatory variables. Treatment center is treated as a random effect; all other explanatory variables are treated as fixed effects. Model-based point estimates (e.g., least squares means, 95% confidence intervals, and p-values) are reported for each time point. With a sample size of 50 participants per treatment group, this study has 90% power to detect a significant treatment effect, using a two-sided test with an alpha value of 0.05. Additional participants may be enrolled with conditional power analysis conducted at a group-unblinded interim analysis time point for efficacy when 200 participants are enrolled and at least 60% of the blinded participants (N=120) have completed a final CAPS-5 assessment and reached Study Conclusion.

Results

The results may indicate that the primary objective is achieved. At the point of Study Conclusion, racemic MBDB-treated, S-MBDB-treated, and R-MBDB-treated participants may demonstrate a significant mean reduction in CAPS-5 assessment compared to the placebo group. The S-MBDB-treated subgroup may achieve a significant mean reduction in CAPS-5 assessment with a lower total dosage of drug compared to the racemic MBDB-treated subgroup. The R-MBDB-treated subgroup may achieve a significant mean reduction in CAPS-5 assessment with a lower total dosage of drug compared to the racemic MBDB-treated subgroup. Significant improvements in CAPS-5 assessments may be observed for racemic MBDB-treated, S-MBDB-treated, and R-MBDB-treated participants at time points of Intervening Session 1C, Intervening Session 2C, Intervening Session 3C and Study Conclusion, compared to placebo-treated controls. Significant improvements in CAPS-5 assessments may be observed for S-MBDB-treated participants at time points of Intervening Session 1C, Intervening Session 2C, Intervening Session 3C, compared to placebo-treated controls without a significant increase in adverse anxiogenic incidents in S-MBDB-treated participants.

The results may indicate that the secondary objectives of this study are also achieved. Racemic MBDB-treated, S-MBDB-treated, and R-MBDB-treated participants may demonstrate a significant improvement in clinician-rated functional impairment score as measured by SDS compared to placebo-treated controls. Racemic MBDB-treated, S-MBDB-treated, and R-MBDB-treated participants may demonstrate a significant improvement depression as measured by HAM-D compared to placebo-treated controls. Racemic MBDB-treated, S-MBDB-treated, and R-MBDB-treated participants may demonstrate a significant improvement in lessening daytime sleepiness as measured by ESS. S-MBDB-treated participants may demonstrate a significant improvement in clinician-rated functional impairment score, in depression, and in lessening daytime sleepiness compared to placebo-treated controls without a significant increase in adverse anxiogenic incidents in S-MBDB-treated participants.

Example 29: Effect of Administration of MDAI and Chlordiazepoxide on Behavior in a Rat 0-Maze Study 35 male Sprague-Dawley rats in treatment groups of 2 or 5, was intraperitoneally dosed with either Vehicle 1 (saline) or MDAI at 1 of 5 dose levels (0.15, 0.31, 0.625, 1.25 and 2.5) or chlordiazepoxide (6 mg/kg) in 5 mL/kg injection volumes. Thirty min later at T=0, rats were individually placed in a closed arm of the zero-maze and behavior assessed by a "blind" observer using remote video monitoring over the subsequent 5 min. The animal was then removed and the maze carefully wiped with 5% methanol/water solution before the next test was begun. Three rats from the vehicle group, 3 rats from the 2.5 mg/kg MDAI group, and 3 rats from the CDP group were tested on a separate day from the other rats.

TABLE Ex13

Synopsis of testing schedule MDAI and chlordiazepoxide in the rat elevated zero maze model of anxiety.

| n | Rat Strain & sex | 0.5 Pretest in Veh 1 5 mL/kg ip | T = 0 Zero-maze |
|---|---|---|---|
| 5 | Male SD | Vehicle 1 | Test |
| 5 | Male SD | MDAI 0.15 mg/kg | Test |
| 5 | Male SD | MDAI 0.31 mg/kg | Test |
| 5 | Male SD | MDAI 0.625 mg/kg | Test |
| 5 | Male SD | MDAI 1.25 mg/kg | Test |
| 5 | Male SD | MDAI 1.25 mg/kg | Test |
| 5 | Male SD | CDP 6 mg/kg | Test |

Statistical Analysis

Data was analysed with Statistica software (Statsoft USA version 10.0). All data was expressed as means±SEM. Data was analyzed by 1 way ANOVA and Dunnett's or Newman-Keuls test. Statistical significance in all analyses was assumed when $P<0.05$.

Figure 124:
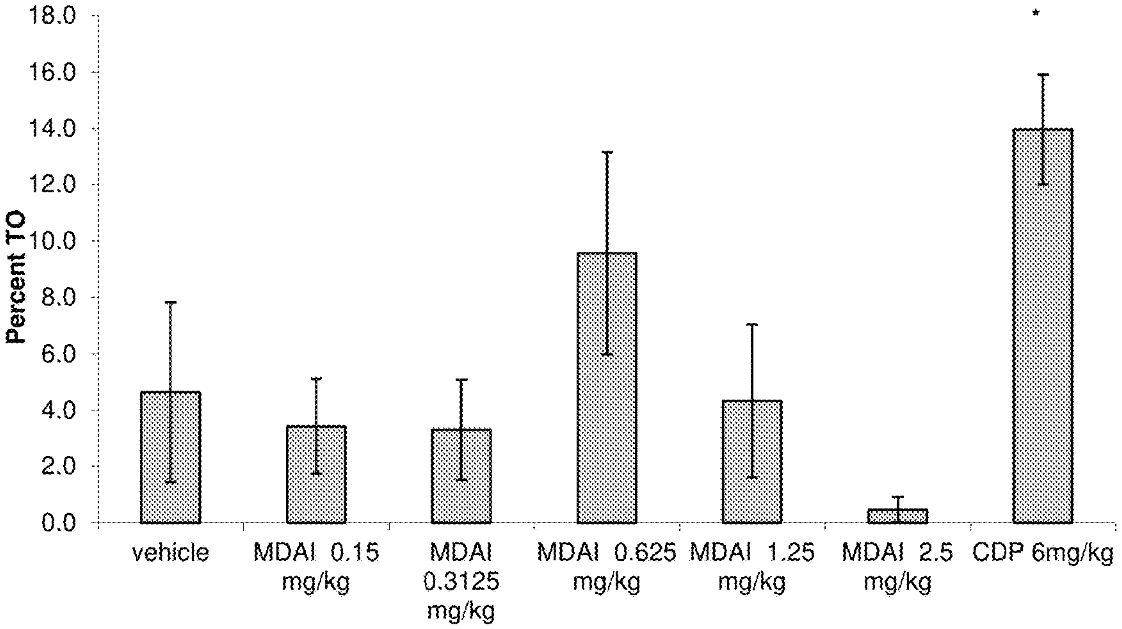
Figure 125:
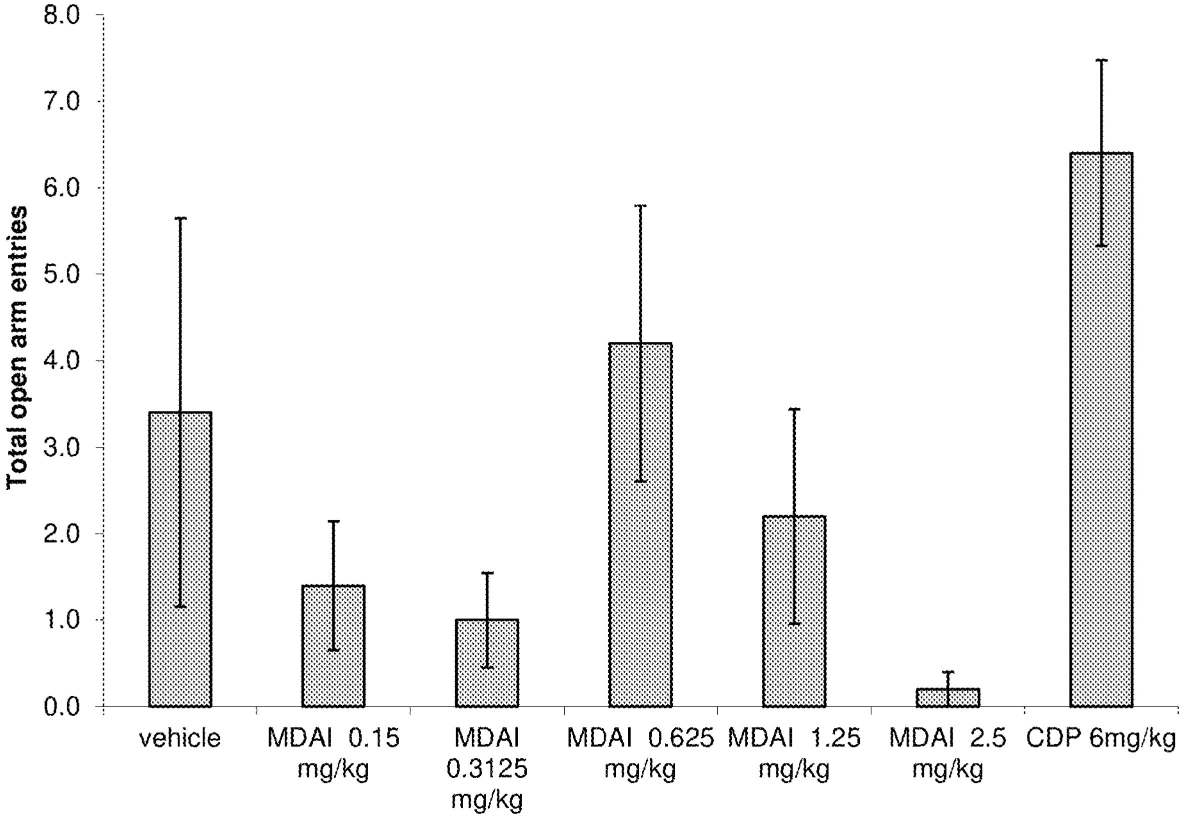
Figure 126:
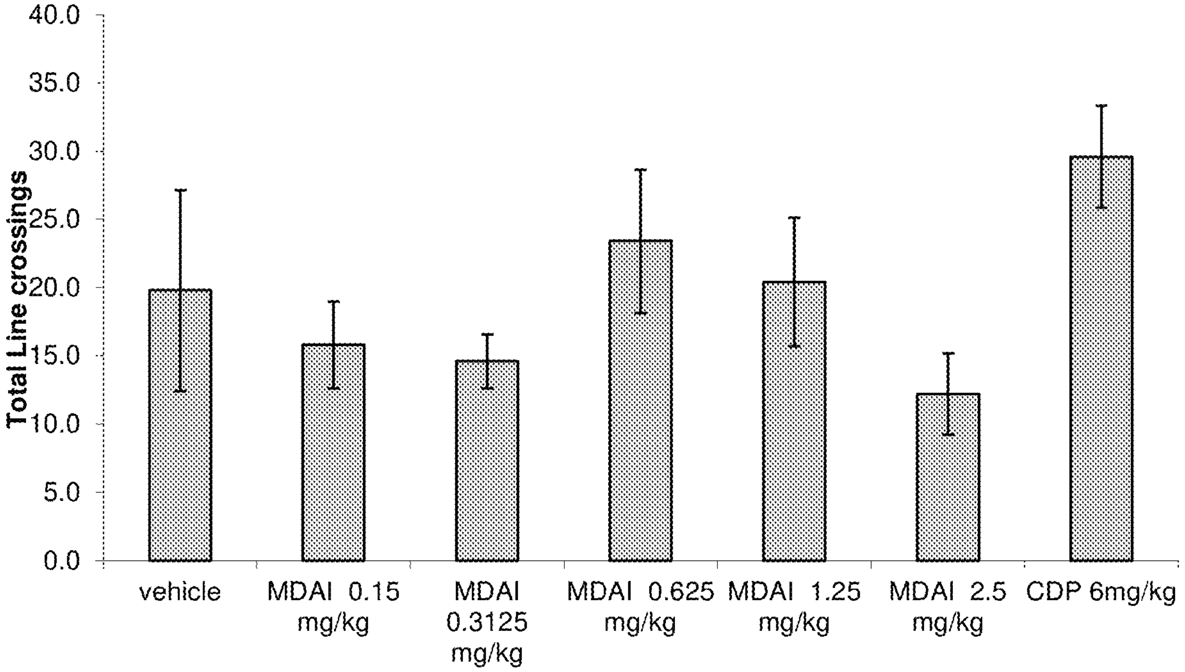
Figure 127:
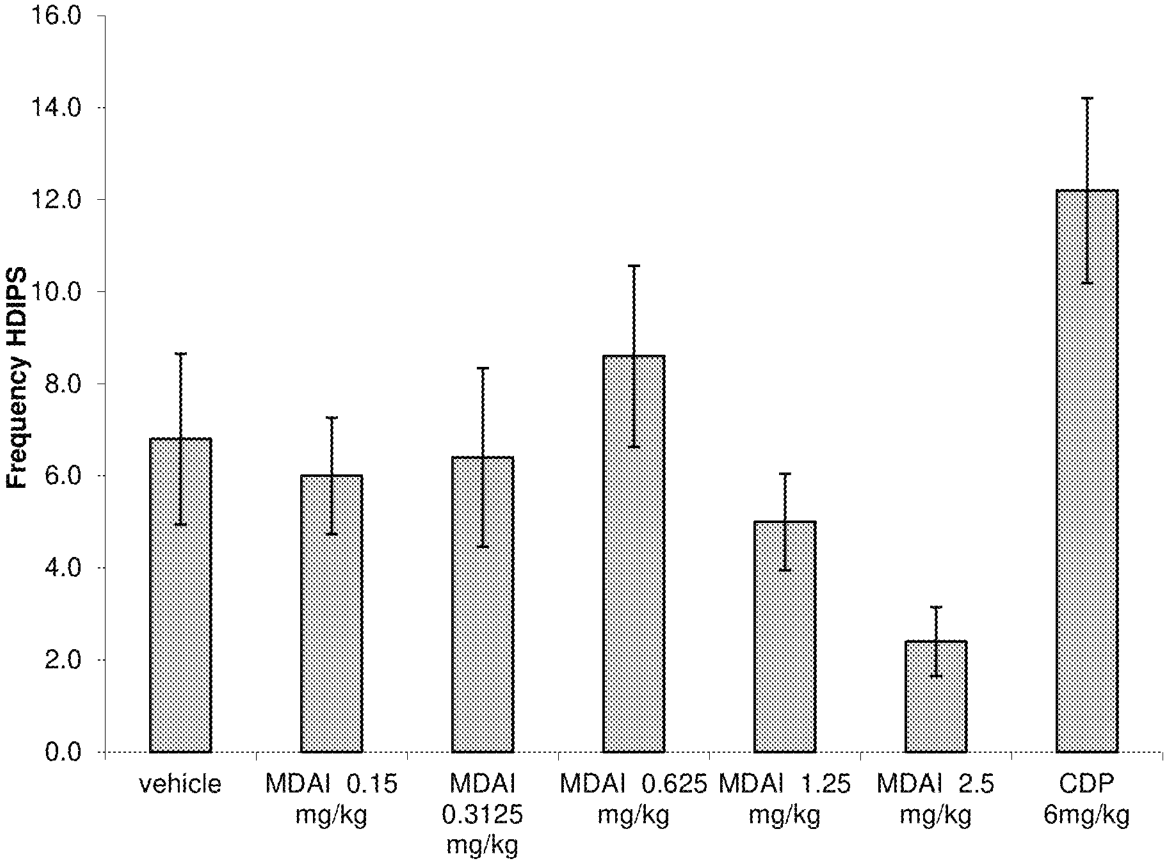

MDAI Discussion:

CDP showed a significant increase in the percentage of time in the open arms (% TO) but only showed a trend towards increased total open arm entries, the total line crossings, and the frequency of HDIPS which showed that the study was underpowered to detect an effect. An increase in total open arm entries, total line crossings, and the frequency of HDIPS all indicates an anxiolytic effect. We found that MDAI dosed at 0.625 mg/kg showed a numerical increase in % TO that was greater than vehicle or any other dose of MDAI (FIG. 124). This indicates that this middle dose of MDAI was anxiolytic. This also shows that doses of MDAI that are too low or too high induce an anxiogenic effect as we saw the opposite effect on % TO with these doses. This trend towards an anxiolytic effect with the middle dose of MDAI was also seen with total open arm entries with only the middle dose showing an increase vs placebo that trended towards significance. The higher and lower doses all trended towards an anxiogenic effect on that measure (FIG. 125). This was further confirmed with total line crossings (FIG. 126) and frequency of HDIPS (FIG. 127). These data show that MDAI has anxiolytic effects in a specific dose range. Additionally, we found the surprising finding that low doses of MDAI are anxiogenic which means that patients who take MDAI would need to be titrated up to the effective dose.

There are several critical implications of this finding. The first is that patients treated with any form of MDAI must receive a dose high enough to reach the anxiolytic threshold since lower doses may cause anxiety as a side effect and result in worsening of the disorder being treated. This could have especially severe implications for anxiety disorders or depressive disorders including post-traumatic stress disorder, generalized anxiety disorder, panic disorder, major depressive disorder, or treatment resistant depression. All of these indications are associated with an increased level of anxiety as a major symptom. In these cases, a drug-induced increase in anxiety due to improper dosing of MDAI could have severe side effects on patients and worsen their underlying disorder. The data presented herein show that patients treated MDAI must be especially careful to titrate up to the therapeutic dose to avoid the anxiogenic effects and to reach the anxiolytic effect level. The data show that in some embodiments a Risk Evaluation and Mitigation Strategy (REMS) program should be utilized so that patients treated with MDAI should undergo an initial dose titration to determine the effective range specific to that patient. This dose titrating protocol would decrease the side effects related to underdosing MDAI. The data also inform Phase 2 and Phase 3 clinical trial design. Clinical trials for neurological and psychiatric disorders often include one or more low dose arms to show a dose dependent effect of the full dose on the disease of interest. However, this data shows that MDAI should only be dosed at the full effective dose and a low dose arm should not be included as a comparator as this may lead to harmful side effects on the patients. This data shows that studies of MDAI should only use inactive matched placebo or a different standard of care therapeutic as a control. In clinical trials MDAI should only be dosed at its effective dose range to avoid harmful side effects to the patients. This would be especially critical in clinical studies of anxiety disorders or depression including post-traumatic stress disorder, generalized anxiety disorder, panic disorder, major depressive disorder, or treatment resistant depression where increased anxiety could worsen the underlying disorder and lead to potentially devastating effects on the patients.

Example 30: MDAI Dose Titration Risk Evaluation and Mitigation Strategy (REMS) Protocol General Information on MDAI Treatment Session Initial MDAI dosing and subsequent dosing adjustments must be done under the supervision of a qualified healthcare professional in a clinic or inpatient setting. The patient must remain under supervision of the healthcare professional for at least 6 hours and up to approximately 24 hours after the final MDAI dose adjustment. The patient will be assessed periodically during the session for anxiety and other effects of MDAI. Dose adjustments within a MDAI treatment session will be based on changes from baseline levels of anxiety. Postdose anxiety measurement timing and duration of observation after dosing are shown here (https://psychonautwiki.org/wiki/MDAI):

Duration of Effects of MDAI

| Effects | Time After Dose |
|---|---|
| Onset | 20 min-40 min |
| Coming Up | 30 min-60 min |
| Peak | 2 hours-2.5 hours |
| Offset | 60 min-120 min |
| Duration | 4 hours-6 hours |

MDAI dosing is shown here:

MDAI Dosages

| Drug Activity Level | Oral MBDB Dose |
|---|---|
| Threshold | 40 mg |
| Light | 420 mg-100 mg |
| Common | 100 mg-175 mg |
| Strong | 175 mg-300 mg |
| Very Strong | ≥300 mg |

Predose Assessment

The patient's baseline level of anxiety will be measured and recorded.

Initial MDAI Dosing

The patient will receive an initial single oral dose of MDAI in the range of approximately 100 mg-200 mg based on oral doses reported as producing moderate effects (https://psychonautwiki.org/wiki/MDAI).

Postdose Assessment

Change from baseline anxiety level will be measured at approximately 0.75 to 2 hours after dosing based on reported time to achieve peak effects (https://psychonautwiki.org/wiki/MDAI).

MDAI Dose Adjustment

MDAI effects have been maintained by taking a larger initial dose followed by smaller doses (30 mg to 100 mg p.o.). Re-dose of one-third to one-half the initial dose usually prolongs duration (https://psychonautwiki.org/wiki/MDAI). Accordingly, the dose of MDAI will be adjusted based on change from baseline in anxiety as follows:

MDAI Dose Adjustment

| Change from Baseline Anxiety | MBDB Dose Adjustment |
|---|---|
| Increased | Increase dose 30%-50% and reassess anxiety in approximately 1 hour |
| No Change | Increase dose 30%-50% and reassess anxiety in approximately 1 hour |
| Decreased | Maintain dose if therapeutic effect achieved or Increase to a maximum of 300 mg total dose to optimize therapeutic effect |

MDAI Discontinuation

The patient will be observed for at least 6 hours after final MDAI dose is administered. The patient may be confined to the inpatient unit for prolonged observation up to approximately 24 hours after last MDAI dose if indicated based on persistent effects.

Anxiety that appears after the final MDAI titration dose is administered can be managed with an appropriate anxiolytic agent. If this is necessary, the patient must remain under observation and undergo periodic reassessment until the supervising healthcare professional determines the patient can be discharged from care.

Example 31: A Double-Blind, Randomized, Placebo-Controlled Clinical Trial of MDAI-Assisted Psychotherapy in PTSD A multicenter, randomized, double-blind, placebo-controlled trial is conducted to assess the efficacy and safety of MDAI-assisted psychotherapy versus psychotherapy with placebo control in participants diagnosed with at least moderate post-traumatic stress disorder (PTSD).

Rationale

PTSD is a debilitating and often times chronic disorder associated with profound mental, physical, occupational, and functional impairment. PTSD can develop due to exposure to a traumatic event or persistent or recurring threats to an individual. Studies indicate that approximately 10% of individuals exposed to a traumatic event eventually go on to be diagnosed with PTSD (American Psychiatric Association. *Diagnostic and statistical manual of mental disorders*, $5^{th}$ edition, 2013). PTSD is a complex psychiatric disorder characterized by symptom heterogeneity including avoidance of trauma-related material, emotional blunting and distancing, hyper-vigilance, hyper-arousal, persistent negative alterations in mood, persistent alterations in cognition, disturbing thoughts, disruptions in sleep and/or dreams, and physical or mental distress. Symptoms can be severe and long lasting. Although this symptom heterogeneity may suggest a wide spectrum of separate disturbances, emotional dysregulation is considered to be a core component of this disorder. Particularly germane to the pathogenesis and progression of PTSD, emotional dysregulation in affected individuals is believed to give rise to observable and measurable features such as presence of hypervigilance and attentional biases, enhanced startle response, hyper-arousal, apathetic feeling or emotional numbness, irritability, enhanced memories associated with traumatic events, difficulty in discerning danger versus safety, a generalization of fear, and avoidance of reminders of trauma. Emotional dysregulation may be defined and also measured by elevated emotional reactivity based on abnormal detection or appraisal of emotional triggers involving bottom-up sensory detection and neuronal processing. Biochemical alterations found in individuals diagnosed with PTSD suggest abnormalities in the hypothalamic-pituitary-adrenal (HPA) axis. The HPA axis is known to regulate reactions to stress and controls significant aspects of the neuroendocrine system impacting many homeostatic systems in the body. In a typical flight-or-flight response in a healthy individual, catecholamine and cortisol levels detected in urine rise after exposure to a stressor. In PTSD, many individuals show a low secretion of cortisol and high secretion of catecholamine in response to a stressor indicating a change in catecholamine to cortisol ratio in the urine. More evidence that the HPA axis is impacted in PTSD is found in elevated levels of catecholamines and corticotropin-releasing factor in the brain of many affected individuals.

The initiation and/or maintenance of emotional dysregulation in PTSD may be due to abnormalities in top-down control of emotional responses indicating that cognitive influences and higher order representations may impinge on information and emotional processing. Certainly, some aspects of abnormalities in neuronal processing in PTSD occur either implicitly (e.g., unconsciously) or explicitly (e.g., consciously) indicating involvement of distinct cognitive processes. Exaggerated responses in the amygdala and insular cortex have been demonstrated in meta-analyses in PTSD pathology, as have decreases in activity in other brain regions including the anterior cingulate cortex and aspects the prefrontal cortex including the ventromedial prefrontal cortex. In addition to changes in patterns of neuronal activity in individuals with PTSD, several neuroanatomical changes in PTSD have also been demonstrated. A reduction of total brain volume, intracranial volume, and the volumes in regions such as the hippocampus (particularly localized to the CA3 and dentate gyrus regions), insular cortex, and anterior cingulate cortex have been indicated in occurring in some individuals with PTSD through meta-analyses of structural MRI studies. Animal studies have shown that severe chronic stress leads to atrophy of apical dendrites in the CA3 region of the hippocampus, reduced hippocampus neurogenesis, and elevated granule cell death in the dentate gyrus due to elevated levels of glucocorticoids (Gould E. and Tanapat. (1999). *Stress and hippocampal neurogenesis*. Biol. Psychiatry 46, 1472-1479.) Connections between brain areas such as the amygdala, hippocampus, prefrontal cortex, and hypothalamus can facilitate activation of the HPA axis to illustrate interactions between brain regions with structural changes and affected biochemical regulatory systems in PTSD.

MDAI is a synthetic analog of the psychedelic phenethylamine class of compounds known to act as a mixed reuptake inhibitor/releasing agent of serotonin and administration of MDAI can produce acute modulations of neurotransmission. MDAI administration also has indirect effects on neurohormone release. MDAI can function as a psychoplastogen promoting neuronal growth, modulating neuronal connectivity, and regulating neuronal plasticity through longer term neuronal changes. The combined neurobiological effects of MDAI administration on individuals reduce fear of emotional injury or distress, enhance introspection and communication, and increase empathetic feelings and compassion. Additionally, MDAI may serve to enhance fear extinction. These combined effects may yield acute and longer-term productive psychological states to enhance behavioral or cognitive-behavioral therapies. MDAI administration may enhance neuronal function at the biochemical and cellular levels to generate or restore favorable neural network pathways and connectivity to increase behavioral or cognitive-behavioral therapy productiveness.

Study Design

This multicenter, randomized, double-blind, placebo-controlled trial is conducted at various sites in the United States with IRB approval from each study site. A flexible dose of MDAI hydrochloride salt or placebo, followed by a supplemental half-dose unless contraindicated by patient's previous response or medical history, is also administered during the Treatment Period with psychotherapy in at least 3 blinded monthly Experimental Sessions. The Supplemental Dose extends the duration of drug effects on the participants during an Experimental Session. An optional Risk Evaluation and Mitigation Strategy (REMS) Protocol may be implemented for MDAI and placebo-groups. The Treatment Period lasts for approximately 12 weeks. During the Treatment Period, each Experimental Session is followed by three Intervening Sessions of non-drug psychotherapy. Each Experimental Session involves an overnight stay. The Primary Outcome measure, the change in Clinician Administered PTSD Scale for DSM-5 (CAPS-5), is determined by a blinded Independent Rater (IR) pool multiple times throughout the study. The study consists of separate periods for each participant. Initially, prospective participants undergo a Screening Period involving an initial eligibility assessment, a medical history intake, informed consent, and enrollment of eligible participants. Next, a Preparation Period is undertaken for enrolled participants involving medication tapering and clinical baseline assessments to confirm each participant meets enrollment criteria. As part of the Preparation Period, a detailed assessment of co-morbidities to PTSD is recorded. Participants may remain on prescribed courses of selective serotonin reuptake inhibitor (SSRI) or serotonin and norepinephrine reuptake inhibitor (SNRI) treatment. Dosages and/or frequency of administration of a prescribed SSRI or SNRI may be adjusted to fit within study parameters. Participants may be required to taper a prescribed course of medication in order to maintain eligibility within the study. The Treatment Period consists of three monthly Experimental Sessions and associated Intervening Sessions of integrative behavioral psychotherapy. The Treatment Period lasts approximately 12 weeks. Following the Treatment Period is a Follow-up Period and Study Conclusion. During the Follow-up Period and Study Conclusion, participants complete 4 weeks with no study visits, followed by a Study Conclusion visit.

| Screening Period - from initial consent to beginning of enrollment (approx. 4 weeks) | | | |
|---|---|---|---|
| Study Visit | | Visit Timing | Description |
| Screening | Screening | Several visits taking place 5-30 days after initial phone call screen | Informed consent obtained and assessment measures of pre-study medications, complete personal and family medical history and all assessed screening measures undertaken. These measures may include any of: PTSD checklist for DSM-5 (PCL-5), Columbia-Suicide Severity Rating Scale (C-SSRS), Montgomery-Asberg Depression Rating Scale (MADRS), Hamilton Depression Rating Scale (HAM-D), Hamilton Anxiety Rating Scale (HAM-A), General Anxiety Disorder-7 (GAD-7), Beck Anxiety Inventory (BAI), Impact of Events Scale (IES), State-Trait Anxiety Inventory (STAI), Edinburgh Postnatal Depression Scale (EPDS), Clinical Global Impressions Scale (CGI-I), Epworth Sleepiness Scale (ESS), and Pittsburgh Sleep Quality Scale. Medical providers are contacted and medical records and laboratory results are obtained. All results and records are reviewed along with interview notes. If eligible, results of Life Events Checklist for DSM-5 (LEC-5) and Structured Clinical Interview for DSM-5 Personality Questionnaire (SCID-5-SPQ) are forwarded to IR. |
| | IR Screening | 2-10 days after initial eligibility determined during Screening Period | Initial eligibility after PCL-5 and initial eligibility are reviewed. Next, IR conducts a since last visit C-SSRS, SCID-5-PD, Dissociative Disorders Interview Schedule (DDIS), and/or International Neuropsychiatric Interview (MINI). Results of IR assessment confirmed over Preparatory Period. |
| Enrollment | Enrollment | 1-14 days after IR Screening | Prior to enrollment, all screening measures are reviewed and any clarification needed with participant is completed by telephone interview. If enrolled, and if it has been determined to taper an ongoing medication, begin a tapering treatment plan of at least 5 half-lives plus at least 5 days for stabilization. Begin collection of Adverse Events (AE). |

| Preparation Period (between 1-12 weeks) | | | |
|---|---|---|---|
| Study Visit | | Visit Timing | Description |
| Preparatory Period | Preparatory Session 1 | Undertaken 0-14 days post-enrollment | Schedule visit timing according to medication tapering needs. Schedule calls in between visits for safety concerns, tapering questions, or other issues related to medical history. Confirm enrollment. |
| | Preparatory Session 2 | Undertaken 2-21 days following Preparation Session 1 | Schedule upcoming visits if medication tapering is not needed or is already completed. If still tapering, schedule additional telephone call for continuing assessment of readiness to enter study. |
| | Taper follow-up | 0-7 days following end of medication taper | Schedule baseline CAPS-5. |
| Baseline and Enrollment Confirmation | Baseline Assessments | Following Preparatory Session 2 | Complete CAPS-5, Sheehan Disability Score (SDS), and Dissociative Subtype of PTSD Scale (DSPS) by IR via in-person or telemedicine appointment. Scores forwarded to therapy monitoring team. Resumption of tapered medicine in symptom management requires. Withdrawal of participants not meeting eligibility criteria at this point. |
| | Preparatory Session 3 | 1-7 days following baseline CAPS-5 | Participants complete baseline self-report metrics and schedule Experimental Session 1. |

The Treatment Period schedule follows the Screening Period and the Preparatory Period

| Treatment Period (lasts approximately 12 weeks) | | | |
|---|---|---|---|
| Study Visit | | Visit Timing | Description |
| Treatment 1 | Randomization | 0-10 days following Baseline assessments | Complete following verification participant is still enrolled and Experimental Session 1 is scheduled. Double-blind randomization. |
| | Experimental Session 1 | 8 hours plus overnight observation | Patient's weight is determined for dosage calculation. Baseline STAI assessment. Dose is 180-210 mg p.o. Placebo administered in placebo group at same time interval. |
| | | Optional. Following anxiety assessment 0.75-2 hours after first dose administration | REMS Protocol: Considered for administration of MDAI treatment groups and associated placebo controls. Underdosing of MDAI may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 350 mg. Placebo administered in placebo group at same time interval. If anxiety is decreased, no REMS protocol dose is given at this time. |
| | | 1.5-2 hours after first dose administration | Supplemental Dose: Supplemental half-dose of 50-100 mg administered 1.5-2 hours following initial dose administration unless contraindicated. If initial plus REMS protocol doses total a cumulative dose of 300 mg, no Supplemental Dose is given. If initial plus any REMS protocol dose is less than 300 mg, Supplemental Dose is administered 2 to 2.5 hours following initial dose administration. Placebo administered in placebo group at same time intervals. |
| | Intervening Session 1A | Morning following Experimental Session 1 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 1B | 3 to 14 days following Experimental Session 1 | Behavioral or cognitive-behavioral therapy session lasting 60-120 minutes. CAPS-5 assessment. |
| | Intervening Session 1C | 18-34 days following Experimental Session 1 | Behavioral or cognitive-behavioral therapy session lasting 60-120 minutes. Assessments include LEC-5, HAM-A, C-SSRS and CAPS-5. |
| Treatment 2 | Experimental Session 2 | 8 hours plus overnight observation. 19-35 days following Experimental Session 1. | Patient's weight is determined for dosage calculation. Baseline STAI assessment. Dose is 180-210 mg p.o. Placebo administered in placebo group at same time interval. |
| | | Optional. Following anxiety assessment 0.75-2 hours after first dose administration | REMS Protocol: Considered for administration of MDAI treatment groups and associated placebo controls. Underdosing of MDAI may lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 300 mg. Placebo administered in placebo group at same time interval. If anxiety is decreased, no REMS protocol dose is given at this time. |

-continued

| Treatment Period (lasts approximately 12 weeks) | | | |
|---|---|---|---|
| Study Visit | | Visit Timing | Description |
| | | 2-2.5 hours after first dose administration | Supplemental Dose: Supplemental half-dose of 30-100 mg administered 2 to 2.5 hours following initial dose administration unless contraindicated. If initial plus REMS protocol doses total a cumulative dose of 300 mg, no Supplemental Dose is given. If initial plus any REMS protocol dose is less than 300 mg, Supplemental Dose is administered 2 to 2.5 hours following initial dose administration. Placebo administered in placebo group at same time intervals. |
| | Intervening Session 2A | Morning following Experimental Session 2 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 2B | 3 to 14 days following Experimental Session 2 | Behavioral or cognitive-behavioral therapy session lasting 60-120 minutes. CAPS-5 assessment. |
| | Intervening Session 2C | 18-34 days following Experimental Session 2 | Behavioral or cognitive-behavioral therapy session lasting 60-120 minutes. Assessments include LEC-5, HAM-A, and C-SSRS and CAPS-5.. |
| Treatment 3 | Experimental Session 3 | 8 hours plus overnight observation. 19-35 days following Experimental Session 2. | Patient's weight is determined for dosage calculation. Baseline STAI assessment. Dose is 100-200 mg p.o. Placebo administered in placebo group at same time interval. |
| | | Optional. Following anxiety assessment 0.75-2 hours after first dose administration | REMS Protocol: Considered for administration of MDAI treatment groups and associated placebo controls. Underdosing of MDSI lead to exacerbation of anxiogenic features necessitating careful assessment of worsening of symptoms. Patients are assessed for anxiety about 0.75 hours after first dose. With no change or increase in anxiety, patients are given a dose of 30%-50% of first dose and anxiety reassessed in about 1 hour. Dose titration up to a maximum cumulative dose of 300 mg. Placebo administered in placebo group at same time interval. If anxiety is decreased, no REMS protocol dose is given at this time. |
| | | 2-2.5 hours after first dose administration | Supplemental Dose: Supplemental half-dose of 30-100 mg administered 2 to 2.5 hours following initial dose administration unless contraindicated. If initial plus REMS protocol doses total a cumulative dose of 300 mg, no Supplemental Dose is given. If initial plus any REMS protocol dose is less than 300 mg, Supplemental Dose is administered 2 to 2.5 hours following initial dose administration. Placebo administered in placebo group at same time intervals. |
| | Intervening Session 3A | Morning following Experimental Session 3 | Behavioral or cognitive-behavioral therapy session lasting 90-120 minutes. Assessment of potential anxiogenic, mixed anxiogenic-anxiolytic, or anxiolytic treatment effects. CAPS-5 assessment. Instructions for participants to complete C-SSRS assessments on every two days following Experimental Session 1. |
| | Intervening Session 3B | 3 to 14 days following Experimental Session 3 | Behavioral or cognitive-behavioral therapy session lasting 60-120 minutes. CAPS-5 assessment. |

-continued

| Treatment Period (lasts approximately 12 weeks) | | |
|---|---|---|
| Study Visit | Visit Timing | Description |
| Intervening Session 3C | 18-34 days following Experimental Session 3 | Behavioral or cognitive-behavioral therapy session lasting 60-120 minutes. Assessments include LEC-5, HAM-A, C-SSRS and CAPS-5. |

The Follow-up Period schedule and Study Conclusion follow the Screening Period and the Treatment Period.

| Follow-up Period and Study Conclusion | | |
|---|---|---|
| Study Visit | Visit Timing | Description |
| Follow-up Period | Occurs 2-10 days after Intervening Session 3C. | Occurs about 100-150 days following Baseline assessment. Complete self-reported assessments and patient safety measures. Create exit treatment plan for participant based on results. Final CAPS-5 assessment. Final SDS, HAM-D, and ESS assessments. |
| Study Conclusion | At time of unblinding of group. | Inform participants who finished study protocol of unblinding of groups. If a participant was in a placebo group, offer opportunity to enroll in a open-label safety extension study using MDAI. |

Dose Selection

This study compares the effects of three blinded Experimental Sessions of psychotherapy in combination with flexible doses of MDAI or placebo administered as described below. Non-drug preparatory and intervening psychotherapy sessions are also included. Patient's weight is determined for dosage calculation. Initial dose is 100 mg unless this will result in a dosage of less than 1.5 mg/kg of patient weight. Initial dose thereby adjusted upward in 50 mg increments to deliver the lowest dose possible of at least 1.5 mg/kg of patient weight. Initial dose for Experimental Session 2 and 3 is cumulative dose calculated by adding the initial dose plus REMS protocol dose used the previous Experimental Session for each patient.

| Double-blinded treatment group | Experimental Session | Initial Dose | Optional (REMS) protocol: Dose Titration if underdosing occurs | Supplemental Dose (unless contraindicated) | Cumulative Dose |
|---|---|---|---|---|---|
| MDAI | 1 | 100-200 mg | 30-100 mg | 50-100 mg | 100-300 mg |
| MDAI | 2 | 100-200 mg | 30-100 mg | 50-100 mg | 100-300 mg |
| MDAI | 3 | 100-200 mg | 30-100 mg | 50-100 mg | 100-300 mg |

Randomization and Masking

Randomization occurs prior to the initiation of Experimental Session 1. Each participant is provided the next randomized number in a sequence by a blinded study monitor. Participants are then randomized, according to a computer-generated randomization schedule, 1:1:1:1 to MDAI or placebo. The randomization schedule is prepared and implemented by an independent statistician. Participants, clinicians, and study teams are blinded to treatment allocation. MDAI treatment groups may be subjected to anxiogenic effects due to underdosing of participants. As such, an optional dose titration schedule (REMS protocol) exists for MDAI treatment groups if a participant displays no change or a significant worsening of assessed anxiety symptomatology. Participants are assessed for general well-being and anxiety by a medical practitioner about 0.75 hours after the first dose is administered. Assessments performed may include general assessments of physical and mental well-being, a structured clinical interview for DSM-5 (SCID-5) module A1, and/or a STAI assessment and may continue throughout the period of overnight observation.

Subjects then undergo three Intervening Sessions with the first session the morning after the initial dose administration. MDAI treatment group or placebo group participants qualifying with a significant worsening of assessed anxiety symptomatology would undergo a placebo dose titration administration. Subjects would then undergo three Intervening Sessions with the first session the morning after the placebo dose titration administration. The pharmacist at each site, who prepares the treatments according to the randomization schedule, and an unblinded monitor, who performs drug accountability during the study, are unblinded. No other study personnel are unblinded until after formal locking of the study database. In the event of a medical emergency, the pharmacist is to reveal actual treatment contents to the primary investigator, who is to alert the Sponsor of the emergency. If the participant or study center personnel are unblinded, the subject is to be removed from the study.

Outcomes

The primary objective of this study is to evaluate the efficacy and safety of MDAI treatment combined with psychotherapy to treat moderate to severe PTSD compared to identical psychotherapy combined with placebo treatment. Treatment outcomes are determined based on a change in CAPS-5 Total Severity.

Several secondary objectives are designed for this study. One is an evaluation of clinician-rated functional impairment of MDAI treatment combined with psychotherapy to treat moderate to severe PTSD compared to identical psychotherapy combined with placebo treatment. Treatment outcomes are determined based on a change in SDS. Another secondary objective of this study is to evaluate clinician-rated depression of MDAI treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in HAM-D. An additional secondary objective of this study is to evaluate sleep assessments of MDAI treatment combined with psychotherapy to treat moderate to severe PTSD compared to identical psychotherapy combined with placebo treatment. Identical study parameters are in place as for the clinician-rated functional impairment assessment except that treatment outcomes are determined based on a change in ESS. Co-morbidities present in participants with a strong positive response to MDAI treatment are correlated. Co-morbidities present in participants with weak-to-no positive response to MDAI treatment are correlated. Changes to presence or severity of co-morbidities from the Preparation Period to the Study Conclusion are recorded to determine if MDAI treatment combined with psychotherapy in moderate to severe PTSD subjects affects co-morbid phenotypes not falling under the constellation of PTSD symptoms.

Participant Populations

Participants are recruited through referrals by other treatment providers or through print or internet advertisements. The Sponsor monitors demographics of individuals assessed for enrollment to encourage diversity and an unbiased representation of the total PTSD population. Participants must be 18 years of age or older, have a confirmed diagnosis of at least moderate PTSD according to PCL-5 at the Screening Period. Medical history intake must indicate a presence of PTSD symptoms for at least 6 months prior to the Screening Period. Participants may be enrolled in the study while remaining on a treatment regimen involving SSRI or SNRI treatment prescribed for PTSD. In some cases, enrolled participants currently taking an SSRI, an SNRI, or another medication are tapered off these medications and stabilized prior to baseline assessments. Participants with a confirmed personality disorder diagnosis are excluded from this study. Participants must be in good general physical health without one or more severe chronic conditions that could affect the safety or tolerability of MDAI treatment.

Statistical Analysis

The change from baseline in CAPS-5, SDS, HAM-D, and ESS in participants is analyzed using a mixed effects model for repeated measures (MMRM) to obtain covariance parameter estimates. The model includes treatment center, treatment subtype, baseline assessments, assessment time point, and time point-by-treatment as explanatory variables. Treatment center is treated as a random effect; all other explanatory variables are treated as fixed effects. Model-based point estimates (e.g., least squares means, 95% confidence intervals, and p-values) are reported for each time point. With a sample size of 50 participants per treatment group, this study has 90% power to detect a significant treatment effect, using a two-sided test with an alpha value of 0.05. Additional participants may be enrolled with conditional power analysis conducted at a group-unblinded interim analysis time point for efficacy when 200 participants are enrolled and at least 60% of the blinded participants (N=120) have completed a final CAPS-5 assessment and reached Study Conclusion.

Results

The results may indicate that the primary objective is achieved. At the point of Study Conclusion, MDAI-treated participants may demonstrate a significant mean reduction in CAPS-5 assessment compared to the placebo group. Significant improvements in CAPS-5 assessments may be observed for MDAI-treated participants at time points of Intervening Session 1C, Intervening Session 2C, Intervening Session 3C and Study Conclusion, compared to placebo-treated controls. The results may indicate that the secondary objectives of this study are also achieved. At the point of Study Conclusion MDAI-treated participants may demonstrate a significant improvement in clinician-rated functional impairment score as measured by SDS compared to placebo-treated controls. At the point of Study Conclusion, MDAI-treated participants may demonstrate a significant improvement depression as measured by HAM-D compared to placebo-treated controls. At the point of Study Conclusion, MDAI-treated participants may demonstrate a significant improvement in lessening daytime sleepiness as measured by ESS. At the point of Study Conclusion MDAI-treated participants may demonstrate a significant improvement in clinician-rated functional impairment score, in depression, and in lessening daytime sleepiness compared to placebo-treated controls without a significant increase in adverse anxiogenic incidents.

EMBODIMENTS

1. A solid form of MDMA, (S)-MDMA, (R)-MDMA, MDE, (S)-MDE, (R)-MDE, MBDB, (S)-MBDB, (R)-MBDB, MDAI, MEAI, or 5,6-Dimethoxy-2-aminoindane.

2 The solid form of embodiment 1, wherein the solid form is a solid form of MDMA. 3. The compound of embodiment 1, wherein the solid form of MDMA is a salt of MDMA.

4. The compound of embodiment 1, wherein the salt of MDMA is a crystalline salt.

5. The compound of embodiment 1, wherein the solid form of MDMA fumarate Form 1 is a crystalline polymorph of MDMA fumarate characterized by two or more, or three or more XRPD signals selected from the group consisting of 17.3° 2θ, 18.6° 2θ, and 21.9° 2θ (±0.2° 2θ; ±0.1° 2θ; or ±0.0° 2θ; Cu Kα1 radiation).

6 The compound of embodiment 1, wherein the solid form of MDMA fumarate Form 1 is a crystalline polymorph of MDMA fumarate characterized by two or more, or three or more XRPD signals selected from the group consisting of 16.7° 2θ, 17.3° 2θ, 18.6° 2θ, 19.2° 2θ, and 21.9° 2θ (±0.2° 2θ; ±0.1° 2θ; or ±0.0° 2θ; Cu Kα1 radiation).

7. The compound of embodiment 1, wherein the solid form of MDMA fumarate Form 1 is a crystalline polymorph of MDMA fumarate characterized by two or more, or three or more XRPD signals selected from the group consisting of 10.9° 2θ, 13.1° 2θ, and 16.7° 2θ (±0.2° 2θ; ±0.1° 2θ; or ±0.0° 2θ; Cu Kα1 radiation).

8. The compound of embodiment 1, wherein the solid form of MDMA fumarate Form 1 is a crystalline polymorph of MDMA fumarate characterized by two or more, or three or more XRPD signals selected from the group consisting of 10.9° 2θ, 13.1° 2θ, 16.7° 2θ, 17.3° 2θ, and 18.6° 2θ (±0.2° 2θ; ±0.1° 2θ; or ±0.0° 2θ; Cu Kα1 radiation).

9. The compound of embodiment 1, wherein the solid form of MDMA fumarate Form 1 is a crystalline polymorph of MDMA fumarate characterized by any combination of the XRPD peaks set forth in Table 2 (±0.2° 2θ; ±0.1° 2θ; or ±0.0° 2θ; Cu Kα1 radiation).

10. The compound of embodiment 1, wherein the solid form of MDMA fumarate Form 1 is a crystalline polymorph of MDMA fumarate characterized by a XRPD diffractogram substantially similar to that shown in FIG. 1.

11. The compound of embodiment 1, wherein the solid form of MDMA fumarate Form 1 is a crystalline polymorph of MDMA fumarate characterized by a $^1$H NMR spectrum substantially similar to that shown in FIG. 44.

12. The compound of embodiment 1, wherein the solid form of MDMA fumarate Form 1 is a crystalline polymorph of MDMA fumarate characterized by a TGA profile is substantially similar to that shown in FIG. 45.

13. The compound of embodiment 1, wherein the solid form of MDMA fumarate Form 1 is a crystalline polymorph of MDMA fumarate characterized by a DSC profile is substantially similar to that shown in FIG. 45.

14. The compound of embodiment 1, wherein the solid form of MDMA fumarate Form 2 is a crystalline polymorph of MDMA fumarate characterized by two or more, or three or more XRPD signals selected from the group consisting of 14.5° 2θ, 22.2° 2θ, and 27.3° 2θ (±0.2° 2θ; ±0.1° 2θ; or ±0.0° 2θ; Cu Kα1 radiation).

15. The compound of embodiment 1, wherein the solid form of MDMA fumarate Form 2 is a crystalline polymorph of MDMA fumarate characterized by two or more, or three or more XRPD signals selected from the group consisting of 14.5° 2θ, 17.8° 2θ, 22.2° 2θ, 25.7° 2θ, and 27.3° 2θ (±0.2° 2θ; ±0.1° 2θ; or ±0.0° 2θ; Cu Kα1 radiation).

16. The compound of embodiment 1, wherein the solid form of MDMA fumarate Form 2 is a crystalline polymorph of MDMA fumarate characterized by two or more, or three or more XRPD signals selected from the group consisting of 12.2° 2θ, 12.8° 2θ, and 14.5° 2θ (±0.2° 2θ; ±0.1° 2θ; or ±0.0° 2θ; Cu Kα1 radiation).

17. The compound of embodiment 1, wherein the solid form of MDMA fumarate Form 2 is a crystalline polymorph of MDMA fumarate characterized by two or more, or three or more XRPD signals selected from the group consisting of 12.2° 2θ, 12.8° 2θ, 14.5° 2θ, 16.0° 2θ, and 16.6° 2θ (±0.2° 2θ; ±0.1° 2θ; or ±0.0° 2θ; Cu Kα1 radiation).

18. The compound of embodiment 1, wherein the solid form of MDMA fumarate Form 2 is a crystalline polymorph of MDMA fumarate characterized by any combination of the XRPD peaks set forth in Table 12 (±0.2° 2θ; ±0.1° 2θ; or ±0.0° 2θ; Cu Kα1 radiation).

19. The compound of embodiment 1, wherein the mixture of solid forms of MDMA fumarate Forms 1 and 2 are crystalline polymorphs of MDMA fumarate characterized by a XRPD diffractogram substantially similar to that shown in FIG. 10.

20 The compound of embodiment 1, wherein the solid form of MDMA maleate Form 1 is a crystalline polymorph of MDMA maleate characterized by two or more, or three or more XRPD signals selected from the group consisting of 14.9° 2θ, 18.1° 2θ, and 25.0° 2θ (±0.2° 2θ; ±0.1° 2θ; or ±0.0° 2θ; Cu Kα1 radiation).

21. The compound of embodiment 1, wherein the solid form of MDMA maleate Form 1 is a crystalline polymorph of MDMA maleate characterized by two or more, or three or more XRPD signals selected from the group consisting of 14.9° 2θ, 18.1° 2θ, 25.0° 2θ, 25.3° 2θ, and 29.2° 2θ (±0.2° 2θ; ±0.1° 2θ; or ±0.0° 2θ; Cu Kα1 radiation).

22. The compound of embodiment 1, wherein the solid form of MDMA maleate Form 1 is a crystalline polymorph of MDMA maleate characterized by two or more, or three or more XRPD signals selected from the group consisting of 10.1° 2θ, 14.9° 2θ, and 18.1° 2θ (±0.2° 2θ; ±0.1° 2θ; or ±0.0° 2θ; Cu Kα1 radiation).

23. The compound of embodiment 1, wherein the solid form of MDMA maleate Form 1 is a crystalline polymorph of MDMA maleate characterized by two or more, or three or more XRPD signals selected from the group consisting of 10.1° 2θ, 14.9° 2θ, 18.1° 2θ, 25.0° 2θ, and 28.8° 2θ (±0.2° 2θ; ±0.1° 2θ; or ±0.0° 2θ; Cu Kα1 radiation).

24. The compound of embodiment 1, wherein the solid form of MDMA maleate Form 1 is a crystalline polymorph of MDMA maleate characterized by any combination of the XRPD peaks set forth in Table 3 (±0.2° 2θ; ±0.1° 2θ; or ±0.0° 2θ; Cu Kα1 radiation).

25. The compound of embodiment 1, wherein the solid form of MDMA maleate Form 1 is a crystalline polymorph of MDMA maleate characterized by a XRPD diffractogram substantially similar to that shown in FIG. 2.

26. The compound of embodiment 1, wherein the solid form of MDMA maleate Form 1 is a crystalline polymorph of MDMA maleate characterized by a $^1$H NMR spectrum substantially similar to that shown in FIG. 51.

Figure 52:
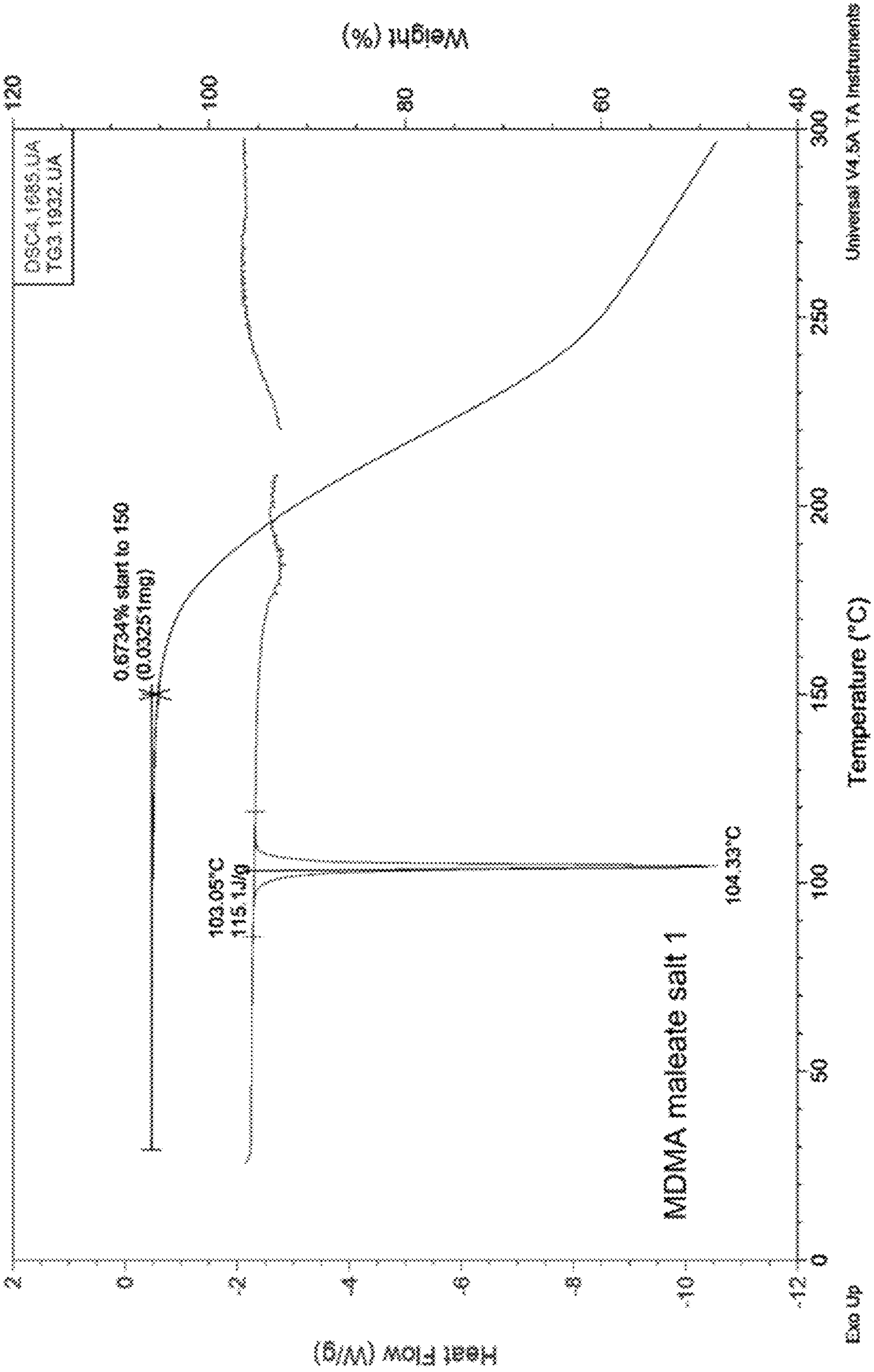
FIG. 52 provides TGA and DSC profiles for MDMA maleate Form 1.

27 The compound of embodiment 1, wherein the solid form of MDMA maleate Form 1 is a crystalline polymorph of MDMA maleate characterized by a TGA profile is substantially similar to that shown in FIG. 52.

28. The compound of embodiment 1, wherein the solid form of MDMA maleate Form 1 is a crystalline polymorph of MDMA maleate characterized by a DSC profile is substantially similar to that shown in FIG. 52.

29. The compound of embodiment 1, wherein the solid form of MDMA maleate Form 2 is a crystalline polymorph of MDMA maleate characterized by two or more, or three or more XRPD signals selected from the group consisting of 9.4° 2θ, 18.5° 2θ, and 26.8° 2θ (±0.2° 2θ; ±0.1° 2θ; or ±0.0° 2θ; Cu Kα1 radiation).

30. The compound of embodiment 1, wherein the solid form of MDMA maleate Form 2 is a crystalline polymorph of MDMA maleate characterized by two or more, or three or more XRPD signals selected from the group consisting of 9.4° 2θ, 15.6° 2θ, 15.9° 2θ, 18.5° 2θ, and 26.8° 2θ (±0.2° 2θ; ±0.1° 2θ; or ±0.0° 2θ; Cu Kα1 radiation).

31. The compound of embodiment 1, wherein the solid form of MDMA maleate Form 2 is a crystalline polymorph of MDMA maleate characterized by two or more, or three or more XRPD signals selected from the group consisting of 9.4° 2θ, 13.8° 2θ, and 14.8° 2θ (±0.2° 2θ; ±0.1° 2θ; or ±0.0° 2θ; Cu Kα1 radiation).

32. The compound of embodiment 1, wherein the solid form of MDMA maleate Form 2 is a crystalline polymorph of MDMA maleate characterized by two or more, or three or more XRPD signals selected from the group consisting of 9.4° 2θ, 13.8° 2θ, 14.8° 2θ, 18.5° 2θ, and 26.8° 2θ (±0.2° 2θ; ±0.1° 2θ; or ±0.0° 2θ; Cu Kα1 radiation).

33. The compound of embodiment 1, wherein the solid form of MDMA maleate Form 2 is a crystalline polymorph of MDMA maleate characterized by any combination of the XRPD peaks set forth in Table 13 (±0.2° 2θ; ±0.1° 2θ; or ±0.0° 2θ; Cu Kα1 radiation).

Figure 11:
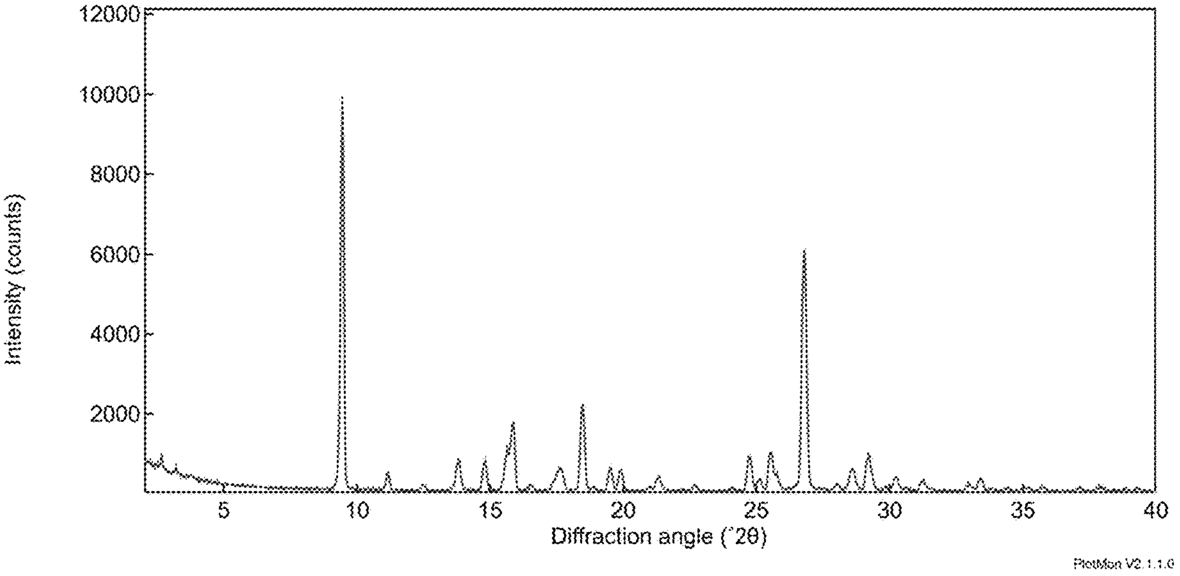
FIG. 11 provides an XRPD diffractogram of a sample comprising crystalline MDMA·maleate Form 2.

34 The compound of embodiment 1, wherein the solid form of MDMA maleate Form 2 is a crystalline polymorph of MDMA maleate characterized by a XRPD diffractogram substantially similar to that shown in FIG. 11.

35. The compound of embodiment 1, wherein the solid form of MDMA maleate Form 2 is a crystalline polymorph of MDMA maleate characterized by a $^{1}$H NMR spectrum substantially similar to that shown in FIG. 53.

36. The compound of embodiment 1, wherein the solid form of MDMA maleate Form 2 is a crystalline polymorph of MDMA maleate characterized by a TGA profile is substantially similar to that shown in FIG. 54.

37. The compound of embodiment 1, wherein the solid form of MDMA maleate Form 2 is a crystalline polymorph of MDMA maleate characterized by a DSC profile is substantially similar to that shown in FIG. 54.

38. The compound of embodiment 1, wherein the solid form of MDMA phosphate is a crystalline polymorph of MDMA phosphate characterized by two or more, or three or more XRPD signals selected from the group consisting of 12.4° 2θ, 19.0° 2θ, and 22.0° 2θ (±0.2° 2θ; ±0.1° 2θ; or ±0.0° 2θ; Cu Kα1 radiation).

39. The compound of embodiment 1, wherein the solid form of MDMA phosphate is a crystalline polymorph of MDMA phosphate characterized by two or more, or three or more XRPD signals selected from the group consisting of 6.2° 2θ, 12.4° 2θ, 18.8° 2θ, 19.0° 2θ, and 22.0° 2θ (±0.2° 2θ; ±0.1° 2θ; or ±0.0° 2θ; Cu Kα1 radiation).

40. The compound of embodiment 1, wherein the solid form of MDMA phosphate is a crystalline polymorph of MDMA phosphate characterized by two or more, or three or more XRPD signals selected from the group consisting of 6.2° 2θ, 12.4° 2θ, and 22.0° 2θ (±0.2° 2θ; ±0.1° 2θ; or ±0.0° 2θ; Cu Kα1 radiation).

41. The compound of embodiment 1, wherein the solid form of MDMA phosphate is a crystalline polymorph of MDMA phosphate characterized by two or more, or three or more XRPD signals selected from the group consisting of 6.2° 2θ, 12.4° 2θ, 17.9° 2θ, 19.3° 2θ, and 22.0° 2θ (±0.2° 2θ; ±0.1° 2θ; or ±0.0° 2θ; Cu Kα1 radiation).

42. The compound of embodiment 1, wherein the solid form of MDMA phosphate is a crystalline polymorph of MDMA phosphate characterized by two or more, or three or more XRPD signals selected from the group consisting of 6.3° 2θ, 12.5° 2θ, and 22.0° 2θ (±0.2° 2θ; ±0.1° 2θ; or ±0.0° 2θ; Cu Kα1 radiation).

43. The compound of embodiment 1, wherein the solid form of MDMA phosphate is a crystalline polymorph of MDMA phosphate characterized by two or more, or three or more XRPD signals selected from the group consisting of 6.3° 2θ, 12.5° 2θ, 19.0° 2θ, 22.0° 2θ, and 23.0° 2θ (±0.2° 2θ; ±0.1° 2θ; or ±0.0° 2θ; Cu Kα1 radiation).

44. The compound of embodiment 1, wherein the solid form of MDMA phosphate is a crystalline polymorph of MDMA phosphate characterized by two or more, or three or more XRPD signals selected from the group consisting of 6.3° 2θ, 12.5° 2θ, 17.9° 2θ, 19.4° 2θ, and 22.0° 2θ (±0.2° 2θ; ±0.1° 2θ; or ±0.0° 2θ; Cu Kα1 radiation).

45. The compound of embodiment 1, wherein the solid form of MDMA phosphate is a crystalline polymorph of MDMA phosphate characterized by any combination of the XRPD peaks set forth in Table 4 or Table 5 (±0.2° 2θ; ±0.1° 2θ; or ±0.0° 2θ; Cu Kα1 radiation).

46. The compound of embodiment 1, wherein the solid form of MDMA phosphate is a crystalline polymorph of MDMA phosphate characterized by a XRPD diffractogram substantially similar to that shown in FIG. 4 or FIG. 47.

47. The compound of embodiment 1, wherein the solid form of MDMA phosphate is a crystalline polymorph of MDMA phosphate characterized by a $^{1}$H NMR spectrum substantially similar to that shown in FIG. 57.

48. The compound of embodiment 1, wherein the solid form of MDMA phosphate is a crystalline polymorph of MDMA phosphate characterized by a TGA profile is substantially similar to that shown in FIG. 58.

Figure 58:
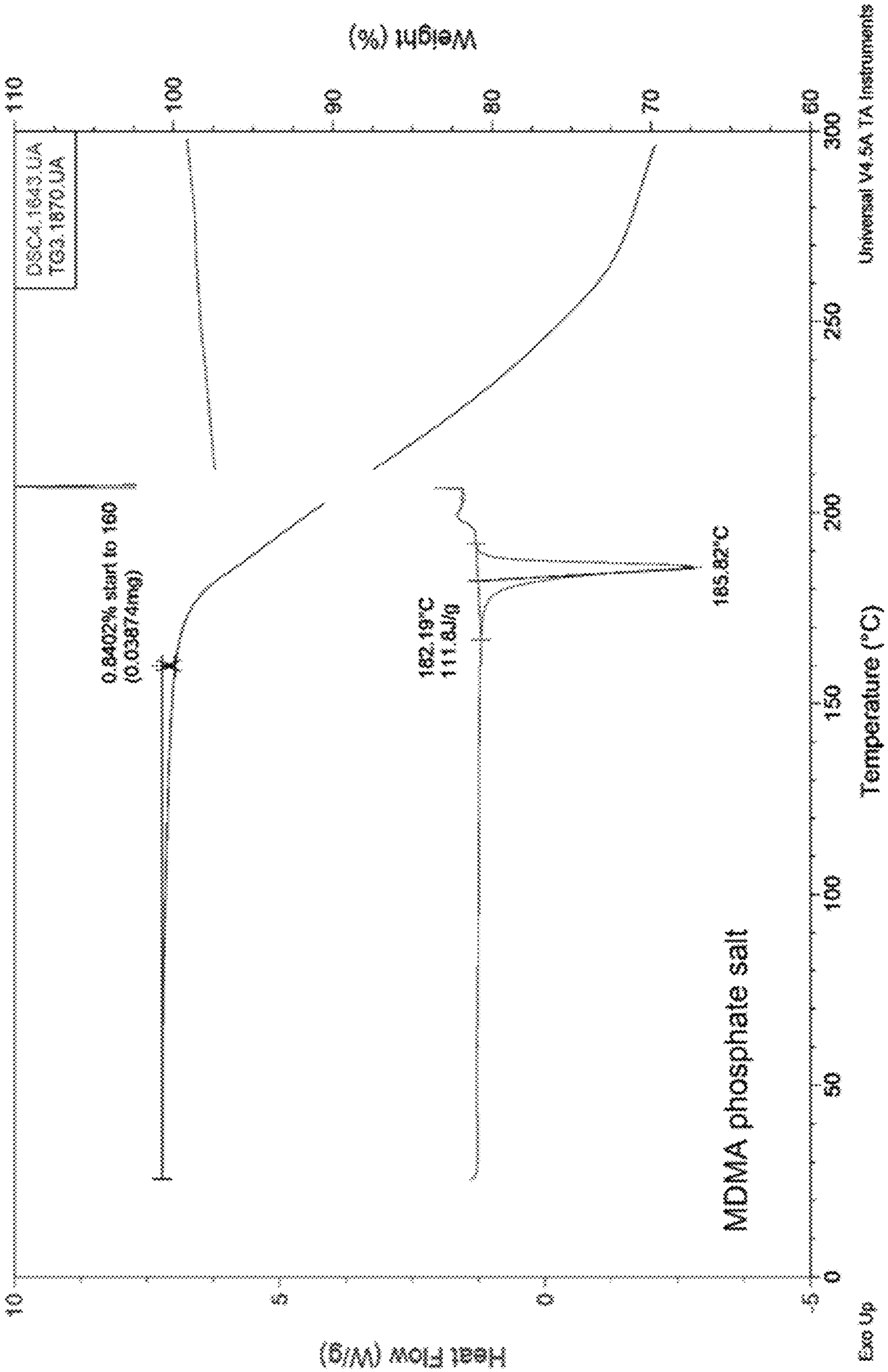
FIG. 58 provides TGA and DSC profiles for MDMA phosphate.

49 The compound of embodiment 1, wherein the solid form of MDMA phosphate is a crystalline polymorph of MDMA phosphate characterized by a DSC profile is substantially similar to that shown in FIG. 58.

50. The compound of embodiment 1, wherein the solid form of MDMA tartrate Form 1 is a crystalline polymorph of MDMA tartrate characterized by two or more, or three or more XRPD signals selected from the group consisting of 12.5° 2θ, 18.0° 2θ, and 18.3° 2θ (±0.2° 2θ; ±0.1° 2θ; or ±0.0° 2θ; Cu Kα1 radiation).

51. The compound of embodiment 1, wherein the solid form of MDMA tartrate Form 1 is a crystalline polymorph of MDMA tartrate characterized by two or more, or three or more XRPD signals selected from the group consisting of 6.3° 2θ, 12.5° 2θ, 18.0° 2θ, 18.3° 2θ, and 18.5° 2θ (±0.2° 2θ; ±0.1° 2θ; or ±0.0° 2θ; Cu Kα1 radiation).

52. The compound of embodiment 1, wherein the solid form of MDMA tartrate Form 1 is a crystalline polymorph of MDMA tartrate characterized by two or more, or three or more XRPD signals selected from the group consisting of 6.3° 2θ, 11.7° 2θ, and 12.5° 2θ (±0.2° 2θ; ±0.1° 2θ; or ±0.0° 2θ; Cu Kα1 radiation).

53. The compound of embodiment 1, wherein the solid form of MDMA tartrate Form 1 is a crystalline polymorph of MDMA tartrate characterized by two or more, or three or more XRPD signals selected from the group consisting of 6.3° 2θ, 11.7° 2θ, 12.5° 2θ, 17.2° 2θ, and 18.0° 2θ (±0.2° 2θ; ±0.1° 2θ; or ±0.0° 2θ; Cu Kα1 radiation).

54. The compound of embodiment 1, wherein the solid form of MDMA tartrate Form 1 is a crystalline polymorph of MDMA tartrate characterized by any combination of the XRPD peaks set forth in Table 6 (±0.2° 2θ; ±0.1° 2θ; or ±0.0° 2θ; Cu Kα1 radiation).

55. The compound of embodiment 1, wherein the solid form of MDMA tartrate Form 1 is a crystalline polymorph of MDMA tartrate characterized by a XRPD diffractogram substantially similar to that shown in FIG. 5.

Figure 61:
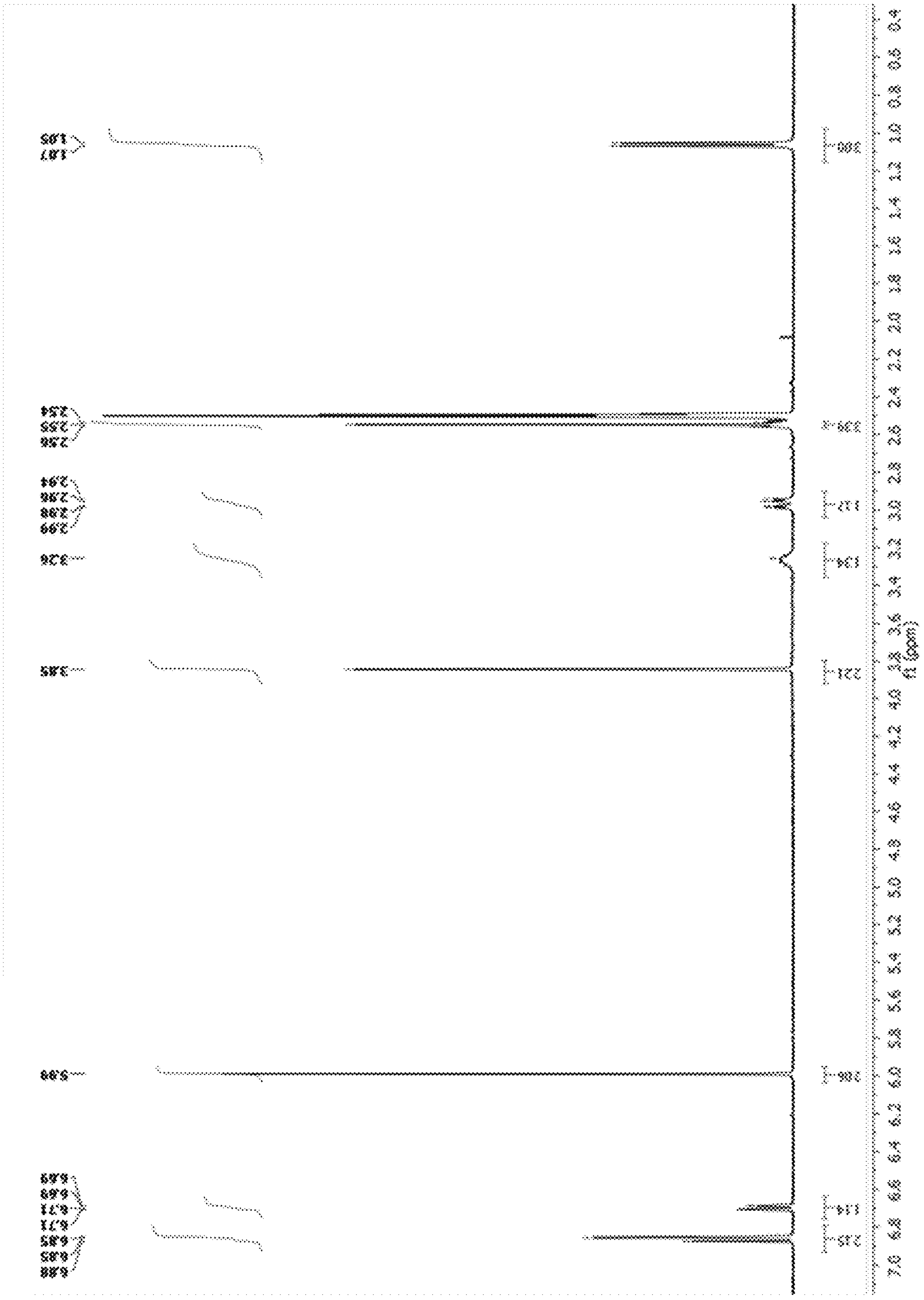
FIG. 61 provides a $^1$H NMR spectrum for MDMA L-tartrate Form 1.
Figure 62:
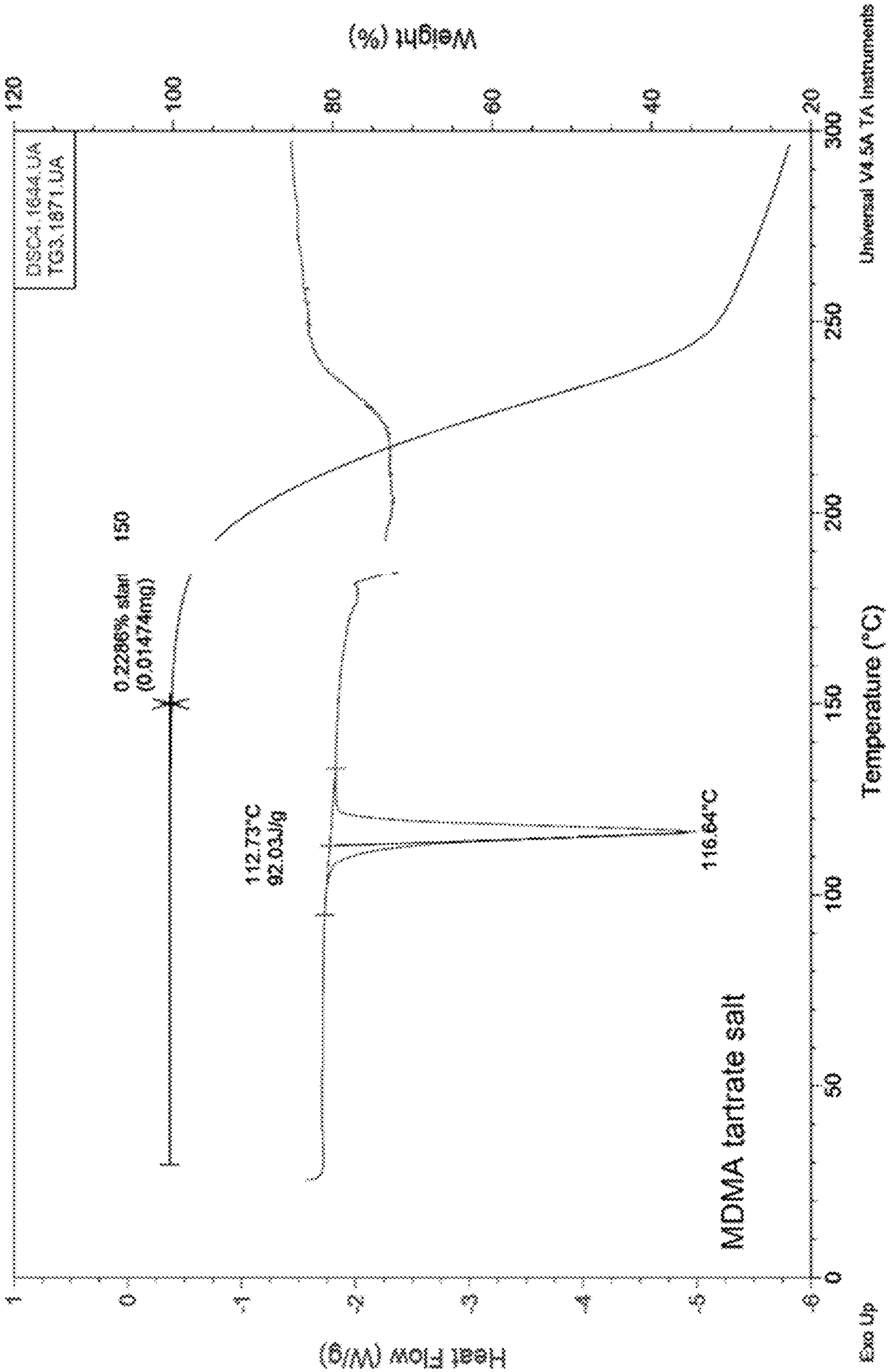
FIG. 62 provides TGA and DSC profiles for MDMA L-tartrate Form 1.

56 The compound of embodiment 1, wherein the solid form of MDMA tartrate Form 1 is a crystalline polymorph of MDMA tartrate characterized by a $^{1}$H NMR spectrum substantially similar to that shown in FIG. 61.

57. The compound of embodiment 1, wherein the solid form of MDMA tartrate Form 1 is a crystalline polymorph of MDMA tartrate characterized by a TGA profile is substantially similar to that shown in FIG. 62.

58. The compound of embodiment 1, wherein the solid form of MDMA tartrate Form 1 is a crystalline polymorph of MDMA tartrate characterized by a DSC profile is substantially similar to that shown in FIG. 62.

59. The compound of embodiment 1, wherein the solid form of MDMA tartrate Form 2 is a crystalline polymorph of MDMA tartrate characterized by two or more, or three or more XRPD signals selected from the group consisting of 5.2° 2θ, 18.9° 2θ, and 19.5° 2θ (±0.2° 2θ; ±0.1° 2θ; or ±0.0° 2θ; Cu Kα1 radiation).

60. The compound of embodiment 1, wherein the solid form of MDMA tartrate Form 2 is a crystalline polymorph of MDMA tartrate characterized by two or more, or three or more XRPD signals selected from the group consisting of 5.2° 2θ, 11.7° 2θ, 15.4° 2θ, 18.9° 2θ, and 19.5° 2θ (±0.2° 2θ; ±0.1° 2θ; or ±0.0° 2θ; Cu Kα1 radiation).

61. The compound of embodiment 1, wherein the solid form of MDMA tartrate Form 2 is a crystalline polymorph of MDMA tartrate characterized by two or more, or three or more XRPD signals selected from the group consisting of 5.2° 2θ, 10.3° 2θ, and 11.7° 2θ (±0.2° 2θ; ±0.1° 2θ; or ±0.0° 2θ; Cu Kα1 radiation).

62. The compound of embodiment 1, wherein the solid form of MDMA tartrate Form 2 is a crystalline polymorph of MDMA tartrate characterized by two or more, or three or more XRPD signals selected from the group consisting of 5.2° 2θ, 10.3° 2θ, 11.7° 2θ, 15.4° 2θ, and 19.5° 2θ (±0.2° 2θ; ±0.1° 2θ; or ±0.0° 2θ; Cu Kα1 radiation).

63 The compound of embodiment 1, wherein the solid form of MDMA tartrate Form 2 is a crystalline polymorph of MDMA tartrate characterized by any combination of the XRPD peaks set forth in Table 14 (±0.2° 2θ; ±0.1° 2θ; or ±0.0° 2θ; Cu Kα1 radiation).

64. The compound of embodiment 1, wherein the mixture of solid forms of MDMA tartrate Forms 1 and 2 are crystalline polymorphs of MDMA tartrate characterized by a XRPD diffractogram substantially similar to that shown in FIG. 12.

65. The compound of embodiment 1, wherein the solid form of MDMA malate is a crystalline polymorph of MDMA malate characterized by two or more, or three or more XRPD signals selected from the group consisting of 17.2° 2θ, 18.0° 2θ, and 19.2° 2θ (±0.2° 2θ; =0.1° 2θ; or ±0.0° 2θ; Cu Kα1 radiation).

66. The compound of embodiment 1, wherein the solid form of MDMA malate is a crystalline polymorph of MDMA malate characterized by two or more, or three or more XRPD signals selected from the group consisting of 17.2° 2θ, 18.0° 2θ, 19.2° 2θ, 20.8° 2θ, and 24.2° 2θ (±0.2° 2θ; ±0.1° 2θ; or ±0.0° 2θ; Cu Kα1 radiation).

67. The compound of embodiment 1, wherein the solid form of MDMA malate is a crystalline polymorph of MDMA malate characterized by two or more, or three or more XRPD signals selected from the group consisting of 11.9° 2θ, 13.1° 2θ, and 13.7° 2θ (±0.2° 2θ; ±0.1° 2θ; or ±0.0° 2θ; Cu Kα1 radiation).

68. The compound of embodiment 1, wherein the solid form of MDMA malate is a crystalline polymorph of MDMA malate characterized by two or more, or three or more XRPD signals selected from the group consisting of 11.9° 2θ, 13.1° 2θ, 13.7° 2θ, 17.2° 2θ, and 18.0° 2θ (±0.2° 2θ; ±0.1° 2θ; or ±0.0° 2θ; Cu Kα1 radiation).

69. The compound of embodiment 1, wherein the solid form of MDMA malate is a crystalline polymorph of MDMA malate characterized by any combination of the XRPD peaks set forth in Table 7 (±0.2° 2θ; ±0.1° 2θ; or ±0.0° 2θ; Cu Kα1 radiation).

70. The compound of embodiment 1, wherein the solid form of MDMA malate is a crystalline polymorph of MDMA malate characterized by a XRPD diffractogram substantially similar to that shown in FIG. 6.

Figure 49:
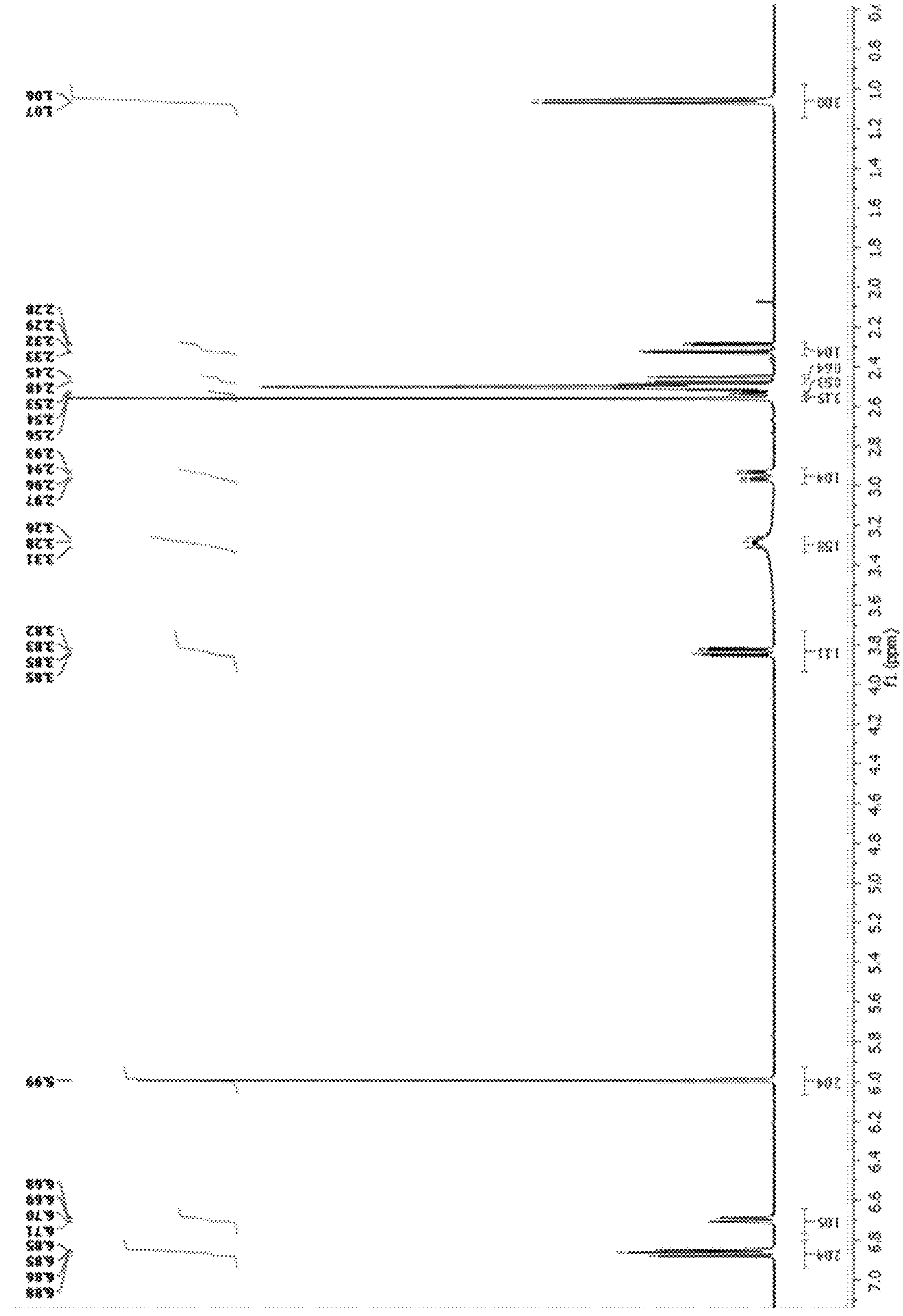
FIG. 49 provides a $^1$H NMR spectrum for MDMA L-malate.
Figure 50:
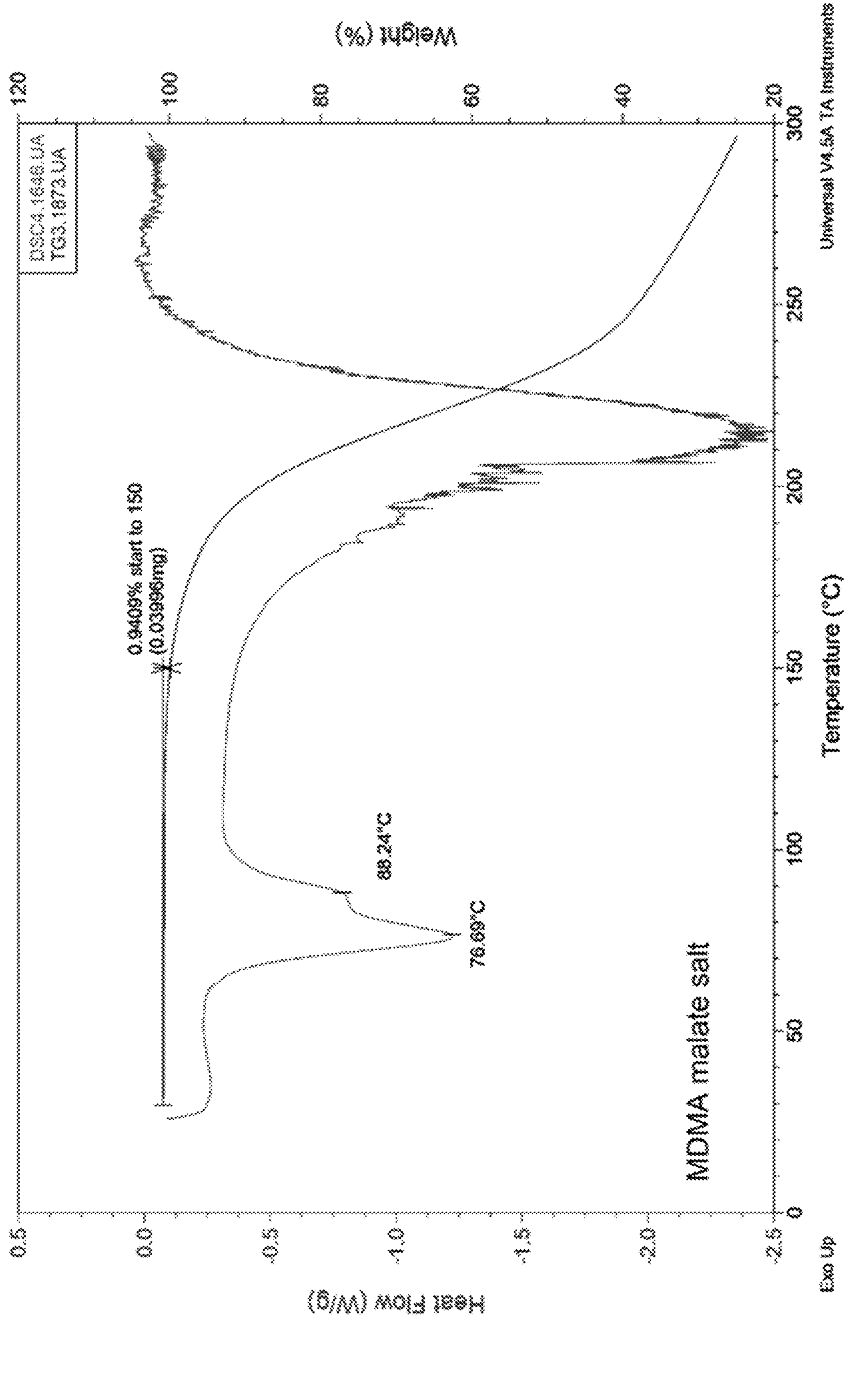
FIG. 50 provides TGA and DSC profiles for MDMA L-malate.

71 The compound of embodiment 1, wherein the solid form of MDMA malate is a crystalline polymorph of MDMA malate characterized by a $^{1}$H NMR spectrum substantially similar to that shown in FIG. 49.

72. The compound of embodiment 1, wherein the solid form of MDMA malate is a crystalline polymorph of MDMA malate characterized by a TGA profile is substantially similar to that shown in FIG. 50.

73. The compound of embodiment 1, wherein the solid form of MDMA malate is a crystalline polymorph of MDMA malate characterized by a DSC profile is substantially similar to that shown in FIG. 50.

74. The compound of embodiment 1, wherein the solid form of MDMA galactarate is a crystalline polymorph of MDMA galactarate characterized by two or more, or three or more XRPD signals selected from the group consisting of 4.6° 2θ, 18.8° 2θ, and 19.6° 2θ (±0.2° 2θ; ±0.1° 2θ; or ±0.0° 2θ; Cu Kα1 radiation).

75. The compound of embodiment 1, wherein the solid form of MDMA galactarate is a crystalline polymorph of MDMA galactarate characterized by two or more, or three or more XRPD signals selected from the group consisting of 4.6° 2θ, 18.4° 2θ, 18.8° 2θ, 19.6° 2θ, and 30.8° 2θ (±0.2° 2θ; ±0.1° 2θ; or ±0.0° 2θ; Cu Kα1 radiation).

76 The compound of embodiment 1, wherein the solid form of MDMA galactarate is a crystalline polymorph of MDMA galactarate characterized by two or more, or three or more XRPD signals selected from the group consisting of 4.6° 2θ, 9.0° 2θ, and 13.6° 2θ (±0.2° 2θ; ±0.1° 2θ; or ±0.0° 2θ; Cu Kα1 radiation).

77. The compound of embodiment 1, wherein the solid form of MDMA galactarate is a crystalline polymorph of MDMA galactarate characterized by two or more, or three or more XRPD signals selected from the group consisting of 4.6° 2θ, 9.0° 2θ, 13.6° 2θ, 18.4° 2θ, and 18.8° 2θ (±0.2° 2θ; ±0.1° 2θ; or ±0.0° 2θ; Cu Kα1 radiation).

78. The compound of embodiment 1, wherein the solid form of MDMA galactarate is a crystalline polymorph of MDMA galactarate characterized by two or more, or three or more XRPD signals selected from the group consisting of 4.6° 2θ, 18.3° 2θ, and 18.8° 2θ (±0.2° 2θ; ±0.1° 2θ; or ±0.0° 2θ; Cu Kα1 radiation).

79. The compound of embodiment 1, wherein the solid form of MDMA galactarate is a crystalline polymorph of MDMA galactarate characterized by two or more, or three or more XRPD signals selected from the group consisting of 4.6° 2θ, 9.1° 2θ, 13.6° 2θ, 18.3° 2θ, and 18.6° 2θ (±0.2° 2θ; ±0.1° 2θ; or ±0.0° 2θ; Cu Kα1 radiation).

80 The compound of embodiment 1, wherein the solid form of MDMA galactarate is a crystalline polymorph of MDMA galactarate characterized by two or more, or three or more XRPD signals selected from the group consisting of 4.6° 2θ, 9.1° 2θ, and 13.6° 2θ (±0.2° 2θ; ±0.1° 2θ; or ±0.0° 2θ; Cu Kα1 radiation).

81. The compound of embodiment 1, wherein the solid form of MDMA galactarate is a crystalline polymorph of MDMA galactarate characterized by two or more, or three or more XRPD signals selected from the group consisting of 4.6° 2θ, 9.1° 2θ, 13.6° 2θ, 18.3° 2θ, and 18.8° 2θ (±0.2° 2θ; ±0.1° 2θ; or ±0.0° 2θ; Cu Kα1 radiation).

82. The compound of embodiment 1, wherein the solid form of MDMA galactarate is a crystalline polymorph of MDMA galactarate characterized by any combination of the XRPD peaks set forth in Table 8 or Table 9 (±0.2° 2θ; ±0.1° 2θ; or ±0.0° 2θ; Cu Kα1 radiation).

83. The compound of embodiment 1, wherein the solid form of MDMA galactarate is a crystalline polymorph of MDMA galactarate characterized by a XRPD diffractogram substantially similar to that shown in FIG. 7 or FIG. 46.

84. The compound of embodiment 1, wherein the solid form of MDMA galactarate is a crystalline polymorph of MDMA galactarate characterized by a $^{1}$H NMR spectrum substantially similar to that shown in FIG. 55.

85. The compound of embodiment 1, wherein the solid form of MDMA galactarate is a crystalline polymorph of MDMA galactarate characterized by a TGA profile is substantially similar to that shown in FIG. 56.

86. The compound of embodiment 1, wherein the solid form of MDMA galactarate is a crystalline polymorph of MDMA galactarate characterized by a DSC profile is substantially similar to that shown in FIG. 56.

87. The compound of embodiment 1, wherein the solid form of MDMA succinate is a crystalline polymorph of MDMA succinate characterized by two or more, or three or more XRPD signals selected from the group consisting of 13.0° 2θ, 21.8° 2θ, and 22.2° 2θ (±0.2° 2θ; ±0.1° 2θ; or ±0.0° 2θ; Cu Kα1 radiation).

88. The compound of embodiment 1, wherein the solid form of MDMA succinate is a crystalline polymorph of MDMA succinate characterized by two or more, or three or more XRPD signals selected from the group consisting of 6.5° 2θ, 13.0° 2θ, 18.9° 2θ, 21.8° 2θ, and 22.2° 2θ (±0.2° 2θ; ±0.1° 2θ; or ±0.0° 2θ; Cu Kα1 radiation).

89. The compound of embodiment 1, wherein the solid form of MDMA succinate is a crystalline polymorph of MDMA succinate characterized by two or more, or three or more XRPD signals selected from the group consisting of 6.5° 2θ, 12.6° 2θ, and 13.0° 2θ (±0.2° 2θ; ±0.1° 2θ; or ±0.0° 2θ; Cu Kα1 radiation).

90 The compound of embodiment 1, wherein the solid form of MDMA succinate is a crystalline polymorph of MDMA succinate characterized by two or more, or three or more XRPD signals selected from the group consisting of 6.5° 2θ, 12.6° 2θ, 13.0° 2θ, 17.1° 2θ, and 18.9° 2θ (±0.2° 2θ; ±0.1° 2θ; or ±0.0° 2θ; Cu Kα1 radiation).

91. The compound of embodiment 1, wherein the solid form of MDMA succinate is a crystalline polymorph of MDMA succinate characterized by any combination of the XRPD peaks set forth in Table 10 (±0.2° 2θ; ±0.1° 2θ; or ±0.0° 2θ; Cu Kα1 radiation).

92. The compound of embodiment 1, wherein the solid form of MDMA succinate is a crystalline polymorph of MDMA succinate characterized by a XRPD diffractogram substantially similar to that shown in FIG. 8.

93. The compound of embodiment 1, wherein the solid form of MDMA succinate is a crystalline polymorph of MDMA succinate characterized by a $^1$H NMR spectrum substantially similar to that shown in FIG. 59.

Figure 60:
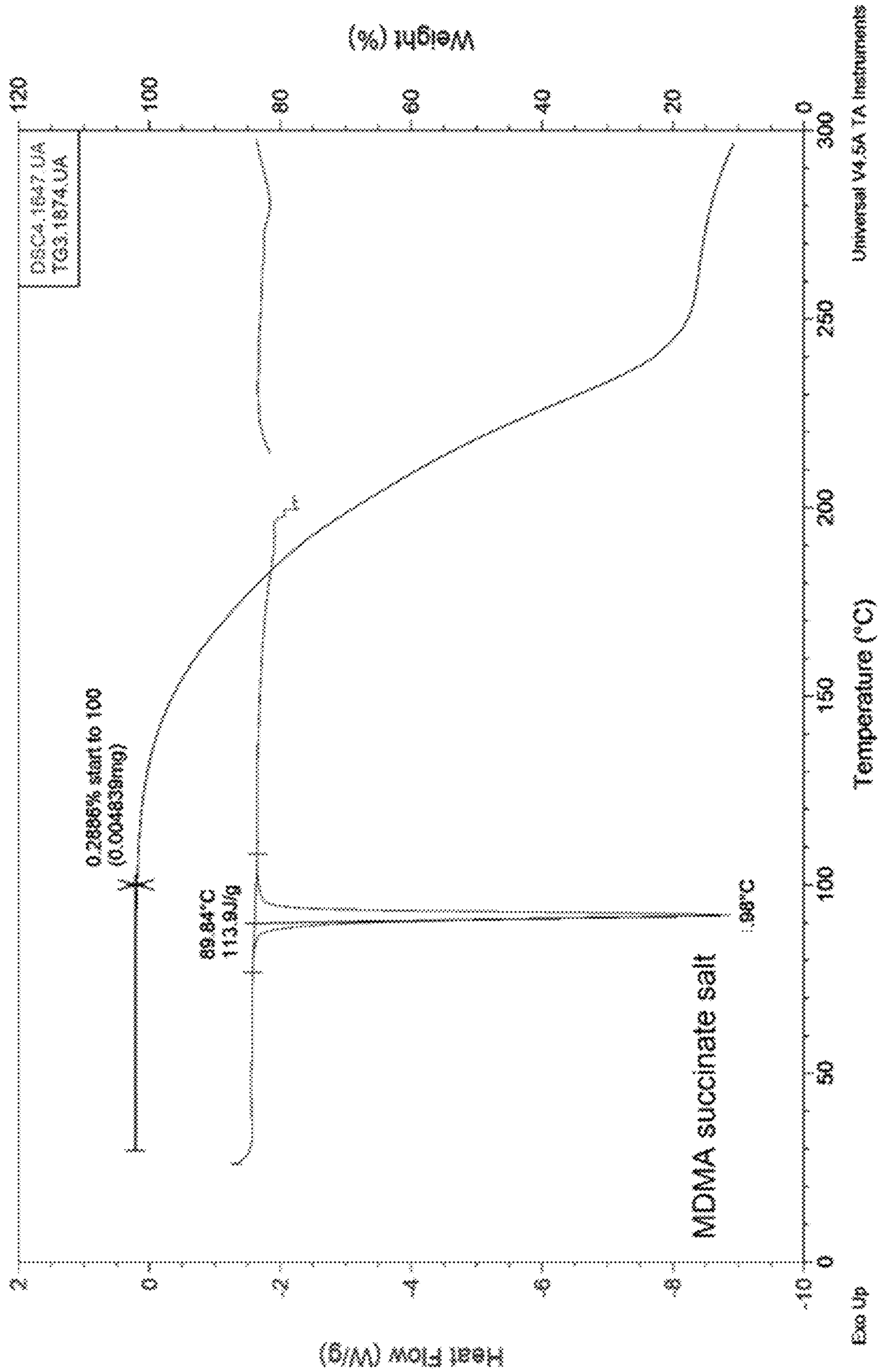
FIG. 60 provides TGA and DSC profiles for MDMA succinate.

94 The compound of embodiment 1, wherein the solid form of MDMA succinate is a crystalline polymorph of MDMA succinate characterized by a TGA profile is substantially similar to that shown in FIG. 60.

95. The compound of embodiment 1, wherein the solid form of MDMA succinate is a crystalline polymorph of MDMA succinate characterized by a DSC profile is substantially similar to that shown in FIG. 60.

96. The compound of embodiment 1, wherein the solid form of MDMA tosylate is a crystalline polymorph of MDMA tosylate characterized by two or more, or three or more XRPD signals selected from the group consisting of 15.4° 2θ, 20.5° 2θ, and 21.9° 2θ (±0.2° 2θ; ±0.1° 2θ; or ±0.0° 2θ; Cu Kα1 radiation).

97. The compound of embodiment 1, wherein the solid form of MDMA tosylate is a crystalline polymorph of MDMA tosylate characterized by two or more, or three or more XRPD signals selected from the group consisting of 13.6° 2θ, 15.4° 2θ, 20.5° 2θ, 21.3° 2θ, and 21.9° 2θ (±0.2° 2θ; ±0.1° 2θ; or ±0.0° 2θ; Cu Kα1 radiation).

98. The compound of embodiment 1, wherein the solid form of MDMA tosylate is a crystalline polymorph of MDMA tosylate characterized by two or more, or three or more XRPD signals selected from the group consisting of 8.0° 2θ, 12.3° 2θ, and 13.6° 2θ (±0.2° 2θ; =0.1° 2θ; or ±0.0° 2θ; Cu Kα1 radiation).

99. The compound of embodiment 1, wherein the solid form of MDMA tosylate is a crystalline polymorph of MDMA tosylate characterized by two or more, or three or more XRPD signals selected from the group consisting of 8.0° 2θ, 12.3° 2θ, 13.6° 2θ, 15.4° 2θ, and 20.5° 2θ (±0.2° 2θ; ±0.1° 2θ; or ±0.0° 2θ; Cu Kα1 radiation).

100. The compound of embodiment 1, wherein the solid form of MDMA tosylate is a crystalline polymorph of MDMA tosylate characterized by any combination of the XRPD peaks set forth in Table 11 (±0.2° 2θ; ±0.1° 2θ; or ±0.0° 2θ; Cu Kα1 radiation).

101. The compound of embodiment 1, wherein the solid form of MDMA tosylate is a crystalline polymorph of MDMA tosylate characterized by a XRPD diffractogram substantially similar to that shown in FIG. 9.

102. The compound of embodiment 1, wherein the solid form of MDMA tosylate is a crystalline polymorph of MDMA tosylate characterized by a $^1$H NMR spectrum substantially similar to that shown in FIG. 63.

103. The compound of embodiment 1, wherein the solid form of MDMA tosylate is a crystalline polymorph of MDMA tosylate characterized by a TGA profile is substantially similar to that shown in FIG. 64.

104. The compound of embodiment 1, wherein the solid form of MDMA tosylate is a crystalline polymorph of MDMA tosylate characterized by a DSC profile is substantially similar to that shown in FIG. 64.

105. The compound of embodiment 1, wherein the solid form of MDMA HCl is a crystalline polymorph of MDMA HCl characterized by two or more, or three or more XRPD signals selected from the group consisting of 15.9° 2θ, 18.5° 2θ, and 21.5° 2θ (±0.2° 2θ; ±0.1° 2θ; or ±0.0° 2θ; Cu Kα1 radiation).

106. The compound of embodiment 1, wherein the solid form of MDMA HCl is a crystalline polymorph of MDMA HCl characterized by two or more, or three or more XRPD signals selected from the group consisting of 15.9° 2θ, 18.5° 2θ, 19.5° 2θ, 21.5° 2θ, and 27.1° 2θ (±0.2° 2θ; ±0.1° 2θ; or ±0.0° 2θ; Cu Kα1 radiation).

107. The compound of embodiment 1, wherein the solid form of MDMA HCl is a crystalline polymorph of MDMA HCl characterized by two or more, or three or more XRPD signals selected from the group consisting of 9.8° 2θ, 12.6° 2θ, and 15.9° 2θ (±0.2° 2θ; =0.1° 2θ; or ±0.0° 2θ; Cu Kα1 radiation).

108. The compound of embodiment 1, wherein the solid form of MDMA HCl is a crystalline polymorph of MDMA HCl characterized by two or more, or three or more XRPD signals selected from the group consisting of 9.8° 2θ, 12.6° 2θ, 15.9° 2θ, 18.5° 2θ, and 19.5° 2θ (±0.2° 2θ; ±0.1° 2θ; or ±0.0° 2θ; Cu Kα1 radiation).

109. The compound of embodiment 1, wherein the solid form of MDMA HCl is a crystalline polymorph of MDMA HCl characterized by any combination of the XRPD peaks set forth in Table 15 (±0.2° 2θ; ±0.1° 2θ; or ±0.0° 2θ; Cu Kα1 radiation).

110. The compound of embodiment 1, wherein the solid form of MDMA HCl is a crystalline polymorph of MDMA HCl characterized by a XRPD diffractogram substantially similar to that shown in FIG. 48.

111. The compound of embodiment 1, wherein the solid form of MDMA HCl is a crystalline polymorph of MDMA HCl characterized by a $^1$H NMR spectrum substantially similar to that shown in FIG. 95.

112. The solid form of embodiment 1, wherein the solid form is a solid form of MDE.

113. The compound of embodiment 1, wherein the solid form of MDE is a salt of MDE.

114. The compound of embodiment 1, wherein the salt of MDE is a crystalline salt.

115. The compound of embodiment 1, wherein the solid form of MDE HCl is a crystalline polymorph of MDE HCl characterized by XRPD signals at 15.6° 2θ and 21.6° 2θ (±0.2° 2θ; ±0.1° 2θ; or ±0.0° 2θ; Cu Kα1 radiation).

116. The compound of embodiment 1, wherein the solid form of MDE HCl is a crystalline polymorph of MDE HCl characterized by two or more, or three or more XRPD signals selected from the group consisting of 15.6° 2θ, 21.6° 2θ, 22.1° 2θ, and 23.5° 2θ (±0.2° 2θ; ±0.1° 2θ; or ±0.0° 2θ; Cu Kα1 radiation).

117. The compound of embodiment 1, wherein the solid form of MDE HCl is a crystalline polymorph of MDE HCl characterized by two or more, or three or more XRPD signals selected from the group consisting of 14.0° 2θ, 14.4° 2θ, and 23.5° 2θ (±0.2° 2θ; ±0.1° 2θ; or ±0.0° 2θ; Cu Kα1 radiation).

118. The compound of embodiment 1, wherein the solid form of MDE HCl is a crystalline polymorph of MDE HCl characterized by two or more, or three or more XRPD signals selected from the group consisting of 14.0° 2θ, 14.4° 2θ, 23.5° 2θ, 24.9° 2θ, and 28.0° 2θ (±0.2° 2θ; ±0.1° 2θ; or ±0.0° 2θ; Cu Kα1 radiation).

119. The compound of embodiment 1, wherein the solid form of MDE HCl is a crystalline polymorph of MDE HCl characterized by two or more, or three or more XRPD signals selected from the group consisting of 14.1° 2θ, 14.5° 2θ, and 15.7° 2θ (±0.2° 2θ; ±0.1° 2θ; or ±0.0° 2θ; Cu Kα1 radiation).

120. The compound of embodiment 1, wherein the solid form of MDE HCl is a crystalline polymorph of MDE HCl characterized by two or more, or three or more XRPD signals selected from the group consisting of 14.1° 2θ, 14.5° 2θ, 15.7° 2θ, 18.5° 2θ, and 18.9° 2θ (±0.2° 2θ; ±0.1° 2θ; or ±0.0° 2θ; Cu Kα1 radiation).

121. The compound of embodiment 1, wherein the solid form of MDE HCl is a crystalline polymorph of MDE HCl characterized by two or more, or three or more XRPD signals selected from the group consisting of 14.5° 2θ, 23.5° 2θ, and 28.1° 2θ (±0.2° 2θ; ±0.1° 2θ; or ±0.0° 2θ; Cu Kα1 radiation).

122. The compound of embodiment 1, wherein the solid form of MDE HCl is a crystalline polymorph of MDE HCl characterized by two or more, or three or more XRPD signals selected from the group consisting of 14.1° 2θ, 14° 2θ, 23.5° 2θ, 25.2° 2θ, and 28.1° 2θ (±0.2° 2θ; ±0.1° 2θ; or ±0.0° 2θ; Cu Kα1 radiation).

123. The compound of embodiment 1, wherein the solid form of MDE HCl is a crystalline polymorph of MDE HCl characterized by any combination of the XRPD peaks set forth in Table 16 (±0.2° 2θ; ±0.1° 2θ; or ±0.0° 2θ; Cu Kα1 radiation).

124. The compound of embodiment 1, wherein the solid form of MDE HCl is a crystalline polymorph of MDE HCl characterized by any combination of the XRPD peaks set forth in Table 17 (±0.2° 2θ; ±0.1° 2θ; or ±0.0° 2θ; Cu Kα1 radiation).

125. The compound of embodiment 1, wherein the solid form of MDE HCl is a crystalline polymorph of MDE HCl characterized by a XRPD diffractogram substantially similar to that shown in FIG. 17.

126. The compound of embodiment 1, wherein the solid form of MDE HCl is a crystalline polymorph of MDE HCl characterized by a XRPD diffractogram substantially similar to that shown in FIG. 108.

127. The compound of embodiment 1, wherein the solid form of (R)-MDE HCl is a crystalline polymorph of (R)-MDE HCl characterized by two or more, or three or more XRPD signals selected from the group consisting of 14.5° 2θ, 17.0° 2θ, and 22.2° 2θ (±0.2° 2θ; ±0.1° 2θ; or ±0.0° 2θ; Cu Kα1 radiation).

128. The compound of embodiment 1, wherein the solid form of (R)-MDE HCl is a crystalline polymorph of (R)-MDE HCl characterized by two or more, or three or more XRPD signals selected from the group consisting of 14.5° 2θ, 17.0° 2θ, 22.2° 2θ, 22.6° 2θ, and 23.4° 2θ (±0.2° 2θ; ±0.1° 2θ; or ±0.0° 2θ; Cu Kα1 radiation).

129. The compound of embodiment 1, wherein the solid form of (R)-MDE HCl is a crystalline polymorph of (R)-MDE HCl characterized by two or more, or three or more XRPD signals selected from the group consisting of 14.5° 2θ, 23.4° 2θ, and 24.8° 2θ (±0.2° 2θ; ±0.1° 2θ; or ±0.0° 2θ; Cu Kα1 radiation).

130. The compound of embodiment 1, wherein the solid form of (R)-MDE HCl is a crystalline polymorph of (R)-MDE HCl characterized by two or more, or three or more XRPD signals selected from the group consisting of 14.5° 2θ, 23.4° 2θ, 24.8° 2θ, 27.4° 2θ, and 27.7° 2θ (±0.2° 2θ; ±0.1° 2θ; or ±0.0° 2θ; Cu Kα1 radiation).

131. The compound of embodiment 1, wherein the solid form of (R)-MDE HCl is a crystalline polymorph of (R)-MDE HCl characterized by any combination of the XRPD peaks set forth in Table 58 (±0.2° 2θ; ±0.1° 2θ; or ±0.0° 2θ; Cu Kα1 radiation).

132. The compound of embodiment 1, wherein the solid form of (R)-MDE HCl is a crystalline polymorph of (R)-MDE HCl characterized by a XRPD diffractogram substantially similar to that shown in FIG. 102.

133. The compound of embodiment 1, wherein the solid form of (S)-MDE HCl is a crystalline polymorph of (S)-MDE HCl characterized by two or more, or three or more XRPD signals selected from the group consisting of 14.5° 2θ, 27.6° 2θ, and 31.8° 2θ (±0.2° 2θ; ±0.1° 2θ; or ±0.0° 2θ; Cu Kα1 radiation).

134. The compound of embodiment 1, wherein the solid form of (S)-MDE HCl is a crystalline polymorph of (S)-MDE HCl characterized by two or more, or three or more XRPD signals selected from the group consisting of 14.5° 2θ, 23.4° 2θ, and 25.0° 2θ (±0.2° 2θ; ±0.1° 2θ; or ±0.0° 2θ; Cu Kα1 radiation).

135. The compound of embodiment 1, wherein the solid form of (S)-MDE HCl is a crystalline polymorph of (S)-MDE HCl characterized by two or more, or three or more XRPD signals selected from the group consisting of 14.5° 2θ, 23.4° 2θ, 25.0° 2θ, 27.6° 2θ, and 31.8° 2θ (±0.2° 2θ; ±0.1° 2θ; or ±0.0° 2θ; Cu Kα1 radiation).

136. The compound of embodiment 1, wherein the solid form of (S)-MDE HCl is a crystalline polymorph of (S)-MDE HCl characterized by any combination of the XRPD peaks set forth in Table 59 (±0.2° 2θ; ±0.1° 2θ; or ±0.0° 2θ; Cu Kα1 radiation).

137. The compound of embodiment 1, wherein the solid form of (S)-MDE HCl is a crystalline polymorph of (S)-MDE HCl characterized by a XRPD diffractogram substantially similar to that shown in FIG. 103.

138. The compound of embodiment 1, wherein the solid form of S-MDE tosylate is a crystalline polymorph of S-MDE tosylate characterized by two or more, or three or more XRPD signals selected from the group consisting of 13.9° 2θ, 19.8° 2θ, and 21.8° 2θ (±0.2° 2θ; ±0.1° 2θ; or ±0.0° 2θ; Cu Kα1 radiation).

139. The compound of embodiment 1, wherein the solid form of S-MDE tosylate is a crystalline polymorph of S-MDE tosylate characterized by two or more, or three or more XRPD signals selected from the group consisting of 13.9° 2θ, 19.8° 2θ, 21.8° 2θ, 24.3° 2θ, and 26.9° 2θ (±0.2° 2θ; ±0.1° 2θ; or ±0.0° 2θ; Cu Kα1 radiation).

140. The compound of embodiment 1, wherein the solid form of S-MDE tosylate is a crystalline polymorph of S-MDE tosylate characterized by two or more, or three or more XRPD signals selected from the group consisting of 12.1° 2θ, 13.9° 2θ, and 15.1° 2θ (±0.2° 2θ; ±0.1° 2θ; or ±0.0° 2θ; Cu Kα1 radiation).

141. The compound of embodiment 1, wherein the solid form of S-MDE tosylate is a crystalline polymorph of S-MDE tosylate characterized by two or more, or three or more XRPD signals selected from the group consisting of 12.1° 2θ, 13.9° 2θ, 15.1° 2θ, 15.6° 2θ, and 16.1° 2θ (±0.2° 2θ; ±0.1° 2θ; or ±0.0° 2θ; Cu Kα1 radiation).

142. The compound of embodiment 1, wherein the solid form of S-MDE tosylate is a crystalline polymorph of S-MDE tosylate characterized by any combination of the XRPD peaks set forth in Table 18 (±0.2° 2θ; ±0.1° 2θ; or ±0.0° 2θ; Cu Kα1 radiation).

143. The compound of embodiment 1, wherein the solid form of S-MDE tosylate is a crystalline polymorph of S-MDE tosylate characterized by a XRPD diffractogram substantially similar to that shown in FIG. 19.

144. The solid form of embodiment 1, wherein the solid form is a solid form of MDAI.

145. The compound of embodiment 1, wherein the solid form of MDAI is a salt of MDAI.

146. The compound of embodiment 1, wherein the salt of MDAI is a crystalline salt.

147. The compound of embodiment 1, wherein the solid form of MDAI HCl is a crystalline polymorph of MDAI HCl characterized by two or more, or three or more XRPD signals selected from the group consisting of 16.9° 2θ, 23.6° 2θ, and 24.2° 2θ (±0.2° 2θ; ±0.1° 2θ; or ±0.0° 2θ; Cu Kα1 radiation).

148. The compound of embodiment 1, wherein the solid form of MDAI HCl is a crystalline polymorph of MDAI HCl characterized by two or more, or three or more XRPD signals selected from the group consisting of 16.9° 2θ, 23.6° 2θ, 24.2° 2θ, 26.4° 2θ, and 27.2° 2θ (±0.2° 2θ; ±0.1° 2θ; or ±0.0° 2θ; Cu Kα1 radiation).

149. The compound of embodiment 1, wherein the solid form of MDAI HCl is a crystalline polymorph of MDAI HCl characterized by any combination of the XRPD peaks set forth in Table 19 (±0.2° 2θ; ±0.1° 2θ; or ±0.0° 2θ; Cu Kα1 radiation).

150. The compound of embodiment 1, wherein the solid form of MDAI HCl is a crystalline polymorph of MDAI HCl characterized by two or more, or three or more XRPD signals selected from the group consisting of 24.2° 2θ, 27.2° 2θ, and 45.8° 2θ (±0.2° 2θ; ±0.1° 2θ; or ±0.0° 2θ; Cu Kα1 radiation).

151. The compound of embodiment 1, wherein the solid form of MDAI HCl is a crystalline polymorph of MDAI HCl characterized by two or more, or three or more XRPD signals selected from the group consisting of 23.6° 2θ, 24.2° 2θ, 26.4° 2θ, 27.2° 2θ, and 45.8° 2θ (±0.2° 2θ; ±0.1° 2θ; or ±0.0° 2θ; Cu Kα1 radiation).

152. The compound of embodiment 1, wherein the solid form of MDAI HCl is a crystalline polymorph of MDAI HCl characterized by any combination of the XRPD peaks set forth in Table 19 (±0.2° 2θ; ±0.1° 2θ; or ±0.0° 2θ; Cu Kα1 radiation).

153. The compound of embodiment 1, wherein the solid form of MDAI HCl is a crystalline polymorph of MDAI HCl characterized by a XRPD diffractogram substantially similar to that shown in FIG. 22.

154. The compound of embodiment 1, wherein the solid form of MDAI HCl is a crystalline polymorph of MDAI HCl characterized by two or more, or three or more XRPD signals selected from the group consisting of 23.5° 2θ, 24.1° 2θ, and 27.0° 2θ (±0.2° 2θ; ±0.1° 2θ; or ±0.0° 2θ; Cu Kα1 radiation).

155. The compound of embodiment 1, wherein the solid form of MDAI HCl is a crystalline polymorph of MDAI HCl characterized by two or more, or three or more XRPD signals selected from the group consisting of 15.2° 2θ, 23.2° 2θ, 23.5° 2θ, 24.1° 2θ, and 27.0° 2θ (±0.2° 2θ; ±0.1° 2θ; or ±0.0° 2θ; Cu Kα1 radiation).

156. The compound of embodiment 1, wherein the solid form of MDAI HCl is a crystalline polymorph of MDAI HCl characterized by any combination of the XRPD peaks set forth in Table 63 (±0.2° 2θ; ±0.1° 2θ; or ±0.0° 2θ; Cu Kα1 radiation).

157. The compound of embodiment 1, wherein the solid form of MDAI HCl is a crystalline polymorph of MDAI HCl characterized by a XRPD diffractogram substantially similar to that shown in FIG. 107.

158. The solid form of embodiment 1, wherein the solid form is a solid form of MBDB.

159. The compound of embodiment 1, wherein the solid form of MBDB is a salt of MBDB.

160. The compound of embodiment 1, wherein the salt of MBDB is a crystalline salt.

161. The compound of embodiment 1, wherein the solid form of MBDB citrate is a crystalline polymorph of MBDB citrate characterized by two or more, or three or more XRPD signals selected from the group consisting of 6.3° 2θ, 19.0° 2θ, and 25.4° 2θ (±0.2° 2θ; ±0.1° 2θ; or ±0.0° 2θ; Cu Kα1 radiation).

162. The compound of embodiment 1, wherein the solid form of MBDB citrate is a crystalline polymorph of MBDB citrate characterized by two or more, or three or more XRPD signals selected from the group consisting of 6.3° 2θ, 12.6° 2θ, 19.0° 2θ, 21.4° 2θ, and 25.4° 2θ (±0.2° 2θ; ±0.1° 2θ; or ±0.0° 2θ; Cu Kα1 radiation).

163. The compound of embodiment 1, wherein the solid form of MBDB citrate is a crystalline polymorph of MBDB citrate characterized by two or more, or three or more XRPD signals selected from the group consisting of 6.3° 2θ, 12.6° 2θ, and 19.0° 2θ (±0.2° 2θ; =0.1° 2θ; or ±0.0° 2θ; Cu Kα1 radiation).

164. The compound of embodiment 1, wherein the solid form of MBDB citrate is a crystalline polymorph of MBDB citrate characterized by two or more, or three or more XRPD signals selected from the group consisting of 6.3° 2θ, 19.0° 2θ, and 25.5° 2θ (±0.2° 2θ; =0.1° 2θ; or ±0.0° 2θ; Cu Kα1 radiation).

165. The compound of embodiment 1, wherein the solid form of MBDB citrate is a crystalline polymorph of MBDB citrate characterized by two or more, or three or more XRPD signals selected from the group consisting of 6.3° 2θ, 15.9° 2θ, 17.1° 2θ, 19.0° 2θ, and 25.5° 2θ (±0.2° 2θ; ±0.1° 2θ; or ±0.0° 2θ; Cu Kα1 radiation).

166. The compound of embodiment 1, wherein the solid form of MBDB citrate is a crystalline polymorph of MBDB citrate characterized by two or more, or three or more XRPD signals selected from the group consisting of 6.3° 2θ, 11.7° 2θ, and 12.7° 2θ (±0.2° 2θ; ±0.1° 2θ; or ±0.0° 2θ; Cu Kα1 radiation).

167. The compound of embodiment 1, wherein the solid form of MBDB citrate is a crystalline polymorph of MBDB citrate characterized by two or more, or three or more XRPD signals selected from the group consisting of 6.3° 2θ, 11.7° 2θ, 12.7° 2θ, 15.9° 2θ, and 17.1° 2θ (±0.2° 2θ; ±0.1° 2θ; or ±0.0° 2θ; Cu Kα1 radiation).

168. The compound of embodiment 1, wherein the solid form of MBDB citrate is a crystalline polymorph of MBDB citrate characterized by any combination of the XRPD peaks set forth in Table 21 or Table 22 (±0.2° 2θ; ±0.1° 2θ; or ±0.0° 2θ; Cu Kα1 radiation).

169. The compound of embodiment 1, wherein the solid form of MBDB citrate is a crystalline polymorph of MBDB citrate characterized by a XRPD diffractogram substantially similar to that shown in FIG. 26 or FIG. 84.

170. The compound of embodiment 1, wherein the solid form of MBDB citrate is a crystalline polymorph of MBDB citrate characterized by a $^1$H NMR spectrum substantially similar to that shown in FIG. 65.

171. The compound of embodiment 1, wherein the solid form of MBDB citrate is a crystalline polymorph of MBDB citrate characterized by a TGA profile is substantially similar to that shown in FIG. 66.

172. The compound of embodiment 1, wherein the solid form of MBDB citrate is a crystalline polymorph of MBDB citrate characterized by a DSC profile is substantially similar to that shown in FIG. 66.

173. The compound of embodiment 1, wherein the solid form of MBDB fumarate is a crystalline polymorph of MBDB fumarate characterized by two or more, or three or more XRPD signals selected from the group consisting of 12.9° 2θ, 20.2° 2θ, and 20.5° 2θ (±0.2° 2θ; ±0.1° 2θ; or ±0.0° 2θ; Cu Kα1 radiation).

174. The compound of embodiment 1, wherein the solid form of MBDB fumarate is a crystalline polymorph of MBDB fumarate characterized by two or more, or three or more XRPD signals selected from the group consisting of 12.9° 2θ, 20.2° 2θ, 20.5° 2θ, 22.5° 2θ, and 26.0° 2θ (±0.2° 2θ; ±0.1° 2θ; or ±0.0° 2θ; Cu Kα1 radiation).

175. The compound of embodiment 1, wherein the solid form of MBDB fumarate is a crystalline polymorph of MBDB fumarate characterized by two or more, or three or more XRPD signals selected from the group consisting of 11.7° 2θ, 12.9° 2θ, 20.2° 2θ, 20.5° 2θ, and 26.0° 2θ (±0.2° 2θ; ±0.1° 2θ; or ±0.0° 2θ; Cu Kα1 radiation).

176. The compound of embodiment 1, wherein the solid form of MBDB fumarate is a crystalline polymorph of MBDB fumarate characterized by two or more, or three or more XRPD signals selected from the group consisting of 12.9° 2θ, 21.6° 2θ, and 22.3° 2θ (±0.2° 2θ; ±0.1° 2θ; or ±0.0° 2θ; Cu Kα1 radiation).

177. The compound of embodiment 1, wherein the solid form of MBDB fumarate is a crystalline polymorph of MBDB fumarate characterized by two or more, or three or more XRPD signals selected from the group consisting of 11.8° 2θ, 12.9° 2θ, 20.2° 2θ, 21.6° 2θ, and 22.3° 2θ (±0.2° 2θ; ±0.1° 2θ; or ±0.0° 2θ; Cu Kα1 radiation).

178. The compound of embodiment 1, wherein the solid form of MBDB fumarate is a crystalline polymorph of MBDB fumarate characterized by two or more, or three or more XRPD signals selected from the group consisting of 11.8° 2θ, 12.9° 2θ, and 21.6° 2θ (±0.2° 2θ; ±0.1° 2θ; or ±0.0° 2θ; Cu Kα1 radiation).

179. The compound of embodiment 1, wherein the solid form of MBDB fumarate is a crystalline polymorph of MBDB fumarate characterized by two or more, or three or more XRPD signals selected from the group consisting of 11.8° 2θ, 12.9° 2θ, 20.2° 2θ, 20.5° 2θ, and 21.6° 2θ (±0.2° 2θ; ±0.1° 2θ; or ±0.0° 2θ; Cu Kα1 radiation).

180. The compound of embodiment 1, wherein the solid form of MBDB fumarate is a crystalline polymorph of MBDB fumarate characterized by any combination of the XRPD peaks set forth in Table 23 or Table 24 (±0.2° 2θ; ±0.1° 2θ; or ±0.0° 2θ; Cu Kα1 radiation).

181. The compound of embodiment 1, wherein the solid form of MBDB fumarate is a crystalline polymorph of MBDB fumarate characterized by a XRPD diffractogram substantially similar to that shown in FIG. 27 or FIG. 85.

182. The compound of embodiment 1, wherein the solid form of MBDB fumarate is a crystalline polymorph of MBDB fumarate characterized by a $^1$H NMR spectrum substantially similar to that shown in FIG. 67.

183. The compound of embodiment 1, wherein the solid form of MBDB fumarate is a crystalline polymorph of MBDB fumarate characterized by a TGA profile is substantially similar to that shown in FIG. 68.

184. The compound of embodiment 1, wherein the solid form of MBDB fumarate is a crystalline polymorph of MBDB fumarate characterized by a DSC profile is substantially similar to that shown in FIG. 68.

185. The compound of embodiment 1, wherein the solid form of MBDB galactarate is a crystalline polymorph of MBDB galactarate characterized by two or more, or three or more XRPD signals selected from the group consisting of 9.2° 2θ, 19.6° 2θ, and 23.1° 2θ (±0.2° 2θ; ±0.1° 2θ; or ±0.0° 2θ; Cu Kα1 radiation).

186. The compound of embodiment 1, wherein the solid form of MBDB galactarate is a crystalline polymorph of MBDB galactarate characterized by two or more, or three or more XRPD signals selected from the group consisting of 4.6° 2θ, 9.2° 2θ, 19.6° 2θ, 23.1° 2θ, and 30.7° 2θ (±0.2° 2θ; ±0.1° 2θ; or ±0.0° 2θ; Cu Kα1 radiation).

187. The compound of embodiment 1, wherein the solid form of MBDB galactarate is a crystalline polymorph of MBDB galactarate characterized by two or more, or three or more XRPD signals selected from the group consisting of 4.6° 2θ, 9.2° 2θ, and 19.6° 2θ (±0.2° 2θ; ±0.1° 2θ; or ±0.0° 2θ; Cu Kα1 radiation).

188. The compound of embodiment 1, wherein the solid form of MBDB galactarate is a crystalline polymorph of MBDB galactarate characterized by two or more, or three or more XRPD signals selected from the group consisting of 4.6° 2θ, 9.2° 2θ, 18.5° 2θ, 19.6° 2θ, and 23.1° 2θ (±0.2° 2θ; ±0.1° 2θ; or ±0.0° 2θ; Cu Kα1 radiation).

189. The compound of embodiment 1, wherein the solid form of MBDB galactarate is a crystalline polymorph of MBDB galactarate characterized by two or more, or three or more XRPD signals selected from the group consisting of 4.6° 2θ, 9.2° 2θ, and 19.6° 2θ (±0.2° 2θ; ±0.1° 2θ; or ±0.0° 2θ; Cu Kα1 radiation).

190. The compound of embodiment 1, wherein the solid form of MBDB galactarate is a crystalline polymorph of MBDB galactarate characterized by two or more, or three or more XRPD signals selected from the group consisting of 4.6° 2θ, 9.2° 2θ, 19.6° 2θ, 23.1° 2θ, and 30.7° 2θ (±0.2° 2θ; ±0.1° 2θ; or ±0.0° 2θ; Cu Kα1 radiation).

191. The compound of embodiment 1, wherein the solid form of MBDB galactarate is a crystalline polymorph of MBDB galactarate characterized by two or more, or three or more XRPD signals selected from the group consisting of 4.6° 2θ, 9.2° 2θ, 17.7° 2θ, 18.1° 2θ, and 19.6° 2θ (±0.2° 2θ; ±0.1° 2θ; or ±0.0° 2θ; Cu Kα1 radiation).

192. The compound of embodiment 1, wherein the solid form of MBDB galactarate is a crystalline polymorph of MBDB galactarate characterized by any combination of the XRPD peaks set forth in Table 25 or Table 26 (±0.2° 2θ; ±0.1° 2θ; or ±0.0° 2θ; Cu Kα1 radiation).

193. The compound of embodiment 1, wherein the solid form of MBDB galactarate is a crystalline polymorph of MBDB galactarate characterized by a XRPD diffractogram substantially similar to that shown in FIG. 28 or FIG. 89.

194. The compound of embodiment 1, wherein the solid form of MBDB galactarate is a crystalline polymorph of MBDB galactarate characterized by a $^1H$ NMR spectrum substantially similar to that shown in FIG. 69.

195. The compound of embodiment 1, wherein the solid form of MBDB galactarate is a crystalline polymorph of MBDB galactarate characterized by a TGA profile is substantially similar to that shown in FIG. 70.

196. The compound of embodiment 1, wherein the solid form of MBDB galactarate is a crystalline polymorph of MBDB galactarate characterized by a DSC profile is substantially similar to that shown in FIG. 70.

197. The compound of embodiment 1, wherein the solid form of MBDB maleate Form 1 is a crystalline polymorph of MBDB maleate characterized by two or more, or three or more XRPD signals selected from the group consisting of 13.8° 2θ, 22.4° 2θ, and 23.8° 2θ (±0.2° 2θ; ±0.1° 2θ; or ±0.0° 2θ; Cu Kα1 radiation).

198. The compound of embodiment 1, wherein the solid form of MBDB maleate Form 1 is a crystalline polymorph of MBDB maleate characterized by two or more, or three or more XRPD signals selected from the group consisting of 12.6° 2θ, 13.8° 2θ, 15.2° 2θ, 22.4° 2θ, and 23.8° 2θ (±0.2° 2θ; ±0.1° 2θ; or ±0.0° 2θ; Cu Kα1 radiation).

199. The compound of embodiment 1, wherein the solid form of MBDB maleate Form 1 is a crystalline polymorph of MBDB maleate characterized by two or more, or three or more XRPD signals selected from the group consisting of 12.6° 2θ, 13.8° 2θ, and 15.2° 2θ (±0.2° 2θ; ±0.1° 2θ; or ±0.0° 2θ; Cu Kα1 radiation).

200. The compound of embodiment 1, wherein the solid form of MBDB maleate Form 1 is a crystalline polymorph of MBDB maleate characterized by two or more, or three or more XRPD signals selected from the group consisting of 12.6° 2θ, 13.8° 2θ, 15.2° 2θ, 16.2° 2θ, and 18.3° 2θ (±0.2° 2θ; ±0.1° 2θ; or ±0.0° 2θ; Cu Kα1 radiation).

201. The compound of embodiment 1, wherein the solid form of MBDB maleate Form 1 is a crystalline polymorph of MBDB maleate characterized by two or more, or three or more XRPD signals selected from the group consisting of 13.8° 2θ, 23.6° 2θ, and 23.8° 2θ (±0.2° 2θ; ±0.1° 2θ; or ±0.0° 2θ; Cu Kα1 radiation).

202. The compound of embodiment 1, wherein the solid form of MBDB maleate Form 1 is a crystalline polymorph of MBDB maleate characterized by two or more, or three or more XRPD signals selected from the group consisting of 13.8° 2θ, 21.5° 2θ, 22.4° 2θ, 23.6° 2θ, and 23.8° 2θ (±0.2° 2θ; ±0.1° 2θ; or ±0.0° 2θ; Cu Kα1 radiation).

203. The compound of embodiment 1, wherein the solid form of MBDB maleate Form 1 is a crystalline polymorph of MBDB maleate characterized by any combination of the XRPD peaks set forth in Table 27, Table 28, or Table 28A (±0.2° 2θ; ±0.1° 2θ; or ±0.0° 2θ; Cu Kα1 radiation).

204. The compound of embodiment 1, wherein the solid form of MBDB maleate Form 1 is a crystalline polymorph of MBDB maleate characterized by a XRPD diffractogram substantially similar to that shown in FIG. 29 or FIG. 88.

205. The compound of embodiment 1, wherein the solid form of MBDB maleate Form 1 is a crystalline polymorph of MBDB maleate characterized by two or more, or three or more XRPD signals selected from the group consisting of 12.6° 2θ, 13.9° 2θ, and 15.3° 2θ (±0.2° 2θ; ±0.1° 2θ; or ±0.0° 2θ; Cu Kα1 radiation).

206. The compound of embodiment 1, wherein the solid form of MBDB maleate Form 1 is a crystalline polymorph of MBDB maleate characterized by two or more, or three or more XRPD signals selected from the group consisting of 12.6° 2θ, 13.9° 2θ, 15.3° 2θ, 18.4° 2θ, and 19.0° 2θ (±0.2° 2θ; ±0.1° 2θ; or ±0.0° 2θ; Cu Kα1 radiation).

207. The compound of embodiment 1, wherein the solid form of MBDB maleate Form 1 is a crystalline polymorph of MBDB maleate characterized by a $^1H$ NMR spectrum substantially similar to that shown in FIG. 71.

208. The compound of embodiment 1, wherein the solid form of MBDB maleate Form 1 is a crystalline polymorph of MBDB maleate characterized by a TGA profile is substantially similar to that shown in FIG. 72.

209. The compound of embodiment 1, wherein the solid form of MBDB maleate Form 1 is a crystalline polymorph of MBDB maleate characterized by a DSC profile is substantially similar to that shown in FIG. 72.

210. The compound of embodiment 1, wherein the solid form of MBDB maleate Form 2 is a crystalline polymorph of MBDB maleate characterized by two or more, or three or more XRPD signals selected from the group consisting of 9.7° 2θ, 11.8° 2θ, and 14.5° 2θ (±0.2° 2θ; ±0.1° 2θ; or ±0.0° 2θ; Cu Kα1 radiation).

211. The compound of embodiment 1, wherein the solid form of MBDB maleate Form 2 is a crystalline polymorph of MBDB maleate characterized by two or more, or three or more XRPD signals selected from the group consisting of 9.7° 2θ, 11.8° 2θ, 14.5° 2θ, 15.3° 2θ, and 19.3° 2θ (±0.2° 2θ; ±0.1° 2θ; or ±0.0° 2θ; Cu Kα1 radiation).

212. The compound of embodiment 1, wherein the solid form of MBDB maleate Form 2 is a crystalline polymorph of MBDB maleate characterized by any combination of the XRPD peaks set forth in Table 42A (±0.2° 2θ; ±0.1° 2θ; or ±0.0° 2θ; Cu Kα1 radiation).

213. The compound of embodiment 1, wherein the solid form of MBDB maleate Form 2 is a crystalline polymorph of MBDB maleate characterized by a XRPD diffractogram substantially similar to that shown in FIG. 96

214. The compound of embodiment 1, wherein the solid form of MBDB maleate Form 2 is a crystalline polymorph of MBDB maleate characterized by a $^1H$ NMR spectrum substantially similar to that shown in FIG. 98.

215. The compound of embodiment 1, wherein the solid form of MBDB maleate Form 2 is a crystalline polymorph of MBDB maleate characterized by a TGA profile is substantially similar to that shown in FIG. 100.

216. The compound of embodiment 1, wherein the solid form of MBDB maleate Form 2 is a crystalline polymorph of MBDB maleate characterized by a DSC profile is substantially similar to that shown in FIG. 100.

217. The compound of embodiment 1, wherein the solid form of MBDB maleate Form 3 is a crystalline polymorph of MBDB maleate characterized by two or more, or three or more XRPD signals selected from the group consisting of 9.3° 2θ, 9.7° 2θ, and 10.9° 2θ (±0.2° 2θ; ±0.1° 2θ; or ±0.0° 2θ; Cu Kα1 radiation).

218. The compound of embodiment 1, wherein the solid form of MBDB maleate Form 3 is a crystalline polymorph of MBDB maleate characterized by two or more, or three or more XRPD signals selected from the group consisting of 9.3° 2θ, 9.7° 2θ, 10.9° 2θ, 14.7° 2θ, and 17.0° 2θ (±0.2° 2θ; ±0.1° 2θ; or ±0.0° 2θ; Cu Kα1 radiation).

219. The compound of embodiment 1, wherein the solid form of MBDB maleate Form 3 is a crystalline polymorph of MBDB maleate characterized by any combination of the XRPD peaks set forth in Table 42B (±0.2° 2θ; ±0.1° 2θ; or ±0.0° 2θ; Cu Kα1 radiation).

220. The compound of embodiment 1, wherein the solid form of MBDB maleate Form 3 is a crystalline polymorph of MBDB maleate characterized by a XRPD diffractogram substantially similar to that shown in FIG. 97.

221. The compound of embodiment 1, wherein the solid form of MBDB maleate Form 3 is a crystalline polymorph of MBDB maleate characterized by a $^1$H NMR spectrum substantially similar to that shown in FIG. 99.

222. The compound of embodiment 1, wherein the solid form of MBDB maleate Form 3 is a crystalline polymorph of MBDB maleate characterized by a TGA profile is substantially similar to that shown in FIG. 101.

223. The compound of embodiment 1, wherein the solid form of MBDB maleate Form 3 is a crystalline polymorph of MBDB maleate characterized by a DSC profile is substantially similar to that shown in FIG. 101.

224. The compound of embodiment 1, wherein the solid form of MBDB phosphate is a crystalline polymorph of MBDB phosphate characterized by two or more, or three or more XRPD signals selected from the group consisting of 6.4° 2θ, 12.7° 2θ, and 21.5° 2θ (±0.2° 2θ; ±0.1° 2θ; or ±0.0° 2θ; Cu Kα1 radiation).

225. The compound of embodiment 1, wherein the solid form of MBDB phosphate is a crystalline polymorph of MBDB phosphate characterized by two or more, or three or more XRPD signals selected from the group consisting of 6.4° 2θ, 12.7° 2θ, 17.3° 2θ, 18.4° 2θ, and 21.5° 2θ (±0.2° 2θ; ±0.1° 2θ; or ±0.0° 2θ; Cu Kα1 radiation).

226. The compound of embodiment 1, wherein the solid form of MBDB phosphate is a crystalline polymorph of MBDB phosphate characterized by two or more, or three or more XRPD signals selected from the group consisting of 6.4° 2θ, 12.7° 2θ, and 14.5° 2θ (±0.2° 2θ; ±0.1° 2θ; or ±0.0° 2θ; Cu Kα1 radiation).

227. The compound of embodiment 1, wherein the solid form of MBDB phosphate is a crystalline polymorph of MBDB phosphate characterized by two or more, or three or more XRPD signals selected from the group consisting of 6.4° 2θ, 12.7° 2θ, 14.5° 2θ, 14.8° 2θ, and 17.3° 2θ (±0.2° 2θ; ±0.1° 2θ; or ±0.0° 2θ; Cu Kα1 radiation).

228. The compound of embodiment 1, wherein the solid form of MBDB phosphate is a crystalline polymorph of MBDB phosphate characterized by any combination of the XRPD peaks set forth in Table 29 (±0.2° 2θ; ±0.1° 2θ; or ±0.0° 2θ; Cu Kα1 radiation).

229. The compound of embodiment 1, wherein the solid form of MBDB phosphate is a crystalline polymorph of MBDB phosphate characterized by a XRPD diffractogram substantially similar to that shown in FIG. 30.

230. The compound of embodiment 1, wherein the solid form of MBDB phosphate is a crystalline polymorph of MBDB phosphate characterized by a $^1$H NMR spectrum substantially similar to that shown in FIG. 75.

231. The compound of embodiment 1, wherein the solid form of MBDB phosphate is a crystalline polymorph of MBDB phosphate characterized by a TGA profile is substantially similar to that shown in FIG. 76.

232. The compound of embodiment 1, wherein the solid form of MBDB phosphate is a crystalline polymorph of MBDB phosphate characterized by a DSC profile is substantially similar to that shown in FIG. 76.

233. The compound of embodiment 1, wherein the solid form of MBDB succinate Form 1 is a crystalline polymorph of MBDB succinate characterized by two or more, or three or more XRPD signals selected from the group consisting of 13.1° 2θ, 20.5° 2θ, and 21.9° 2θ (±0.2° 2θ; ±0.1° 2θ; or ±0.0° 2θ; Cu Kα1 radiation).

234. The compound of embodiment 1, wherein the solid form of MBDB succinate Form 1 is a crystalline polymorph of MBDB succinate characterized by two or more, or three or more XRPD signals selected from the group consisting of 13.1° 2θ, 20.5° 2θ, 21.9° 2θ, 22.9° 2θ, and 26.3° 2θ (±0.2° 2θ; ±0.1° 2θ; or ±0.0° 2θ; Cu Kα1 radiation).

235. The compound of embodiment 1, wherein the solid form of MBDB succinate Form 1 is a crystalline polymorph of MBDB succinate characterized by two or more, or three or more XRPD signals selected from the group consisting of 11.7° 2θ, 13.1° 2θ, and 20.5° 2θ (±0.2° 2θ; ±0.1° 2θ; or ±0.0° 2θ; Cu Kα1 radiation).

236. The compound of embodiment 1, wherein the solid form of MBDB succinate Form 1 is a crystalline polymorph of MBDB succinate characterized by two or more, or three or more XRPD signals selected from the group consisting of 11.7° 2θ, 13.1° 2θ, 20.5° 2θ, 21.9° 2θ, and 22.9° 2θ (±0.2° 2θ; ±0.1° 2θ; or ±0.0° 2θ; Cu Kα1 radiation).

237. The compound of embodiment 1, wherein the solid form of MBDB succinate Form 1 is a crystalline polymorph of MBDB succinate characterized by any combination of the XRPD peaks set forth in Table 30 (±0.2° 2θ; ±0.1° 2θ; or ±0.0° 2θ; Cu Kα1 radiation).

238. The compound of embodiment 1, wherein the solid form of MBDB succinate Form 1 is a crystalline polymorph of MBDB succinate characterized by a XRPD diffractogram substantially similar to that shown in FIG. 31.

239. The compound of embodiment 1, wherein the solid form of MBDB succinate Form 1 is a crystalline polymorph of MBDB succinate characterized by a $^1$H NMR spectrum substantially similar to that shown in FIG. 77.

240. The compound of embodiment 1, wherein the solid form of MBDB succinate Form 1 is a crystalline polymorph of MBDB succinate characterized by a TGA profile is substantially similar to that shown in FIG. 78.

241. The compound of embodiment 1, wherein the solid form of MBDB succinate Form 1 is a crystalline polymorph of MBDB succinate characterized by a DSC profile is substantially similar to that shown in FIG. 78.

242. The compound of embodiment 1, wherein the solid form of MBDB succinate Form 2 is a crystalline polymorph of MBDB succinate characterized by two or more, or three or more XRPD signals selected from the group consisting of 13.0° 2θ, 20.3° 2θ, and 21.5° 2θ (±0.2° 2θ; ±0.1° 2θ; or ±0.0° 2θ; Cu Kα1 radiation).

243. The compound of embodiment 1, wherein the solid form of MBDB succinate Form 2 is a crystalline polymorph of MBDB succinate characterized by two or more, or three or more XRPD signals selected from the group consisting of 11.6° 2θ, 13.0° 2θ, 20.3° 2θ, 20.7° 2θ, and 21.5° 2θ (±0.2° 2θ; ±0.1° 2θ; or ±0.0° 2θ; Cu Kα1 radiation).

244. The compound of embodiment 1, wherein the solid form of MBDB succinate Form 2 is a crystalline polymorph of MBDB succinate characterized XRPD signals at 11.6° 2θ, 13.0° 2θ, and 21.5° 2θ (±0.2° 2θ; ±0.1° 2θ; or ±0.0° 2θ; Cu Kα1 radiation).

245. The compound of embodiment 1, wherein the solid form of MBDB succinate Form 2 is a crystalline polymorph of MBDB succinate characterized by any combination of the XRPD peaks set forth in Table 30 (±0.2° 2θ; ±0.1° 2θ; or ±0.0° 2θ; Cu Kα1 radiation).

246. The compound of embodiment 1, wherein the solid form of MBDB succinate Form 2 is a crystalline polymorph of MBDB succinate characterized by a XRPD diffractogram substantially similar to that shown in FIG. 36.

247. The compound of embodiment 1, wherein the solid form of MBDB succinate Form 2 is a crystalline polymorph of MBDB succinate characterized by a $^{1}$H NMR spectrum substantially similar to that shown in FIG. 79.

248. The compound of embodiment 1, wherein the solid form of MBDB succinate Form 2 is a crystalline polymorph of MBDB succinate characterized by a TGA profile is substantially similar to that shown in FIG. 80.

249. The compound of embodiment 1, wherein the solid form of MBDB succinate Form 2 is a crystalline polymorph of MBDB succinate characterized by a DSC profile is substantially similar to that shown in FIG. 80.

250. The compound of embodiment 1, wherein the solid form of MBDB sulfate is a crystalline polymorph of MBDB sulfate characterized by two or more, or three or more XRPD signals selected from the group consisting of 8.8° 2θ, 17.5° 2θ, and 26.4° 2θ (±0.2° 2θ; ±0.1° 2θ; or ±0.0° 2θ; Cu Kα1 radiation).

251. The compound of embodiment 1, wherein the solid form of MBDB sulfate is a crystalline polymorph of MBDB sulfate characterized by two or more, or three or more XRPD signals selected from the group consisting of 8.8° 2θ, 13.7° 2θ, 17.5° 2θ, 21.0° 2θ, and 26.4° 2θ (±0.2° 2θ; ±0.1° 2θ; or ±0.0° 2θ; Cu Kα1 radiation).

252. The compound of embodiment 1, wherein the solid form of MBDB sulfate is a crystalline polymorph of MBDB sulfate characterized by two or more, or three or more XRPD signals selected from the group consisting of 8.8° 2θ, 15.0° 2θ, 17.5° 2θ, 22.3° 2θ, and 26.4° 2θ (±0.2° 2θ; ±0.1° 2θ; or ±0.0° 2θ; Cu Kα1 radiation).

253. The compound of embodiment 1, wherein the solid form of MBDB sulfate is a crystalline polymorph of MBDB sulfate characterized by two or more, or three or more XRPD signals selected from the group consisting of 17.4° 2θ, 22.4° 2θ, and 24.9° 2θ (±0.2° 2θ; ±0.1° 2θ; or ±0.0° 2θ; Cu Kα1 radiation).

254. The compound of embodiment 1, wherein the solid form of MBDB sulfate is a crystalline polymorph of MBDB sulfate characterized by two or more, or three or more XRPD signals selected from the group consisting of 17.4° 2θ, 18.9° 2θ, 21.5° 2θ, 22.4° 2θ, and 24.9° 2θ (±0.2° 2θ; ±0.1° 2θ; or ±0.0° 2θ; Cu Kα1 radiation).

255. The compound of embodiment 1, wherein the solid form of MBDB sulfate is a crystalline polymorph of MBDB sulfate characterized by two or more, or three or more XRPD signals selected from the group consisting of 8.8° 2θ, 17.4° 2θ, and 18.9° 2θ (±0.2° 2θ; ±0.1° 2θ; or ±0.0° 2θ; Cu Kα1 radiation).

256. The compound of embodiment 1, wherein the solid form of MBDB sulfate is a crystalline polymorph of MBDB sulfate characterized by two or more, or three or more XRPD signals selected from the group consisting of 8.8° 2θ, 17.4° 2θ, 18.9° 2θ, 21.1° 2θ, and 22.4° 2θ (±0.2° 2θ; ±0.1° 2θ; or ±0.0° 2θ; Cu Kα1 radiation).

257. The compound of embodiment 1, wherein the solid form of MBDB sulfate is a crystalline polymorph of MBDB sulfate characterized by any combination of the XRPD peaks set forth in Table 31 or Table 32 (±0.2° 2θ; ±0.1° 2θ; or ±0.0° 2θ; Cu Kα1 radiation).

258. The compound of embodiment 1, wherein the solid form of MBDB sulfate is a crystalline polymorph of MBDB sulfate characterized by a XRPD diffractogram substantially similar to that shown in FIG. 32 or FIG. 34.

259. The compound of embodiment 1, wherein the solid form of MBDB sulfate is a crystalline polymorph of MBDB sulfate characterized by a TGA profile is substantially similar to that shown in FIG. 81.

260. The compound of embodiment 1, wherein the solid form of MBDB sulfate is a crystalline polymorph of MBDB sulfate characterized by a DSC profile is substantially similar to that shown in FIG. 81.

261. The compound of embodiment 1, wherein the solid form of MBDB tartrate is a crystalline polymorph of MBDB tartrate characterized by two or more, or three or more XRPD signals selected from the group consisting of 5.8° 2θ, 11.5° 2θ, and 17.2° 2θ (±0.2° 2θ; =0.1° 2θ; or ±0.0° 2θ; Cu Kα1 radiation).

262. The compound of embodiment 1, wherein the solid form of MBDB tartrate is a crystalline polymorph of MBDB tartrate characterized by two or more, or three or more XRPD signals selected from the group consisting of 5.8° 2θ, 11.5° 2θ, 17.2° 2θ, 18.7° 2θ, and 24.7° 2θ (±0.2° 2θ; ±0.1° 2θ; or ±0.0° 2θ; Cu Kα1 radiation).

263. The compound of embodiment 1, wherein the solid form of MBDB tartrate is a crystalline polymorph of MBDB tartrate characterized by two or more, or three or more XRPD signals selected from the group consisting of 5.8° 2θ, 8.6° 2θ, 11.5° 2θ, 17.2° 2θ, and 18.7° 2θ (±0.2° 2θ; ±0.1° 2θ; or ±0.0° 2θ; Cu Kα1 radiation).

264. The compound of embodiment 1, wherein the solid form of MBDB tartrate is a crystalline polymorph of MBDB tartrate characterized by any combination of the XRPD peaks set forth in Table 33 (±0.2° 2θ; ±0.1° 2θ; or ±0.0° 2θ; Cu Kα1 radiation).

265. The compound of embodiment 1, wherein the solid form of MBDB tartrate is a crystalline polymorph of MBDB tartrate characterized by a XRPD diffractogram substantially similar to that shown in FIG. 33.

266. The compound of embodiment 1, wherein the solid form of MBDB malonate is a crystalline polymorph of MBDB malonate characterized by two or more, or three or more XRPD signals selected from the group consisting of 18.1° 2θ, 20.4° 2θ, and 22.7° 2θ (±0.2° 2θ; ±0.1° 2θ; or ±0.0° 2θ; Cu Kα1 radiation).

267. The compound of embodiment 1, wherein the solid form of MBDB malonate is a crystalline polymorph of MBDB malonate characterized by two or more, or three or more XRPD signals selected from the group consisting of 14.2° 2θ, 18.1° 2θ, 20.4° 2θ, 22.7° 2θ, and 27.5° 2θ (±0.2° 2θ; ±0.1° 2θ; or ±0.0° 2θ; Cu Kα1 radiation).

268. The compound of embodiment 1, wherein the solid form of MBDB malonate is a crystalline polymorph of MBDB malonate characterized by two or more, or three or more XRPD signals selected from the group consisting of 10.2° 2θ, 14.2° 2θ, and 16.5° 2θ (±0.2° 2θ; ±0.1° 2θ; or ±0.0° 2θ; Cu Kα1 radiation).

269. The compound of embodiment 1, wherein the solid form of MBDB malonate is a crystalline polymorph of MBDB malonate characterized by two or more, or three or more XRPD signals selected from the group consisting of 10.2° 2θ, 14.2° 2θ, 16.5° 2θ, 18.1° 2θ, and 22.7° 2θ (±0.2° 2θ; ±0.1° 2θ; or ±0.0° 2θ; Cu Kα1 radiation).

270. The compound of embodiment 1, wherein the solid form of MBDB malonate is a crystalline polymorph of MBDB malonate characterized by any combination of the XRPD peaks set forth in Table 34 (±0.2° 2θ; ±0.1° 2θ; or ±0.0° 2θ; Cu Kα1 radiation).

271. The compound of embodiment 1, wherein the solid form of MBDB malonate is a crystalline polymorph of MBDB malonate characterized by a XRPD diffractogram substantially similar to that shown in FIG. 35.

272. The compound of embodiment 1, wherein the solid form of MBDB malonate is a crystalline polymorph of MBDB malonate characterized by a $^1$H NMR spectrum substantially similar to that shown in FIG. 73.

273. The compound of embodiment 1, wherein the solid form of MBDB malonate is a crystalline polymorph of MBDB malonate characterized by a TGA profile is substantially similar to that shown in FIG. 74.

274. The compound of embodiment 1, wherein the solid form of MBDB malonate is a crystalline polymorph of MBDB malonate characterized by a DSC profile is substantially similar to that shown in FIG. 74.

275. The compound of embodiment 1, wherein the solid form of MBDB tosylate is a crystalline polymorph of MBDB tosylate characterized by two or more, or three or more XRPD signals selected from the group consisting of 13.1° 2θ, 18.1° 2θ, and 19.1° 2θ (±0.2° 2θ; ±0.1° 2θ; or ±0.0° 2θ; Cu Kα1 radiation).

276. The compound of embodiment 1, wherein the solid form of MBDB tosylate is a crystalline polymorph of MBDB tosylate characterized by two or more, or three or more XRPD signals selected from the group consisting of 6.1° 2θ, 13.1° 2θ, 18.1° 2θ, 19.1° 2θ, and 23.2° 2θ (±0.2° 2θ; ±0.1° 2θ; or ±0.0° 2θ; Cu Kα1 radiation).

277. The compound of embodiment 1, wherein the solid form of MBDB tosylate is a crystalline polymorph of MBDB tosylate characterized by two or more, or three or more XRPD signals selected from the group consisting of 6.1° 2θ, 11.3° 2θ, and 13.1° 2θ (±0.2° 2θ; ±0.1° 2θ; or ±0.0° 2θ; Cu Kα1 radiation).

278. The compound of embodiment 1, wherein the solid form of MBDB tosylate is a crystalline polymorph of MBDB tosylate characterized by two or more, or three or more XRPD signals selected from the group consisting of 6.1° 2θ, 10.0° 2θ, 11.3° 2θ, 12.1° 2θ, and 13.1° 2θ (±0.2° 2θ; ±0.1° 2θ; or ±0.0° 2θ; Cu Kα1 radiation).

279. The compound of embodiment 1, wherein the solid form of MBDB tosylate is a crystalline polymorph of MBDB tosylate characterized by any combination of the XRPD peaks set forth in Table 35 (±0.2° 2θ; ±0.1° 2θ; or ±0.0° 2θ; Cu Kα1 radiation).

280. The compound of embodiment 1, wherein the solid form of MBDB tosylate is a crystalline polymorph of MBDB tosylate characterized by a XRPD diffractogram substantially similar to that shown in FIG. 37.

281. The compound of embodiment 1, wherein the solid form of MBDB tosylate is a crystalline polymorph of MBDB tosylate characterized by a $^1$H NMR spectrum substantially similar to that shown in FIG. 82.

282. The compound of embodiment 1, wherein the solid form of MBDB tosylate is a crystalline polymorph of MBDB tosylate characterized by a TGA profile is substantially similar to that shown in FIG. 83.

283. The compound of embodiment 1, wherein the solid form of MBDB tosylate is a crystalline polymorph of MBDB tosylate characterized by a DSC profile is substantially similar to that shown in FIG. 83.

284. The compound of embodiment 1, wherein the solid form of MBDB HCl Form A is a crystalline polymorph of MBDB HCl characterized by two or more, or three or more XRPD signals selected from the group consisting of 14.3° 2θ, 14.9° 2θ, and 25.4° 2θ (±0.2° 2θ; ±0.1° 2θ; or ±0.0° 2θ; Cu Kα1 radiation).

285. The compound of embodiment 1, wherein the solid form of MBDB HCl Form A is a crystalline polymorph of MBDB HCl characterized by two or more, or three or more XRPD signals selected from the group consisting of 7.1° 2θ, 14.3° 2θ, 14.9° 2θ, 25.4° 2θ, and 26.1° 2θ (±0.2° 2θ; ±0.1° 2θ; or ±0.0° 2θ; Cu Kα1 radiation).

286. The compound of embodiment 1, wherein the solid form of MBDB HCl Form A is a crystalline polymorph of MBDB HCl characterized by two or more, or three or more XRPD signals selected from the group consisting of 7.1° 2θ, 12.3° 2θ, and 14.3° 2θ (±0.2° 2θ; ±0.1° 2θ; or ±0.0° 2θ; Cu Kα1 radiation).

287. The compound of embodiment 1, wherein the solid form of MBDB HCl Form A is a crystalline polymorph of MBDB HCl characterized by two or more, or three or more XRPD signals selected from the group consisting of 7.1° 2θ, 12.3° 2θ, 14.3° 2θ, 14.9° 2θ, and 16.2° 2θ (±0.2° 2θ; ±0.1° 2θ; or ±0.0° 2θ; Cu Kα1 radiation).

288. The compound of embodiment 1, wherein the solid form of MBDB HCl Form A is a crystalline polymorph of MBDB HCl characterized by two or more, or three or more XRPD signals selected from the group consisting of 14.4° 2θ, 15.0° 2θ, and 25.4° 2θ (±0.2° 2θ; ±0.1° 2θ; or ±0.0° 2θ; Cu Kα1 radiation).

289. The compound of embodiment 1, wherein the solid form of MBDB HCl Form A is a crystalline polymorph of MBDB HCl characterized by two or more, or three or more XRPD signals selected from the group consisting of 14.4° 2θ, 15.0° 2θ, 16.2° 2θ, 21.6° 2θ, and 25.4° 2θ (±0.2° 2θ; ±0.1° 2θ; or ±0.0° 2θ; Cu Kα1 radiation).

290. The compound of embodiment 1, wherein the solid form of MBDB HCl Form A is a crystalline polymorph of MBDB HCl characterized by two or more, or three or more XRPD signals selected from the group consisting of 7.2° 2θ, 12.4° 2θ, and 14.4° 2θ (±0.2° 2θ; ±0.1° 2θ; or ±0.0° 2θ; Cu Kα1 radiation).

291. The compound of embodiment 1, wherein the solid form of MBDB HCl Form A is a crystalline polymorph of MBDB HCl characterized by two or more, or three or more XRPD signals selected from the group consisting of 7.2° 2θ, 12.4° 2θ, 14.4° 2θ, 15.0° 2θ, and 16.2° 2θ (±0.2° 2θ; ±0.1° 2θ; or ±0.0° 2θ; Cu Kα1 radiation).

292. The compound of embodiment 1, wherein the solid form of MBDB HCl Form A is a crystalline polymorph of MBDB HCl characterized by any combination of the XRPD peaks set forth in Table 36 or Table 37 (±0.2° 2θ; ±0.1° 2θ; or ±0.0° 2θ; Cu Kα1 radiation).

293. The compound of embodiment 1, wherein the solid form of MBDB HCl Form A is a crystalline polymorph of MBDB HCl characterized by a XRPD diffractogram substantially similar to that shown in FIG. 38 or FIG. 86.

294. The compound of embodiment 1, wherein the solid form of MBDB HCl Form A is a crystalline polymorph of MBDB HCl characterized by a $^1$H NMR spectrum substantially similar to that shown in FIG. 90.

295. The compound of embodiment 1, wherein the solid form of MBDB HCl Form A is a crystalline polymorph of MBDB HCl characterized by a TGA profile is substantially similar to that shown in FIG. 91.

296. The compound of embodiment 1, wherein the solid form of MBDB HCl Form A is a crystalline polymorph of MBDB HCl characterized by a DSC profile is substantially similar to that shown in FIG. 91.

297. The compound of embodiment 1, wherein the solid form of MBDB HCl Form B is a crystalline polymorph of MBDB HCl characterized by two or more, or three or more XRPD signals selected from the group consisting of 19.7° 2θ, 25.0° 2θ, and 30.7° 2θ (±0.2° 2θ; ±0.1° 2θ; or ±0.0° 2θ; Cu Kα1 radiation).

298. The compound of embodiment 1, wherein the solid form of MBDB HCl Form B is a crystalline polymorph of MBDB HCl characterized by two or more, or three or more XRPD signals selected from the group consisting of 7.6° 2θ, 18.5° 2θ, 19.7° 2θ, 25.0° 2θ, and 30.7° 2θ (±0.2° 2θ; ±0.1° 2θ; or ±0.0° 2θ; Cu Kα1 radiation).

299. The compound of embodiment 1, wherein the solid form of MBDB HCl Form B is a crystalline polymorph of MBDB HCl characterized by two or more, or three or more XRPD signals selected from the group consisting of 7.6° 2θ, 13.3° 2θ, and 14.2° 2θ (±0.2° 2θ; ±0.1° 2θ; or ±0.0° 2θ; Cu Kα1 radiation).

300. The compound of embodiment 1, wherein the solid form of MBDB HCl Form B is a crystalline polymorph of MBDB HCl characterized by two or more, or three or more XRPD signals selected from the group consisting of 7.6° 2θ, 13.3° 2θ, 14.2° 2θ, 18.5° 2θ, and 19.7° 2θ (±0.2° 2θ; ±0.1° 2θ; or ±0.0° 2θ; Cu Kα1 radiation).

301. The compound of embodiment 1, wherein the solid form of MBDB HCl Form B is a crystalline polymorph of MBDB HCl characterized by two or more, or three or more XRPD signals selected from the group consisting of 18.5° 2θ, 19.6° 2θ, and 24.9° 2θ (±0.2° 2θ; ±0.1° 2θ; or ±0.0° 2θ; Cu Kα1 radiation).

302. The compound of embodiment 1, wherein the solid form of MBDB HCl Form B is a crystalline polymorph of MBDB HCl characterized by two or more, or three or more XRPD signals selected from the group consisting of 16.8° 2θ, 18.5° 2θ, 19.6° 2θ, 24.9° 2θ, and 27.8° 2θ (±0.2° 2θ; ±0.1° 2θ; or ±0.0° 2θ; Cu Kα1 radiation).

303. The compound of embodiment 1, wherein the solid form of MBDB HCl Form B is a crystalline polymorph of MBDB HCl characterized by two or more, or three or more XRPD signals selected from the group consisting of 13.4° 2θ, 14.2° 2θ, and 16.8° 2θ (±0.2° 2θ; ±0.1° 2θ; or ±0.0° 2θ; Cu Kα1 radiation).

304. The compound of embodiment 1, wherein the solid form of MBDB HCl Form B is a crystalline polymorph of MBDB HCl characterized by two or more, or three or more XRPD signals selected from the group consisting of 13.4° 2θ, 14.2° 2θ, 16.8° 2θ, 18.5° 2θ, and 19.6° 2θ (±0.2° 2θ; ±0.1° 2θ; or ±0.0° 2θ; Cu Kα1 radiation).

305. The compound of embodiment 1, wherein the solid form of MBDB HCl Form B is a crystalline polymorph of MBDB HCl characterized by any combination of the XRPD peaks set forth in Table 38 or Table 39 (±0.2° 2θ; ±0.1° 2θ; or ±0.0° 2θ; Cu Kα1 radiation).

306. The compound of embodiment 1, wherein the solid form of MBDB HCl Form B is a crystalline polymorph of MBDB HCl characterized by a XRPD diffractogram substantially similar to that shown in FIG. 39 or FIG. 87.

307. The compound of embodiment 1, wherein the solid form of MBDB HCl Form B is a crystalline polymorph of MBDB HCl characterized by a $^1$H NMR spectrum substantially similar to that shown in FIG. 93.

308. The compound of embodiment 1, wherein the solid form of MBDB HCl Form B is a crystalline polymorph of MBDB HCl characterized by a TGA profile is substantially similar to that shown in FIG. 94.

309. The compound of embodiment 1, wherein the solid form of MBDB HCl Form B is a crystalline polymorph of MBDB HCl characterized by a DSC profile is substantially similar to that shown in FIG. 94.

310. The compound of embodiment 1, wherein the solid form of MBDB HCl Form A is a crystalline polymorph of MBDB HCl characterized by two or more, or three or more XRPD signals selected from the group consisting of 16.7° 2θ, 18.4° 2θ, and 19.6° 2θ (±0.2° 2θ; ±0.1° 2θ; or ±0.0° 2θ; Cu Kα1 radiation).

311. The compound of embodiment 1, wherein the solid form of MBDB HCl Form A is a crystalline polymorph of MBDB HCl characterized by two or more, or three or more XRPD signals selected from the group consisting of 16.7° 2θ, 18.4° 2θ, 19.6° 2θ, 24.6° 2θ, and 24.9° 2θ (±0.2° 2θ; ±0.1° 2θ; or ±0.0° 2θ; Cu Kα1 radiation).

312. The compound of embodiment 1, wherein the solid form of MBDB HCl Form A is a crystalline polymorph of MBDB HCl characterized by any combination of the XRPD peaks set forth in Table 62 (±0.2° 2θ; ±0.1° 2θ; or ±0.0° 2θ; Cu Kα1 radiation).

313. The compound of embodiment 1, wherein the solid form of MBDB HCl Form A is a crystalline polymorph of MBDB HCl characterized by a XRPD diffractogram substantially similar to that shown in FIG. 106.

314. The compound of embodiment 1, wherein the solid form of (R)-MBDB HCl is a crystalline polymorph of (R)-MBDB HCl characterized by two or more, or three or more XRPD signals selected from the group consisting of 13.2° 2θ, 14.1° 2θ, and 16.7° 2θ (±0.2° 2θ; ±0.1° 2θ; or ±0.0° 2θ; Cu Kα1 radiation).

315. The compound of embodiment 1, wherein the solid form of (R)-MBDB HCl is a crystalline polymorph of (R)-MBDB HCl characterized by two or more, or three or more XRPD signals selected from the group consisting of 13.2° 2θ, 14.1° 2θ, 16.7° 2θ, 19.6° 2θ, and 24.9° 2θ (±0.2° 2θ; ±0.1° 2θ; or ±0.0° 2θ; Cu Kα1 radiation).

316. The compound of embodiment 1, wherein the solid form of (R)-MBDB HCl is a crystalline polymorph of (R)-MBDB HCl characterized by two or more, or three or more XRPD signals selected from the group consisting of 18.4° 2θ, 19.6° 2θ, and 24.9° 2θ (±0.2° 2θ; ±0.1° 2θ; or ±0.0° 2θ; Cu Kα1 radiation).

317. The compound of embodiment 1, wherein the solid form of (R)-MBDB HCl is a crystalline polymorph of (R)-MBDB HCl characterized by two or more, or three or more XRPD signals selected from the group consisting of 16.7° 2θ, 18.4° 2θ, 19.6° 2θ, 24.9° 2θ, and 27.9° 2θ (±0.2° 2θ; ±0.1° 2θ; or ±0.0° 2θ; Cu Kα1 radiation).

318. The compound of embodiment 1, wherein the solid form of (R)-MBDB HCl is a crystalline polymorph of (R)-MBDB HCl characterized by any combination of the XRPD peaks set forth in Table 60 (±0.2° 2θ; ±0.1° 2θ; or ±0.0° 2θ; Cu Kα1 radiation).

319. The compound of embodiment 1, wherein the solid form of (R)-MBDB HCl is a crystalline polymorph of (R)-MBDB HCl characterized by a XRPD diffractogram substantially similar to that shown in FIG. 104.

320. The compound of embodiment 1, wherein the solid form of (S)-MBDB HCl is a crystalline polymorph of (S)-MBDB HCl characterized by two or more, or three or more XRPD signals selected from the group consisting of 13.3° 2θ, 16.7° 2θ, and 19.6° 2θ (±0.2° 2θ; ±0.1° 2θ; or ±0.0° 2θ; Cu Kα1 radiation).

321. The compound of embodiment 1, wherein the solid form of (S)-MBDB HCl is a crystalline polymorph of (S)-MBDB HCl characterized by two or more, or three or more XRPD signals selected from the group consisting of 13.3° 2θ, 16.7° 2θ, 19.6° 2θ, 22.2° 2θ, and 24.6° 2θ (±0.2° 2θ; ±0.1° 2θ; or ±0.0° 2θ; Cu Kα1 radiation).

322. The compound of embodiment 1, wherein the solid form of (S)-MBDB HCl is a crystalline polymorph of (S)-MBDB HCl characterized by two or more, or three or more XRPD signals selected from the group consisting of 18.4° 2θ, 19.6° 2θ, and 24.9° 2θ (±0.2° 2θ; =0.1° 2θ; or ±0.0° 2θ; Cu Kα1 radiation).

323. The compound of embodiment 1, wherein the solid form of (S)-MBDB HCl is a crystalline polymorph of (S)-MBDB HCl characterized by two or more, or three or more XRPD signals selected from the group consisting of 16.7° 2θ, 18.4° 2θ, 19.6° 2θ, 24.6° 2θ, and 24.9° 2θ (±0.2° 2θ; ±0.1° 2θ; or ±0.0° 2θ; Cu Kα1 radiation).

324. The compound of embodiment 1, wherein the solid form of (S)-MBDB HCl is a crystalline polymorph of (S)-MBDB HCl characterized by any combination of the XRPD peaks set forth in Table 61 (±0.2° 2θ; ±0.1° 2θ; or ±0.0° 2θ; Cu Kα1 radiation).

325. The compound of embodiment 1, wherein the solid form of (S)-MBDB HCl is a crystalline polymorph of (S)-MBDB HCl characterized by a XRPD diffractogram substantially similar to that shown in FIG. 105.

326. The solid form of embodiment 1, wherein the solid form is a solid form of MEAI. 327. The compound of embodiment 1, wherein the solid form of MEAI is a salt of MEAI.

328. The compound of embodiment 1, wherein the salt of MEAI is a crystalline salt.

329. The compound of embodiment 1, wherein the solid form of MEAI HCl is a crystalline polymorph of MEAI HCl characterized by two or more, or three or more XRPD signals selected from the group consisting of 21.6° 2θ, 21.7° 2θ, and 32.7° 2θ (±0.2° 2θ; ±0.1° 2θ; or ±0.0° 2θ; Cu Kα1 radiation).

330. The compound of embodiment 1, wherein the solid form of MEAI HCl is a crystalline polymorph of MEAI HCl characterized by two or more, or three or more XRPD signals selected from the group consisting of 21.6° 2θ, 21.7° 2θ, 24.5° 2θ, 32.7° 2θ, and 32.8° 2θ (±0.2° 2θ; ±0.1° 2θ; or ±0.0° 2θ; Cu Kα1 radiation).

331. The compound of embodiment 1, wherein the solid form of MEAI HCl is a crystalline polymorph of MEAI HCl characterized by any combination of the XRPD peaks set forth in Table 40 (±0.2° 2θ; ±0.1° 2θ; or ±0.0° 2θ; Cu Kα1 radiation).

332. The compound of embodiment 1, wherein the solid form of MEAI HCl is a crystalline polymorph of MEAI HCl characterized by a XRPD diffractogram substantially similar to that shown in FIG. 40.

333. The solid form of embodiment 1, wherein the solid form is a solid form of 5,6-dimethoxy-2-aminoindane.

334. The compound of embodiment 1, wherein the solid form of 5,6-dimethoxy-2-aminoindane is a salt of 5,6-dimethoxy-2-aminoindane.

335. The compound of embodiment 1, wherein the salt of 5,6-dimethoxy-2-aminoindane is a crystalline salt.

336. The compound of embodiment 1, wherein the solid form of 5,6-dimethoxy-2-aminoindane HCl is a crystalline polymorph of 5,6-dimethoxy-2-aminoindane HCl characterized by two or more, or three or more XRPD signals selected from the group consisting of 11.7° 2θ, 18.2° 2θ, and 18.9° 2θ (±0.2° 2θ; ±0.1° 2θ; or ±0.0° 2θ; Cu Kα1 radiation).

337. The compound of embodiment 1, wherein the solid form of 5,6-dimethoxy-2-aminoindane HCl is a crystalline polymorph of 5,6-dimethoxy-2-aminoindane HCl characterized by two or more, or three or more XRPD signals selected from the group consisting of 11.7° 2θ, 18.2° 2θ, 18.9° 2θ, 23.0° 2θ, and 23.5° 2θ (±0.2° 2θ; ±0.1° 2θ; or ±0.0° 2θ; Cu Kα1 radiation).

338. The compound of embodiment 1, wherein the solid form of 5,6-dimethoxy-2-aminoindane HCl is a crystalline polymorph of 5,6-dimethoxy-2-aminoindane HCl characterized by two or more, or three or more XRPD signals selected from the group consisting of 11.7° 2θ, 27.3° 2θ, and 27.5° 2θ (±0.2° 2θ; ±0.1° 2θ; or ±0.0° 2θ; Cu Kα1 radiation).

339. The compound of embodiment 1, wherein the solid form of 5,6-dimethoxy-2-aminoindane HCl is a crystalline polymorph of 5,6-dimethoxy-2-aminoindane HCl characterized by two or more, or three or more XRPD signals selected from the group consisting of 9.0° 2θ, 9.1 020, 11.7° 2θ, 27.3° 2θ, and 27.5° 2θ (±0.2° 2θ; ±0.1° 2θ; or ±0.0° 2θ; Cu Kα1 radiation).

340. The compound of embodiment 1, wherein the solid form of 5,6-dimethoxy-2-aminoindane HCl is a crystalline polymorph of 5,6-dimethoxy-2-aminoindane HCl characterized by any combination of the XRPD peaks set forth in Table 41 (±0.2° 2θ; ±0.1° 2θ; or ±0.0° 2θ; Cu Kα1 radiation).

341. The compound of embodiment 1, wherein the solid form of 5,6-dimethoxy-2-aminoindane HCl is a crystalline polymorph of 5,6-dimethoxy-2-aminoindane HCl characterized by a XRPD diffractogram substantially similar to that shown in FIG. 42.

342. The solid form of embodiment 1, wherein a stoichiometric ratio of acid to free base is from about 0.4 molar equivalent to about 2.2 molar equivalents of the acid.

343. The solid form of embodiment 1, wherein a stoichiometric ratio of acid to free base is from about 0.5 molar equivalent to about 2 molar equivalents of the acid.

344. The solid from of embodiment 1, wherein a stoichiometric ratio of acid to free base is selected from about 0.5, 1, or 2 molar equivalents of the acid.

345. The compound of embodiment 1, wherein the solid form of MDMA hemifumarate Form A is a crystalline polymorph of MDMA hemifumarate characterized by two or more, or three or more XRPD signals selected from the group consisting of 8.3° 2θ, 10.9° 2θ, and 13.0° 2θ (±0.2° 2θ; ±0.1° 2θ; or ±0.0° 2θ; Cu Kα1 radiation).

346. The compound of embodiment 1, wherein the solid form of MDMA hemifumarate Form A is a crystalline polymorph of MDMA hemifumarate characterized by two or more, or three or more XRPD signals selected from the group consisting of 8.3° 2θ, 10.9° 2θ, 13.0° 2θ, 16.7° 2θ, and 17.3° 2θ (±0.2° 2θ; ±0.1° 2θ; or ±0.0° 2θ; Cu Kα1 radiation).

347. The compound of embodiment 1, wherein the solid form of MDMA hemifumarate Form A is a crystalline polymorph of MDMA hemifumarate characterized by two or more, or three or more XRPD signals selected from the group consisting of 8.4° 2θ, 10.9° 2θ, and 13.1° 2θ (±0.2° 2θ; ±0.1° 2θ; or ±0.0° 2θ; Cu Kα1 radiation).

348. The compound of embodiment 1, wherein the solid form of MDMA hemifumarate Form A is a crystalline polymorph of MDMA hemifumarate characterized by two or more, or three or more XRPD signals selected from the group consisting of 8.4° 2θ, 10.9° 2θ, 13.1° 2θ, 16.7° 2θ, and 17.3° 2θ (±0.2° 2θ; ±0.1° 2θ; or ±0.0° 2θ; Cu Kα1 radiation).

349. The compound of embodiment 1, wherein the solid form of MDMA hemifumarate Form A is a crystalline polymorph of MDMA hemifumarate characterized by any combination of the XRPD peaks set forth in Table 64 (±0.2° 2θ; ±0.1° 2θ; or ±0.0° 2θ; Cu Kα1 radiation).

350. The compound of embodiment 1, wherein the solid form of MDMA hemifumarate Form A is a crystalline polymorph of MDMA hemifumarate characterized by any combination of the XRPD peaks set forth in Table 65 (±0.2° 2θ; ±0.1° 2θ; or ±0.0° 2θ; Cu Kα1 radiation).

351. The compound of embodiment 1, wherein the solid form of MDMA hemifumarate Form A is a crystalline polymorph of MDMA hemifumarate characterized by a XRPD diffractogram substantially similar to that shown in FIG. 115.

352. The compound of embodiment 1, wherein the solid form of MDMA hemifumarate Form A is a crystalline polymorph of MDMA hemifumarate characterized by a XRPD diffractogram substantially similar to that shown in FIG. 116.

353. The compound of embodiment 1, wherein the solid form of (S)-MDMA HCl is a crystalline polymorph of (S)-MDMA HCl characterized by two or more, or three or more XRPD signals selected from the group consisting of 15.7° 2θ, 17.4° 2θ, and 20.6° 2θ (±0.2° 2θ; ±0.1° 2θ; or ±0.0° 2θ; Cu Kα1 radiation).

354. The compound of embodiment 1, wherein the solid form of (S)-MDMA HCl is a crystalline polymorph of (S)-MDMA HCl characterized by two or more, or three or more XRPD signals selected from the group consisting of 15.7° 2θ, 17.4° 2θ, 20.6° 2θ, 24.7° 2θ, and 29.1° 2θ (±0.2° 2θ; ±0.1° 2θ; or ±0.0° 2θ; Cu Kα1 radiation).

355. The compound of embodiment 1, wherein the solid form of (S)-MDMA HCl is a crystalline polymorph of (S)-MDMA HCl characterized by two or more, or three or more XRPD signals selected from the group consisting of 7.9° 2θ, 14.0° 2θ, and 15.7° 2θ (±0.2° 2θ; ±0.1° 2θ; or ±0.0° 2θ; Cu Kα1 radiation).

356. The compound of embodiment 1, wherein the solid form of (S)-MDMA HCl is a crystalline polymorph of (S)-MDMA HCl characterized by two or more, or three or more XRPD signals selected from the group consisting of 7.9° 2θ, 14.0° 2θ, 15.7° 2θ, 19.6° 2θ, and 20.6° 2θ (±0.2° 2θ; ±0.1° 2θ; or ±0.0° 2θ; Cu Kα1 radiation).

357. The compound of embodiment 1, wherein the solid form of (S)-MDMA HCl is a crystalline polymorph of (S)-MDMA HCl characterized by any combination of the XRPD peaks set forth in Table 67A (±0.2° 2θ; ±0.1° 2θ; or ±0.0° 2θ; Cu Kα1 radiation).

358. The compound of embodiment 1, wherein the solid form of (S)-MDMA HCl is a crystalline polymorph of (S)-MDMA HCl characterized by a XRPD diffractogram substantially similar to that shown in FIG. 13.

359. The compound of embodiment 1, wherein the solid form of (S)-MDMA HCl is a crystalline polymorph of (S)-MDMA HCl characterized by a XRPD diffractogram substantially similar to that shown in FIG. 14.

360. The compound of embodiment 1, wherein the solid form of (R)-MDMA HCl is a crystalline polymorph of (R)-MDMA HCl characterized by two or more, or three or more XRPD signals selected from the group consisting of 15.7° 2θ, 17.4° 2θ, and 20.6° 2θ (±0.2° 2θ; ±0.1° 2θ; or ±0.0° 2θ; Cu Kα1 radiation).

361. The compound of embodiment 1, wherein the solid form of (R)-MDMA HCl is a crystalline polymorph of (R)-MDMA HCl characterized by two or more, or three or more XRPD signals selected from the group consisting of 15.7° 2θ, 17.4° 2θ, 20.6° 2θ, 24.7° 2θ, and 29.1° 2θ (±0.2° 2θ; ±0.1° 2θ; or ±0.0° 2θ; Cu Kα1 radiation).

362. The compound of embodiment 1, wherein the solid form of (R)-MDMA HCl is a crystalline polymorph of (R)-MDMA HCl characterized by two or more, or three or more XRPD signals selected from the group consisting of 7.9° 2θ, 14.0° 2θ, and 15.7° 2θ (±0.2° 2θ; ±0.1° 2θ; or ±0.0° 2θ; Cu Kα1 radiation).

363. The compound of embodiment 1, wherein the solid form of (R)-MDMA HCl is a crystalline polymorph of (R)-MDMA HCl characterized by two or more, or three or more XRPD signals selected from the group consisting of 7.9° 2θ, 14.0° 2θ, 15.7° 2θ, 19.6° 2θ, and 20.6° 2θ (±0.2° 2θ; ±0.1° 2θ; or ±0.0° 2θ; Cu Kα1 radiation).

364. The compound of embodiment 1, wherein the solid form of (R)-MDMA HCl is a crystalline polymorph of (R)-MDMA HCl characterized by any combination of the XRPD peaks set forth in Table 67B (±0.2° 2θ; ±0.1° 2θ; or ±0.0° 2θ; Cu Kα1 radiation).

365. The compound of embodiment 1, wherein the solid form of (R)-MDMA HCl is a crystalline polymorph of (R)-MDMA HCl characterized by a XRPD diffractogram substantially similar to that shown in FIG. 15.

366. The compound of embodiment 1, wherein the solid form of (R)-MDMA HCl is a crystalline polymorph of (R)-MDMA HCl characterized by a XRPD diffractogram substantially similar to that shown in FIG. 16.

367. A pharmaceutical composition, comprising a solid form of a compound according to of any one of the preceding embodiments, and a pharmaceutically acceptable excipient.

368. A method comprising administering to a subject an effective amount of a solid form of any one of the preceding embodiments, or a pharmaceutical composition thereof.

369. The method of embodiment 368, wherein the subject has a neurological disorder or a psychiatric disorder, or both.

370. The method of embodiment 368, wherein subject has a neurological disorder which is a neurodegenerative disorder.

371. The method of embodiment 369, wherein the neurological disorder or psychiatric disorder, or both, comprises depression, addiction, anxiety, or a post-traumatic stress disorder.

372. The method of embodiment 369, wherein the neurological disorder or psychiatric disorder, or both, comprises treatment resistant depression, suicidal ideation, major depressive disorder, bipolar disorder, schizophrenia, or substance use disorder.

373. The method of embodiment 369, wherein the neurological disorder or psychiatric disorder, or both, comprises stroke, traumatic brain injury, or a combination thereof.

374. The method of any of the preceding embodiments, wherein administering comprises oral, parenteral, or topical administration.

375. The method of any of the preceding embodiments, wherein administering comprises oral administration.

376. The method of any of the preceding embodiments, wherein administering comprises administering by injection, inhalation, intraocular, intravaginal, intrarectal or transdermal routes.

377. The method of any of the preceding embodiments, further comprising administering to the subject an effective amount of an empathogenic agent.

378. The method of any of the preceding embodiments, further comprising administering a 5-$HT_{2A}$ antagonist to the subject.

379. The method of embodiment 378, wherein the 5-$HT_{2A}$ antagonist is selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, pruvanserin, nelotanserin and lorcaserin.

380. Use of a compound or composition of any of the preceding embodiments, in a method of treating a subject with a neurological disorder or a psychiatric disorder, or both.

381. Use of a compound or composition of any of the preceding embodiments, in a method of treating a subject with a neurological disorder which is a neurodegenerative disorder.

382. The use of embodiment 381, wherein the neurological disorder or psychiatric disorder, or both, comprises depression, addiction, anxiety, or a post-traumatic stress disorder.

383. The use of embodiment 381, wherein the neurological disorder or psychiatric disorder, or both, comprises treatment resistant depression, suicidal ideation, major depressive disorder, bipolar disorder, schizophrenia, or substance use disorder.

384. The use of embodiment 381, wherein the neurological disorder or psychiatric disorder, or both, comprises stroke, traumatic brain injury, or a combination thereof.

385. The use of any of the preceding embodiments, wherein administering comprises oral, parenteral, or topical administration.

386. The use of any of the preceding embodiments, wherein administering comprises oral administration.

387. The use of any of the preceding embodiments, wherein administering comprises administering by injection, inhalation, intraocular, intravaginal, intrarectal or transdermal routes.

388. The use of any of the preceding embodiments, further comprising administering to the subject an effective amount of an empathogenic agent.

389. The use of any of the preceding embodiments, further comprising administering a 5-$HT_{2A}$ antagonist to the subject.

390. The use of embodiment 389, wherein the 5-$HT_{2A}$ antagonist is selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, pruvanserin, nelotanserin and lorcaserin.

391. Use of a compound or composition of any of the preceding embodiments, in the manufacture of a medicament for treating a subject with a neurological disorder or a psychiatric disorder, or both.

392. Use of a compound or composition of any of the preceding embodiments, in the manufacture of a medicament for treating a subject with a neurological disorder which is a neurodegenerative disorder.

393. The use of embodiment 392, wherein the neurological disorder or psychiatric disorder, or both, comprises depression, addiction, anxiety, or a post-traumatic stress disorder.

394. The use of embodiment 392, wherein the neurological disorder or psychiatric disorder, or both, comprises treatment resistant depression, suicidal ideation, major depressive disorder, bipolar disorder, schizophrenia, or substance use disorder.

395. The use of embodiment 392, wherein the neurological disorder or psychiatric disorder, or both, comprises stroke, traumatic brain injury, or a combination thereof.

396. The use of any of the preceding embodiments, wherein administering comprises oral, parenteral, or topical administration.

397. The use of any of the preceding embodiments, wherein administering comprises oral administration.

398. The use of any of the preceding embodiments, wherein administering comprises administering by injection, inhalation, intraocular, intravaginal, intrarectal or transdermal routes.

399. The use of any of the preceding embodiments, further comprising administering to the subject an effective amount of an empathogenic agent.

400. The use of any of the preceding embodiments, further comprising administering a 5-$HT_{2A}$ antagonist to the subject.

401. The use of embodiment 400, wherein the 5-$HT_{2A}$ antagonist is selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, pruvanserin, nelotanserin and lorcaserin.

What is claimed is:

1. A solid form of (R)-3,4-methylenedioxy-methamphetamine ((R)-MDMA) HCl salt, wherein the solid form is characterized by an XRPD spectrum comprising two or three XRPD signals at 7.9° 2θ, 14.0° 2θ, and 15.7° 2θ (±0.2° 2θ; ±0.1° 2θ; or ±0.0° 2θ; Cu Kα1 radiation).

2. The solid form of (R)-MDMA HCl salt of claim 1, wherein the solid form of (R)-MDMA HCl XRPD spectrum is further characterized by one or more additional XRPD signal selected from the group consisting of 19.6° 2θ, and 20.6° 2θ (±0.2° 2θ; ±0.1° 2θ; or ±0.0° 2θ; Cu Kα1 radiation).

3. The solid form of (R)-MDMA HCl salt of claim 1, wherein the solid form of (R)-MDMA HCl XRPD spectrum is further characterized by one or more additional XRPD signal selected from the group consisting of 19.6° 2θ, 20.6° 2θ, 17.4° 2θ, and 24.7° 2θ, (±0.2° 2θ; ±0.1° 2θ; or ±0.0° 2θ; Cu Kα1 radiation).

4. A solid form of (R)-3,4-methylenedioxy-methamphetamine ((R)-MDMA) HCl salt wherein the solid form of (R)-MDMA HCl is characterized by an XRPD spectrum comprising two or more XRPD signals in Table 67B (±0.2° 2θ; ±0.1° 2θ; or ±0.0° 2θ; Cu Kα1 radiation).

5. A solid form of (R)-3,4-methylenedioxy-methamphetamine ((R)-MDMA) HCl salt wherein the solid form of (R)-MDMA HCl is characterized by an XRPD spectrum substantially similar to that shown in FIG. 15 or FIG. 16.

6. A pharmaceutical composition comprising the solid form of claim 1, and a pharmaceutically acceptable excipient.

7. A method of treating post-traumatic stress disorder (PTSD) in a subject in need thereof, comprising administering to the subject the solid form of claim 1.

8. The pharmaceutical composition of claim 6, wherein the (R)-MDMA is present in enantiomeric excess of at least 70%, at least 80%, at least 90%, at least 94%, at least 96%, at least 98%, or at least 99% enantiomeric excess.

9. A solid form of (R)-MDMA HCl salt, wherein the solid form is characterized an XRPD spectrum comprising two or three XRPD signals at 15.7° 2θ, 17.4° 2θ, and 20.6° 2θ (±0.2° 2θ; ±0.1° 2θ; or ±0.0° 2θ; Cu Kα1 radiation).

10. The solid form of (R)-MDMA HCl salt of claim 9, wherein the solid form of (R)-MDMA HCl XRPD spectrum is further characterized by one or more additional XRPD signal selected from the group consisting of 24.7° 2θ, and 29.1° 2θ (±0.2° 2θ; ±0.1° 2θ; or ±0.0° 2θ; Cu Kα1 radiation).

11. A pharmaceutical composition comprising the solid form of claim 9, and a pharmaceutically acceptable excipient.

12. A method of treating PTSD in a subject in need thereof, comprising administering to the subject the solid form of claim 9.

13. The pharmaceutical composition of claim 11, wherein the (R)-MDMA is present in enantiomeric excess of at least 70%, at least 80%, at least 90%, at least 94%, at least 96%, at least 98%, or at least 99% enantiomeric excess.

14. A solid form of(S)-3,4-methylenedioxy-methamphetamine ((S)-MDMA) HCl salt, wherein the solid form is characterized by an XRPD spectrum comprising two or three XRPD signals at 7.9° 2θ, 14.0° 2θ, and 15.7° 2θ (±0.2° 2θ; ±0.1° 2θ; or ±0.0° 2θ; Cu Kα1 radiation).

15. The solid form of(S)-MDMA HCl salt of claim 14, wherein the solid form of(S)-MDMA HCl XRPD spectrum is further characterized by one or more additional XRPD signal selected from the group consisting of 19.6° 2θ, and 20.6° 2θ (±0.2° 2θ; ±0.1° 2θ; or ±0.0° 2θ; Cu Kα1 radiation).

16. The solid form of(S)-3,4-methylenedioxy-methamphetamine ((S)-MDMA) HCl salt of claim 14, wherein the solid form of(S)-MDMA HCl XRPD spectrum is further characterized by one or more additional XRPD signal selected from the group consisting of 19.6° 2θ, 20.6° 2θ, 17.4° 2θ, and 24.7° 2θ, (±0.2° 2θ; ±0.1° 2θ; or ±0.0° 2θ; Cu Kα1 radiation).

17. A solid form of(S)-3,4-methylenedioxy-methamphetamine ((S)-MDMA) HCl salt, wherein the solid form of(S)-MDMA HCl is characterized by an XRPD spectrum comprising two or more XRPD signals in Table 67A (±0.2° 2θ; ±0.1° 2θ; or ±0.0° 2θ; Cu Kα1 radiation).

18. A solid form of(S)-3,4-methylenedioxy-methamphetamine ((S)-MDMA) HCl salt, wherein the solid form of(S)-MDMA HCl is further characterized by a XRPD spectrum substantially similar to that shown in FIG. 13 or FIG. 14.

19. A pharmaceutical composition comprising the solid form of claim 14, and a pharmaceutically acceptable excipient.

20. A method of treating PTSD in a subject in need thereof, comprising administering to the subject the solid form of claim 14.

21. The pharmaceutical composition of claim 19, wherein the(S)-MDMA is present in enantiomeric excess of at least 70%, at least 80%, at least 90%, at least 94%, at least 96%, at least 98%, or at least 99% enantiomeric excess.

22. A solid form of(S)-MDMA HCl salt, wherein the solid form is characterized by an XRPD spectrum comprising two or three XRPD signals at 15.7° 2θ, 17.4° 2θ, and 20.6° 2θ (±0.2° 2θ; ±0.1° 2θ; or ±0.0° 2θ; Cu Kα1 radiation).

23. The solid form of(S)-MDMA HCl salt of claim 22, wherein the solid form of(S)-MDMA HCl XRPD spectrum is further characterized by one or more additional XRPD signals selected from the group consisting of 24.7° 2θ, and 29.1° 2θ (±0.2° 2θ; ±0.1° 2θ; or ±0.0° 2θ; Cu Kα1 radiation).

24. A pharmaceutical composition comprising the solid form of claim 22, and a pharmaceutically acceptable excipient.

25. A method of treating PTSD in a subject in need thereof, comprising administering to the subject the solid form of claim 22.

26. The pharmaceutical composition of claim 24, wherein the(S)-MDMA is present in enantiomeric excess of at least 70%, at least 80%, at least 90%, at least 94%, at least 96%, at least 98%, or at least 99% enantiomeric excess.

27. A pharmaceutical composition comprising the solid form of claim 4, and a pharmaceutically acceptable excipient.

28. A method of treating post-traumatic stress disorder (PTSD) in a subject in need thereof, comprising administering to the subject the solid form of claim 4.

29. The pharmaceutical composition of claim 27, wherein the (R)-MDMA is present in enantiomeric excess of at least 70%, at least 80%, at least 90%, at least 94%, at least 96%, at least 98%, or at least 99% enantiomeric excess.

30. A pharmaceutical composition comprising the solid form of claim 5, and a pharmaceutically acceptable excipient.

31. A method of treating post-traumatic stress disorder (PTSD) in a subject in need thereof, comprising administering to the subject the solid form of claim 5.

32. The pharmaceutical composition of claim 30, wherein the (R)-MDMA is present in enantiomeric excess of at least 70%, at least 80%, at least 90%, at least 94%, at least 96%, at least 98%, or at least 99% enantiomeric excess.

33. A pharmaceutical composition comprising the solid form of claim 17, and a pharmaceutically acceptable excipient.

34. A method of treating post-traumatic stress disorder (PTSD) in a subject in need thereof, comprising administering to the subject the solid form of claim 17.

35. The pharmaceutical composition of claim 33, wherein the (R)-MDMA is present in enantiomeric excess of at least 70%, at least 80%, at least 90%, at least 94%, at least 96%, at least 98%, or at least 99% enantiomeric excess.

36. A pharmaceutical composition comprising the solid form of claim 18, and a pharmaceutically acceptable excipient.

37. A method of treating post-traumatic stress disorder (PTSD) in a subject in need thereof, comprising administering to the subject the solid form of claim 18.

38. The pharmaceutical composition of claim 36, wherein the (R)-MDMA is present in enantiomeric excess of at least 70%, at least 80%, at least 90%, at least 94%, at least 96%, at least 98%, or at least 99% enantiomeric excess.

* * * * *